(12) United States Patent
Bluemling et al.

(10) Patent No.: US 11,192,914 B2
(45) Date of Patent: Dec. 7, 2021

(54) ALKYNE CONTAINING NUCLEOTIDE AND NUCLEOSIDE THERAPEUTIC COMPOSITIONS AND USES RELATED THERETO

(71) Applicant: Emory University, Atlanta, GA (US)

(72) Inventors: Gregory Bluemling, Decatur, GA (US); Abel De La Rosa, Alpharetta, GA (US); George Painter, Atlanta, GA (US); Damien Kuiper, Atlanta, GA (US); Alexander Kolykhalov, Atlanta, GA (US)

(73) Assignee: Emory University, Atlanta, GA (US)

( * ) Notice: Subject to any disclaimer, the term of this patent is extended or adjusted under 35 U.S.C. 154(b) by 20 days.

(21) Appl. No.: 16/097,382

(22) PCT Filed: Apr. 28, 2017

(86) PCT No.: PCT/US2017/030080
§ 371 (c)(1),
(2) Date: Oct. 29, 2018

(87) PCT Pub. No.: WO2017/189978
PCT Pub. Date: Nov. 2, 2017

(65) Prior Publication Data
US 2019/0144484 A1    May 16, 2019

Related U.S. Application Data

(60) Provisional application No. 62/328,857, filed on Apr. 28, 2016.

(51) Int. Cl.
| | |
|---|---|
| *C07H 19/06* | (2006.01) |
| *A61K 45/06* | (2006.01) |
| *C07H 19/10* | (2006.01) |
| *C07H 19/12* | (2006.01) |
| *C07H 19/14* | (2006.01) |
| *C07H 19/20* | (2006.01) |
| *C07H 19/11* | (2006.01) |
| *C07H 19/213* | (2006.01) |
| *A61P 31/14* | (2006.01) |
| *A61K 31/706* | (2006.01) |
| *A61K 31/7068* | (2006.01) |
| *A61K 31/7072* | (2006.01) |
| *A61K 31/7076* | (2006.01) |
| *C07H 19/16* | (2006.01) |

(52) U.S. Cl.
CPC .......... *C07H 19/06* (2013.01); *A61K 31/706* (2013.01); *A61K 31/7068* (2013.01); *A61K 31/7072* (2013.01); *A61K 31/7076* (2013.01); *A61K 45/06* (2013.01); *A61P 31/14* (2018.01); *C07H 19/10* (2013.01); *C07H 19/11* (2013.01); *C07H 19/12* (2013.01); *C07H 19/14* (2013.01); *C07H 19/16* (2013.01); *C07H 19/20* (2013.01); *C07H 19/213* (2013.01)

(58) Field of Classification Search
CPC ................ A61K 45/06; A61K 31/7068; A61K 31/7064; A61K 31/7072; A61K 31/7076; A61K 31/706; A61K 2300/00; C07H 19/06; C07H 19/12; C07H 19/213; C07H 19/10; C07H 19/14; C07H 19/20; C07H 19/16; C07H 19/11; A61P 31/14; A61P 31/12; A61P 31/18; A61P 31/16
See application file for complete search history.

(56) References Cited

U.S. PATENT DOCUMENTS

| | | |
|---|---|---|
| 5,607,925 A | 3/1997 | Matthews et al. |
| 6,056,961 A | 5/2000 | Lavie et al. |
| 6,143,752 A | 11/2000 | Oren |
| 6,369,086 B1 | 4/2002 | Davis et al. |
| 6,369,087 B1 | 4/2002 | Whittle et al. |

(Continued)

FOREIGN PATENT DOCUMENTS

| | | |
|---|---|---|
| CA | 2518115 C | 3/2012 |
| DE | 102005038768 A1 | 2/2007 |

(Continued)

OTHER PUBLICATIONS

International Search Report and Written Opinion issued for International Application No. PCT/US2017/030080, dated Oct. 6, 2017.

(Continued)

*Primary Examiner* — Lawrence E Crane
(74) *Attorney, Agent, or Firm* — Meunier Carlin & Curfman LLC

(57) ABSTRACT

This disclosure relates to nucleotide and nucleoside therapeutic compositions and uses in treating infectious diseases, viral infections, and cancer, where the nucleotide or nucleoside is defined by Formula I below,

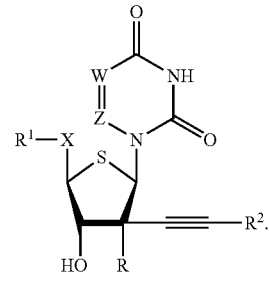

Formula I

18 Claims, No Drawings

(56) References Cited

U.S. PATENT DOCUMENTS

| | | |
|---|---|---|
| 6,372,733 B1 | 4/2002 | Caldwell et al. |
| 6,372,778 B1 | 4/2002 | Tung et al. |
| 6,403,564 B1 | 6/2002 | Ganguly et al. |
| 6,475,985 B1 | 11/2002 | Wagner et al. |
| 6,610,835 B1 | 8/2003 | Liotta et al. |
| 6,689,814 B1 | 2/2004 | Argy et al. |
| 6,849,254 B1 | 2/2005 | Brass et al. |
| 6,936,629 B2 | 8/2005 | Kong et al. |
| 6,995,174 B2 | 2/2006 | Wang et al. |
| 7,012,066 B2 | 3/2006 | Saksena et al. |
| 7,105,499 B2 | 9/2006 | Carroll et al. |
| 7,125,855 B2 | 10/2006 | Bhat et al. |
| 7,153,848 B2 | 12/2006 | Hudyma et al. |
| 7,202,224 B2 | 4/2007 | Eldrup et al. |
| 7,205,330 B2 | 4/2007 | Bogen et al. |
| 7,244,721 B2 | 7/2007 | Saksena et al. |
| 7,348,425 B2 | 3/2008 | Hudyma et al. |
| RE40,525 E | 9/2008 | Llinas-Brunet et al. |
| 7,423,058 B2 | 9/2008 | Bogen et al. |
| 7,429,572 B2 | 9/2008 | Clark |
| 7,470,664 B2 | 12/2008 | Holloway et al. |
| 7,491,794 B2 | 2/2009 | Blatt et al. |
| 7,514,557 B2 | 4/2009 | Busacca et al. |
| 7,585,845 B2 | 9/2009 | Llinas et al. |
| 7,592,316 B2 | 9/2009 | Njoroge et al. |
| 7,601,820 B2 | 10/2009 | Wang et al. |
| 7,608,600 B2 | 10/2009 | Storer et al. |
| 7,648,998 B2 | 1/2010 | Bondy et al. |
| 7,728,027 B2 | 6/2010 | Pack et al. |
| 7,754,699 B2 | 7/2010 | Chun et al. |
| 7,772,178 B2 | 8/2010 | Malcolm et al. |
| 7,777,395 B2 | 8/2010 | Xu et al. |
| 7,793,040 B2 | 9/2010 | Bittner |
| 7,820,671 B2 | 10/2010 | Babine et al. |
| 7,893,264 B2 | 2/2011 | Casarez et al. |
| 7,906,619 B2 | 3/2011 | Phadke et al. |
| 7,910,595 B2 | 3/2011 | Betebenner et al. |
| 7,910,728 B2 | 3/2011 | Hildbrand et al. |
| 7,915,291 B2 | 3/2011 | Wang et al. |
| 7,939,667 B2 | 5/2011 | Llinas-Brunet et al. |
| 7,951,787 B2 | 5/2011 | Mcguigan |
| 7,951,789 B2 | 5/2011 | Sommadossi et al. |
| 7,964,580 B2 | 6/2011 | Sofia et al. |
| 7,973,040 B2 | 7/2011 | Harper et al. |
| 8,017,771 B2 | 9/2011 | Busacca et al. |
| 8,067,438 B2 | 11/2011 | Llinas-Brunet et al. |
| 8,080,654 B2 | 12/2011 | Harper et al. |
| 8,088,368 B2 | 1/2012 | Guo et al. |
| 8,101,765 B2 | 1/2012 | Busacca et al. |
| 8,106,187 B2 | 1/2012 | Scalone et al. |
| 8,119,602 B2 | 2/2012 | Zhang et al. |
| RE43,298 E | 4/2012 | Saksena et al. |
| 8,148,399 B2 | 4/2012 | Simmen et al. |
| 8,178,491 B2 | 5/2012 | Cho et al. |
| 8,216,999 B2 | 7/2012 | Holloway et al. |
| 8,252,923 B2 | 8/2012 | Babine et al. |
| 8,466,159 B2 | 6/2013 | Bernstein et al. |
| 8,492,386 B2 | 7/2013 | Bernstein et al. |
| 8,575,119 B2 * | 11/2013 | Wang ............... C07H 19/12 514/43 |
| 8,685,984 B2 | 4/2014 | Bernstein et al. |
| 8,809,265 B2 | 8/2014 | Bernstein et al. |
| 8,853,176 B2 | 10/2014 | Bernstein et al. |
| 8,889,159 B2 | 11/2014 | Cleary et al. |
| 8,969,357 B2 | 3/2015 | Bernstein et al. |
| 8,980,865 B2 * | 3/2015 | Wang ............... C07H 19/20 514/47 |
| 8,993,578 B2 | 3/2015 | Bernstein et al. |
| 9,243,022 B2 * | 1/2016 | Beigelman ............ A61P 31/14 |
| 9,556,216 B2 * | 1/2017 | Anandan ............ C07H 19/06 |
| 9,598,457 B2 * | 3/2017 | Smith ............... C07H 19/207 |
| 9,603,863 B2 * | 3/2017 | Blatt ............... A61K 31/7068 |
| 9,603,864 B2 * | 3/2017 | Blatt ............... A61K 31/7076 |
| 9,605,018 B2 * | 3/2017 | Wang ............... C07H 19/207 |
| 9,732,111 B2 * | 8/2017 | Bennett ............ C07H 19/06 |
| 9,758,544 B2 * | 9/2017 | Beigelman ......... A61K 31/7076 |
| 9,814,739 B2 * | 11/2017 | Anandan ................ A61P 31/12 |
| 9,815,864 B2 * | 11/2017 | Beigelman ............ C07H 19/20 |
| 9,862,743 B2 * | 1/2018 | Beigelman ............ C07H 19/06 |
| 10,023,626 B2 * | 7/2018 | Bolen ............... A61K 31/7115 |
| 10,052,342 B2 * | 8/2018 | Blatt ................ A61K 31/7068 |
| 10,112,966 B2 * | 10/2018 | Beigelman ............ C07H 19/10 |
| 10,144,755 B2 * | 12/2018 | Beigelman ............ C07H 19/16 |
| 10,307,439 B2 * | 6/2019 | Blatt .................... A61K 31/708 |
| 10,370,401 B2 * | 8/2019 | Beigelman ......... A61K 31/7076 |
| 10,487,104 B2 * | 11/2019 | Beigelman ............ A61K 31/14 |
| 2002/0022015 A1 | 2/2002 | Okushin |
| 2002/0119122 A1 | 8/2002 | Stalgis et al. |
| 2002/0183690 A1 | 12/2002 | Arnisolle |
| 2003/0004119 A1 | 1/2003 | Ganguly et al. |
| 2003/0032590 A1 | 2/2003 | Dieterich |
| 2003/0044824 A1 | 3/2003 | Abe |
| 2003/0109697 A1 | 6/2003 | Shepard |
| 2003/0138403 A1 | 7/2003 | Drustrup |
| 2003/0187000 A1 | 10/2003 | Yao |
| 2003/0199518 A1 | 11/2003 | Dubuisson |
| 2004/0167123 A1 | 8/2004 | Pratt et al. |
| 2004/0198840 A1 | 10/2004 | Deloach |
| 2004/0202641 A1 | 10/2004 | Wei et al. |
| 2005/0085528 A1 | 4/2005 | Ahola et al. |
| 2005/0123628 A1 | 6/2005 | Zabrecky |
| 2005/0187170 A1 | 8/2005 | Bantia et al. |
| 2005/0245502 A1 | 11/2005 | Keller |
| 2005/0249702 A1 | 11/2005 | Njoroge et al. |
| 2005/0288245 A1 | 12/2005 | Sarnow et al. |
| 2006/0083785 A1 | 4/2006 | Kerrish |
| 2006/0100148 A1 | 5/2006 | Liu et al. |
| 2006/0105063 A1 | 5/2006 | Hann et al. |
| 2006/0142238 A1 | 6/2006 | Mcguigan |
| 2006/0228333 A1 | 10/2006 | Paik |
| 2006/0229293 A1 | 10/2006 | Lotsof |
| 2006/0275366 A1 | 12/2006 | Malcolm et al. |
| 2006/0276404 A1 | 12/2006 | Ghosal et al. |
| 2006/0276406 A1 | 12/2006 | Gupta et al. |
| 2006/0276407 A1 | 12/2006 | Albrecht et al. |
| 2006/0281689 A1 | 12/2006 | Malcolm |
| 2006/0287248 A1 | 12/2006 | Malcolm |
| 2006/0293267 A1 | 12/2006 | Zamore et al. |
| 2007/0021351 A1 | 1/2007 | Glukhovsky |
| 2007/0092512 A1 | 4/2007 | Daaka et al. |
| 2007/0105781 A1 | 5/2007 | Lyons et al. |
| 2007/0207949 A1 | 9/2007 | Ghosal et al. |
| 2007/0224167 A1 | 9/2007 | Emini et al. |
| 2007/0004635 A1 | 10/2007 | Albrecht et al. |
| 2007/0232527 A1 | 10/2007 | Ghosal et al. |
| 2007/0237818 A1 | 10/2007 | Malcolm et al. |
| 2007/0274951 A1 | 11/2007 | Tong et al. |
| 2007/0287664 A1 | 12/2007 | Ralston et al. |
| 2008/0004236 A1 | 1/2008 | Comper |
| 2008/0019950 A1 | 1/2008 | Heins et al. |
| 2008/0050336 A1 | 2/2008 | Bachand et al. |
| 2008/0070861 A1 | 3/2008 | Clark |
| 2008/0081791 A1 | 4/2008 | Huang et al. |
| 2008/0161232 A1 | 7/2008 | Hummel et al. |
| 2008/0261906 A1 | 10/2008 | Glenn et al. |
| 2008/0269205 A1 | 10/2008 | Loebel et al. |
| 2008/0275005 A1 | 11/2008 | Murphy et al. |
| 2008/0275141 A1 | 11/2008 | Whiteford |
| 2009/0017457 A1 | 1/2009 | Lu et al. |
| 2009/0028824 A1 | 1/2009 | Chiang et al. |
| 2009/0041716 A1 | 2/2009 | Kim et al. |
| 2009/0047245 A1 | 2/2009 | Younossi |
| 2009/0053263 A1 | 2/2009 | Cunningham et al. |
| 2009/0076100 A1 | 3/2009 | Czarnik |
| 2009/0082366 A1 | 3/2009 | Czarnik |
| 2009/0082414 A1 | 3/2009 | Czarnik |
| 2009/0098123 A1 | 4/2009 | Rice et al. |
| 2009/0105471 A1 | 4/2009 | Blatt et al. |
| 2009/0156545 A1 | 6/2009 | Hostetler et al. |
| 2009/0202476 A1 | 8/2009 | Perrone et al. |
| 2009/0234102 A1 | 9/2009 | Kohara et al. |
| 2009/0286843 A1 | 11/2009 | Blatt et al. |
| 2009/0297518 A1 | 12/2009 | Honjo et al. |
| 2009/0298916 A1 | 12/2009 | Kauppinen et al. |

(56) References Cited

U.S. PATENT DOCUMENTS

| | | |
|---|---|---|
| 2010/0009970 A1 | 1/2010 | Johansen et al. |
| 2010/0028301 A1 | 2/2010 | Bondy et al. |
| 2010/0034839 A1 | 2/2010 | Newell et al. |
| 2010/0041617 A1 | 2/2010 | Trepel et al. |
| 2010/0055055 A1 | 3/2010 | Albeck et al. |
| 2010/0056770 A1 | 3/2010 | Axt et al. |
| 2010/0068182 A1 | 3/2010 | Huang et al. |
| 2010/0081672 A1 | 4/2010 | Wan et al. |
| 2010/0093792 A1 | 4/2010 | Berkenbusch et al. |
| 2010/0099695 A1 | 4/2010 | Liverton et al. |
| 2010/0144608 A1 | 6/2010 | Ku et al. |
| 2010/0158866 A1 | 6/2010 | Zhu |
| 2010/0166661 A1 | 7/2010 | Zheng et al. |
| 2010/0168384 A1 | 7/2010 | Mcdaniel et al. |
| 2010/0216725 A1 | 8/2010 | Phadke et al. |
| 2010/0221217 A1 | 9/2010 | Porter et al. |
| 2010/0226885 A1 | 9/2010 | Albrecht et al. |
| 2010/0233122 A1 | 9/2010 | Qiu et al. |
| 2010/0234585 A1 | 9/2010 | Wang et al. |
| 2010/0254942 A1 | 10/2010 | Ewart et al. |
| 2010/0256217 A1 | 10/2010 | Weiner et al. |
| 2010/0272682 A1 | 10/2010 | Tran |
| 2010/0286083 A1 | 11/2010 | Bao et al. |
| 2010/0291034 A1 | 11/2010 | Ralston, II et al. |
| 2010/0297080 A1 | 11/2010 | Bertelsen et al. |
| 2010/0298257 A1 | 11/2010 | Ross et al. |
| 2010/0310512 A1 | 12/2010 | Guo et al. |
| 2010/0316594 A1 | 12/2010 | Sommadossi et al. |
| 2010/0317568 A1 | 12/2010 | Degoey et al. |
| 2010/0330173 A1 | 12/2010 | Rossignol et al. |
| 2011/0020272 A1 | 1/2011 | Schubert |
| 2011/0038833 A1 | 1/2011 | Clark |
| 2011/0045001 A1 | 2/2011 | Klosel et al. |
| 2011/0117055 A1 | 5/2011 | Macdonald et al. |
| 2011/0117057 A1 | 5/2011 | Saksena et al. |
| 2011/0160149 A1 | 6/2011 | Chen et al. |
| 2011/0200582 A1 | 8/2011 | Baryza et al. |
| 2011/0245484 A1 | 10/2011 | Ross et al. |
| 2011/0250176 A1 | 10/2011 | Lemm et al. |
| 2011/0251152 A1 | 10/2011 | Ross et al. |
| 2011/0257122 A1 | 10/2011 | Sofia et al. |
| 2011/0268697 A1 | 11/2011 | Kim et al. |
| 2011/0306541 A1 | 12/2011 | Delaney, IV et al. |
| 2011/0311482 A1 | 12/2011 | Wang et al. |
| 2011/0312973 A1 | 12/2011 | Liepold et al. |
| 2011/0319323 A1 | 12/2011 | Schricker et al. |
| 2012/0009148 A1 | 1/2012 | Smith |
| 2012/0010170 A1 | 1/2012 | Painter |
| 2012/0052046 A1 | 3/2012 | Chamberlain et al. |
| 2012/0058084 A1 | 3/2012 | Rad et al. |
| 2012/0059033 A1 | 3/2012 | Yang et al. |
| 2012/0071434 A1 | 3/2012 | Smith et al. |
| 2012/0101049 A1 | 4/2012 | Chen |
| 2012/0107278 A1 | 5/2012 | Berrey et al. |
| 2012/0115918 A1 | 5/2012 | Degoey et al. |
| 2012/0135949 A1 | 5/2012 | Boecher et al. |
| 2012/0151158 A1 | 6/2012 | Yeh |
| 2012/0157404 A1 | 6/2012 | Guo et al. |
| 2012/0171157 A1 | 7/2012 | Simmen |
| 2012/0172290 A1 | 7/2012 | Krueger |
| 2012/0196272 A1 | 8/2012 | Chu et al. |
| 2012/0196794 A1 | 8/2012 | Gao et al. |
| 2012/0232247 A1 | 9/2012 | Song et al. |
| 2012/0245335 A1 | 9/2012 | Clark |
| 2013/0102526 A1 | 4/2013 | Bernstein et al. |
| 2013/0102557 A1 | 4/2013 | Bernstein et al. |
| 2013/0137084 A1 | 5/2013 | Benayed |
| 2013/0164261 A1 | 6/2013 | Wang et al. |
| 2014/0080868 A1 | 3/2014 | Ng et al. |
| 2014/0080886 A1 | 3/2014 | Pilot-Matia et al. |
| 2015/0174194 A1 | 6/2015 | Bernstein et al. |
| 2015/0232501 A1 | 8/2015 | Anandan et al. |
| 2015/0299243 A1 | 10/2015 | Bennett et al. |

FOREIGN PATENT DOCUMENTS

| | | |
|---|---|---|
| EP | 1627641 A1 | 2/2006 |
| EP | 1646639 A2 | 4/2006 |
| EP | 1827450 A2 | 9/2007 |
| EP | 1970372 B1 | 11/2010 |
| JP | 2000212099 A | 8/2000 |
| KR | 20010068676 A | 7/2001 |
| MD | 2549 F1 | 9/2004 |
| MD | 20060037 A | 7/2007 |
| MD | 3477 F1 | 1/2008 |
| MX | PA05012606 A | 2/2006 |
| RO | 0118842 B | 12/2003 |
| RU | 2158604 C2 | 11/2000 |
| RU | 2212248 C1 | 9/2003 |
| RU | 2293572 C1 | 2/2007 |
| RU | 2306134 C2 | 9/2007 |
| RU | 2306934 C1 | 9/2007 |
| RU | 2336096 C1 | 10/2008 |
| RU | 2345787 C2 | 2/2009 |
| RU | 2348412 C1 | 3/2009 |
| RU | 2373952 C1 | 11/2009 |
| RU | 2398582 C1 | 9/2010 |
| RU | 2400229 C1 | 9/2010 |
| RU | 2424794 C1 | 7/2011 |
| RU | 2429877 C1 | 9/2011 |
| UA | 6419 A | 2/2004 |
| UA | 68233 A | 7/2004 |
| WO | 1991009605 A1 | 7/1991 |
| WO | 1994001125 A1 | 1/1994 |
| WO | 1996018419 A1 | 6/1996 |
| WO | 1996029336 A1 | 9/1996 |
| WO | 1996036351 A1 | 11/1996 |
| WO | 1997027866 A1 | 8/1997 |
| WO | 1997033565 A1 | 9/1997 |
| WO | 1998014181 A1 | 4/1998 |
| WO | 1998019670 A2 | 5/1998 |
| WO | 1998048621 A1 | 11/1998 |
| WO | 1998049281 A1 | 11/1998 |
| WO | 1999015194 A1 | 4/1999 |
| WO | 1999018993 A1 | 4/1999 |
| WO | 1999029321 A1 | 6/1999 |
| WO | 1999030721 A1 | 6/1999 |
| WO | 2000001715 A1 | 1/2000 |
| WO | 2000023454 A1 | 4/2000 |
| WO | 2000037097 A1 | 6/2000 |
| WO | 2000037110 A2 | 6/2000 |
| WO | 2000047240 A1 | 8/2000 |
| WO | 2000061161 A2 | 10/2000 |
| WO | 2001007454 A1 | 2/2001 |
| WO | 2001012214 A2 | 2/2001 |
| WO | 2001077091 A2 | 10/2001 |
| WO | 2001079540 A2 | 10/2001 |
| WO | 2002003886 A1 | 1/2002 |
| WO | 2002010743 A1 | 2/2002 |
| WO | 2002018369 A2 | 3/2002 |
| WO | 2002030259 A2 | 4/2002 |
| WO | 2002030455 A2 | 4/2002 |
| WO | 2002032414 A2 | 4/2002 |
| WO | 2002053096 A2 | 7/2002 |
| WO | 2002055100 A2 | 7/2002 |
| WO | 2002079234 A1 | 10/2002 |
| WO | 2002089731 A2 | 11/2002 |
| WO | 2002091989 A2 | 11/2002 |
| WO | 2003002152 A2 | 1/2003 |
| WO | 2003007981 A1 | 1/2003 |
| WO | 2003024461 A1 | 3/2003 |
| WO | 2003028754 A1 | 4/2003 |
| WO | 2003028755 A1 | 4/2003 |
| WO | 2003030923 A1 | 4/2003 |
| WO | 2003037312 A2 | 5/2003 |
| WO | 2003037908 A1 | 5/2003 |
| WO | 2003040104 A1 | 5/2003 |
| WO | 2003042377 A1 | 5/2003 |
| WO | 2003049760 A1 | 6/2003 |
| WO | 2003072135 A2 | 9/2003 |
| WO | 2003101199 A1 | 12/2003 |
| WO | 2003101478 A1 | 12/2003 |
| WO | 2004019934 A1 | 3/2004 |

(56) References Cited

FOREIGN PATENT DOCUMENTS

| | | |
|---|---|---|
| WO | 2004039996 A1 | 5/2004 |
| WO | 2004043435 A2 | 5/2004 |
| WO | 2004047673 A2 | 6/2004 |
| WO | 2004073599 A2 | 9/2004 |
| WO | 2004078127 A2 | 9/2004 |
| WO | 2004078191 A1 | 9/2004 |
| WO | 2004078194 A1 | 9/2004 |
| WO | 2004094452 A2 | 11/2004 |
| WO | 2004103396 A1 | 12/2004 |
| WO | 2004112720 A2 | 12/2004 |
| WO | 2005000308 A2 | 1/2005 |
| WO | 2005010143 A2 | 2/2005 |
| WO | 2005012327 A2 | 2/2005 |
| WO | 2005016288 A2 | 2/2005 |
| WO | 2005018330 A1 | 3/2005 |
| WO | 2005023289 A1 | 3/2005 |
| WO | 2005025583 A2 | 3/2005 |
| WO | 2005037214 A2 | 4/2005 |
| WO | 2005037274 A1 | 4/2005 |
| WO | 2005038056 A1 | 4/2005 |
| WO | 2005040816 A1 | 5/2005 |
| WO | 2005042020 A2 | 5/2005 |
| WO | 2005043118 A2 | 5/2005 |
| WO | 2005062949 A2 | 7/2005 |
| WO | 2005063281 A2 | 7/2005 |
| WO | 2005067454 A2 | 7/2005 |
| WO | 2005067963 A1 | 7/2005 |
| WO | 2005102353 A1 | 11/2005 |
| WO | 2005108418 A1 | 11/2005 |
| WO | 2005123076 A2 | 12/2005 |
| WO | 2006005610 A1 | 1/2006 |
| WO | 2006016930 A2 | 2/2006 |
| WO | 2006038088 A1 | 2/2006 |
| WO | 2006039488 A2 | 4/2006 |
| WO | 2006043153 A2 | 4/2006 |
| WO | 2006046039 A2 | 5/2006 |
| WO | 2006050250 A2 | 5/2006 |
| WO | 2006063149 A1 | 6/2006 |
| WO | 2006064026 A1 | 6/2006 |
| WO | 2006067606 A1 | 6/2006 |
| WO | 2006072347 A2 | 7/2006 |
| WO | 2006084141 A2 | 8/2006 |
| WO | 2006085747 A1 | 8/2006 |
| WO | 2006089113 A2 | 8/2006 |
| WO | 2006096285 A2 | 9/2006 |
| WO | 2006110656 A2 | 10/2006 |
| WO | 2006113937 A2 | 10/2006 |
| WO | 2006119646 A1 | 11/2006 |
| WO | 2006127289 A1 | 11/2006 |
| WO | 2006127482 A1 | 11/2006 |
| WO | 2006127757 A2 | 11/2006 |
| WO | 2006130532 A2 | 12/2006 |
| WO | 2006130626 A2 | 12/2006 |
| WO | 2006130686 A2 | 12/2006 |
| WO | 2006133092 A1 | 12/2006 |
| WO | 2007021494 A2 | 2/2007 |
| WO | 2007022459 A2 | 2/2007 |
| WO | 2007049265 A2 | 5/2007 |
| WO | 2007056016 A2 | 5/2007 |
| WO | 2007058384 A1 | 5/2007 |
| WO | 2007059221 A2 | 5/2007 |
| WO | 2007062272 A1 | 5/2007 |
| WO | 2007064691 A1 | 6/2007 |
| WO | 2007075896 A2 | 7/2007 |
| WO | 2007081974 A2 | 7/2007 |
| WO | 2007098270 A2 | 8/2007 |
| WO | 2007109080 A2 | 9/2007 |
| WO | 2007109604 A2 | 9/2007 |
| WO | 2007109605 A2 | 9/2007 |
| WO | 2007111866 A2 | 10/2007 |
| WO | 2007112028 A2 | 10/2007 |
| WO | 2007138116 A2 | 12/2007 |
| WO | 2007143164 A1 | 12/2007 |
| WO | 2007146712 A2 | 12/2007 |
| WO | 2007149382 A2 | 12/2007 |
| WO | 2008005511 A2 | 1/2008 |
| WO | 2008008502 A1 | 1/2008 |
| WO | 2008017692 A2 | 2/2008 |
| WO | 2008022006 A2 | 2/2008 |
| WO | 2008024763 A2 | 2/2008 |
| WO | 2008024843 A2 | 2/2008 |
| WO | 2008033413 A2 | 3/2008 |
| WO | 2008033466 A2 | 3/2008 |
| WO | 2008153610 A2 | 3/2008 |
| WO | 2008039179 A1 | 4/2008 |
| WO | 2008058393 A1 | 5/2008 |
| WO | 2008063727 A2 | 5/2008 |
| WO | 2008086161 A1 | 7/2008 |
| WO | 2008089034 A2 | 7/2008 |
| WO | 2008091763 A1 | 7/2008 |
| WO | 2008092954 A2 | 8/2008 |
| WO | 2008095993 A1 | 8/2008 |
| WO | 2008106151 A2 | 9/2008 |
| WO | 2008106167 A1 | 9/2008 |
| WO | 2008116194 A2 | 9/2008 |
| WO | 2008118013 A2 | 10/2008 |
| WO | 2008121634 A3 | 10/2008 |
| WO | 2008124384 A2 | 10/2008 |
| WO | 2008137126 A2 | 11/2008 |
| WO | 2008137779 A2 | 11/2008 |
| WO | 2008141227 A1 | 11/2008 |
| WO | 2008143647 A2 | 11/2008 |
| WO | 2008144072 A1 | 11/2008 |
| WO | 2009009951 A1 | 1/2009 |
| WO | 2009015336 A2 | 1/2009 |
| WO | 2009026292 A1 | 2/2009 |
| WO | 2009032198 A1 | 3/2009 |
| WO | 2009033183 A2 | 3/2009 |
| WO | 2009038663 A1 | 3/2009 |
| WO | 2009039127 A1 | 3/2009 |
| WO | 2009039134 A1 | 3/2009 |
| WO | 2009039135 A1 | 3/2009 |
| WO | 2009039248 A2 | 3/2009 |
| WO | 2009043176 A1 | 4/2009 |
| WO | 2009061395 A2 | 5/2009 |
| WO | 2009062737 A1 | 5/2009 |
| WO | 2009046369 A3 | 7/2009 |
| WO | 2009082701 A1 | 7/2009 |
| WO | 2009085267 A1 | 7/2009 |
| WO | 2009085659 A1 | 7/2009 |
| WO | 2009131696 A1 | 10/2009 |
| WO | 2009134616 A2 | 11/2009 |
| WO | 2009138146 A2 | 11/2009 |
| WO | 2009149179 A2 | 12/2009 |
| WO | 2009149377 A1 | 12/2009 |
| WO | 2009150194 A1 | 12/2009 |
| WO | 2009152589 A1 | 12/2009 |
| WO | 2010015637 A1 | 2/2010 |
| WO | 2010017178 A1 | 2/2010 |
| WO | 2010017432 A1 | 2/2010 |
| WO | 2010020676 A1 | 2/2010 |
| WO | 2010021681 A2 | 2/2010 |
| WO | 2010024384 A1 | 3/2010 |
| WO | 2010025380 A2 | 3/2010 |
| WO | 2010027921 A1 | 3/2010 |
| WO | 2010030359 A2 | 3/2010 |
| WO | 2010031832 A3 | 3/2010 |
| WO | 2010033443 A1 | 3/2010 |
| WO | 2010034670 A2 | 4/2010 |
| WO | 2010036799 A1 | 4/2010 |
| WO | 2010038796 A1 | 4/2010 |
| WO | 2010039801 A2 | 4/2010 |
| WO | 2010042683 A1 | 4/2010 |
| WO | 2010045266 A1 | 4/2010 |
| WO | 2010049438 A2 | 5/2010 |
| WO | 2010053942 A1 | 5/2010 |
| WO | 2010075376 A2 | 7/2010 |
| WO | 2010076323 A1 | 7/2010 |
| WO | 2010093843 A2 | 8/2010 |
| WO | 2010099458 A1 | 9/2010 |
| WO | 2010101649 A2 | 9/2010 |
| WO | 2010111436 A2 | 9/2010 |
| WO | 2010111437 A1 | 9/2010 |
| WO | 2010120935 A1 | 10/2010 |

(56) References Cited

FOREIGN PATENT DOCUMENTS

| | | |
|---|---|---|
| WO | 2010122538 A1 | 10/2010 |
| WO | 2010132601 A1 | 11/2010 |
| WO | 2010151472 A1 | 12/2010 |
| WO | 2010151487 A1 | 12/2010 |
| WO | 2010151488 A1 | 12/2010 |
| WO | 2011009961 A1 | 1/2011 |
| WO | 2011013019 A1 | 2/2011 |
| WO | 2011014882 A1 | 2/2011 |
| WO | 2011038224 A1 | 3/2011 |
| WO | 2011041551 A1 | 4/2011 |
| WO | 2011046811 A1 | 4/2011 |
| WO | 2011053617 A1 | 5/2011 |
| WO | 2011056630 A2 | 5/2011 |
| WO | 2011056650 A2 | 5/2011 |
| WO | 2011066082 A2 | 6/2011 |
| WO | 2011066260 A2 | 6/2011 |
| WO | 2011072370 A1 | 6/2011 |
| WO | 2011079016 A1 | 6/2011 |
| WO | 2011094489 A1 | 8/2011 |
| WO | 2011112558 A2 | 9/2011 |
| WO | 2011156337 A2 | 12/2011 |
| WO | 2011156578 A1 | 12/2011 |
| WO | 2011156757 A1 | 12/2011 |
| WO | 2012009503 A1 | 1/2012 |
| WO | 2012009699 A2 | 1/2012 |
| WO | 2012015712 A1 | 2/2012 |
| WO | 2012016995 A1 | 2/2012 |
| WO | 2012018829 A1 | 2/2012 |
| WO | 2012041771 A1 | 4/2012 |
| WO | 2012050850 A1 | 4/2012 |
| WO | 2012051361 A1 | 4/2012 |
| WO | 2012083170 A1 | 6/2012 |
| WO | 2012087596 A1 | 6/2012 |
| WO | 2012087833 A1 | 6/2012 |
| WO | 2012092411 A2 | 7/2012 |
| WO | 2012139028 A2 | 10/2012 |
| WO | 2012175733 A1 | 12/2012 |
| WO | 2013000855 A1 | 1/2013 |
| WO | 2013000856 A1 | 1/2013 |
| WO | 2013024155 A1 | 2/2013 |
| WO | 2013025975 A1 | 2/2013 |
| WO | 2013028953 A1 | 2/2013 |
| WO | 2013040492 A2 | 3/2013 |
| WO | 2013044030 A1 | 3/2013 |
| WO | 2013066753 A1 | 5/2013 |
| WO | 2013096680 A1 | 6/2013 |
| WO | 2014078463 A1 | 5/2014 |
| WO | 2014100505 A1 | 6/2014 |
| WO | 2014152514 A1 | 9/2014 |
| WO | 2014152635 A1 | 9/2014 |
| WO | 2015200219 A1 | 12/2015 |

OTHER PUBLICATIONS

International Preliminary Report on Patentability issued for International Application No. PCT/US2017/030080, dated Oct. 6, 2018.
Boumendjel, Ahcene and Miller, Synthesis of sphingosine-1-phosphate and dihydrosphingosine-1-phosphate. Stephen Journal of Lipid Research 1994, 35, 2305.
Bushnev et al., An efficient asymmetric synthesis of Enigmols (1-deoxy-5-hydroxysphingoid bases), an important class of bioactive lipid modulators, ARKIVOC, 2010, (viii):263-277.
Chojnowski et al., Methods of Synthesis of O,O-Bis TrimethylSilyl Phosphorothiolates. Synthesis-Stuttgart 1977, 10, 683-686.
Dembinski et al., An Expedient Synthesis of Symmetrical Tetra-Alkyl Mono-thiopyrophosphates, Tetrahedron Letters 1994, 35 (34), 6331-6334.
Dougherty et al., Synthesis of 1-deoxysphingosine derivatives with conformationally restricted pyrrolidinediol head groups, Org. Lett. 2006, 8(4), 649-652.
Imai, Human carboxylesterase isozymes: catalytic properties and rational drug design, Drug Metab Pharmacokinet. (2006) 21(3):173-85.
Jessen et al., Bioreversible Protection of Nucleoside Diphosphates, Angewandte Chemie-International Edition English 2008, 47 (45), 8719-8722.
McGuigan et al., Application of Phosphoramidate Pronucleotide Technology to Abacavir Leads to a Significant Enhancement of Antiviral Potency, J Med Chem, 2005, 48(10), 3504-3515.
Meier et al., Comparative study of bis(benzyl)phosphate triesters of 2',3'-dideoxy-2',3'-didehydrothymidine (d4T) and cycloSal-d4TMP-hydrolysis, mechanistic insights and anti-HIV activity, Antiviral Chemistry and Chemotherapy 2002, 13,101-114.
Painter et al., Evaluation of Hexadecyloxypropyl-9-R-[2-(Phosphonomethoxy)Propyl]-Adenine, CMX157, as a Potential Treatment for Human Immunodeficiency Virus Type 1 and Hepatitis B Virus Infections, Antimicrob Agents Chemother, 2007, 51(10), 3505-3509.
Pruett et al., Thematic Review Series: Sphingolipids. Biodiversity of sphingoid bases ("sphingosines") and related amino alcohols, J. Lipid Res. 2008, 49(8), 1621-1639.
Routledge et al., Synthesis, Bioactivation and Anti-HIV Activity of 4-Acyloxybenzyl-bis(nucleosid-5'-yl) Phosphates, Nucleosides & Nucleotides 1995, 14 (7), 1545-1558.
Serpi et al., Novel Phosphoramidate Prodrugs of N-Acetyl-(d)-Glucosamine with Antidegenerative Activity on Bovine and Human Cartilage Explants, J med Chem, 2012, 55(10):4629-4639.
Skowronska et al., Novel Synthesis of Symmetrical Tetre-Alkyl Monothiophosphates, Tetrahedron Letters 1987, 28 (36), 4209-4210.
Skowronska et al., Reaction of Oxophosphorane-Sulfenyl and Oxophosphorane-Selenenyl Chlorides with Dialkyl Trimethylsilyl Phosphites—Novel Synthesis of Compounds Containing a Sulfur or Selenium Bridge Between 2 Phosphoryl Centers, Journal of the Chemical Society-Perkin Transactions 1 1988, 8, 2197-2201.
Wiseman et al., 1-Deoxy-5-hydroxysphingolipids as new anticancer principles: An Efficient Procedure for stereoselective syntheses of 2-amino-3, 5-diols, Org. Lett. 2005, 7(15), 3155-3157.
Harry-O'kuru, et al., A Short, Flexible Route toward 2'-C-Branched Ribonucleosides, J. Org. Chem. 1997, 62: 1754-1759.
Fenaux, et al., Antiviral Nucleotide Incorporation by Recombinant Human Mitochondrial RNA Polymerase Is Predictive of Increased In Vivo Mitochondrial Toxicity Risk, Antimicrobial Agents and Chemotherapy, 2016, 60, 12:7077-7085.
Extended European Search Report dated Nov. 22, 2019 for Application No. 17790519.
English translation of Office Action issued in Eurasian Application No. 201892448/28 dated Apr. 20, 2020.
English translation of Office Action issued for Chinese Application No. 201780038569.9 dated Sep. 23, 2020.
English translation of Office Action issued for Eurasian Application No. 201892448 dated Oct. 20, 2020.
Communication received from the European Patent Office dated Feb. 19, 2021 for Application No. 17790519.7.
Office Action and English Language (Machine) translation issued in Japanese Application No. 2018-556819 dated Mar. 16, 2021.
Office Action and English translation issued in Eurasian Application No. 201892448 dated Apr. 3, 2021.

* cited by examiner

ALKYNE CONTAINING NUCLEOTIDE AND NUCLEOSIDE THERAPEUTIC COMPOSITIONS AND USES RELATED THERETO

CROSS-REFERENCE TO RELATED APPLICATIONS

This application is a 371 national phase of International Application No. PCT/US2017/30080, filed Apr. 28, 2017, which claims benefit of U.S. Provisional Application No. 62/328,857, filed Apr. 28, 2016, which are hereby incorporated herein by reference in their entirety.

FIELD

This disclosure relates to alkyne containing nucleotide and nucleoside therapeutic compositions and uses related thereto. In certain embodiments, the disclosure relates to nucleosides optionally conjugated to a phosphorus oxide or salts thereof. In certain embodiments, the disclosure relates to conjugate compounds or salts thereof comprising an amino acid ester, a lipid or a sphingolipid or derivative linked by a phosphorus oxide to a nucleotide or nucleoside. In certain embodiments, the disclosure contemplates pharmaceutical compositions comprising these compounds for uses in treating infectious diseases, viral infections, and cancer.

BACKGROUND

Nucleoside and nucleotide phosphates and phosphonates are clinically useful as antiviral agents. Two examples are tenofovir disoproxil fumarate for the treatment of human immunodeficiency virus and adefovir dipivoxil for the treatment of hepatitis B virus infections. Administration of three or more antiretroviral agents in combination, e.g., Highly Active Antiretroviral Therapy (HAART), has significantly reduced the morbidity and mortality associated with HIV infection. However, there is a growing need for new antiviral agents to address the critical issues of resistance and penetration into viral sanctuaries (commonly referred to as privileged compartments). Permeability into privileged compartments may be partially responsible for the current inability of chemotherapy to totally clear a patient of HIV infection and the emergence of resistance.

Anti-viral agents that are unphosphorylated nucleotides and nucleotide derivatives need to be phosphorylated to actively inhibit viral replication. Nucleoside analogues enter a cell via two types of broad-specificity transporters, concentrative nucleoside transporters (CNTs) and equilibrative nucleoside transporters (ENTs). Once inside, they utilize the host's nucleoside salvage pathway for sequential phosphorylation by deoxynucleoside kinases (dNKs), deoxynucleoside monophosphate kinases (dNMPKs) and nucleoside diphosphate kinase (NDPK). However, intracellular activation of these compounds is often compromised by the high substrate specificity of the host's endogenous kinases. In vitro and in vivo studies have demonstrated that the first and/or second phosphorylation, catalyzed by dNKs and dNMPKs, often represent the rate-limiting steps in nucleoside analogue activation. Thus, there is a need to identifying improved antiviral nucleoside analogues with structural features that are sufficiently activated by cellular kinases.

McGuigan et al., J Med Chem, 2005, 48(10), 3504-3515, report phenylmethoxyalaninyl phosphoramidate of abacavir as a prodrug leads to enhancement of antiviral potency. Painter et al., Antimicrob Agents Chemother, 2007, 51(10), 3505-3509, report promoting the oral availability of tenofovir with a hexadecyloxypropyl prodrug ester, designated CMX157.

Sphingolipids play roles in cell-cell and cell-substratum interactions, and help regulate growth and differentiation by a variety of mechanisms, such as inhibition of growth factor receptor kinases and effects on numerous cellular signal transduction systems. U.S. Pat. No. 6,610,835 discloses sphingosine analogues. It also discloses methods of treating infections and cancer. Pruett et al., J. Lipid Res. 2008, 49(8), 1621-1639, report on sphingosine and derivatives. Bushnev et al., ARKIVOC, 2010, (viii):263-277, report an asymmetric synthetic method for preparing sphingolipid derivatives. Dougherty et al., Org. Lett. 2006, 8(4), 649-652, report the synthesis of 1-deoxysphingosine derivatives. Wiseman et al., Org. Lett. 2005, 7(15), 3155-3157, report 1-deoxy-5-hydroxysphingolipids in anticancer and stereoselective syntheses of 2-amino-3,5-diols.

References cited herein are not an admission of prior art.

SUMMARY

This disclosure relates to alkyne containing nucleotide and nucleoside therapeutic compositions and uses related thereto. Included are nucleosides optionally conjugated to a phosphorus oxide or salts thereof, prodrugs or conjugate compounds or salts thereof comprising an amino acid ester, lipid or a sphingolipid or derivative linked by a phosphorus oxide to a nucleotide or nucleoside.

DETAILED DESCRIPTION

This disclosure relates to alkyne containing nucleotide and nucleoside therapeutic compositions and uses related thereto. In certain embodiments, the disclosure relates to nucleosides optionally conjugated to a phosphorus oxide or salts thereof. In certain embodiments, the disclosure relates to conjugate compounds or salts thereof comprising an amino acid ester, a lipid or a sphingolipid or derivative linked by a phosphorus oxide to a nucleotide or nucleoside. In certain embodiments, the disclosure contemplates pharmaceutical compositions comprising these compounds for uses in treating infectious diseases, viral infections, and cancer.

In certain embodiments, the disclosure relates to phosphorus oxide prodrugs of 2'-alkyne containing nucleosides for the treatment of positive-sense and negative-sense RNA viral infections through targeting of the virally encoded RNA-dependent RNA polymerase (RdRp). This disclosure also provides the general use of lipids and sphingolipids to deliver nucleoside analogs for the treatment of infectious disease and cancer.

In certain embodiments, the disclosure relates to conjugate compounds or salts thereof comprising a sphingolipid or derivative linked by a phosphorus oxide to a nucleotide or nucleoside. In certain embodiments, the phosphorus oxide is a phosphate, phosphonate, polyphosphate, or polyphosphonate, wherein the phosphate, phosphonate or a phosphate in the polyphosphate or polyphosphonate is optionally a phosphorothioate or phosphoroamidate. In certain embodiments, the lipid or sphingolipid is covalently bonded to the phosphorus oxide through an amino group or a hydroxyl group.

The nucleotide or nucleoside comprises a heterocycle comprising two or more nitrogen heteroatoms, wherein the substituted heterocycle is optionally substituted with one or more, the same or different alkyl, halogen, or cycloalkyl.

In certain embodiments, the sphingolipid is saturated or unsaturated 2-aminoalkyl or 2-aminooctadecane optionally substituted with one or more substituents. In certain embodiments, the sphingolipid derivative is saturated or unsaturated 2-aminooctadecane-3-ol optionally substituted with one or more substituents. In certain embodiments, the sphingolipid derivative is saturated or unsaturated 2-aminooctadecane-3,5-diol optionally substituted with one or more substituents.

In certain embodiments, the disclosure contemplates pharmaceutical compositions comprising any of the compounds disclosed herein and a pharmaceutically acceptable excipient. In certain embodiments, the pharmaceutical composition is in the form of a pill, capsule, tablet, or saline buffer comprising a saccharide. In certain embodiments, the composition may contain a second active agent such as a pain reliever, anti-inflammatory agent, non-steroidal anti-inflammatory agent, anti-viral agent, anti-biotic, or anti-cancer agent.

In certain embodiments, the disclosure relates to methods of treating or preventing an infection comprising administering an effective amount of a compound disclosed herein to a subject in need thereof. Typically, the subject is diagnosed with or at risk of an infection from a virus, bacteria, fungi, protozoa, or parasite.

In certain embodiments, the disclosure relates the methods of treating a viral infection comprising administering an effective amount of a pharmaceutical composition disclosed herein to a subject in need thereof. In certain embodiments, the subject is a mammal, for example, a human. In certain embodiments, the subject is diagnosed with a chronic viral infection. In certain embodiments, administration is under conditions such that the viral infection is no longer detected. In certain embodiments, the subject is diagnosed with a RNA virus, DNA virus, or retroviruses. In certain embodiments, the subject is diagnosed with a virus that is a double stranded DNA virus, sense single stranded DNA virus, double stranded RNA virus, sense single stranded RNA virus, antisense single stranded RNA virus, sense single stranded RNA retrovirus or a double stranded DNA retrovirus.

In certain embodiments, the subject is diagnosed with influenza A virus including subtype H1N1, H3N2, H7N9, or H5N1, influenza B virus, influenza C virus, rotavirus A, rotavirus B, rotavirus C, rotavirus D, rotavirus E, human coronavirus, SARS coronavirus, MERS coronavirus, human adenovirus types (HAdV-1 to 55), human papillomavirus (HPV) Types 16, 18, 31, 33, 35, 39, 45, 51, 52, 56, 58, and 59, parvovirus B19, molluscum contagiosum virus, JC virus (JCV), BK virus, Merkel cell polyomavirus, coxsackie A virus, norovirus, Rubella virus, lymphocytic choriomeningitis virus (LCMV), Dengue virus, chikungunya, Eastern equine encephalitis virus (EEEV), Western equine encephalitis virus (WEEV), Venezuelan equine encephalitis virus (VEEV), Ross River virus, Barmah Forest virus, yellow fever virus, measles virus, mumps virus, respiratory syncytial virus, rinderpest virus, California encephalitis virus, hantavirus, rabies virus, ebola virus, marburg virus, herpes simplex virus-1 (HSV-1), herpes simplex virus-2 (HSV-2), varicella zoster virus (VZV), Epstein-Barr virus (EBV), cytomegalovirus (CMV), herpes lymphotropic virus, roseolovirus, or Kaposi's sarcoma-associated herpesvirus, hepatitis A, hepatitis B, hepatitis C, hepatitis D, hepatitis E or human immunodeficiency virus (HIV).

In certain embodiments, the subject is diagnosed with influenza A virus including subtypes H1N1, H3N2, H7N9, H5N1 (low path), and H5N1 (high path) influenza B virus, influenza C virus, rotavirus A, rotavirus B, rotavirus C, rotavirus D, rotavirus E, SARS coronavirus, MERS-CoV, human adenovirus types (HAdV-1 to 55), human papillomavirus (HPV) Types 16, 18, 31, 33, 35, 39, 45, 51, 52, 56, 58, and 59, parvovirus B19, molluscum contagiosum virus, JC virus (JCV), BK virus, Merkel cell polyomavirus, coxsackie A virus, norovirus, Rubella virus, lymphocytic choriomeningitis virus (LCMV), yellow fever virus, measles virus, mumps virus, respiratory syncytial virus, parainfluenza viruses 1 and 3, rinderpest virus, chikungunya, eastern equine encephalitis virus (EEEV), Venezuelan equine encephalitis virus (VEEV), western equine encephalitis virus (WEEV), California encephalitis virus, Japanese encephalitis virus, Rift Valley fever virus (RVFV), hantavirus, Dengue virus serotypes 1, 2, 3 and 4, West Nile virus, Zika virus, Powassan virus, Tacaribe virus, Junin, rabies virus, ebola virus, marburg virus, adenovirus, herpes simplex virus-1 (HSV-1), herpes simplex virus-2 (HSV-2), varicella zoster virus (VZV), Epstein-Barr virus (EBV), cytomegalovirus (CMV), herpes lymphotropic virus, roseolovirus, or Kaposi's sarcoma-associated herpesvirus, hepatitis A, hepatitis B, hepatitis C, hepatitis D, hepatitis E or human immunodeficiency virus (HIV). In certain embodiments, the subject is diagnosed with gastroenteritis, acute respiratory disease, severe acute respiratory syndrome, post-viral fatigue syndrome, viral hemorrhagic fevers, acquired immunodeficiency syndrome or hepatitis.

In certain embodiments, the pharmaceutical compositions disclosed herein can be administered in combination with a any of U.S. Pat. Nos. 8,466,159; 8,492,386; 6,056,961, 6,143,752, 6,403,564, 6,475,985, 6,689,814, 6,849,254, 6,936,629, 6,995,174, 7,012,066, 7,105,499, 7,125,855, 7,153,848, 7,202,224, 7,205,330, 7,244,721, 7,348,425, 7,423,058, 7,429,572, 7,470,664, 7,491,794, 7,514,557, 7,585,845, 7,592,316, 7,601,820, 7,608,600, 7,648,998, 7,728,027, 7,754,699, 7,772,178, 7,777,395, 7,793,040, 7,820,671, 7,893,264, 7,906,619, 7,910,728, 7,915,291, 7,939,667, 7,951,787, 7,951,789, 7,964,580, 7,973,040, 8,017,771, 8,067,438, 8,080,654, 8,088,368, 8,101,765, 8,106,187, 8,119,602, 8,148,399, 8,178,491, 8,216,999, 8,252,923, 8,466,159, 8,492,386, US20020022015, US20020119122, US20020183690, US20030004119, US20030032590, US20030044824, US20030109697, US20030138403, US20030187000, US20030199518, US20040198840, US20040202641, US20050095528, US20050123628, US20050187170, US20050245502, US20050249702, US20050288245, US20060083785, US20060100148, US20060105063, US20060142238, US20060228333, US20060229293, US20060275366, US20060276404, US20060276406, US20060276407, US20060281689, US20060287248, US20060293267, US20070004635, US20070021351, US20070092512, US20070105781, US20070207949, US20070224167, US20070232527, US20070237818, US20070274951, US20070287664, US20080004236, US20080019950, US20080050336, US20080070861, US20080081791, US20080161232, US20080261906, US20080269205, US20080275005, US20080275141, US20090017457, US20090028824, US20090041716, US20090047245, US20090053263, US20090076100, US20090082366, US20090082414, US20090098123, US20090105471, US20090156545, US20090202476, US20090234102, US20090286843, US20090297518, US20090298916, US20100009970, US20100028301, US20100034839, US20100041617, US20100055055, US20100056770, US20100068182, US20100081672, US20100093792, US20100099695, US20100158866, US20100166661, US20100216725, US20100221217, US20100226885, US20100233122, US20100234585, US20100254942, WO2006038088A1, WO2006039488A2,
US20100256217, US20100272682, US20100286083, WO2006043153A2, WO2006046039A2,
US20100291034, US20100297080, US20100298257, WO2006050250A2, WO2006063149A1,
US20100310512, US20100316594, US20100317568, WO2006064026A1, WO2006067606A1,
US20100330173, US20110020272, US20110038833, WO2006072347A2, WO2006084141A2,
US20110045001, US20110117055, US20110117057, WO2006085747A1, WO2006089113A2,
US20110160149, US20110200582, US20110245484, WO2006096285A2, WO2006110656A2,
US20110250176, US20110251152, US20110257122, WO2006113937A2, WO2006119646A1,
US20110268697, US20110306541, US20110311482, WO2006127289A1, WO2006127482A1,
US20110312973, US20110319323, US20120009148, WO2006127757A2, WO2006130532A2,
US20120010170, US20120052046, US20120058084, WO2006130626A2, WO2006130686A2,
US20120059033, US20120071434, US20120101049, WO2006133092A1, WO2007021494A2,
US20120107278, US20120135949, US20120157404, WO2007022459A2, WO2007049265A2,
US20120171157, US20120196272, US20120196794, WO2007056016A2, WO2007058384A1,
US20120232247, US20130102526, US20130102557, WO2007059221A2, WO2007062272A1,
US20130137084, US20130164261, USRE40525, WO2007064691A1, WO2007075896A2,
USRE43298, CA2518115C, DE102005038768A1, WO2007081974A2, WO2007098270A2,
EP1627641A1, EP1646639A2, EP1827450A2, WO2007109080A2, WO2007109604A2,
EP1970372B1, JP2000212099A, KR20010068676A, WO2007109605A2, WO2007111866A2,
MD2549F1, MD3477F1, MD20060037A, WO2007112028A2, WO2007138116A2,
MXPA05012606A, RO118842B, RU2158604C2, WO2007143164A1, WO2007146712A2,
RU2212248C1, RU2293572C1, RU2306134C2, WO2007149382A2, WO2008005511A2,
RU2306934C1, RU2336096C1, RU2345787C2, WO2008008502A1, WO2008017692A2,
RU2348412C1, RU2373952C1, RU2398582C1, WO2008022006A2, WO2008024763A2,
RU2400229C1, RU2424794C1, RU2429877C1, WO2008024843A2, WO2008033413A2,
UA64191A, UA68233A, WO1991009605A1, WO2008033466A2, WO2008039179A1,
WO1994001125A1, WO1996018419A1, WO2008058393A1, WO2008063727A2,
WO1996029336A1, WO1996036351A1, WO2008086161A1, WO2008089034A2,
WO1997027866A1, WO1997033565A1, WO2008091763A1, WO2008092954A2,
WO1998014181A1, WO1998019670A2, WO2008106151A2, WO2008106167A1,
WO1998048621A1, WO1998049281A1, WO2008116194A2, WO2008118013A2,
WO1999015194A1, WO1999018993A1, WO2008121634A3, WO2008124384A2,
WO1999029321A1, WO1999030721A1, WO2008137126A2, WO2008137779A2,
WO2000001715A1, WO2000023454A1, WO2008141227A1, WO2008143647A2,
WO2000037097A1, WO2000037110A2, WO2008144072A1, WO2008153610A2,
WO2000047240A1, WO2000061161A2, WO2009009951A1, WO2009015336A2,
WO2001007454A1, WO2001012214A2, WO2009026292A1, WO2009032198A1,
WO2001077091A2, WO2001079540A2, WO2009033183A2, WO2009038663A1,
WO2002003886A1, WO2002010743A1, WO2009039127A1, WO2009039134A1,
WO2002018369A2, WO2002030259A2, WO2009039248A2, WO2009043176A1,
WO2002030455A2, WO2002032414A2, WO2009046369A2, WO2009061395A2,
WO2002053096A2, WO2002055100A2, WO2009062737A1, WO2009082701A1,
WO2002079234A1, WO2002089731A2, WO2009085267A1, WO2009085659A1,
WO2002091989A2, WO2003002152A2, WO2009131696A1, WO2009134616A2,
WO2003007981A1, WO2003024461A1, WO2009138146A2, WO2009149179A2,
WO2003028754A1, WO2003028755A1, WO2009149377A1, WO2009150194A1,
WO2003030923A1, WO2003037312A2, WO2009152589A1, WO2010017178A1,
WO2003037908A1, WO2003040104A1, WO2010017432A1, WO2010020676A1,
WO2003042377A1, WO2003049760A1, WO2010021681A2, WO2010024384A1,
WO2003072135A2, WO2003101199A1, WO2010025380A2, WO2010027921A1,
WO2003101478A1, WO2004019934A1, WO2010030359A2, WO2010031832A2,
WO2004039996A1, WO2004043435A2, WO2010033443A1, WO2010034670A2,
WO2004047673A2, WO2004073599A2, WO2010036799A1, WO2010038796A1,
WO2004078127A2, WO2004078191A1, WO2010039801A2, WO2010042683A1,
WO2004078194A1, WO2004094452A2, WO2010045266A1, WO2010049438A2,
WO2004103396A1, WO2004112720A2, WO2010053942A1, WO2010076323A1,
WO2005000308A2, WO2005010143A2, WO2010081082A2, WO2010093843A2,
WO2005012327A2, WO2005016288A2, WO2010099458A1, WO2010101649A2,
WO2005018330A1, WO2005023289A1, WO2010122538A1, WO2010132601A1,
WO2005025583A2, WO2005037214A2, WO2010151472A1, WO2010151487A1,
WO2005037274A1, WO2005038056A1, WO2010151488A1, WO2011009961A1,
WO2005040816A1, WO2005042020A2, WO2011013019A1, WO2011014882A1,
WO2005043118A2, WO2005062949A1, WO2011038224A1, WO2011041551A1,
WO2005063281A2, WO2005067454A2, WO2011046811A1, WO2011053617A1,
WO2005067963A1, WO2005102353A1, WO2011056630A2, WO2011056650A2,
WO2005108418A1, WO2005123076A2, WO2011066082A2, WO2011066260A2,
WO2006005610A1, WO2006016930A2, WO2011072370A1, WO2011079016A1, WO2011094489A1, WO2011112558A2, WO2011156578A1, WO2011156757A1, WO2012009503A1, WO2012015712A1, WO2012016995A1, WO2012018829A1, WO2012041771A1, WO2012050850A1, WO2012087596A1, WO2012139028A2, WO2012175733A1, WO2013000855A1, WO2013000856A1, WO2013024155A1, WO2013024158A1, WO2013025975A1, WO2013028953A1, WO2013040492A2, WO2013066753A1, U.S. Pat. Nos. 8,680,106, 8,685,984, 8,809,265, 8,853,176, 8,889,159, 8,969,357, 8,993,578, US20140080868 US20140080886, US20150174194, WO2014152514A1, or WO2014152635A1.

In certain embodiments, pharmaceutical compositions disclosed herein are administered in combination with a second antiviral agent, such as ABT-450, ABT-267, ABT-333, ABT-493, ABT-530, abacavir, acyclovir, acyclovir, adefovir, amantadine, amprenavir, ampligen, arbidol, atazanavir, atripla, boceprevir, cidofovir, combivir, daclatasvir, darunavir, dasabuvir, delavirdine, didanosine, docosanol, edoxudine, efavirenz, emtricitabine, enfuvirtide, entecavir, famciclovir, fomivirsen, fosamprenavir, foscamet, fosfonet, ganciclovir, ibacitabine, imunovir, idoxuridine, imiquimod, indinavir, inosine, interferon type III, interferon type II, interferon type I, lamivudine, ledipasvir, lopinavir, loviride, maraviroc, moroxydine, methisazone, nelfinavir, nevirapine, nexavir, ombitasvir, oseltamivir, paritaprevir, peginterferon alfa-2a, penciclovir, peramivir, pleconaril, podophyllotoxin, raltegravir, ribavirin, rimantadine, ritonavir, pyramidine, saquinavir, simeprevir, sofosbuvir, stavudine, telaprevir, telbivudine, tenofovir, tenofovir disoproxil, tipranavir, trifluridine, trizivir, tromantadine, truvada, valaciclovir, valganciclovir, vicriviroc, vidarabine, viramidine zalcitabine, zanamivir, or zidovudine and combinations thereof.

In certain embodiments, the disclosure relates to methods of treating a cancer comprising administering an effective amount of a pharmaceutical composition disclosed herein to subject in need thereof. In certain embodiments, the cancer is selected from bladder cancer, lung cancer, breast cancer, melanoma, colon and rectal cancer, non-Hodgkins lymphoma, endometrial cancer, pancreatic cancer, kidney cancer, prostate cancer, leukemia, thyroid cancer, and brain cancer.

In certain embodiments, the compositions are administered in combination with a second anti-cancer agent, such as temozolamide, bevacizumab, procarbazine, lomustine, vincristine, gefitinib, erlotinib, docetaxel, cis-platin, 5-fluorouracil, gemcitabine, tegafur, raltitrexed, methotrexate, cytosine arabinoside, hydroxyurea, adriamycin, bleomycin, doxorubicin, daunomycin, epirubicin, idarubicin, mitomycin-C, dactinomycin and mithramycin, vinblastine, vindesine, vinorelbine, taxol, taxotere, etoposide, teniposide, amsacrine, topotecan, camptothecin, bortezomib, anagrelide, tamoxifen, toremifene, raloxifene, droloxifene, iodoxyfene, fulvestrant, bicalutamide, flutamide, nilutamide, cyproterone, goserelin, leuprorelin, buserelin, megestrol, anastrozole, letrozole, vorazole, exemestane, finasteride, marimastat, trastuzumab, cetuximab, dasatinib, imatinib, combretastatin, thalidomide, and/or lenalidomide or combinations thereof.

In certain embodiment, the disclosure relates to uses of compounds disclosed herein in the production or manufacture of a medicament for the treatment or prevention of an infectious disease, viral infection, or cancer.

In certain embodiments, the disclosure relates to derivatives of compounds disclosed herein or any of the formula.

Additional advantages of the disclosure will be set forth in part in the description which follows. It is to be understood that both the foregoing general description and the following detailed description are exemplary and explanatory only and are not restrictive of the disclosure, as claimed.

It is to be understood that this disclosure is not limited to the particular embodiments described. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

Prior to describing the various embodiments, the following definitions are provided and should be used unless otherwise indicated.

As used herein, the term "phosphorus oxide" refers to any variety of chemical moieties that contain a phosphorus-oxygen (P—O or P=O) bond. When used as linking groups herein, the joined molecules may bond to oxygen or directly to the phosphorus atoms. The term is intended to include, but are not limited to phosphates, in which the phosphorus is typically bonded to four oxygens and phosphonates, in which the phosphorus is typically bonded to one carbon and three oxygens. A "polyphosphate" generally refers to phosphates linked together by at least one phosphorus-oxygen-phosphorus (P—O—P) bond. A "polyphosphonate" refers to a polyphosphate that contains at least one phosphorus-carbon (C—P—O—P) bond. In addition to containing phosphorus-oxygen bond, phosphorus oxides may contain a phosphorus-thiol (P—S or P=S) bond and/or a phosphorus-amine (P—N) bond, respectively referred to as phosphorothioate or phosphoroamidate. In phosphorus oxides, the oxygen atom may form a double or single bond to the phosphorus or combinations, and the oxygen may further bond with other atoms such as carbon or may exist as an anion which is counter balanced with a cation, e.g., metal or quaternary amine.

As used herein, "alkyl" means a noncyclic, cyclic, linear or branched, unsaturated or saturated hydrocarbon such as those containing from 1 to 22 carbon atoms, and specifically includes methyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The term includes both substituted and unsubstituted alkyl groups. Alkyl groups can be optionally substituted with one or more moieties selected from, for example, hydroxyl, amino, halo, deutero, alkylamino, arylamino, alkoxy, aryloxy, nitro, cyano, sulfonic acid, sulfate, phosphonic acid, phosphate, or phosphonate, or any other viable functional group that does not inhibit the pharmacological activity of this compound, either unprotected, or protected, as necessary, as known to those skilled in the art, for example, as taught in T. W. Greene and P. G. M. Wuts, "Protective Groups in Organic Synthesis," 3 ed., John Wiley & Sons, 1999, hereby incorporated by reference.

The term "lower alkyl," as used herein, and unless otherwise specified, refers to a C1 to C4 saturated straight, branched, or if appropriate, a cyclic (for example, cyclopropyl) alkyl group, including both substituted and unsubstituted forms. Unless otherwise specifically stated in this application, when alkyl is a suitable moiety, lower alkyl is preferred.

The term "halo" or "halogen," as used herein, includes chloro, bromo, iodo and fluoro.

Non-aromatic mono or polycyclic alkyls are referred to herein as "carbocycles" or "carbocyclyl" groups that contain 3 to 30 carbon atoms. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Aryl" means an aromatic carbocyclic monocyclic or polycyclic ring that contains 6 to 32 carbon atoms, such as phenyl or naphthyl. Polycyclic ring systems may, but are not required to, contain one or more non-aromatic rings, as long as one of the rings is aromatic.

As used herein, "heteroaryl" refers an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkylthio" refers to an alkyl group as defined above attached through a sulfur bridge. An example of an alkylthio is methylthio, (i.e., —S—CH$_3$).

"Alkoxy" refers to an alkyl group as defined above attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, and t-butoxy.

"Alkylamino" refers an alkyl group as defined above attached through an amino bridge. An example of an alkylamino is methylamino, (i.e., —NH—CH$_3$).

"Alkanoyl" refers to an alkyl as defined above attached through a carbonyl bride (i.e., —(C=O)alkyl).

"Alkylsulfonyl" refers to an alkyl as defined above attached through a sulfonyl bridge (i.e., —S(=O)$_2$alkyl) such as mesyl and the like, and "Arylsulfonyl" refers to an aryl attached through a sulfonyl bridge (i.e., —S(=O)$_2$aryl).

"Alkylsulfinyl" refers to an alkyl as defined above attached through a sulfinyl bridge (i.e. —S(=O)alkyl).

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(=O)Rb, —NRaC(=O)NRaNRb, —NRaC(=O)ORb, —NRaSO$_2$Rb, —C(=O)Ra, —C(=O)ORa, —C(=O)NRaRb, —OC(=O)NRaRb, —ORa, —SRa, —SORa, —S(=O)$_2$Ra, —OS(=O)$_2$Ra and —S(=O)$_2$ORa. Ra and Rb in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

The term "optionally substituted," as used herein, means that substitution is optional and therefore it is possible for the designated atom to be unsubstituted.

As used herein, "salts" refer to derivatives of the disclosed compounds where the parent compound is modified making acid or base salts thereof. Examples of salts include, but are not limited to, mineral or organic acid salts of basic residues such as amines, alkylamines, or dialkylamines; alkali or organic salts of acidic residues such as carboxylic acids; and the like. In typical embodiments, the salts are conventional nontoxic pharmaceutically acceptable salts including the quaternary ammonium salts of the parent compound formed, and non-toxic inorganic or organic acids. Preferred salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

"Subject" refers any animal, preferably a human patient, livestock, rodent, monkey or domestic pet.

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis.

As used herein, the term "derivative" refers to a structurally similar compound that retains sufficient functional attributes of the identified analogue. The derivative may be structurally similar because it is lacking one or more atoms, substituted with one or more substituents, a salt, in different hydration/oxidation states, e.g., substituting a single or double bond, substituting a hydroxy group for a ketone, or because one or more atoms within the molecule are switched, such as, but not limited to, replacing an oxygen atom with a sulfur or nitrogen atom or replacing an amino group with a hydroxyl group or vice versa. Replacing a carbon with nitrogen in an aromatic ring is a contemplated derivative. The derivative may be a prodrug. Derivatives may be prepared by any variety of synthetic methods or appropriate adaptations presented in the chemical literature or as in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

As used herein, the terms "prevent" and "preventing" include the full or partial inhibition of the recurrence, spread or onset of a referenced pathological condition or disease. It is not intended that the present disclosure be limited to complete prevention. In some embodiments, the onset is delayed, or the severity of the disease is reduced.

As used herein, the terms "treat" and "treating" are not limited to the case where the subject (e.g., patient) is cured and the disease is eradicated. Rather, embodiments, of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

Nucleoside Analogues as Antiviral Agents

Nucleoside analogs utilize the host's nucleoside salvage pathway for sequential phosphorylation by deoxynucleoside kinases (dNKs), deoxynucleoside monophosphate kinases (dNMPKs) and nucleoside diphosphate kinase (NDPK). However, intracellular activation of these compounds is often compromised by the high substrate specificity of the host's endogenous kinases. In vitro and in vivo studies have demonstrated that the first and/or second phosphorylation, catalyzed by dNKs and dNMPKs, often represent the rate-limiting steps in nucleoside analog activation. These significant blockades in the phosphorylation cascade of a given nucleoside analog will result in the lack of any observable activity in cellular assays. To circumvent these blockades, several kinase bypass strategies have been developed. For example, McGuigan phosphoramidates are chemical conjugates used for kinase bypass. See Serpi et al., J Med Chem, 2012, 55(10):4629-4639. The metabolism of these prodrugs begins with an esterase-catalyzed cleavage of the carboxylic ester, followed by several chemical rearrangement steps resulting in an amino acid phosphoramidate. The final cleavage is carried out by one of several endogenous phosphoramidases, one of which has been identified to be the histidine triad nucleotide binding protein 1 (hINT1).

An alternative prodrug strategy to circumvent these blockades is to utilize sphingoid bases to mask nucleotide analog phosphates. Sphingoid bases have the potential for delivering nucleotide analog phosphates to critical tissues such as the brain. The design concept driving the use of sphingoid bases to form nucleoside-lipid conjugates is based on observations that the sphingoid base analogs are: (a) well absorbed after oral administration, (b) resistant to oxidative catabolism in enterocytes, and (c) achieve high concentrations in the brain. Based on data for intestinal uptake of traditional phospholipid drug conjugates in mice and our data for sphingoid base oral absorption in rats, our sphingoid base conjugates should be well absorbed and resist first pass metabolism. After absorption, sphingoid bases, including sphingosine-1-phosphate, are transported in blood via both lipoproteins and free plasma proteins like albumin. Active epithelial cell uptake of sphingoid base phosphates has been demonstrated to occur via the ABC transporter, CFTR, but passive protein transport and endocytotic uptake are also possible; it is believed that extracellularly delivered drug conjugates would be processed similarly by target cells in the central nervous system (CNS) and the gut-associated lymphoid tissue (GALT). The rat sphingolipid PK studies mentioned above resulted in 24 hour tissue concentrations exceeding plasma Cmax concentrations by 10 to 300+ fold, with lung and brain levels being particularly high and without evidence of toxicity. This approach has significant potential for conjugate delivery of high drug concentrations to critical tissues.

Compounds

In certain embodiments, the disclosure relates to nucleosides conjugated to a phosphorus moiety or pharmaceutically acceptable salts thereof.

In certain embodiments, the present invention relates to compounds of the following formula:

Formula I

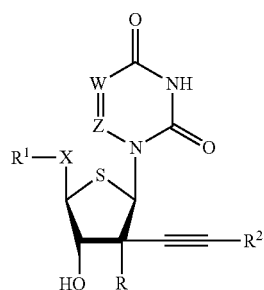

or pharmaceutically acceptable salts thereof wherein,
X is $OCH_2$, OCHMe, $OCMe_2$, OCHF, $OCF_2$, or $OCD_2$;

R is OH, F, Cl, or NH$_2$;

W is N or CR$^7$;

Z is N or CR$^8$;

R$^1$ is selected from H or from one of the following formulae:

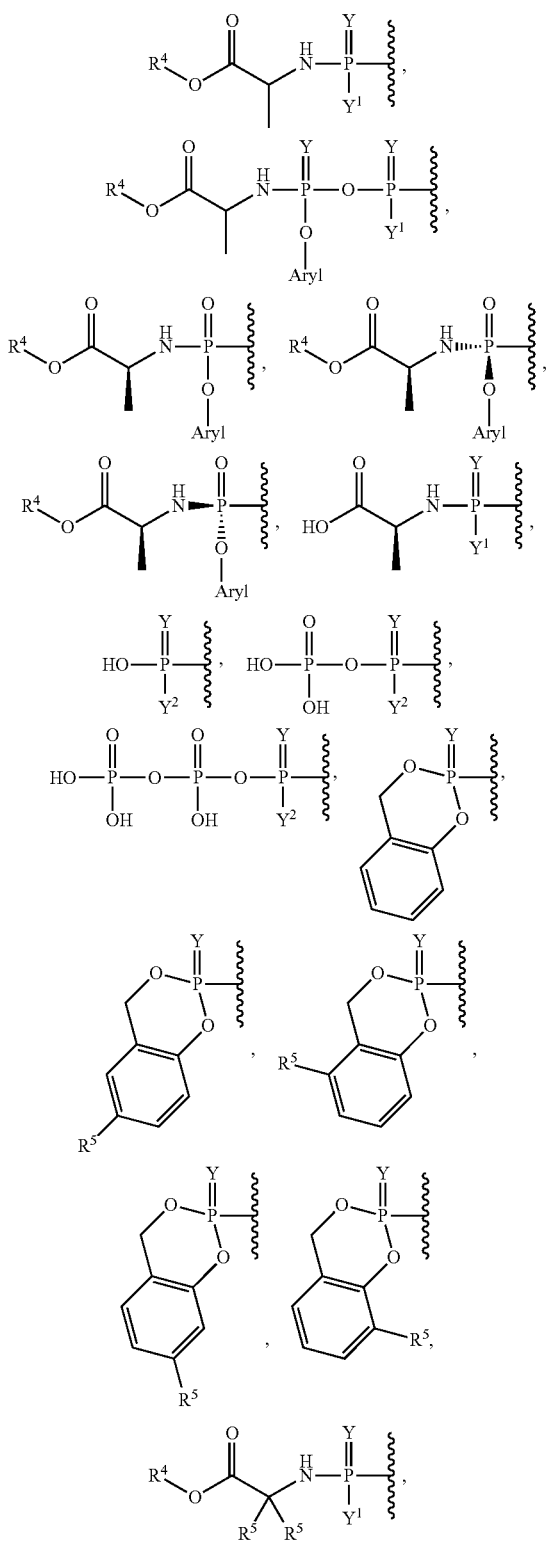

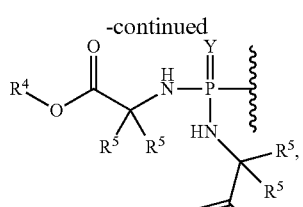

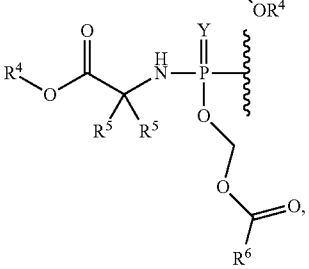

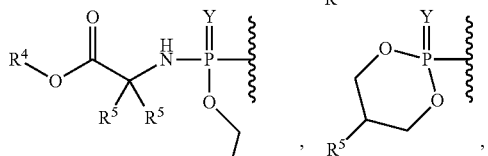

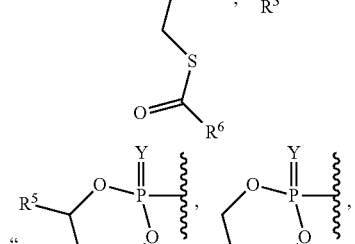

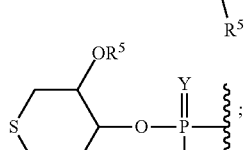

Y is O or S;

Y$^1$ is OH, OAryl, OAlkyl, or BH$_3^-$M$^+$;

Y$^2$ is OH or BH$_3^-$M$^+$;

Aryl is phenyl, 1-naphthyl, 2-naphthyl, aromatic, heteroaromatic, 4-substituted phenyl, 4-chlorophenyl, or 4-bromophenyl;

R$^2$ is hydrogen, methyl, fluoromethyl, difluoromethyl, trifluoromethyl, ethyl, cyclopropyl, fluoro, chloro, hydroxymethyl, aminomethyl, vinyl, or cyclobutyl;

R$^4$ is hydrogen, methyl, ethyl, isopropyl, cyclopentyl, cyclohexyl, neopentyl, benzyl, alkyl, branched alkyl, cycloalkyl, or lipid;

R$^5$ is hydrogen, deuterium, hydroxyl, cyano, azido, amino, substituted amino, aryl, heteroaryl, substituted aryl, lipid, C$_{1-22}$ alkoxy, C$_{1-22}$ alkyl, C$_{2-22}$ alkenyl, C$_{2-22}$ alkynyl, or substituted heteroaryl;

R$^6$ is methyl, ethyl, tert-butyl, C$_{1-22}$ alkoxy, C$_{1-22}$ alkyl, branched alkyl, cycloalkyl, aryl, substituted aryl, or alkyoxy;

R$^7$ is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano;

R⁸ is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano.

In certain embodiments, the present invention relates to compounds of the following Formula II

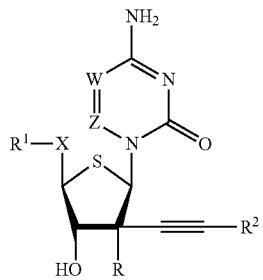

or pharmaceutically acceptable salts thereof wherein,

X is $OCH_2$, OCHMe, $OCMe_2$, OCHF, $OCF_2$, or $OCD_2$;

R is OH, F, Cl, or $NH_2$;

W is N or $CR^7$;

Z is N or $CR^8$;

$R^1$ is selected from H or from one of the following formulae:

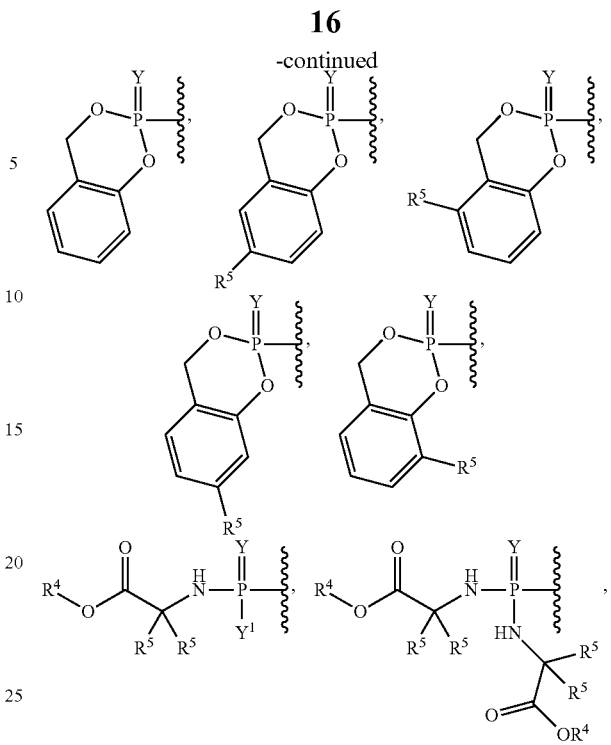

Y is O or S;

$Y^1$ is OH, OAryl, OAlkyl, or $BH_3^-M^+$;

$Y^2$ is OH or $BH_3^-M^+$;

Aryl is phenyl, 1-naphthyl, 2-naphthyl, aromatic, heteroaromatic, 4-substituted phenyl, 4-chlorophenyl, or 4-bromophenyl;

R[2] is hydrogen, methyl, fluoromethyl, difluoromethyl, trifluoromethyl, ethyl, cyclopropyl, fluoro, chloro, hydroxymethyl, aminomethyl, vinyl, or cyclobutyl;

R[4] is hydrogen, methyl, ethyl, isopropyl, cyclopentyl, cyclohexyl, neopentyl, benzyl, alkyl, branched alkyl, cycloalkyl, or lipid;

R[5] is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;

R[6] is methyl, ethyl, tert-butyl, $C_{1-22}$ alkoxy, $C_{1-22}$ alkyl, branched alkyl, cycloalkyl, aryl, substituted aryl, or alkyoxy;

R[7] is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano;

R[8] is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano.

In certain embodiments, the present invention relates to compounds of the following formula:

Formula IIIa

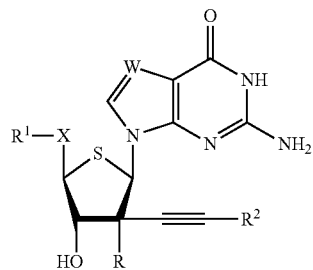

Formula IIIb

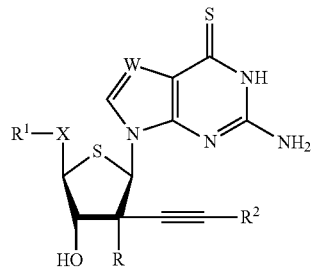

Formula IIIc

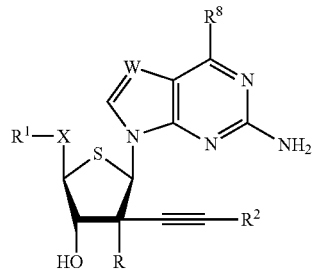

or pharmaceutically acceptable salts thereof wherein,

X is $OCH_2$, OCHMe, $OCMe_2$, OCHF, $OCF_2$, or $OCD_2$;

R is OH, F, Cl, or $NH_2$;

W is N or CR[7];

R[1] is selected from H or from one of the following formulae:

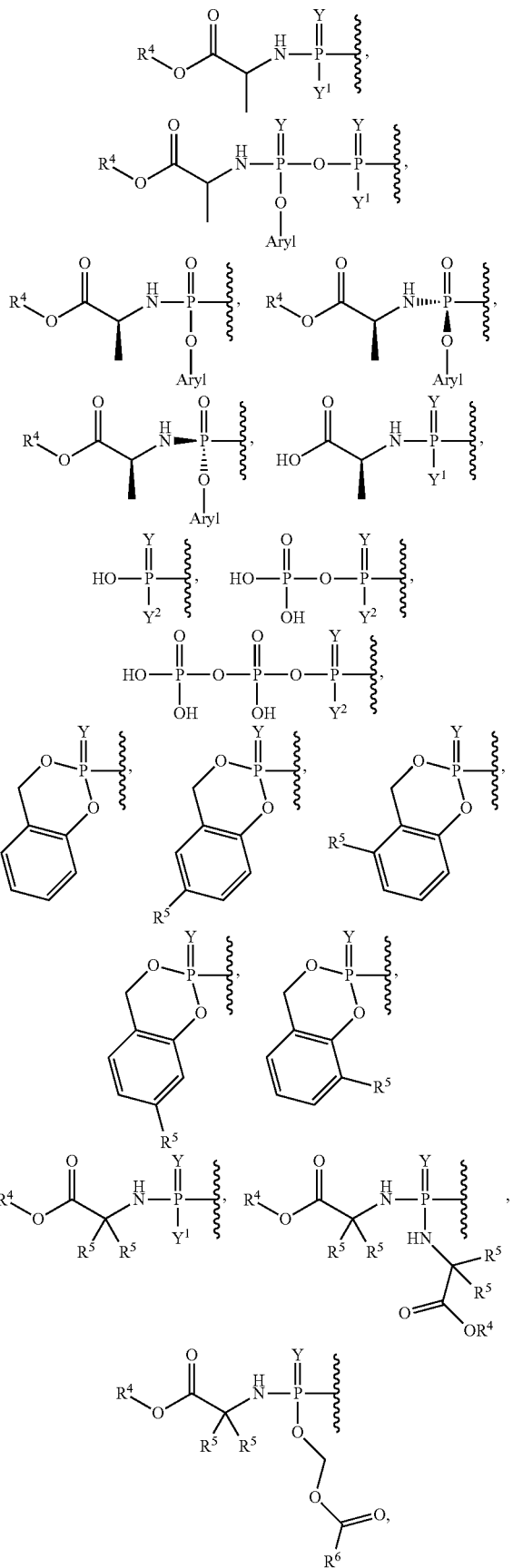

-continued

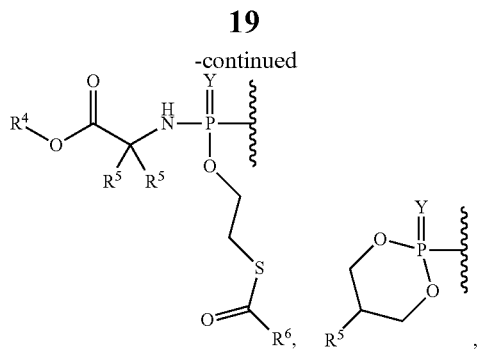

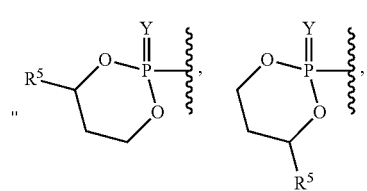

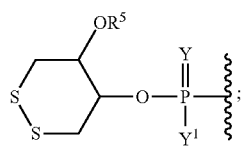

Y is O or S;
Y¹ is OH, OAryl, OAlkyl, or $BH_3^-M^+$;
Y² is OH or $BH_3^-M^+$;
Aryl is phenyl, 1-naphthyl, 2-naphthyl, aromatic, heteroaromatic, 4-substituted phenyl, 4-chlorophenyl, or 4-bromophenyl;
$R^2$ is hydrogen, methyl, fluoromethyl, difluoromethyl, trifluoromethyl, ethyl, cyclopropyl, fluoro, chloro, hydroxymethyl, aminomethyl, vinyl, or cyclobutyl;
$R^4$ is hydrogen, methyl, ethyl, isopropyl, cyclopentyl, cyclohexyl, neopentyl, benzyl, alkyl, branched alkyl, cycloalkyl, or lipid;
$R^5$ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;
$R^6$ is methyl, ethyl, tert-butyl, $C_{1-22}$ alkoxy, $C_{1-22}$ alkyl, branched alkyl, cycloalkyl, aryl, substituted aryl, or alkyoxy;
$R^7$ is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano;
$R^8$ is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, methoxy, ethoxy, alkoxy, substituted amino, or cyano.

In certain embodiments, the present invention relates to compounds of the following formula:

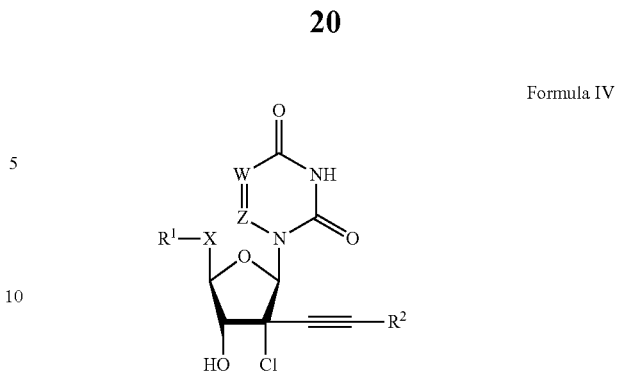

Formula IV or pharmaceutically acceptable salts thereof wherein,
X is $OCH_2$, OCHMe, $OCMe_2$, OCHF, $OCF_2$, or $OCD_2$;
W is N or $CR^7$;
Z is N or $CR^8$;
$R^1$ is selected from H or from one of the following formulae:

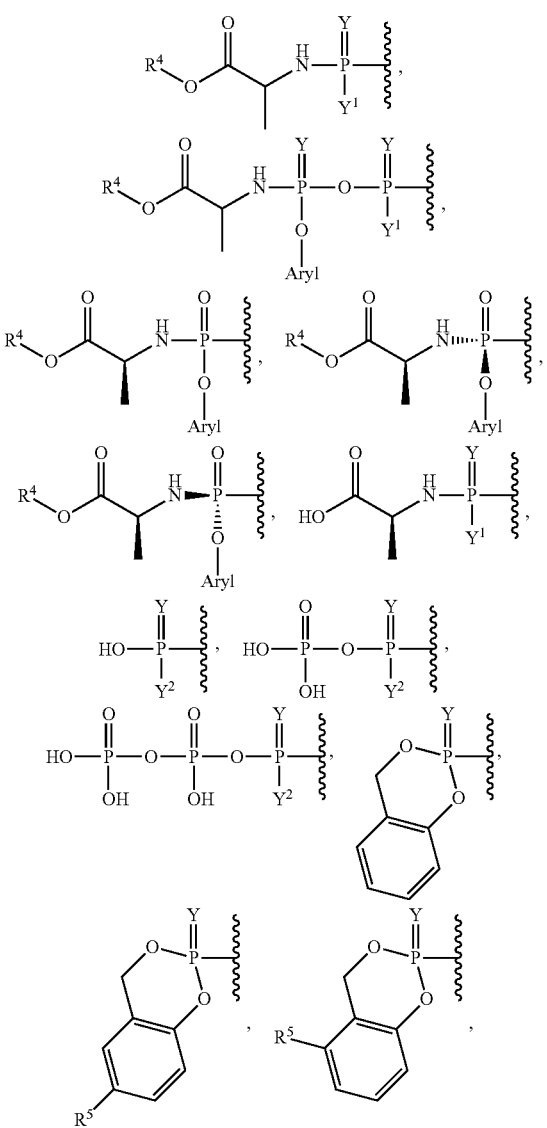

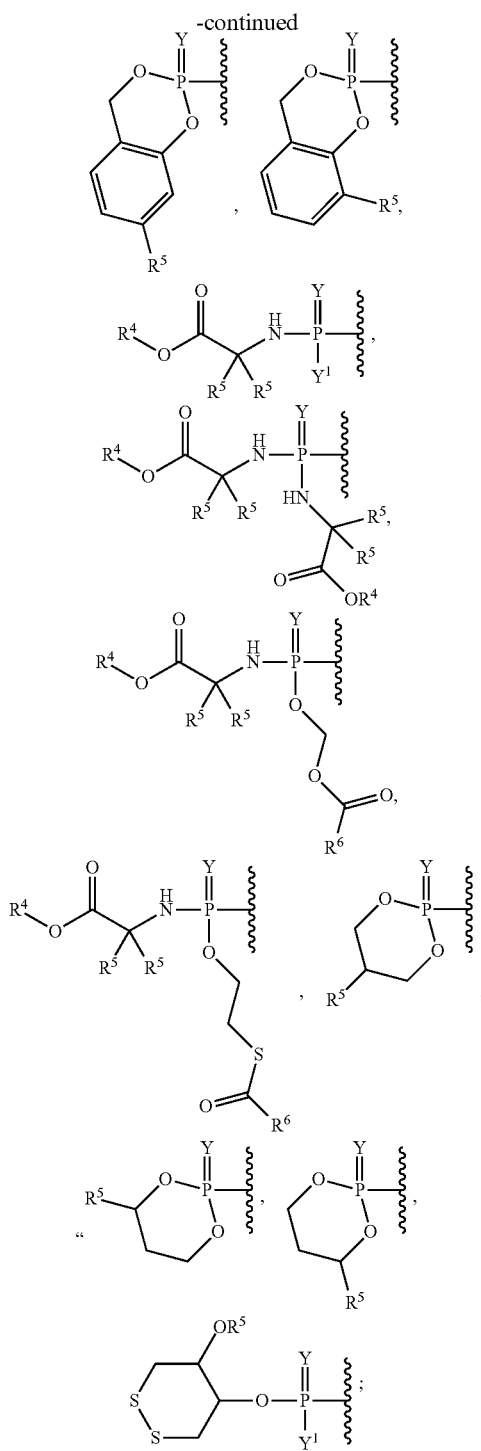

Y is O or S;
Y¹ is OH, OAryl, OAlkyl, or $BH_3^-M^+$;
Y² is OH or $BH_3^-M^+$;
Aryl is phenyl, 1-naphthyl, 2-naphthyl, aromatic, heteroaromatic, 4-substituted phenyl, 4-chlorophenyl, or 4-bromophenyl;
$R^2$ is hydrogen, methyl, fluoromethyl, difluoromethyl, trifluoromethyl, ethyl, cyclopropyl, fluoro, chloro, hydroxymethyl, aminomethyl, vinyl, or cyclobutyl;
$R^4$ is hydrogen, methyl, ethyl, isopropyl, cyclopentyl, cyclohexyl, neopentyl, benzyl, alkyl, branched alkyl, cycloalkyl, or lipid;
$R^5$ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;
$R^6$ is methyl, ethyl, tert-butyl, $C_{1-22}$ alkoxy, $C_{1-22}$ alkyl, branched alkyl, cycloalkyl, aryl, substituted aryl, or alkyoxy;
$R^7$ is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano;
$R^8$ is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano.

In certain embodiments, the present invention relates to compounds of the following Formula V

or pharmaceutically acceptable salts thereof wherein,
X is $OCH_2$, OCHMe, $OCMe_2$, OCHF, $OCF_2$, or $OCD_2$;
W is N or $CR^7$;
Z is N or $CR^8$;
$R^1$ is selected from H or from one of the following formulae:

-continued

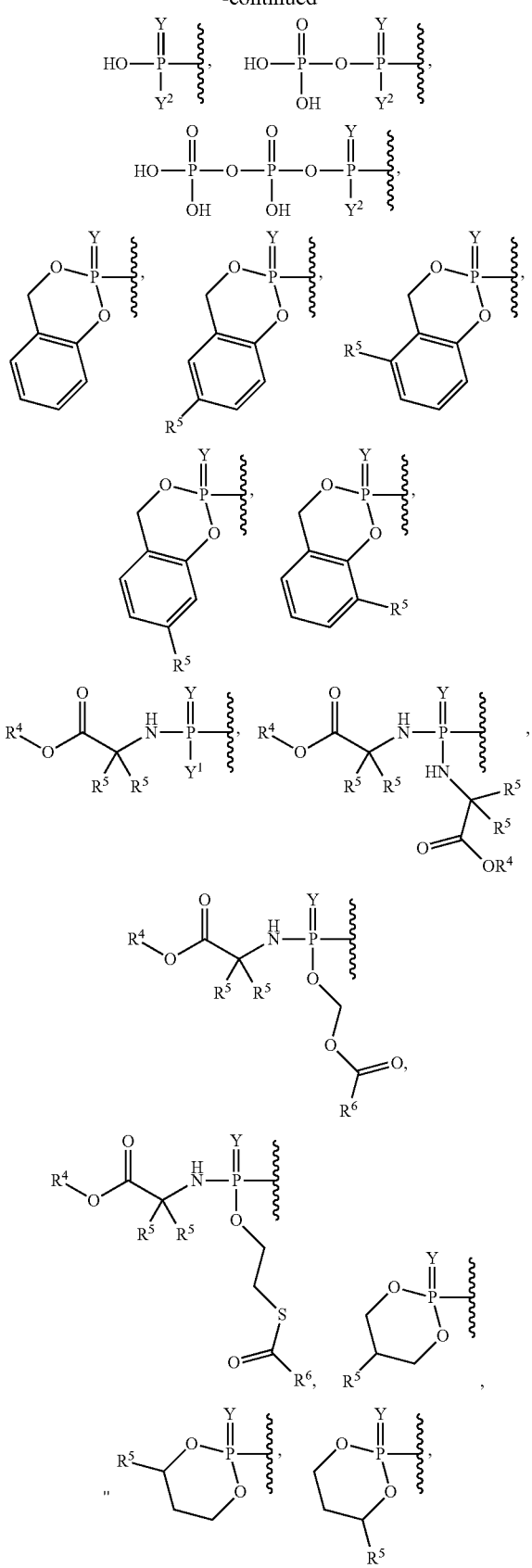

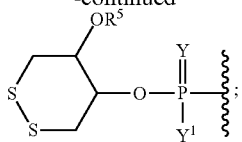

Y is O or S;

Y is OH, OAryl, OAlkyl, or $BH_3^-M^+$;

$Y^2$ is OH or $BH_3^-M^+$;

Aryl is phenyl, 1-naphthyl, 2-naphthyl, aromatic, heteroaromatic, 4-substituted phenyl, 4-chlorophenyl, or 4-bromophenyl;

$R^2$ is hydrogen, methyl, fluoromethyl, difluoromethyl, trifluoromethyl, ethyl, cyclopropyl, fluoro, chloro, hydroxymethyl, aminomethyl, vinyl, or cyclobutyl;

$R^4$ is hydrogen, methyl, ethyl, isopropyl, cyclopentyl, cyclohexyl, neopentyl, benzyl, alkyl, branched alkyl, cycloalkyl, or lipid;

$R^5$ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;

$R^6$ is methyl, ethyl, tert-butyl, $C_{1-22}$ alkoxy, $C_{1-22}$ alkyl, branched alkyl, cycloalkyl, aryl, substituted aryl, or alkyoxy;

$R^7$ is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano;

$R^8$ is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano.

In certain embodiments, the present invention relates to compounds of the following formula:

Formula VIa

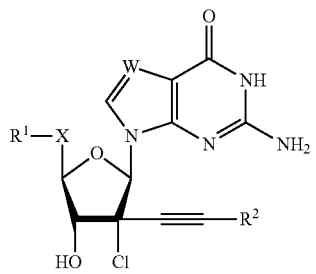

Formula VIb

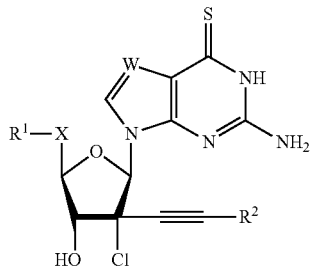

Formula VIc

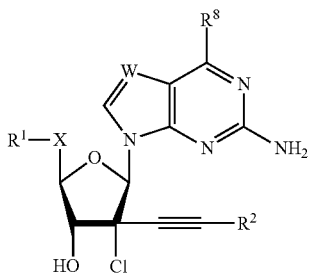

or pharmaceutically acceptable salts thereof wherein,

X is $OCH_2$, $OCHMe$, $OCMe_2$, $OCHF$, $OCF_2$, or $OCD_2$;

W is N or $CR^7$;

$R^1$ is selected from H or from one of the following formulae:

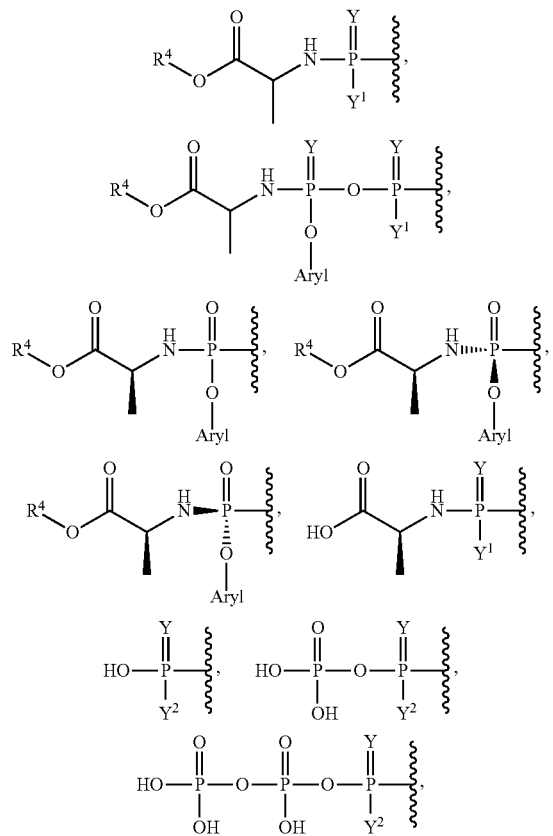

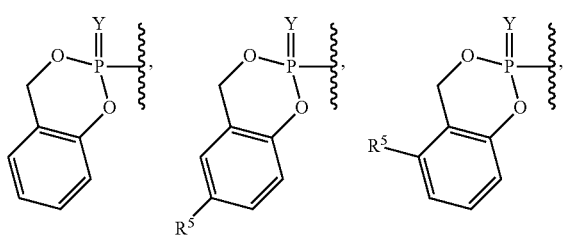

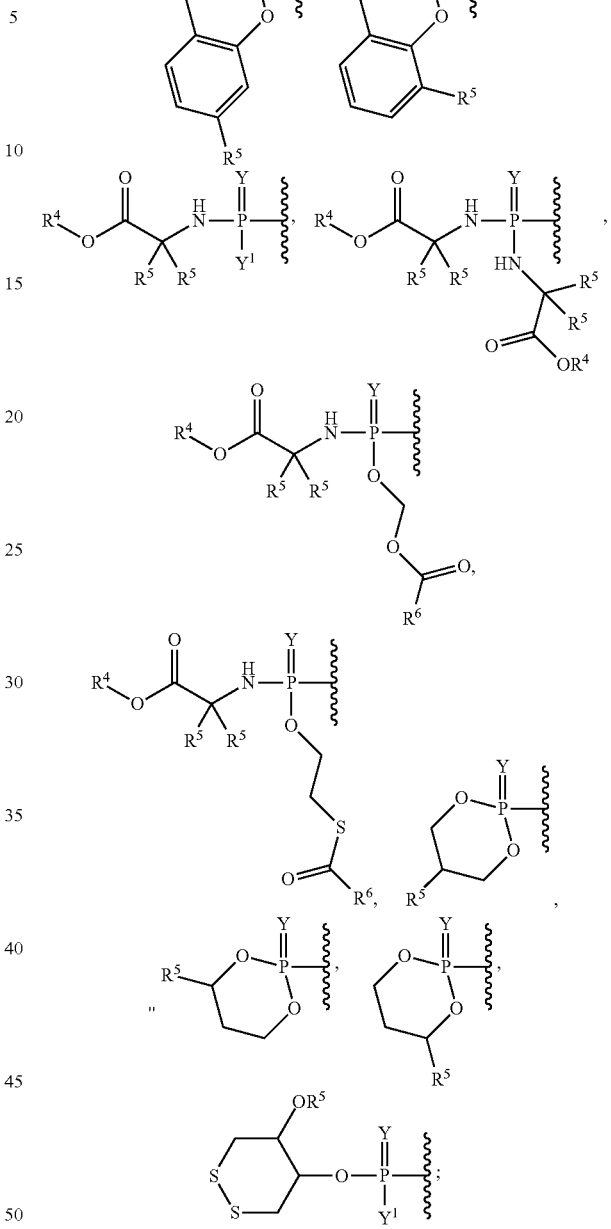

Y is O or S;

$Y^1$ is OH, OAryl, OAlkyl, or $BH_3^-M^+$;

$Y^2$ is OH or $BH_3^-M^+$;

Aryl is phenyl, 1-naphthyl, 2-naphthyl, aromatic, heteroaromatic, 4-substituted phenyl, 4-chlorophenyl, or 4-bromophenyl;

$R^2$ is hydrogen, methyl, fluoromethyl, difluoromethyl, trifluoromethyl, ethyl, cyclopropyl, fluoro, chloro, hydroxymethyl, aminomethyl, vinyl, or cyclobutyl;

$R^4$ is hydrogen, methyl, ethyl, isopropyl, cyclopentyl, cyclohexyl, neopentyl, benzyl, alkyl, branched alkyl, cycloalkyl, or lipid;

$R^5$ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;

R[6] is methyl, ethyl, tert-butyl, $C_{1-22}$ alkoxy, $C_{1-22}$ alkyl, branched alkyl, cycloalkyl, aryl, substituted aryl, or alkyoxy;

R[7] is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano;

R[8] is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, methoxy, ethoxy, alkoxy, substituted amino, or cyano.

In certain embodiments, the present invention relates to compounds of the following formula:

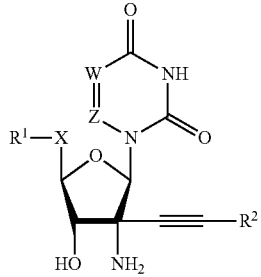

Formula VII or pharmaceutically acceptable salts thereof wherein,

X is $OCHMe$, $OCMe_2$, $OCHF$, $OCF_2$, or $OCD_2$;

W is N or CR[7];

Z is N or CR[8];

R[1] is selected from H or from one of the following formulae:

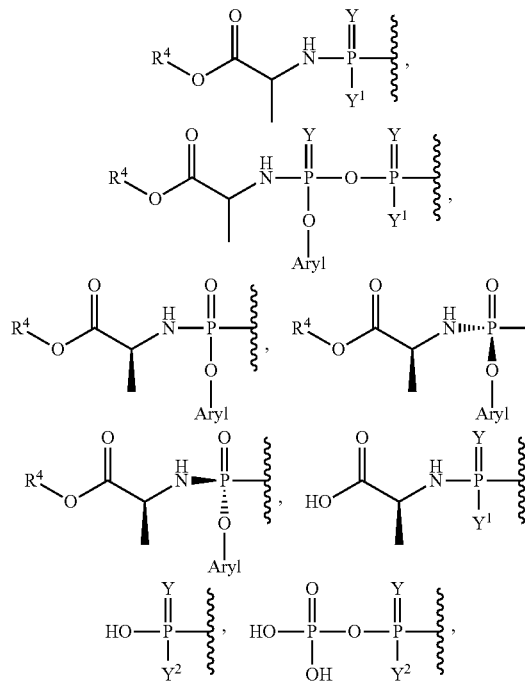

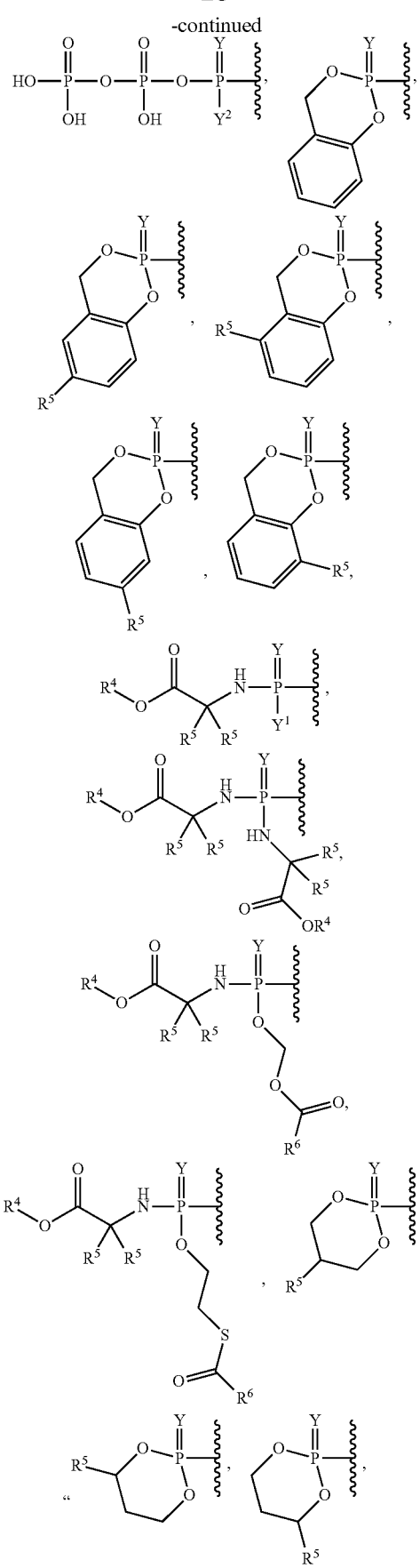

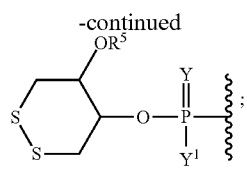

Y is O or S;
Y¹ is OH, OAryl, OAlkyl, or $BH_3^-M^+$;
Y² is OH or $BH_3^-M^+$;
Aryl is phenyl, 1-naphthyl, 2-naphthyl, aromatic, heteroaromatic, 4-substituted phenyl, 4-chlorophenyl, or 4-bromophenyl;
$R^2$ is hydrogen, methyl, fluoromethyl, difluoromethyl, trifluoromethyl, ethyl, cyclopropyl, fluoro, chloro, hydroxymethyl, aminomethyl, vinyl, or cyclobutyl;
$R^4$ is hydrogen, methyl, ethyl, isopropyl, cyclopentyl, cyclohexyl, neopentyl, benzyl, alkyl, branched alkyl, cycloalkyl, or lipid;
$R^5$ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;
$R^6$ is methyl, ethyl, tert-butyl, $C_{1-22}$ alkoxy, $C_{1-22}$ alkyl, branched alkyl, cycloalkyl, aryl, substituted aryl, or alkyoxy;
$R^7$ is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano;
$R^8$ is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano.

In certain embodiments, the present invention relates to compounds of the following formula:

Formula VIII

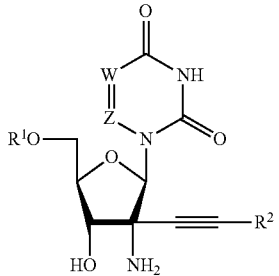

or pharmaceutically acceptable salts thereof wherein,
W is N or $CR^7$;
Z is N or $CR^8$;
$R^1$ is selected from H or from one of the following formulae:

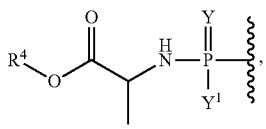

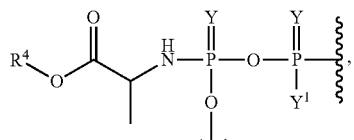

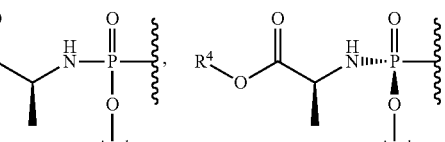

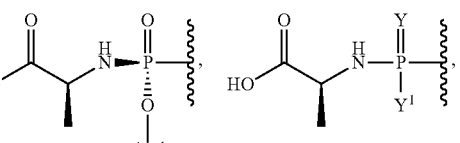

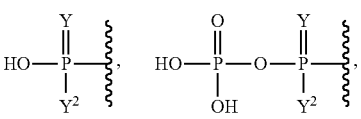

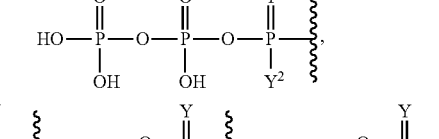

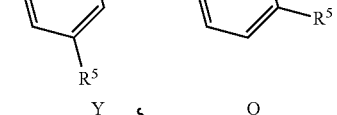

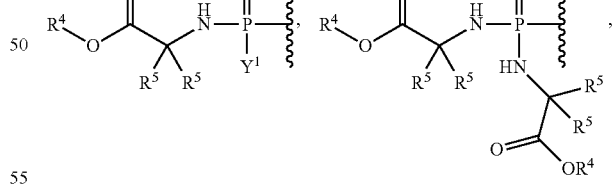

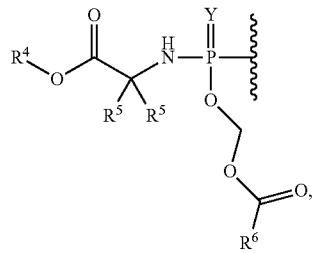

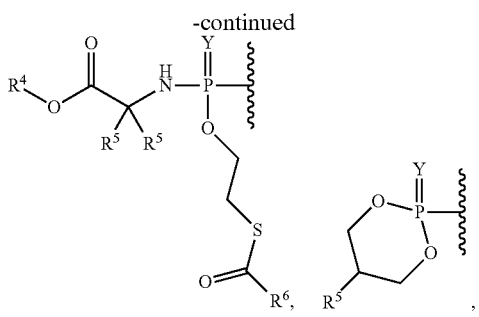

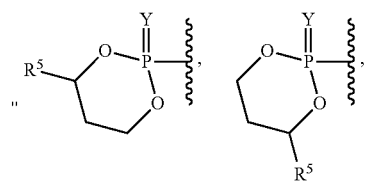

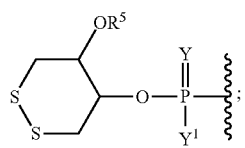

Y is O or S;

Y¹ is OH, OAryl, OAlkyl, or $BH_3^-M^+$;

Y² is OH or $BH_3^-M^+$;

Aryl is phenyl, 1-naphthyl, 2-naphthyl, aromatic, heteroaromatic, 4-substituted phenyl, 4-chlorophenyl, or 4-bromophenyl;

$R^2$ is hydrogen, methyl, fluoromethyl, difluoromethyl, trifluoromethyl, ethyl, cyclopropyl, fluoro, chloro, hydroxymethyl, aminomethyl, vinyl, or cyclobutyl;

$R^4$ is hydrogen, methyl, ethyl, isopropyl, cyclopentyl, cyclohexyl, neopentyl, benzyl, alkyl, branched alkyl, cycloalkyl, or lipid;

$R^5$ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;

$R^6$ is methyl, ethyl, tert-butyl, $C_{1-22}$ alkoxy, $C_{1-22}$ alkyl, branched alkyl, cycloalkyl, aryl, substituted aryl, or alkyoxy;

$R^7$ is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano;

$R^8$ is D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano.

In certain embodiments, the present invention relates to compounds of the following formula:

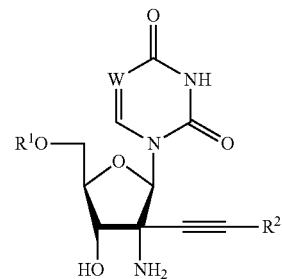

Formula IX or pharmaceutically acceptable salts thereof wherein,

W is N or $CR^7$;

$R^1$ is selected from H or from one of the following formulae:

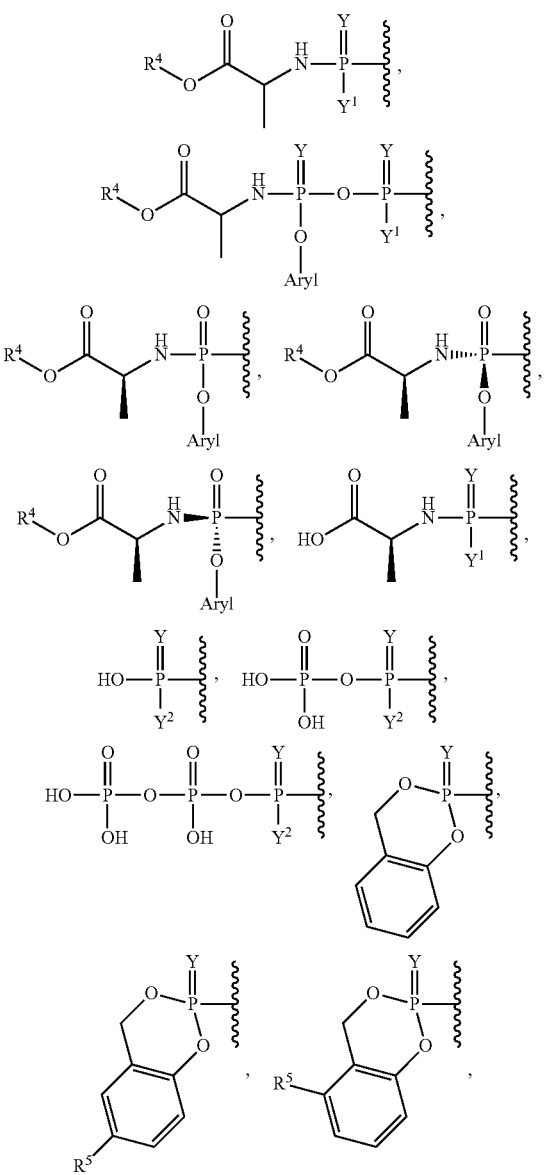

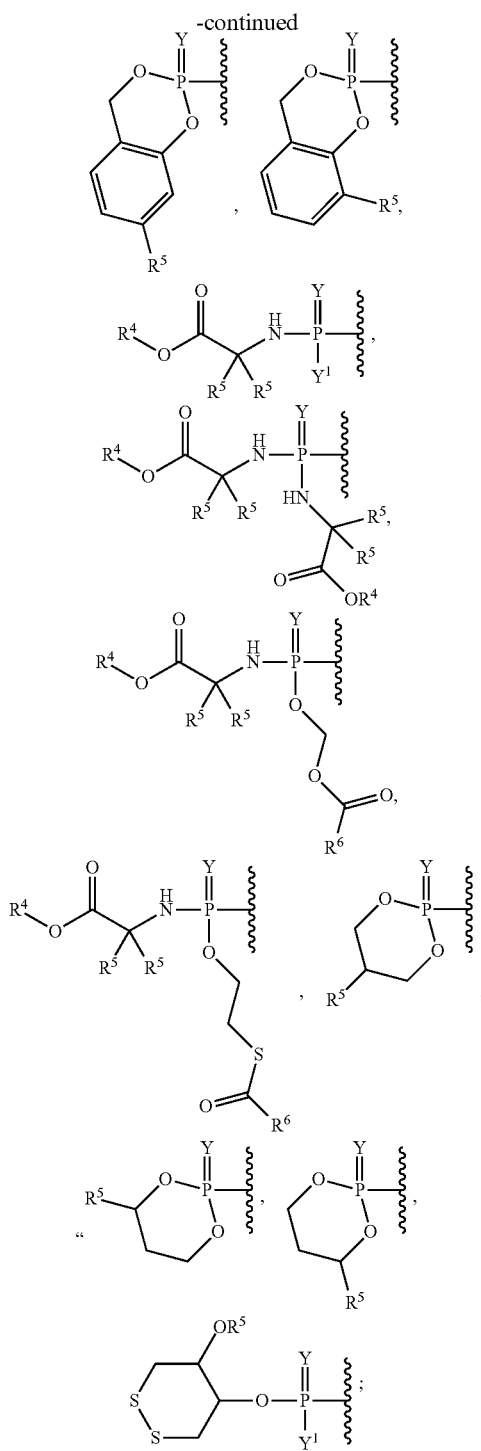

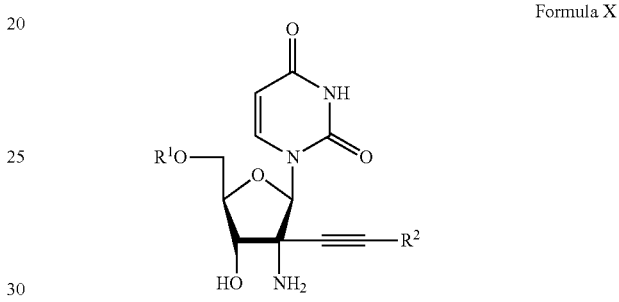

Y is O or S;

Y$^1$ is OH, OAryl, OAlkyl, or BH$_3^-$M$^+$;

Y$^2$ is OH or BH$_3^-$M$^+$;

Aryl is phenyl, 1-naphthyl, 2-naphthyl, aromatic, heteroaromatic, 4-substituted phenyl, 4-chlorophenyl, or 4-bromophenyl;

R$^2$ is hydrogen, methyl, fluoromethyl, difluoromethyl, trifluoromethyl, ethyl, cyclopropyl, fluoro, chloro, hydroxymethyl, aminomethyl, vinyl, or cyclobutyl;

R$^4$ is hydrogen, methyl, ethyl, isopropyl, cyclopentyl, cyclohexyl, neopentyl, benzyl, alkyl, branched alkyl, cycloalkyl, or lipid;

R$^5$ is hydrogen, deuterium, hydroxyl, cyano, azido, amino, substituted amino, aryl, heteroaryl, substituted aryl, lipid, C$_{1-22}$ alkoxy, C$_{1-22}$ alkyl, C$_{2-22}$ alkenyl, C$_{2-22}$ alkynyl, or substituted heteroaryl;

R$^6$ is methyl, ethyl, tert-butyl, C$_{1-22}$ alkoxy, C$_{1-22}$ alkyl, branched alkyl, cycloalkyl, aryl, substituted aryl, or alkyoxy;

R$^7$ is D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano.

In certain embodiments, the present invention relates to compounds of the following formula:

Formula X or pharmaceutically acceptable salts thereof wherein,

R$^1$ is selected from H or from one of the following formulae:

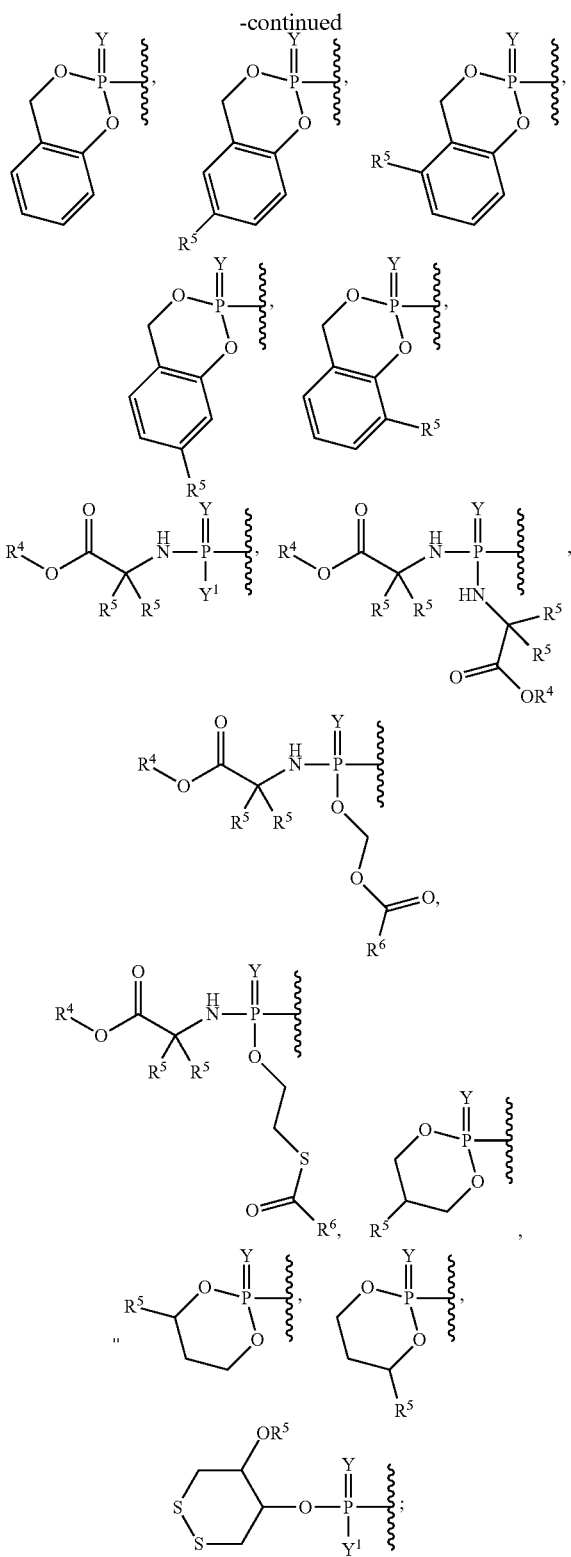

Y is O or S;
Y¹ is OH, OAryl, OAlkyl, or $BH_3^- M^+$;
Y² is OH or $BH_3^- M^+$;
Aryl is phenyl, 1-naphthyl, 2-naphthyl, aromatic, heteroaromatic, 4-substituted phenyl, 4-chlorophenyl, or 4-bromophenyl;

$R^2$ is methyl, fluoromethyl, difluoromethyl, trifluoromethyl, ethyl, cyclopropyl, fluoro, chloro, hydroxymethyl, aminomethyl, vinyl, or cyclobutyl;

$R^4$ is hydrogen, methyl, ethyl, isopropyl, cyclopentyl, cyclohexyl, neopentyl, benzyl, alkyl, branched alkyl, cycloalkyl, or lipid;

$R^5$ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;

$R^6$ is methyl, ethyl, tert-butyl, $C_{1-22}$ alkoxy, $C_{1-22}$ alkyl, branched alkyl, cycloalkyl, aryl, substituted aryl, or alkyoxy.

In certain embodiments, the present invention relates to compounds of the following formula:

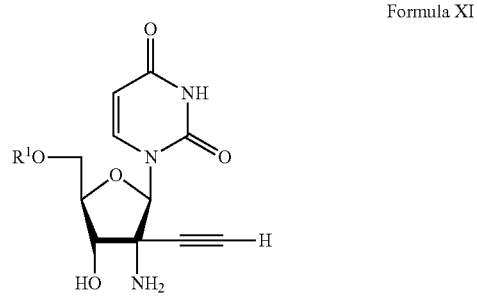

Formula XI or pharmaceutically acceptable salts thereof wherein,
$R^1$ is selected from one of the following formulae:

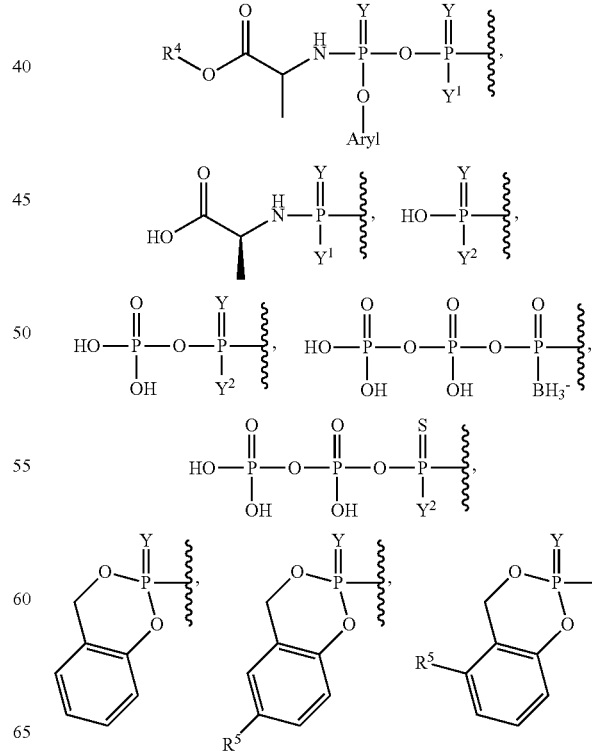

-continued

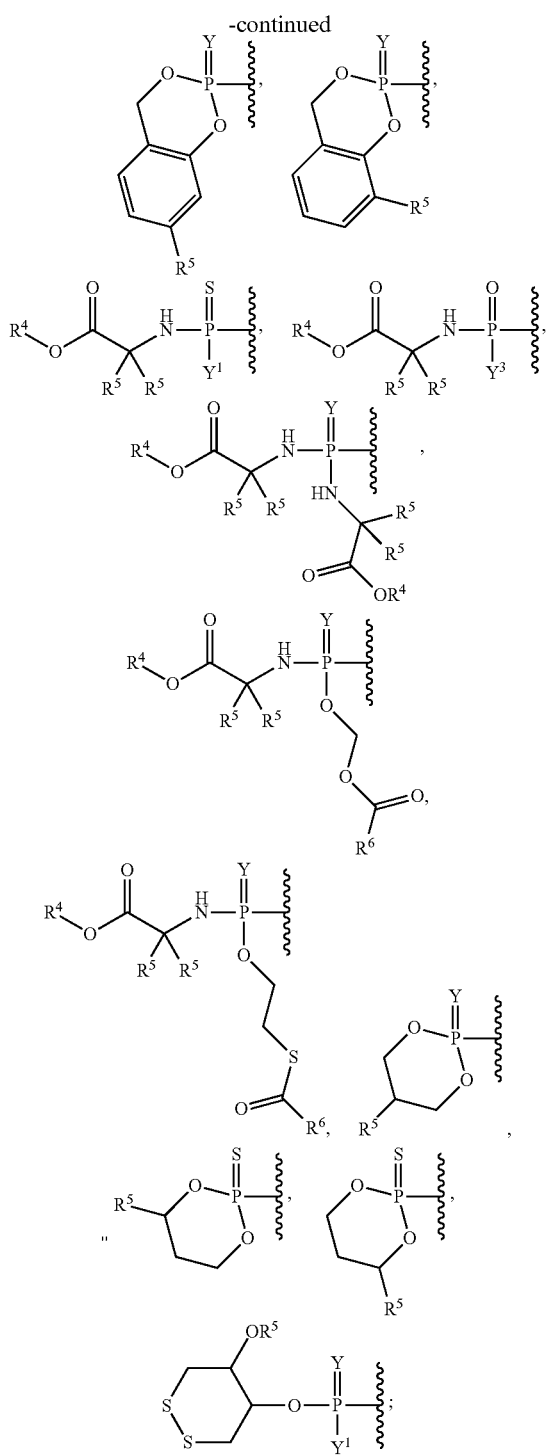

Y is O or S;
Y$^1$ is OH, OAryl, OAlkyl, or BH$_3^-$M$^+$;
Y$^2$ is OH or BH$_3^-$M$^+$;
Y$^3$ is OH, OAlkyl, or BH$_3^-$M$^+$;
Aryl is phenyl, 1-naphthyl, 2-naphthyl, aromatic, heteroaromatic, 4-substituted phenyl, 4-chlorophenyl, or 4-bromophenyl;
R$^4$ is hydrogen, methyl, ethyl, isopropyl, cyclopentyl, cyclohexyl, neopentyl, benzyl, alkyl, branched alkyl, cycloalkyl, or lipid;
R$^5$ is hydrogen, deuterium, hydroxyl, cyano, azido, amino, substituted amino, aryl, heteroaryl, substituted aryl, lipid, C$_{1-22}$ alkoxy, C$_{1-22}$ alkyl, C$_{2-22}$ alkenyl, C$_{2-22}$ alkynyl, or substituted heteroaryl;
R$^6$ is methyl, ethyl, tert-butyl, C$_{1-22}$ alkoxy, C$_{1-22}$ alkyl, branched alkyl, cycloalkyl, aryl, substituted aryl, or alkyoxy.

In certain embodiments, the present invention relates to compounds of the following formula:

Formula XII

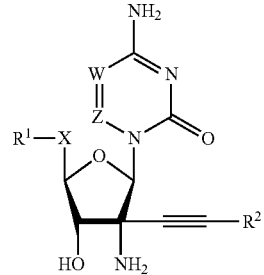

or pharmaceutically acceptable salts thereof wherein,
X is OCH$_2$, OCHMe, OCMe$_2$, OCHF, OCF$_2$, or OCD$_2$;
W is N or CR$^7$;
Z is N or CR$^8$;
R$^1$ is selected from H or from one of the following formulae:

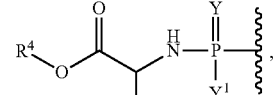

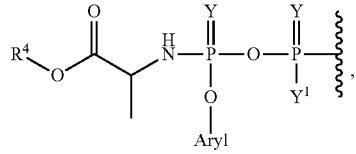

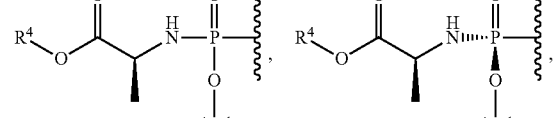

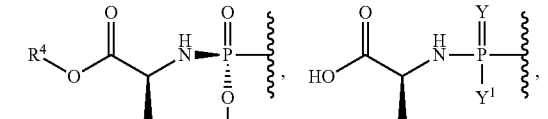

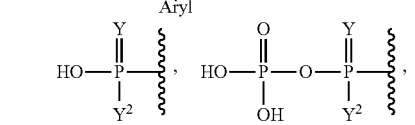

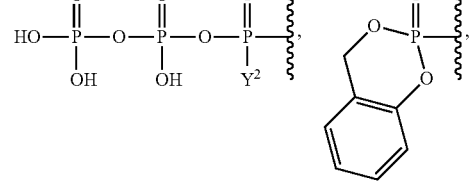

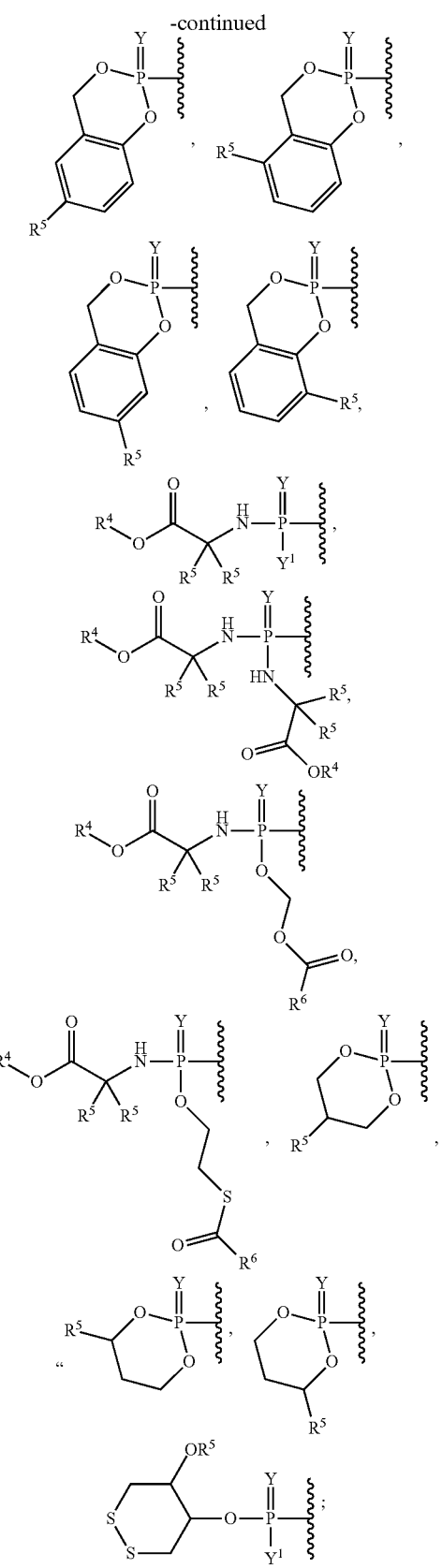

Y is O or S;
Y¹ is OH, OAryl, OAlkyl, or $BH_3^-M^+$;

Y² is OH or $BH_3^-M^+$;
Aryl is phenyl, 1-naphthyl, 2-naphthyl, aromatic, heteroaromatic, 4-substituted phenyl, 4-chlorophenyl, or 4-bromophenyl;
$R^2$ is hydrogen, methyl, fluoromethyl, difluoromethyl, trifluoromethyl, ethyl, cyclopropyl, fluoro, chloro, hydroxymethyl, aminomethyl, vinyl, or cyclobutyl;
$R^4$ is hydrogen, methyl, ethyl, isopropyl, cyclopentyl, cyclohexyl, neopentyl, benzyl, alkyl, branched alkyl, cycloalkyl, or lipid;
$R^5$ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;
$R^6$ is methyl, ethyl, tert-butyl, $C_{1-22}$ alkoxy, $C_{1-22}$ alkyl, branched alkyl, cycloalkyl, aryl, substituted aryl, or alkyoxy;
$R^7$ is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano;
$R^8$ is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano.

In certain embodiments, the present invention relates to compounds of the following formula:

Formula XIIIa

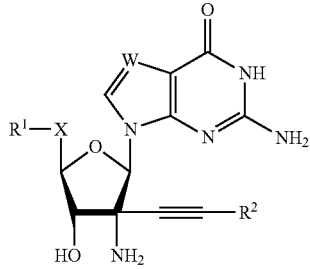

Formula XIIIb

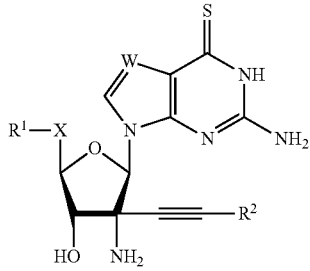

Formula XIIIc

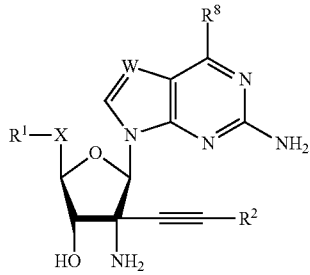

or pharmaceutically acceptable salts thereof wherein,

X is $OCH_2$, OCHMe, $OCMe_2$, OCHF, $OCF_2$, or $OCD_2$;

W is N or $CR^7$;

$R^1$ is selected from H or from one of the following formulae:

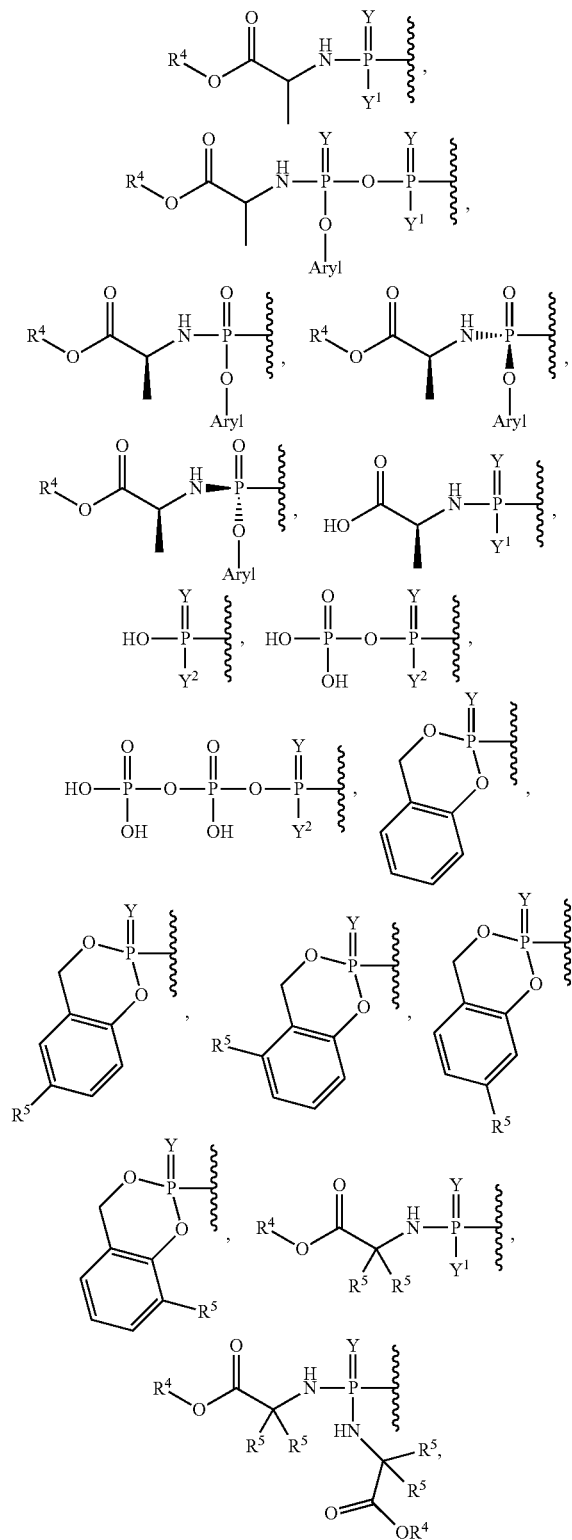
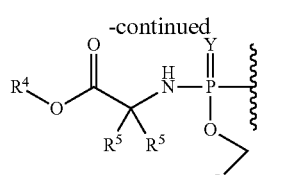
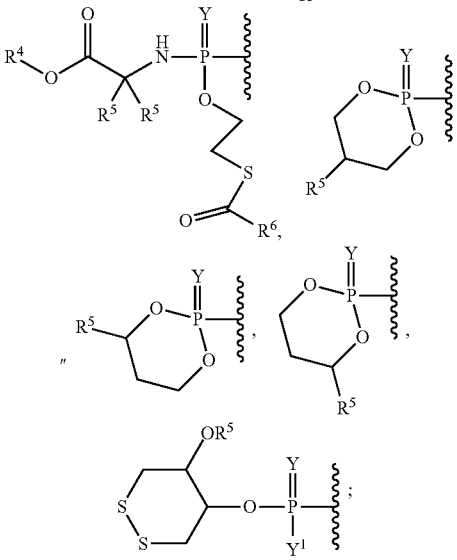

Y is O or S;

$Y^1$ is OH, OAryl, OAlkyl, or $BH_3^-M^+$; $Y^2$ is OH or $BH_3^-M^+$;

Aryl is phenyl, 1-naphthyl, 2-naphthyl, aromatic, heteroaromatic, 4-substituted phenyl, 4-chlorophenyl, or 4-bromophenyl;

$R^2$ is hydrogen, methyl, fluoromethyl, difluoromethyl, trifluoromethyl, ethyl, cyclopropyl, fluoro, chloro, hydroxymethyl, aminomethyl, vinyl, or cyclobutyl;

$R^4$ is hydrogen, methyl, ethyl, isopropyl, cyclopentyl, cyclohexyl, neopentyl, benzyl, alkyl, branched alkyl, cycloalkyl, or lipid;

$R^5$ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;

$R^6$ is methyl, ethyl, tert-butyl, $C_{1-22}$ alkoxy, $C_{1-22}$ alkyl, branched alkyl, cycloalkyl, aryl, substituted aryl, or alkyoxy;

$R^7$ is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano;

$R^8$ is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, methoxy, ethoxy, alkoxy, substituted amino, or cyano.

In certain embodiments, the present invention relates to compounds of the following formula:

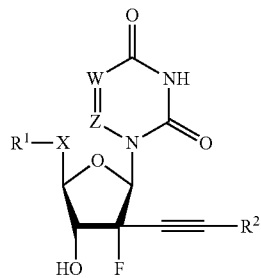

Formula XIV

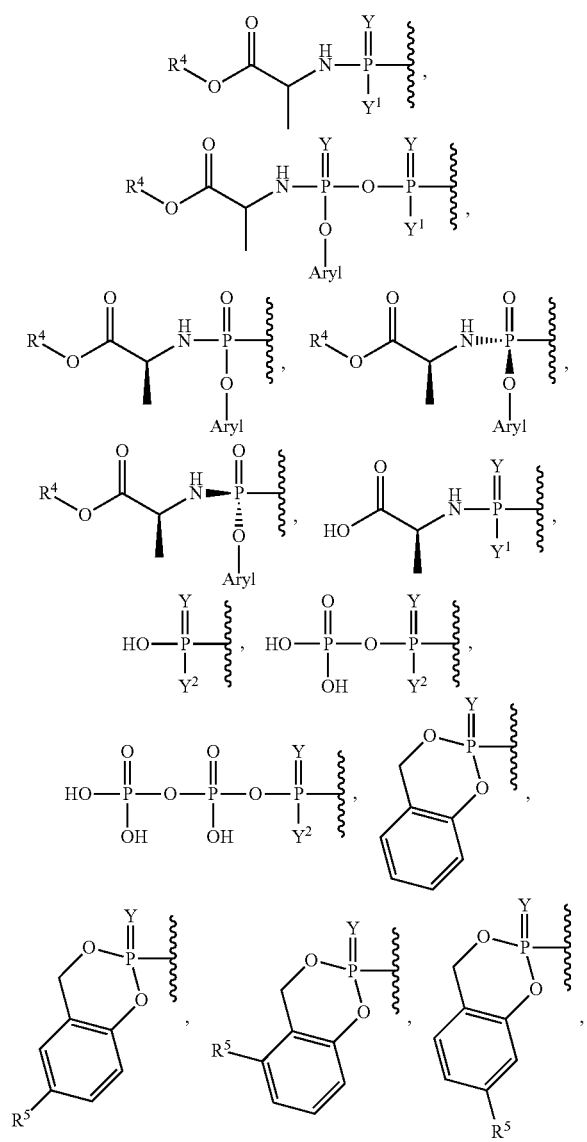

or pharmaceutically acceptable salts thereof wherein,

X is OCMe$_2$, OCHF, OCF$_2$, or OCD$_2$;

W is N or CR$^7$;

Z is N or CR$^8$;

R$^1$ is selected from H or from one of the following formulae:

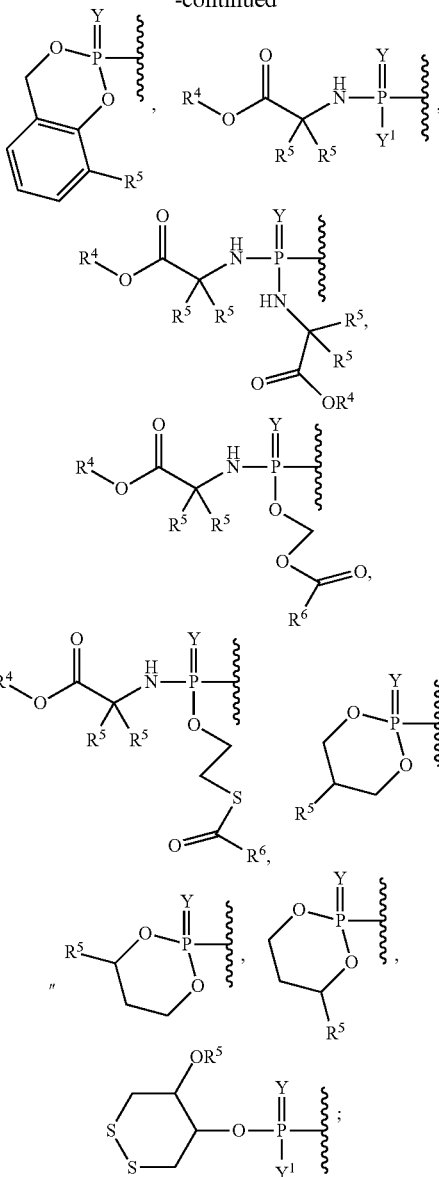

Y is O or S;

Y$^1$ is OH, OAryl, OAlkyl, or BH$_3^-$M$^+$;

Y$^2$ is OH or BH$_3^-$M$^+$;

Aryl is phenyl, 1-naphthyl, 2-naphthyl, aromatic, heteroaromatic, 4-substituted phenyl, 4-chlorophenyl, or 4-bromophenyl;

R$^2$ is hydrogen, methyl, fluoromethyl, difluoromethyl, trifluoromethyl, ethyl, cyclopropyl, fluoro, chloro, hydroxymethyl, aminomethyl, vinyl, or cyclobutyl;

R$^4$ is hydrogen, methyl, ethyl, isopropyl, cyclopentyl, cyclohexyl, neopentyl, benzyl, alkyl, branched alkyl, cycloalkyl, or lipid;

R$^5$ is hydrogen, deuterium, hydroxyl, cyano, azido, amino, substituted amino, aryl, heteroaryl, substituted aryl, lipid, C$_{1-22}$ alkoxy, C$_{1-22}$ alkyl, C$_{2-22}$ alkenyl, C$_{2-22}$ alkynyl, or substituted heteroaryl;

R$^6$ is methyl, ethyl, tert-butyl, C$_{1-22}$ alkoxy, C$_{1-22}$ alkyl, branched alkyl, cycloalkyl, aryl, substituted aryl, or alkyoxy;

R$^7$ is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano;

$R^8$ is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano.

In certain embodiments, the present invention relates to compounds of the following formula:

Formula XV

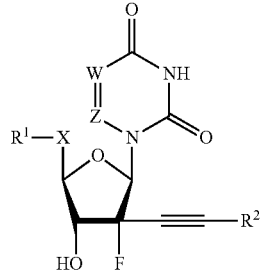

or pharmaceutically acceptable salts thereof wherein,

X is OCHMe;
W is N or $CR^7$;
Z is N or $CR^8$;
$R^1$ is selected from H or from one of the following formulae:

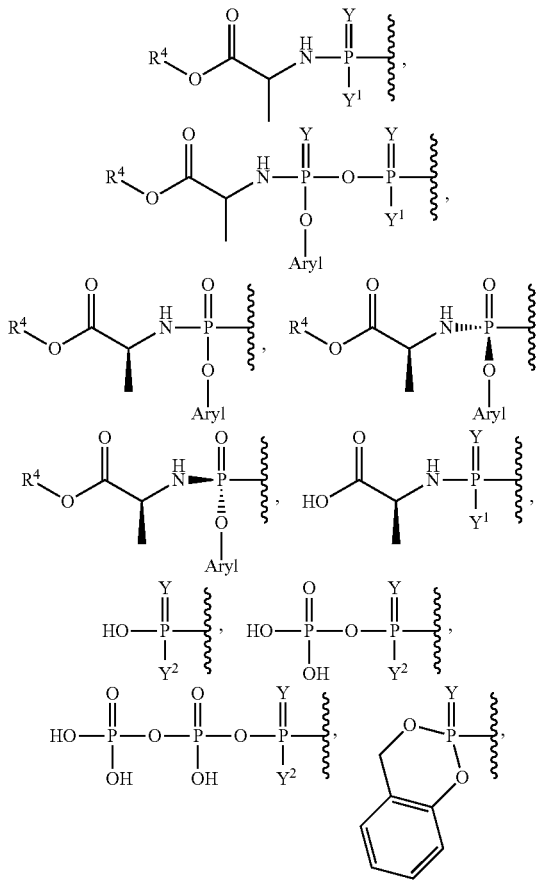

-continued

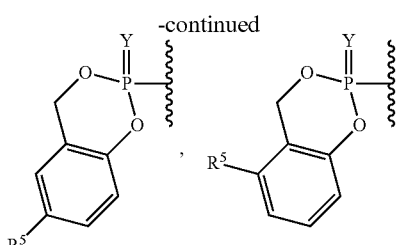

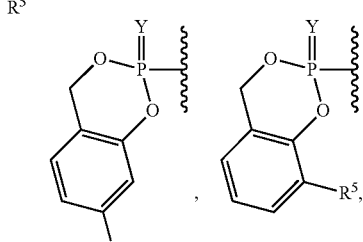

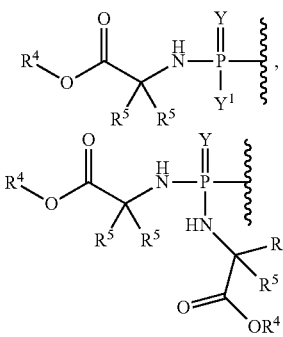

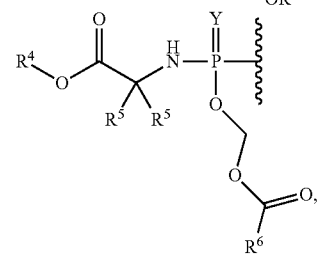

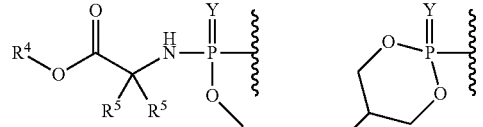

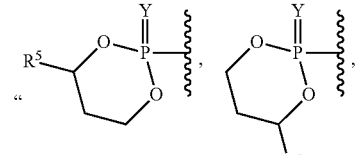

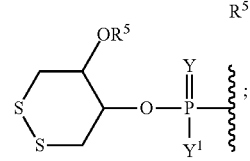

Y is O or S;
$Y^1$ is OH, OAryl, OAlkyl, or $BH_3^-M^+$;

$Y^2$ is OH or $BH_3^-M^+$;

Aryl is phenyl, 1-naphthyl, 2-naphthyl, aromatic, heteroaromatic, 4-substituted phenyl, 4-chlorophenyl, or 4-bromophenyl;

$R^2$ is hydrogen, methyl, fluoromethyl, difluoromethyl, trifluoromethyl, ethyl, cyclopropyl, fluoro, hydroxymethyl, aminomethyl, vinyl, or cyclobutyl;

$R^4$ is hydrogen, methyl, ethyl, isopropyl, cyclopentyl, cyclohexyl, neopentyl, benzyl, alkyl, branched alkyl, cycloalkyl, or lipid;

$R^5$ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;

$R^6$ is methyl, ethyl, tert-butyl, $C_{1-22}$ alkoxy, $C_{1-22}$ alkyl, branched alkyl, cycloalkyl, aryl, substituted aryl, or alkyoxy;

$R^7$ is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano;

$R^8$ is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano.

In certain embodiments, the present invention relates to compounds of the following formula:

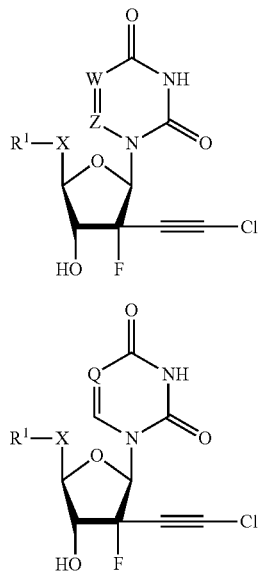

Formula XVIa

Formula XVIb or pharmaceutically acceptable salts thereof wherein,

X is OCHMe;

W is N or $CR^7$;

Z is N or $CR^8$;

Q is N or $CR^9$;

$R^1$ is selected from H or from one of the following formulae:

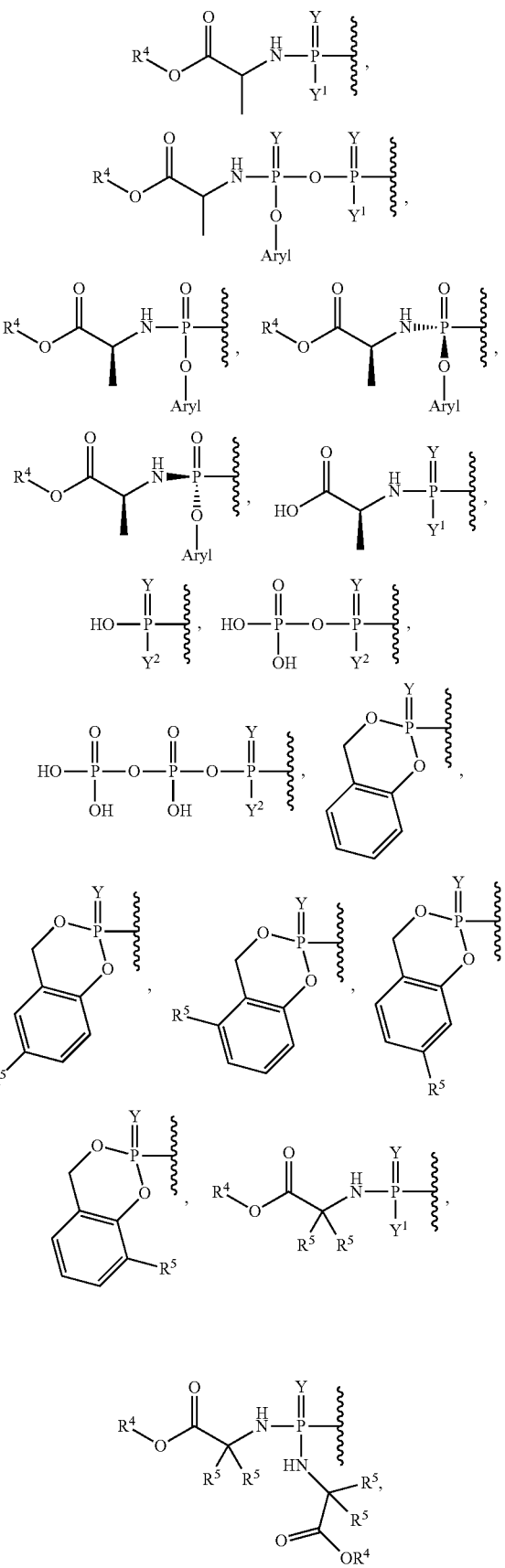

-continued

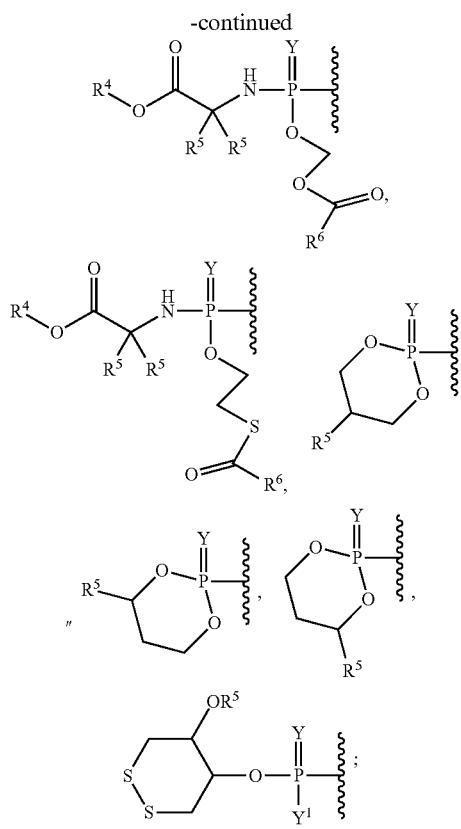

Y is O or S;

Y$^1$ is OH, OAryl, OAlkyl, or BH$_3^-$M$^+$;

Y$^2$ is OH or BH$_3^-$M$^+$; Aryl is phenyl, 1-naphthyl, 2-naphthyl, aromatic, heteroaromatic, 4-substituted phenyl, 4-chlorophenyl, or 4-bromophenyl;

R$^4$ is hydrogen, methyl, ethyl, isopropyl, cyclopentyl, cyclohexyl, neopentyl, benzyl, alkyl, branched alkyl, cycloalkyl, or lipid;

R$^5$ is hydrogen, deuterium, hydroxyl, cyano, azido, amino, substituted amino, aryl, heteroaryl, substituted aryl, lipid, C$_{1-22}$ alkoxy, C$_{1-22}$ alkyl, C$_{2-22}$ alkenyl, C$_{2-22}$ alkynyl, or substituted heteroaryl;

R$^6$ is methyl, ethyl, tert-butyl, C$_{1-22}$ alkoxy, C$_{1-22}$ alkyl, branched alkyl, cycloalkyl, aryl, substituted aryl, or alkyoxy;

R$^7$ is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano;

R$^8$ is D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano;

R$^9$ is D, hydroxyl, thiol, amino, alkyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano.

In certain embodiments, the present invention relates to compounds of the following formula:

Formula XVII

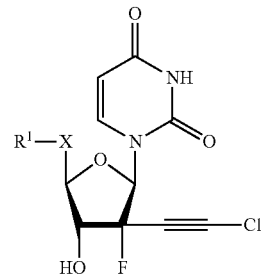

or pharmaceutically acceptable salts thereof wherein,

X is OCHMe;

R$^1$ is selected from one of the following formulae:

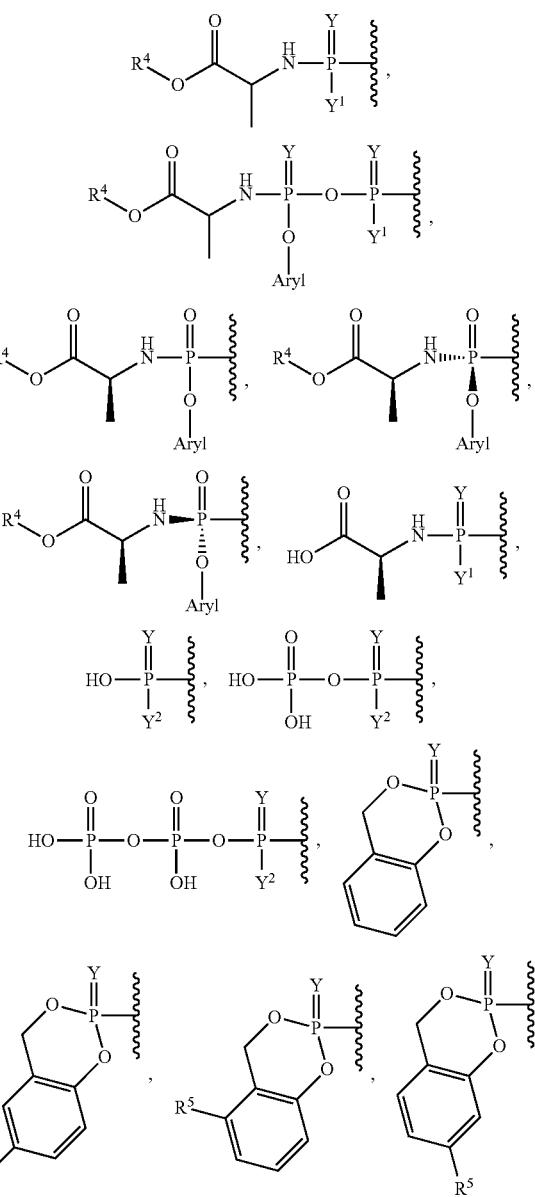

-continued

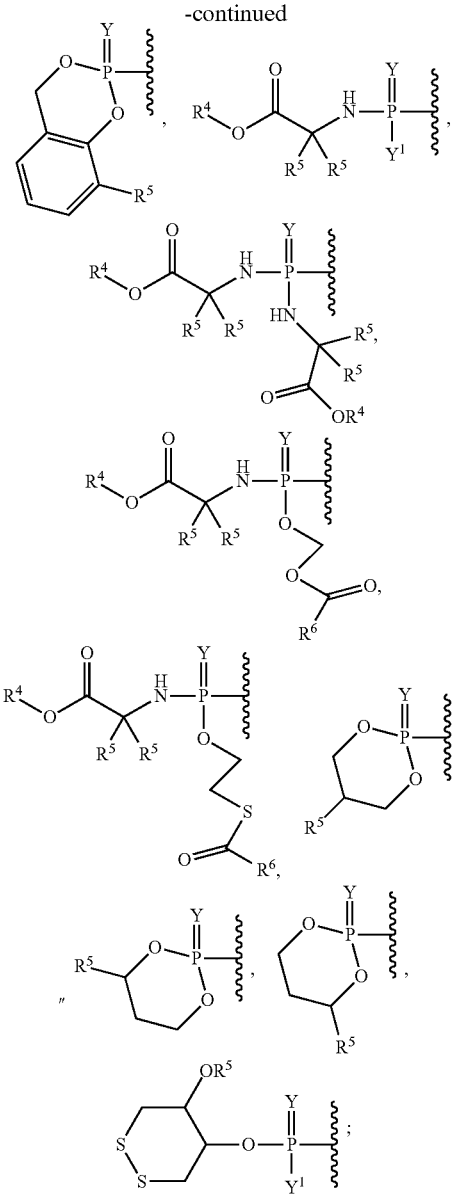

Y is O or S;

Y$^1$ is OH, OAryl, OAlkyl, or BH$_3^-$M$^+$;

Y$^2$ is OH or BH$_3^-$M$^+$;

Aryl is phenyl, 1-naphthyl, 2-naphthyl, aromatic, heteroaromatic, 4-substituted phenyl, 4-chlorophenyl, or 4-bromophenyl;

R$^4$ is hydrogen, methyl, ethyl, isopropyl, cyclopentyl, cyclohexyl, neopentyl, benzyl, alkyl, branched alkyl, cycloalkyl, or lipid;

R$^5$ is hydrogen, deuterium, hydroxyl, cyano, azido, amino, substituted amino, aryl, heteroaryl, substituted aryl, lipid, C$_{1-22}$ alkoxy, C$_{1-22}$ alkyl, C$_{2-22}$ alkenyl, C$_{2-22}$ alkynyl, or substituted heteroaryl;

R$^6$ is methyl, ethyl, tert-butyl, C$_{1-22}$ alkoxy, C$_{1-22}$ alkyl, branched alkyl, cycloalkyl, aryl, substituted aryl, or alkyoxy.

In certain embodiments, the present invention relates to compounds of the following formula:

Formula XVIII

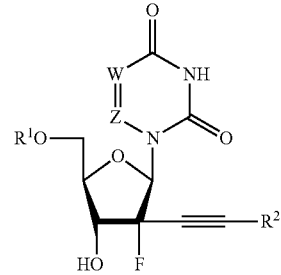

or pharmaceutically acceptable salts thereof wherein,

W is N or CR$^7$;

Z is N or CR$^8$;

R$^1$ is selected from H or from one of the following formulae:

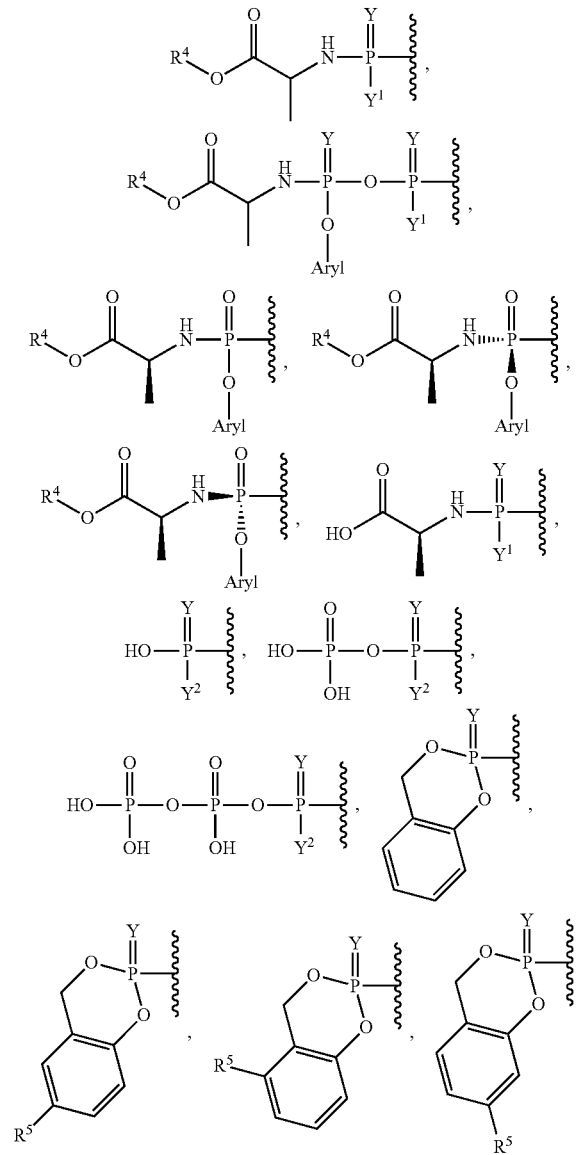

-continued

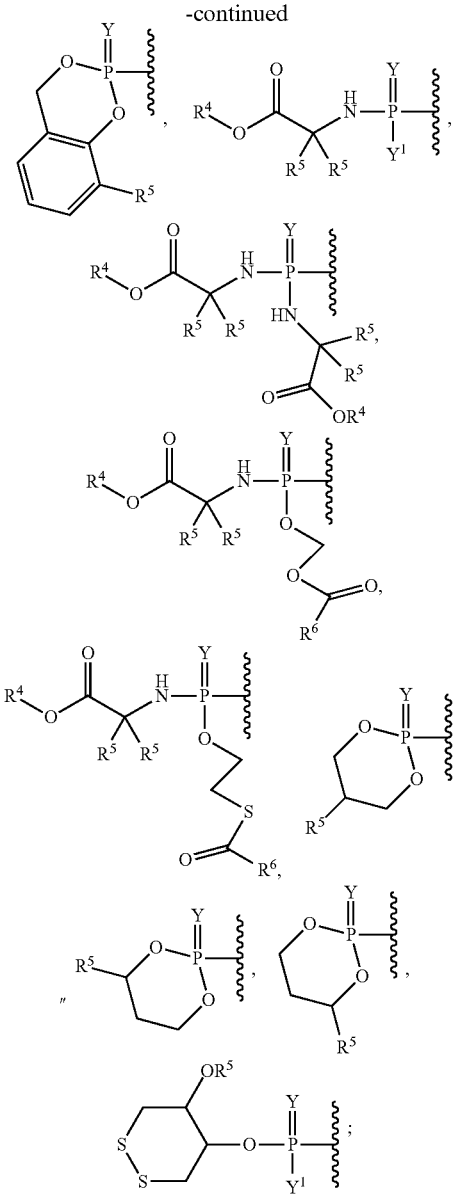

Y is O or S;
Y$^1$ is OH, OAryl, OAlkyl, or BH$_3^-$M$^+$;
Y$^2$ is OH or BH$_3^-$M$^+$;
Aryl is phenyl, 1-naphthyl, 2-naphthyl, aromatic, heteroaromatic, 4-substituted phenyl, 4-chlorophenyl, or 4-bromophenyl;
R$^2$ is fluoromethyl, difluoromethyl, trifluoromethyl, ethyl, cyclopropyl, fluoro, hydroxymethyl, aminomethyl, vinyl, or cyclobutyl;
R$^4$ is hydrogen, methyl, ethyl, isopropyl, cyclopentyl, cyclohexyl, neopentyl, benzyl, alkyl, branched alkyl, cycloalkyl, or lipid;
R$^5$ is hydrogen, deuterium, hydroxyl, cyano, azido, amino, substituted amino, aryl, heteroaryl, substituted aryl, lipid, C$_{1-22}$ alkoxy, C$_{1-22}$ alkyl, C$_{2-22}$ alkenyl, C$_{2-22}$ alkynyl, or substituted heteroaryl;
R$^6$ is methyl, ethyl, tert-butyl, C$_{1-22}$ alkoxy, C$_{1-22}$ alkyl, branched alkyl, cycloalkyl, aryl, substituted aryl, or alkyoxy;
R$^7$ is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano;
R$^8$ is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano.

In certain embodiments, the present invention relates to compounds of the following formula:

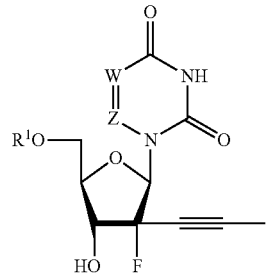

Formula XIX or pharmaceutically acceptable salts thereof wherein,
W is N or CR$^7$;
Z is N or CR$^8$;
R$^1$ is selected from H or from one of the following formulae:

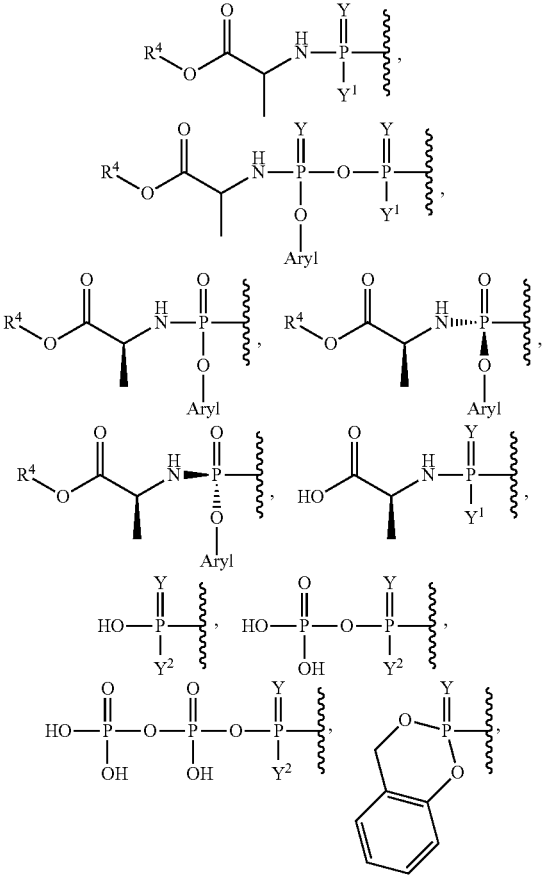

$Y^2$ is OH or $BH_3^-M^+$;

Aryl is phenyl, 1-naphthyl, 2-naphthyl, aromatic, heteroaromatic, 4-substituted phenyl, 4-chlorophenyl, or 4-bromophenyl;

$R^4$ is hydrogen, methyl, ethyl, isopropyl, cyclopentyl, cyclohexyl, neopentyl, benzyl, alkyl, branched alkyl, cycloalkyl, or lipid;

$R^5$ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;

$R^6$ is methyl, ethyl, tert-butyl, $C_{1-22}$ alkoxy, $C_{1-22}$ alkyl, branched alkyl, cycloalkyl, aryl, substituted aryl, or alkyoxy;

$R^7$ is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano;

$R^8$ is D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano.

In certain embodiments, the present invention relates to compounds of the following formula:

Formula XX or pharmaceutically acceptable salts thereof wherein,

W is N or $CR^7$;

$R^1$ is selected from H or from one of the following formulae:

Y is O or S;
$Y^1$ is OH, OAryl, OAlkyl, or $BH_3^-M^+$;

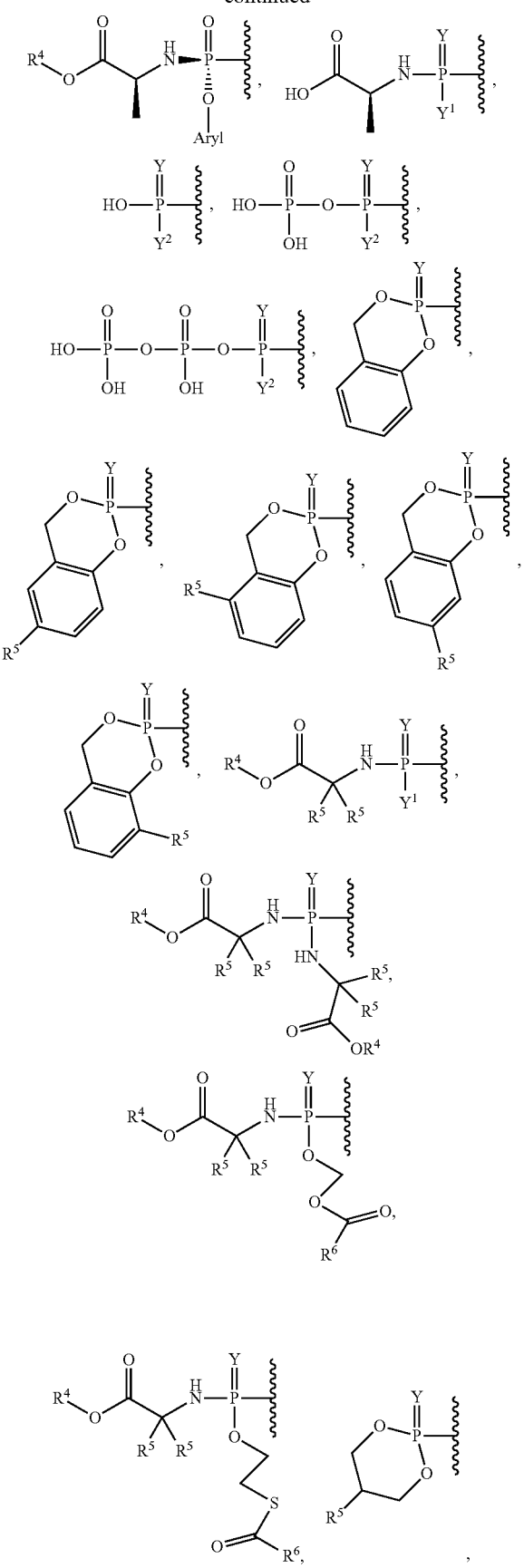

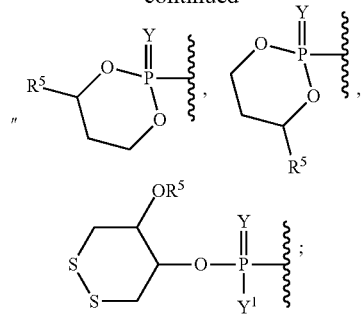

Y is O or S;

$Y^1$ is OH, OAryl, OAlkyl, or $BH_3^-M^+$;

$Y^2$ is OH or $BH_3^-M^+$;

Aryl is phenyl, 1-naphthyl, 2-naphthyl, aromatic, heteroaromatic, 4-substituted phenyl, 4-chlorophenyl, or 4-bromophenyl;

$R^4$ is hydrogen, methyl, ethyl, isopropyl, cyclopentyl, cyclohexyl, neopentyl, benzyl, alkyl, branched alkyl, cycloalkyl, or lipid;

$R^5$ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;

$R^6$ is methyl, ethyl, tert-butyl, $C_{1-22}$ alkoxy, $C_{1-22}$ alkyl, branched alkyl, cycloalkyl, aryl, substituted aryl, or alkyoxy;

$R^7$ is D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano.

In certain embodiments, the present invention relates to compounds of the following formula:

Formula XXI

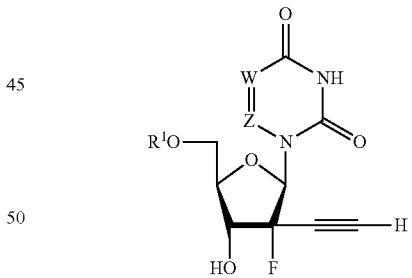

or pharmaceutically acceptable salts thereof wherein,

W is N or $CR^7$;

Z is N or $CR^8$;

$R^1$ is selected from H or from one of the following formulae:

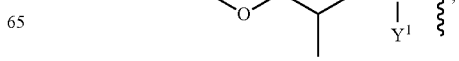

-continued

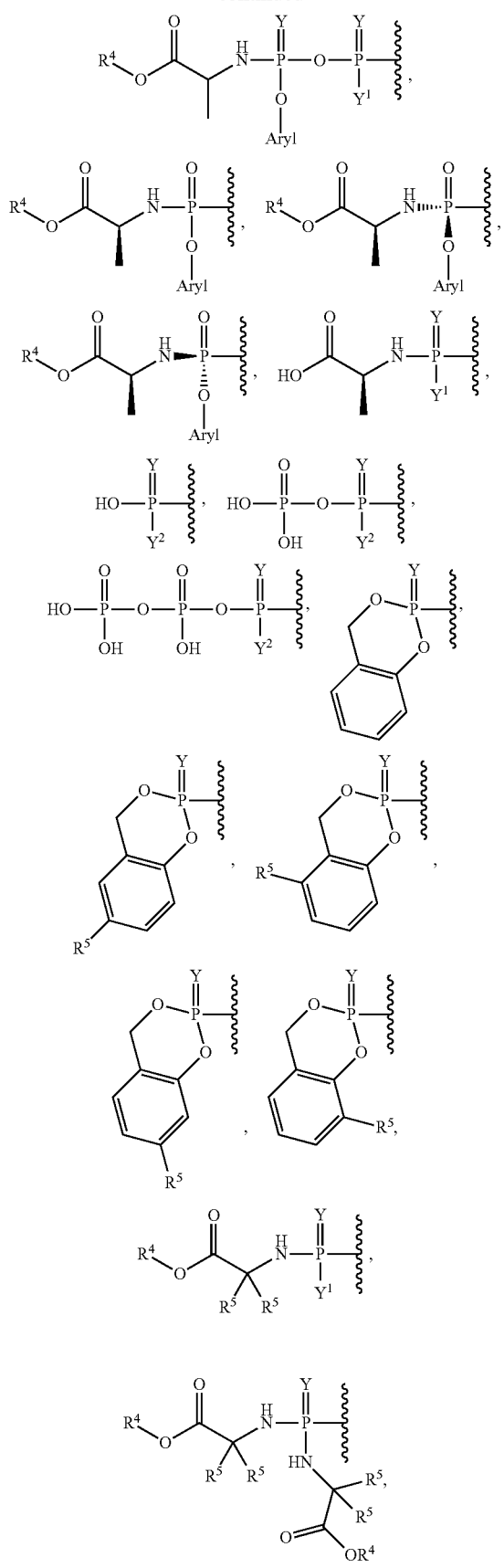

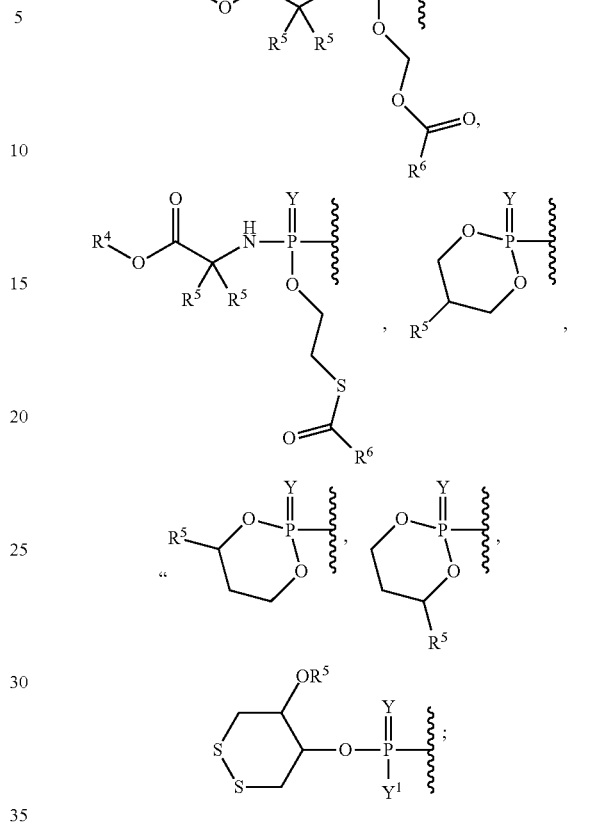

Y is O or S;

Y$^1$ is OH, OAryl, OAlkyl, or BH$_3^-$M$^+$;

Y$^2$ is OH or BH$_3^-$M$^+$;

Aryl is phenyl, 1-naphthyl, 2-naphthyl, aromatic, heteroaromatic, 4-substituted phenyl, 4-chlorophenyl, or 4-bromophenyl;

R$^4$ is hydrogen, methyl, ethyl, isopropyl, cyclopentyl, cyclohexyl, neopentyl, benzyl, alkyl, branched alkyl, cycloalkyl, or lipid;

R$^5$ is hydrogen, deuterium, hydroxyl, cyano, azido, amino, substituted amino, aryl, heteroaryl, substituted aryl, lipid, C$_{1-22}$ alkoxy, C$_{1-22}$ alkyl, C$_{2-22}$ alkenyl, C$_{2-22}$ alkynyl, or substituted heteroaryl;

R$^6$ is methyl, ethyl, tert-butyl, C$_{1-22}$ alkoxy, C$_{1-22}$ alkyl, branched alkyl, cycloalkyl, aryl, substituted aryl, or alkyoxy;

R$^7$ is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano;

R$^8$ is D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano.

In certain embodiments, the present invention relates to compounds of the following formula:

Formula XXII

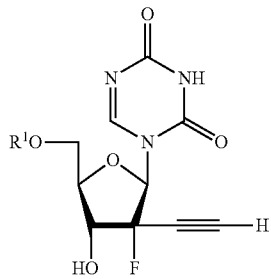

or pharmaceutically acceptable salts thereof wherein,

R¹ is selected from H or from one of the following formulae:

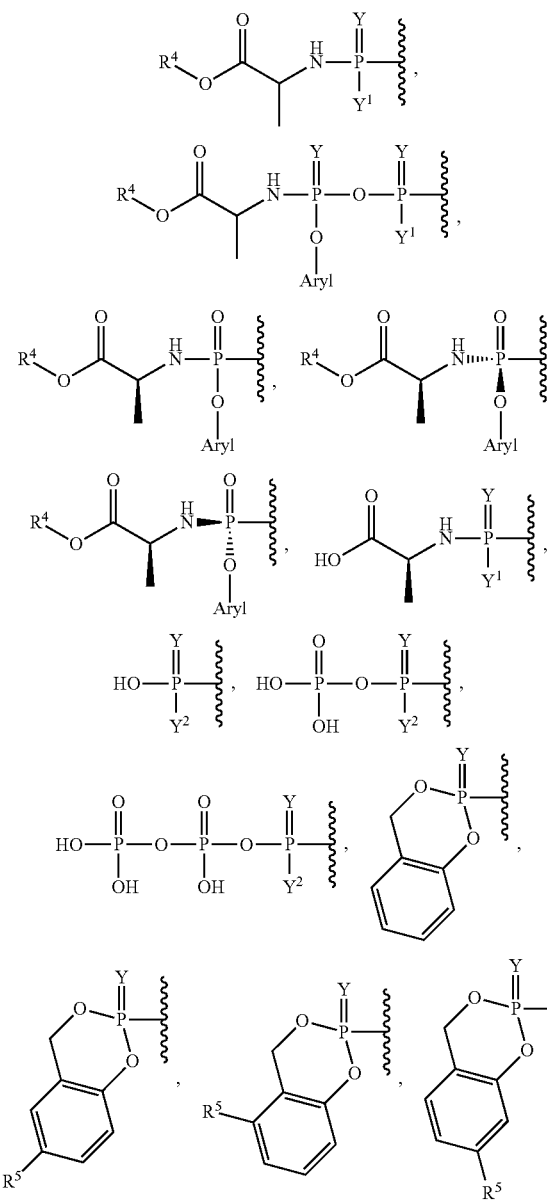

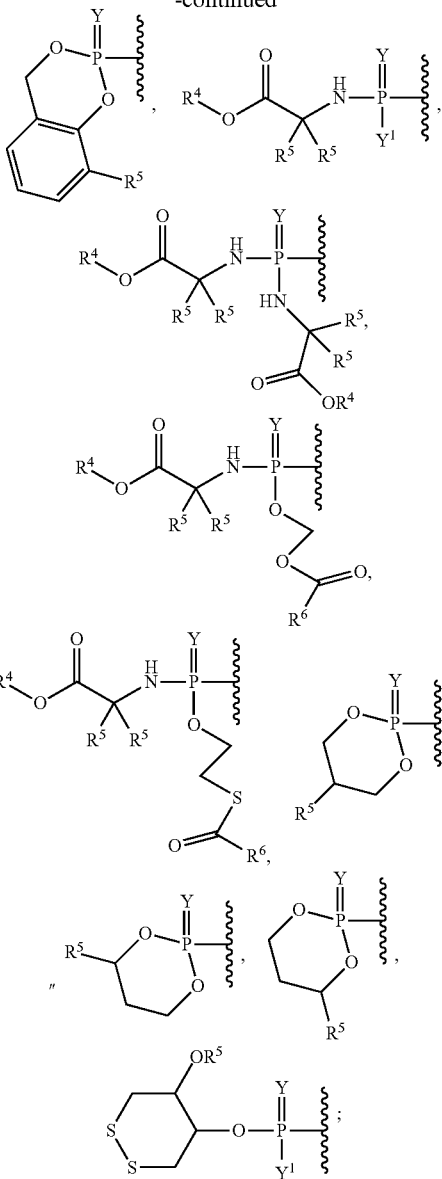

Y is O or S;

Y¹ is OH, OAryl, OAlkyl, or $BH_3^-M^+$;

Y² is OH or $BH_3^-M^+$;

Aryl is phenyl, 1-naphthyl, 2-naphthyl, aromatic, heteroaromatic, 4-substituted phenyl, 4-chlorophenyl, or 4-bromophenyl;

R⁴ is hydrogen, methyl, ethyl, isopropyl, cyclopentyl, cyclohexyl, neopentyl, benzyl, alkyl, branched alkyl, cycloalkyl, or lipid;

R⁵ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;

R⁶ is methyl, ethyl, tert-butyl, $C_{1-22}$ alkoxy, $C_{1-22}$ alkyl, branched alkyl, cycloalkyl, aryl, substituted aryl, or alkyoxy.

In certain embodiments, the present invention relates to compounds of the following formula:

Formula XXIII

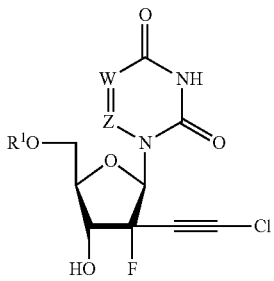

or pharmaceutically acceptable salts thereof wherein,

W is N or $CR^7$;

Z is N or $CR^8$;

$R^1$ is selected from H or from one of the following formulae:

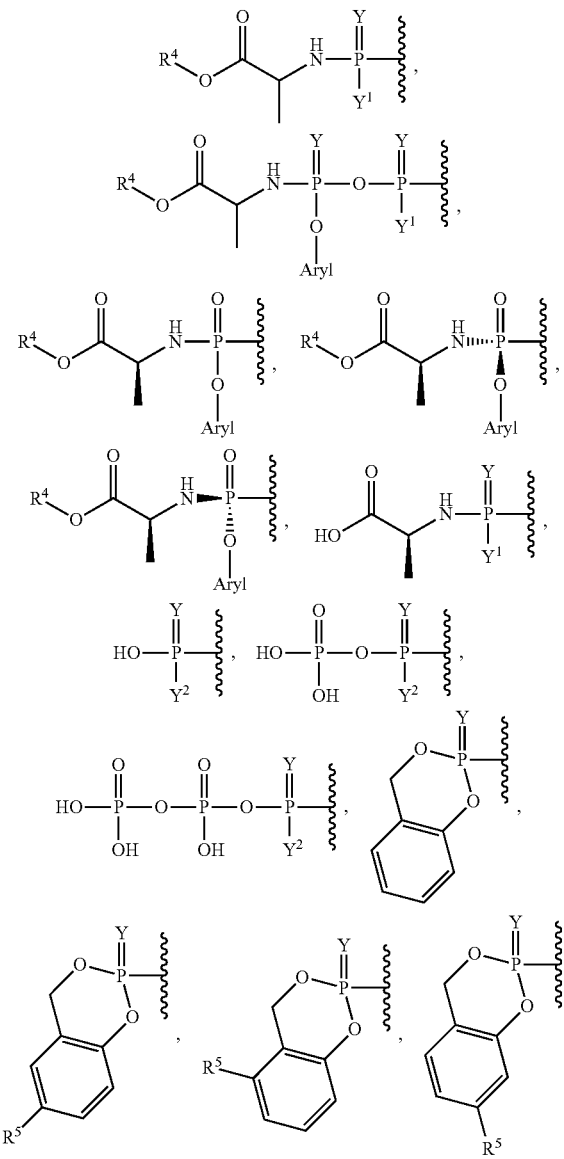

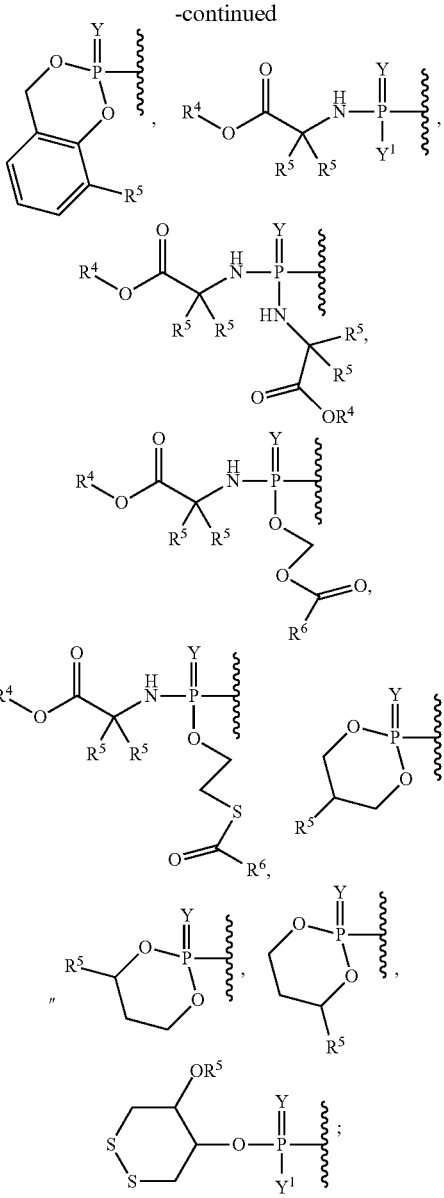

Y is O or S;

$Y^1$ is OH, OAryl, OAlkyl, $BH_3^-M^+$;

$Y^2$ is OH or $BH_3^-M^+$;

Aryl is phenyl, 1-naphthyl, 2-naphthyl, aromatic, heteroaromatic, 4-substituted phenyl, 4-chlorophenyl, or 4-bromophenyl;

$R^4$ is hydrogen, methyl, ethyl, isopropyl, cyclopentyl, cyclohexyl, neopentyl, benzyl, alkyl, branched alkyl, cycloalkyl, or lipid;

$R^5$ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;

$R^6$ is methyl, ethyl, tert-butyl, $C_{1-22}$ alkoxy, $C_{1-22}$ alkyl, branched alkyl, cycloalkyl, aryl, substituted aryl, or alkyoxy;

$R^7$ is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano;

$R^8$ is D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano.

In certain embodiments, the present invention relates to compounds of the following formula:

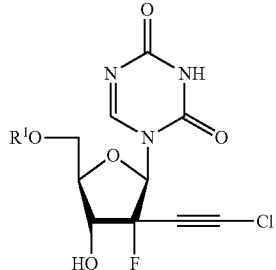

Formula XXIV or pharmaceutically acceptable salts thereof wherein, $R^1$ is selected from H or from one of the following formulae:

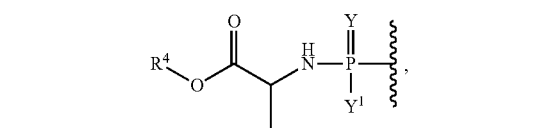

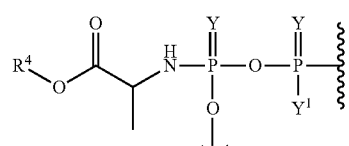

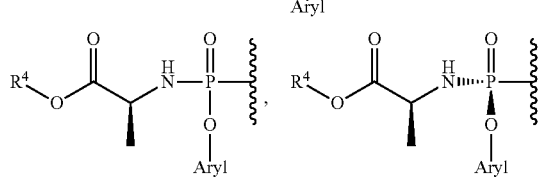

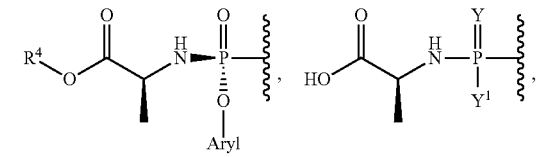

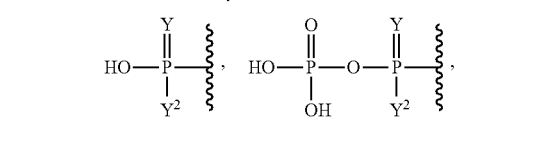

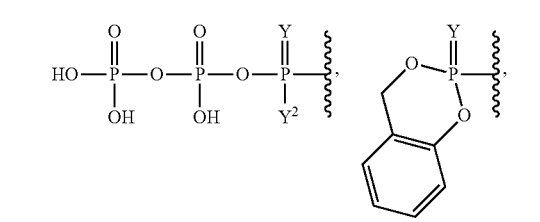

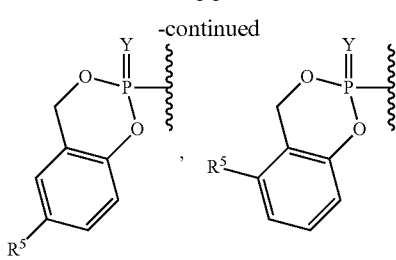

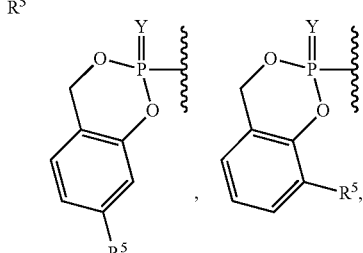

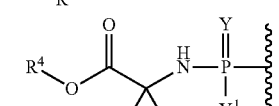

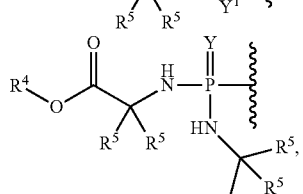

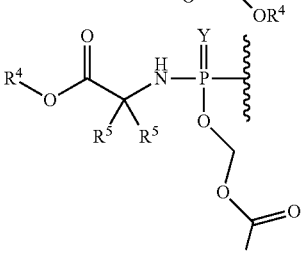

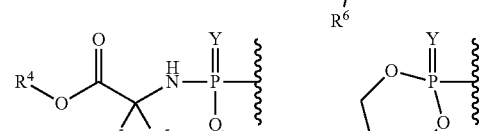

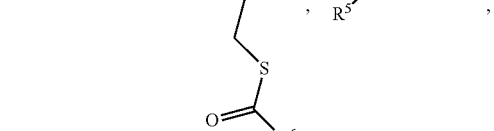

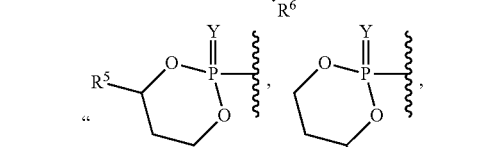

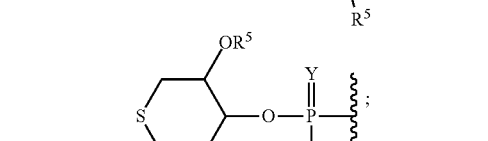

Y is O or S;

$Y^1$ is OH, OAryl, OAlkyl, or $BH_3^- M^+$;

$Y^2$ is OH or $BH_3^-M^+$;

Aryl is phenyl, 1-naphthyl, 2-naphthyl, aromatic, heteroaromatic, 4-substituted phenyl, 4-chlorophenyl, or 4-bromophenyl;

$R^4$ is hydrogen, methyl, ethyl, isopropyl, cyclopentyl, cyclohexyl, neopentyl, benzyl, alkyl, branched alkyl, cycloalkyl, or lipid;

$R^5$ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;

$R^6$ is methyl, ethyl, tert-butyl, $C_{1-22}$ alkoxy, $C_{1-22}$ alkyl, branched alkyl, cycloalkyl, aryl, substituted aryl, or alkyoxy.

In certain embodiments, the present invention relates to compounds of the following Formula XXV

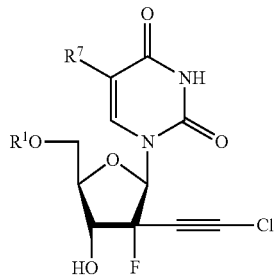

or pharmaceutically acceptable salts thereof wherein, $R^1$ is selected from H or from one of the following formulae:

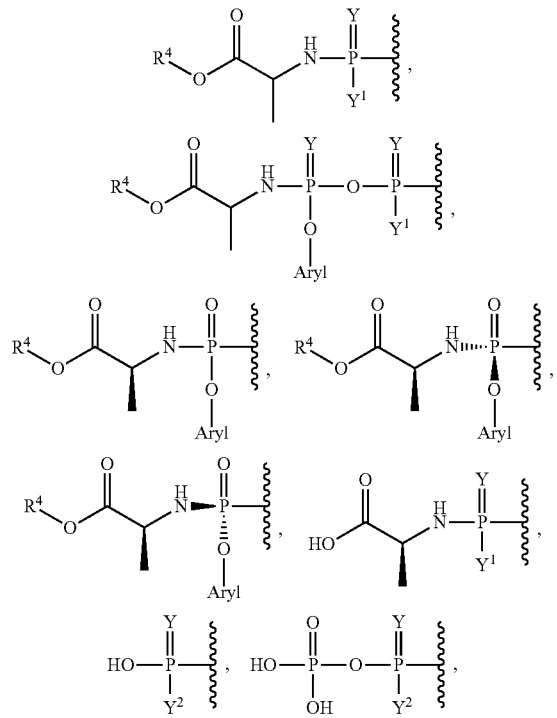

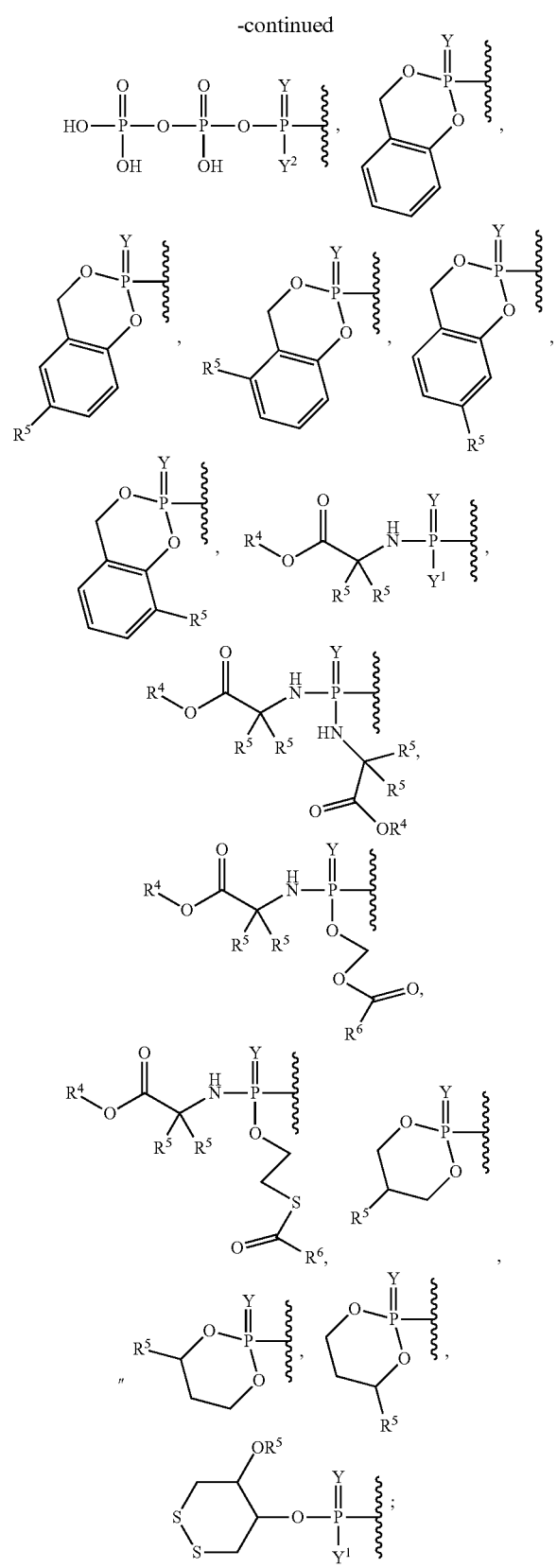

$Y$ is O or S;
$Y^1$ is OH, OAryl, OAlkyl, or $BH_3^-M^+$;
$Y^2$ is OH or $BH_3^-M^+$;

Aryl is phenyl, 1-naphthyl, 2-naphthyl, aromatic, heteroaromatic, 4-substituted phenyl, 4-chlorophenyl, or 4-bromophenyl;

$R^4$ is hydrogen, methyl, ethyl, isopropyl, cyclopentyl, cyclohexyl, neopentyl, benzyl, alkyl, branched alkyl, cycloalkyl, or lipid;

$R^5$ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;

$R^6$ is methyl, ethyl, tert-butyl, $C_{1-22}$ alkoxy, $C_{1-22}$ alkyl, branched alkyl, cycloalkyl, aryl, substituted aryl, or alkyoxy;

$R^7$ is D, hydroxyl, thiol, amino, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano.

In certain embodiments, the present invention relates to compounds of the following formula:

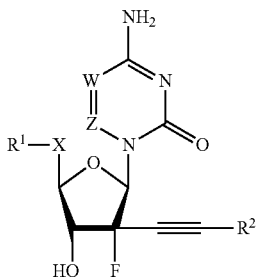

Formula XXVI or pharmaceutically acceptable salts thereof wherein,

X is $OCH_2$, OCHMe, $OCMe_2$, OCHF, $OCF_2$, or $OCD_2$;

W is N or $CR^7$;

Z is N or $CR^8$;

$R^1$ is selected from H or from one of the following formulae:

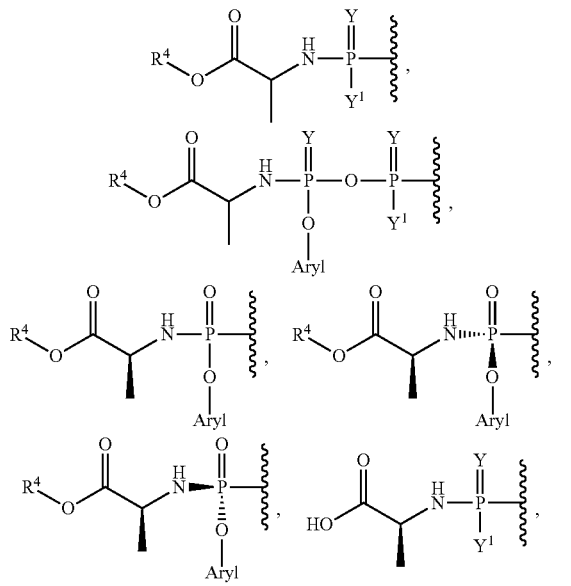

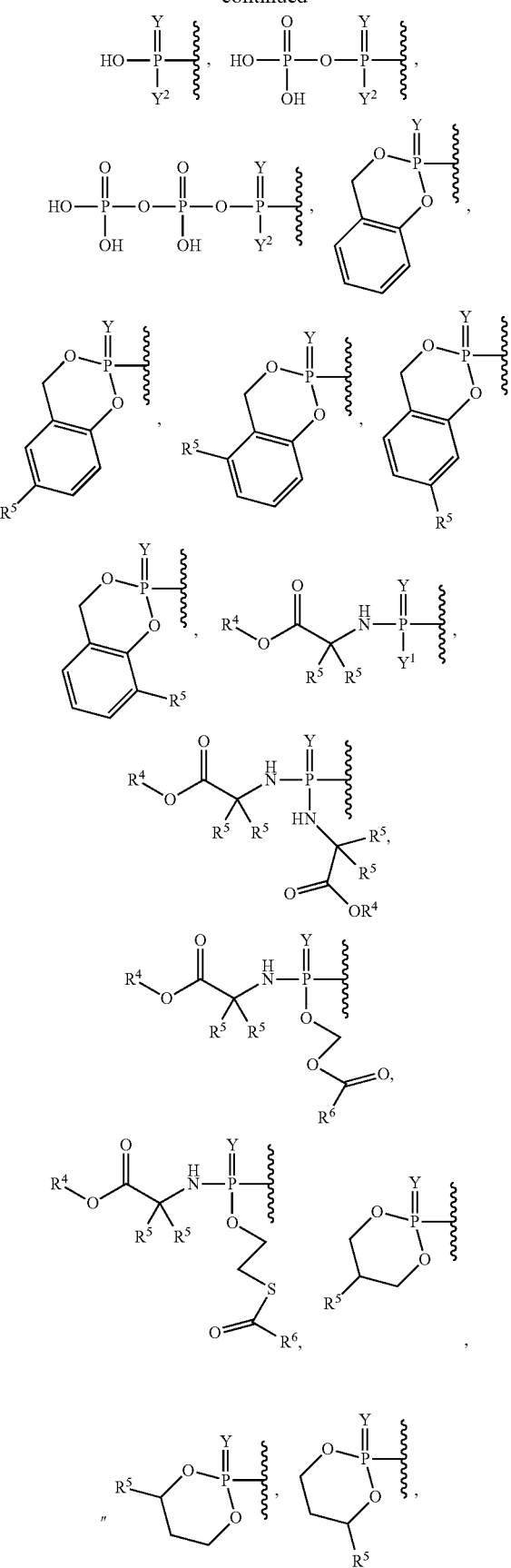

-continued

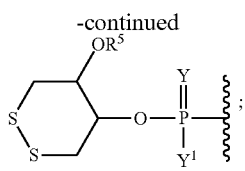

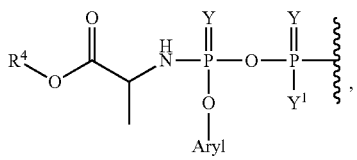

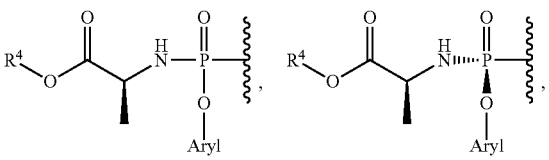

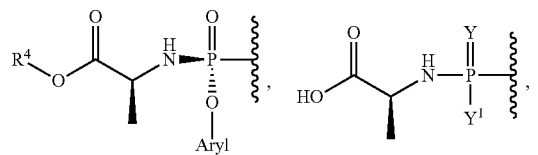

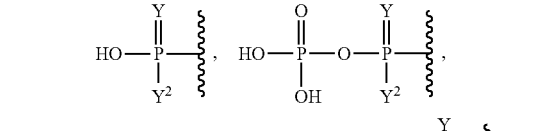

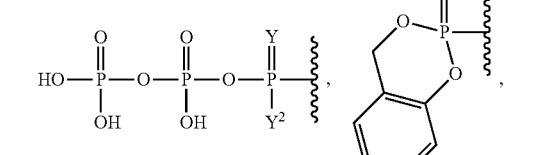

Y is O or S;
Y$^1$ is OH, OAryl, OAlkyl, or BH$_3^-$M$^+$;
Y$^2$ is OH or BH$_3^-$M$^+$;
Aryl is phenyl, 1-naphthyl, 2-naphthyl, aromatic, heteroaromatic, 4-substituted phenyl, 4-chlorophenyl, or 4-bromophenyl;
R$^2$ is methyl, fluoromethyl, difluoromethyl, trifluoromethyl, ethyl, cyclopropyl, fluoro, hydroxymethyl, aminomethyl, vinyl, or cyclobutyl;
R$^4$ is hydrogen, methyl, ethyl, isopropyl, cyclopentyl, cyclohexyl, neopentyl, benzyl, alkyl, branched alkyl, cycloalkyl, or lipid;
R$^5$ is hydrogen, deuterium, hydroxyl, cyano, azido, amino, substituted amino, aryl, heteroaryl, substituted aryl, lipid, C$_{1-22}$ alkoxy, C$_{1-22}$ alkyl, C$_{2-22}$ alkenyl, C$_{2-22}$ alkynyl, or substituted heteroaryl;
R$^6$ is methyl, ethyl, tert-butyl, C$_{1-22}$ alkoxy, C$_{1-22}$ alkyl, branched alkyl, cycloalkyl, aryl, substituted aryl, or alkyoxy;
R$^7$ is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano;
R$^8$ is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano. In certain embodiments, the present invention relates to compounds of the following formula:

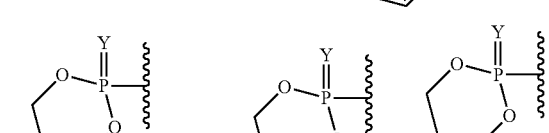

Formula XXVII

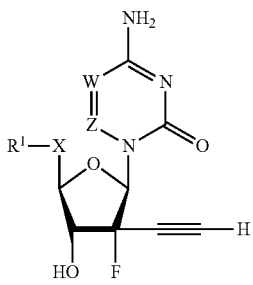

or pharmaceutically acceptable salts thereof wherein,
X is OCHMe, OCMe$_2$, OCHF, OCF$_2$, or OCD$_2$;
W is N or CR$^7$;
Z is N or CR$^8$;
R$^1$ is selected from H or from one of the following formulae:

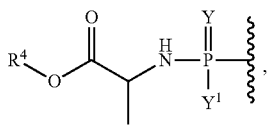

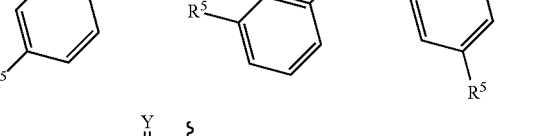

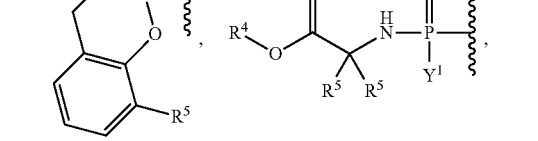

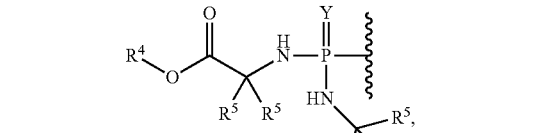

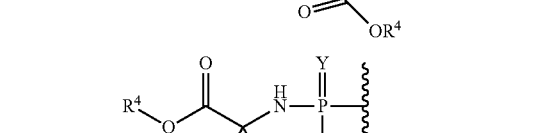

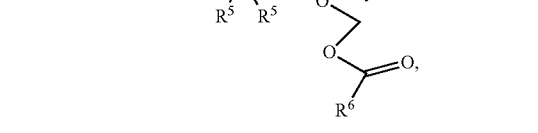

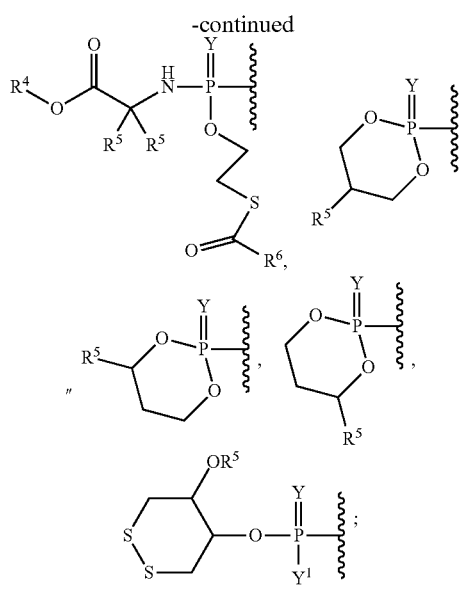

Y is O or S;
Y¹ is OH, OAryl, OAlkyl, or $BH_3^-M^+$;
Y² is OH or $BH_3^-M^+$;
Aryl is phenyl, 1-naphthyl, 2-naphthyl, aromatic, heteroaromatic, 4-substituted phenyl, 4-chlorophenyl, or 4-bromophenyl;
$R^4$ is hydrogen, methyl, ethyl, isopropyl, cyclopentyl, cyclohexyl, neopentyl, benzyl, alkyl, branched alkyl, cycloalkyl, or lipid;
$R^5$ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;
$R^6$ is methyl, ethyl, tert-butyl, $C_{1-22}$ alkoxy, $C_{1-22}$ alkyl, branched alkyl, cycloalkyl, aryl, substituted aryl, or alkyoxy;
$R^7$ is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano;
$R^8$ is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano.

In certain embodiments, the present invention relates to compounds of the following formula:

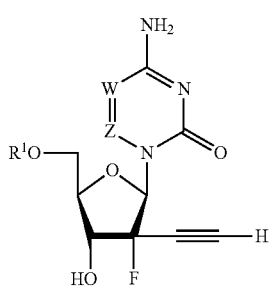

Formula XXVIII or pharmaceutically acceptable salts thereof wherein,

W is N or $CR^7$;
Z is N or $CR^8$;
$R^1$ is selected from H or from one of the following formulae:

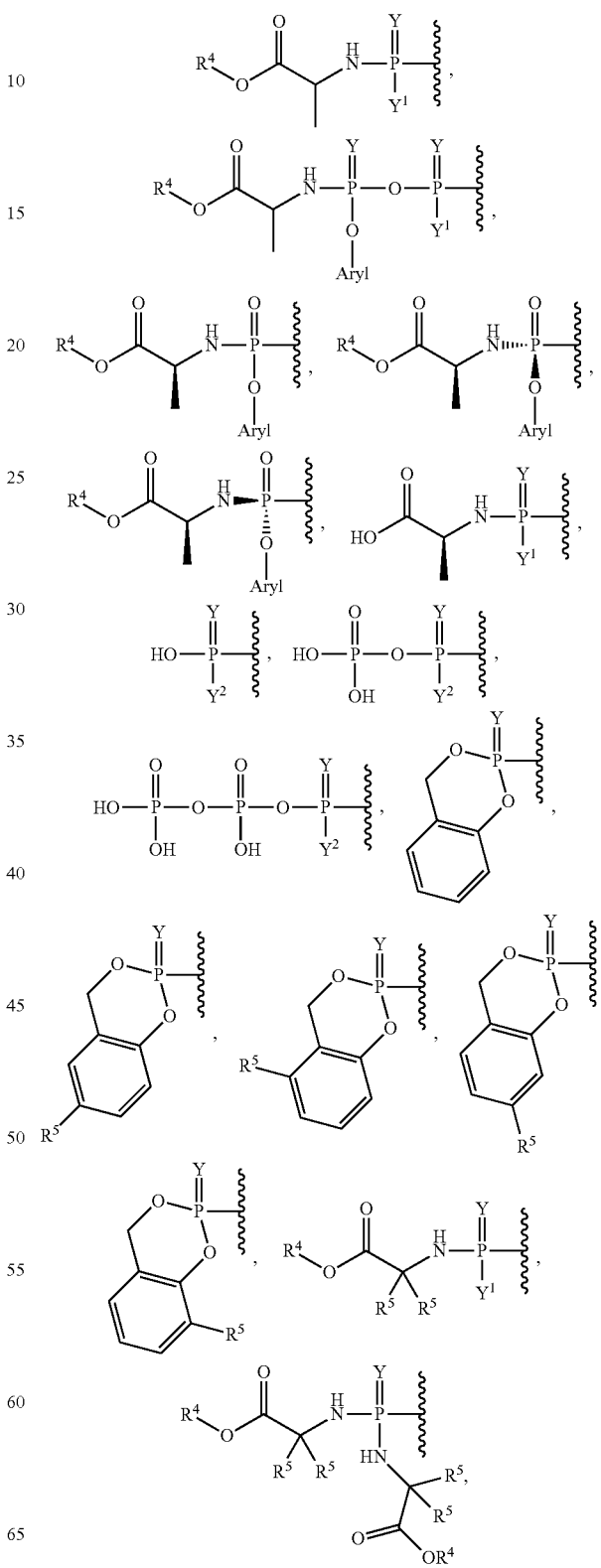

-continued

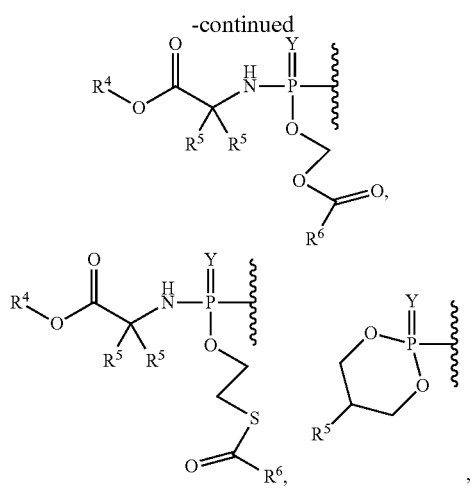

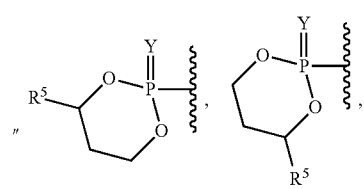

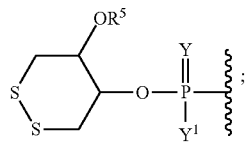

Y is O or S;
Y¹ is OH, OAryl, OAlkyl, or $BH_3^-M^+$;
Y² is OH or $BH_3^-M^+$;
Aryl is phenyl, 1-naphthyl, 2-naphthyl, aromatic, heteroaromatic, 4-substituted phenyl, 4-chlorophenyl, or 4-bromophenyl;
$R^4$ is hydrogen, methyl, ethyl, isopropyl, cyclopentyl, cyclohexyl, neopentyl, benzyl, alkyl, branched alkyl, cycloalkyl, or lipid;
$R^5$ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;
$R^6$ is methyl, ethyl, tert-butyl, $C_{1-22}$ alkoxy, $C_{1-22}$ alkyl, branched alkyl, cycloalkyl, aryl, substituted aryl, or alkyoxy;
$R^7$ is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano;
$R^8$ is D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano.

In certain embodiments, the present invention relates to compounds of the following formula:

Formula XXIX

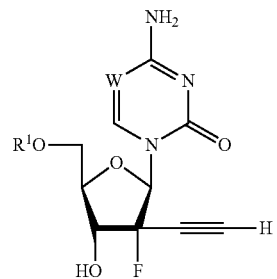

or pharmaceutically acceptable salts thereof wherein,
W is N or $CR^7$;
$R^1$ is selected from H or from one of the following formulae:

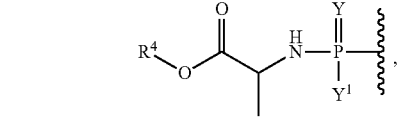

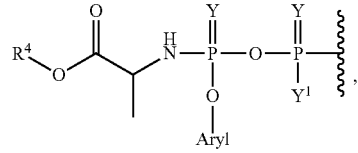

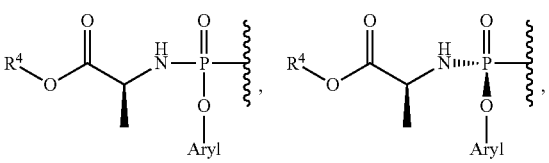

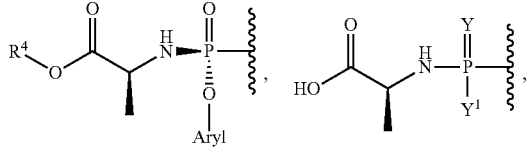

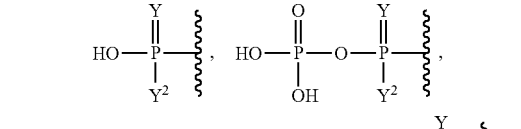

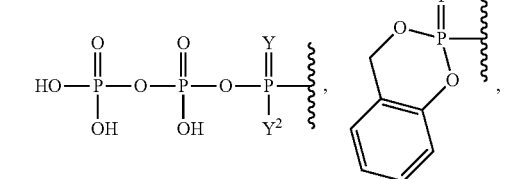

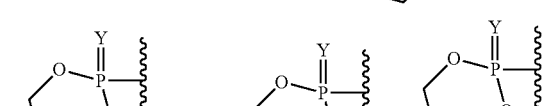

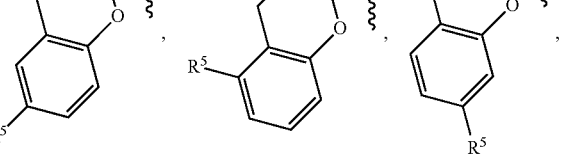

-continued

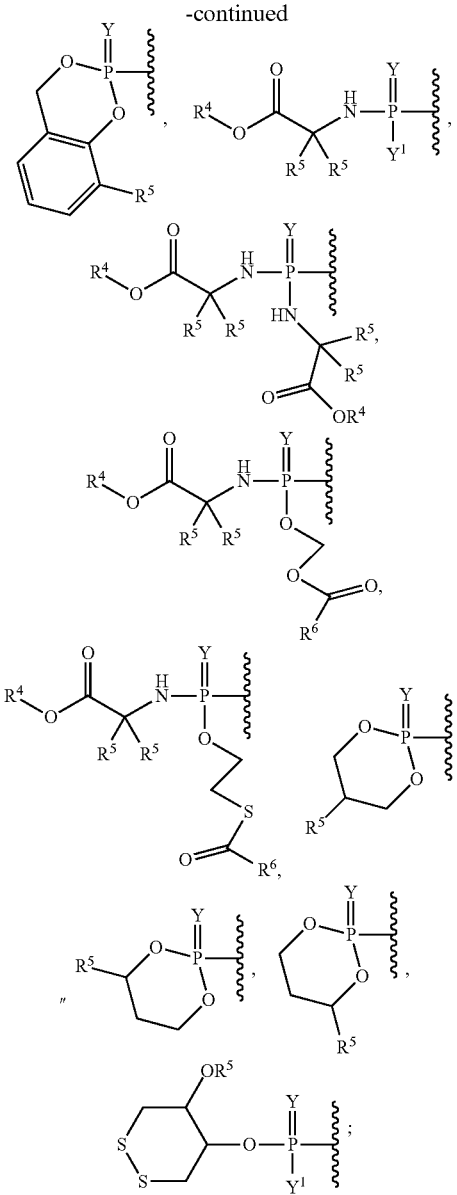

Y is O or S;
Y¹ is OAryl, OAlkyl, or $BH_3^-M^+$;
Y² is OH or $BH_3^-M^+$;
Aryl is phenyl, 1-naphthyl, 2-naphthyl, aromatic, heteroaromatic, 4-substituted phenyl, 4-chlorophenyl, or 4-bromophenyl;
$R^4$ is hydrogen, methyl, ethyl, isopropyl, cyclopentyl, cyclohexyl, neopentyl, benzyl, alkyl, branched alkyl, cycloalkyl, or lipid;
$R^5$ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;
$R^6$ is methyl, ethyl, tert-butyl, $C_{1-22}$ alkoxy, $C_{1-22}$ alkyl, branched alkyl, cycloalkyl, aryl, substituted aryl, or alkyoxy;
$R^7$ is D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano.

In certain embodiments, the present invention relates to compounds of the following formula:

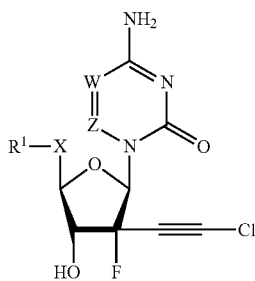

Formula XXX or pharmaceutically acceptable salts thereof wherein,
X is $OCMe_2$, OCHF, $OCF_2$, or $OCD_2$;
W is N or $CR^7$;
Z is N or $CR^8$;
$R^1$ is selected from H or from one of the following formulae:

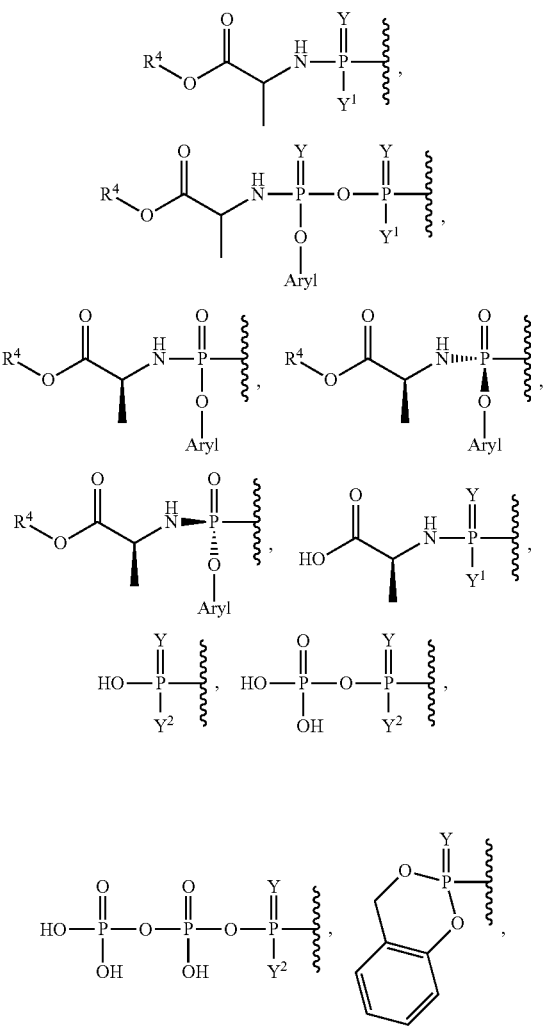

-continued

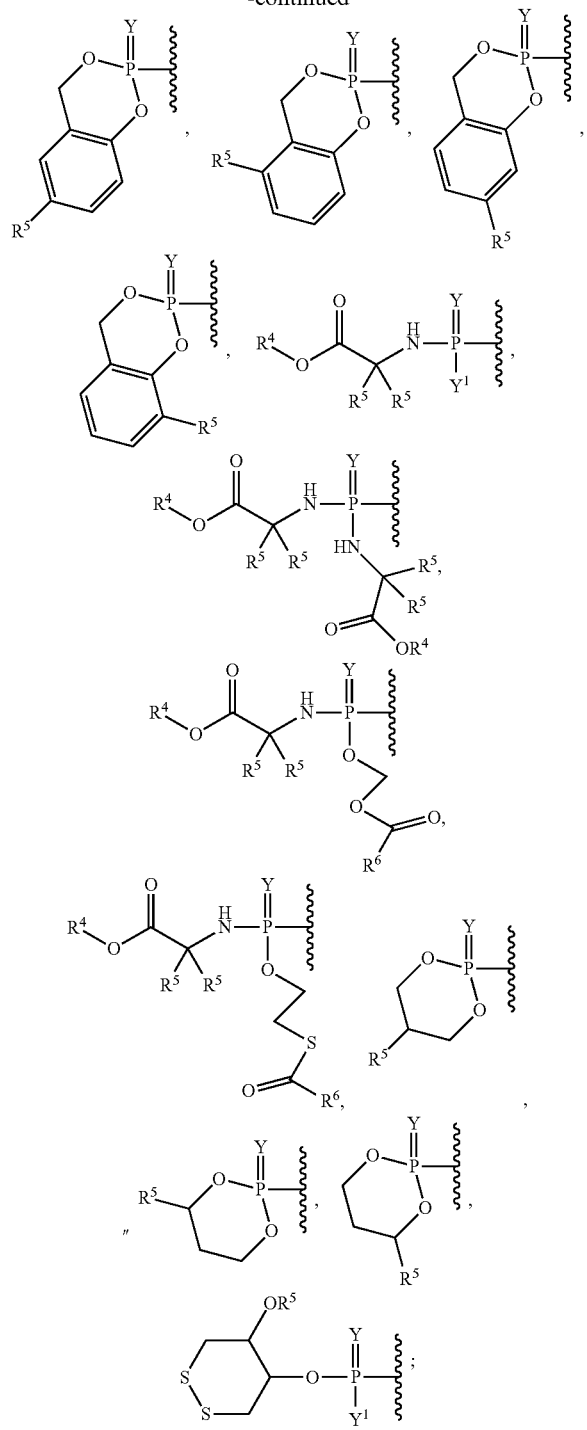

Y is O or S;
Y¹ is OH, OAryl, OAlkyl, or $BH_3^-M^+$;
Y² is OH or $BH_3^-M^+$;
Aryl is phenyl, 1-naphthyl, 2-naphthyl, aromatic, heteroaromatic, 4-substituted phenyl, 4-chlorophenyl, or 4-bromophenyl;
$R^4$ is hydrogen, methyl, ethyl, isopropyl, cyclopentyl, cyclohexyl, neopentyl, benzyl, alkyl, branched alkyl, cycloalkyl, or lipid;

$R^5$ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;

$R^6$ is methyl, ethyl, tert-butyl, $C_{1-22}$ alkoxy, $C_{1-22}$ alkyl, branched alkyl, cycloalkyl, aryl, substituted aryl, or alkyoxy;

$R^7$ is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano;

$R^8$ is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano.

In certain embodiments, the present invention relates to compounds of the following formula:

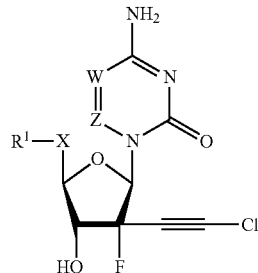

Formula XXXI or pharmaceutically acceptable salts thereof wherein,
X is OCHMe or $OCH_2$;
W is N or $CR^7$;
Z is N or $CR^8$;
$R^1$ is selected from H or from one of the following formulae:

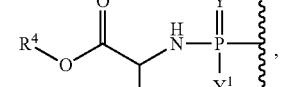

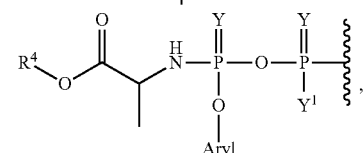

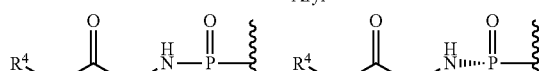

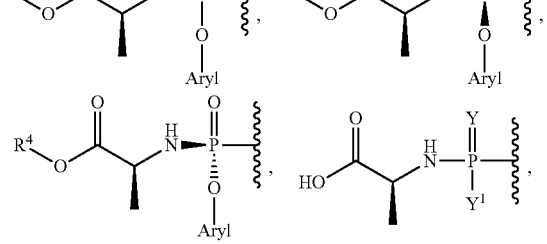

-continued

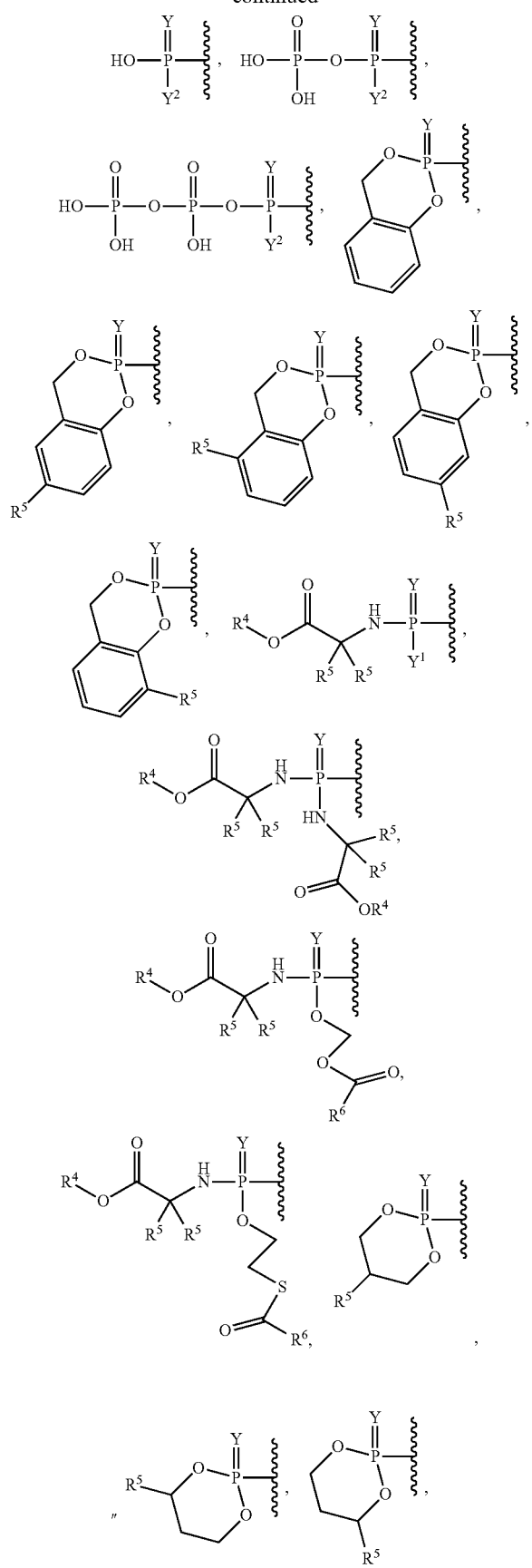

-continued

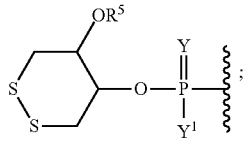

Y is O or S;

$Y^1$ is OH, OAryl, OAlkyl, or $BH_3^-M^+$;

$Y^2$ is OH or $BH_3^-M^+$;

Aryl is phenyl, 1-naphthyl, 2-naphthyl, aromatic, heteroaromatic, 4-substituted phenyl, 4-chlorophenyl, or 4-bromophenyl;

$R^4$ is hydrogen, methyl, ethyl, isopropyl, cyclopentyl, cyclohexyl, neopentyl, benzyl, alkyl, branched alkyl, cycloalkyl, or lipid;

$R^5$ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;

$R^6$ is methyl, ethyl, tert-butyl, $C_{1-22}$ alkoxy, $C_{1-22}$ alkyl, branched alkyl, cycloalkyl, aryl, substituted aryl, or alkyoxy;

$R^7$ is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano;

$R^8$ is D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano.

In certain embodiments, the present invention relates to compounds of the following Formula XXXIIa

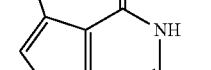

Formula XXXIIb

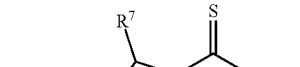

Formula XXXIIc

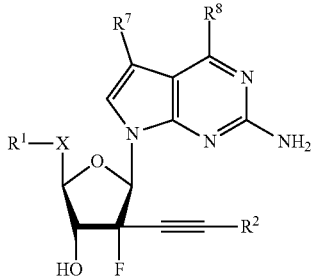

or pharmaceutically acceptable salts thereof wherein,

X is $OCH_2$, $OCHMe$, $OCMe_2$, $OCHF$, $OCF_2$, or $OCD_2$;

$R^1$ is selected from H or from one of the following formulae:

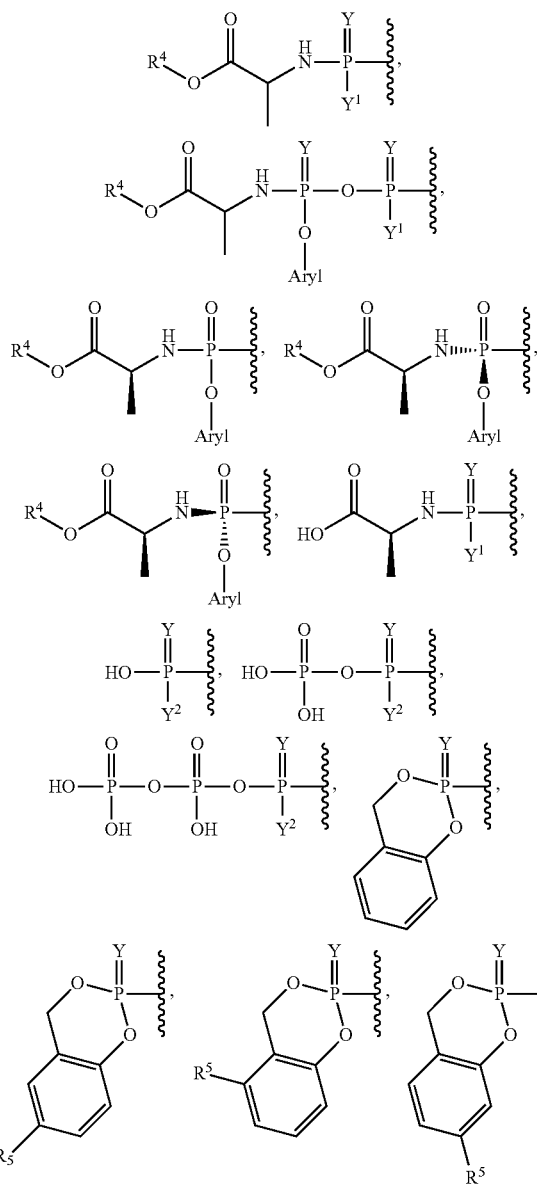

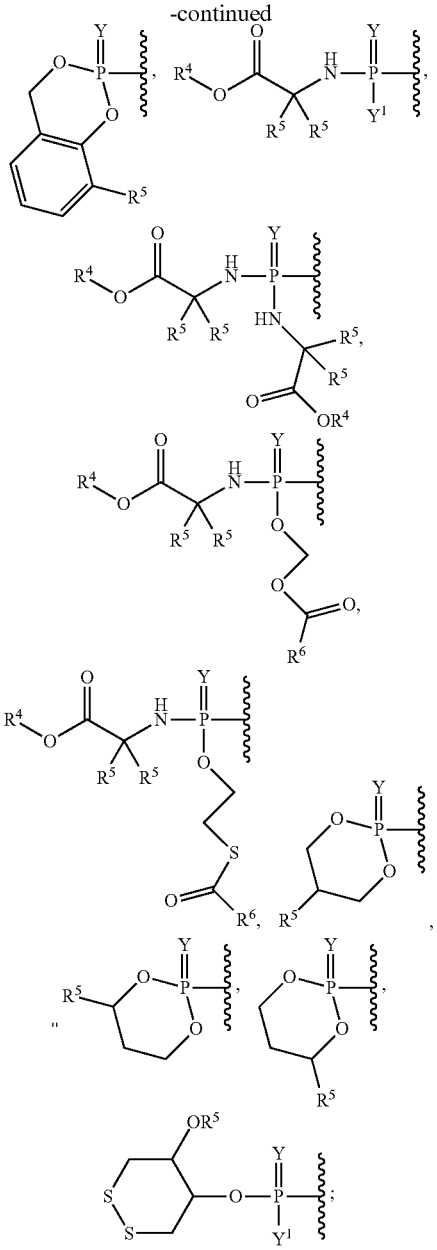

Y is O or S;
$Y^1$ is OH, OAryl, OAlkyl, or $BH_3^-M^+$;
$Y^2$ is OH or $BH_3^-M^+$;
Aryl is phenyl, 1-naphthyl, 2-naphthyl, aromatic, heteroaromatic, 4-substituted phenyl, 4-chlorophenyl, or 4-bromophenyl;
$R^2$ is hydrogen, methyl, fluoromethyl, difluoromethyl, trifluoromethyl, ethyl, cyclopropyl, fluoro, chloro, hydroxymethyl, aminomethyl, vinyl, or cyclobutyl;
$R^4$ is hydrogen, methyl, ethyl, isopropyl, cyclopentyl, cyclohexyl, neopentyl, benzyl, alkyl, branched alkyl, cycloalkyl, or lipid;
$R^5$ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;
$R^6$ is methyl, ethyl, tert-butyl, $C_{1-22}$ alkoxy, $C_{1-22}$ alkyl, branched alkyl, cycloalkyl, aryl, substituted aryl, or alkyoxy;

R[7] is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano;

R[8] is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, methoxy, ethoxy, alkoxy, substituted amino, or cyano.

In certain embodiments, the present invention relates to compounds of the following formula:

Formula XXXIIIa
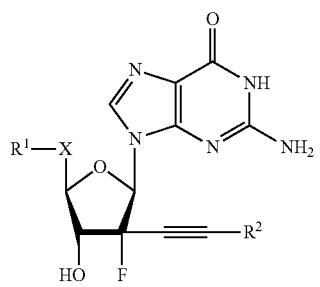

Formula XXXIIIb
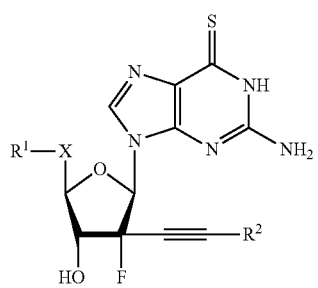

Formula XXXIIIc
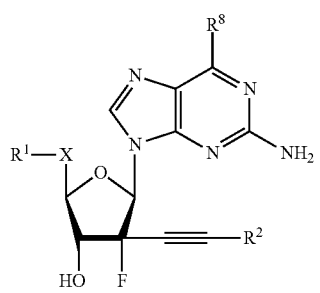

or pharmaceutically acceptable salts thereof wherein,

X is $OCH_2$, OCHMe, $OCMe_2$, OCHF, $OCF_2$, or $OCD_2$;

R[1] is selected from H or from one of the following formulae:

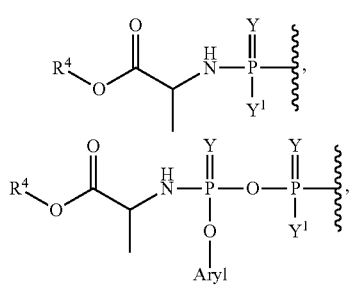

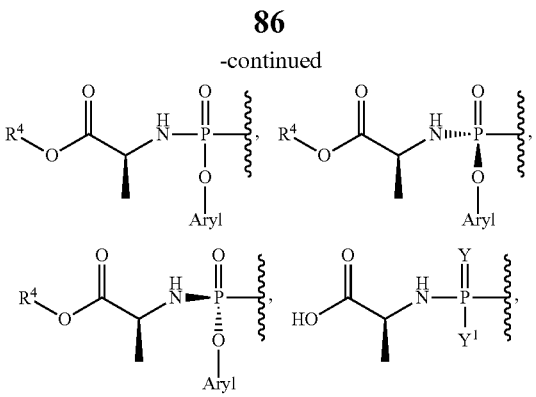

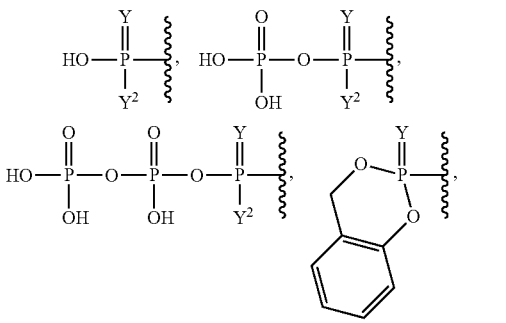

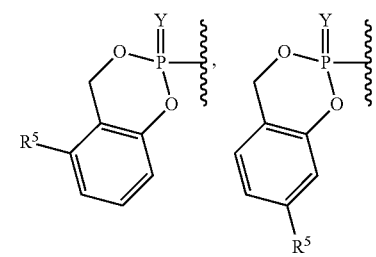

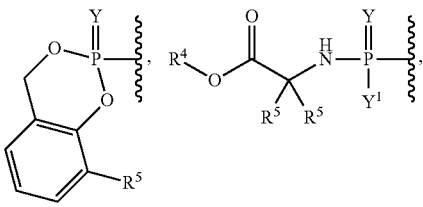

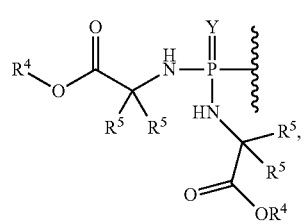

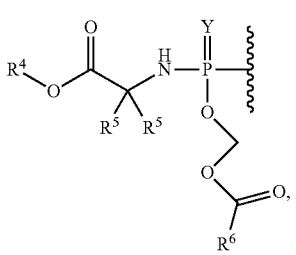

-continued

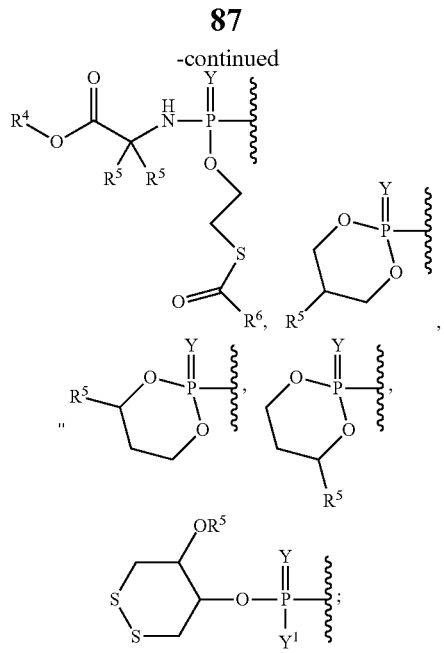

Y is O or S;
Y$^1$ is OH, OAryl, OAlkyl, or BH$_3^-$M$^+$;
Y$^2$ is OH or BH$_3^-$M$^+$;
Aryl is phenyl, 1-naphthyl, 2-naphthyl, aromatic, heteroaromatic, 4-substituted phenyl, 4-chlorophenyl, or 4-bromophenyl;
R$^2$ is methyl, fluoromethyl, difluoromethyl, trifluoromethyl, ethyl, cyclopropyl, fluoro, hydroxymethyl, aminomethyl, vinyl, or cyclobutyl;
R$^4$ is hydrogen, methyl, ethyl, isopropyl, cyclopentyl, cyclohexyl, neopentyl, benzyl, alkyl, branched alkyl, cycloalkyl, or lipid;
R$^5$ is hydrogen, deuterium, hydroxyl, cyano, azido, amino, substituted amino, aryl, heteroaryl, substituted aryl, lipid, C$_{1-22}$ alkoxy, C$_{1-22}$ alkyl, C$_{2-22}$ alkenyl, C$_{2-22}$ alkynyl, or substituted heteroaryl;
R$^6$ is methyl, ethyl, tert-butyl, C$_{1-22}$ alkoxy, C$_{1-22}$ alkyl, branched alkyl, cycloalkyl, aryl, substituted aryl, or alkyoxy;
R$^8$ is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, methoxy, ethoxy, alkoxy, substituted amino, or cyano.

In certain embodiments, the present invention relates to compounds of the following formula:

Formula XXXIVa

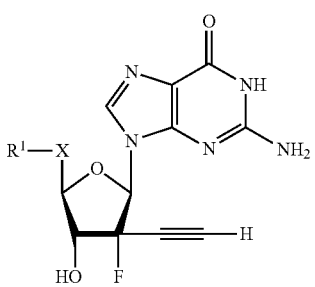

Formula XXXIVb

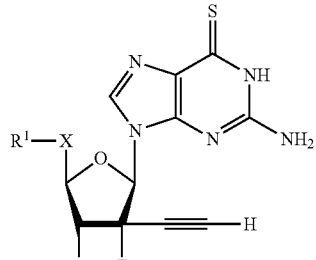

Formula XXXIVc

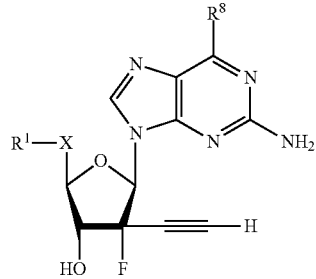

or pharmaceutically acceptable salts thereof wherein,
X is OCHMe, OCMe$_2$, OCHF, OCF$_2$, or OCD$_2$;
R$^1$ is selected from H or from one of the following formulae:

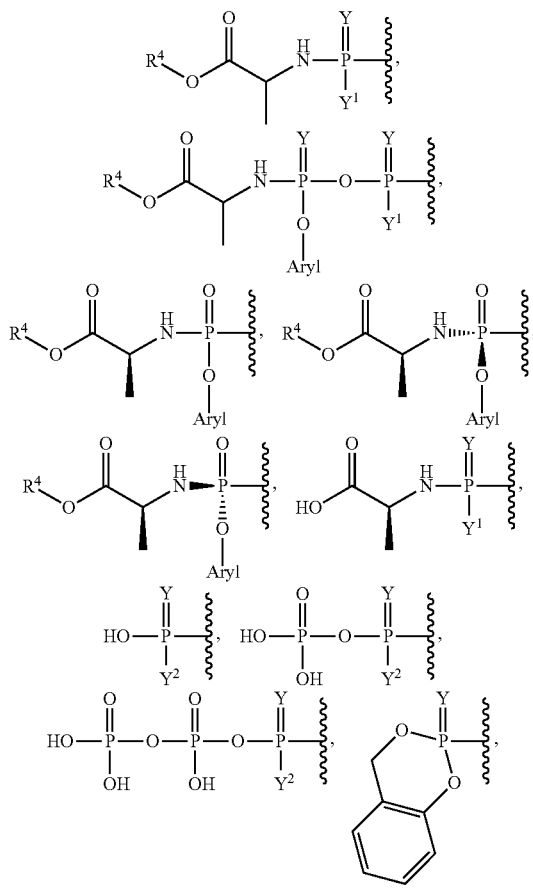

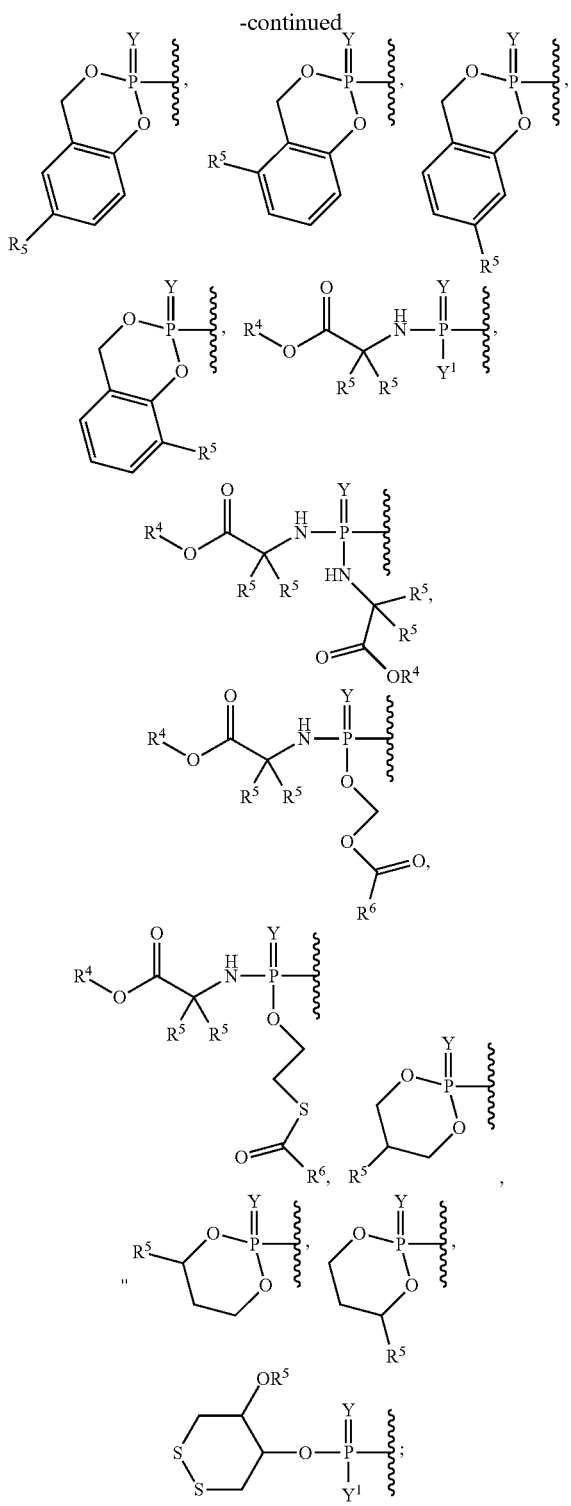

Y is O or S;
Y¹ is OH, OAryl, OAlkyl, or $BH_3^-M^+$;
Y² is OH or $BH_3^-M^+$;
Aryl is phenyl, 1-naphthyl, 2-naphthyl, aromatic, heteroaromatic, 4-substituted phenyl, 4-chlorophenyl, or 4-bromophenyl;
$R^4$ is hydrogen, methyl, ethyl, isopropyl, cyclopentyl, cyclohexyl, neopentyl, benzyl, alkyl, branched alkyl, cycloalkyl, or lipid;

$R^5$ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;
$R^6$ is methyl, ethyl, tert-butyl, $C_{1-22}$ alkoxy, $C_{1-22}$ alkyl, branched alkyl, cycloalkyl, aryl, substituted aryl, or alkyoxy;
$R^8$ is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, methoxy, ethoxy, alkoxy, substituted amino, or cyano.

In certain embodiments, the present invention relates to compounds of the following formula:

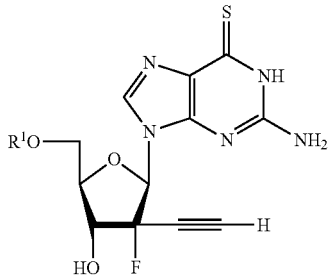

Formula XXXVa

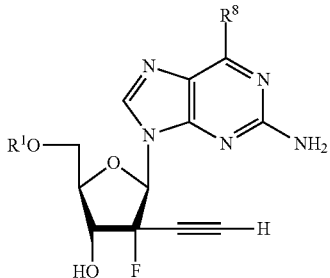

Formula XXXVb or pharmaceutically acceptable salts thereof wherein,
R¹ is selected from H or from one of the following formulae:

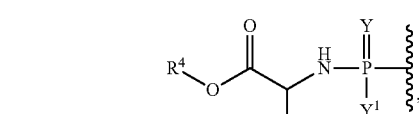

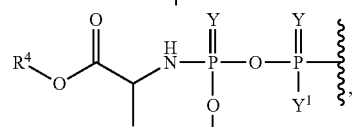

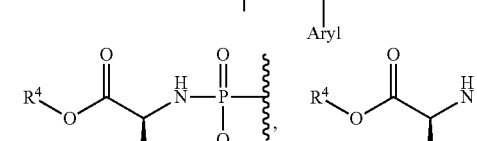


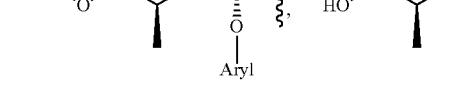

-continued

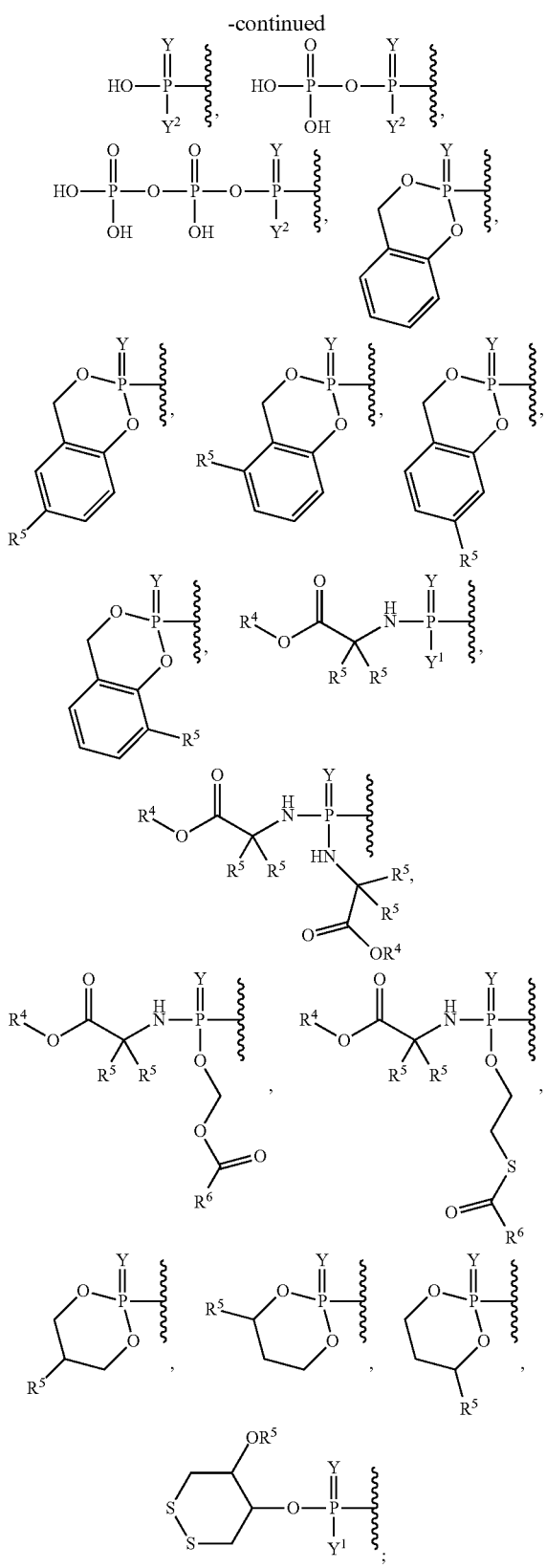

Y is O or S;
Y$^1$ is OH, OAryl, OAlkyl, or BH$_3^-$M$^+$;
Y$^2$ is OH or BH$_3^-$M$^+$;

Aryl is phenyl, 1-naphthyl, 2-naphthyl, aromatic, heteroaromatic, 4-substituted phenyl, 4-chlorophenyl, or 4-bromophenyl;
R$^4$ is hydrogen, methyl, ethyl, isopropyl, cyclopentyl, cyclohexyl, neopentyl, benzyl, alkyl, branched alkyl, cycloalkyl, or lipid;
R$^5$ is hydrogen, deuterium, hydroxyl, cyano, azido, amino, substituted amino, aryl, heteroaryl, substituted aryl, lipid, C$_{1-22}$ alkoxy, C$_{1-22}$ alkyl, C$_{2-22}$ alkenyl, C$_{2-22}$ alkynyl, or substituted heteroaryl;
R$^6$ is methyl, ethyl, tert-butyl, C$_{1-22}$ alkoxy, C$_{1-22}$ alkyl, branched alkyl, cycloalkyl, aryl, substituted aryl, or alkyoxy;
R$^8$ is H, D, thiol, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, or cyano.

In certain embodiments, the present invention relates to compounds of the following formula:

Formula XXXVIa
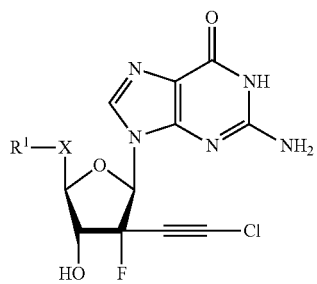

Formula XXXVIb
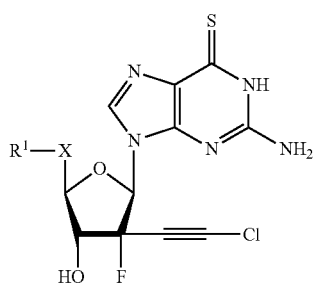

Formula XXXVIc
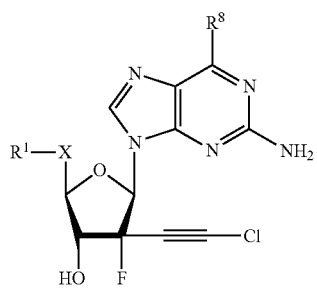

or pharmaceutically acceptable salts thereof wherein,
X is OCMe$_2$, OCHF, OCF$_2$, or OCD$_2$;
R$^1$ is selected from H or from one of the following formulae:

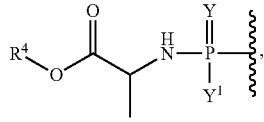

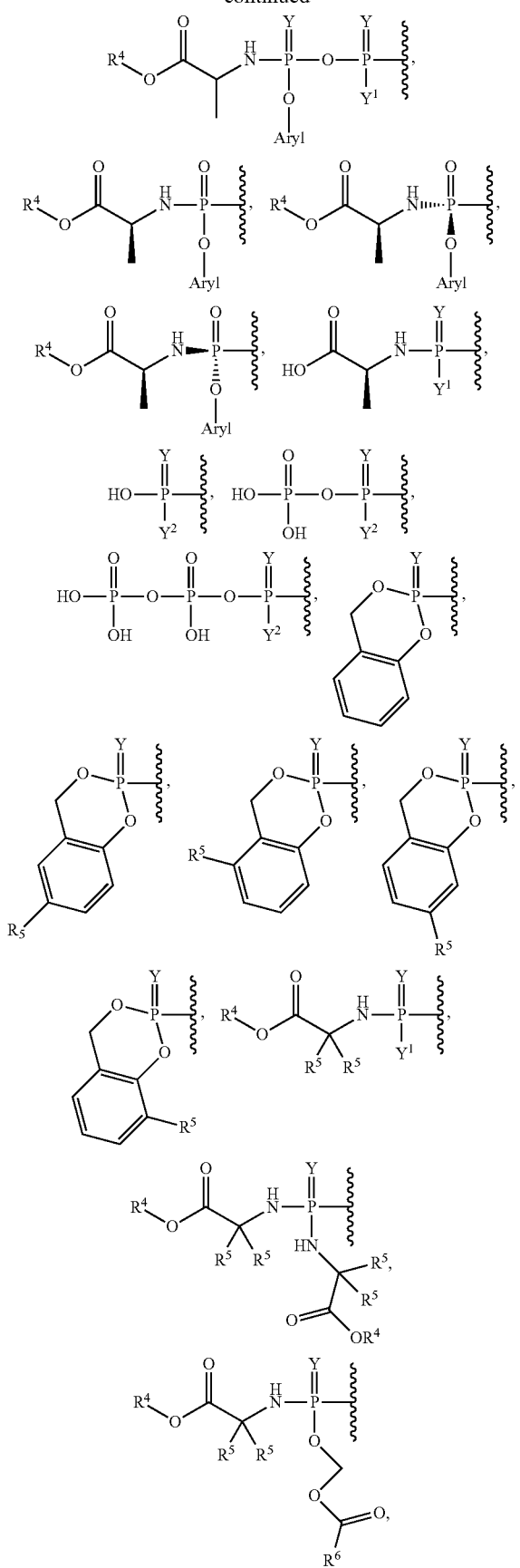

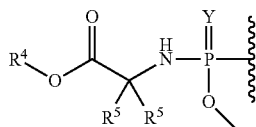

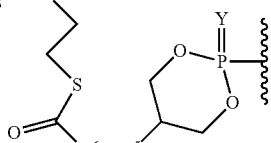

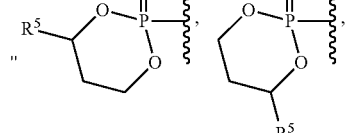

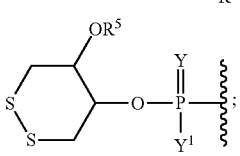

Y is O or S;

$Y^1$ is OH, OAryl, OAlkyl, or $BH_3^-M^+$;

$Y^2$ is OH or $BH_3^-M^+$;

Aryl is phenyl, 1-naphthyl, 2-naphthyl, aromatic, heteroaromatic, 4-substituted phenyl, 4-chlorophenyl, or 4-bromophenyl;

$R^4$ is hydrogen, methyl, ethyl, isopropyl, cyclopentyl, cyclohexyl, neopentyl, benzyl, alkyl, branched alkyl, cycloalkyl, or lipid;

$R^5$ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;

$R^6$ is methyl, ethyl, tert-butyl, $C_{1-22}$ alkoxy, $C_{1-22}$ alkyl, branched alkyl, cycloalkyl, aryl, substituted aryl, or alkyoxy;

$R^8$ is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, methoxy, ethoxy, alkoxy, substituted amino, or cyano.

In certain embodiments, the present invention relates to compounds of the following formula:

Formula XXXVIIa

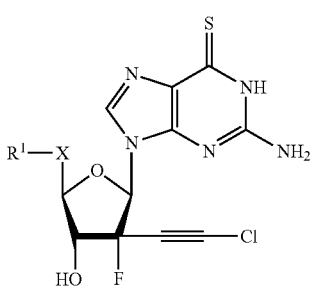

Formula XXXVIIb

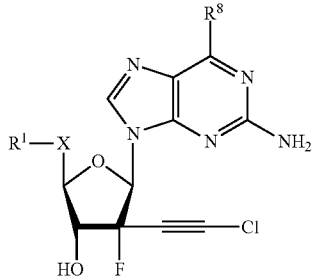

or pharmaceutically acceptable salts thereof wherein,

X is OCH$_2$ or OCHMe;

R$^1$ is selected from H or from one of the following formulae:

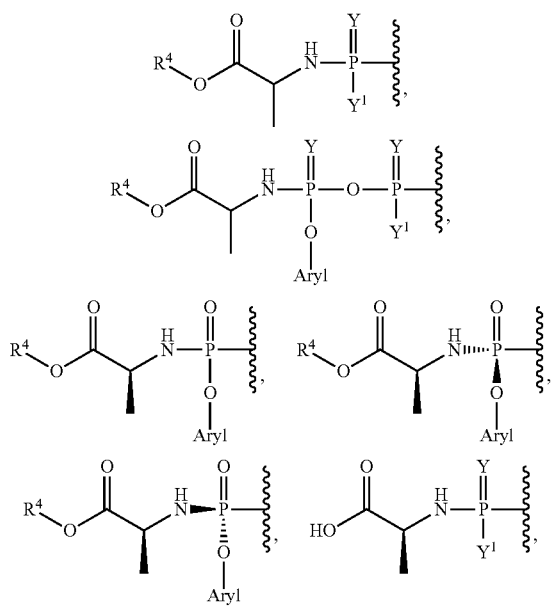

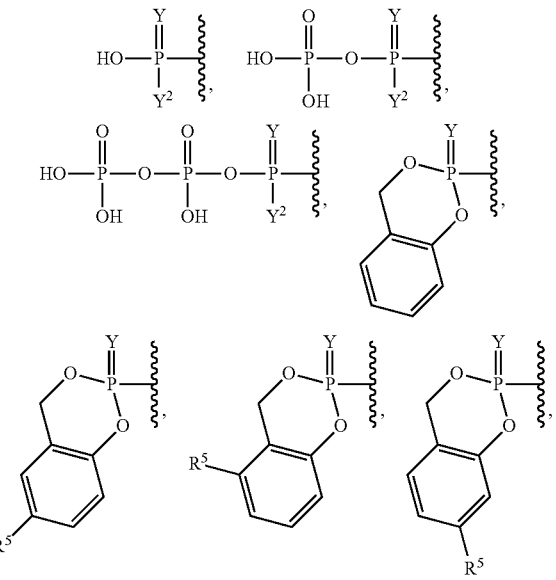

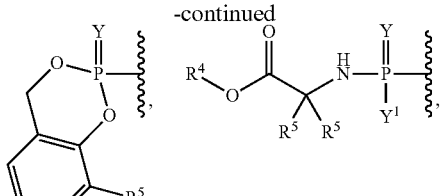

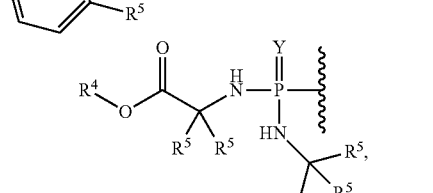

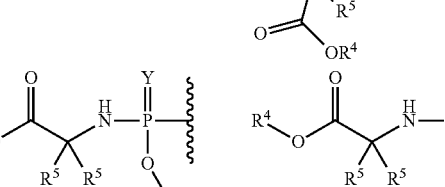

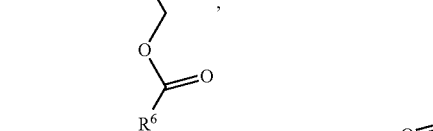

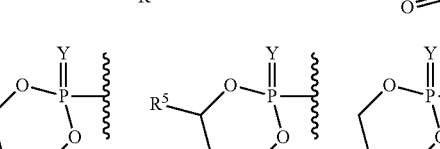

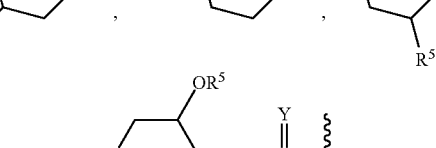

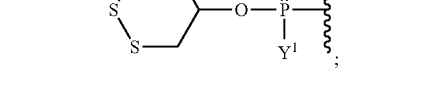

Y is O or S;

Y$^1$ is OH, OAryl, OAlkyl, or BH$_3^-$M$^+$;

Y$^2$ is OH or BH$_3^-$M$^+$;

Aryl is phenyl, 1-naphthyl, 2-naphthyl, aromatic, heteroaromatic, 4-substituted phenyl, 4-chlorophenyl, or 4-bromophenyl;

R$^4$ is hydrogen, methyl, ethyl, isopropyl, cyclopentyl, cyclohexyl, neopentyl, benzyl, alkyl, branched alkyl, cycloalkyl, or lipid;

R$^5$ is hydrogen, deuterium, hydroxyl, cyano, azido, amino, substituted amino, aryl, heteroaryl, substituted aryl, lipid, C$_{1-22}$ alkoxy, C$_{1-22}$ alkyl, C$_{2-22}$ alkenyl, C$_{2-22}$ alkynyl, or substituted heteroaryl;

R$^6$ is methyl, ethyl, tert-butyl, C$_{1-22}$ alkoxy, C$_{1-22}$ alkyl, branched alkyl, cycloalkyl, aryl, substituted aryl, or alkyoxy;

R$^8$ is H, D, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, substituted amino, or cyano.

In certain embodiments, the present invention relates to compounds of the following formula:

Formula XXXVIII

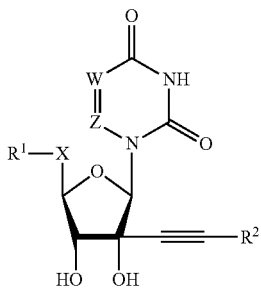

or pharmaceutically acceptable salts thereof wherein,

X is $OCH_2$, OCHMe, $OCMe_2$, OCHF, $OCF_2$, or $OCD_2$;

W is N or $CR^7$;

Z is N or $CR^8$;

$R^1$ is selected from H or from one of the following formulae:

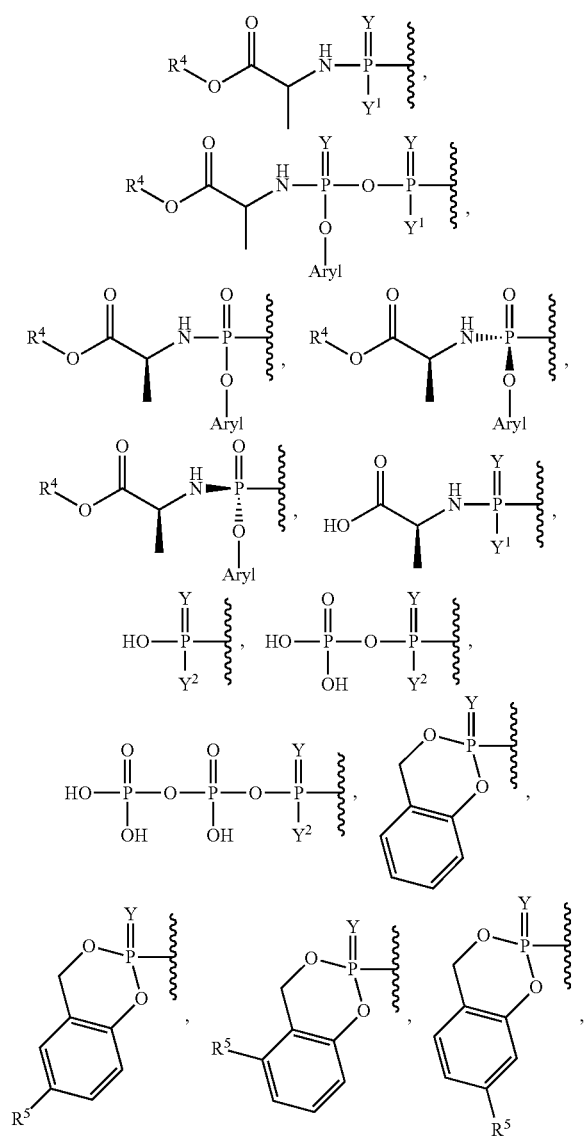

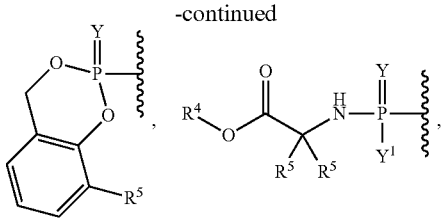

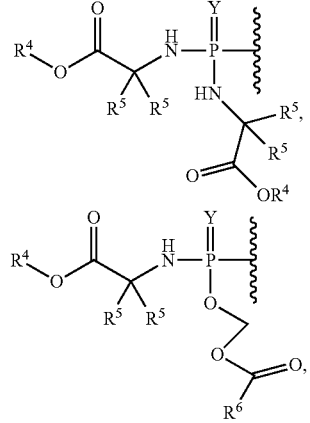

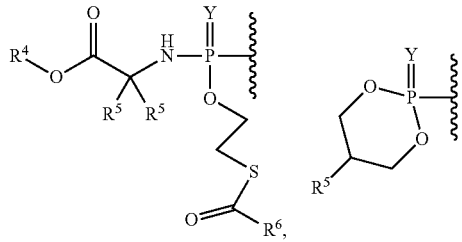

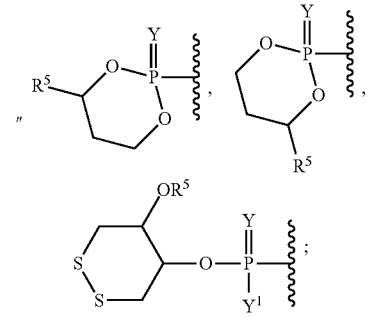

Y is O or S;

$Y^1$ is OH, OAryl, OAlkyl, or $BH_3^-M^+$;

$Y^2$ is OH or $BH_3^-M^+$;

Aryl is phenyl, 1-naphthyl, 2-naphthyl, aromatic, heteroaromatic, 4-substituted phenyl, 4-chlorophenyl, or 4-bromophenyl;

$R^2$ is hydrogen, methyl, fluoromethyl, difluoromethyl, trifluoromethyl, ethyl, cyclopropyl, fluoro, chloro, hydroxymethyl, aminomethyl, vinyl, or cyclobutyl;

$R^4$ is hydrogen, methyl, ethyl, isopropyl, cyclopentyl, cyclohexyl, neopentyl, benzyl, alkyl, branched alkyl, cycloalkyl, or lipid;

$R^5$ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;

$R^6$ is methyl, ethyl, tert-butyl, $C_{1-22}$ alkoxy, $C_{1-22}$ alkyl, branched alkyl, cycloalkyl, aryl, substituted aryl, or alkyoxy;

$R^7$ is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano;

R[8] is D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano.

In certain embodiments, the present invention relates to compounds of the following formula:

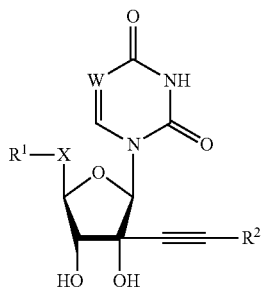

Formula XXXIX or pharmaceutically acceptable salts thereof wherein,

X is $OCH_2$, OCHMe, $OCMe_2$, OCHF, $OCF_2$, or $OCD_2$;

W is N or CR[7];

R[1] is selected from H or from one of the following formulae:

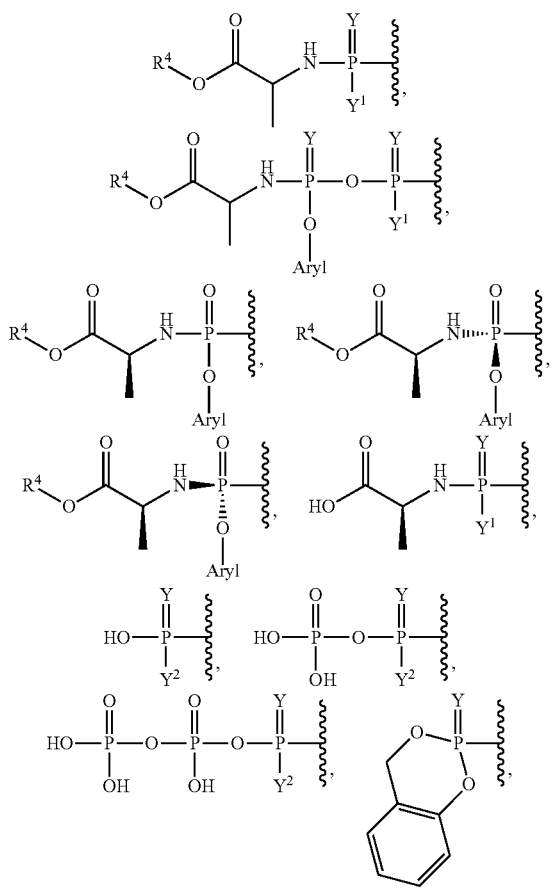

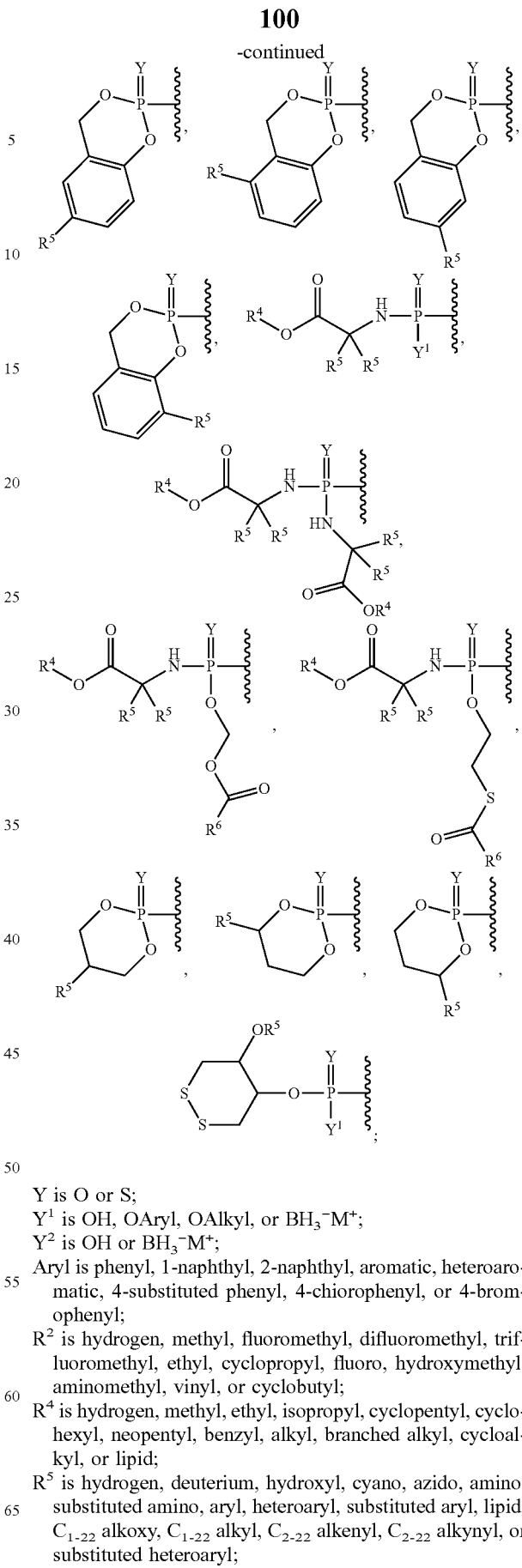

Y is O or S;

Y[1] is OH, OAryl, OAlkyl, or $BH_3^-M^+$;

Y[2] is OH or $BH_3^-M^+$;

Aryl is phenyl, 1-naphthyl, 2-naphthyl, aromatic, heteroaromatic, 4-substituted phenyl, 4-chiorophenyl, or 4-bromophenyl;

R[2] is hydrogen, methyl, fluoromethyl, difluoromethyl, trifluoromethyl, ethyl, cyclopropyl, fluoro, hydroxymethyl, aminomethyl, vinyl, or cyclobutyl;

R[4] is hydrogen, methyl, ethyl, isopropyl, cyclopentyl, cyclohexyl, neopentyl, benzyl, alkyl, branched alkyl, cycloalkyl, or lipid;

R[5] is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;

R⁶ is methyl, ethyl, tert-butyl, $C_{1-22}$ alkoxy, $C_{1-22}$ alkyl, branched alkyl, cycloalkyl, aryl, substituted aryl, or alkyoxy;

R⁷ is D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano.

In certain embodiments, the present invention relates to compounds of the following formula:

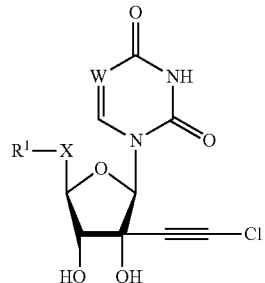

Formula XL or pharmaceutically acceptable salts thereof wherein,

X is $OCMe_2$, OCHF, $OCF_2$, or $OCD_2$;

W is N or $CR^7$;

R¹ is selected from H or from one of the following formulae:

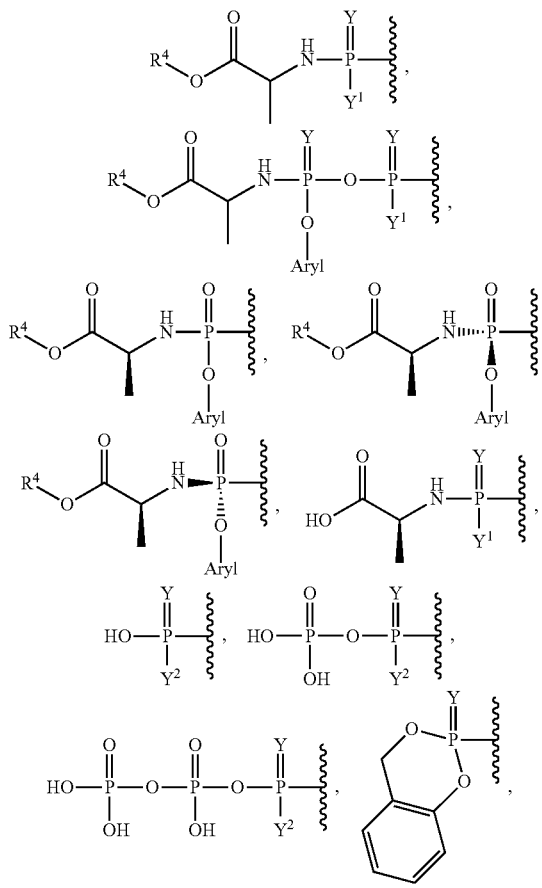

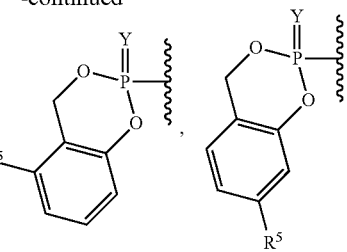

-continued

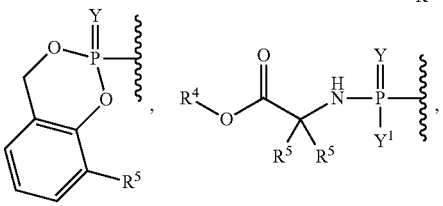

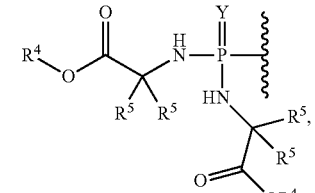

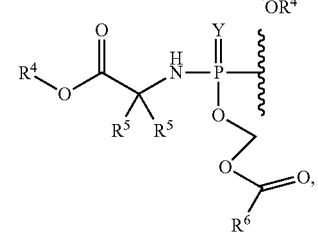

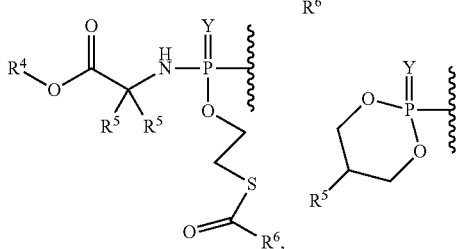

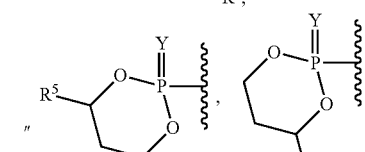

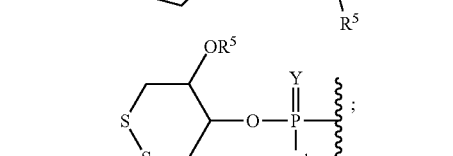

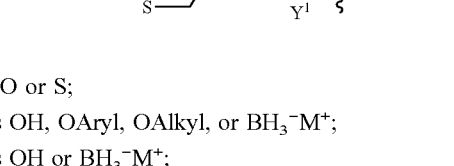

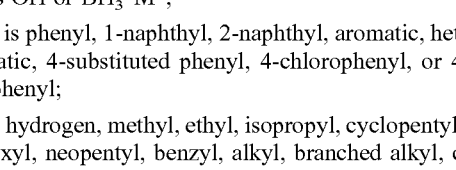

Y is O or S;

Y¹ is OH, OAryl, OAlkyl, or $BH_3^-M^+$;

Y² is OH or $BH_3^-M^+$;

Aryl is phenyl, 1-naphthyl, 2-naphthyl, aromatic, heteroaromatic, 4-substituted phenyl, 4-chlorophenyl, or 4-bromophenyl;

R⁴ is hydrogen, methyl, ethyl, isopropyl, cyclopentyl, cyclohexyl, neopentyl, benzyl, alkyl, branched alkyl, cycloalkyl, or lipid;

103

R⁵ is hydrogen, deuterium, hydroxyl, cyano, azido, amino, substituted amino, aryl, heteroaryl, substituted aryl, lipid, C$_{1-22}$ alkoxy, C$_{1-22}$ alkyl, C$_{2-22}$ alkenyl, C$_{2-22}$ alkynyl, or substituted heteroaryl;

R⁶ is methyl, ethyl, tert-butyl, C$_{1-22}$ alkoxy, C$_{1-22}$ alkyl, branched alkyl, cycloalkyl, aryl, substituted aryl, or alkyoxy;

R⁷ is D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano.

In certain embodiments, the present invention relates to compounds of the following formula:

Formula XLI

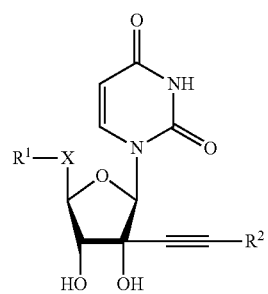

or pharmaceutically acceptable salts thereof wherein,

X is OCMe₂, OCHF, OCF₂, or OCD₂;

R¹ is selected from H or from one of the following formulae:

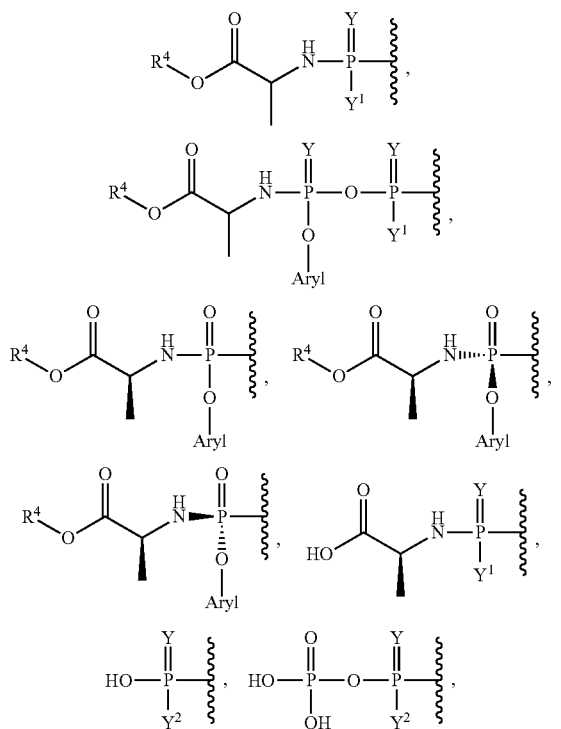

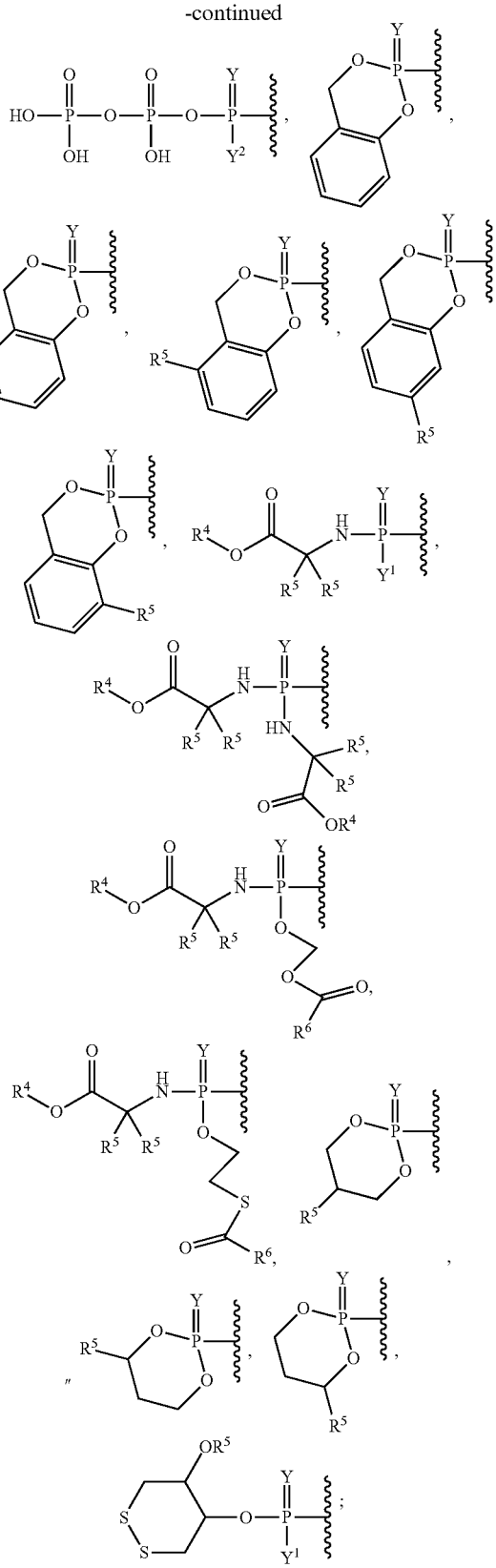

Y is O or S;
Y¹ is OH, OAryl, OAlkyl, or BH₃⁻M⁺;
Y² is OH or BH₃⁻M⁺;

Aryl is phenyl, 1-naphthyl, 2-naphthyl, aromatic, heteroaromatic, 4-substituted phenyl, 4-chlorophenyl, or 4-bromophenyl;

$R^2$ is hydrogen, methyl, fluoromethyl, difluoromethyl, trifluoromethyl, ethyl, cyclopropyl, fluoro, chloro, hydroxymethyl, aminomethyl, vinyl, or cyclobutyl;

$R^4$ is hydrogen, methyl, ethyl, isopropyl, cyclopentyl, cyclohexyl, neopentyl, benzyl, alkyl, branched alkyl, cycloalkyl, or lipid;

$R^5$ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;

$R^6$ is methyl, ethyl, tert-butyl, $C_{1-22}$ alkoxy, $C_{1-22}$ alkyl, branched alkyl, cycloalkyl, aryl, substituted aryl, or alkyoxy.

In certain embodiments, the present invention relates to compounds of the following formula:

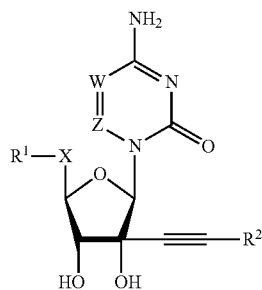

Formula XLII or pharmaceutically acceptable salts thereof wherein,

X is $OCH_2$, OCHMe, $OCMe_2$, OCHF, $OCF_2$, or $OCD_2$;
W is N or $CR^7$;
Z is N or $CR^8$;
$R^1$ is selected from H or from one of the following formulae:

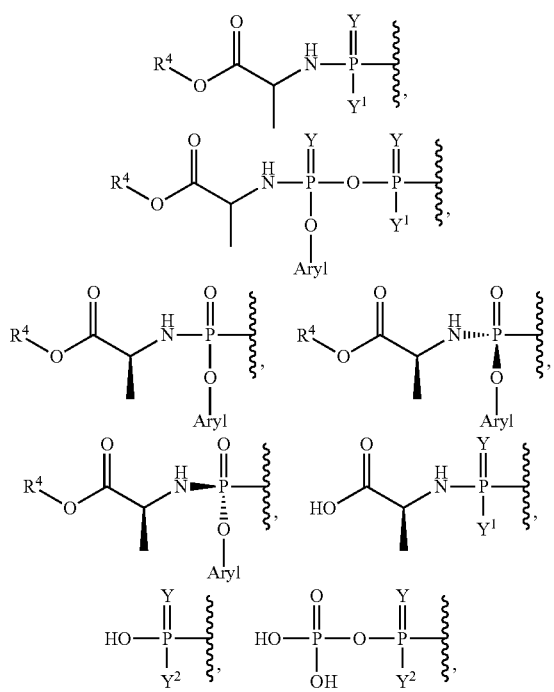

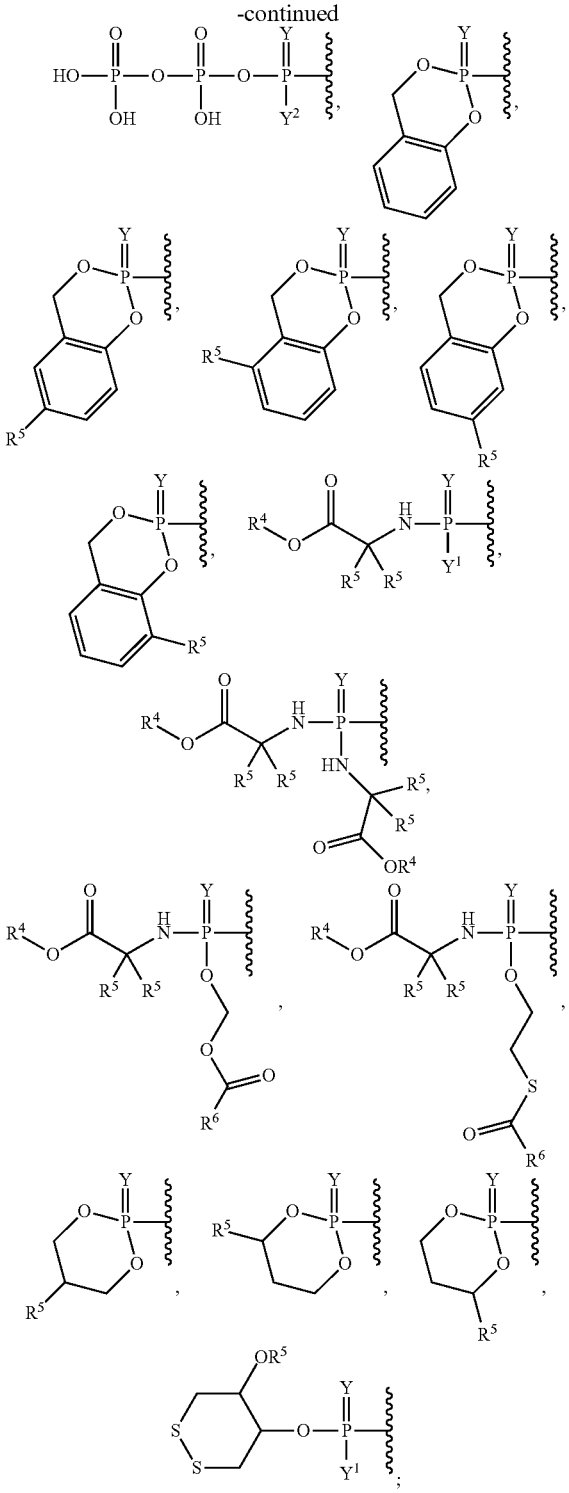

Y is O or S;
$Y^1$ is OH, OAryl, OAlkyl, or $BH_3^-M^+$;
$Y^2$ is OH or $BH_3^-M^+$;
Aryl is phenyl, 1-naphthyl, 2-naphthyl, aromatic, heteroaromatic, 4-substituted phenyl, 4-chlorophenyl, or 4-bromophenyl;
$R^2$ is hydrogen, methyl, fluoromethyl, difluoromethyl, trifluoromethyl, ethyl, cyclopropyl, fluoro, hydroxymethyl, aminomethyl, vinyl, or cyclobutyl;

R[4] is hydrogen, methyl, ethyl, isopropyl, cyclopentyl, cyclohexyl, neopentyl, benzyl, alkyl, branched alkyl, cycloalkyl, or lipid;

R[5] is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;

R[6] is methyl, ethyl, tert-butyl, $C_{1-22}$ alkoxy, $C_{1-22}$ alkyl, branched alkyl, cycloalkyl, aryl, substituted aryl, or alkyoxy;

R[7] is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano;

R[8] is D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano.

In certain embodiments, the present invention relates to compounds of the following formula:

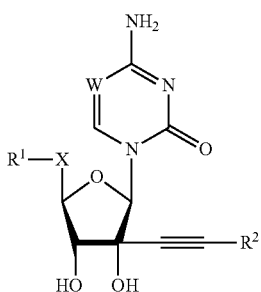

Formula XLIII or pharmaceutically acceptable salts thereof wherein,

X is $OCH_2$, OCHMe, $OCMe_2$, OCHF, $OCF_2$, or $OCD_2$;

W is N or CR[7];

R[1] is selected from H or from one of the following formulae:

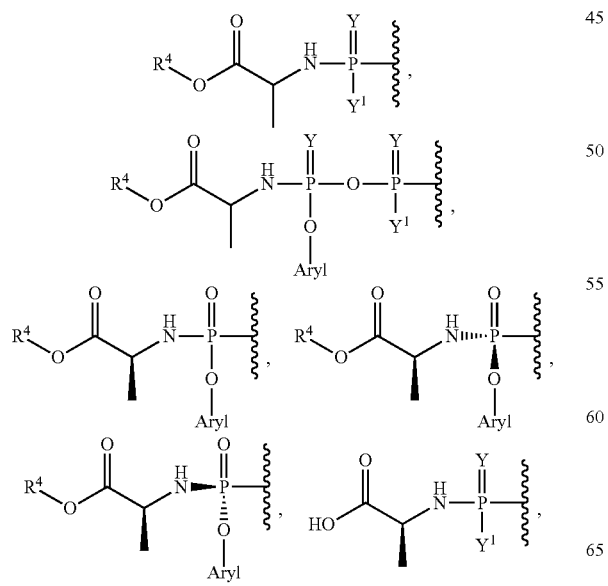

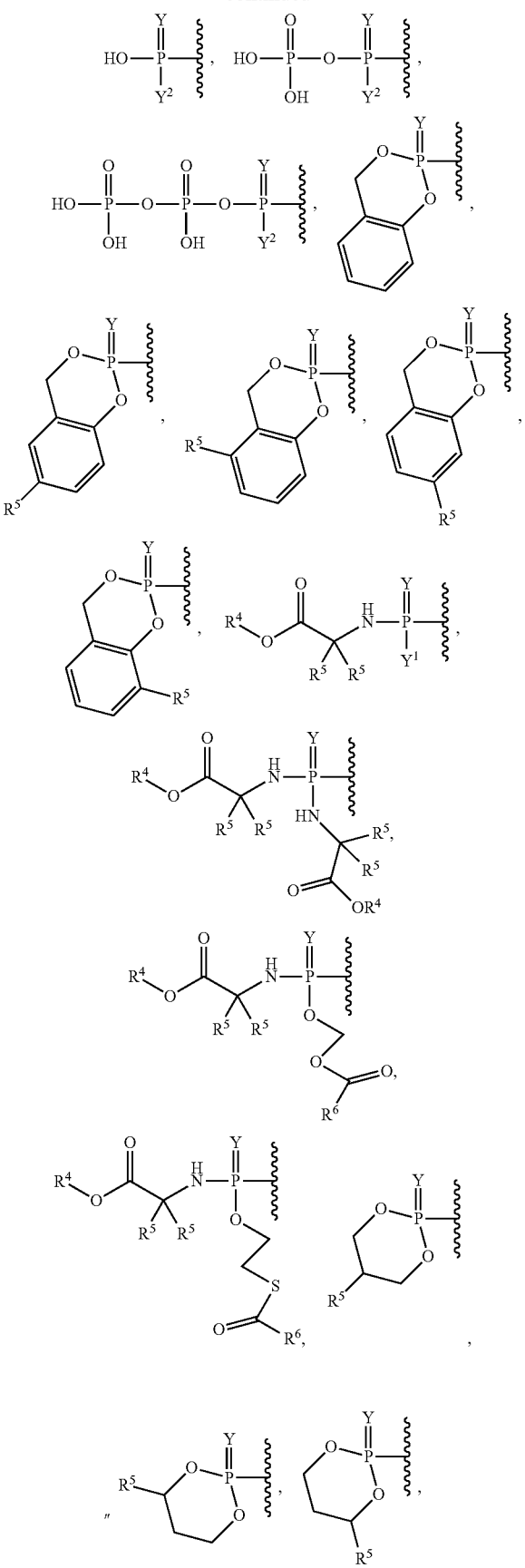

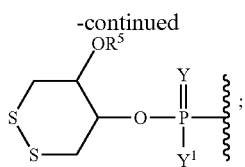

Y is O or S;
Y¹ is OH, OAryl, OAlkyl, or $BH_3^-M^+$;
Y² is OH or $BH_3^-M^+$;
Aryl is phenyl, 1-naphthyl, 2-naphthyl, aromatic, heteroaromatic, 4-substituted phenyl, 4-chlorophenyl, or 4-bromophenyl;
$R^2$ is hydrogen, methyl, fluoromethyl, difluoromethyl, trifluoromethyl, ethyl, cyclopropyl, fluoro, hydroxymethyl, aminomethyl, vinyl, or cyclobutyl;
$R^4$ is hydrogen, methyl, ethyl, isopropyl, cyclopentyl, cyclohexyl, neopentyl, benzyl, alkyl, branched alkyl, cycloalkyl, or lipid;
$R^5$ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;
$R^6$ is methyl, ethyl, tert-butyl, $C_{1-22}$ alkoxy, $C_{1-22}$ alkyl, branched alkyl, cycloalkyl, aryl, substituted aryl, or alkyoxy;
$R^7$ is D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano.

In certain embodiments, the present invention relates to compounds of the following formula:

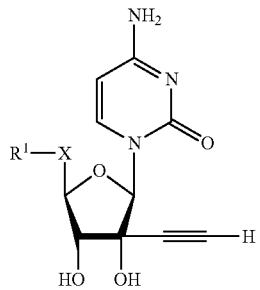

Formula XLIV or pharmaceutically acceptable salts thereof wherein,
X is $OCHMe$, $OCMe_2$, $OCHF$, $OCF_2$, or $OCD_2$;
$R^1$ is selected from H or from one of the following formulae:

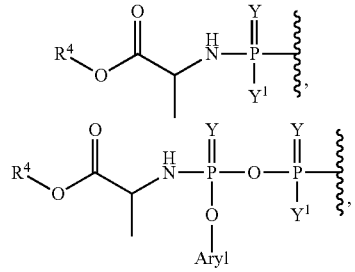

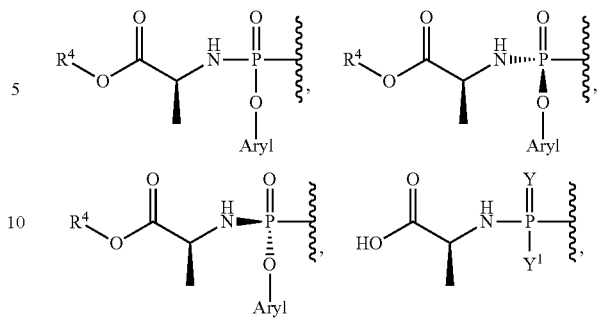

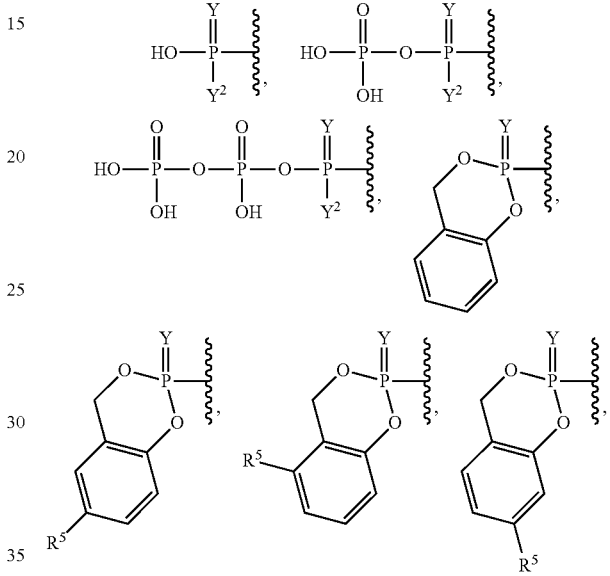

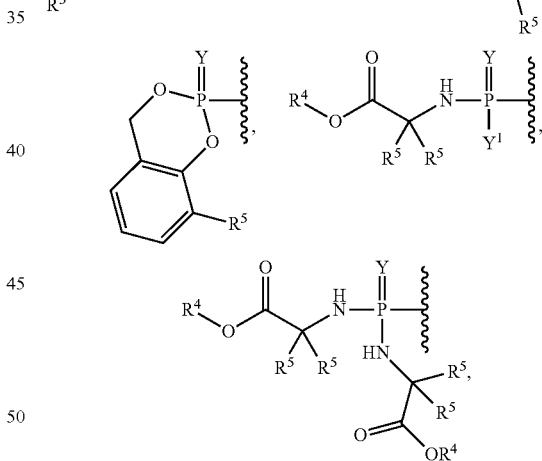

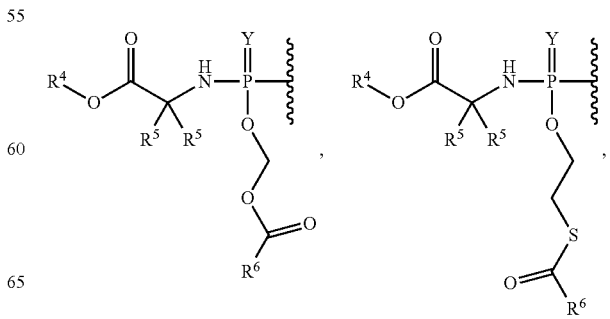

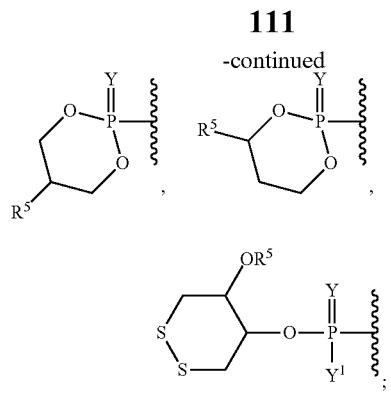

Y is O or S;
Y¹ is OH, OAryl, OAlkyl, or $BH_3^-M^+$;
Y² is OH or $BH_3^-M^+$;
Aryl is phenyl, 1-naphthyl, 2-naphthyl, aromatic, heteroaromatic, 4-substituted phenyl, 4-chlorophenyl, or 4-bromophenyl;
R⁴ is hydrogen, methyl, ethyl, isopropyl, cyclopentyl, cyclohexyl, neopentyl, benzyl, alkyl, branched alkyl, cycloalkyl, or lipid;
R⁵ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;
R⁶ is methyl, ethyl, tert-butyl, $C_{1-22}$ alkoxy, $C_{1-22}$ alkyl, branched alkyl, cycloalkyl, aryl, substituted aryl, or alkyoxy.

In certain embodiments, the present invention relates to compounds of the following formula:

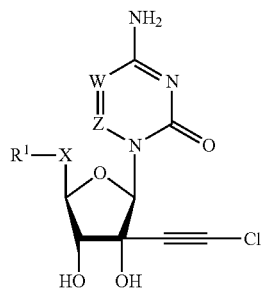

Formula XLV or pharmaceutically acceptable salts thereof wherein,
X is $OCH_2$, $OCHMe$, $OCMe_2$, $OCHF$, $OCF_2$, or $OCD_2$;
W is N or CR⁷;
Z is N or CR⁸;
R¹ is selected from H or from one of the following formulae:

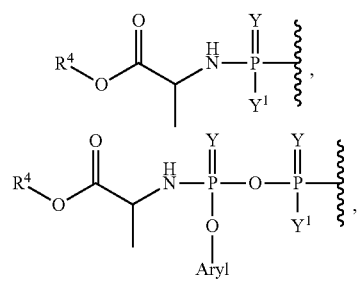

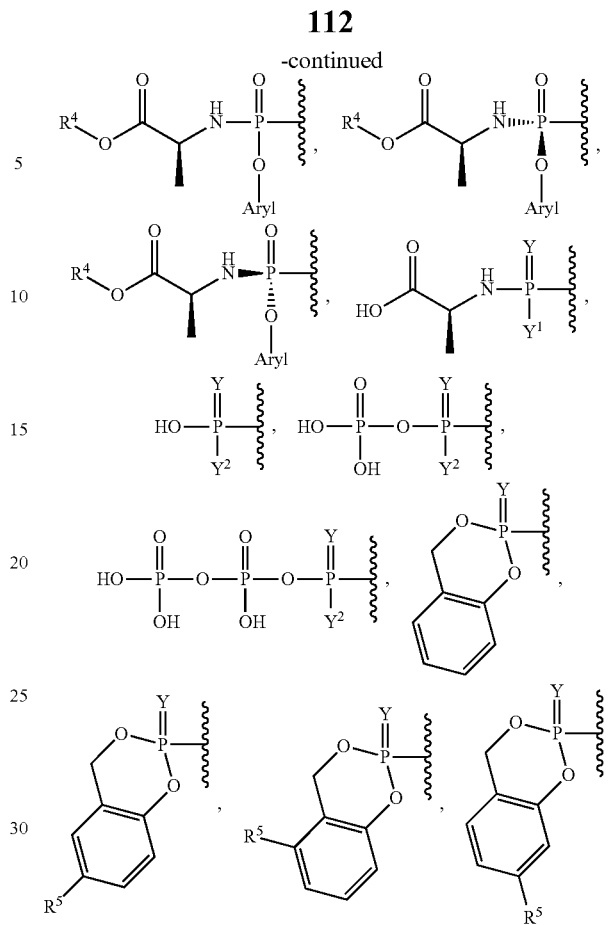

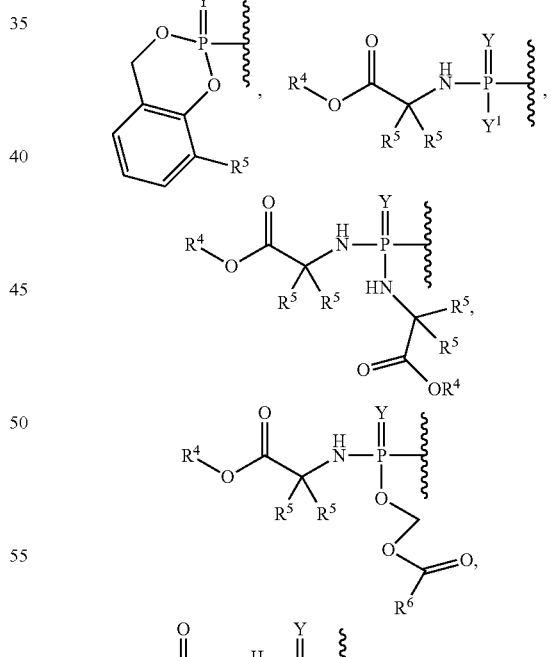

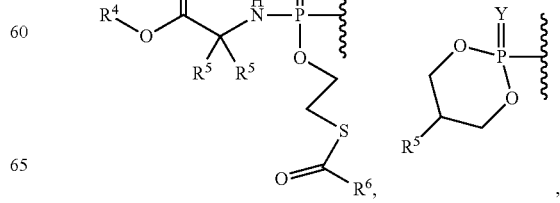

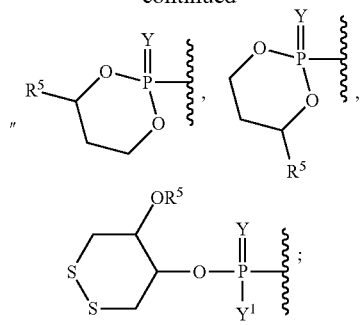

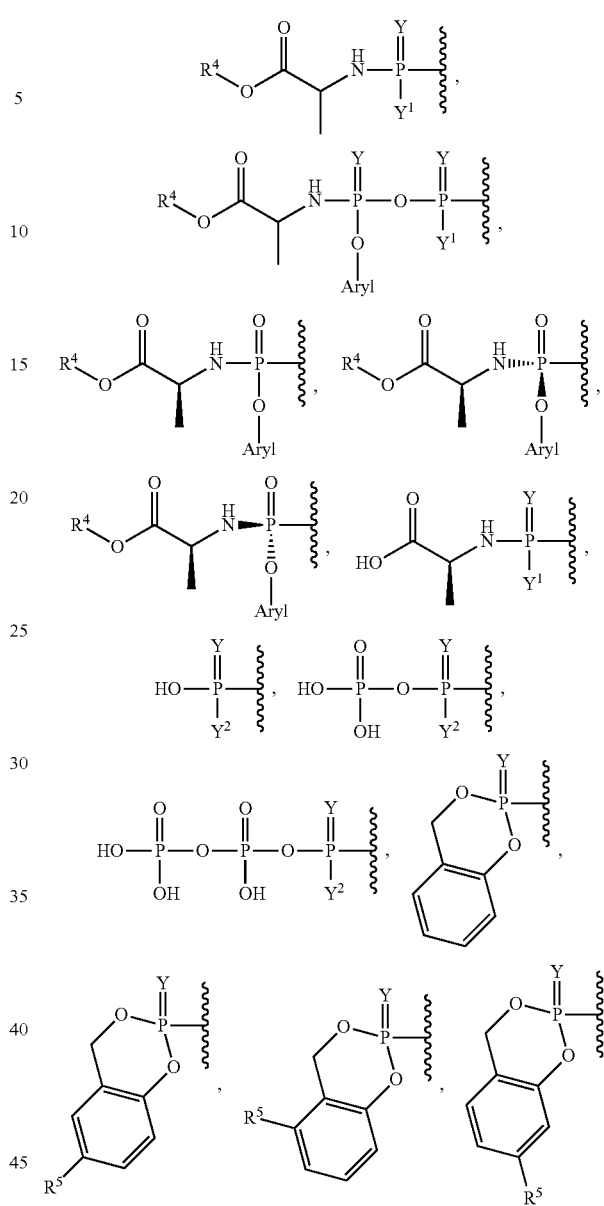

Y is O or S;

Y[1] is OH, OAryl, OAlkyl, or $BH_3^-M^+$;

Y[2] is OH or $BH_3^-M^+$;

Aryl is phenyl, 1-naphthyl, 2-naphthyl, aromatic, heteroaromatic, 4-substituted phenyl, 4-chlorophenyl, or 4-bromophenyl;

$R^4$ is hydrogen, methyl, ethyl, isopropyl, cyclopentyl, cyclohexyl, neopentyl, benzyl, alkyl, branched alkyl, cycloalkyl, or lipid;

$R^5$ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;

$R^6$ is methyl, ethyl, tert-butyl, $C_{1-22}$ alkoxy, $C_{1-22}$ alkyl, branched alkyl, cycloalkyl, aryl, substituted aryl, or alkyoxy;

$R^7$ is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano;

$R^8$ is D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano. In certain embodiments, the present invention relates to compounds of the following formula:

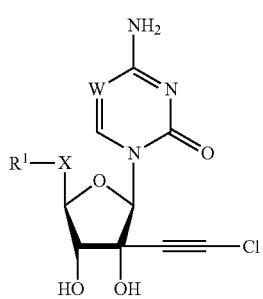

Formula XLVI or pharmaceutically acceptable salts thereof wherein,

X is $OCMe_2$, OCHF, $OCF_2$, or $OCD_2$;

W is N or $CR^7$;

$R^1$ is selected from H or from one of the following formulae:

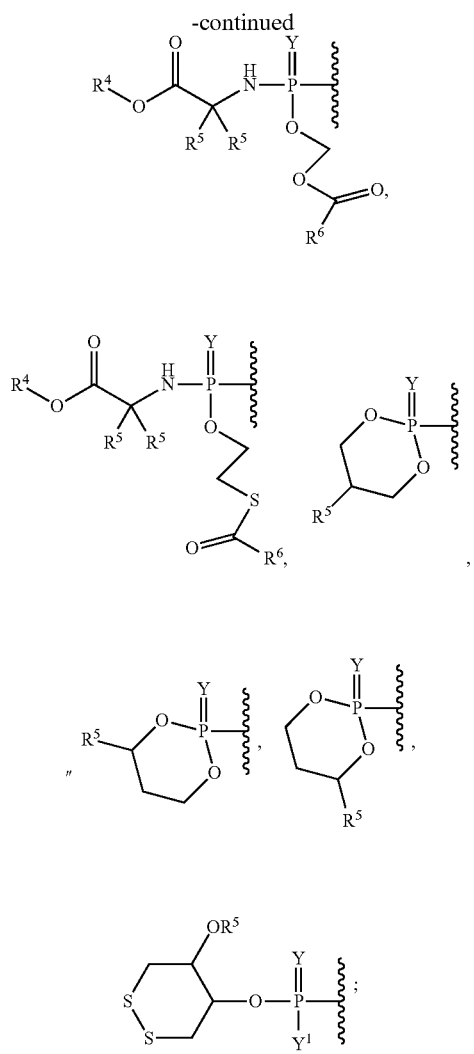

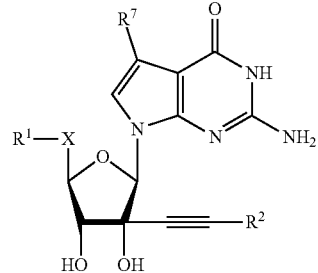
Formula XLVIIa

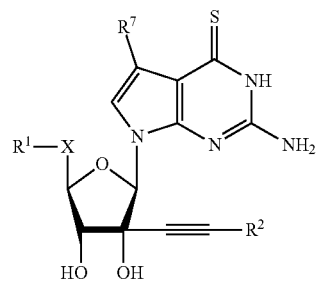
Formula XLVIIb

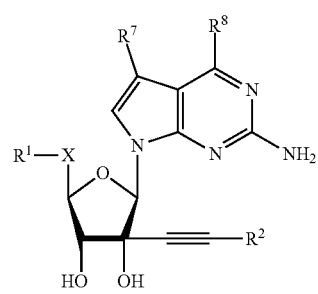
Formula XLVIIc or pharmaceutically acceptable salts thereof wherein, $X$ is $OCH_2$, $OCHMe$, $OCMe_2$, $OCHF$, $OCF_2$, or $OCD_2$;

$R^1$ is selected from H or from one of the following formulae:

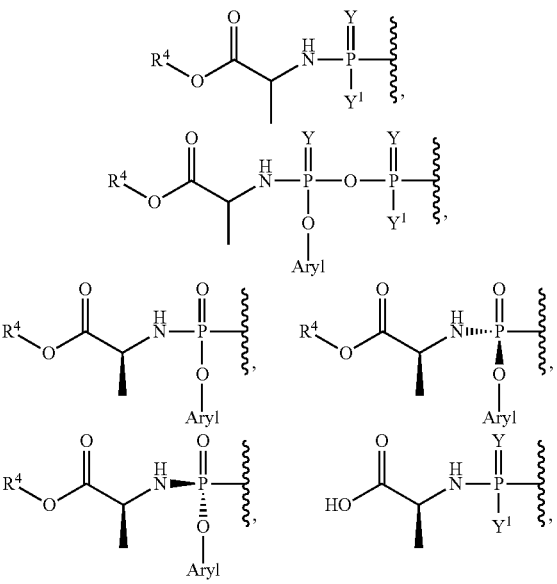

Y is O or S;

$Y^1$ is OH, OAryl, OAlkyl, or $BH_3^-M^+$;

$Y^2$ is OH or $BH_3^-M^+$;

Aryl is phenyl, 1-naphthyl, 2-naphthyl, aromatic, heteroaromatic, 4-substituted phenyl, 4-chlorophenyl, or 4-bromophenyl;

$R^4$ is hydrogen, methyl, ethyl, isopropyl, cyclopentyl, cyclohexyl, neopentyl, benzyl, alkyl, branched alkyl, cycloalkyl, or lipid;

$R^5$ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;

$R^6$ is methyl, ethyl, tert-butyl, $C_{1-22}$ alkoxy, $C_{1-22}$ alkyl, branched alkyl, cycloalkyl, aryl, substituted aryl, or alkyoxy;

$R^7$ is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano.

In certain embodiments, the present invention relates to compounds of the following formula:

117
-continued

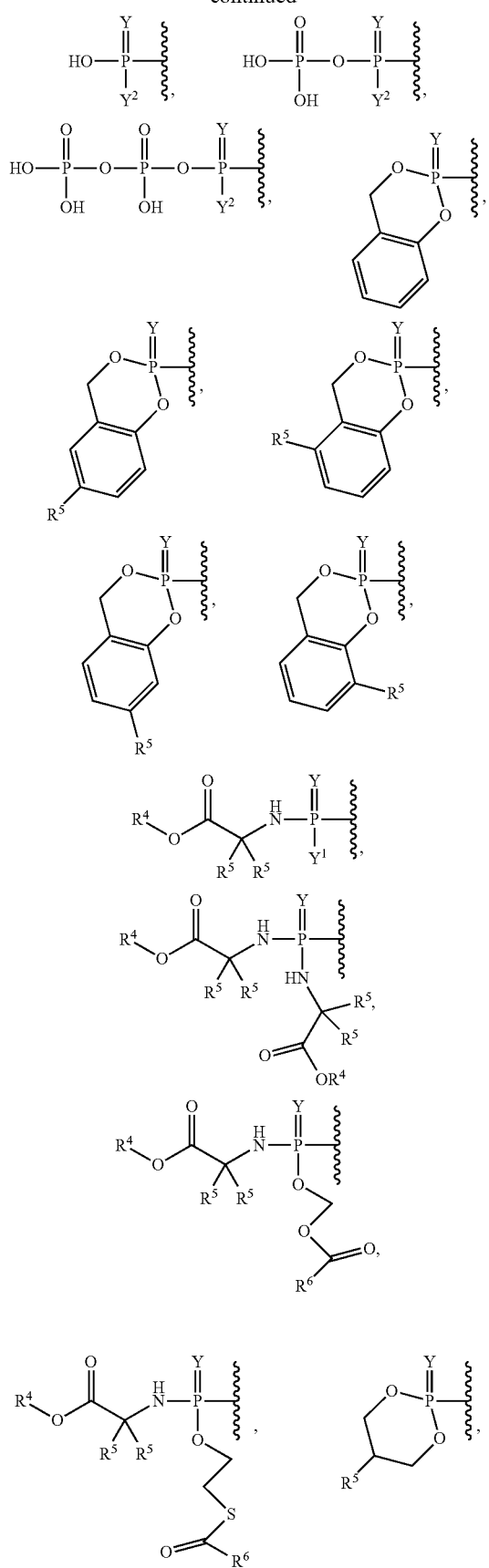

118
-continued

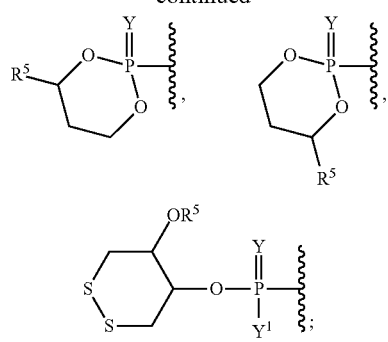

Y is O or S;

$Y^1$ is OH, OAryl, OAlkyl, or $BH_3^-M^+$;

$Y^2$ is OH or $BH_3^-M^+$;

Aryl is phenyl, 1-naphthyl, 2-naphthyl, aromatic, heteroaromatic, 4-substituted phenyl, 4-chlorophenyl, or 4-bromophenyl;

$R^2$ is hydrogen, methyl, fluoromethyl, difluoromethyl, trifluoromethyl, ethyl, cyclopropyl, fluoro, chloro, hydroxymethyl, aminomethyl, vinyl, or cyclobutyl;

$R^4$ is hydrogen, methyl, ethyl, isopropyl, cyclopentyl, cyclohexyl, neopentyl, benzyl, alkyl, branched alkyl, cycloalkyl, or lipid;

$R^5$ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;

$R^6$ is methyl, ethyl, tert-butyl, $C_{1-22}$ alkoxy, $C_{1-22}$ alkyl, branched alkyl, cycloalkyl, aryl, substituted aryl, or alkyoxy;

$R^7$ is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano;

$R^8$ is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, methoxy, ethoxy, alkoxy, substituted amino, or cyano.

In certain embodiments, the present invention relates to compounds of the following formula:

Formula XLVIIIa

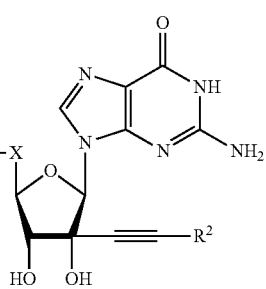

Formula XLVIIIb

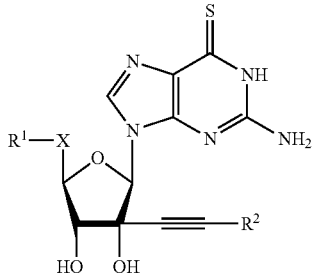

Formula XLVIIIc

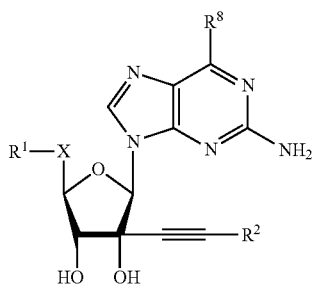

or pharmaceutically acceptable salts thereof wherein,

X is $OCH_2$, OCHMe, $OCMe_2$, OCHF, $OCF_2$, or $OCD_2$;

$R^1$ is selected from H or from one of the following formulae:

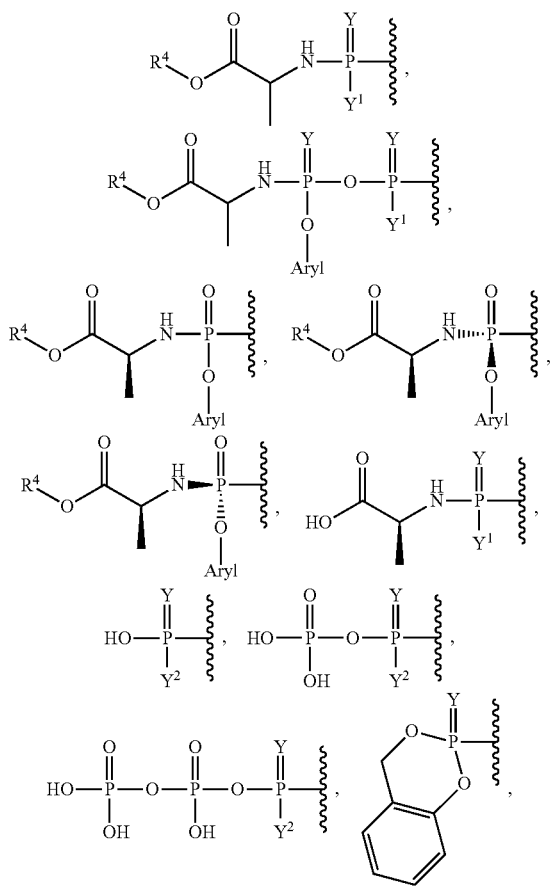

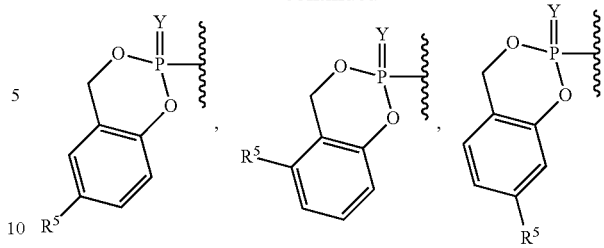

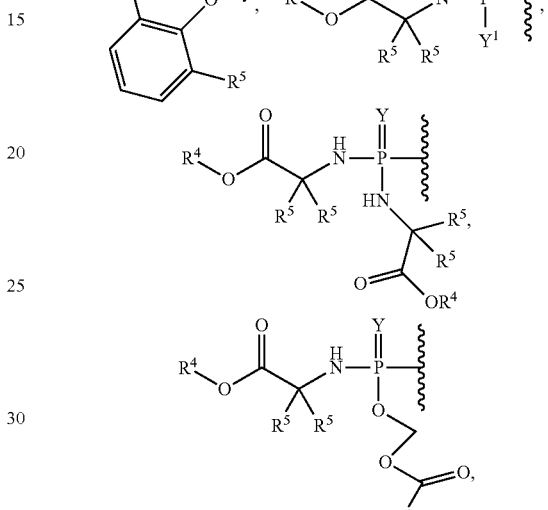

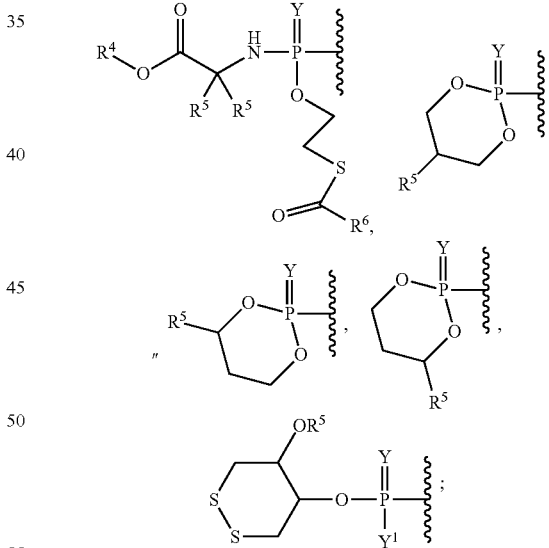

Y is O or S;

$Y^1$ is OH, OAryl, OAlkyl, or $BH_3^-M^+$;

$Y^2$ is OH or $BH_3^-M^+$;

Aryl is phenyl, 1-naphthyl, 2-naphthyl, aromatic, heteroaromatic, 4-substituted phenyl, 4-chlorophenyl, or 4-bromophenyl;

$R^2$ is methyl, fluoromethyl, difluoromethyl, trifluoromethyl, cyclopropyl, fluoro, hydroxymethyl, aminomethyl, vinyl, or cyclobutyl;

R[4] is hydrogen, methyl, ethyl, isopropyl, cyclopentyl, cyclohexyl, neopentyl, benzyl, alkyl, branched alkyl, cycloalkyl, or lipid;

R[5] is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;

R[6] is methyl, ethyl, tert-butyl, $C_{1-22}$ alkoxy, $C_{1-22}$ alkyl, branched alkyl, cycloalkyl, aryl, substituted aryl, or alkyoxy;

R[8] is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, methoxy, ethoxy, alkoxy, substituted amino, or cyano.

In certain embodiments, the present invention relates to compounds of the following formula:

Formula XLIXa

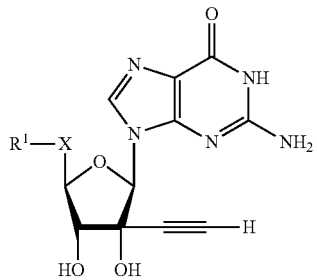

Formula XLIXb

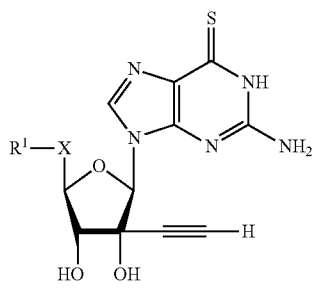

Formula XLIXc

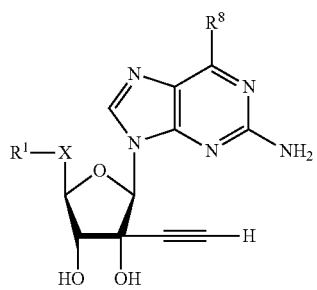

or pharmaceutically acceptable salts thereof wherein,

X is $OCHMe$, $OCMe_2$, $OCHF$, $OCF_2$, or $OCD_2$;

R[1] is selected from H or from one of the following formulae:

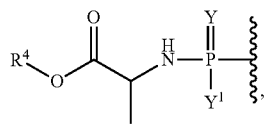

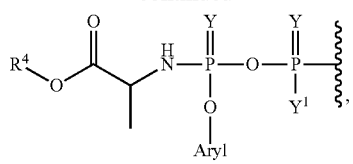

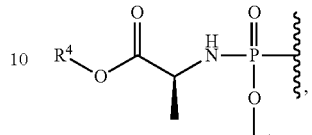
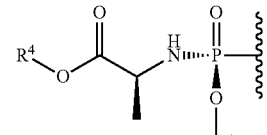

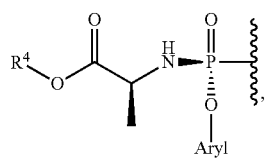
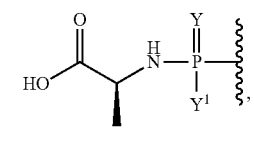

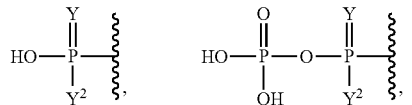

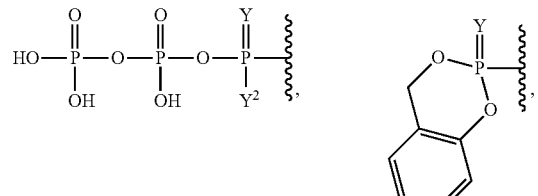

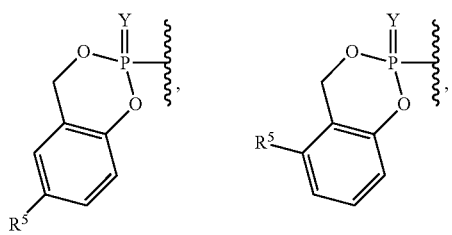

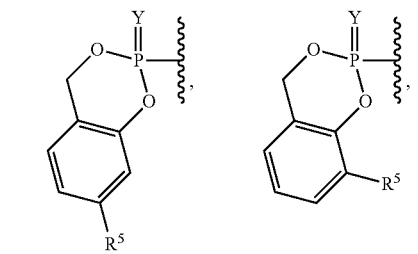

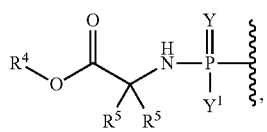

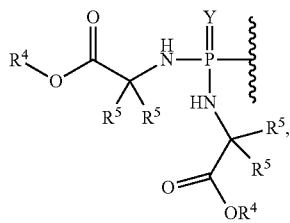

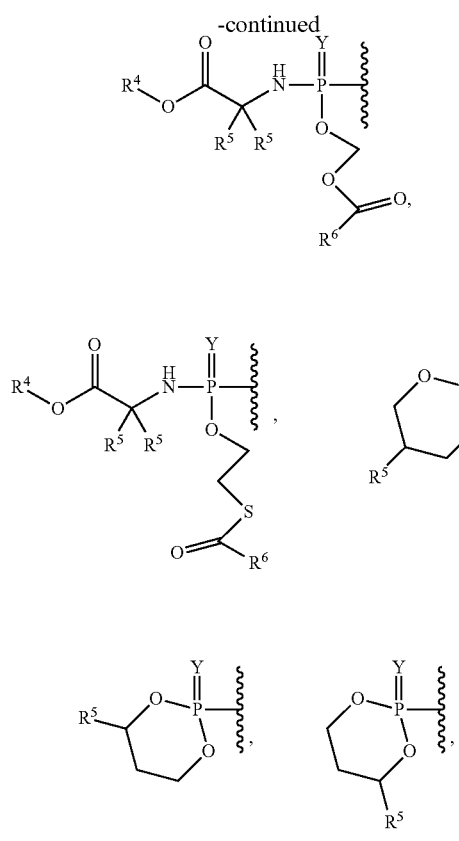

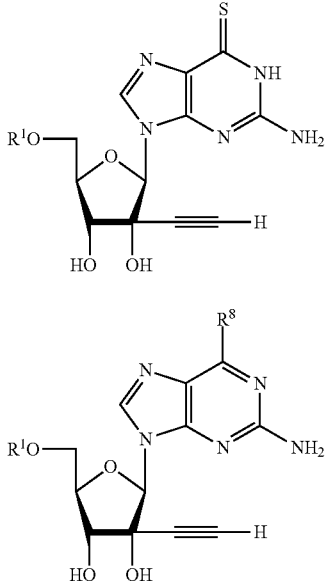

Formula La

Formula Lb or pharmaceutically acceptable salts thereof wherein, $R^1$ is selected from H or from one of the following formulae:

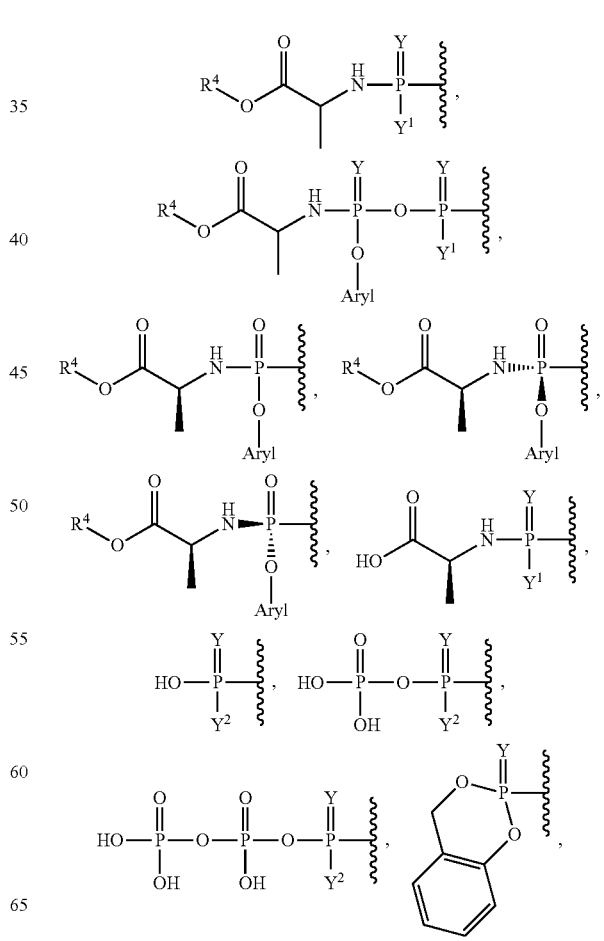

Y is O or S;

$Y^1$ is OH, OAryl, OAlkyl, or $BH_3^-M^+$;

$Y^2$ is OH or $BH_3^-M^+$;

Aryl is phenyl, 1-naphthyl, 2-naphthyl, aromatic, heteroaromatic, 4-substituted phenyl, 4-chlorophenyl, or 4-bromophenyl;

$R^4$ is hydrogen, methyl, ethyl, isopropyl, cyclopentyl, cyclohexyl, neopentyl, benzyl, alkyl, branched alkyl, cycloalkyl, or lipid;

$R^5$ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;

$R^6$ is methyl, ethyl, tert-butyl, $C_{1-22}$ alkoxy, $C_{1-22}$ alkyl, branched alkyl, cycloalkyl, aryl, substituted aryl, or alkyoxy;

$R^8$ is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, methoxy, ethoxy, alkoxy, substituted amino, or cyano.

In certain embodiments, the present invention relates to compounds of the following formula:

-continued

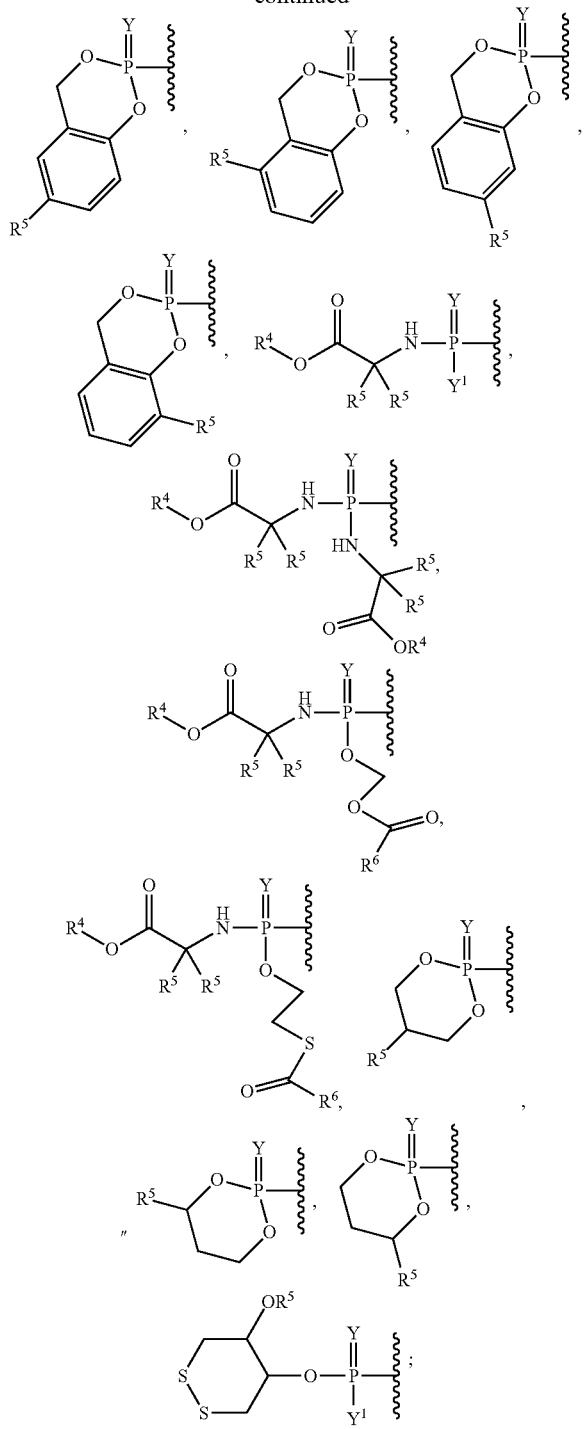

Y is O or S;

Y¹ is OH, OAryl, OAlkyl, or $BH_3^-M^+$;

Y² is OH or $BH_3^-M^+$;

Aryl is phenyl, 1-naphthyl, 2-naphthyl, aromatic, heteroaromatic, 4-substituted phenyl, 4-chlorophenyl, or 4-bromophenyl;

R⁴ is hydrogen, methyl, ethyl, isopropyl, cyclopentyl, cyclohexyl, neopentyl, benzyl, alkyl, branched alkyl, cycloalkyl, or lipid;

R⁵ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;

R⁶ is methyl, ethyl, tert-butyl, $C_{1-22}$ alkoxy, $C_{1-22}$ alkyl, branched alkyl, cycloalkyl, aryl, substituted aryl, or alkyoxy;

R⁸ is H, D, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, substituted amino, or cyano.

In certain embodiments, the present invention relates to compounds of the following formula:

Formula LIa

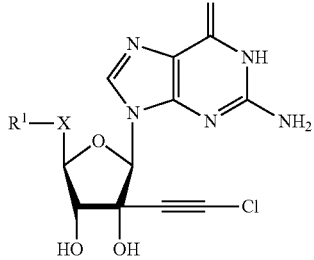

Formula LIb

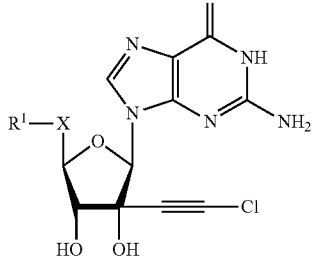

Formula LIc

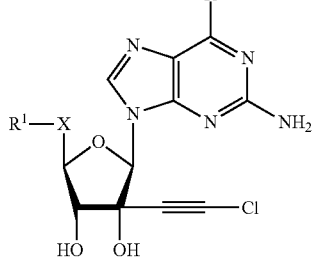

or pharmaceutically acceptable salts thereof wherein,

X is $OCMe_2$, $OCHF$, $OCF_2$, or $OCD_2$;

R¹ is selected from H or from one of the following formulae:

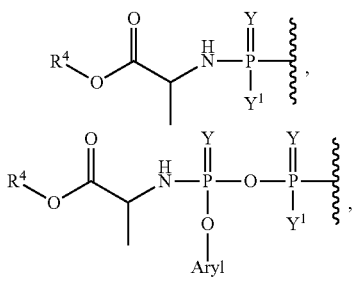

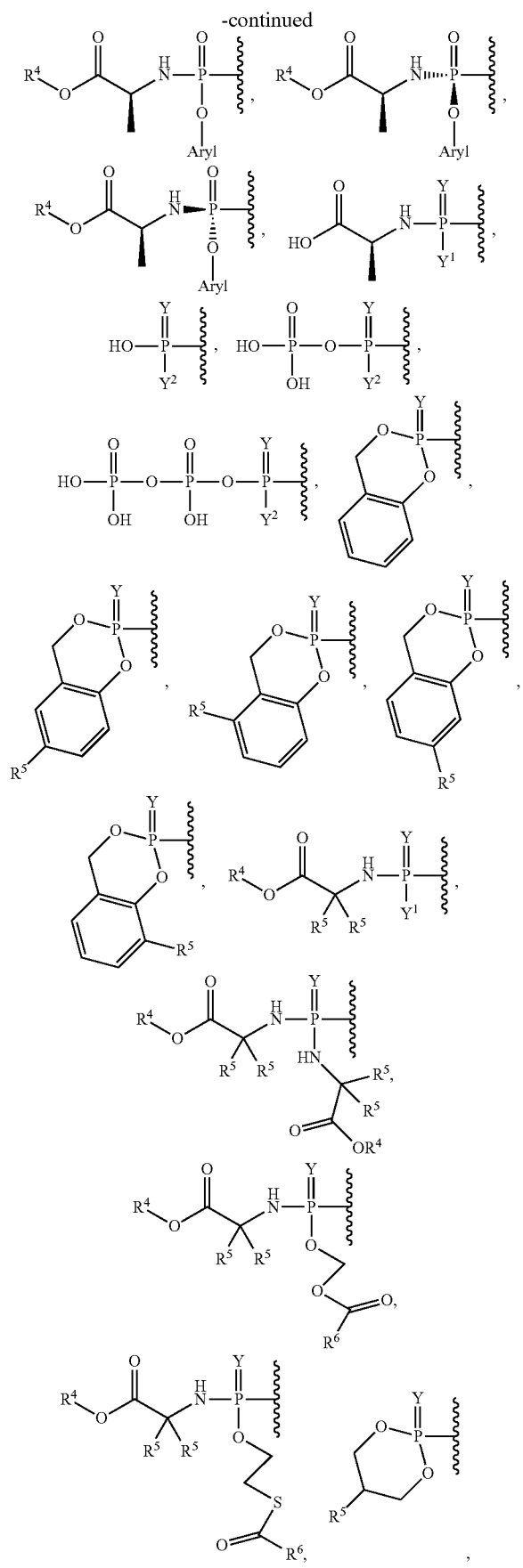

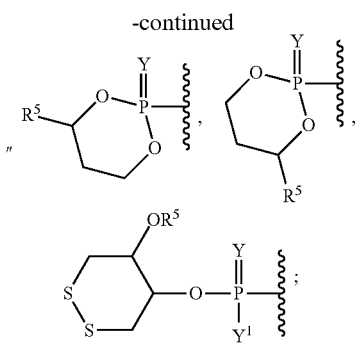

Y is O or S;
Y$^1$ is OH, OAryl, OAlkyl, or BH$_3^-$M$^+$;
Y$^2$ is OH or BH$_3^-$M$^+$;
Aryl is phenyl, 1-naphthyl, 2-naphthyl, aromatic, heteroaromatic, 4-substituted phenyl, 4-chlorophenyl, or 4-bromophenyl;
R$^4$ is hydrogen, methyl, ethyl, isopropyl, cyclopentyl, cyclohexyl, neopentyl, benzyl, alkyl, branched alkyl, cycloalkyl, or lipid;
R$^5$ is hydrogen, deuterium, hydroxyl, cyano, azido, amino, substituted amino, aryl, heteroaryl, substituted aryl, lipid, C$_{1-22}$ alkoxy, C$_{1-22}$ alkyl, C$_{2-22}$ alkenyl, C$_{2-22}$ alkynyl, or substituted heteroaryl;
R$^6$ is methyl, ethyl, tert-butyl, C$_{1-22}$ alkoxy, C$_{1-22}$ alkyl, branched alkyl, cycloalkyl, aryl, substituted aryl, or alkyoxy;
R$^8$ is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, methoxy, ethoxy, alkoxy, substituted amino, or cyano.

In certain embodiments, the present invention relates to compounds of the following formula:

Formula LIIa

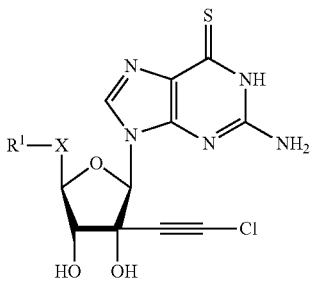

Formula LIIb

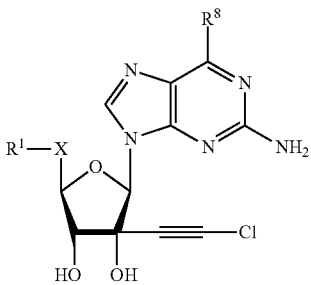

or pharmaceutically acceptable salts thereof wherein,
X is OCH$_2$ or OCHMe;
R$^1$ is selected from H or from one of the following formulae:

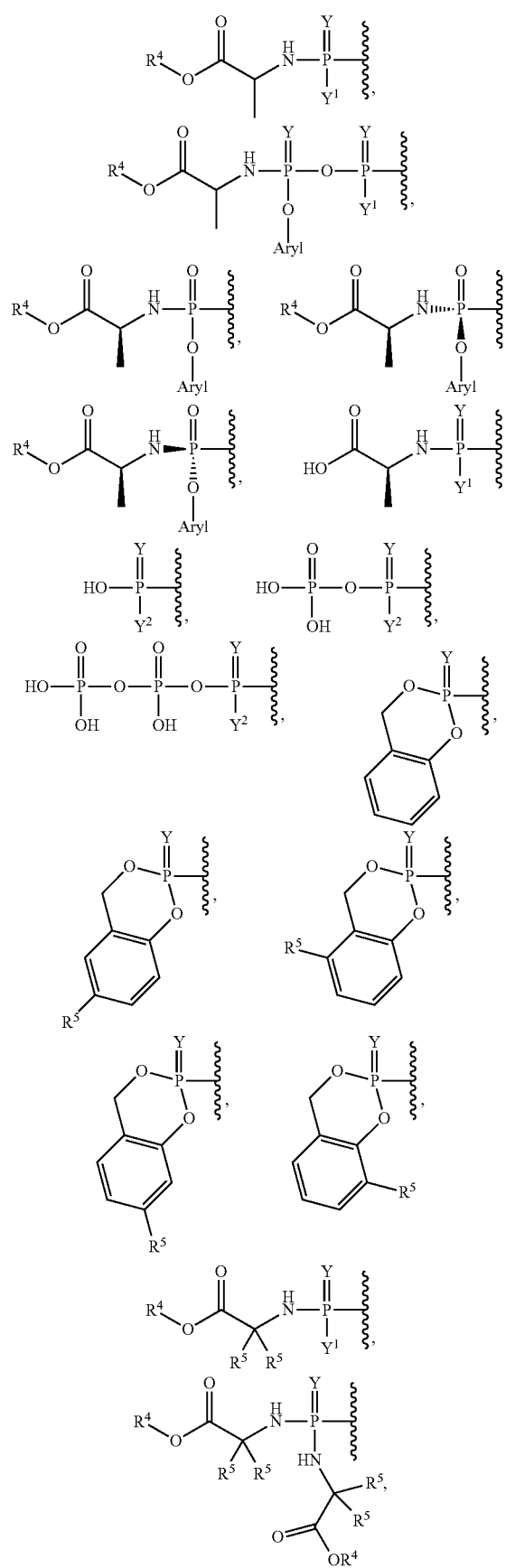
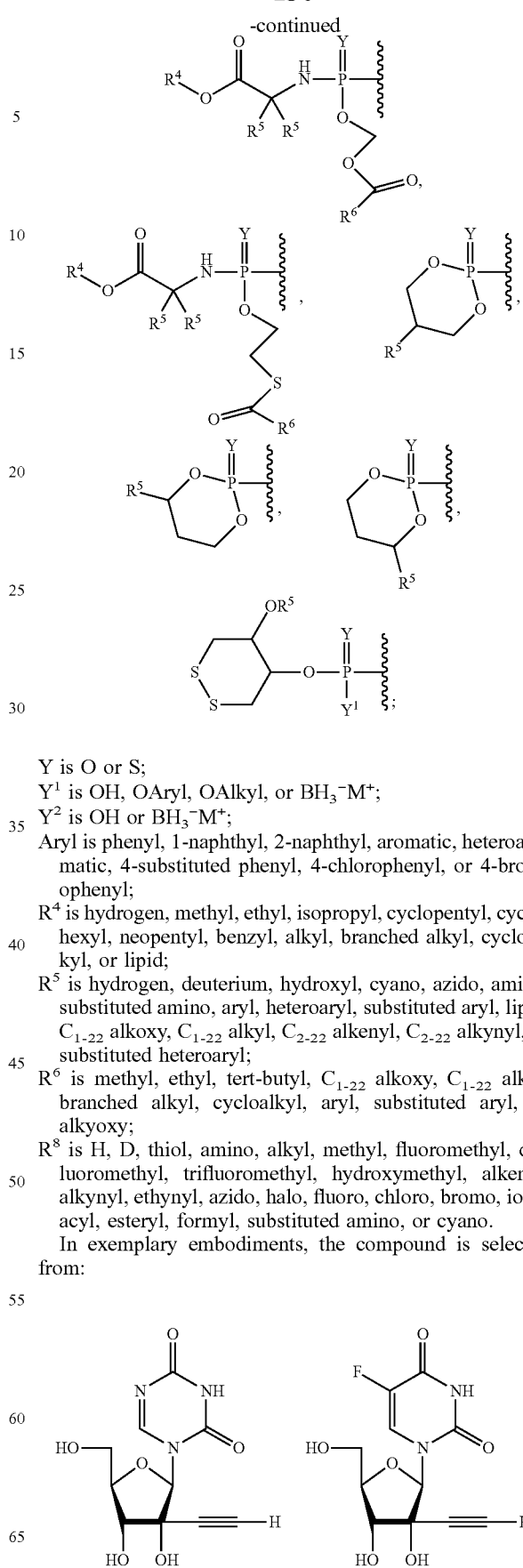

Y is O or S;
Y¹ is OH, OAryl, OAlkyl, or $BH_3^-M^+$;
Y² is OH or $BH_3^-M^+$;
Aryl is phenyl, 1-naphthyl, 2-naphthyl, aromatic, heteroaromatic, 4-substituted phenyl, 4-chlorophenyl, or 4-bromophenyl;
$R^4$ is hydrogen, methyl, ethyl, isopropyl, cyclopentyl, cyclohexyl, neopentyl, benzyl, alkyl, branched alkyl, cycloalkyl, or lipid;
$R^5$ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;
$R^6$ is methyl, ethyl, tert-butyl, $C_{1-22}$ alkoxy, $C_{1-22}$ alkyl, branched alkyl, cycloalkyl, aryl, substituted aryl, or alkyoxy;
$R^8$ is H, D, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, substituted amino, or cyano.

In exemplary embodiments, the compound is selected from:

131
-continued
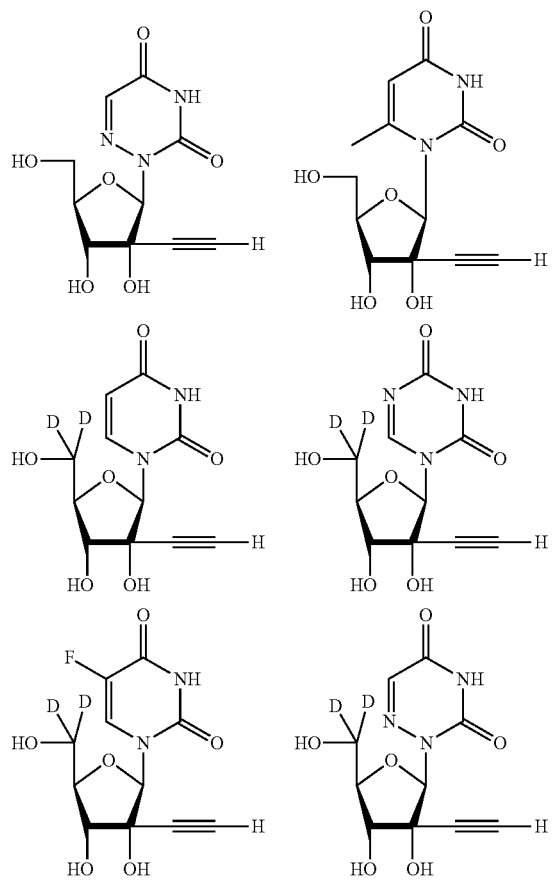
132
-continued
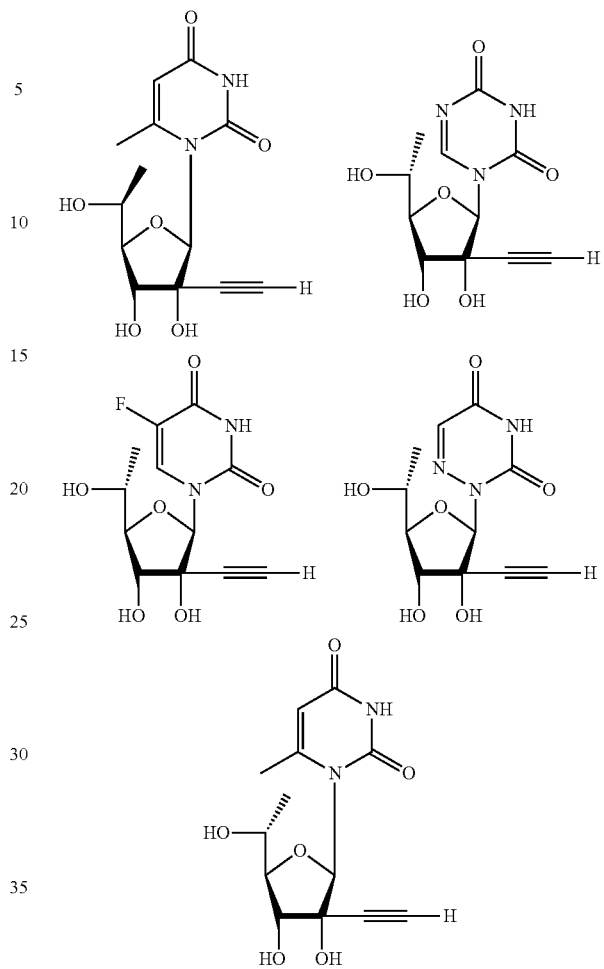
In exemplary embodiments, the compound is selected from:
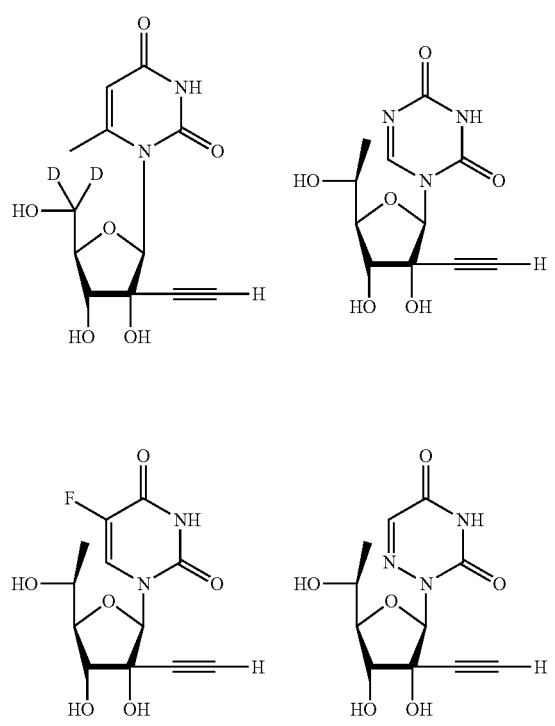

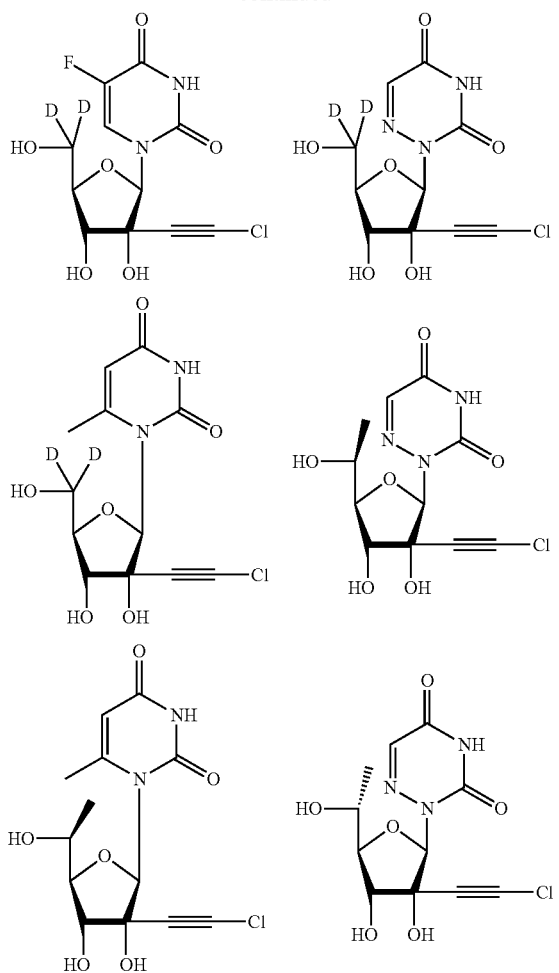
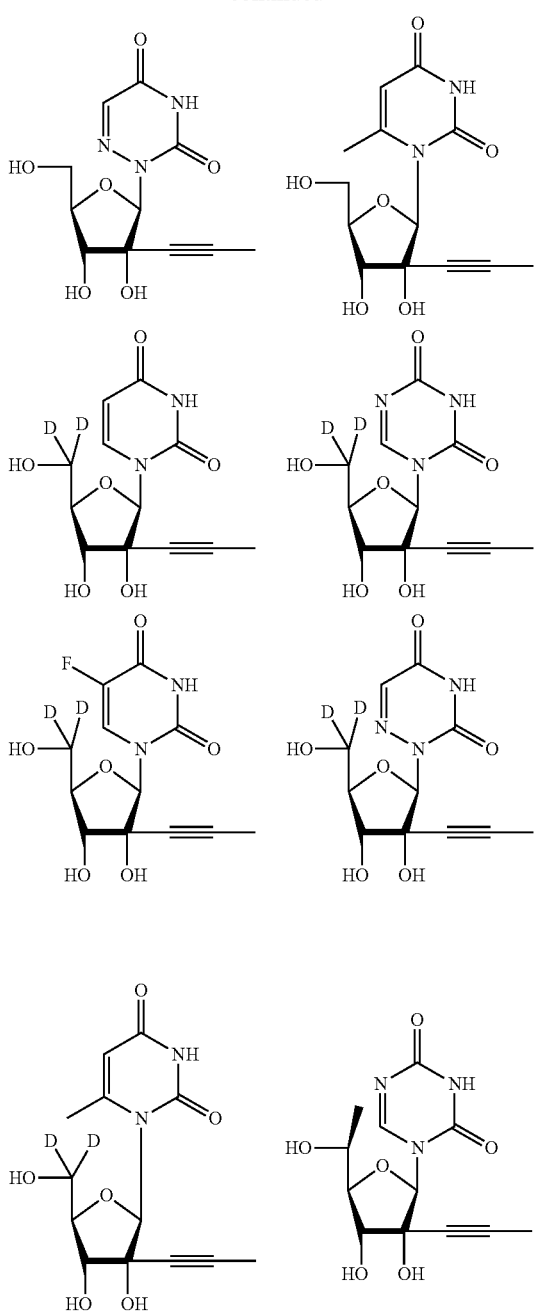
In exemplary embodiments, the compound is selected from:
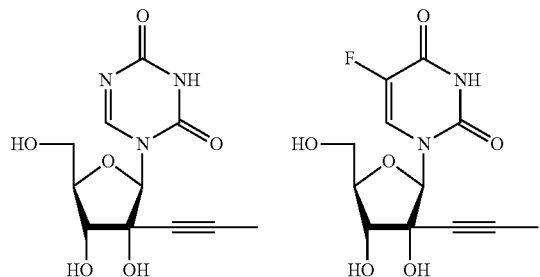
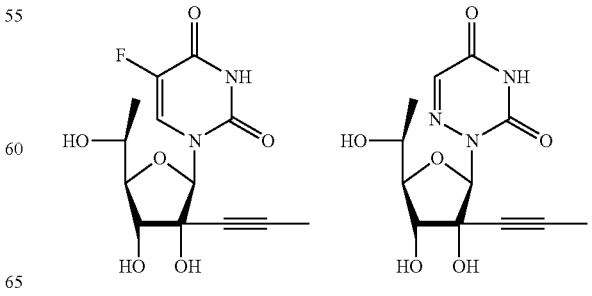

135
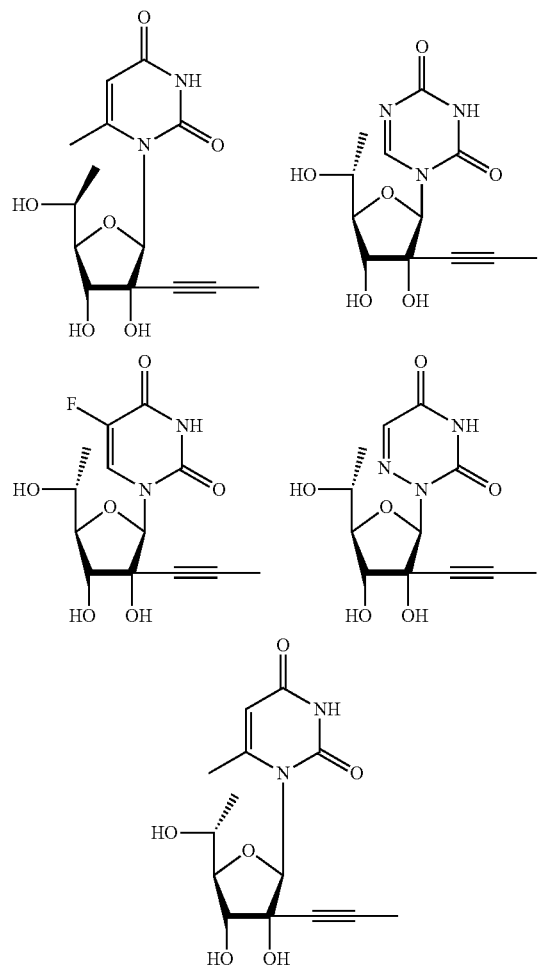
In exemplary embodiments, the compound is selected from:
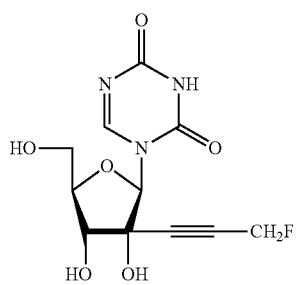
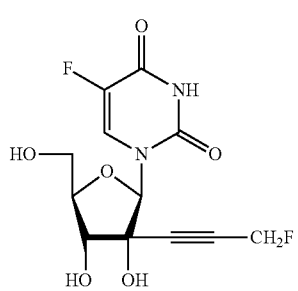
136
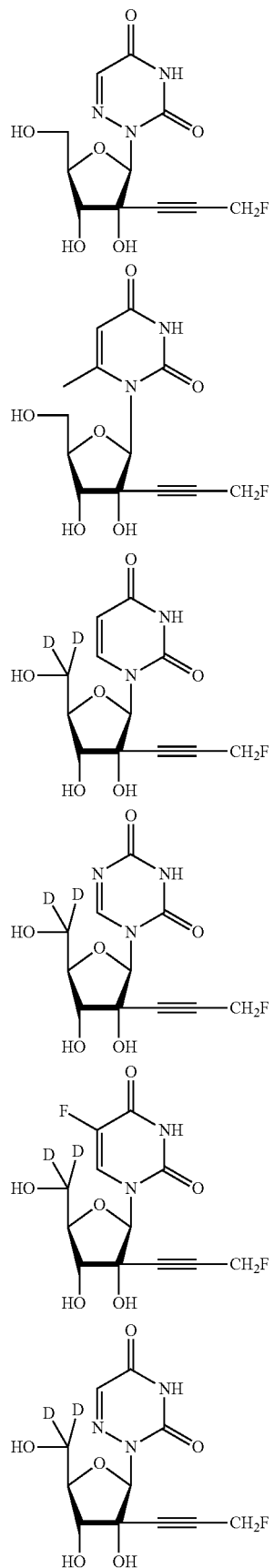

-continued
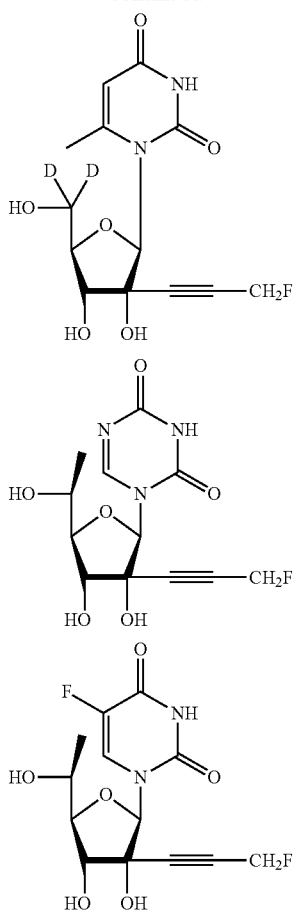
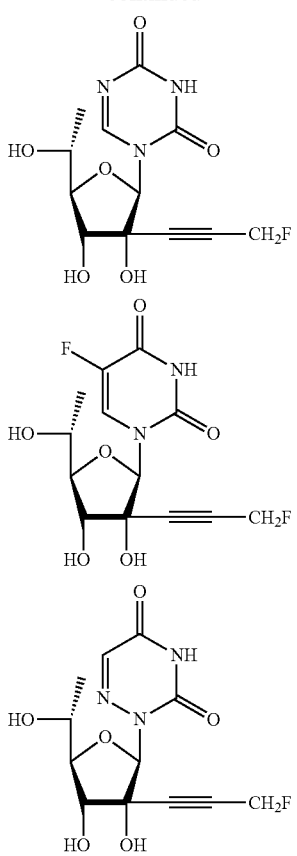
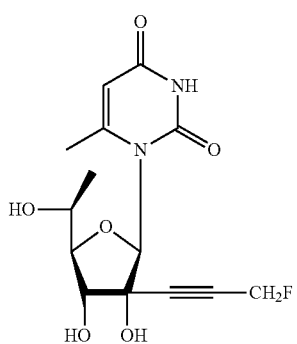
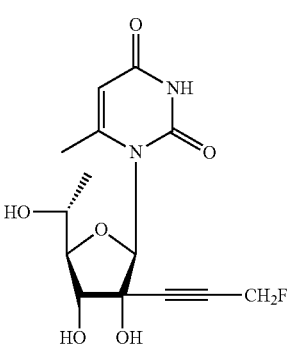
In exemplary embodiments, the compound is selected from:
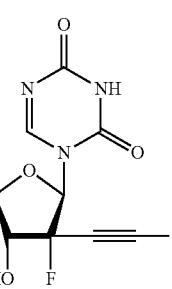 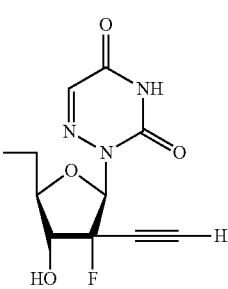

-continued
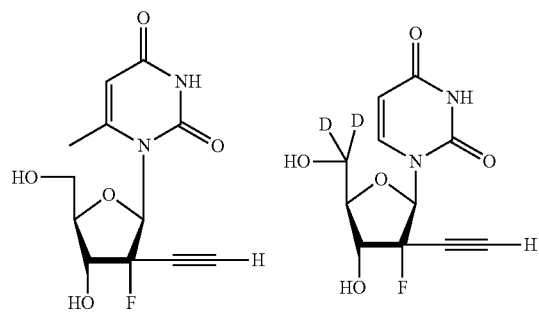
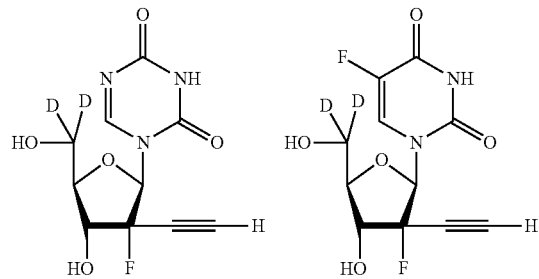
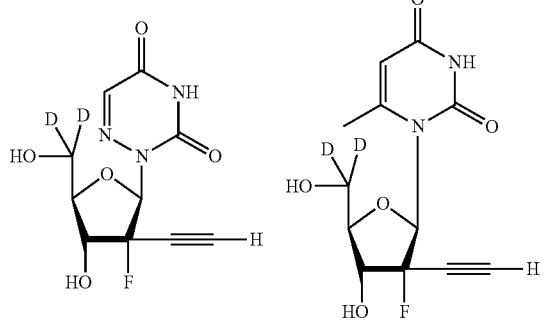
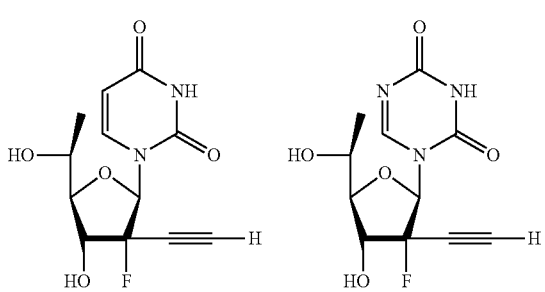
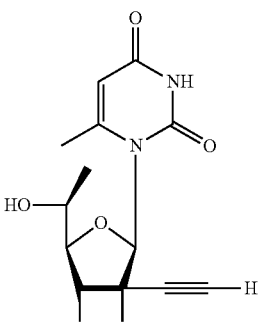
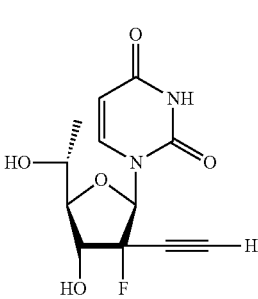
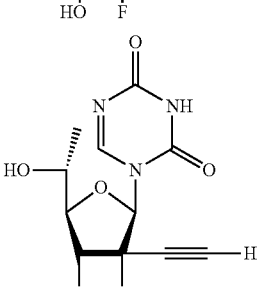
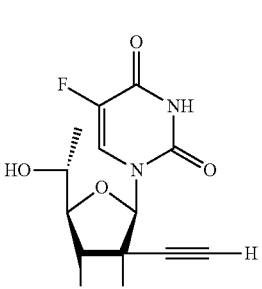
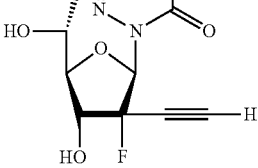
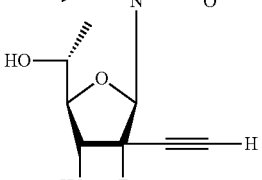
In exemplary embodiments, the compound is selected from:
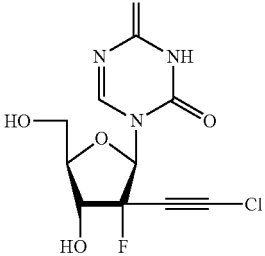
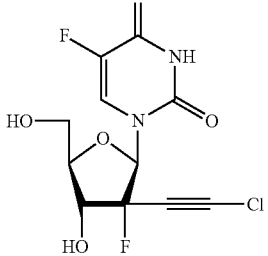
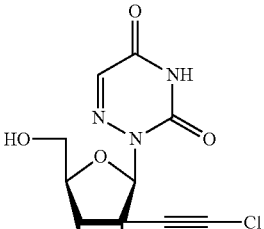
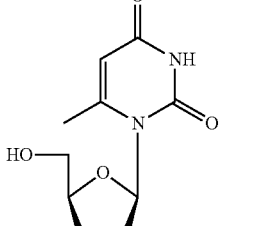
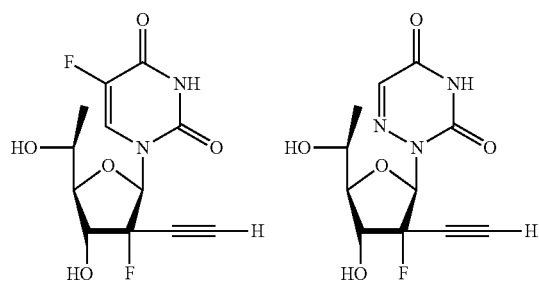

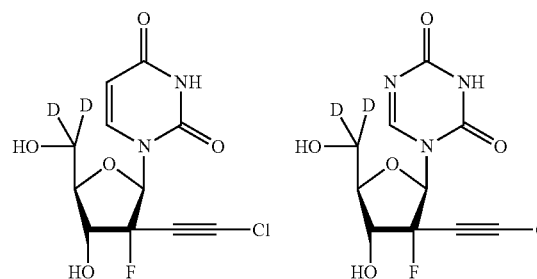
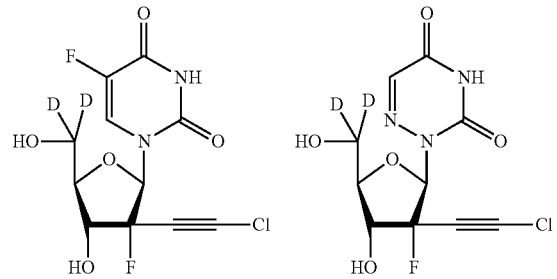
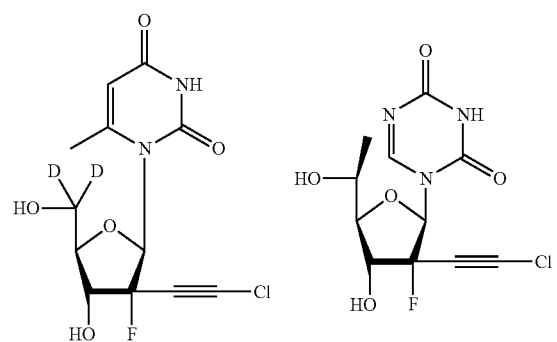
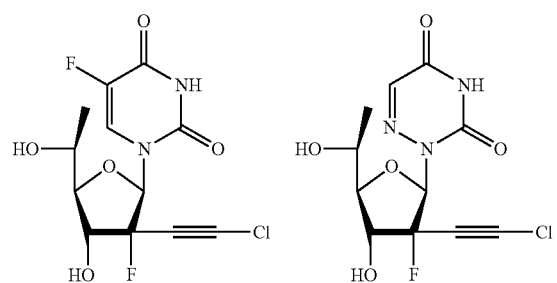
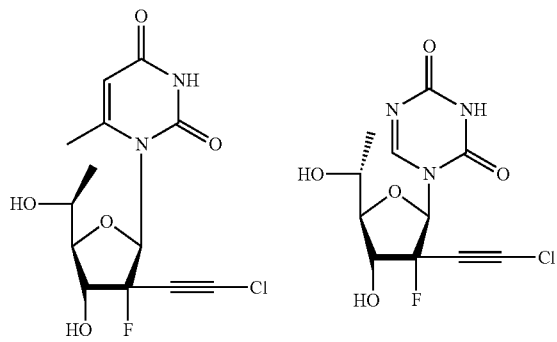
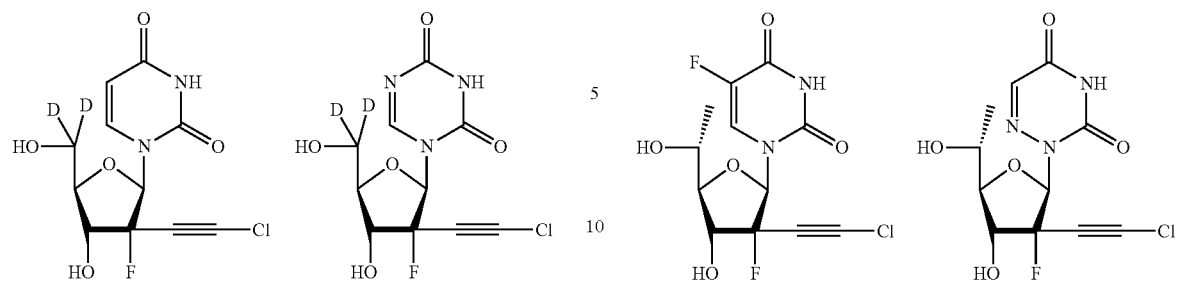
In exemplary embodiments, the compound is selected from:
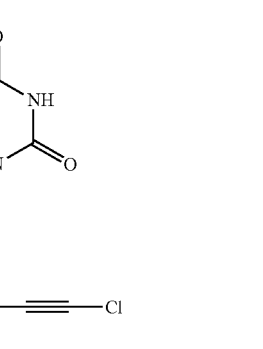

-continued
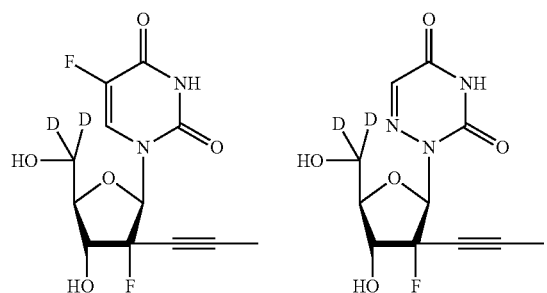
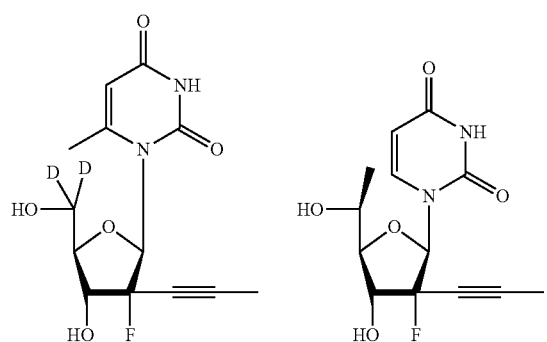
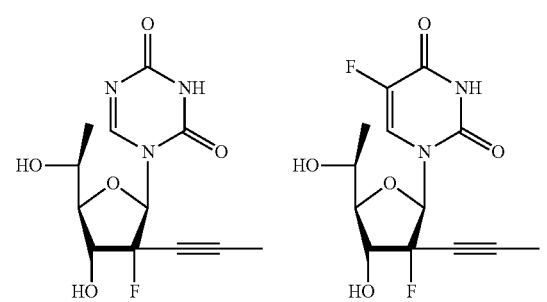
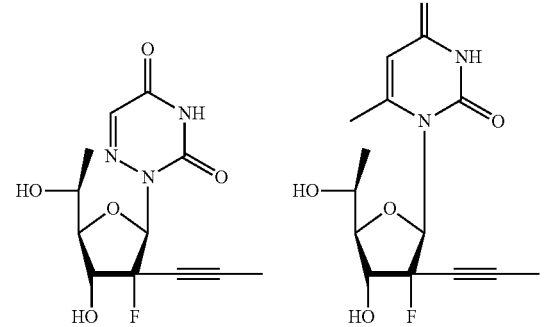
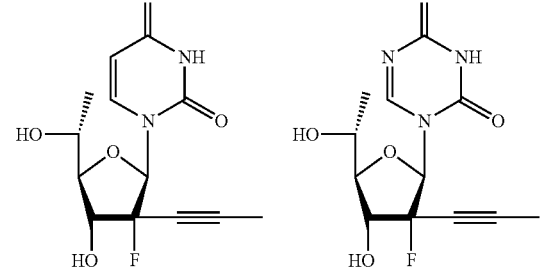
-continued
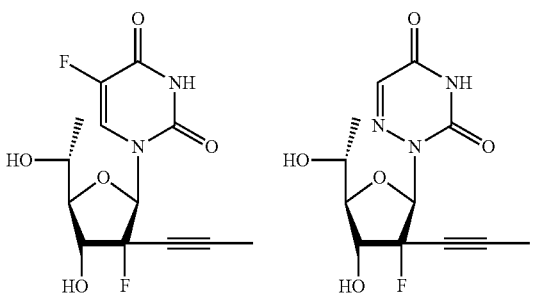
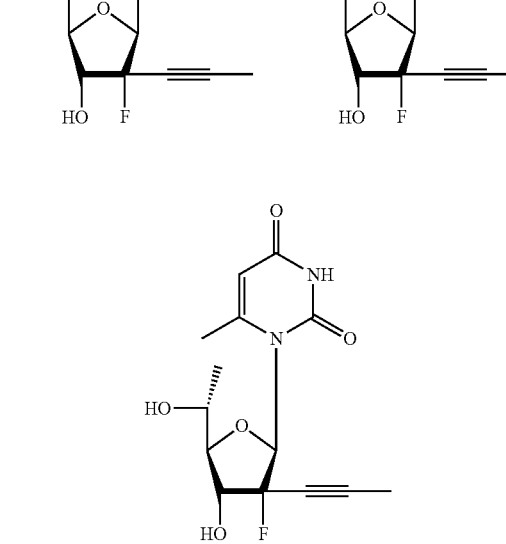
In exemplary embodiments, the compound is selected from:
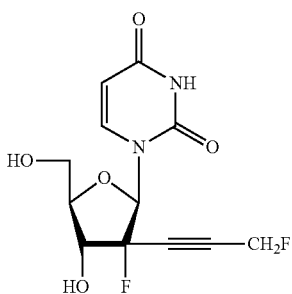
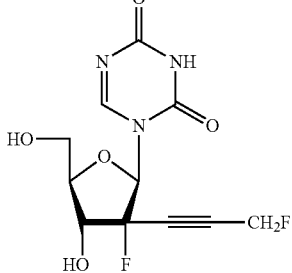
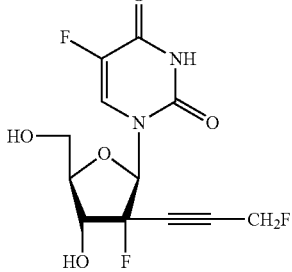

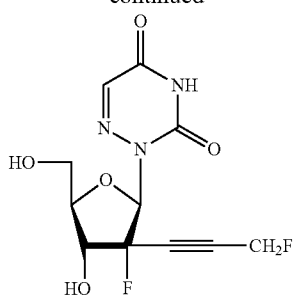
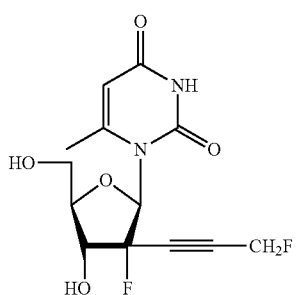

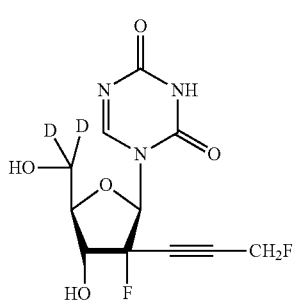

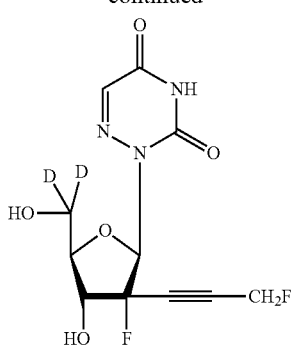
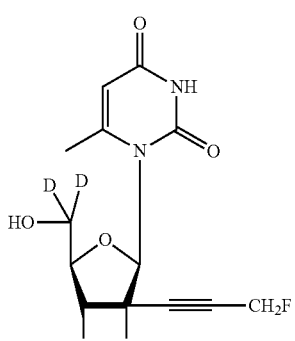
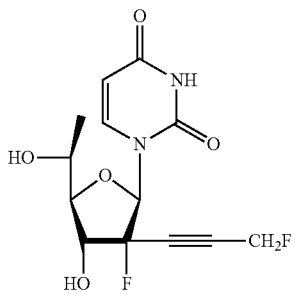
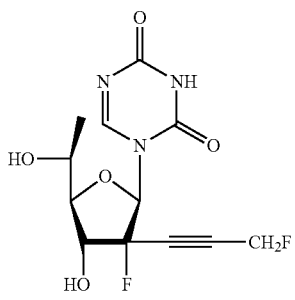
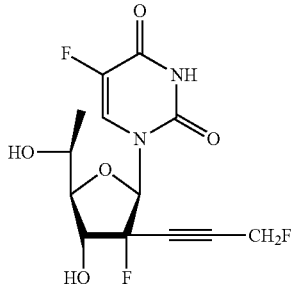

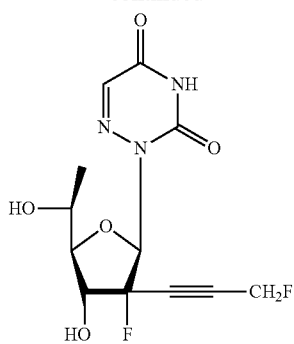
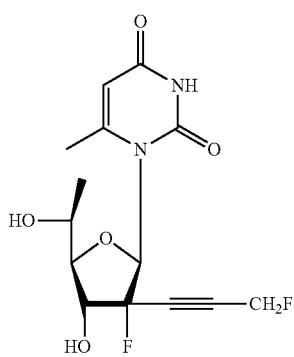
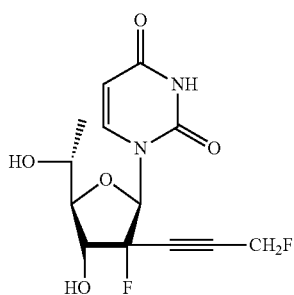
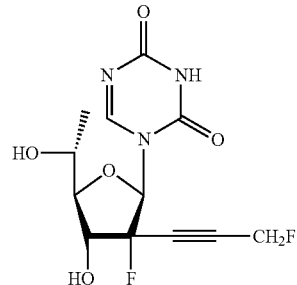
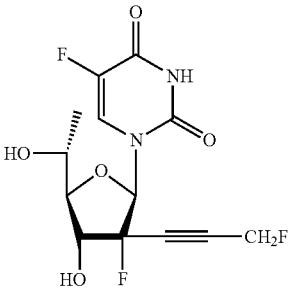
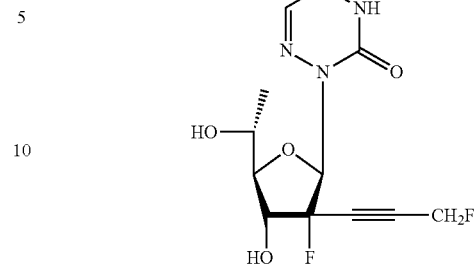
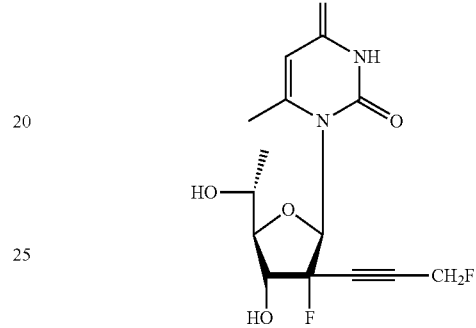
In exemplary embodiments, the compound is selected from:
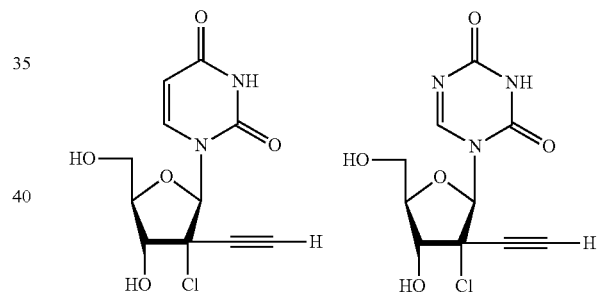
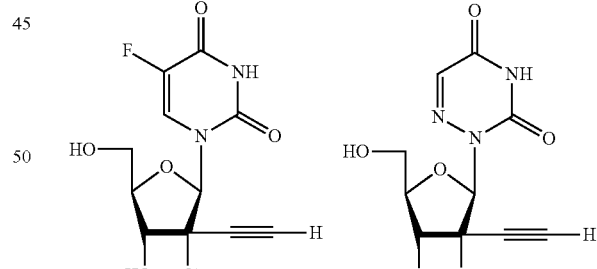
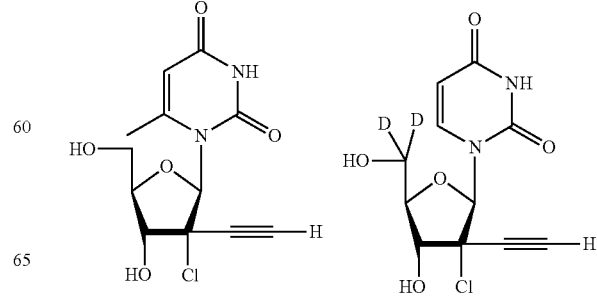

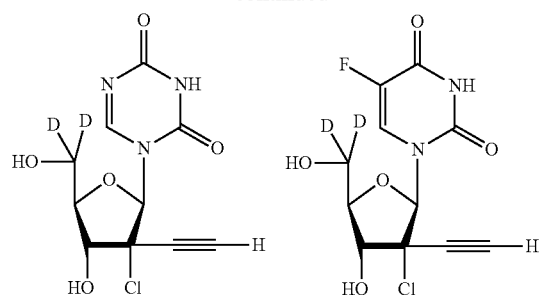
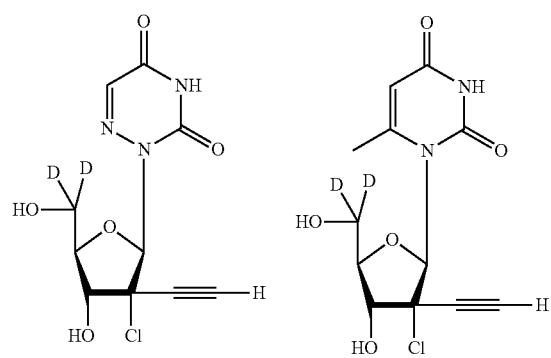
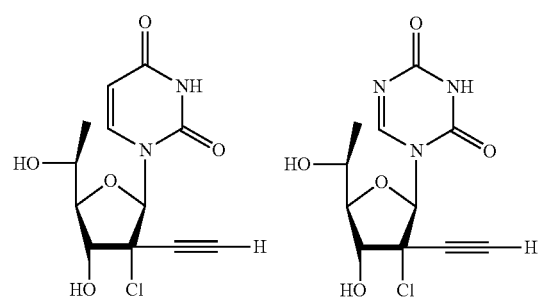
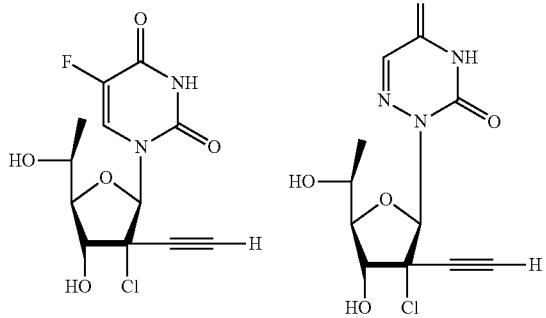
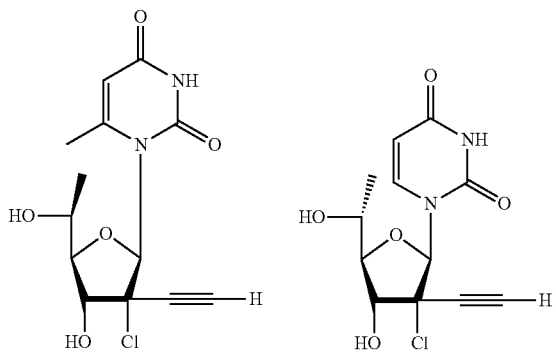
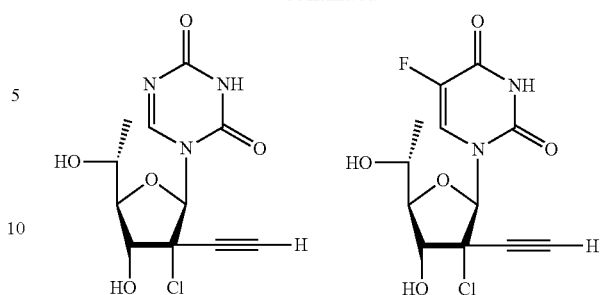
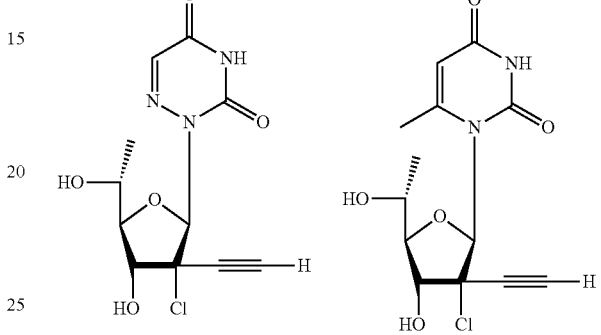
In exemplary embodiments, the compound is selected from:
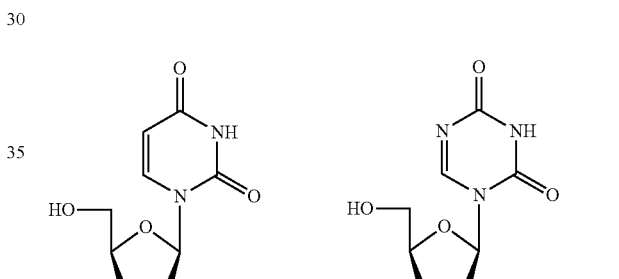
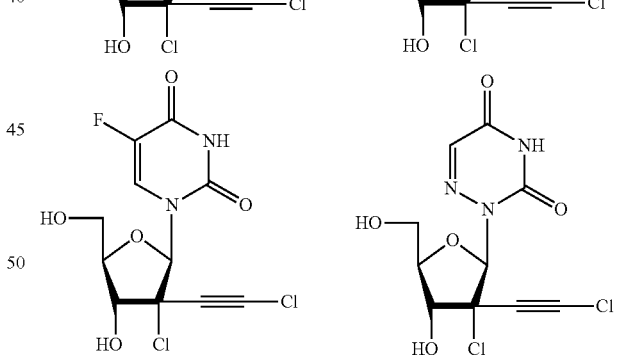
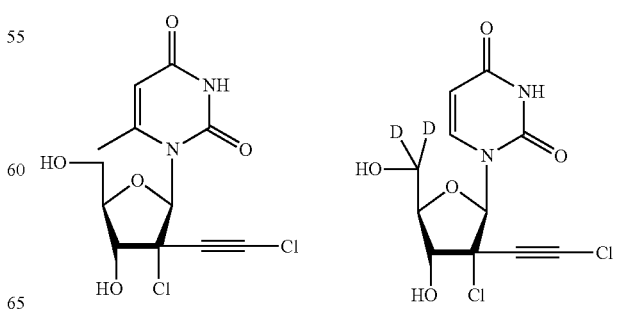

-continued
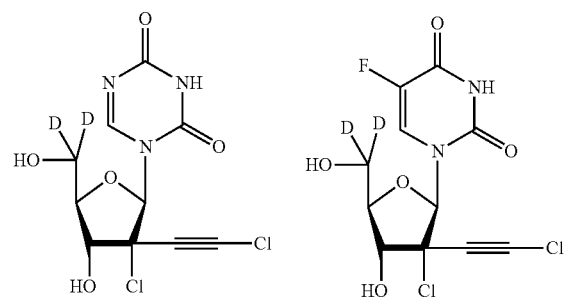
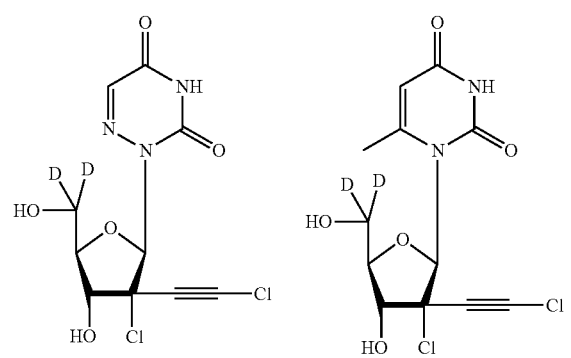
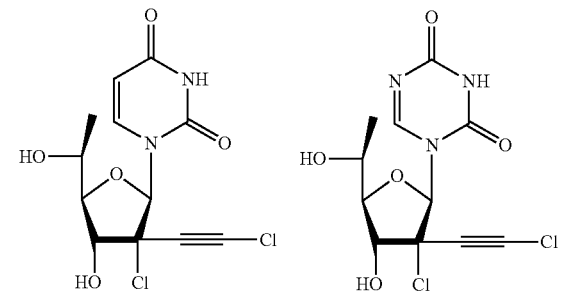
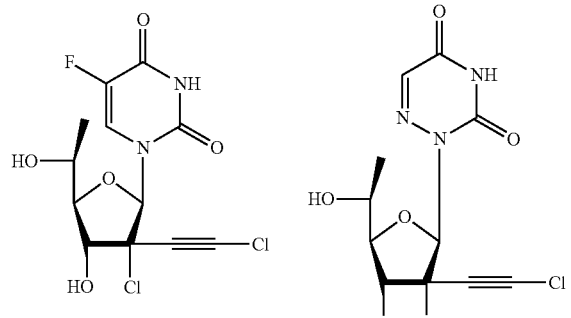
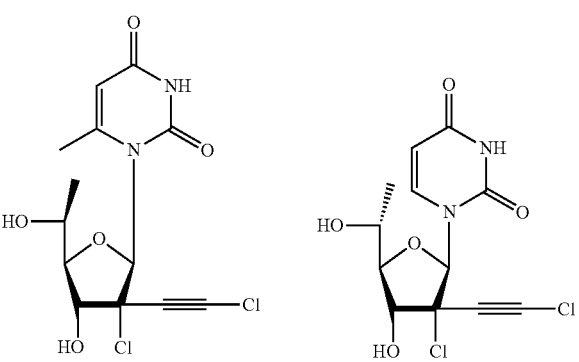
-continued
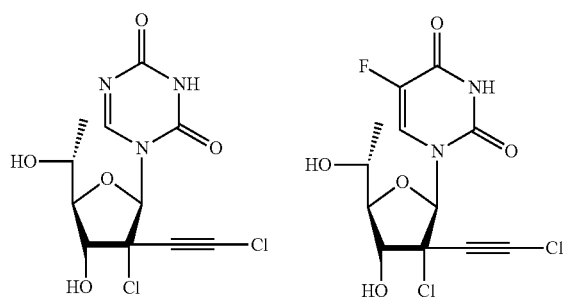
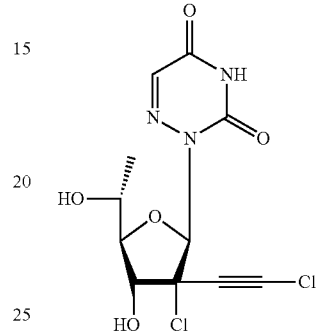
In exemplary embodiments, the compound is selected from:
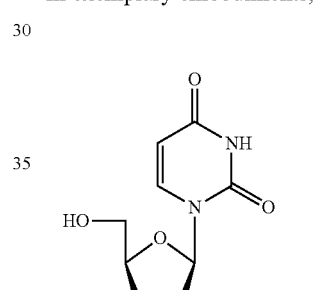
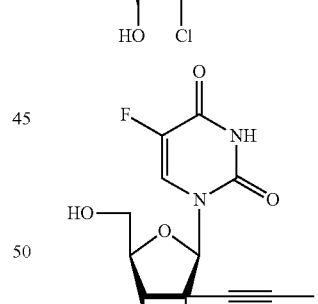
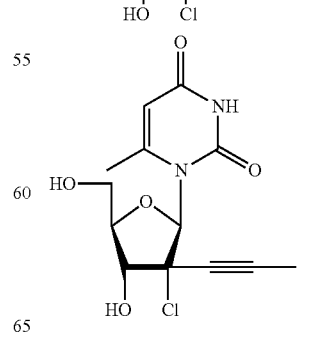

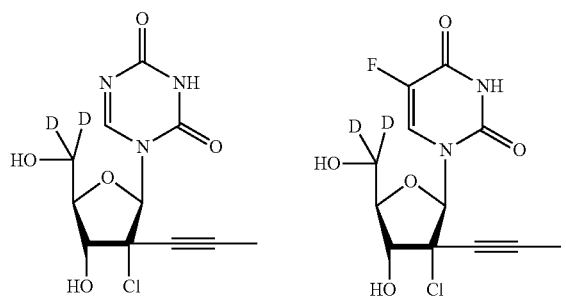
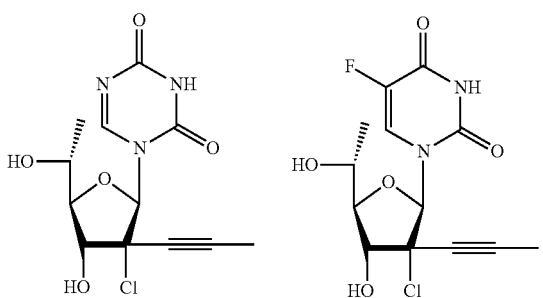
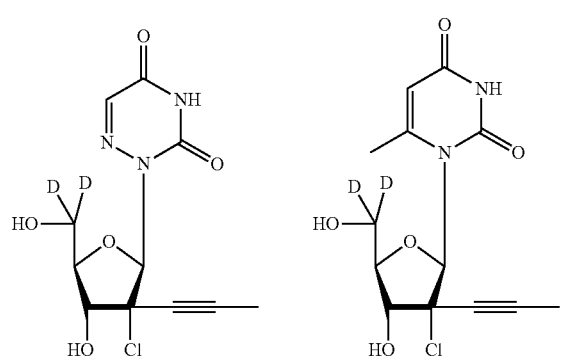
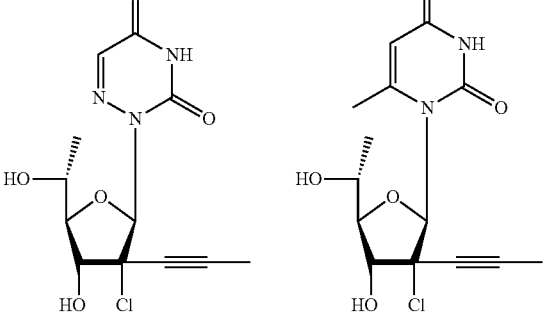
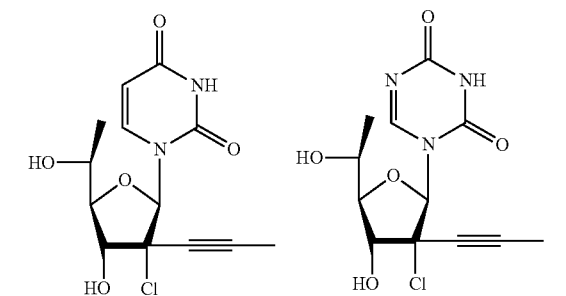
In exemplary embodiments, the compound is selected from:
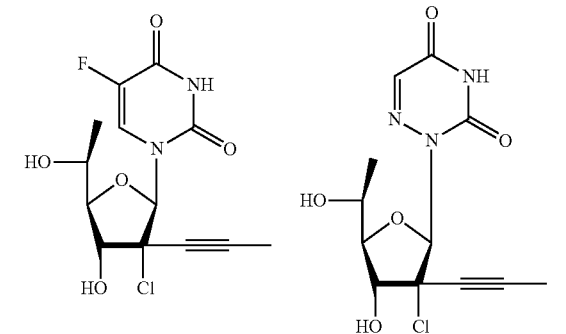
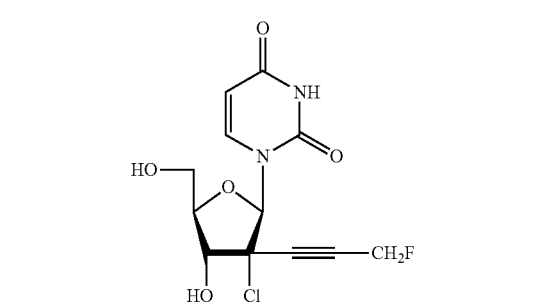
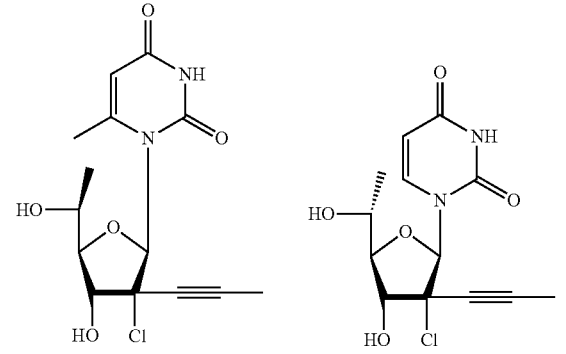
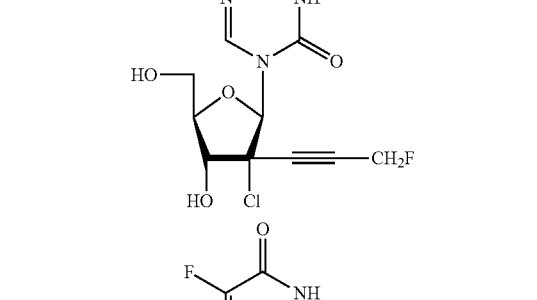
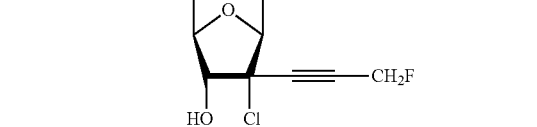

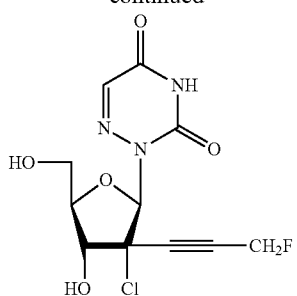
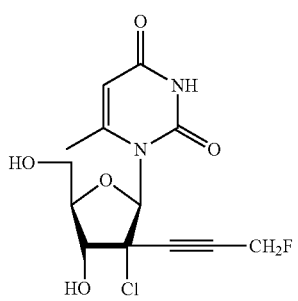
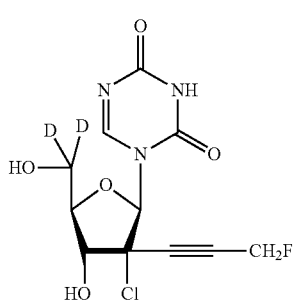
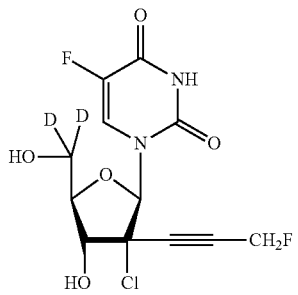
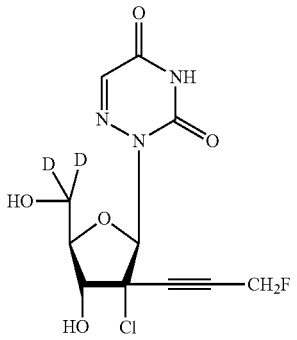
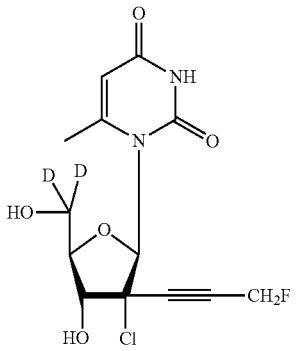
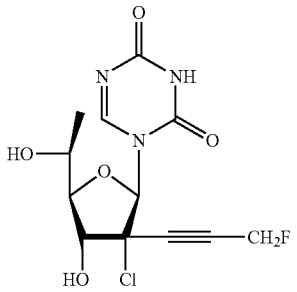
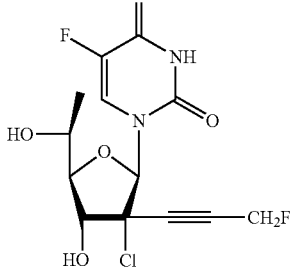

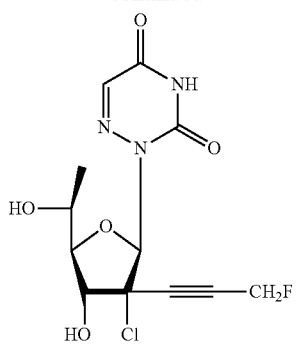
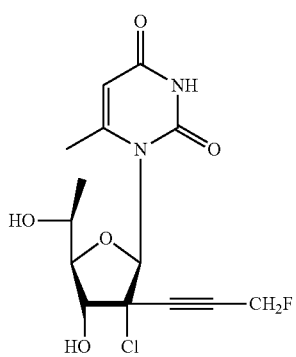
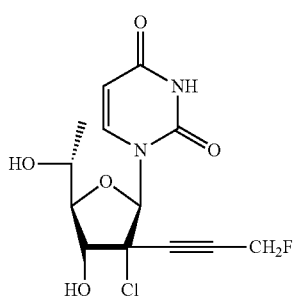
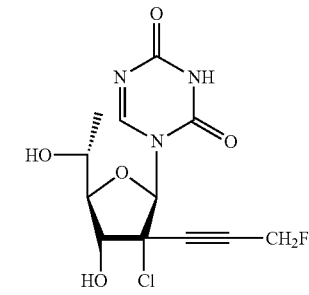
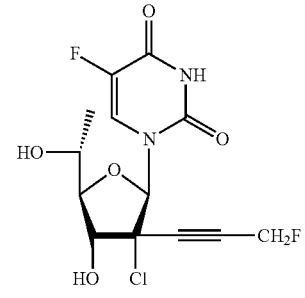
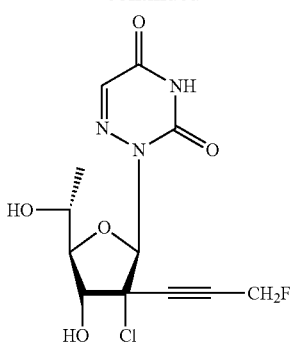
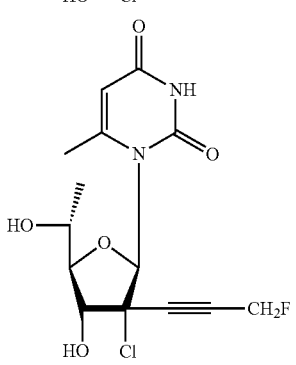
In exemplary embodiments, the compound is selected from:
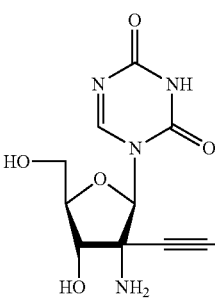 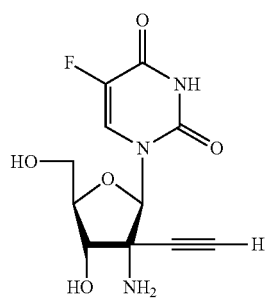
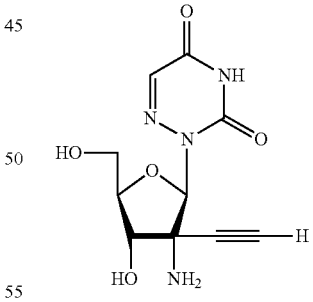
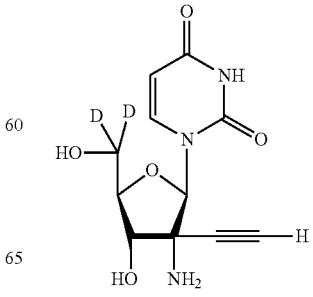 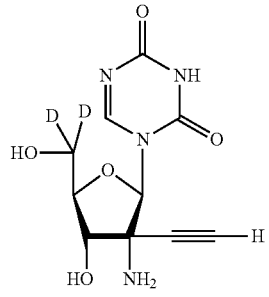

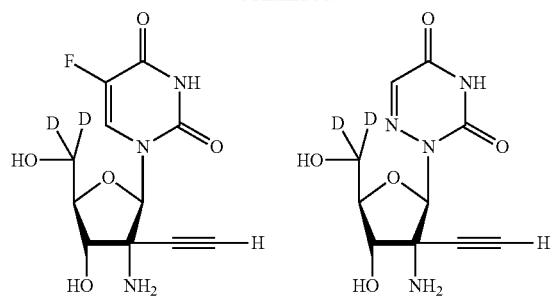
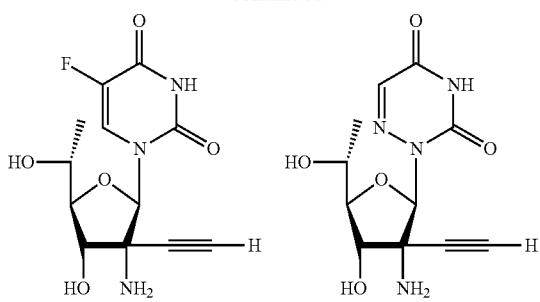
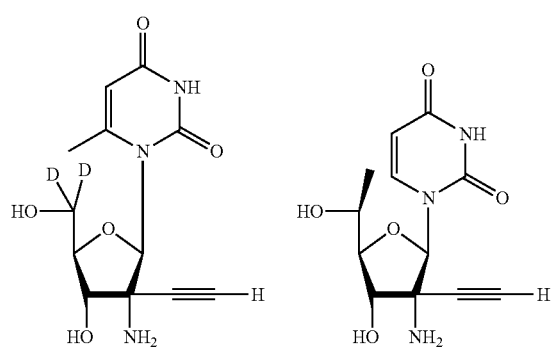
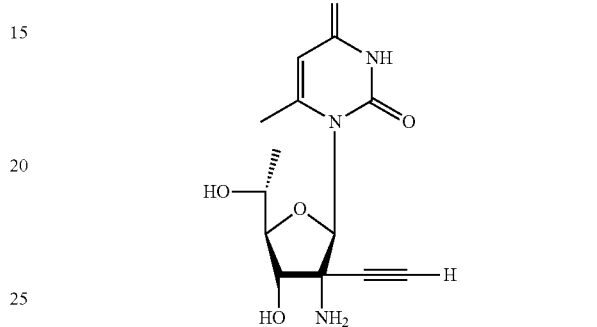
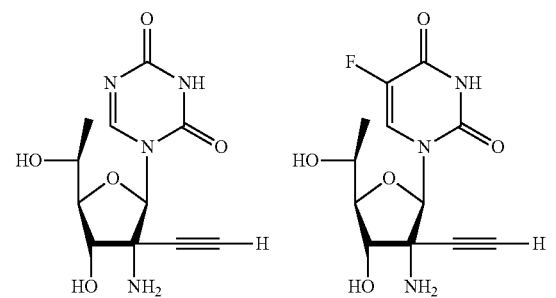
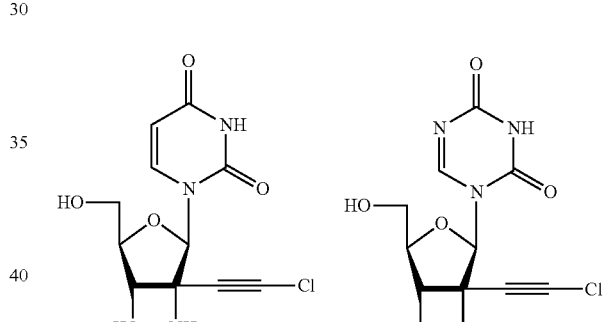
In exemplary embodiments, the compound is selected from:
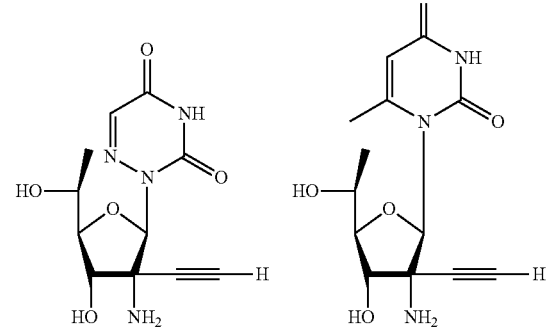
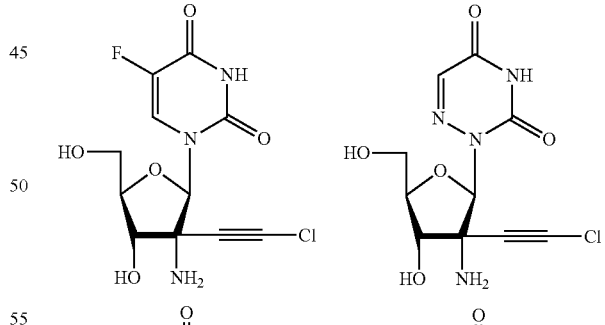
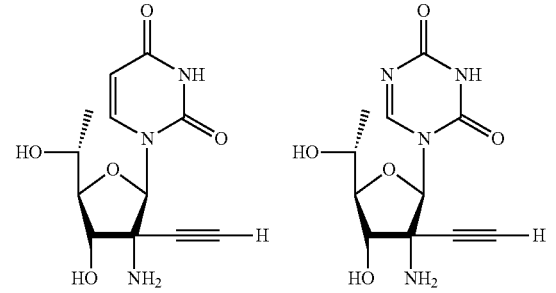
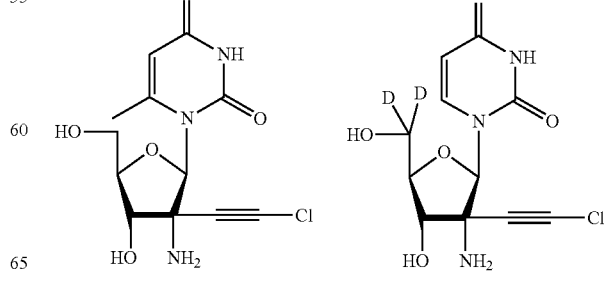

161
-continued
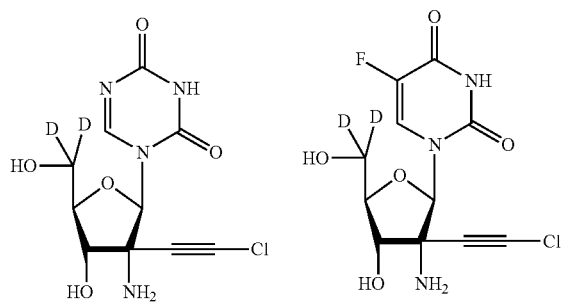
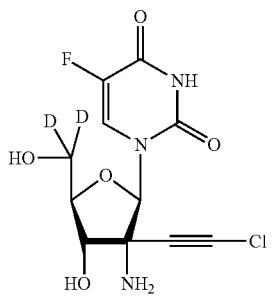
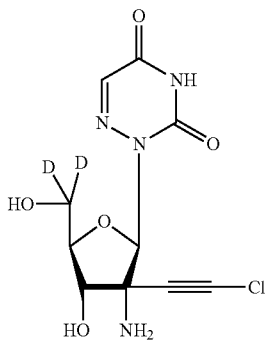
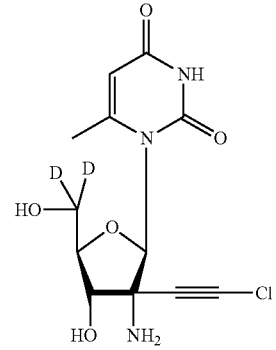
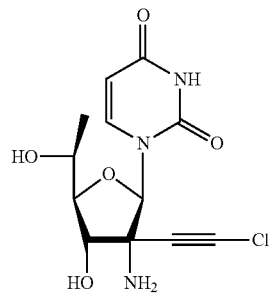
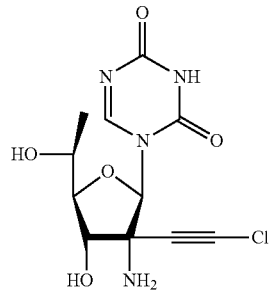
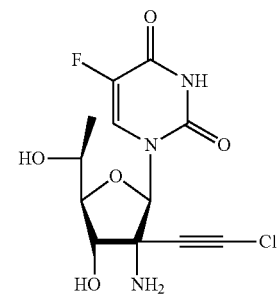
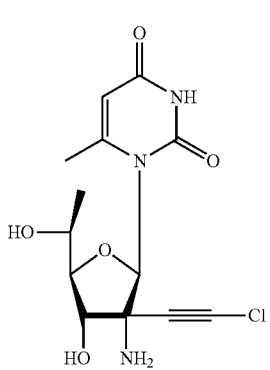
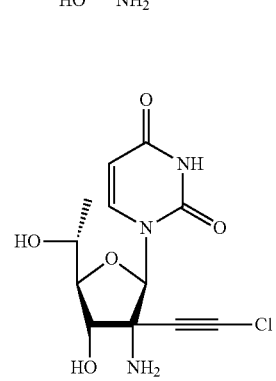
162
-continued
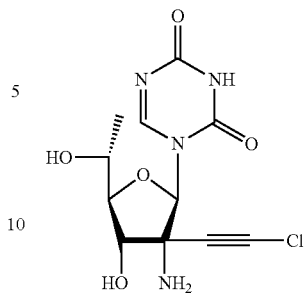
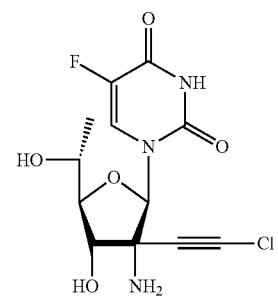
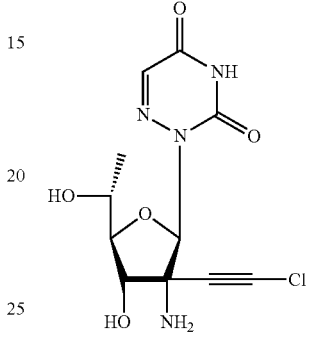
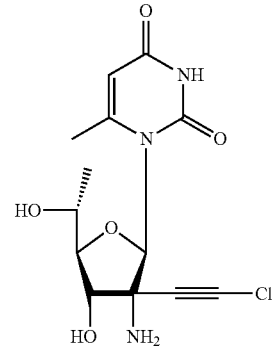
In exemplary embodiments, the compound is selected from:
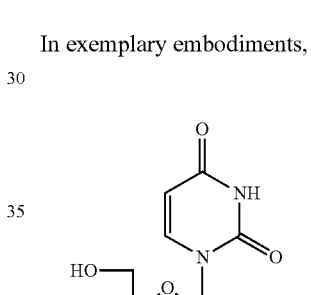
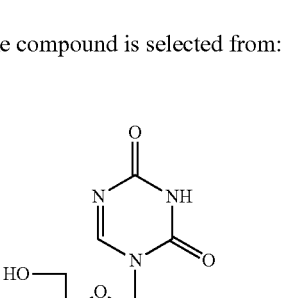
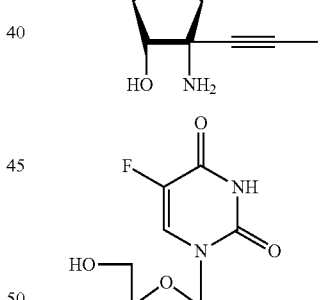
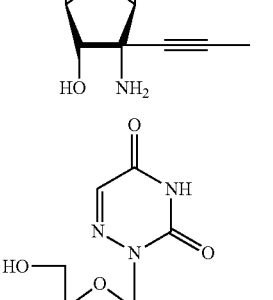
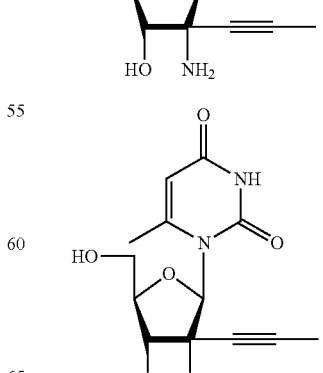
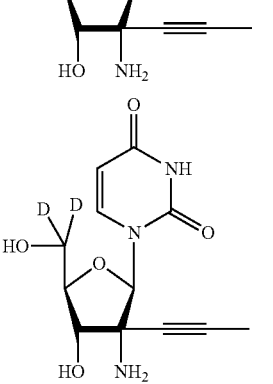

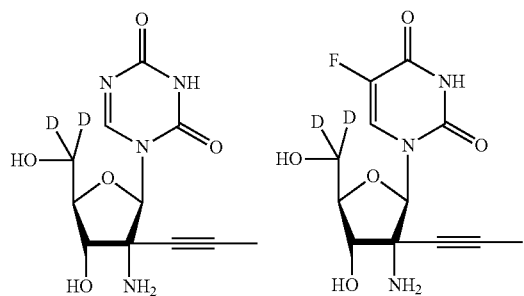
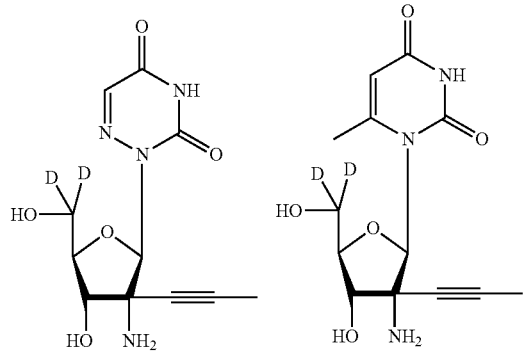
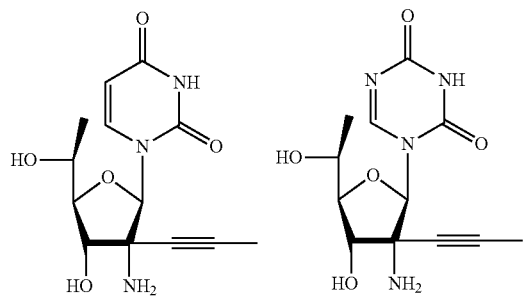
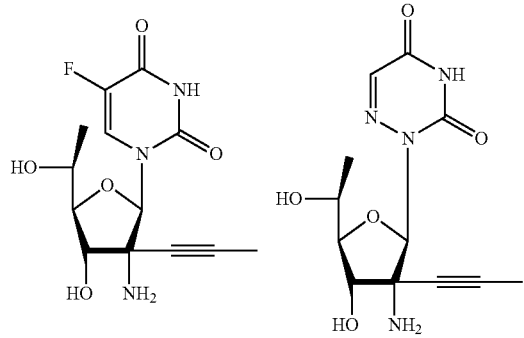
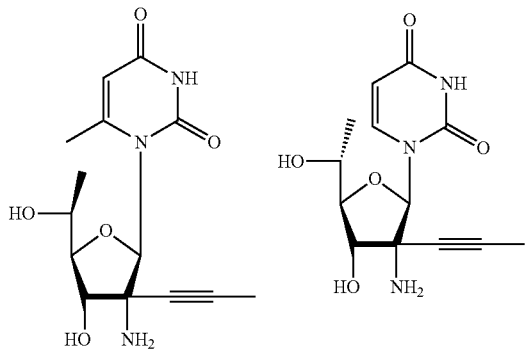
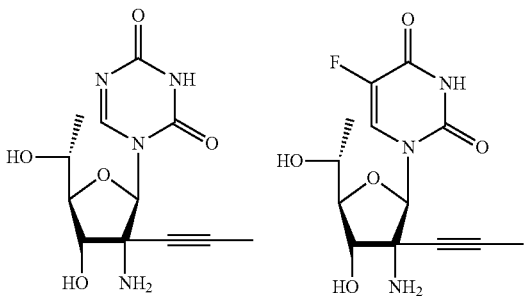
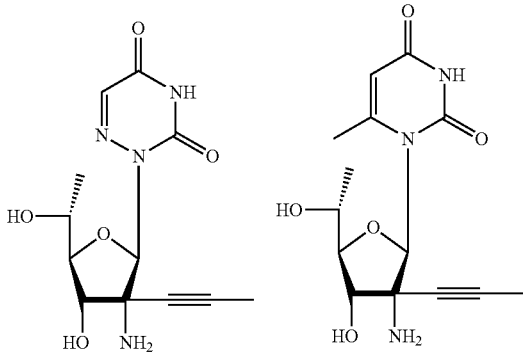
In exemplary embodiments, the compound is selected from:
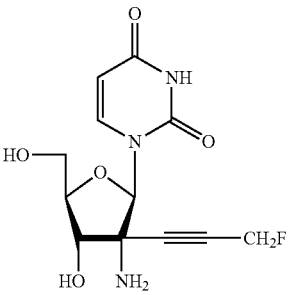
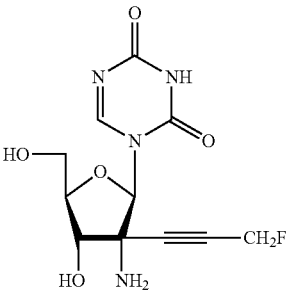
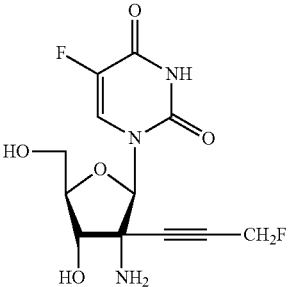

165
-continued
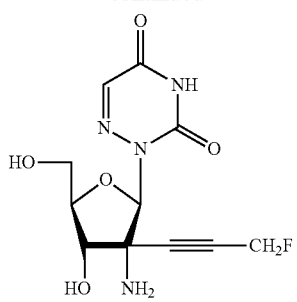
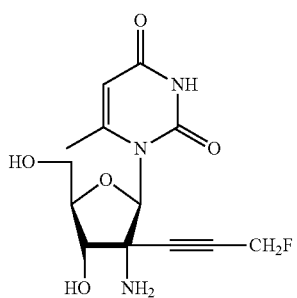
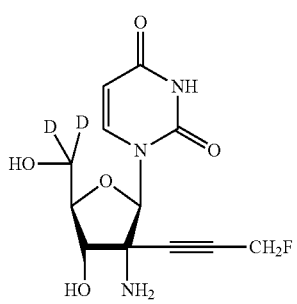
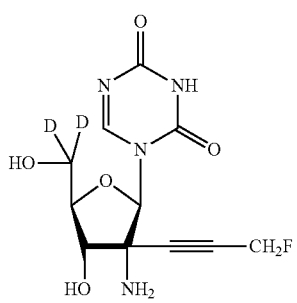
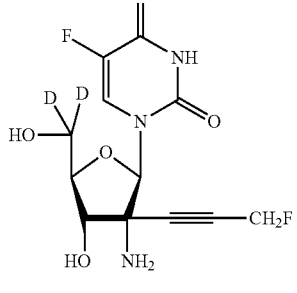
166
-continued
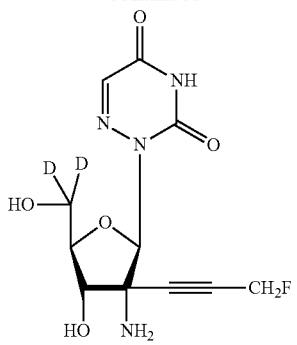
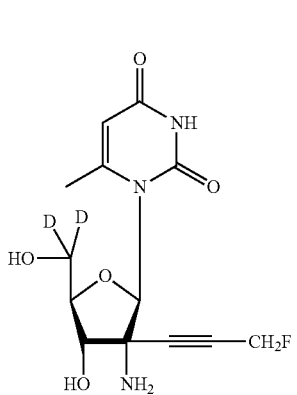
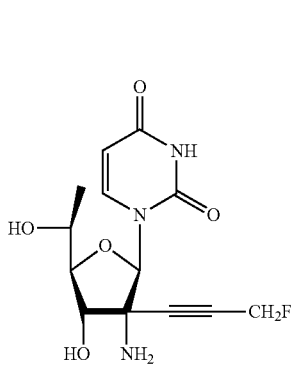
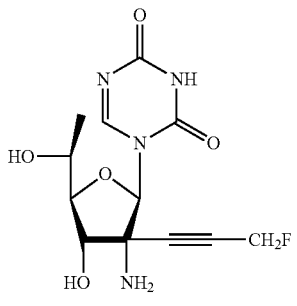
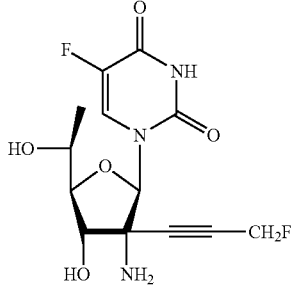

-continued

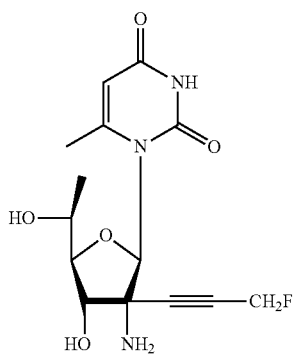
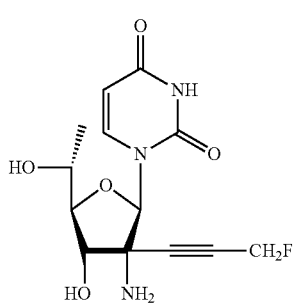
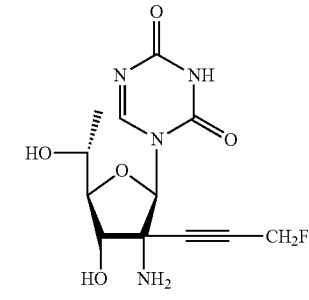
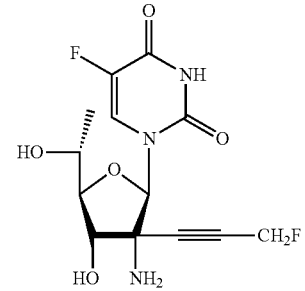
-continued
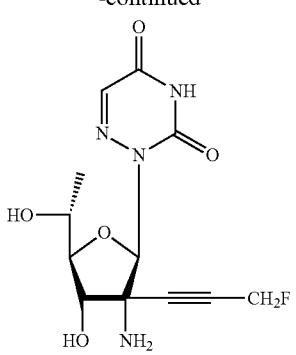
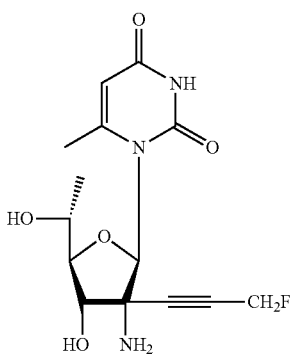
In exemplary embodiments, the compound is selected from:
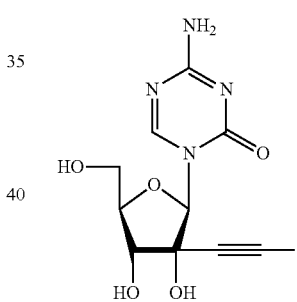 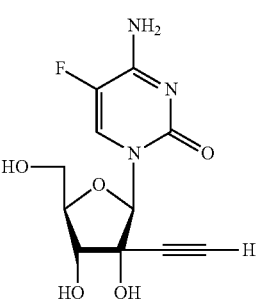
 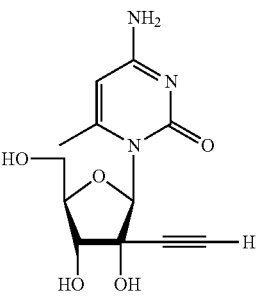
 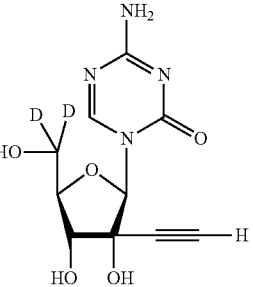

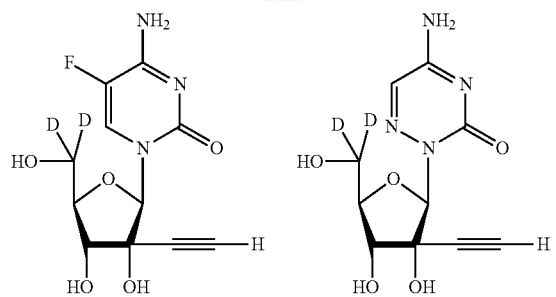
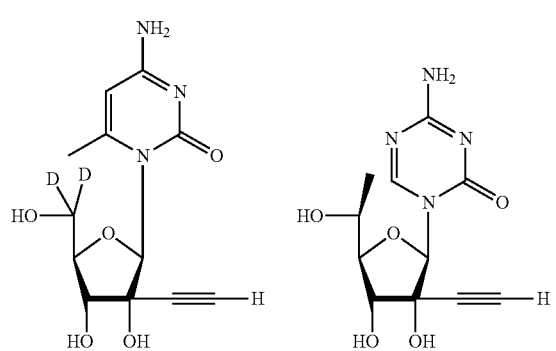
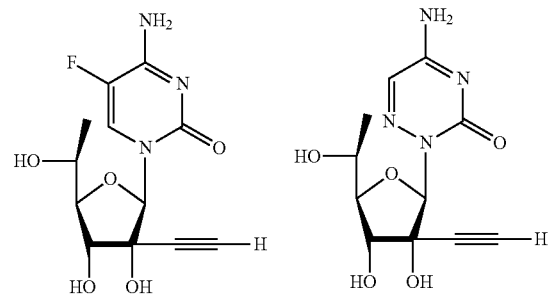
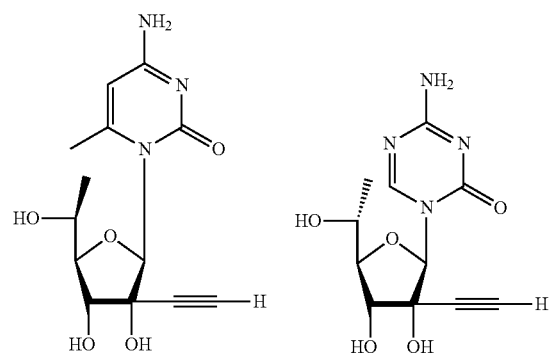
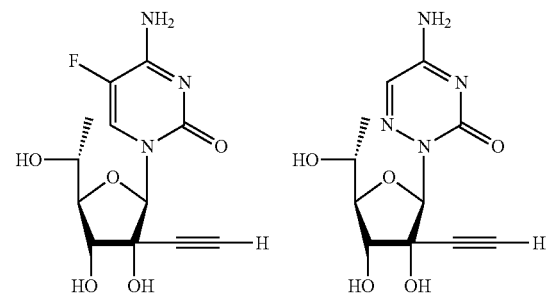
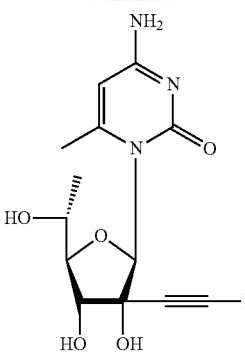
In exemplary embodiments, the compound is selected from:
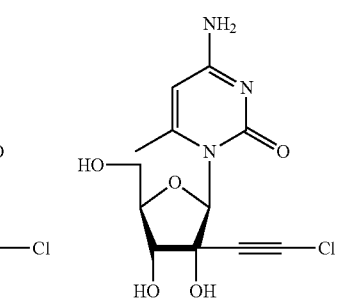
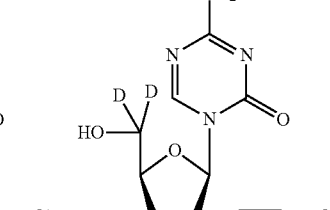
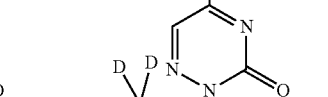
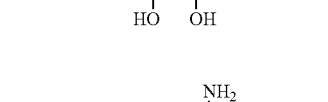
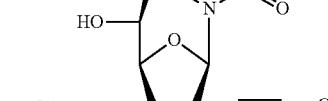

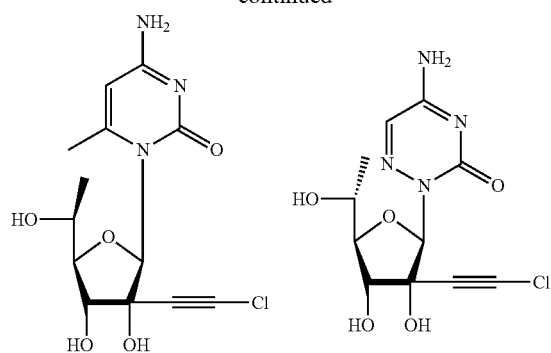
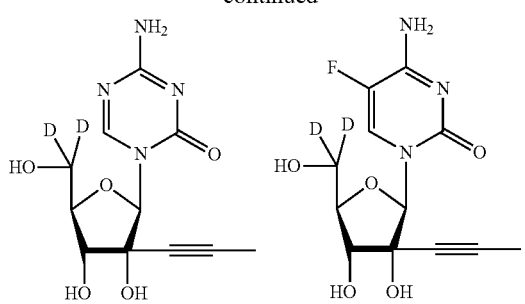
In exemplary embodiments, the compound is selected from:
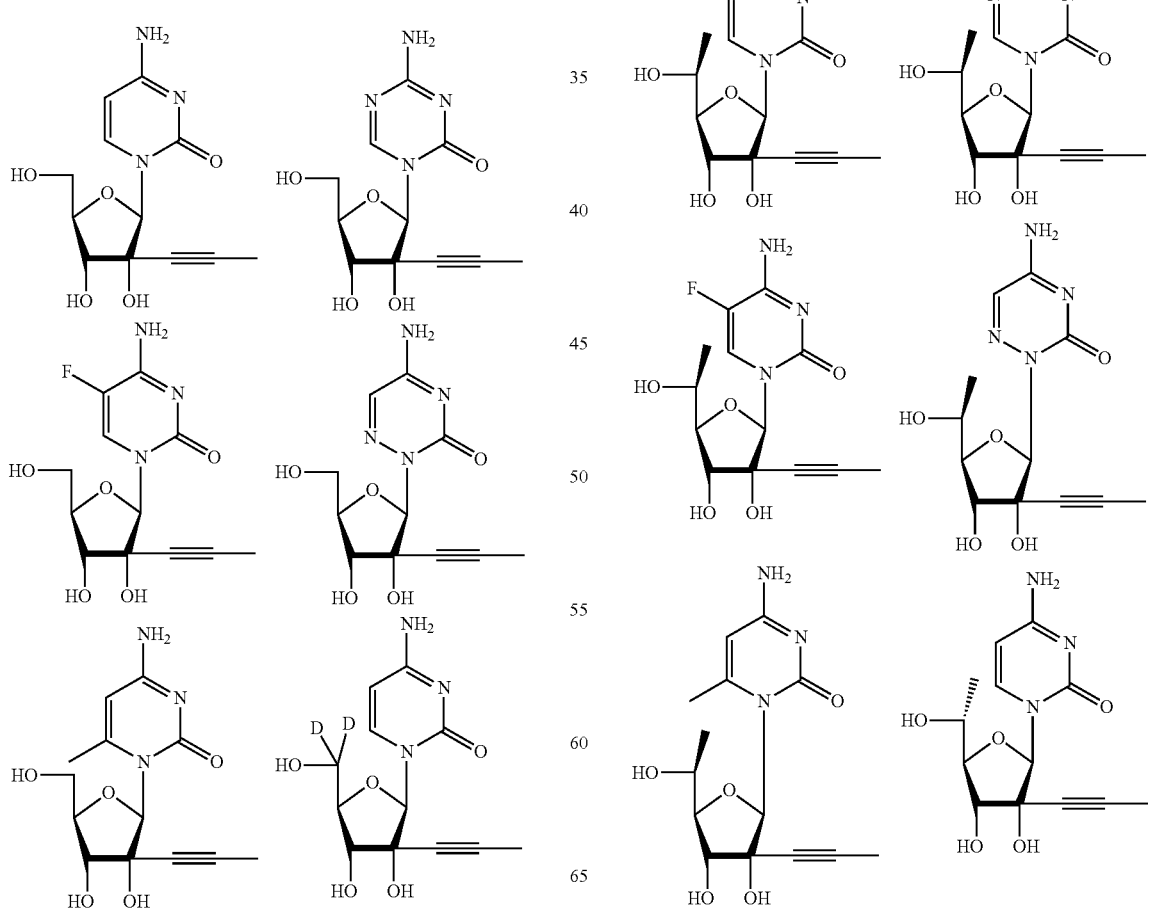

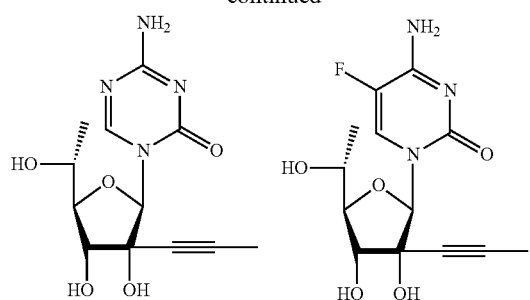
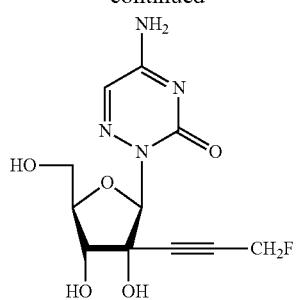
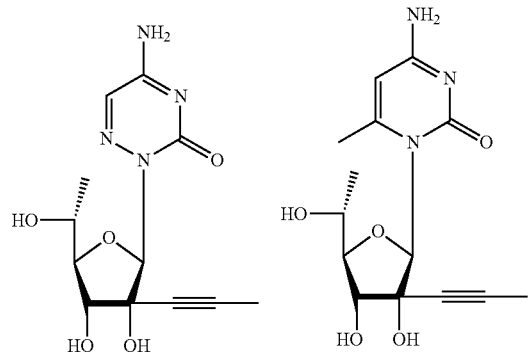
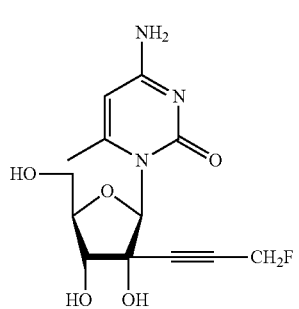
In exemplary embodiments, the compound is selected from:
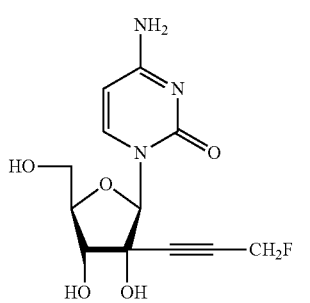
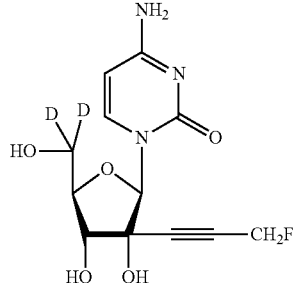
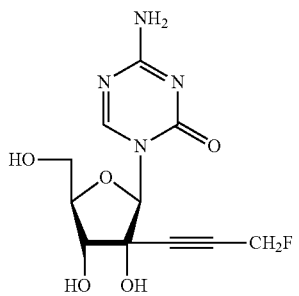
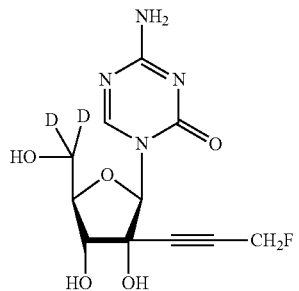
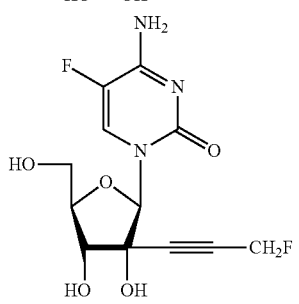
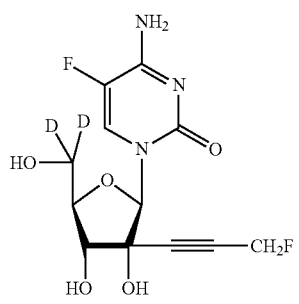

175
-continued
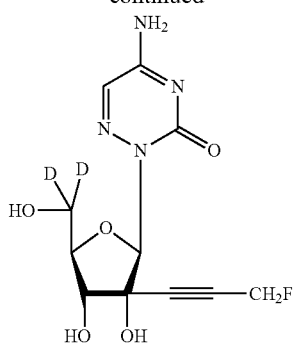
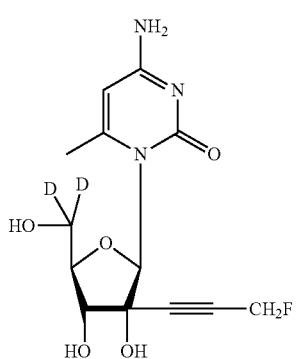
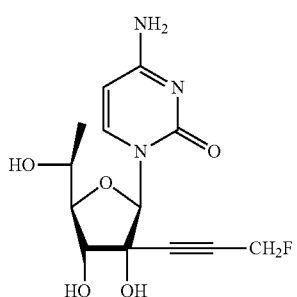
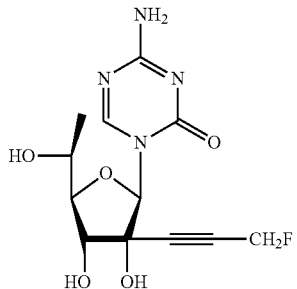
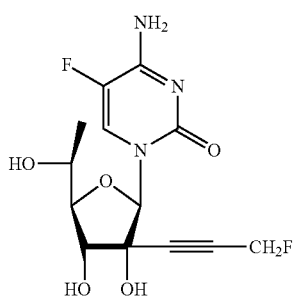
176
-continued
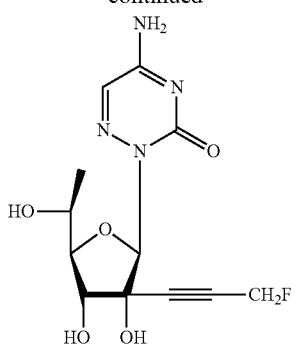
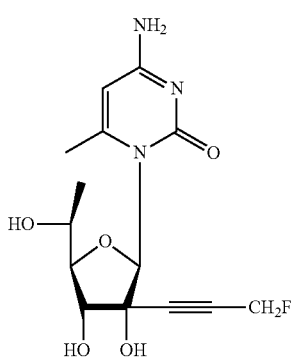
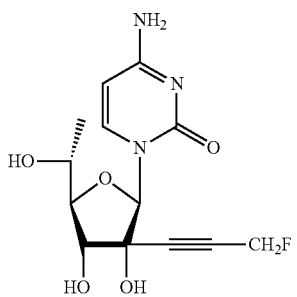
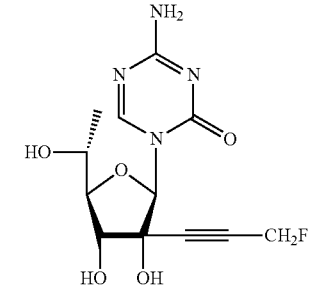
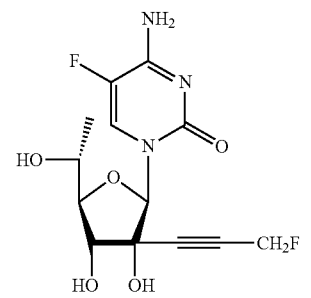

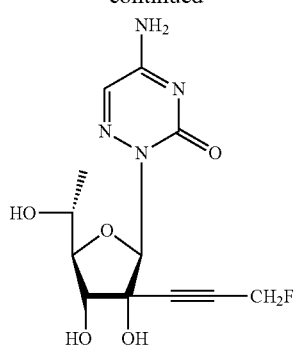
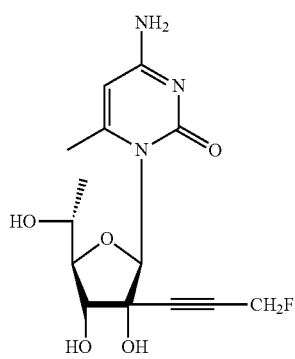
In exemplary embodiments, the compound is selected from:
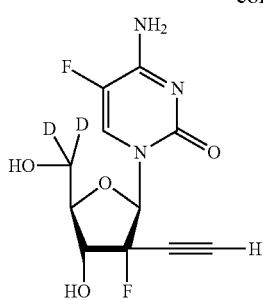
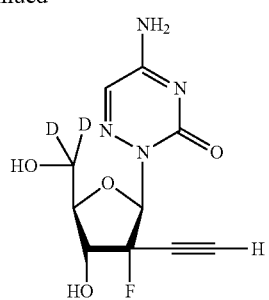
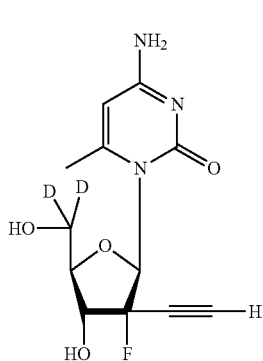
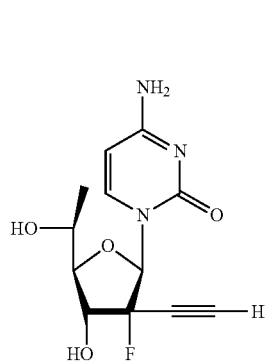
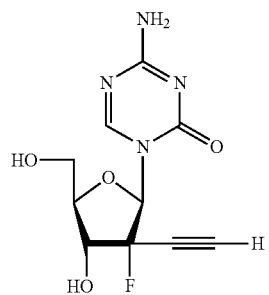
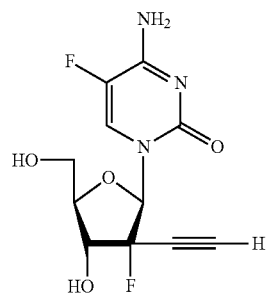
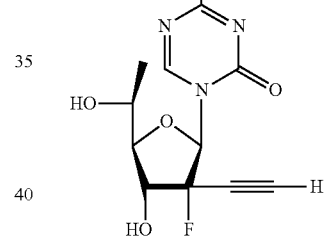
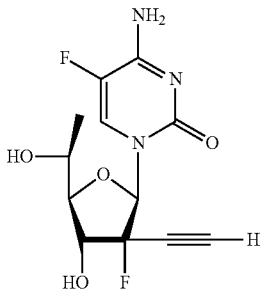
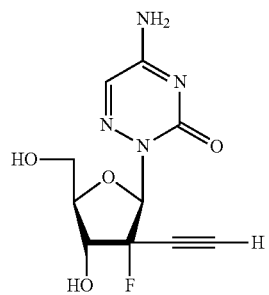
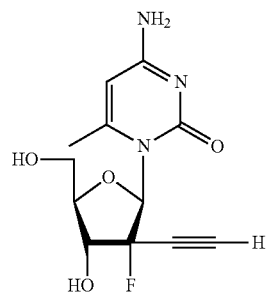
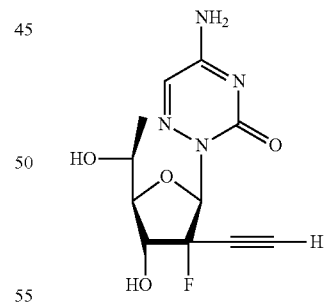
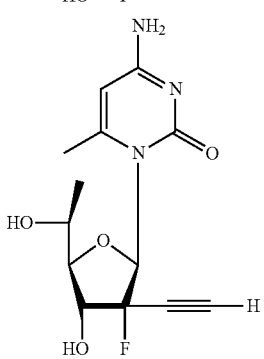
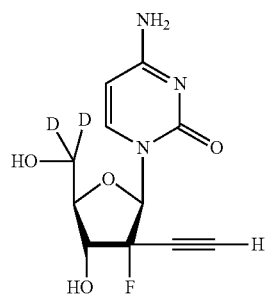
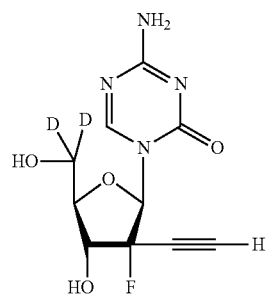
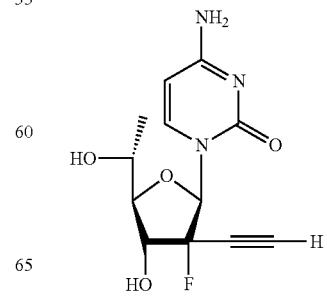
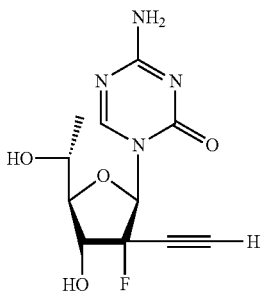

-continued
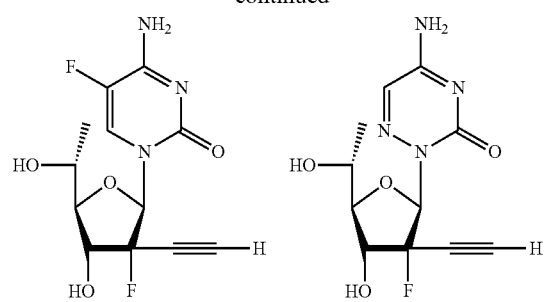
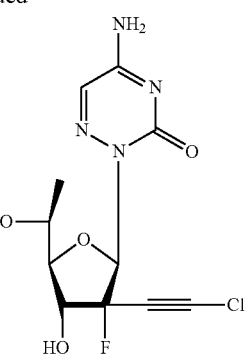
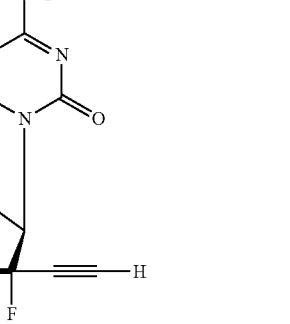
In exemplary embodiments, the compound is selected from:
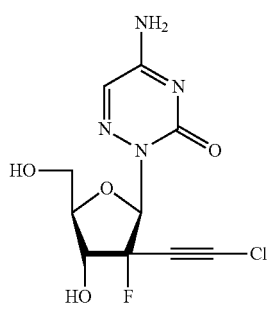
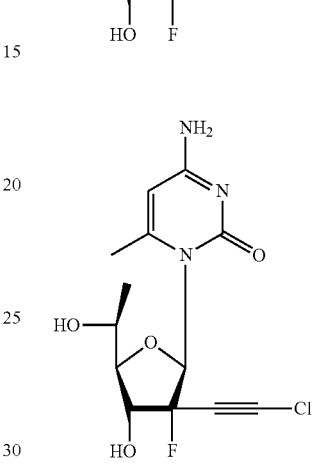
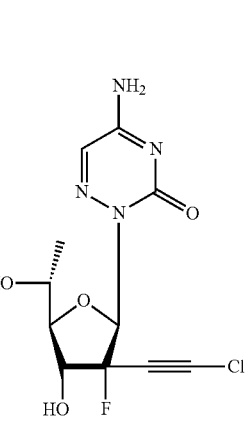
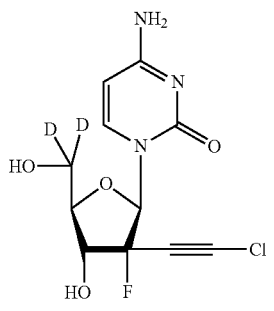
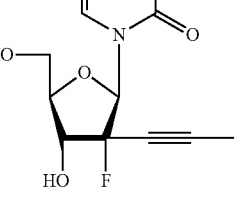
In exemplary embodiments, the compound is selected from:
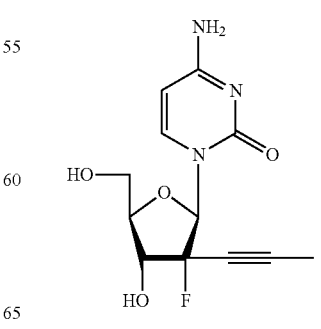 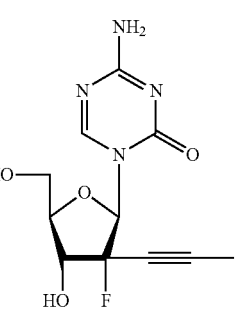

-continued
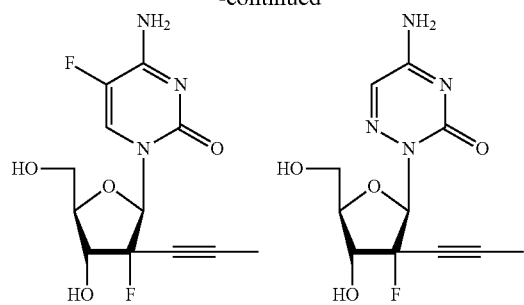
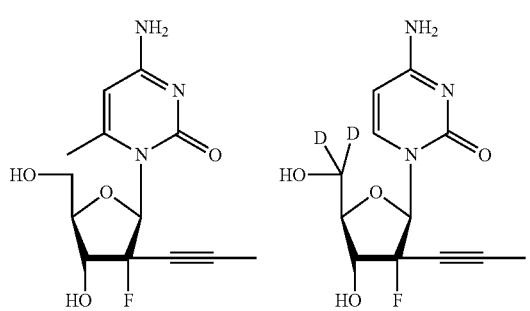
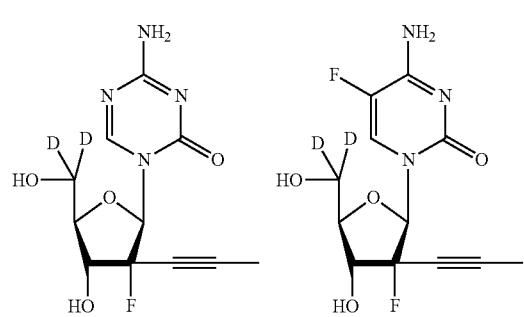
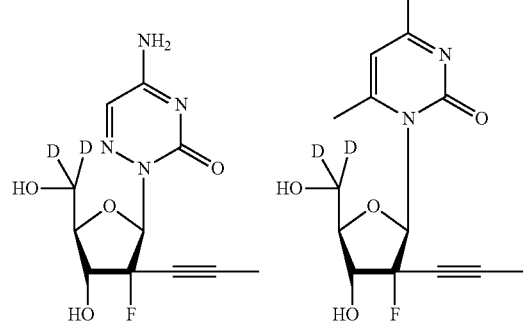
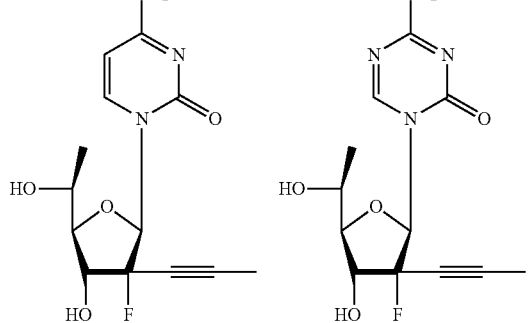
-continued
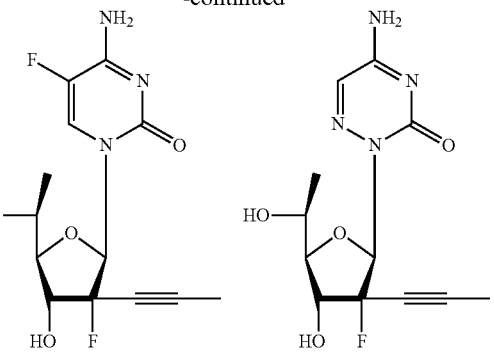
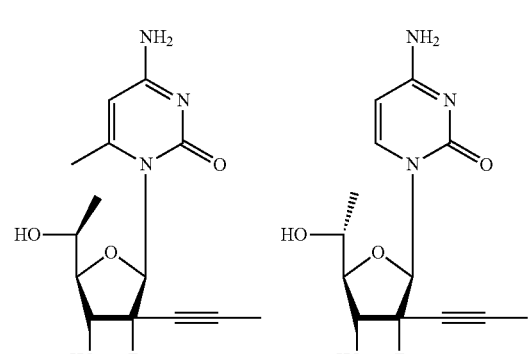
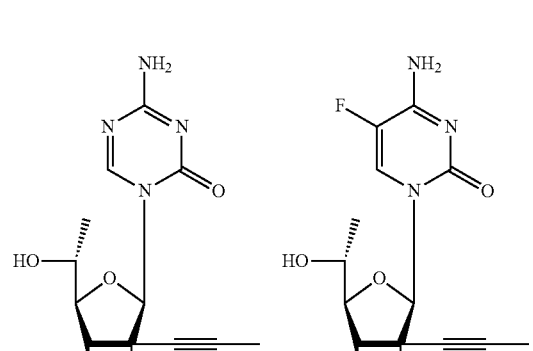
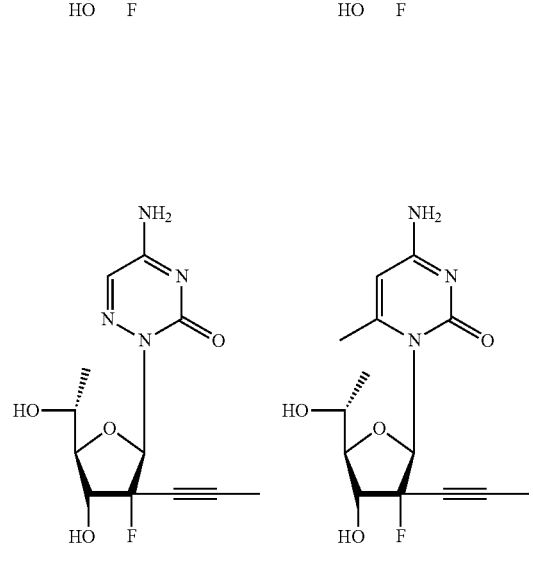

In exemplary embodiments, the compound is selected from:
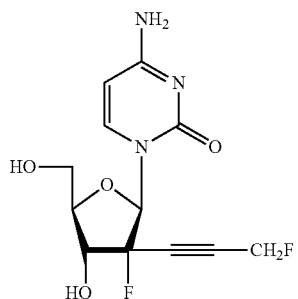
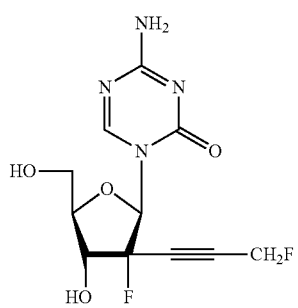
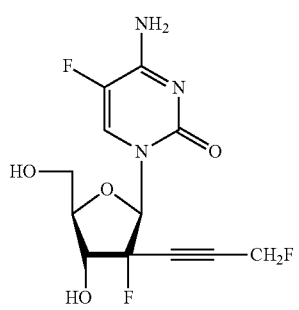
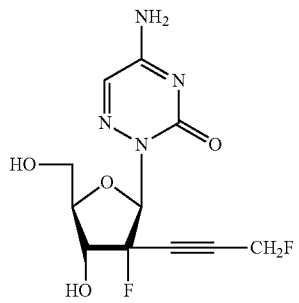
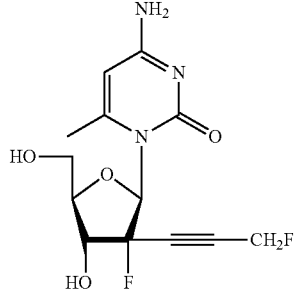
-continued
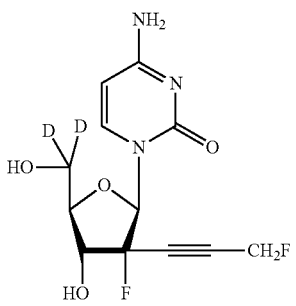
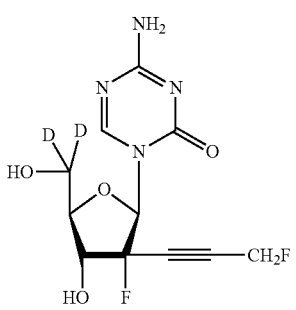
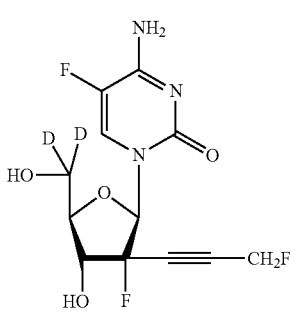
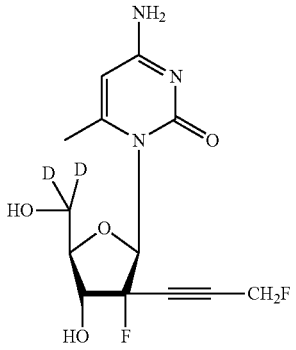

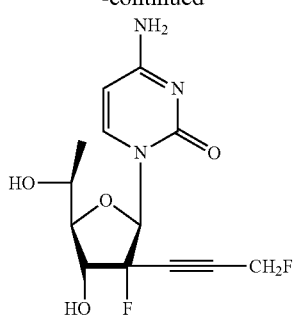
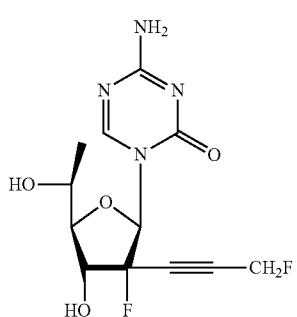
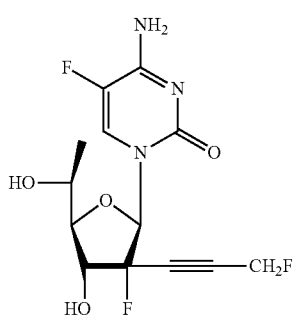
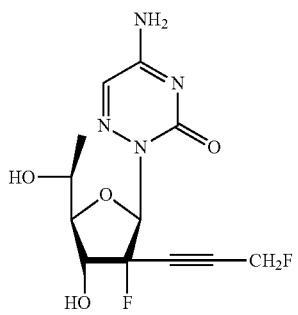
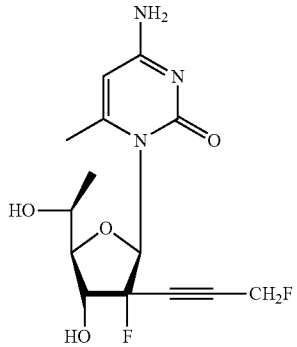
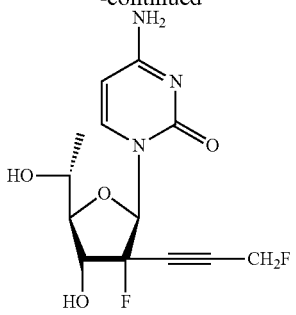
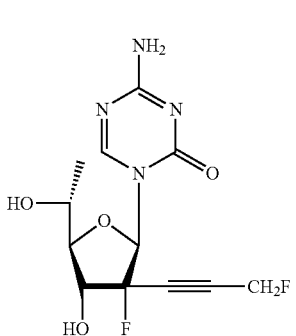
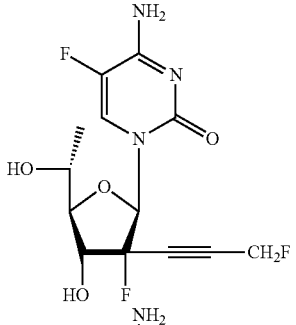
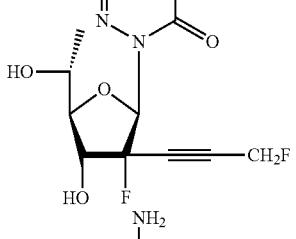
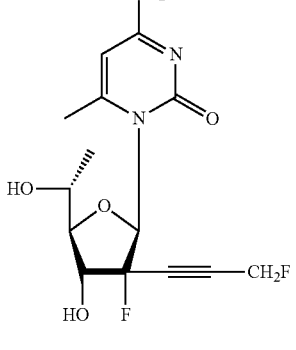

In exemplary embodiments, the compound is selected from:
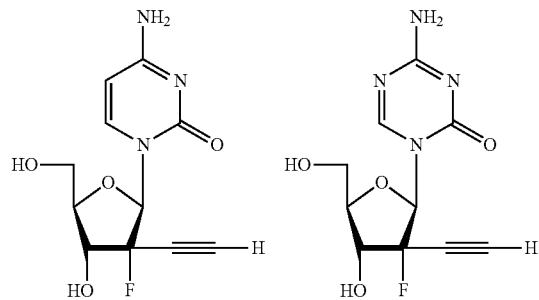
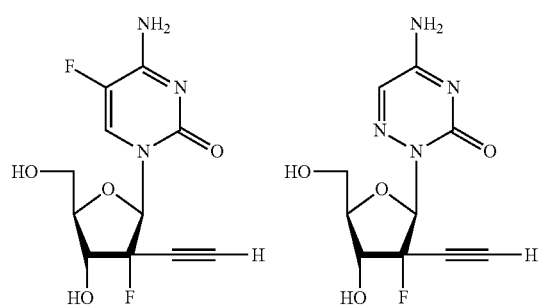
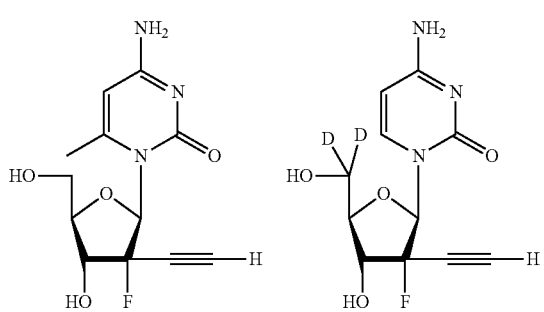
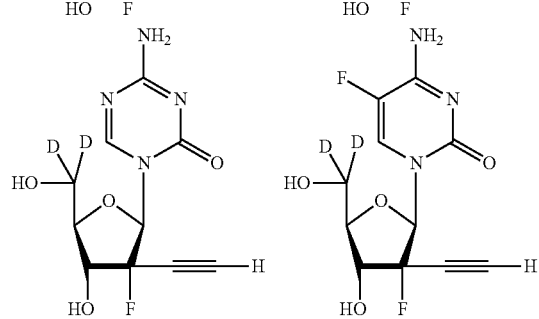
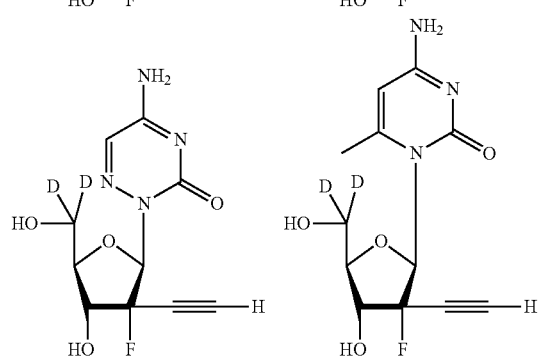
-continued
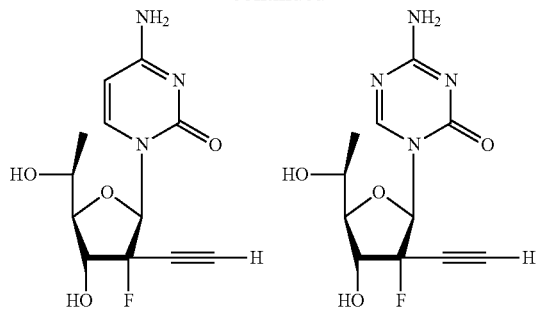

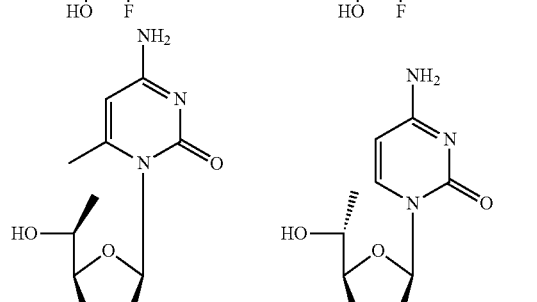
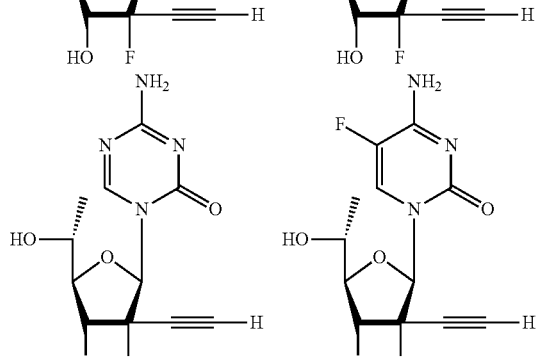
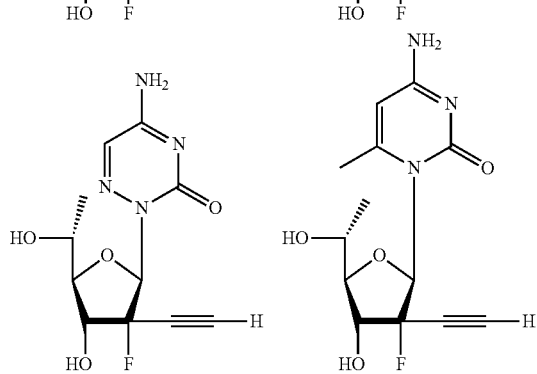

In exemplary embodiments, the compound is selected from:
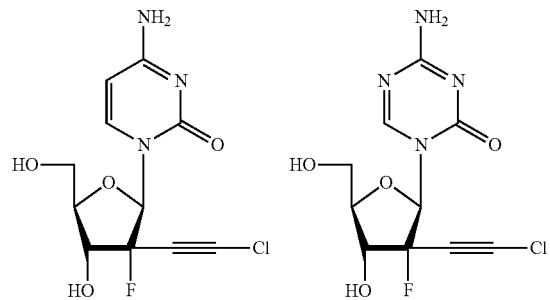
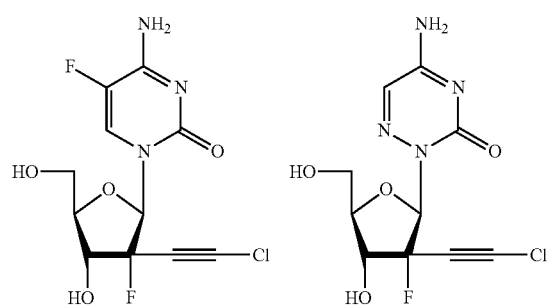
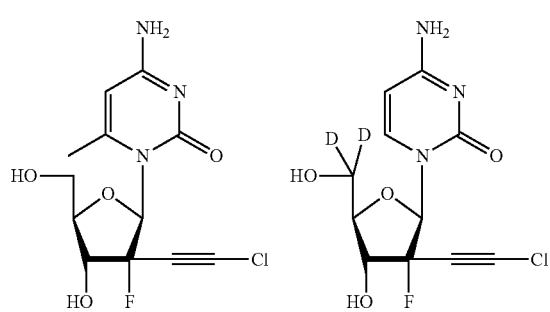
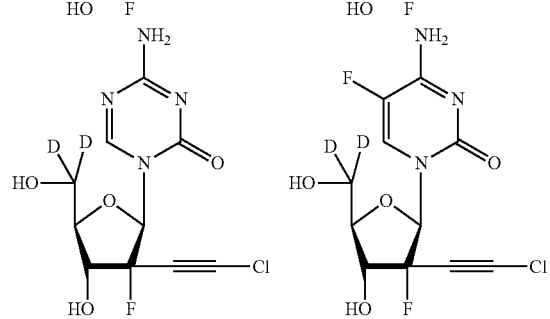
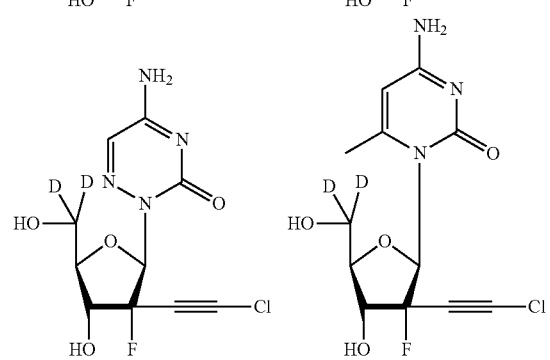
-continued
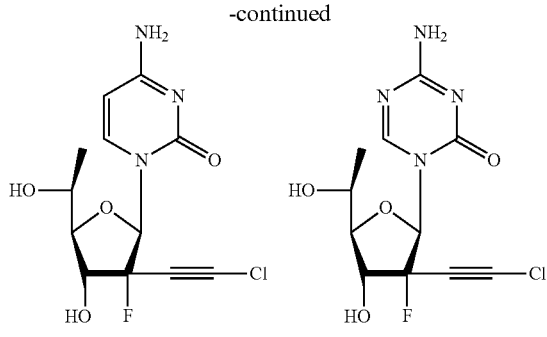
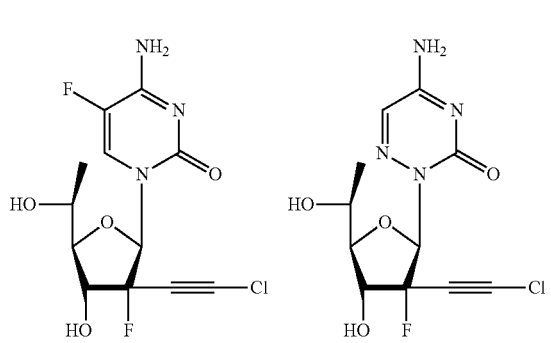
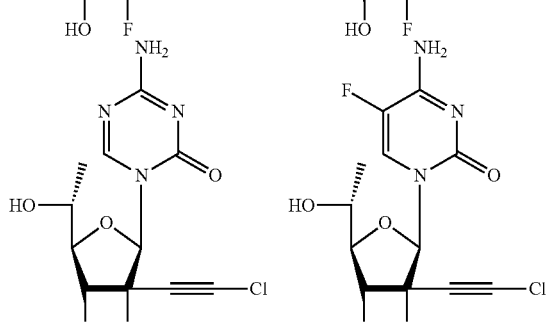
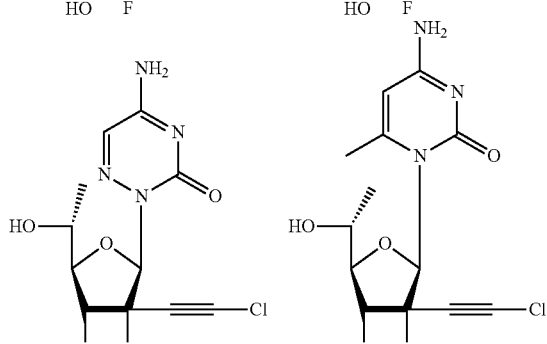

In exemplary embodiments, the compound is selected from:
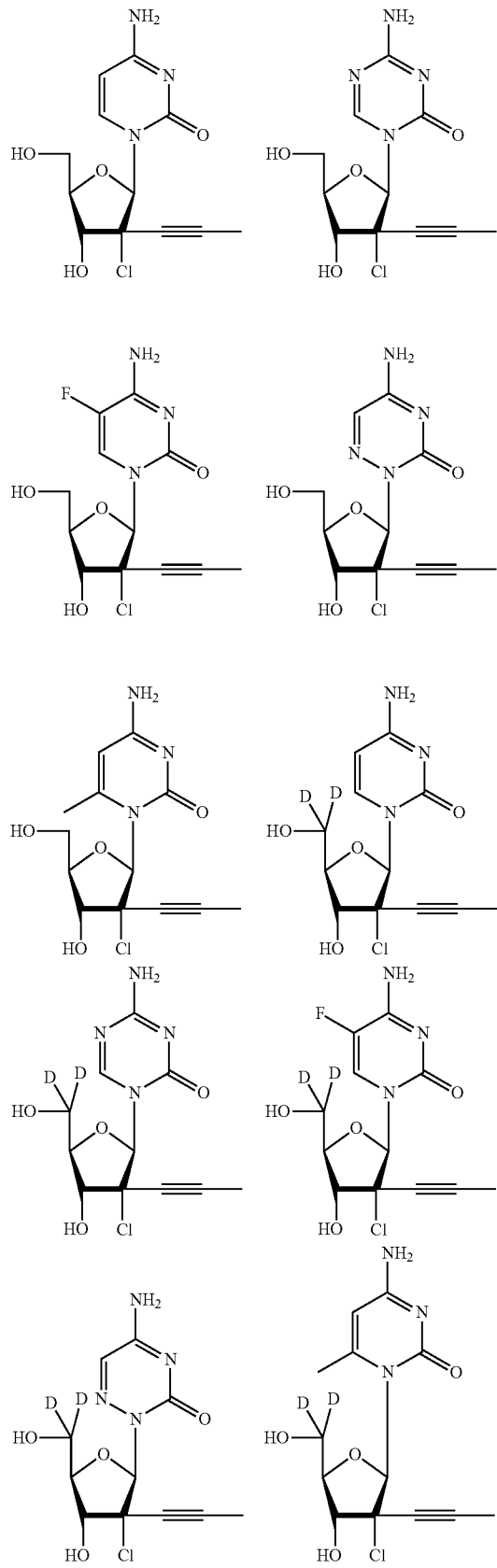
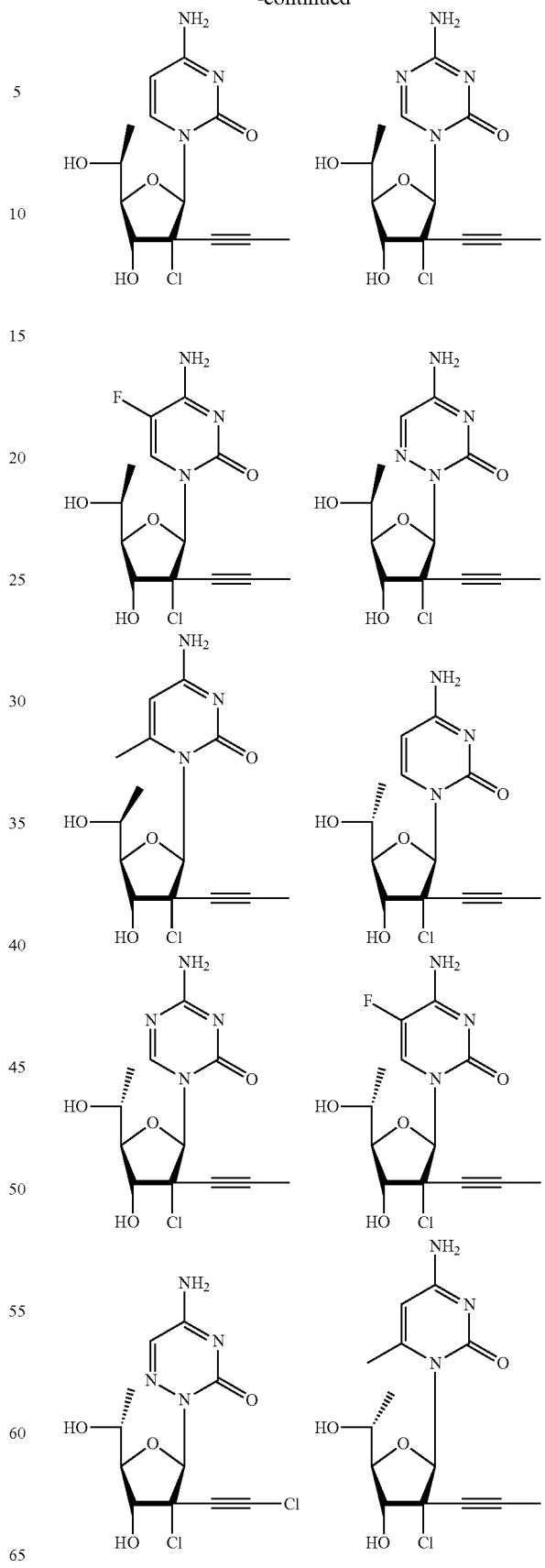
-continued In exemplary embodiments, the compound is selected from:
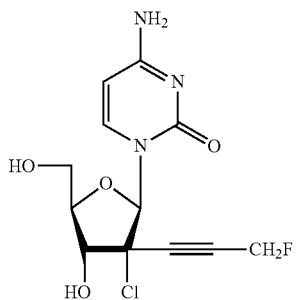
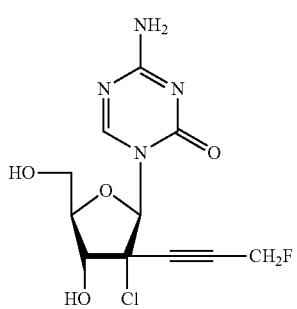
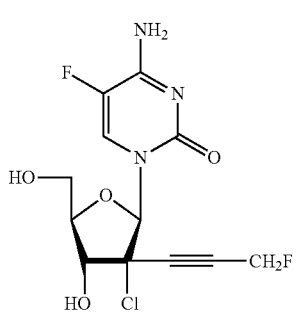
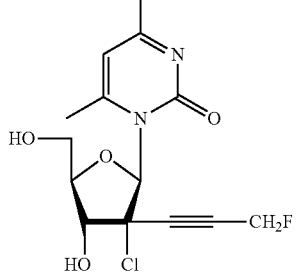
-continued
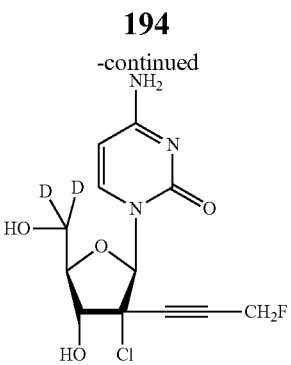
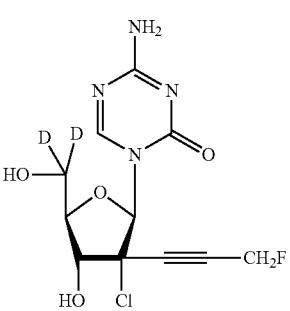
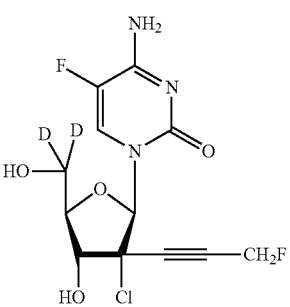
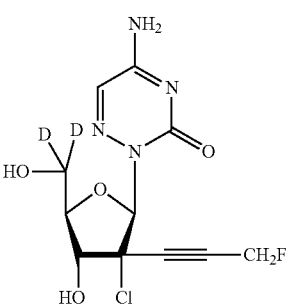
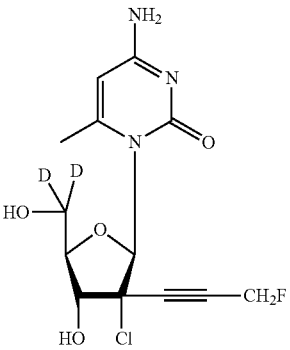

195
-continued
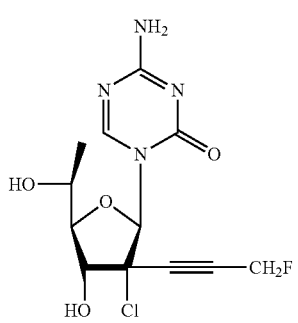
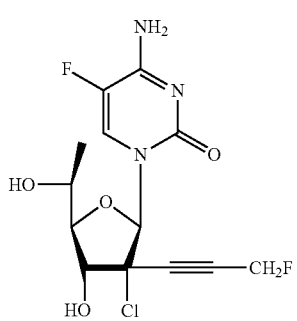
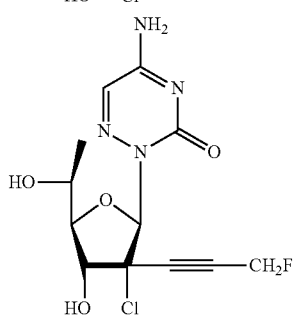
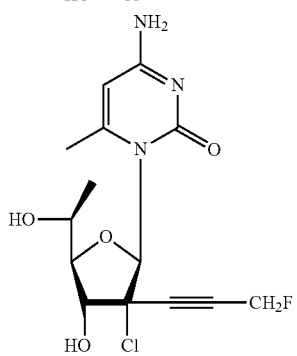
196
-continued

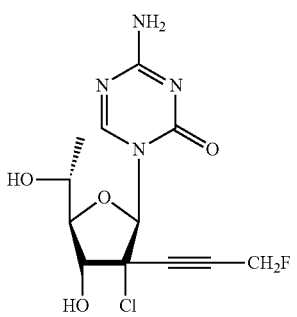
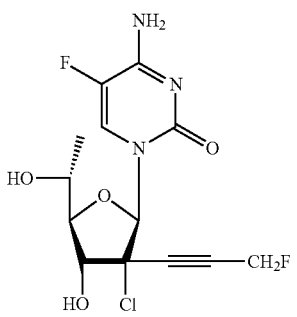
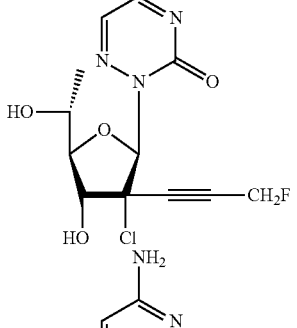
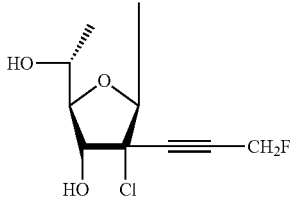

In exemplary embodiments, the compound is selected from:
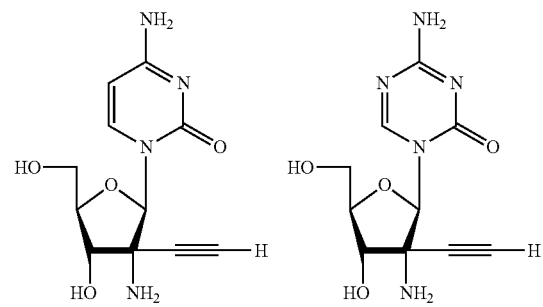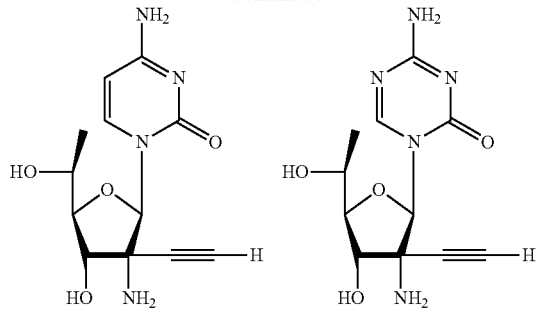
-continued
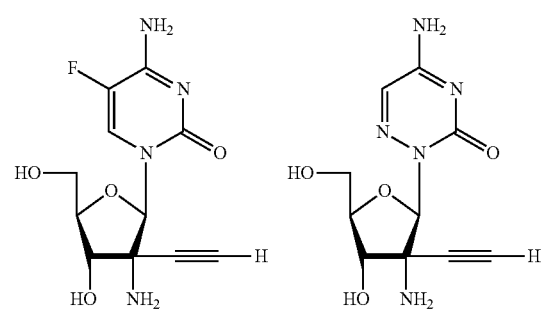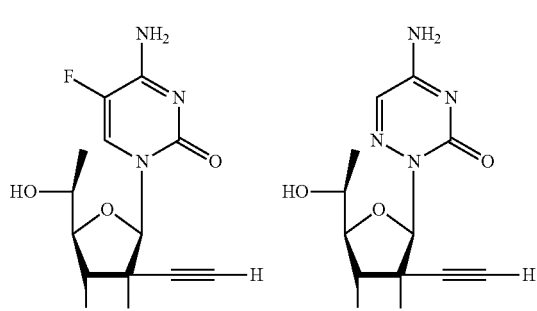
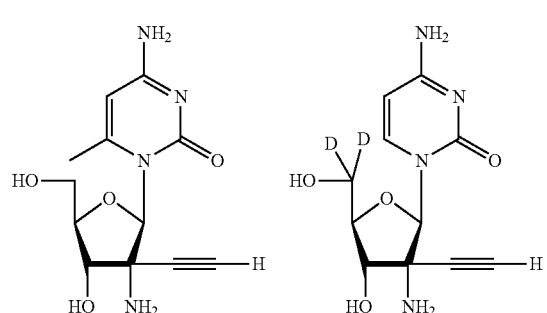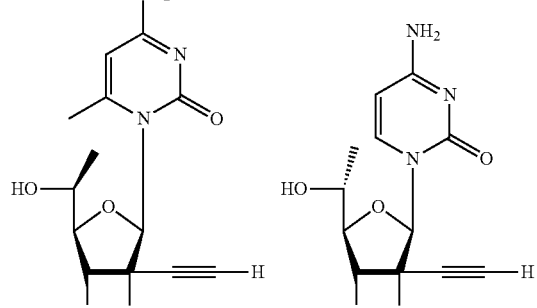
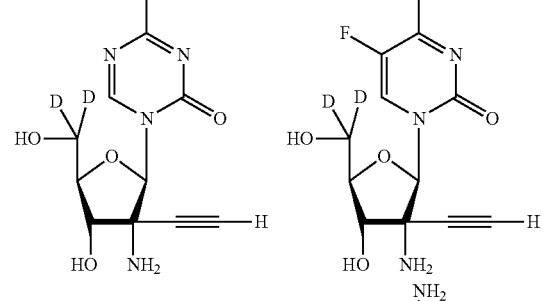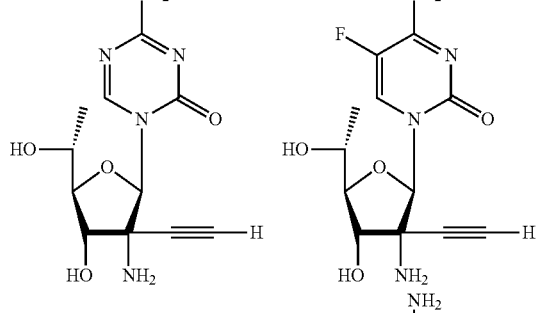
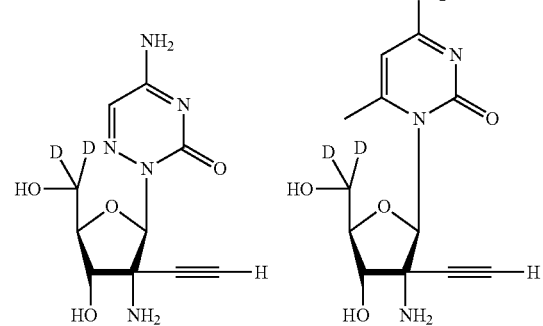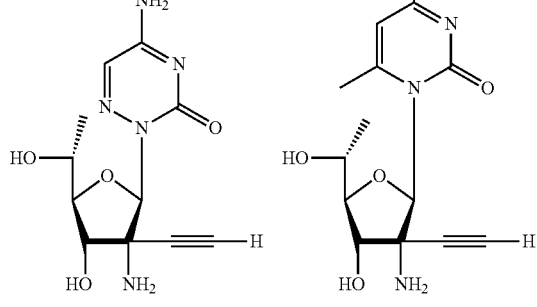

In exemplary embodiments, the compound is selected from:
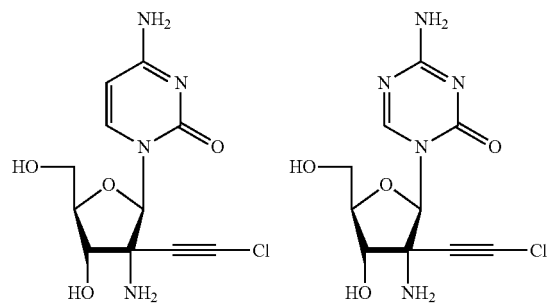
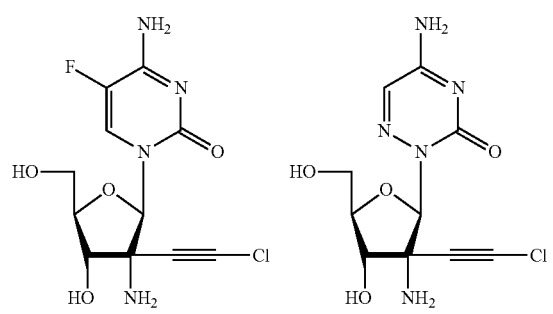
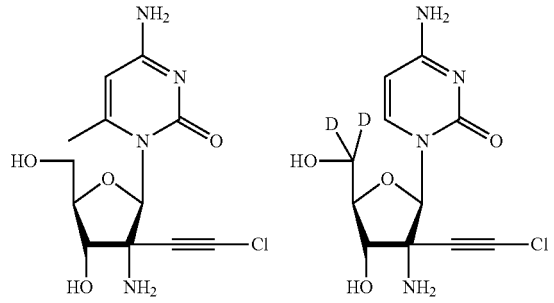
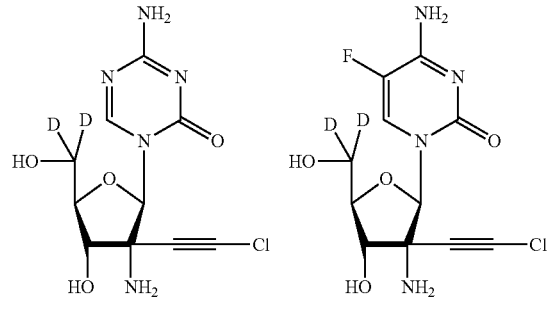
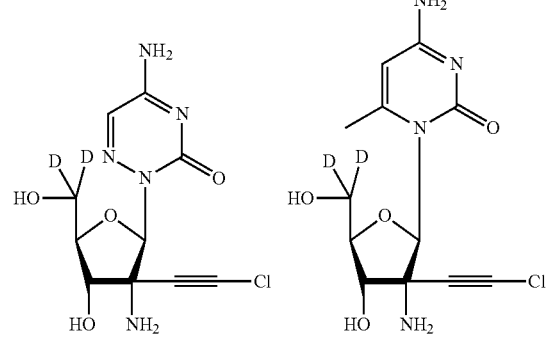
-continued
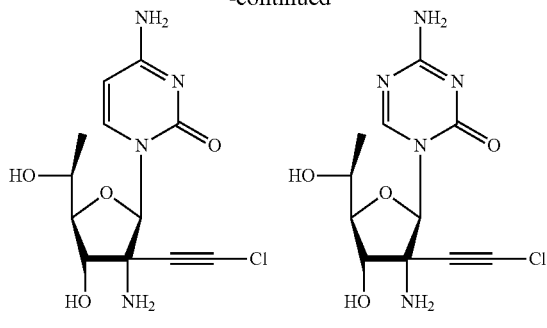
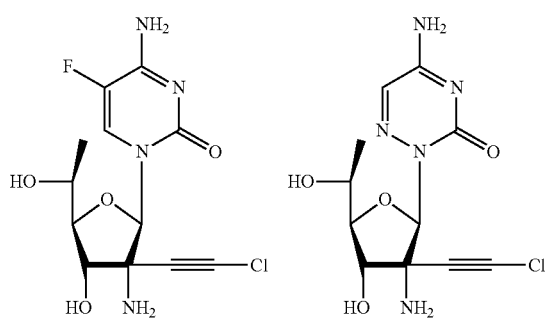

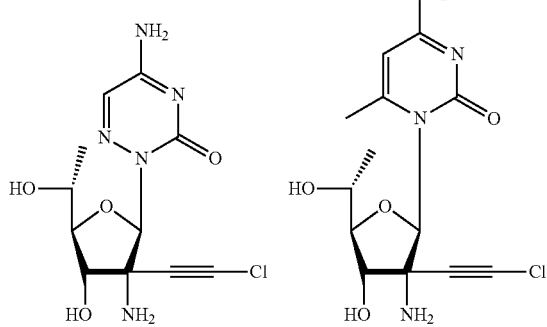

201
In exemplary embodiments, the compound is selected from:
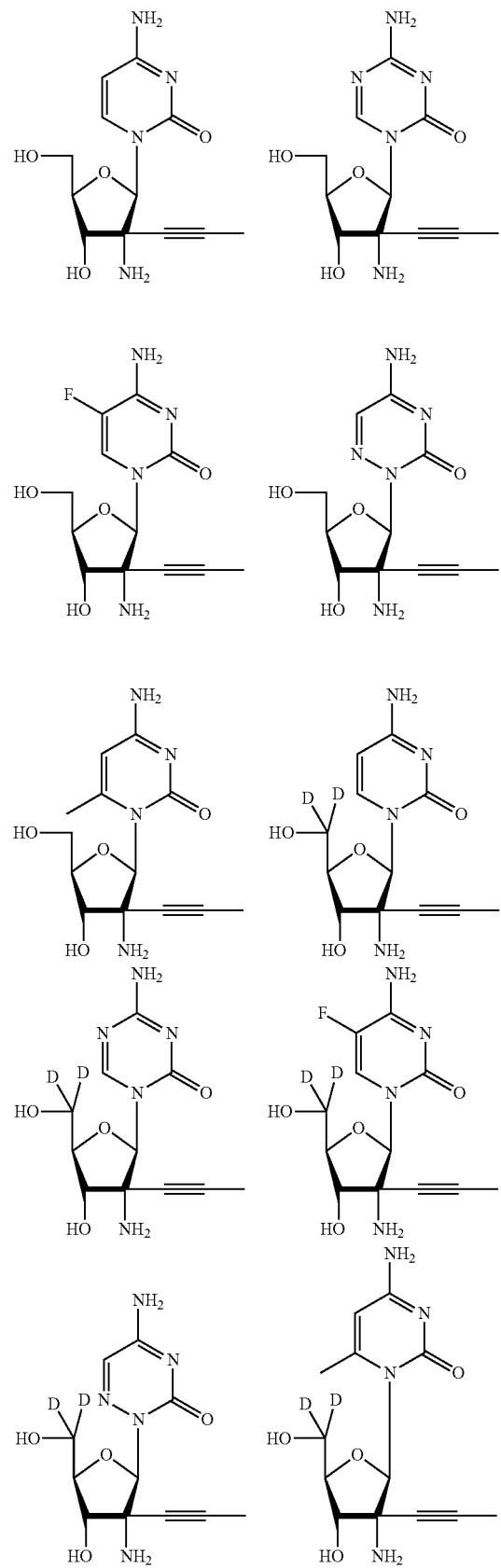
-continued
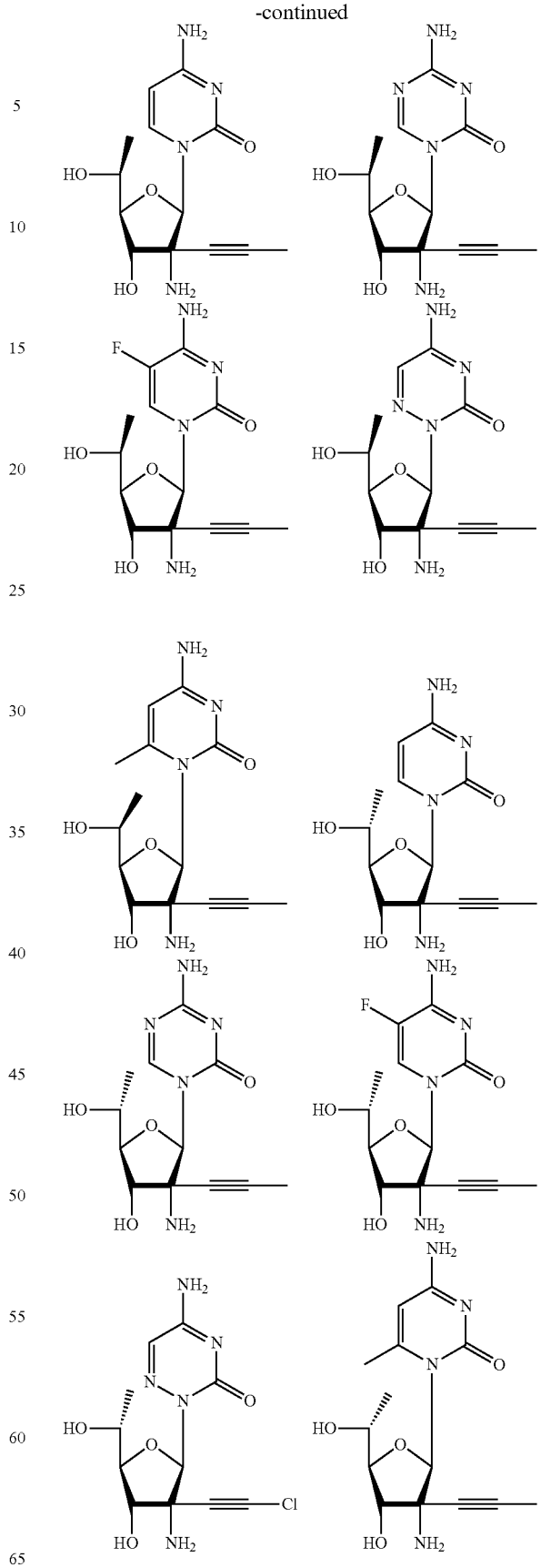

In exemplary embodiments, the compound is selected from:
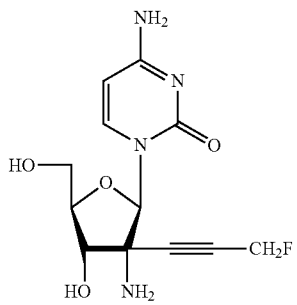
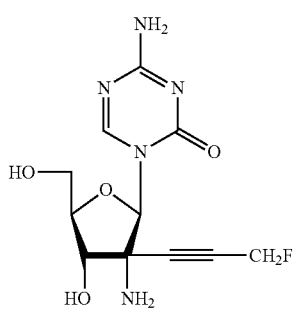
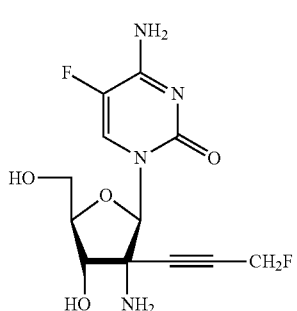
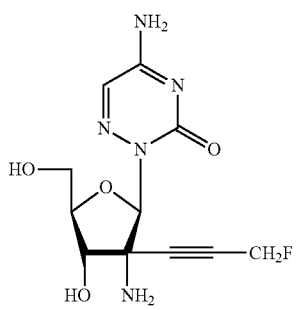
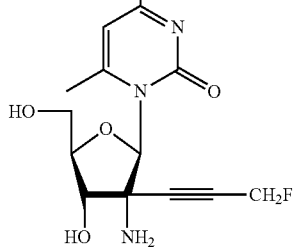
-continued
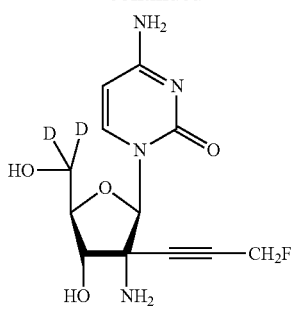
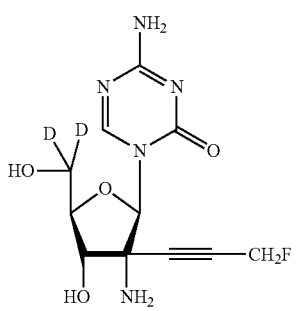
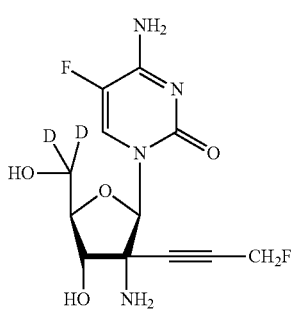
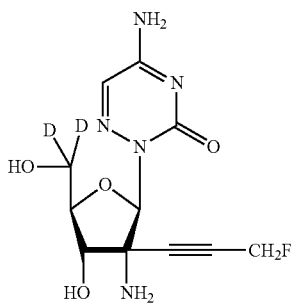
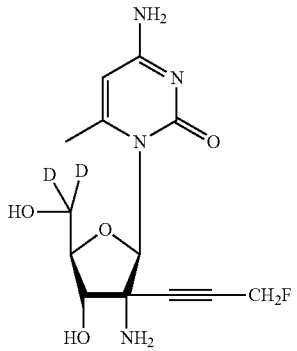

-continued
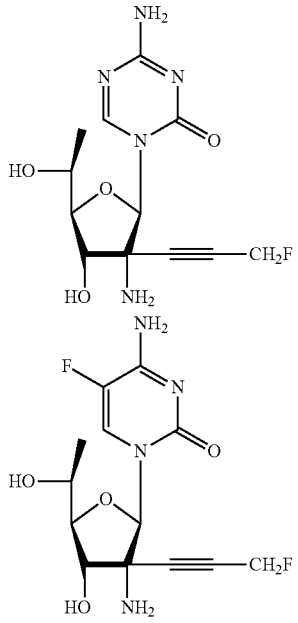
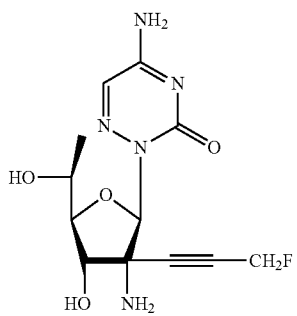
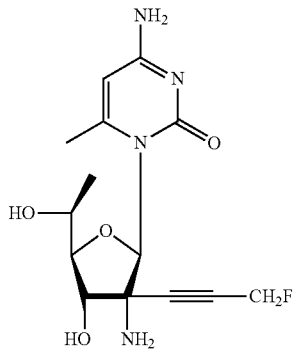
-continued
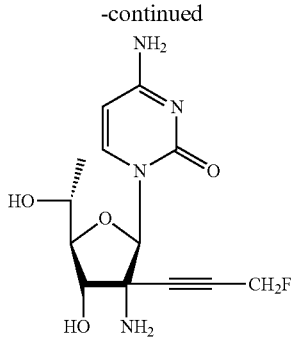
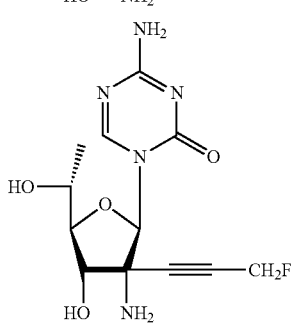
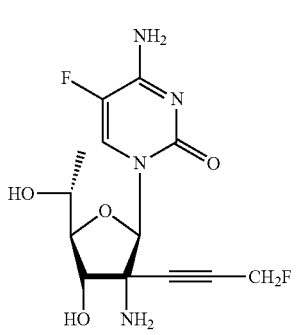
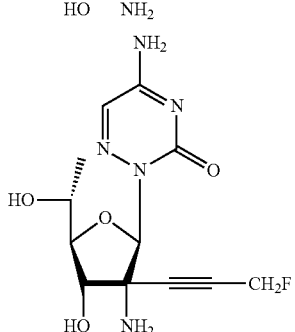
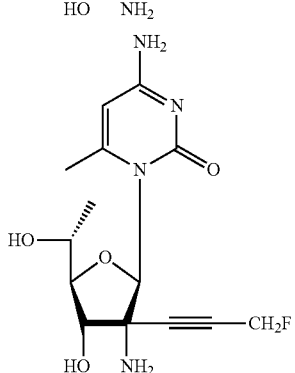

In exemplary embodiments, the compound is selected from:
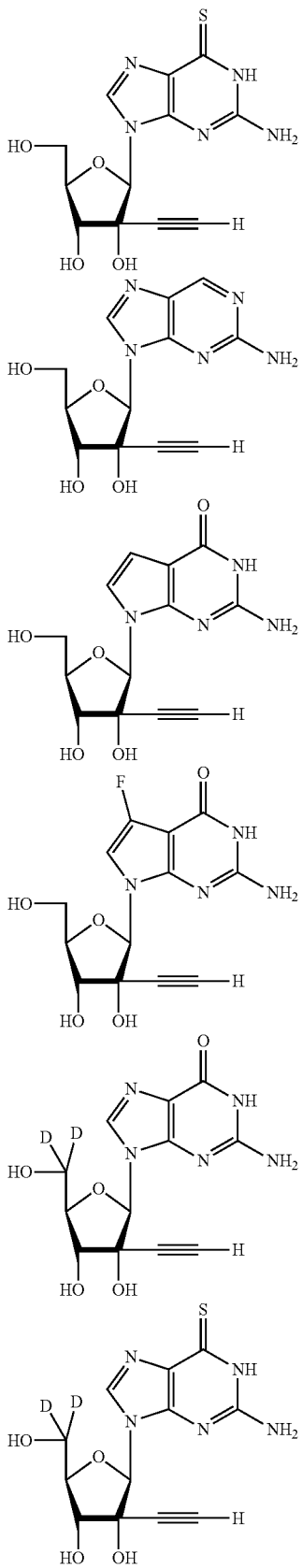
-continued
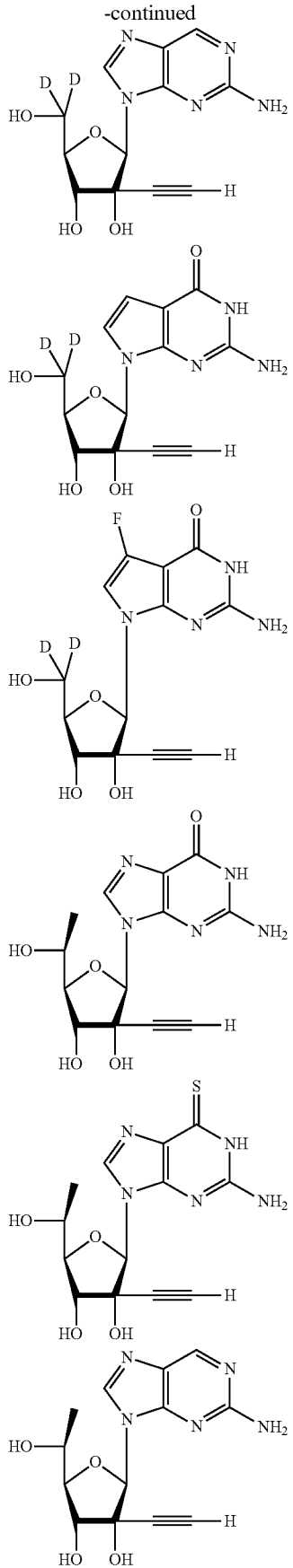

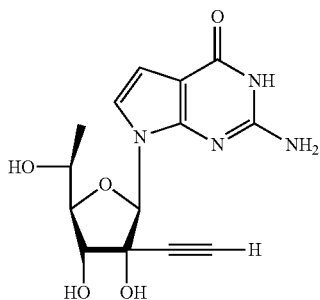
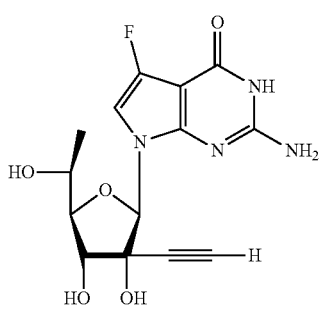
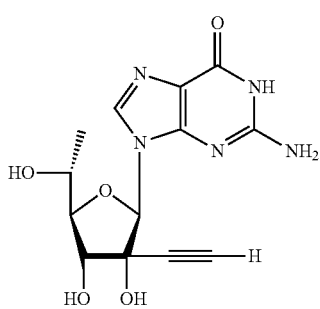
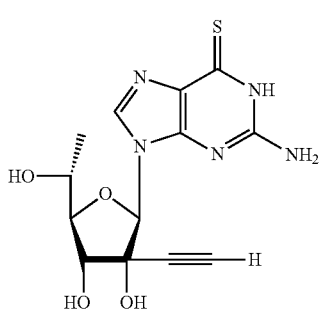
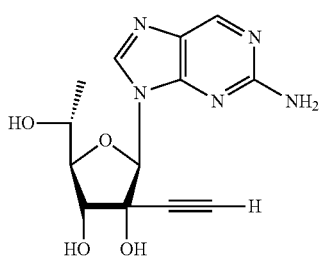
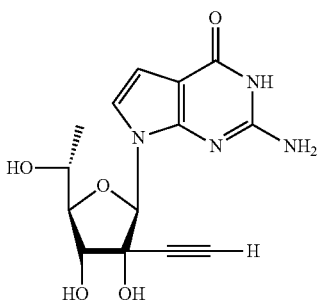
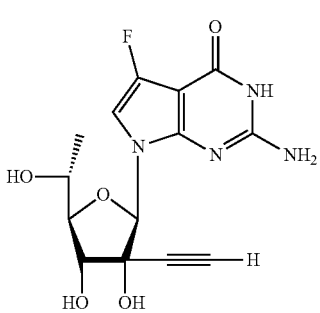
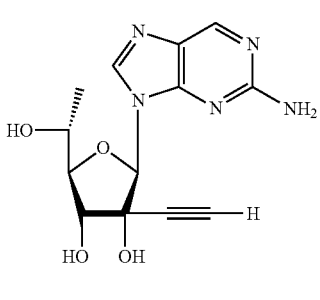
In exemplary embodiments, the compound is selected from:
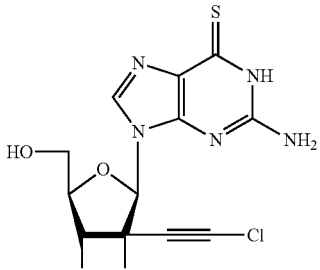
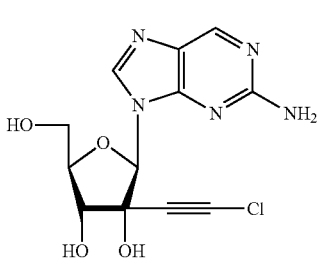

211
-continued
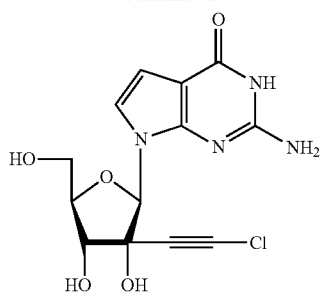
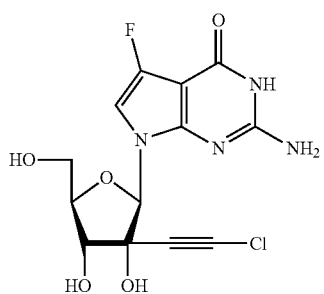
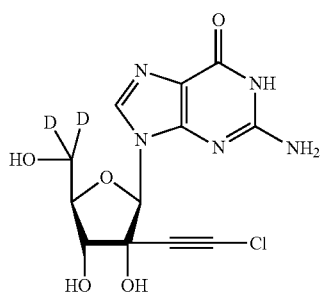
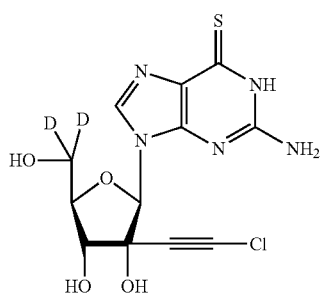
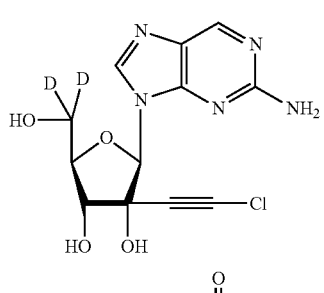
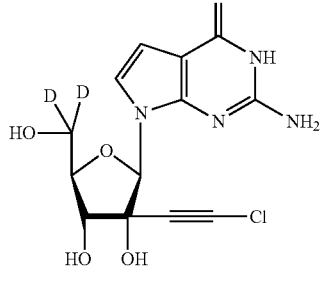
212
-continued
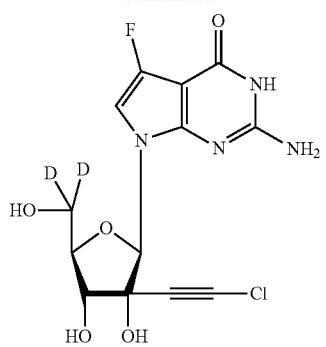
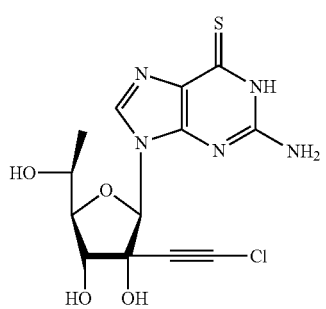
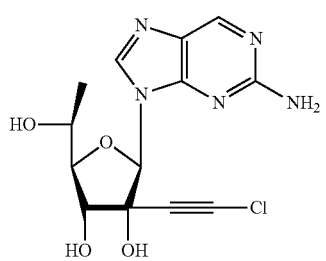
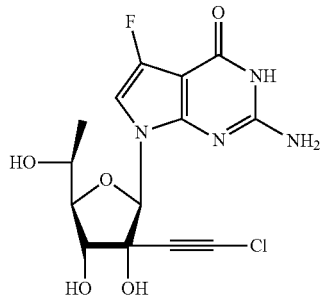

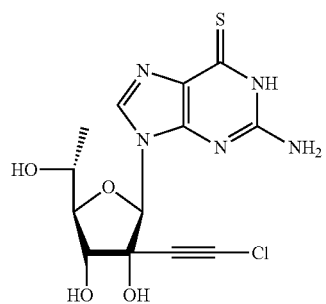
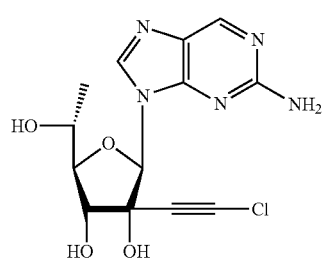
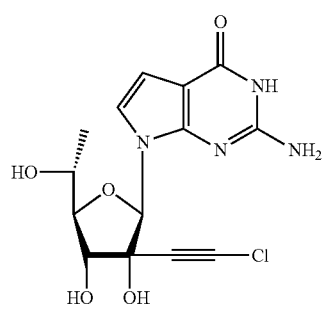
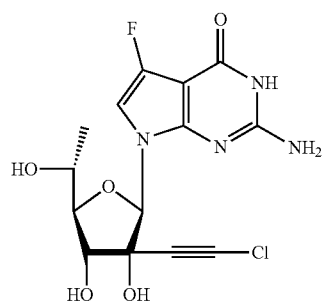
In exemplary embodiments, the compound is selected from:
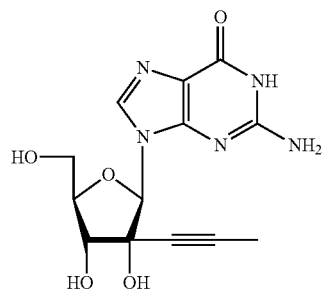
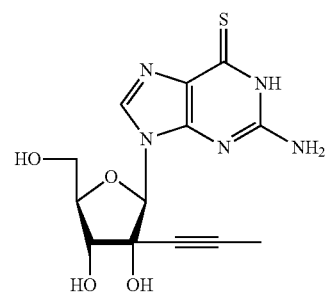
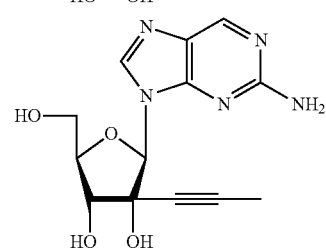
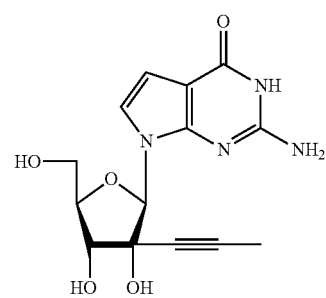
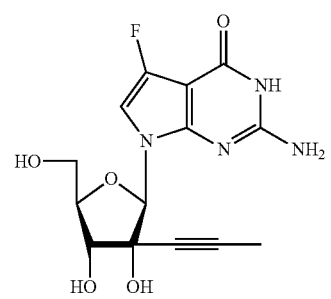
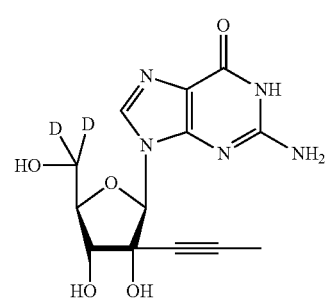
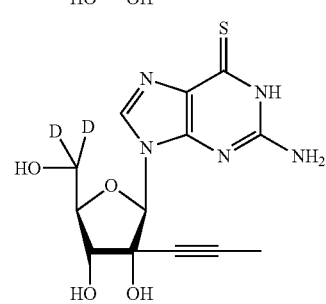

215
-continued
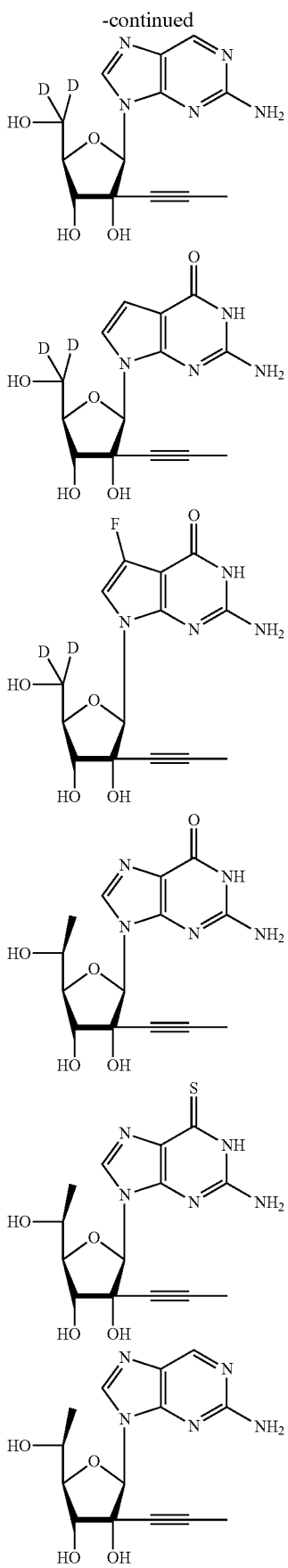
216
-continued
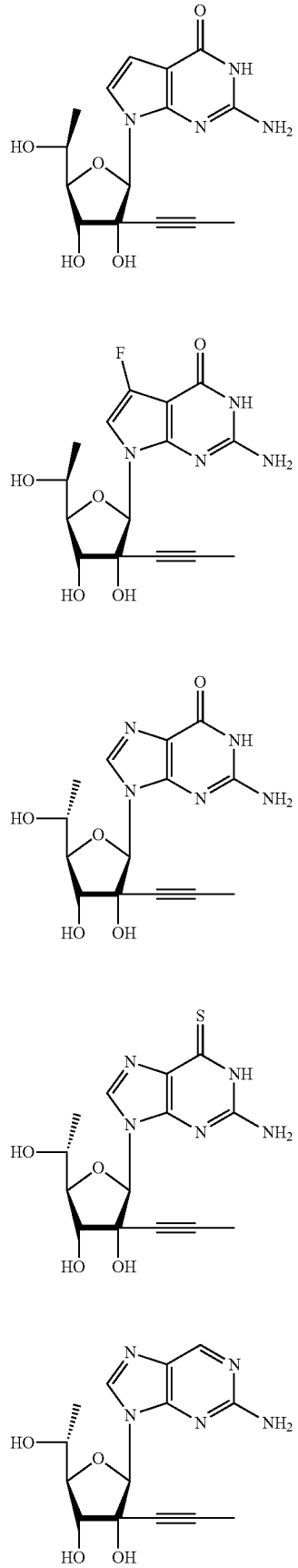

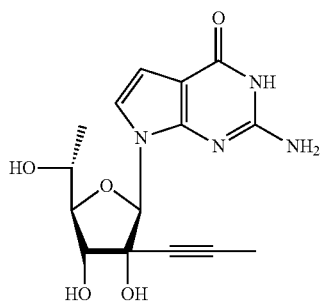
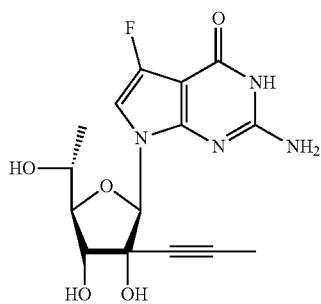
In exemplary embodiments, the compound is selected from:
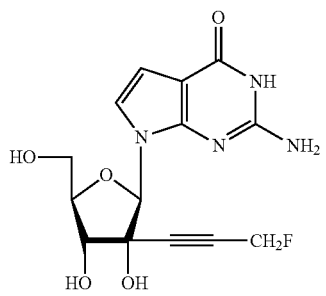
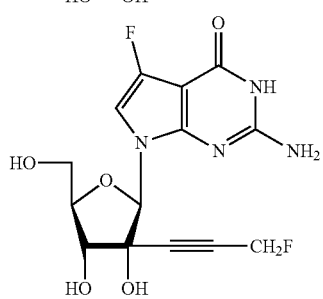
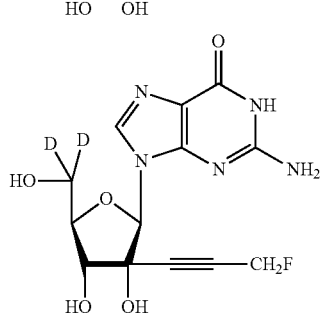
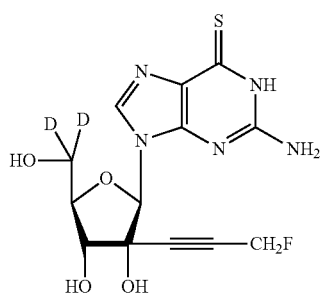
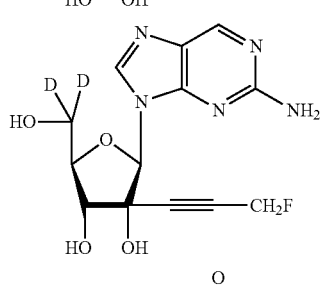
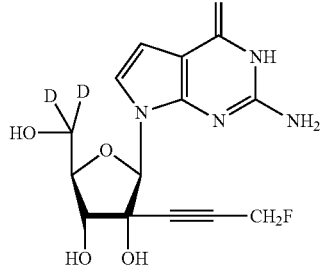

219
-continued
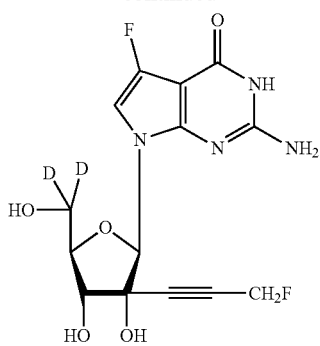
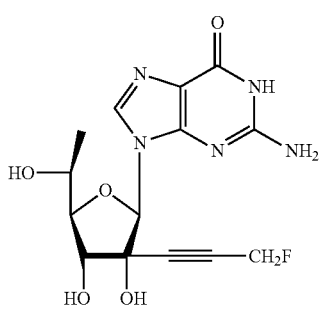
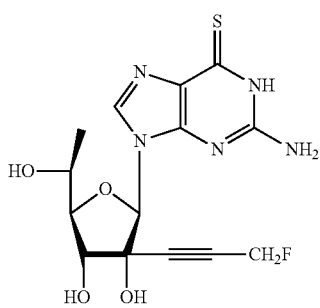
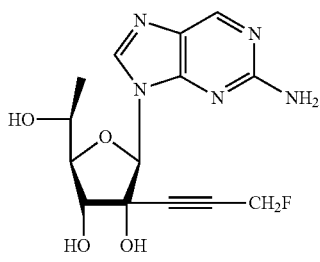
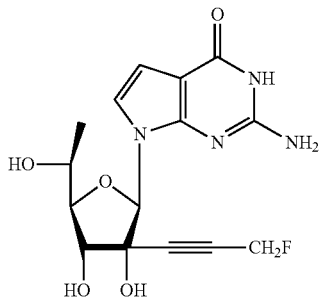
220
-continued
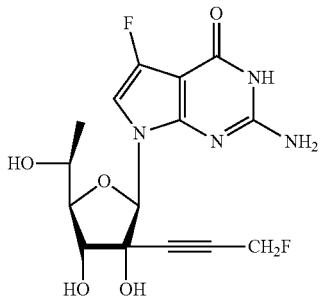
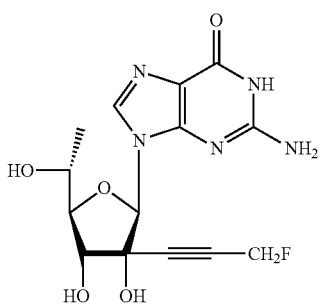
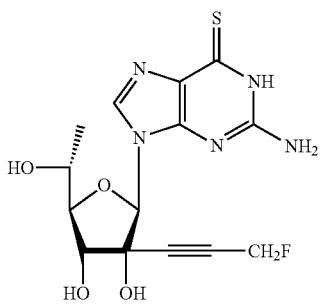
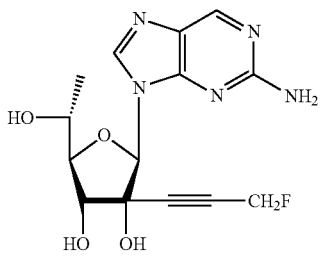
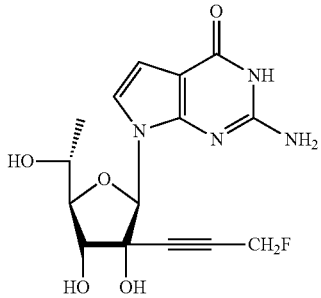

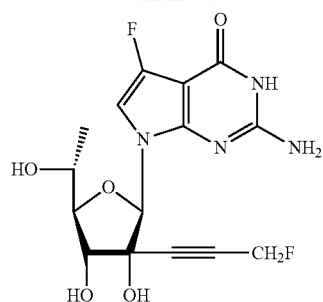
In exemplary embodiments, the compound is selected from:
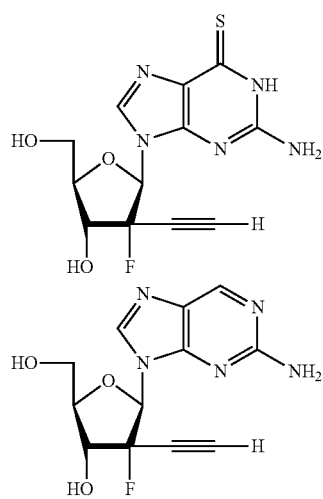
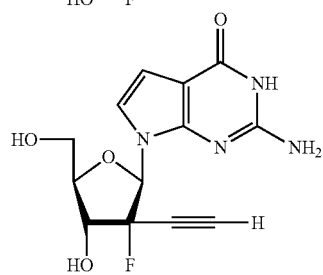
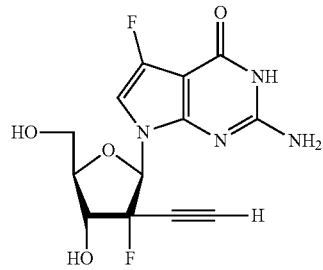
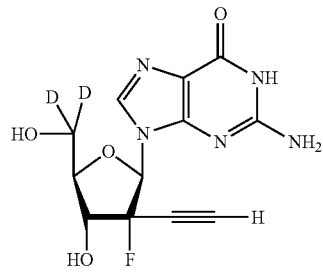
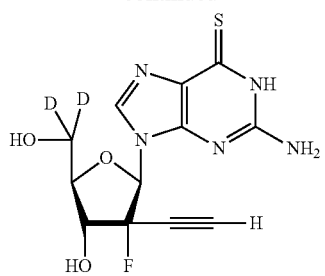
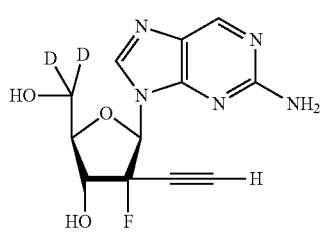
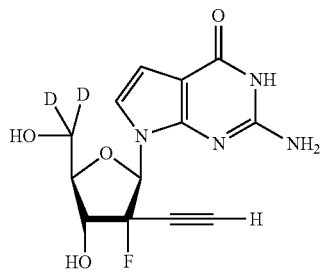
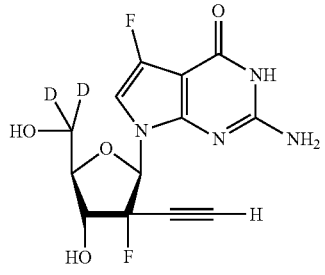
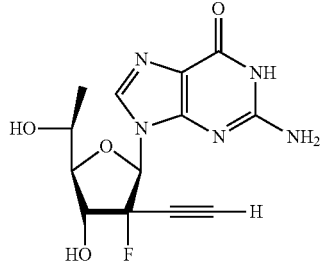
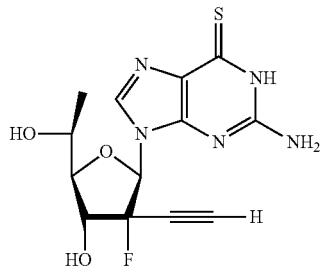

223
-continued
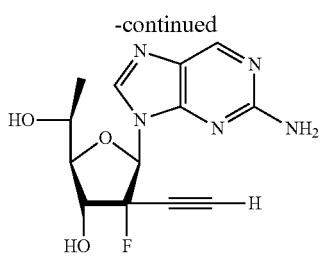
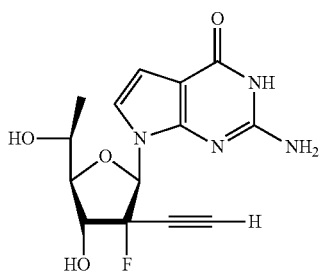
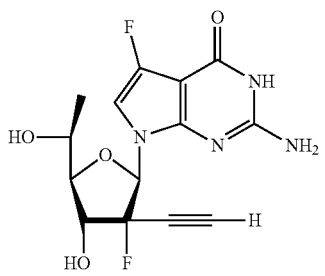
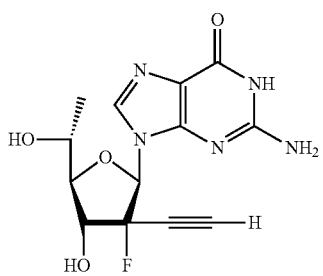
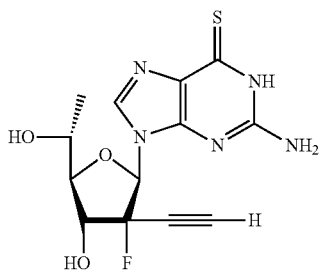
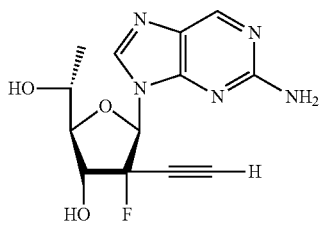
224
-continued
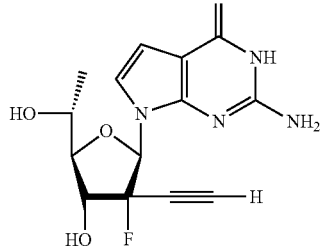
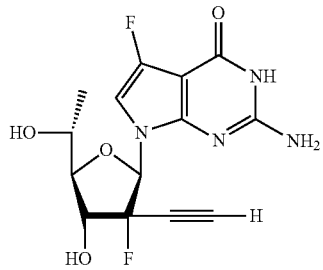
In exemplary embodiments, the compound is selected from:
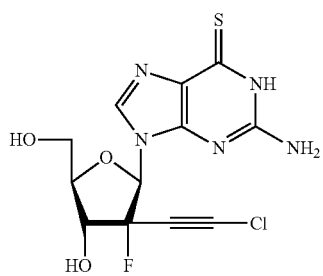
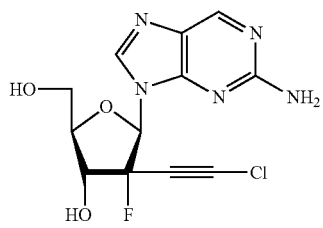
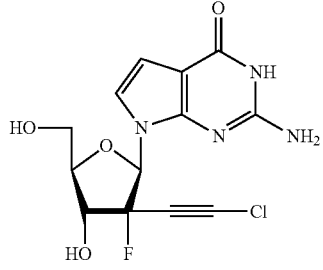
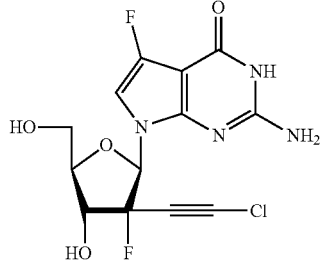

225
-continued
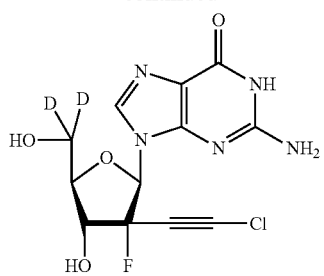
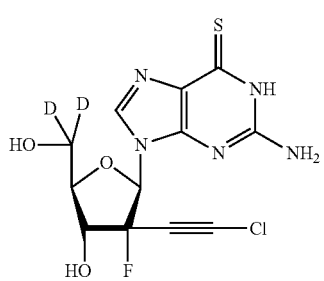
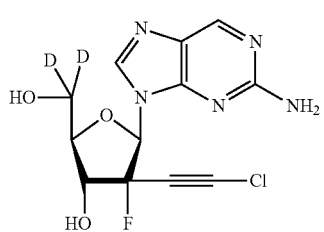
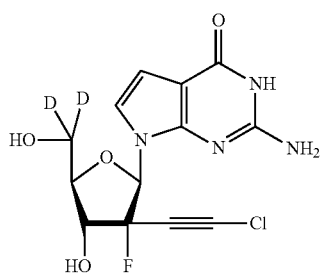
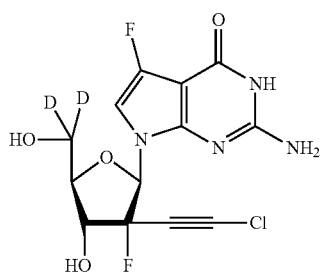
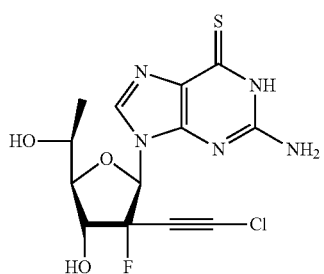
226
-continued
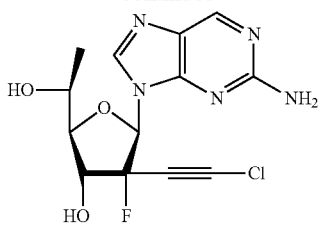
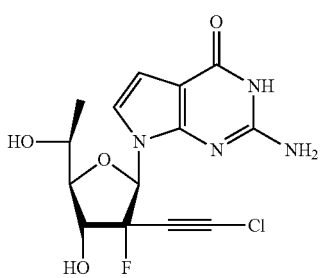
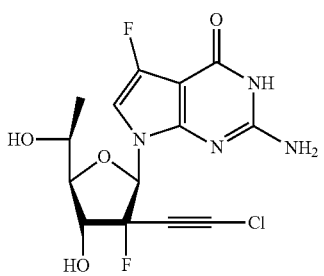
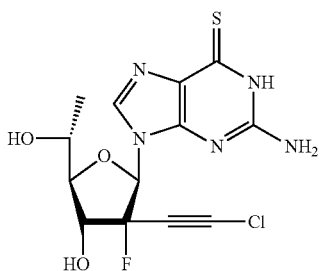
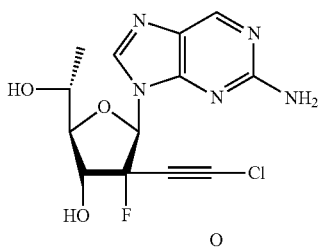
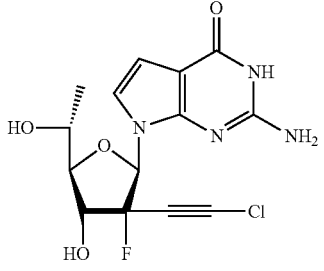

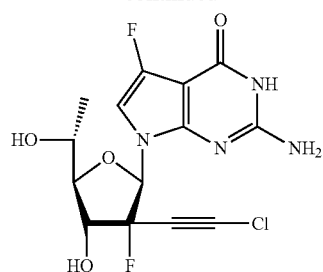
In exemplary embodiments, the compound is selected from:
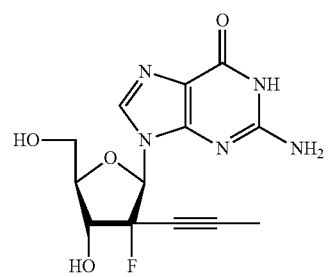
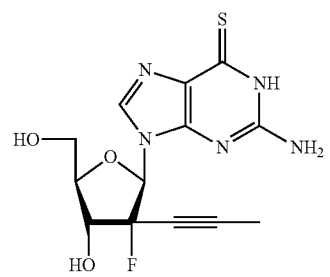
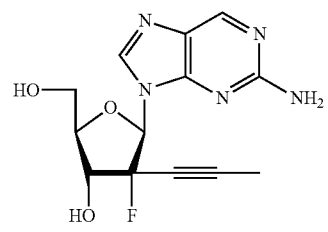
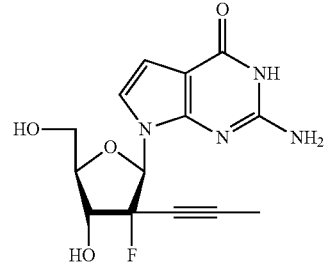
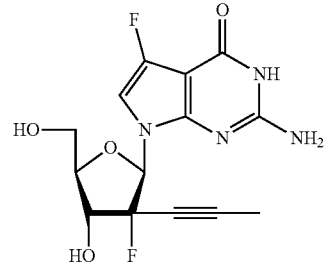
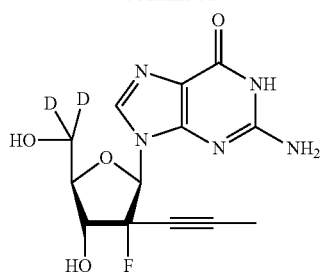
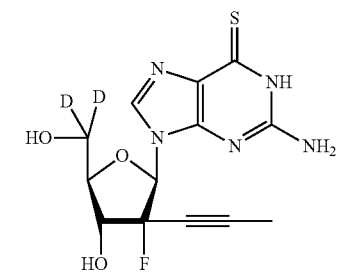
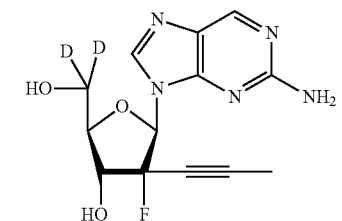
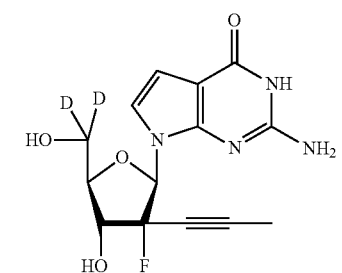
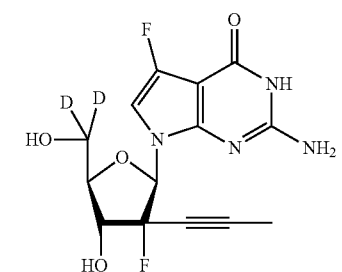
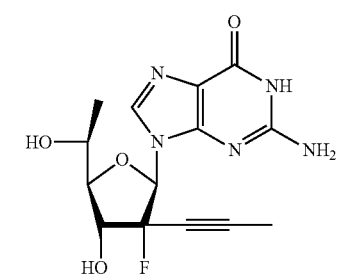

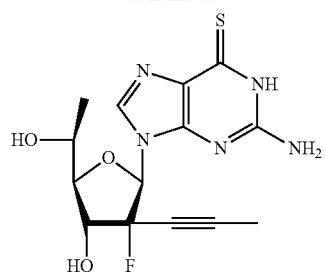
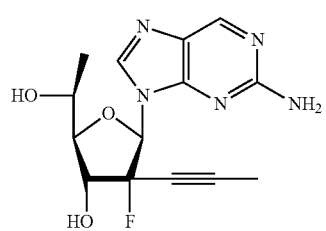
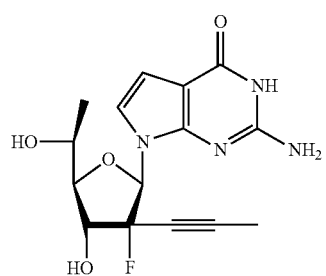
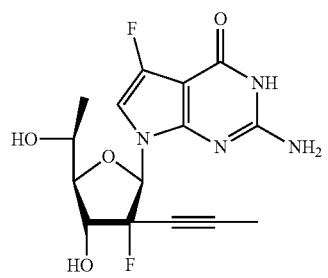
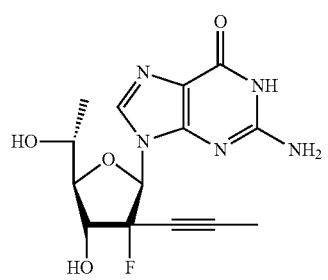
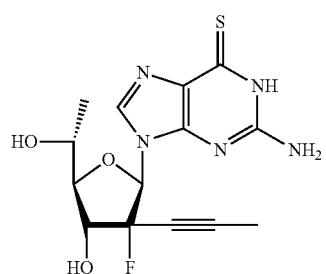
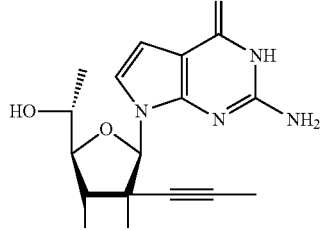
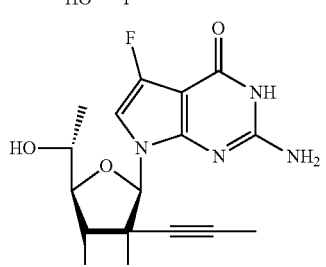
In exemplary embodiments, the compound is selected from:
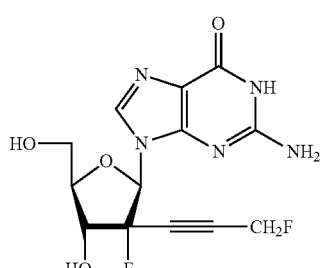
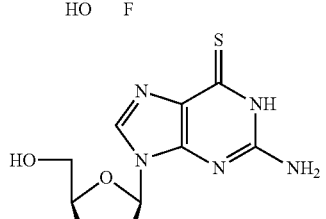
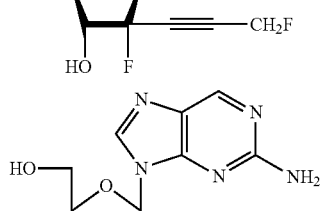
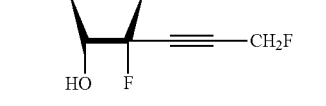

231
-continued
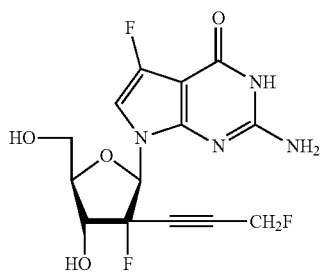
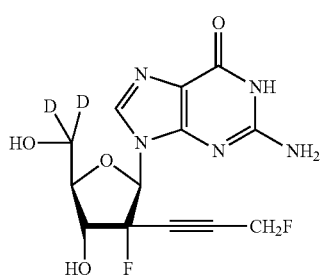
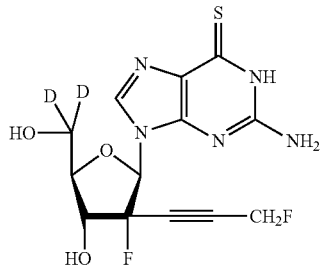
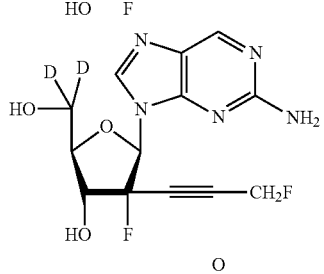
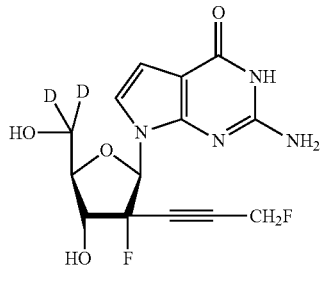
232
-continued

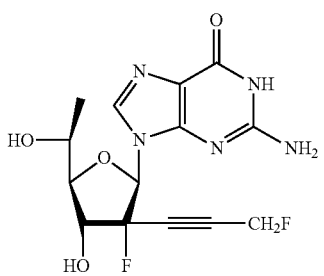
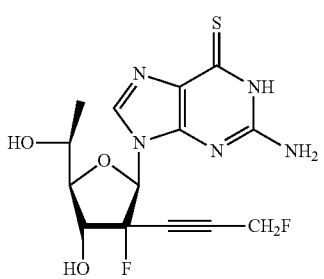
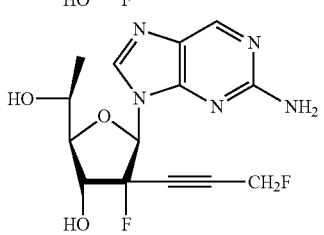
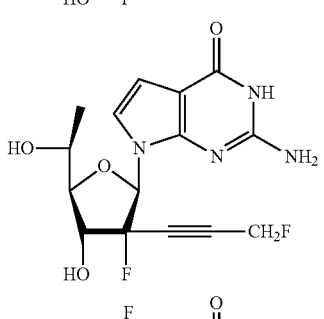
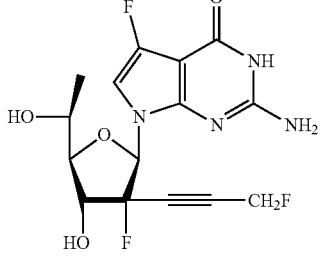

233
-continued
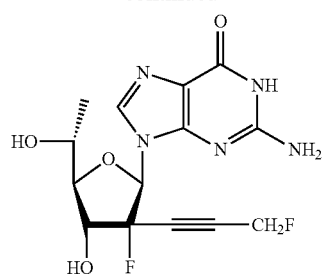
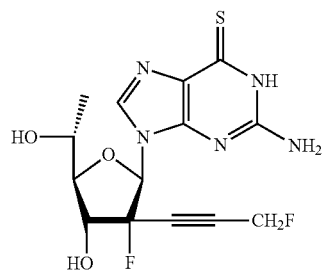
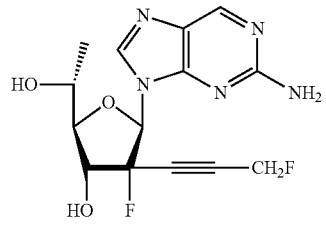
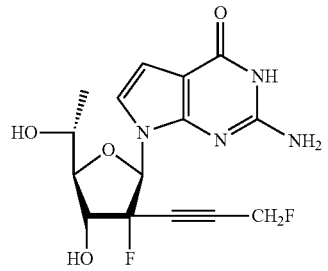
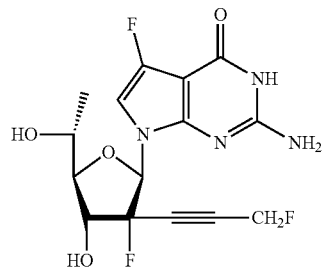
In exemplary embodiments, the compound is selected from:
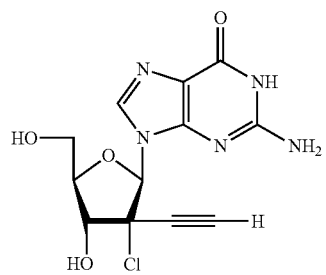
234
-continued
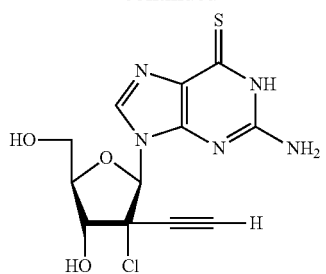
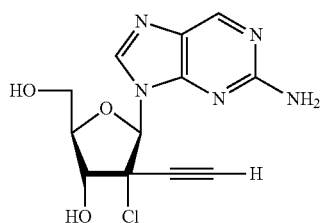
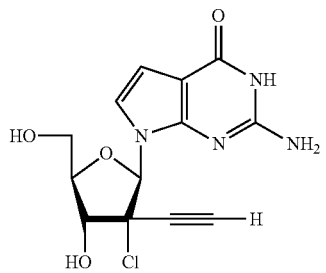
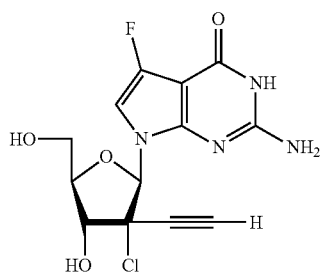
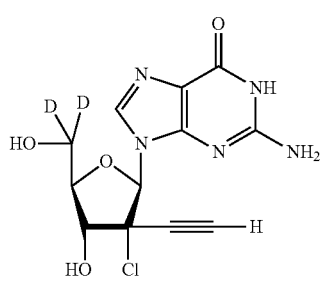
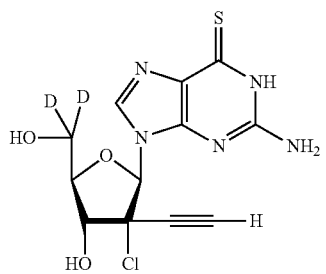

235
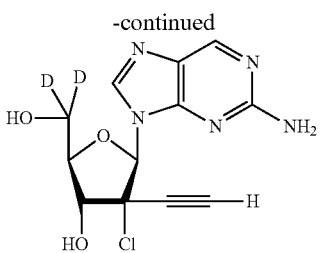
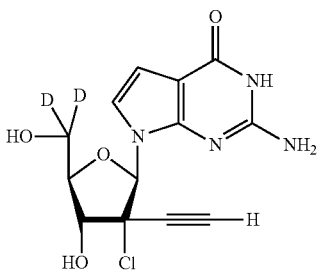
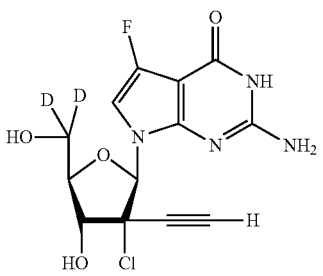
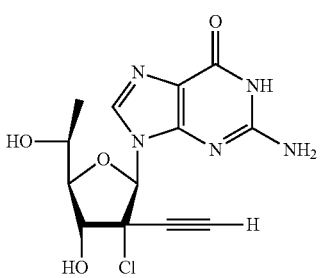
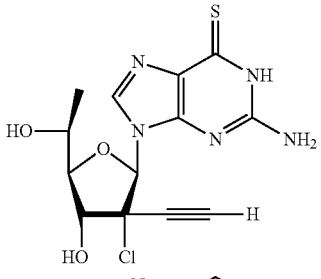
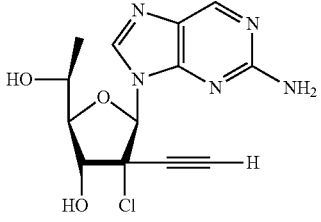
236
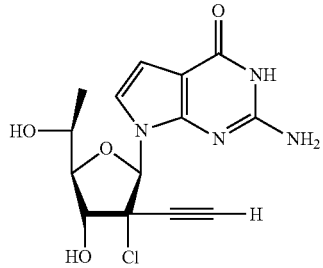
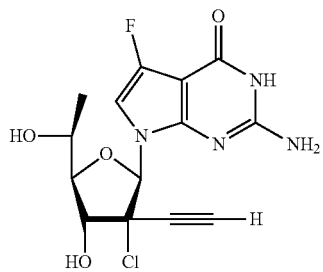
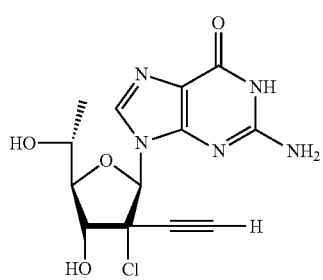
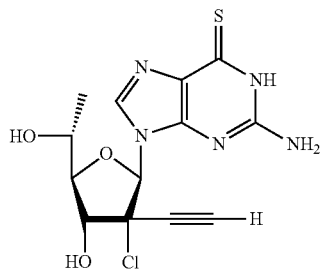
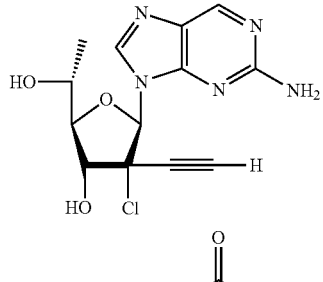
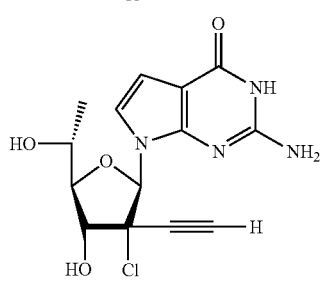

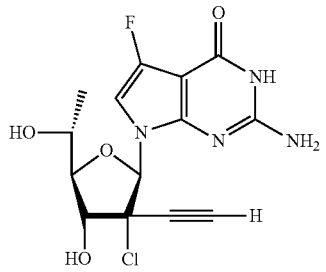
In exemplary embodiments, the compound is selected from:
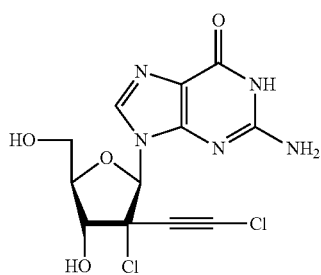
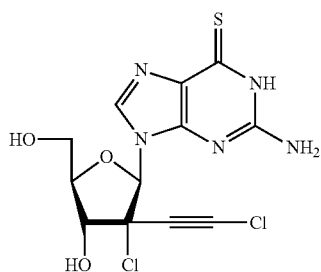
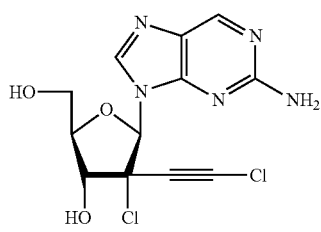
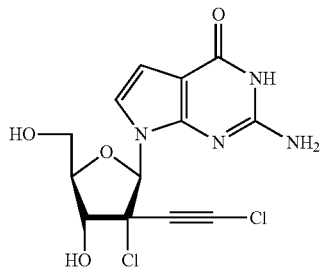
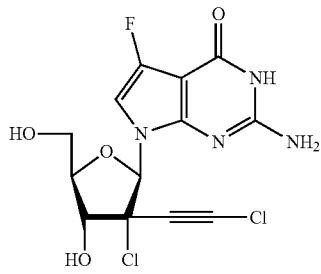
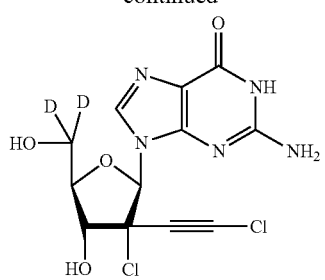
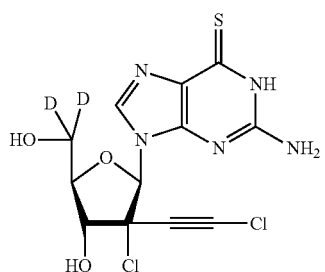
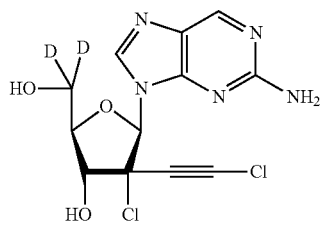
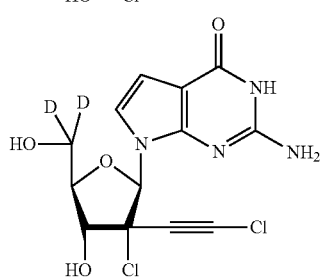
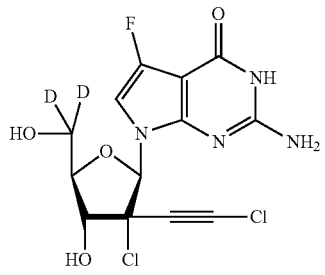
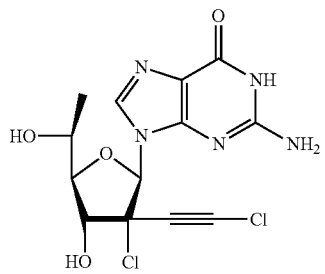

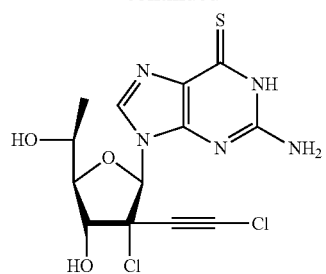
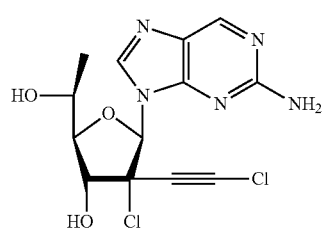
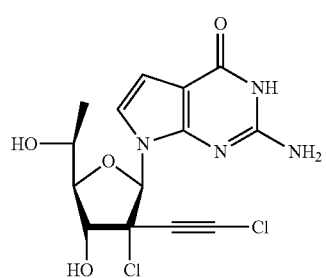
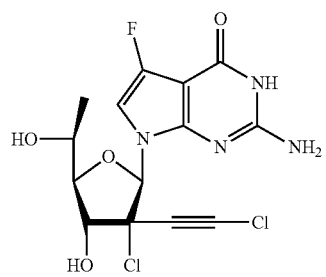
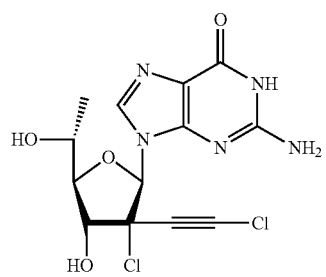
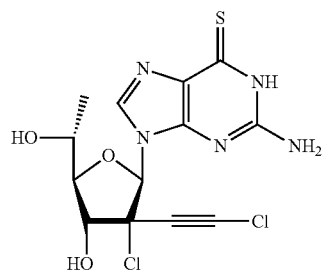
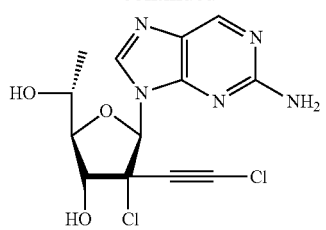
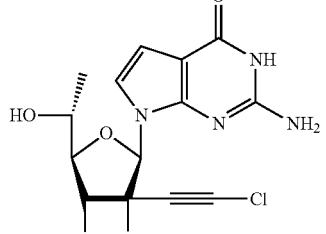
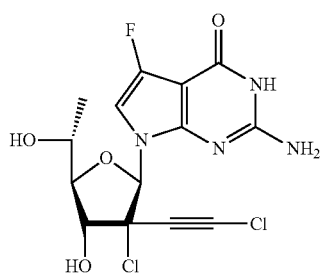
In exemplary embodiments, the compound is selected from:
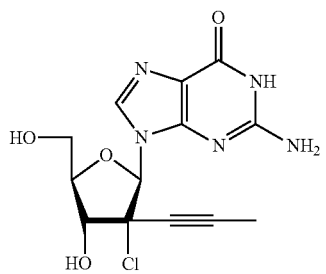
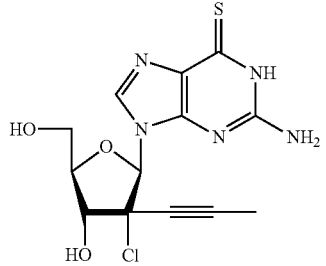
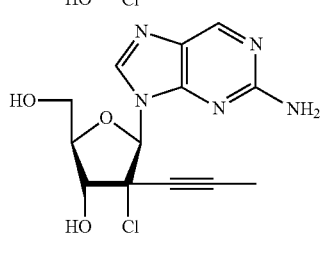

-continued
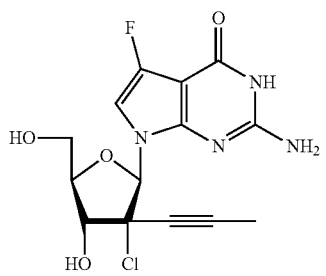
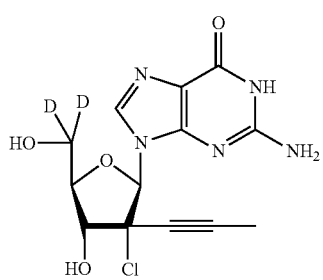
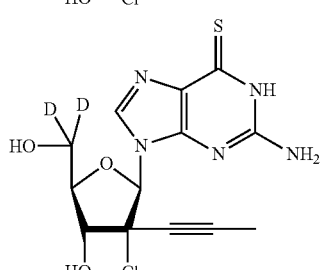
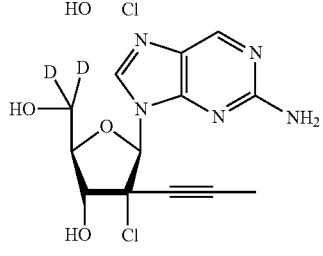
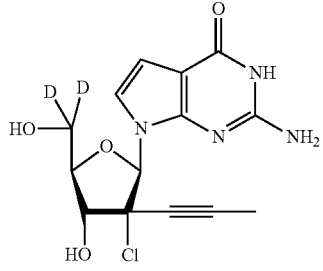
-continued
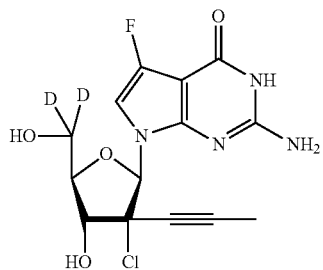
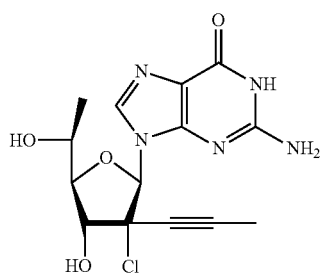
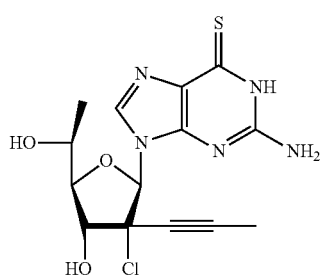
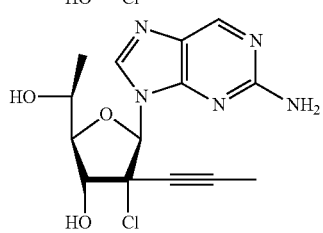
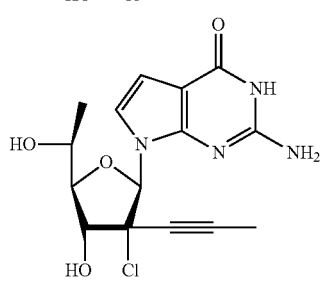
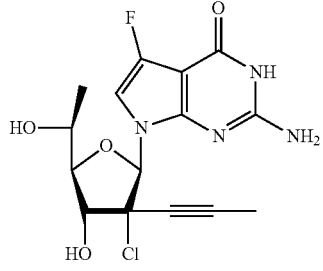

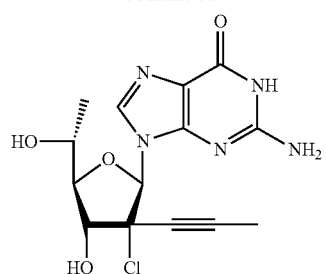
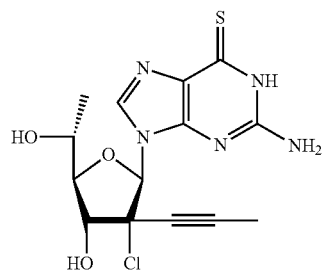
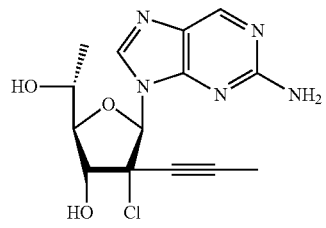
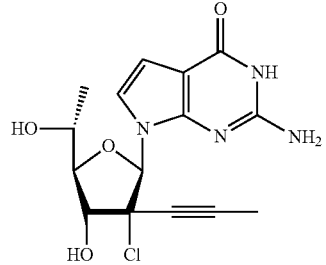
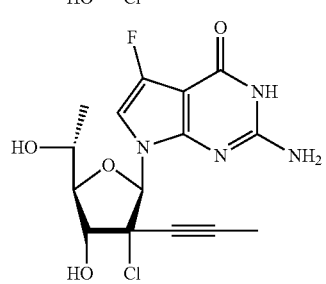
In exemplary embodiments, the compound is selected from:
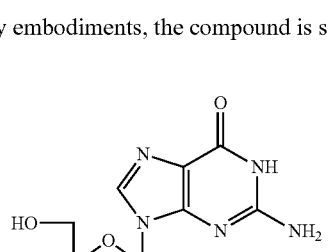
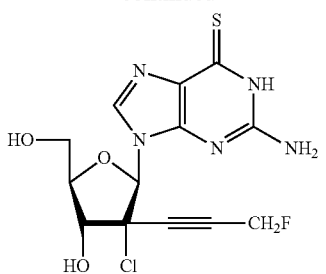
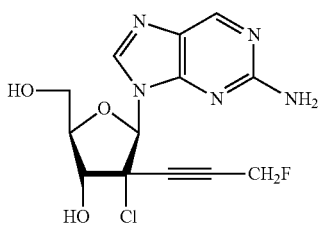
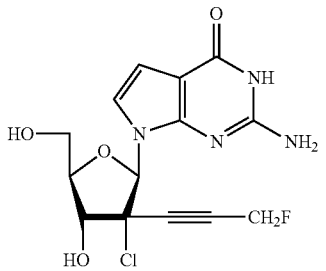
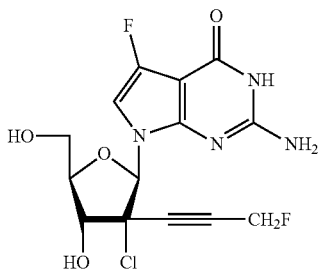
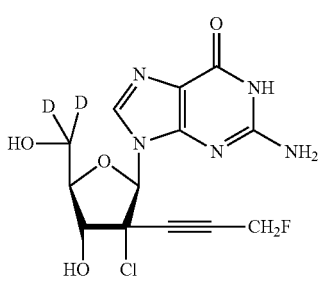
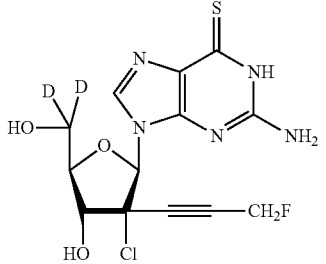

245
-continued
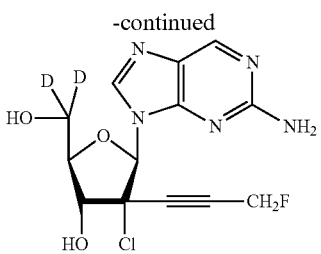
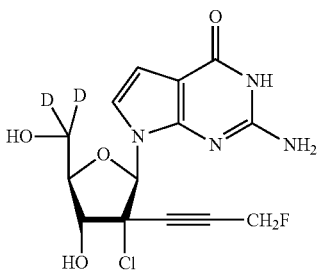
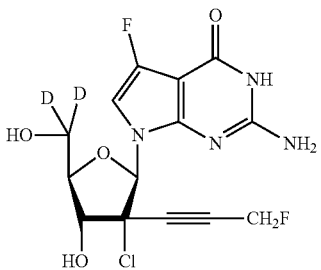
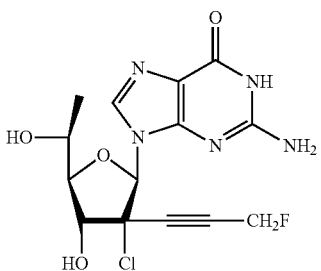
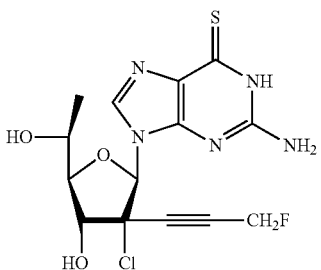
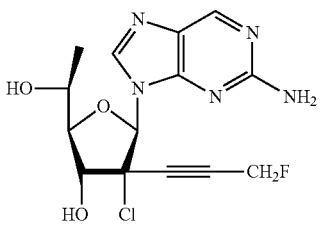
246
-continued
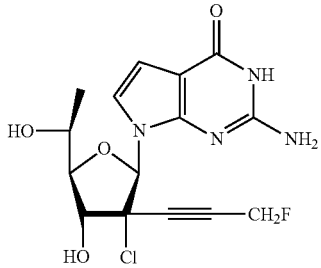
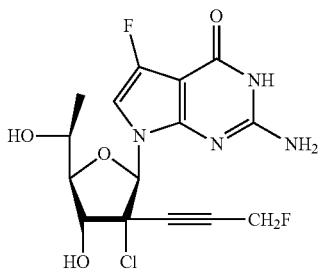
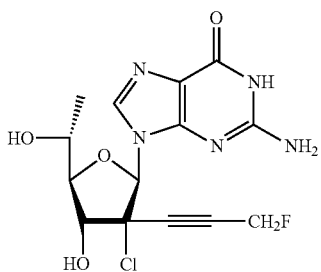
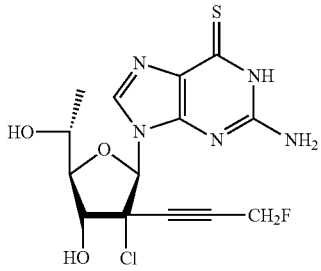
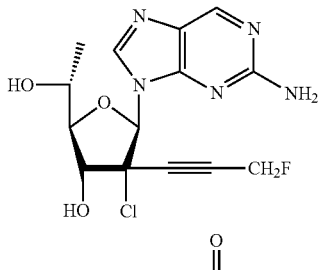
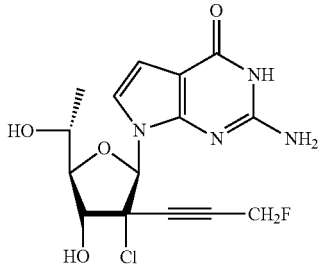

247
-continued
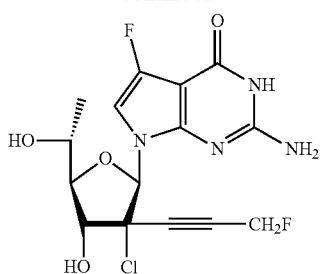
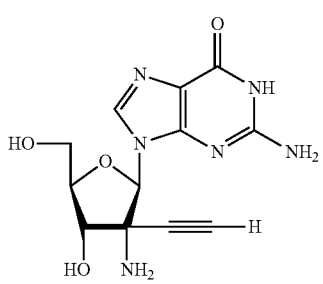
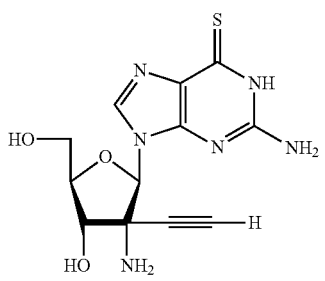
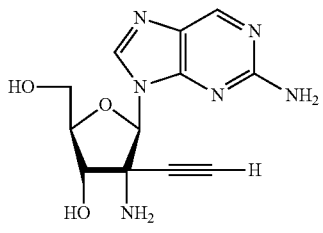
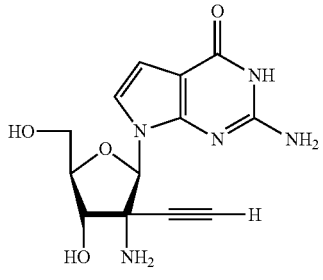
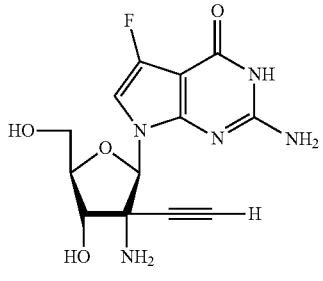
248
-continued
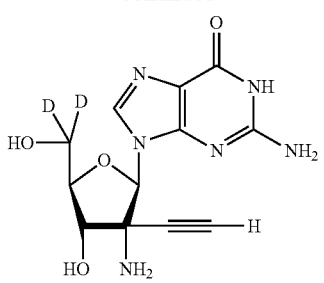
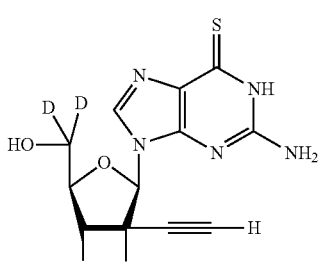
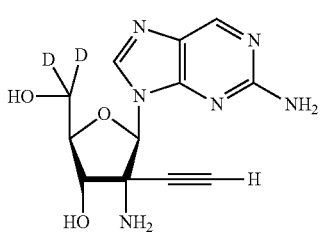
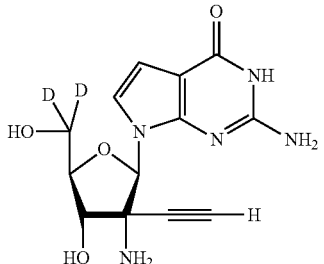
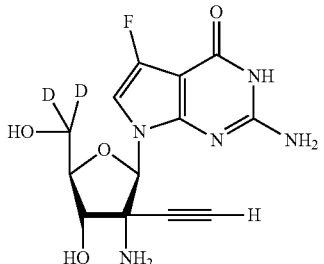
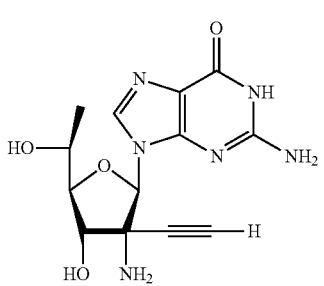

-continued
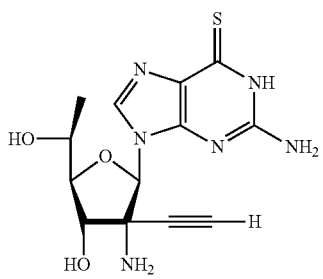
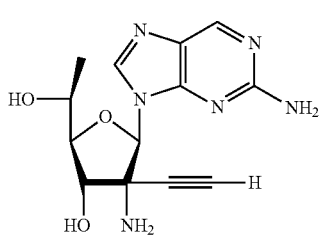
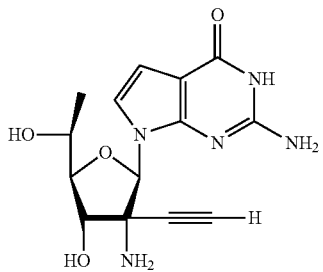
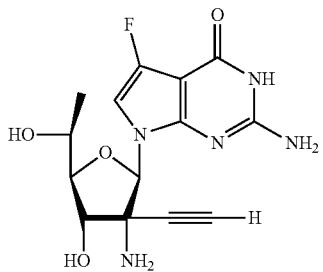
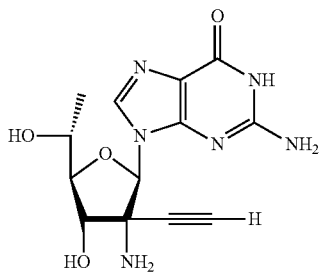
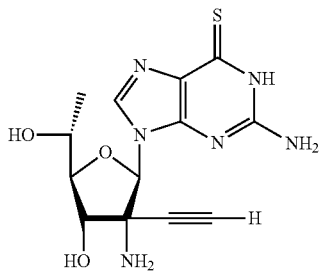
-continued
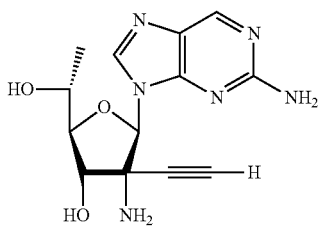
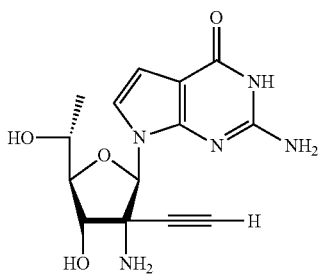
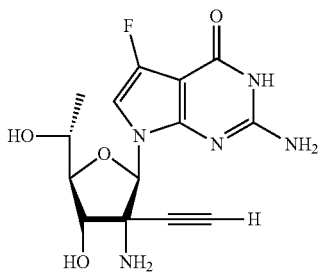
In exemplary embodiments, the compound is selected from:
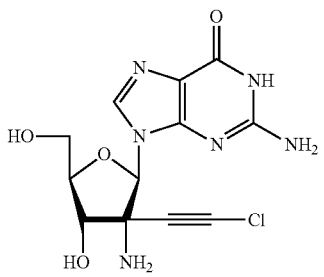
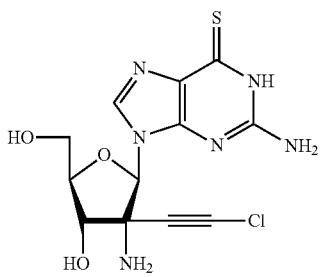
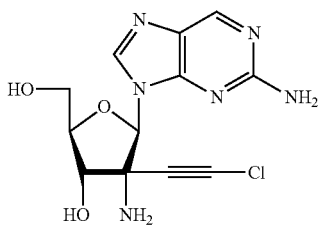

251
-continued
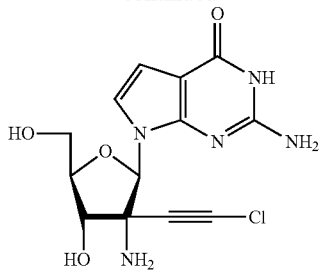
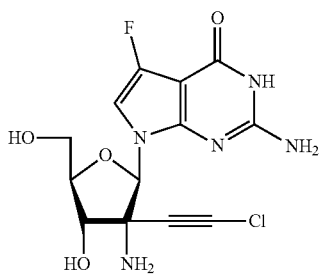
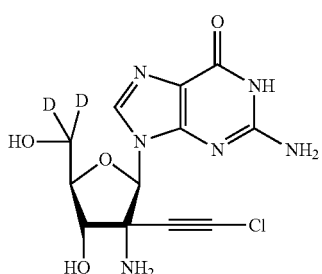
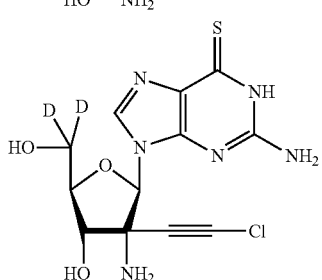
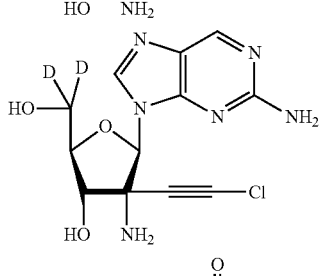
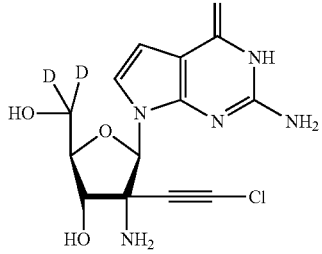
252
-continued
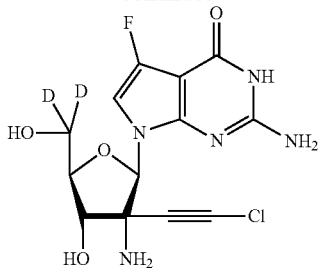
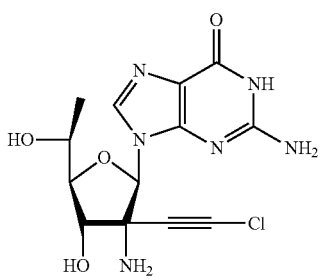
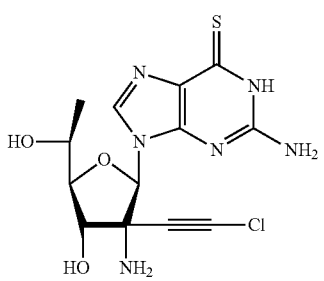
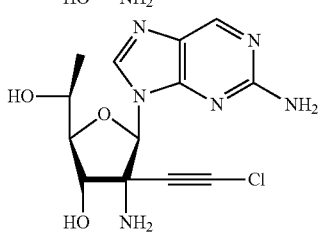
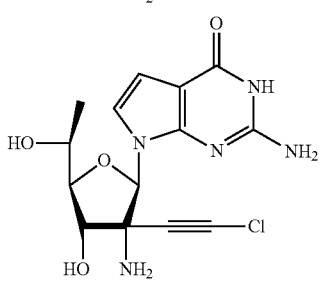
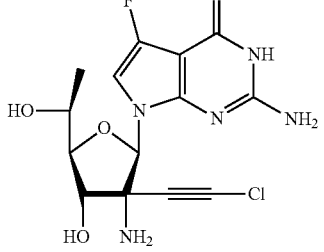

-continued
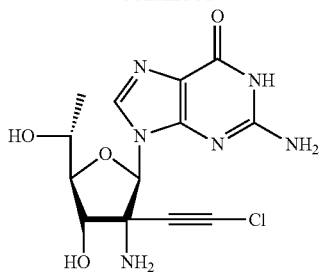
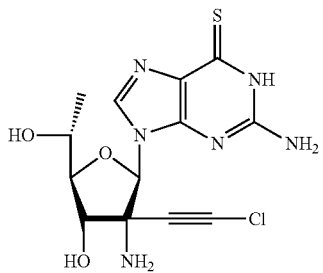
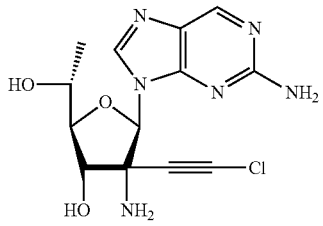

In exemplary embodiments, the compound is selected from:
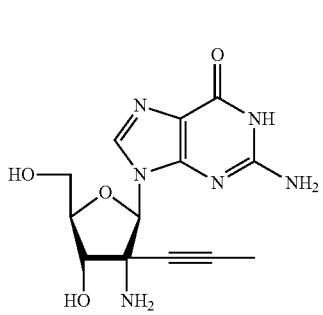
-continued
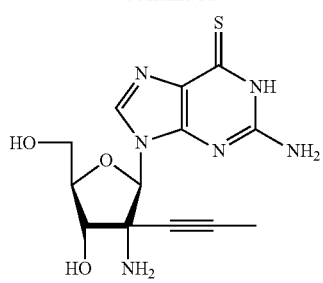
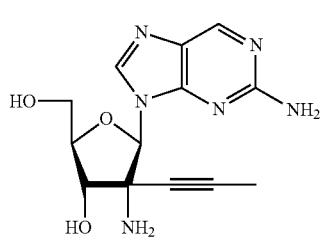
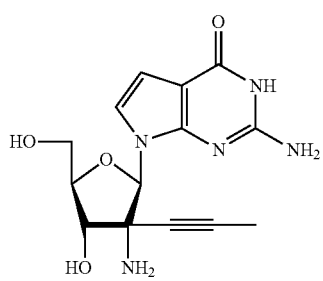
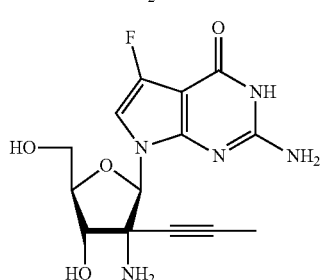
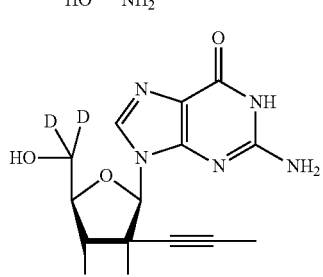
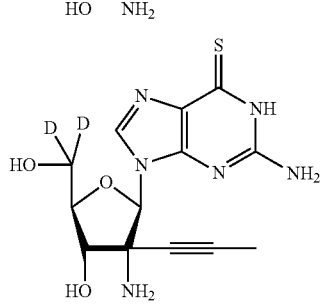

255 -continued

256 -continued

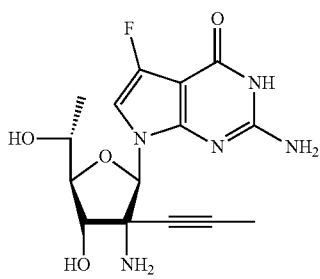
In exemplary embodiments, the compound is selected from:
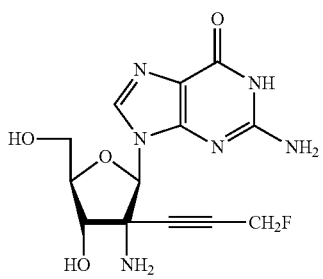

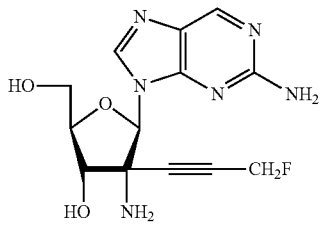
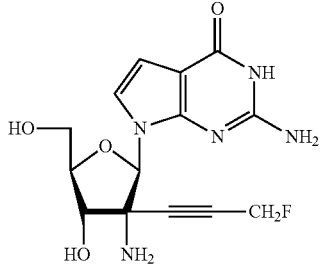
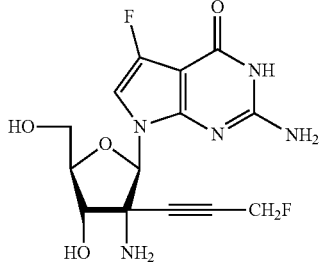
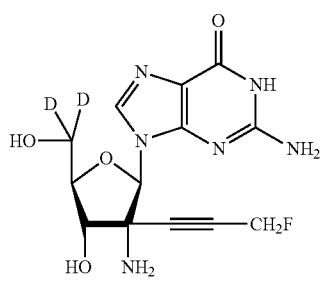
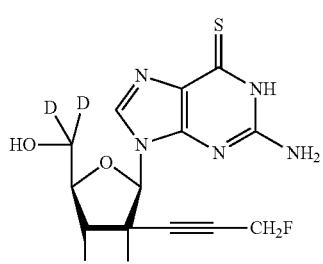
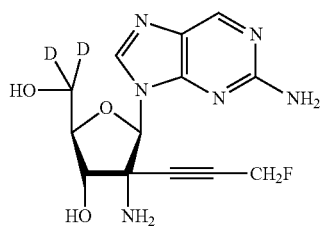
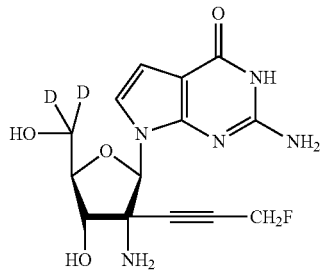
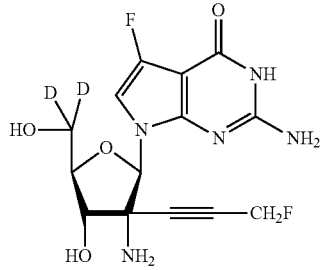
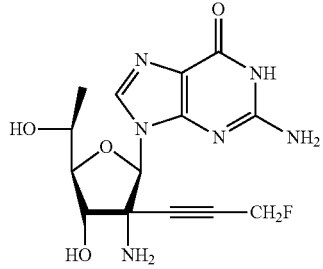

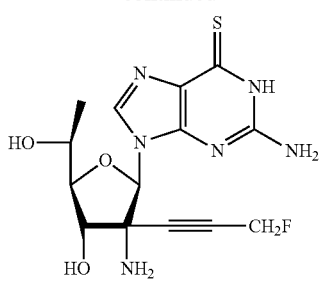
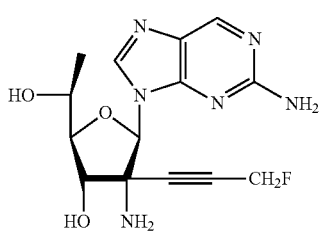
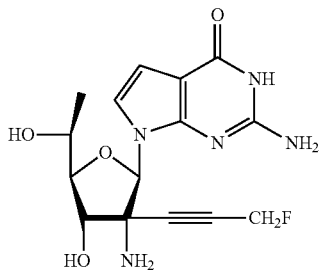
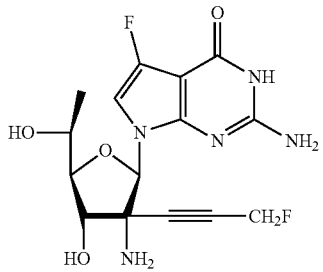
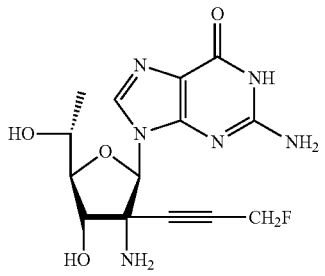
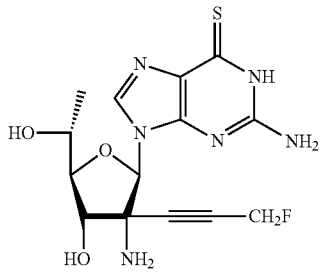
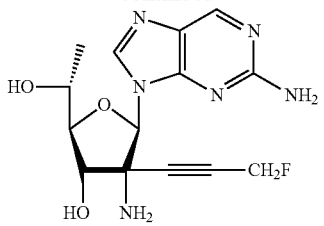
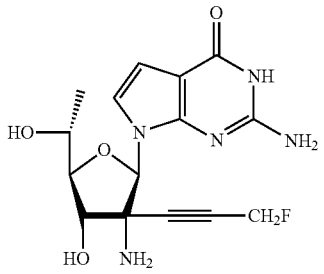
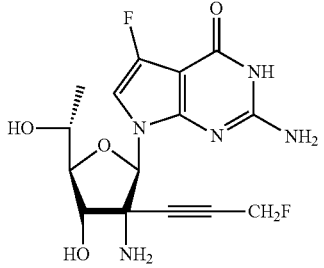
In exemplary embodiments, the compound is selected from:
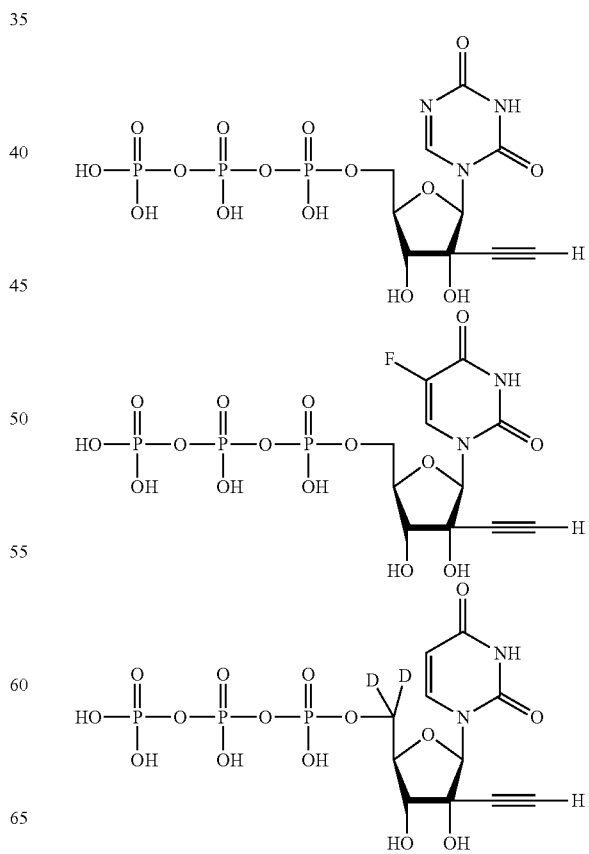

261
-continued
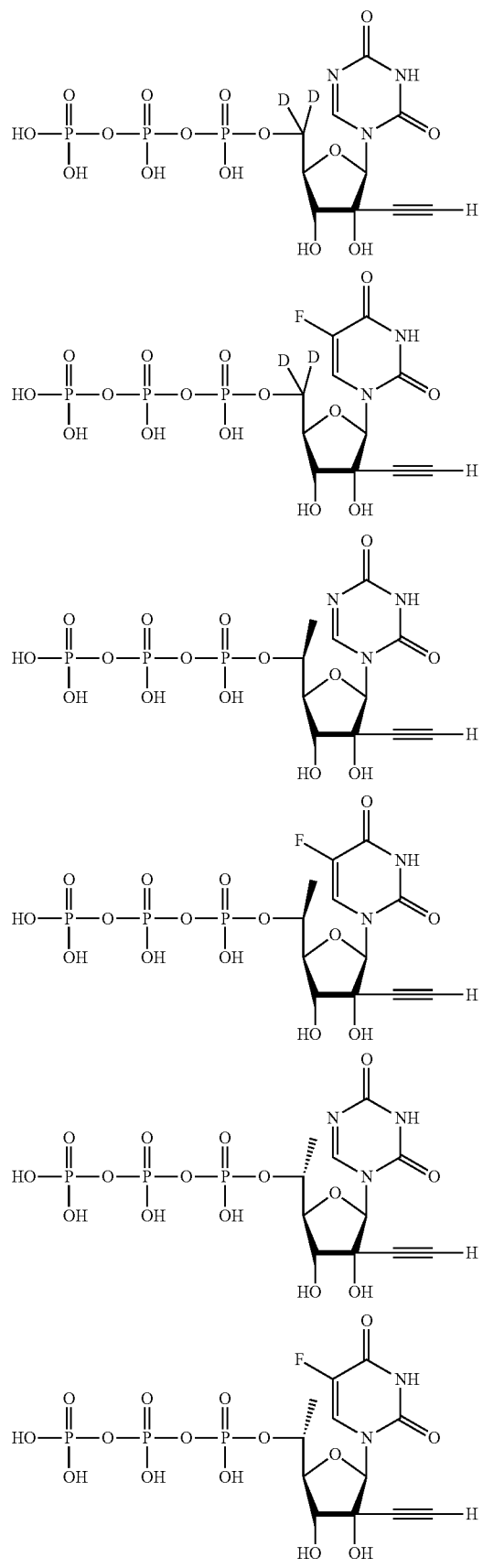
262
-continued
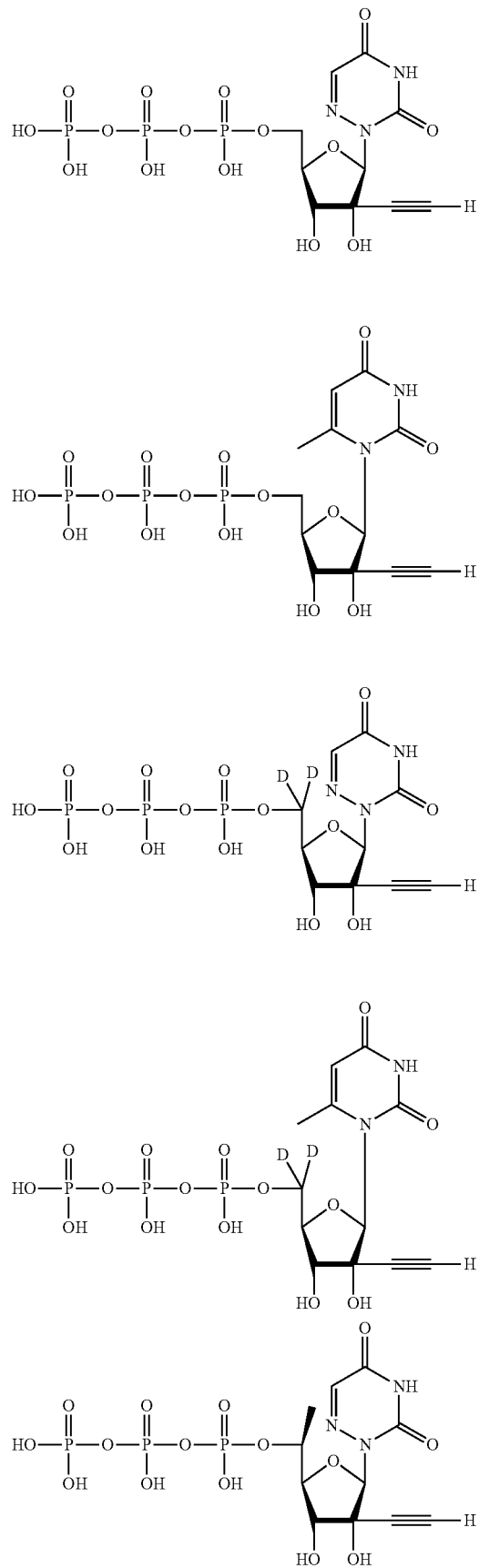

263
-continued
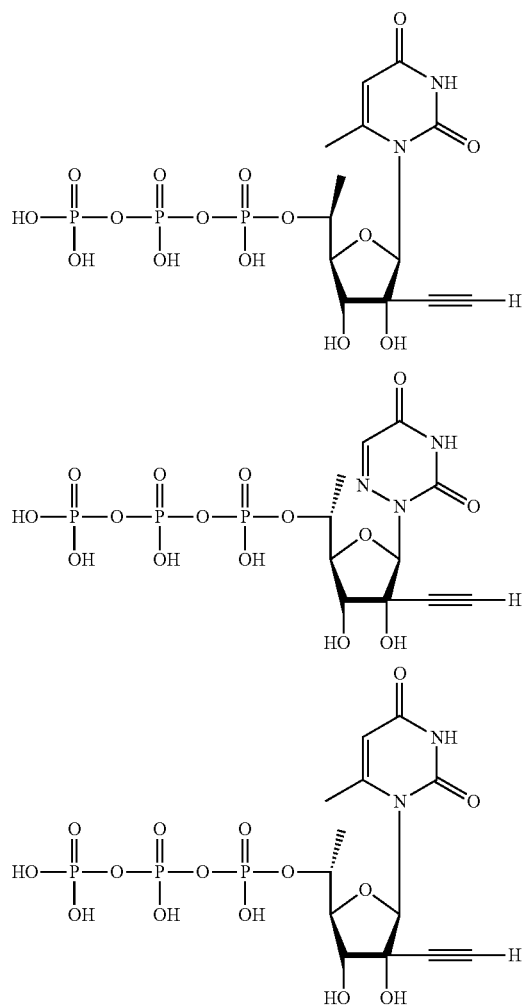
In exemplary embodiments, the compound is selected from:
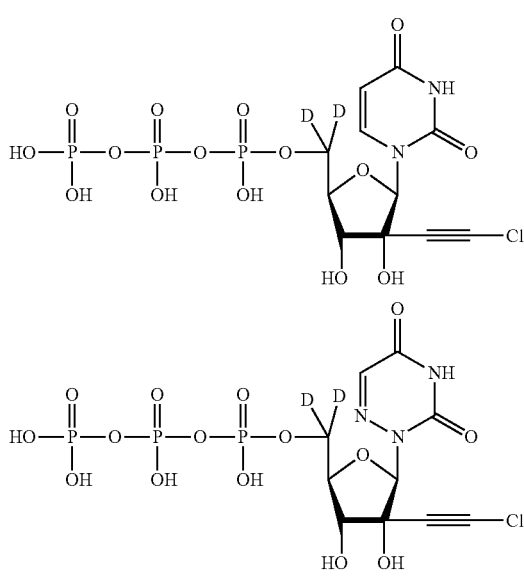
264
-continued
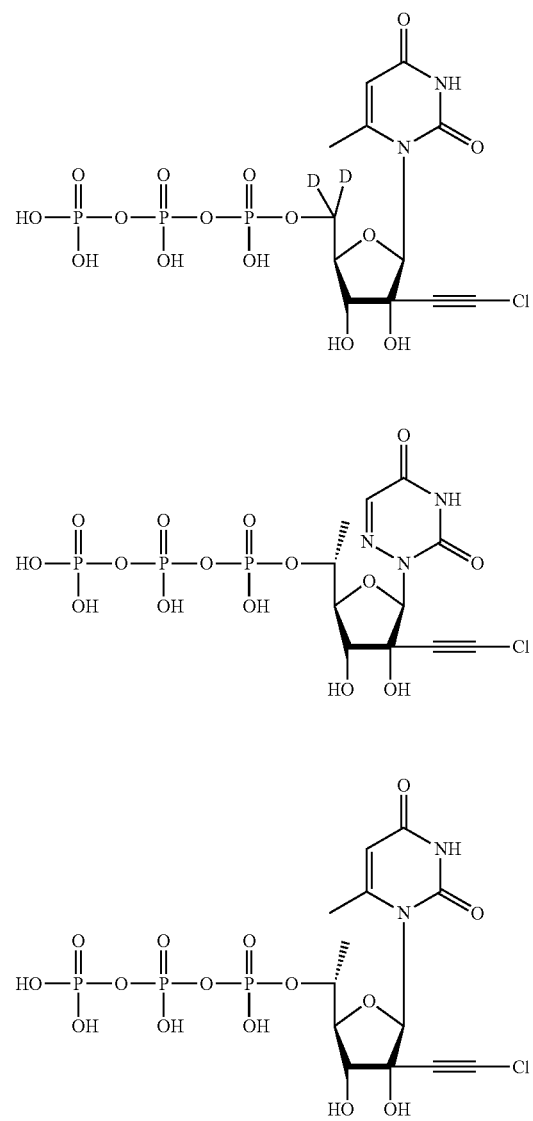
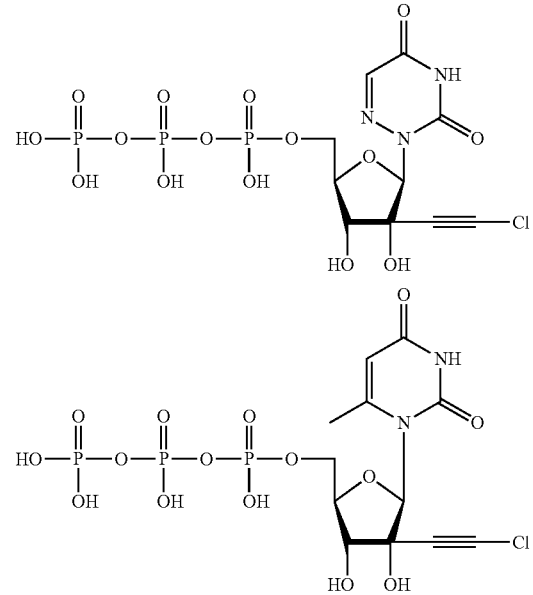

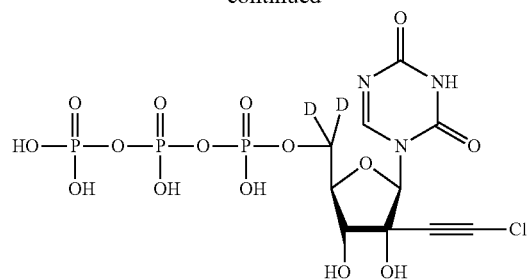
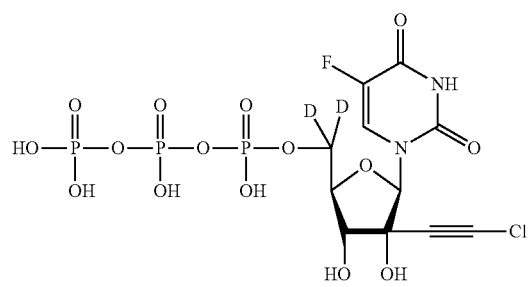
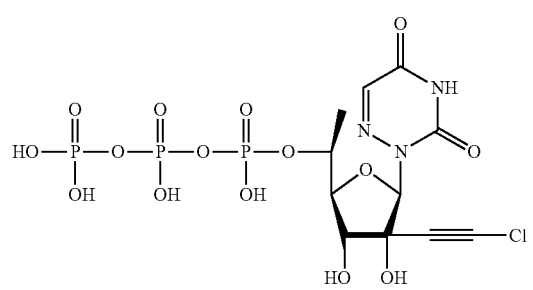
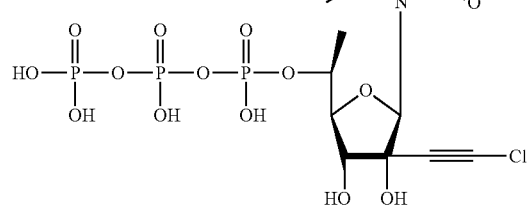
In exemplary embodiments, the compound is selected from:
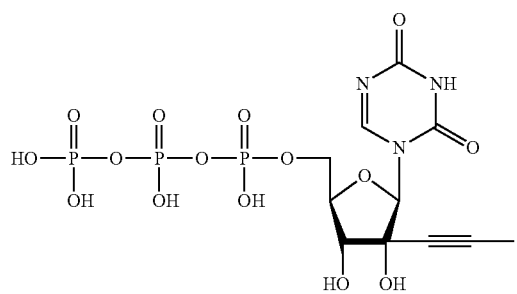
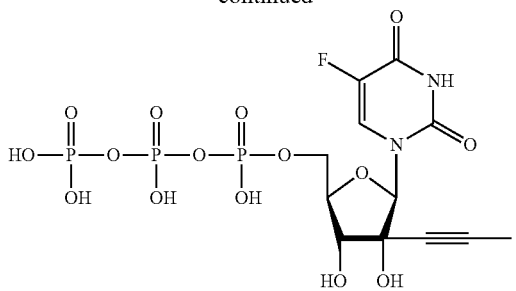
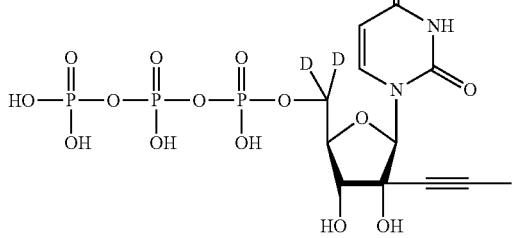
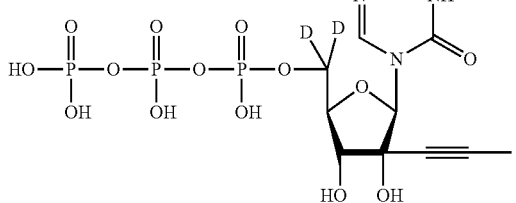

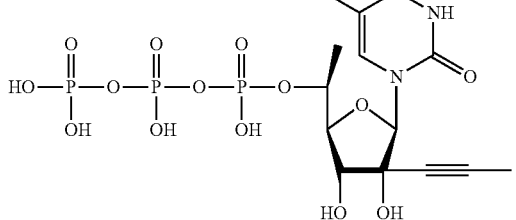

267
-continued
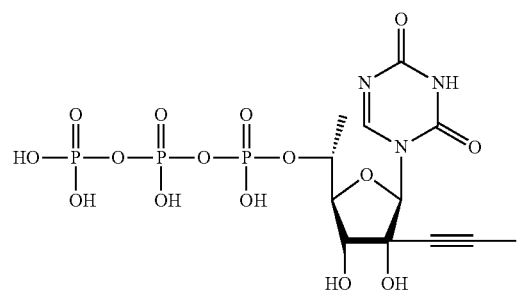
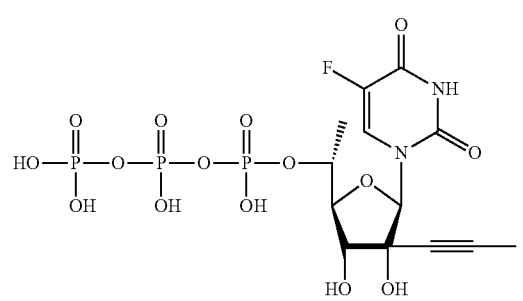
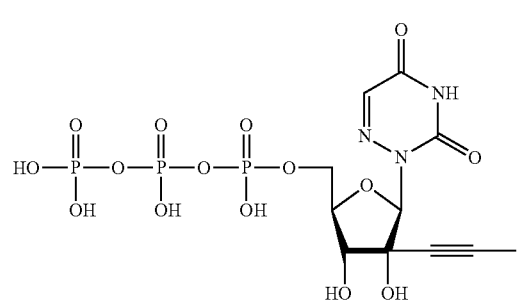
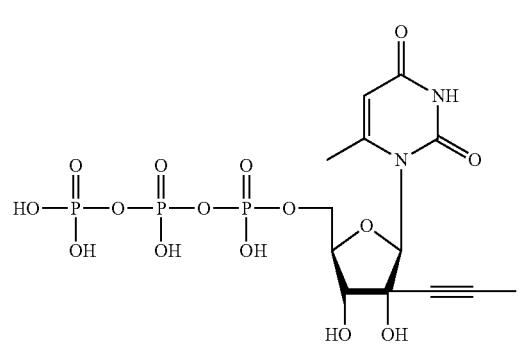
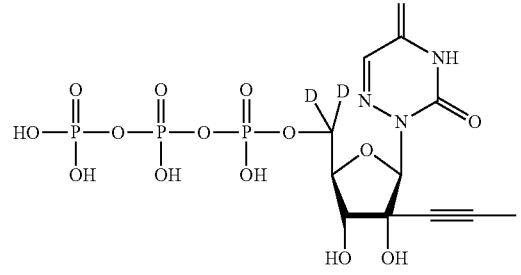
268
-continued
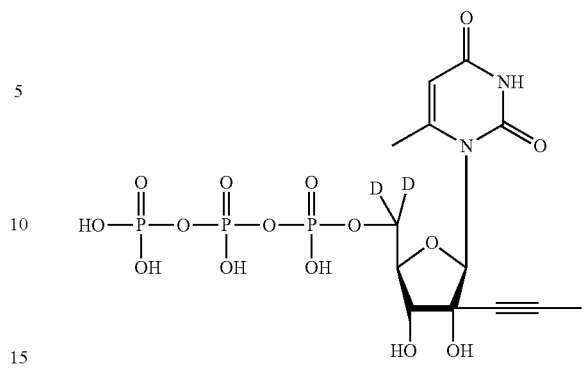
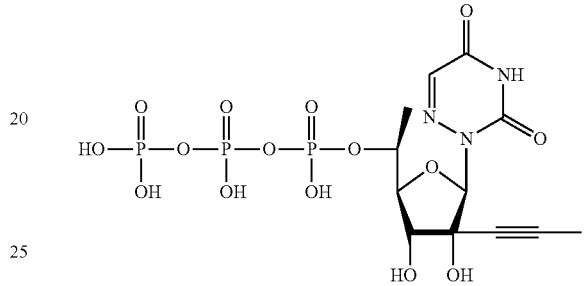
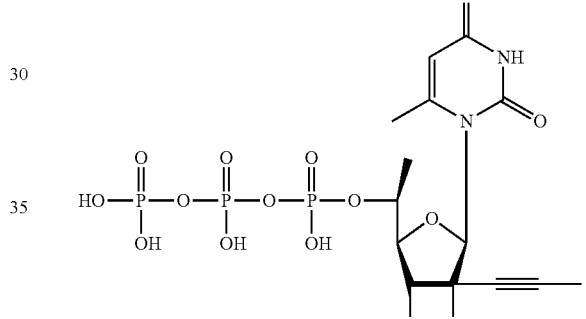
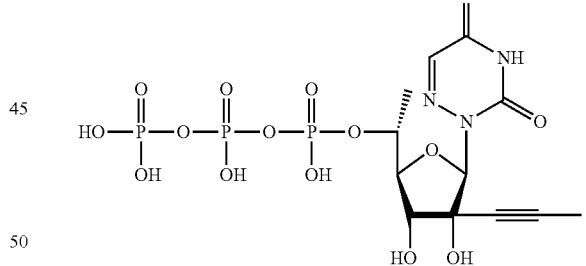
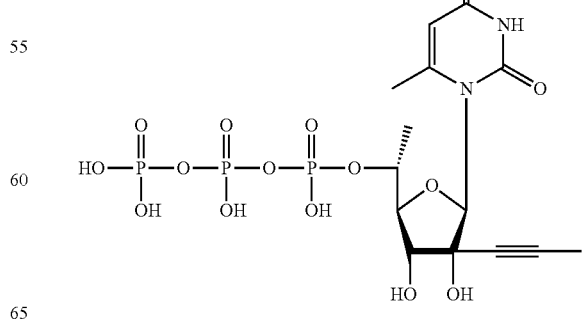

In exemplary embodiments, the compound is selected from:
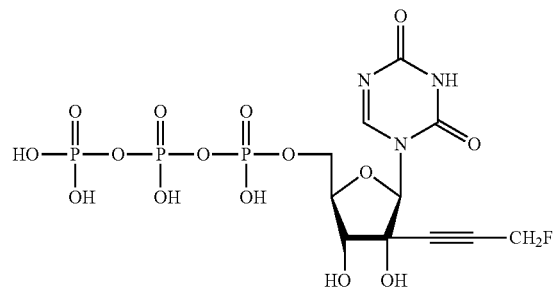
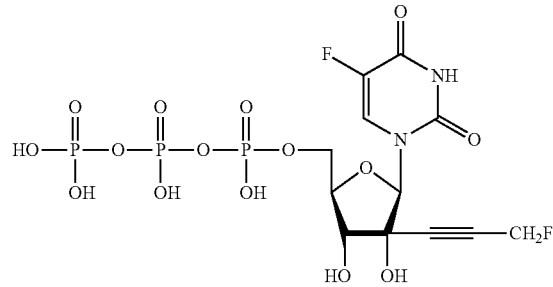
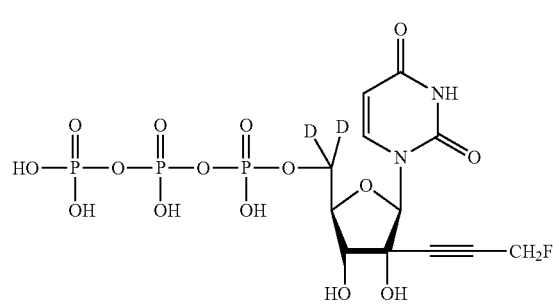
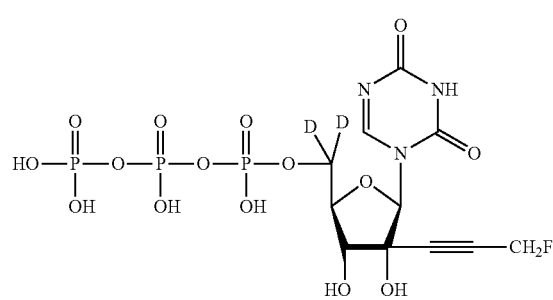
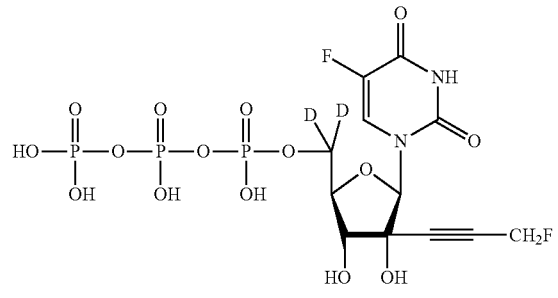
-continued
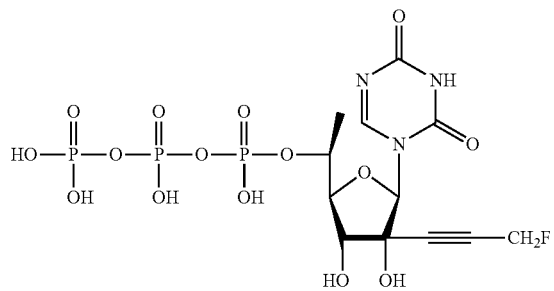
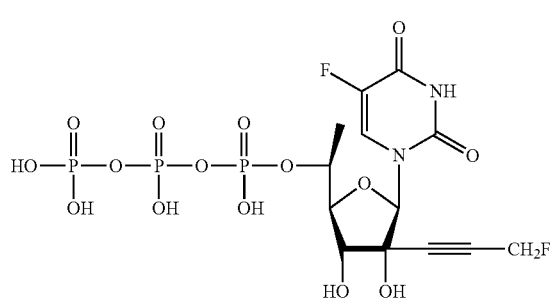
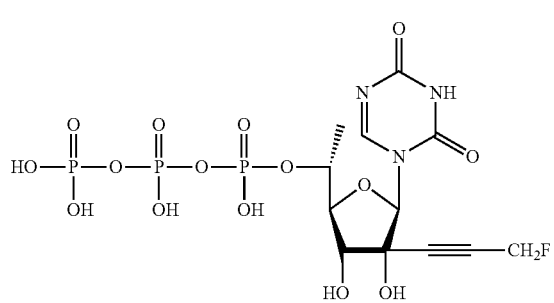
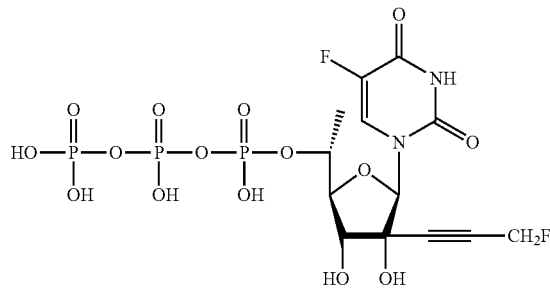
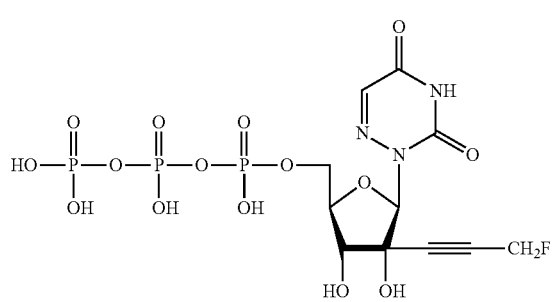

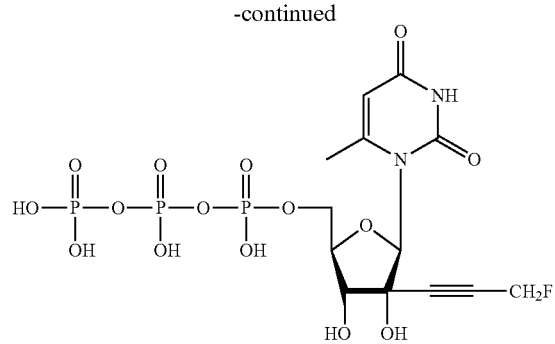
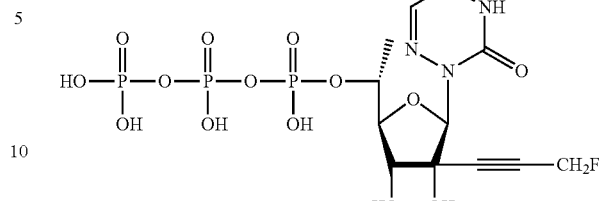
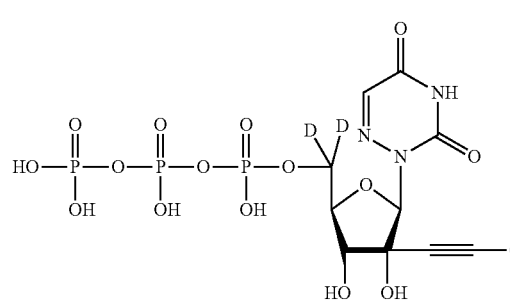
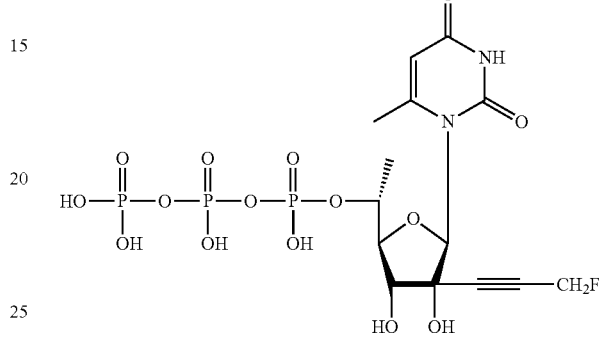
In exemplary embodiments, the compound is selected from:
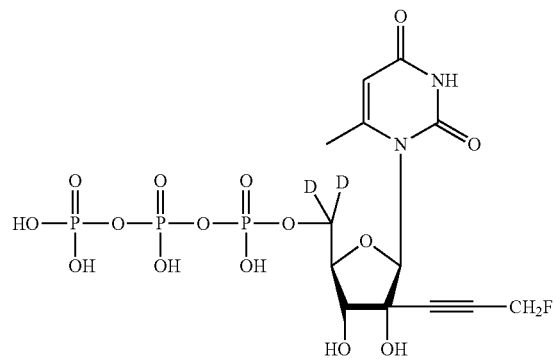
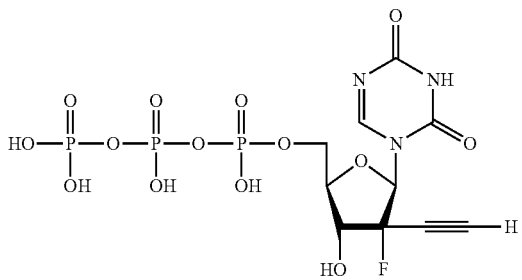
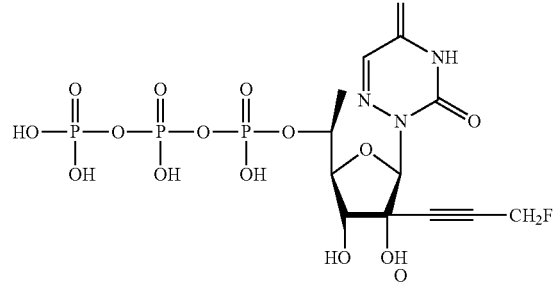
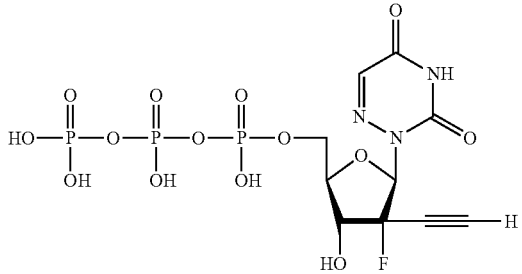
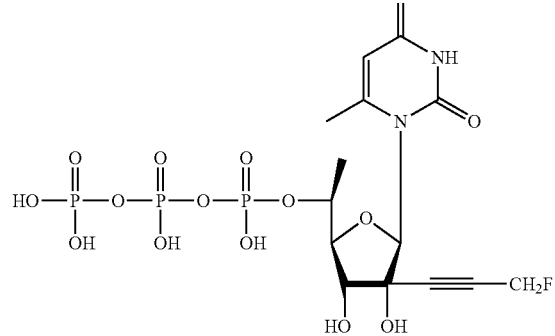
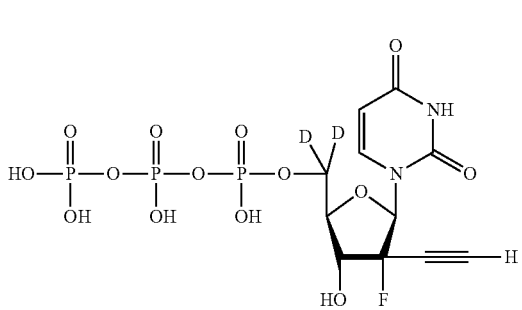

273
-continued
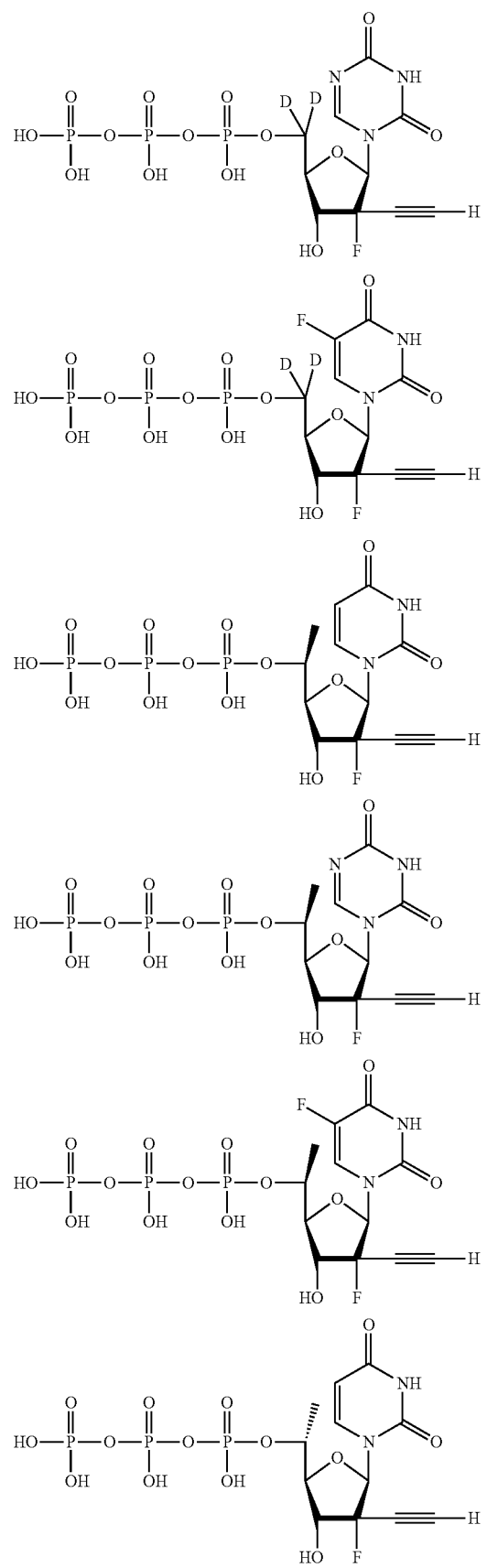
274
-continued
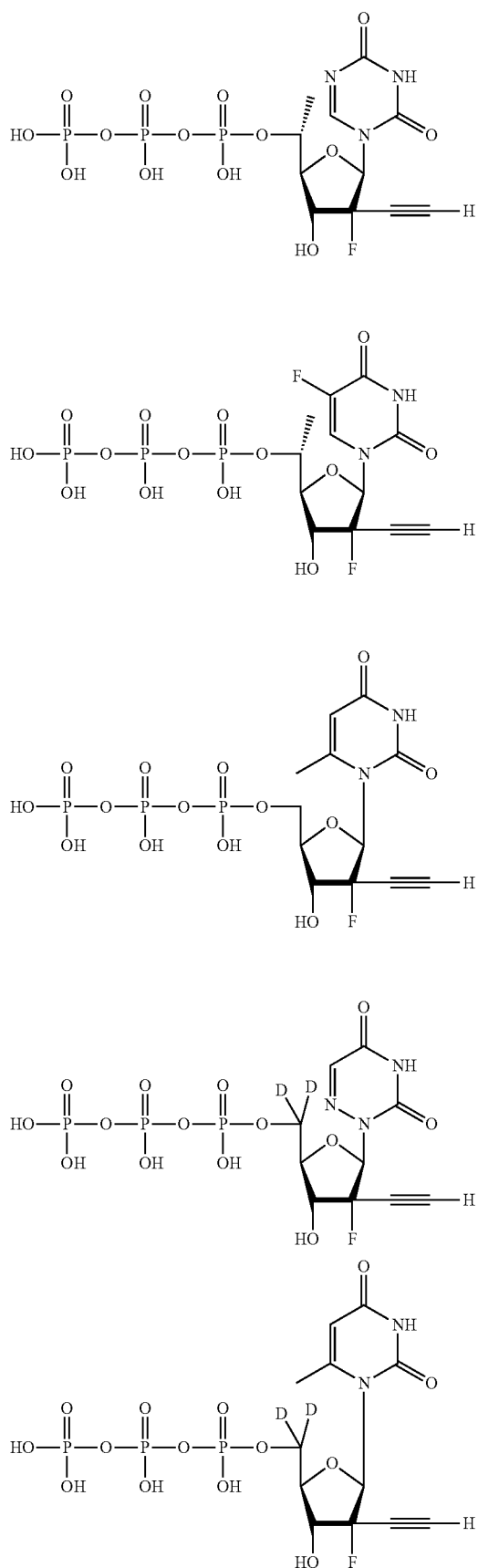

275
-continued
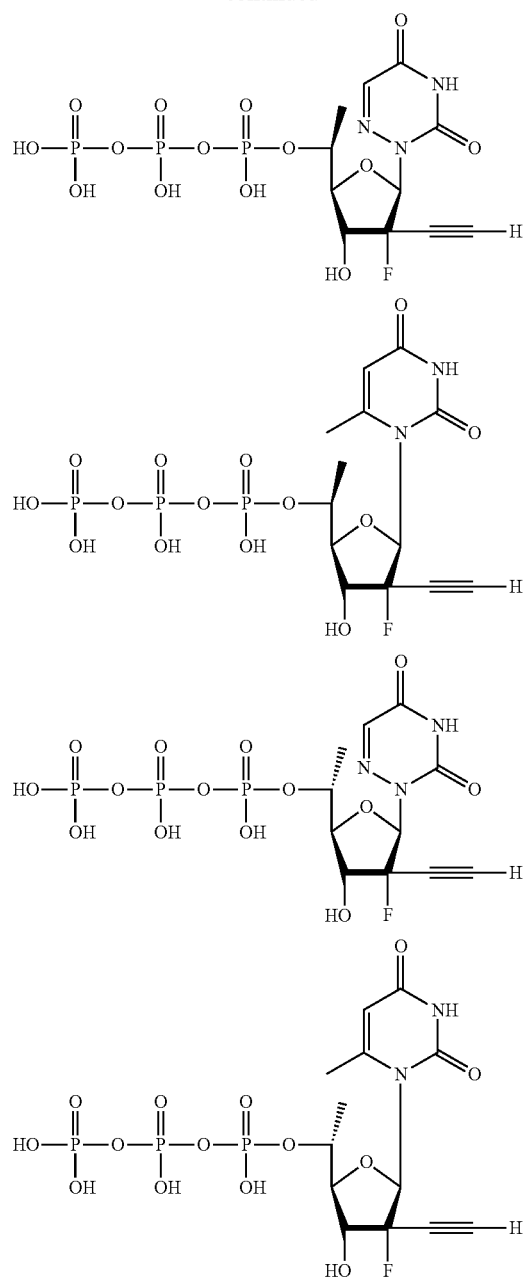
In exemplary embodiments, the compound is selected from:
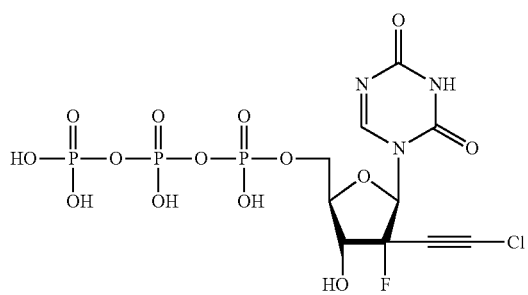
276
-continued
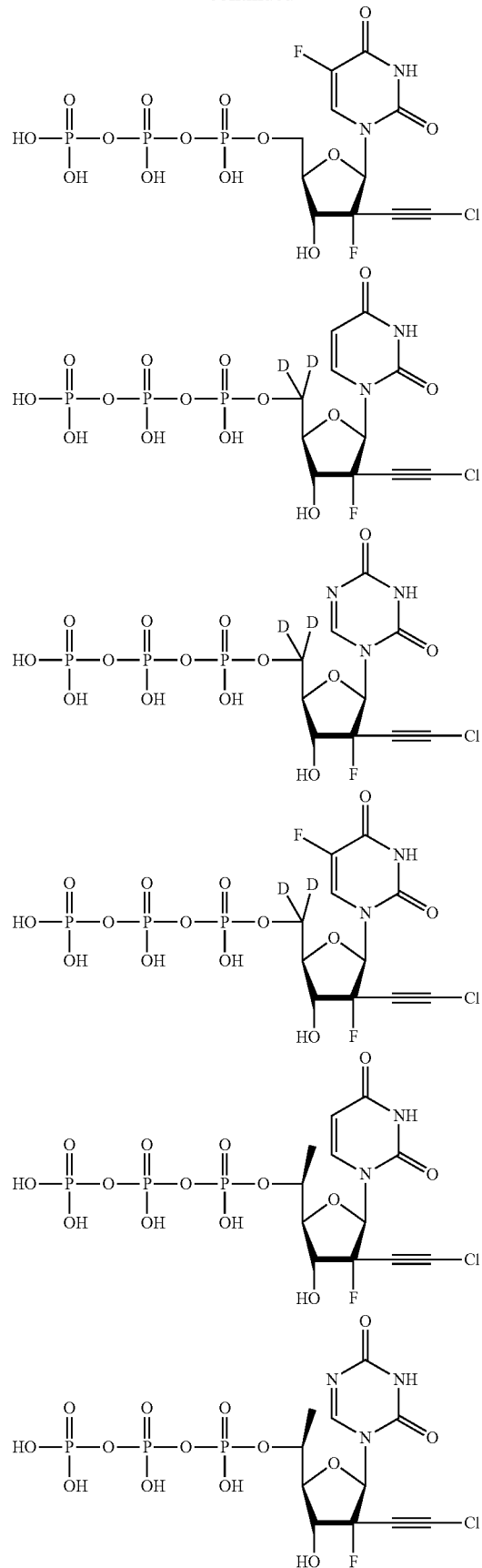

277
-continued
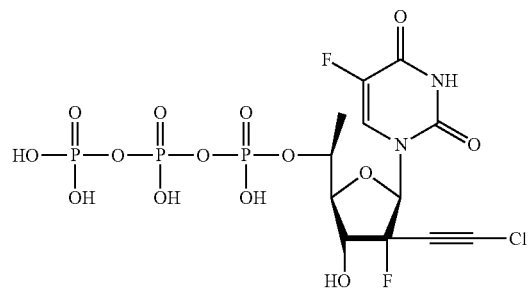
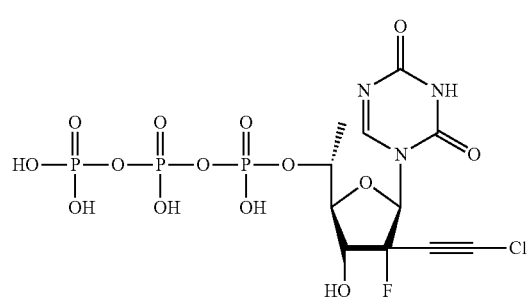
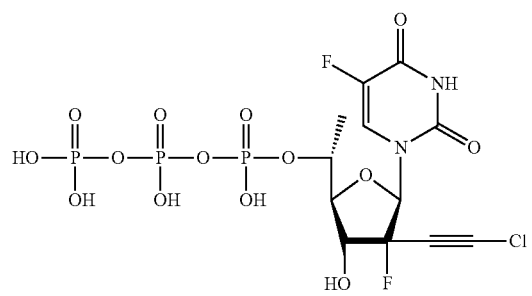
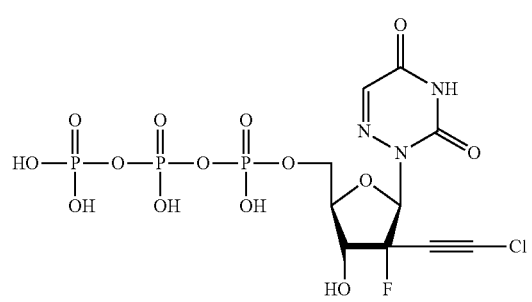
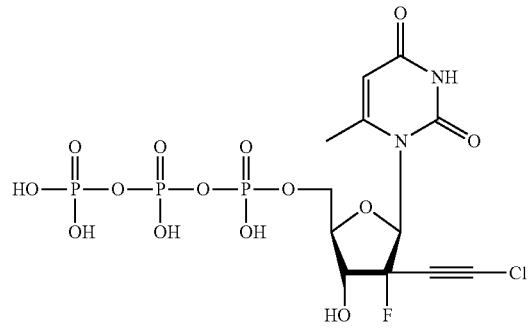
278
-continued
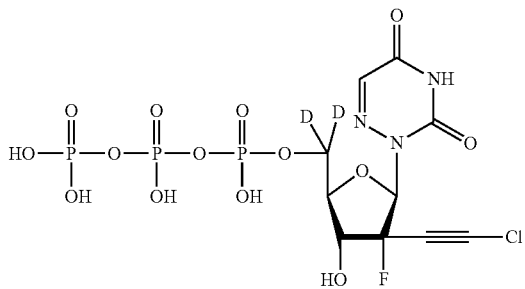
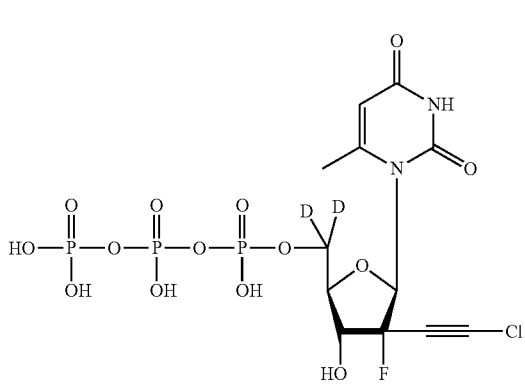
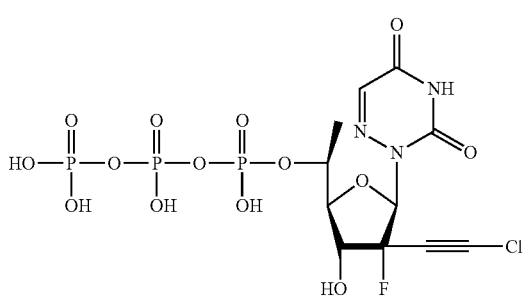
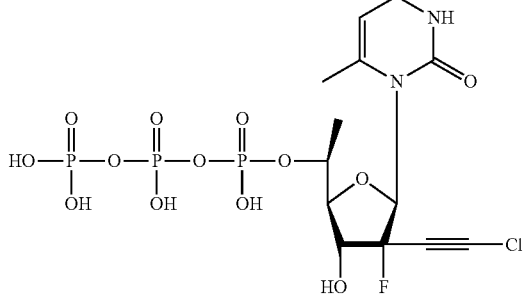
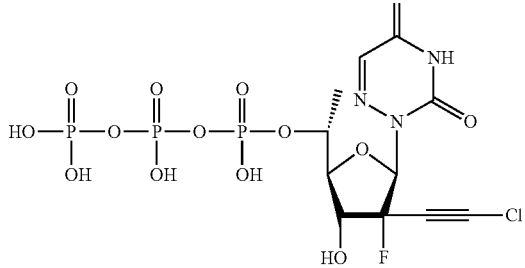

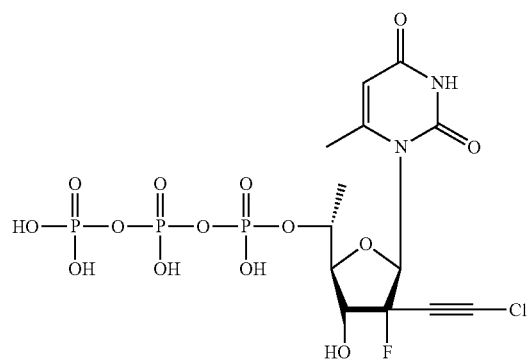
In exemplary embodiments, the compound is selected from:
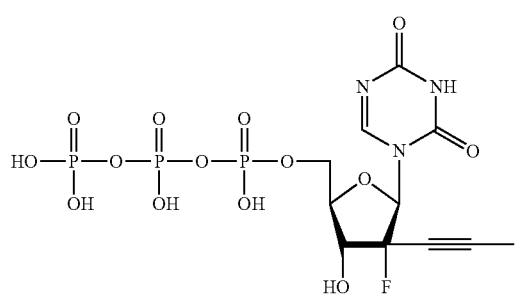
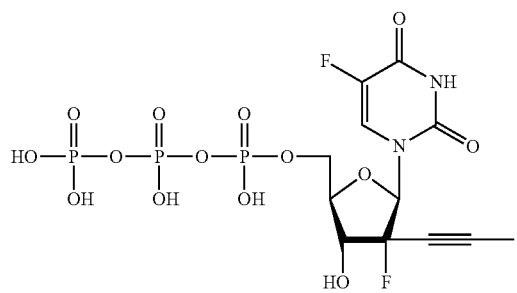
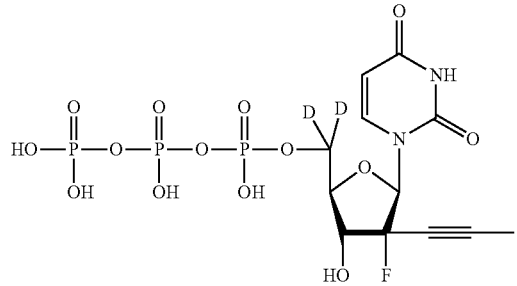
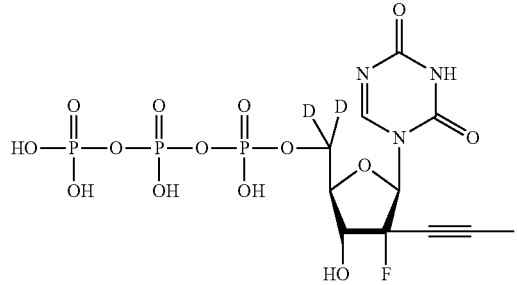
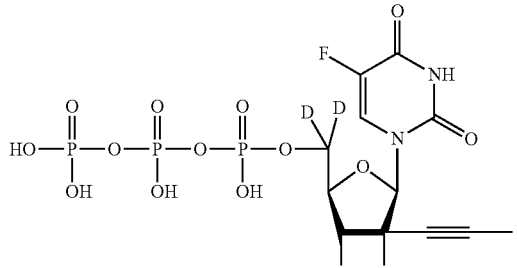

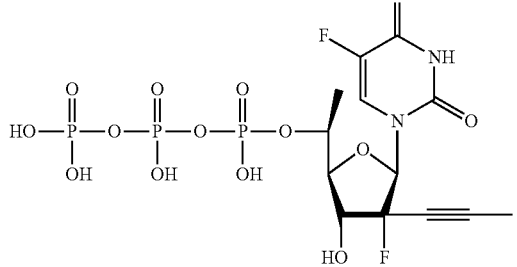
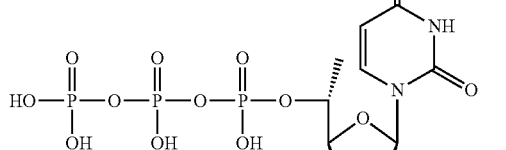

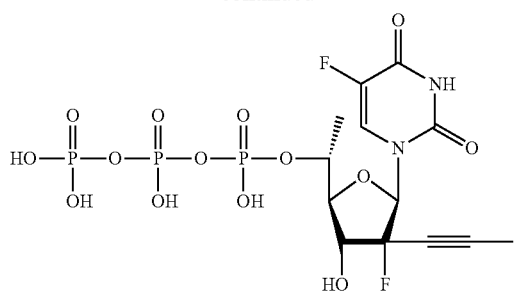
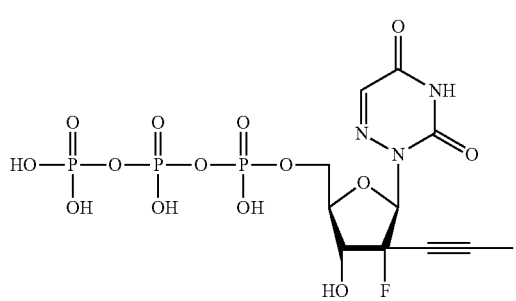
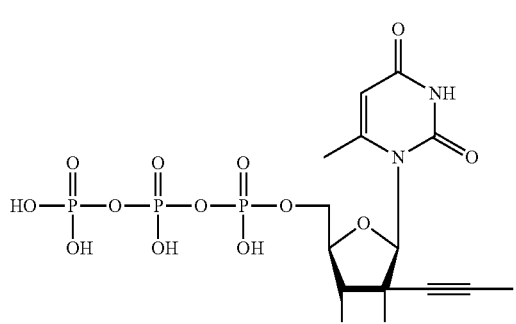
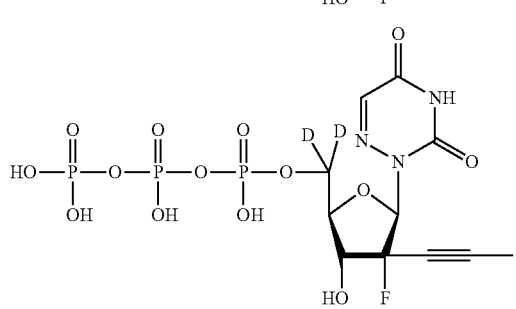
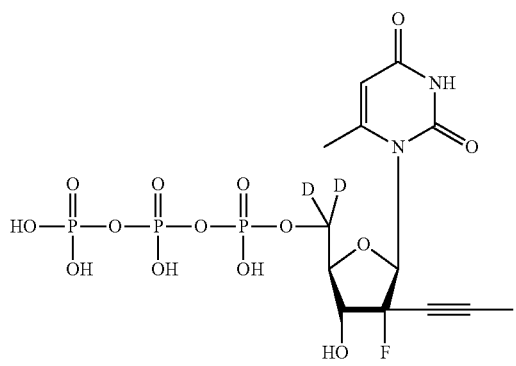
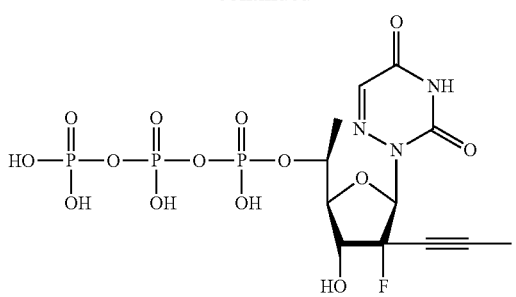
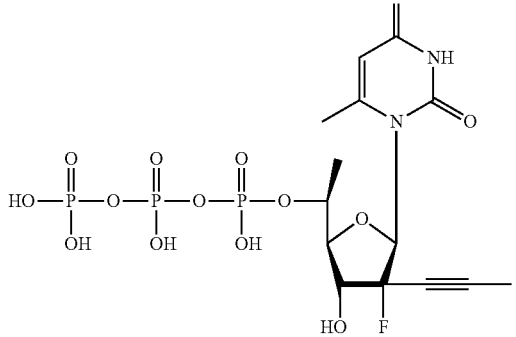
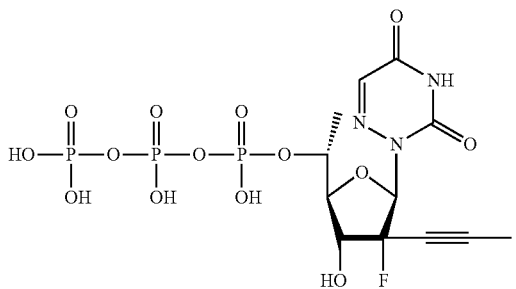
In exemplary embodiments, the compound is selected from:
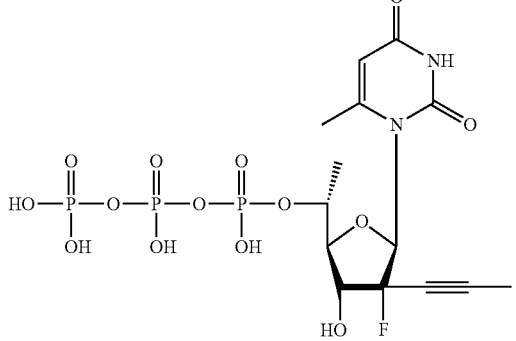

283
-continued
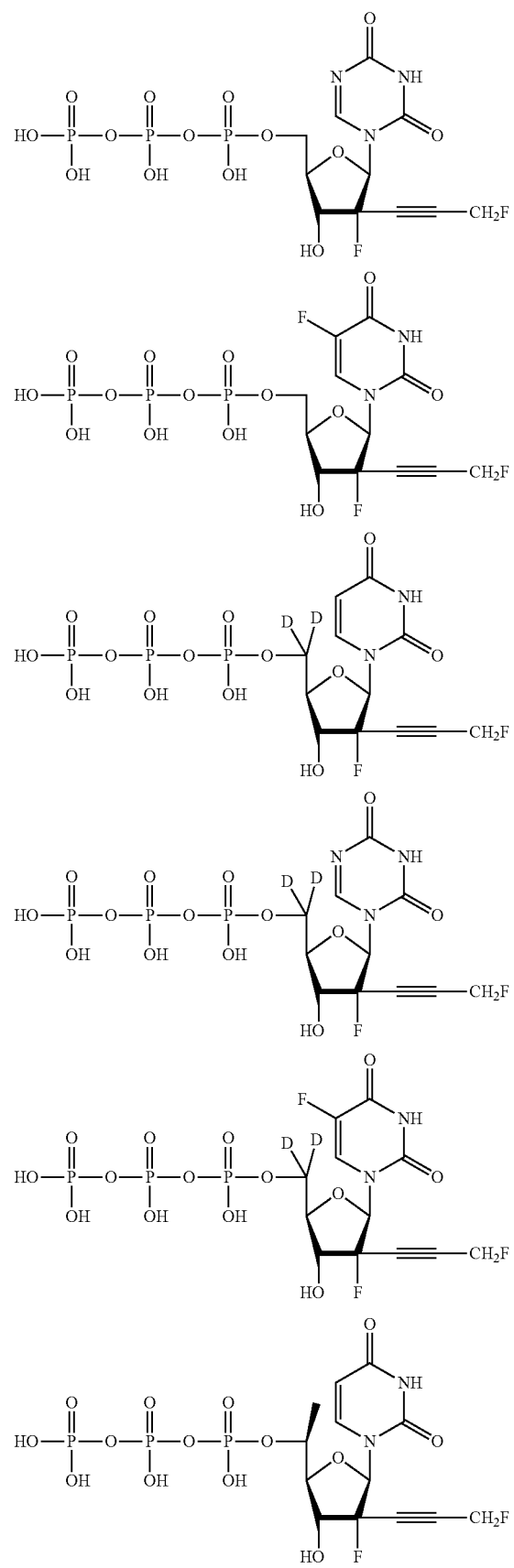
284
-continued
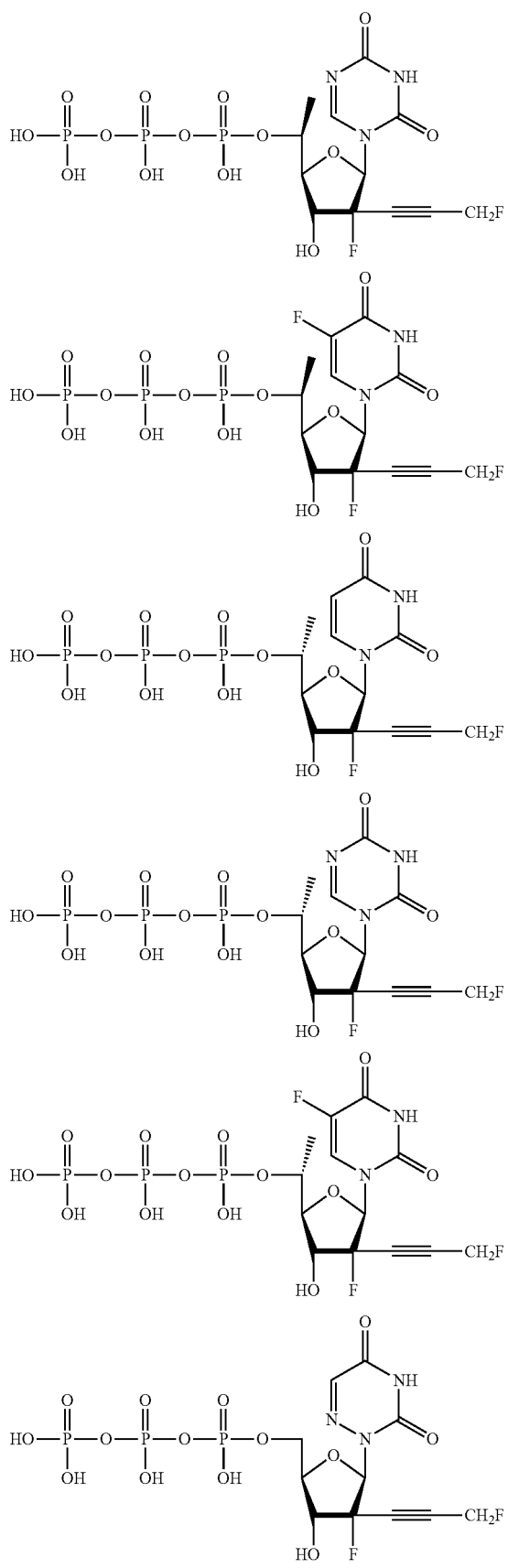

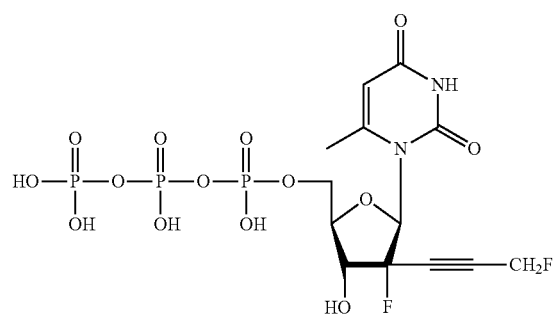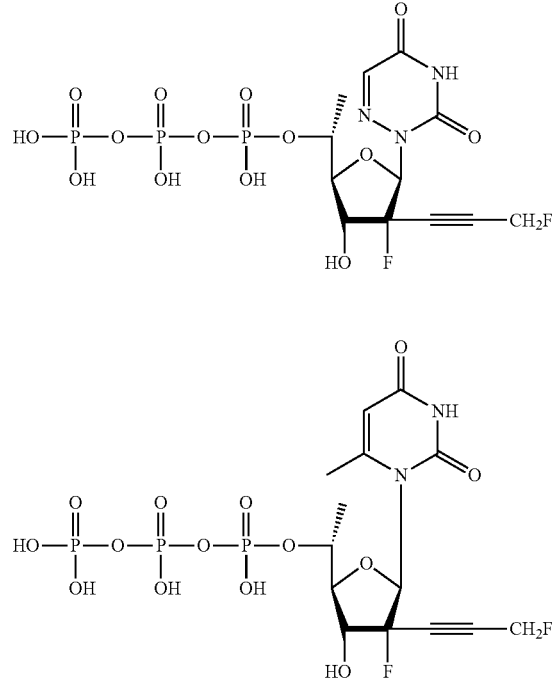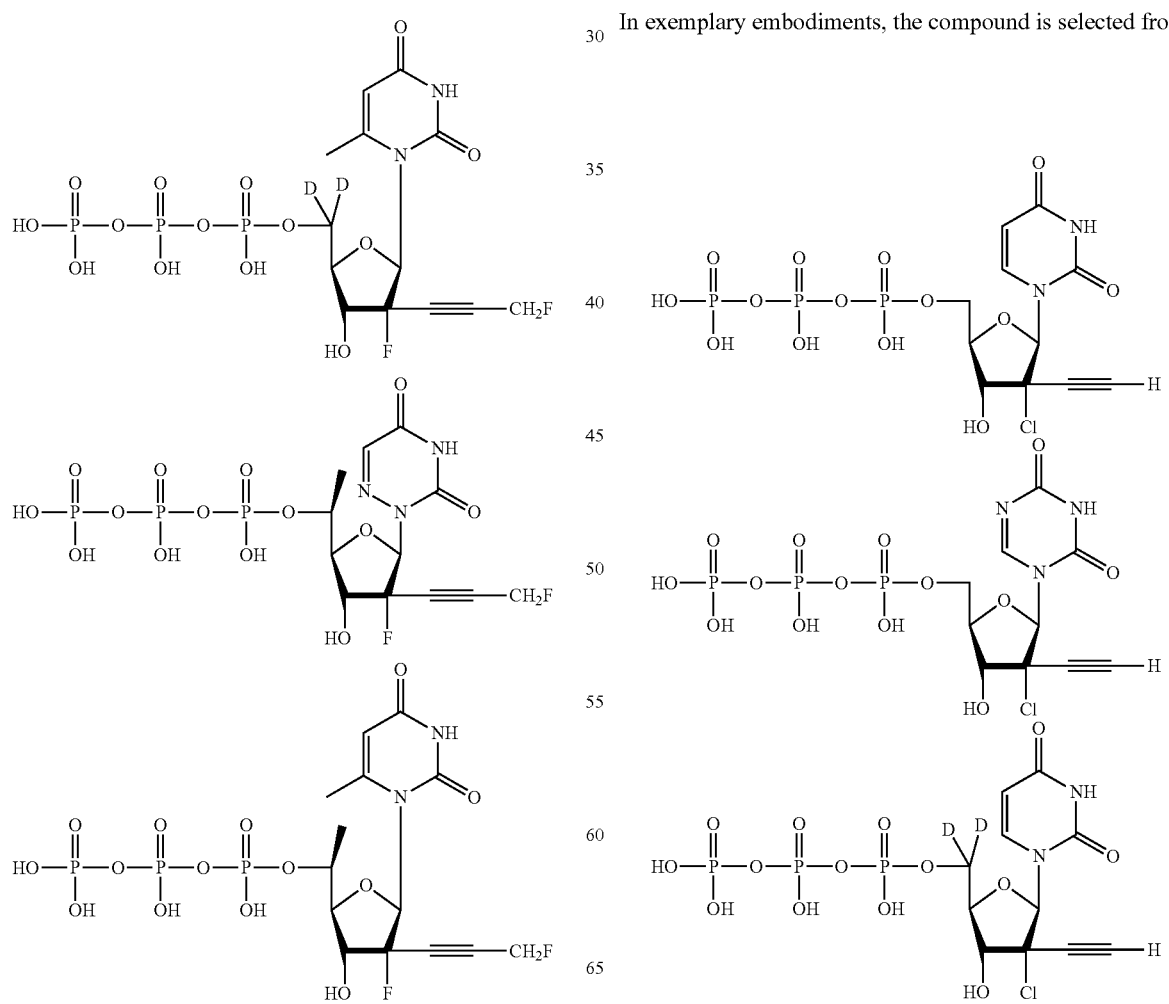
In exemplary embodiments, the compound is selected from:

287
-continued
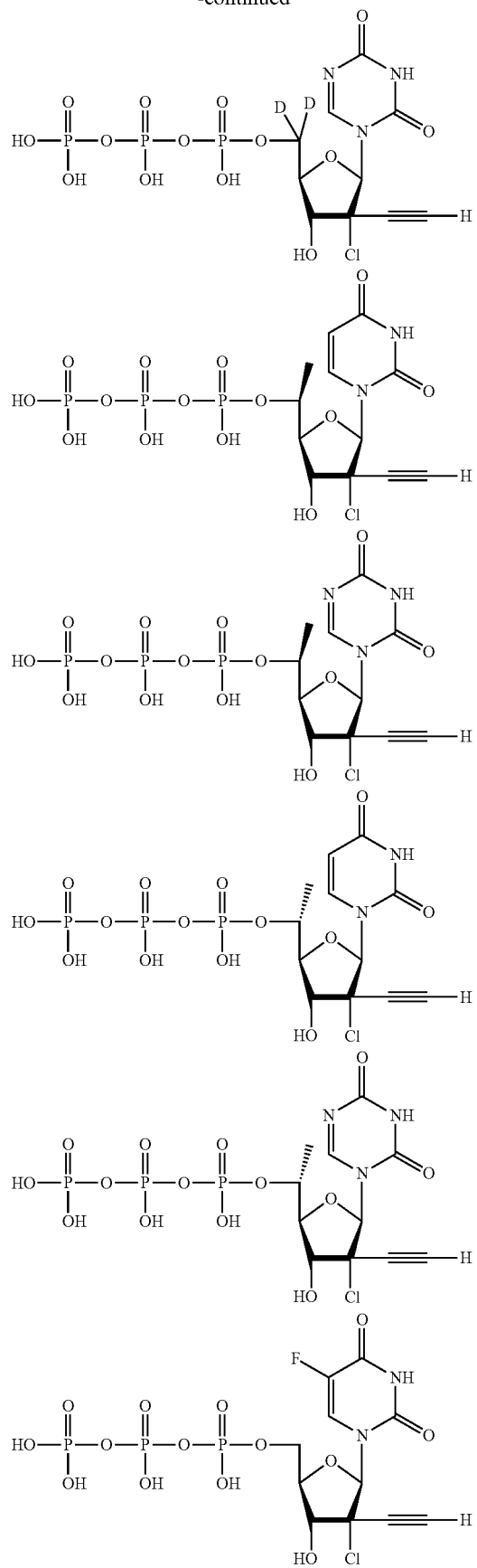
288
-continued
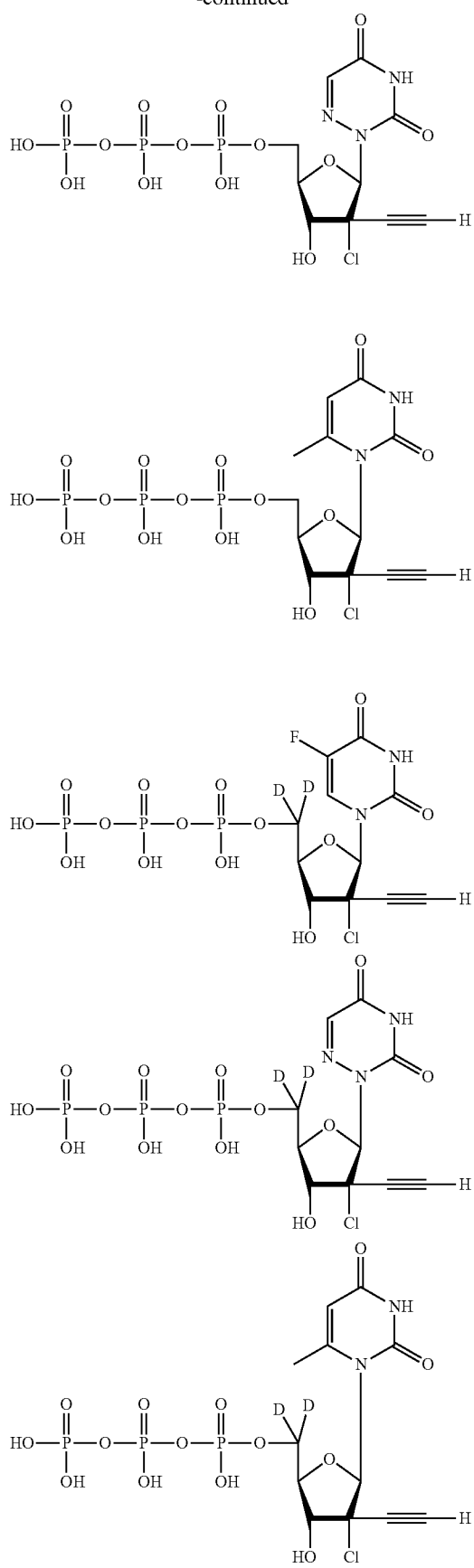

-continued
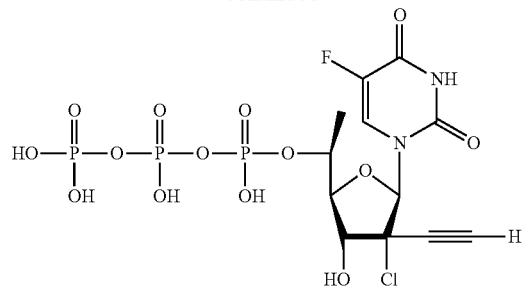
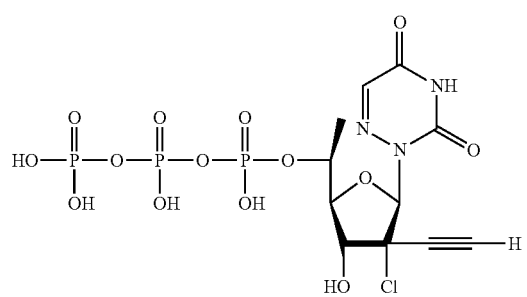
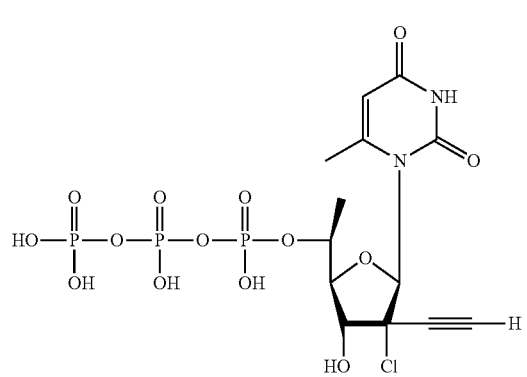
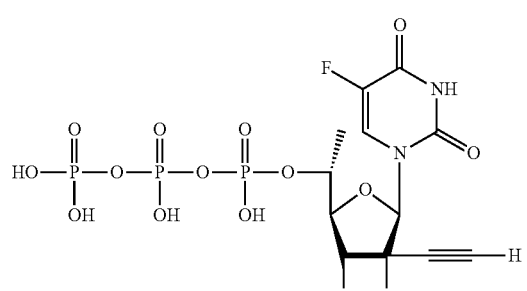
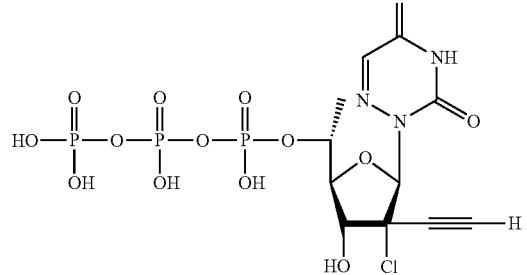
-continued
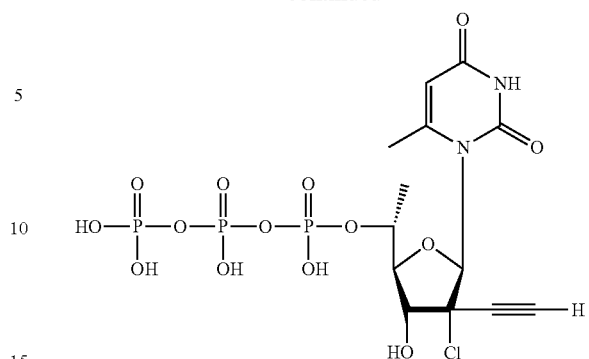
In exemplary embodiments, the compound is selected from:
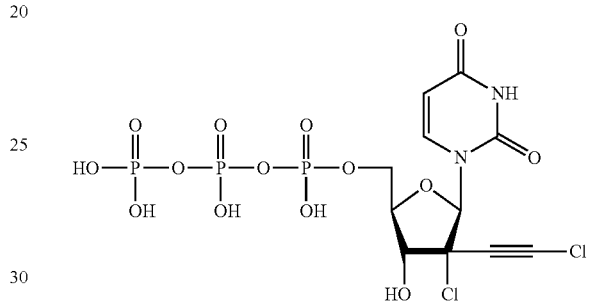

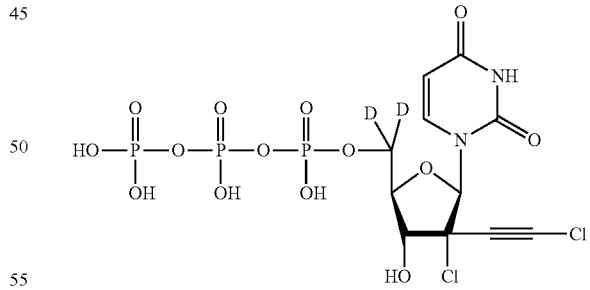
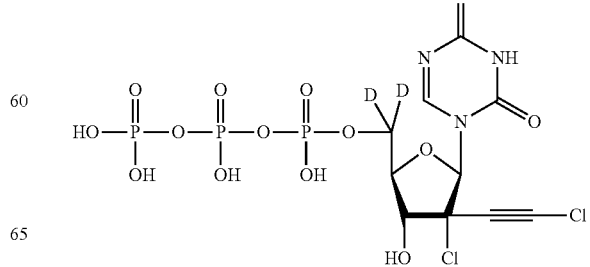

291
-continued
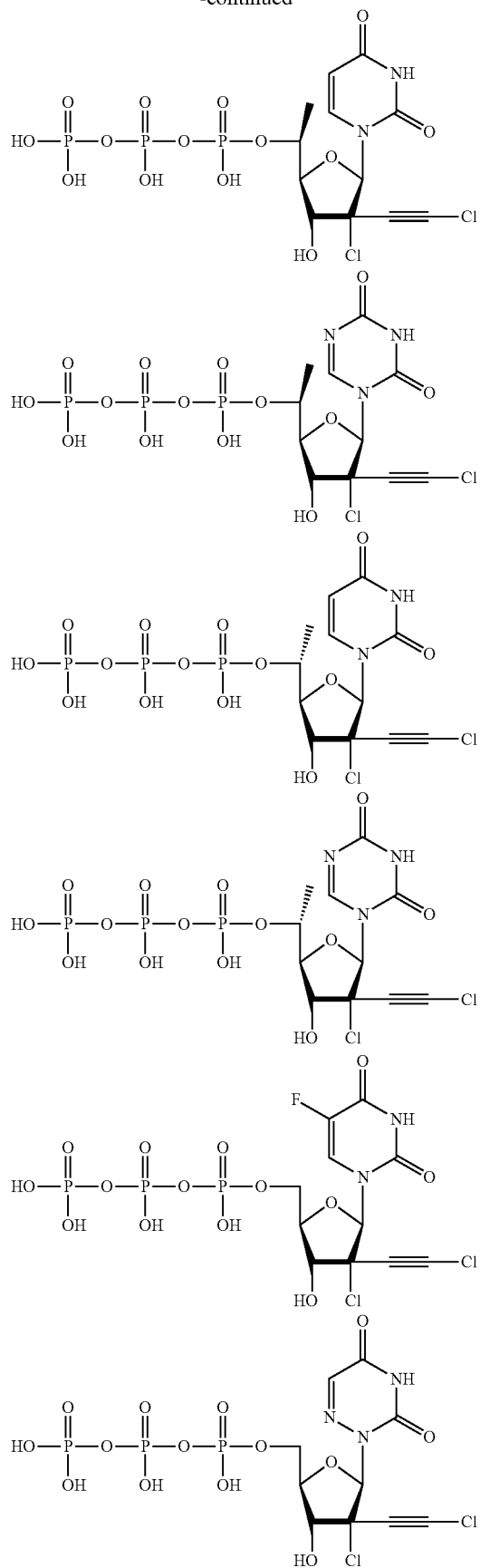
292
-continued
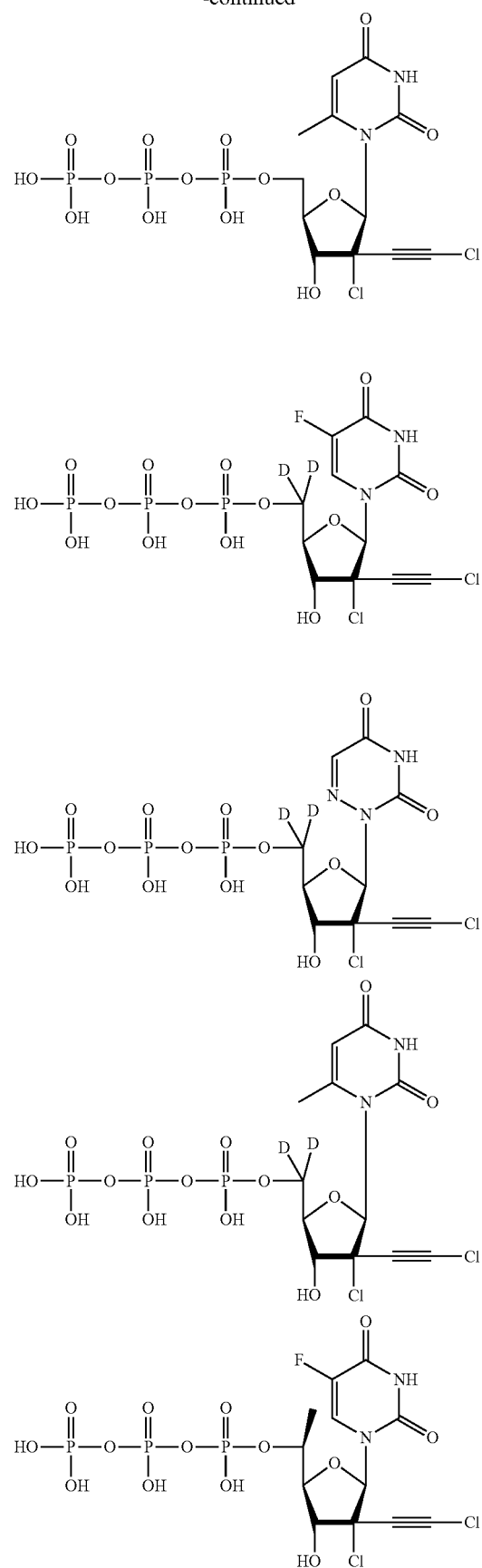

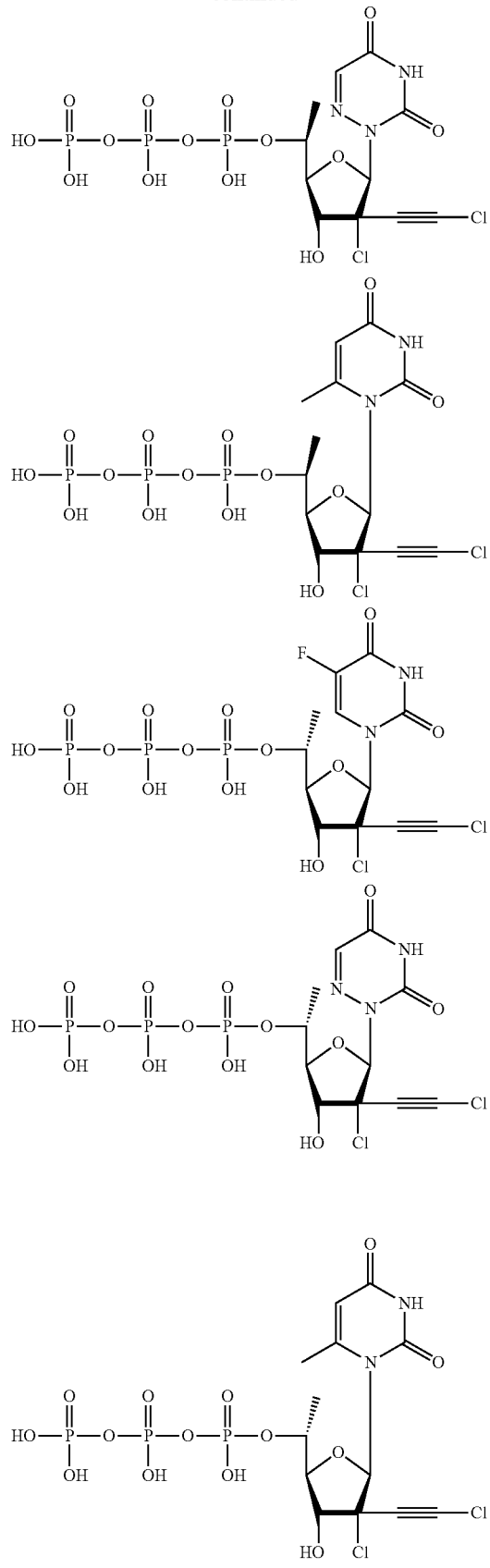
In exemplary embodiments, the compound is selected from:
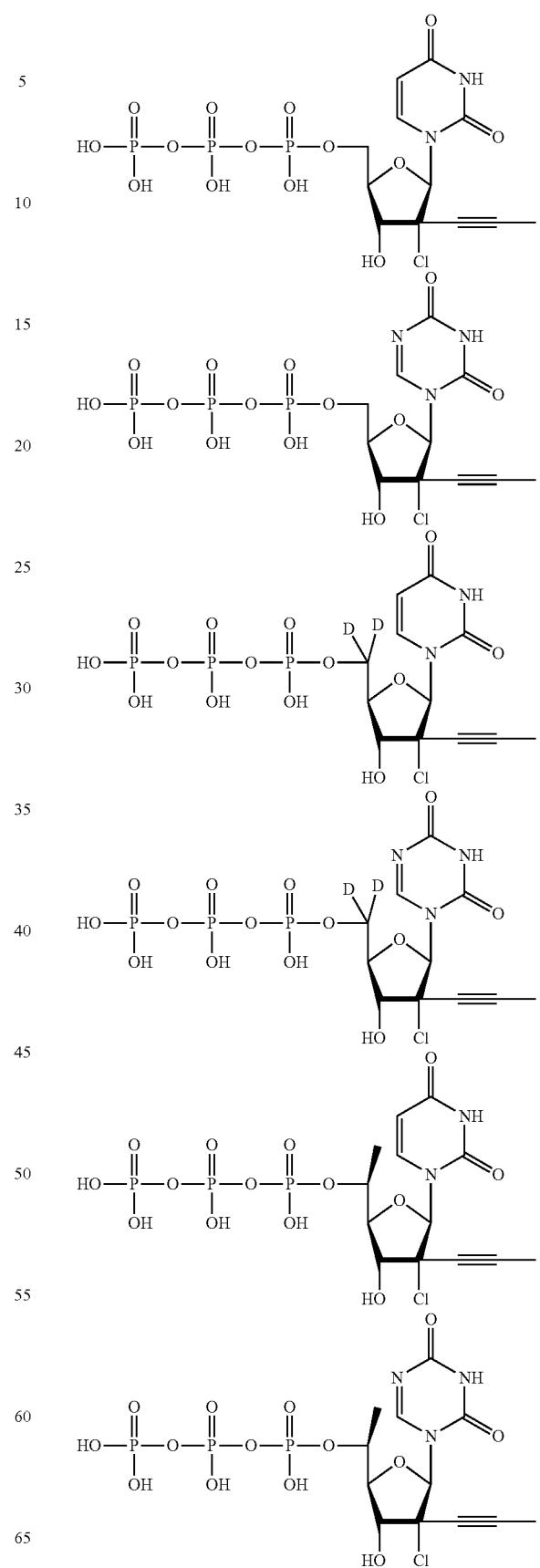

295
-continued
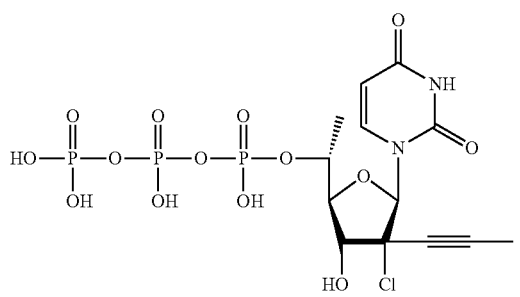
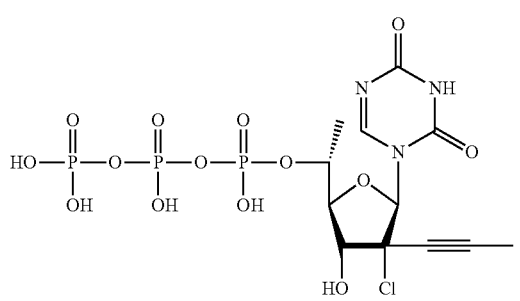
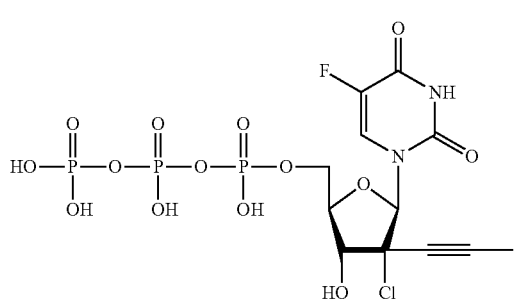
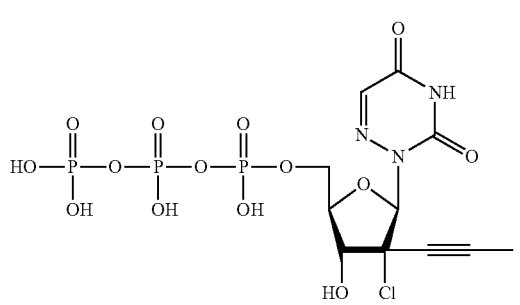
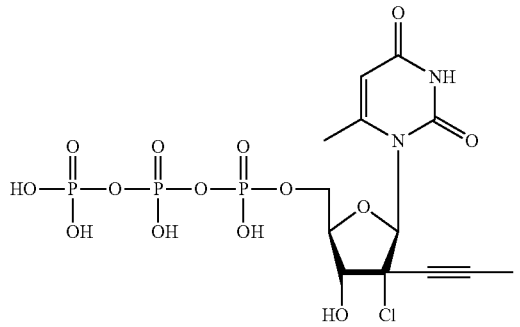
296
-continued
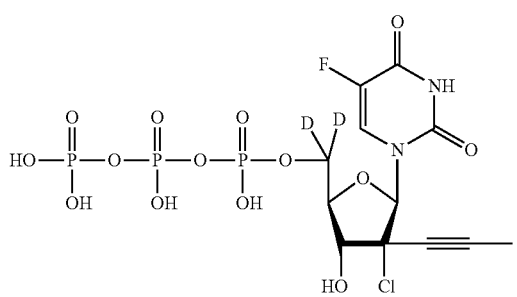
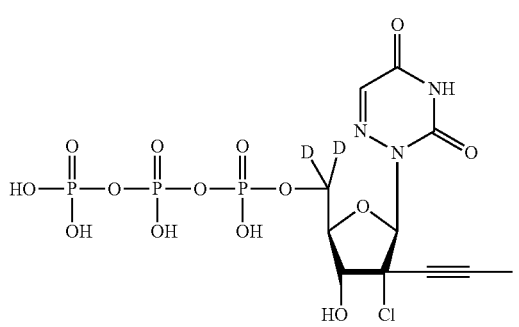
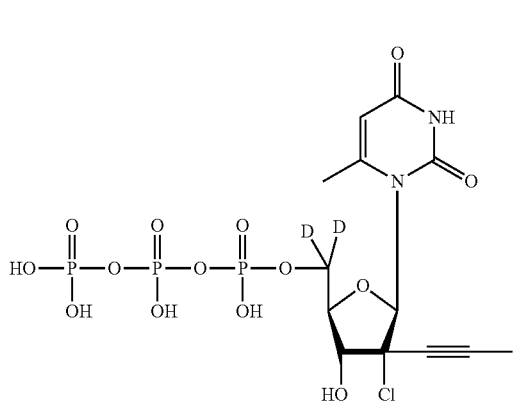
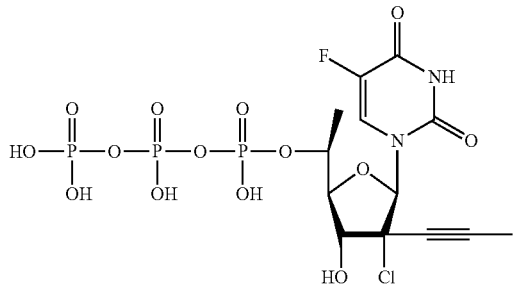
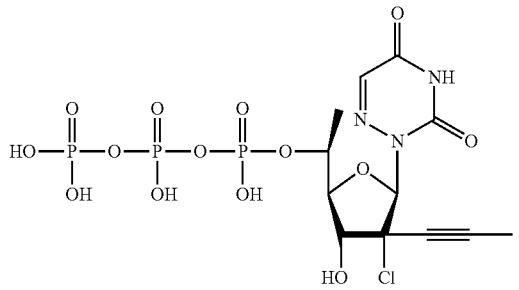

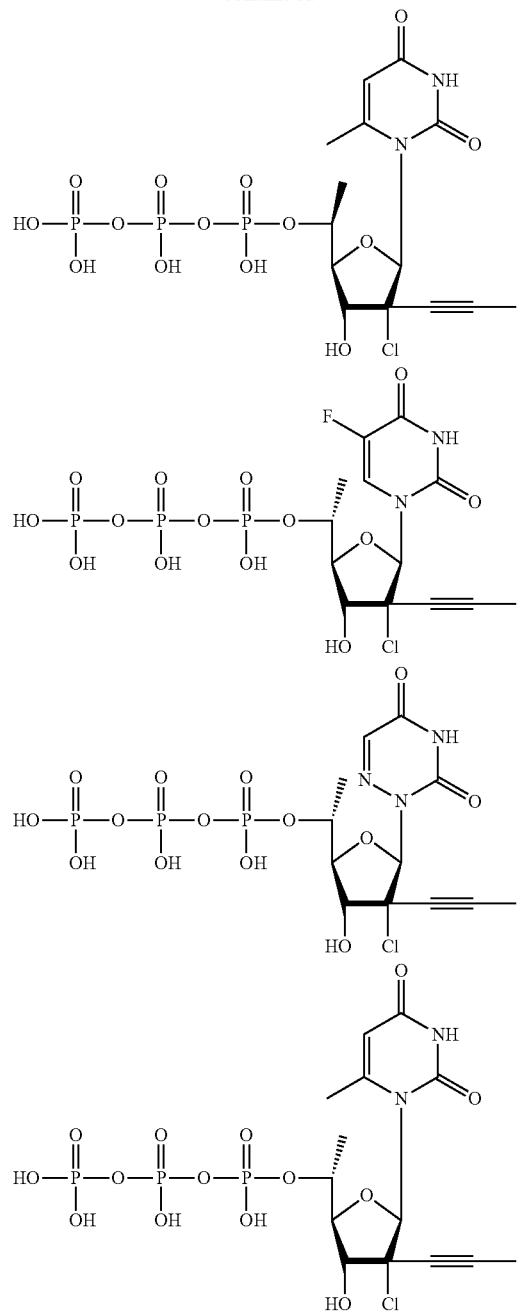
In exemplary embodiments, the compound is selected from:
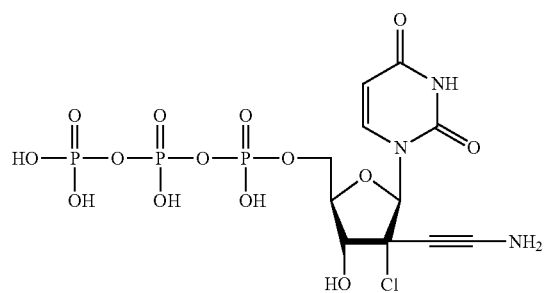
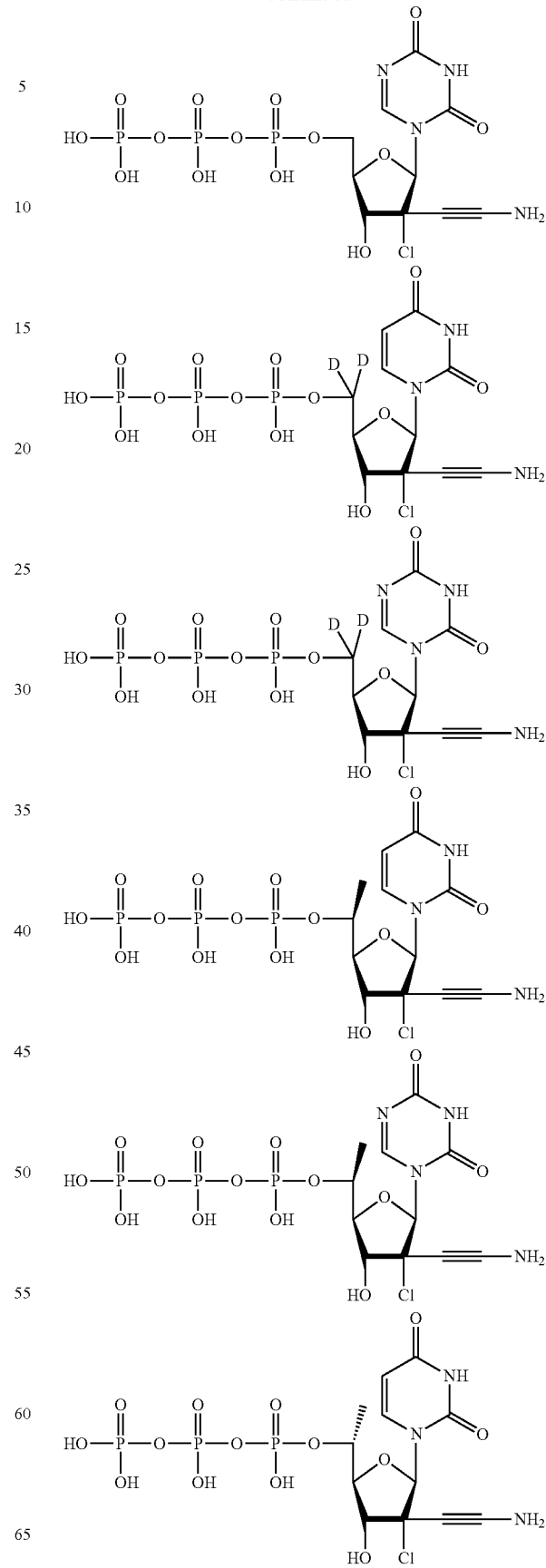

299
300
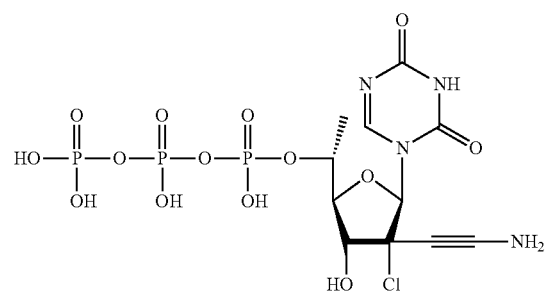
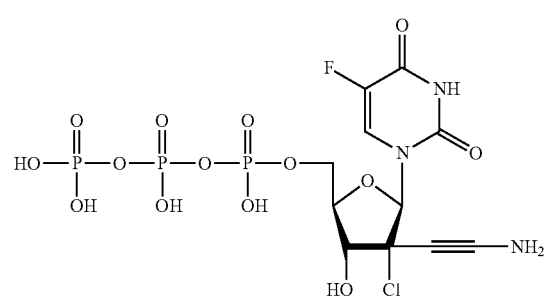
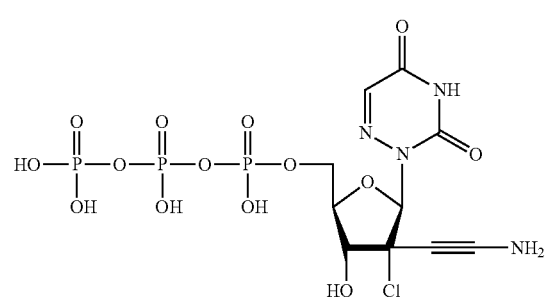
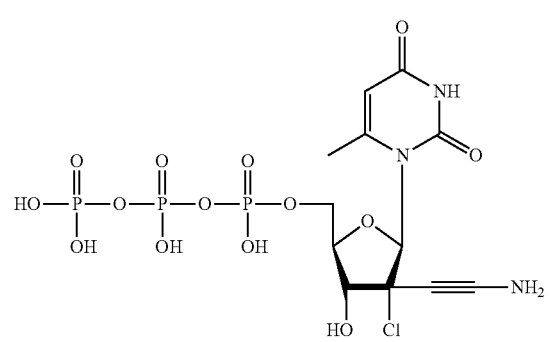
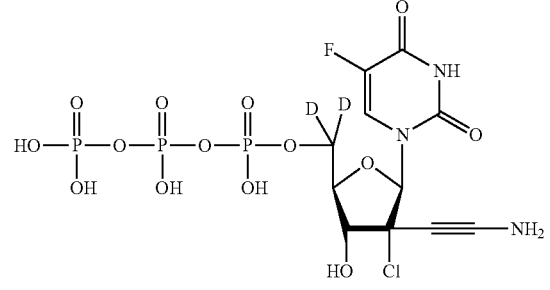
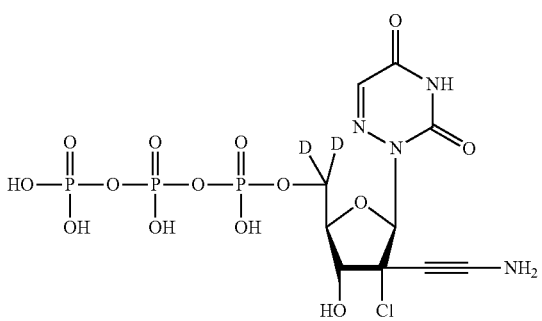
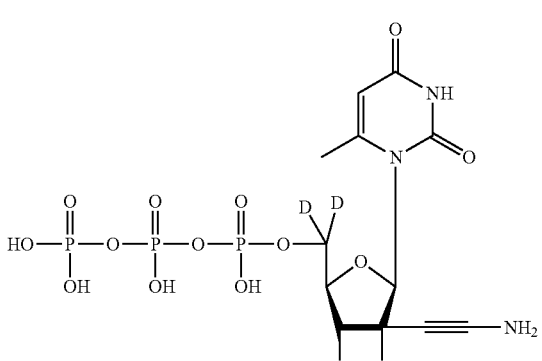
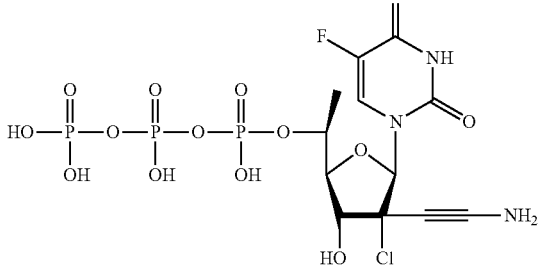
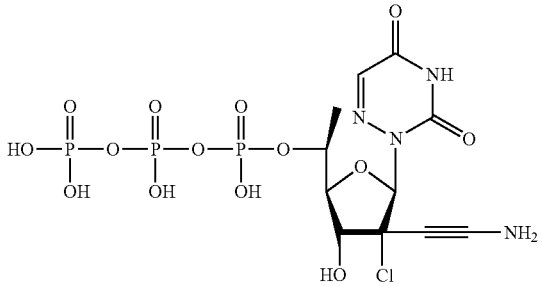
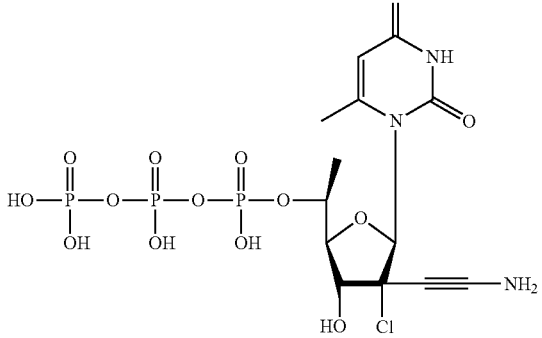

301
-continued
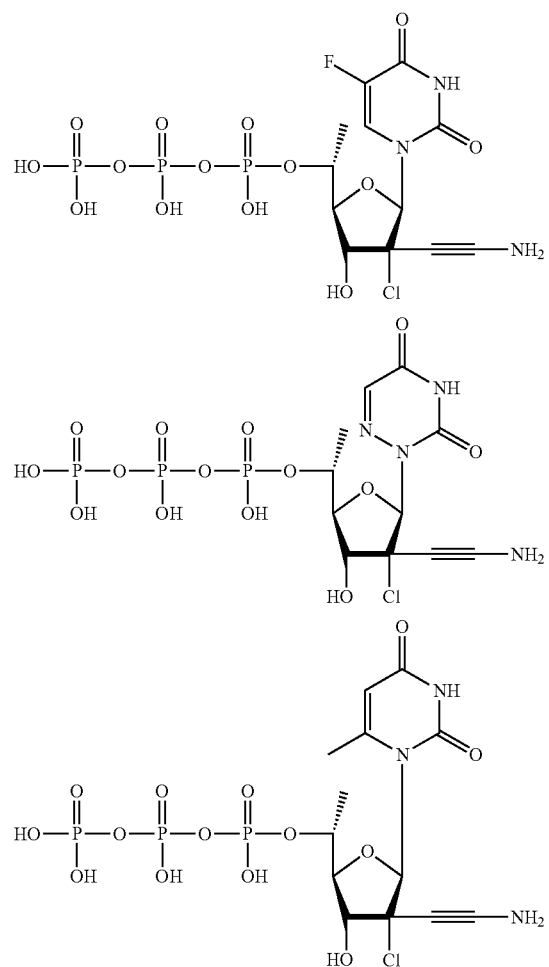
In exemplary embodiments, the compound is selected from:
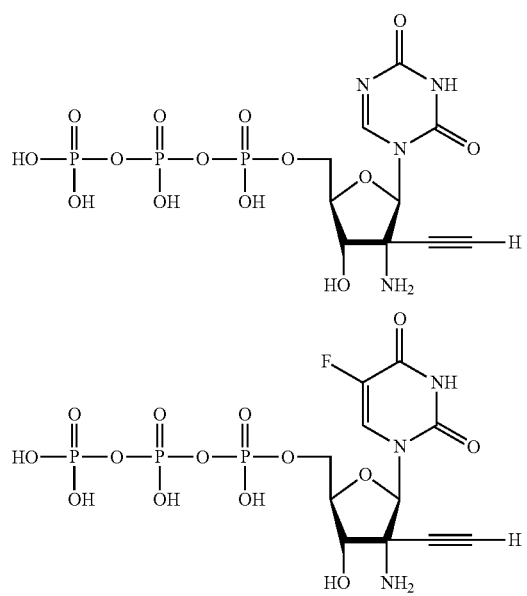
302
-continued
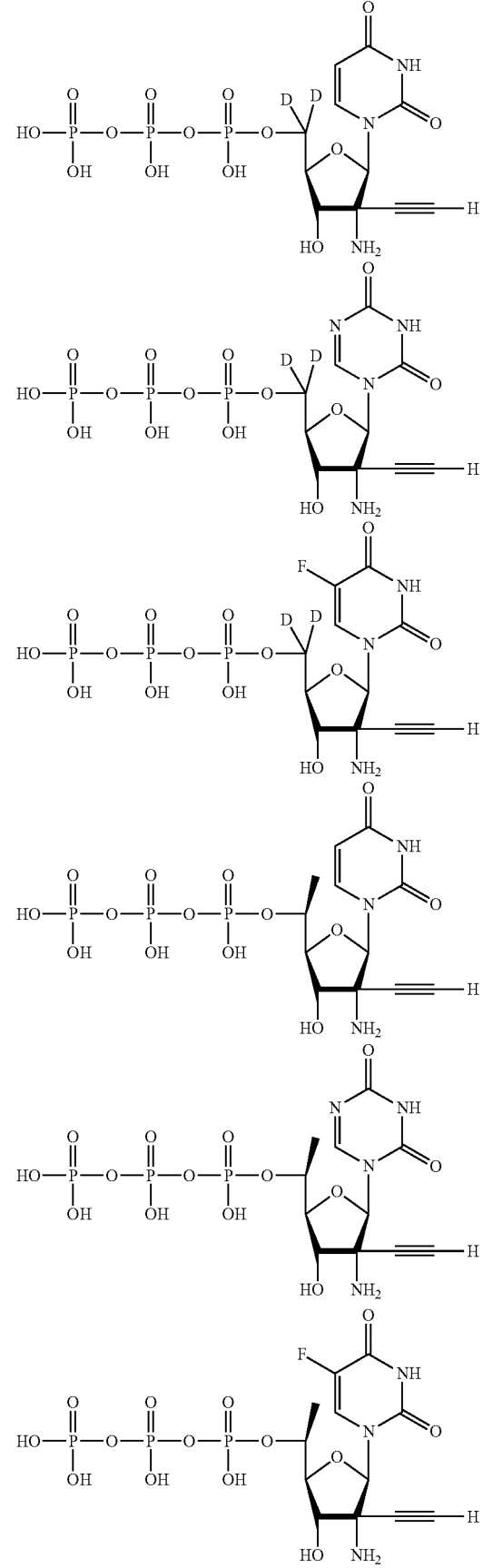

303
-continued
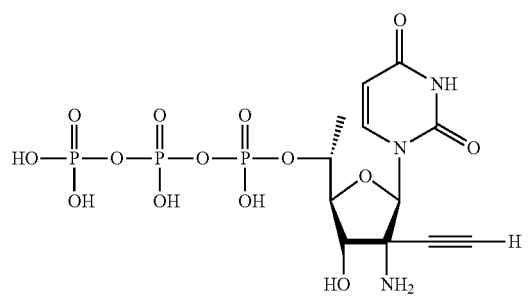
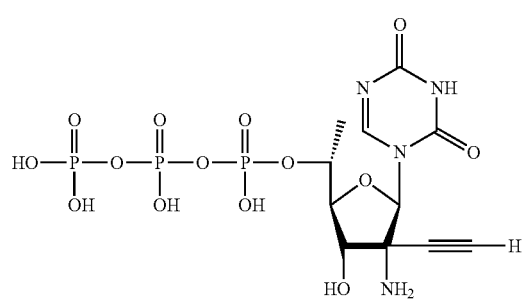
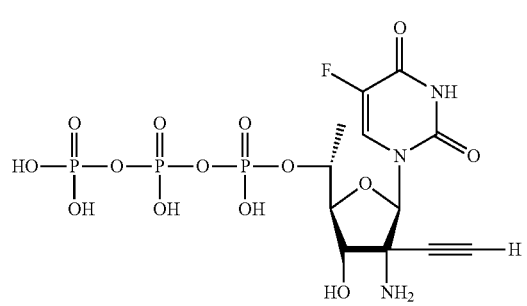
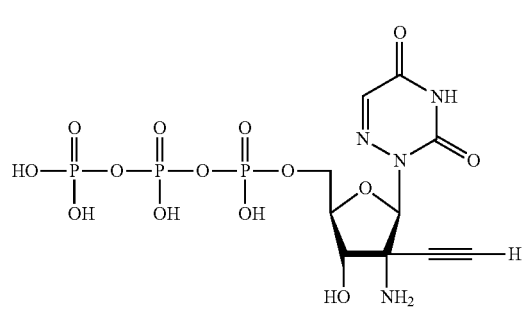
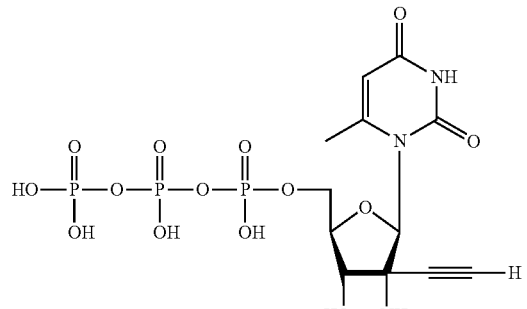
304
-continued
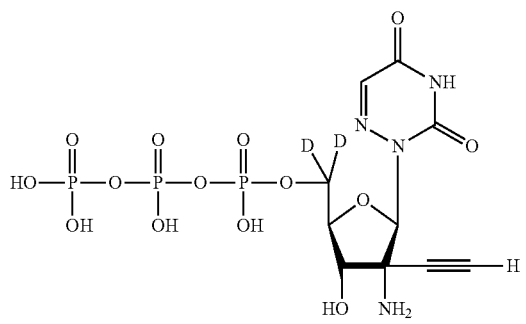
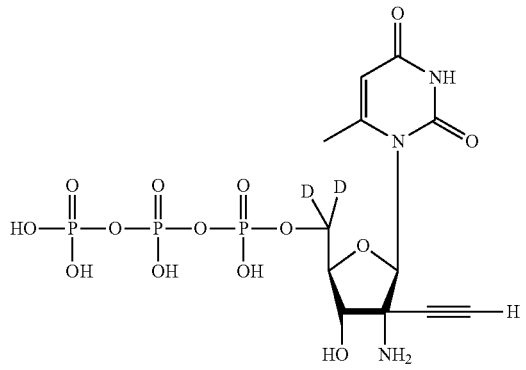
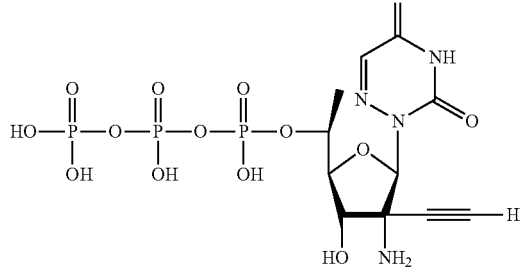
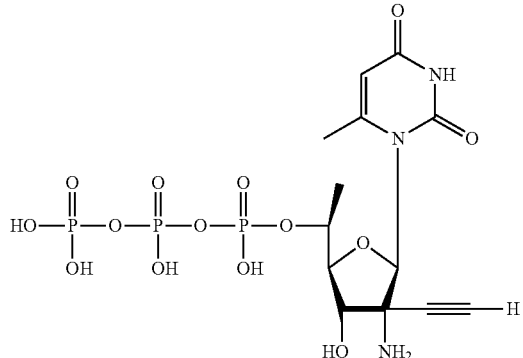
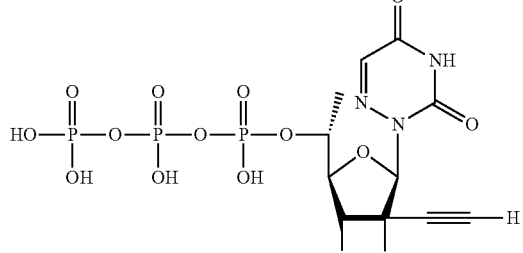

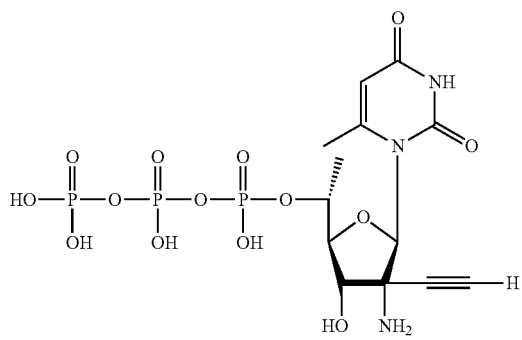
In exemplary embodiments, the compound is selected from:
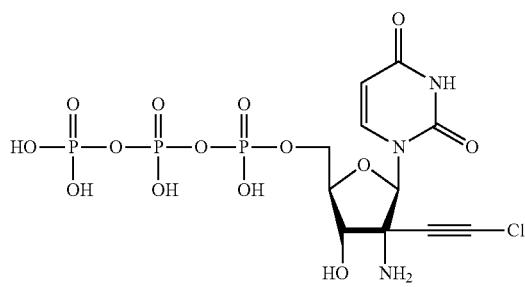
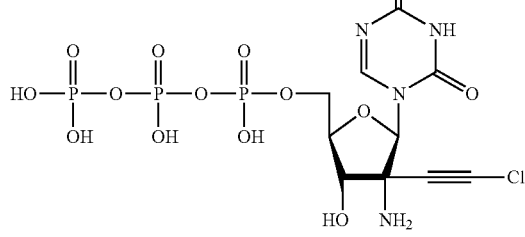
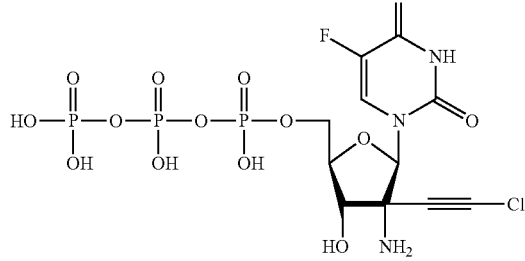
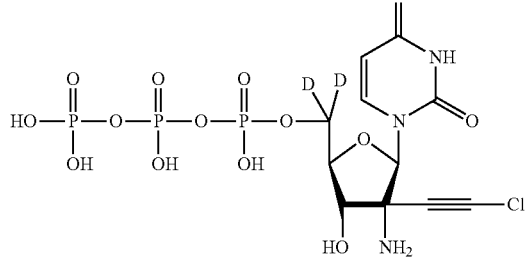
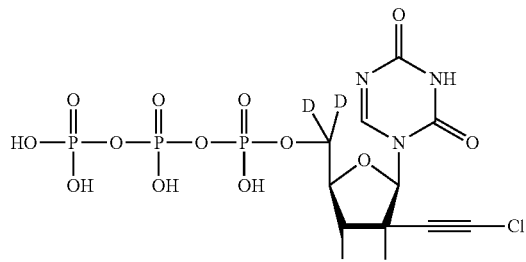
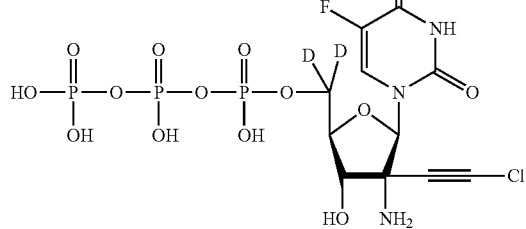
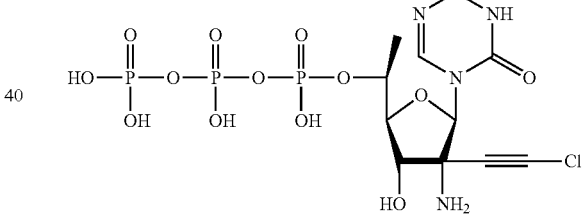
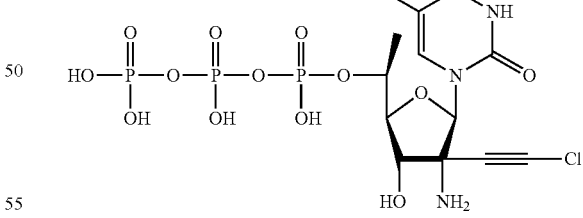
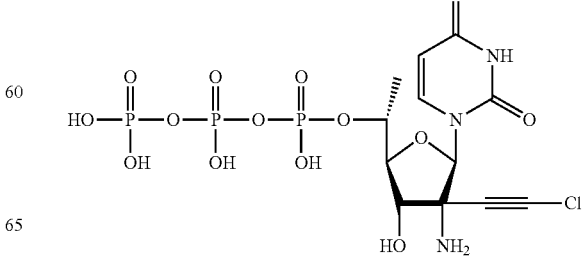

307
-continued
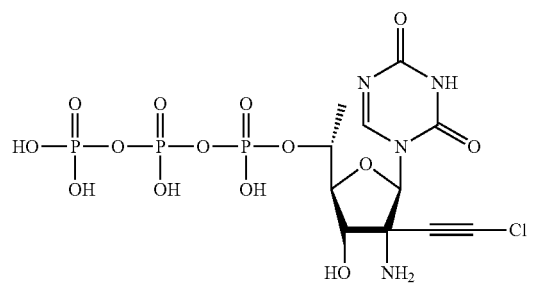
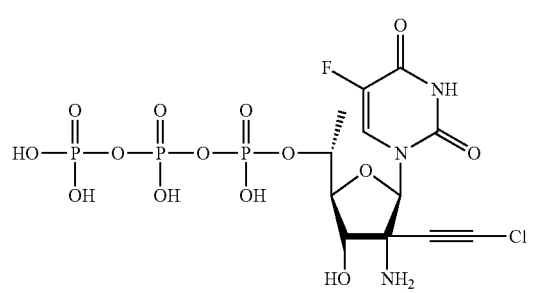
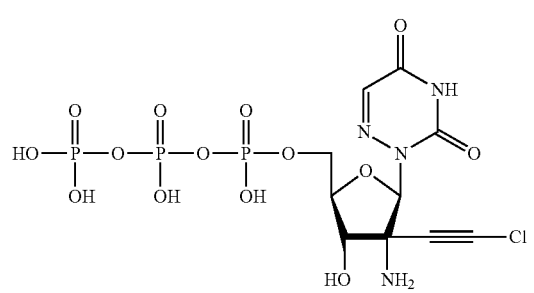
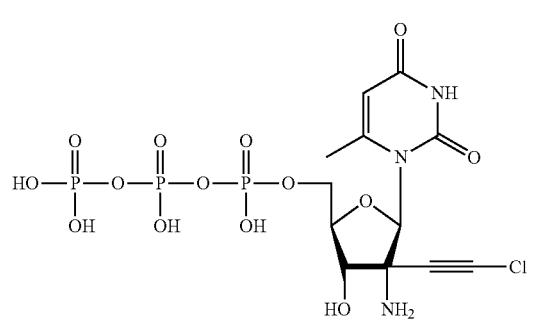
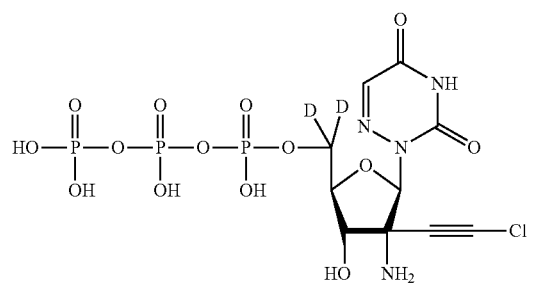
308
-continued
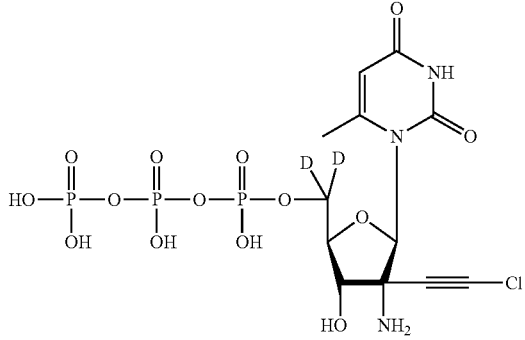
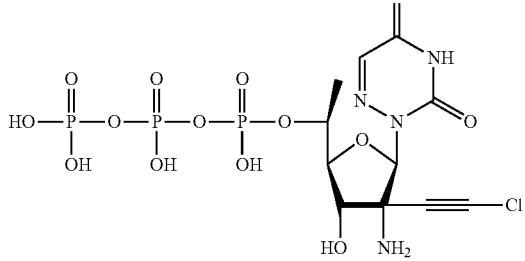
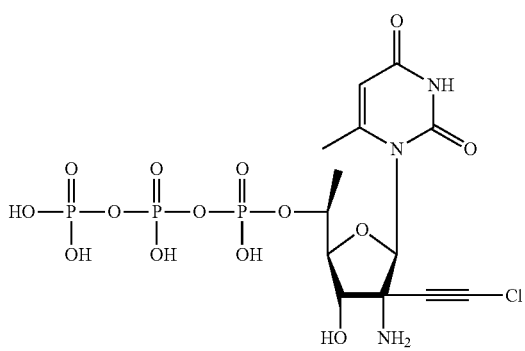
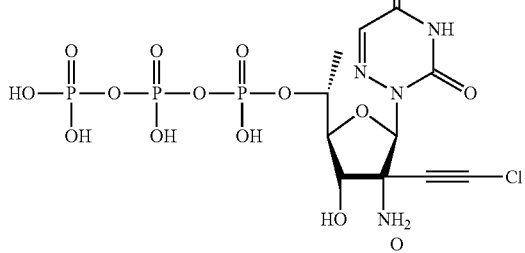
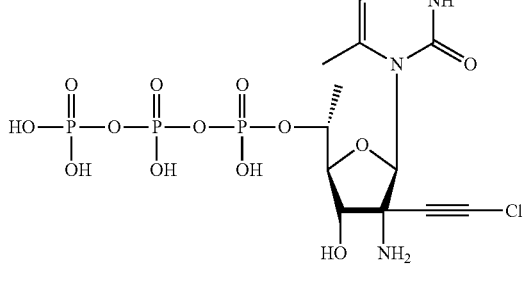

309
In exemplary embodiments, the compound is selected from:
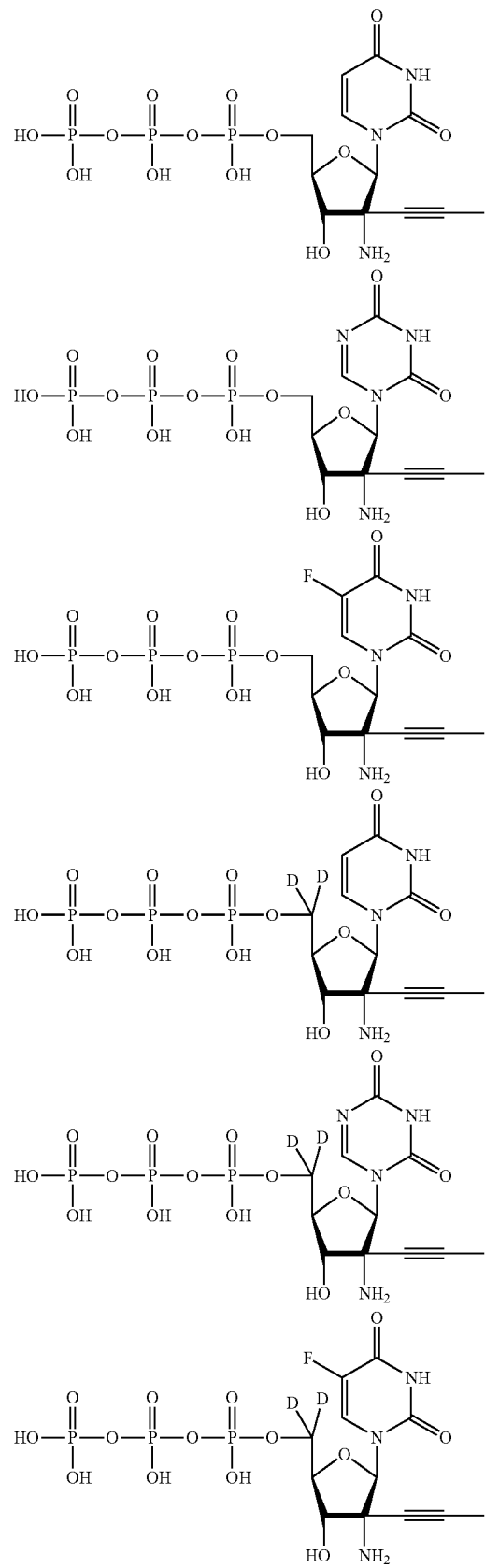
310
-continued
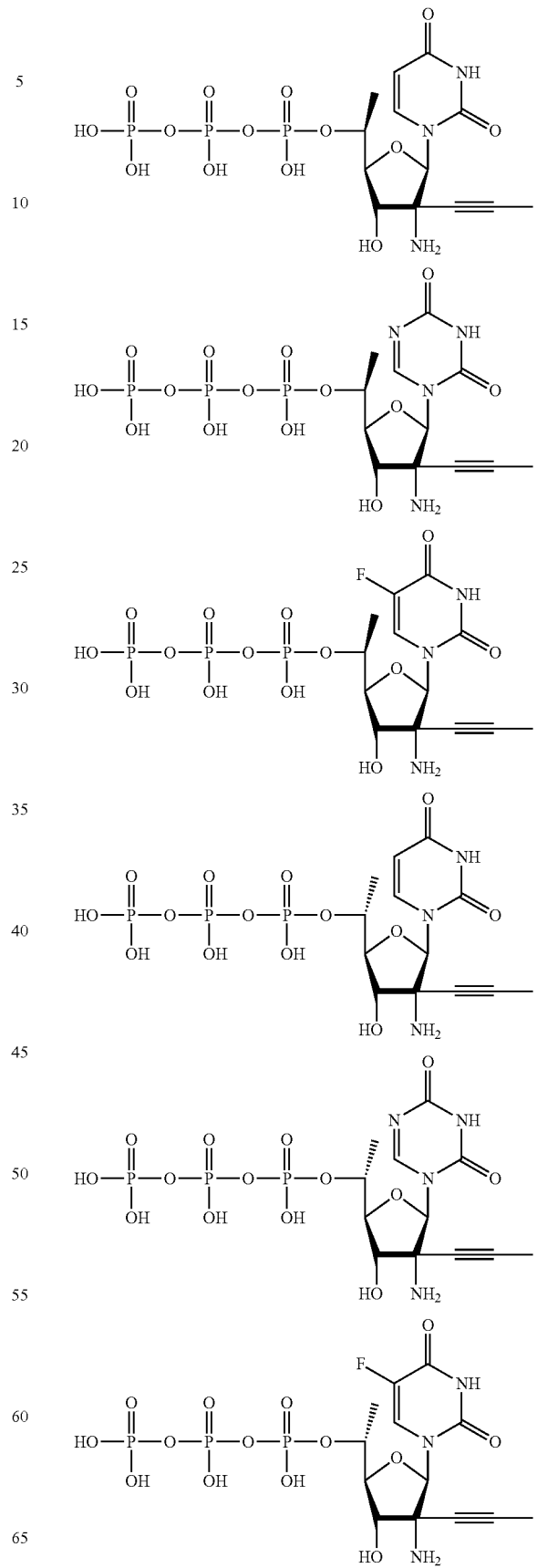

-continued
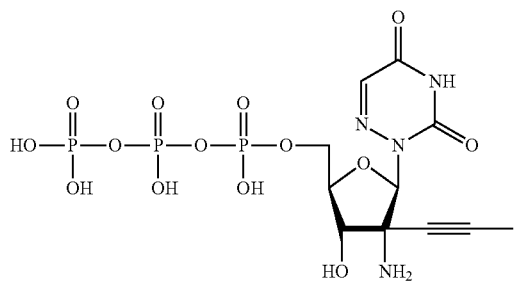
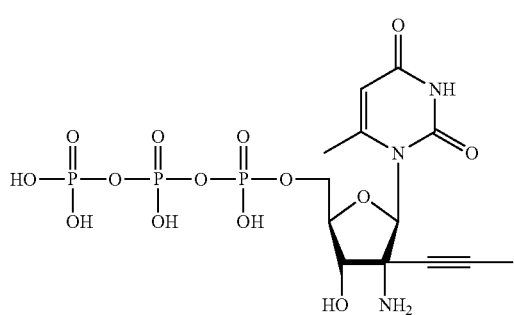
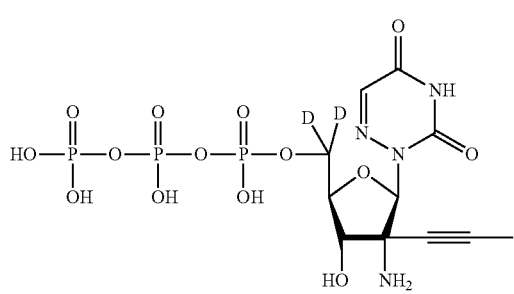
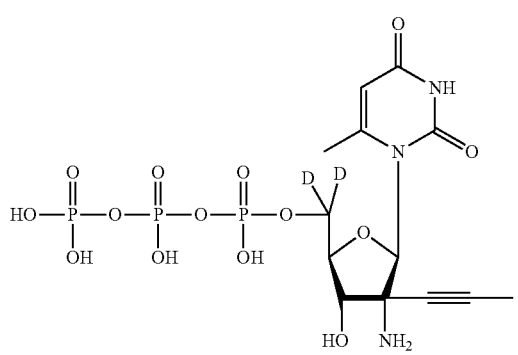
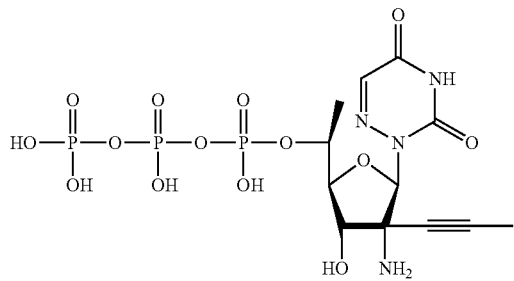
-continued
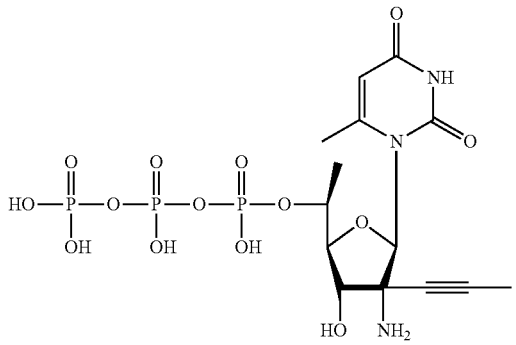
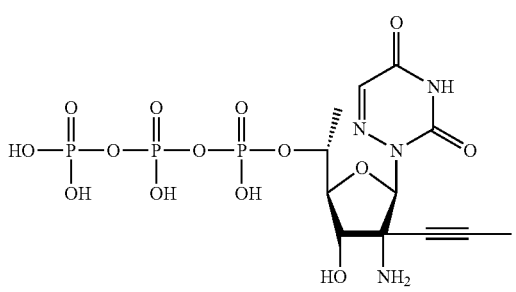
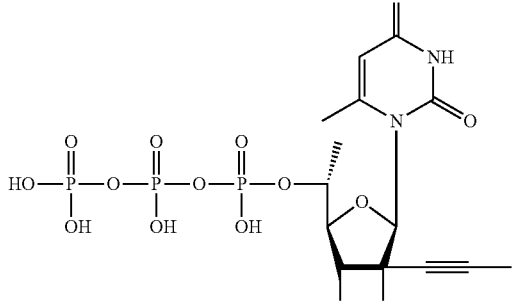
In exemplary embodiments, the compound is selected from:
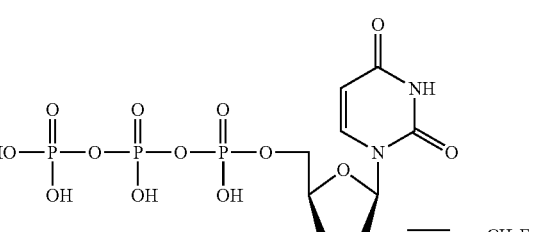
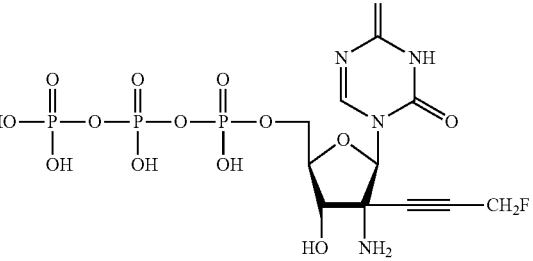

313
-continued
314
-continued
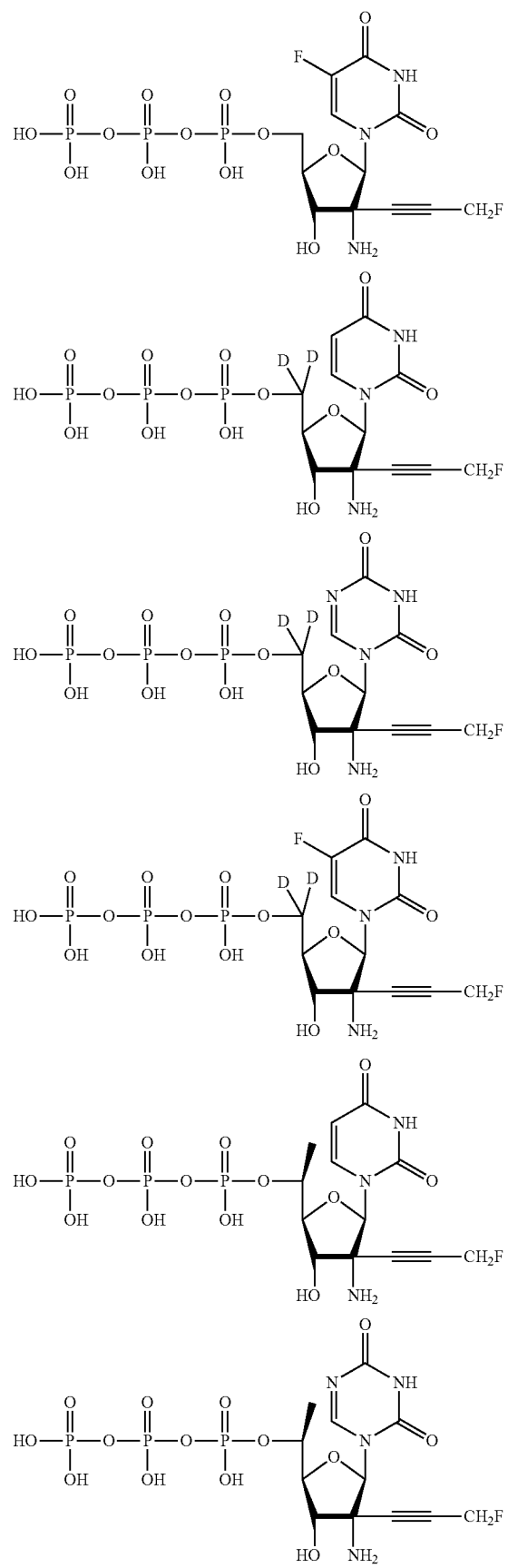
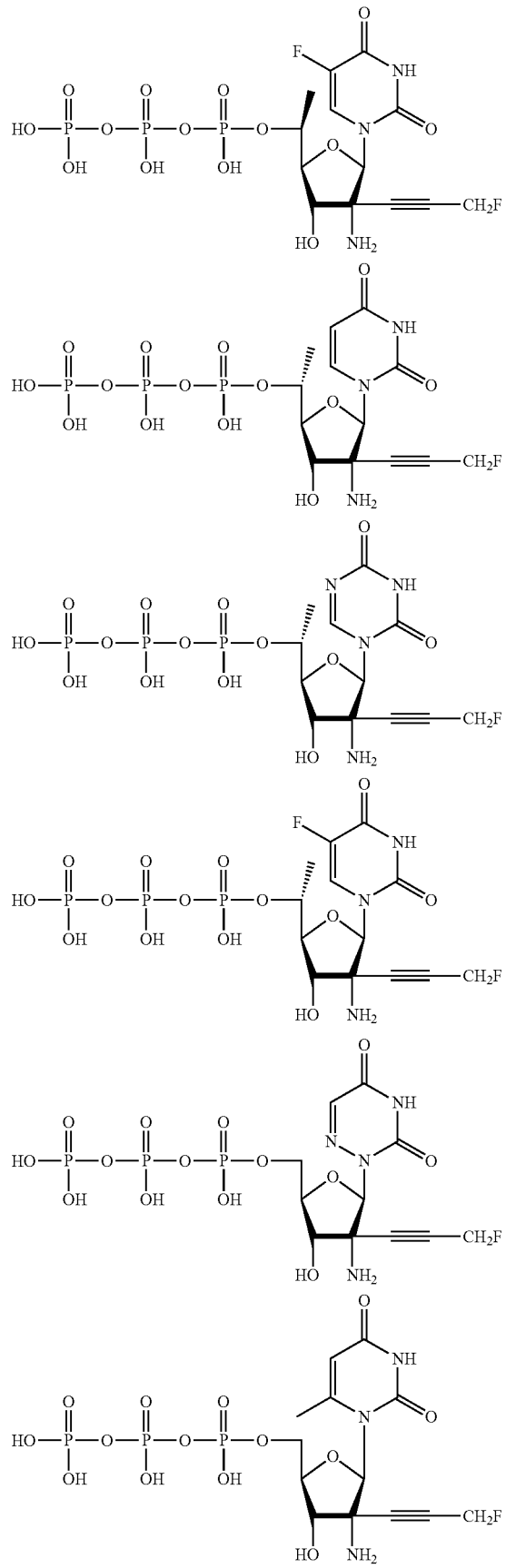

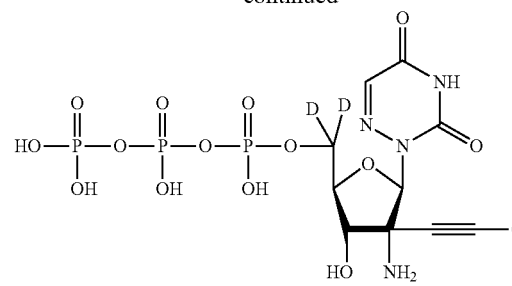
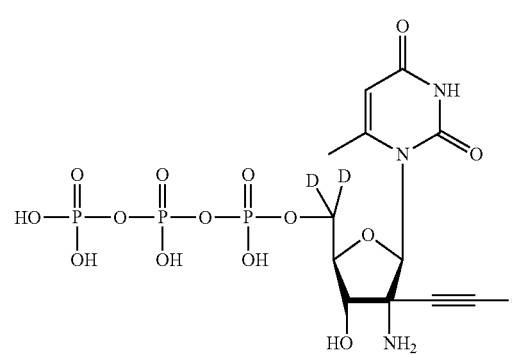
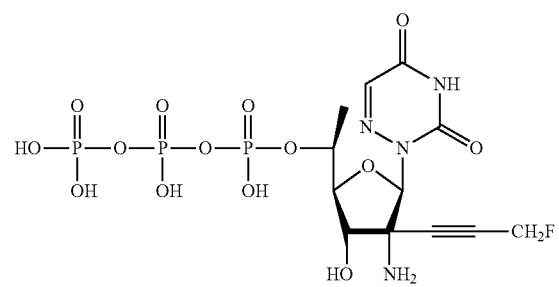
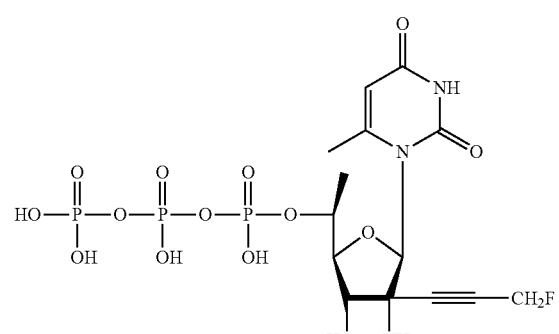
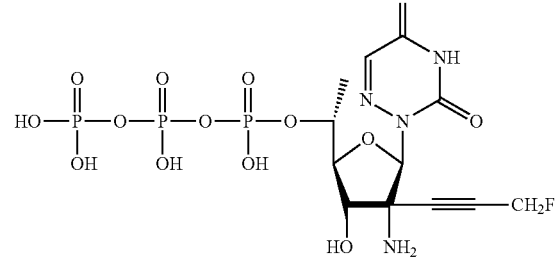
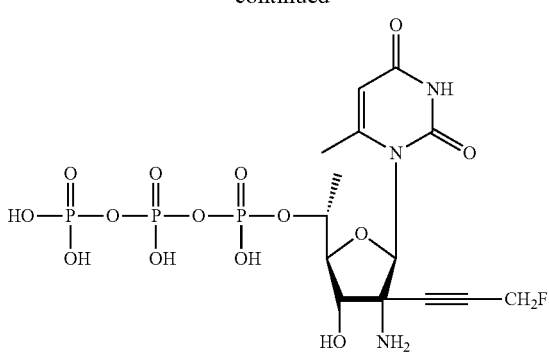
In exemplary embodiments, the compound is selected from:
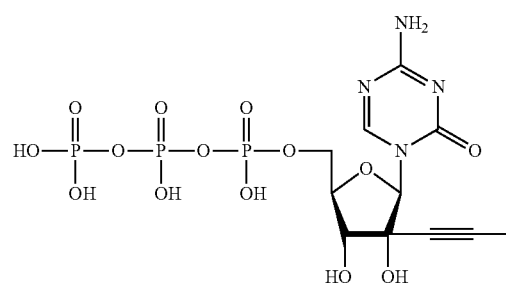
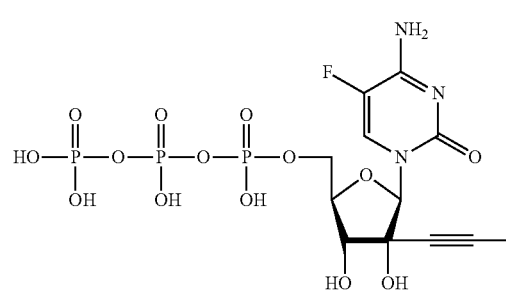
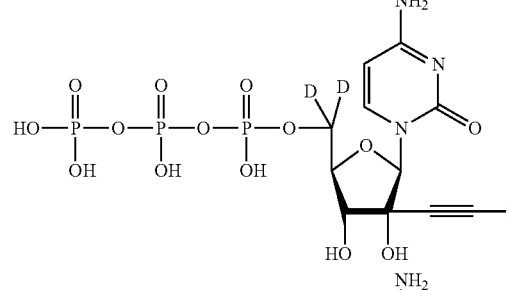
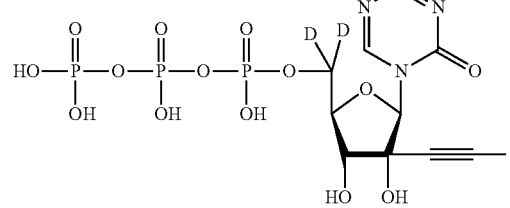

317
-continued
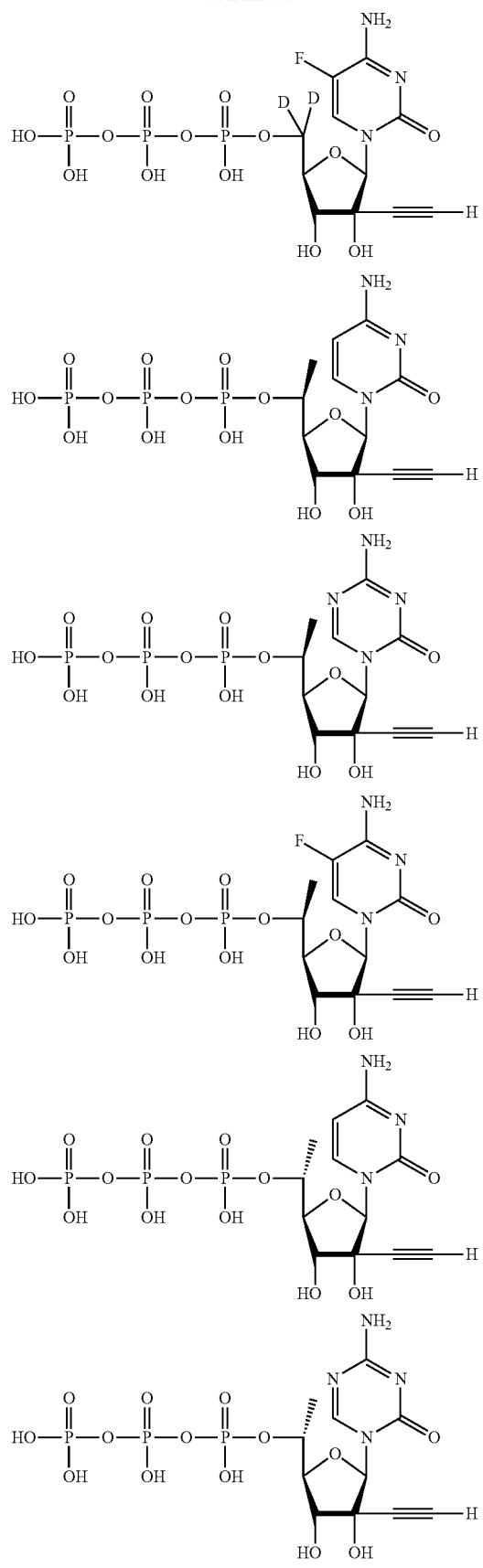
318
-continued
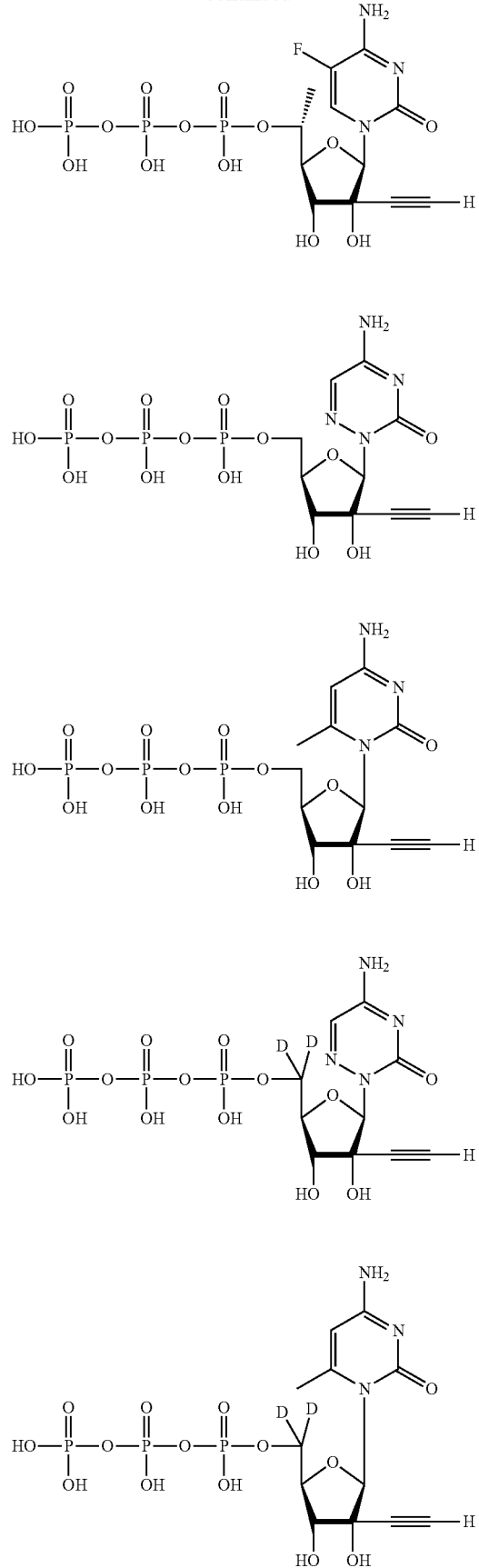

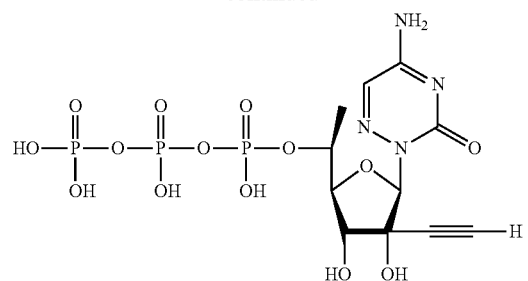
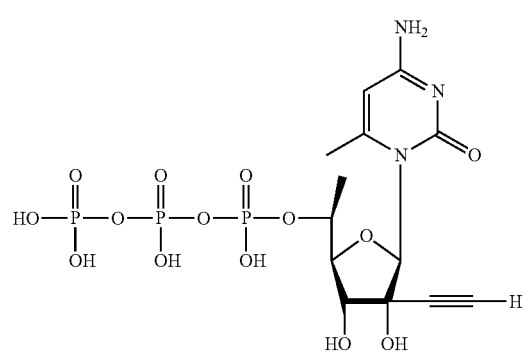
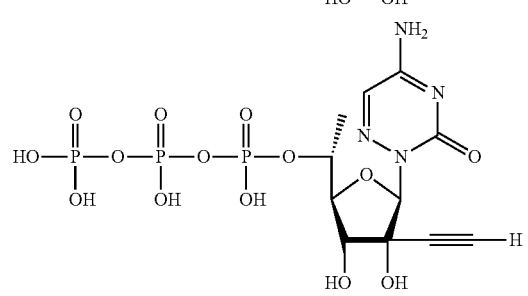
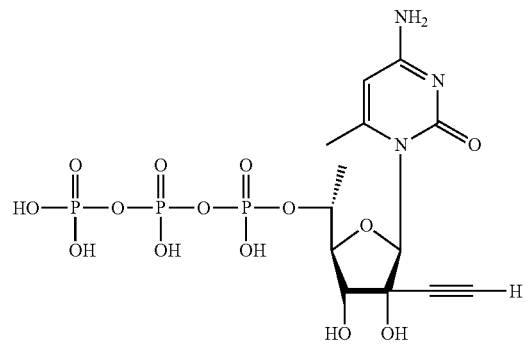
In exemplary embodiments, the compound is selected from:
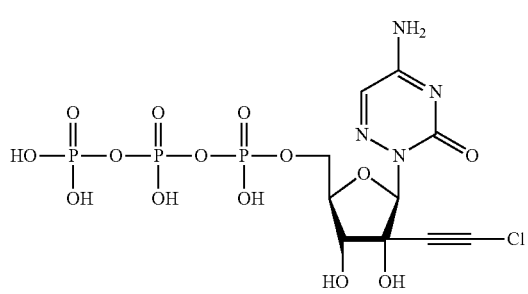
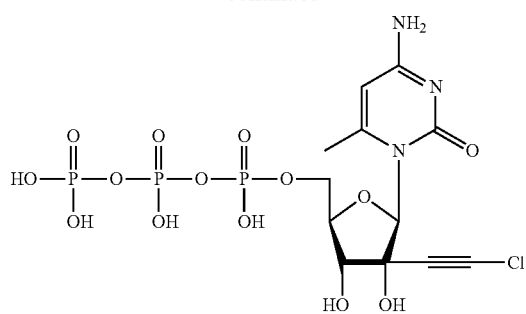
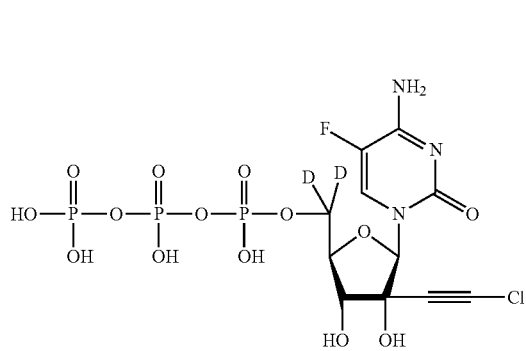
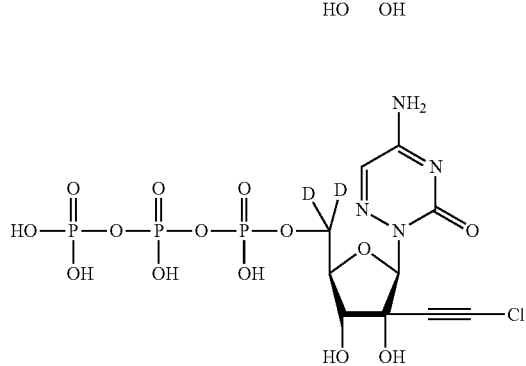
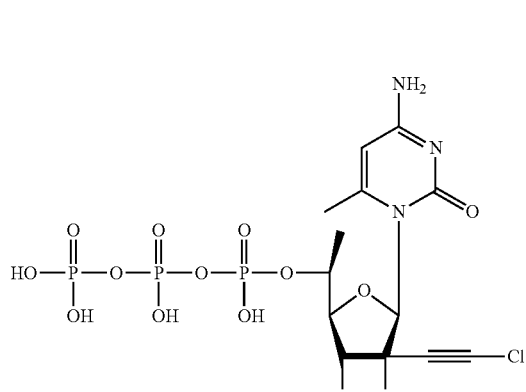
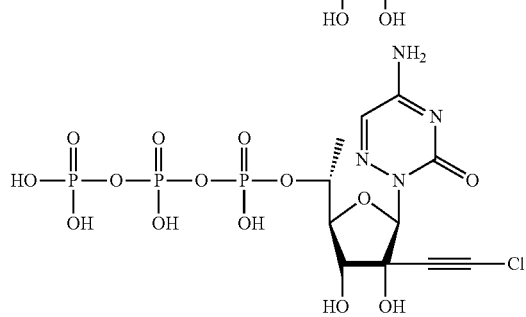

321
-continued
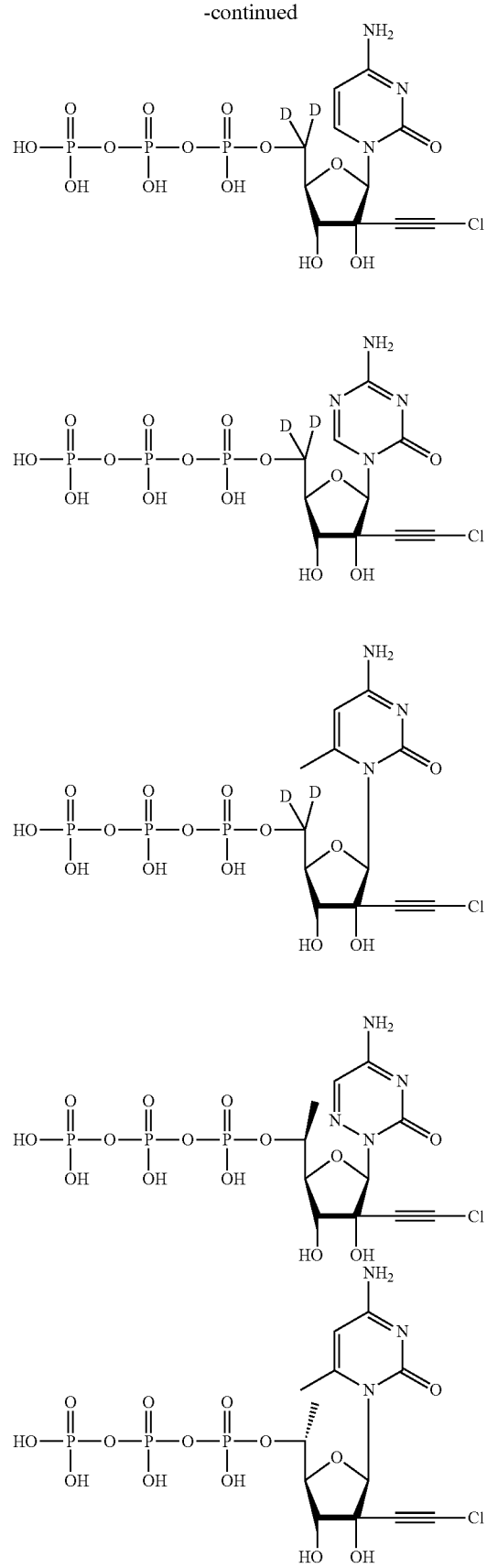
322
In exemplary embodiments, the compound is selected from:
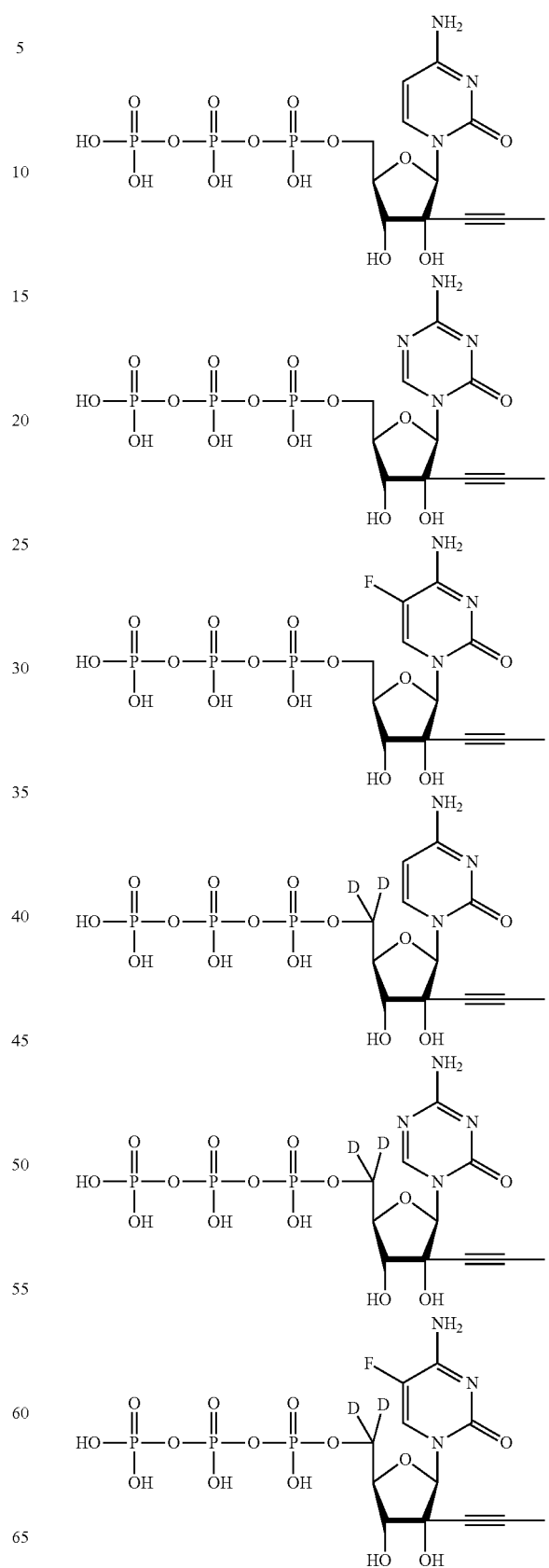

323
-continued
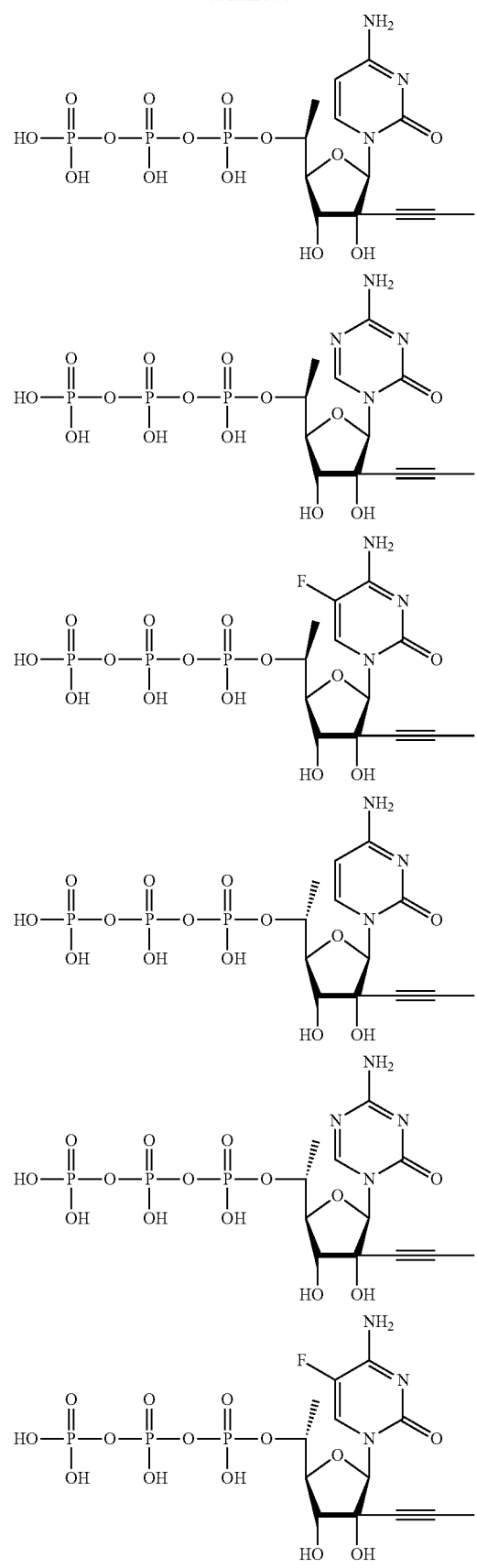
324
-continued
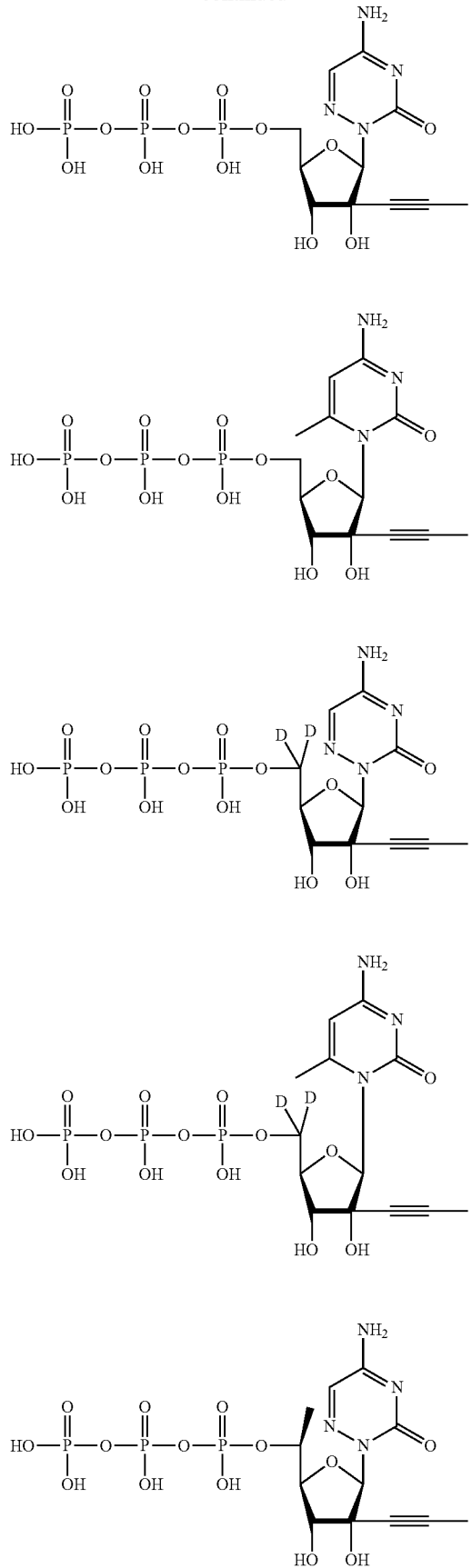

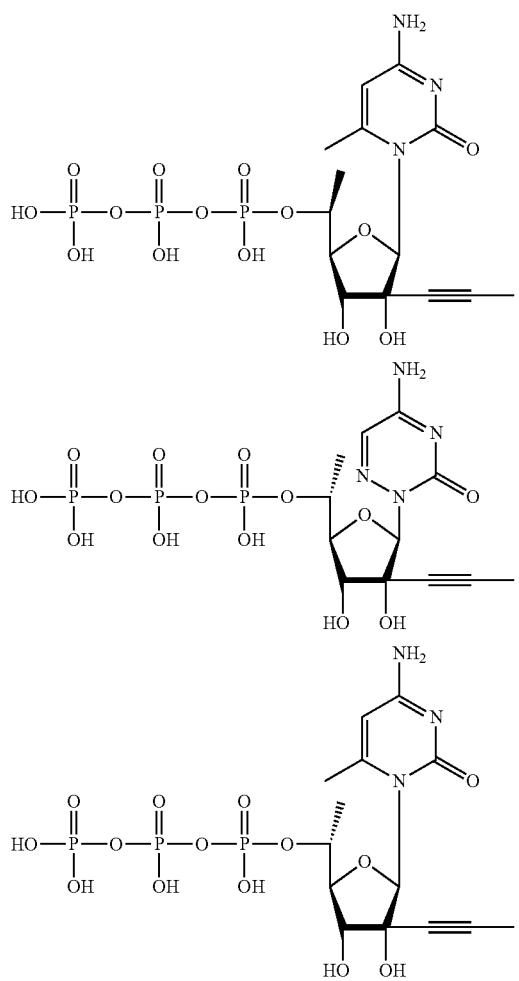
In exemplary embodiments, the compound is selected from:
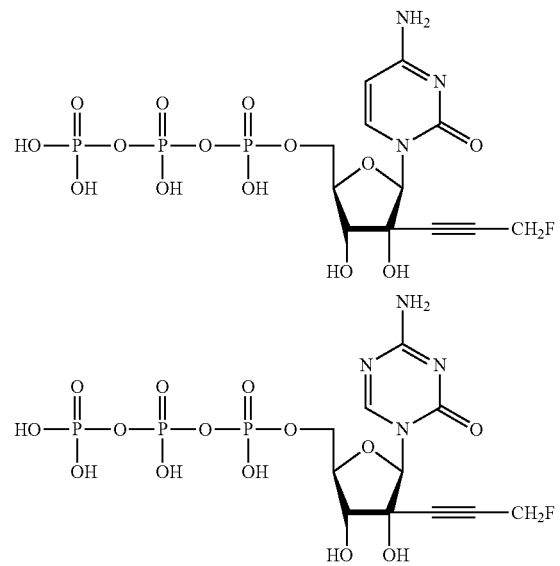
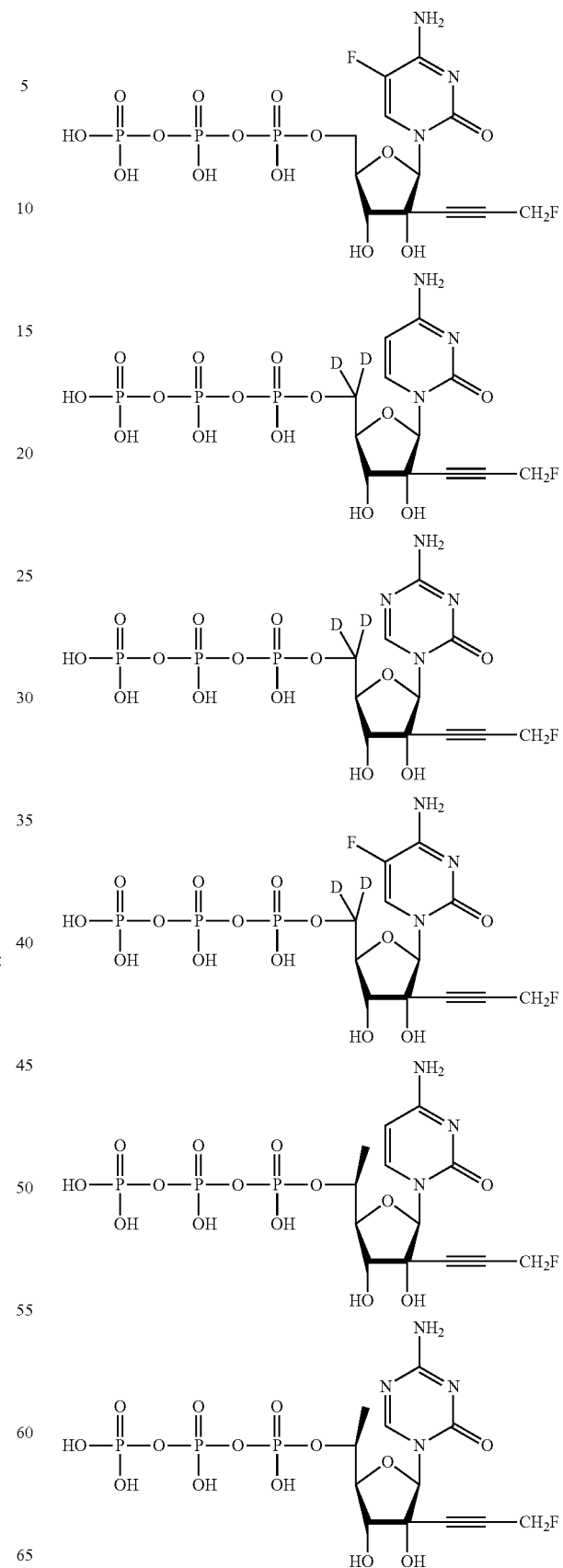

327
-continued
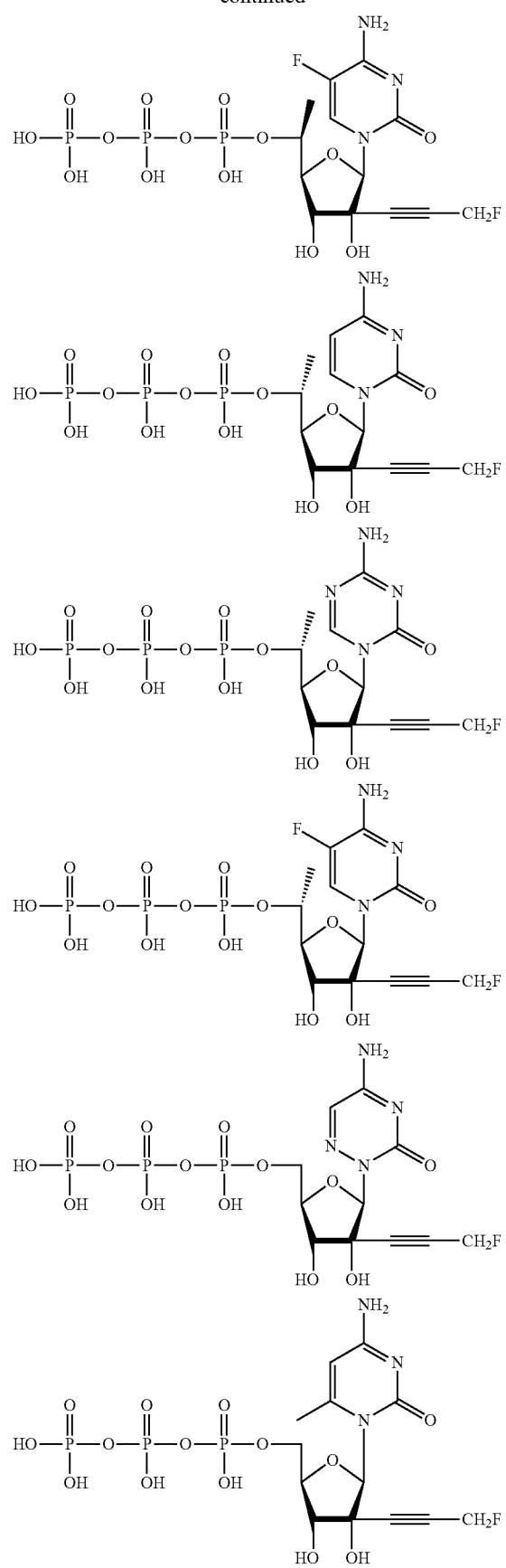
328
-continued
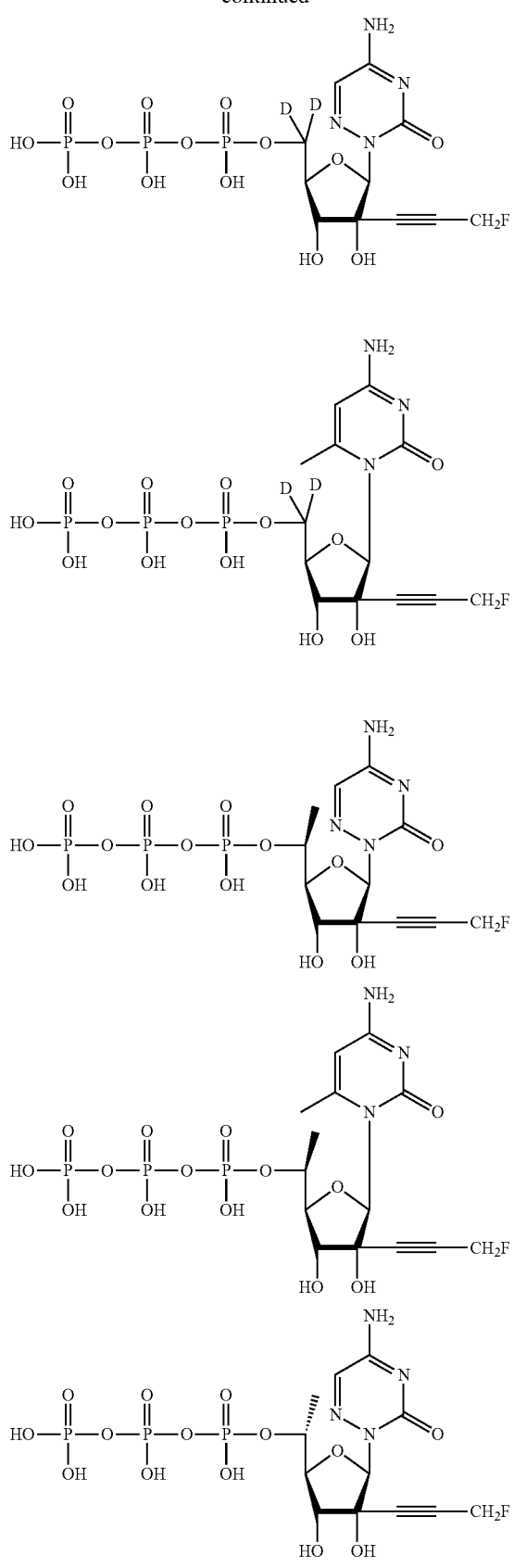

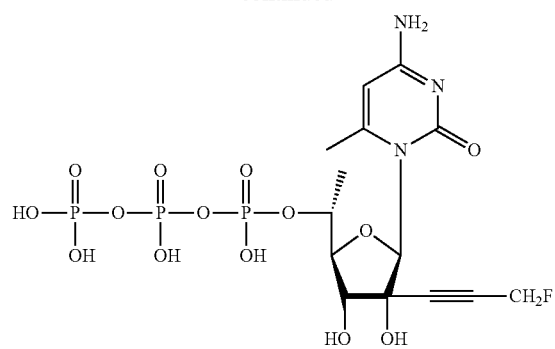
In exemplary embodiments, the compound is selected from:
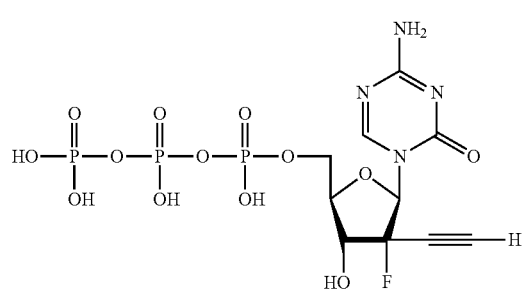
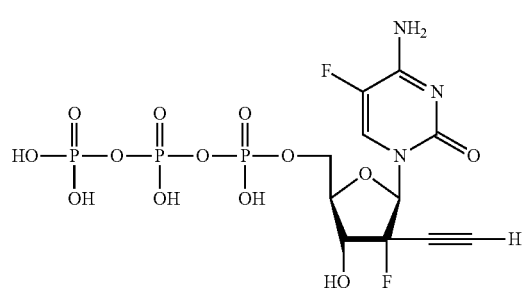
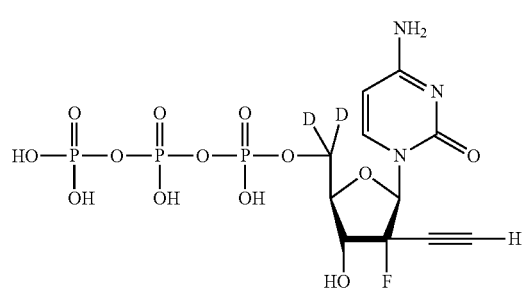
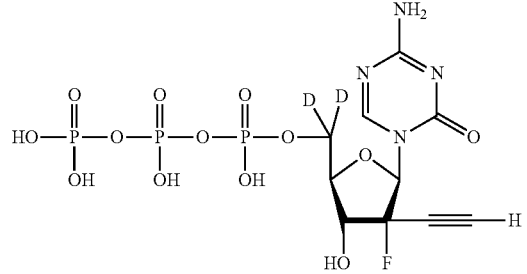
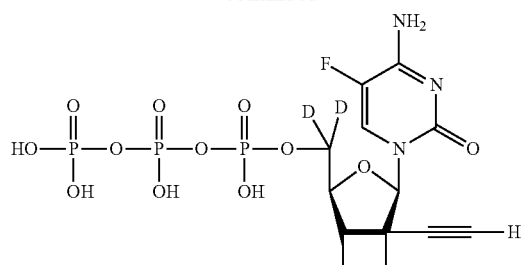
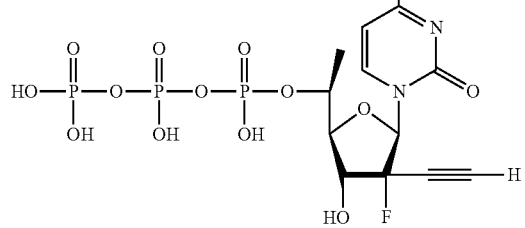
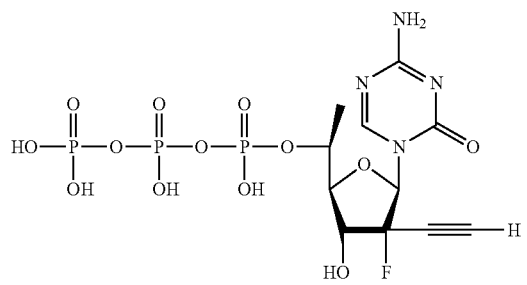
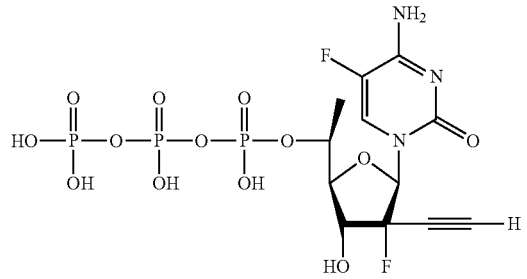
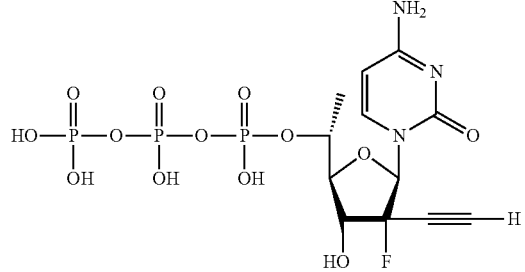

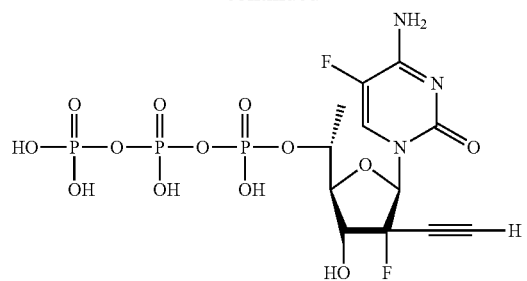
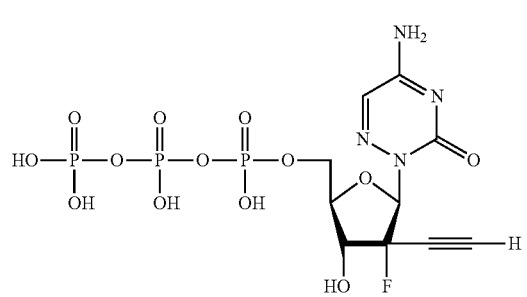
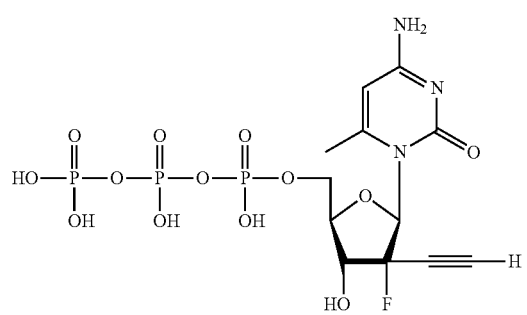
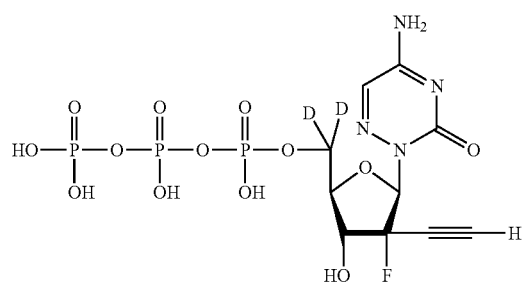
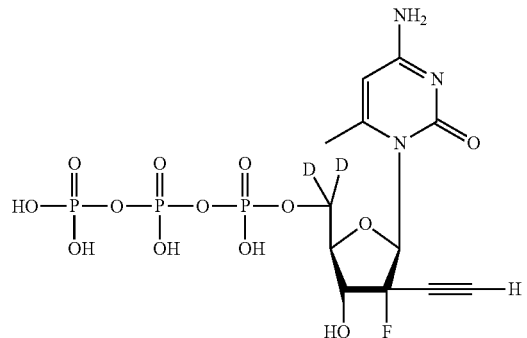
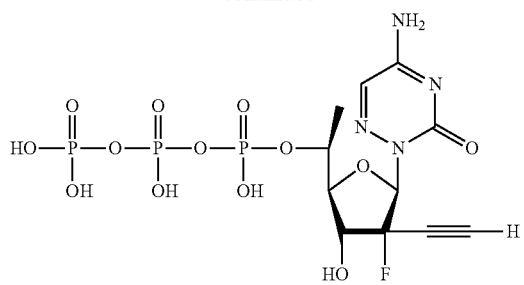
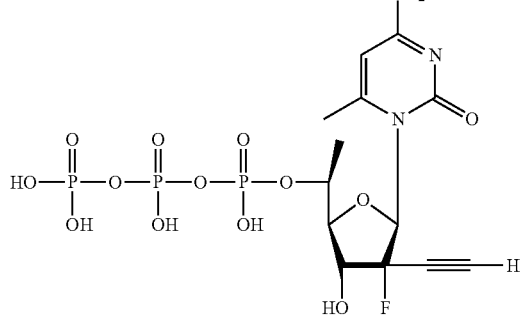
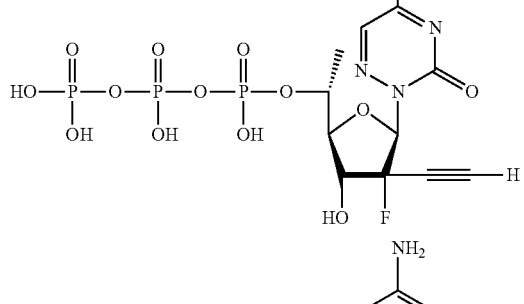
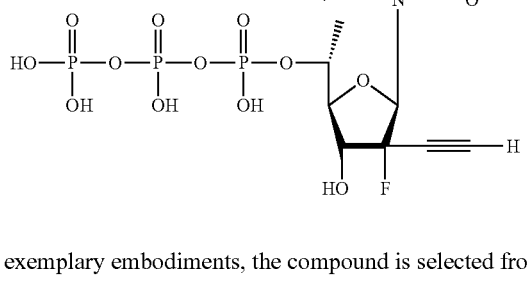
In exemplary embodiments, the compound is selected from:
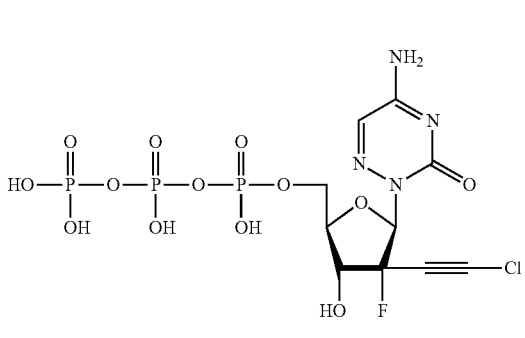

333
-continued
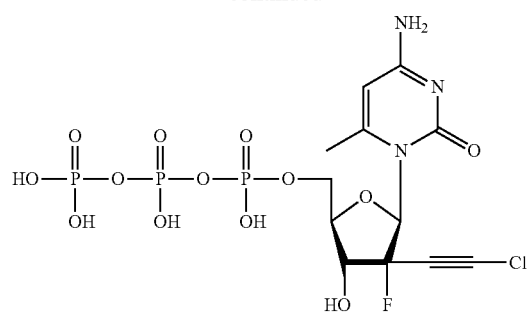
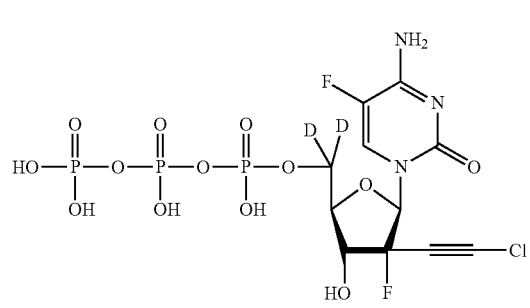
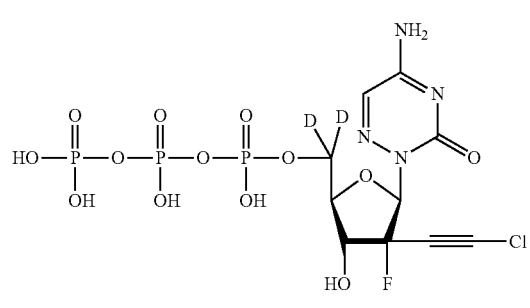
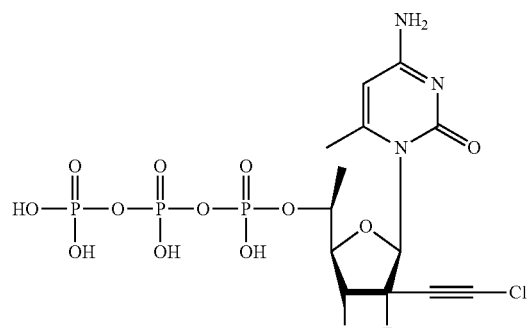
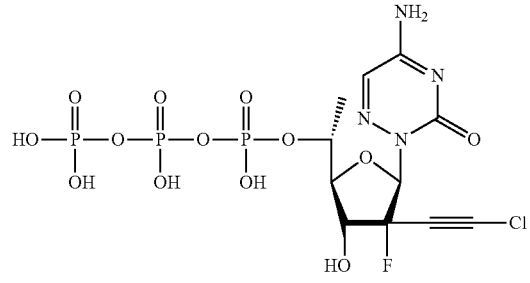
334
-continued
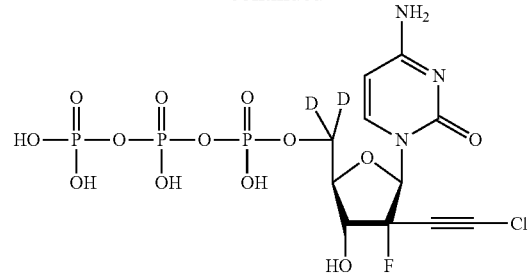
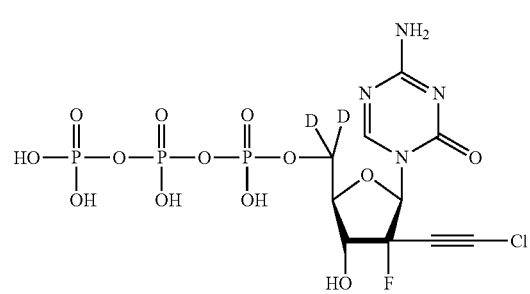
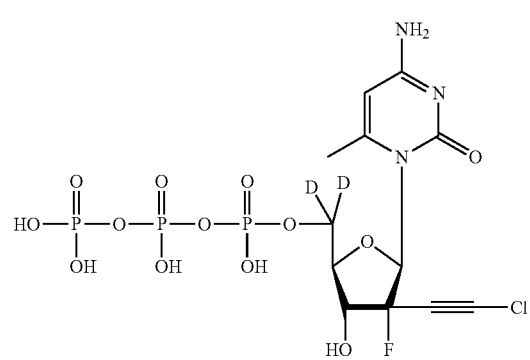
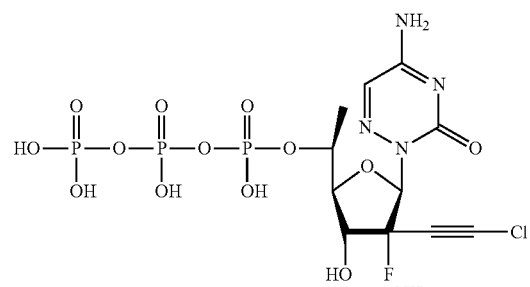
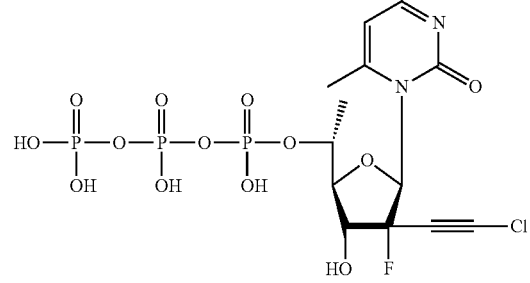

In exemplary embodiments, the compound is selected from:
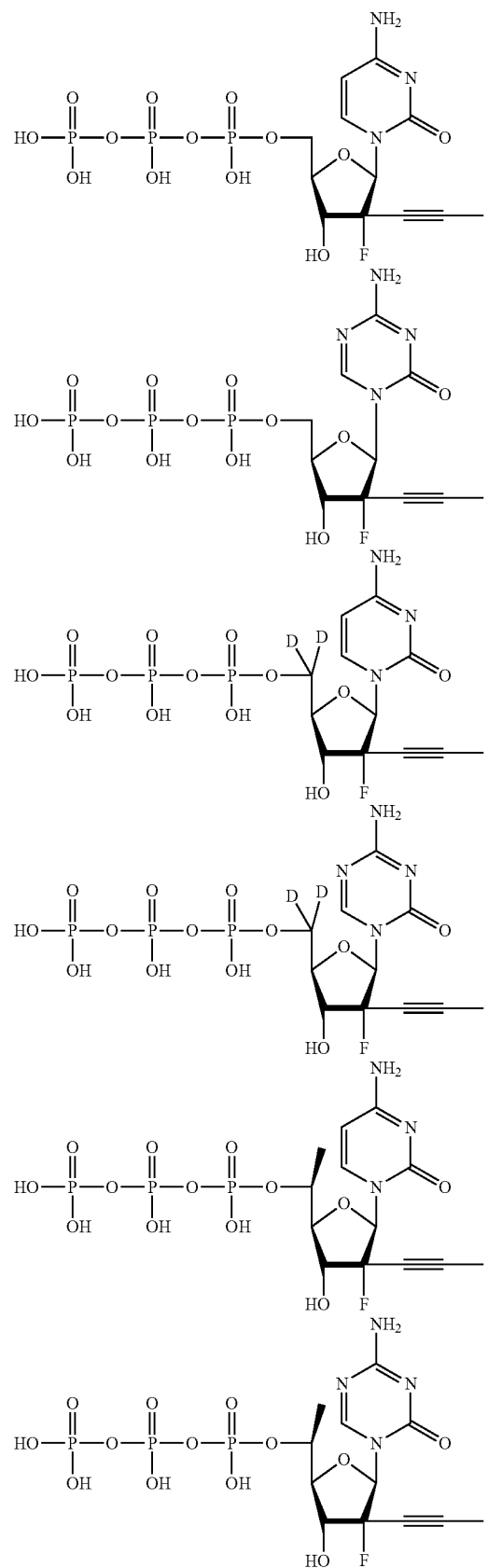
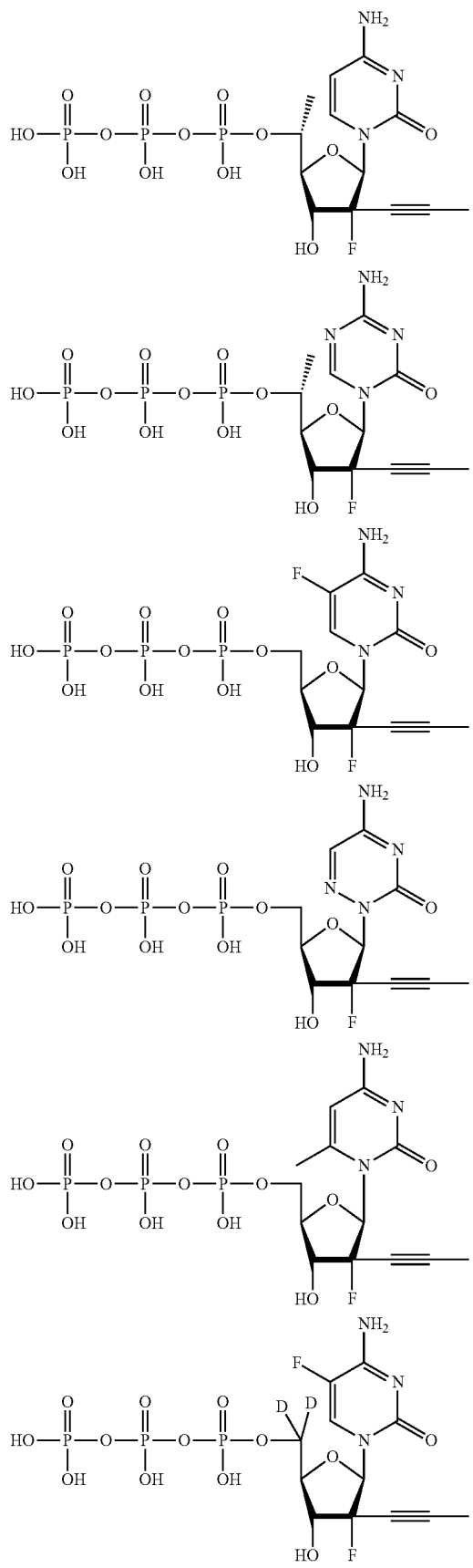

337
-continued
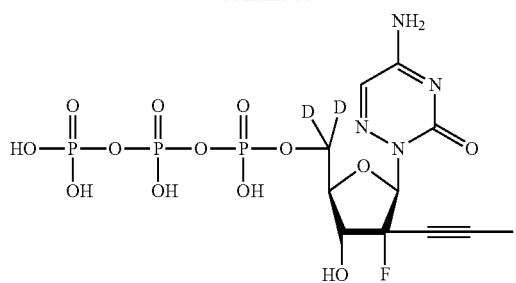
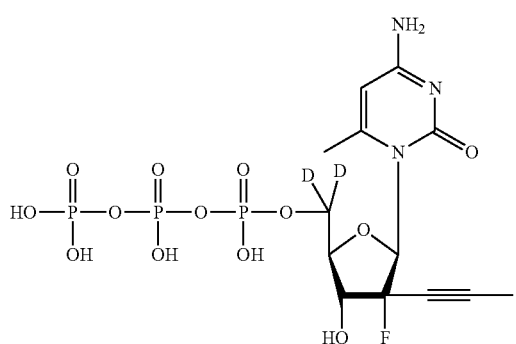
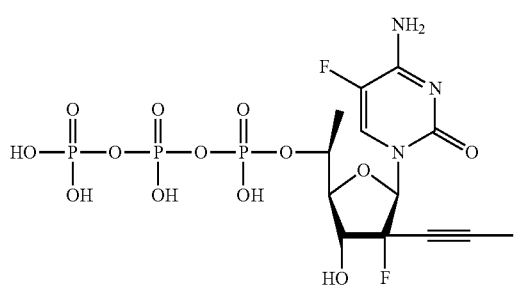
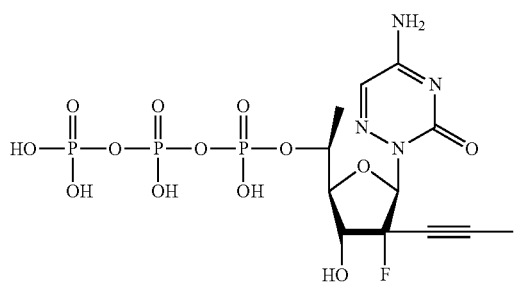
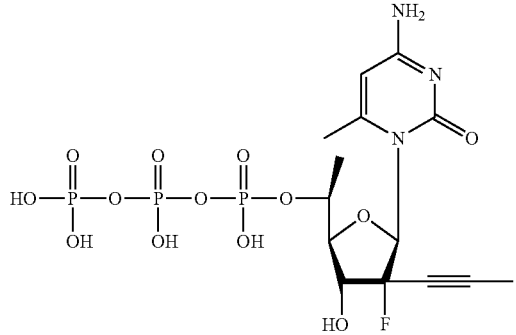
338
-continued
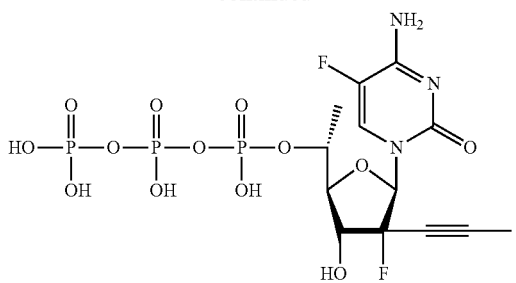
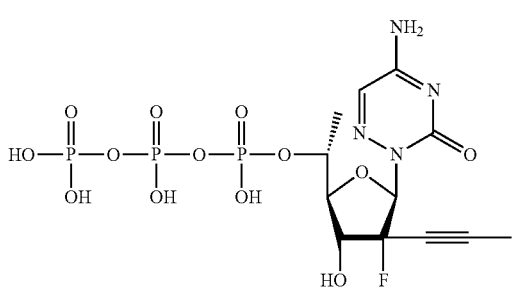
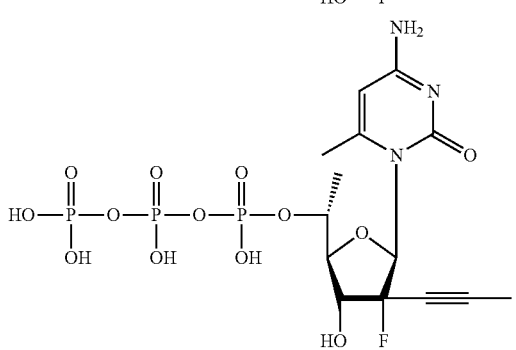
In exemplary embodiments, the compound is selected from:
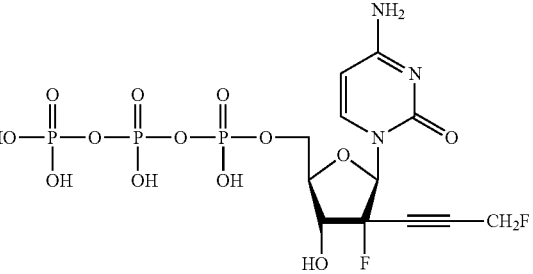
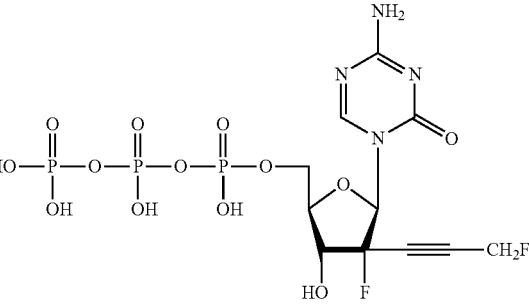

339
-continued
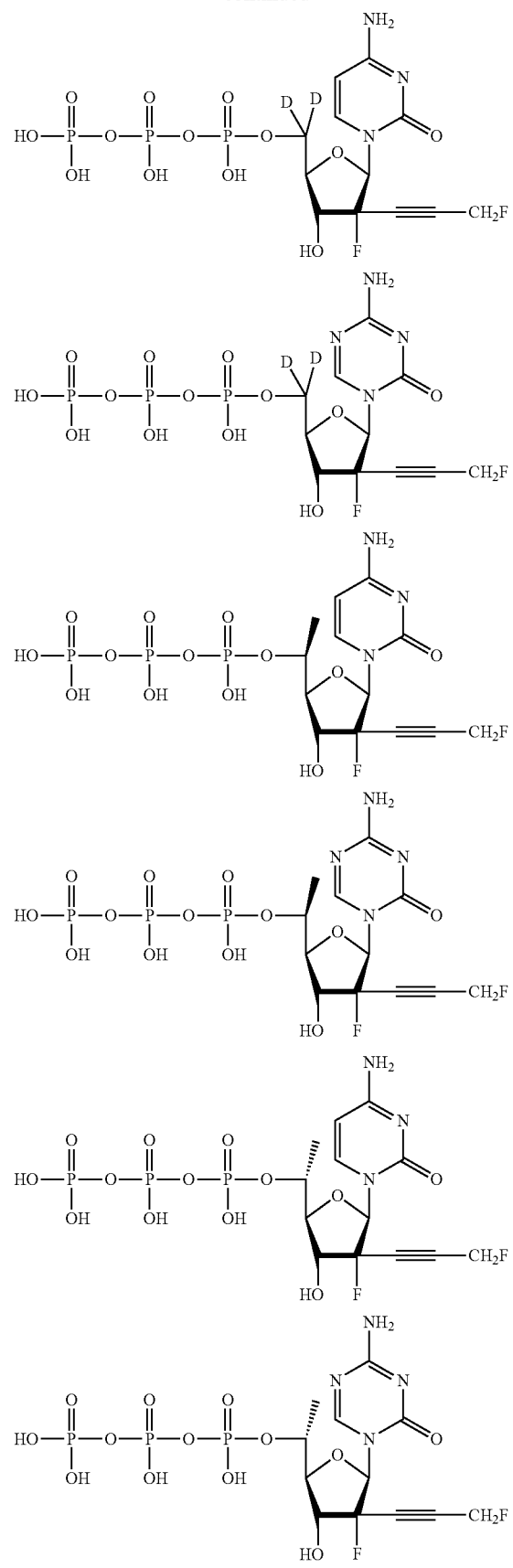
340
-continued
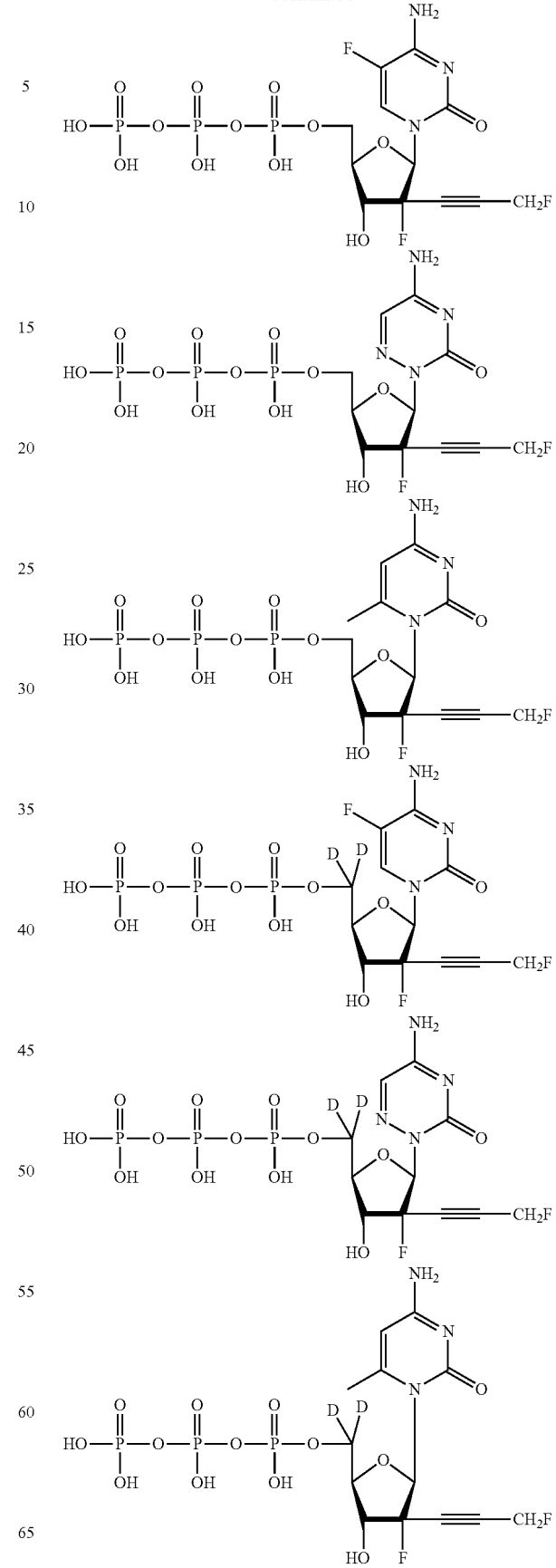

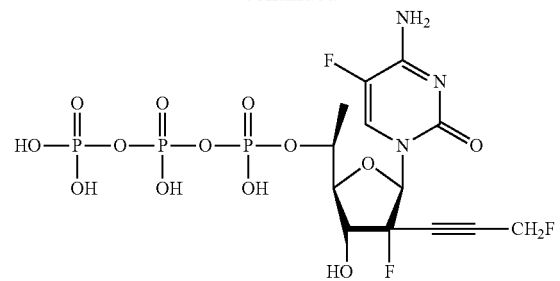
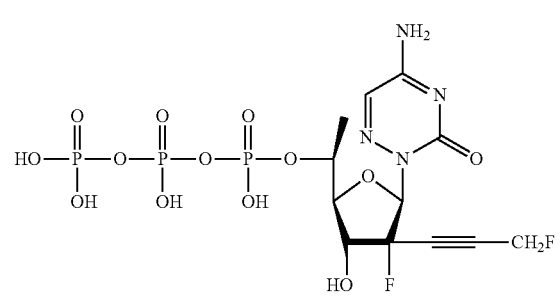
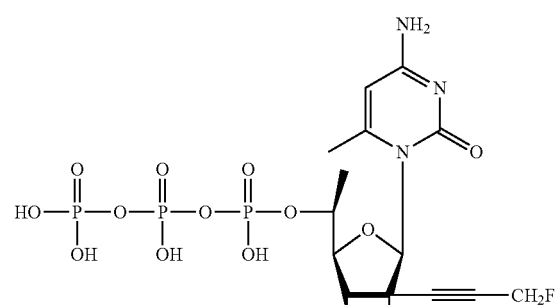
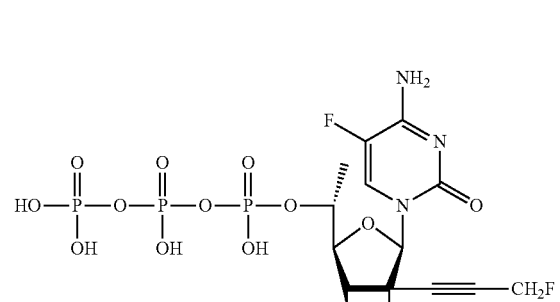
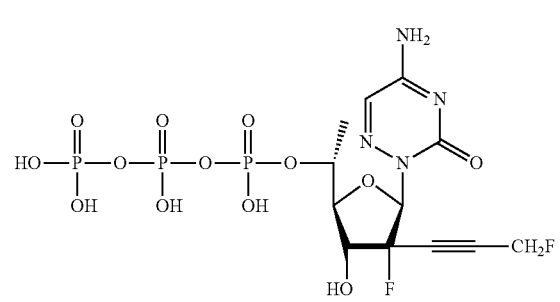
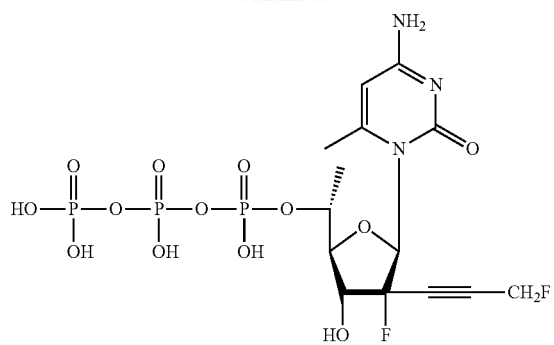
In exemplary embodiments, the compound is selected from:
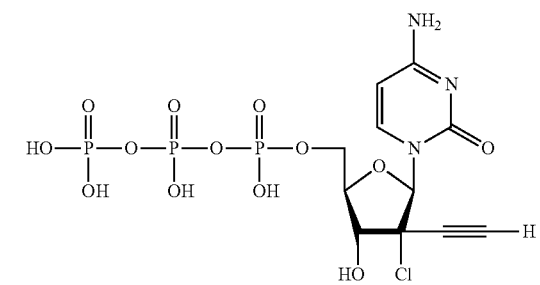
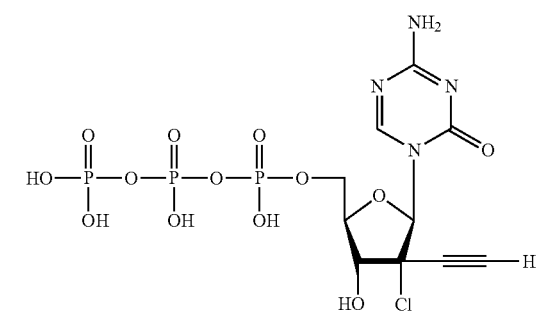
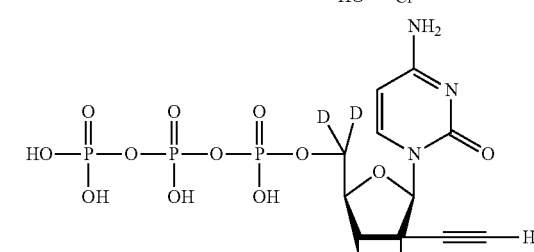
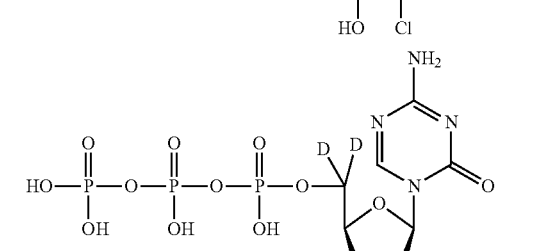

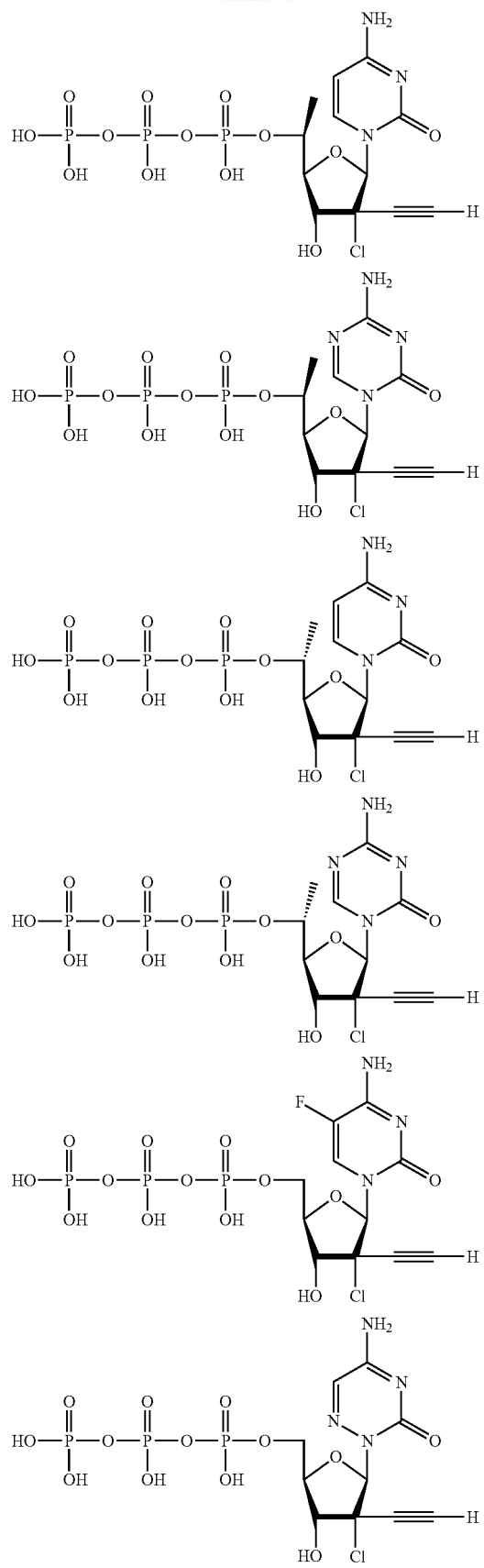
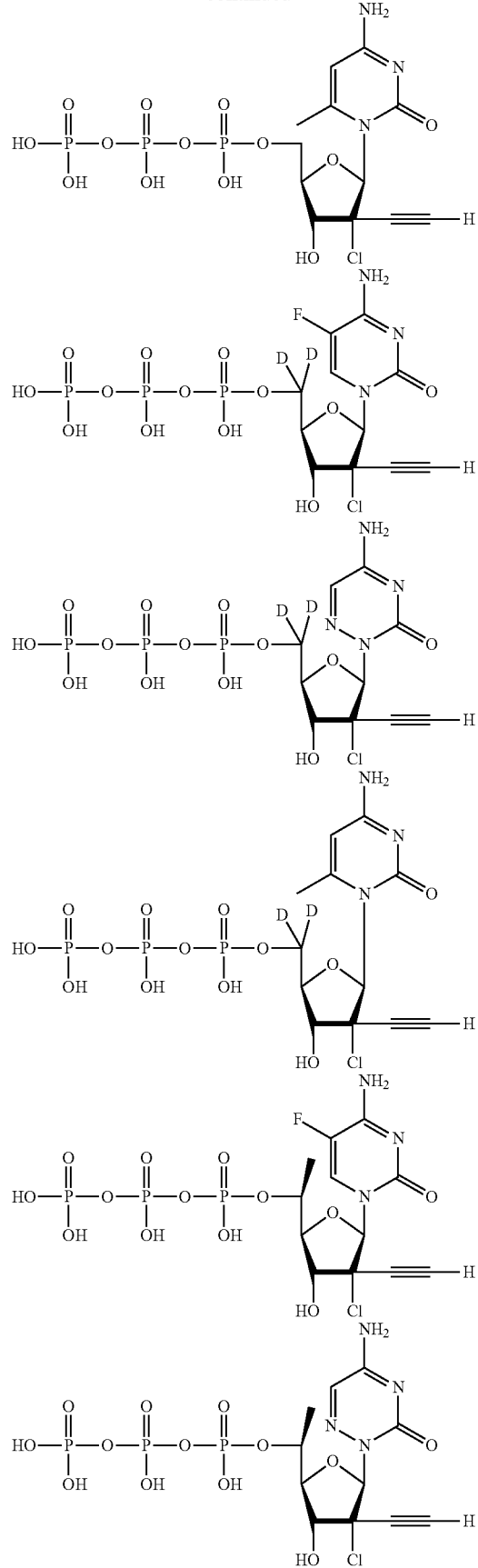

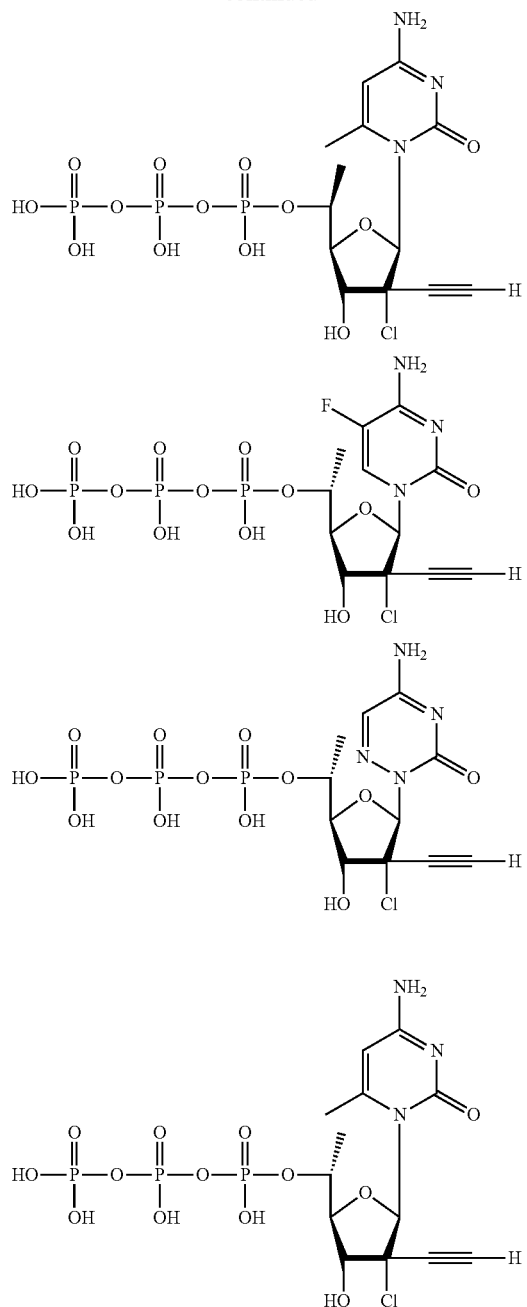
In exemplary embodiments, the compound is selected from:
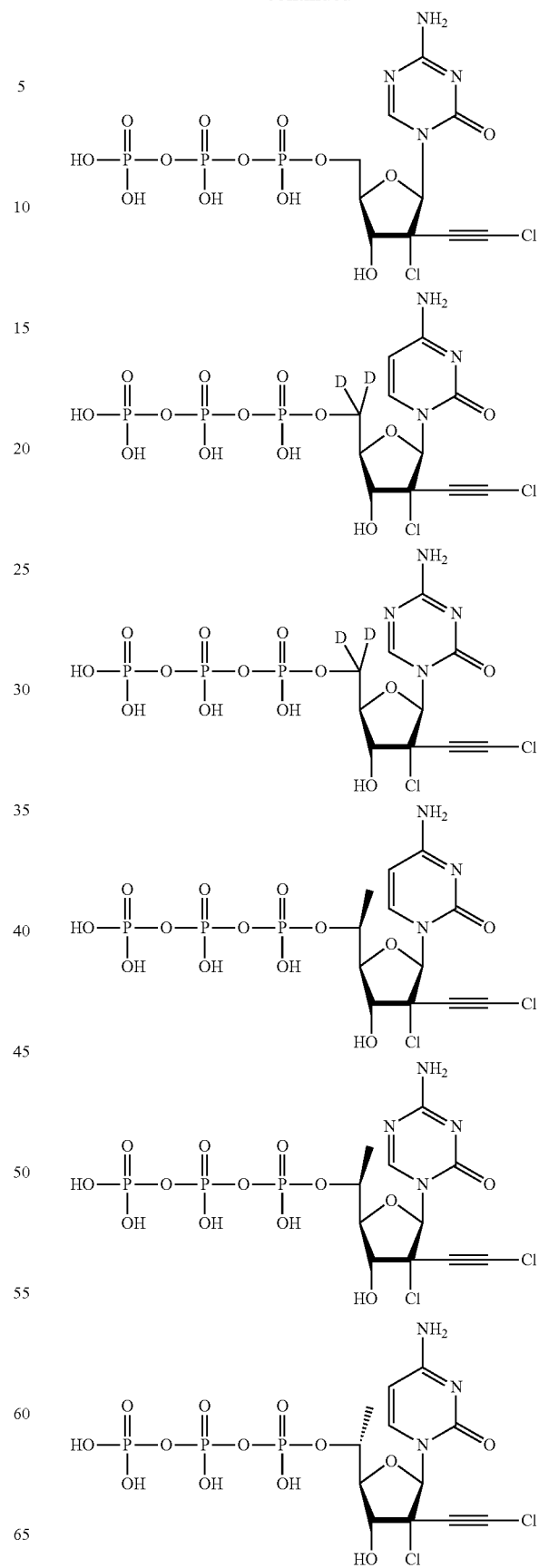

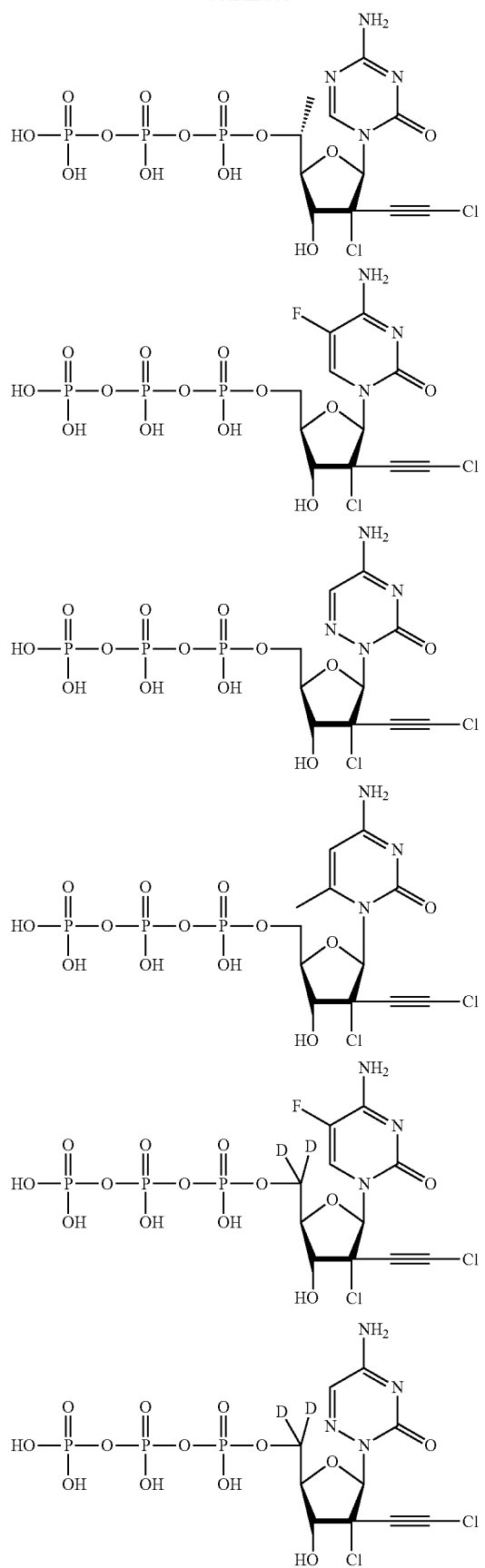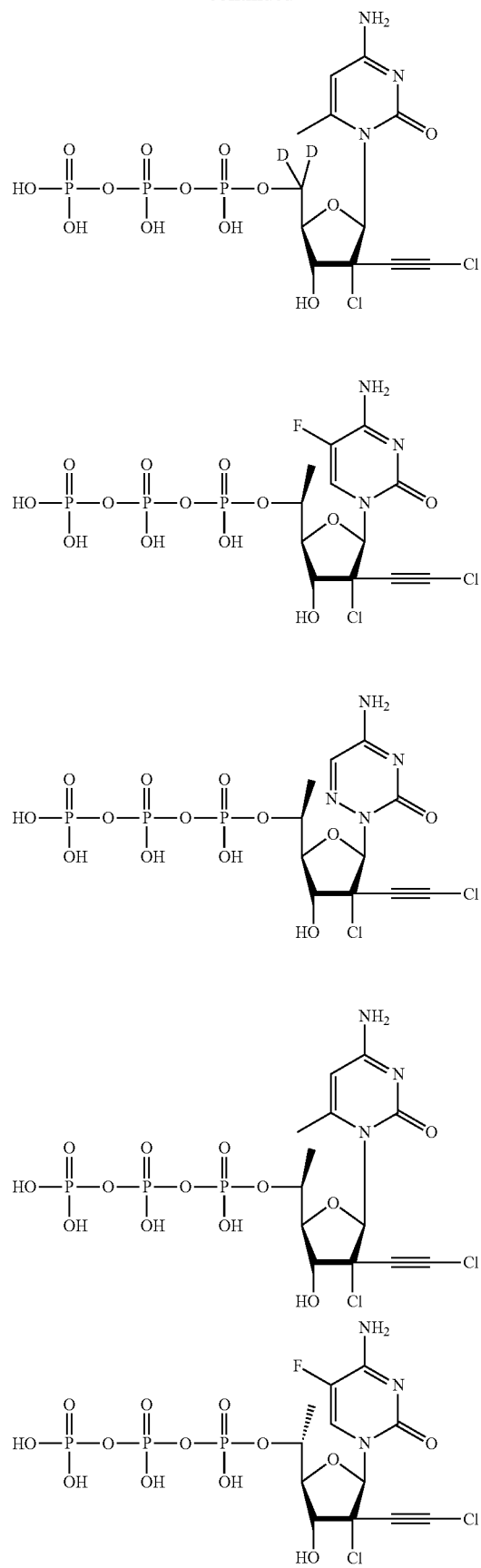

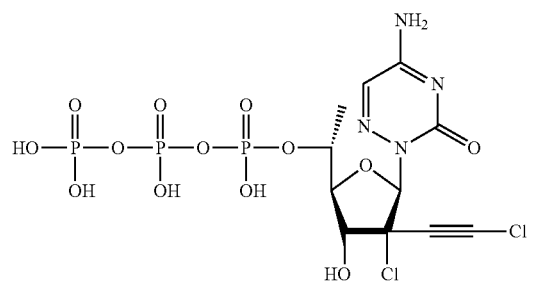
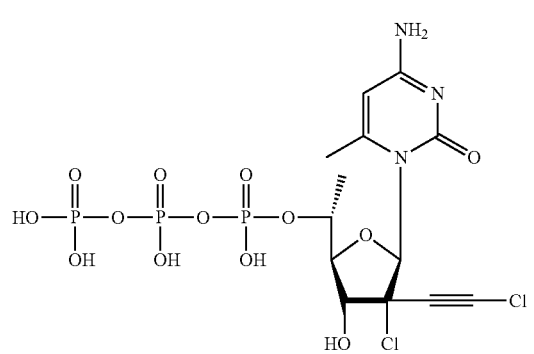
In exemplary embodiments, the compound is selected from:
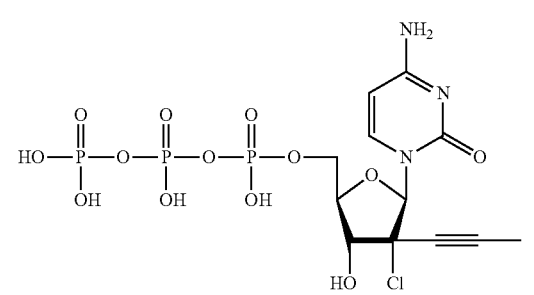
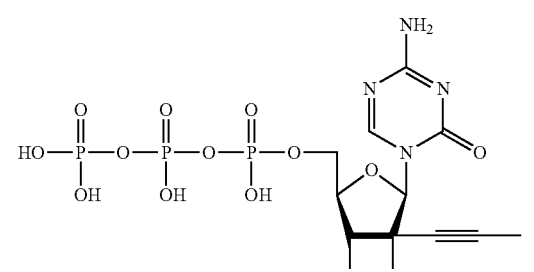
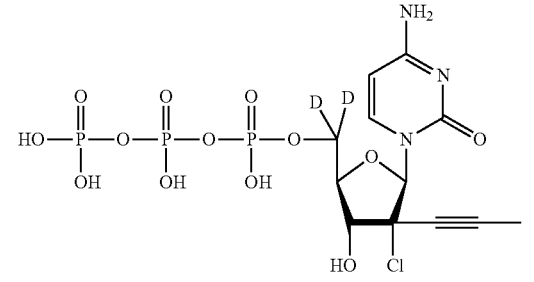
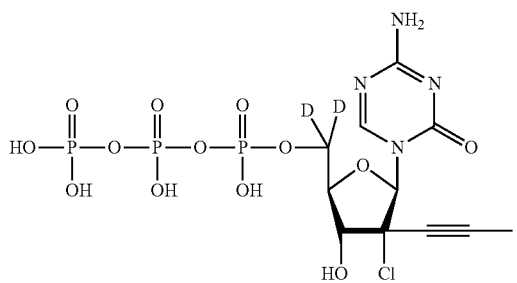
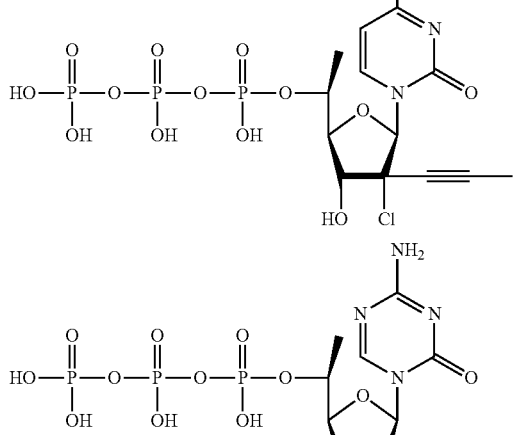
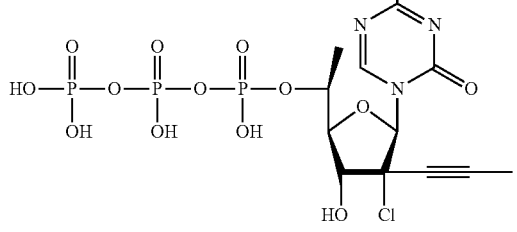
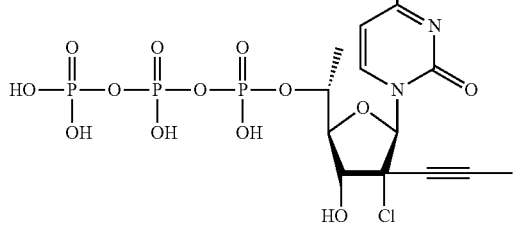
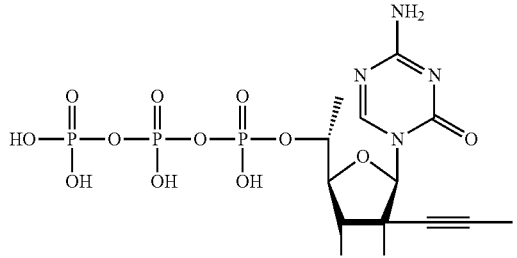
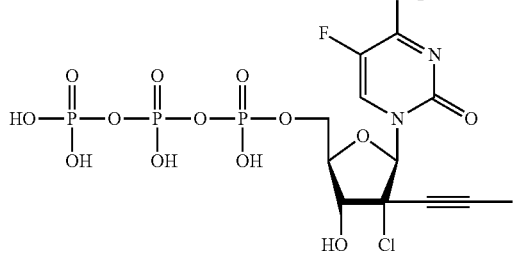

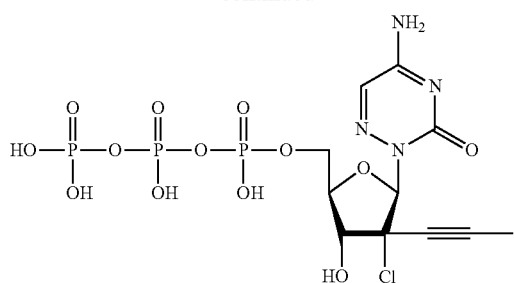
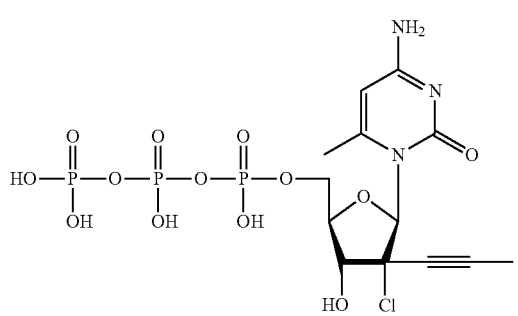
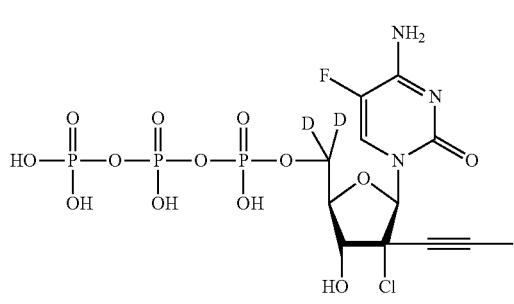
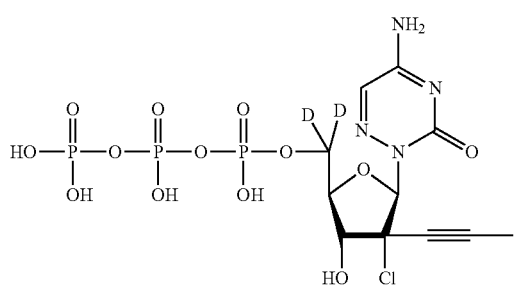
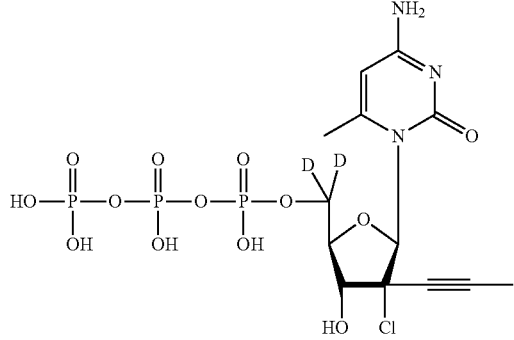
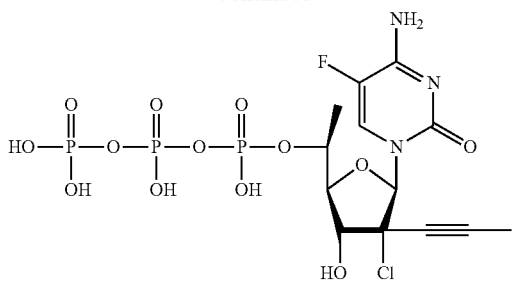
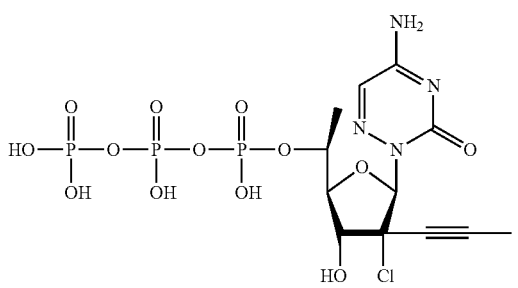
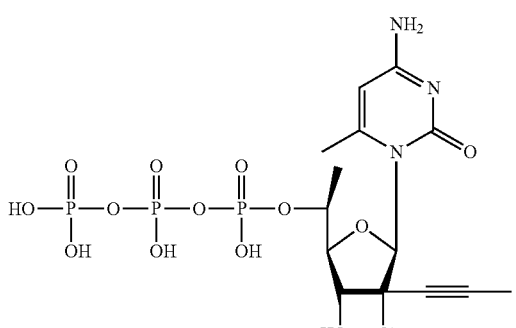
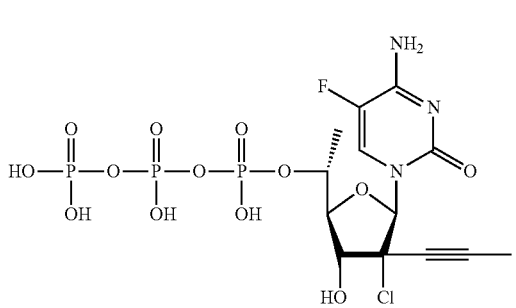
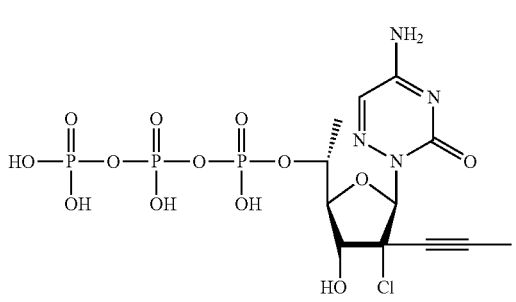

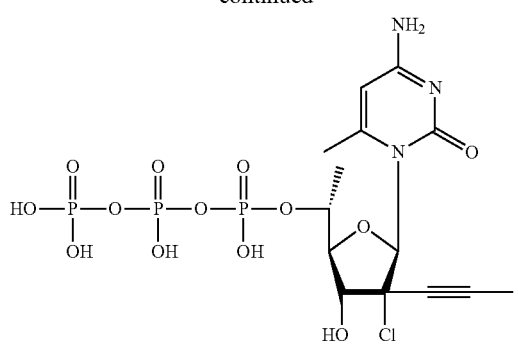
In exemplary embodiments, the compound is selected from:
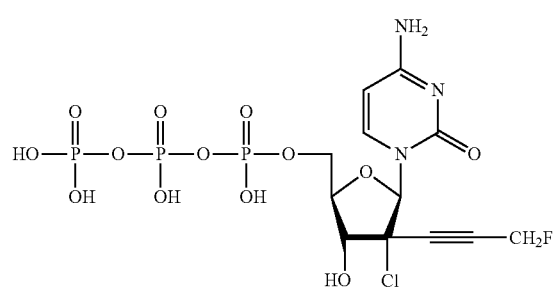
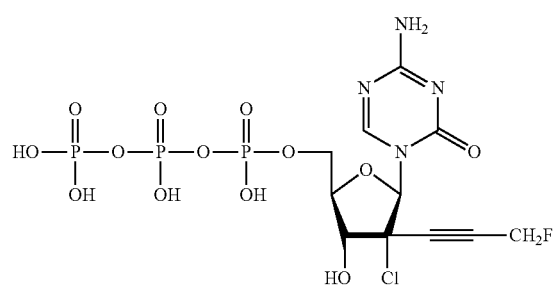
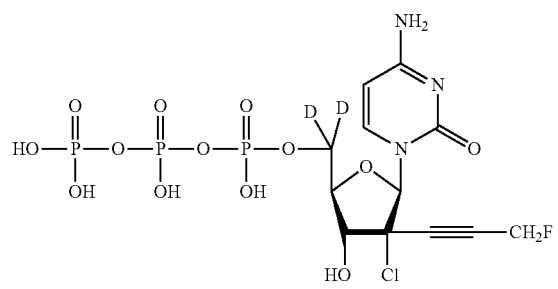
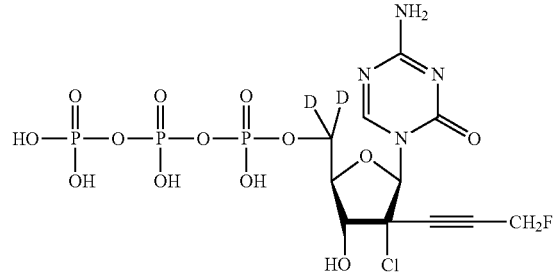
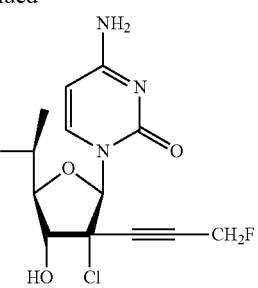
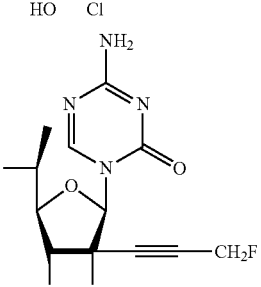
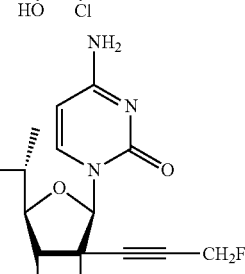
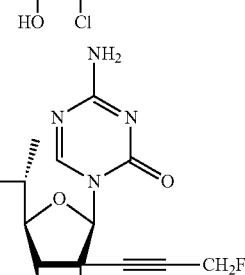
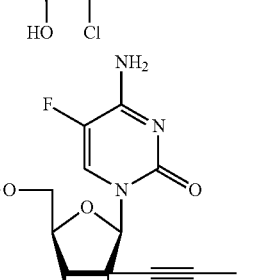
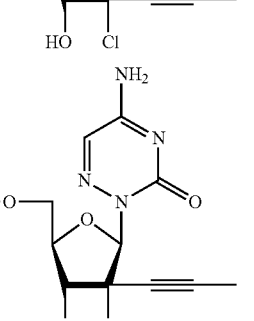

355
-continued
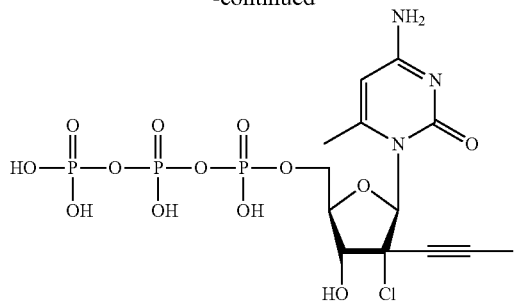
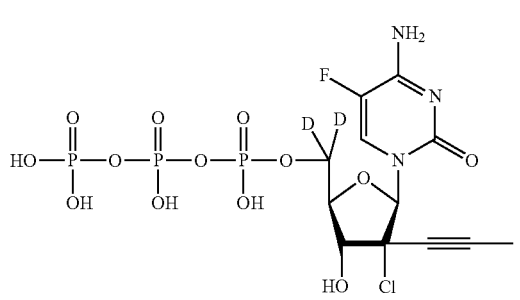
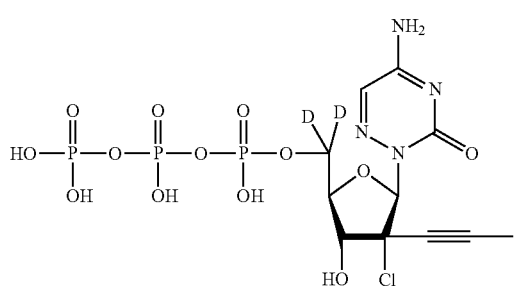
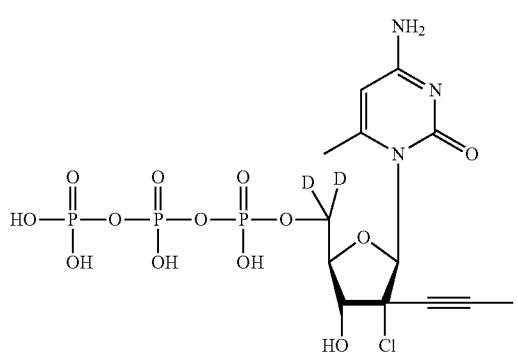
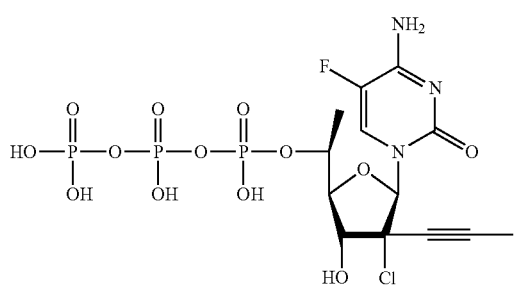
356
-continued
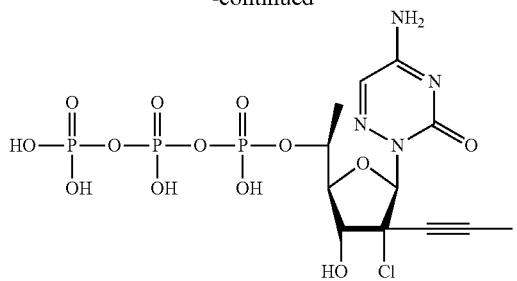
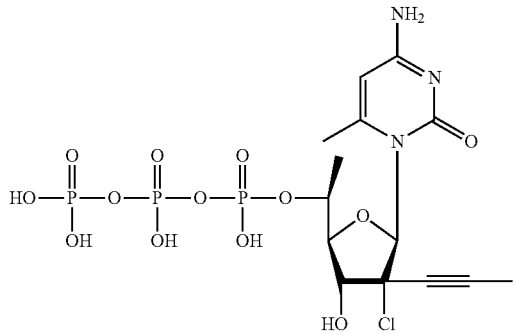
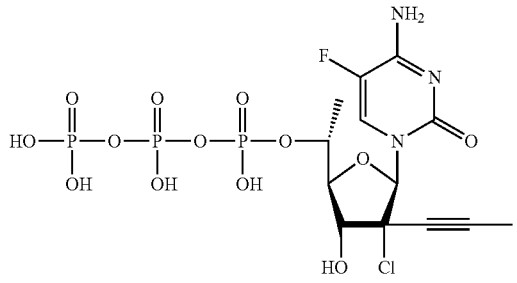
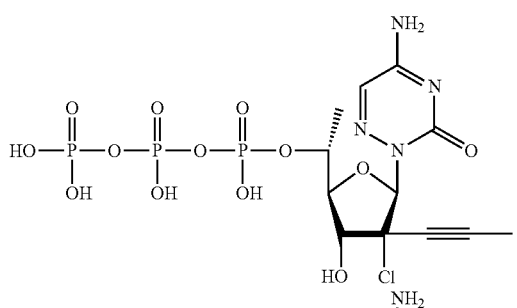
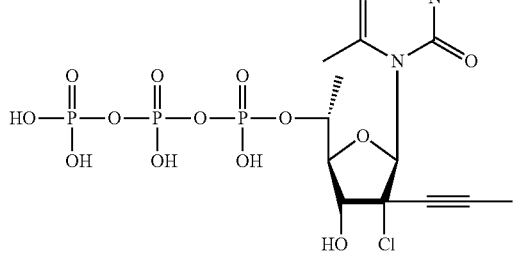

In exemplary embodiments, the compound is selected from:
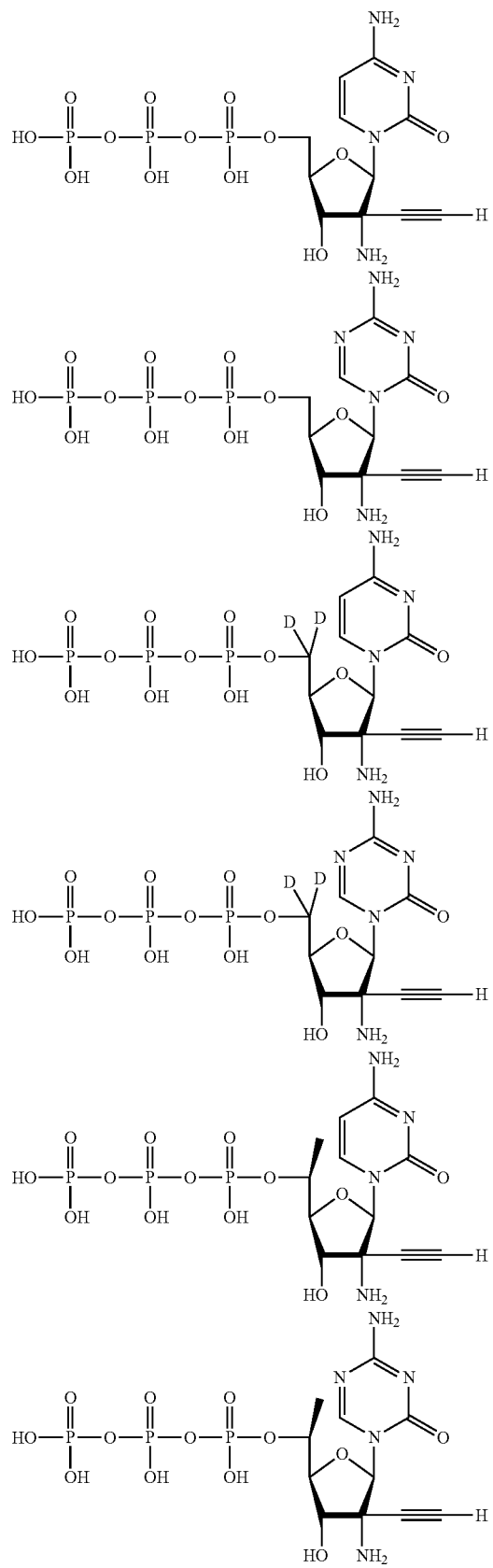
-continued
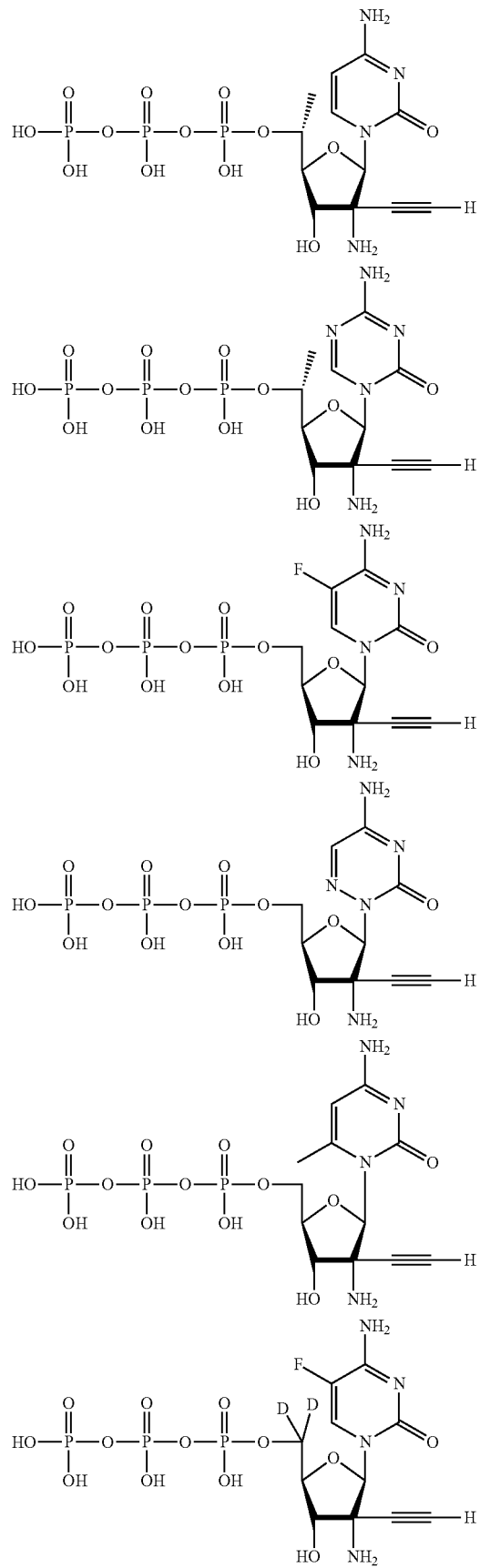

-continued
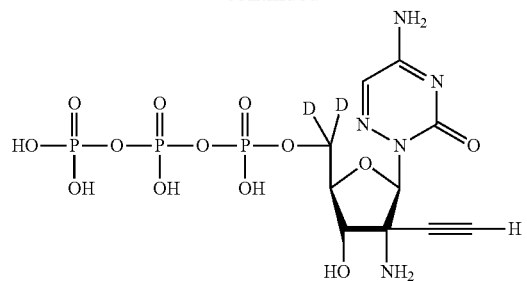
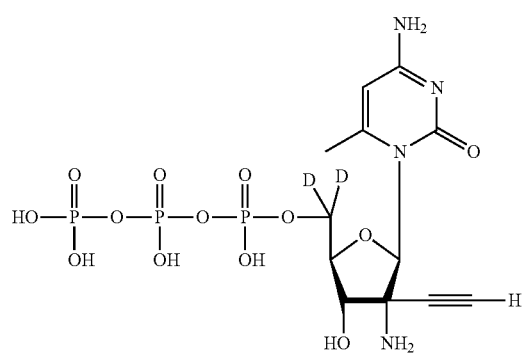
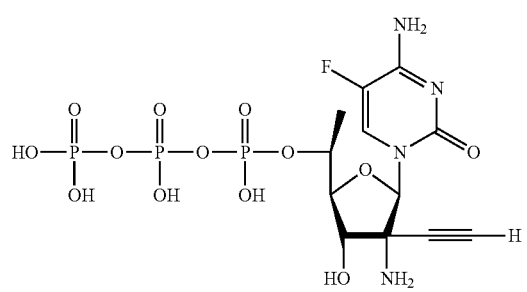
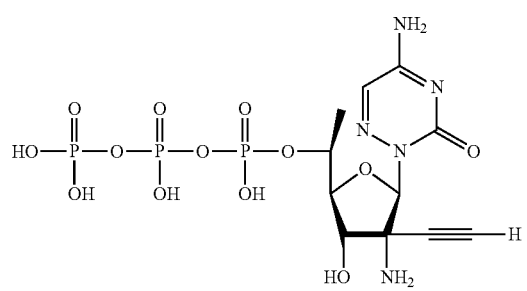
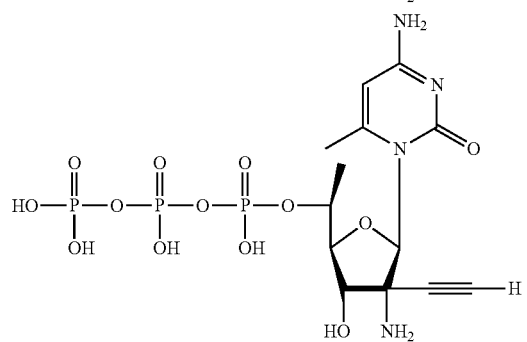
-continued
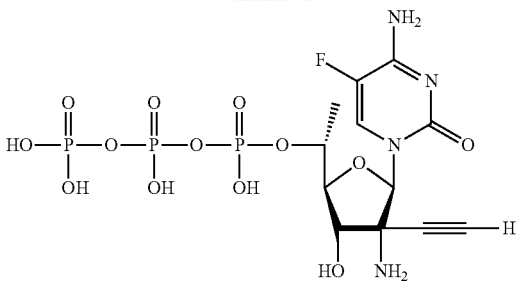
In exemplary embodiments, the compound is selected from:
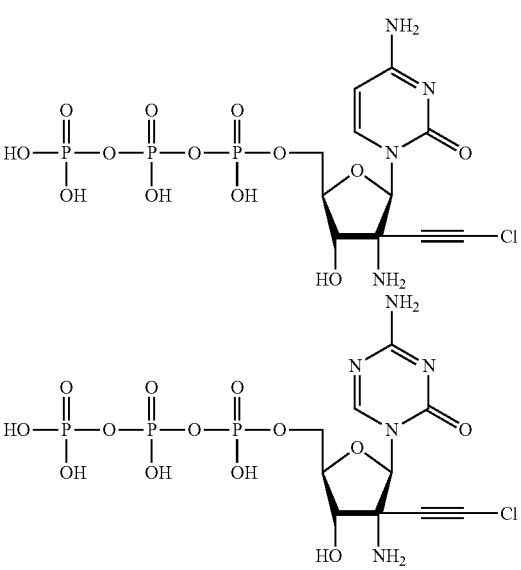

361
-continued
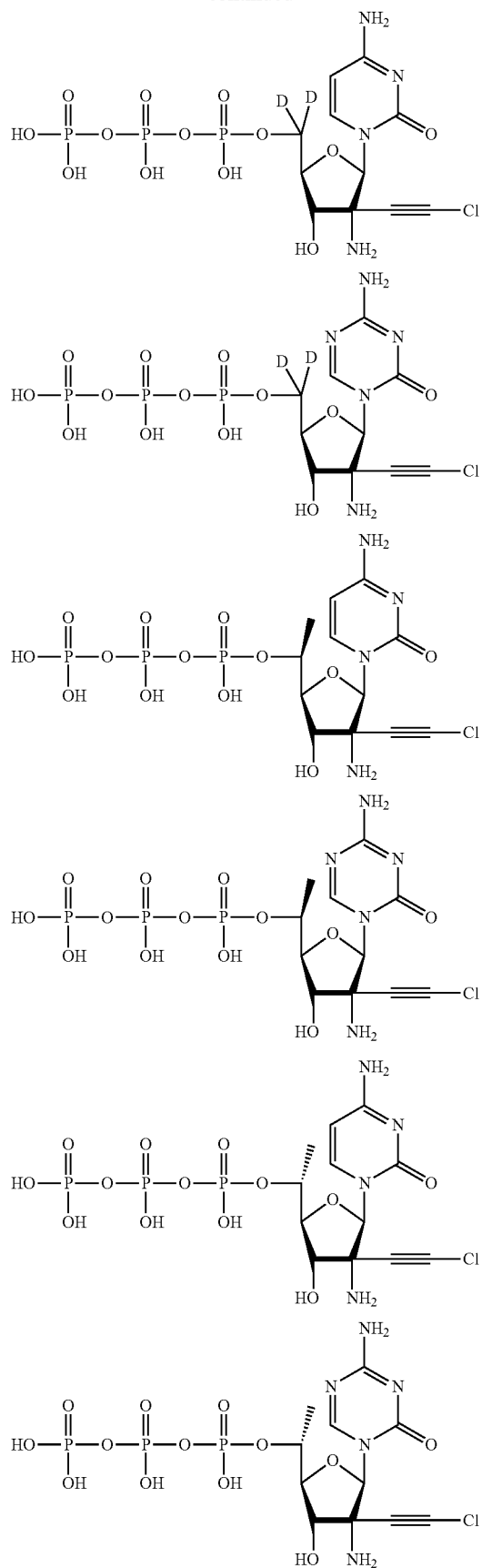
362
-continued
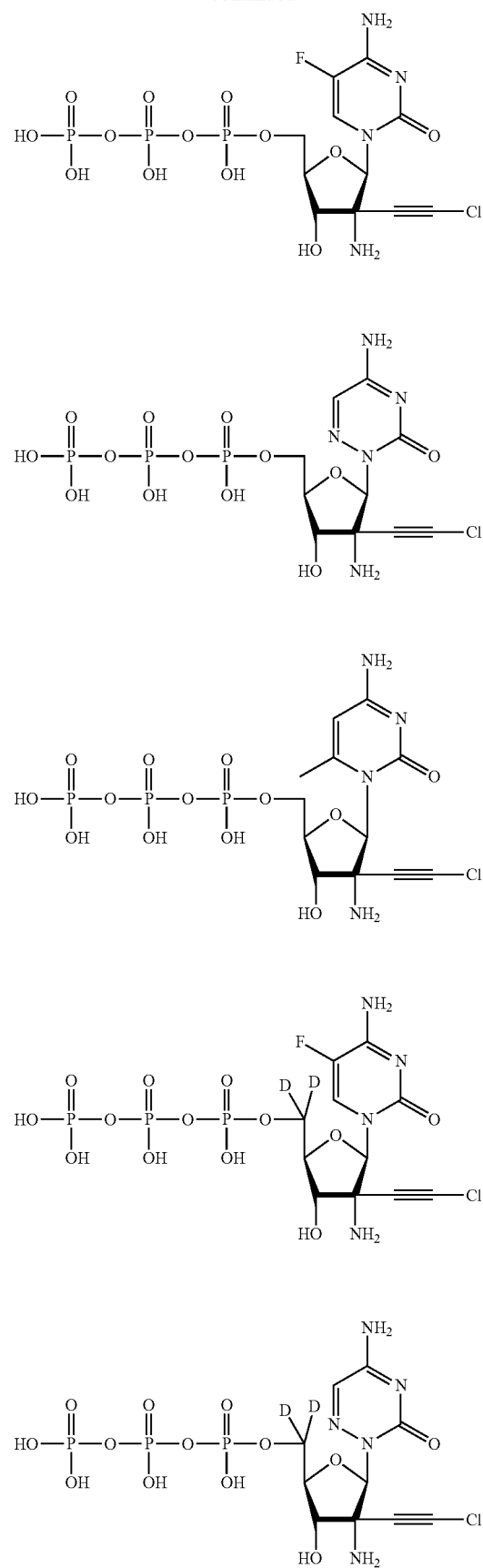

363
-continued
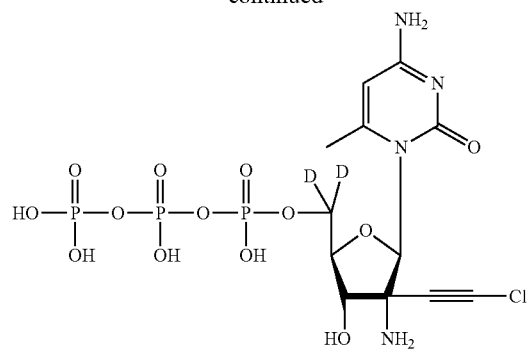
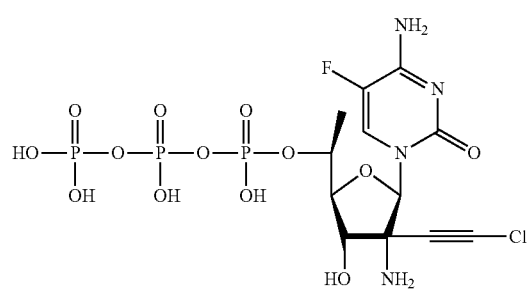
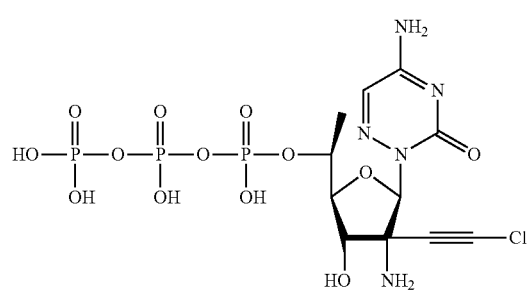
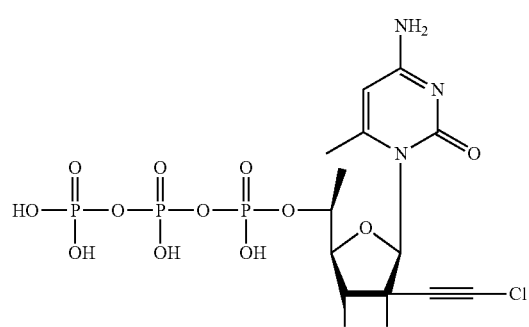
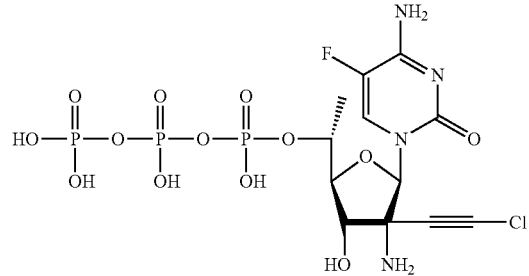
364
-continued
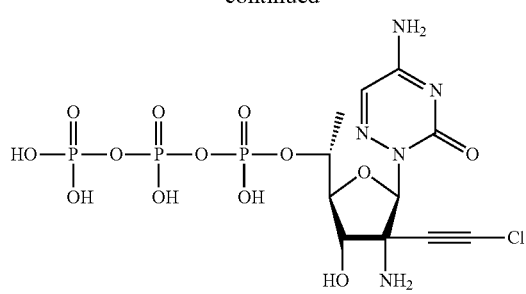
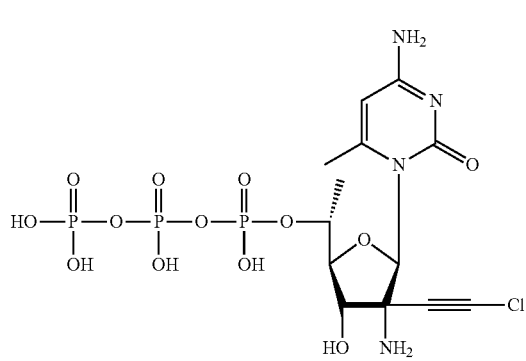
In exemplary embodiments, the compound is selected from:
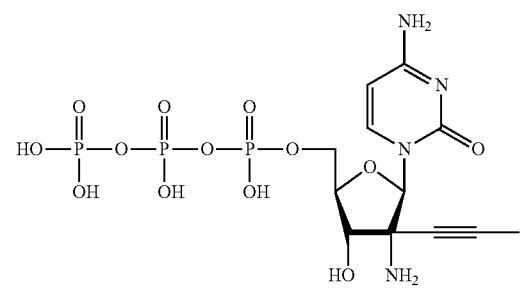
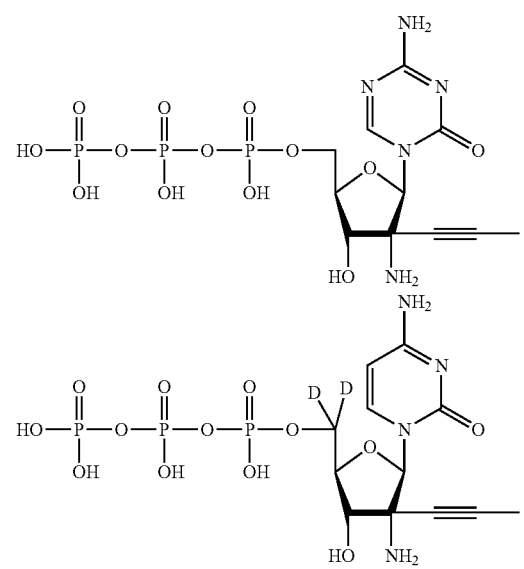

365
-continued
366
-continued
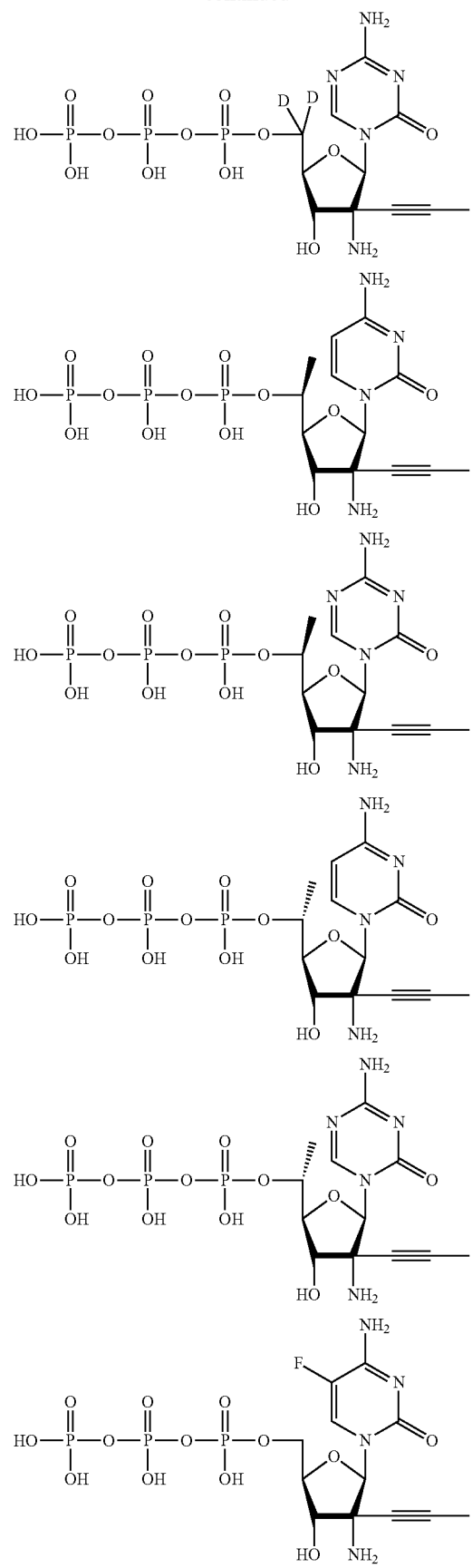
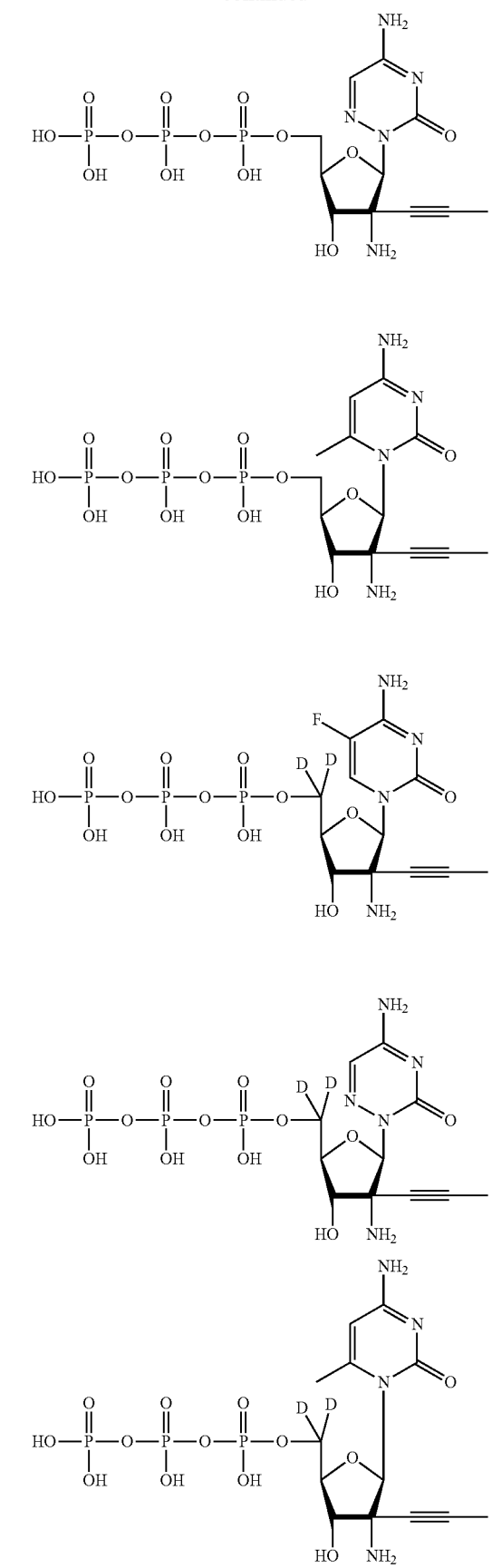

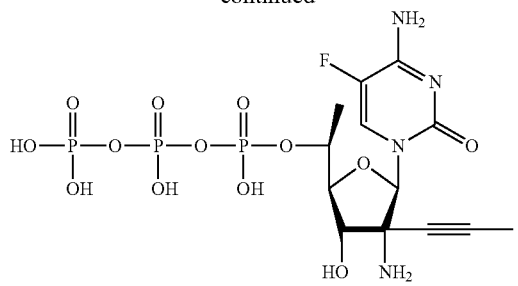
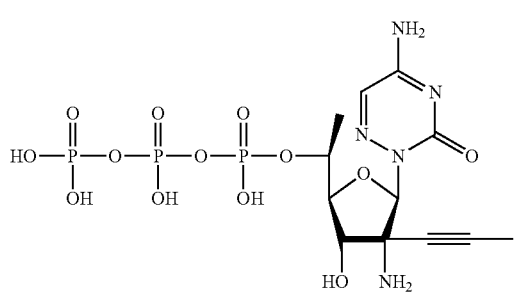
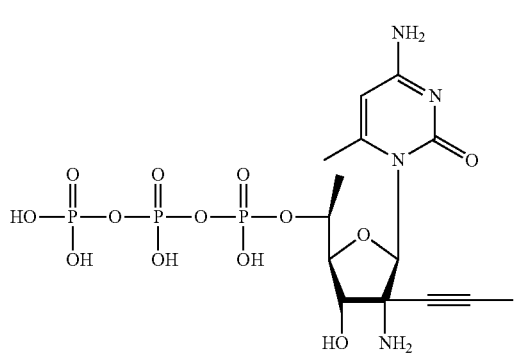
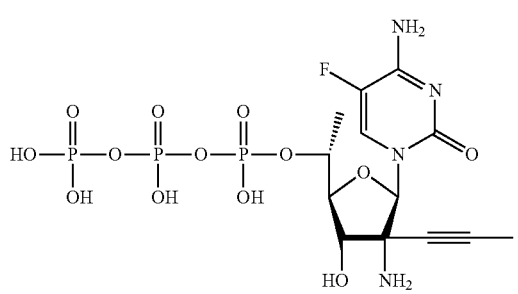
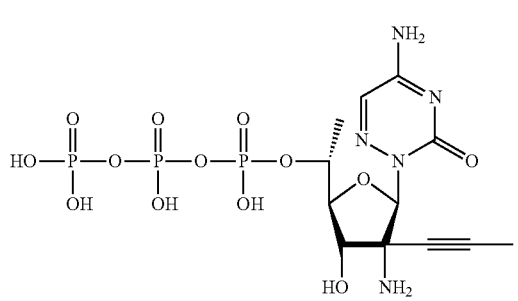
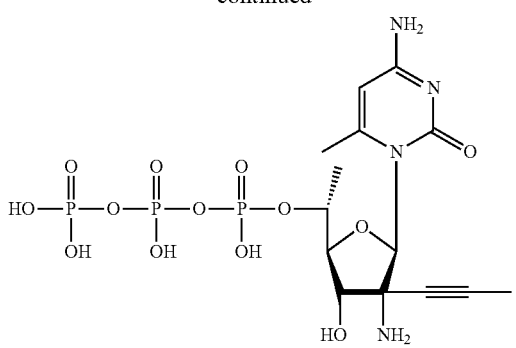
In exemplary embodiments, the compound is selected from:
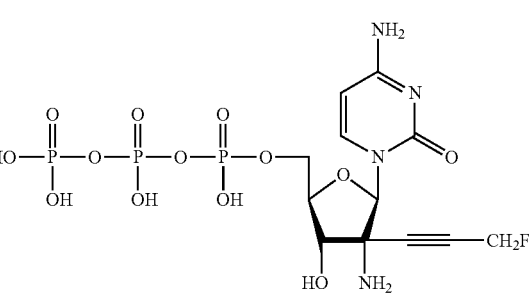
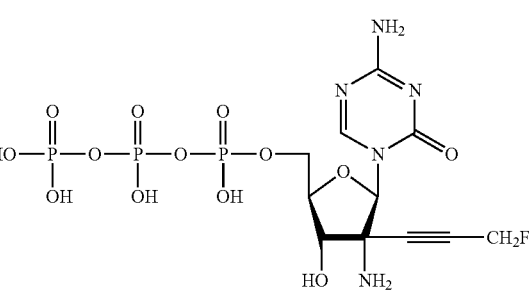
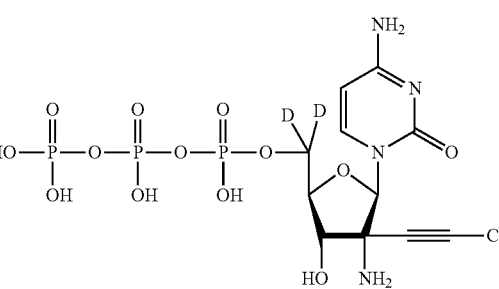
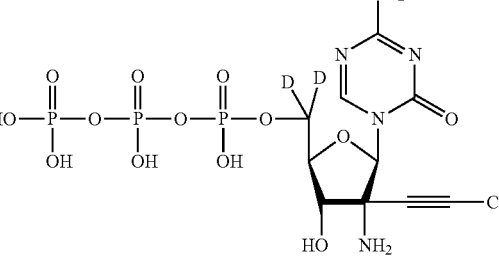

369
-continued
370
-continued
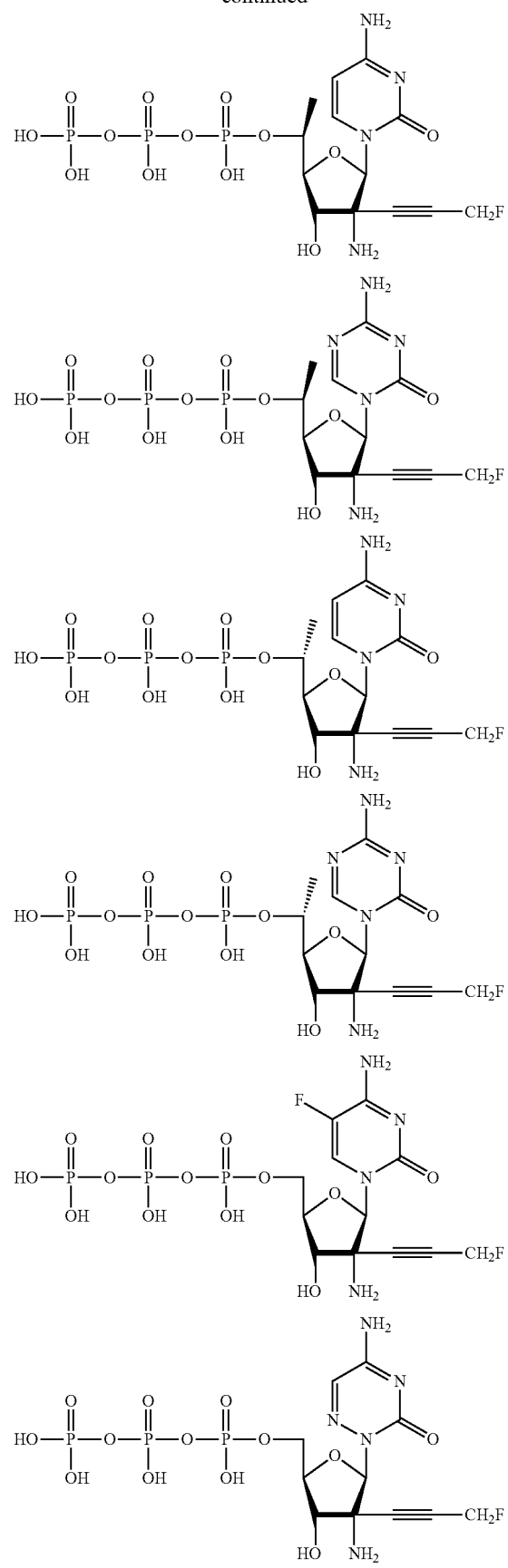
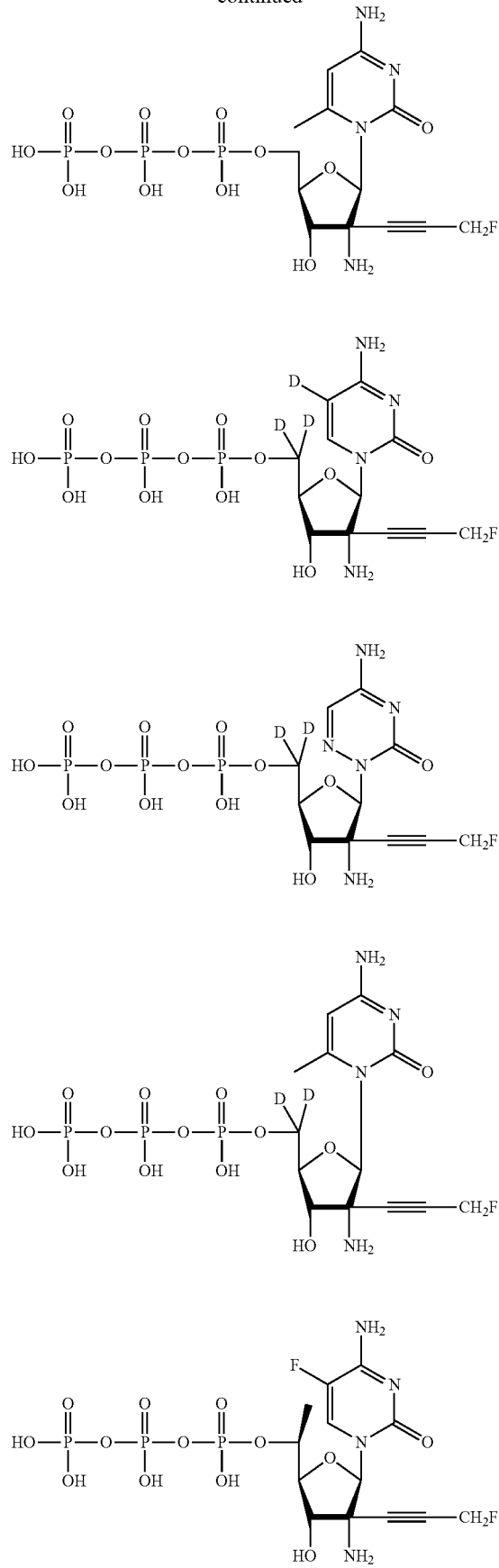

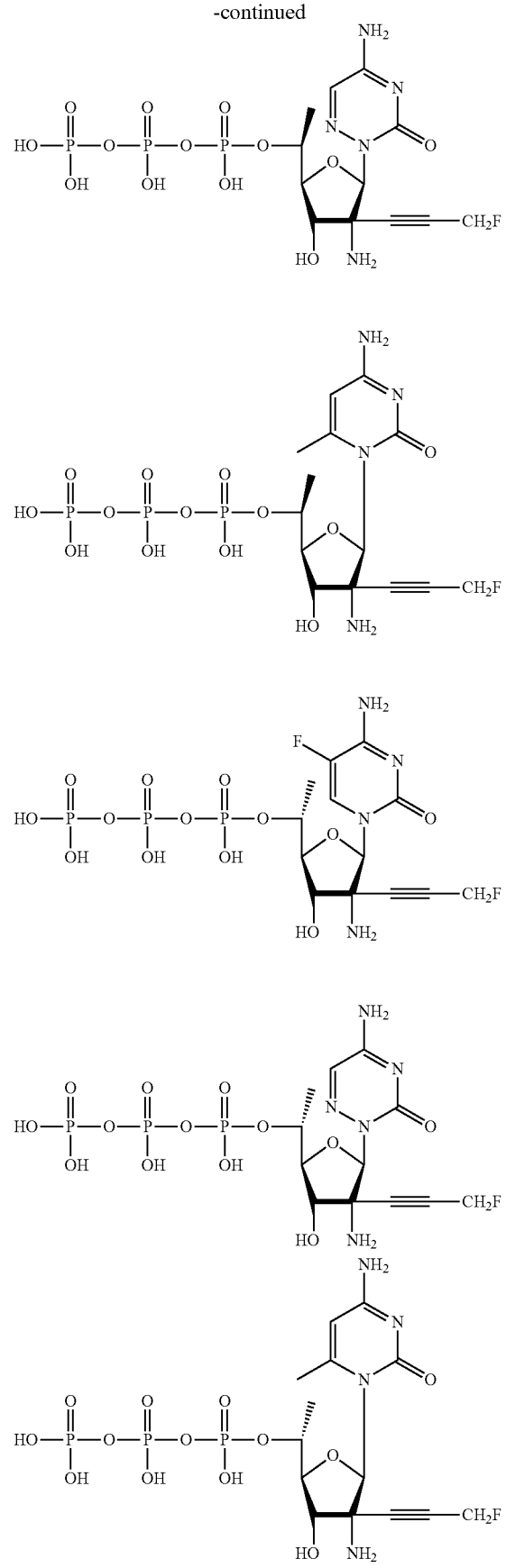
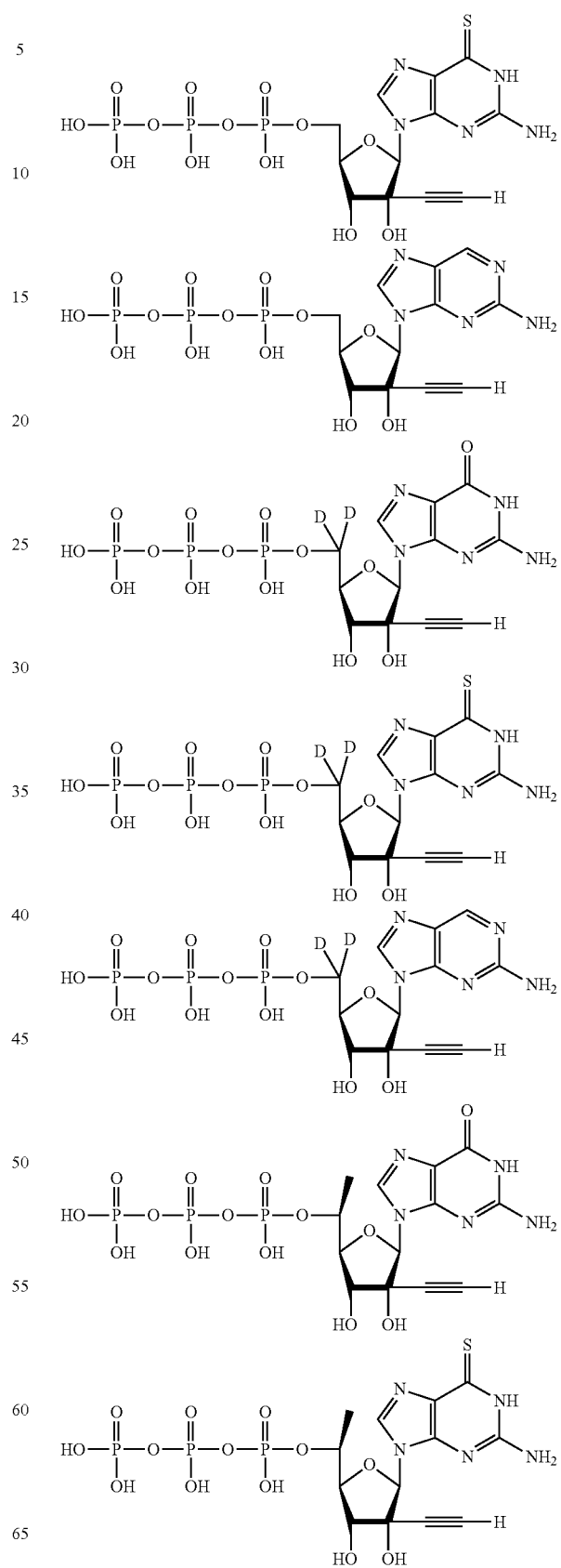
In exemplary embodiments, the compound is selected from:

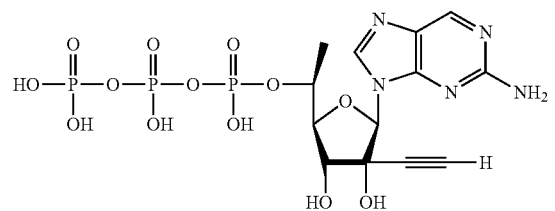
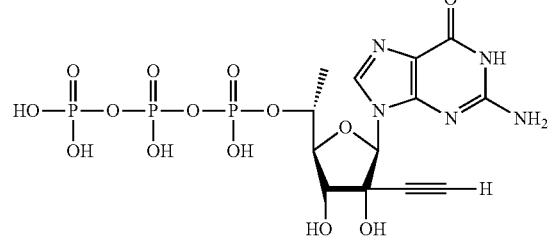
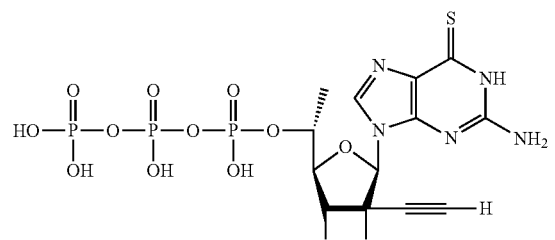
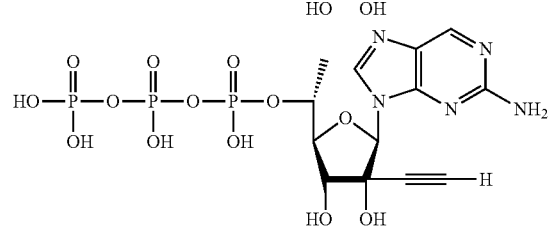
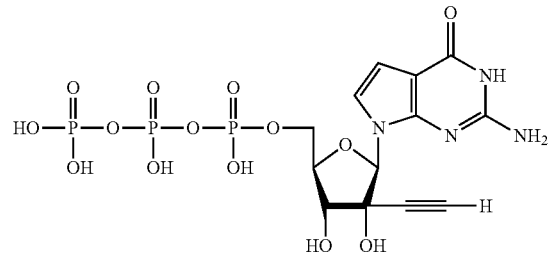
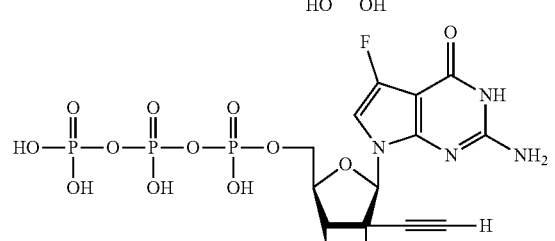
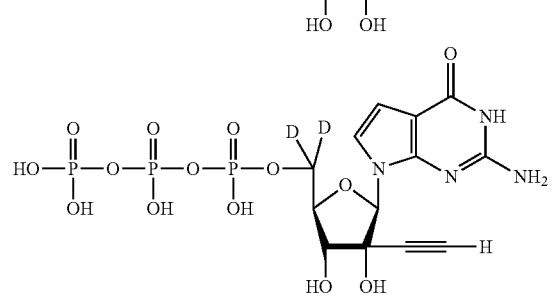
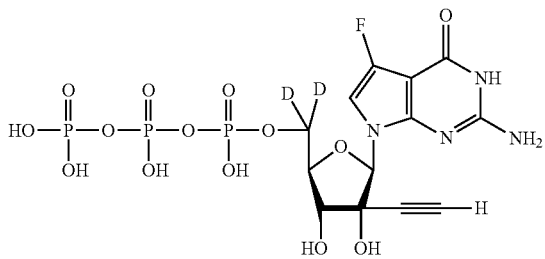
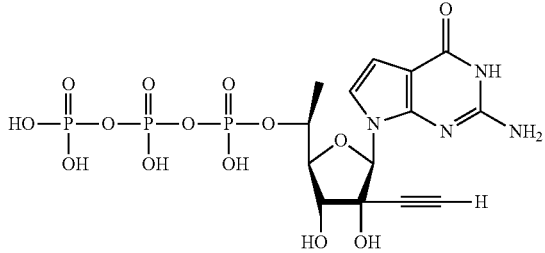
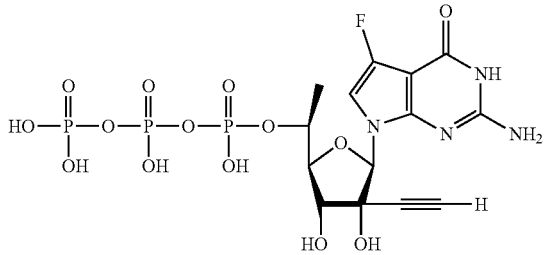
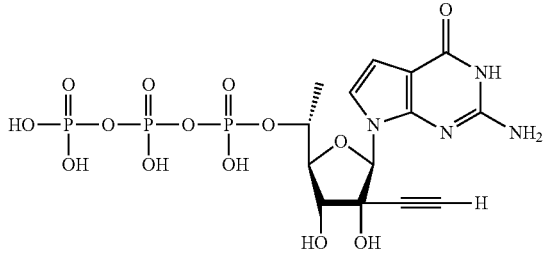
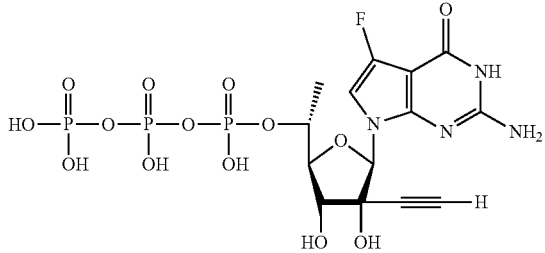
In exemplary embodiments, the compound is selected from:
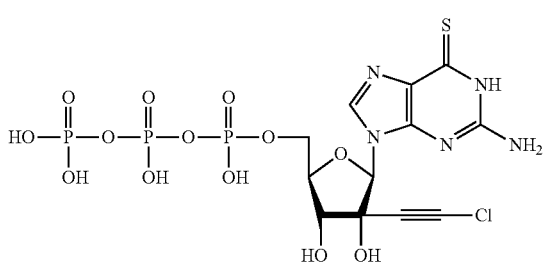

375
-continued
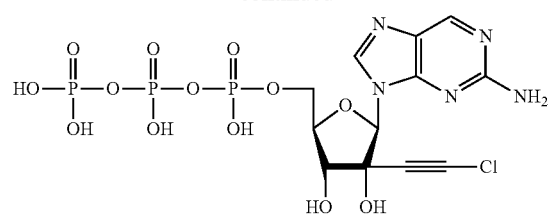
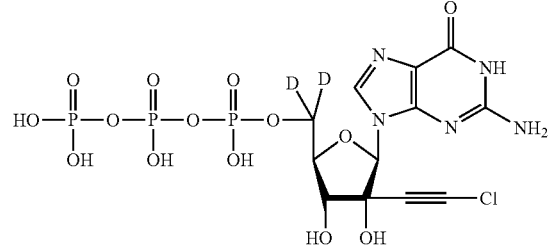
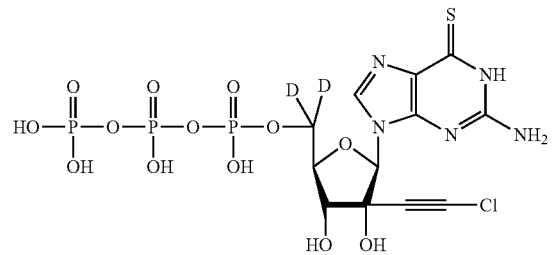
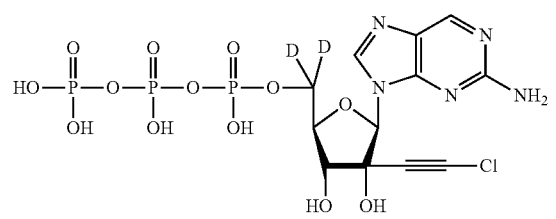
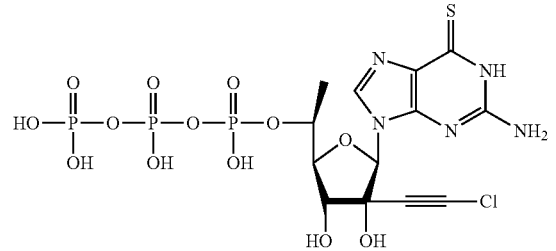
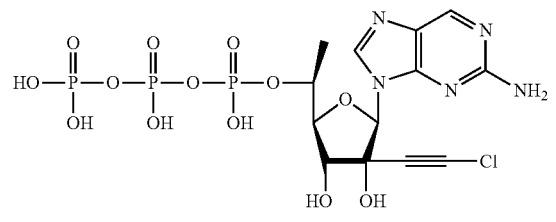
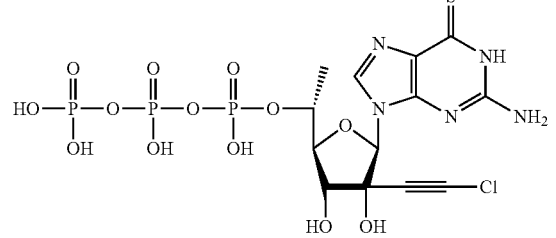
376
-continued
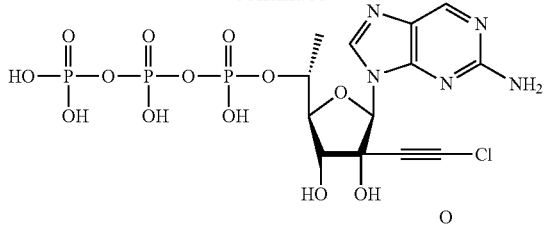
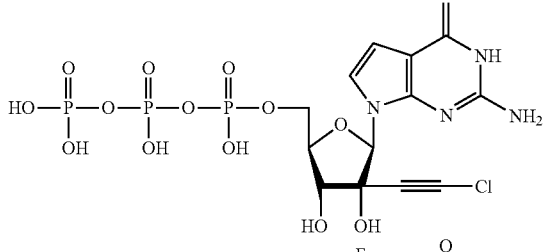
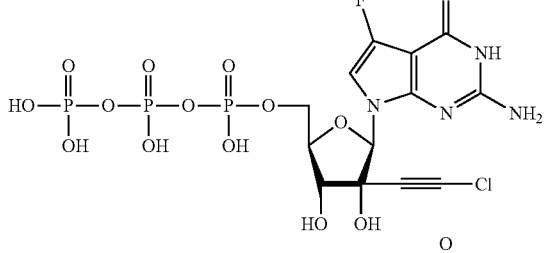
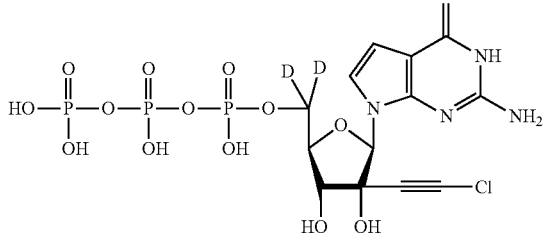
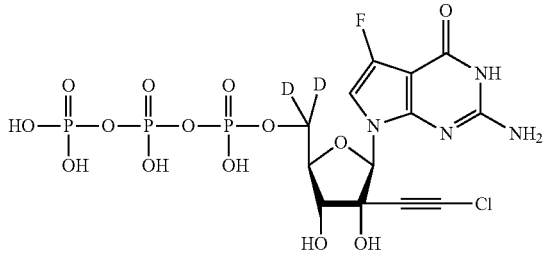
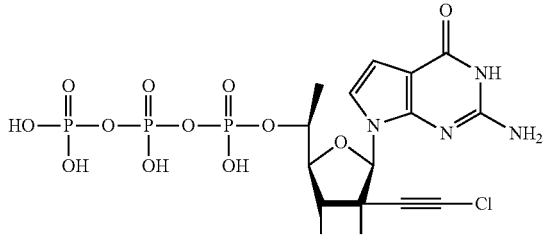
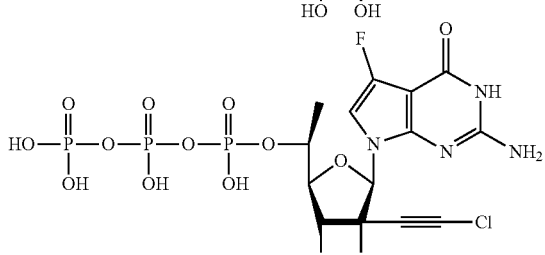

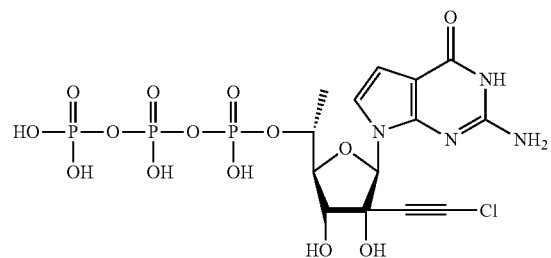
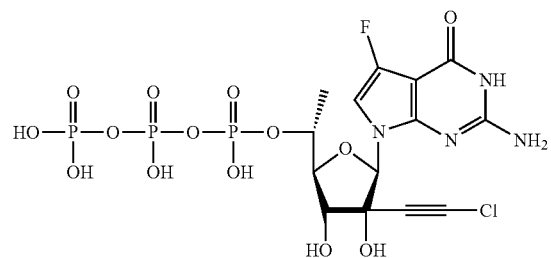
In exemplary embodiments, the compound is selected from:
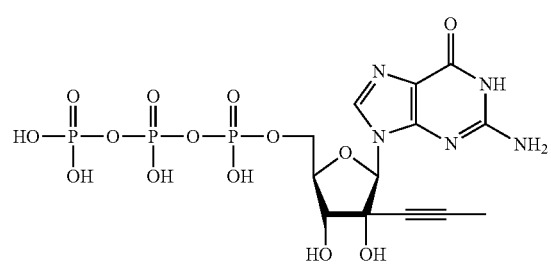
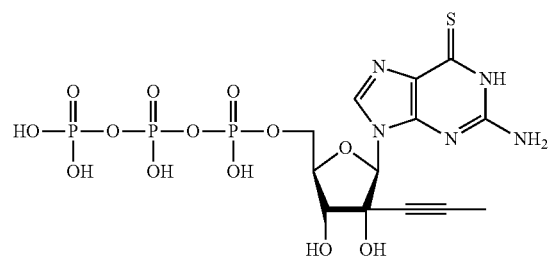
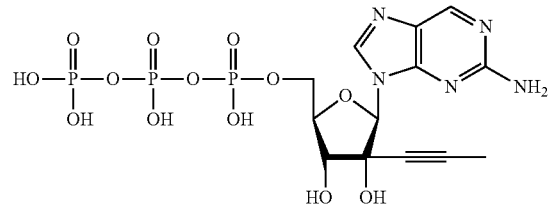
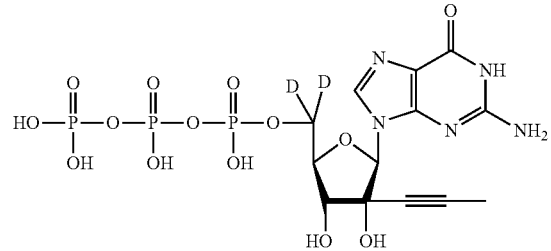
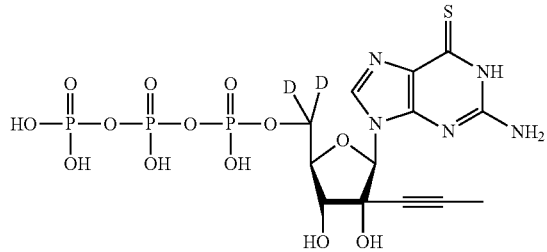
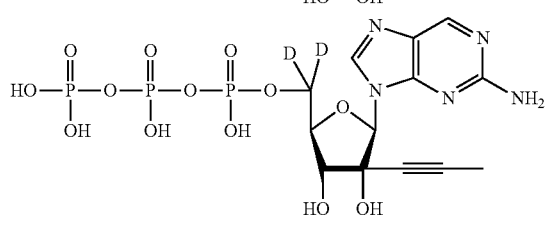
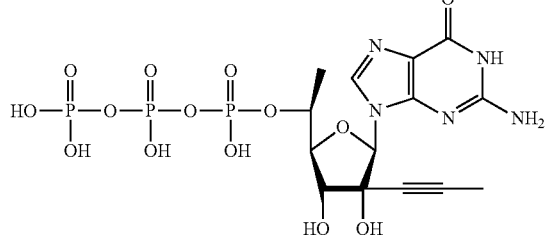
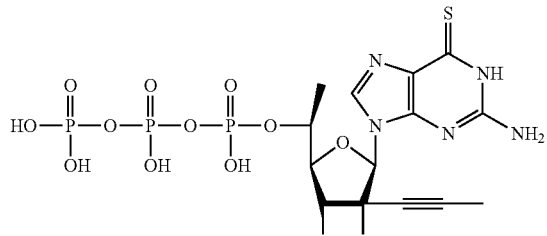
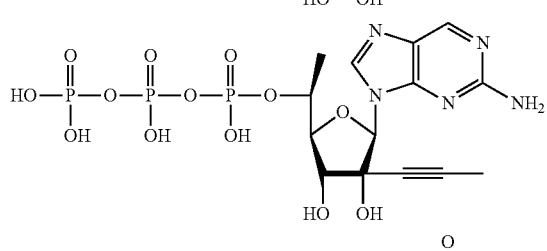
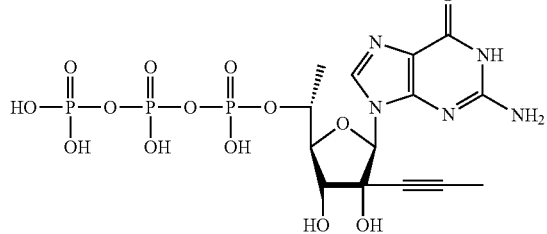
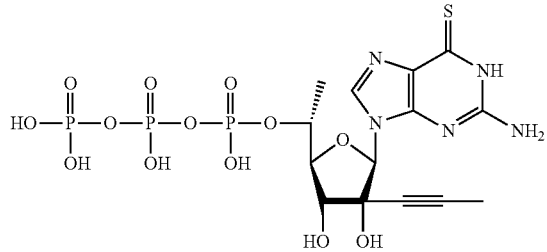

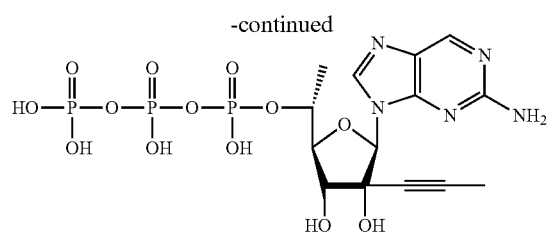
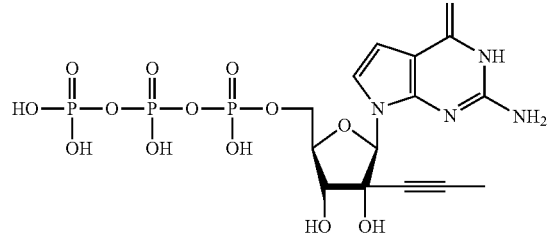
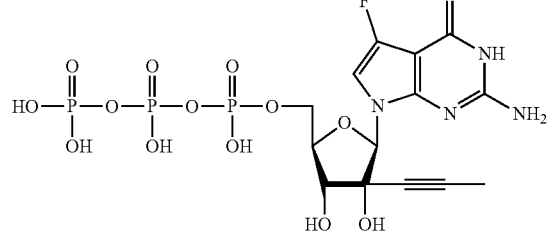
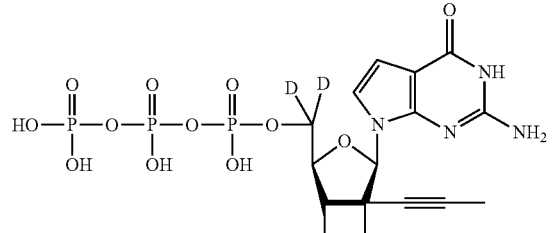
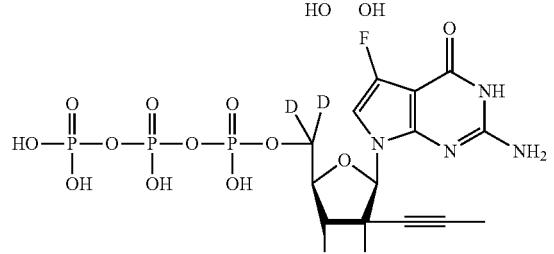
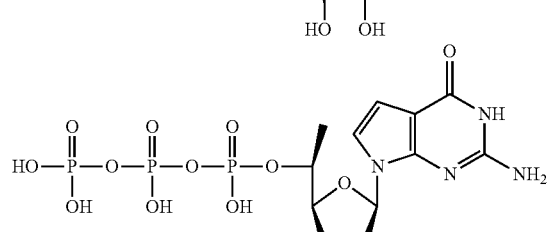
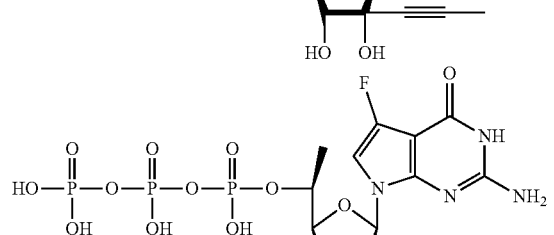
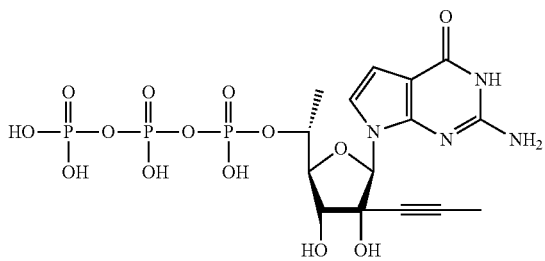
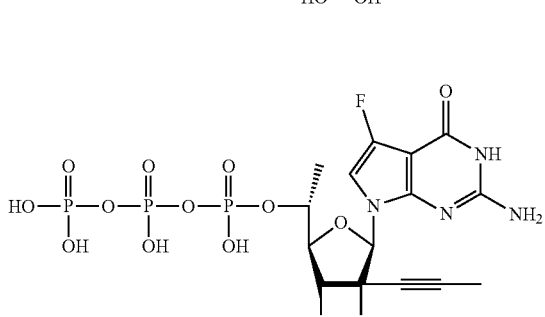
In exemplary embodiments, the compound is selected from:
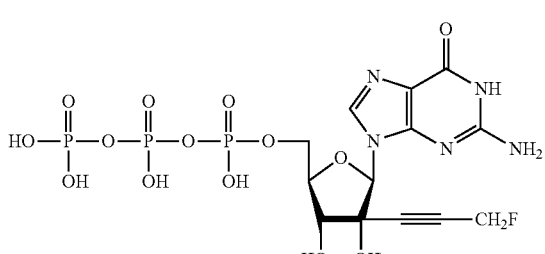
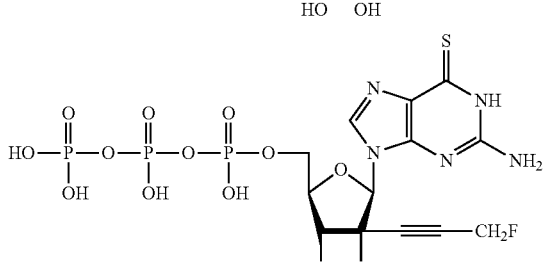
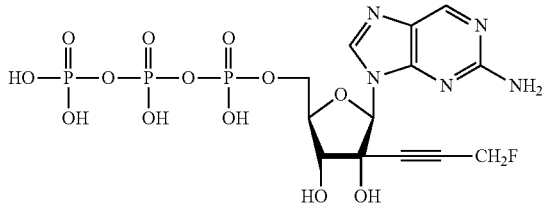
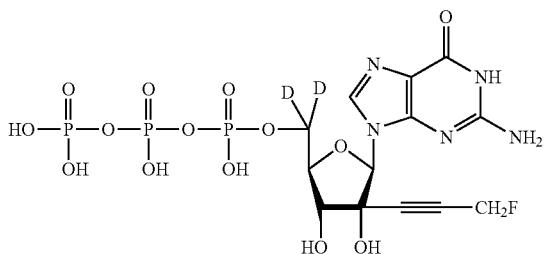

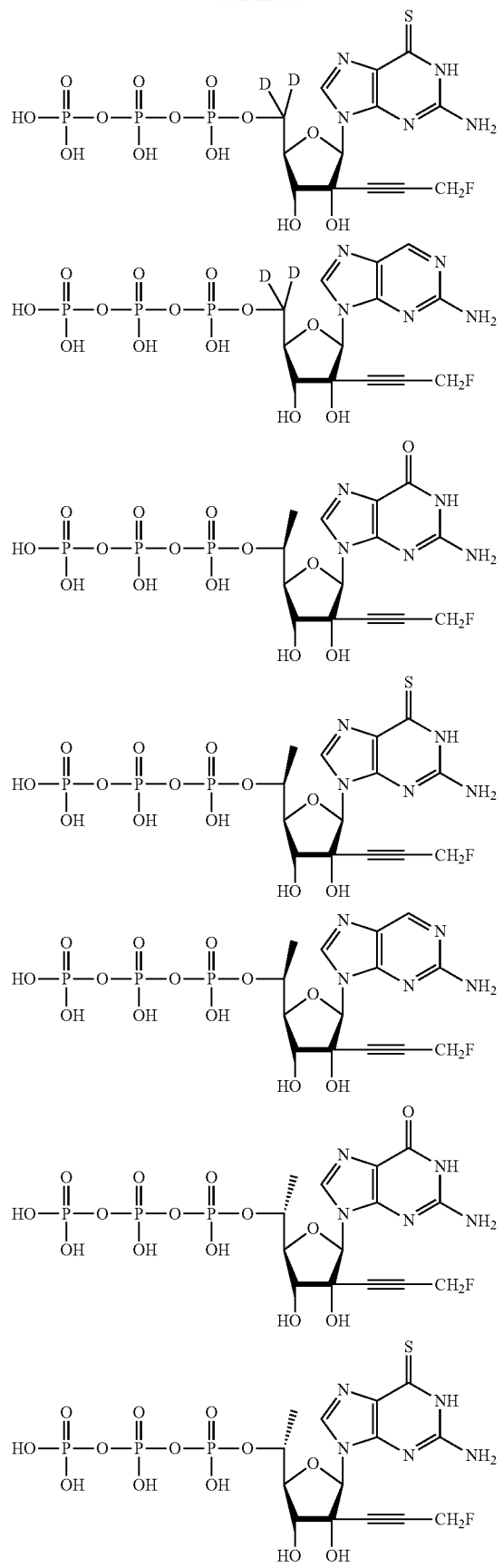
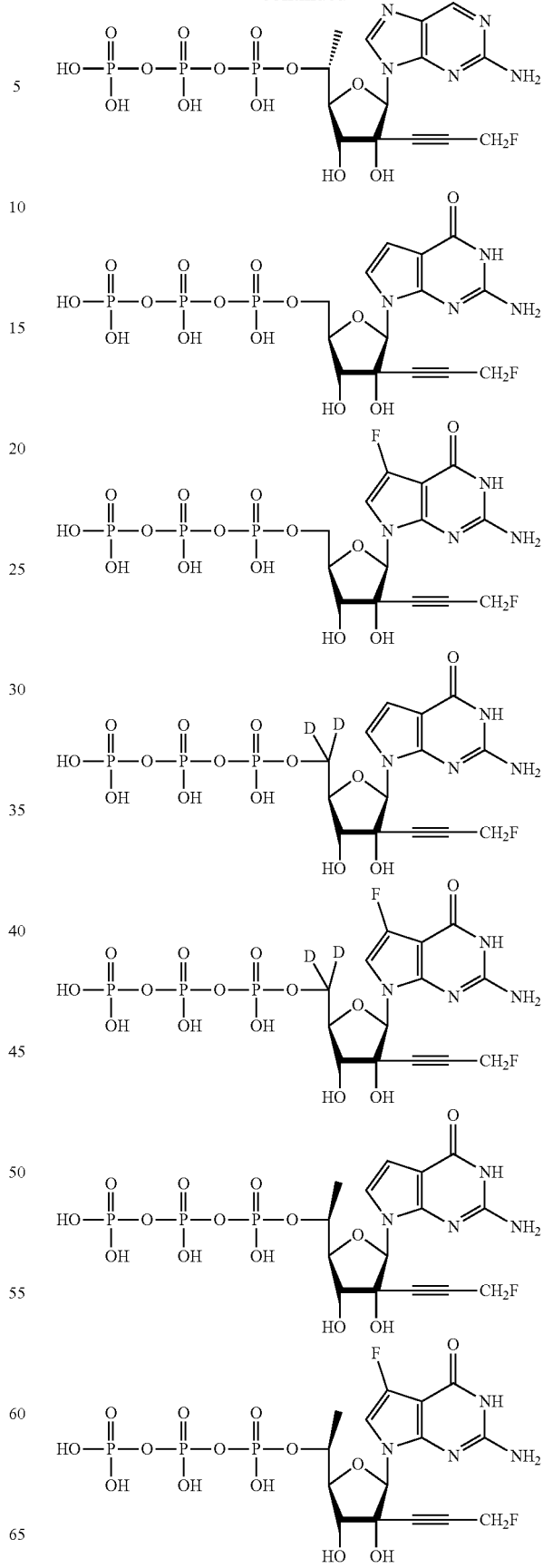

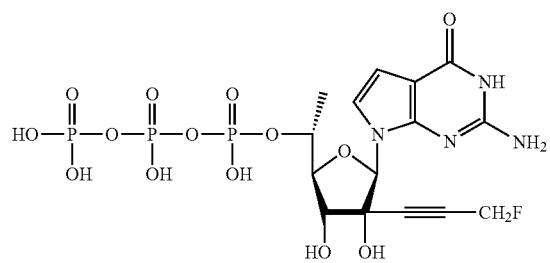
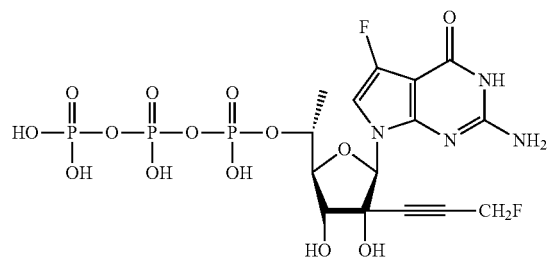
In exemplary embodiments, the compound is selected from:
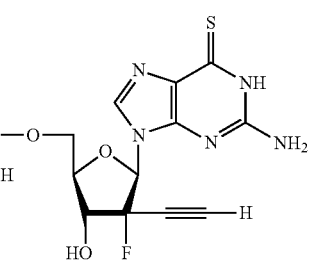
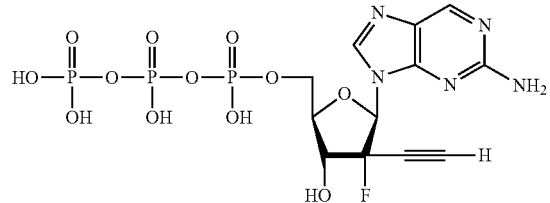
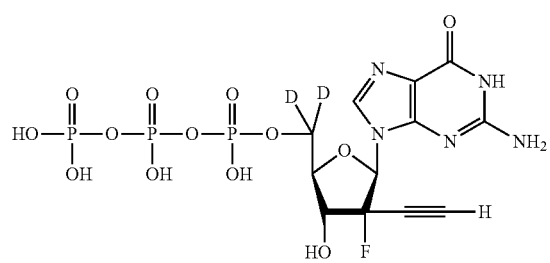
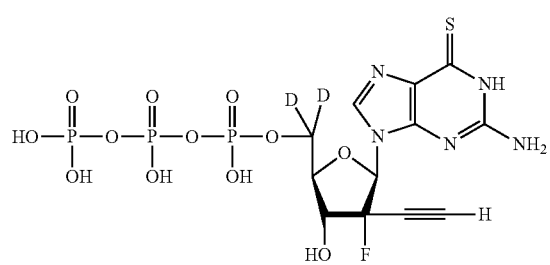
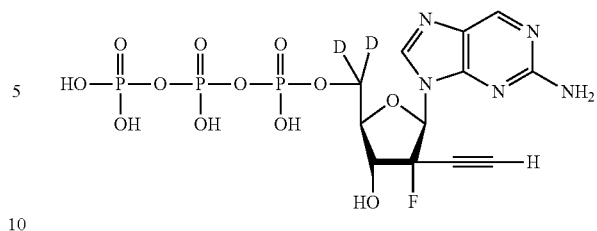
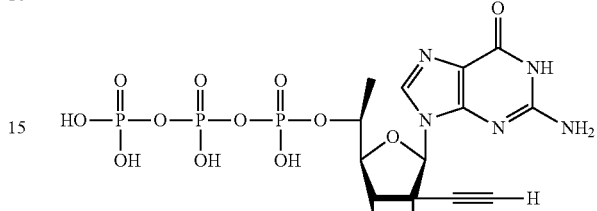
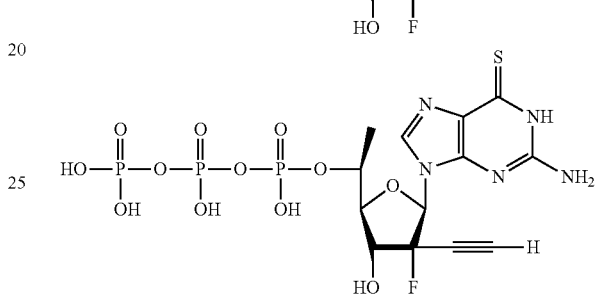
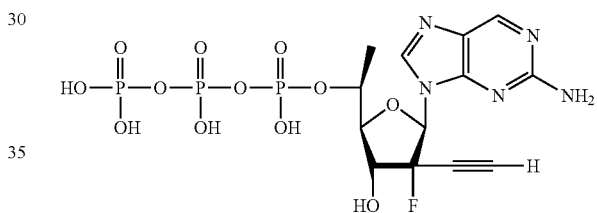
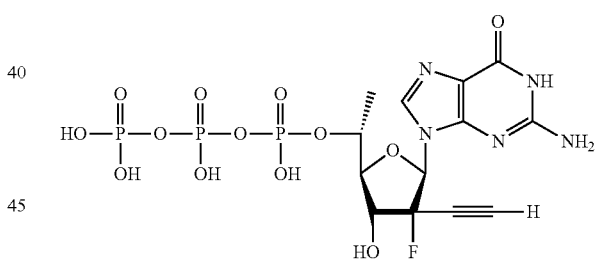
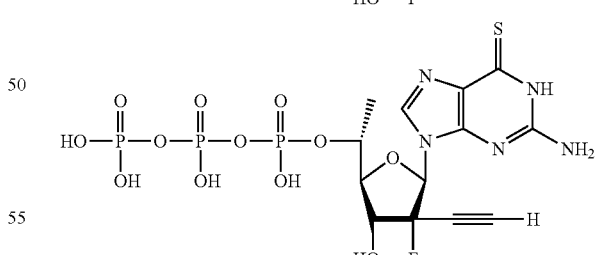
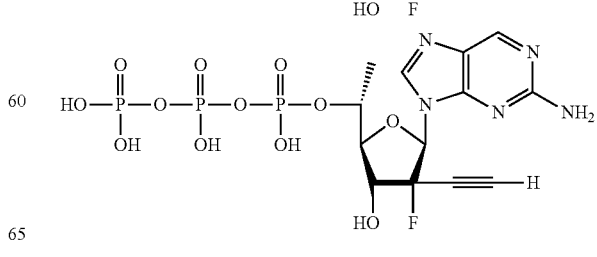

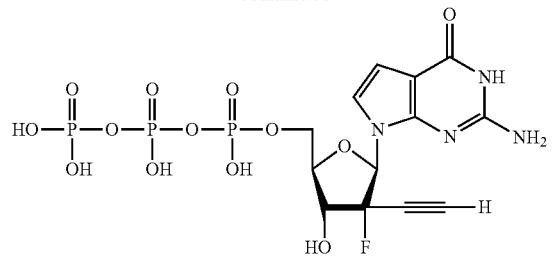
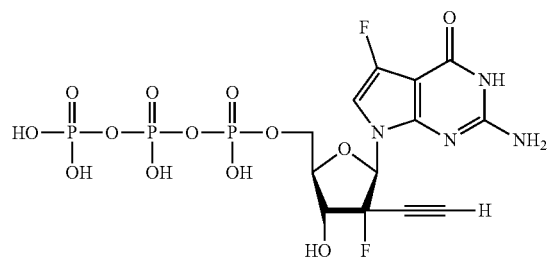
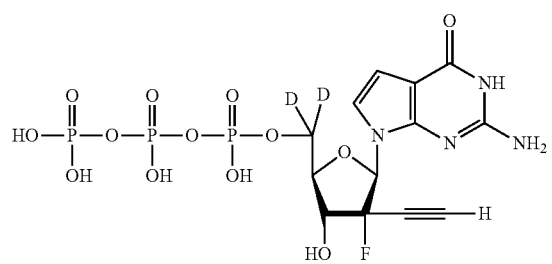
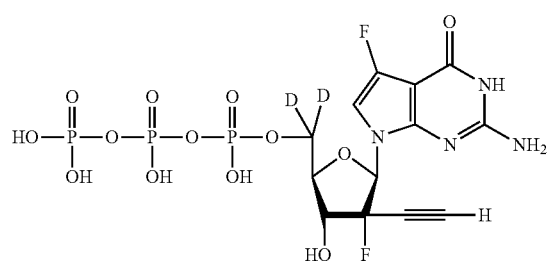
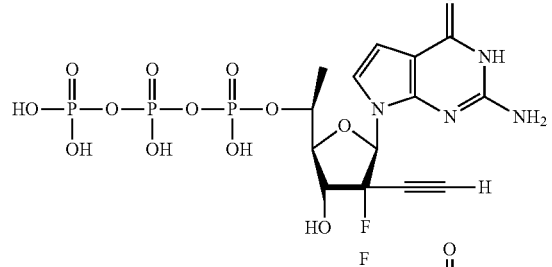
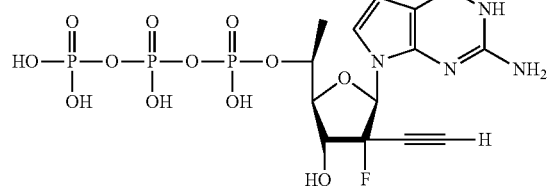
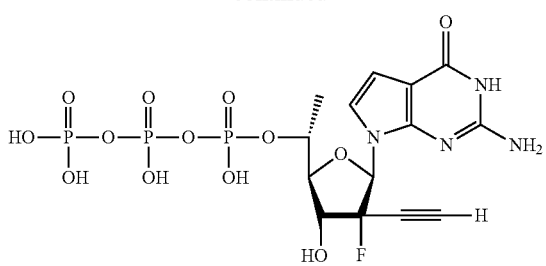
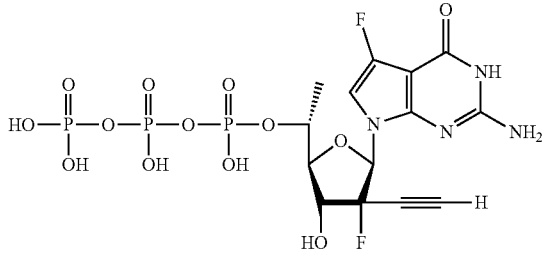
In exemplary embodiments, the compound is selected from:
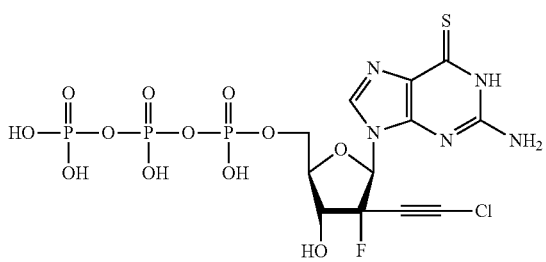
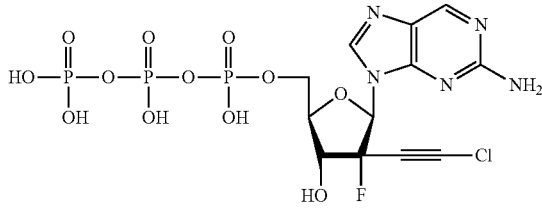
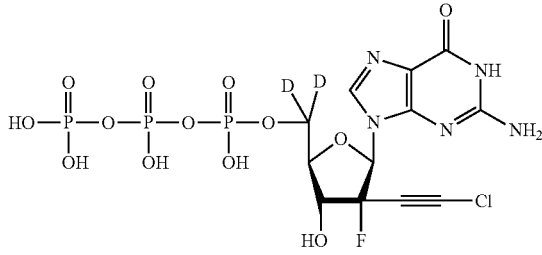
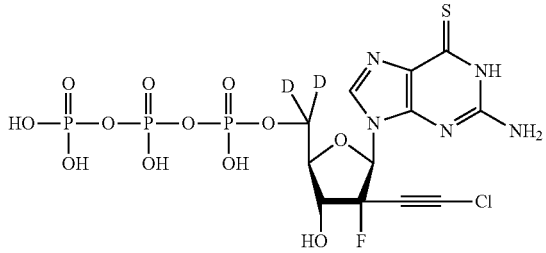

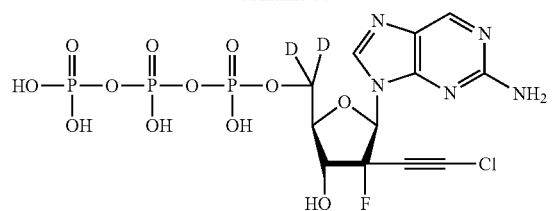
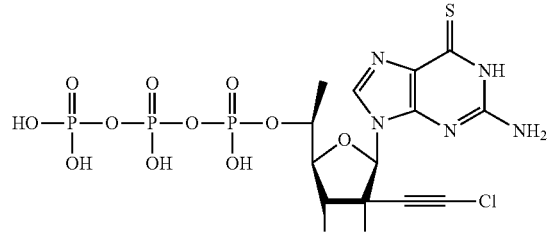
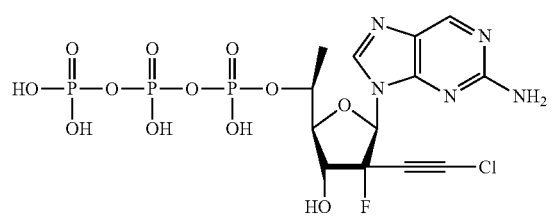
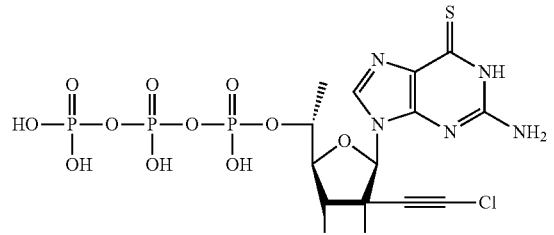
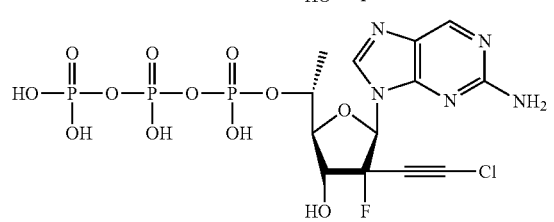
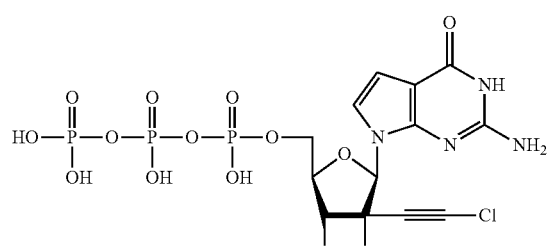
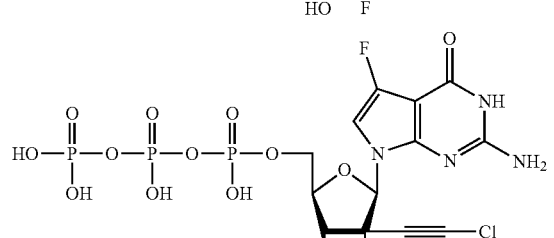
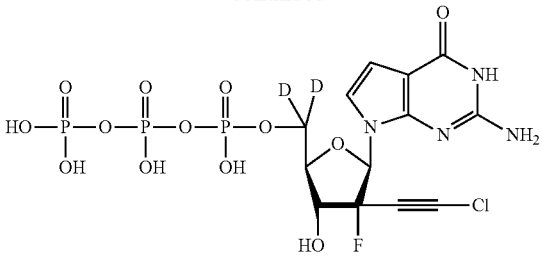
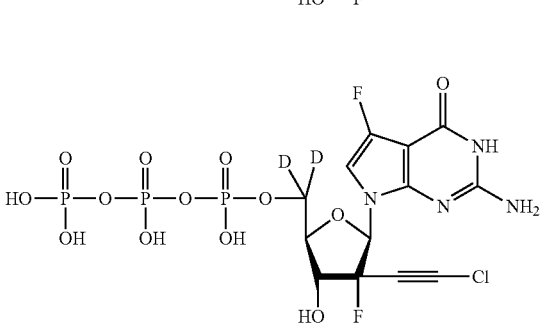
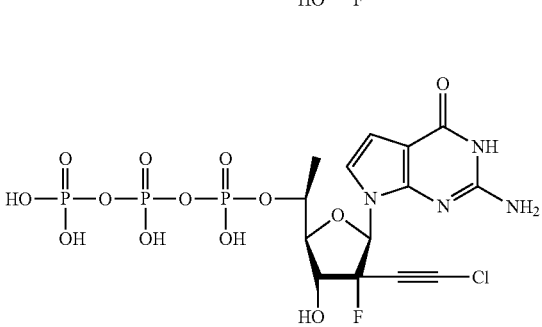
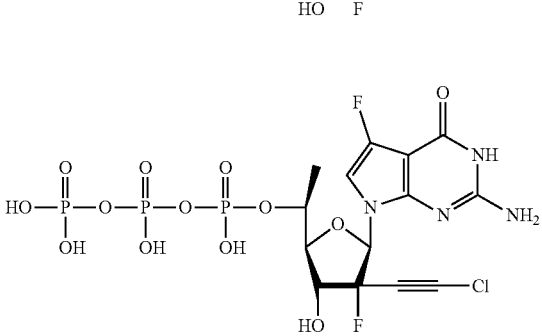
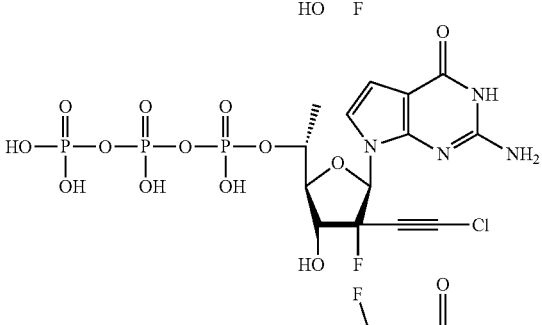
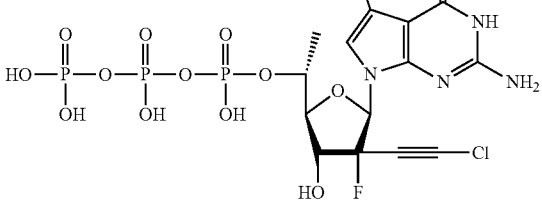

In exemplary embodiments, the compound is selected from:
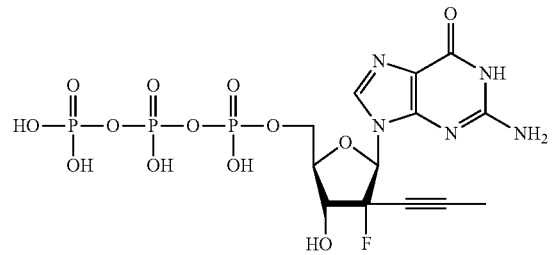
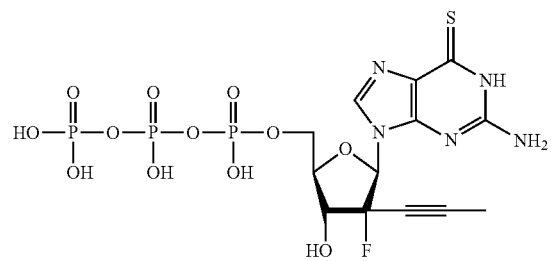
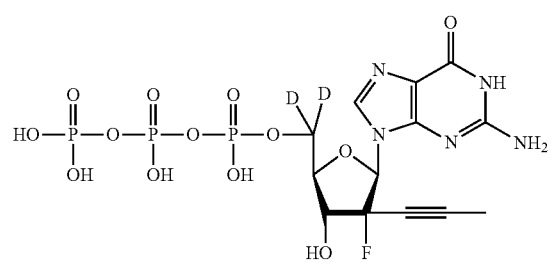
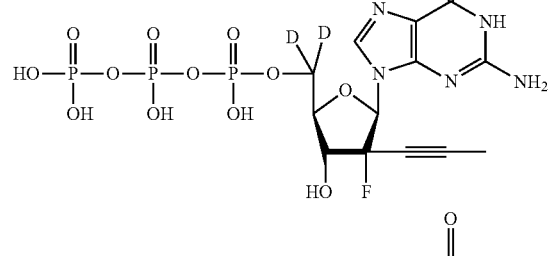
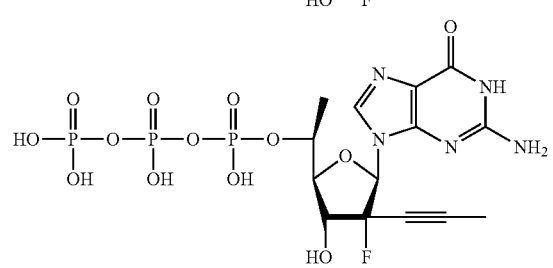
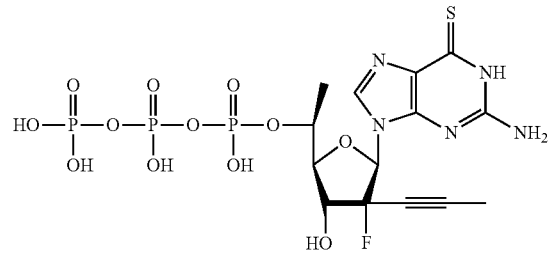
-continued
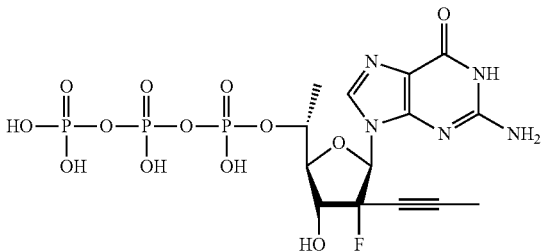
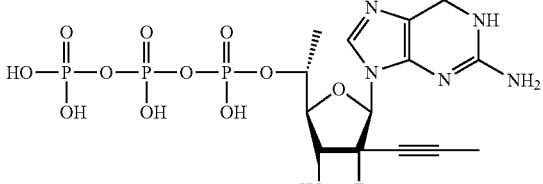
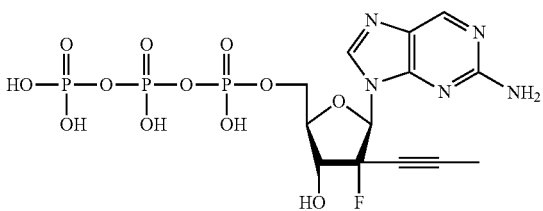
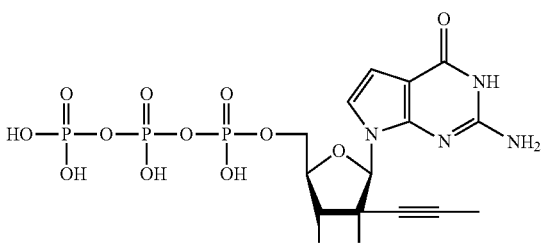
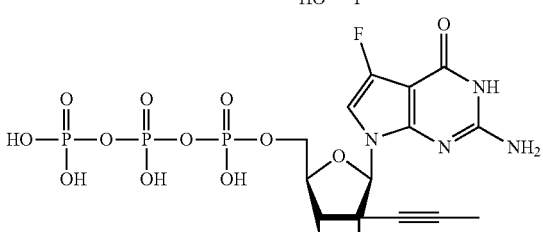
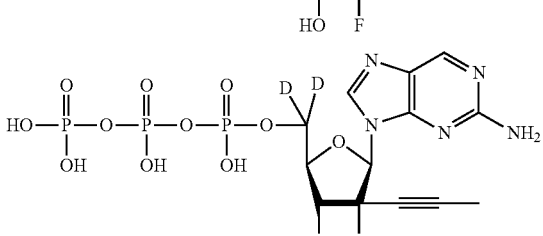
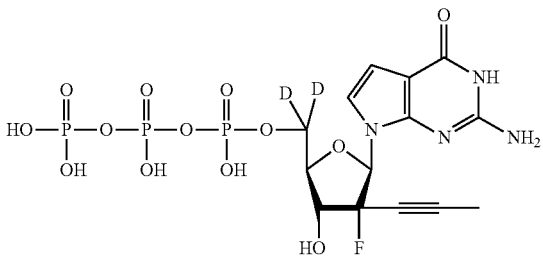

-continued
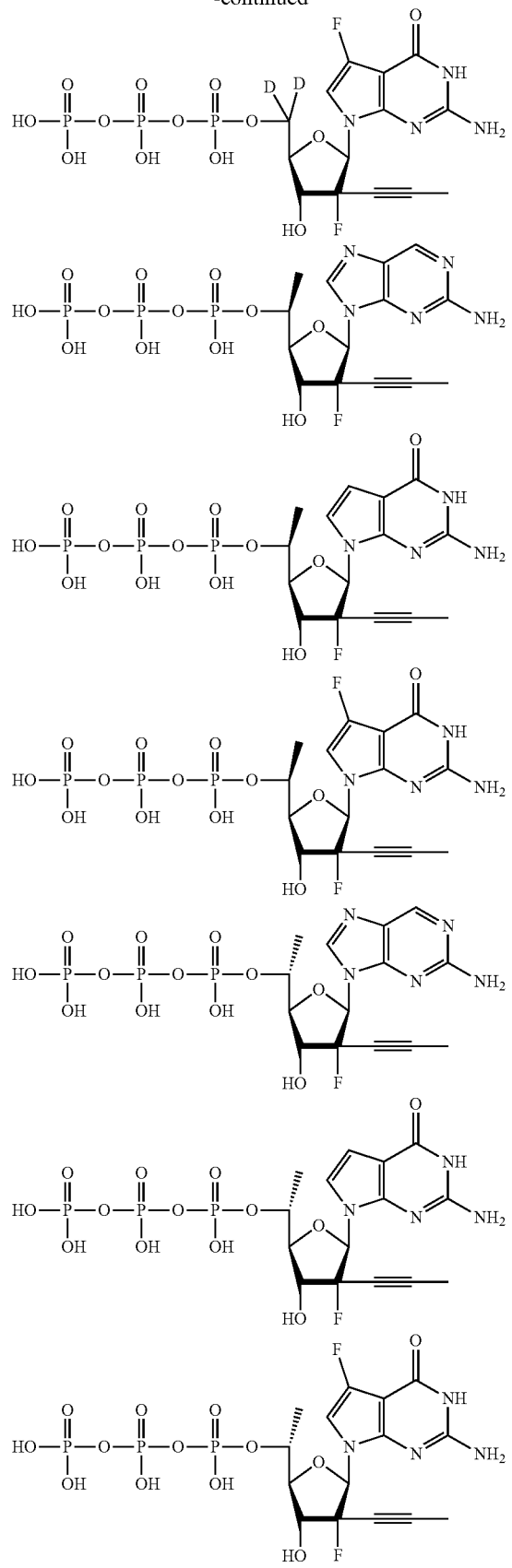
In exemplary embodiments, the compound is selected from:
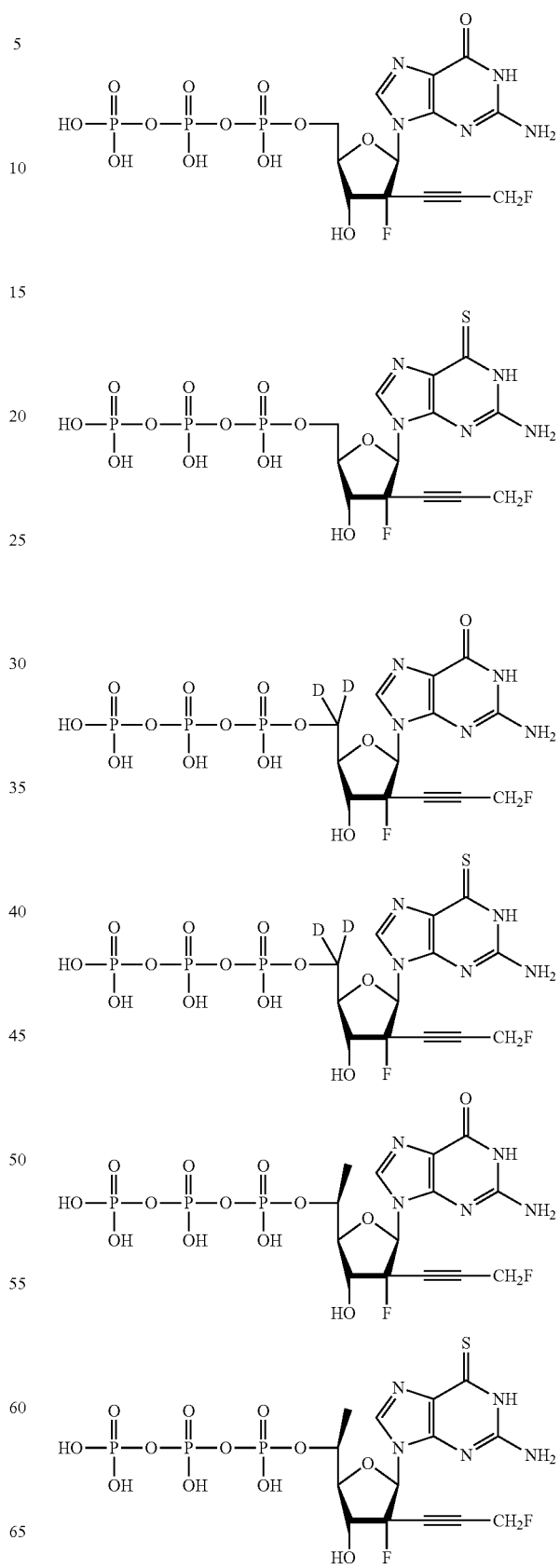

393
-continued
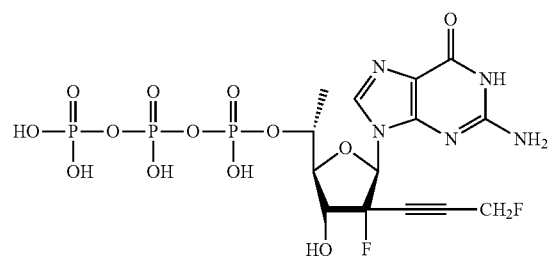
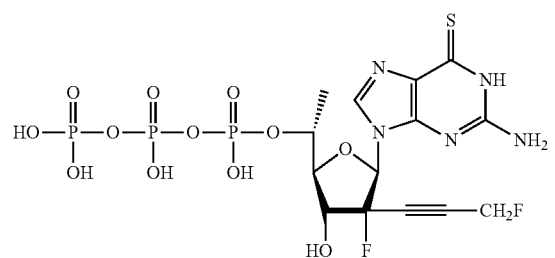
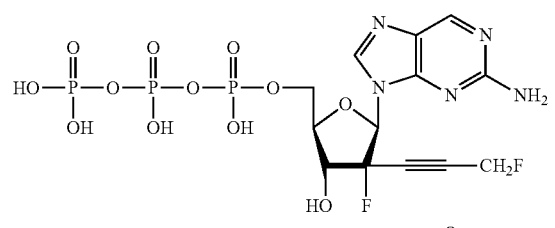
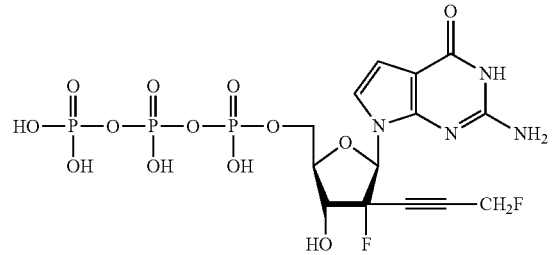
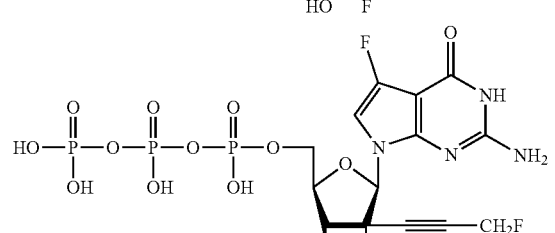
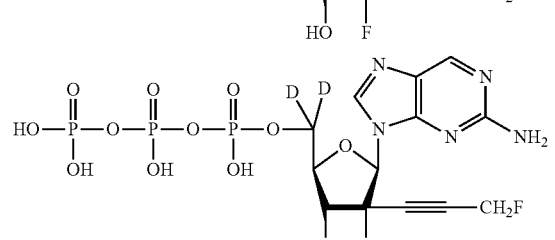
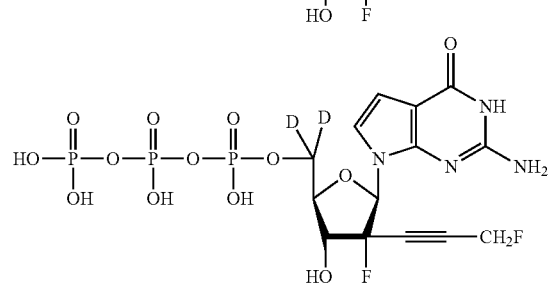
394
-continued
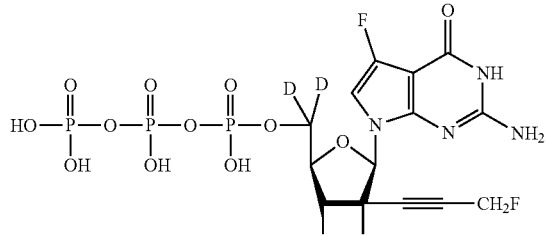
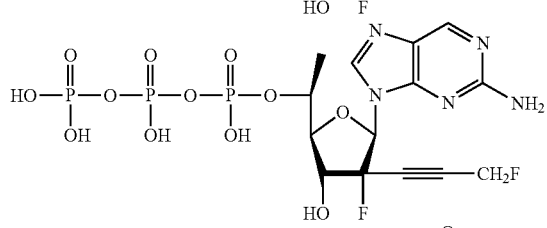
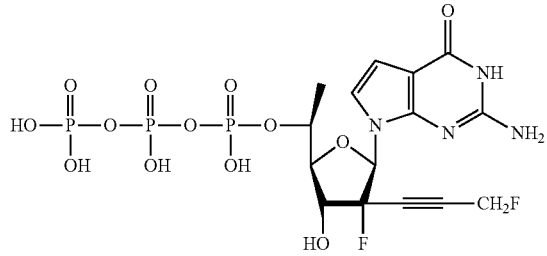
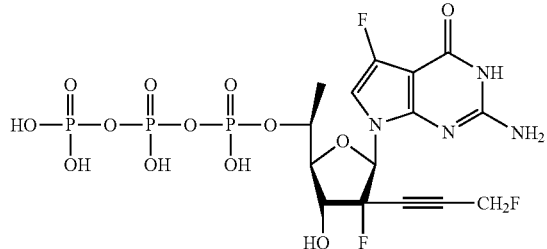
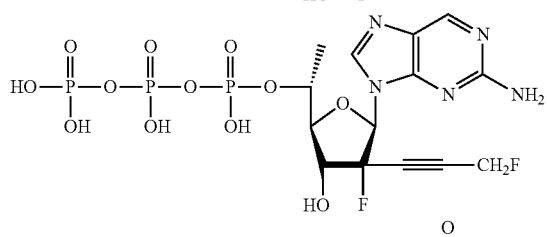
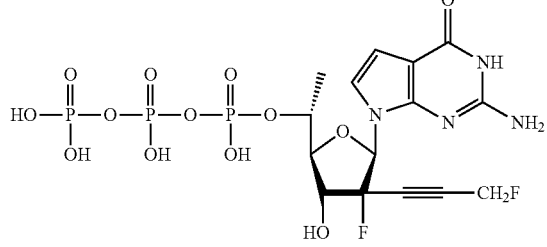
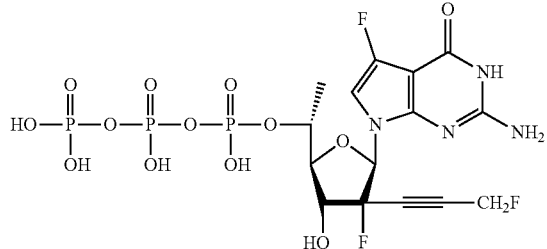

In exemplary embodiments, the compound is selected from:
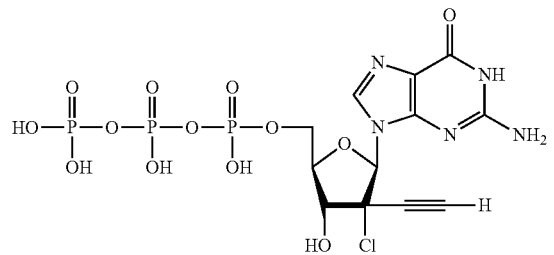
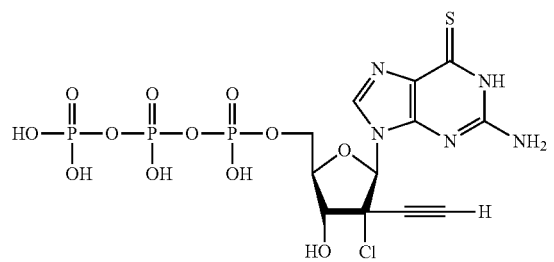
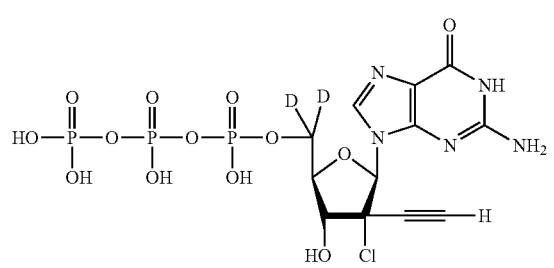
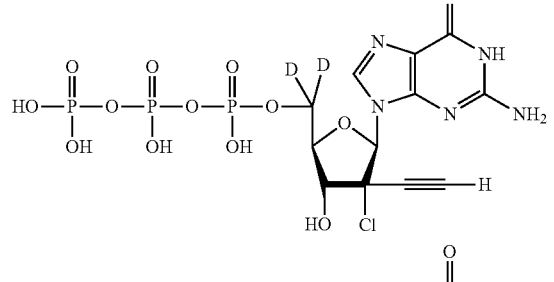
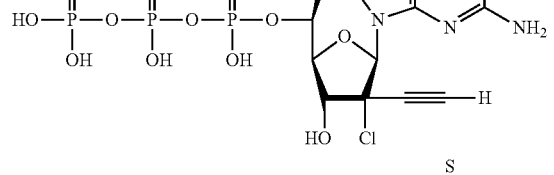
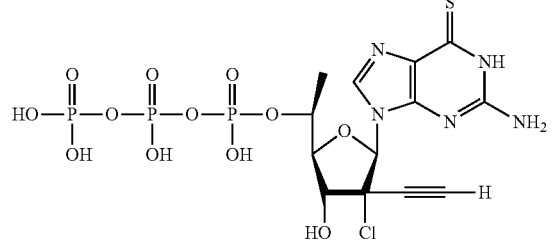
-continued
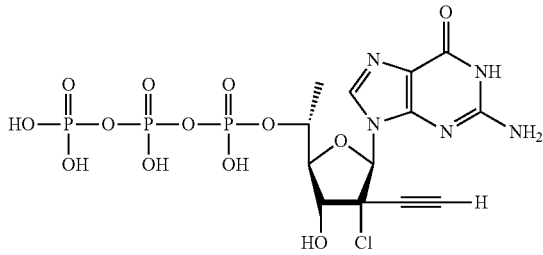
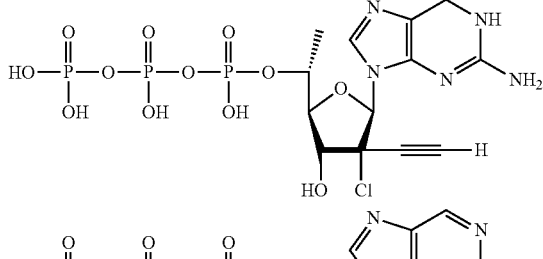
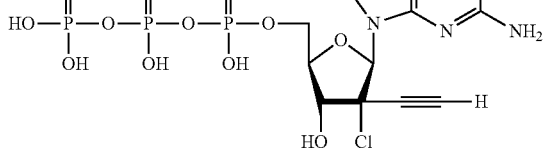
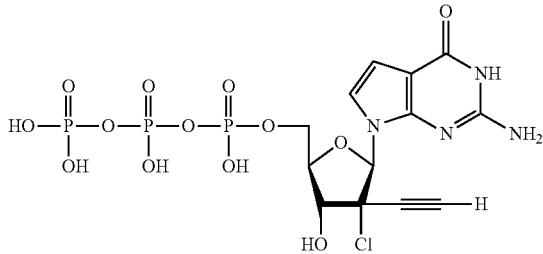
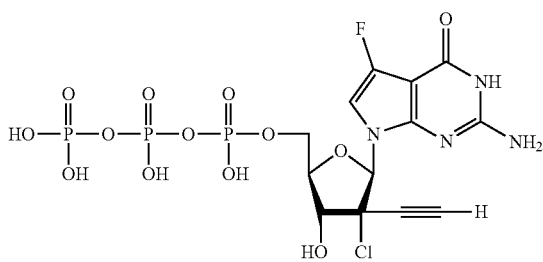
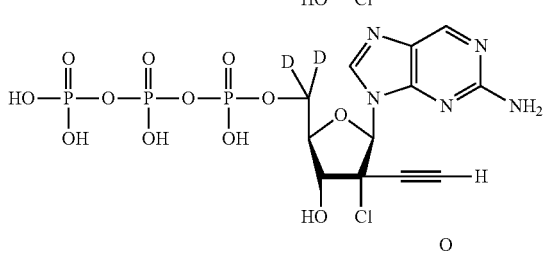
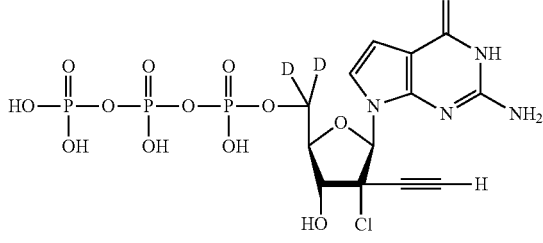

397
-continued
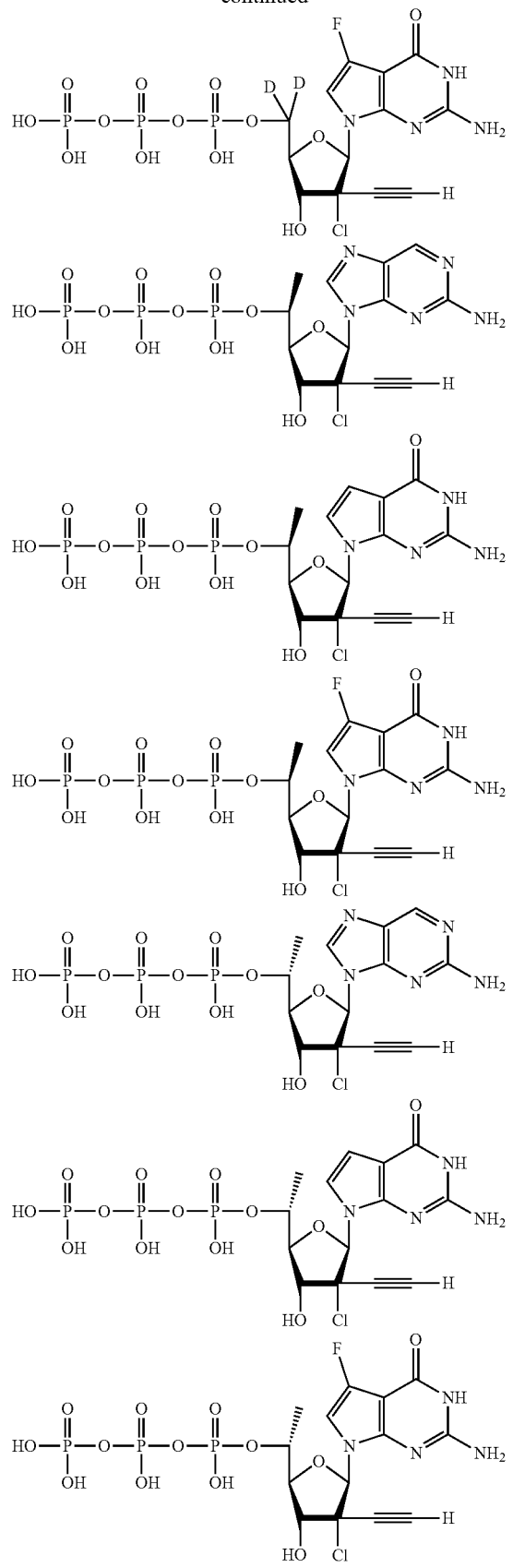
398
In exemplary embodiments, the compound is selected from:
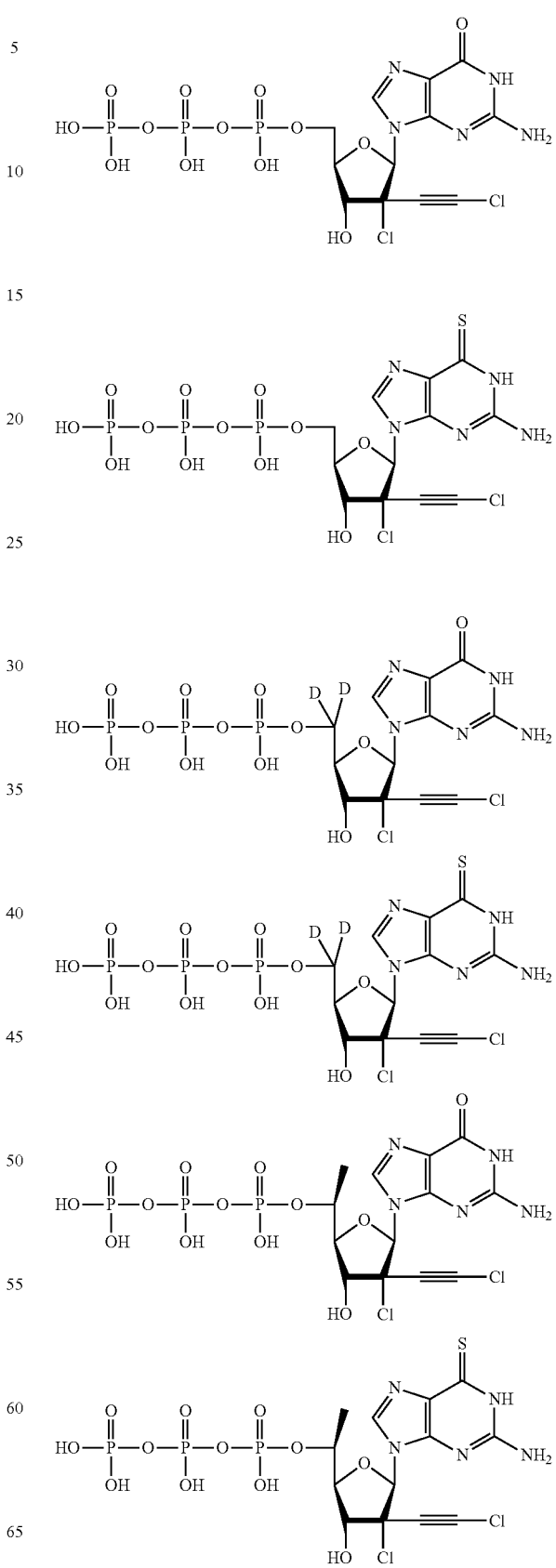

399
-continued
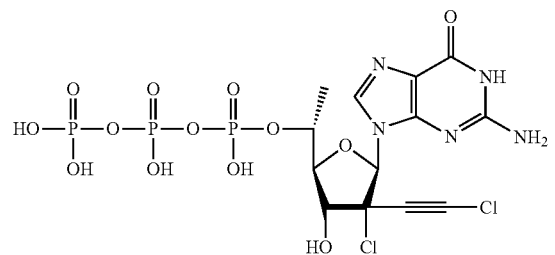
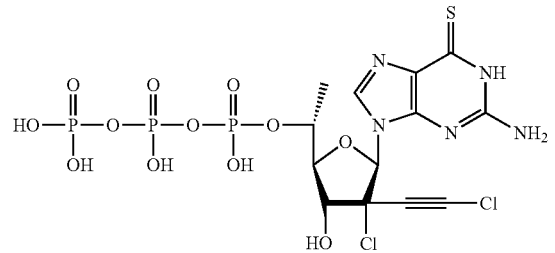
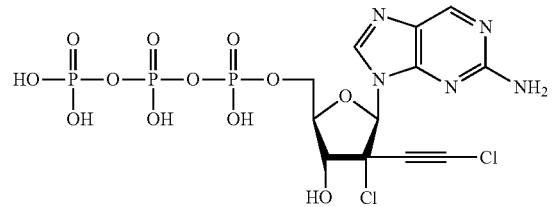
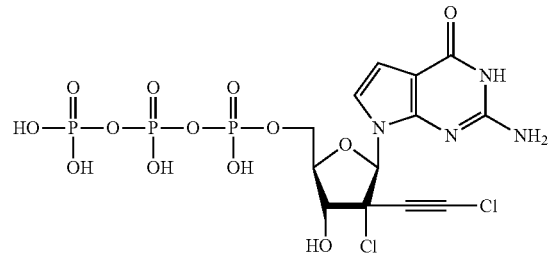
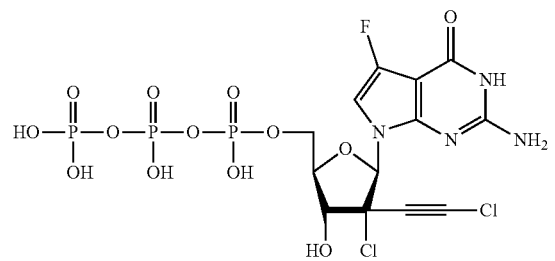
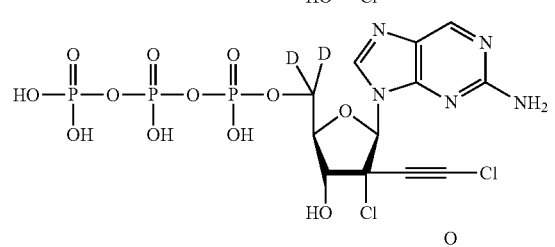
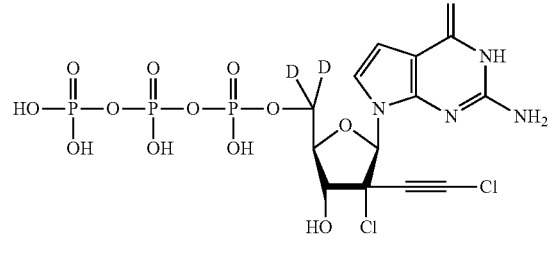
400
-continued
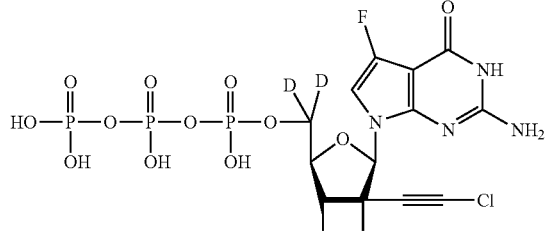
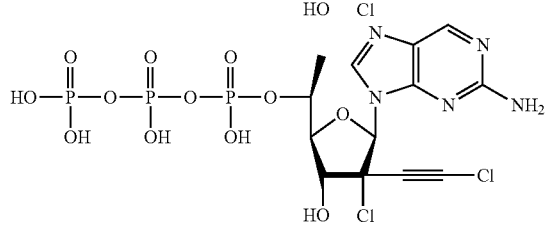
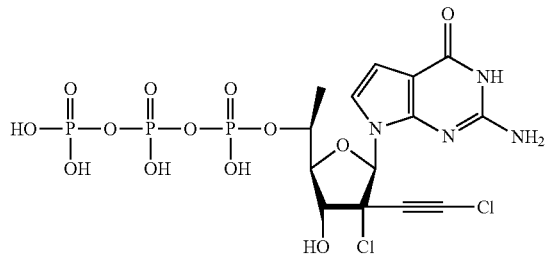
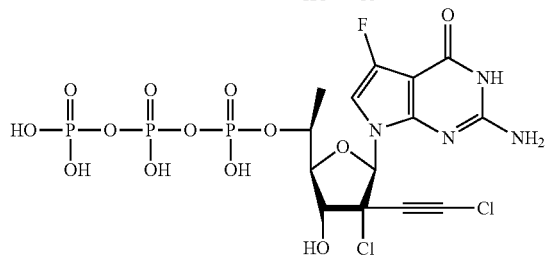
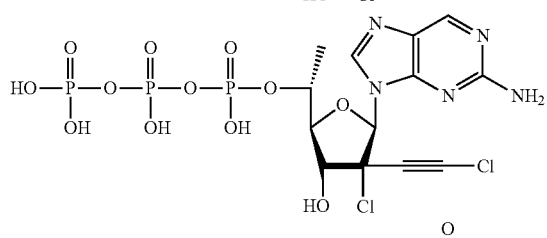
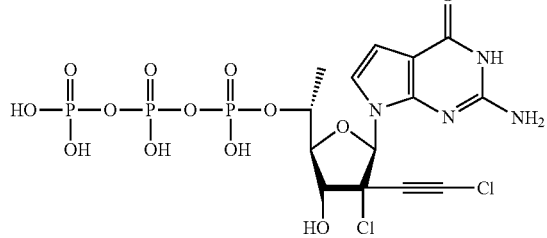
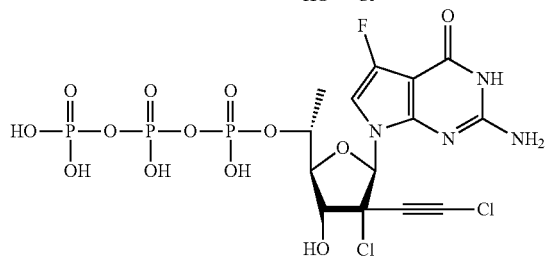

In exemplary embodiments, the compound is selected from:
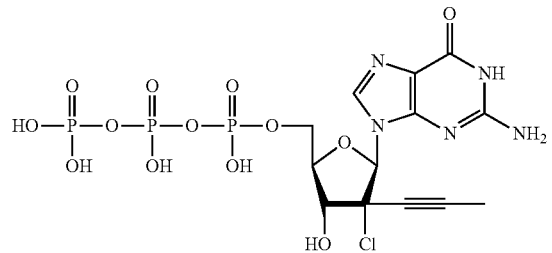
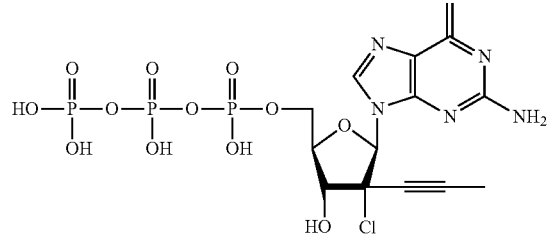
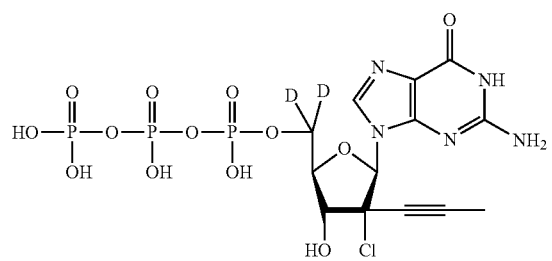
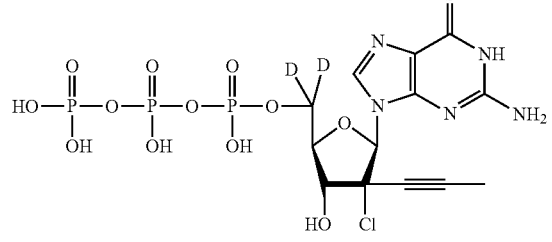
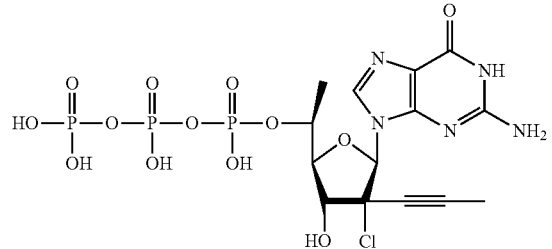
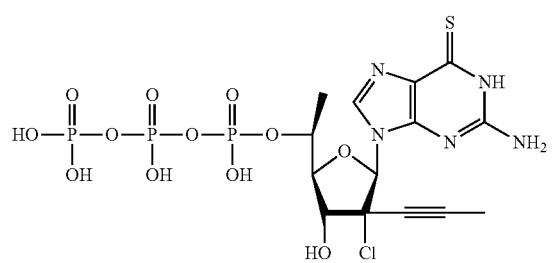
-continued
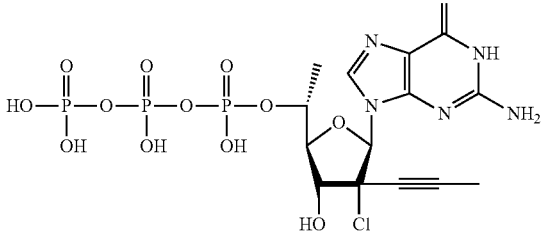
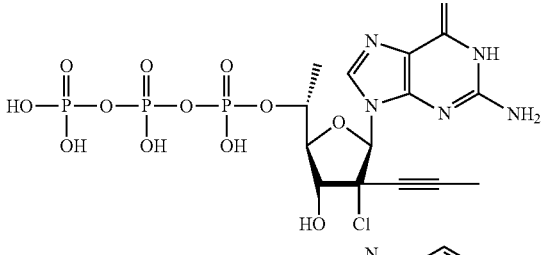
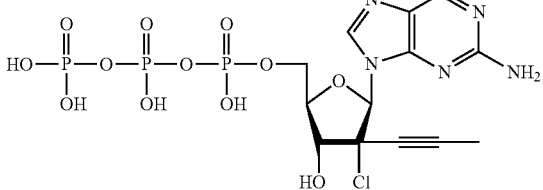
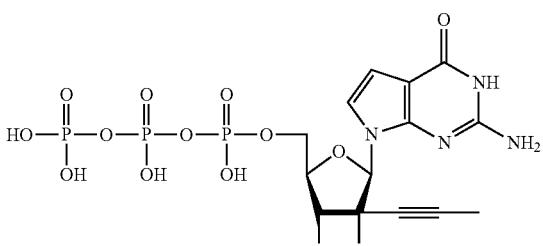
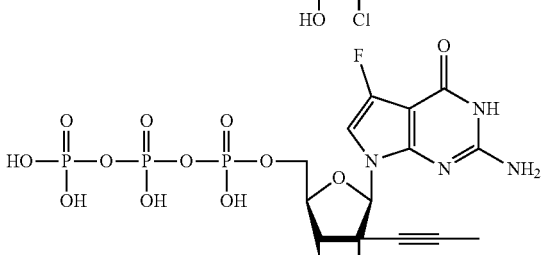
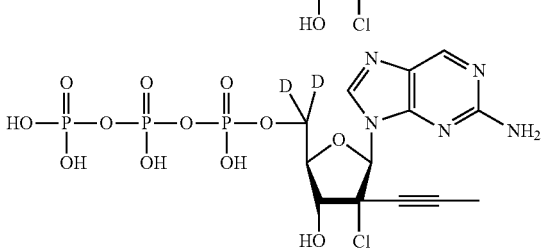
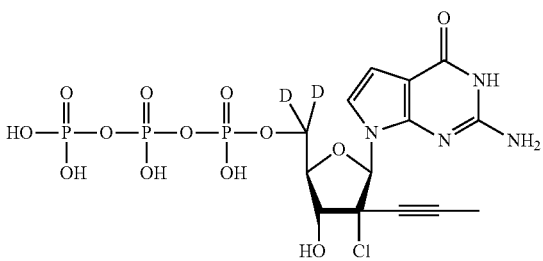

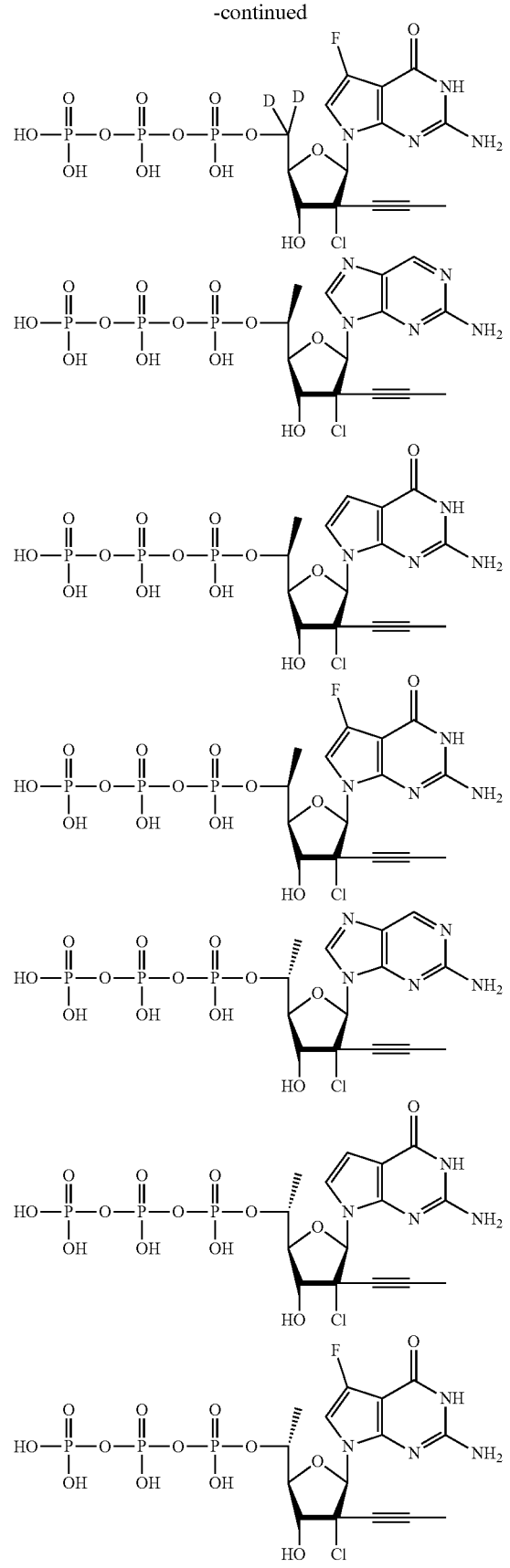
In exemplary embodiments, the compound is selected from:
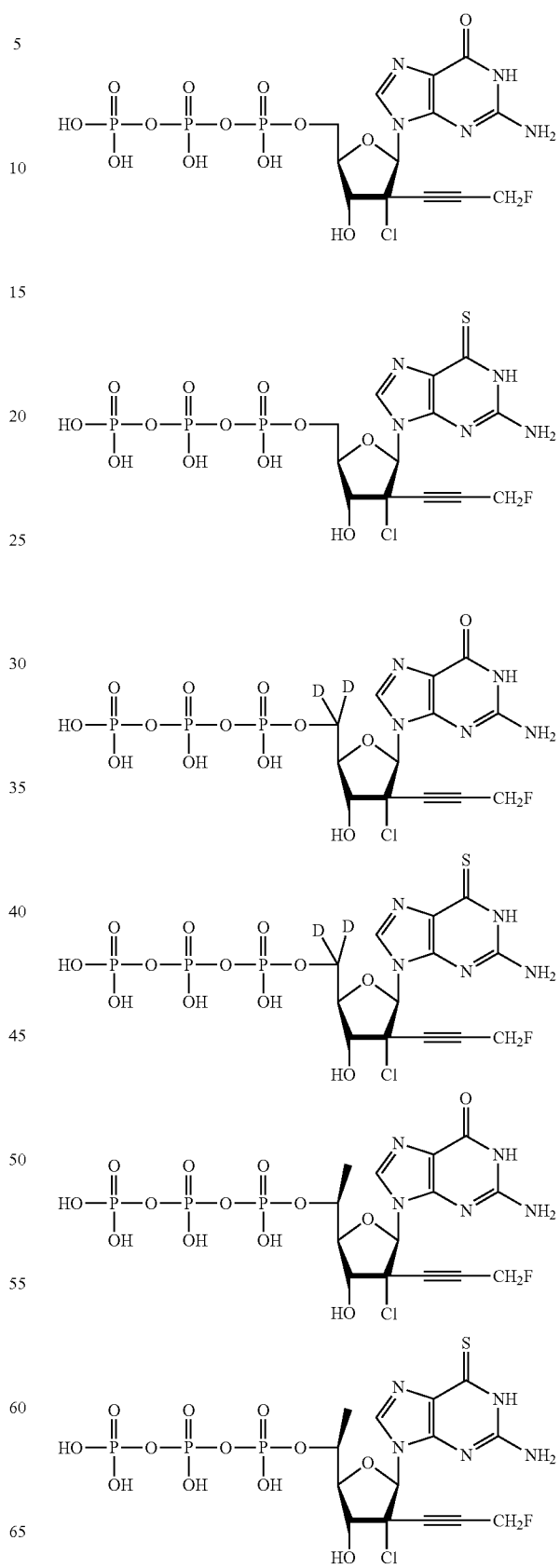

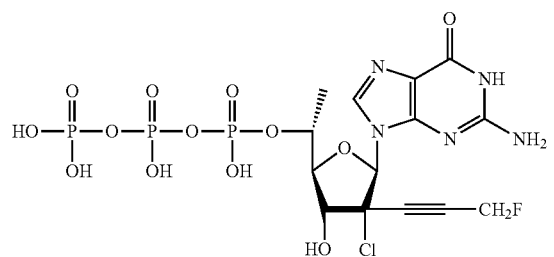
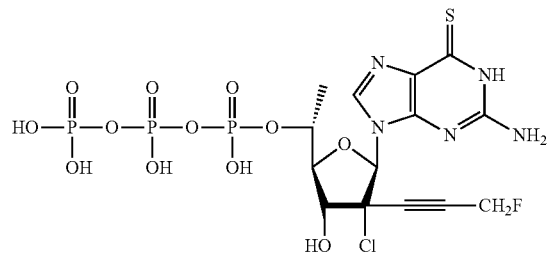
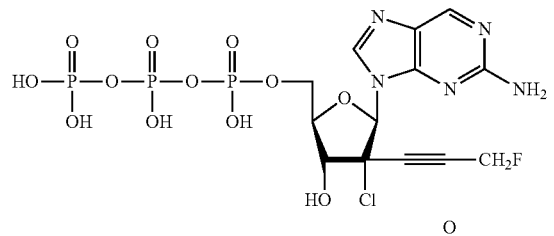
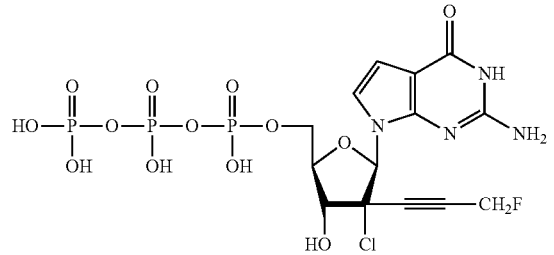
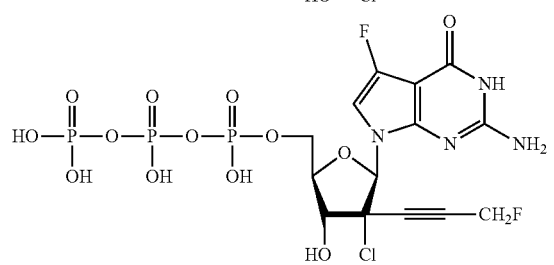
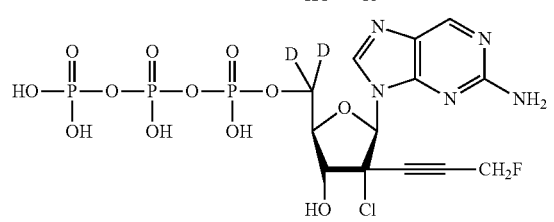
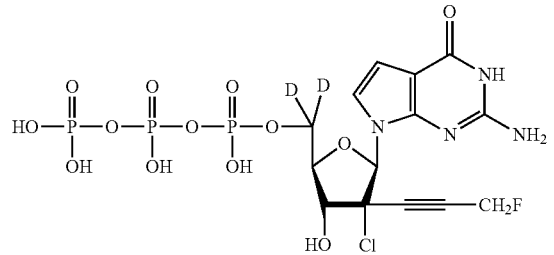
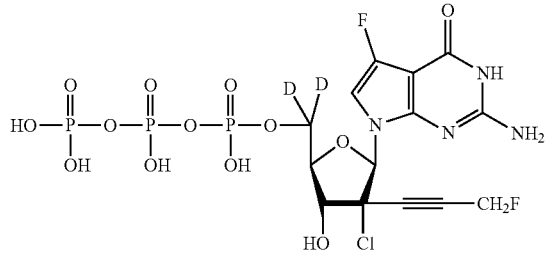
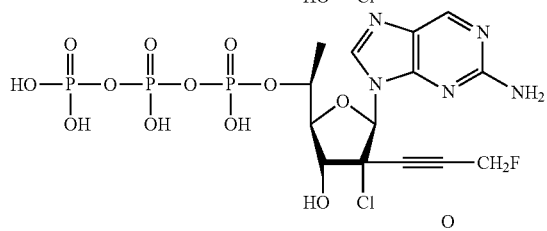
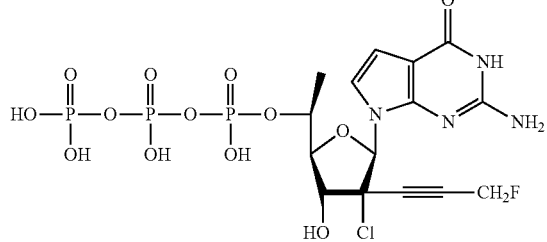
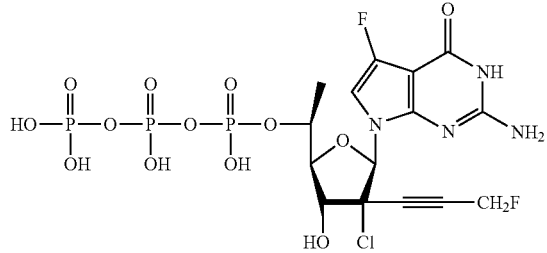
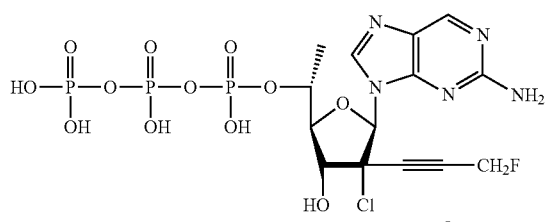
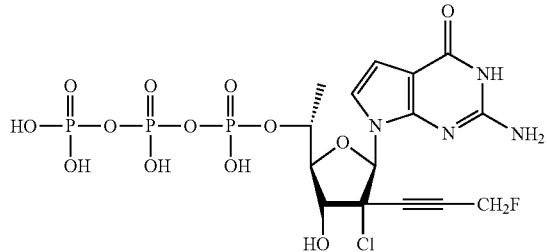
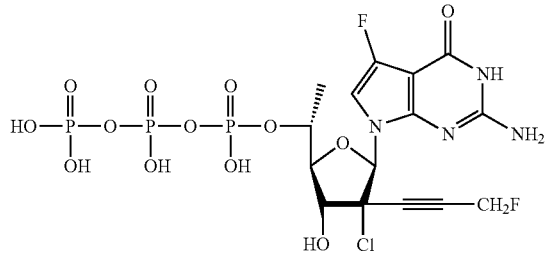

In exemplary embodiments, the compound is selected from:
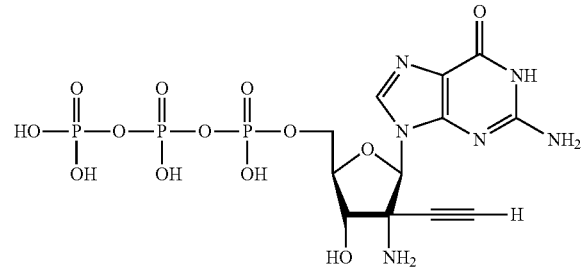
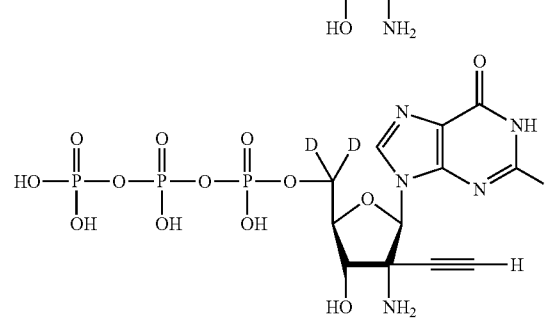
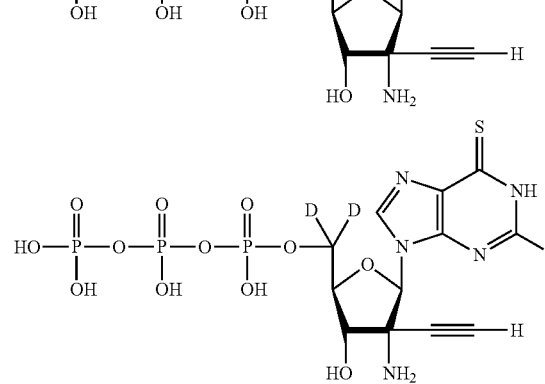
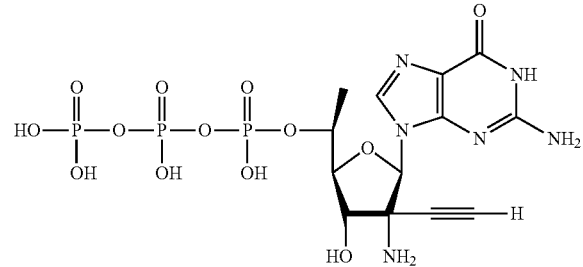
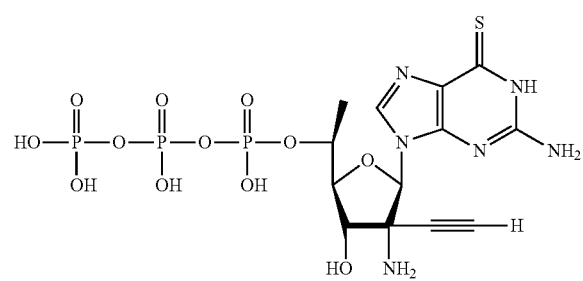
-continued
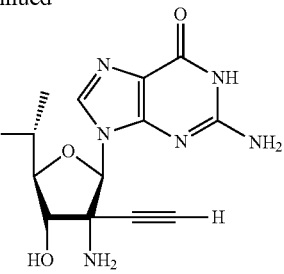
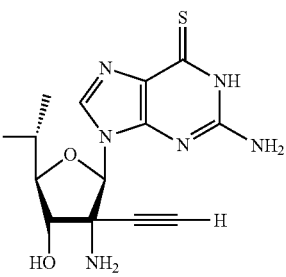
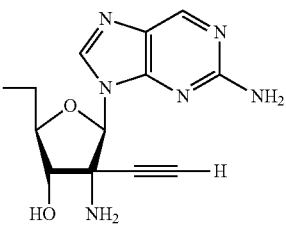
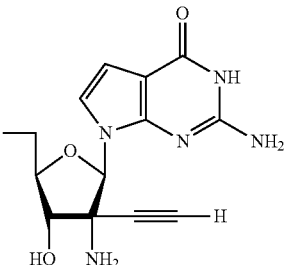
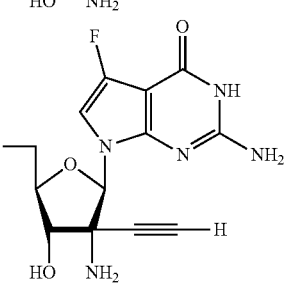
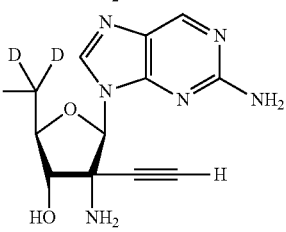

409
-continued
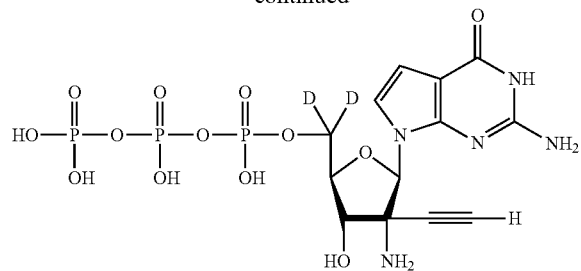
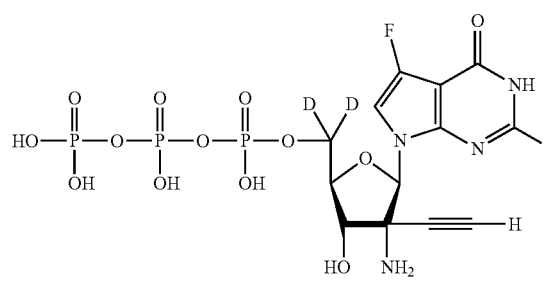
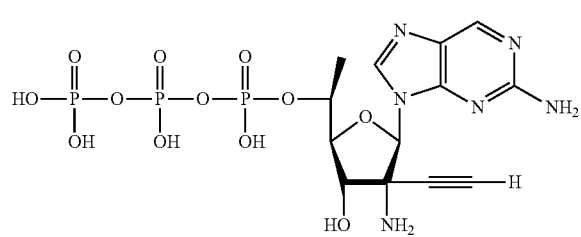
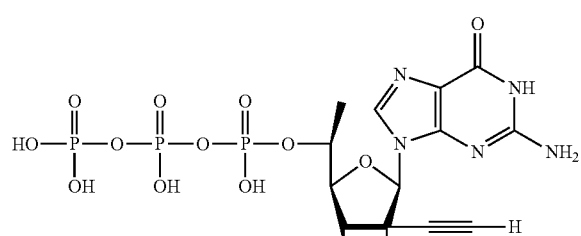
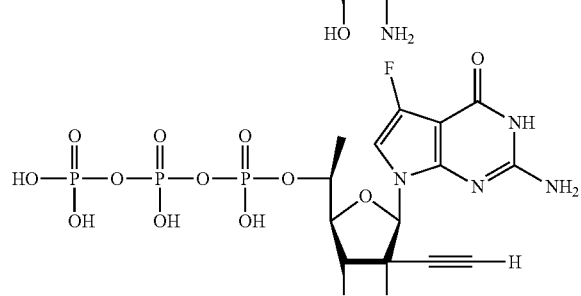
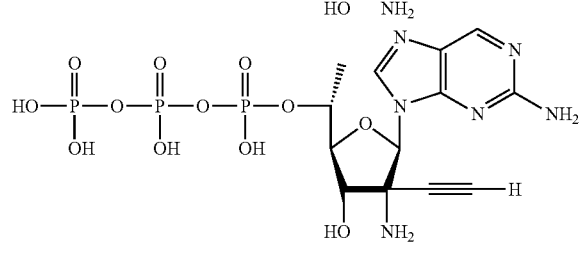
410
-continued
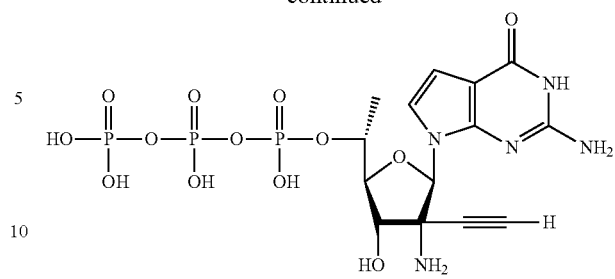
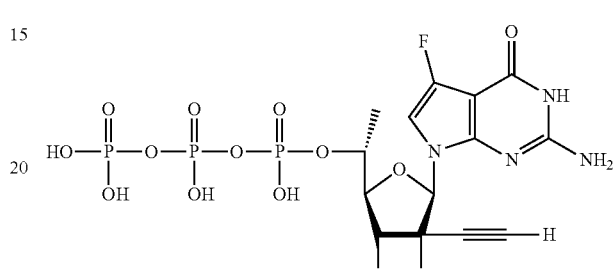
In exemplary embodiments, the compound is selected from:
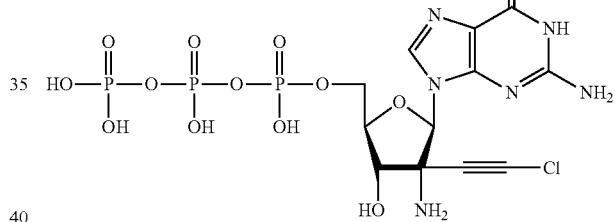
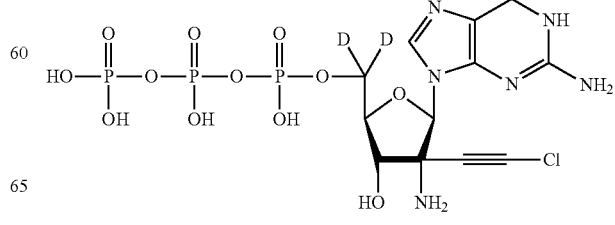
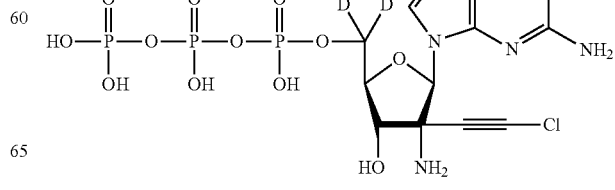

-continued
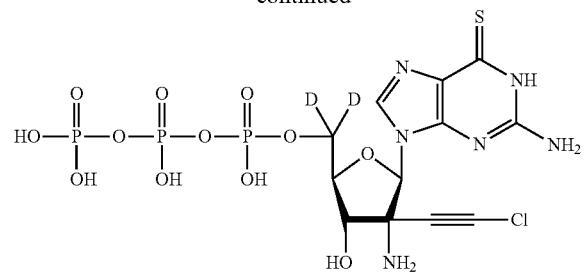
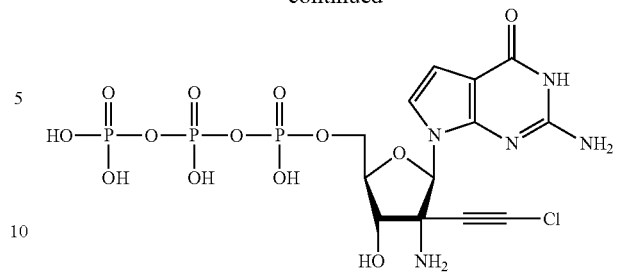
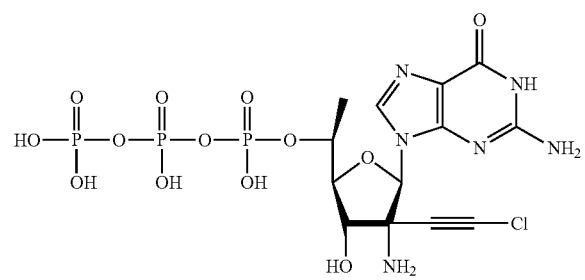
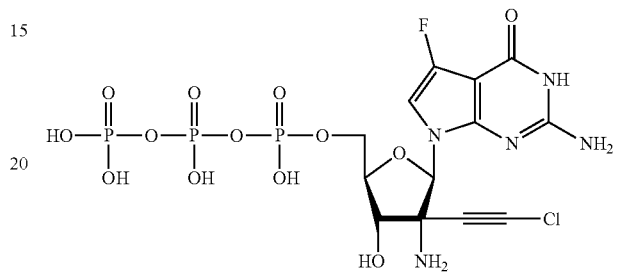
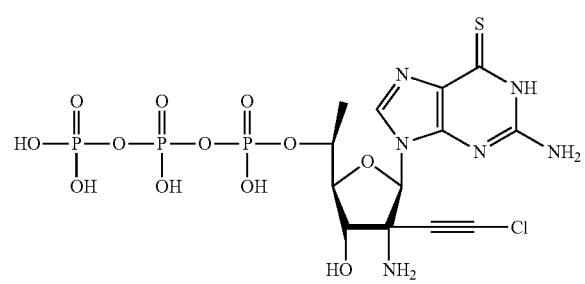
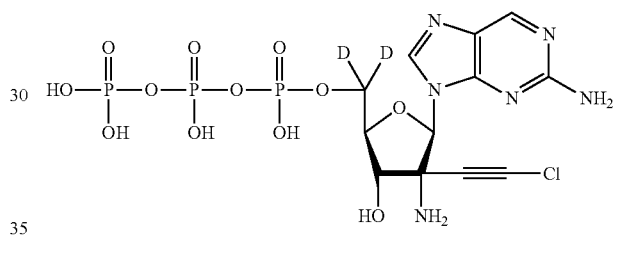
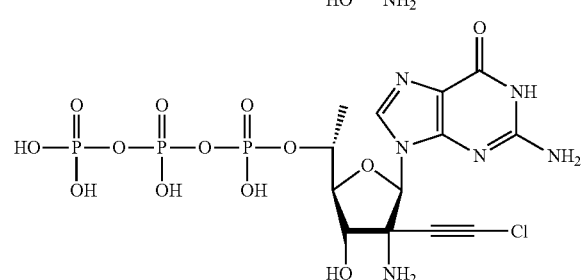
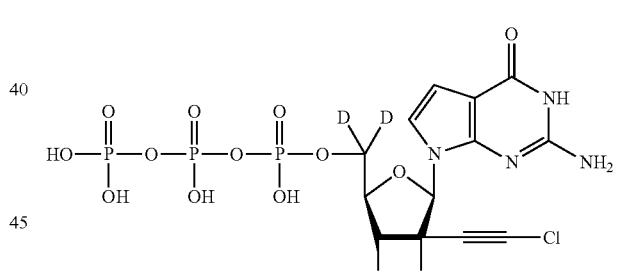
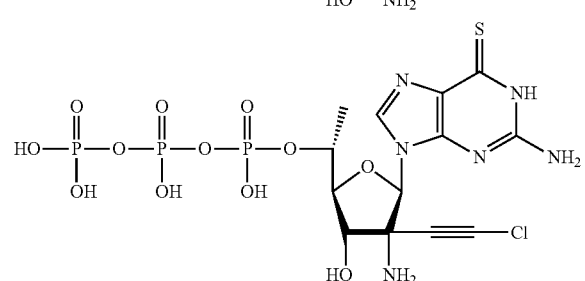
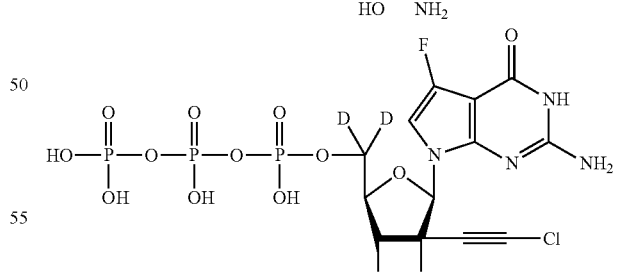
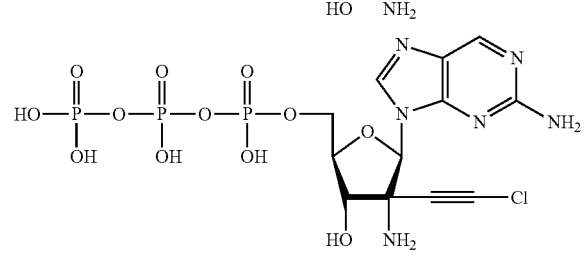
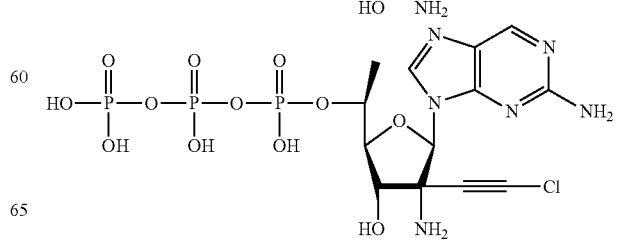

413
-continued
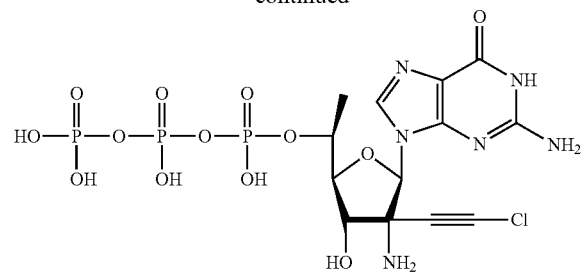
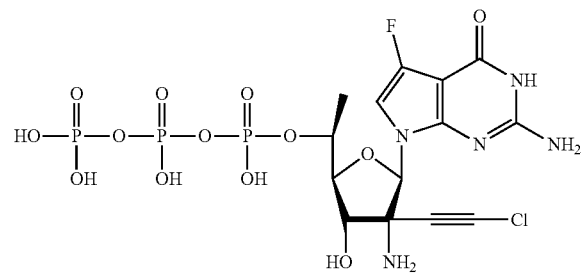
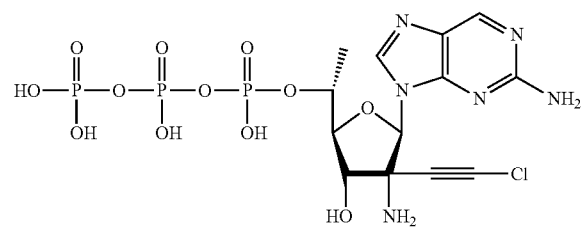
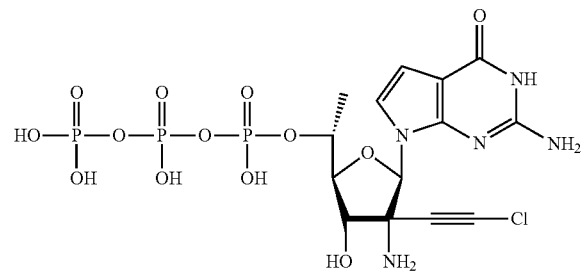
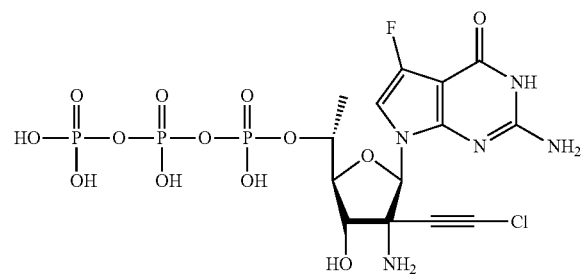
In exemplary embodiments, the compound is selected from:
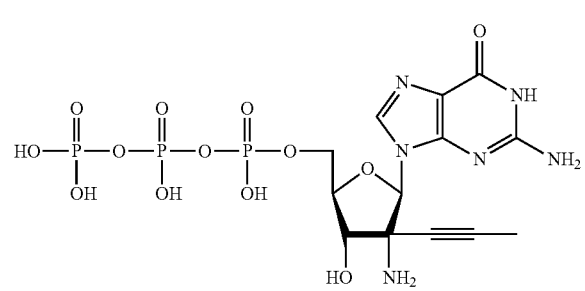
414
-continued
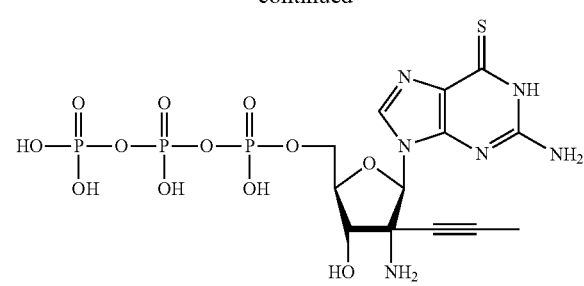
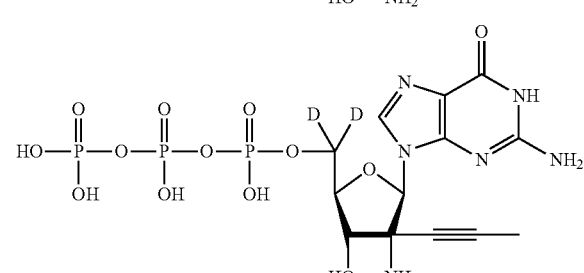
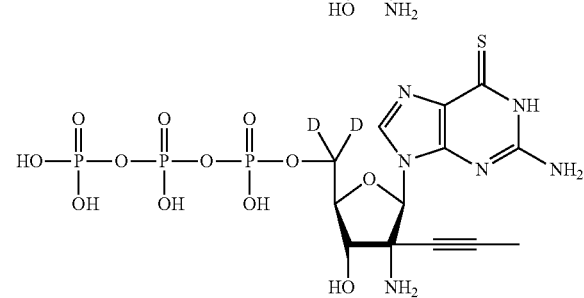
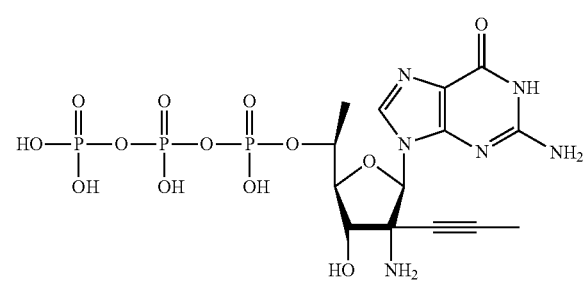
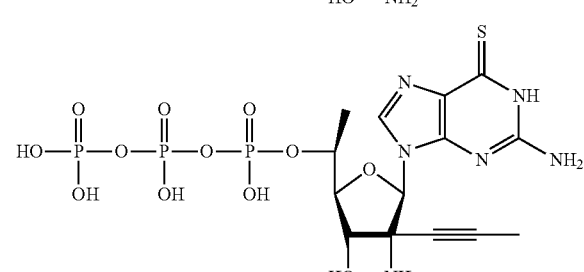
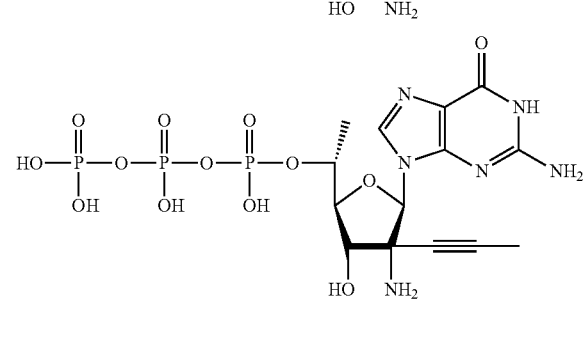

415
416
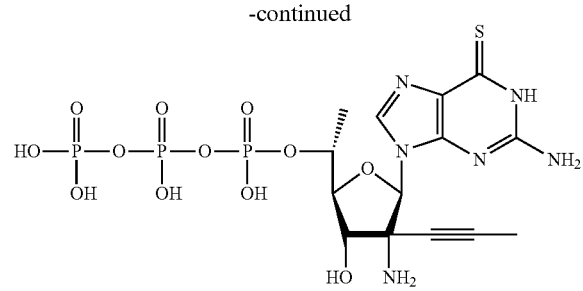
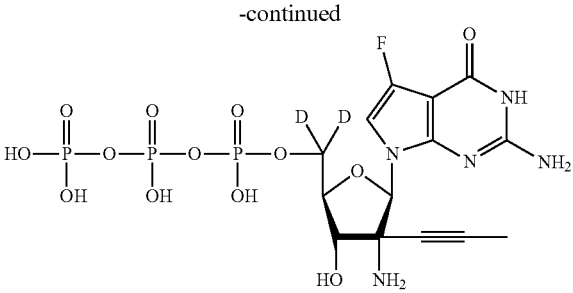
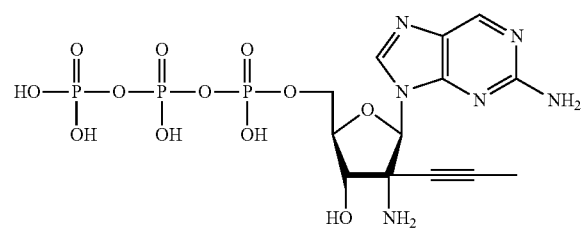
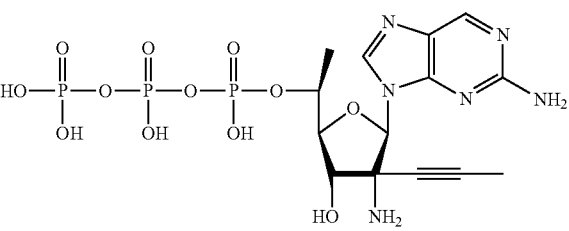
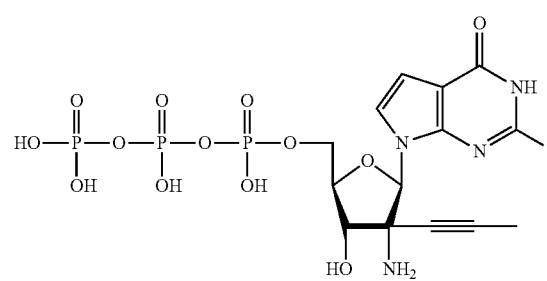
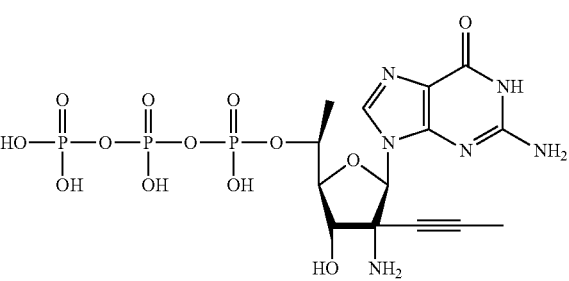
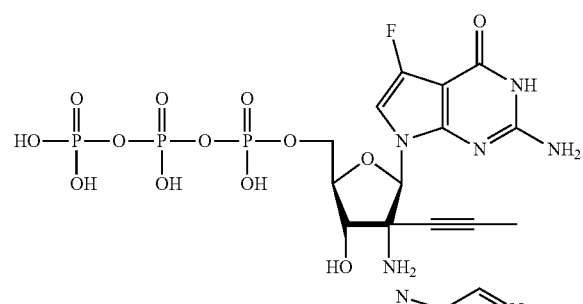
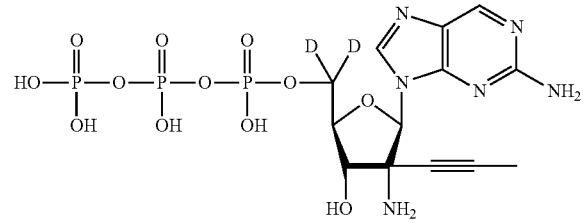
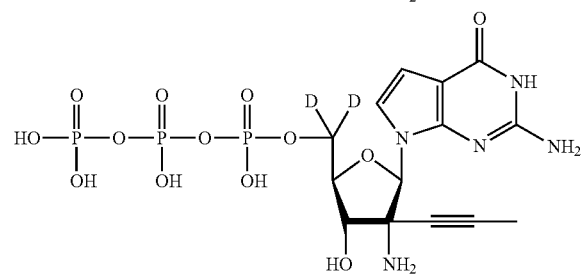

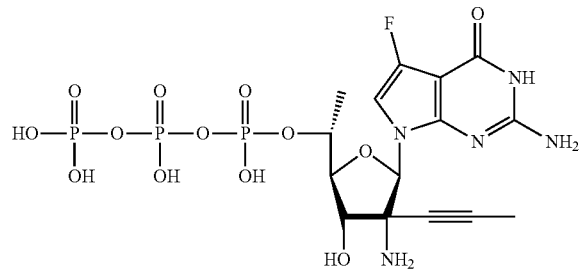
In exemplary embodiments, the compound is selected from:
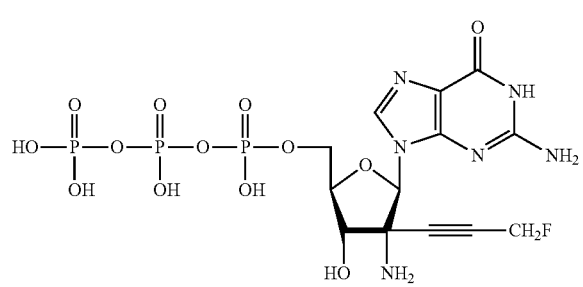
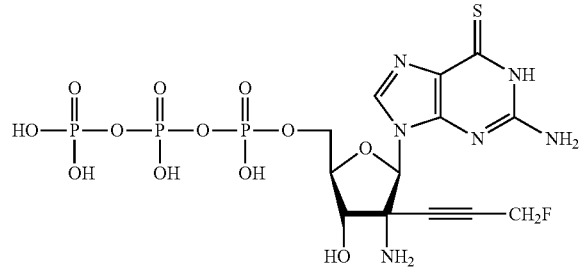
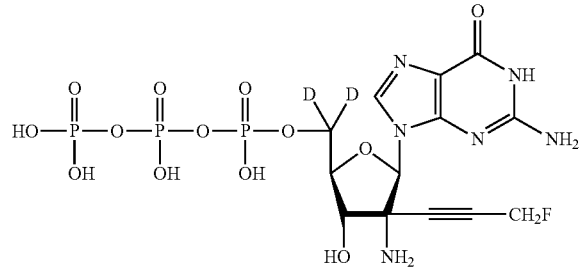
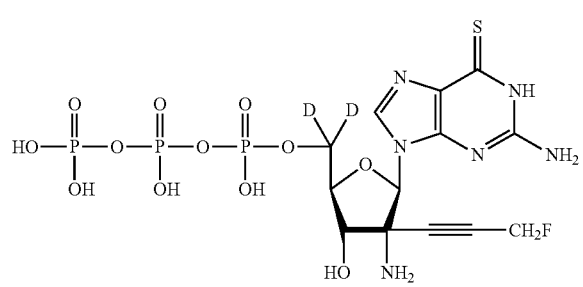
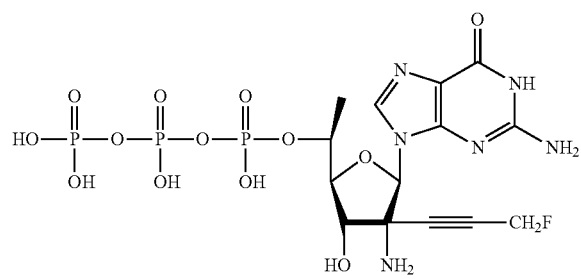
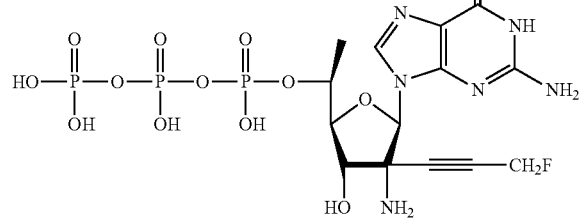
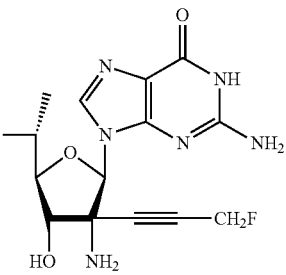
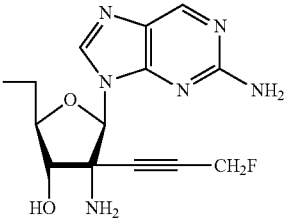
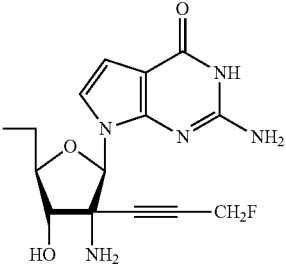

419
-continued
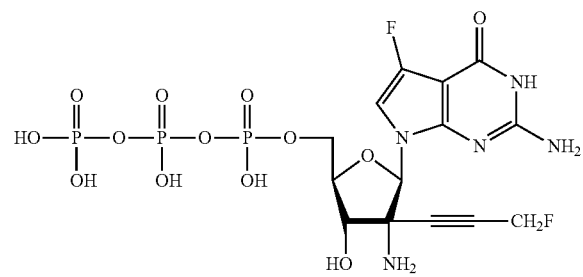
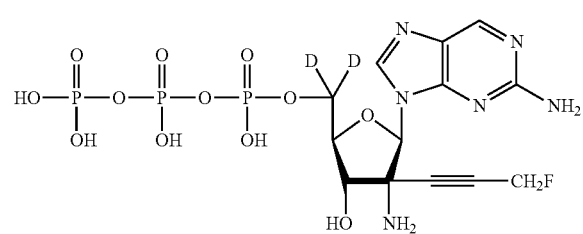
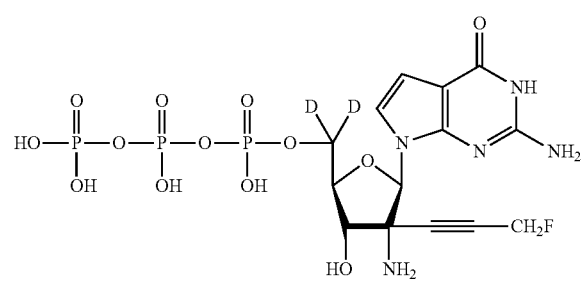
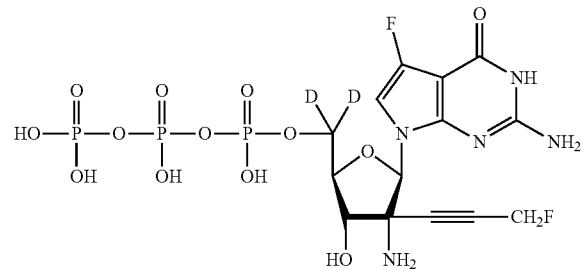
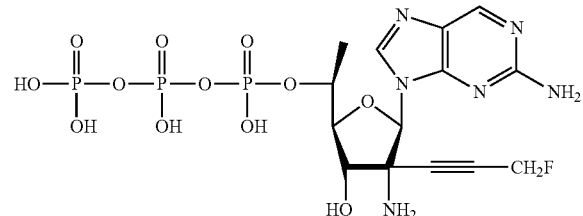
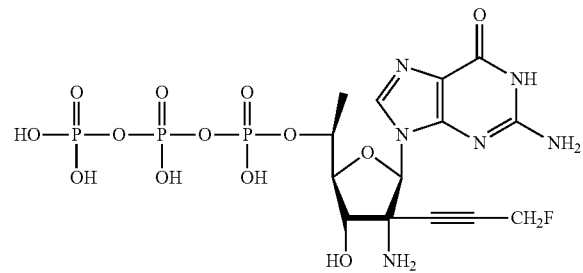
420
-continued
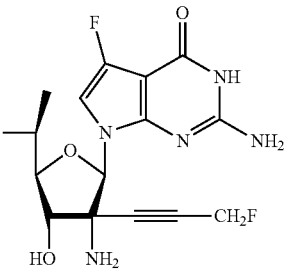
In exemplary embodiments, the compound is selected from:
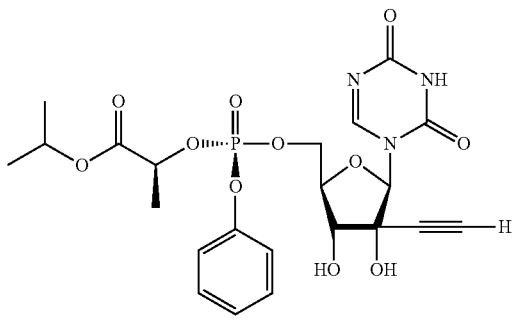

421
-continued
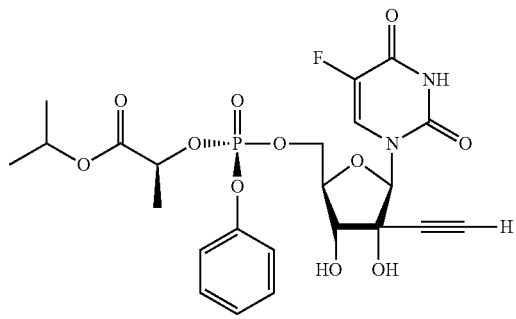
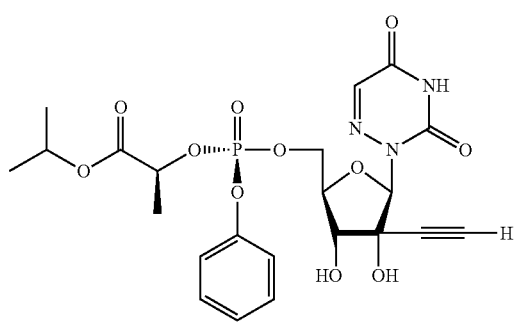
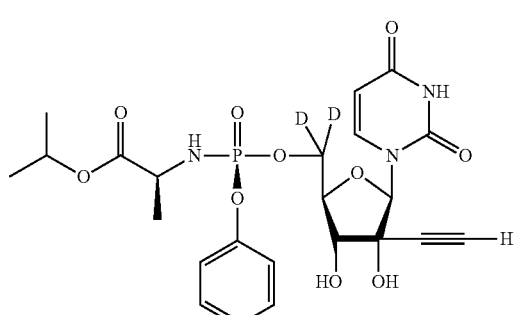
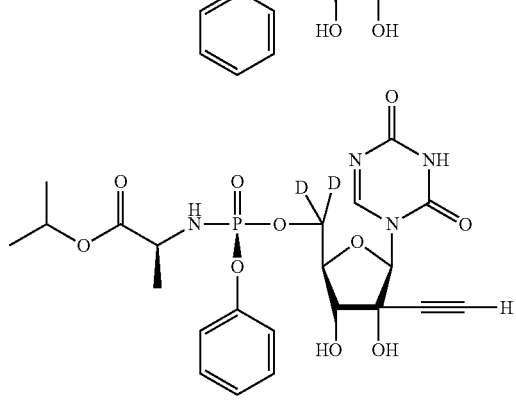
422
-continued
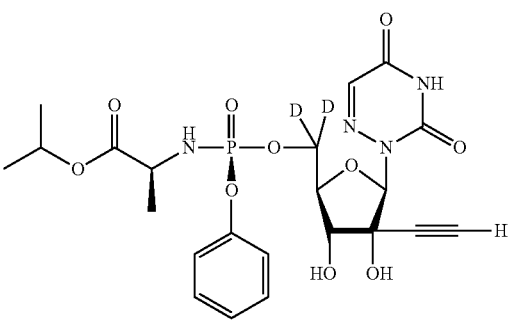
In exemplary embodiments, the compound is selected from:
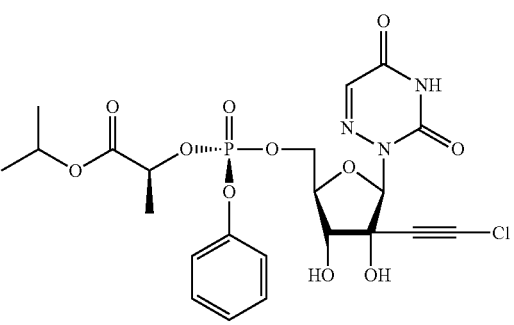
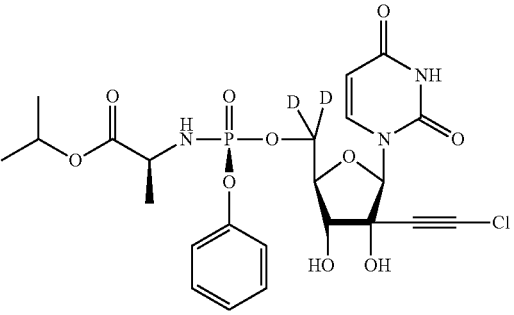
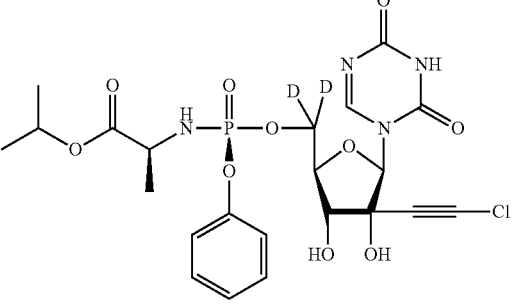
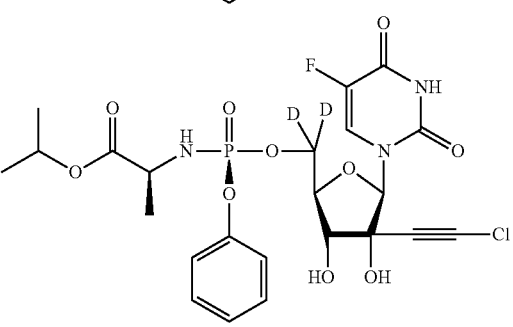

423
-continued
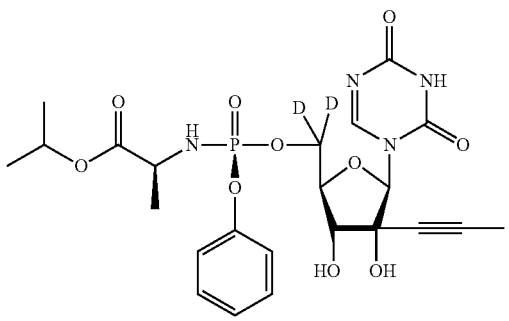
In exemplary embodiments, the compound is selected from:
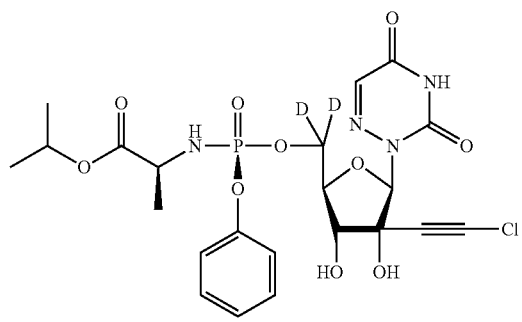
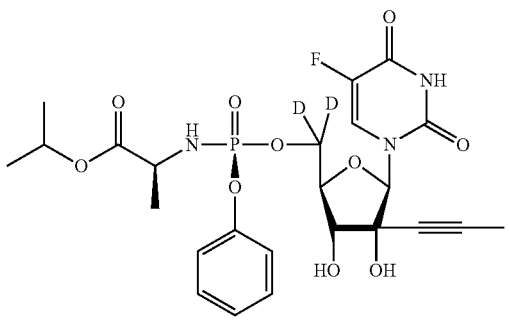
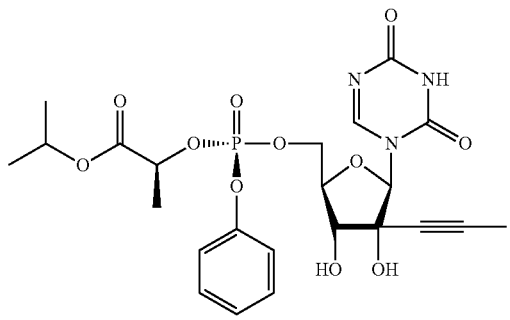
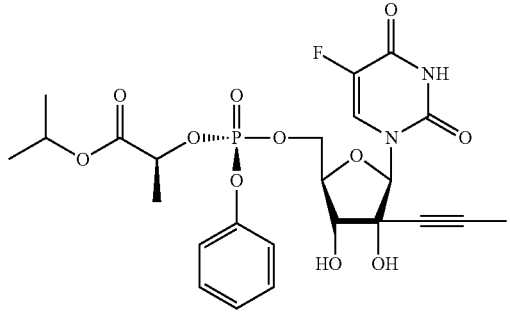
In exemplary embodiments, the compound is selected from:
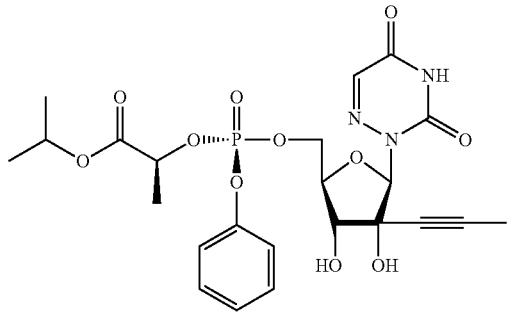
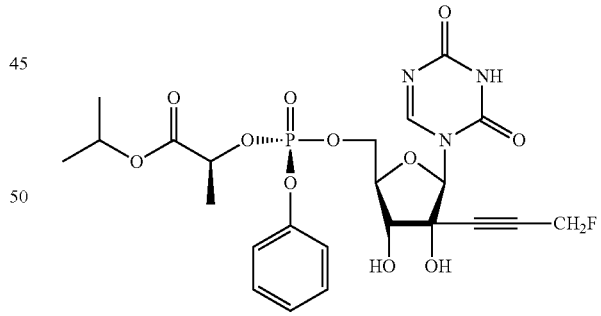
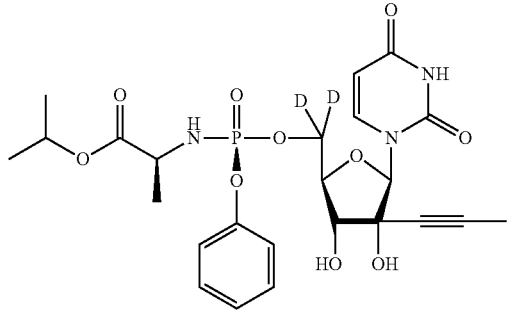
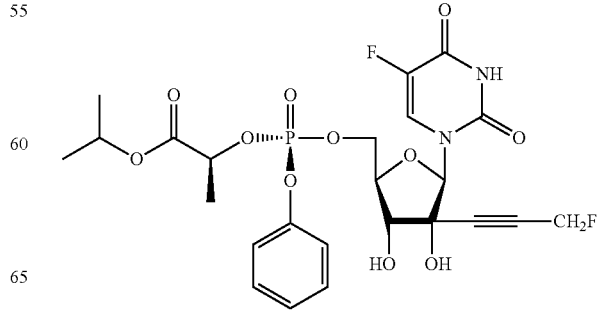

-continued
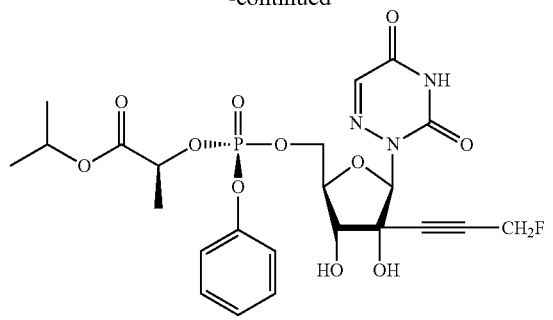
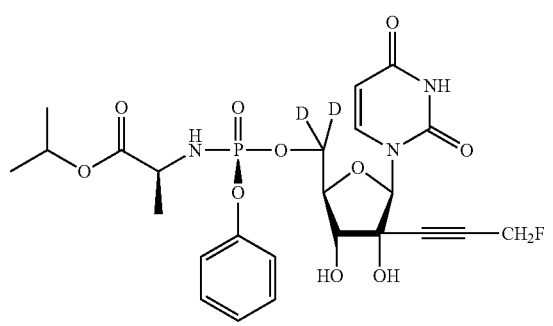
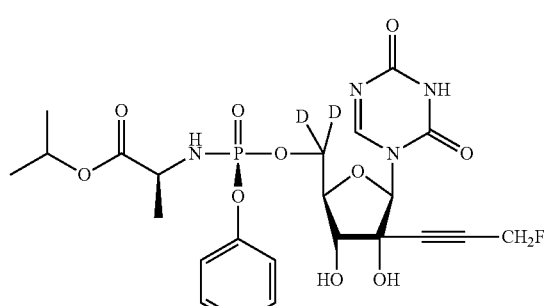
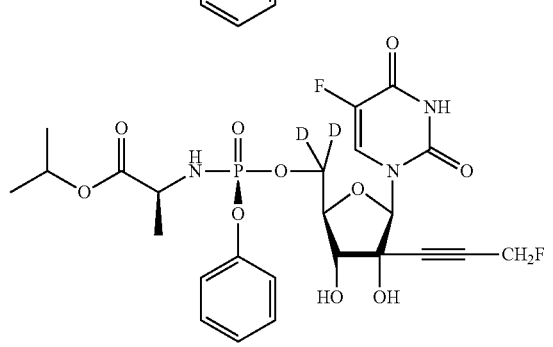
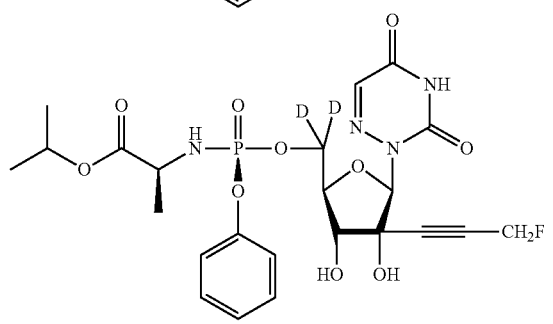
In exemplary embodiments, the compound is selected from:
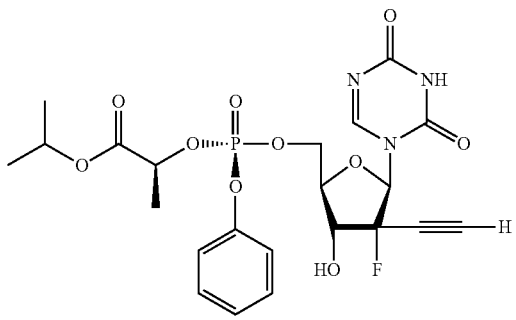
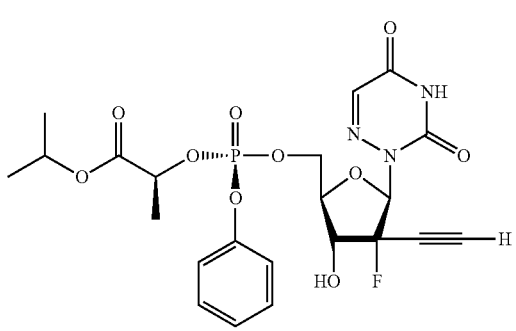
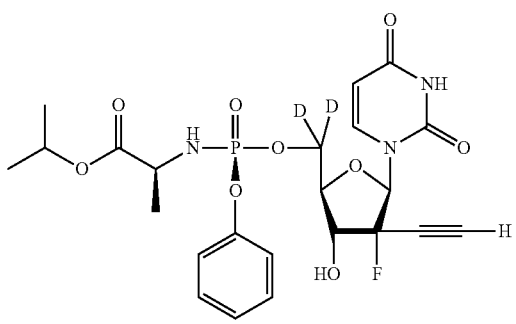
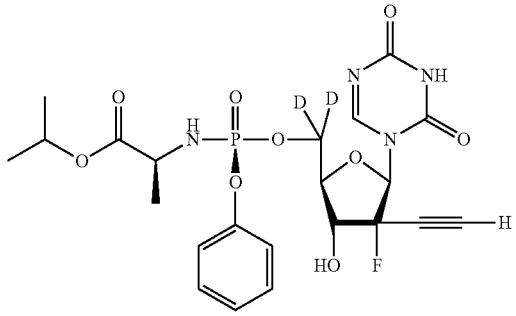
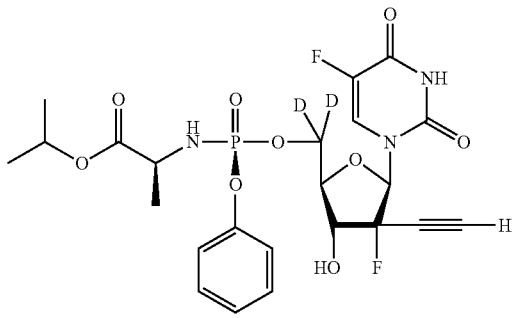

427
-continued
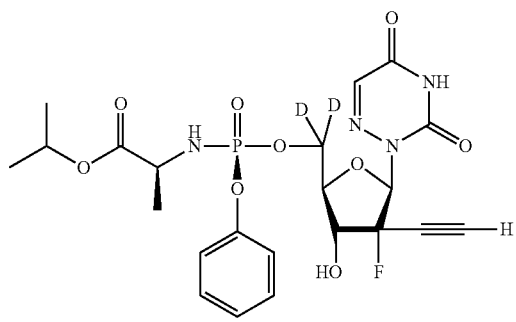
In exemplary embodiments, the compound is selected from:
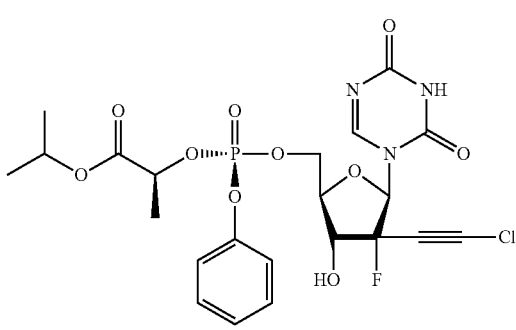
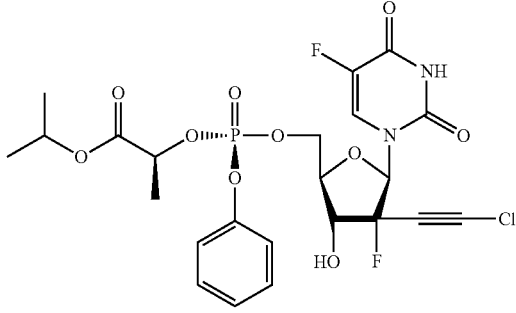
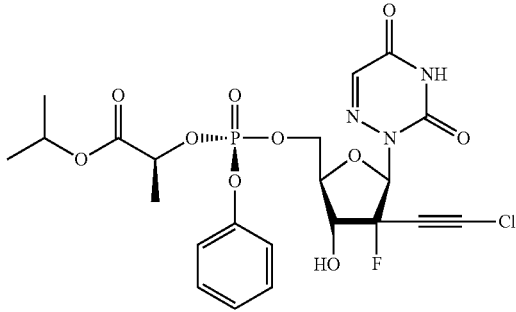
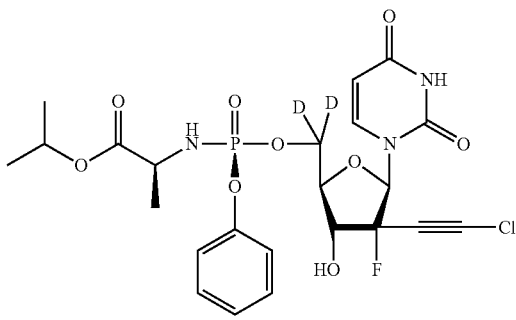
428
-continued
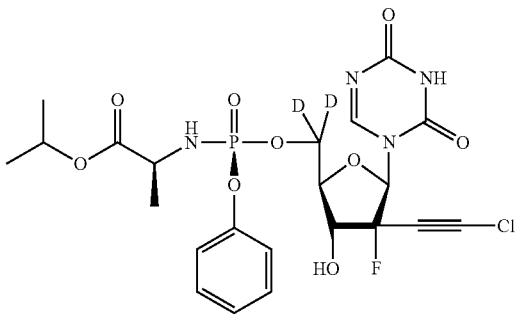
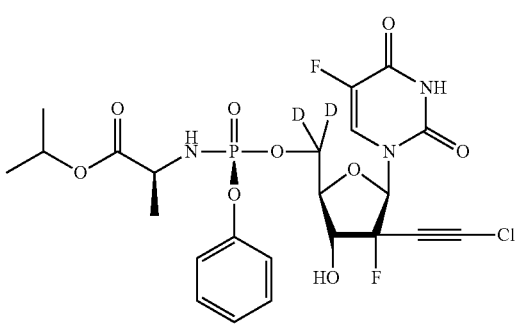
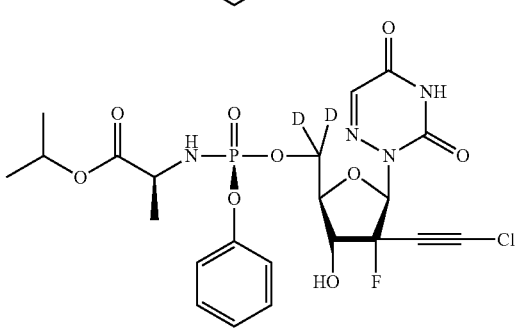
In exemplary embodiments, the compound is selected from:
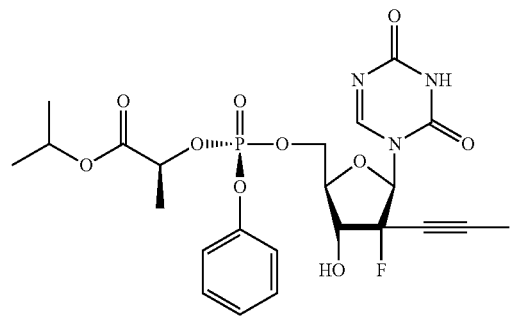
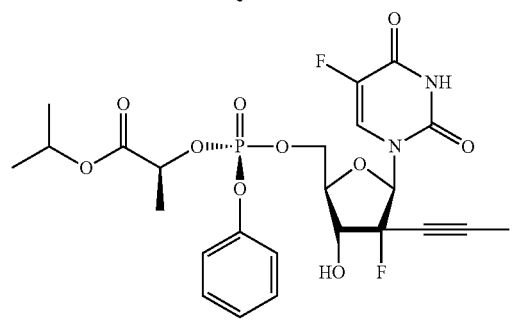

-continued
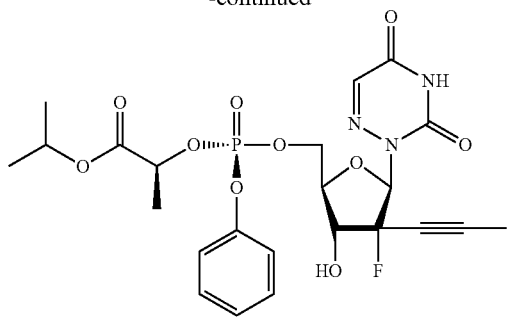
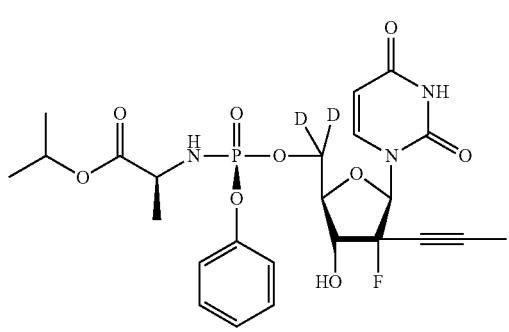
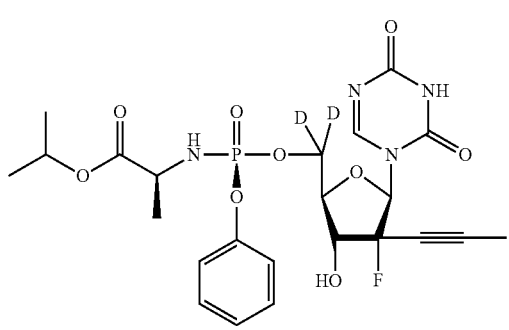
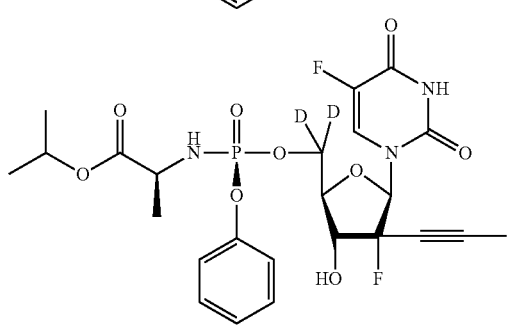
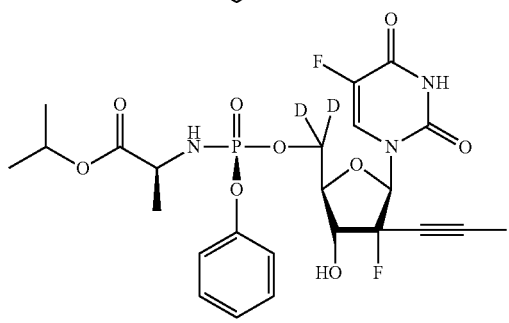
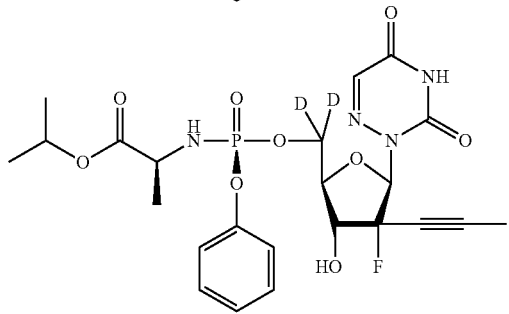
In exemplary embodiments, the compound is selected from:
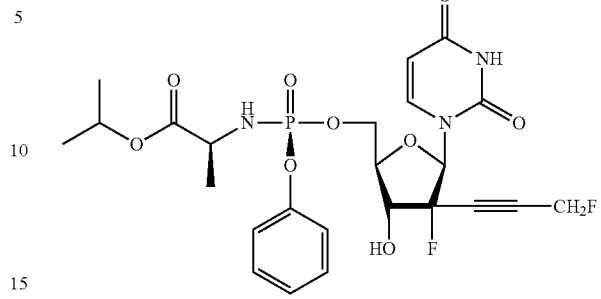
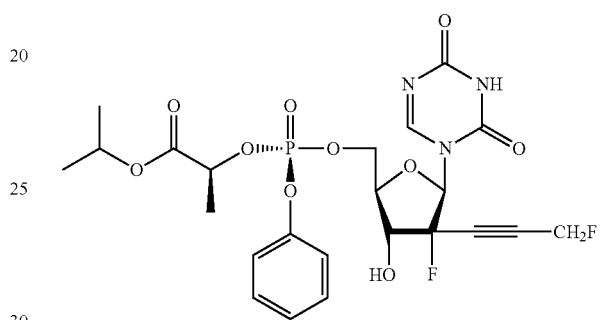
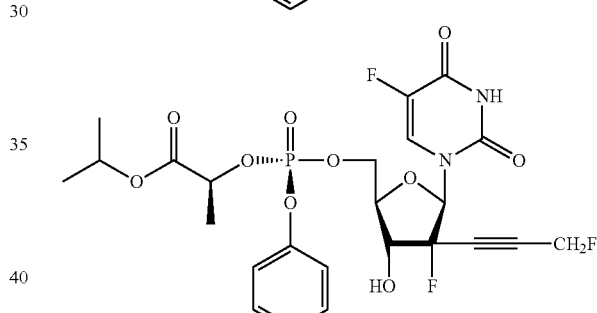
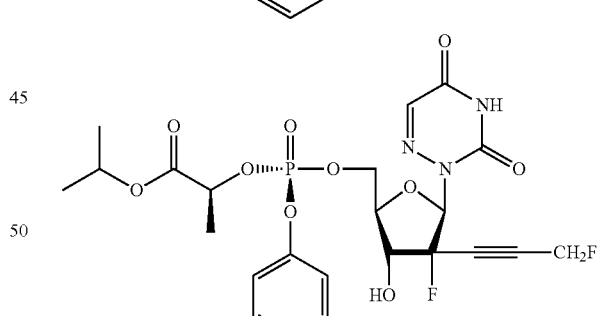
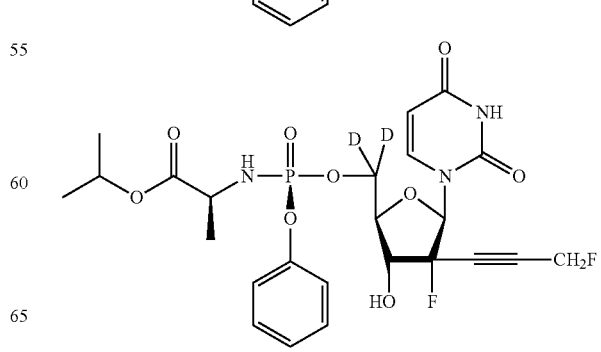

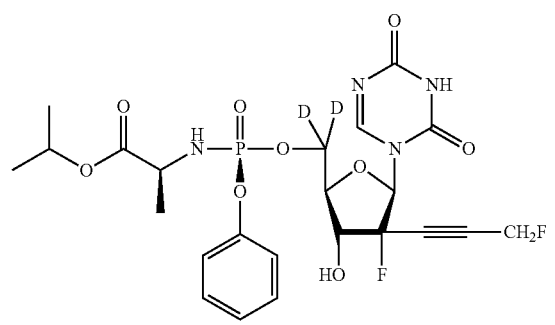
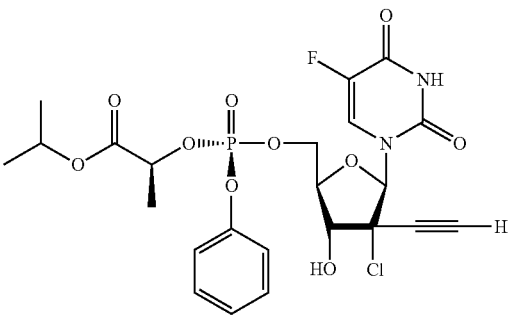
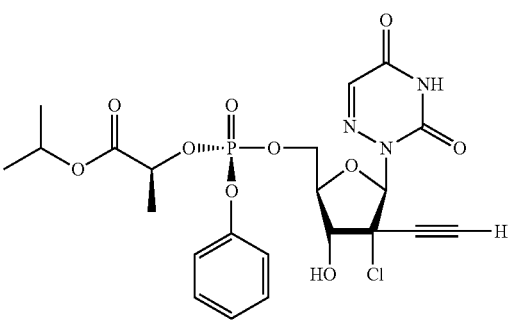
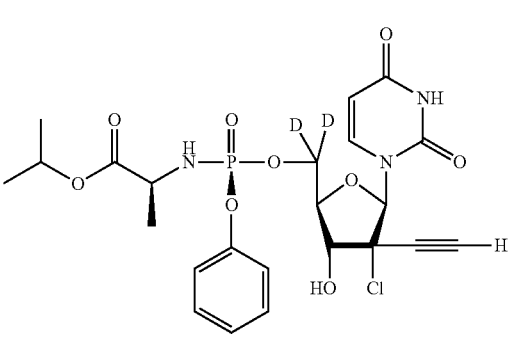
In exemplary embodiments, the compound is selected from:
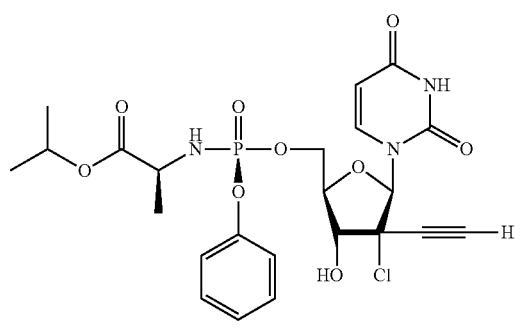
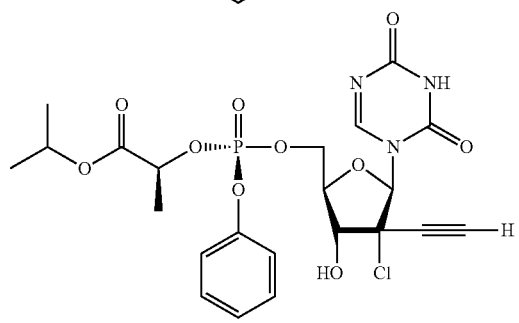

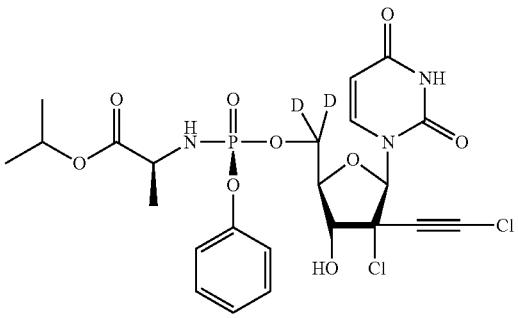
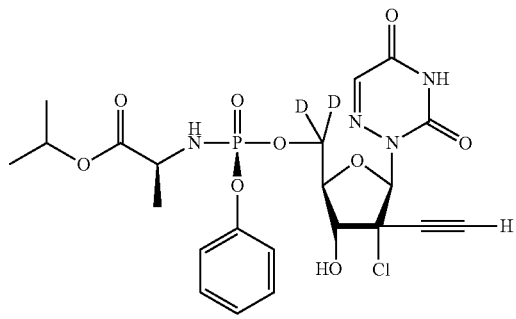
In exemplary embodiments, the compound is selected from:
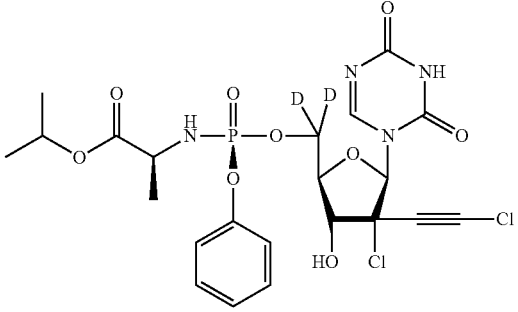
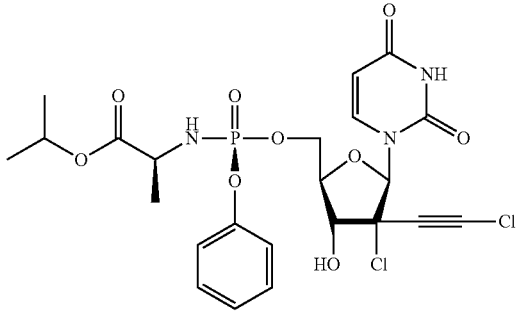
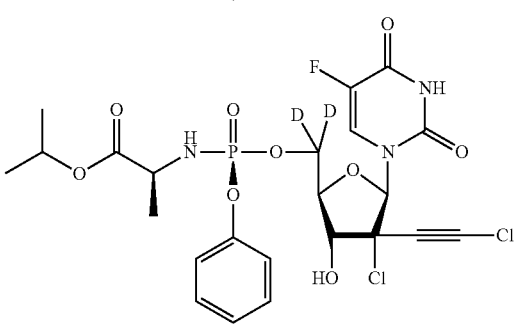
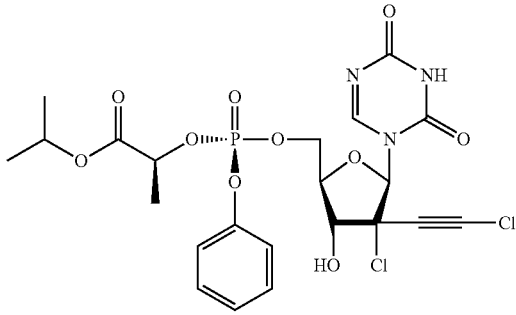
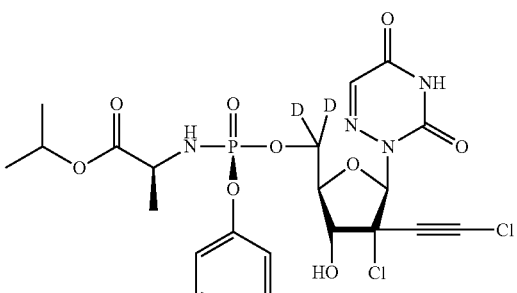
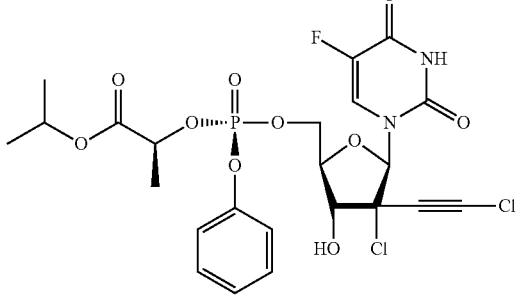
In exemplary embodiments, the compound is selected from:
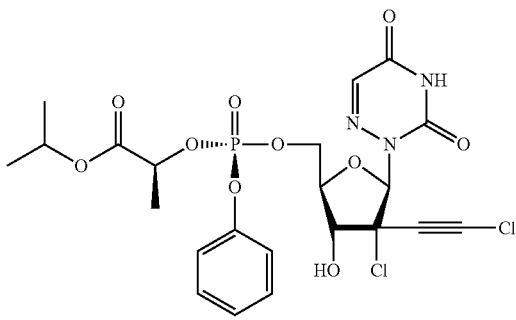
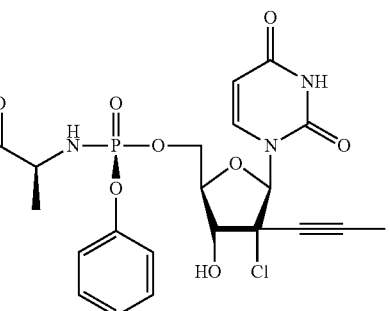

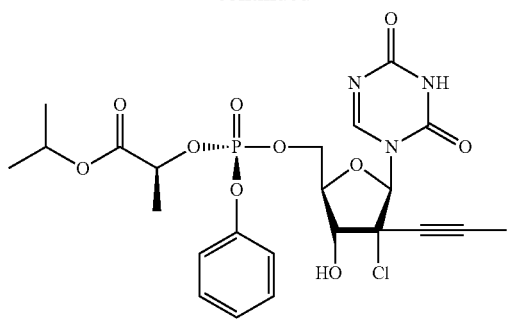
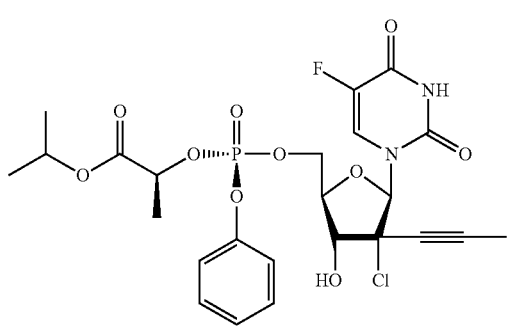
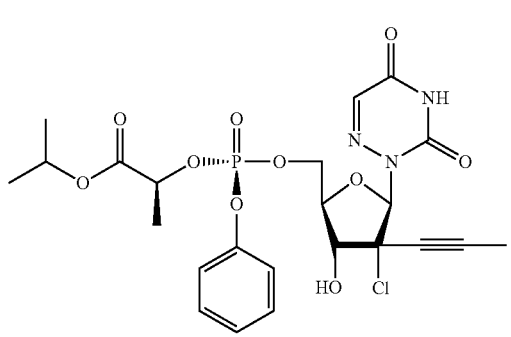
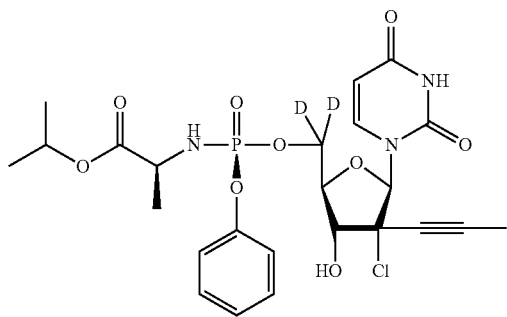
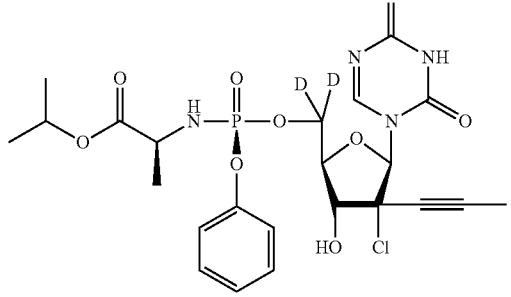
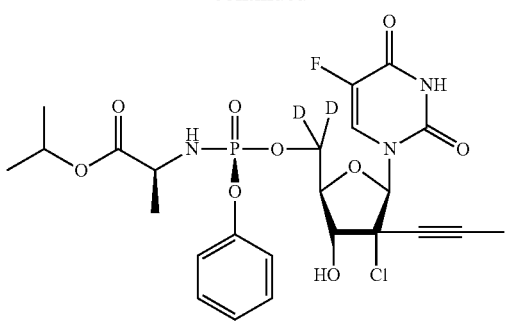
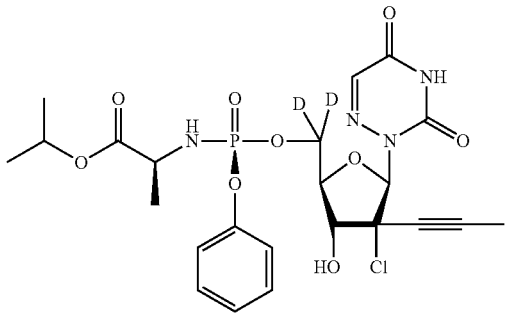
In exemplary embodiments, the compound is selected from:
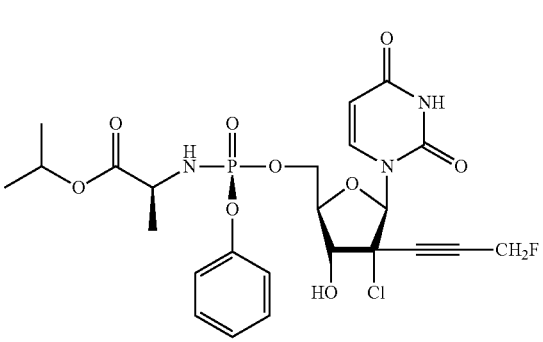
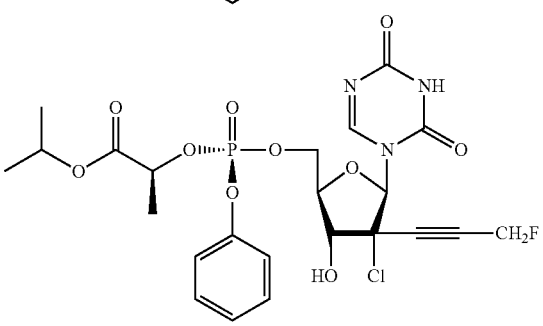
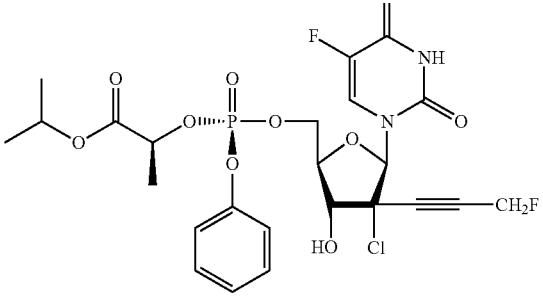

-continued
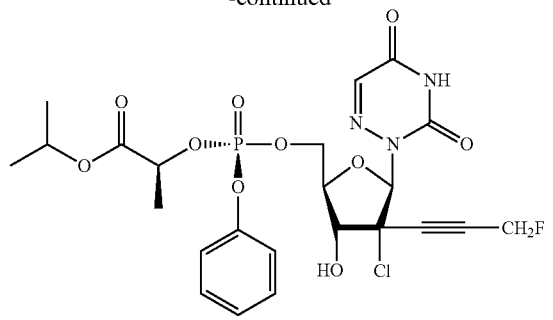
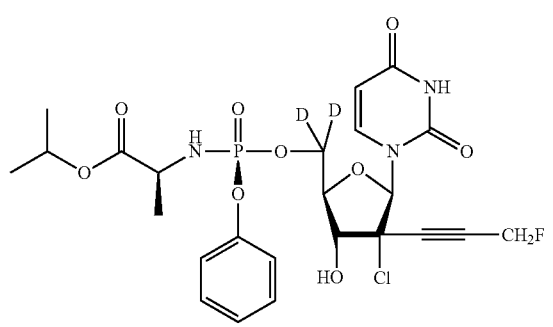
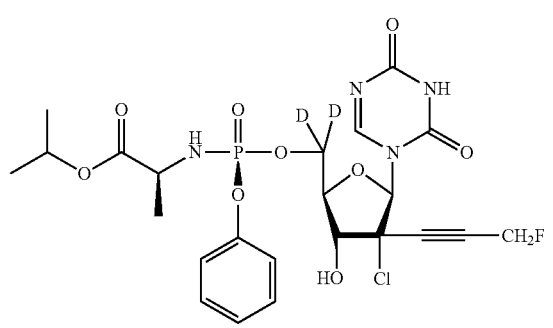
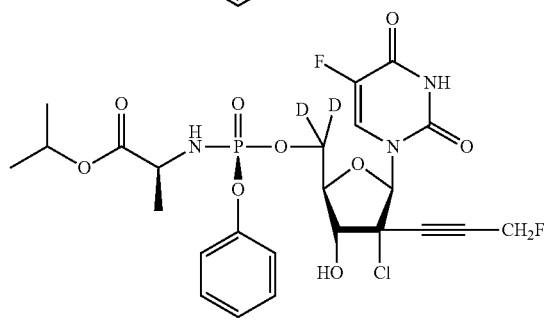
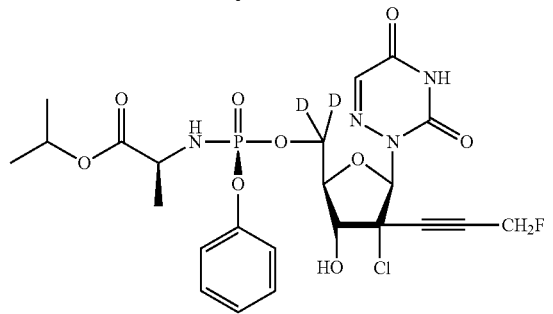
In exemplary embodiments, the compound is selected from:
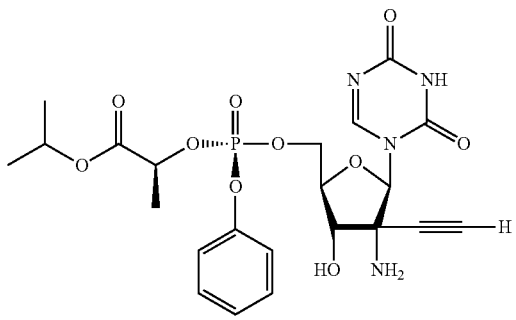
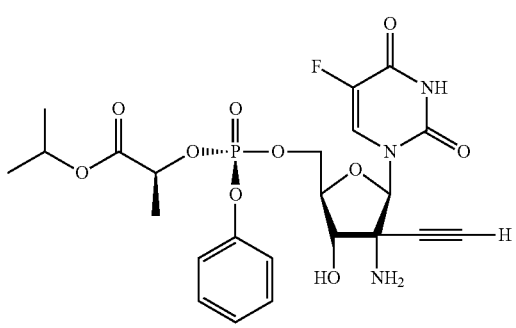
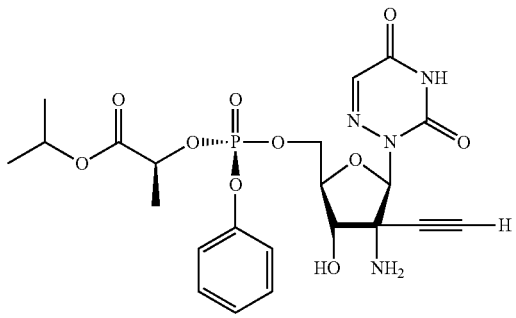
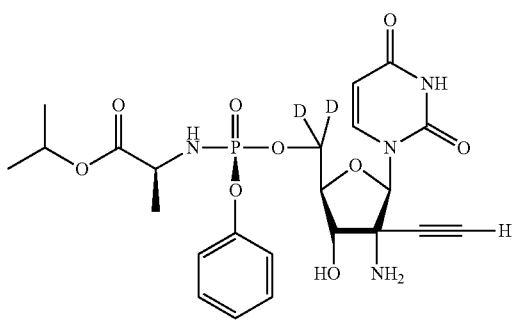
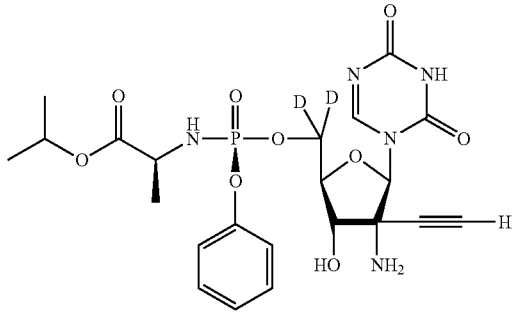

439
-continued

440
-continued

In exemplary embodiments, the compound is selected from:

In exemplary embodiments, the compound is selected from:
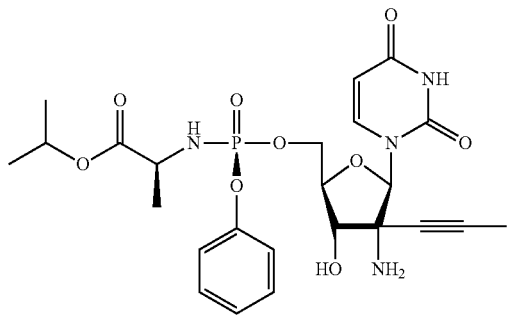
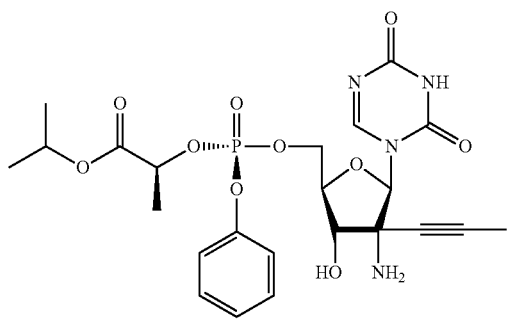
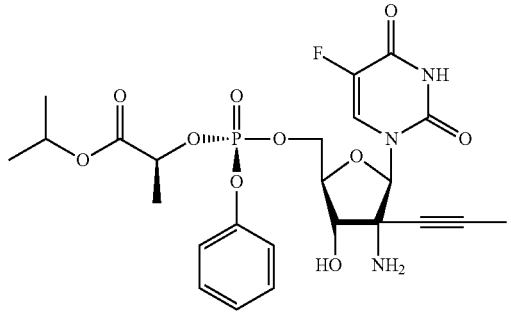
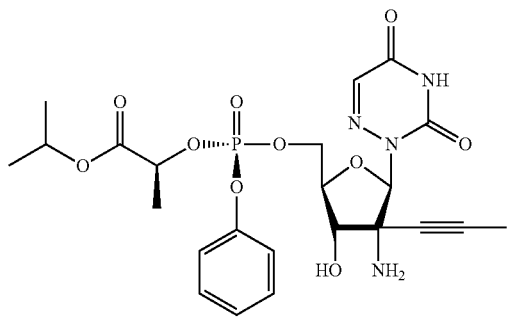
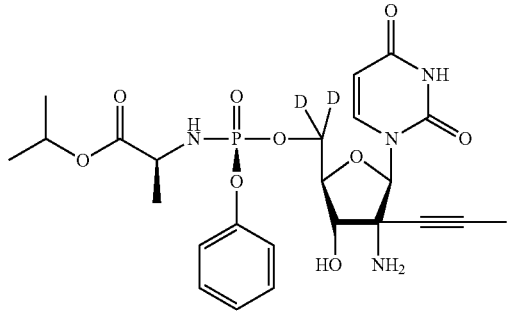
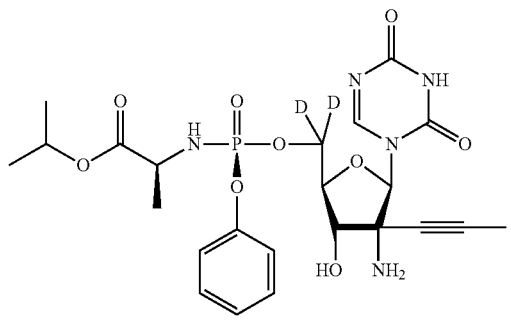
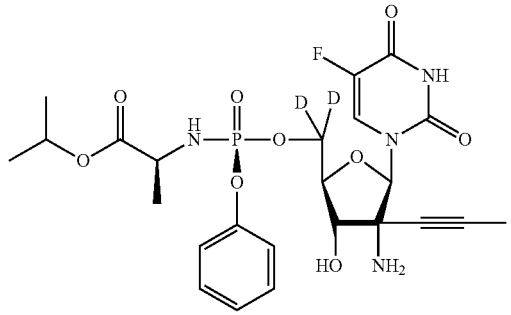
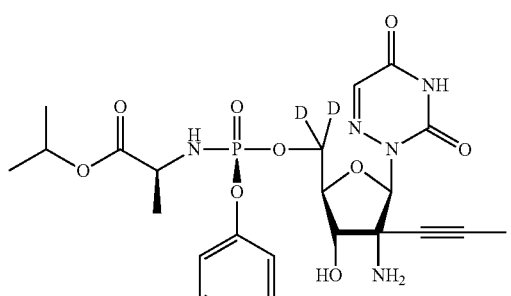
In exemplary embodiments, the compound is selected from:
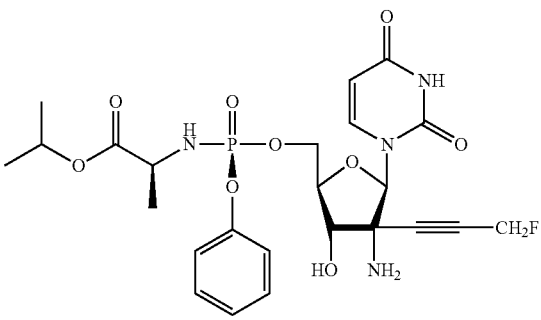
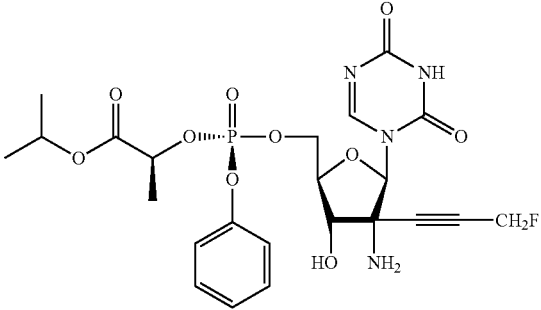

443
-continued
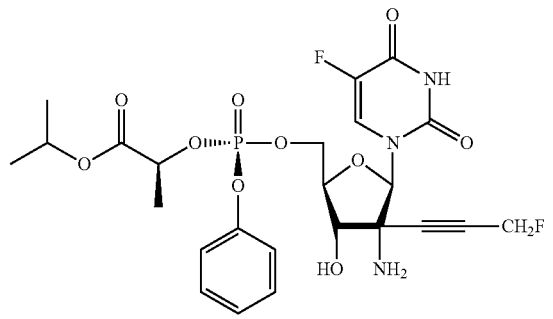
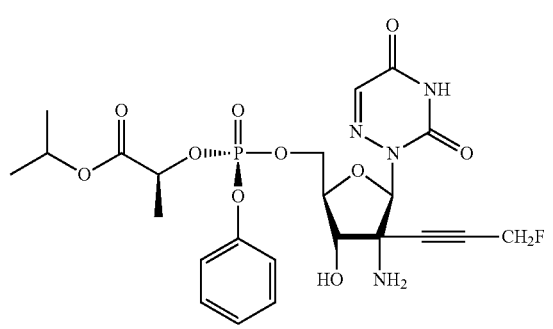
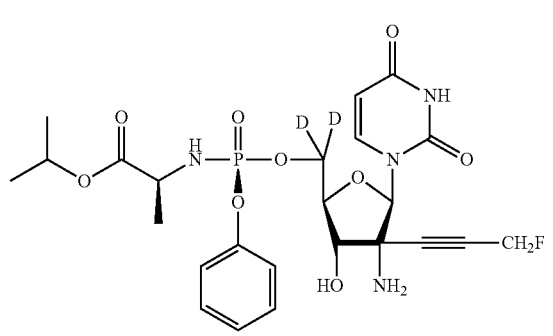
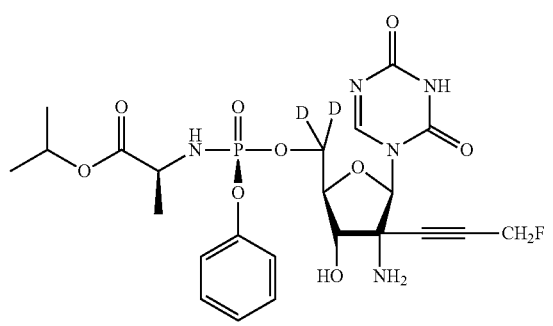
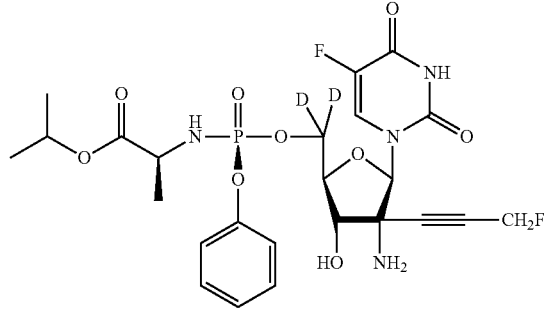
444
-continued
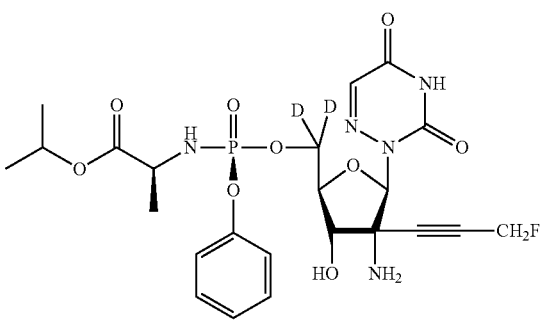
In exemplary embodiments, the compound is selected from:
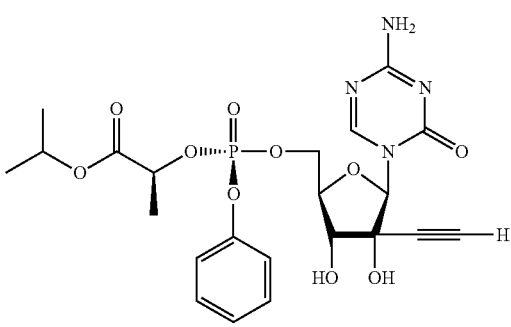
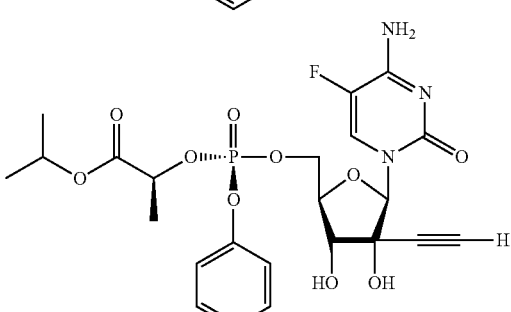
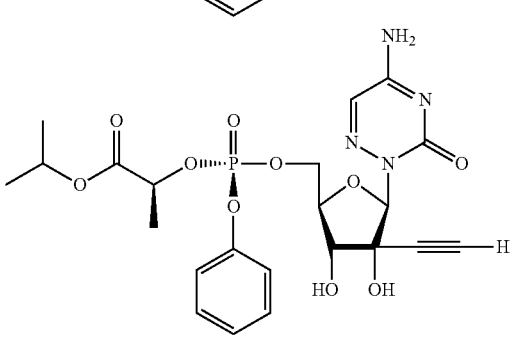
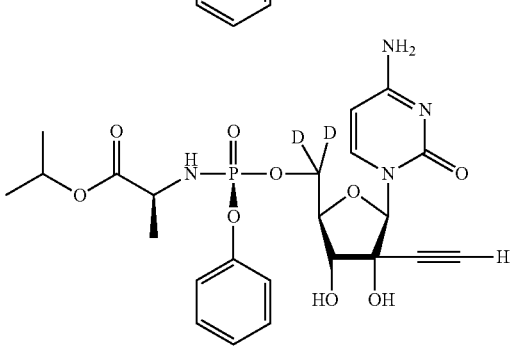

445
-continued
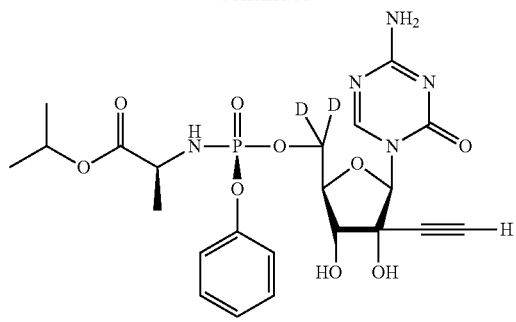
446
-continued
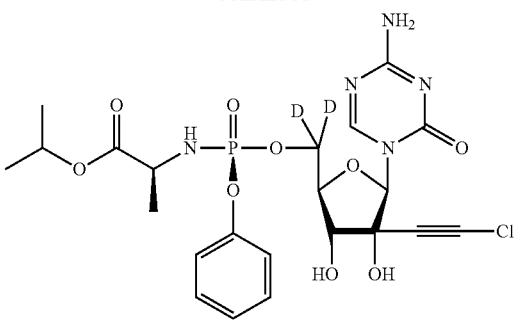
In exemplary embodiments, the compound is selected from:
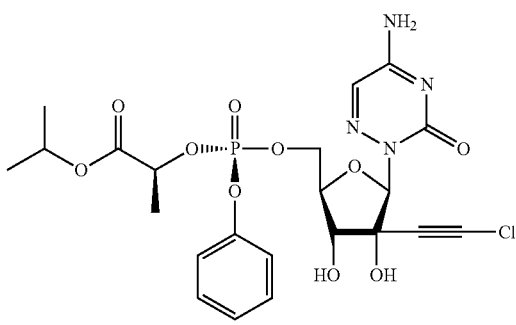
In exemplary embodiments, the compound is selected from:
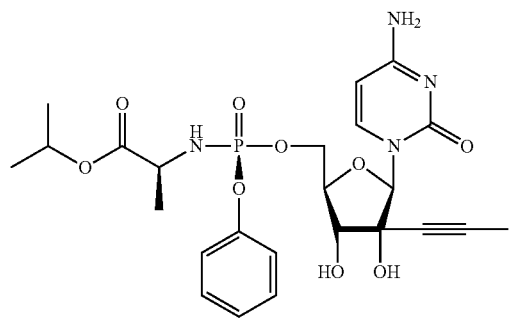
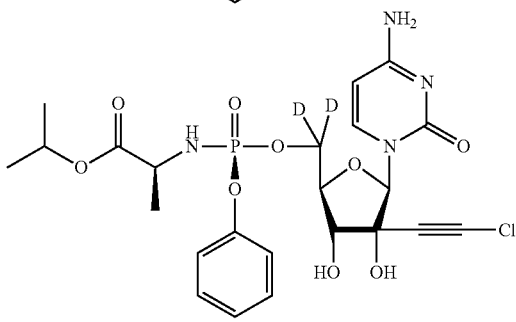
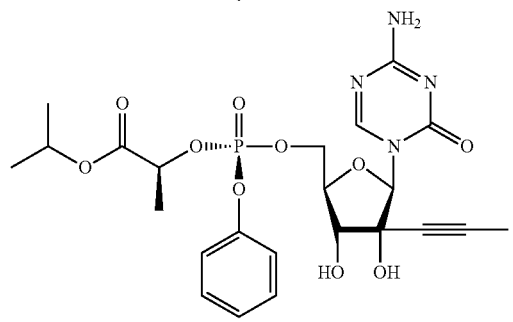

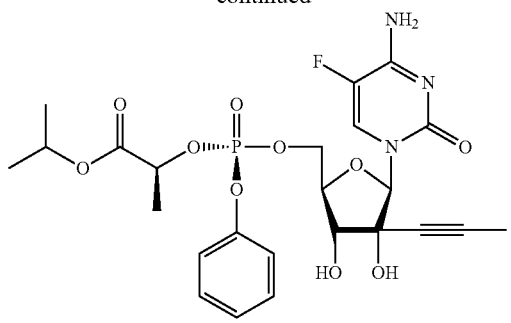
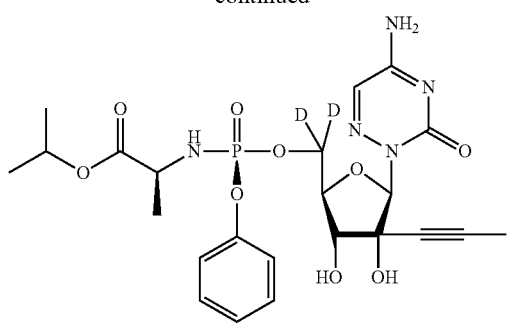
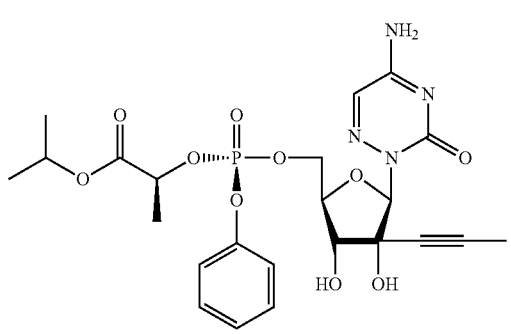
In exemplary embodiments, the compound is selected from:
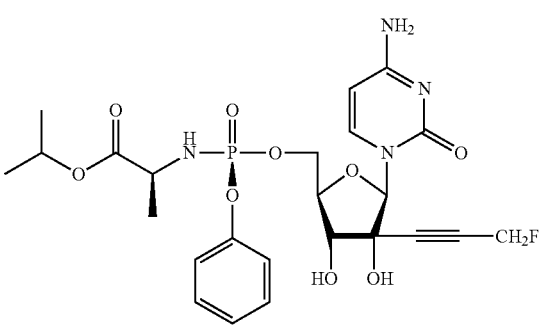
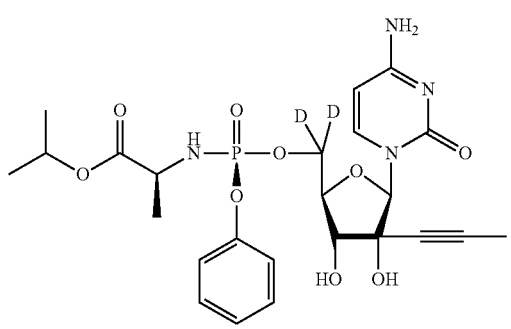
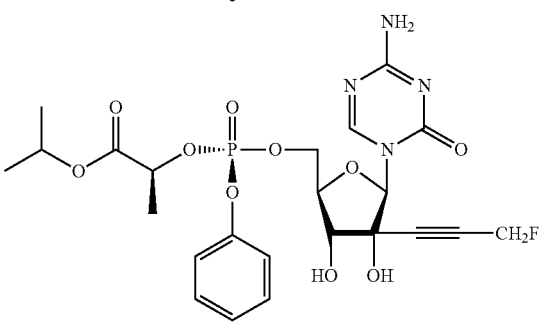
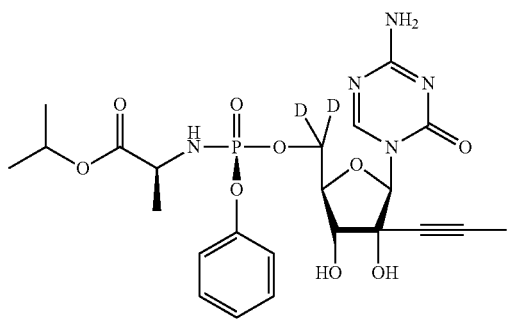
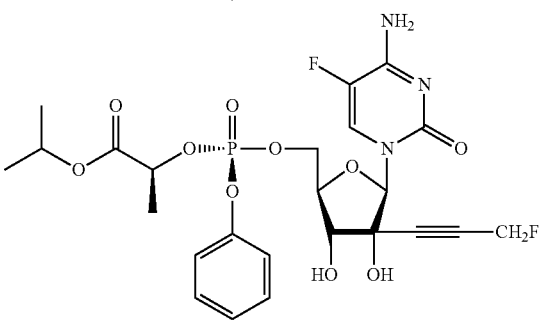
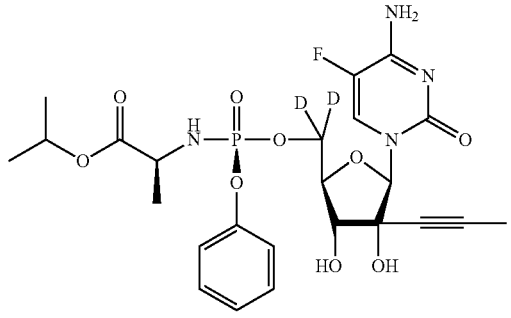
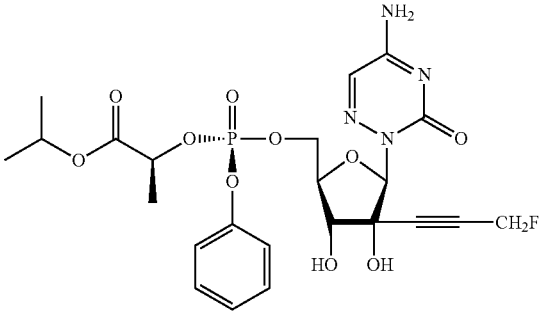

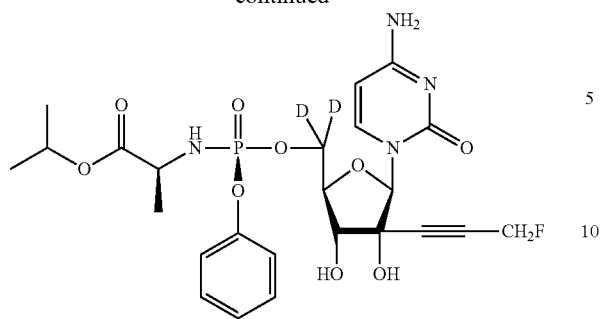
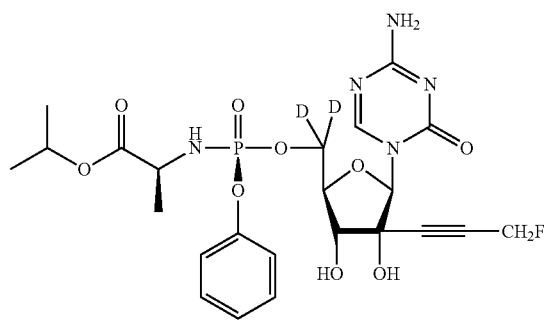
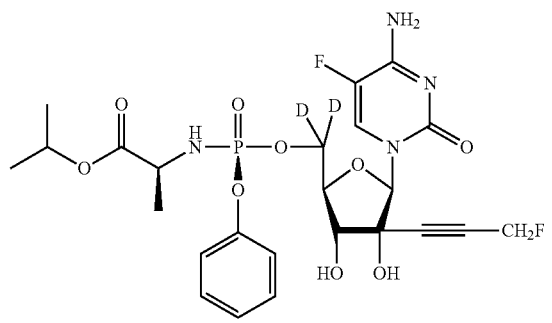
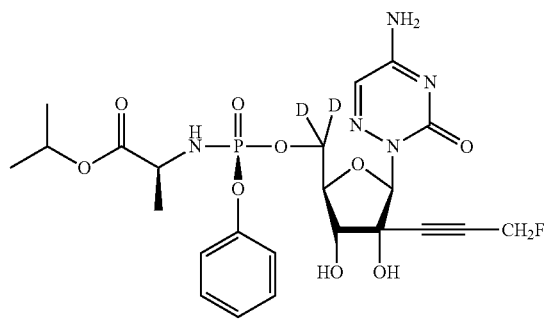
In exemplary embodiments, the compound is selected from:
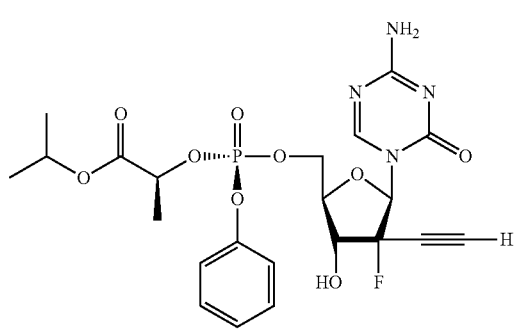
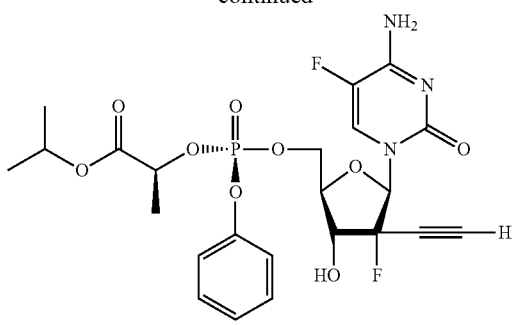
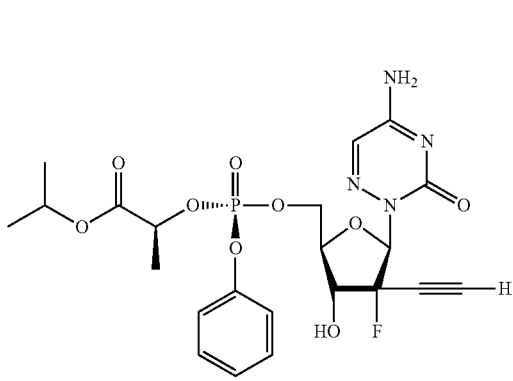
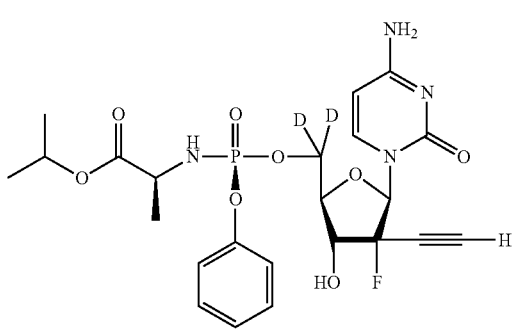
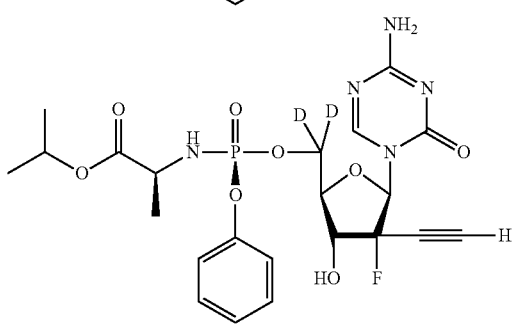
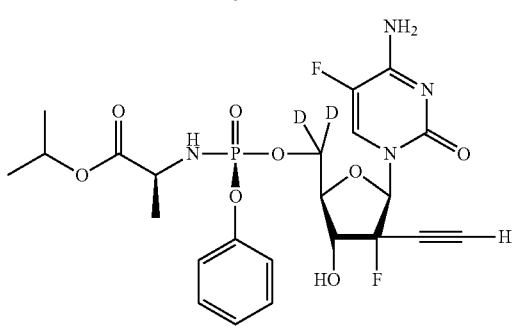

-continued
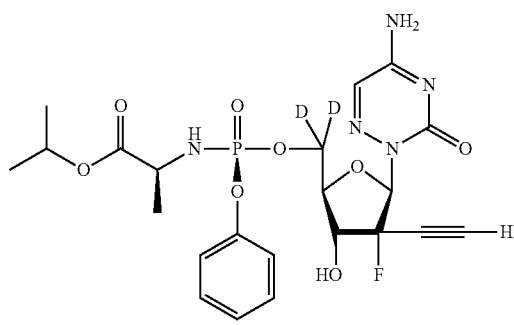
In exemplary embodiments, the compound is selected from:
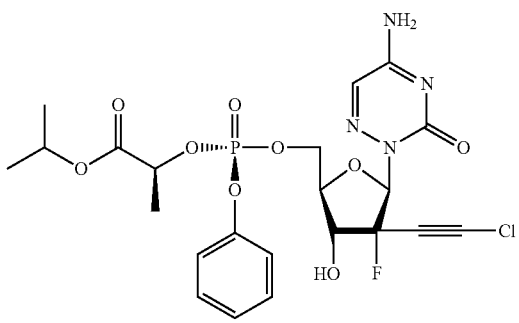
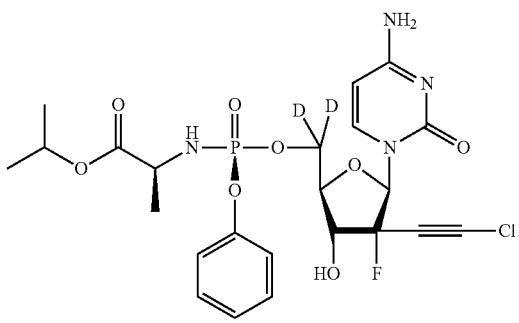
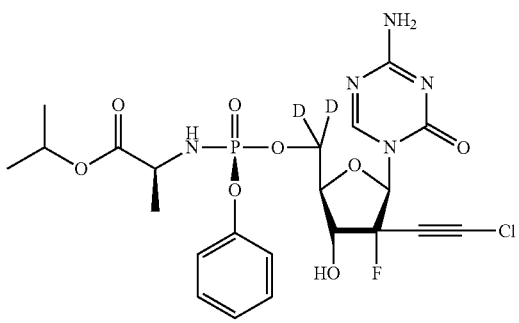
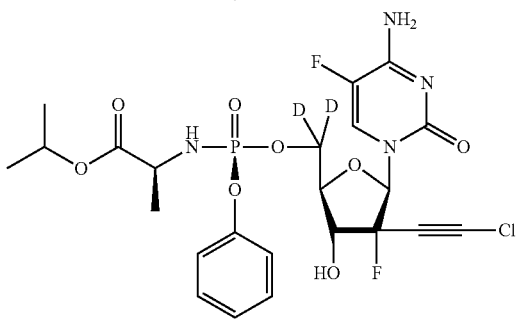
-continued
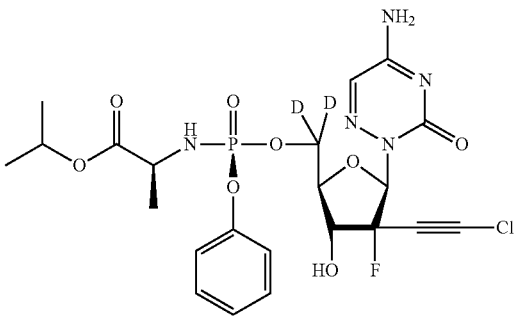
In exemplary embodiments, the compound is selected from:
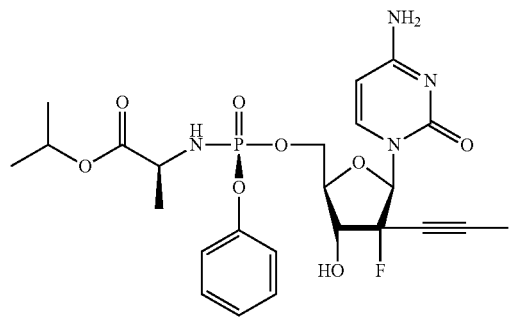
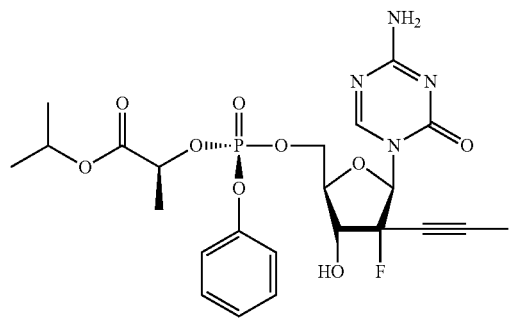
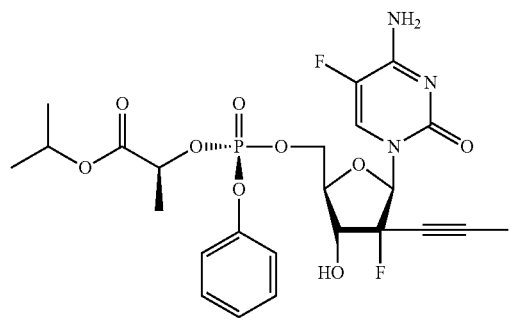

453
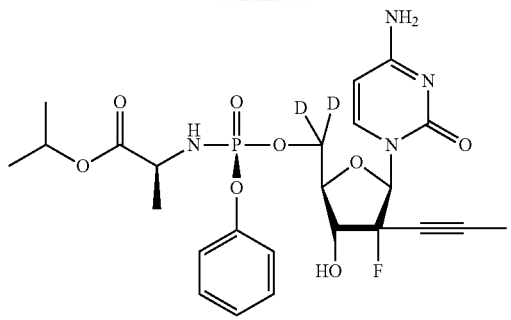
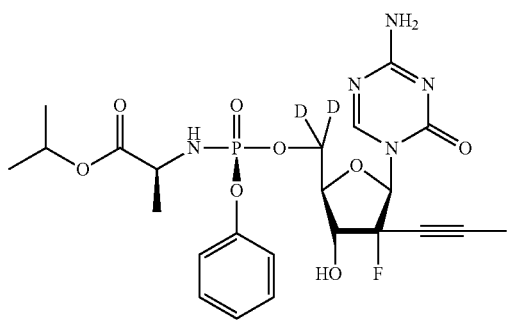
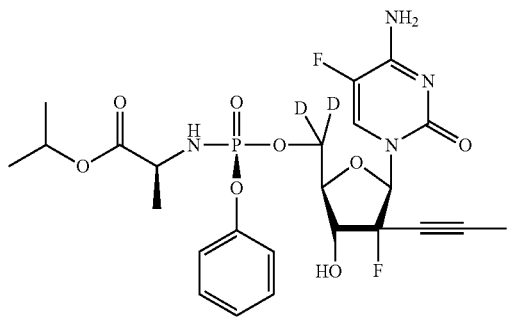
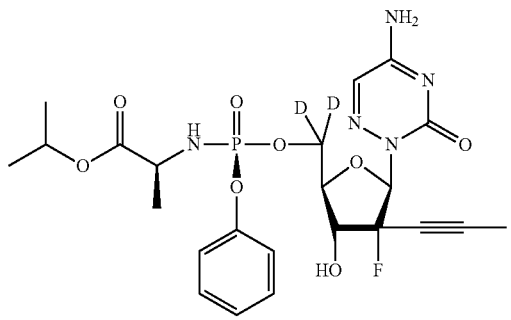
In exemplary embodiments, the compound is selected from:
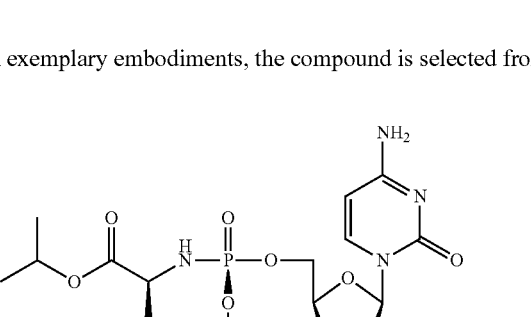
454
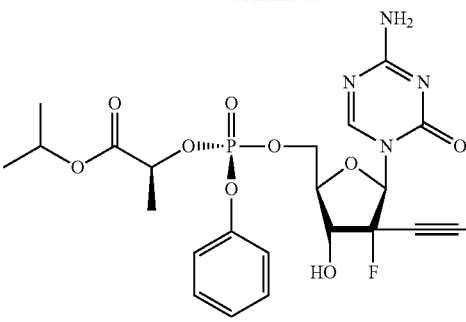
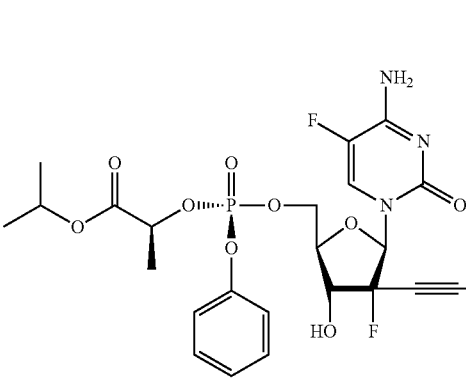
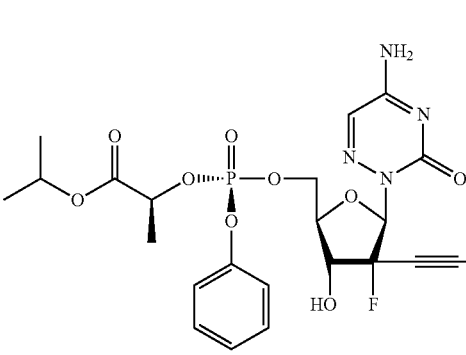
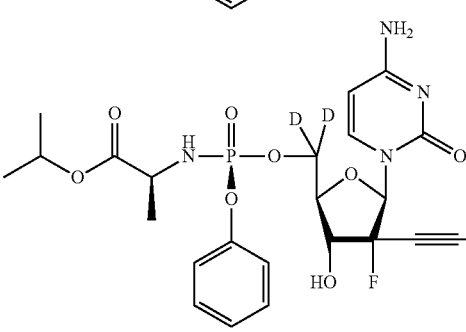
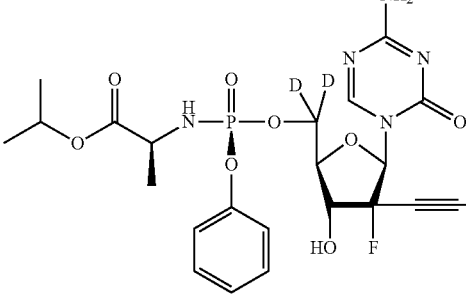

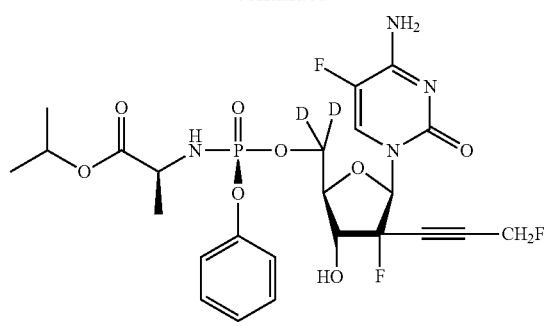
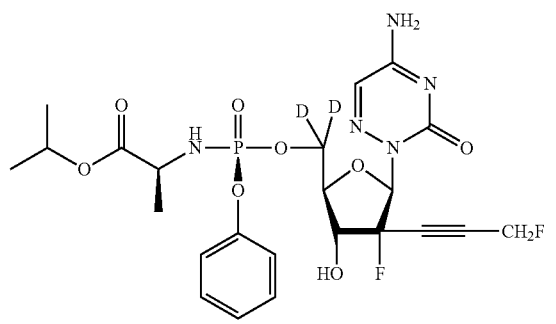
In exemplary embodiments, the compound is selected from:
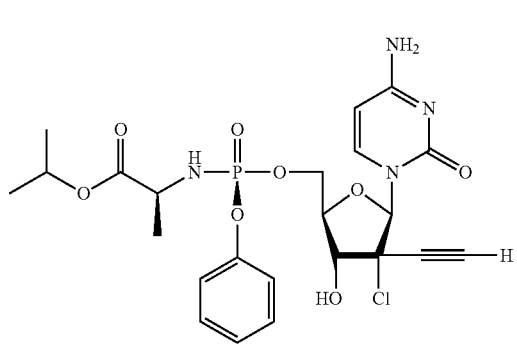
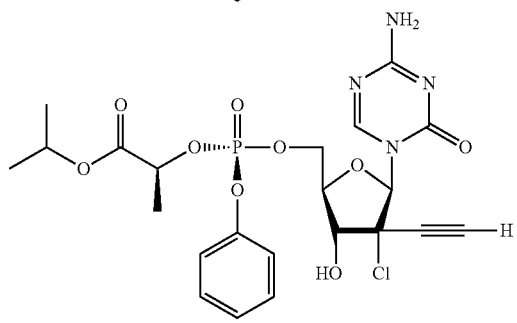
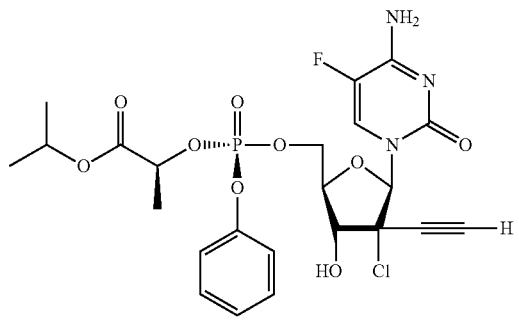
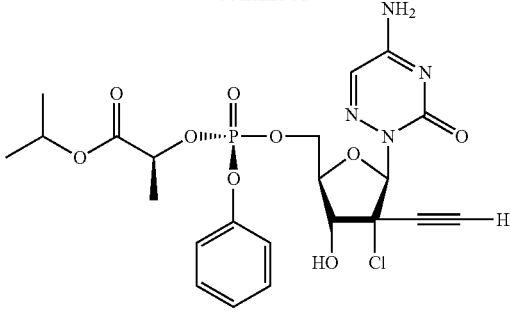
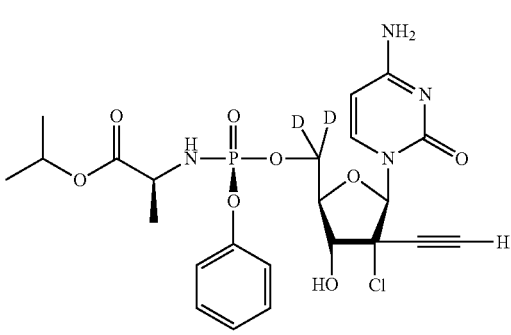
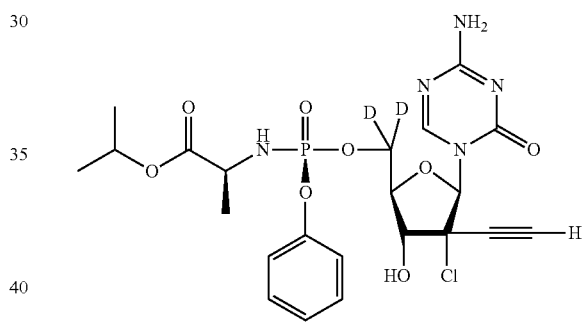
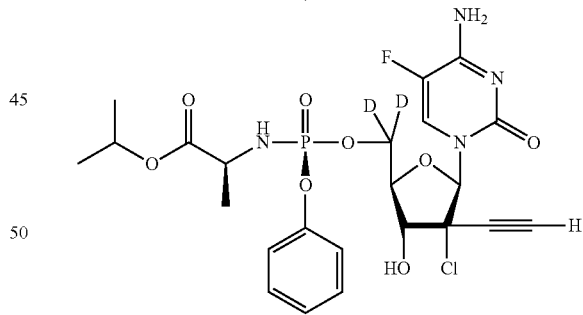

In exemplary embodiments, the compound is selected from:
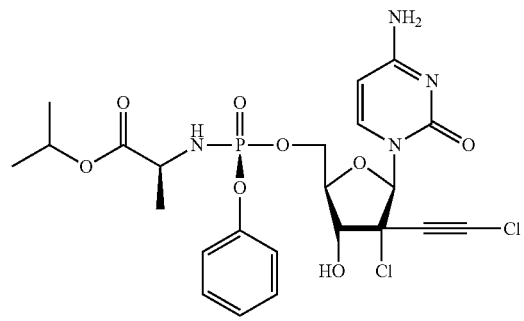
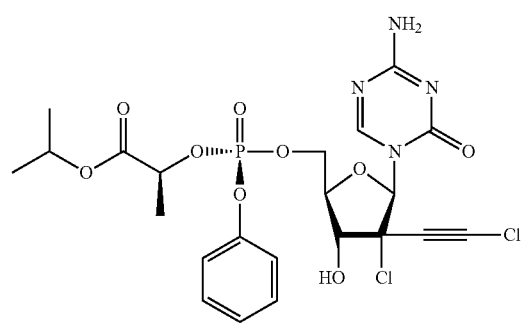
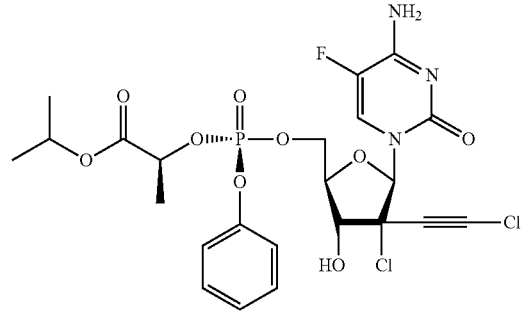
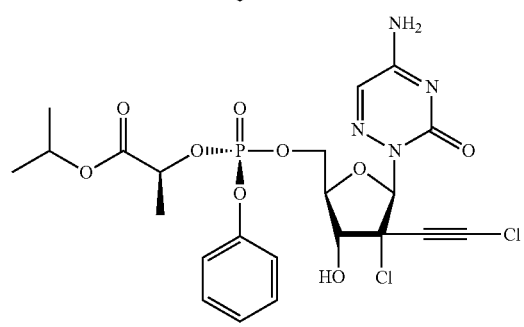
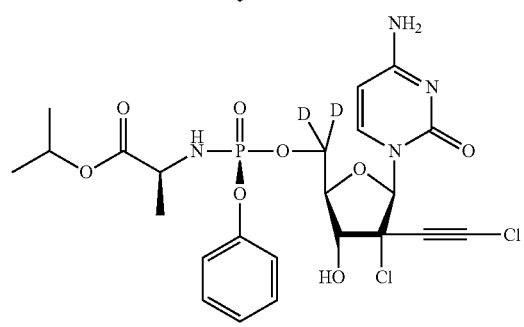
-continued
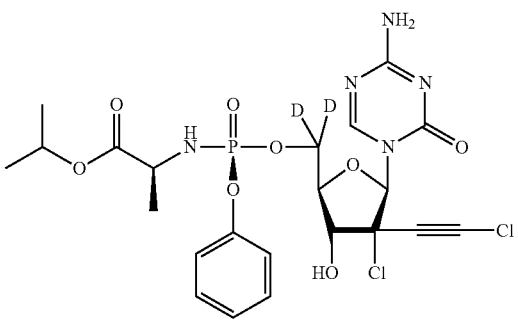
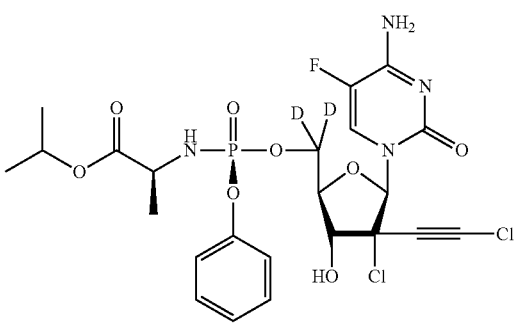
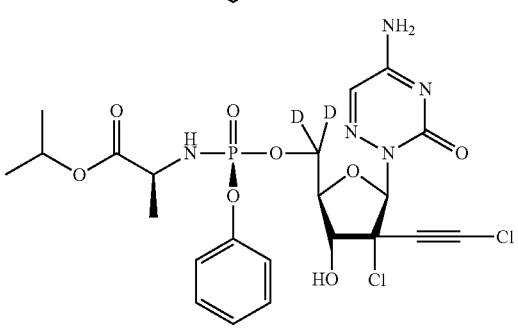
In exemplary embodiments, the compound is selected from:
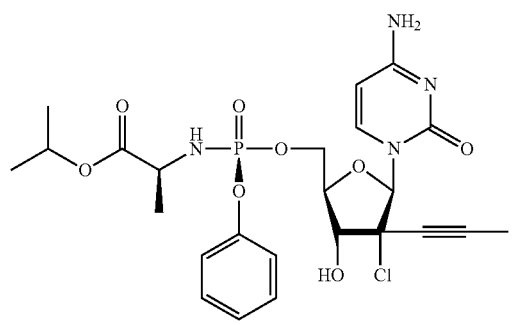
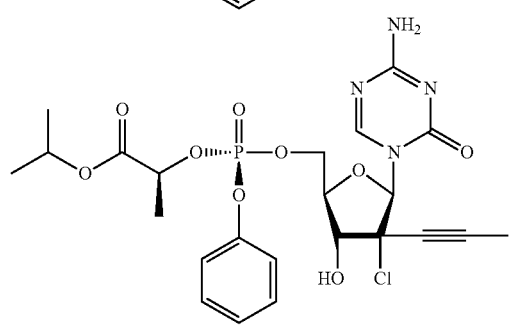

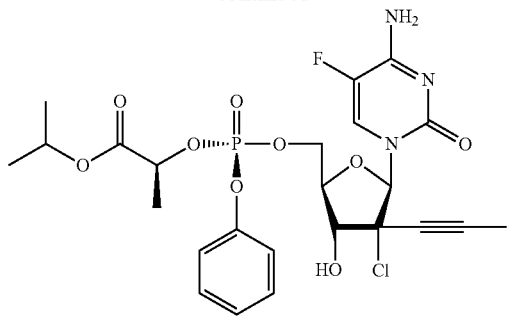
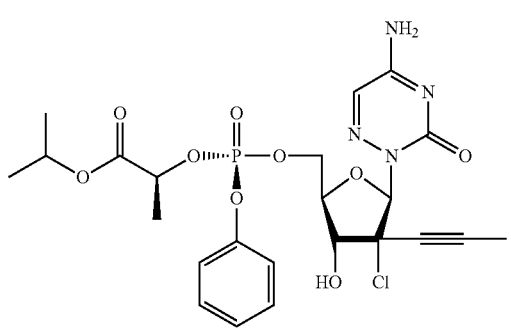
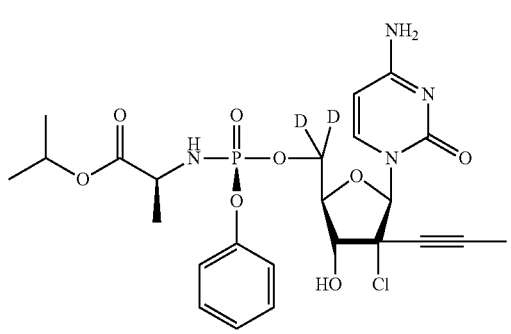
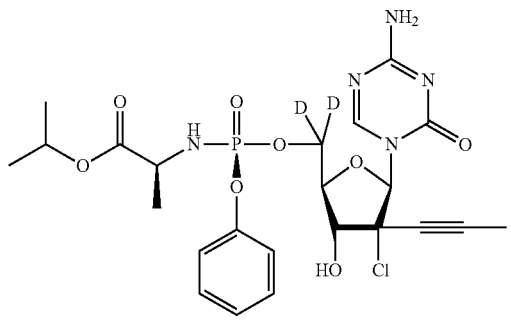
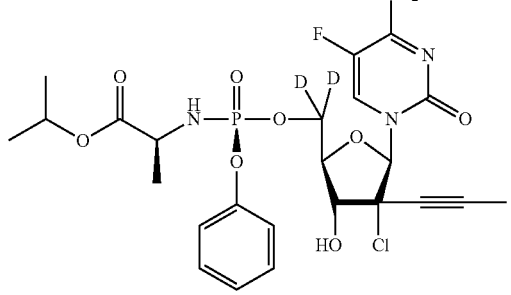
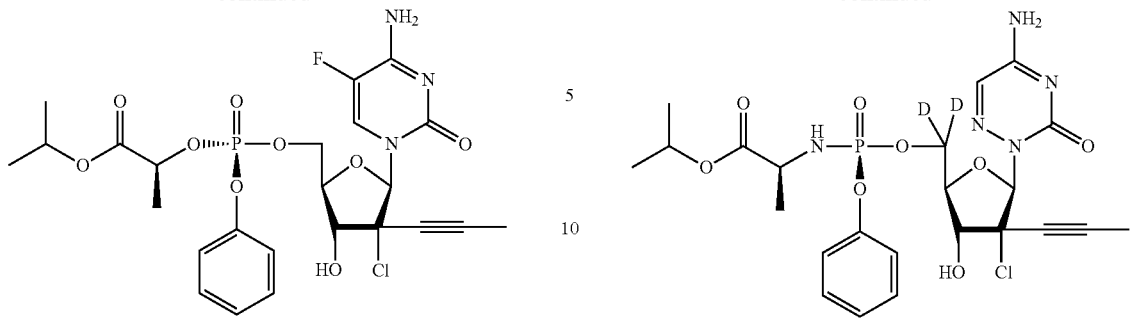
In exemplary embodiments, the compound is selected from:
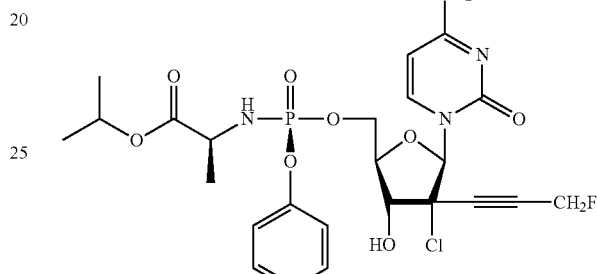
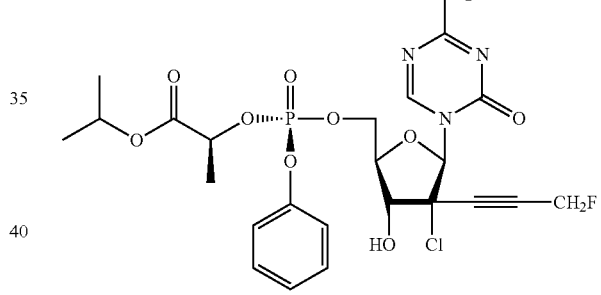
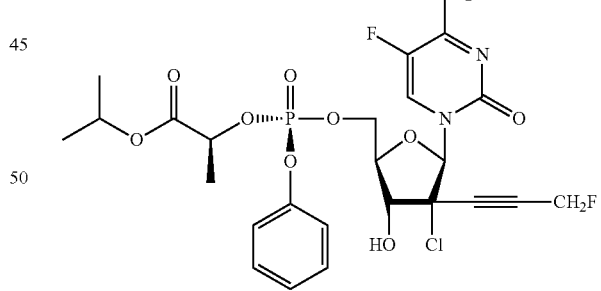
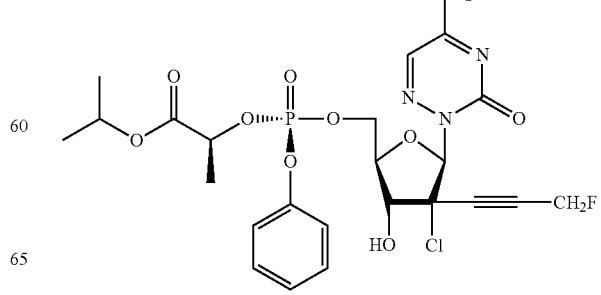

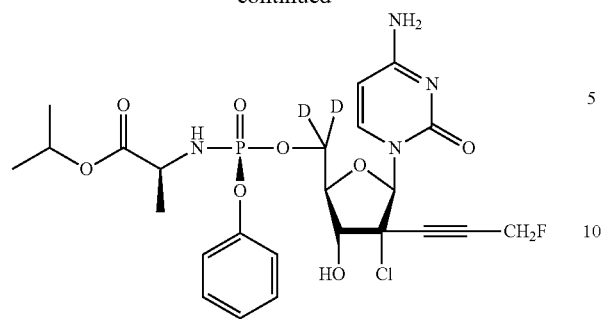
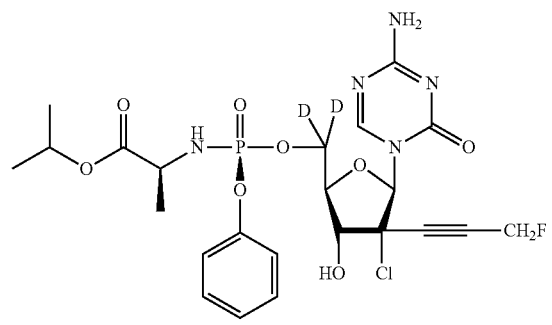
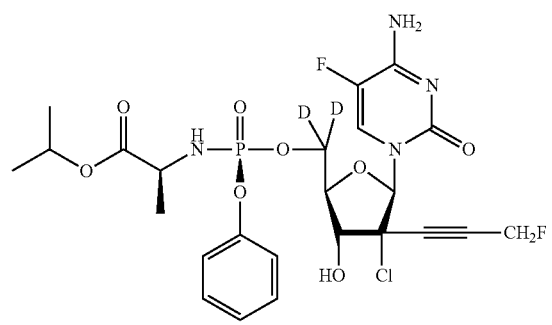
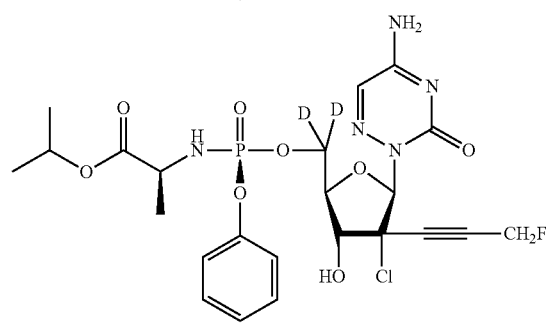
In exemplary embodiments, the compound is selected from:
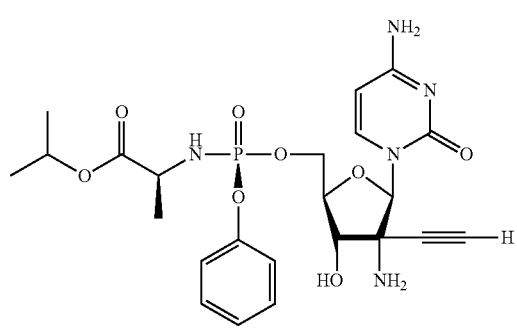
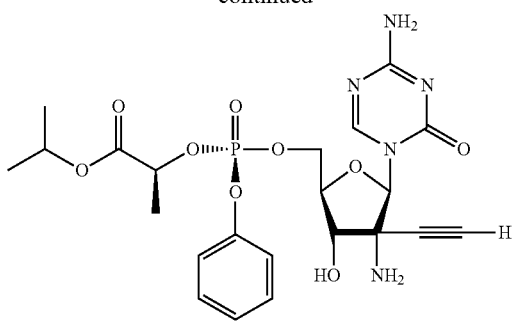
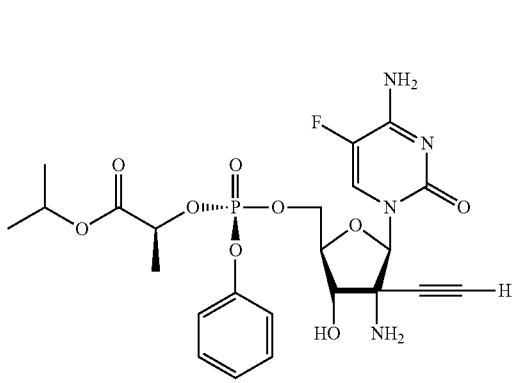
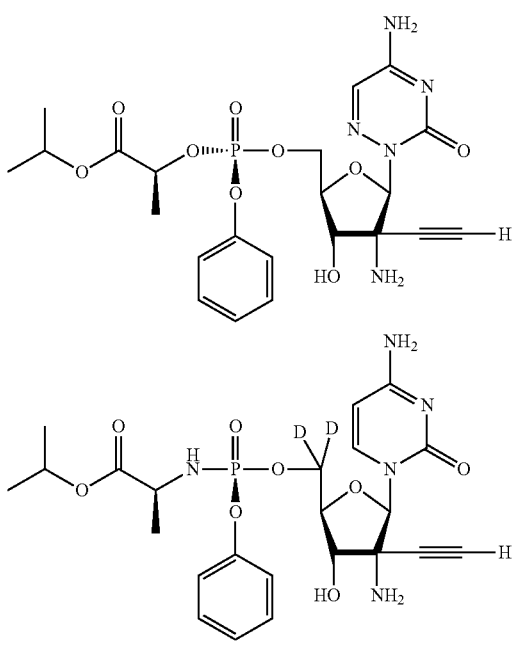
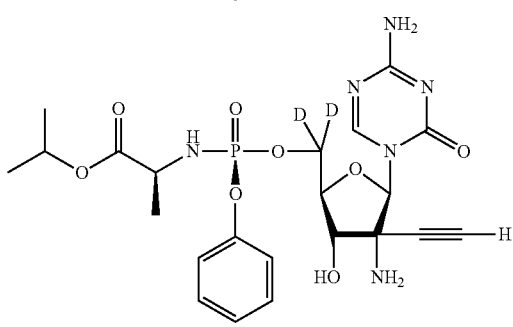

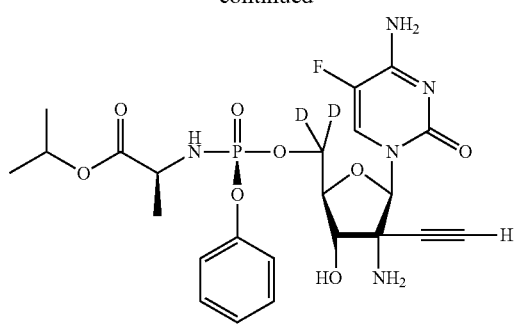
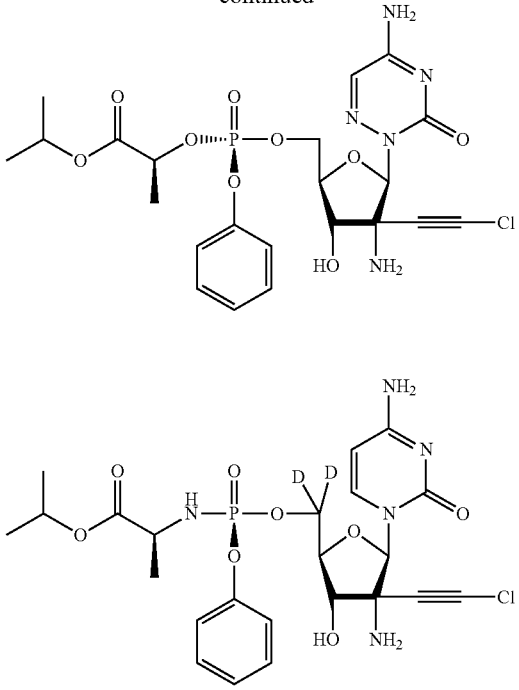
In exemplary embodiments, the compound is selected from:
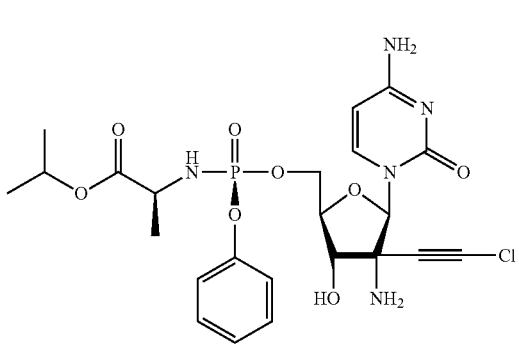
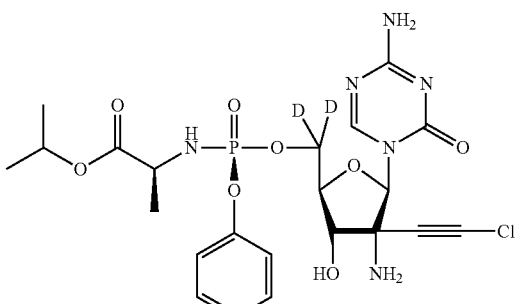
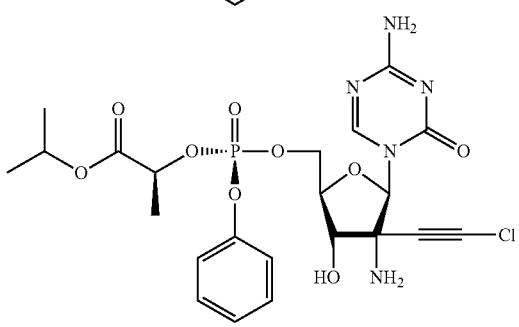
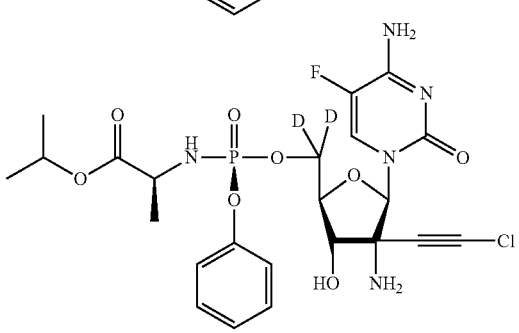
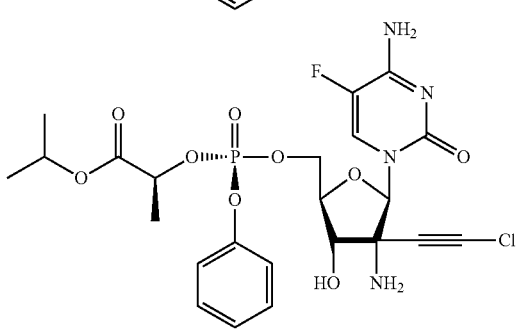
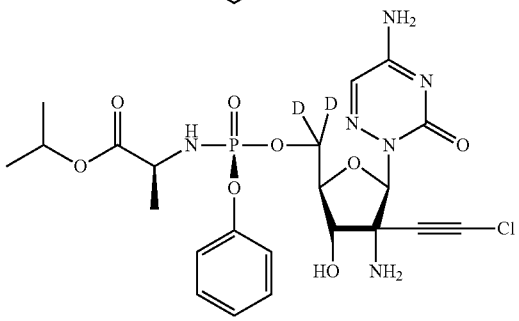

In exemplary embodiments, the compound is selected from:
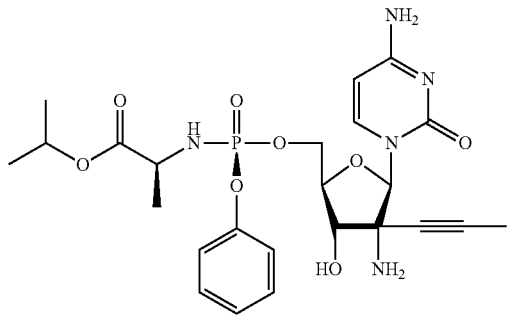
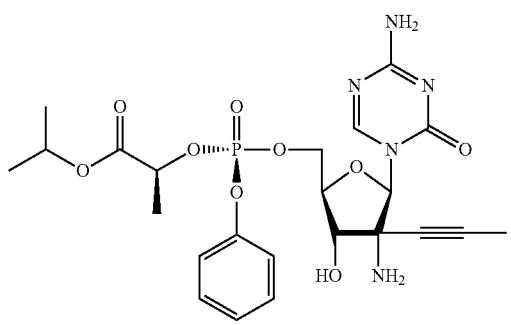
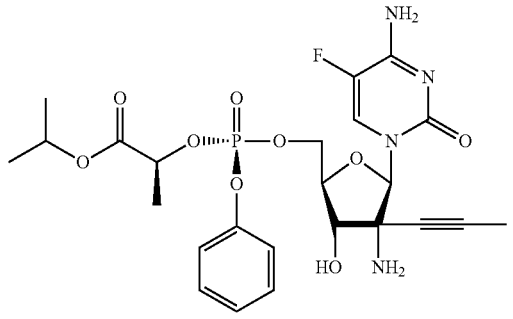
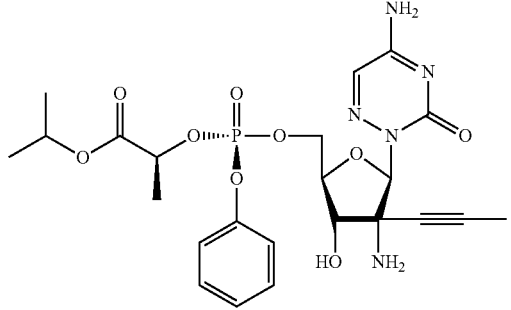
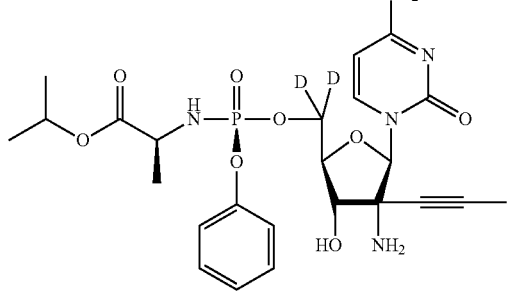
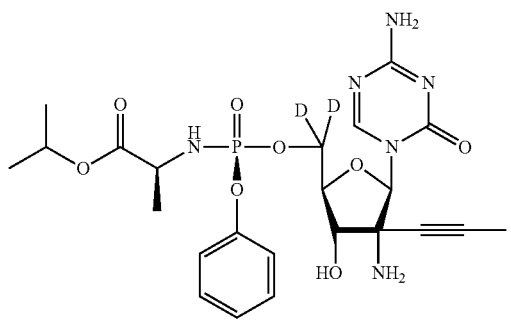
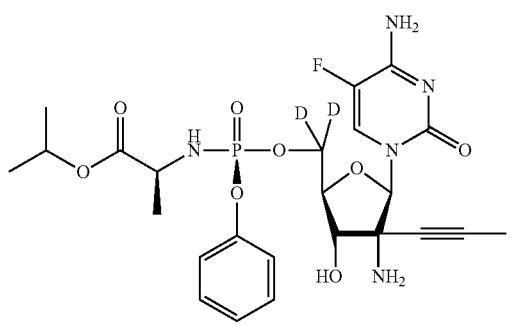
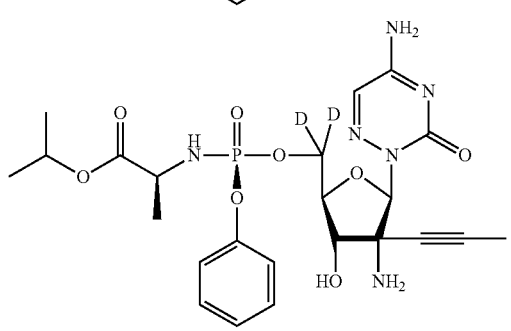
In exemplary embodiments, the compound is selected from:
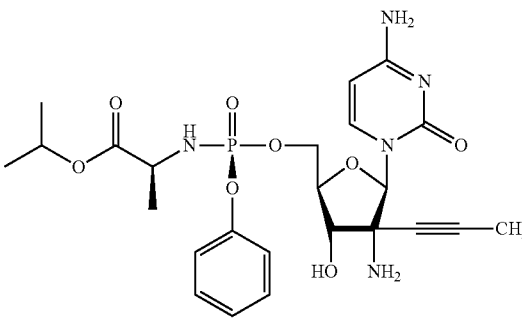
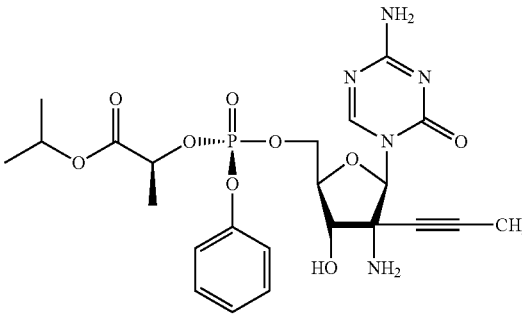

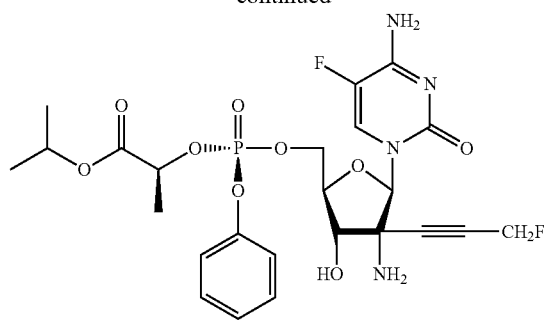
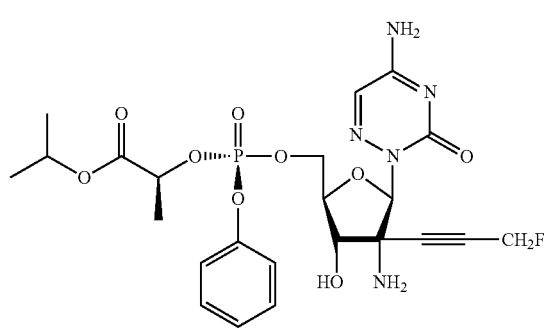
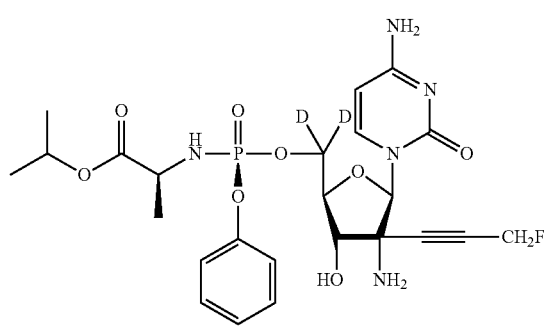
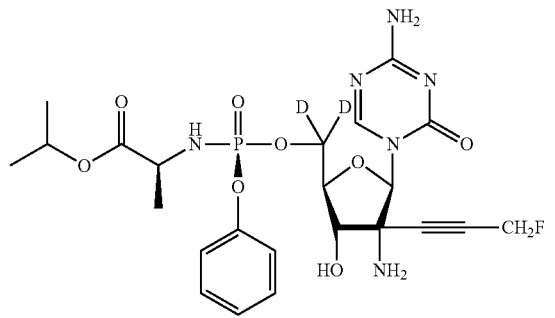
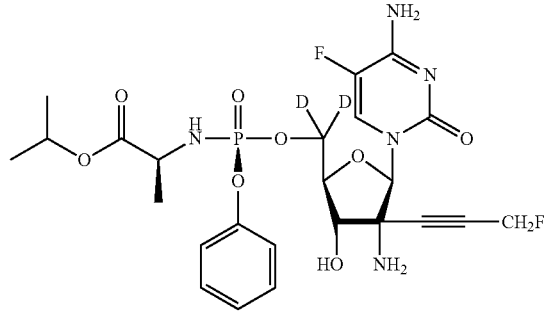
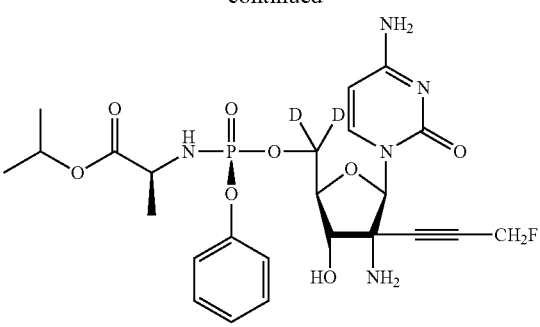
In exemplary embodiments, the compound is selected from:
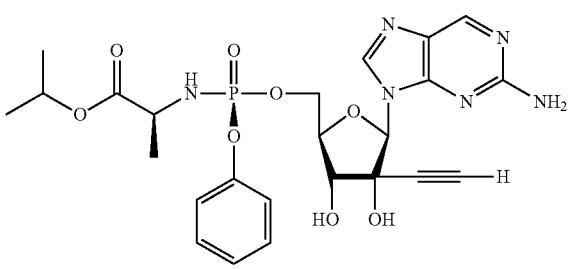
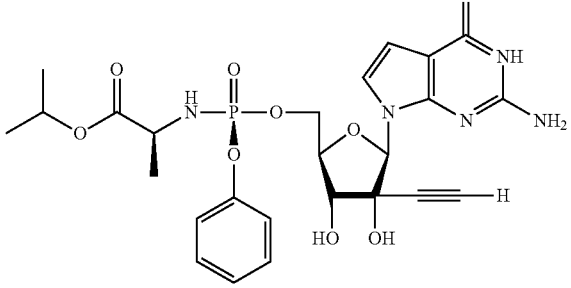
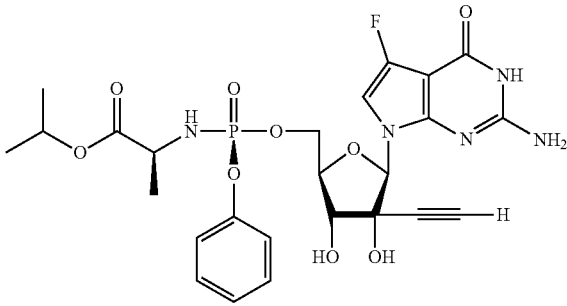
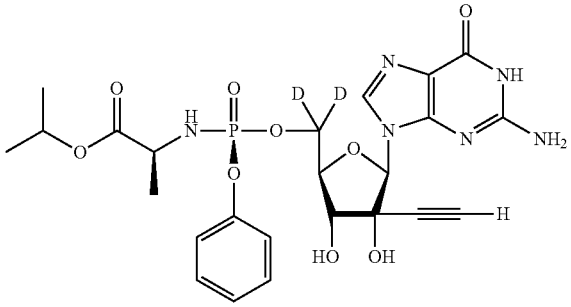

469
-continued
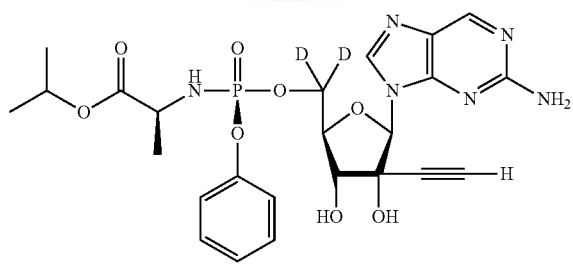
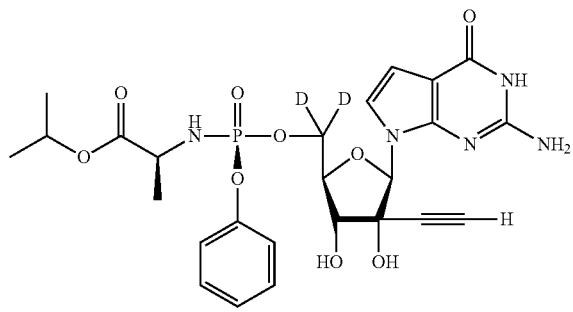
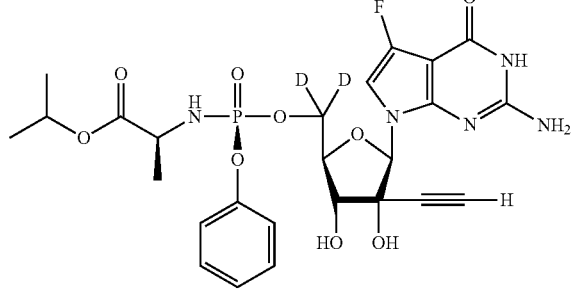
In exemplary embodiments, the compound is selected from:
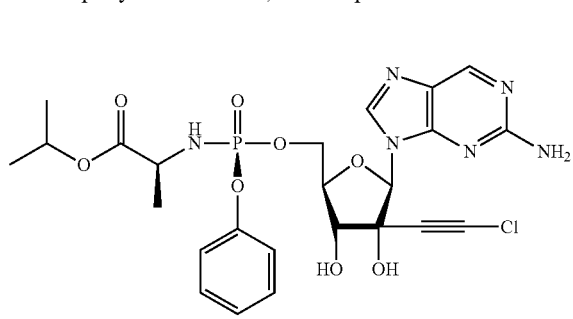
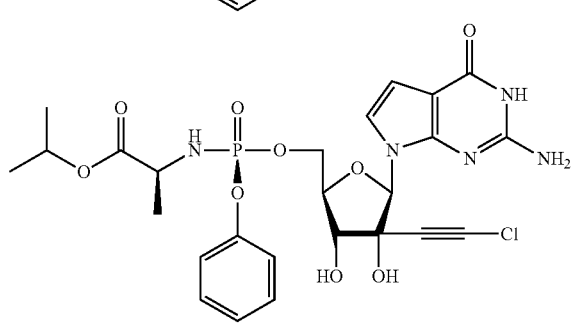
470
-continued
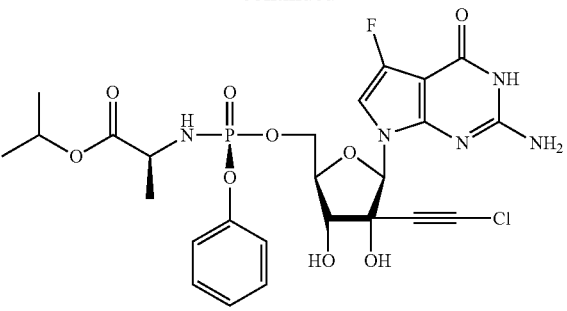
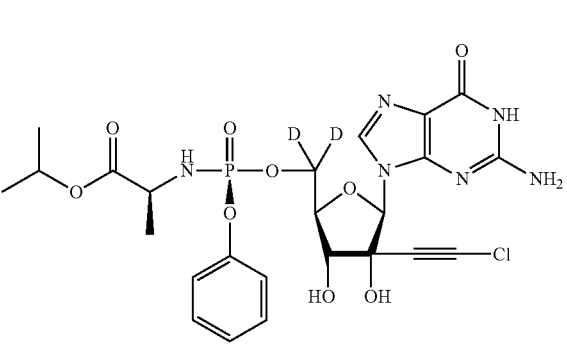
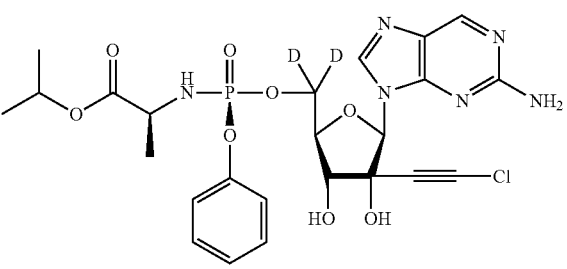
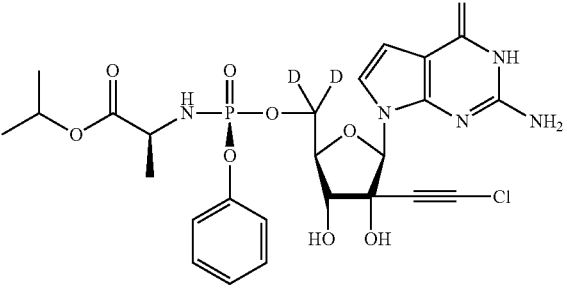
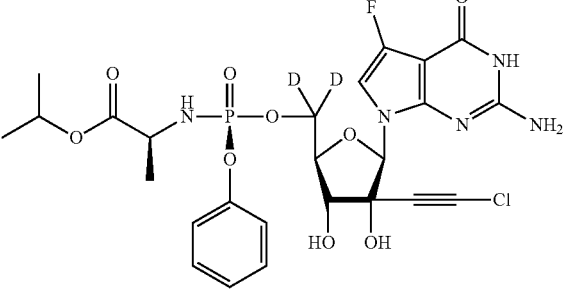

471
In exemplary embodiments, the compound is selected from:
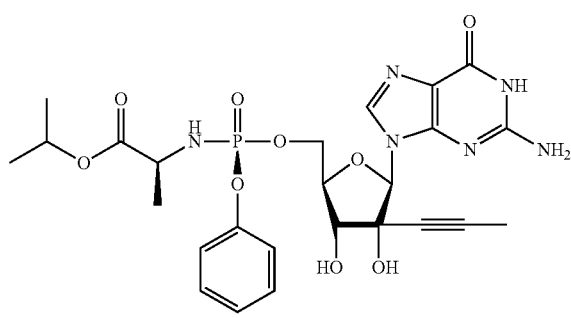
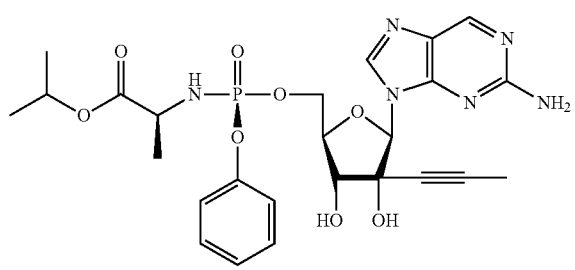
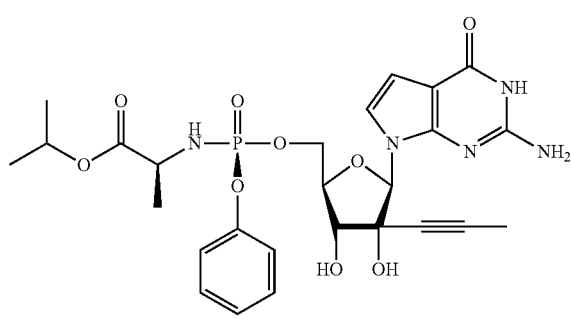
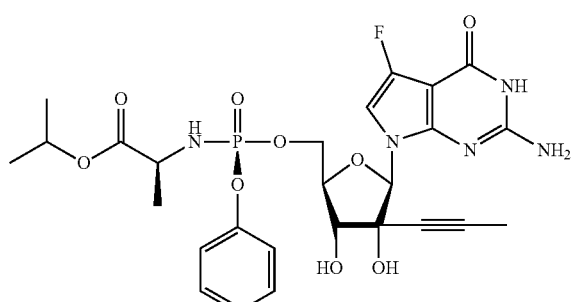
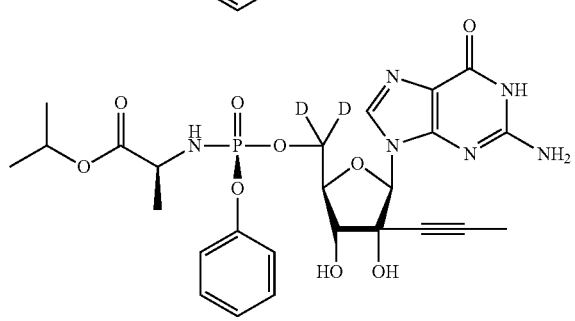
472
-continued
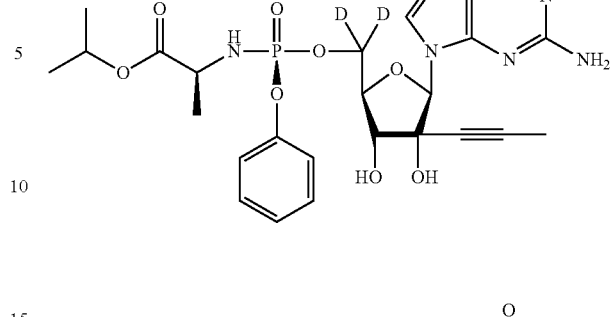
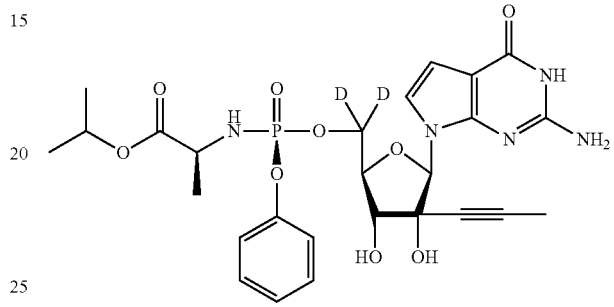
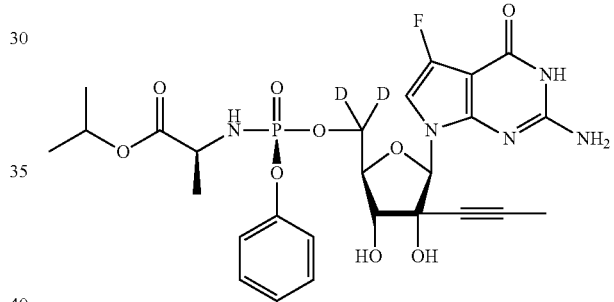
In exemplary embodiments, the compound is selected from:
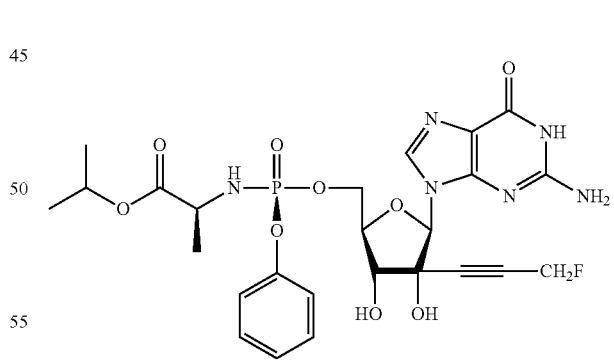
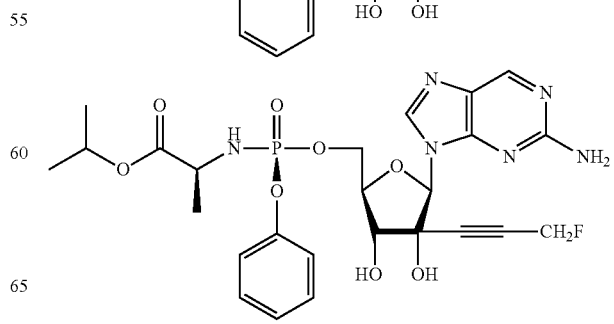

473
-continued
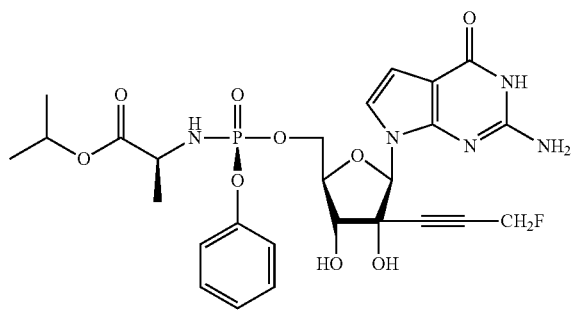
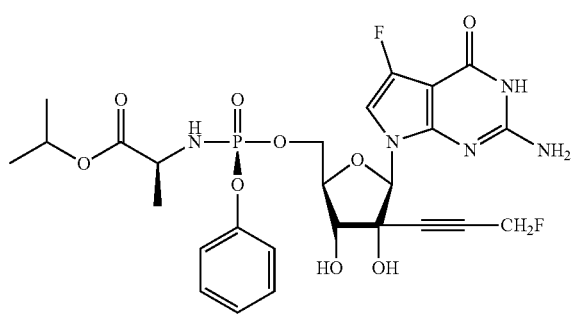
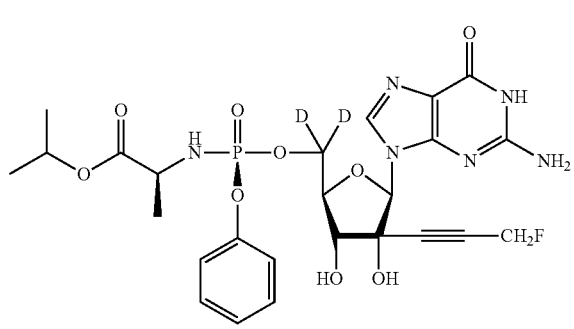
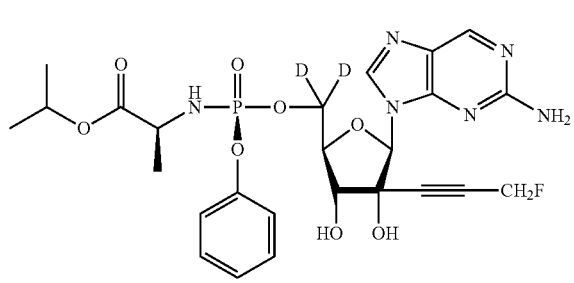
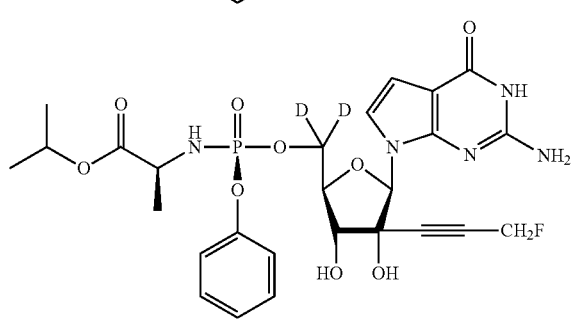
474
-continued
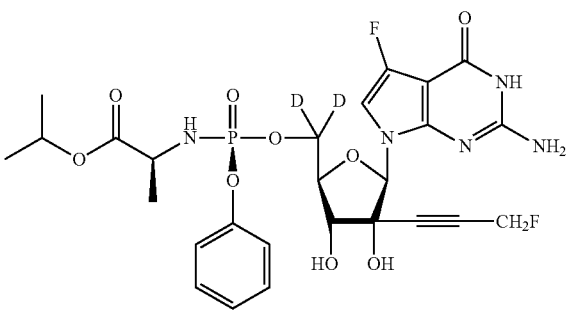
In exemplary embodiments, the compound is selected from:
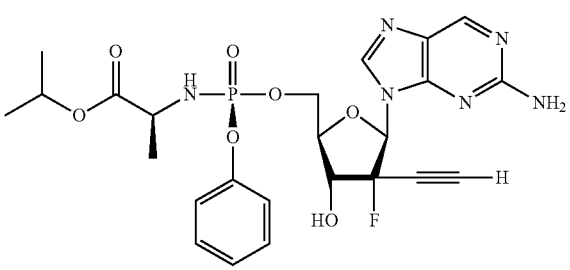
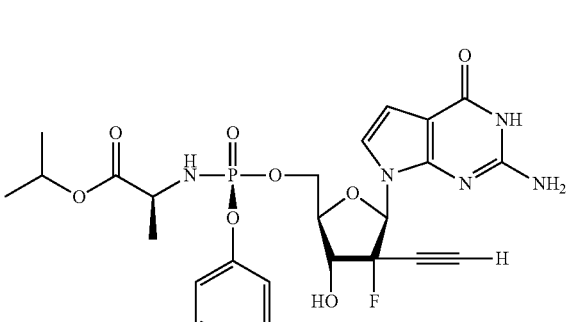
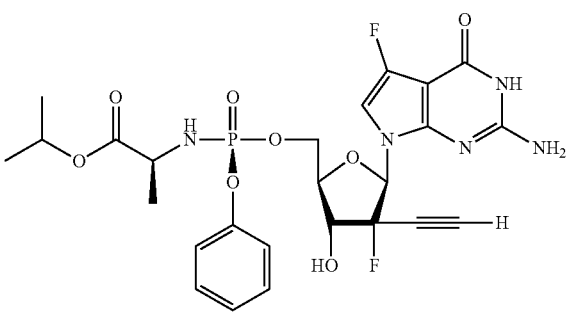
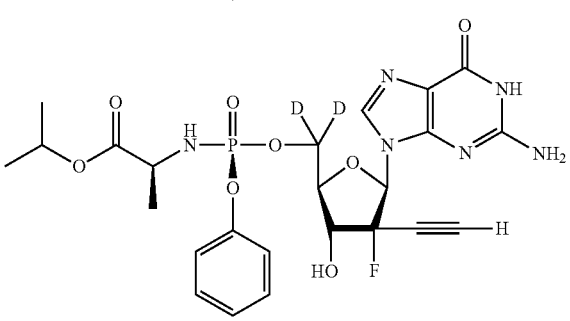

475
-continued
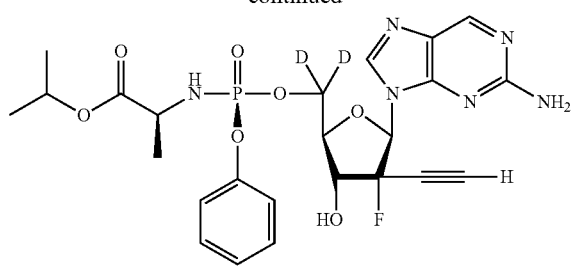
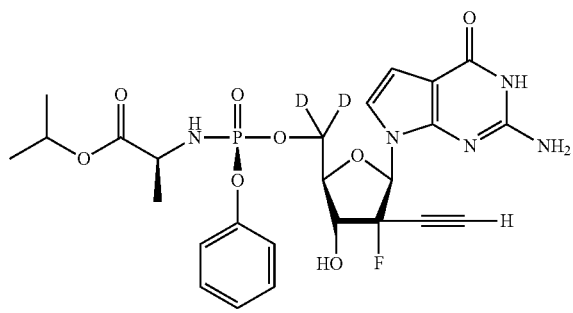
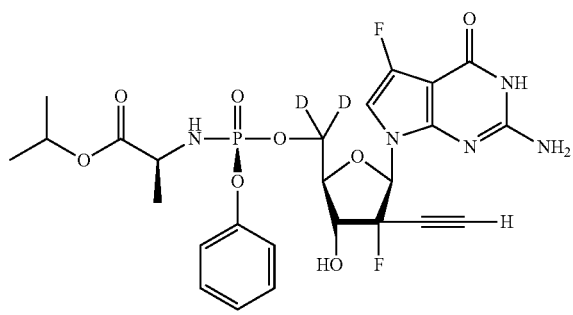
In exemplary embodiments, the compound is selected from:
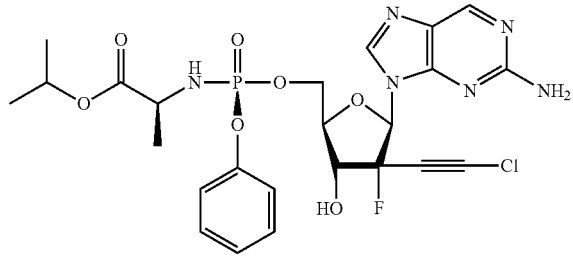
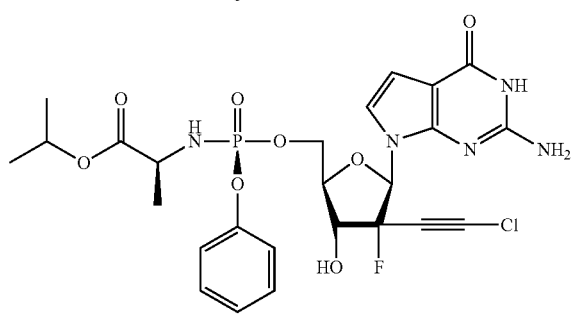
476
-continued
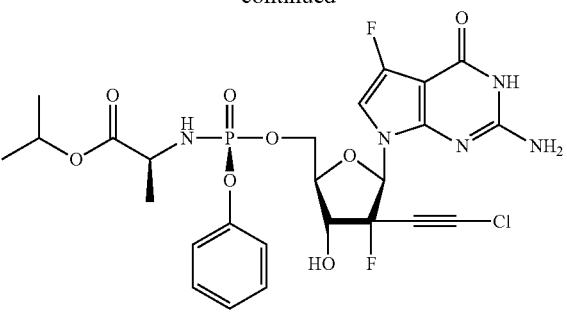
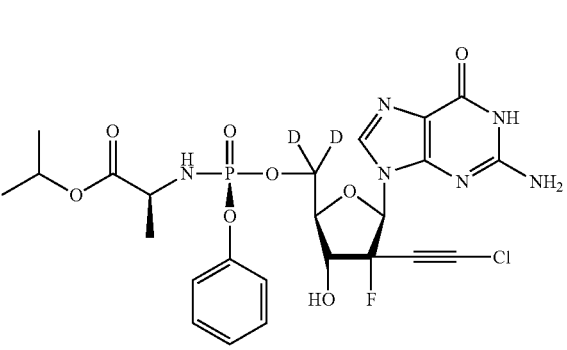
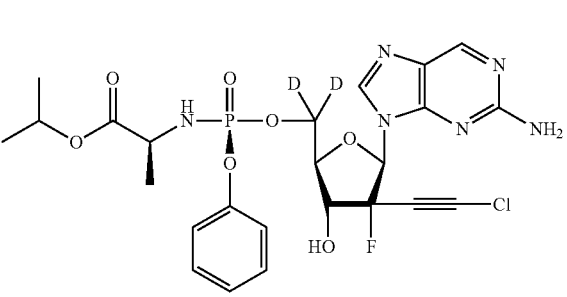
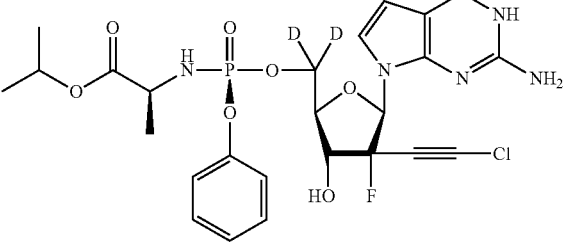
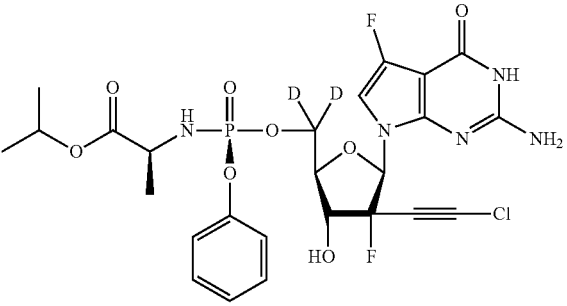

In exemplary embodiments, the compound is selected from:
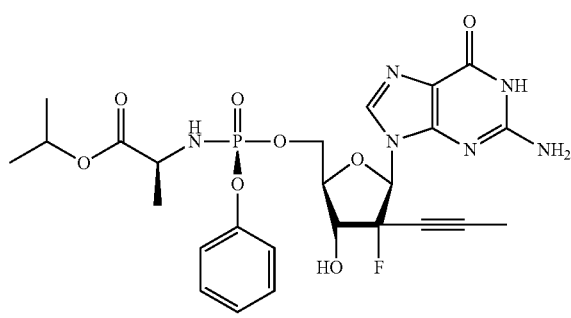
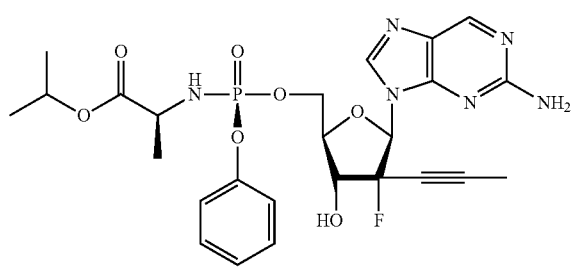
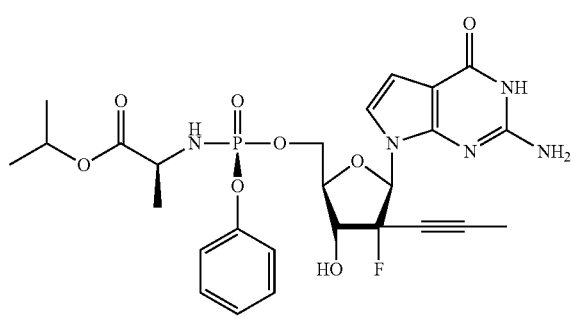
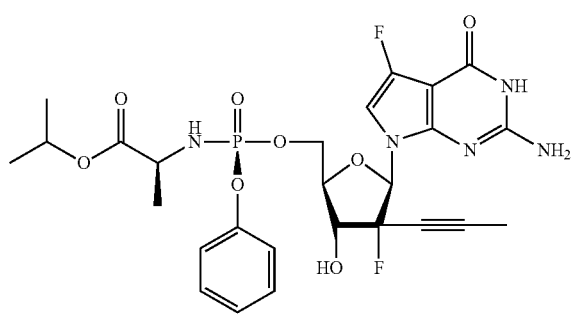
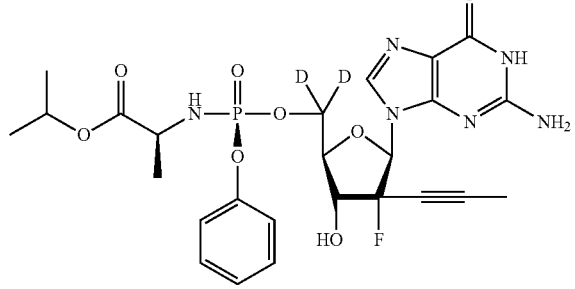
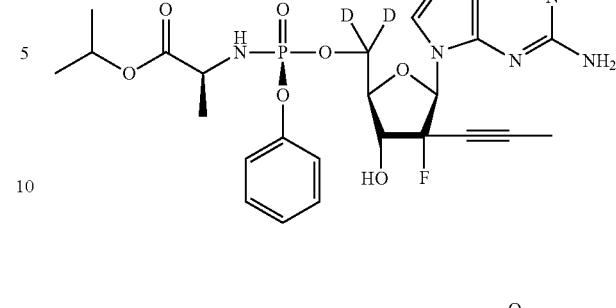
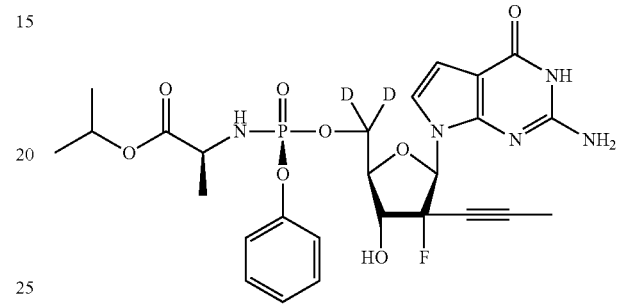
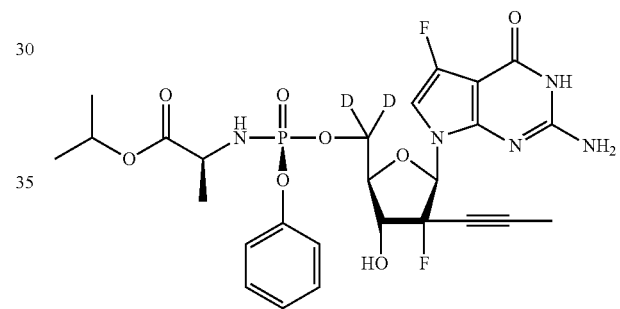
In exemplary embodiments, the compound is selected from:
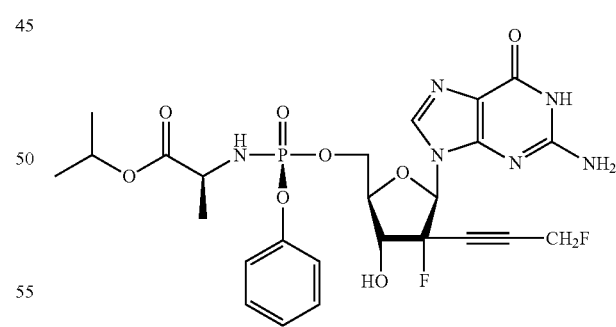
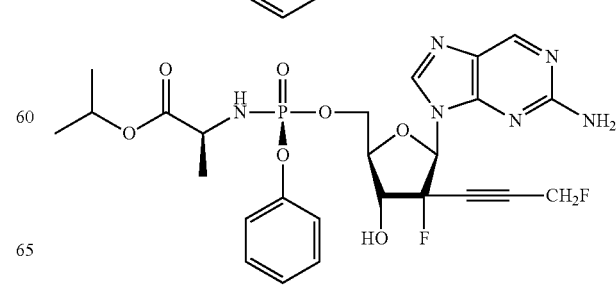

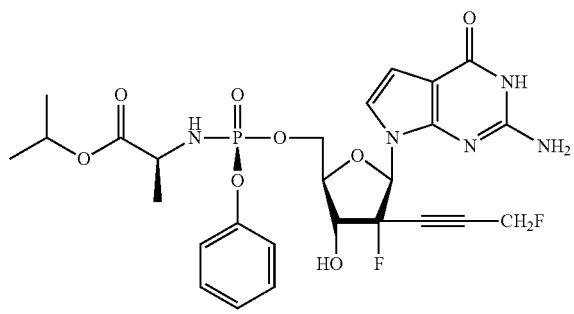
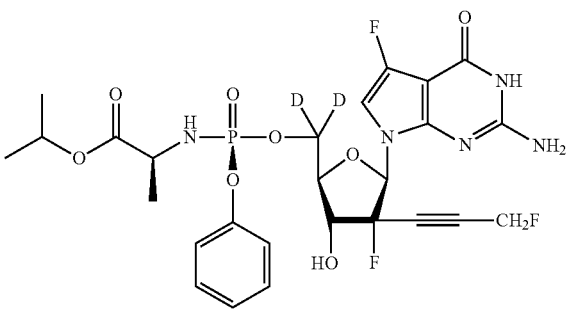
In exemplary embodiments, the compound is selected from:
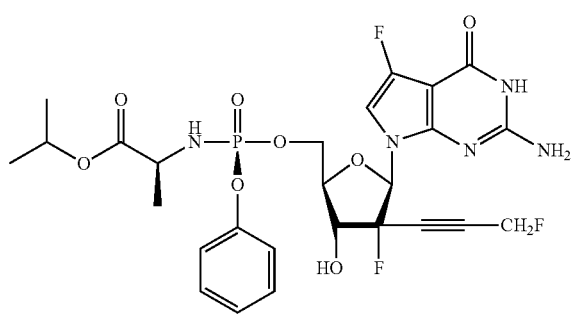
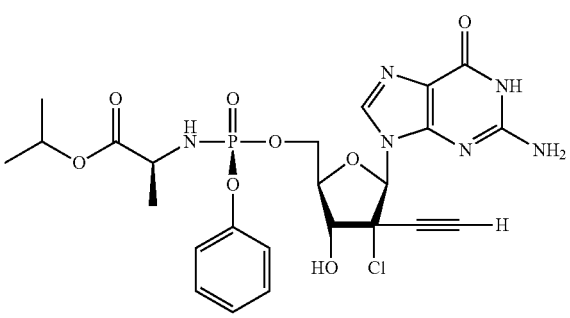
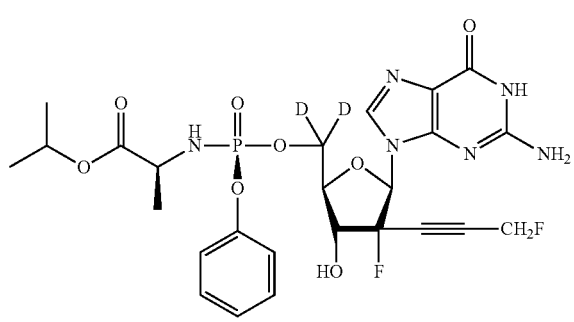
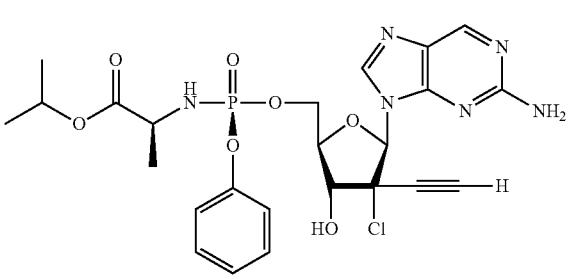
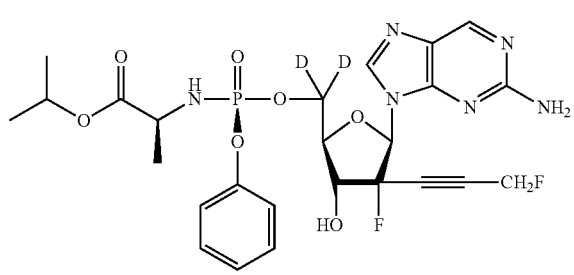
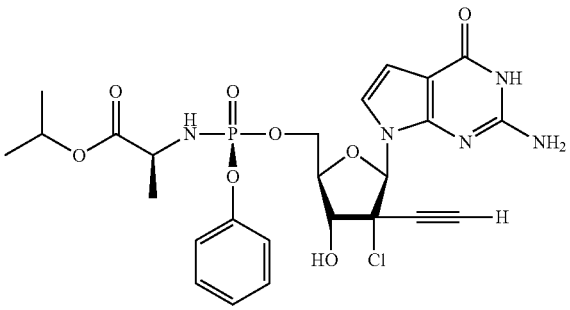
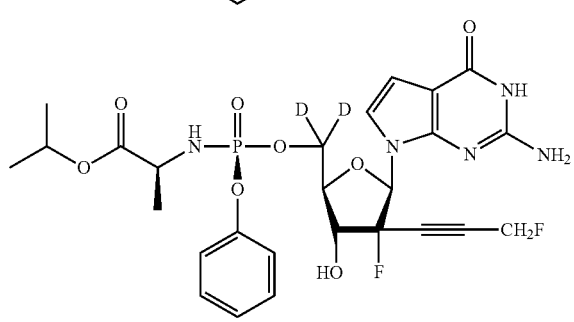
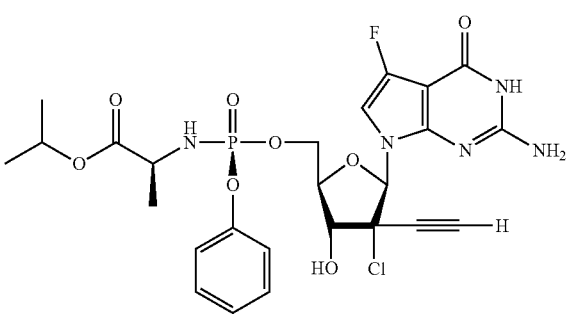

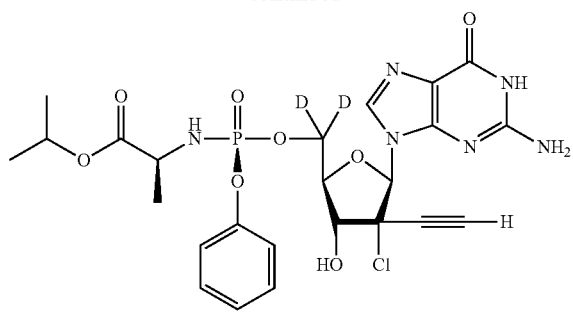
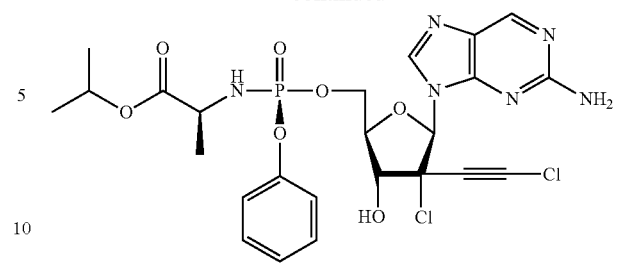
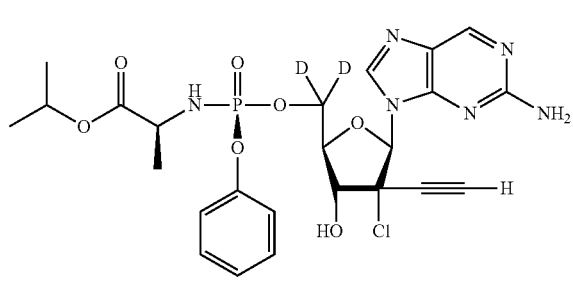
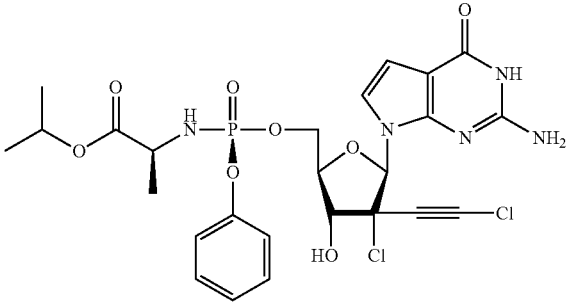
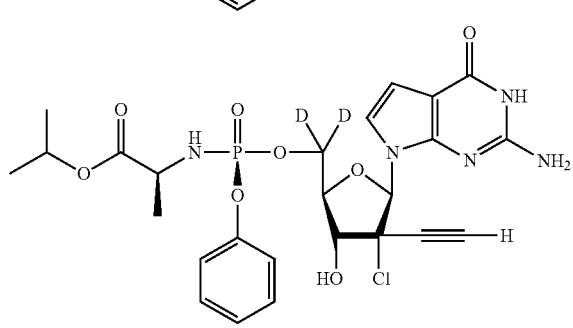
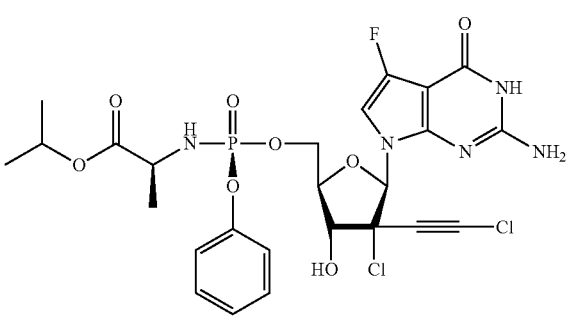
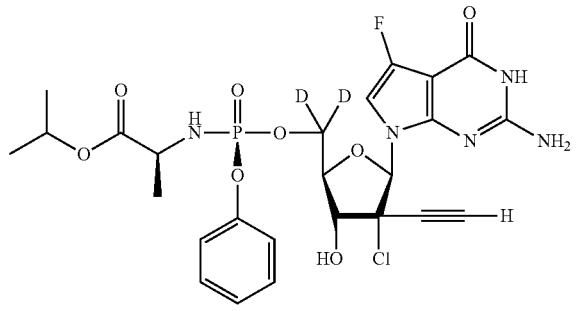
In exemplary embodiments, the compound is selected from:
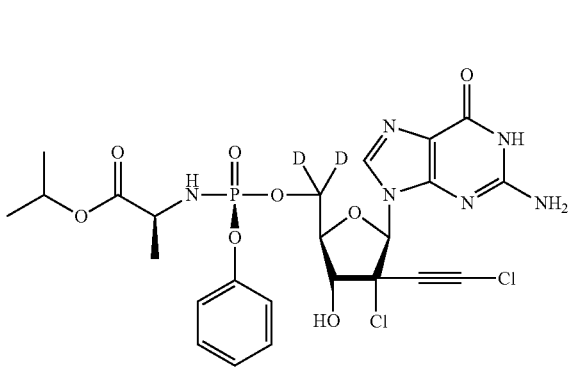
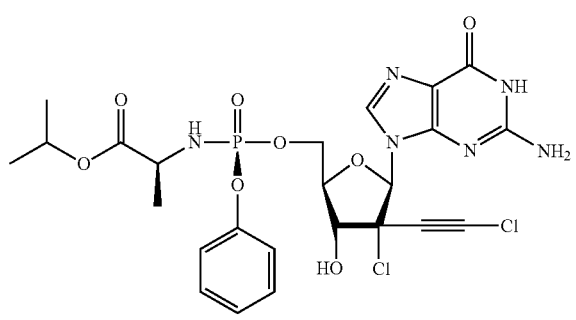
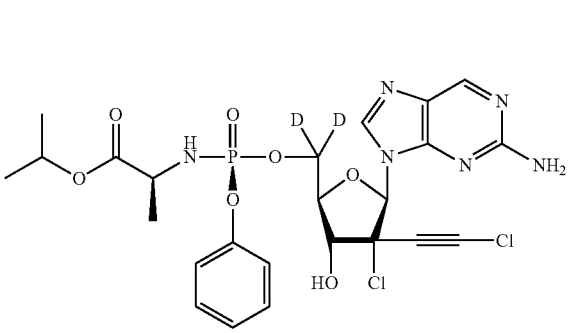

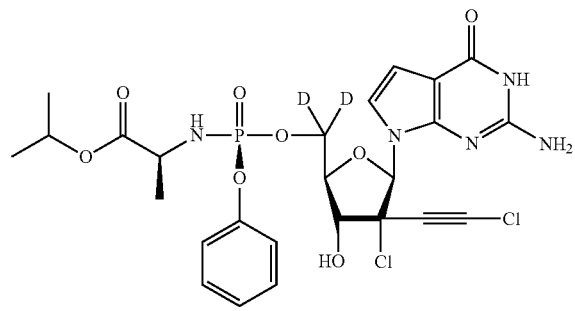
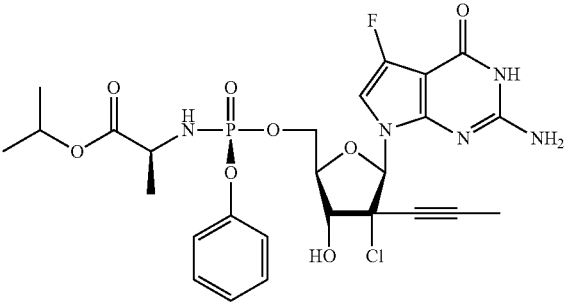
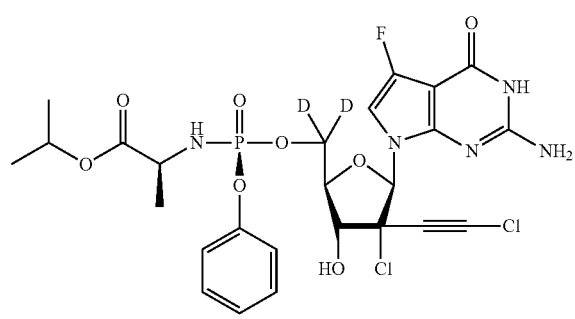
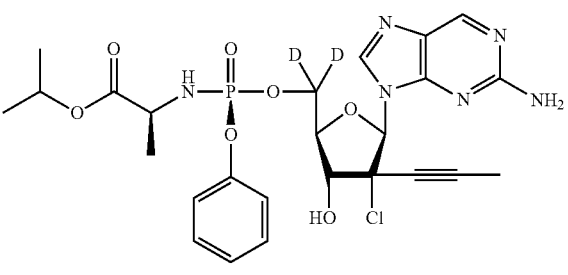
In exemplary embodiments, the compound is selected from:
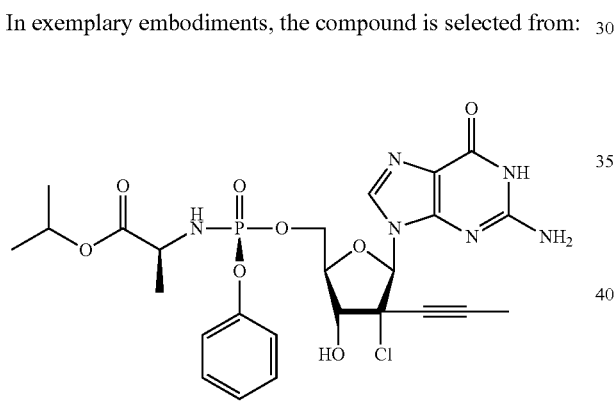
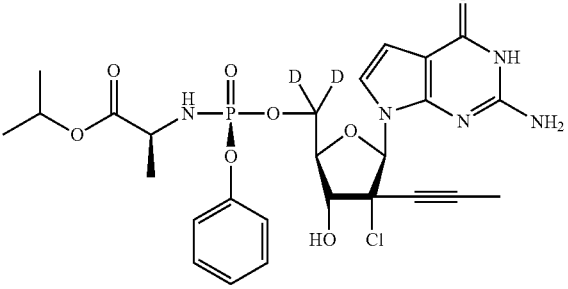
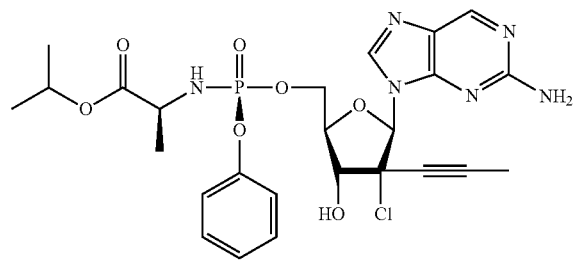
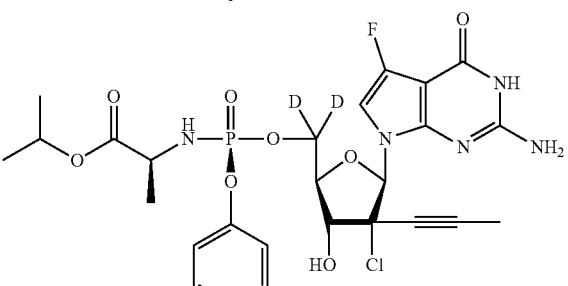
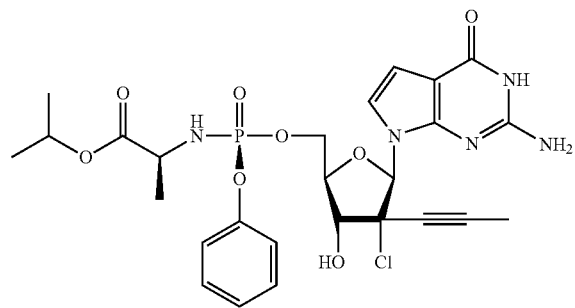

In exemplary embodiments, the compound is selected from:
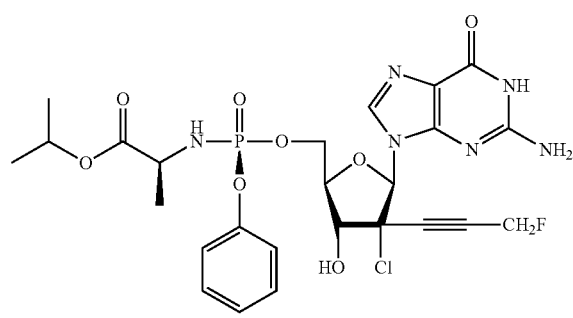
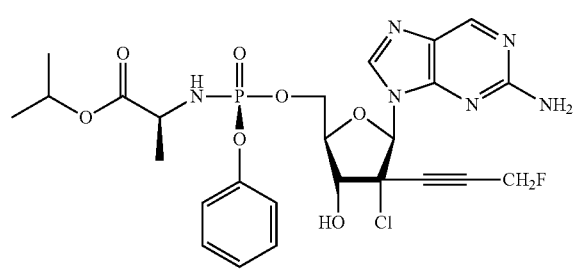
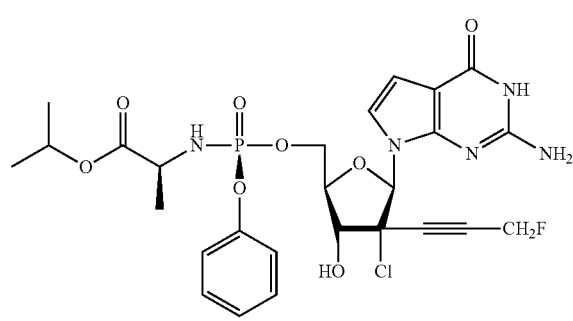
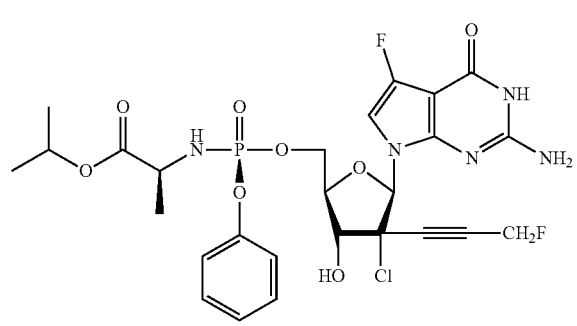
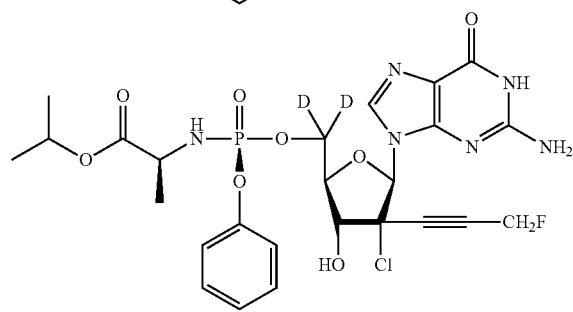
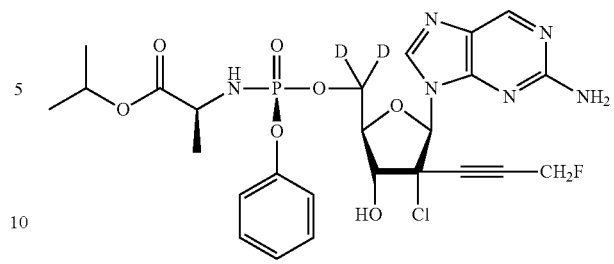
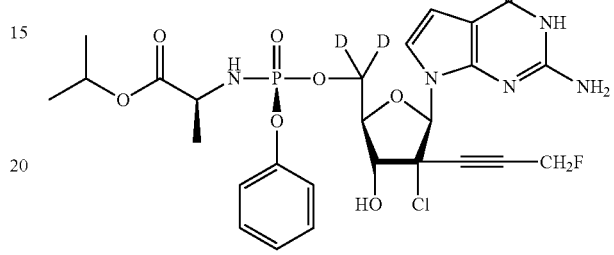
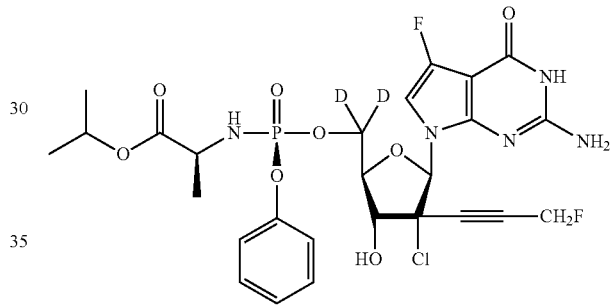
In exemplary embodiments, the compound is selected from:
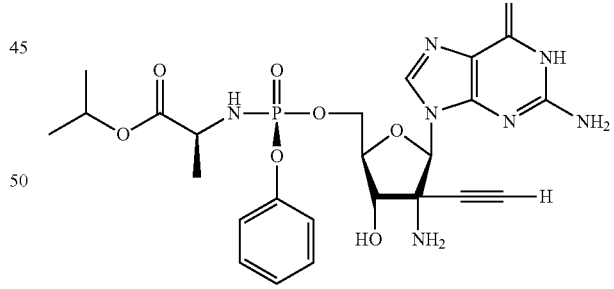
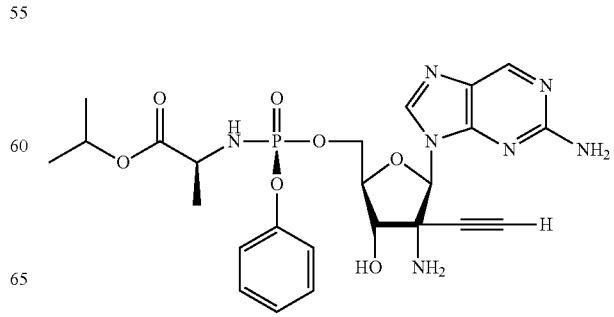

487
-continued
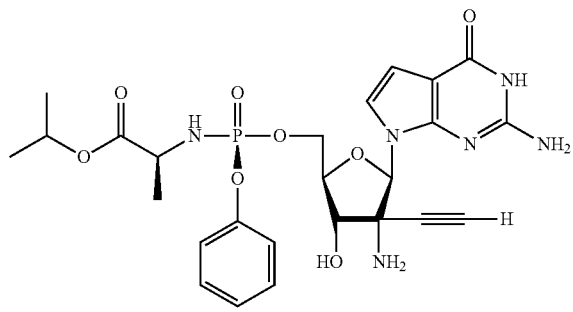
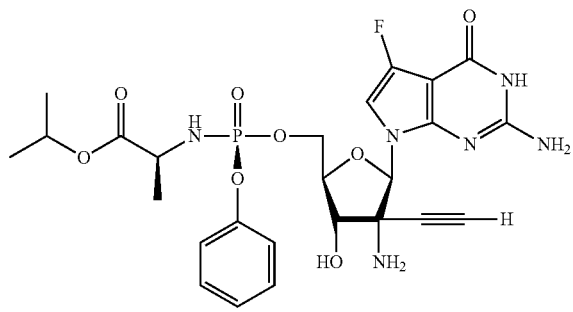
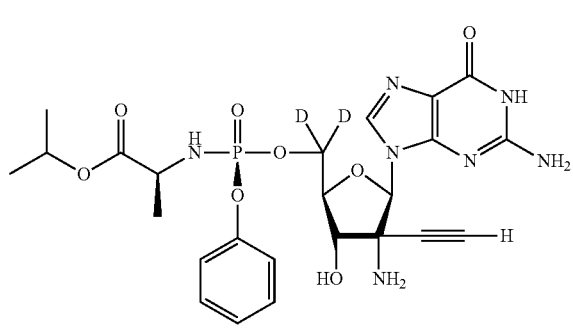
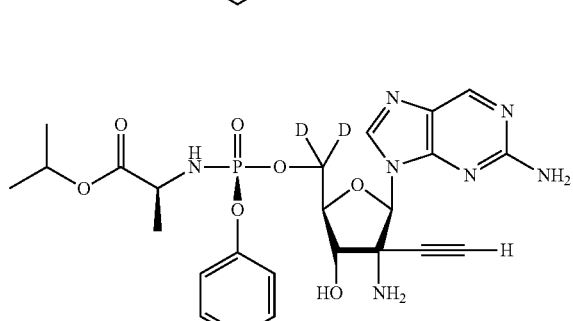
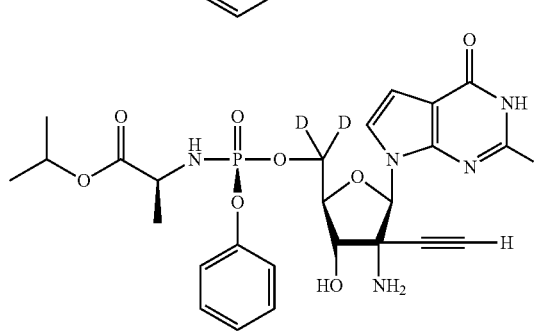
488
-continued
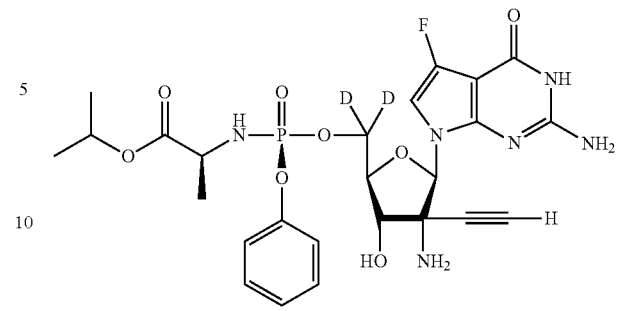
In exemplary embodiments, the compound is selected from:
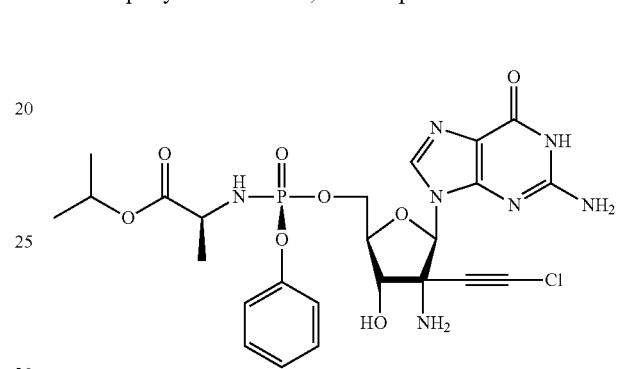
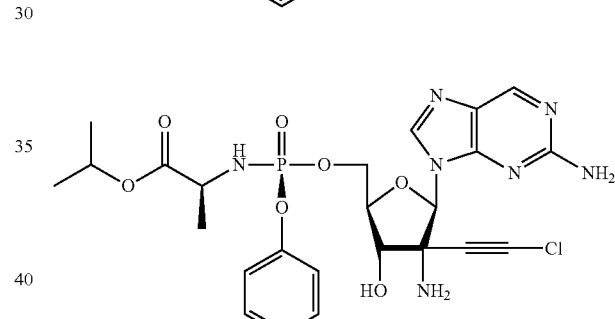
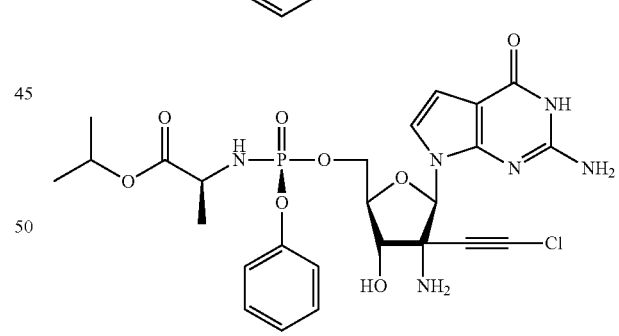
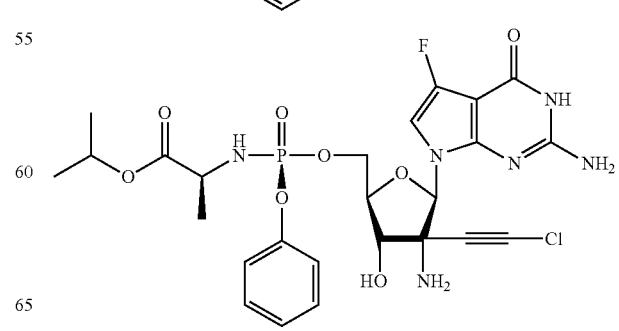

489
-continued
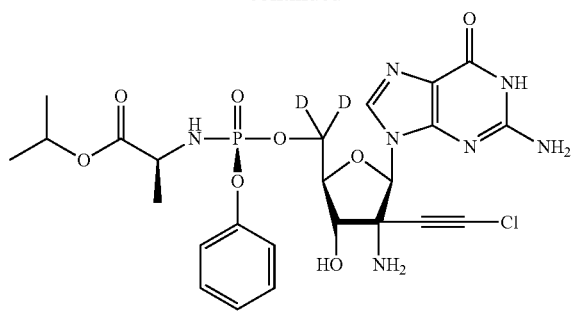
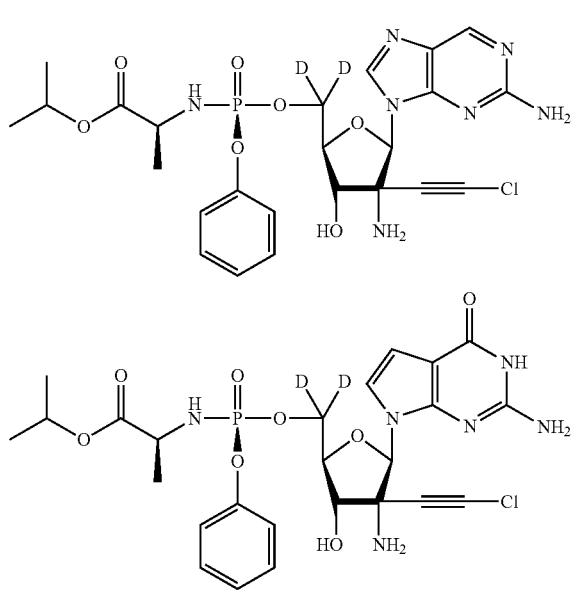
490
-continued
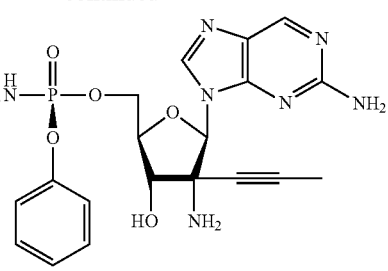
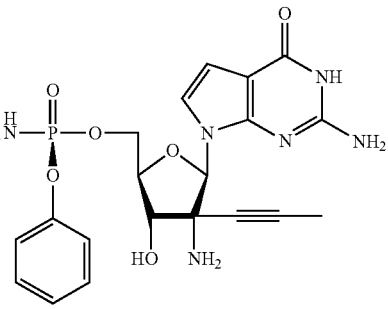

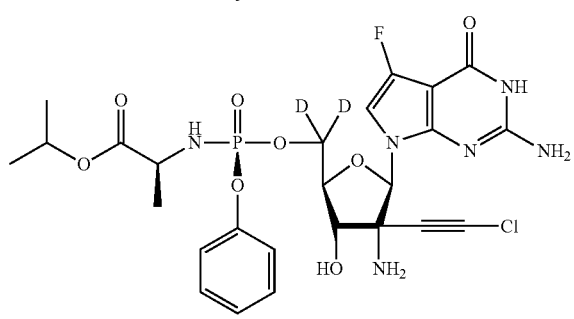
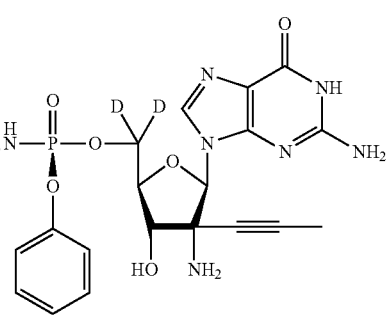
In exemplary embodiments, the compound is selected from:
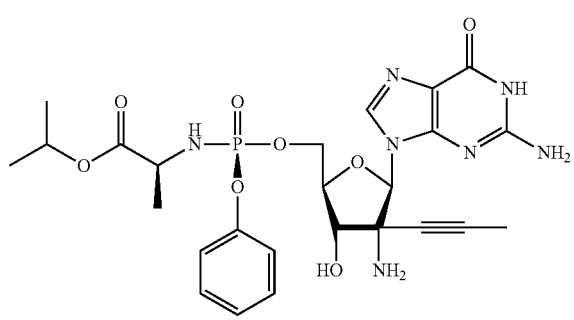
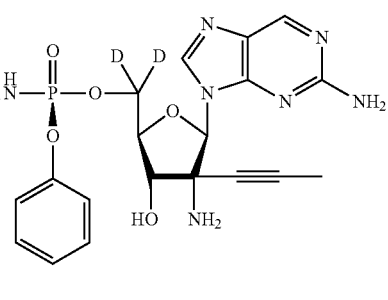

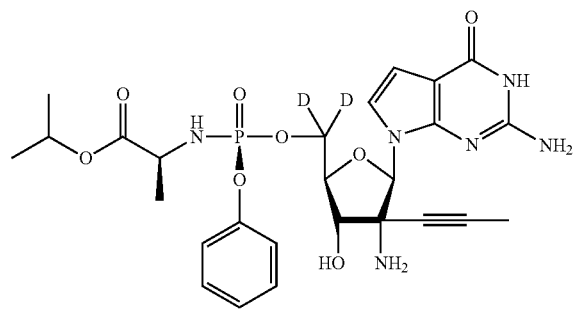
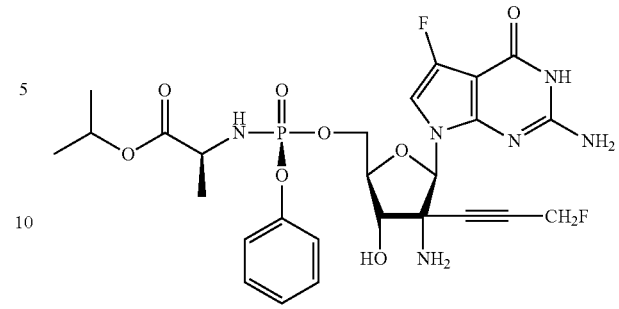
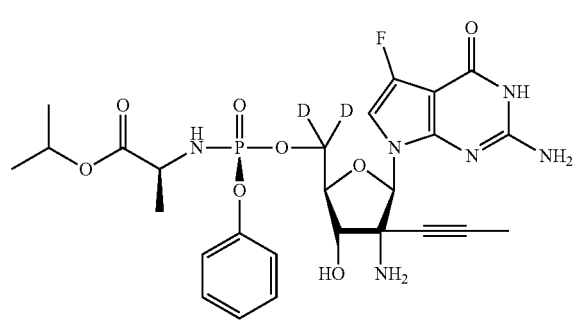
In exemplary embodiments, the compound is selected from:
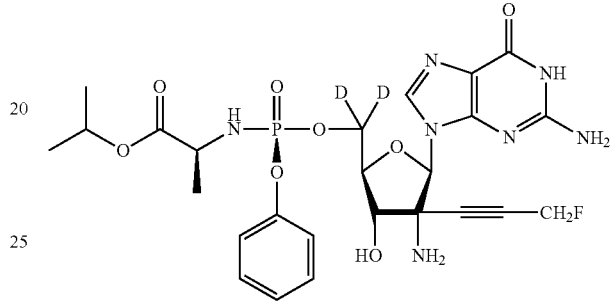
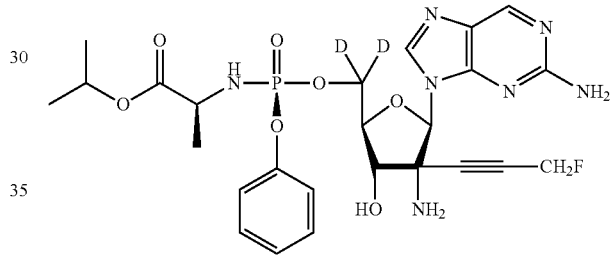
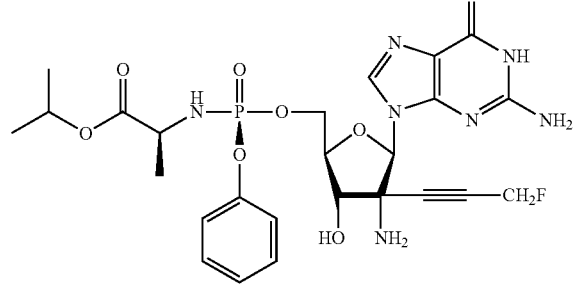
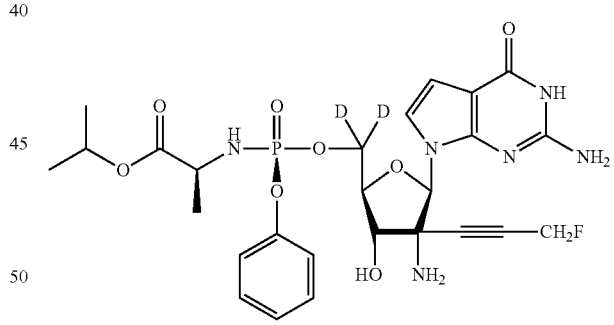
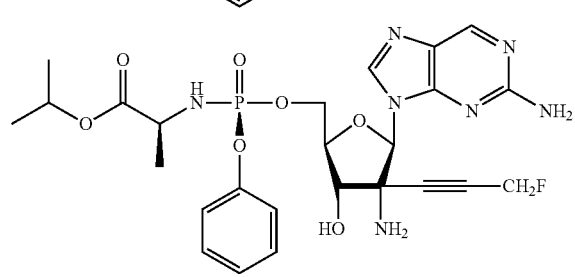
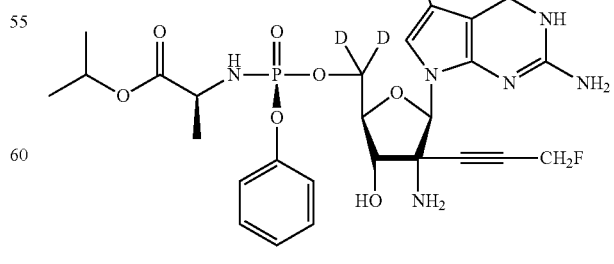
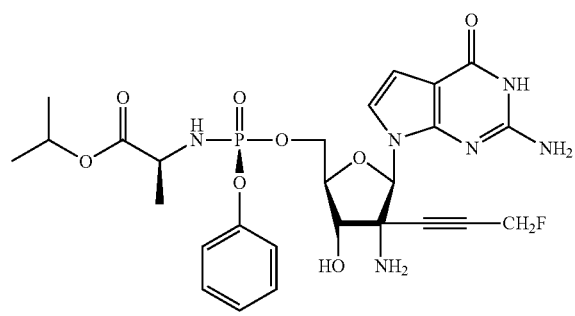
In certain embodiments, the present invention relates to compounds of the following formula:

Formula LIII

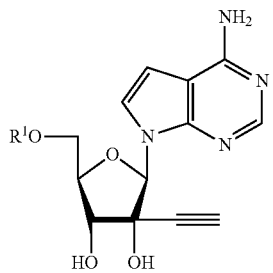

or pharmaceutically acceptable salts thereof wherein, R¹ is selected from one of the following formulae:

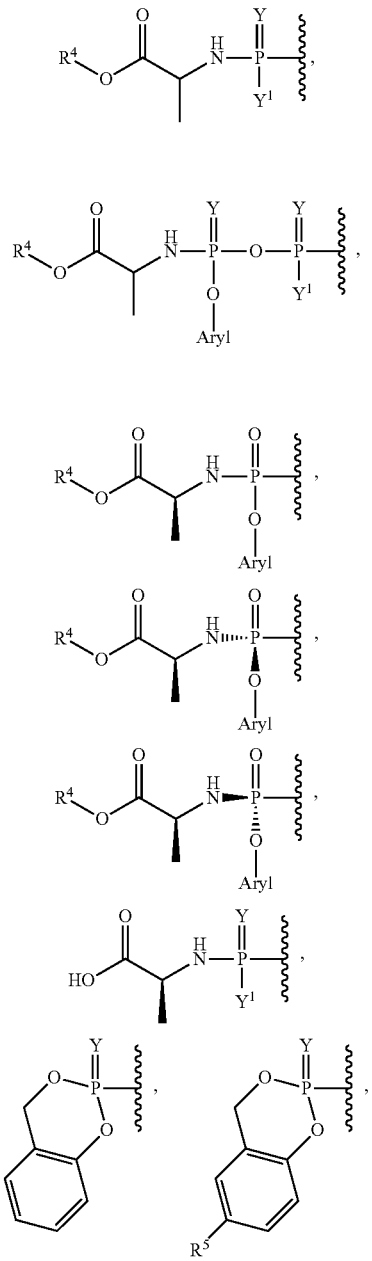

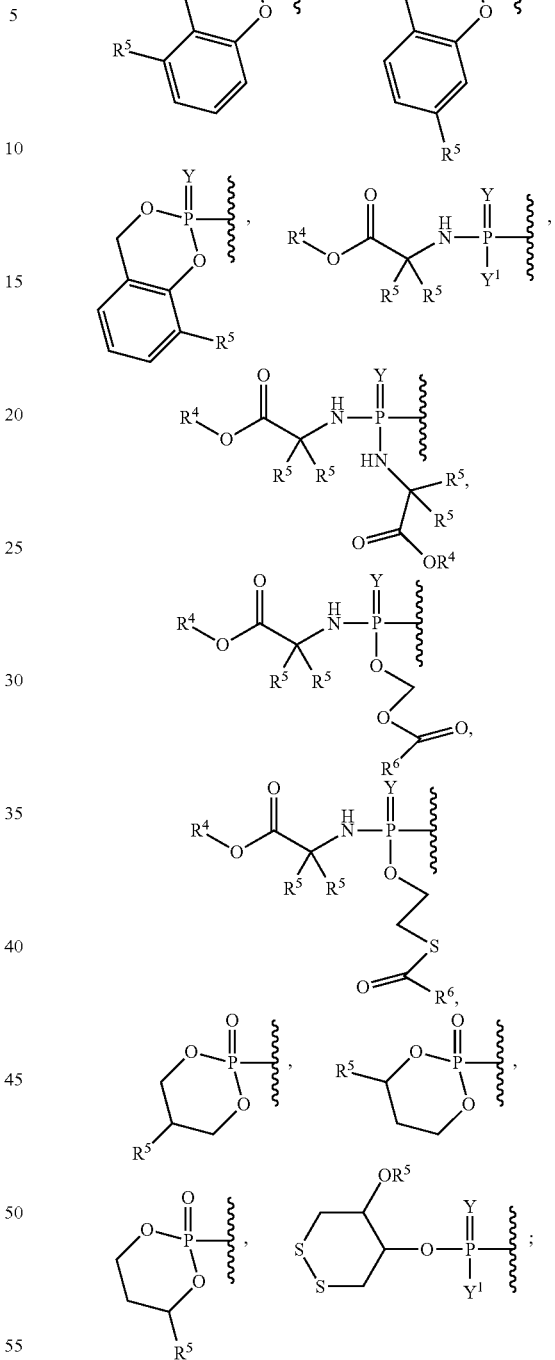

Y is O or S;
Y¹ is OH, OAryl, OAlkyl, or $BH_3^- M^+$;
Y² is OH or $BH_3^- M^+$;
Aryl is phenyl, 1-naphthyl, 2-naphthyl, aromatic, heteroaromatic, 4-substituted phenyl, 4-chlorophenyl, or 4-bromophenyl;
R⁴ is hydrogen, methyl, ethyl, isopropyl, cyclopentyl, cyclohexyl, neopentyl, benzyl, alkyl, branched alkyl, cycloalkyl, or lipid;

$R^5$ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;

$R^6$ is methyl, ethyl, tert-butyl, $C_{1-22}$ alkoxy, $C_{1-22}$ alkyl, branched alkyl, cycloalkyl, aryl, substituted aryl, or alkyoxy.

In certain embodiments, the present invention relates to compounds of the following formula:

Formula LIV

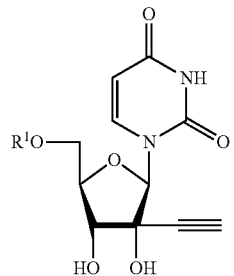

or pharmaceutically acceptable salts thereof wherein, $R^1$ is selected from one of the following formulae:

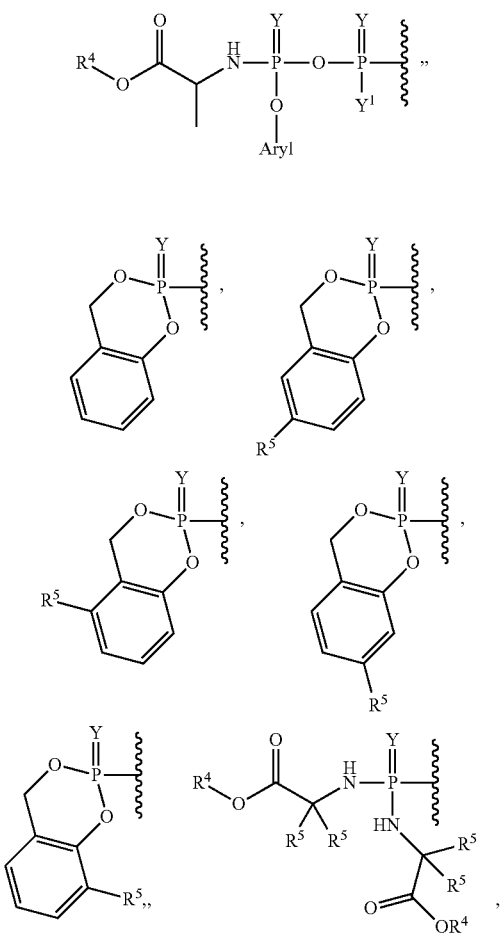

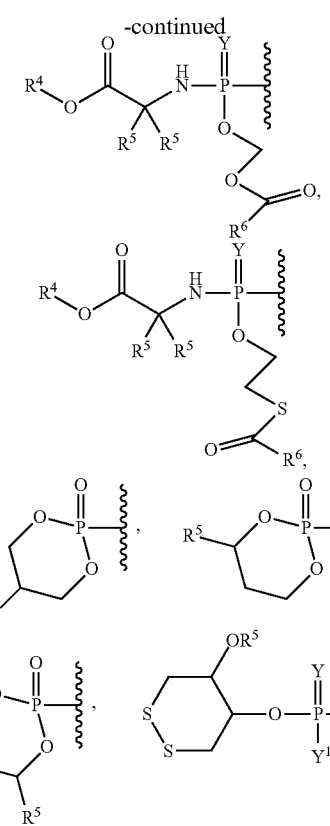

Y is O or S;
$Y^1$ is OH, OAryl, OAlkyl, or $BH_3^-M^+$;
$Y^2$ is OH or $BH_3^-M^+$;
Aryl is phenyl, 1-naphthyl, 2-naphthyl, aromatic, heteroaromatic, 4-substituted phenyl, 4-chlorophenyl, or 4-bromophenyl;
$R^4$ is hydrogen, methyl, ethyl, isopropyl, cyclopentyl, cyclohexyl, neopentyl, benzyl, alkyl, branched alkyl, cycloalkyl, or lipid;
$R^5$ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;
$R^6$ is methyl, ethyl, tert-butyl, $C_{1-22}$ alkoxy, $C_{1-22}$ alkyl, branched alkyl, cycloalkyl, aryl, substituted aryl, or alkyoxy.

In certain embodiments, the present invention relates to compounds of the following formula:

Formula LV

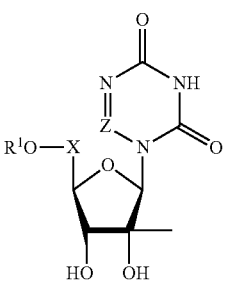

or pharmaceutically acceptable salts thereof wherein,
X is $OCH_2$, OCHMe, $OCMe_2$, OCHF, $OCF_2$, or $OCD_2$;
Z is N or $CR^8$;

$R^1$ is selected from H or from one of the following formulae:

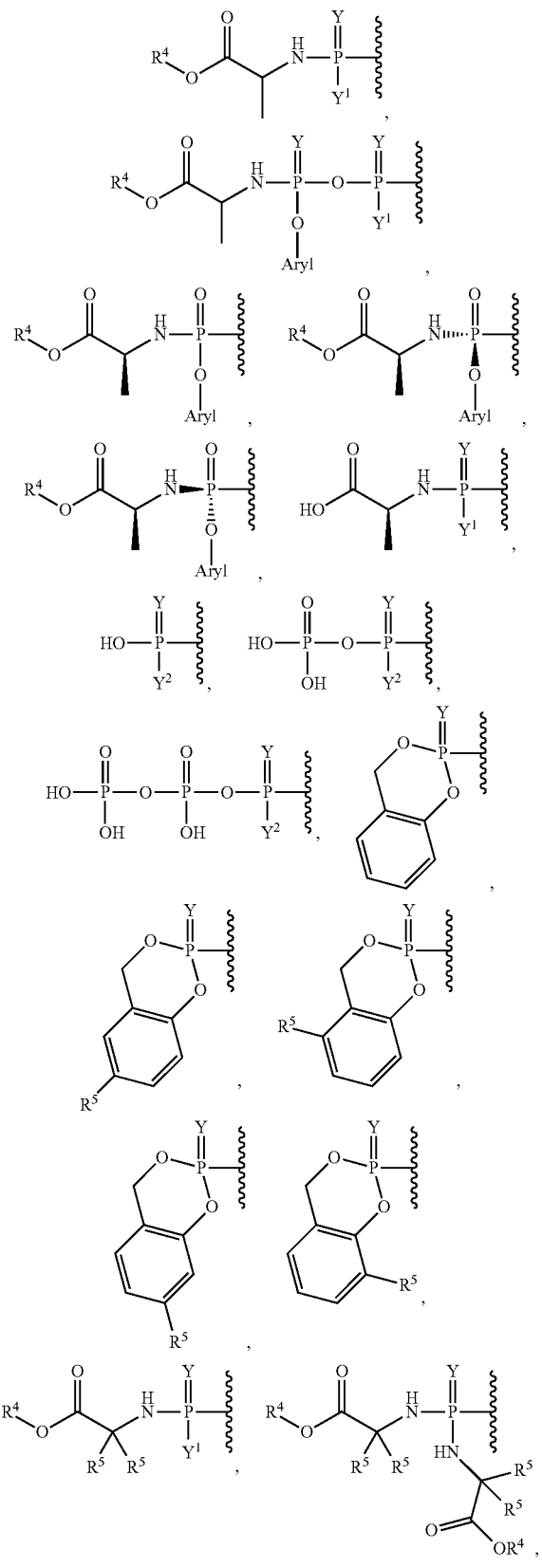

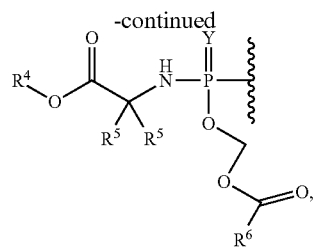

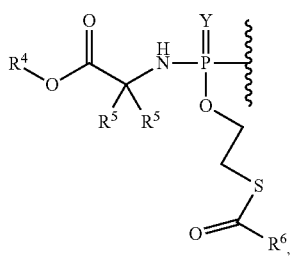

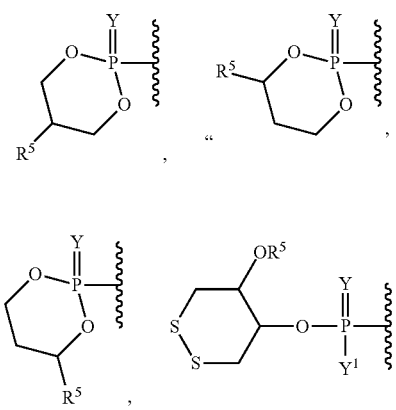

Y is O or S;

$Y^1$ is OH, OAryl, OAlkyl, or $BH_3^-M^+$;

$Y^2$ is OH or $BH_3^-M^+$;

Aryl is phenyl, 1-naphthyl, 2-naphthyl, aromatic, heteroaromatic, 4-substituted phenyl, 4-chlorophenyl, or 4-bromophenyl;

$R^4$ is hydrogen, methyl, ethyl, isopropyl, cyclopentyl, cyclohexyl, neopentyl, benzyl, alkyl, branched alkyl, cycloalkyl, or lipid;

$R^5$ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;

$R^6$ is methyl, ethyl, tert-butyl, $C_{1-22}$ alkoxy, $C_{1-22}$ alkyl, branched alkyl, cycloalkyl, aryl, substituted aryl, or alkyoxy;

$R^8$ is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano.

In certain embodiments, the present invention relates to compounds of the following formula:

Formula LVI
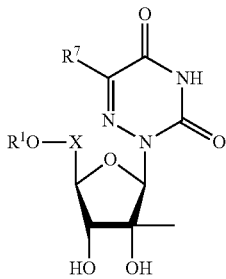
or pharmaceutically acceptable salts thereof wherein,
X is OCHMe, OCMe$_2$, OCHF, OCF$_2$, or OCD$_2$;
R$^1$ is selected from H or from one of the following formulae:
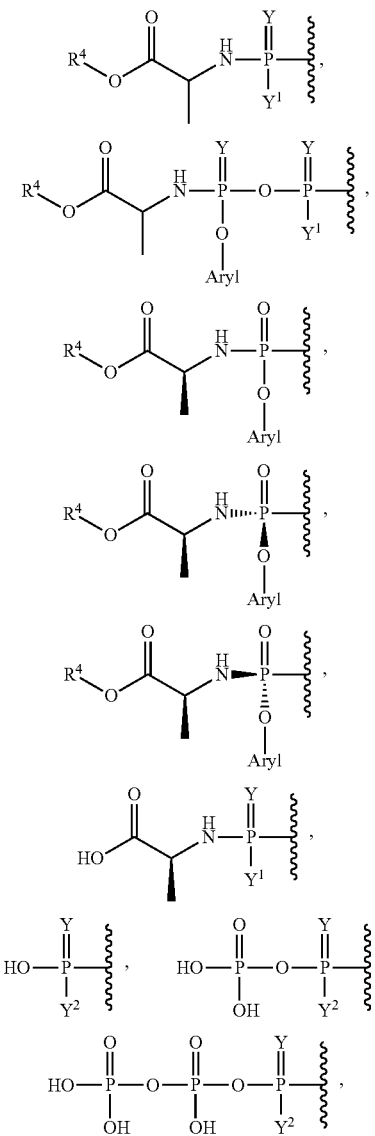
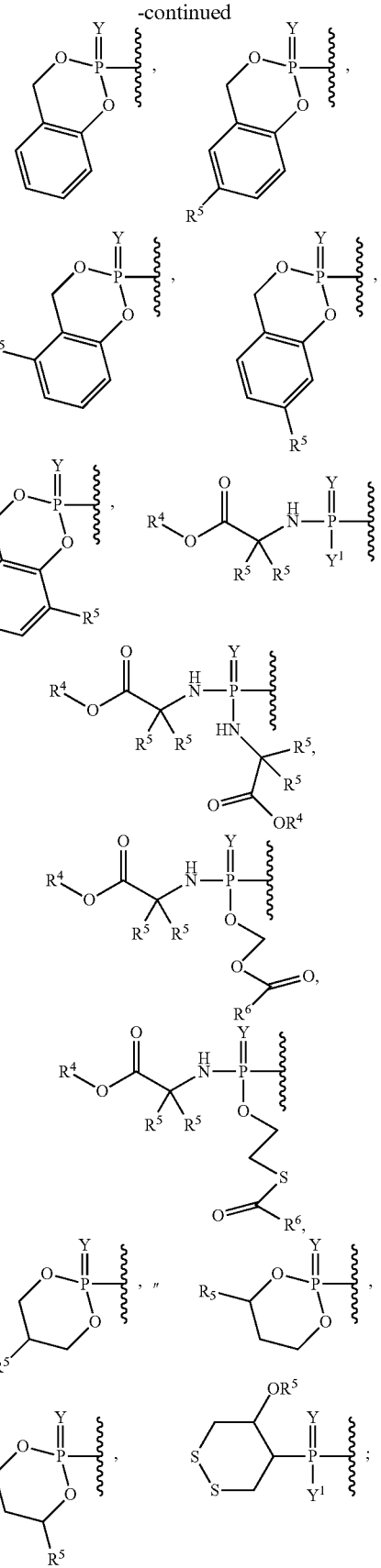

Y is O or S;

Y$^1$ is OH, OAryl, OAlkyl, or BH$_3^-$M$^+$;

Y$^2$ is OH or BH$_3^-$M$^+$;

Aryl is phenyl, 1-naphthyl, 2-naphthyl, aromatic, heteroaromatic, 4-substituted phenyl, 4-chlorophenyl, or 4-bromophenyl;

R$^4$ is hydrogen, methyl, ethyl, isopropyl, cyclopentyl, cyclohexyl, neopentyl, benzyl, alkyl, branched alkyl, cycloalkyl, or lipid;

R$^5$ is hydrogen, deuterium, hydroxyl, cyano, azido, amino, substituted amino, aryl, heteroaryl, substituted aryl, lipid, C$_{1-22}$ alkoxy, C$_{1-22}$ alkyl, C$_{2-22}$ alkenyl, C$_{2-22}$ alkynyl, or substituted heteroaryl;

R$^6$ is methyl, ethyl, tert-butyl, C$_{1-22}$ alkoxy, C$_{1-22}$ alkyl, branched alkyl, cycloalkyl, aryl, substituted aryl, or alkyoxy;

R$^7$ is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano.

In certain embodiments, the present invention relates to compounds of the following formula:

Formula LVII

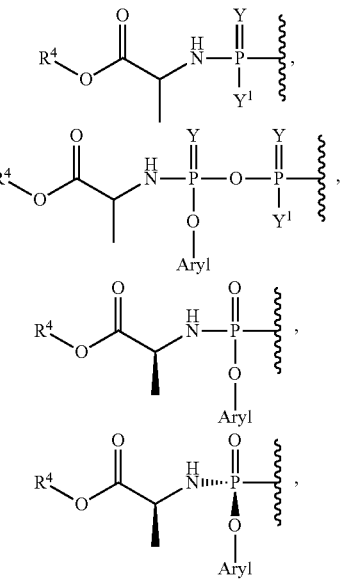

or pharmaceutically acceptable salts thereof wherein,

R$^1$ is selected from H or from one of the following formulae:

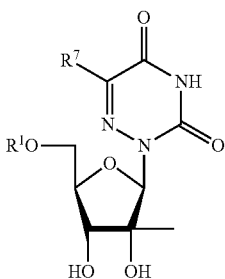

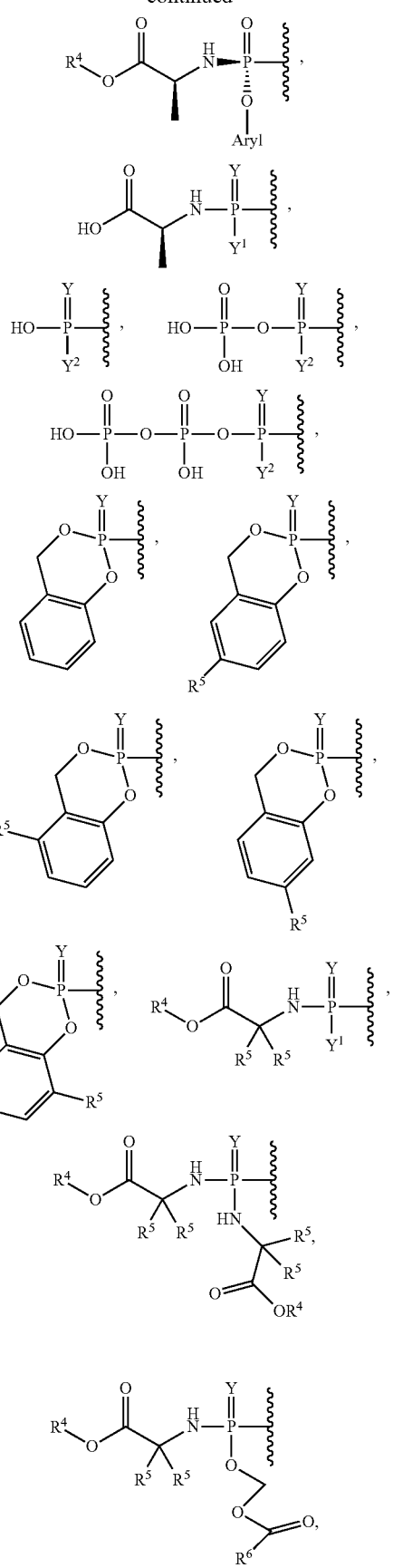

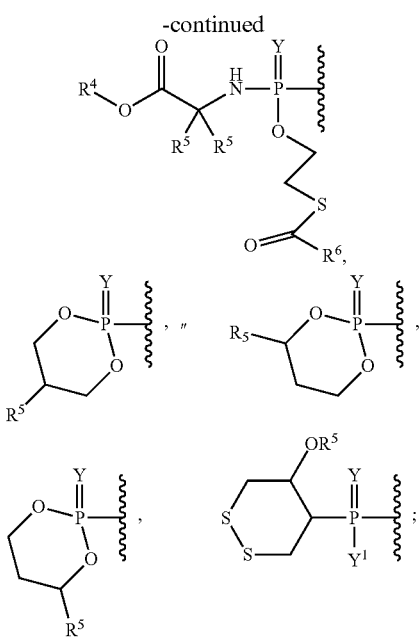

Y is O or S;
Y¹ is OH, OAryl, OAlkyl, or $BH_3^-M^+$;
Y² is OH or $BH_3^-M^+$;
Aryl is phenyl, 1-naphthyl, 2-naphthyl, aromatic, heteroaromatic, 4-substituted phenyl, 4-chlorophenyl, or 4-bromophenyl;
$R^4$ is hydrogen, methyl, ethyl, isopropyl, cyclopentyl, cyclohexyl, neopentyl, benzyl, alkyl, branched alkyl, cycloalkyl, or lipid;
$R^5$ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;
$R^6$ is methyl, ethyl, tert-butyl, $C_{1-22}$ alkoxy, $C_{1-22}$ alkyl, branched alkyl, cycloalkyl, aryl, substituted aryl, or alkyoxy;
$R^7$ is D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano.

In certain embodiments, the present invention relates to compounds of the following formula:

Formula LVIII

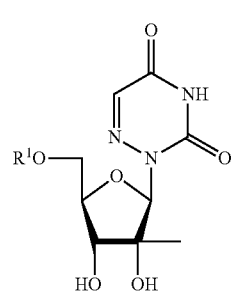

or pharmaceutically acceptable salts thereof wherein, $R^1$ is selected from one of the following formulae:

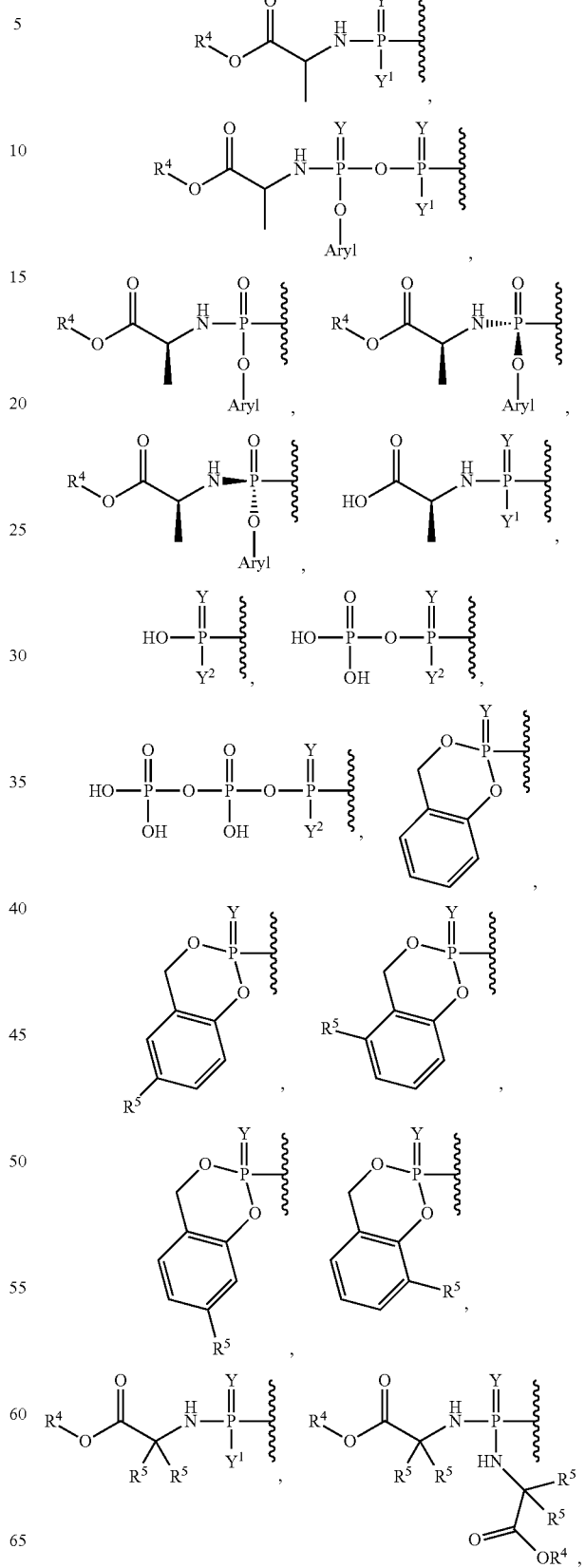

-continued

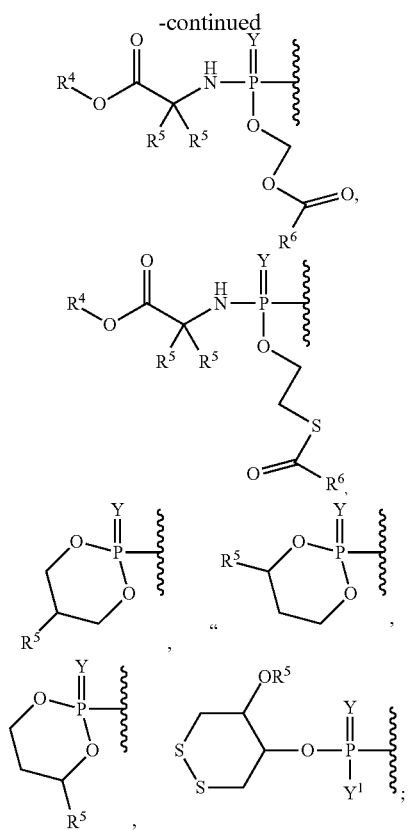

Y is O or S;
Y¹ is OH, OAryl, OAlkyl, or $BH_3^-M^+$;
Y² is OH or $BH_3^-M^+$;
Aryl is phenyl, 1-naphthyl, 2-naphthyl, aromatic, heteroaromatic, 4-substituted phenyl, 4-chlorophenyl, or 4-bromophenyl;
$R^4$ is hydrogen, methyl, ethyl, isopropyl, cyclopentyl, cyclohexyl, neopentyl, benzyl, alkyl, branched alkyl, cycloalkyl, or lipid;
$R^5$ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;
$R^6$ is methyl, ethyl, tert-butyl, $C_{1-22}$ alkoxy, $C_{1-22}$ alkyl, branched alkyl, cycloalkyl, aryl, substituted aryl, or alkyoxy.

In certain embodiments, the present invention relates to compounds of the following formula:

Formula LIX

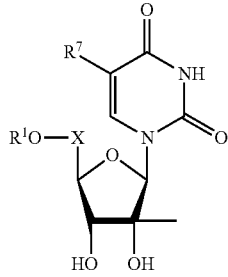

or pharmaceutically acceptable salts thereof wherein,

X is OCHMe, $OCMe_2$, OCHF, or $OCF_2$;
$R^1$ is selected from H or from one of the following formulae:

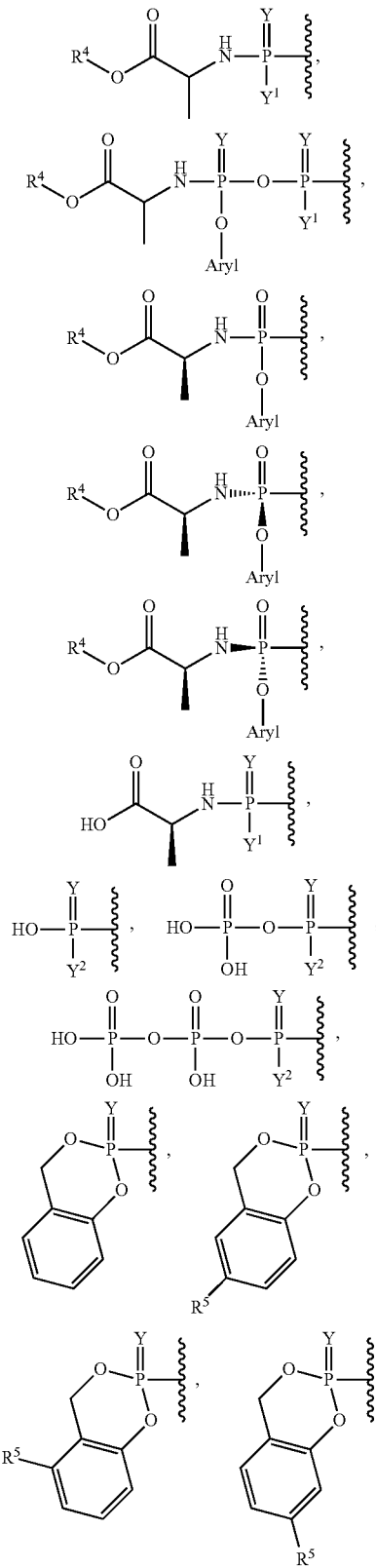

-continued

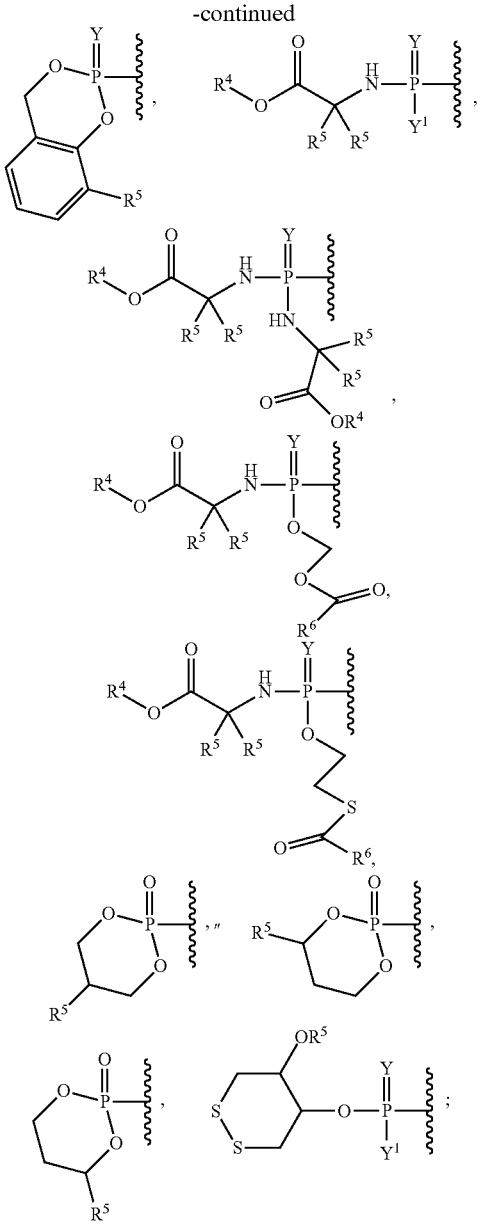

Y is O or S;
Y¹ is OH, OAryl, OAlkyl, or $BH_3^-M^+$;
Y² is OH or $BH_3^-M^+$;
Aryl is phenyl, 1-naphthyl, 2-naphthyl, aromatic, heteroaromatic, 4-substituted phenyl, 4-chlorophenyl, or 4-bromophenyl;
$R^4$ is hydrogen, methyl, ethyl, isopropyl, cyclopentyl, cyclohexyl, neopentyl, benzyl, alkyl, branched alkyl, cycloalkyl, or lipid;
$R^5$ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;
$R^6$ is methyl, ethyl, tert-butyl, $C_{1-22}$ alkoxy, $C_{1-22}$ alkyl, branched alkyl, cycloalkyl, aryl, substituted aryl, or alkyoxy;
$R^7$ is D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano.

In certain embodiments, the present invention relates to compounds of the following formula:

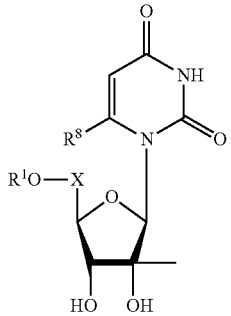

Formula LX or pharmaceutically acceptable salts thereof wherein,
X is OCHMe, OCMe₂, OCHF, OCF₂, or CD₂;
$R^1$ is selected from H or from one of the following formulae:

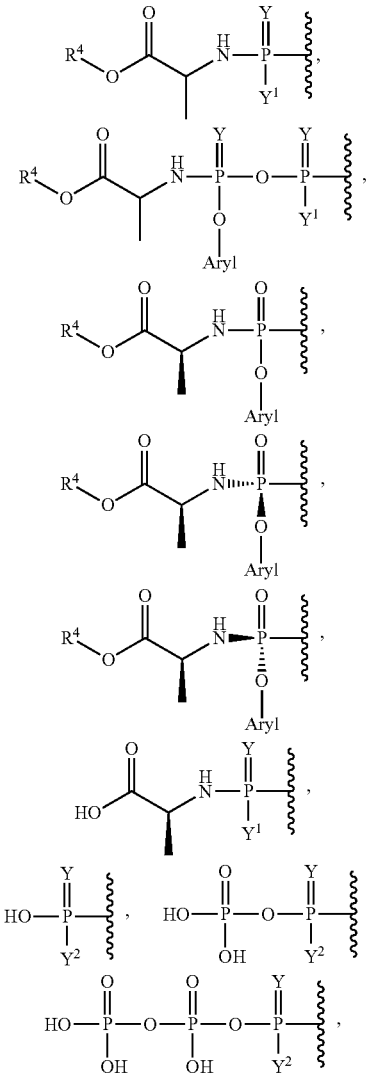

Y is O or S;
Y¹ is OH, OAryl, OAlkyl, or $BH_3^-M^+$;
Y² is OH or $BH_3^-M^+$;
Aryl is phenyl, 1-naphthyl, 2-naphthyl, aromatic, heteroaromatic, 4-substituted phenyl, 4-chlorophenyl, or 4-bromophenyl;
R⁴ is hydrogen, methyl, ethyl, isopropyl, cyclopentyl, cyclohexyl, neopentyl, benzyl, alkyl, branched alkyl, cycloalkyl, or lipid;
R⁵ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;
R⁶ is methyl, ethyl, tert-butyl, $C_{1-22}$ alkoxy, $C_{1-22}$ alkyl, branched alkyl, cycloalkyl, aryl, substituted aryl, or alkyoxy;
R⁸ is D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano.

In certain embodiments, the present invention relates to compounds of the following formula:

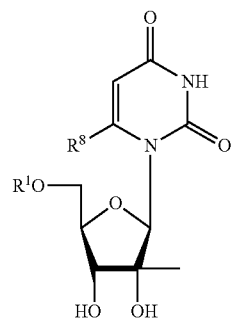

Formula LXI or pharmaceutically acceptable salts thereof wherein,
R¹ is selected from H or from one of the following formulae:

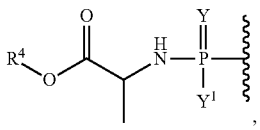

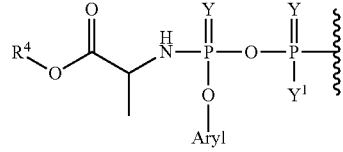

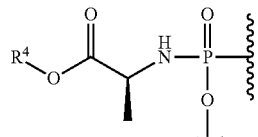

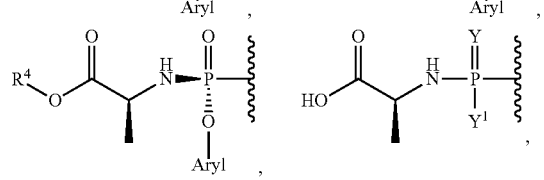

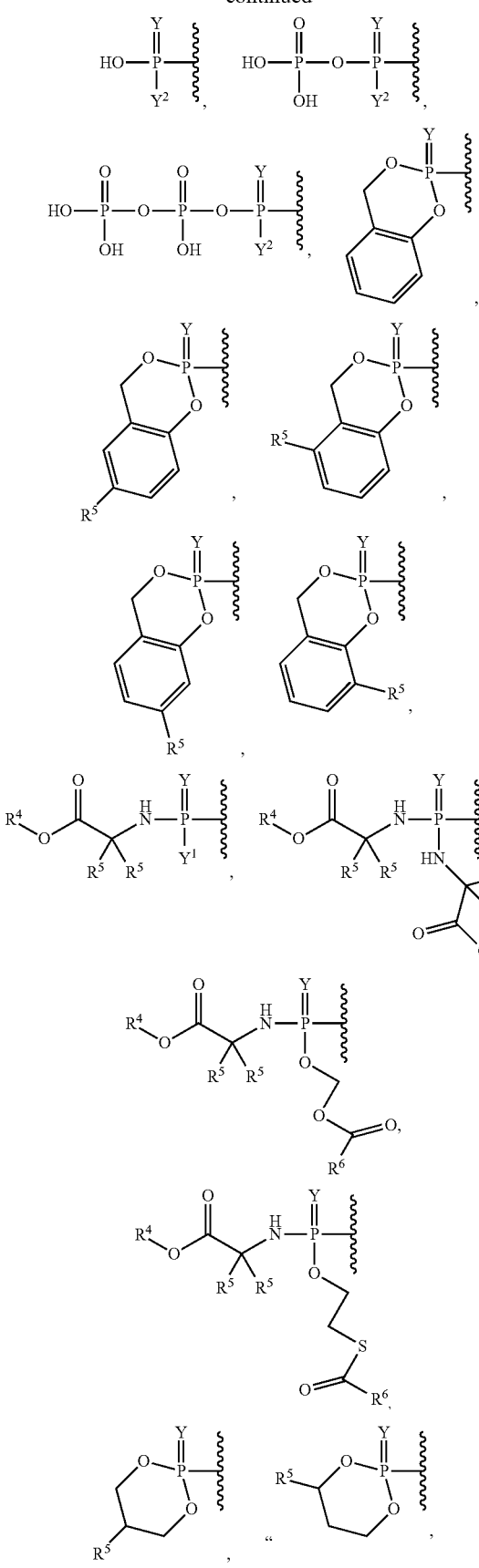

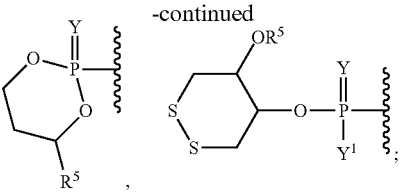

Y is O or S;
Y$^1$ is OH, OAryl, OAlkyl, or BH$_3^-$M$^+$;
Y$^2$ is OH or BH$_3^-$M$^+$;
Aryl is phenyl, 1-naphthyl, 2-naphthyl, aromatic, heteroaromatic, 4-substituted phenyl, 4-chlorophenyl, or 4-bromophenyl;
R$^4$ is hydrogen, methyl, ethyl, isopropyl, cyclopentyl, cyclohexyl, neopentyl, benzyl, alkyl, branched alkyl, cycloalkyl, or lipid;
R$^5$ is hydrogen, deuterium, hydroxyl, cyano, azido, amino, substituted amino, aryl, heteroaryl, substituted aryl, lipid, C$_{1-22}$ alkoxy, C$_{1-22}$ alkyl, C$_{2-22}$ alkenyl, C$_{2-22}$ alkynyl, or substituted heteroaryl;
R$^6$ is methyl, ethyl, tert-butyl, C$_{1-22}$ alkoxy, C$_{1-22}$ alkyl, branched alkyl, cycloalkyl, aryl, substituted aryl, or alkyoxy;
R$^8$ is D, hydroxyl, thiol, amino, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, or substituted amino.

In certain embodiments, the present invention relates to compounds of the following formula:

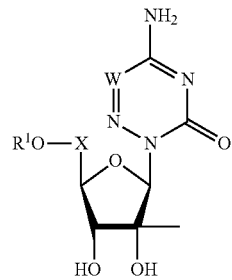

Formula LXII or pharmaceutically acceptable salts thereof wherein,
X is OCHMe, OCMe$_2$, OCHF, OCF$_2$, or OCD$_2$;
W is N or CR$^7$;
R$^1$ is selected from H or from one of the following formulae:

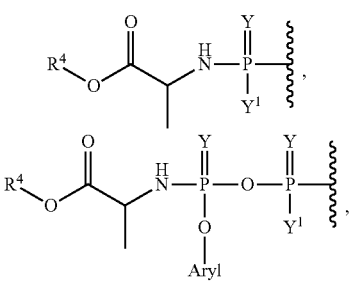

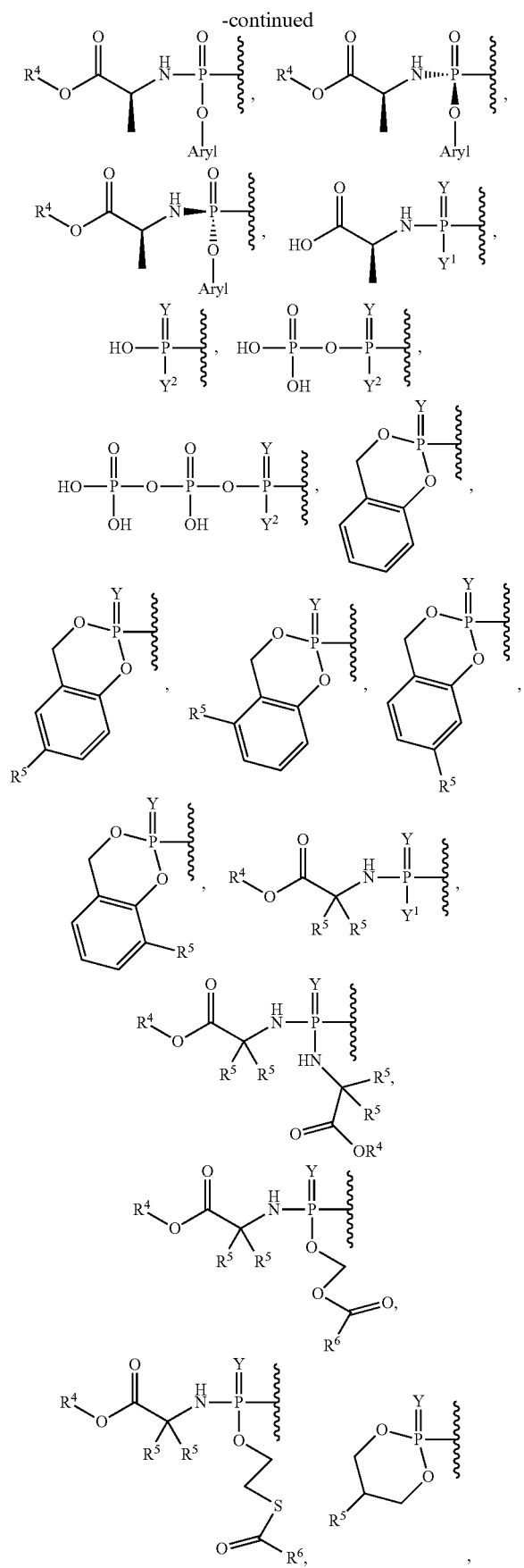

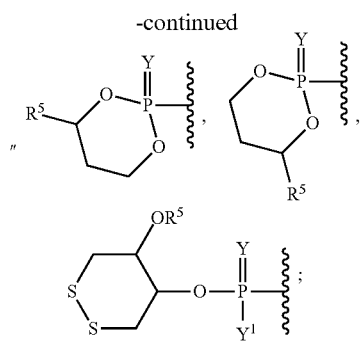

Y is O or S;

Y$^1$ is OH, OAryl, OAlkyl, or BH$_3^-$M$^+$;

Y$^2$ is OH or BH$_3^-$M$^+$;

Aryl is phenyl, 1-naphthyl, 2-naphthyl, aromatic, heteroaromatic, 4-substituted phenyl, 4-chlorophenyl, or 4-bromophenyl;

R$^4$ is hydrogen, methyl, ethyl, isopropyl, cyclopentyl, cyclohexyl, neopentyl, benzyl, alkyl, branched alkyl, cycloalkyl, or lipid;

R$^5$ is hydrogen, deuterium, hydroxyl, cyano, azido, amino, substituted amino, aryl, heteroaryl, substituted aryl, lipid, C$_{1-22}$ alkoxy, C$_{1-22}$ alkyl, C$_{2-22}$ alkenyl, C$_{2-22}$ alkynyl, or substituted heteroaryl;

R$^6$ is methyl, ethyl, tert-butyl, C$_{1-22}$ alkoxy, C$_{1-22}$ alkyl, branched alkyl, cycloalkyl, aryl, substituted aryl, or alkyoxy;

R$^7$ is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano.

In certain embodiments, the present invention relates to compounds of the following formula:

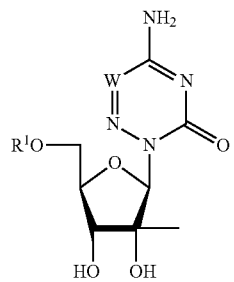

Formula LXIII or pharmaceutically acceptable salts thereof wherein,

W is N or CR$^7$;

R$^1$ is selected from H or from one of the following formulae:

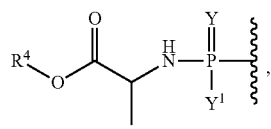

515
-continued

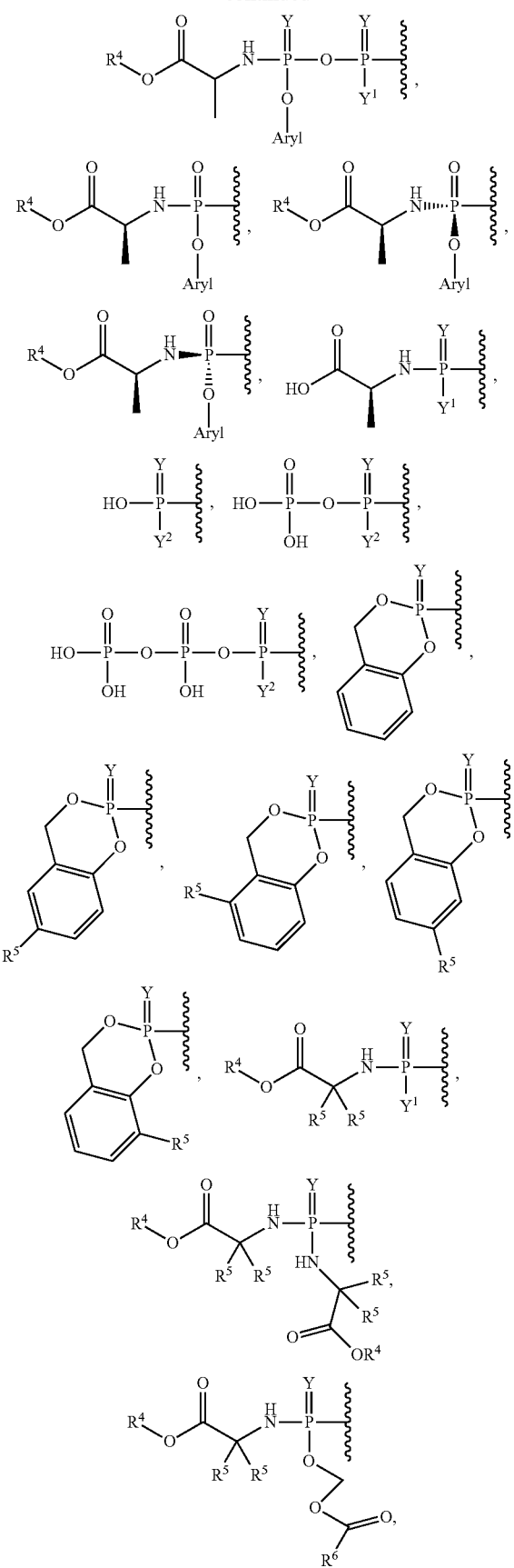

516
-continued

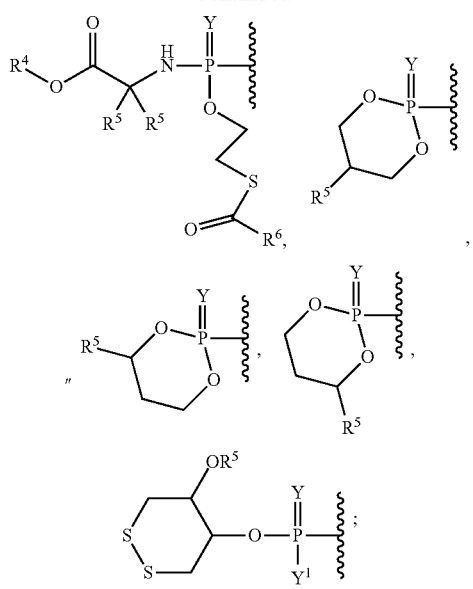

Y is O or S;

$Y^1$ is OH, OAryl, OAlkyl, or $BH_3^-M^+$;

$Y^2$ is OH or $BH_3^-M^+$;

Aryl is phenyl, 1-naphthyl, 2-naphthyl, aromatic, heteroaromatic, 4-substituted phenyl, 4-chlorophenyl, or 4-bromophenyl;

$R^4$ is hydrogen, methyl, ethyl, isopropyl, cyclopentyl, cyclohexyl, neopentyl, benzyl, alkyl, branched alkyl, cycloalkyl, or lipid;

$R^5$ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;

$R^6$ is methyl, ethyl, tert-butyl, $C_{1-22}$ alkoxy, $C_{1-22}$ alkyl, branched alkyl, cycloalkyl, aryl, substituted aryl, or alkyoxy;

$R^7$ is D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano.

In certain embodiments, the present invention relates to compounds of the following formula:

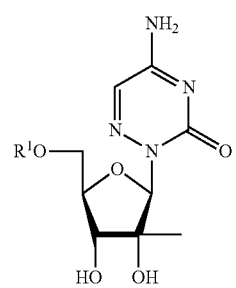

Formula LXIV or pharmaceutically acceptable salts thereof wherein, $R^1$ is selected from one of the following formulae:

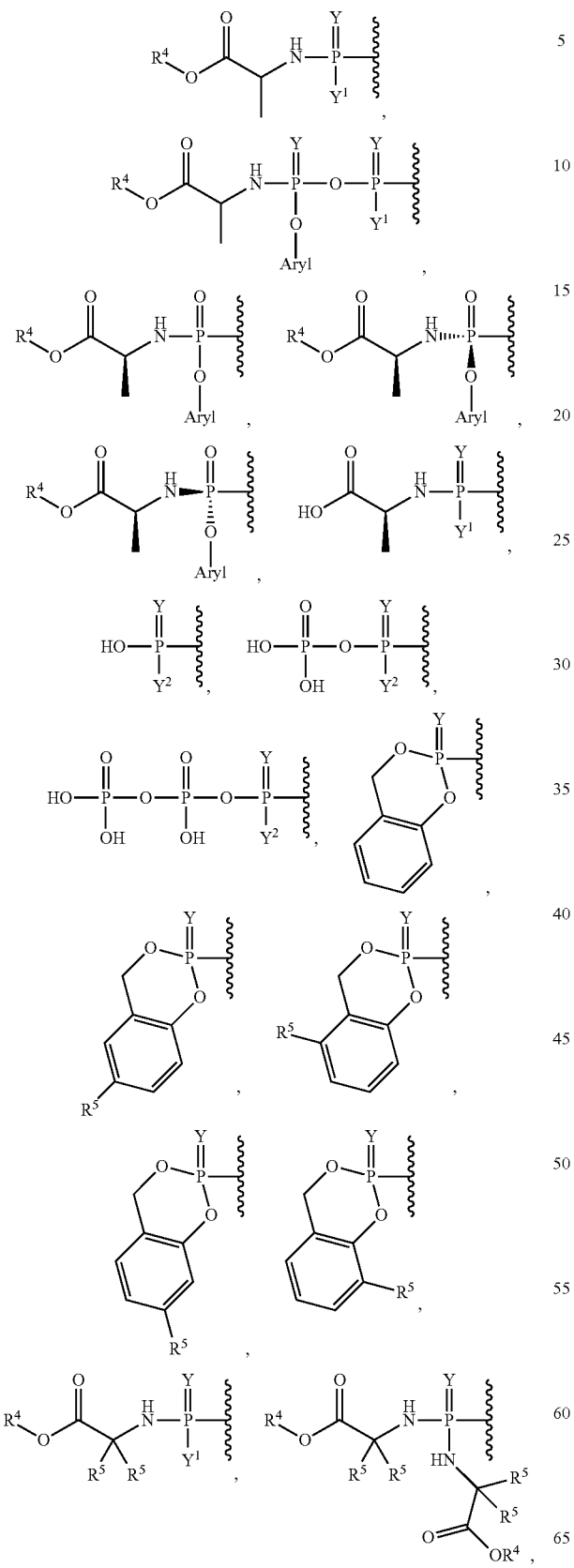

Y is O or S;
$Y^1$ is OH, OAryl, OAlkyl, or $BH_3^- M^+$;
$Y^2$ is OH or $BH_3^- M^+$; Aryl is phenyl, 1-naphthyl, 2-naphthyl, aromatic, heteroaromatic, 4-substituted phenyl, 4-chlorophenyl, or 4-bromophenyl;
$R^4$ is hydrogen, methyl, ethyl, isopropyl, cyclopentyl, cyclohexyl, neopentyl, benzyl, alkyl, branched alkyl, cycloalkyl, or lipid;
$R^5$ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;
$R^6$ is methyl, ethyl, tert-butyl, $C_{1-22}$ alkoxy, $C_{1-22}$ alkyl, branched alkyl, cycloalkyl, aryl, substituted aryl, or alkyoxy.

In certain embodiments, the present invention relates to compounds of the following formula:

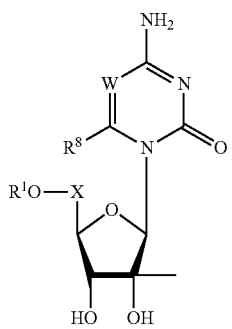

Formula LXV or pharmaceutically acceptable salts thereof wherein,

X is OCHMe, OCMe$_2$, OCHF, OCF$_2$, or OCD$_2$;

W is N or CR$^7$;

R$^1$ is selected from H or from one of the following formulae:

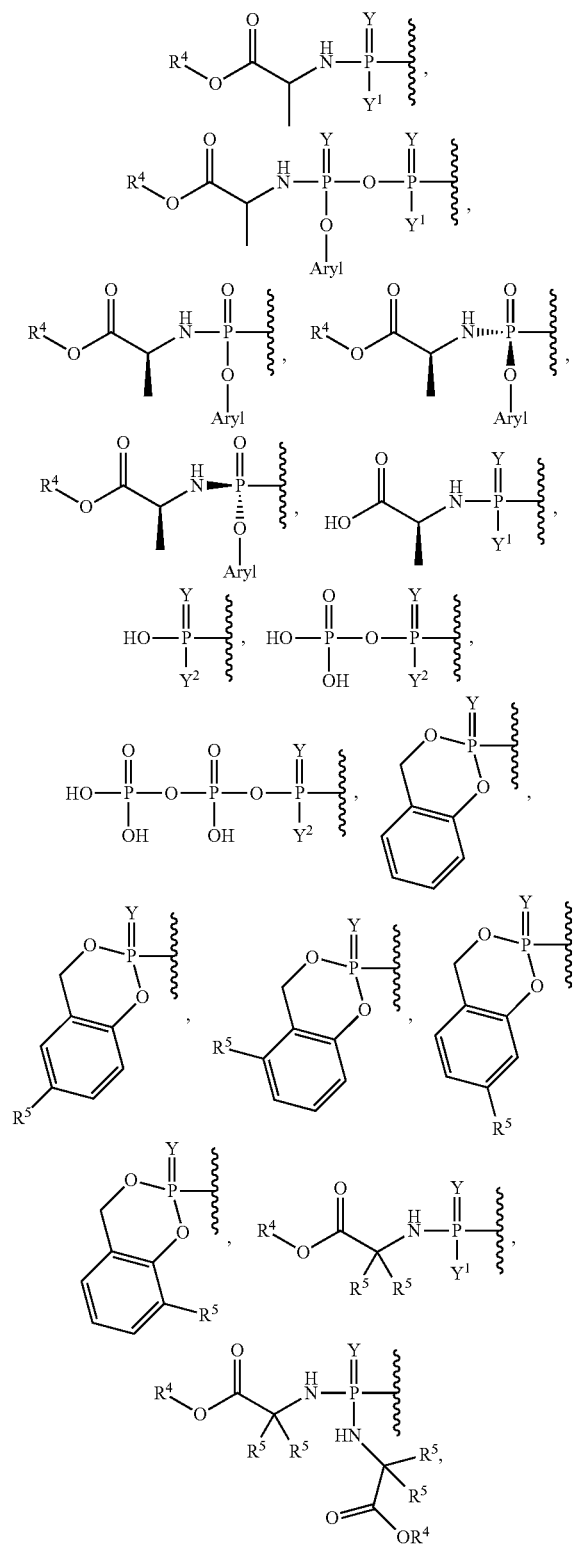

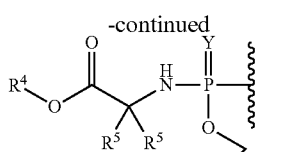

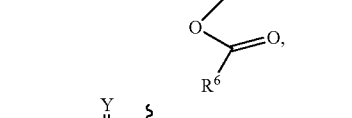

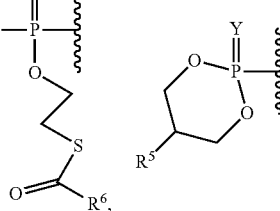

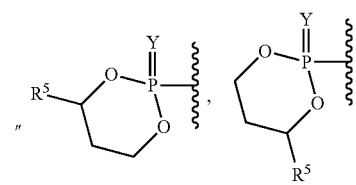

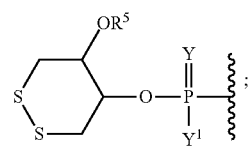

Y is O or S;

Y$^1$ is OH, OAryl, OAlkyl, or BH$_3^-$M$^+$;

Y$^2$ is OH or BH$_3^-$M$^+$;

Aryl is phenyl, 1-naphthyl, 2-naphthyl, aromatic, heteroaromatic, 4-substituted phenyl, 4-chlorophenyl, or 4-bromophenyl;

R$^4$ is hydrogen, methyl, ethyl, isopropyl, cyclopentyl, cyclohexyl, neopentyl, benzyl, alkyl, branched alkyl, cycloalkyl, or lipid;

R$^5$ is hydrogen, deuterium, hydroxyl, cyano, azido, amino, substituted amino, aryl, heteroaryl, substituted aryl, lipid, C$_{1-22}$ alkoxy, C$_{1-22}$ alkyl, C$_{2-22}$ alkenyl, C$_{2-22}$ alkynyl, or substituted heteroaryl;

R$^6$ is methyl, ethyl, tert-butyl, C$_{1-22}$ alkoxy, C$_{1-22}$ alkyl, branched alkyl, cycloalkyl, aryl, substituted aryl, or alkyoxy;

R$^7$ is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano;

R$^8$ is D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano.

In certain embodiments, the present invention relates to compounds of the following formula:

Formula LXVI

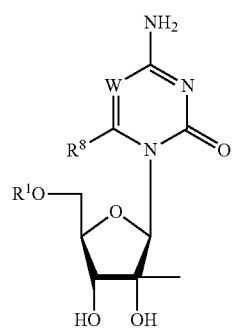

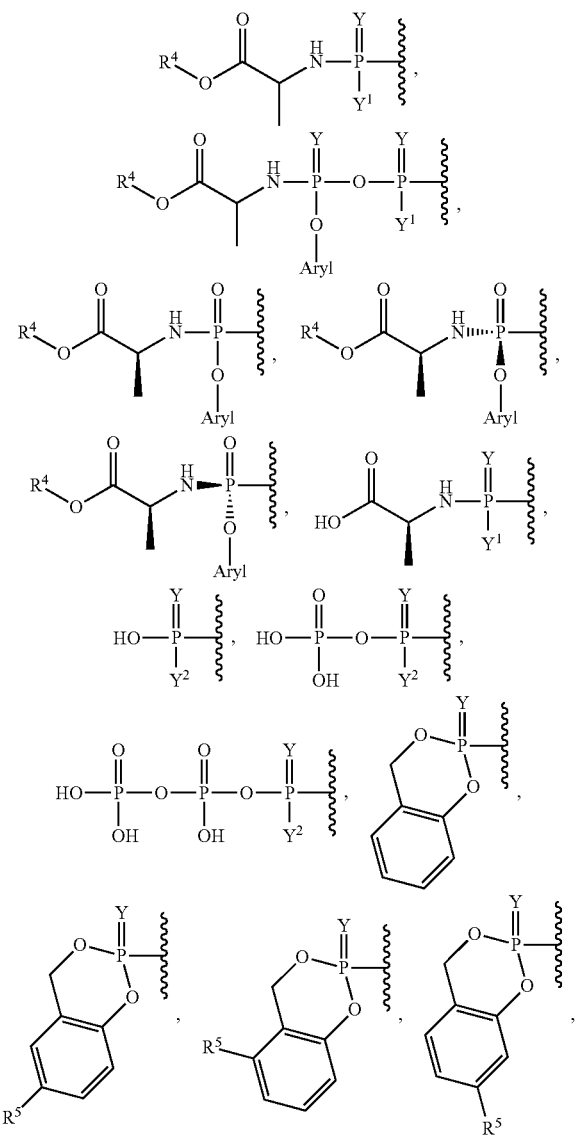

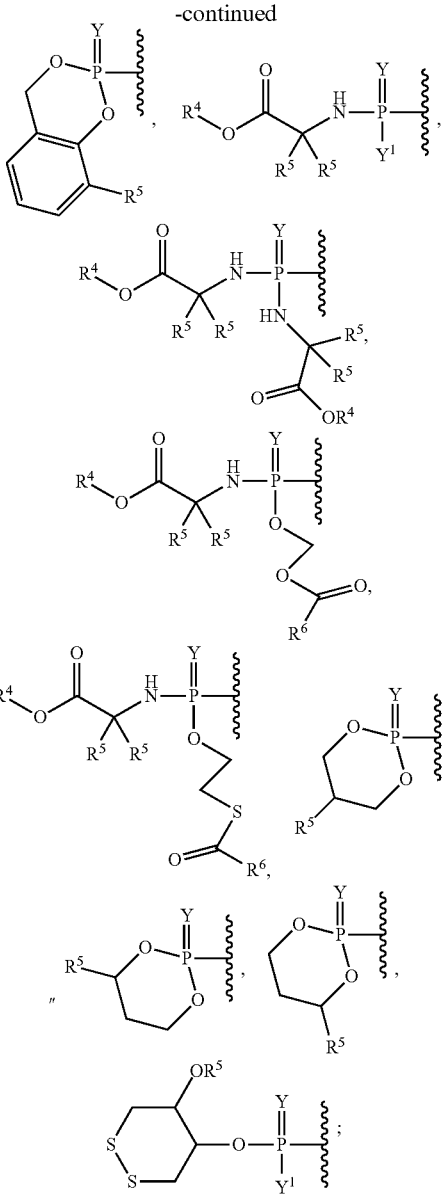

or pharmaceutically acceptable salts thereof wherein,

W is N or $CR^7$;

$R^1$ is selected from H or from one of the following formulae:

Y is O or S;
$Y^1$ is OH, OAryl, OAlkyl, or $BH_3^-M^+$;
$Y^2$ is OH or $BH_3^-M^+$;
Aryl is phenyl, 1-naphthyl, 2-naphthyl, aromatic, heteroaromatic, 4-substituted phenyl, 4-chlorophenyl, or 4-bromophenyl;
$R^4$ is hydrogen, methyl, ethyl, isopropyl, cyclopentyl, cyclohexyl, neopentyl, benzyl, alkyl, branched alkyl, cycloalkyl, or lipid;
$R^5$ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;
$R^6$ is methyl, ethyl, tert-butyl, $C_{1-22}$ alkoxy, $C_{1-22}$ alkyl, branched alkyl, cycloalkyl, aryl, substituted aryl, or alkyoxy;
$R^7$ is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano;

R[8] is D, hydroxyl, thiol, amino, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano.

In certain embodiments, the present invention relates to compounds of the following formula:

Formula LXVII

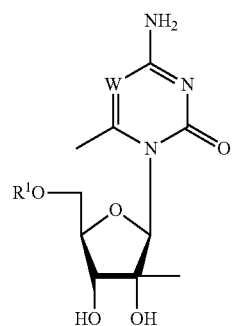

or pharmaceutically acceptable salts thereof wherein,

W is N or CR[7];

R[1] is selected from H or from one of the following formulae:

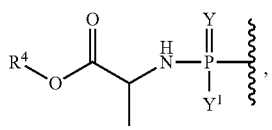

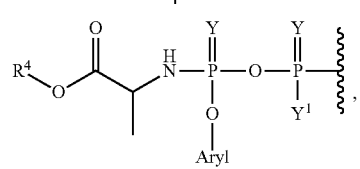

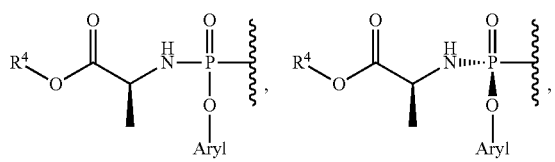

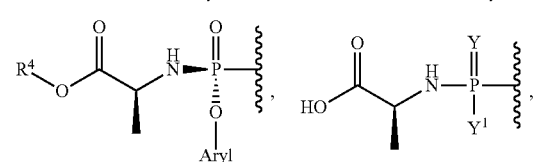

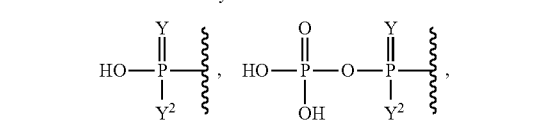

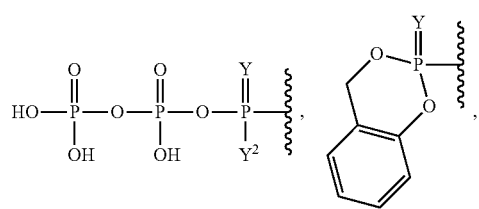

-continued

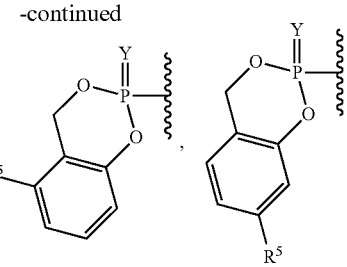

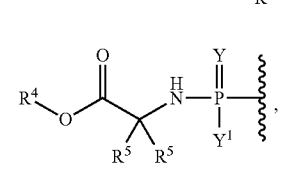

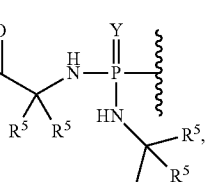

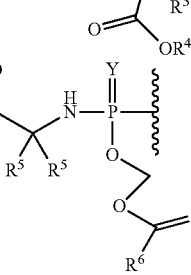

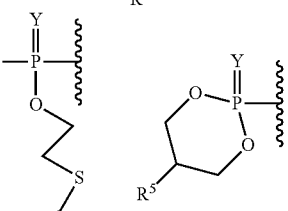

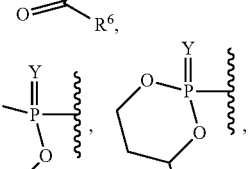

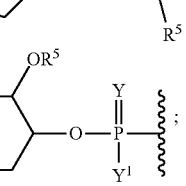

Y is O or S;

Y[1] is OH, OAryl, OAlkyl, or $BH_3^- M^+$;

Y[2] is OH or $BH_3^- M^+$;

Aryl is phenyl, 1-naphthyl, 2-naphthyl, aromatic, heteroaromatic, 4-substituted phenyl, 4-chlorophenyl, or 4-bromophenyl;

R[4] is hydrogen, methyl, ethyl, isopropyl, cyclopentyl, cyclohexyl, neopentyl, benzyl, alkyl, branched alkyl, cycloalkyl, or lipid;

R[5] is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;

R[6] is methyl, ethyl, tert-butyl, $C_{1-22}$ alkoxy, $C_{1-22}$ alkyl, branched alkyl, cycloalkyl, aryl, substituted aryl, or alkyoxy;

R[7] is D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano.

In certain embodiments, the present invention relates to compounds of the following formula:

Formula LXVIII

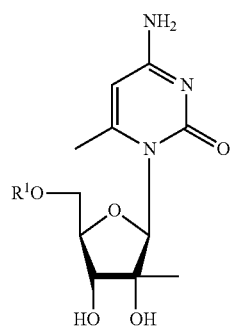

or pharmaceutically acceptable salts thereof wherein, R[1] is selected from one of the following formulae:

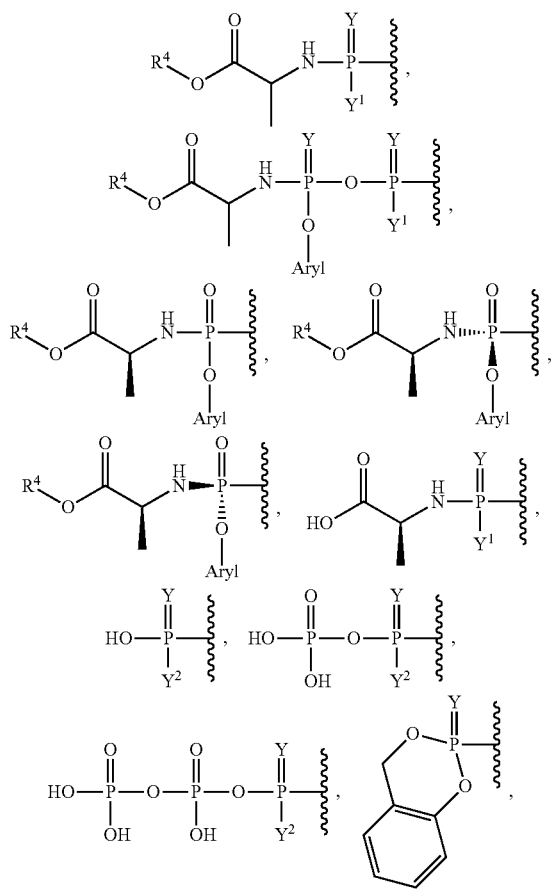

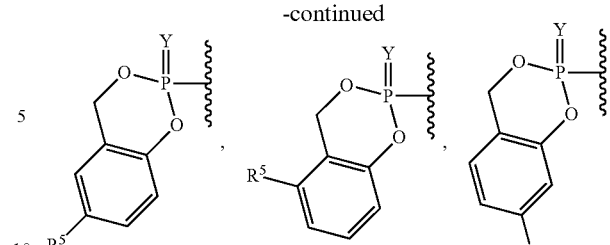

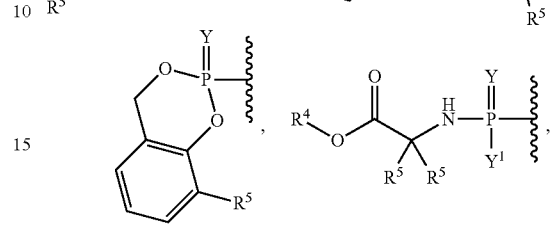

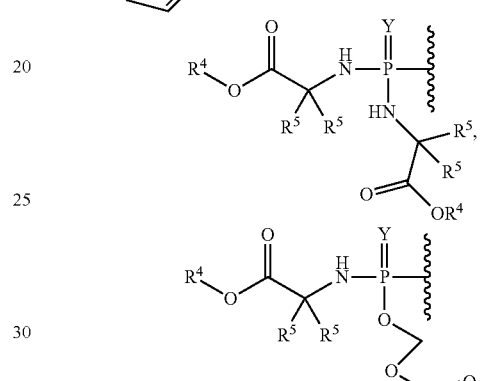

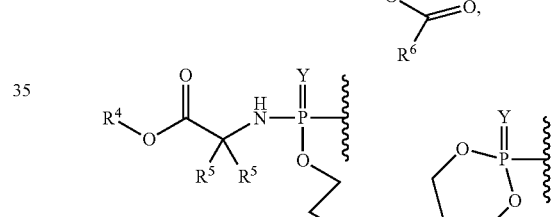

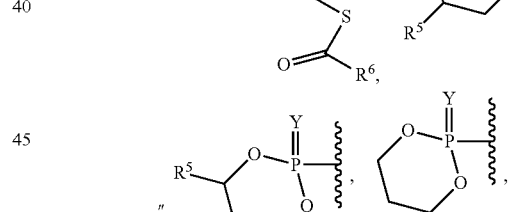

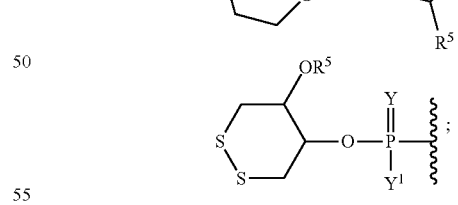

Y is O or S;

Y[1] is OH, OAryl, OAlkyl, or $BH_3^-M^+$;

Y[2] is OH or $BH_3^-M^+$;

Aryl is phenyl, 1-naphthyl, 2-naphthyl, aromatic, heteroaromatic, 4-substituted phenyl, 4-chlorophenyl, or 4-bromophenyl;

R[4] is hydrogen, methyl, ethyl, isopropyl, cyclopentyl, cyclohexyl, neopentyl, benzyl, alkyl, branched alkyl, cycloalkyl, or lipid;

R⁵ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;

R⁶ is methyl, ethyl, tert-butyl, $C_{1-22}$ alkoxy, $C_{1-22}$ alkyl, branched alkyl, cycloalkyl, aryl, substituted aryl, or alkyoxy.

In certain embodiments, the present invention relates to compounds of the following formula:

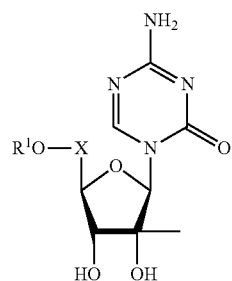

Formula LXIX or pharmaceutically acceptable salts thereof wherein,

X is OCHMe, OCMe₂, OCHF, OCF₂, or OCD₂;

R¹ is selected from H or from one of the following formulae:

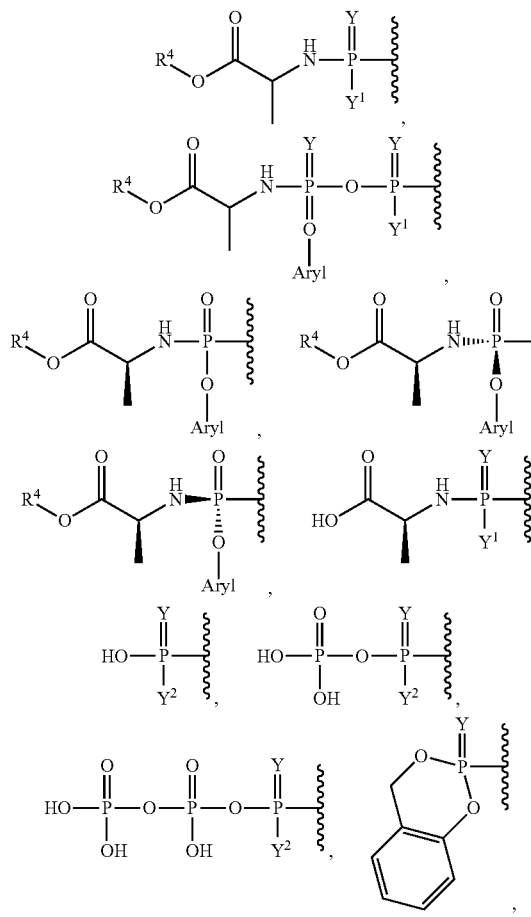

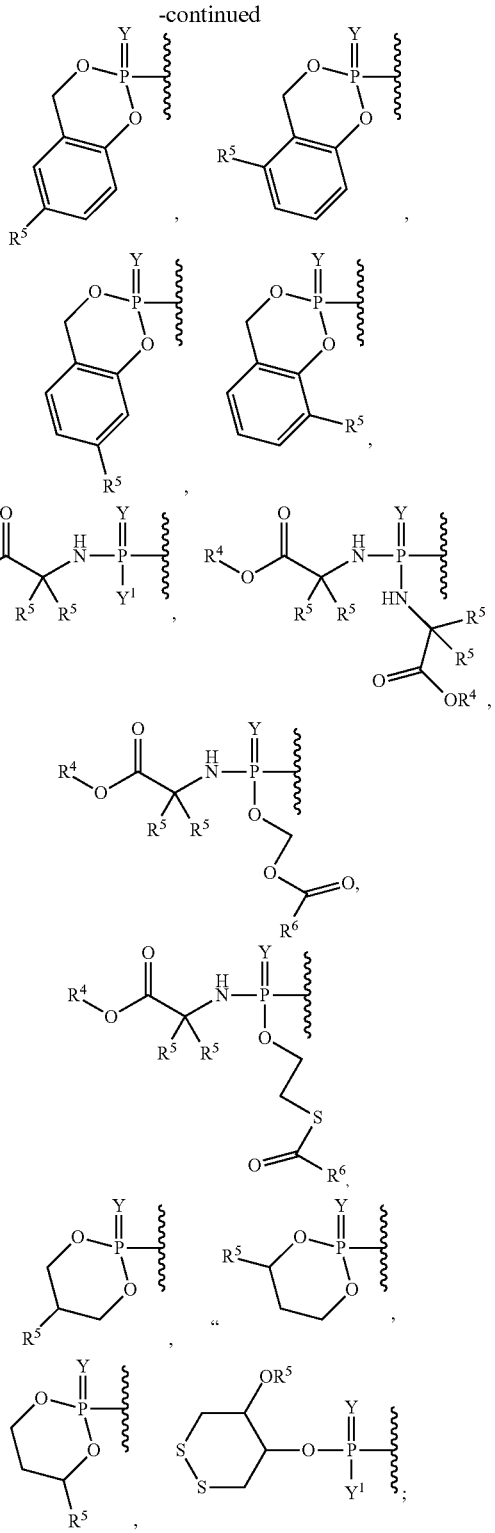

Y is O or S;

Y¹ is OH, OAryl, OAlkyl, or $BH_3^- M^+$;

Y² is OH or $BH_3^- M^+$;

Aryl is phenyl, 1-naphthyl, 2-naphthyl, aromatic, heteroaromatic, 4-substituted phenyl, 4-chlorophenyl, or 4-bromophenyl;

$R^4$ is hydrogen, methyl, ethyl, isopropyl, cyclopentyl, cyclohexyl, neopentyl, benzyl, alkyl, branched alkyl, cycloalkyl, or lipid;

$R^5$ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;

$R^6$ is methyl, ethyl, tert-butyl, $C_{1-22}$ alkoxy, $C_{1-22}$ alkyl, branched alkyl, cycloalkyl, aryl, substituted aryl, or alkyoxy.

In certain embodiments, the present invention relates to compounds of the following formula:

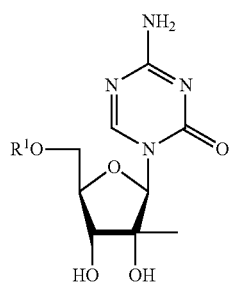

Formula LXX or pharmaceutically acceptable salts thereof wherein,
$R^1$ is selected from one of the following formulae:

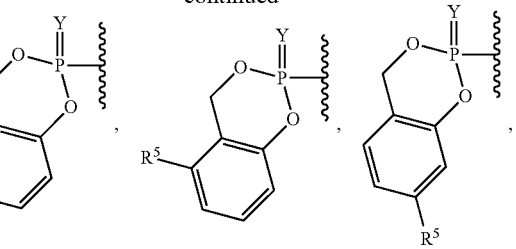

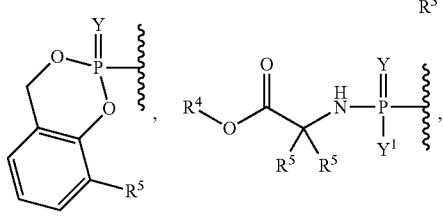

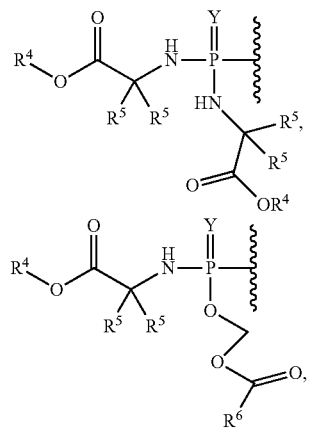

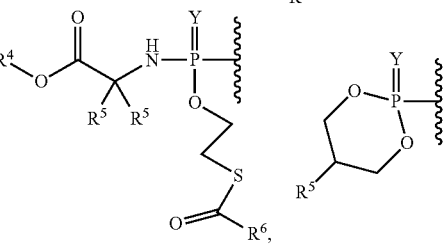

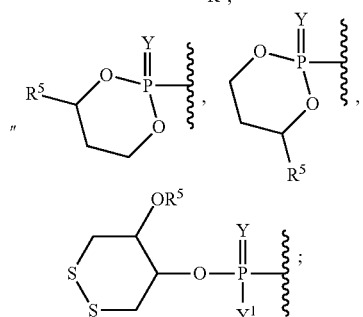

Y is O or S;
$Y^1$ is OH, OAryl, OAlkyl, or $BH_3^- M^+$;
$Y^2$ is OH or $BH_3^- M^+$;
Aryl is phenyl, 1-naphthyl, 2-naphthyl, aromatic, heteroaromatic, 4-substituted phenyl, 4-chlorophenyl, or 4-bromophenyl;
$R^4$ is hydrogen, methyl, ethyl, isopropyl, cyclopentyl, cyclohexyl, neopentyl, benzyl, alkyl, branched alkyl, cycloalkyl, or lipid;

R⁵ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;

R⁶ is methyl, ethyl, tert-butyl, $C_{1-22}$ alkoxy, $C_{1-22}$ alkyl, branched alkyl, cycloalkyl, aryl, substituted aryl, or alkyoxy.

In certain embodiments, the present invention relates to compounds of the following formula:

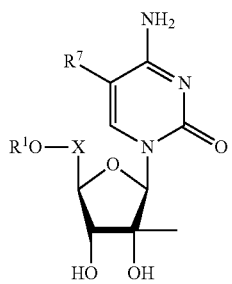

Formula LXXI or pharmaceutically acceptable salts thereof wherein,

X is OCHMe, OCMe₂, OCHF, OCF₂, or OCD₂;

R¹ is selected from H or from one of the following formulae:

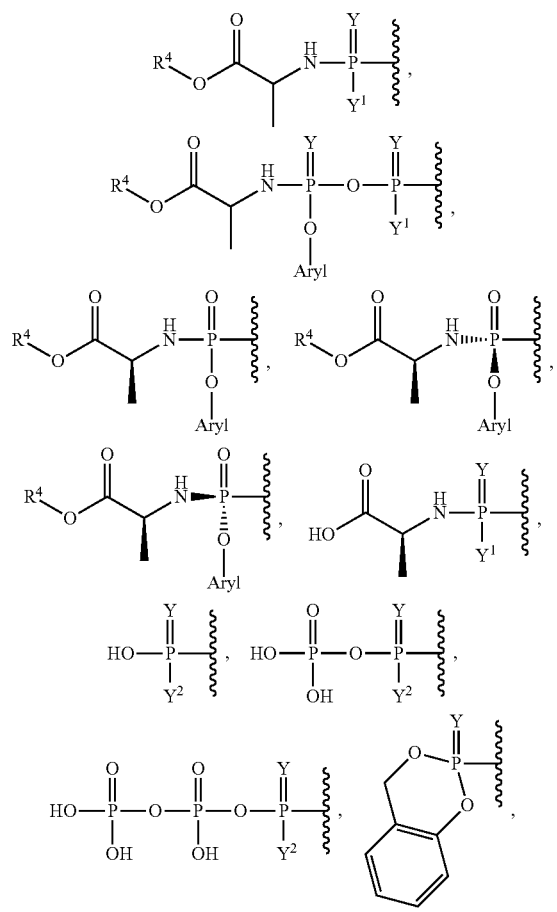

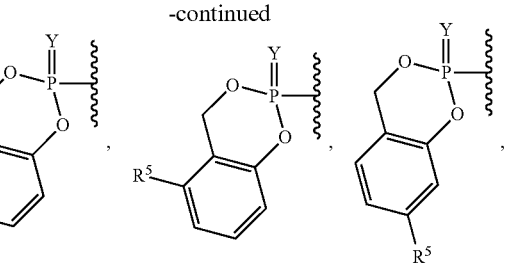

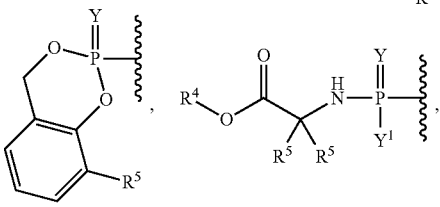

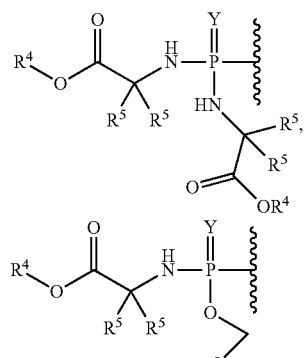

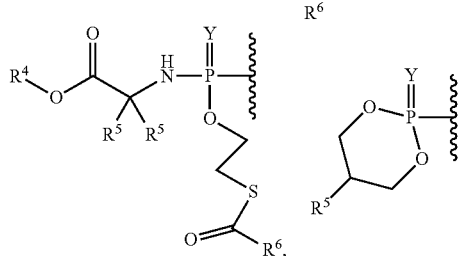

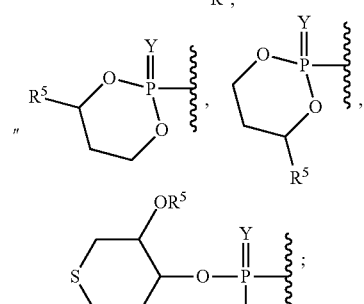

Y is O or S;

Y¹ is OH, OAryl, OAlkyl, or $BH_3^- M^+$;

Y² is OH or $BH_3^- M^+$;

Aryl is phenyl, 1-naphthyl, 2-naphthyl, aromatic, heteroaromatic, 4-substituted phenyl, 4-chlorophenyl, or 4-bromophenyl;

R⁴ is hydrogen, methyl, ethyl, isopropyl, cyclopentyl, cyclohexyl, neopentyl, benzyl, alkyl, branched alkyl, cycloalkyl, or lipid;

R⁵ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;

R⁶ is methyl, ethyl, tert-butyl, $C_{1-22}$ alkoxy, $C_{1-22}$ alkyl, branched alkyl, cycloalkyl, aryl, substituted aryl, or alkyoxy;

R⁷ is D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano.

In certain embodiments, the present invention relates to compounds of the following formula:

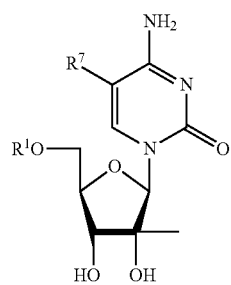

Formula LXXII or pharmaceutically acceptable salts thereof wherein,

R¹ is selected from one of the following formulae:

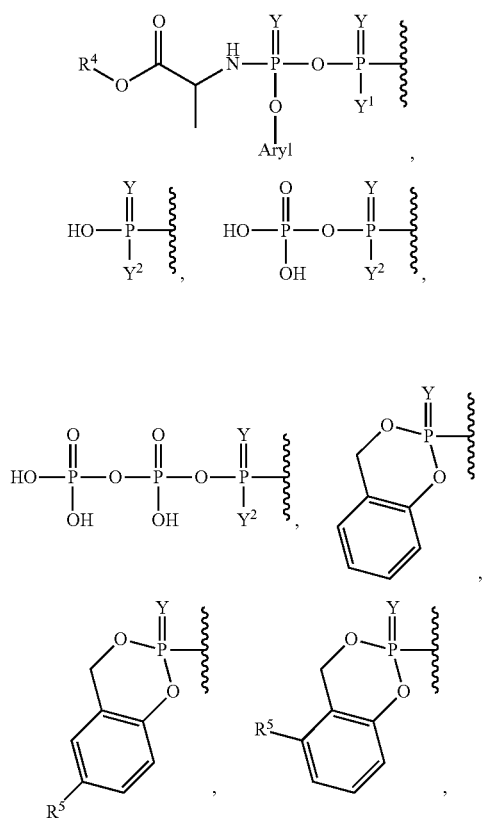

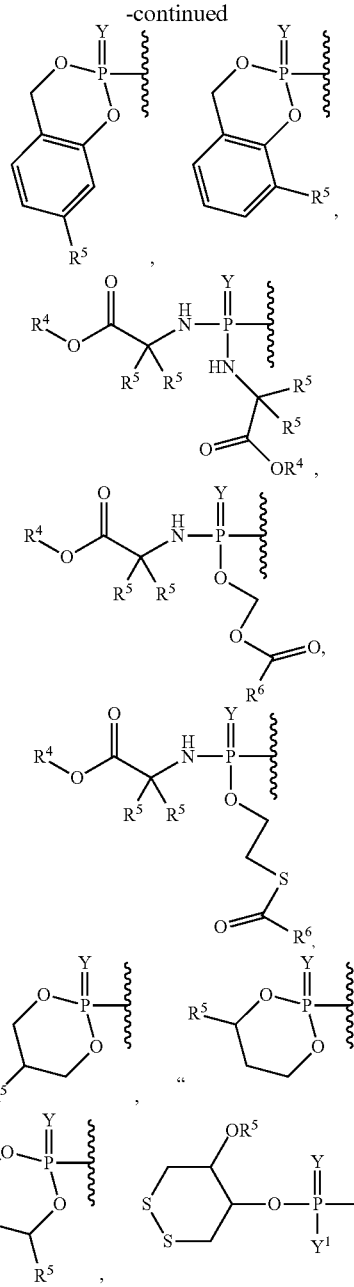

Y is O or S;

Y¹ is OH, OAryl, OAlkyl, or $BH_3^-M^+$;

Y² is OH or $BH_3^-M^+$;

Aryl is phenyl, 1-naphthyl, 2-naphthyl, aromatic, heteroaromatic, 4-substituted phenyl, 4-chlorophenyl, or 4-bromophenyl;

R⁴ is hydrogen, methyl, ethyl, isopropyl, cyclopentyl, cyclohexyl, neopentyl, benzyl, alkyl, branched alkyl, cycloalkyl, or lipid;

R⁵ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;

R⁶ is methyl, ethyl, tert-butyl, $C_{1-22}$ alkoxy, $C_{1-22}$ alkyl, branched alkyl, cycloalkyl, aryl, substituted aryl, or alkyoxy;

R⁷ is D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano.

In certain embodiments, the present invention relates to compounds of the following formula:

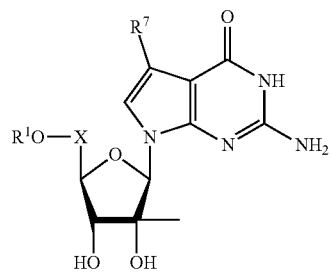

Formula LXXIIIa

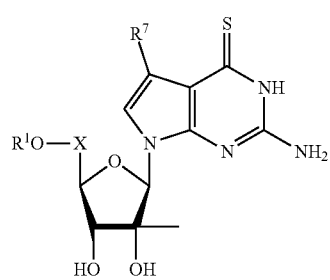

Formula LXXIIIb

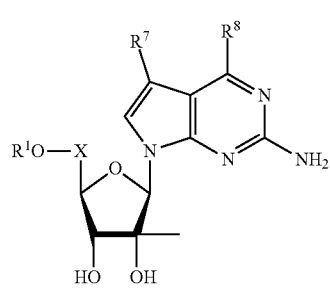

Formula LXXIIIc or pharmaceutically acceptable salts thereof wherein,

X is OCHMe, OCMe₂, OCHF, OCF₂, or OCD₂;

R¹ is selected from H or from one of the following formulae:

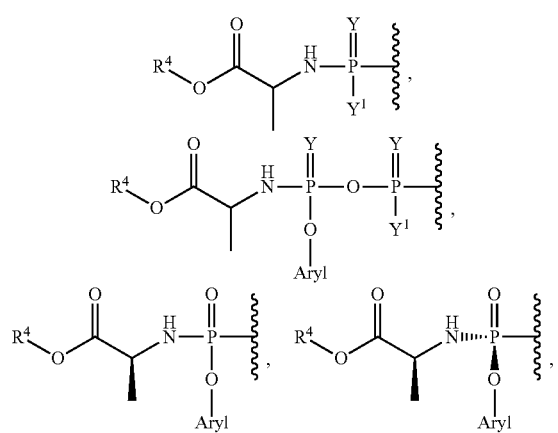

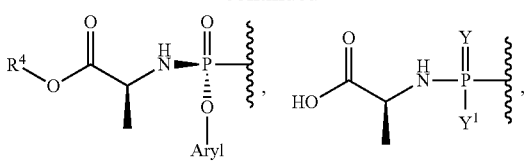

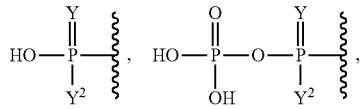

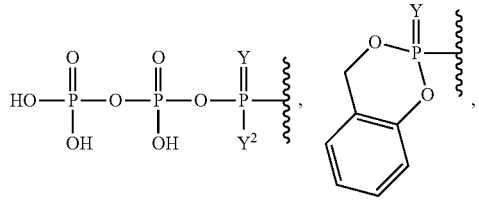

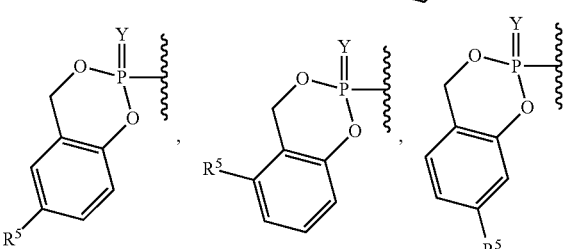

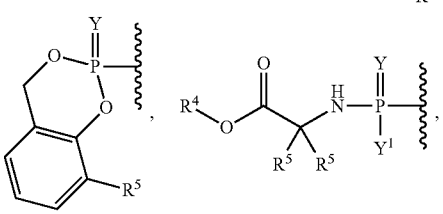

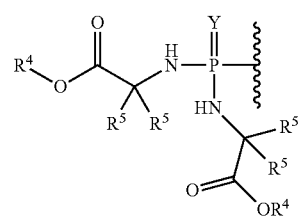

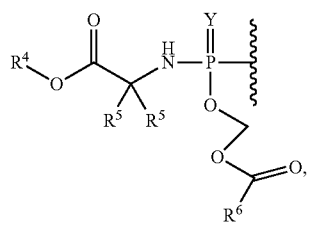

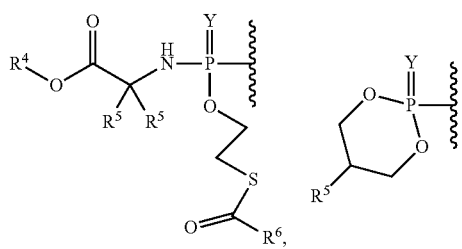

-continued

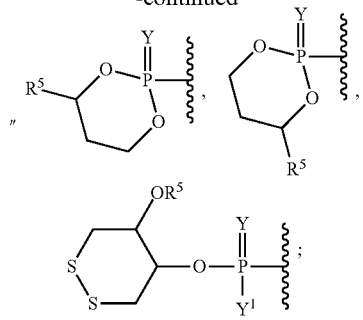

Y is O or S;
Y$^1$ is OH, OAryl, OAlkyl, or BH$_3^-$M$^+$;
Y$^2$ is OH or BH$_3^-$M$^+$;
Aryl is phenyl, 1-naphthyl, 2-naphthyl, aromatic, heteroaromatic, 4-substituted phenyl, 4-chlorophenyl, or 4-bromophenyl;
R$^4$ is hydrogen, methyl, ethyl, isopropyl, cyclopentyl, cyclohexyl, neopentyl, benzyl, alkyl, branched alkyl, cycloalkyl, or lipid;
R$^5$ is hydrogen, deuterium, hydroxyl, cyano, azido, amino, substituted amino, aryl, heteroaryl, substituted aryl, lipid, C$_{1-22}$ alkoxy, C$_{1-22}$ alkyl, C$_{2-22}$ alkenyl, C$_{2-22}$ alkynyl, or substituted heteroaryl;
R$^6$ is methyl, ethyl, tert-butyl, C$_{1-22}$ alkoxy, C$_{1-22}$ alkyl, branched alkyl, cycloalkyl, aryl, substituted aryl, or alkyoxy;
R$^7$ is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano;
R$^8$ is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, methoxy, ethoxy, alkoxy, substituted amino, or cyano.

In certain embodiments, the present invention relates to compounds of the following formula:

Formula LXXIV

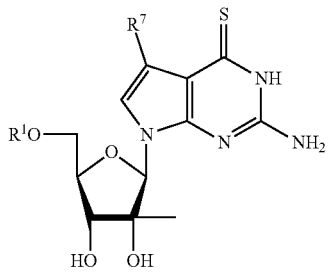

or pharmaceutically acceptable salts thereof wherein,
R$^1$ is selected from H or from one of the following formulae:

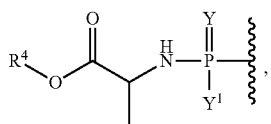

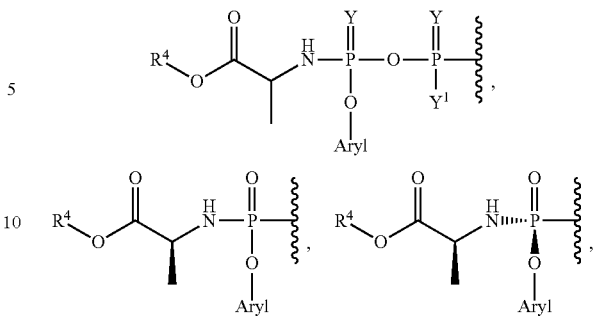

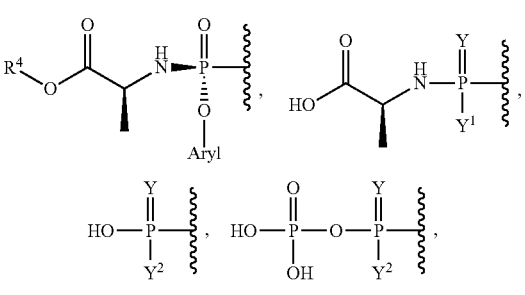

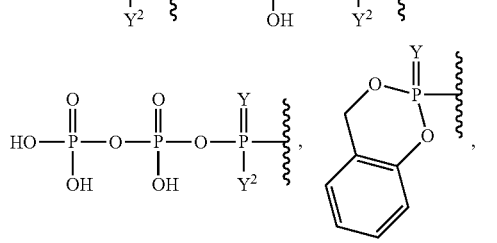

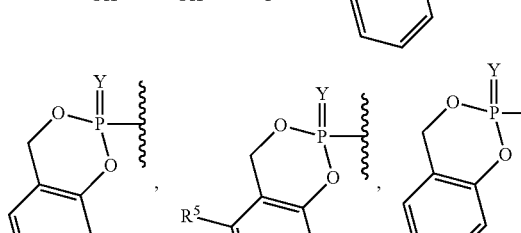

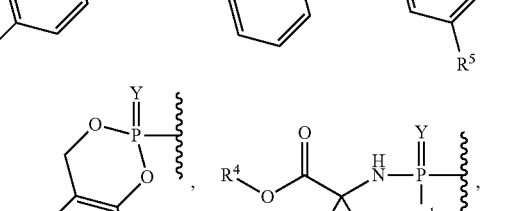

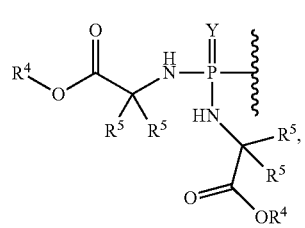

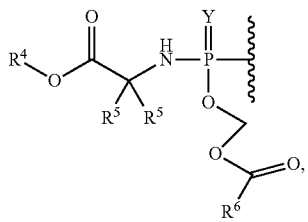

539

-continued

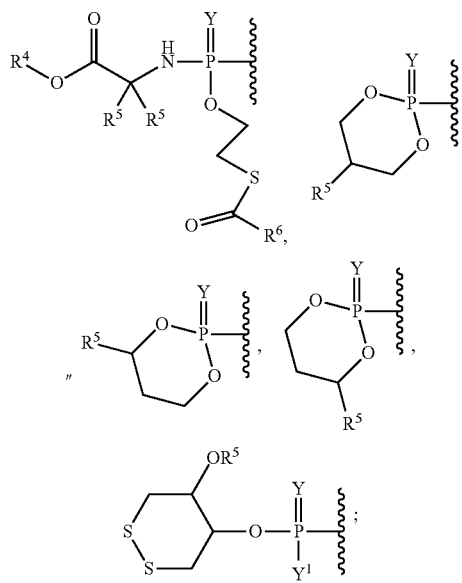

Y is O or S;

$Y^1$ is OH, OAryl, OAlkyl, or $BH_3^-M^+$;

$Y^2$ is OH or $BH_3^-M^+$;

Aryl is phenyl, 1-naphthyl, 2-naphthyl, aromatic, heteroaromatic, 4-substituted phenyl, 4-chlorophenyl, or 4-bromophenyl;

$R^4$ is hydrogen, methyl, ethyl, isopropyl, cyclopentyl, cyclohexyl, neopentyl, benzyl, alkyl, branched alkyl, cycloalkyl, or lipid;

$R^5$ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;

$R^6$ is methyl, ethyl, tert-butyl, $C_{1-22}$ alkoxy, $C_{1-22}$ alkyl, branched alkyl, cycloalkyl, aryl, substituted aryl, or alkyoxy;

$R^7$ is D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano.

In certain embodiments, the present invention relates to compounds of the following formula:

Formula LXXV

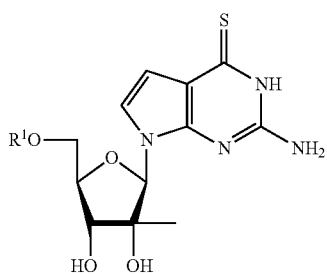

or pharmaceutically acceptable salts thereof wherein,

540

$R^1$ is selected from one of the following formulae:

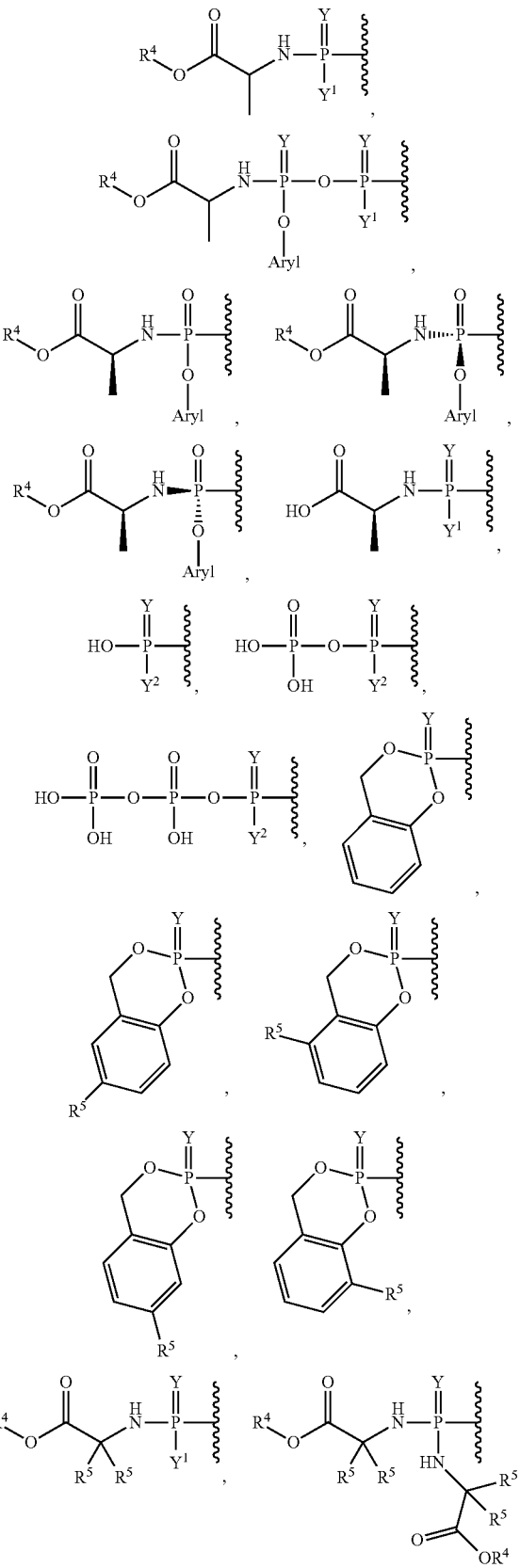

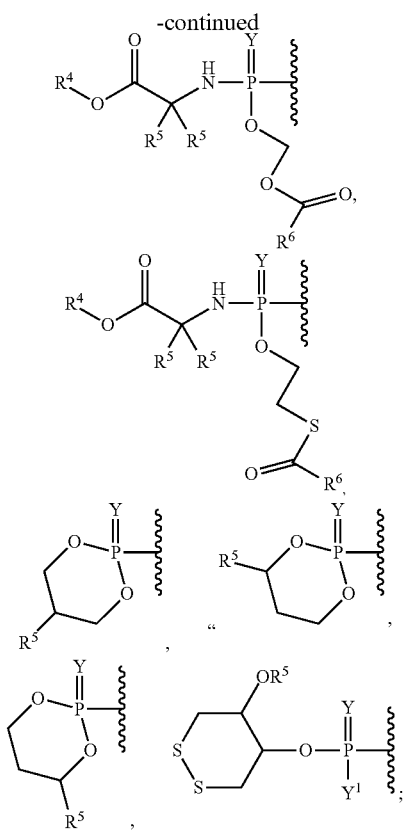

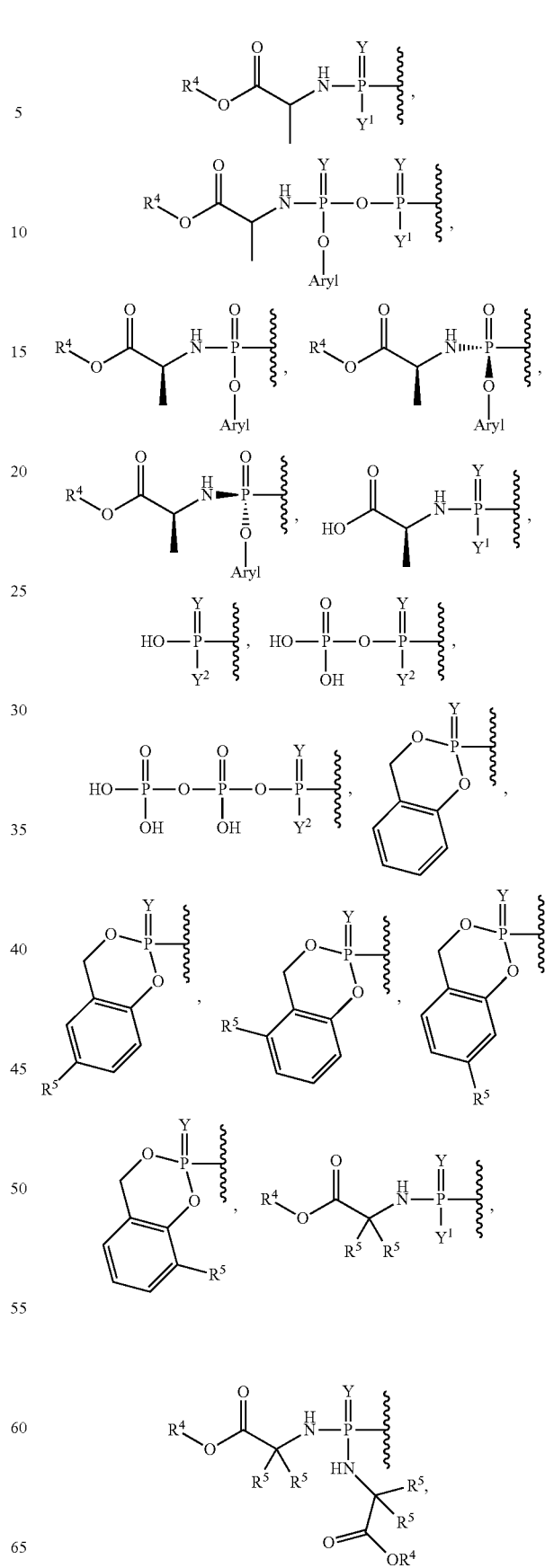

Y is O or S;
Y$^1$ is OH, OAryl, OAlkyl, or BH$_3^-$M$^+$;
Y$^2$ is OH or BH$_3^-$M$^+$;
Aryl is phenyl, 1-naphthyl, 2-naphthyl, aromatic, heteroaromatic, 4-substituted phenyl, 4-chlorophenyl, or 4-bromophenyl;
R$^4$ is hydrogen, methyl, ethyl, isopropyl, cyclopentyl, cyclohexyl, neopentyl, benzyl, alkyl, branched alkyl, cycloalkyl, or lipid;
R$^5$ is hydrogen, deuterium, hydroxyl, cyano, azido, amino, substituted amino, aryl, heteroaryl, substituted aryl, lipid, C$_{1-22}$ alkoxy, C$_{1-22}$ alkyl, C$_{2-22}$ alkenyl, C$_{2-22}$ alkynyl, or substituted heteroaryl;
R$^6$ is methyl, ethyl, tert-butyl, C$_{1-22}$ alkoxy, C$_{1-22}$ alkyl, branched alkyl, cycloalkyl, aryl, substituted aryl, or alkyoxy.

In certain embodiments, the present invention relates to compounds of the following formula:

Formula LXXVI

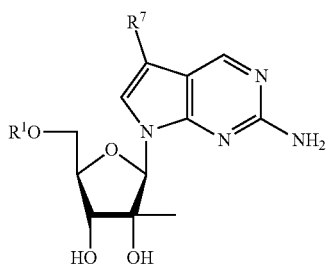

or pharmaceutically acceptable salts thereof wherein,
R$^1$ is selected from H or from one of the following formulae:

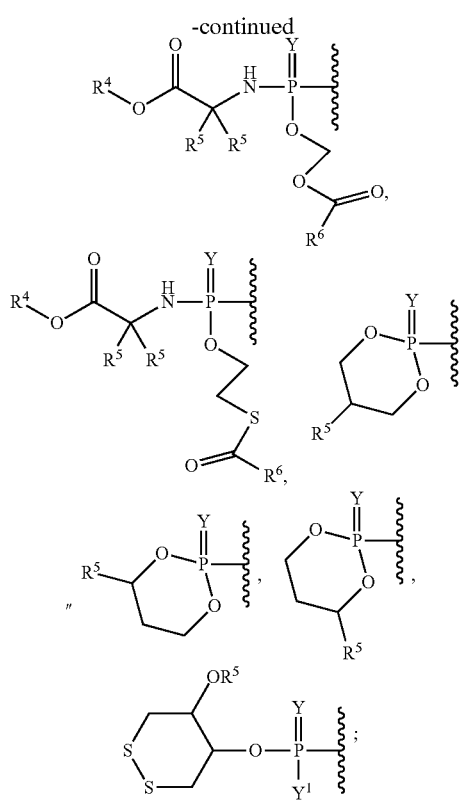

Y is O or S;
Y$^1$ is OH, OAryl, OAlkyl, or BH$_3^-$M$^+$;
Y$^2$ is OH or BH$_3^-$M$^+$;
Aryl is phenyl, 1-naphthyl, 2-naphthyl, aromatic, heteroaromatic, 4-substituted phenyl, 4-chlorophenyl, or 4-bromophenyl;
R$^4$ is hydrogen, methyl, ethyl, isopropyl, cyclopentyl, cyclohexyl, neopentyl, benzyl, alkyl, branched alkyl, cycloalkyl, or lipid;
R$^5$ is hydrogen, deuterium, hydroxyl, cyano, azido, amino, substituted amino, aryl, heteroaryl, substituted aryl, lipid, C$_{1-22}$ alkoxy, C$_{1-22}$ alkyl, C$_{2-22}$ alkenyl, C$_{2-22}$ alkynyl, or substituted heteroaryl;
R$^6$ is methyl, ethyl, tert-butyl, C$_{1-22}$ alkoxy, C$_{1-22}$ alkyl, branched alkyl, cycloalkyl, aryl, substituted aryl, or alkyoxy;
R$^7$ is D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano.

In certain embodiments, the present invention relates to compounds of the following formula:

Formula LXXVII or pharmaceutically acceptable salts thereof wherein,

R$^1$ is selected from one of the following formulae:

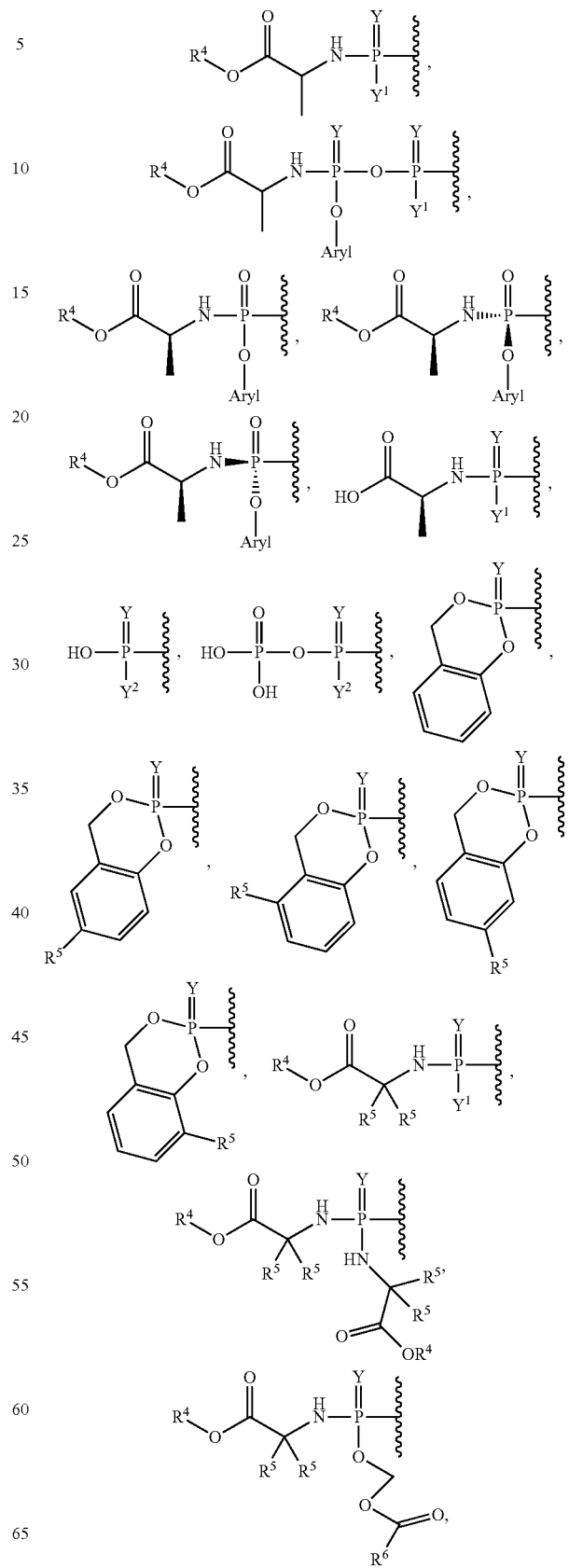

-continued

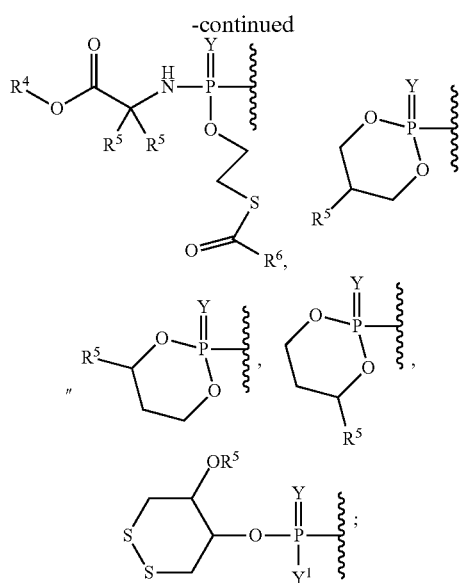

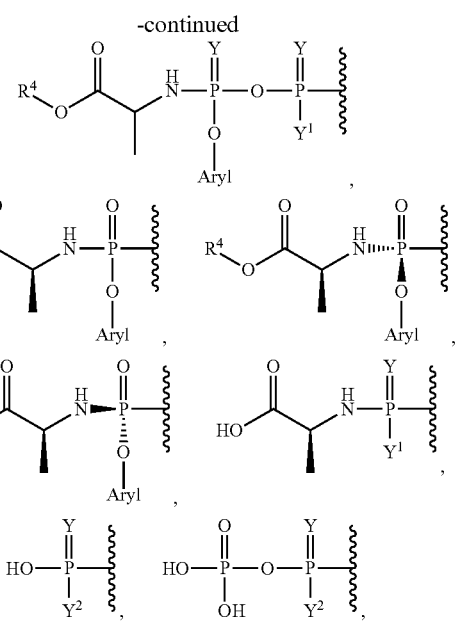

Y is O or S;

Y¹ is OH, OAryl, OAlkyl, or $BH_3^- M^+$;

Y² is OH or $BH_3^- M^+$; Aryl is phenyl, 1-naphthyl, 2-naphthyl, aromatic, heteroaromatic, 4-substituted phenyl, 4-chlorophenyl, or 4-bromophenyl;

R⁴ is hydrogen, methyl, ethyl, isopropyl, cyclopentyl, cyclohexyl, neopentyl, benzyl, alkyl, branched alkyl, cycloalkyl, or lipid;

R⁵ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;

R⁶ is methyl, ethyl, tert-butyl, $C_{1-22}$ alkoxy, $C_{1-22}$ alkyl, branched alkyl, cycloalkyl, aryl, substituted aryl, or alkyoxy.

In certain embodiments, the present invention relates to methods of use for compounds of the following formula:

Formula LXXVIII

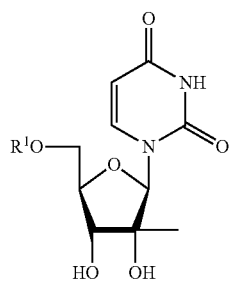

or pharmaceutically acceptable salts thereof wherein,

R¹ is selected from H or from one of the following formulae:

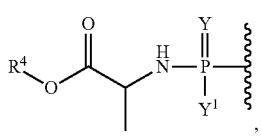

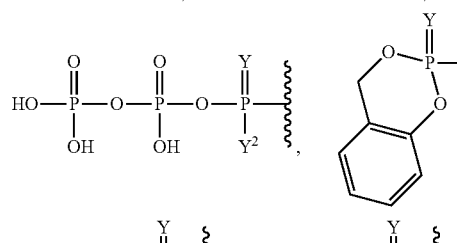

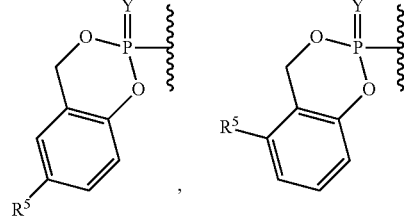

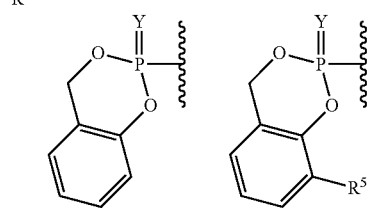

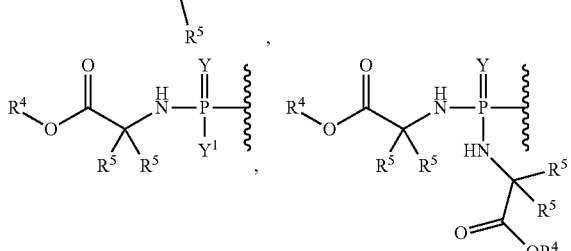

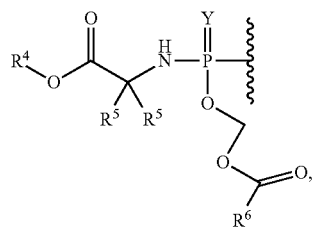

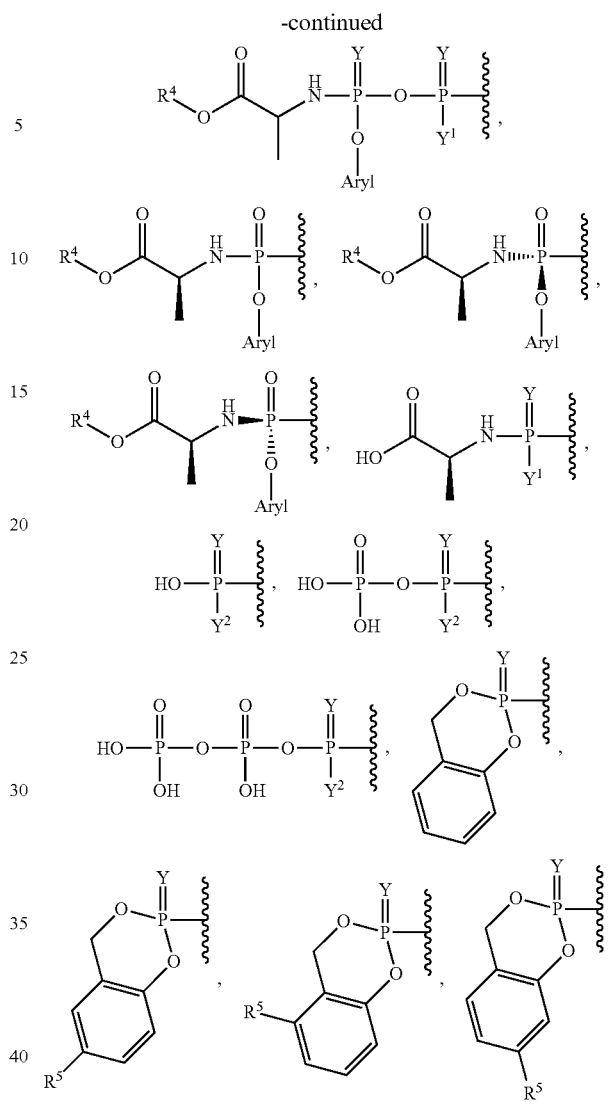

Y is O or S;
Y¹ is OH, OAryl, OAlkyl, or $BH_3^- M^+$;
Y² is OH or $BH_3^- M^+$;
Aryl is phenyl, 1-naphthyl, 2-naphthyl, aromatic, heteroaromatic, 4-substituted phenyl, 4-chlorophenyl, or 4-bromophenyl;
$R^4$ is hydrogen, methyl, ethyl, isopropyl, cyclopentyl, cyclohexyl, neopentyl, benzyl, alkyl, branched alkyl, cycloalkyl, or lipid;
$R^5$ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;
$R^6$ is methyl, ethyl, tert-butyl, $C_{1-22}$ alkoxy, $C_{1-22}$ alkyl, branched alkyl, cycloalkyl, aryl, substituted aryl, or alkyoxy.

In certain embodiments, the present invention relates to methods of use for compounds of the following formula:

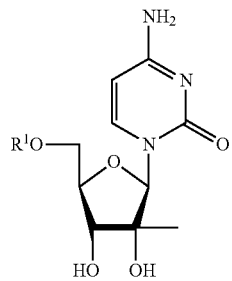

Formula LXXIX or pharmaceutically acceptable salts thereof wherein,
$R^1$ is selected from H or from one of the following formulae:

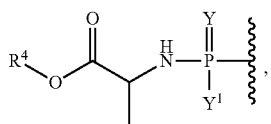

-continued

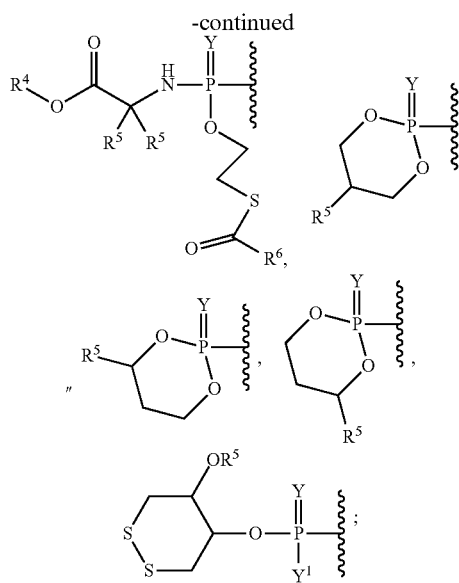

Y is O or S;
Y¹ is OH, OAryl, OAlkyl, or $BH_3^-M^+$;
Y² is OH or $BH_3^-M^+$;
Aryl is phenyl, 1-naphthyl, 2-naphthyl, aromatic, heteroaromatic, 4-substituted phenyl, 4-chlorophenyl, or 4-bromophenyl;
R⁴ is hydrogen, methyl, ethyl, isopropyl, cyclopentyl, cyclohexyl, neopentyl, benzyl, alkyl, branched alkyl, cycloalkyl, or lipid;
R⁵ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;
R⁶ is methyl, ethyl, tert-butyl, $C_{1-22}$ alkoxy, $C_{1-22}$ alkyl, branched alkyl, cycloalkyl, aryl, substituted aryl, or alkyoxy.

In certain embodiments, the present invention relates to methods of use for compounds of the following formula:

Formula LXXX

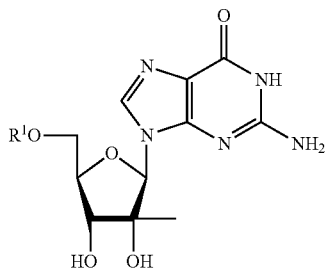

or pharmaceutically acceptable salts thereof wherein,
R¹ is selected from H or from one of the following formulae:

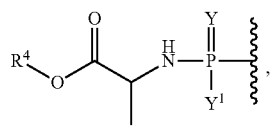

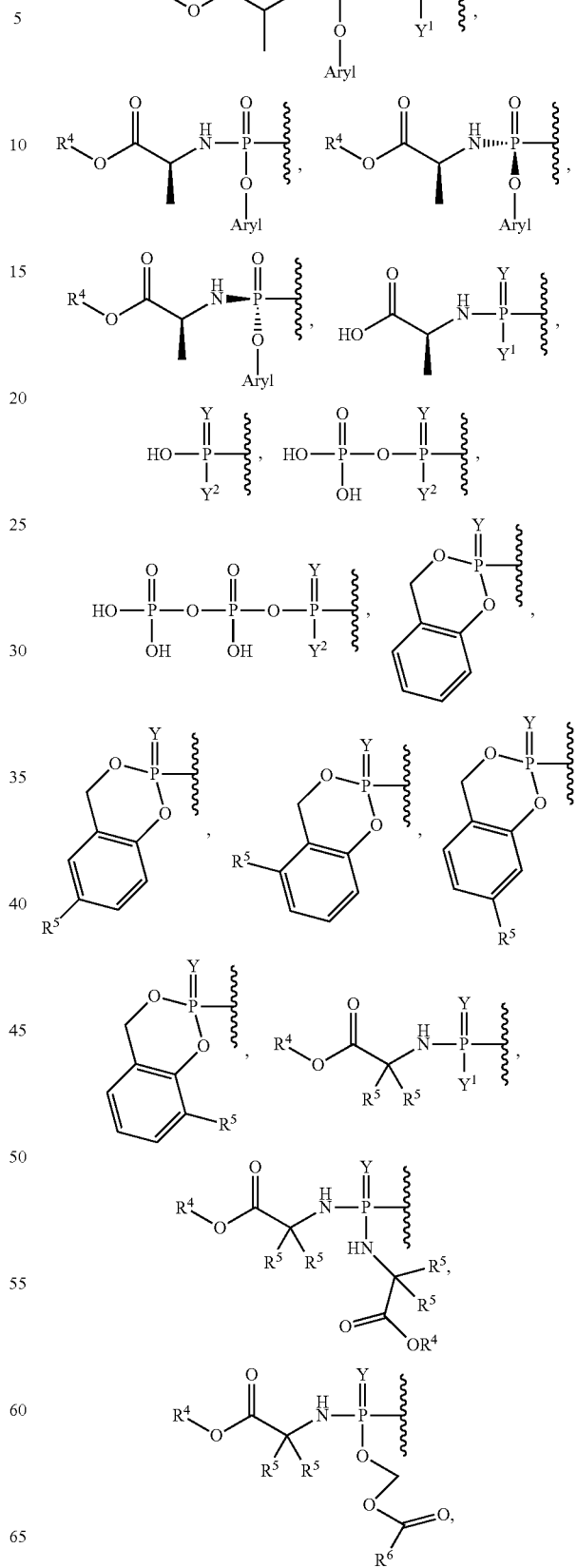

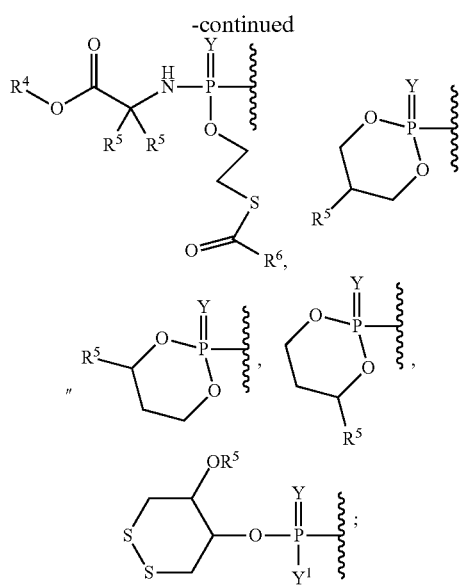

Y is O or S;
Y¹ is OH, OAryl, OAlkyl, or $BH_3^-M^+$;
Y² is OH or $BH_3^-M^+$;
Aryl is phenyl, 1-naphthyl, 2-naphthyl, aromatic, heteroaromatic, 4-substituted phenyl, 4-chlorophenyl, or 4-bromophenyl;
R⁴ is hydrogen, methyl, ethyl, isopropyl, cyclopentyl, cyclohexyl, neopentyl, benzyl, alkyl, branched alkyl, cycloalkyl, or lipid;
R⁵ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;
R⁶ is methyl, ethyl, tert-butyl, $C_{1-22}$ alkoxy, $C_{1-22}$ alkyl, branched alkyl, cycloalkyl, aryl, substituted aryl, or alkyoxy.
In certain embodiments, the present invention relates to methods of use for compounds of the following formula:

Formula LXXXI

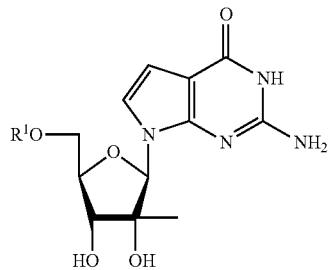

or pharmaceutically acceptable salts thereof wherein,
R¹ is selected from H or from one of the following formulae:

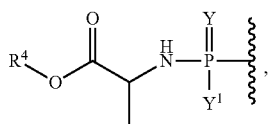

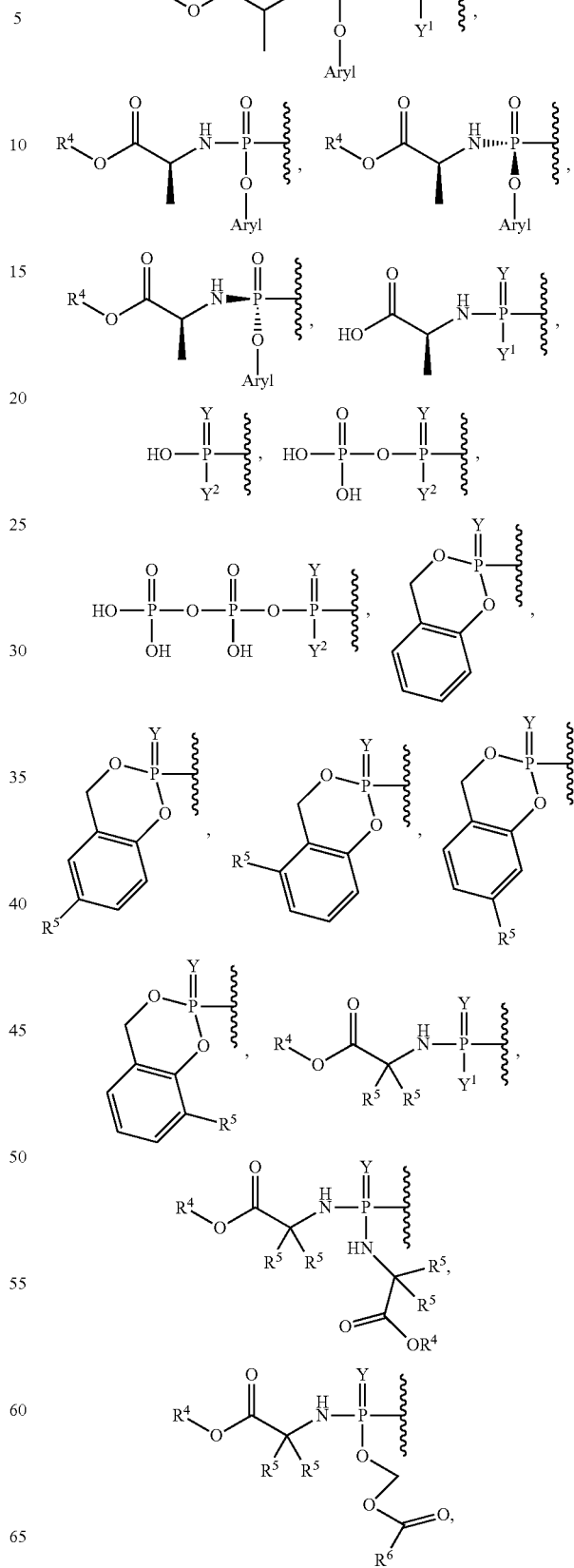

553

-continued

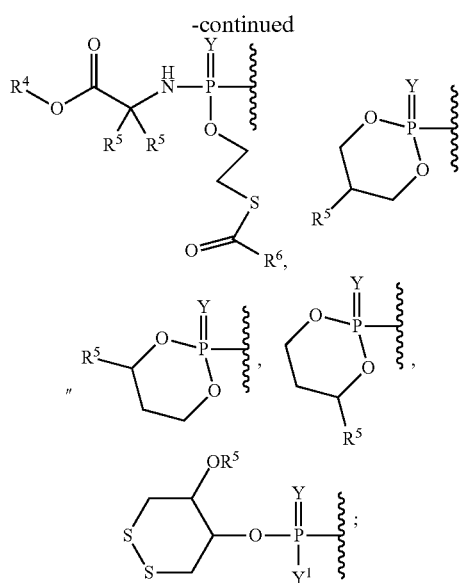

Y is O or S;
Y¹ is OH, OAryl, OAlkyl, or $BH_3^-M^+$;
Y² is OH or $BH_3^-M^+$;
Aryl is phenyl, 1-naphthyl, 2-naphthyl, aromatic, heteroaromatic, 4-substituted phenyl, 4-chlorophenyl, or 4-bromophenyl;
R⁴ is hydrogen, methyl, ethyl, isopropyl, cyclopentyl, cyclohexyl, neopentyl, benzyl, alkyl, branched alkyl, cycloalkyl, or lipid;
R⁵ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;
R⁶ is methyl, ethyl, tert-butyl, $C_{1-22}$ alkoxy, $C_{1-22}$ alkyl, branched alkyl, cycloalkyl, aryl, substituted aryl, or alkyoxy.

In certain embodiments, the present invention relates to methods of use for compounds of the following formula:

Formula LXXXII

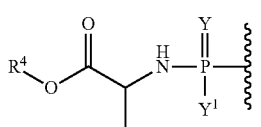

or pharmaceutically acceptable salts thereof wherein,
R¹ is selected from H or from one of the following formulae:

554

-continued

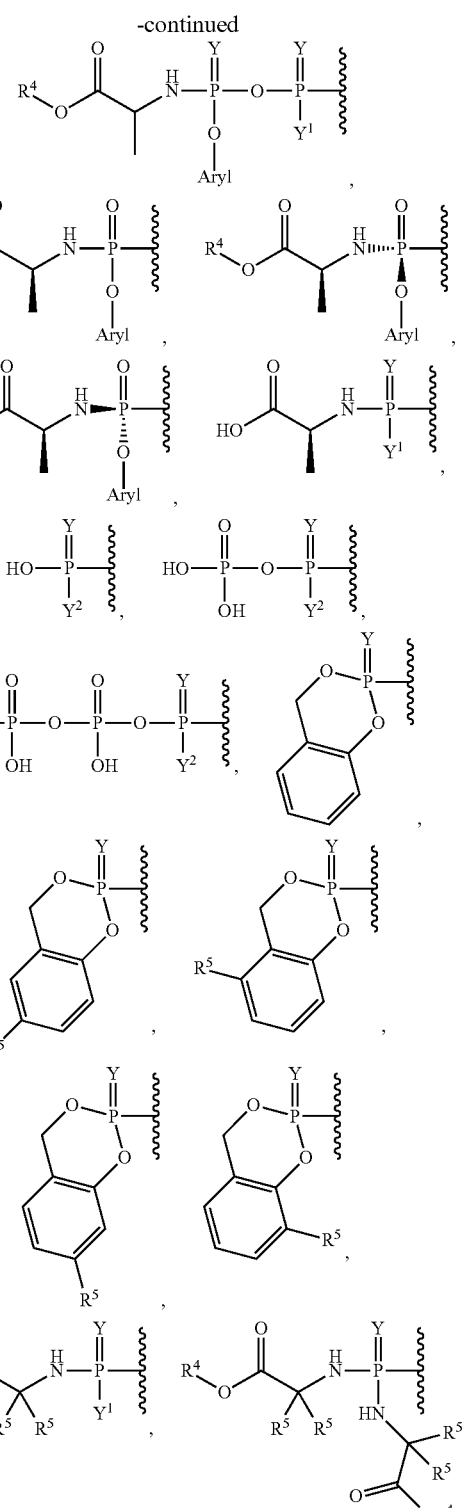

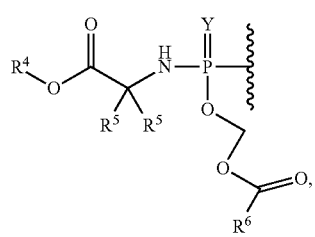

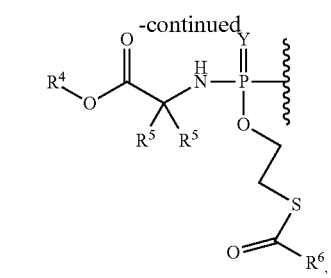

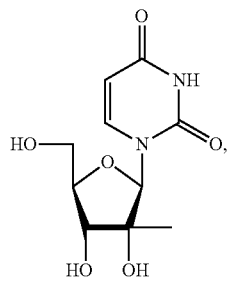

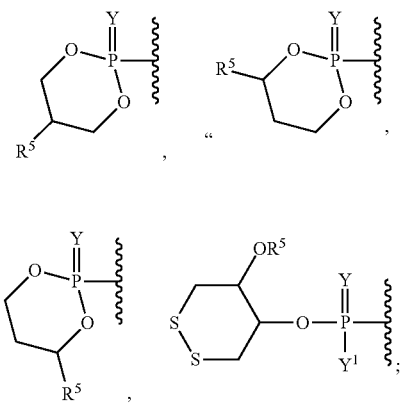

Y is O or S;

Y$^1$ is OH, OAryl, OAlkyl, or BH$_3^-$M$^+$;

Y$^2$ is OH or BH$_3^-$M$^+$;

Aryl is phenyl, 1-naphthyl, 2-naphthyl, aromatic, heteroaromatic, 4-substituted phenyl, 4-chlorophenyl, or 4-bromophenyl;

R$^4$ is hydrogen, methyl, ethyl, isopropyl, cyclopentyl, cyclohexyl, neopentyl, benzyl, alkyl, branched alkyl, cycloalkyl, or lipid;

R$^5$ is hydrogen, deuterium, hydroxyl, cyano, azido, amino, substituted amino, aryl, heteroaryl, substituted aryl, lipid, C$_{1-22}$ alkoxy, C$_{1-22}$ alkyl, C$_{2-22}$ alkenyl, C$_{2-22}$ alkynyl, or substituted heteroaryl;

R$^6$ is methyl, ethyl, tert-butyl, C$_{1-22}$ alkoxy, C$_{1-22}$ alkyl, branched alkyl, cycloalkyl, aryl, substituted aryl, or alkyoxy.

In certain embodiments, the present invention relates to compounds with the following structure:

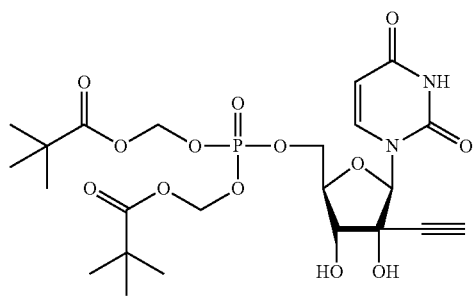

In certain embodiments, the present invention relates to methods of use for compounds of the following formula:

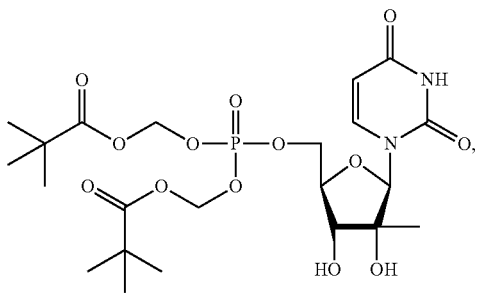

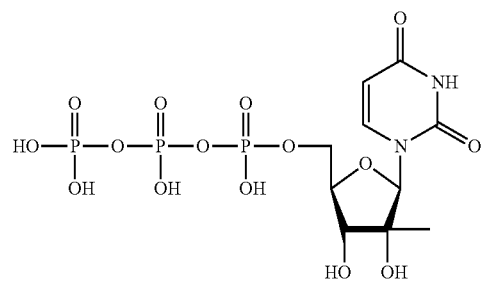

In certain embodiments, the present invention relates to methods of use for compounds of the following formula:

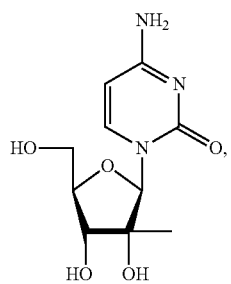

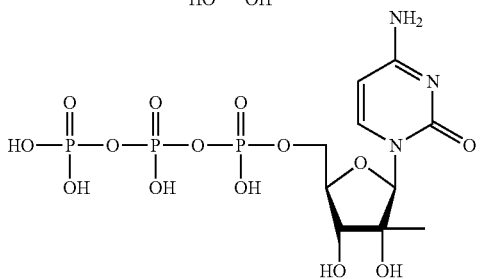

In certain embodiments, the present invention relates to methods of use for compounds of the following formula:

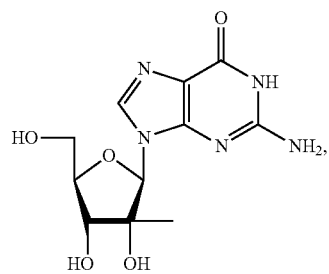

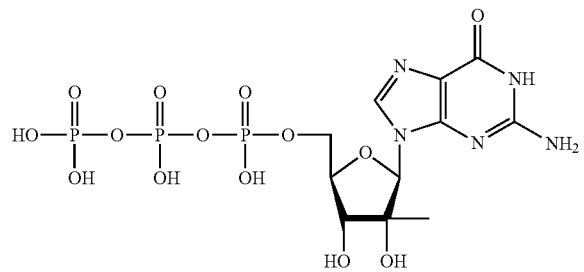

In certain embodiments, the present invention relates to methods of use for compounds of the following formula:

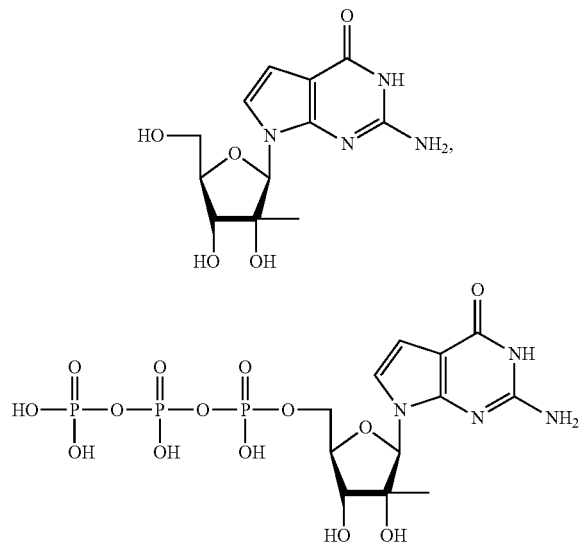

In certain embodiments, the present invention relates to methods of use for compounds of the following formula:

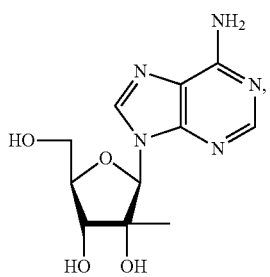

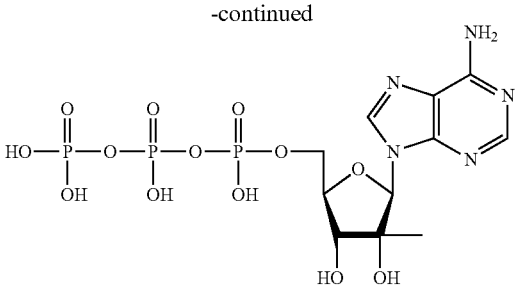

In certain embodiments, the present invention relates to methods of use for compounds of the following formula:

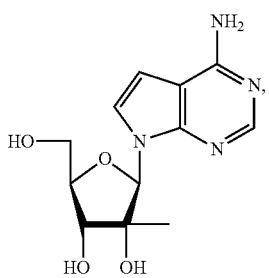

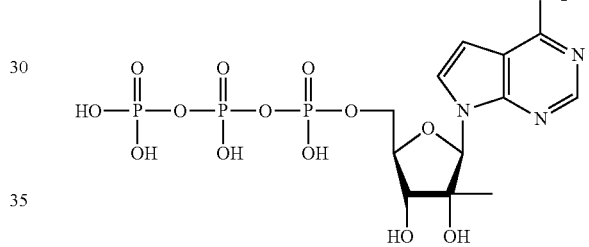

Lipid, as used herein, is a $C_{6-22}$ alkyl, alkoxy, polyethylene glycol, or aryl substituted with an alkyl group.

In certain embodiments, the lipid is a fatty alcohol, fatty amine, or fatty thiol derived from essential and non-essential fatty acids.

In certain embodiments, the lipid is an unsaturated, polyunsaturated, omega unsaturated, or omega polyunsaturated fatty alcohol, fatty amine, or fatty thiol derived from essential and non-essential fatty acids.

In certain embodiments, the lipid is a fatty alcohol, fatty amine, or fatty thiol derived from essential and non-essential fatty acids that have one or more of its carbon units substituted with an oxygen, nitrogen, or sulfur.

In certain embodiments, the lipid is an unsaturated, polyunsaturated, omega unsaturated, or omega polyunsaturated fatty alcohol, fatty amine, or fatty thiol derived from essential and non-essential fatty acids that have one or more of its carbon units substituted with an oxygen, nitrogen, or sulfur.

In certain embodiments, the lipid is a fatty alcohol, fatty amine, or fatty thiol derived from essential and non-essential fatty acids that is optionally substituted. In certain embodiments, the lipid is an unsaturated, polyunsaturated, omega unsaturated, or omega polyunsaturated fatty alcohol, fatty amine, or fatty thiol derived from essential and non-essential fatty acids that is optionally substituted.

In certain embodiments, the lipid is a fatty alcohol, fatty amine, or fatty thiol derived from essential and non-essential fatty acids that have one or more of its carbon units substituted with an oxygen, nitrogen, or sulfur that is optionally substituted.

In certain embodiments, the lipid is an unsaturated, polyunsaturated, omega unsaturated, or omega polyunsaturated fatty alcohol, fatty amine, or fatty thiol derived from essential and non-essential fatty acids that have one or more of its carbon units substituted with an oxygen, nitrogen, or sulfur that is also optionally substituted.

In certain embodiments, the lipid is hexadecyloxypropyl.

In certain embodiments, the lipid is 2-aminohexadecyloxypropyl.

In certain embodiments, the lipid is 2-aminoarachidyl.

In certain embodiments, the lipid is 2-benzyloxyhexadecyloxypropyl.

In certain embodiments, the lipid is lauryl, myristyl, palmityl, stearyl, arachidyl, behenyl, or lignoceryl.

In certain embodiments, the lipid is a sphingolipid having the formula:

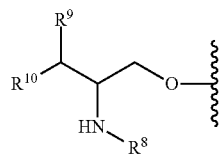

wherein, $R^8$ of the sphingolipid is hydrogen, alkyl, $C(=O)R^{12}$, $C(=O)OR^{12}$, or $C(=O)NHR^{12}$;

$R^9$ of the sphingolipid is hydrogen, fluoro, $OR^{12}$, $OC(=O)R^{12}$, $OC(=O)OR^{12}$, or $OC(=O)NHR^{12}$;

$R^{10}$ of the sphingolipid is a saturated or unsaturated alkyl chain of greater than 6 and less than 22 carbons optionally substituted with one or more halogen or hydroxy or a structure of the following formula:

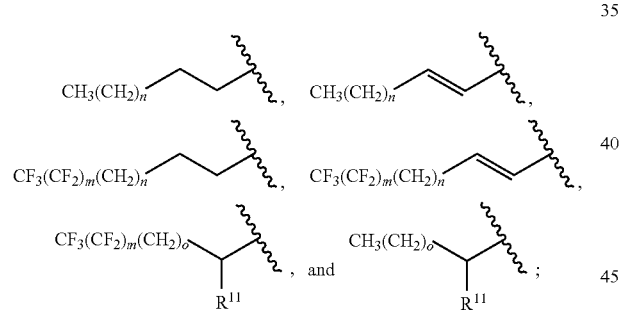

n is 8 to 14 or less than or equal to 8 to less than or equal to 14, o is 9 to 15 or less than or equal to 9 to less than or equal to 15, the total or m and n is 8 to 14 or less than or equal to 8 to less than or equal to 14, the total of m and o is 9 to 15 or less than or equal to 9 to less than or equal to 15; or

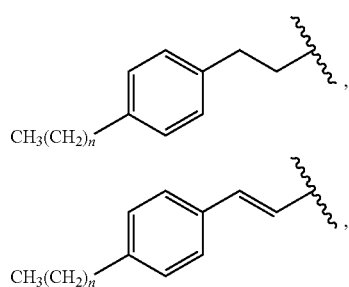

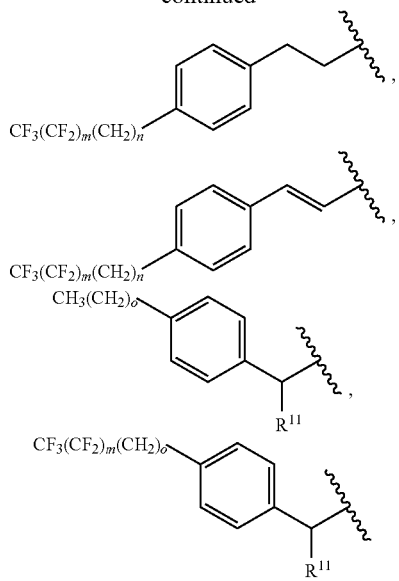

n is 4 to 10 or less than or equal to 4 to less than or equal to 10, o is 5 to 11 or less than or equal to 5 to less than or equal to 11, the total of m and n is 4 to 10 or less than or equal to 4 to less than or equal to 10, and the total of m and o is 5 to 11 or less than or equal to 5 to less than or equal to 11; or

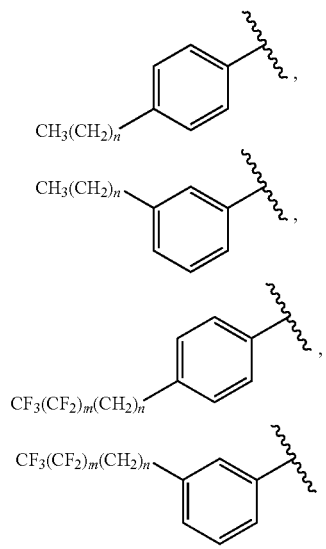

n is 6 to 12 or n is less than or equal to 6 to less than or equal to 12, the total of m and n is 6 to 12 or n is less than or equal to 6 to less than or equal to 12;

$R^{11}$ of the sphingolipid is $OR^{12}$, $OC(=O)R^{12}$, $OC(=O)OR^{12}$, or $OC(=O)NHR^{12}$;

$R^{12}$ of the sphingolipid is hydrogen, a branched or strait chain $C_{1-12}$alkyl, $C_{13-22}$alkyl, cycloalkyl, or aryl selected from benzyl or phenyl, wherein the aryl is optionally substituted with one or more, the same or different $R^{13}$; and $R^{13}$ of the sphingolipid is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^{12}$ of the sphingolipid is H, alkyl, methyl, ethyl, propyl, n-butyl, branched alkyl, isopropyl, 2-butyl, 1-ethylpropyl, 1-propylbutyl, cycloalkyl, cyclopropyl, cyclobutyl, cyclopentyl, cyclohexyl, benzyl, phenyl, monosubstituted phenyl, disubstituted phenyl, tri-substituted phenyl, or saturated or unsaturated C12-C19 long chain alkyl.

In certain embodiments, the sphingolipid has the formula:

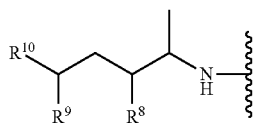

wherein,
$R^8$ of the sphingolipid is hydrogen, hydroxy, fluoro, $OR^{12}$, $OC(=O)R^{12}$, $OC(=O)OR^{12}$, or $OC(=O)NHR^{12}$;
$R^9$ of the sphingolipid is hydrogen, hydroxy, fluoro, $OR^{12}$, $OC(=O)R^{12}$, $OC(=O)OR^{12}$, or $OC(=O)NHR^{12}$;
$R^{10}$ of the sphingolipid is a saturated or unsaturated alkyl chain of greater than 6 and less than 22 carbons optionally substituted with one or more halogens or a structure of the following formula:

n is 8 to 14 or less than or equal to 8 to less than or equal to 14, the total or m and n is 8 to 14 or less than or equal to 8 to less than or equal to 14;
$R^{12}$ of the sphingolipid is hydrogen, a branched or strait chain $C_{1-12}$alkyl, $C_{13-22}$alkyl, cycloalkyl, or aryl selected from benzyl or phenyl, wherein the aryl is optionally substituted with one or more, the same or different $R^{13}$; and
$R^{13}$ of the sphingolipid is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^{12}$ of the sphingolipid is H, alkyl, methyl, ethyl, propyl, n-butyl, branched alkyl, isopropyl, 2-butyl, 1-ethylpropyl, 1-propylbutyl, cycloalkyl, cyclopropyl, cyclobutyl, cyclopentyl, cyclohexyl, benzyl, phenyl, monosubstituted phenyl, disubstituted phenyl, tri-substituted phenyl, or saturated or unsaturated $C_{12}$-$C_{19}$ long chain alkyl.

Suitable sphingolipids include, but are not limited to, sphingosine, ceramide, or sphingomyelin, or 2-aminoalkyl optionally substituted with one or more substituents.

Other suitable sphingolipids include, but are not limited to, 2-aminooctadecane-3,5-diol; (2S,3S,5S)-2-aminooctadecane-3,5-diol; (2S,3R,5S)-2-aminooctadecane-3,5-diol; 2-(methylamino)octadecane-3,5-diol; (2S,3R,5S)-2-(methylamino)octadecane-3,5-diol; 2-(dimethylamino)octadecane-3,5-diol; (2R,3S,5S)-2-(dimethylamino)octadecane-3,5-diol; 1-(pyrrolidin-2-yl)hexadecane-1,3-diol; (1S,3S)-1-((S)-pyrrolidin-2-yl)hexadecane-1,3-diol; 2-amino-11,11-difluorooctadecane-3,5-diol; (2S,3S,5S)-2-amino-11,11-difluorooctadecane-3,5-diol; 11,11-difluoro-2-(methylamino)octadecane-3,5-diol; (2S,3S,5S)-11,11-difluoro-2-(methylamino)octadecane-3,5-diol; N-((2S,3S,5S)-3,5-dihydroxyoctadecan-2-yl)acetamide; N-((2S,3S,5S)-3,5-dihydroxyoctadecan-2-yl)palmitamide; 1-(1-aminocyclopropyl)hexadecane-1,3-diol; (1S,3R)-1-(1-aminocyclopropyl)hexadecane-1,3-diol; (1S,3S)-1-(1-aminocyclopropyl)hexadecane-1,3-diol; 2-amino-2-methyloctadecane-3,5-diol; (3S,5S)-2-amino-2-methyloctadecane-3,5-diol; (3S,5R)-2-amino-2-methyloctadecane-3,5-diol; (3S,5S)-2-methyl-2-(methylamino)octadecane-3,5-diol; 2-amino-5-hydroxy-2-methyloctadecan-3-one; (Z)-2-amino-5-hydroxy-2-methyloctadecan-3-one oxime; (2S,3R,5R)-2-amino-6,6-difluorooctadecane-3,5-diol; (2S,3S,5R)-2-amino-6,6-difluorooctadecane-3,5-diol; (2S,3S,5S)-2-amino-6,6-difluorooctadecane-3,5-diol; (2S,3R,5S)-2-amino-6,6-difluorooctadecane-3,5-diol; and (2S,3S,5S)-2-amino-18,18,18-trifluorooctadecane-3,5-diol; which may be optionally substituted with one or more substituents.

Infectious Diseases

The compounds provided herein can be used to treat viral infectious diseases. Examples of viral infections include but are not limited to, infections caused by RNA viruses (including negative stranded RNA viruses, positive stranded RNA viruses, double stranded RNA viruses and retroviruses) or DNA viruses. All strains, types, and subtypes of RNA viruses and DNA viruses are contemplated herein.

Examples of RNA viruses include, but are not limited to picornaviruses, which include aphthoviruses (for example, foot and mouth disease virus 0, A, C, Asia 1, SAT1, SAT2 and SAT3), cardioviruses (for example, encephalomyocarditis virus and Theiller's murine encephalomyelitis virus), enteroviruses (for example polioviruses 1, 2 and 3, human enteroviruses A-D, bovine enteroviruses 1 and 2, human coxsackieviruses A1-A22 and A24, human coxsackieviruses B1-B5, human echoviruses 1-7, 9, 11-12, 24, 27, 29-33, human enteroviruses 68-71, porcine enteroviruses 8-10 and simian enteroviruses 1-18), erboviruses (for example, equine rhinitis virus), hepatovirus (for example human hepatitis A virus and simian hepatitis A virus), kobuviruses (for example, bovine kobuvirus and Aichi virus), parechoviruses (for example, human parechovirus 1 and human parechovirus 2), rhinovirus (for example, rhinovirus A, rhinovirus B, rhinovirus C, HRV16, HRV16 (VR-11757), HRV14 (VR-284), or HRViA (VR-1559), human rhinovirus 1-100 and bovine rhinoviruses 1-3) and teschoviruses (for example, porcine teschovirus).

Additional examples of RNA viruses include caliciviruses, which include noroviruses (for example, Norwalk virus), sapoviruses (for example, Sapporo virus), lagoviruses (for example, rabbit hemorrhagic disease virus and European brown hare syndrome) and vesiviruses (for example vesicular exanthema of swine virus and feline calicivirus). Other RNA viruses include astroviruses, which include mamastorviruses and avastroviruses. Togaviruses are also RNA viruses. Togaviruses include alphaviruses (for example, Chikungunya virus, Sindbis virus, Semliki Forest virus, Western equine encephalitis virus, Eastern Getah virus, Everglades virus, Venezuelan equine encephalitis virus, Ross River virus, Barmah Forest virus and Aura virus) and rubella viruses. Additional examples of RNA viruses include the flaviviruses (for example, tick-borne encephalitis virus (Western, Siberian, and Far eastern subtypes), Omsk hemorrhagic fever virus, Kyasanur Forest disease virus, Alkhurma virus, Louping ill virus, Tyuleniy virus, Aroa virus, M virus (types 1 to 4), Kedougou virus, Japanese encephalitis virus (JEV), West Nile virus (WNV), Dengue Virus (including genotypes 1-4), Zika virus, Powassan virus, Kokobera virus, Ntaya virus, Spondweni virus, Yellow fever virus, Entebbe bat virus, Modoc virus, Rio Bravo virus, Cell fusing agent virus, pestivirus, GB virus A, GBV-A like viruses, GB virus C, Hepatitis G virus, hepacivirus (hepatitis C virus (HCV)) all six genotypes), bovine viral diarrhea virus (BVDV) types 1 and 2, and GB virus B).

Other examples of RNA viruses are the coronaviruses, which include, human respiratory coronaviruses such as SARS-CoV, HCoV-229E, HCoV-NL63 and HCoV-OC43. Coronaviruses also include bat SARS-like CoV, Middle East Respiratory Syndrome coronavirus (MERS), turkey coronavirus, chicken coronavirus, feline coronavirus and canine coronavirus. Additional RNA viruses include arteriviruses (for example, equine arterivirus, porcine reproductive and respiratory syndrome virus, lactate dehyrogenase elevating virus of mice and simian hemorraghic fever virus). Other RNA viruses include the rhabdoviruses, which include lyssaviruses (for example, rabies, Lagos bat virus, Mokola virus, Duvenhage virus and European bat lyssavirus), vesiculoviruses (for example, VSV-Indiana, VSV-New Jersey, VSV-Alagoas, Piry virus, Cocal virus, Maraba virus, Isfahan virus and Chandipura virus), and ephemeroviruses (for example, bovine ephemeral fever virus, Adelaide River virus and Berrimah virus). Additional examples of RNA viruses include the filoviruses. These include the Marburg and Ebola viruses (for example, EBOV-Z, EBOV-S, EBOV-IC and EBOV-R).

The paramyxoviruses are also RNA viruses. Examples of these viruses are the rubulaviruses (for example, mumps, parainfluenza virus 5, human parainfluenza virus type 2, Mapuera virus and porcine rubulavirus), avulaviruses (for example, Newcastle disease virus), respoviruses (for example, Sendai virus, human parainfluenza virus type 1 and type 3, bovine parainfluenza virus type 3), henipaviruses (for example, Hendra virus and Nipah virus), morbilliviruses (for example, measles, Cetacean morvilliirus, Canine distemper virus, Peste des-petits-ruminants virus, Phocine distemper virus and Rinderpest virus), pneumoviruses (for example, human respiratory syncytial virus (RSV) A2, B1 and S2, bovine respiratory syncytial virus and pneumonia virus of mice), metapneumoviruses (for example, human metapneumovirus and avian metapneumovirus). Additional paramyxoviruses include Fer-de-Lance virus, Tupaia paramyxovirus, Menangle virus, Tioman virus, Beilong virus, J virus, Mossman virus, Salem virus and Nariva virus.

Additional RNA viruses include the orthomyxoviruses. These viruses include influenza viruses and strains (e.g., influenza A, influenza A strain A/Victoria/3/75, influenza A strain A/Puerto Rico/8/34, influenza A H1N1 (including but not limited to A/WS/33, A/NWS/33 and A/California/04/2009 strains), influenza B, influenza B strain Lee, and influenza C viruses) H2N2, H3N2, H5N1, H7N7, H1N2, H9N2, H7N2, H7N3 and H10N7), as well as avian influenza (for example, strains H5N1, H5N1 Duck/MN/1525/81, H5N2, H7N1, H7N7 and H9N2) thogotoviruses and isaviruses. Orthobunyaviruses (for example, Akabane virus, California encephalitis, Cache Valley virus, Snowshoe hare virus,) nairoviruses (for example, Nairobi sheep virus, Crimean-Congo hemorrhagic fever virus Group and Hughes virus), phleboviruses (for example, Candiru, Punta Toro, Rift Valley Fever, Sandfly Fever, Naples, Toscana, Sicilian and Chagres), and hantaviruses (for example, Hantaan, Dobrava, Seoul, Puumala, Sin Nombre, Bayou, Black Creek Canal, Andes and Thottapalayam) are also RNA viruses. Arenaviruses such as lymphocytic choriomeningitis virus, Lujo virus, Lassa fever virus, Argentine hemorrhagic fever virus, Bolivian hemorrhagic fever virus, Venezuelan hemorrhagic fever virus, SABV and WWAV are also RNA viruses. Borna disease virus is also an RNA virus. Hepatitis D (Delta) virus and hepatitis E are also RNA viruses.

Additional RNA viruses include reoviruses, rotaviruses, birnaviruses, chrysoviruses, cystoviruses, hypoviruses partitiviruses and totoviruses. Orbiviruses such as African horse sickness virus, Blue tongue virus, Changuinola virus, Chenuda virus, Chobar GorgeCorriparta virus, epizootic hemorrhagic disease virus, equine encephalosis virus, Eubenangee virus, Ieri virus, Great Island virus, Lebombo virus, Orungo virus, Palyam virus, Peruvian Horse Sickness virus, St. Croix River virus, Umatilla virus, Wad Medani virus, Wallal virus, Warrego virus and Wongorr virus are also RNA viruses. Retroviruses include alpharetroviruses (for example, Rous sarcoma virus and avian leukemia virus), betaretroviruses (for example, mouse mammary tumor virus, Mason-Pfizer monkey virus and Jaagsiekte sheep retrovirus), gammaretroviruses (for example, murine leukemia virus and feline leukemia virus, deltraretroviruses (for example, human T cell leukemia viruses (HTLV-1, HTLV-2), bovine leukemia virus, STLV-1 and STLV-2), epsilonretriviruses (for example, Walleye dermal sarcoma virus and Walleye epidermal hyperplasia virus 1), reticuloendotheliosis virus (for example, chicken syncytial virus, lentiviruses (for example, human immunodeficiency virus (HIV) type 1, human immunodeficiency virus (HIV) type 2, human immunodeficiency virus (HIV) type 3, simian immunodeficiency virus, equine infectious anemia virus, feline immunodeficiency virus, caprine arthritis encephalitis virus and Visna maedi virus) and spumaviruses (for example, human foamy virus and feline syncytia-forming virus).

Examples of DNA viruses include polyomaviruses (for example, simian virus 40, simian agent 12, BK virus, JC virus, Merkel Cell polyoma virus, bovine polyoma virus and lymphotrophic papovavirus), papillomaviruses (for example, human papillomavirus, bovine papillomavirus, adenoviruses (for example, adenoviruses A-F, canine adenovirus type I, canined adeovirus type 2), circoviruses (for example, porcine circovirus and beak and feather disease virus (BFDV)), parvoviruses (for example, canine parvovirus), erythroviruses (for example, adeno-associated virus types 1-8), betaparvoviruses, amdoviruses, densoviruses, iteraviruses, brevidensoviruses, pefudensoviruses, herpes viruses 1, 2, 3, 4, 5, 6, 7 and 8 (for example, herpes simplex virus 1, herpes simplex virus 2, varicella-zoster virus, Epstein-Barr virus, cytomegalovirus, Kaposi's sarcoma associated herpes virus, human herpes virus-6 variant A, human herpes virus-6 variant B and cercophithecine herpes virus 1 (B virus)), poxviruses (for example, smallpox (variola), cowpox, monkeypox, vaccinia, Uasin Gishu, camelpox, psuedocowpox, pigeonpox, horsepox, fowlpox, turkeypox and swinepox), and hepadnaviruses (for example, hepatitis B and hepatitis B-like viruses). Chimeric viruses comprising portions of more than one viral genome are also contemplated herein.

In some embodiments, the disclosure relates to treating or preventing an infection by viruses, bacteria, fungi, protozoa, and parasites. In some embodiments, the disclosure relates to methods of treating a viral infection comprising administering a compound herein to a subject that is diagnosed with, suspected of, or exhibiting symptoms of a viral infection.

Viruses are infectious agents that can typically replicate inside the living cells of organisms. Virus particles (virions) usually consist of nucleic acids, a protein coat, and in some cases an envelope of lipids that surrounds the protein coat. The shapes of viruses range from simple helical and icosahedral forms to more complex structures. Virally coded protein subunits will self-assemble to form a capsid, generally requiring the presence of the virus genome. Complex viruses can code for proteins that assist in the construction of their capsid. Proteins associated with nucleic acid are known as nucleoproteins, and the association of viral capsid proteins with viral nucleic acid is called a nucleocapsid.

Viruses are transmitted by a variety of methods including direct or bodily fluid contact, e.g., blood, tears, semen, preseminal fluid, saliva, milk, vaginal secretions, lesions, droplet contact, fecal-oral contact, or as a result of an animal bite or birth. A virus has either DNA or RNA genes and is called a DNA virus or a RNA virus respectively. A viral genome is either single-stranded or double-stranded. Some viruses contain a genome that is partially double-stranded and partially single-stranded. For viruses with RNA or single-stranded DNA, the strands are said to be either positive-sense (called the plus-strand) or negative-sense (called the minus-strand), depending on whether it is complementary to the viral messenger RNA (mRNA). Positive-sense viral RNA is identical to viral mRNA and thus can be immediately translated by the host cell. Negative-sense viral RNA is complementary to mRNA and thus must be converted to positive-sense RNA by an RNA polymerase before translation. DNA nomenclature is similar to RNA nomenclature, in that the coding strand for the viral mRNA is complementary to it (negative), and the non-coding strand is a copy of it (positive).

Antigenic shift, or reassortment, can result in novel strains. Viruses undergo genetic change by several mechanisms. These include a process called genetic drift where individual bases in the DNA or RNA mutate to other bases. Antigenic shift occurs when there is a major change in the genome of the virus. This can be a result of recombination or reassortment. RNA viruses often exist as quasispecies or swarms of viruses of the same species but with slightly different genome nucleoside sequences.

The genetic material within viruses, and the method by which the material is replicated, vary between different types of viruses. The genome replication of most DNA viruses takes place in the nucleus of the cell. If the cell has the appropriate receptor on its surface, these viruses enter the cell by fusion with the cell membrane or by endocytosis. Most DNA viruses are entirely dependent on the host DNA and RNA synthesizing machinery, and RNA processing machinery. Replication usually takes place in the cytoplasm. RNA viruses typically use their own RNA replicase enzymes to create copies of their genomes.

The Baltimore classification of viruses is based on the mechanism of mRNA production. Viruses must generate mRNAs from their genomes to produce proteins and replicate themselves, but different mechanisms are used to achieve this. Viral genomes may be single-stranded (ss) or double-stranded (ds), RNA or DNA, and may or may not use reverse transcriptase (RT). Additionally, ssRNA viruses may be either sense (plus) or antisense (minus). This classification places viruses into seven groups: I, dsDNA viruses (e.g. adenoviruses, herpesviruses, poxviruses); II, ssDNA viruses (plus) sense DNA (e.g. parvoviruses); III, dsRNA viruses (e.g. reoviruses); IV, (plus) ssRNA viruses (plus) sense RNA (e.g. picornaviruses, togaviruses); V, (minus) ssRNA viruses (minus) sense RNA (e.g. orthomyxoviruses, Rhabdoviruses); VI, ssRNA-RT viruses (plus) sense RNA with DNA intermediate in life-cycle (e.g. retroviruses); and VII, dsDNA-RT viruses (e.g. hepadnaviruses).

Human immunodeficiency virus (HIV) is a lentivirus (a member of the retrovirus family) that causes acquired immunodeficiency syndrome (AIDS). Lentiviruses are transmitted as single-stranded, positive-sense, enveloped RNA viruses. Upon entry of the target cell, the viral RNA genome is converted to double-stranded DNA by a virally encoded reverse transcriptase. This viral DNA is then integrated into the cellular DNA by a virally encoded integrase, along with host cellular co-factors. There are two species of HIV. HIV-1 is sometimes termed LAV or HTLV-III.

HIV infects primarily vital cells in the human immune system such as helper T cells (CD4+ T cells), macrophages, and dendritic cells. HIV infection leads to low levels of CD4+ T cells. When CD4+ T cell numbers decline below a critical level, cell-mediated immunity is lost, and the body becomes progressively more susceptible to other viral or bacterial infections. Subjects with HIV typically develop malignancies associated with the progressive failure of the immune system.

The viral envelope is composed of two layers of phospholipids taken from the membrane of a human cell when a newly formed virus particle buds from the cell. Embedded in the viral envelope are proteins from the host cell and a HIV protein known as Env. Env contains glycoprotein-sgp120, and gp41. The RNA genome consists of at structural landmarks (LTR, TAR, RRE, PE, SLIP, CRS, and INS) and nine genes (gag, pol, and env, tat, rev, nef, vif, vpr, vpu, and sometimes a tenth tev, which is a fusion of tat env and rev) encoding 19 proteins. Three of these genes, gag, pol, and env, contain information needed to make the structural proteins for new virus particles. HIV-1 diagnosis is typically done with antibodies in an ELISA, Western blot, orimmunoaffinity assays or by nucleic acid testing (e.g., viral RNA or DNA amplification).

HIV is typically treated with a combination of antiviral agent, e.g., two nucleoside-analogue reverse transcription inhibitors and one non-nucleoside-analogue reverse transcription inhibitor or protease inhibitor. The three-drug combination is commonly known as a triple cocktail. In certain embodiments, the disclosure relates to treating a subject diagnosed with HIV by administering a pharmaceutical composition disclosed herein in combination with two nucleoside-analogue reverse transcription inhibitors and one non-nucleoside-analogue reverse transcription inhibitor or protease inhibitor.

In certain embodiments, the disclosure relates to treating a subject by administering a compound disclosed herein, emtricitabine, tenofovir, and efavirenz. In certain embodiments, the disclosure relates to treating a subject by administering a compound disclosed herein, emtricitabine, tenofovir and raltegravir. In certain embodiments, the disclosure relates to treating a subject by administering a compound disclosed herein, emtricitabine, tenofovir, ritonavir and darunavir. In certain embodiments, the disclosure relates to treating a subject by administering a compound disclosed herein, emtricitabine, tenofovir, ritonavir and atazanavir.

Banana lectin (BanLec or BanLec-1) is one of the predominant proteins in the pulp of ripe bananasand has binding specificity for mannose and mannose-containing oligosaccharides. BanLec binds to the HIV-1 envelope protein gp120. In certain embodiments, the disclosure relates to treating viral infections, such as HIV, by administering a compound disclosed herein in combination with a banana lectin.

The hepatitis C virus is a single-stranded, positive sense RNA virus. It is the only known member of the hepacivirus genus in the family Flaviviridae. There are six major genotypes of the hepatitis C virus, which are indicated numerically. The hepatitis C virus particle consists of a core of genetic material (RNA), surrounded by an icosahedral protective shell, and further encased in a lipid envelope. Two viral envelope glycoproteins, E1 and E2, are embedded in the lipid envelope. The genome consists of a single open reading frame translated to produce a single protein. This large pre-protein is later cut by cellular and viral proteases into smaller proteins that allow viral replication within the host cell, or assemble into the mature viral particles, e.g., E1, E2, NS2, NS3, NS4, NS4A, NS4B, NS5, NS5A, and NS5B.

HCV leads to inflammation of the liver, and chronic infection leads to cirrhosis. Most people with hepatitis C infection have the chronic form. Diagnosis of HCV can occur via nucleic acid analysis of the 5'-noncoding region. ELISA assay may be performed to detect hepatitis C antibodies and RNA assays to determine viral load. Subjects infected with HCV may exhibit symptoms of abdominal pain, ascites, dark urine, fatigue, generalized itching, jaundice, fever, nausea, pale or clay-colored stools and vomiting.

Therapeutic agents in some cases may suppress the virus for a long period of time. Typical medications are a combination of interferon alpha and ribavirin. Subjects may receive injections of pegylated interferon alpha. Genotypes 1 and 4 are less responsive to interferon-based treatment than are the other genotypes (2, 3, 5 and 6). In certain embodiments, the disclosure relates to treating a subject with HCV by administering a compound disclosed herein to a subject exhibiting symptoms or diagnosed with HCV. In certain embodiments, the compound is administered in combination with interferon alpha and another antiviral agent such as ribavirin, and/or a protease inhibitor such as telaprevir or boceprevir. In certain embodiments, the subject is diagnosed with genotype 2, 3, 5, or 6. In other embodiments, the subject is diagnosed with genotype 1 or 4.

In certain embodiments, the subject is diagnosed to have a virus by nucleic acid detection or viral antigen detection. Cytomegalovirus (CMV) belongs to the Betaherpesvirinae subfamily of Herpesviridae. In humans it is commonly known as HCMV or Human Herpesvirus 5 (HHV-5). Herpesviruses typically share a characteristic ability to remain latent within the body over long periods. HCMV infection may be life threatening for patients who are immunocompromised. In certain embodiments, the disclosure relates to methods of treating a subject diagnosed with cytomegalovirus or preventing a cytomegalovirus infection by administration of a compound disclosed herein. In certain embodiments, the subject is immunocompromised. In typical embodiments, the subject is an organ transplant recipient, undergoing hemodialysis, diagnosed with cancer, receiving an immunosuppressive drug, and/or diagnosed with an HIV-infection. In certain embodiments, the subject may be diagnosed with cytomegalovirus hepatitis, the cause of fulminant liver failure, cytomegalovirus retinitis (inflammation of the retina, may be detected by ophthalmoscopy), cytomegalovirus colitis (inflammation of the large bowel), cytomegalovirus pneumonitis, cytomegalovirus esophagitis, cytomegalovirus mononucleosis, polyradiculopathy, transverse myelitis, and subacute encephalitis. In certain embodiments, a compound disclosed herein is administered in combination with an antiviral agent such as valganciclovir or ganciclovir. In certain embodiments, the subject undergoes regular serological monitoring.

HCMV infections of a pregnant subject may lead to congenital abnormalities. Congenital HCMV infection occurs when the mother suffers a primary infection (or reactivation) during pregnancy. In certain embodiments, the disclosure relates to methods of treating a pregnant subject diagnosed with cytomegalovirus or preventing a cytomegalovirus infection in a subject at risk for, attempting to become, or currently pregnant by administering compound disclosed herein.

Subjects who have been infected with CMV typically develop antibodies to the virus. A number of laboratory tests that detect these antibodies to CMV have been developed. The virus may be cultured from specimens obtained from urine, throat swabs, bronchial lavages and tissue samples to detect active infection. One may monitor the viral load of CMV-infected subjects using PCR. CMV pp65 antigenemia test is an immunoaffinity based assay for identifying the pp65 protein of cytomegalovirus in peripheral blood leukocytes. CMV should be suspected if a patient has symptoms of infectious mononucleosis but has negative test results for mononucleosis and Epstein-Barr virus, or if they show signs of hepatitis, but have negative test results for hepatitis A, B, and C. A virus culture can be performed at any time the subject is symptomatic. Laboratory testing for antibody to CMV can be performed to determine if a subject has already had a CMV infection.

The enzyme-linked immunosorbent assay (or ELISA) is the most commonly available serologic test for measuring antibody to CMV. The result can be used to determine if acute infection, prior infection, or passively acquired maternal antibody in an infant is present. Other tests include various fluorescence assays, indirect hemagglutination, (PCR), and latex agglutination. An ELISA technique for CMV-specific IgM is available.

Hepatitis B virus is a hepadnavirus. The virus particle, (virion) consists of an outer lipid envelope and an icosahedral nucleocapsid core composed of protein. The genome of HBV is made of circular DNA, but the DNA is not fully double-stranded. One end of the strand is linked to the viral DNA polymerase. The virus replicates through an RNA intermediate form by reverse transcription. Replication typically takes place in the liver where it causes inflammation (hepatitis). The virus spreads to the blood where virus-specific proteins and their corresponding antibodies are found in infected people. Blood tests for these proteins and antibodies are used to diagnose the infection.

Hepatitis B virus gains entry into the cell by endocytosis. Because the virus multiplies via RNA made by a host enzyme, the viral genomic DNA has to be transferred to the cell nucleus by host chaperones. The partially double stranded viral DNA is then made fully double stranded and transformed into covalently closed circular DNA (cccDNA) that serves as a template for transcription of viral mRNAs. The virus is divided into four major serotypes (adr, adw, ayr, ayw) based on antigenic epitopes presented on its envelope proteins, and into eight genotypes (A-H) according to overall nucleotide sequence variation of the genome.

The hepatitis B surface antigen (HBsAg) is typically used to screen for the presence of this infection. It is the first detectable viral antigen to appear during infection. However, early in an infection, this antigen may not be present and it may be undetectable later in the infection if it is being cleared by the host. The infectious virion contains an inner "core particle" enclosing viral genome. The icosahedral core particle is made of core protein, alternatively known as hepatitis B core antigen, or HBcAg. IgM antibodies to the hepatitis B core antigen (anti-HBc IgM) may be used as a serological marker. Hepatitis B e antigen (HBeAg) may appear. The presence of HBeAg in the serum of the host is associated with high rates of viral replication. Certain variants of the hepatitis B virus do not produce the 'e' antigen.

If the host is able to clear the infection, typically the HBsAg will become undetectable and will be followed by IgG antibodies to the hepatitis B surface antigen and core antigen, (anti-HBs and anti HBc IgG). The time between the removal of the HBsAg and the appearance of anti-HBs is called the window period. A person negative for HBsAg but positive for anti-HBs has either cleared an infection or has been vaccinated previously. Individuals who remain HBsAg positive for at least six months are considered to be hepatitis B carriers. Carriers of the virus may have chronic hepatitis B, which would be reflected by elevated serum alanine aminotransferase levels and inflammation of the liver that may be identified by biopsy. Nucleic acid (PCR) tests have been developed to detect and measure the amount of HBV DNA in clinical specimens.

Acute infection with hepatitis B virus is associated with acute viral hepatitis. Acute viral hepatitis typically begins with symptoms of general ill health, loss of appetite, nausea, vomiting, body aches, mild fever, dark urine, and then progresses to development of jaundice. Chronic infection with hepatitis B virus may be either asymptomatic or may be associated with a chronic inflammation of the liver (chronic hepatitis), possibly leading to cirrhosis. Having chronic hepatitis B infection increases the incidence of hepatocellular carcinoma (liver cancer).

During HBV infection, the host immune response causes both hepatocellular damage and viral clearance. The adaptive immune response, particularly virus-specific cytotoxic T lymphocytes (CTLs), contributes to most of the liver injury associated with HBV infection. By killing infected cells and by producing antiviral cytokines capable of purging HBV from viable hepatocytes, CTLs eliminate the virus. Although liver damage is initiated and mediated by the CTLs, antigen-nonspecific inflammatory cells can worsen CTL-induced immunopathology, and platelets activated at the site of infection may facilitate the accumulation of CTLs in the liver.

Therapeutic agents can stop the virus from replicating, thus minimizing liver damage. In certain embodiments, the disclosure relates to methods of treating a subject diagnosed with HBV by administering a compound disclosed herein disclosed herein. In certain embodiments, the subject is immunocompromised. In certain embodiments, the compound is administered in combination with another antiviral agent such as lamivudine, adefovir, tenofovir, telbivudine, and entecavir, and/or immune system modulators interferon alpha-2a and pegylated interferon alpha-2a (Pegasys). In certain embodiments, the disclosure relates to preventing an HBV infection in an immunocompromised subject at risk of infection by administering a pharmaceutical composition disclosed herein and optionally one or more antiviral agents. In certain embodiments, the subject is at risk of an infection because the sexual partner of the subject is diagnosed with HBV.

Zika virus (ZIKV) is an emerging arthropod-borne human pathogen in the family Flaviviridae (genus flavivirus) first isolated in 1947 from a febrile sentinel rhesus monkey in the Zika forest of Uganda. Though mainly transmitted by the *Aedes aegypti* mosquito, current reports strongly suggest that the virus is being transmitted perinatally, sexually and via blood transfusion. ZIKV infections are usually self-limiting with 80% of infected individuals clinically asymptomatic. Symptoms for patients that become ill are usually mild and non-life threating. Symptoms include fever, maculopapular rash, joint pain and/or conjunctivitis, muscle pain, headache and retro-orbital pain. Recently, a higher than normal incidence of Gullain-Barre Syndrome (GBS), the most frequent cause of non-poliovirus associated acute flaccid paralysis, and primary microcephaly cases have been linked to ZIKV outbreaks in French Polynesia and Brazil. GBS is a serious disease believed to be initiated by an immune-mediated response to antigenic exposure from certain viruses or bacterial infections. Roughly 20% of the patients are left with severe disability and approximately 5% of the patients die. Also of great concern is the apparent correlation of ZIKV infections with a 20-fold increase in the incidence of microcephaly cases reported in Brazil in 2015. Among the symptoms, the most common are seizures, mental retardation, development delay, cerebral palsy, hearing and vision loss. Currently there are no vaccines or therapeutic options for the prevention or treatment of ZIKV infections.

The mechanism of infection of ZIKV has not been well studied, but the replication cycle of the virus may be similar to other flaviviruses such as DFV. Human skin inoculated with saliva from a ZIKV infected mosquito leads to infection of epidermal keratinocytes, skin fibroblasts, and Langerhans cells. ZIKV continues to spread throughout the human host by way of lymph nodes and bloodstream. ZIKV genome replication occurs at intracellular compartments in the endoplasmic reticulum by a membrane-bound viral replication complex consisting of viral non-structural proteins, viral RNA, and host proteins, the identity of which are mostly unknown. The genome of ZIKV is a single-stranded (+)-RNA molecule approximately 10.7 kb in length with two non-coding flanking regions (NCR) known as 5'-NCR and 3'-NCR. The ZIKV RNA genome contains a single open reading frame (ORF) encoding a 3,419 amino acid polypeptide, which is cleaved into three structural proteins (C, prM and E) and seven non-structural proteins (NS1, NS2a, NS2b, NS3, NS4a, NS4b and NS5). The complex first transcribes genomic plus-strand RNA into a complementary minus strand RNA intermediate resulting in the formation of a duplex RNA. The minus strand of this duplex serves as a template for multiple rounds of plus-strand RNA synthesis. Viral RNA synthesis occurs through an asymmetric replication cycle in which ten times more plus-strand than minus-strand RNA is synthesized.

In certain embodiments, pharmaceutical compositions disclosed herein are administered in combination with a second antiviral agent, such as ABT-450, ABT-267, ABT-333, ABT-493, ABT-530, abacavir, acyclovir, acyclovir, adefovir, amantadine, amprenavir, ampligen, arbidol, atazanavir, atripla, boceprevir, cidofovir, combivir, daclatasvir, darunavir, dasabuvir, delavirdine, didanosine, docosanol, edoxudine, efavirenz, emtricitabine, enfuvirtide, entecavir, famciclovir, fomivirsen, fosamprenavir, foscarnet, fosfonet, ganciclovir, ibacitabine, imunovir, idoxuridine, imiquimod, indinavir, inosine, interferon type III, interferon type II, interferon type I, lamivudine, ledipasvir, lopinavir, loviride, maraviroc, moroxydine, methisazone, nelfinavir, nevirapine, nexavir, ombitasvir, oseltamivir, paritaprevir, peginterferon alfa-2a, penciclovir, peramivir, pleconaril, podophyllotoxin, raltegravir, ribavirin, rimantadine, ritonavir, pyramidine, saquinavir, simeprevir, sofosbuvir, stavudine, telaprevir, telbivudine, tenofovir, tenofovir disoproxil, tipranavir, trifluridine, trizivir, tromantadine, truvada, valaciclovir, valganciclovir, vicriviroc, vidarabine, viramidine zalcitabine, zanamivir, or zidovudine and combinations thereof.

Methods for treating HCV infection in a subject are also provided. The methods comprise administering the compounds of this invention to provide at least two direct acting antiviral agents (DAAs) with or without ribavirin for a duration of no more than twelve weeks, or for another duration as set forth herein. In one embodiment, the duration of the treatment is no more than twelve weeks. In another embodiment, the duration of the treatment is no more than eight weeks. Preferably, the two or more direct acting antiviral agents (DAAs), with or without ribavirin, are administered in amounts effective to provide a sustained virological response (SVR) or achieve another desired measure of effectiveness in a subject. The subject is not administered interferon during the treatment regimen. Put another way, in one embodiment, the methods exclude the administration of interferon to the subject, thereby avoiding the side effects associated with interferon. In some embodiments, the methods further comprise administering an inhibitor of cytochrome P-450 (such as ritonavir) to the subject to improve the pharmacokinetics or bioavailability of one or more of the DAAs.

As another aspect, methods for treating HCV infection in a subject are provided. The methods comprise administering (a) protease inhibitor, (b) at least one polymerase inhibitor, wherein at least one is a polymerase of this invention and combinations thereof, with or without (c) ribavirin and/or (d) an inhibitor or cytochrome P-450 to the subject for a duration of no more than twelve weeks, or for another duration as set forth herein (e.g., the treatment regimen can last a duration of for no more than 8 weeks). Preferably, the compounds are administered in amounts effective to provide high rates of SVR or another measure of effectiveness in the subject. As non-limiting examples, the compounds can be co-formulated and administered once daily, and the treatment regimen preferably lasts for eight weeks or six weeks.

As still another aspect, methods for treating a population of subjects having HCV infection are provided. The methods comprise administering at least two DAAs, wherein one of the DAAs is a compound of this invention, with or without ribavirin, to the subjects for a duration of no more than 12 or 8 or 6 weeks. Preferably, the at least two DAAs are administered to the subjects in amounts effective to result in SVR or another measure of effectiveness in at least about 70% of the population, preferably at least 90% of the population.

In the foregoing methods as well as methods described herein below, the DAAs can be selected from the group consisting of protease inhibitors, nucleoside or nucleotide polymerase inhibitors (one of which is provided herein), non-nucleoside polymerase inhibitors, NS3B inhibitors, NS4A inhibitors, NS5A inhibitors, NS5B inhibitors, cyclophilin inhibitors, and combinations of any of the foregoing. For example, in some embodiments, the DAAs used in the present methods comprise or consist of at least one HCV protease inhibitor and at least one HCV polymerase inhibitor provided herein.

At least one of the HCV polymerase inhibitors is one of the compounds of this invention (described herein). By way of example, compounds of this invention can be administered a total daily dose of from about 100 mg to about 250 mg, or administered once daily at a dose of from about 150 mg to about 250 mg.

In some embodiments, the at least two DAAs comprise at least on HCV polymerase inhibitors of this invention and at least one NS5A inhibitor. By way of example, the polymerase inhibitor of this invention can be administered at a total daily dosage from about 100 mg to about 250 mg, and the NS5A inhibitor can be administered in a total daily dose from about 25 mg to about 200 mg. Ritonavir (or another cytochrome P-450 3A4 inhibitor) can be co-administered with to improve the pharmacokinetics and bioavailability of the compounds.

In the foregoing methods as well as methods described herein, the DAAs with or without ribavirin can be administered in any effective dosing schemes and/or frequencies, for example, they can each be administered daily. Each DAA can be administered either separately or in combination, and each DAA can be administered at lease once a day, at least twice a day, or at least three times a day. Likewise, the ribavirin can be administered at least once a day, at least twice a day, or at least three times a day, either separately or in combination with one of more of the DAAs. In some preferred embodiments, the compounds are administered once daily.

In some aspects, the present technology provides a method for treating HCV infection comprising administering to a subject in need thereof at least two DAAs with or without ribavirin for a duration of no more than twelve or eight or six weeks, wherein the subject is not administered with interferon during said duration. In some aspects, the at least two DAAs with or without ribavirin are administered in an amount effective to result in SVR. Some methods further comprise administering an inhibitor of cytochrome P450 to the subject. In some aspects, the duration is no more than eight weeks.

In yet another aspect, the at least two direct acting antiviral agents comprises a drug combination selected from the group consisting of: a compound of this invention, with one or more of ABT-450 and/or ABT-267, and/or ABT-333, and/or ABT-493, and/or ABT-530; a novel compound of this invention with a compound disclosed in any of US 2010/0144608; U.S. 61/339,964; US 2011/0312973; WO 2009/039127; US 2010/0317568; 2012/151158; US 2012/0172290; WO 2012/092411; WO 2012/087833; WO 2012/083170; WO 2009/039135; US 2012/0115918; WO 2012/051361; WO 2012/009699; WO 2011/156337; US 2011/0207699; WO 2010/075376; U.S. Pat. No. 7,910,595; WO 2010/120935; WO 2010/111437; WO 2010/111436; US 2010/0168384 or US 2004/0167123; a compound of this invention with one or more of Simeprevir, and/or GSK805; a compound of this invention with one or more of Asunaprevir, and/or Daclastavir, and/or BMS-325; a compound of this invention with one or more of GS-9451, and/or Ledisasvir and/or Sofosbuvir, and/or GS-9669; a compound of this invention with one or more of ACH-2684, and/or ACH-3102, and/or ACH-3422; a compound of this invention with one or more of Boceprevir, and/or MK-8742; a compound of this invention with one or more of Faldaprevir and/or Deleobuvir; a compound of this invention with PPI-668; a compound of this invention with one or more of telaprevir and/or VX-135; a compound of this invention with one or more of Samatasvir and/or IDX-437; a compound of this invention with PSI-7977 and/or PSI-938, a compound of this invention with BMS-790052 and/or BMS-650032; a compound of this invention with GS-5885 and/or GS-9451; a compound of this invention with GS-5885, GS-9190 and/or GS-9451; a compound of this invention in combination with BI-201335 and/or BI-27127; a compound of this invention in combination with telaprevir and/or VX-222; a compound of this invention combination with PSI-7977 and/or TMC-435; and a compound of this invention in combination with danoprevir and/or R7128.

In yet another aspect, the at least two direct acting antiviral agents comprises a compound of this invention in a combination of PSI-7977 and/or BMS-790052 (daclatasvir). In yet another aspect, the at least two direct acting antiviral agents comprises a compound of this invention in a combination of PSI-7977 and/or BMS-650032 (asunaprevir). In still another aspect, the at least direct acting antiviral agents comprise a compound of this invention in combination with PSI-7977, BMS-650032 (asunaprevir) and/or BMS-790052 (daclatasvir). The compounds of this invention can be either added to these combinations or used to replace the listed polymerase.

In another aspect, the present technology features a combination of at least two DAAs for use in treating HCV infection, wherein the duration of the treatment regimen is no more than twelve weeks (e.g., the duration being 12 weeks; or the duration being 11, 10, 9, 8, 7, 6, 5. 4, or 3 weeks). The treatment comprises administering the at least two DAAs to a subject infected with HCV. The duration of the treatment can be 12 weeks and also last, for example, no more than eight weeks (e.g., the duration being 8 weeks; or the duration being 7, 6, 5, 4, or 3 weeks). The treatment can include administering ribavirin but does not include administering interferon. The treatment may also include administering ritonavir or another CYP3A4 inhibitor (e.g., cobicistat) if one of the DAAs requires pharmacokinetic enhancement. The at least two DAAs can be administered concurrently or sequentially. For example, one DAA can be administered once daily, and another DAA can be administered twice daily. For another example, the two DAAs are administered once daily. For yet another example, the two DAAs are co-formulated in a single composition and administered concurrently (e.g., once daily). As a non-limiting example, the patient being treated can be infected with HCV genotype 1, such as genotype 1a or 1b. As another non-limiting example, the patient can be infected with HCV genotype 2 or 3. As yet another non-limiting example, the patient can be a HCV treatment naïve patient, a HCV-treatment experienced patient, an interferon non-responder (e.g., a null responder, a partial responder or a relapser), or not a candidate for interferon treatment.

In another aspect, the present technology features a combination of at least two DAAs for use in treating HCV infection, wherein said combination comprises a compound of this invention in combination with compounds selected from:
a combination of PSI-7977 and/or PSI-938;
a combination of BMS-790052 and/or BMS-650032;
a combination of GS-5885 and/or GS-9451;
a combination of GS-5885, GS-9190 and/or GS-9451;
a combination of BI-201335 and/or BI-27127;
at combination of telaprevir and/or VX-222;
combination of PSI-7977 and/or TMC-435;
a combination of danoprevir and/or R7128;
a combination of ABT-450 and/or ABT-267 and/or ABT-333 and/or ABT-493 and/or ABT-530; one or more of the following protease inhibitors: ABT450, ABT-493, Simeprevir, Asunaprevir, GS-9451, ACH-2684, Boceprevir, MK-5172, Faldaprevir, and Telaprevir; one or more of the following NS5A inhibitors: ABT-267, ABT-530, GSK805, Daclastavir, Dedipasvir, GS-5816, ACH-3102, MK-8742, PPI-668, and Samatasvir; one or more of the following Non-nuc NS5B Inhibitors: ABT-333, TMC055, BMS-325, GS-9669, and Deleobuvir.

In one embodiment, the compound of the present invention used in the combination therapies above is 1911, 2023, or 2024. In a currently preferred embodiment, the novel compound of the present invention used in the combination therapies above is 2023. One or more of 1911, 2033 and 2024 can be combined with one or more of ABT-450, ABT-267 and/or ABT-333 and/or ABT-493 and/or ABT-530 and/or a compound disclosed in US 2010/0144608; U.S. 61/339,964; US 2011/0312973; WO 2009/039127; US 2010/0317568; 2012/151158; US 2012/0172290; WO 2012/092411; WO 2012/087833; WO 2012/083170; WO 2009/039135; US 2012/0115918; WO 2012/051361; WO 2012/009699; WO 2011/156337; US 2011/0207699; WO 2010/075376; U.S. Pat. No. 7,910,595; WO 2010/120935; WO 2010/111437; WO 2010/111436; US 2010/0168384 or US 2004/0167123.

In yet another aspect, the present technology features a combination of at least two DAAs for use in treating HCV infection, wherein said combination comprises a compound of this invention in a combination selected from: ABT-450, and/or ABT-267 and/or ABT-333 and/or a compound disclosed in US 2010/0144608; U.S. 61/339,964; US 2011/0312973; WO 2009/039127; US 2010/0317568; 2012/151158; US 2012/0172290; WO 2012/092411; WO 2012/087833; WO 2012/083170; WO 2009/039135; US 2012/0115918; WO 2012/051361; WO 2012/009699; WO 2011/156337; US 2011/0207699; WO 2010/075376; US 7,9105, 95; WO 2010/120935; WO 2010/111437; WO 2010/111436; US 2010/0168384 or US 2004/0167123;
a combination of PSI-797 and/or BMS-790052;
a combination of PSI-7977 and/or BMS-650032;
a combination of PSI-7977, BMS-790052 and/or BMS-650032;
a combination of INX-189 and/or BMS-790052;
combination of INX-189 and/or BMS-650032; or
a combination of INX-189, BMS-790052 and/or BMS-650032.

In still another aspect, the present technology features PSI-7977, or a combination of at least two DAAs, for use in treating HCV infection, wherein said combination comprises a combination of a compound of this invention and a compound selected from:
a combination of mericitabine and/or danoprevir;
a combination of daclatasvir and/or BMS-791325; and
a combination of PSI-7977 and/or GS-5885.

The treatment comprises administering PSI-7977 or the DAA combination to a subject infected with HCV.

In still another aspect, the present technology features a compound of this invention with PSI-7977, or a combination of at least two DAAs, for use in treating HCV infection, wherein said combination comprises a combination selected from:
a combination of mericitabine and/or danoprevir;
combination of INX-189, daclatasvir and/or BMS-791325; and
a combination of PSI-7977 and/or GS-5885.

The treatment comprises administering PSI-7977 or the DAA combination to a subject infected with HCV.

In still another aspect, the present technology features a combination of at least two DAAs, for use in treating HCV infection, wherein said combination comprises a combination selected from a compound of this invention and:
a combination of tegobuvir and/or GS-9256;
a combination of BMS-791325, asunaprevir and/or daclatasvir; and
a combination of TMC-435 and/or daclatasvir.

The treatment comprises administering the DAA combination to a subject infected with HCV.

In yet another aspect, the present technology features a combination of a compound of this invention with PSI-7977 and/or BMS-790052 for use in treating HCV infection. The treatment comprises administering the DAA combination to a subject infected with HCV.

In yet another aspect, the present technology features a combination of a compound of this invention with PSI-7977 and/or TMC-435 for use in treating HCV infection.

In yet another aspect, the present technology features a combination of a compound of this invention with danoprevir and/or mercitabine for use in treating HCV infection.

In yet another aspect, the present technology features a combination of a compound of this invention with daclatasvir and/or BMS-791325 for use in treating HCV infection. The treatment comprises administering the DAA combination to a subject infected with HCV.

In yet another aspect, the present technology features a combination of a compound of this invention with PSI-7977 and/or GS-5885 for use in treating HCV infection. The treatment comprises administering the DAA combination to a subject infected with HCV.

The duration of the treatment regimens is no more than sixteen weeks (e.g., the duration being 16 weeks; or the duration being 14, 12 or 10, 9, 8, 7, 6, 5, 4, 3, 2, or 1 weeks). The treatment includes administering ribavirin but does not include administering interferon. The treatment may include administering ritonavir or another CYP3A4 inhibitor (e.g., cobicistat) if one of the DAAs requires pharmacokinetic enhancement. The two DAAs can be administered concurrently or sequentially. For example, one DAA can be administered once daily, and the other DAA can be administered twice daily. For another example, the two DAAs are administered once daily. For yet another example, the two DAAs are co-formulated in a single composition and administered concurrently (e.g., once daily). As a non-limiting example, the patient being treated can be infected with HCV genotype 1, such as genotype 1a or 1b. As another non-limiting example, the patient can be infected with HCV genotype 2 or 3. As yet another non-limiting example, the patient can be a HCV-treatment naïve patient, a HCV-treatment experienced patient, an interferon non-responded (e.g., a null responder), or not a candidate for interferon treatment.

In yet another embodiment of this aspect of the invention, the at least two DAAs comprise a HCV protease inhibitor and a HCV polymerase inhibitor of this invention. The treatment can last, for example and without limitation, for no more than 12 weeks, such as 8, 9, 10, 11, or 12 weeks. Preferably, the treatment lasts for 12 weeks. The treatment can also last for 8 weeks. The subject being treated can be, for example, a treatment naïve patient. The subject can also be a treatment-experienced patient, or an interferon non-responder (e.g., a null responder). Preferably, the subject being treated is infected with HCV genotype 1, e.g., HCV genotype Ta. As another non-limiting example, the subject being treatment is infected with HCV genotype 3.

In yet another embodiment of this aspect of the invention, the at least two DAAs comprise a compound of this invention with an HCV protease inhibitor and a non-nucleoside or non-nucleotide HCV polymerase inhibitor. The treatment can last, for example, and without limitation, for no more than 12 weeks, such as 8, 9, 10, 11 or 12 weeks. Preferably, the treatment lasts for 12 weeks. The treatment can also last for 8 weeks. The subject being treated can be, for example, a treatment-naïve patient. The subject can also be a treatment-experienced patient, or an interferon non-responder (e.g., a null responder). Preferably, the subject being treated is infected with HCV genotype 1, e.g., HCV genotype 1a. As another non-limiting example, the subject being treatment is infected with HCV genotype 3.

In yet another embodiment of this aspect of the invention, the DAAs comprise a compound of this invention with HCV protease inhibitor and a HCV NS5A inhibitor.

In yet another embodiment of this aspect of the invention, the at least two DAAs comprise a HCV polymerase inhibitor of this invention and a HCV NS5A inhibitor.

In yet another embodiment of this aspect of the invention, the DAAs comprise a compound of this invention and a HCV non-nucleoside or non-nucleotide polymerase inhibitor and a HCV NS5A inhibitor.

In yet another embodiment of this aspect of the invention, the DAAs can comprise a HCV nucleoside or nucleotide polymerase inhibitor of this invention and a HCV NS5A inhibitor.

In yet another embodiment of this aspect of the invention, the at least two DAAs comprise a compound of this invention with PSI-7977 and/or TMC-435.

In yet another embodiment of this aspect of the invention, the DAAs comprise a compound of this invention with PSI-7977 and/or daclatasvir.

In yet another embodiment of this aspect of the invention, the DAAs comprise a compound of this invention with PSI-7977 and/or GS-5885.

In yet another embodiment of this aspect of the invention, the DAAs comprise a compound of this invention with mericitabine and/or danoprevir.

In yet another embodiment of this aspect of the invention, the DAAs comprise a compound of this invention with BMS-790052 and/or BMS-650032.

In yet another embodiment of this aspect of the invention, the DAAs comprise a compound of this invention and INX-189, daclatasvir and/or BMS-791325.

A treatment regimen of the present technology generally constitutes a complete treatment regimen, i.e., no subsequent interferon-containing regimen is intended. Thus, a treatment or use described herein generally does not include any subsequent interferon-containing treatment.

In one aspect of the disclosure, an "infection" or "bacterial infection" refers to an infection caused by *acinetobacter* spp, *bacteroides* spp, *burkholderia* spp, *campylobacter* spp, *chlamydia* spp, *chlamydophila* spp, *clostridium* spp, *enterobacter* spp, *enterococcus* spp, *escherichia* spp, *fusobacterium* spp, *gardnerella* spp, *haemophilus* spp, *helicobacter* spp, *klebsiella* spp, *legionella* spp, *moraxella* spp, *morganella* spp, *mycoplasma* spp, *neisseria* spp, *peptococcus* spp *peptostreptococcus* spp, *proteus* spp, *pseudomonas* spp, *salmonella* spp, *serratia* spp., *staphylococcus* spp, streptoccocus spp, *stenotrophomonas* spp, or *ureaplasma* spp.

In one aspect of the disclosure, an "infection" or "bacterial infection" refers to an infection caused by *Acinetobacter baumanii, Acinetobacter haemolyticus, Acinetobacter junii, Acinetobacter johnsonii, Acinetobacter* Iwoffi, *Bacteroides bivius, Bacteroides fragilis, Burkholderia cepacia, Campylobacter jejuni, Chlamydia pneumoniae, Chlamydia urealyticus, Chlamydophila pneumoniae, Clostridium difficile, Enterobacter aerogenes, Enterobacter cloacae, Enterococcus faecalis, Enterococcus faecium, Escherichia coli, Gard-* nerella vaginalis, haemophilus par influenzae, Haemophilus influenzae, Helicobacter pylori, Klebsiella pneumoniae, Legionella pneumophila, methicillin-resistant Staphylococcus aureus, methicillin-susceptible Staphylococcus aureus, Moraxella catarrhalis, Morganella morganii, Mycoplasma pneumoniae, Neisseria gonorrhoeae, penicillin-resistant Streptococcus pneumoniae, penicillin-susceptible Streptococcus pneumoniae, Peptostreptococcus magnus, Peptostreptococcus micros, Peptostreptococcus anaerobius, Peptostreptococcus asaccharolyticus, Peptostreptococcus prevotii, Peptostreptococcus tetradius, Peptostreptococcus vaginalis, Proteus mirabilis, Pseudomonas aeruginosa, quino lone-resistant Staphylococcus aureus, quinolone-resistant Staphylococcus epidermis, Salmonella typhi, Salmonella paratyphi, Salmonella enteritidis, Salmonella typhimurium, Serratia marcescens, Staphylococcus aureus, Staphylococcus epidermidis, Staphylococcus saprophyticus, streptoccocus agalactiae, Streptococcus pneumoniae, Streptococcus pyogenes, Stenotrophomonas maltophilia, Ureaplasma urealyticum, vancomycin-resistant Enterococcus faecium, vancomycin-resistant Enterococcus faecalis, vancomycin-resistant Staphylococcus aureus, vancomycin-resistant Staphylococcus epidermis, Mycobacterium tuberculosis, Clostridium perfringens, Klebsiella oxytoca, Neisseria miningitidis, Proteus vulgaris, or coagulase-negative Staphylococcus (including Staphylococcus lugdunensis, Staphylococcus capitis, Staphylococcus hominis, or Staphylococcus saprophytic).

In one aspect of the disclosure "infection" or "bacterial infection" refers to aerobes, obligate anaerobes, facultative anaerobes, gram-positive bacteria, gram-negative bacteria, gram-variable bacteria, or atypical respiratory pathogens.

In some embodiments, the disclosure relates to treating a bacterial infection such as a gynecological infection, a respiratory tract infection (RTI), a sexually transmitted disease, or a urinary tract infection.

In some embodiments, the disclosure relates to treating a bacterial infection such as an infection caused by drug resistant bacteria.

In some embodiments, the disclosure relates to treating a bacterial infection such as community-acquired pneumoniae, hospital-acquired pneumoniae, skin & skin structure infections, gonococcal cervicitis, gonococcal urethritis, febrile neutropenia, osteomyelitis, endocarditis, urinary tract infections and infections caused by drug resistant bacteria such as penicillin-resistant Streptococcus pneumoniae, methicillin-resistant Staphylococcus aureus, methicillin-resistant Staphylococcus epidermidis and vancomycin-resistant enterococci, syphilis, ventilator-associated pneumonia, intra-abdominal infections, gonorrhoeae, meningitis, tetanus, or tuberculosis.

In some embodiments, the disclosure relates to treating a fungal infections such as infections caused by tinea versicolor, microsporum, trichophyton, epidermophyton, candidiasis, cryptococcosis, or aspergillosis.

In some embodiments, the disclosure relates to treating an infection caused by protozoa including, but not limited to, malaria, amoebiasis, giardiasis, toxoplasmosis, cryptosporidiosis, trichomoniasis, leishmaniasis, sleeping sickness, or dysentery.

Certain compounds disclosed herein are useful to prevent or treat an infection of a malarial parasite in a subject and/or for preventing, treating and/or alleviating complications and/or symptoms associated therewith and can then be used in the preparation of a medicament for the treatment and/or prevention of such disease. The malaria may be caused by Plasmodium falciparum, P. vivax, P. ovale, or P. malariae.

In one embodiment, the compound is administered after the subject has been exposed to the malaria parasite. In another embodiment, a compound disclosed herein is administered before the subject travels to a country where malaria is endemic.

The compounds or the above-mentioned pharmaceutical compositions may also be used in combination with one or more other therapeutically useful substances selected from the group comprising antimalarials like quinolines (e.g., quinine, chloroquine, amodiaquine, mefloquine, primaquine, tafenoquine); peroxide antimalarials (e.g., artemisinin, artemether, artesunate); pyrimethamine-sulfadoxine antimalarials (e.g., Fansidar); hydroxynaphtoquinones (e.g., atovaquone); acroline-type antimalarials (e.g., pyronaridine); and antiprotozoal agents such as ethylstibamine, hydroxystilbamidine, pentamidine, stilbamidine, quinapyramine, puromycine, propamidine, nifurtimox, melarsoprol, nimorazole, nifuroxime, aminitrozole and the like.

In an embodiment, compounds disclosed herein can be used in combination one additional drug selected from the group consisting of chloroquine, artemesin, qinghaosu, 8-aminoquinoline, amodiaquine, arteether, artemether, artemisinin, artesunate, artesunic acid, artelinic acid, atovoquone, azithromycine, biguanide, chloroquine phosphate, chlorproguanil, cycloguanil, dapsone, desbutyl halofantrine, desipramine, doxycycline, dihydrofolate reductase inhibitors, dipyridamole, halofantrine, haloperidol, hydroxychloroquine sulfate, imipramine, mefloquine, penfluridol, phospholipid inhibitors, primaquine, proguanil, pyrimethamine, pyronaridine, quinine, quinidine, quinacrineartemisinin, sulfonamides, sulfones, sulfadoxine, sulfalene, tafenoquine, tetracycline, tetrandine, triazine, salts or mixture thereof.

Cancer

In a typical embodiment, the disclosure relates to a method treating cancer comprising administering to a patient a compound disclosed herein. In some embodiments, the disclosure relates to a compound disclosed herein, or a pharmaceutically acceptable salt thereof for uses in treating cancer.

In some embodiments, the disclosure relates to a compound disclosed herein, or a pharmaceutically acceptable salt thereof, as defined herein for use in the treatment of cancer of the breast, colorectum, lung (including small cell lung cancer, non-small cell lung cancer and bronchioalveolar cancer) and prostate.

In some embodiments, the disclosure relates to a compound disclosed herein, or a pharmaceutically acceptable salt thereof, as defined herein for use in the treatment of cancer of the bile duct, bone, bladder, head and neck, kidney, liver, gastrointestinal tissue, oesophagus, ovary, endometrium, pancreas, skin, testes, thyroid, uterus, cervix and vulva, and of leukaemias (including ALL and CML), multiple myeloma and lymphomas.

In some embodiments, the disclosure relates to a compound disclosed herein, or a pharmaceutically acceptable salt thereof, as defined herein for use in the treatment of lung cancer, prostate cancer, melanoma, ovarian cancer, breast cancer, endometrial cancer, kidney cancer, gastric cancer, sarcomas, head and neck cancers, tumors of the central nervous system and their metastases, and also for the treatment of glioblastomas.

In some embodiments, compounds disclosed herein could be used in the clinic either as a single agent by itself or in combination with other clinically relevant agents. This compound could also prevent the potential cancer resistance mechanisms that may arise due to mutations in a set of genes.

The anti-cancer treatment defined herein may be applied as a sole therapy or may involve, in addition to the compound of the disclosure, conventional surgery or radiotherapy or chemotherapy. Such chemotherapy may include one or more of the following categories of anti-tumour agents:

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulfan and nitrosoureas); antimetabolites (for example antifolates such as fluoropyrimidines like 5-fluorouracil and gemcitabine, tegafur, raltitrexed, methotrexate, cytosine arabinoside and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example *vinca* alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin); and proteosome inhibitors (for example bortezomib [Velcade®]); and the agent anegrilide [Agrylin®]; and the agent alpha-interferon;

(ii) cytostatic agents such as anti-estrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) agents that inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbb1 antibody cetuximab), farnesyl transferase inhibitors, tyrosine kinase inhibitors and serine/threonine kinase inhibitors, for example inhibitors of the epidermal growth factor family (for example EGFR family tyrosine kinase inhibitors such as: N-(3-chloro-4-fluorophenyl)-7-methoxy-6-(3-morpholinopropoxy)quinazolin-4-amine (gefitinib), N-(3-ethynylphenyl)-6,7-bis(2-methoxyethoxy)quinazolin-4-amine (erlotinib), and 6-acrylamido-N-(3-chloro-4-fluorophenyl)-7-(3-morpholinopropoxy)quinazolin-4-amine (CI 1033), for example inhibitors of the platelet-derived growth factor family and for example inhibitors of the hepatocyte growth factor family, for example inhibitors or phosphotidylinositol 3-kinase (PI3K) and for example inhibitors of mitogen activated protein kinase kinase (MEK1/2) and for example inhibitors of protein kinase B (PKB/Akt), for example inhibitors of Src tyrosine kinase family and/or Abelson (AbI) tyrosine kinase family such as dasatinib (BMS-354825) and imatinib mesylate (Gleevec™); and any agents that modify STAT signalling;

(v) antiangiogenic agents such as those which inhibit the effects of vascular endothelial growth factor, (for example the anti-vascular endothelial cell growth factor antibody bevacizumab [Avastin™]) and compounds that work by other mechanisms (for example linomide, inhibitors of integrin ocvβ3 function and angiostatin);

(vi) vascular damaging agents such as Combretastatin A4;

(vii) antisense therapies, for example those which are directed to the targets listed above, such as an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies, and approaches using the immunomodulatory drugs thalidomide and lenalidomide [Revlimid®].

Such conjoint treatment may be achieved by way of the simultaneous, sequential or separate dosing of the individual components of the treatment. Such combination products employ the compounds of this disclosure, or pharmaceutically acceptable salts thereof, within the dosage range described hereinbefore and the other pharmaceutically-active agent within its approved dosage range.

Formulations

Pharmaceutical compositions disclosed herein may be in the form of pharmaceutically acceptable salts, as generally described below. Some preferred, but non-limiting examples of suitable pharmaceutically acceptable organic and/or inorganic acids are hydrochloric acid, hydrobromic acid, sulfuric acid, nitric acid, acetic acid and citric acid, as well as other pharmaceutically acceptable acids known per se (for which reference is made to the references referred to below).

When the compounds of the disclosure contain an acidic group as well as a basic group, the compounds of the disclosure may also form internal salts, and such compounds are within the scope of the disclosure. When a compound of the disclosure contains a hydrogen-donating heteroatom (e.g., NH), the disclosure also covers salts and/or isomers formed by the transfer of the hydrogen atom to a basic group or atom within the molecule.

Pharmaceutically acceptable salts of the compounds include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/ dihydrogen phosphate, pyroglutamate, saccharate, stearate, succinate, tannate, tartrate, tosylate, trifluoroacetate and xinofoate salts. Suitable base salts are formed from bases that form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see Handbook of Pharmaceutical Salts: Properties, Selection, and Use by Stahl and Wermuth (Wiley-VCH, 2002), incorporated herein by reference.

The compounds described herein may be administered in the form of prodrugs. A prodrug can include a covalently bonded carrier that releases the active parent drug when administered to a mammalian subject. Prodrugs can be prepared by modifying functional groups present in the compounds in such a way that the modifications are cleaved, either in routine manipulation or in vivo, to the parent compounds. Prodrugs include, for example, compounds wherein a hydroxyl group is bonded to any group that, when administered to a mammalian subject, cleaves to form a free hydroxyl group. Examples of prodrugs include, but are not limited to, acetate, formate and benzoate derivatives of alcohol functional groups in the compounds. Methods of structuring a compound as a prodrug are known, for example, in Testa and Mayer, Hydrolysis in Drug and Prodrug Metabolism, Wiley (2006). Typical prodrugs form the active metabolite by transformation of the prodrug by hydrolytic enzymes, the hydrolysis of amide, lactams, peptides, carboxylic acid esters, epoxides or the cleavage of esters of inorganic acids. It has been shown that ester prodrugs are readily degraded in the body to release the corresponding alcohol. See e.g., Imai, Drug Metab Pharmacokinet. (2006) 21(3):173-85, entitled "Human carboxylesterase isozymes: catalytic properties and rational drug design."

Pharmaceutical compositions for use in the present disclosure typically comprise an effective amount of a compound and a suitable pharmaceutical acceptable carrier. The preparations may be prepared in a manner known per se, which usually involves mixing the at least one compound according to the disclosure with the one or more pharmaceutically acceptable carriers, and, if desired, in combination with other pharmaceutical active compounds, when necessary under aseptic conditions. Reference is made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

Generally, for pharmaceutical use, the compounds may be formulated as a pharmaceutical preparation comprising at least one compound and at least one pharmaceutically acceptable carrier, diluent or excipient, and optionally one or more further pharmaceutically active compounds.

The pharmaceutical preparations of the disclosure are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of the at least one compound of the disclosure, e.g., about 10, 25, 50, 100, 200, 300 or 400 mg per unit dosage.

The compounds can be administered by a variety of routes including the oral, ocular, rectal, transdermal, subcutaneous, intravenous, intramuscular or intranasal routes, depending mainly on the specific preparation used. The compound will generally be administered in an "effective amount", by which is meant any amount of a compound that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the patient per day, more often between 0.1 and 500 mg, such as between 1 and 250 mg, for example about 5, 10, 20, 50, 100, 150, 200 or 250 mg, per kilogram body weight of the patient per day, which may be administered as a single daily dose, divided over one or more daily doses. The amount(s) to be administered, the route of administration and the further treatment regimen may be determined by the treating clinician, depending on factors such as the age, gender and general condition of the patient and the nature and severity of the disease/symptoms to be treated. Reference is made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

For an oral administration form, the compound can be mixed with suitable additives, such as excipients, stabilizers or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, cornstarch. In this case, the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, the compositions may be prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Suitable pharmaceutical formulations for administration in the form of aerosols or sprays are, for example, solutions, suspensions or emulsions of the compounds of the disclosure or their physiologically tolerable salts in a pharmaceutically acceptable solvent, such as ethanol or water, or a mixture of such solvents. If required, the formulation may additionally contain other pharmaceutical auxiliaries such as surfactants, emulsifiers and stabilizers as well as a propellant.

For subcutaneous or intravenous administration, the compounds, if desired with the substances customary therefore such as solubilizers, emulsifiers or further auxiliaries are brought into solution, suspension, or emulsion. The compounds may also be lyophilized and the lyophilizates obtained used, for example, for the production of injection or infusion preparations. Suitable solvents are, for example, water, physiological saline solution or alcohols, e.g. ethanol, propanol, glycerol, sugar solutions such as glucose or mannitol solutions, or mixtures of the various solvents mentioned. The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, the formulations may be prepared by mixing the compounds of formula I with a suitable non-irritating excipient, such as cocoa butter, synthetic glyceride esters or polyethylene glycols, which are solid at ordinary temperatures, but liquefy and/or dissolve in the rectal cavity to release the drug.

In certain embodiments, it is contemplated that these compositions can be extended release formulations. Typical extended release formations utilize an enteric coating. Typically, a barrier is applied to oral medication that controls the location in the digestive system where it is absorbed. Enteric coatings prevent release of medication before it reaches the small intestine. Enteric coatings may contain polymers of polysaccharides, such as maltodextrin, xanthan, scleroglucan dextran, starch, alginates, pullulan, hyaloronic acid, chitin, chitosan and the like; other natural polymers, such as proteins (albumin, gelatin etc.), poly-L-lysine; sodium poly (acrylic acid); poly(hydroxyalkylmethacrylates) (for example poly(hydroxyethylmethacrylate)); carboxypolymethylene (for example Carbopol™); carbomer; polyvinylpyrrolidone; gums, such as guar gum, gum arabic, gum karaya, gum ghatti, locust bean gum, tamarind gum, gellan gum, gum tragacanth, agar, pectin, gluten and the like; poly(vinyl alcohol); ethylene vinyl alcohol; polyethylene glycol (PEG); and cellulose ethers, such as hydroxymethylcellulose (HMC), hydroxyethylcellulose (HEC), hydroxypropylcellulose (HPC), methylcellulose (MC), ethylcellulose (EC), carboxyethylcellulose (CEC), ethylhydroxyethylcellulose (EHEC), carboxymethylhydroxyethylcellulose (CMHEC), hydroxypropylmethyl-cellulose (HPMC), hydroxypropylethylcellulose (HPEC) and sodium carboxymethylcellulose (Na-CMC); as well as copolymers and/or (simple) mixtures of any of the above polymers. Certain of the above-mentioned polymers may further be crosslinked by way of standard techniques.

The choice of polymer will be determined by the nature of the active ingredient/drug that is employed in the composition of the disclosure as well as the desired rate of release. In particular, it will be appreciated by the skilled person, for example in the case of HPMC, that a higher molecular weight will, in general, provide a slower rate of release of drug from the composition. Furthermore, in the case of HPMC, different degrees of substitution of methoxyl groups and hydroxypropoxyl groups will give rise to changes in the rate of release of drug from the composition. In this respect, and as stated above, it may be desirable to provide compositions of the disclosure in the form of coatings in which the polymer carrier is provided by way of a blend of two or more polymers of, for example, different molecular weights in order to produce a particular required or desired release profile.

Microspheres of polylactide, polyglycolide, and their copolymers poly(lactide-co-glycolide) may be used to form sustained-release protein delivery systems. Proteins can be entrapped in the poly(lactide-co-glycolide) microsphere depot by a number of methods, including formation of a water-in-oil emulsion with water-borne protein and organic solvent-borne polymer (emulsion method), formation of a solid-in-oil suspension with solid protein dispersed in a solvent-based polymer solution (suspension method), or by dissolving the protein in a solvent-based polymer solution (dissolution method). One can attach poly(ethylene glycol) to proteins (PEGylation) to increase the in vivo half-life of circulating therapeutic proteins and decrease the chance of an immune response.

Liposomal suspensions (including liposomes targeted to viral antigens) may also be prepared by conventional methods to produce pharmaceutically acceptable carriers. This may be appropriate for the delivery of free nucleosides, acyl nucleosides or phosphate ester prodrug forms of the nucleoside compounds according to the present invention.

It is appreciated that nucleosides of the present invention have several chiral centers and may exist in and be isolated in optically active and racemic forms. Some compounds may exhibit polymorphism. It is to be understood that the present invention encompasses any racemic, optically active, diastereomeric, polymorphic, or stereoisomeric form, or mixtures thereof, of a compound of the invention, which possess the useful properties described herein. It is well known in the art how to prepare optically active forms (for example, by resolution of the racemic form by recrystallization techniques, by synthesis from optically-active starting materials, by chiral synthesis, or by chromatographic separation using a chiral stationary phase).

Carbons of the nucleoside are chiral, their nonhydrogen substituents (the base and the CHOR groups, respectively) can be either cis (on the same side) or trans (on opposite sides) with respect to the sugar ring system. The four optical isomers therefore are represented by the following configurations (when orienting the sugar moiety in a horizontal plane such that the oxygen atom is in the back): cis (with both groups "up", which corresponds to the configuration of naturally occurring β-D nucleosides), cis (with both groups "down", which is a nonnaturally occurring β-L configuration), trans (with the C2' substituent "up" and the C4' substituent "down"), and trans (with the C2' substituent "down" and the C4' substituent "up"). The "D-nucleosides" are cis nucleosides in a natural configuration and the "L-nucleosides" are cis nucleosides in the nonnaturally occurring configuration.

Likewise, most amino acids are chiral (designated as L or D, wherein the L enantiomer is the naturally occurring configuration) and can exist as separate enantiomers.

Examples of methods to obtain optically active materials are known in the art, and include at least the following. i) physical separation of crystals—a technique whereby macroscopic crystals of the individual enantiomers are manually separated. This technique can be used if crystals of the separate enantiomers exist, i.e., the material is a conglomerate, and the crystals are visually distinct; ii) simultaneous crystallization—a technique whereby the individual enantiomers are separately crystallized from a solution of the racemate, possible only if the latter is a conglomerate in the solid state; iii) enzymatic resolutions—a technique whereby partial or complete separation of a racemate by virtue of differing rates of reaction for the enantiomers with an enzyme; iv) enzymatic asymmetric synthesis—a synthetic technique whereby at least one step of the synthesis uses an enzymatic reaction to obtain an enantiomerically pure or enriched synthetic precursor of the desired enantiomer; v) chemical asymmetric synthesis—a synthetic technique whereby the desired enantiomer is synthesized from an achiral precursor under conditions that produce asymmetry (i.e., chirality) in the product, which may be achieved using chiral catalysts or chiral auxiliaries; vi) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer; vii) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer; viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions; ix) enantiospecific synthesis from non-racemic precursors—a synthetic technique whereby the desired enantiomer is obtained from non-chiral starting materials and where the stereochemical integrity is not or is only minimally compromised over the course of the synthesis; x) chiral liquid chromatography—a technique whereby the enantiomers of a racemate are separated in a liquid mobile phase by virtue of their differing interactions with a stationary phase. The stationary phase can be made of chiral material or the mobile phase can contain an additional chiral material to provoke the differing interactions; xi) chiral gas chromatography—a technique whereby the racemate is volatilized and enantiomers are separated by virtue of their differing interactions in the gaseous mobile phase with a column containing a fixed non-racemic chiral adsorbent phase; xii) extraction with chiral solvents—a technique whereby the enantiomers are separated by virtue of preferential dissolution of one enantiomer into a particular chiral solvent; xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane that allows only one enantiomer of the racemate to pass through. Chiral chromatography, including simulated moving bed chromatography, is used in one embodiment. A wide variety of chiral stationary phases are commercially available.

Some of the compounds described herein contain olefinic double bonds and unless otherwise specified, are meant to include both E and Z geometric isomers.

In addition, some of the nucleosides described herein, may exist as tautomers, such as, keto-enol tautomers. The individual tautomers as well as mixtures thereof are intended to be encompassed within the compounds of the present invention.

EXAMPLES

Example 1

Conjugate Preparation

Mono and diphosphate prodrugs have been prepared by several groups. See Jessen et al., Bioreversible Protection of Nucleoside Diphosphates, Angewandte Chemie-International Edition English 2008, 47 (45), 8719-8722, hereby incorporated by reference. In order to prevent rupture of the P—O—P anhydride bond, one utilizes a pendant group that fragments rapidly (e.g. bis-(4-acyloxybenzyl)-nucleoside diphosphates (BAB-NDP) that is deacylated by an endogenous esterase) to generate a negative charge on the second phosphate. See also Routledge et al., Synthesis, Bioactivation and Anti-HIV Activity of 4-Acyloxybenzyl-bis(nucleosid-5'-yl) Phosphates, Nucleosides & Nucleotides 1995, 14 (7), 1545-1558 and Meier et al., Comparative study of bis(benzyl)phosphate triesters of 2',3'-dideoxy-2',3'-didehydrothymidine (d4T) and cycloSal-d4TMP-hydrolysis, mechanistic insights and anti-HIV activity, Antiviral Chemistry and Chemotherapy 2002, 13, 101-114, both hereby incorporated by reference. Once this occurs, the P—O—P anhydride bond is less susceptible to cleavage and the remaining protecting group can then do its final unraveling to produce the nucleoside diphosphate.

Other methods to prepare diphosphate and monothiodiphosphate prodrugs are shown in FIG. 5. Standard coupling conditions are used to prepare sphingolipid-nucleoside monophosphate prodrugs. The corresponding diphosphate prodrugs may be prepared according to the protocols shown in FIG. 5 and as provided in Smith et al., Substituted Nucleotide Analogs. U.S. Patent Application 2012/0071434; Skowronska et al., Reaction of Oxophosphorane-Sulfenyl and Oxophosphorane-Selenenyl Chlorides with Dialkyl Trimethylsilyl Phosphites—Novel Synthesis of Compounds Containing a Sulfur or Selenium Bridge Between 2 Phosphoryl Centers, Journal of the Chemical Society-Perkin Transactions 1 1988, 8, 2197-2201; Dembinski et al., An Expedient Synthesis of Symmetrical Tetra-Alkyl Monothiopyrophosphates, Tetrahedron Letters 1994, 35 (34), 6331-6334; Skowronska et al., Novel Synthesis of Symmetrical Tetra-Alkyl Monothiophosphates, Tetrahedron Letters 1987, 28 (36), 4209-4210; and Chojnowski et al., Methods of Synthesis of O,O-Bis TrimethylSilyl Phosphorothiolates. Synthesis-Stuttgart 1977, 10, 683-686, all hereby incorporated by reference in their entirety.

Example 2

Activity of 2-Fluoronucleosides

Ribonucleoside analogs when activated to their corresponding triphosphate inhibit RNA-dependent RNA viral replication by acting as competitive substrate inhibitors of the virally encoded RdRp. Compounds in this therapeutic class are useful in the treatment of viruses found in but not limited to the arenaviridae, bunyaviridae, flaviviridae, orthomyxoviridae, paramyxoviridae, and togaviridae viral families. Certain compounds disclosed herein are contemplated to have advantages such as a high genetic barrier for antiviral resistance; broad spectrum activity within viral families; and high oral bioavailability with targeted delivery to sites of infection.

The nucleoside analogs were designed with a 2'-alpha-fluorine substituent to mimic natural ribonucleosides. The C—F bond length (1.35 Å) is similar to the C—O bond length (1.43 Å) and fluorine is a hydrogen-bond acceptor making the fluorine substituent an isopolar and isosteric replacement of a hydroxyl group. Unlike ribonucleoside analogs currently in clinical trials for treating HCV infections, in certain embodiments, the 2', 3'-dideoxy-2'-fluoronucleoside analogs covered by this disclosure lack a 3'-hydroxyl group and are thus obligate chain terminators of viral replication. Once the nucleosides are converted to their triphosphates, they act as competitive substrate inhibitors of the virally encoded RdRp. After incorporation of the chain terminator into nascent RNA, viral replication ceases. One advantage to obligate chain terminators is that they are not mutagenic to the host when treating chronic diseases.

Example 3

ZIKV NS5 RNA-Dependent RNA Polymerase Assay Results

The table below shows activity of select analog triphosphates against the ZIKV NS5 RdRp.

| Structure and I.D. | ZIKV Polymerase Assay | |
|---|---|---|
| | Km (μM) | Discrimination |
| EIDD-02596 | 1.26 | 5 |
| EIDD-02404 | 1.45 | 7 |
| EIDD-02296 | 2.82 | 13 |
| (structure shown) | 72.82 | 53 |

-continued
| Structure and I.D. | ZIKV Polymerase Assay | |
|---|---|---|
| | Km (μM) | Discrimination |
| 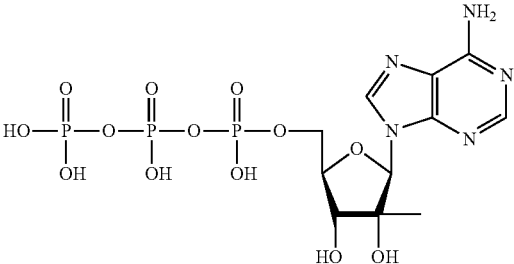 EIDD-01889 | 3.03 | 12 |
| 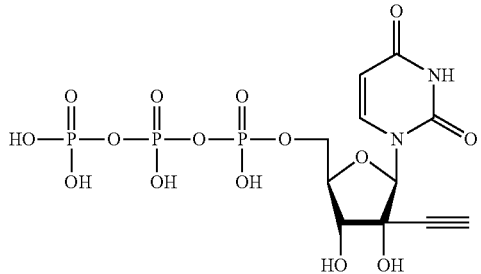 EIDD-02442 | 6.59 | 5 |
Example 4. ZIKV Infectious Assay Results
| Structure and I.D. | ZIKV (EC$_{50}$ μM) | Vero cells CC$_{50}$ (μM) |
|---|---|---|
| 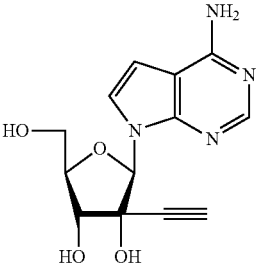 EIDD-02454 | 0.34 | 35.4 |
| 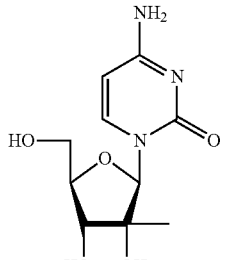 EIDD-01020 | 0.13 | 9.57 |

-continued
| Structure and I.D. | ZIKV (EC$_{50}$ μM) | Vero cells CC$_{50}$ (μM) |
|---|---|---|
| 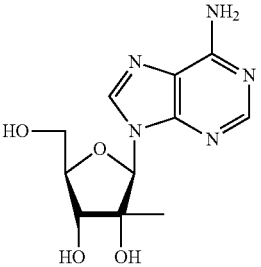 EIDD-02441 | 2.46 | >100 |
| 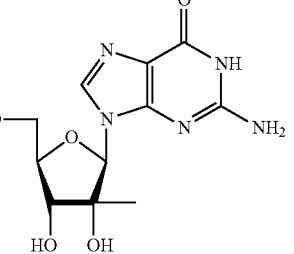 EIDD-01021 | 7.23 | >100 |
| 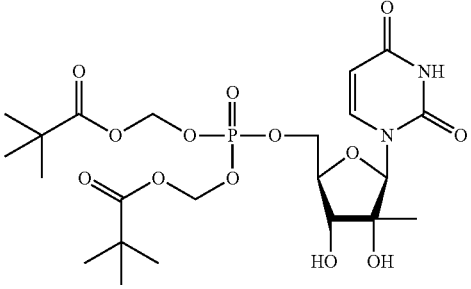 EIDD-02416 | 3.57 | 26.4 |
| 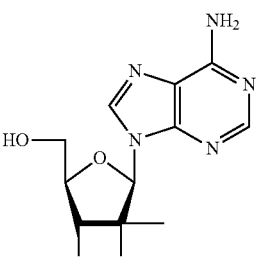 EIDD-01019 | 2.75 | >100 |

| Structure and I.D. | ZIKV (EC$_{50}$ μM) | Vero cells CC$_{50}$ (μM) |
|---|---|---|
| 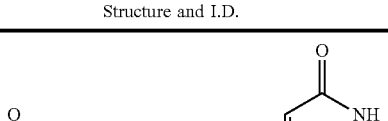 EIDD-02290 | 1.06 | 11 |

Example 5

General Procedure for Base Coupling

The persilylated nucleobase was prepared in a round bottom flask charged with dry nucleobase (15.5 mmol), chlorotrimethylsilane (12.21 mmol), and bis(trimethylsilyl)amine (222 mmol) under nitrogen. The mixture was refluxed with stirring overnight (16 h) until all solids dissolved. The mixture was cooled to room temperature and volatiles were removed by rotary evaporation followed by high vacuum to give persilylated nucleobase. This compound was used immediately in the next step.

The freshly prepared persilylated nucleobase (15.50 mmol) was dissolved in 1,2-dichloroethane (50 mL) or chlorobenzene (50 mL) under nitrogen with stirring at room temperature. A solution of β-D-ribofuranose 1,2,3,5-tetraacetate (7.75 mmol) in 1,2-dichloroethane (50 mL) or chlorobenzene (50 mL) was added all at once to the stirred mixture.

To this mixture was added SnCl$_4$ (11.63 mmol) dropwise via syringe, and the mixture was stirred at room temperature 6 h until all starting material was consumed. The mixture was cooled to 0° C. and a sat. aq. NaHCO$_3$ solution (125 mL) was added. The mixture was warmed to room temperature and stirred 30 min. The mixture was extracted with EtOAc (2×200 mL) and the combined organic layers were washed with brine (1×100 mL), dried over Na$_2$SO$_4$, filtered, and concentrated by rotary evaporation to give 5.5 g crude product. The crude material was taken up in dichloromethane, immobilized on Celite, and subjected to flash chromatography to provide the desired acetate protected product. The ribonucleoside was deprotected using the general deprotection conditions.

Example 6

General Cytosine Analog Coupling

In a flask charged with N$^4$-benzoyl protected cytosine analog (0.793 mmol) was added bis(trimethylsilyl)amine (8.45 mmol) and ammonium sulfate (0.02 mmol) under N2. This was heated at reflux for 2 h, after cooling to rt, solvent was removed in vacuo and further dried under high vacuum for 1 h. The residue was dissolved in dry chlorobenzene (10 ml) and β-D-ribofuranose 1,2,3,5-tetraacetate (0.53 mmol) was added. Then SnCl$_4$ (0.27 ml, 2.3 mmol) was added dropwise. After stirring at rt for 1 h, this was heated to 60° C. overnight. After cooling to 0° C., solid sodium bicarbonate (0.85 g) was added, followed by EtOAc (5 mL). This was allowed to stir for 15 min and then water (0.5 mL) was added slowly. The insoluble material was filtered off and washed with more EtOAc (2.5 mL). The filtrate was washed with water once, bine once, dried (Na$_2$SO$_4$) and concentrated in vacuo. The crude material was purified by SiO$_2$ column chromatography.

Example 7

General Deamination Conditions

A solution of benzoyl protected cytidine ribonucleoside (1.02 mmol) in 80% aqueous AcOH (30 mL) was heated under reflux for 16 h. The solvent was then removed in vacuo and dried under high vacuum. The white solid was triturated with ether, filtered off and washed with more ether to obtain the desired product.

Example 8

General Benzoyl Deprotection Conditions

Benzoyl protected ribonucleoside analog (0.25 mmol) was stirred with 7 N ammonia in MeOH at rt for 15.5 h. The solvent was then removed and the crude material was purified by SiO$_2$ column chromatography to obtain the desired ribonucleoside.

Example 9

Synthesis of Methyl-β-D-2'-spiro-Epoxide Ribose

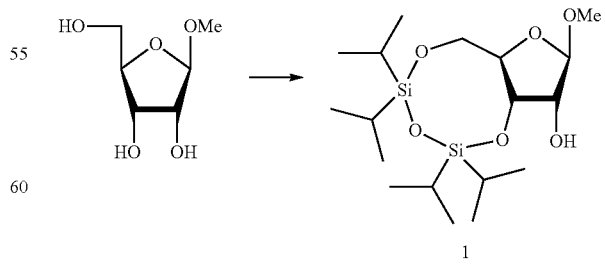

Procedure of the preparation of 1. A solution of methyl β-D-riboside (40.9 mmol, 1.0 eq.) under argon atmosphere, at 0° C. was added 1,3-dichloro-1,1,3,3-tetraisopropyldisiloxane (45.0 mmol, 1.1 eq.) drop wise via syringe over a 15 min period. The reaction mixture was warmed to room temperature and further stirred for 3 hours. The reaction was quenched with MeOH (10 mL) and the solvent was evaporated. The viscous residue was dissolved in DCM (400 mL) and washed with sat. NaCO₃H, brine, and dried over MgSO₄. The solvent was evaporated and coevaporated with toluene to remove traces of pyridine. The product was purified by silica gel column chromatography, eluding with hexane:ethylacetate (3:2) to provide the desried product.

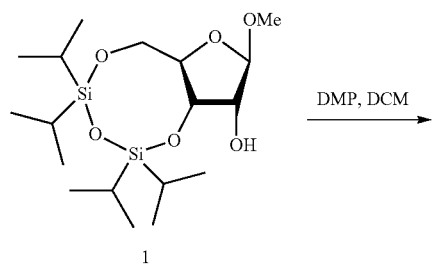

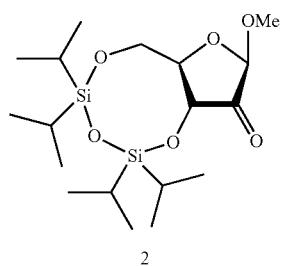

Procedure of the preparation of 2. A solution of protected riboside 1 (32.9 mmol, 1 eq.) in DCM (150 mL) at 0° C. was added Dess-Martin periodinane (18.1 g, 42.7 mmol, 1.3 eq). The reaction mixture was stirred at 25-30° C. for 24 hr. After which, approximately 75 mL of DCM was evaporated, diethyl ether (400 mL) was added to the reaction mixture, and the precipitates were filtered off over celite. The resulting filtrate was washed with 300 mL of saturated NaHCO₃ solution containing 18.5 g of Na₂S₂O₃ and brine respectively. The organic layer was dried over anhydrous Na₂SO₄, and evaporated to give 2, which was used in the next step without further purification.

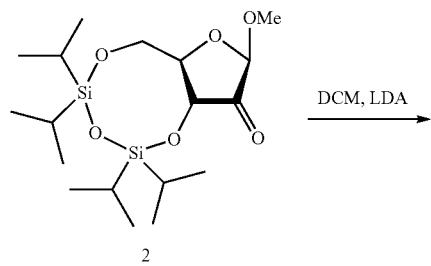

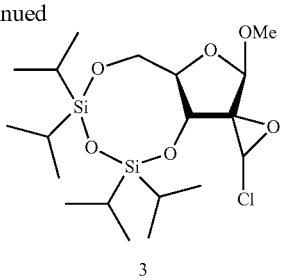

Procedure of the preparation of 3. A solution of ketone 2 (8.87 mmol, 1 eq.) and DCM (2.28 mL, 35.5 mmol, 4.0 eq.) in THF (50 mL) at −78° C., under argon atmosphere was added LDA solution (31.1 mL, 1.0 M, 3.5 eq.) over the course of 20 min. The reaction mixture was stirred at −78° C. for 3 hours, then over night at room temperature. The reaction was quenched with sat. NH₄Cl. The solution was extracted with diethyl ether (150 mL×2). The combined organic layers was washed with brine, dried over MgSO₄, evaporated, and purified by silica gel column chromatography by eluding with hexane ethyl acetate (3:1) to provide 3. The epoxide can then be subjected to general epoxide opening conditions with sodium chloride, sodium azide followed by reduction, and TBAF. After conversion of the resulting aldehyde to an alkyne, the riboside can be subjected to general base coupling conditions followed by the appropriate deprotection conditions.

Example 10

General Conversion of an Aldehyde to an Alkyne

The 2'-aldehyde resulting from epoxide opening above can be converted to an aldehyde using the following protocol. A solution of 2'-aldehyde in dry DCM (10 mL/mmol riboside) under argon at 0° C. was treated with carbon tetrabromide (2.0 eq.) followed by a solution of triphenylphosphine (2.0 eq.) in dry DCM (10 mL/mmol of riboside) over a 10 minute period. The reaction was allowed to stir overnight while warming to room temperature. The reaction mixture was then diluted with petroleum ether, filtered, and concentrated under reduced pressure. The purified product was obtained after silica gel chromatography. The purified intermediate was then dissolved in dry THF (10 mL/mmol) under argon, and the reaction mixture was cooled to −78° C. To the solution was added butyl lithium (2 eq.). The reaction was allowed to stir for 1 hour and quenched with either ammonium chloride or an appropriate electrophile. The reaction mixture was allowed to warm to room temperature and then washed with water and brine. The organic layer was dried over MgSO₄, filtered, and concentrated under reduced pressure. The product was purified on silica. If the product is a carbohydrate, the product can be subjected to general base coupling procedures followed by appropriate deprotection conditions, but it the product is a protected ribonucleoside, the product can be subjected to the appropriate deprotection conditions.

Example 11

General Synthesis of 2'-Chloro-Substituted Spiro Epoxide Ribonucleoside Analogs

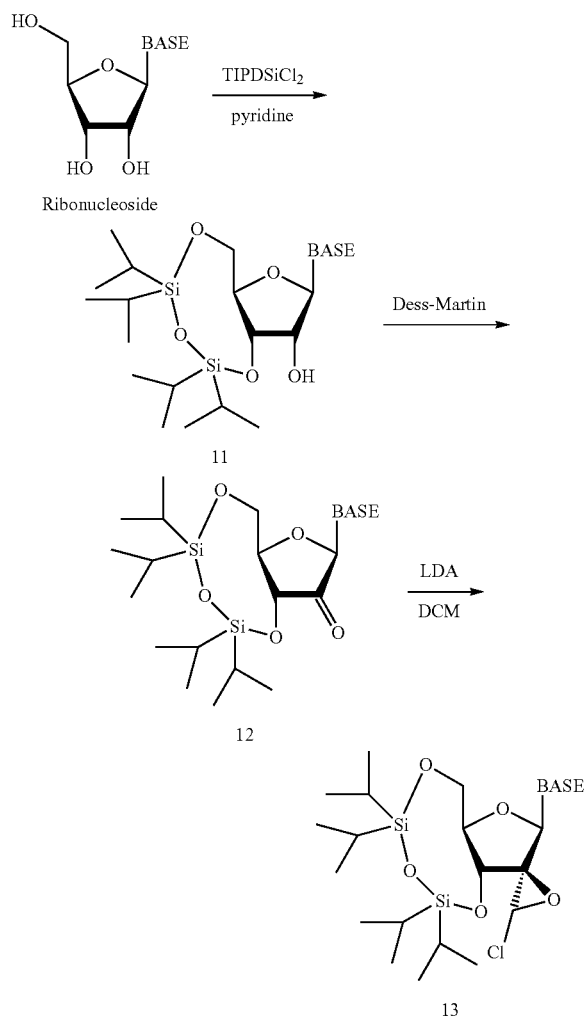

Procedure of the preparation of 11. A solution of ribonucleoside (40.9 mmol, 1.0 eq.) under argon atmosphere, at 0° C. was added 1,3-dichloro-1,1,3,3-tetraisopropyldisiloxane (45.0 mmol, 1.1 eq.) drop wise via syringe over a 15 min period. The reaction mixture was warmed to room temperature and further stirred for 3 hours. The reaction was quenched with MeOH (10 mL) and the solvent was evaporated. The viscous residue was dissolved in DCM (400 mL) and washed with sat. NaCO$_3$H, brine, and dried over MgSO$_4$. The solvent was evaporated and coevaporated with toluene to remove traces of pyridine. The product was purified by silica gel column chromatography, eluding with hexane:ethylacetate (3:2) to provide the desried product.

Procedure of the preparation of 12. A solution of protected ribonucleoside 11 (32.9 mmol, 1 eq.) in DCM (150 mL) at 0° C. was added Dess-Martin periodinane (18.1 g, 42.7 mmol, 1.3 eq). The reaction mixture was stirred at 25-30° C. for 24 hr. After which, approximately 75 mL of DCM was evaporated, diethyl ether (400 mL) was added to the reaction mixture, and the precipitates were filtered off over celite. The resulting filtrate was washed with 300 mL of saturated NaHCO$_3$ solution containing 18.5 g of Na$_2$S$_2$O$_3$ and brine respectively. The organic layer was dried over anhydrous Na$_2$SO$_4$, and evaporated to give 12, which was used in the next step without further purification.

Procedure of the preparation of 13. A solution of ketone 12 (8.87 mmol, 1 eq.) and DCM (2.28 mL, 35.5 mmol, 4.0 eq.) in THF (50 mL) at −78° C., under argon atmosphere was added LDA solution (31.1 mL, 1.0 M, 3.5 eq.) over the course of 20 min. The reaction mixture was stirred at −78° C. for 3 hours, then over night at room temperature. The reaction was quenched with sat. NH$_4$Cl. The solution was extracted with diethyl ether (150 mL×2). The combined organic layers was washed with brine, dried over MgSO$_4$, evaporated, and purified by silica gel column chromatography by eluding with hexane ethyl acetate (3:1) to provide 13. Uridine ribonucleoside analogs were further protected with a PMB group at the N3-position of the nucleobase.

Example 12

General Procedure for PMB Protection

PMBCl (1.2 eq.) and K$_2$CO$_3$ (1.5 eq) was added to a DMF solution of uridine ribonucleoside analog at 0° C. under an argon atmosphere. The mixture was then allowed to stir at room temperature for 12-16 hours. The mixture was quenched with water and extracted with ethyl acetate three times. The organic extracts were combined, washed with brine, dried over MgSO$_4$, filtered, and concentrated under reduced pressure. The crude product was purified on silica gel eluting with hexanes/ethyl acetate or used without further purification.

Example 13

General Conditions for Opening Epoxide with Sodium Chloride

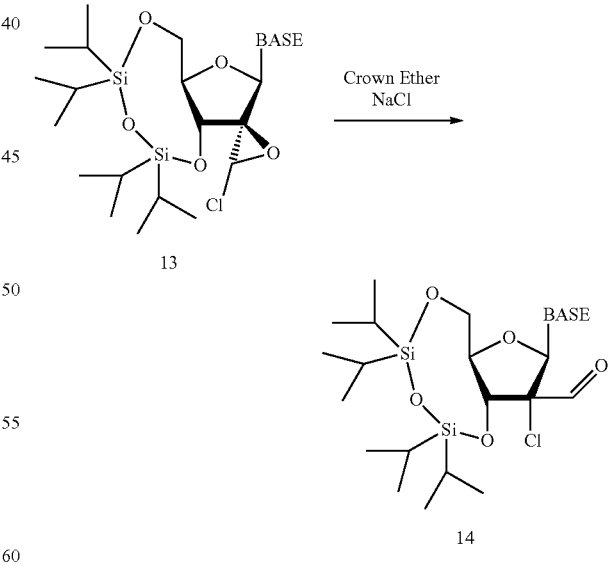

Procedure of the synthesis of 14. A solution of 13 (7.50 mmol, 1.0 eq.), and 15-crown-5 (1.48 mL, 7.50 mmol, 1.0 eq.) in DMF (10 mL) was added sodium chloride (4.38 g, 75.0 mmol, 10.0 eq.) at room temperature. The mixture was stirred at 45° C. for 16 hours. Then cooled to room temperature, and diluted with DCM (150 mL). The solution was washed with water (2×), brine, dried over MgSO₄, evaporated, and purified by silica gel column chromatography by eluding with hexane:ethyacetate to provide the desired product. The product can then be subjected to the general conditions for alkyne formation.

Example 14

General Conditions for Opening Epoxide with Sodium Azide

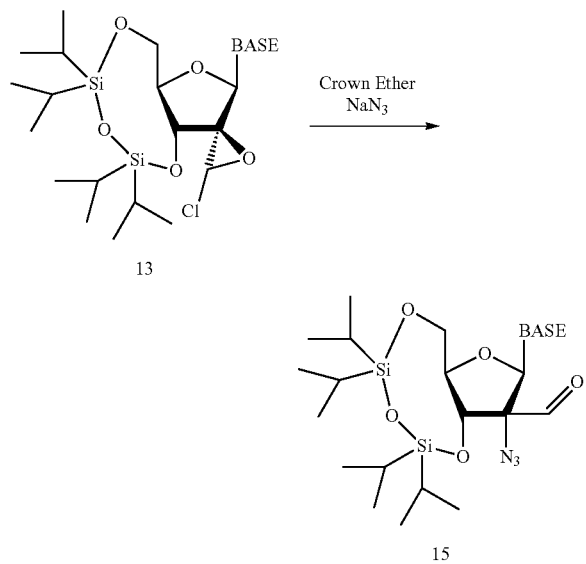

Procedure of the preparation of 15. A solution of 13 (3.75 mmol, 1.0 eq.), and 15-crown-5 (0.74 mL, 3.75 mmol, 1.0 eq.) in DMF (10 mL) was added sodium azide (1.2 g, 18.7 mmol, 5 eq.) at room temperature. The mixture was stirred at 30° C. for 2 hours. Then cooled to room temperature, and diluted with DCM (100 mL). The solution was washed with water (2×), brine, dried over MgSO₄, evaporated, and purified by silica gel column chromatography by eluding with hexane:ethyl acetate (3:1) to provide the desired product. The product can then be subjected to the general conditions for alkyne formation.

Example 15

General Conditions for Opening Epoxide with TBAF

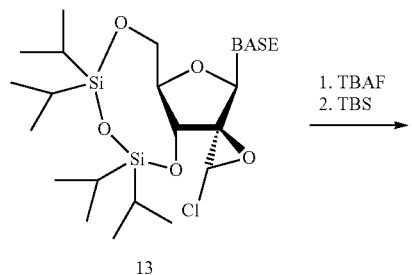

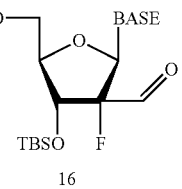

Procedure of the preparation of 16. A solution of 13 (3.75 mmol, 1.0 eq.) and TBAF (6.0 eq.) in DMF (10 mL) was stirred at room temperature. The mixture was stirred at 30° C. for 2 hours. Then cooled to room temperature, and diluted with DCM (100 mL). The solution was washed with water (2×), brine, dried over MgSO₄, evaporated, and purified by silica gel column chromatography by eluding with hexane: ethyl acetate (3:1) to provide the desired product. The desired product was then reprotected with TBSCl. The product can then be subjected to the general conditions for alkyne formation.

Example 16

General Conditions for Azide Reduction

2'-Azido ribonucleoside analogs were reduced to 2'-amino ribonucleoside analogs using the following procedure. The 2'-azido ribonucleoside analog was dissolved in methanol followed by the addition of palladium hydroxide on carbon. The reaction mixture was then allowed to stir under a hydrogen atmosphere for 30 minutes at room temperature. The reaction mixture was filtered through a celite pad, which was washed with methanol. The solvent was removed under reduced pressure, and the product was purified by silica gel chromatography eluting with DCM and methanol.

Example 17

General Desilylation Conditions

Silyl protected ribonucleoside analog was dissolved in THF followed by the addition of 1M TBAF (2.1 eq.) at room temperature. The reaction solution was allowed to stir at room temperature for 20 minutes. The solvent was then removed under reduced pressure, and the resulting residue was dissolved in DCM and loaded onto a silica gel column. The desired ribonucleoside analog was eluted with DCM and methanol.

Example 18

General Debenzylation Conditions

A solution of benzyl protected ribonucleoside analog in dry DCM was treated with a 1M BCl₃ (3 eq.) solution in DCM at −78° C. under an argon atmosphere. The reaction solution was allowed to stir at −78° C. for 2-4 hours. The mixture was quenched with the slow addition of methanol at −78° C., and the solvent was removed under reduced pressure. The desired ribonucleoside analog was purified by silica gel chromatography eluting with DCM and methanol. Alternatively, to a solution of nucleoside in MeOH was added 20% palladium (II) hydroxide on carbon. The reaction vessel was purged with and kept under a hydrogen atmosphere with a balloon for 24 hours. Once the reaction was complete, the catalyst was filtered off, and the solvents were removed under reduced pressure to afford the desired product.

Example 19

General Conditions for the Removal of a PMB Group

To a PMB-protected ribonucleoside analog in MeCN:H$_2$O (3:1) was added CAN (3 eq.). The reaction solution was allowed to stir for 12-16 hours at room temperature. The reaction solution was then extracted with ethyl acetate. The organic extracts were dried over MgSO$_4$, filtered, and concentrated under reduced pressure. The desired product was purified by silica gel chromatography.

Example 20

Uridine Protection

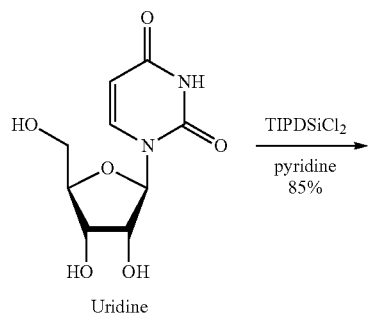

Uridine

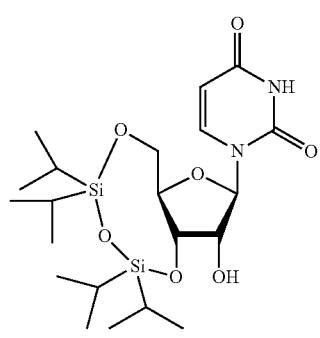

17

A solution of uridine (10.0 g, 40.9 mmol, 1.0 eq.) in dry pyridine under argon atmosphere, at 0° C. was added 1,3-dichloro-1,1,3,3-tetraisopropyldisiloxane (14.4 mL, 45.0 mmol, 1.1 eq.) drop wise via syringe over a 15 min period. The reaction mixture was warmed to room temperature and further stirred for 3 hours. The reaction was quenched with MeOH (10 mL) and the solvent was evaporated. The viscous residue was dissolved in DCM (400 mL) and washed with sat. NaCO$_3$H, brine, and dried over MgSO$_4$. The solvent was evaporated and coevaporated with toluene to remove traces of pyridine. The product was purified by silica gel column chromatography, eluding with hexane:ethylacetate (3:2) to provide 17 (17.0 g, 85% yield) as white foam.

Example 21

Oxidation of Protected Uridine

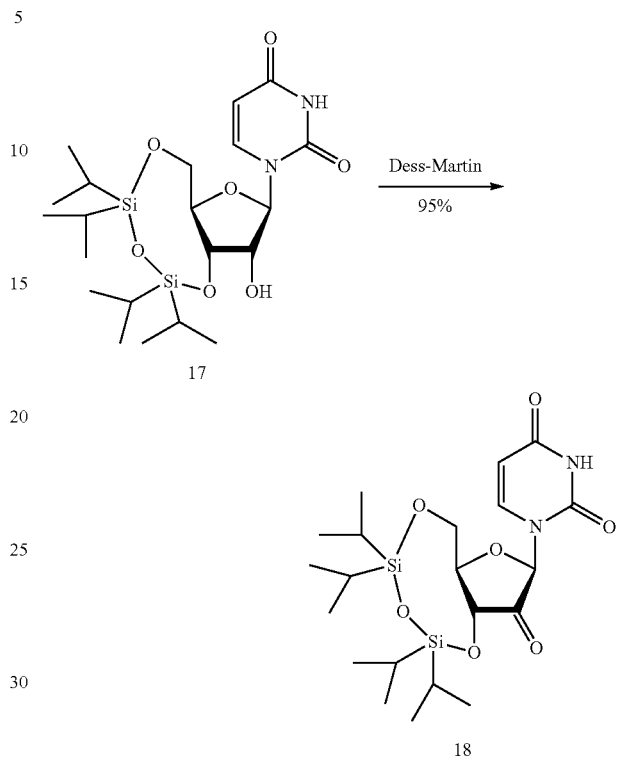

A solution of protected sugar 17 (16.0 g, 32.9 mmol, 1 eq.) in DCM (150 mL) at 0° C. was added Dess-Martin periodinane (18.1 g, 42.7 mmol, 1.3 eq). The reaction mixture was stirred at 25-30° C. for 24 hr. After approximately 75 mL of DCM was evaporated, diethyl ether (400 mL) was added to the reaction mixture, and the precipitates were filtered off over celite. The resulting filtrate was washed with 300 mL of saturated NaHCO$_3$ solution containing 18.5 g of Na$_2$S$_2$O$_3$ and brine respectively. The organic layer was dried over anhydrous Na$_2$SO$_4$, and evaporated to give 18 (15.1 g, 95% yield) as a white foam, which was used in the next step without further purification.

Example 22

Epoxide Formation

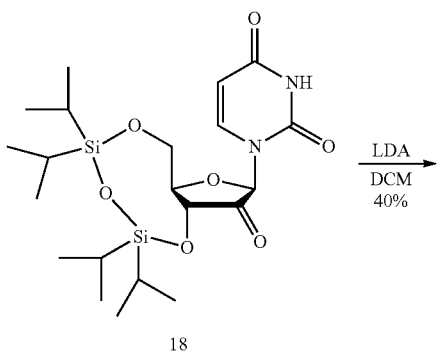

18

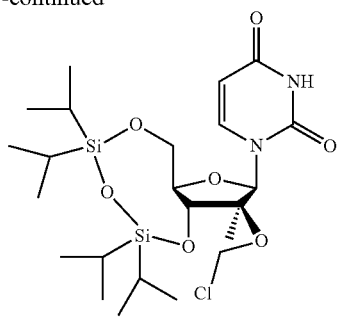

19

A solution of ketone 18 (4.30 g, 8.87 mmol, 1 eq.) and DCM (2.28 mL, 35.5 mmol, 4.0 eq.) in THF (50 mL) at −78° C., under argon atmosphere was added LDA solution (31.1 mL, 1.0 M, 3.5 eq.) over the course of 20 min. The reaction mixture was stirred at −78° C. for 3 hours, then over night at room temperature. The reaction was quenched with sat. NH$_4$Cl. The solution was extracted with diethyl ether (150 mL×2). The combined organic layers was washed with brine, dried over MgSO$_4$, evaporated, and purified by silica gel column chromatography by eluding with hexane ethyl acetate (3:1) to provide 19 (1.90 g, 40% yield) as brown solid.

Example 23

Epoxide Opening with Sodium Azide

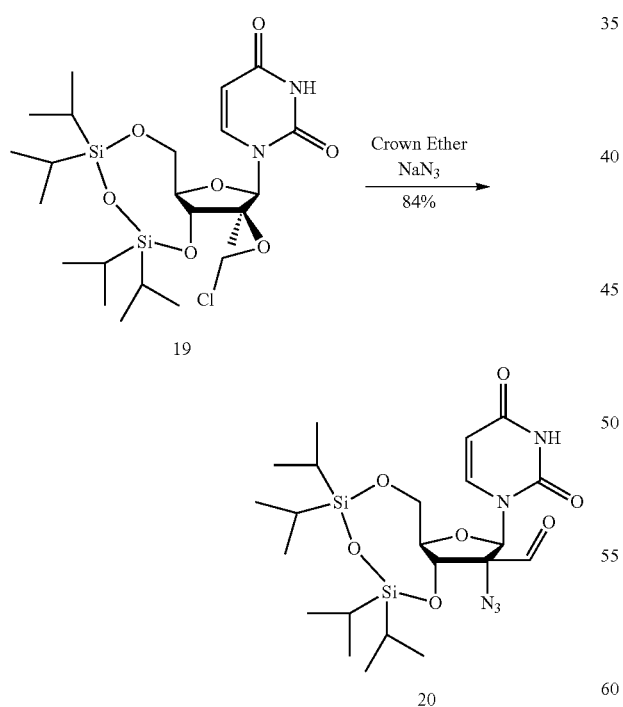

20

A solution of 19 (2.0 g, 3.75 mmol, 1.0 eq.), and 15-crown-5 (0.74 mL, 3.75 mmol, 1.0 eq.) in DMF (10 mL) was added sodium azide (1.2 g, 18.7 mmol, 5 eq.) at room temperature. The mixture was stirred at 30° C. for 2 hours. Then cooled to room temperature, and diluted with DCM (100 mL). The solution was washed with water (2×), brine, dried over MgSO$_4$, evaporated, and purified by silica gel column chromatography by eluding with hexane:ethyacetate (3:1) to provide 20 (1.71 gram, 84% yield) as light brown foam.

Example 24

Epoxide Opening with Sodium Chloride

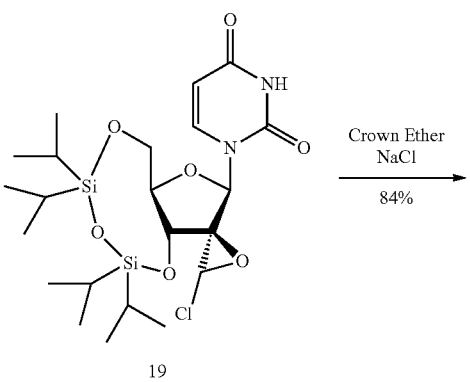

19

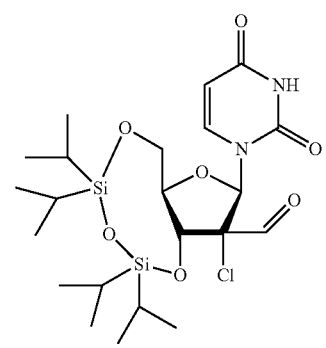

21

A solution of 19 (4.0 g, 7.50 mmol, 1.0 eq.), and 15-crown-5 (1.48 mL, 7.50 mmol, 1.0 eq.) in DMF (10 mL) was added sodium chloride (4.38 g, 75.0 mmol, 10.0 eq.) at room temperature. The mixture was stirred at 45° C. for 16 hours. Then cooled to room temperature, and diluted with DCM (150 mL). The solution was washed with water (2×), brine, dried over MgSO$_4$, evaporated, and purified by silica gel column chromatography by eluding with hexane:ethyacetate (3:1) to provide 21 (2.60 gram, 65% yield) as pale yellow foam.

Example 25

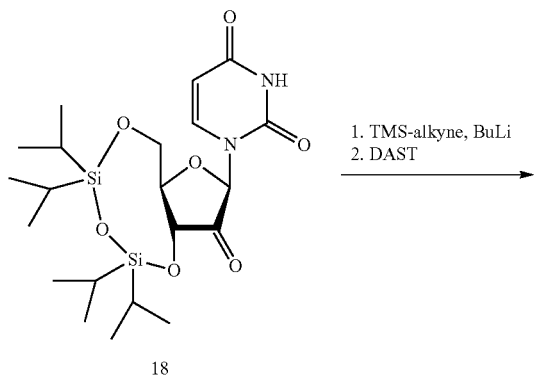

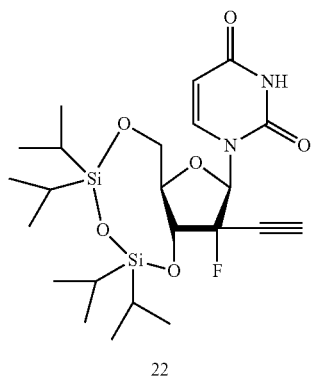

Ethynyltrimethysilane (37 mmol, 3 eq.) was dissolved in anhydrous THF (40 mL) under argon, and the reaction flask was then cool to −78° C. N-butyllithium (37 mmol, 3 eq., 2.5M in hexane) was added dropwise. The resulting mixture was stirred for 30 minutes A solution of ketone (12.4 mmol, 1 eq.) in THF (15 ml) was added dropwise. The reaction was stirred for 3 hours at −78° C. After warm up to room temperature, the reaction was quench with saturated aqueous NH₄Cl and extracted with diethyl ether. The organic layers were combined, dried over MgSO₄, filtered, and concentrated under reduced pressure. The crude residue was purified by silica gel column chromatography eluding with hexane:ethyl acetate (3:1) to provide pure product.

To a stirred solution of the resulting alcohol (1 g, 1.72 mmol) in toluene (8.6 mL, 0.2M) at −78° C. was added DAST (1.13 mL, 8.58 mmol) dropwise. After 3 hours of stirring, the reaction was quenched with saturated aqueous NaHCO₃ (100 mL) and was extracted 3×100 mL ethyl acetate. The extracts were dried over sodium sulfate, filtered, and concentrated under reduced pressure to a paste and purified by silica gel chromatography 25-75% ethyl acetate in hexanes to provide of the desired product.

Example 26

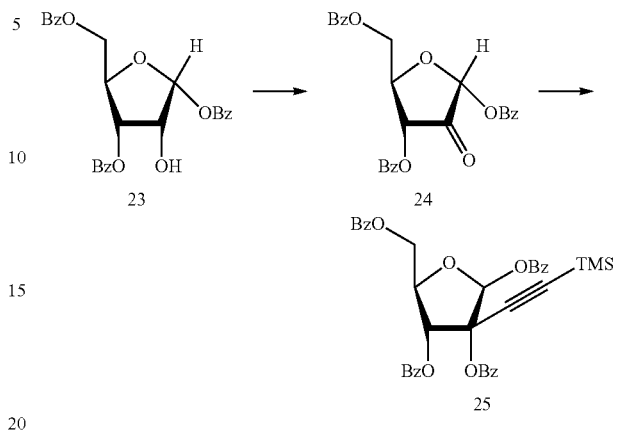

To a stirred solution of DMP (27.5 g, 64.9 mmol) in DCM (162 mL, 0.2M) was cooled to 0° C. and 23 (15 g, 32.4 mmol) was added. The reaction was stirred at 0° C. and allowed to warm to room temperature. After stirring for 18 hours the reaction mixture was concentrated under reduced pressure to a past which was then slurried in 100 mL ethyl ether followed by filtration through a 50 g pad of sillica/mag sulfate 1:1 by mass and washed with a total of 400 mL ethyl ether. The ether layer was washed with 2.5 g of sodium thiosulfate in 15 mL water then 2×30 mL cooled sodium bicarbonate, and finally with 30 mL brine. The filtrate was then dried over sodium sulfate, filtered, and concentrated under reduced pressure to provide a foam which was used without further purification. Before use in the next step, a solution of ketone (32.6 mmol) in DCM (200 mL) was prepared and stirred overnight over 5 g of magnesium sulfate at room temperature. After 18 hours of stirring, the solution was filtered and concentrated under reduced pressure.

To a −78° C. solution of TMS Ethylene (11.4 mL, 80 mmol) in dry THF (100 mL) under argon was added butyl lithium (30.5 mL, 2.5M hexanes, 76 mmol). After 30 minutes of stirring, lithiated alkyne was cannulated into a −78° C. suspension of anhydrous CeCl₃ (33.5 g, 90 mmol, dried overnight 150° C. under high vacuum) in dry THF (130 mL) with 2×15 mL rinses of THF. After 90 minutes of stirring, a solution of 24 (32.4 mmol) in dry THF (50 mL) was added via cannula (2×10 mL rinse THF). After 3 hours of stirring, the resulting solution was quenched with saturated aqueous ammonium chloride (100 mL). The reaction was warmed to room temperature and filtered through a celite pad. The celite pad was washed with ethyl ether (3×100 mL) and with saturated aqueous ammonium chloride (100 mL). The filtrate was separated and the organics were washed with saturated aqueous ammonium chloride (100 mL) and brine (100 mL). The filtrate was dried over sodium sulfate, filtered, and concentrated under reduced pressure to provide an oil which was purified by silica gel chromatography 10-50% ethyl acetate in hexanes to provide the product as a mixture of anomers.

To a stirred 0° C. solution of the above product (32.4 mmol) in dry DCM (163 mL, 0.2M) under argon was added sequentially triethyl amine (18 mL, 130 mmol) DMAP (3.98 g, 32.4 mmol), and benzoyl chloride (9.46 mL, 82 mmol). After stirring for 16 hours, the reaction was concentrated under reduced pressure and then slurried in 200 mL ethyl ether and filtered. The organics were concentrated under reduced pressure to provide a paste which was purified by silica gel chromatography eluting with 10-25% ethyl acetate in hexanes to provide 25 as a mixture of anomers. Compound 25 can then be subjected to general base coupling conditions followed by the appropriate deprotection conditions.

Example 27

2'-Ethynyluridine (27)

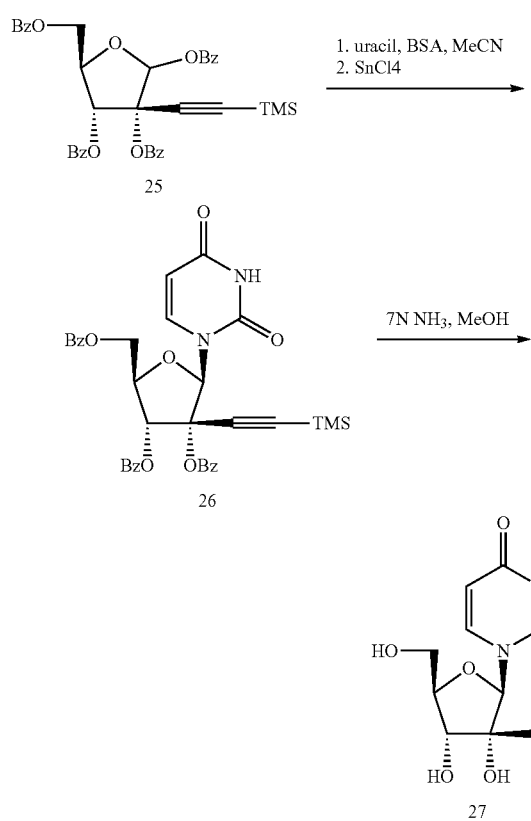

A suspension of uracil (5.19 g, 2.1 eq) in 11 mL acetonitrile and 3 mL BSA (4 eq) was heated to 90° C. for 30 min and then cooled to rt. Compound 25 (14.6 g, 1 eq) was azeotroped in 12 mL of acetonitrile to a paste then redissolved in 6 mL acetonitrile. Compound 25 solution was added to base via cannula with 2×3 mL rinse. $SnCl_4$ (1.5 mL, 4.25 eq) was then added dropwise over 5 min. The reaction was then heated to 90° C. for 2h. The reaction was monitored by TLC (5% methanol in DCM). The reaction was stirred for 30 min and then cooled to 0° C. The reaction was then charged with 5 g of $NaCO_3$ and 5 g of celite. The reaction was then diluted with 20 mL ethyl acetate and charged with 10 mL of saturated aqueous $NaCO_3$ (gas evolution was robust). After 15 min of stirring, the reaction was filtered through a celite pad. The pad was washed 2×50 mL ethyl acetate. The combined organics were washed with 75 mL saturated aqueous $NaCO_3$ and 75 mL brine. The aqueous layer was back extracted with 2×100 mL ethyl acetate. The combined organics were dried with sodium sulfate filtered, filtered, and concentrated under reduced pressure to a foam. Silica gel chromatography, eluting with 0-2.5-5% methanol in DCM, provided 1.74 g of compound 26.

A solution of compound 26 was prepared in 234 mL of 7M ammonia in methanol. The reaction was allowed to stir for 18 h. The reaction was concentrated onto 20 g of celite and purified by silica gel chromatography, eluting with 1-10% methanol in DCM, providing 1 g of compound 27.

Example 28

2'-Ethynyluridine-5'-monophosphate

A stirred solution of compound 27 (0.186 mmol, 1 eq) in $POMe_3$ (1.86 mL) at 0° C. was charged with $POCl3$ (0.317 mmol, 1.7 eq) dropwise over 5 minutes. The reaction was allowed to warm from 0° C. to room temperature (rt) over a 3h period. The reaction was monitored by TLC (7:2:2 IPA, $NH_4OH$, $H_2O$). The reaction was quenched with water (50 mL) and extracted with chloroform (2×100 mL). The pH of the aqueous layer was then made basic using concentrated ammonium hydroxide (500 uL). The aqueous layer was the reextracted with chloroform (2×100 mL). The aqueous layer was then concentrated under reduced pressure. The product was then purified by sillica gel chromatography (eluting with 16:1:1 IPA, $NH_4OH$, $H_2O$ to 8:1:1 IPA, $NH_4OH$, $H_2O$ to 7:2:2 IPA, $NH_4OH$, $H_2O$) several times to provide pure monophosphate in 8% yield after lyophilization.

Example 29

2'-Ethynyl-5-fluorouridine (29)

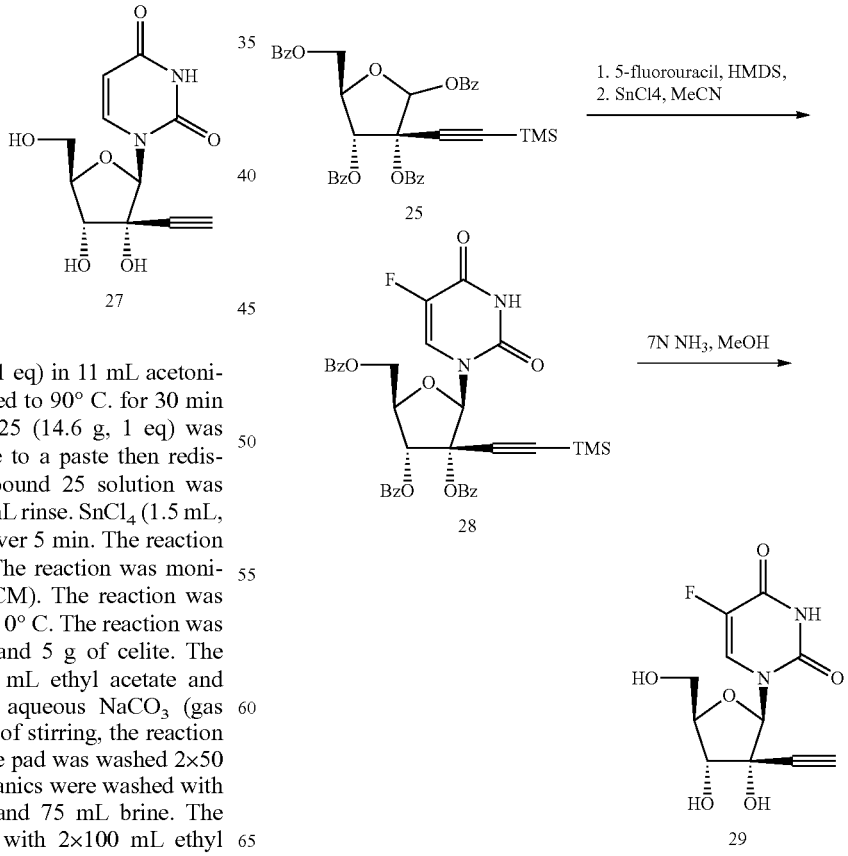

5-Fluorouracil (1.96 g, 15.1 mmol) and ammonium sulfate (50 mg, cat) were suspended in HMDS (25 mL) under argon and heated to 125° C. overnight. The solvent was removed in vacuo and to the residue was added a solution of Compound 25 (5 g, 7.55 mmol) in MeCN (100 mL) then SnCl$_4$ (1M in DCM, 26.5 mL, 26.5 mmol) and heated to 40° C. overnight. Reaction was monitored by TLC (33% EtOAc in hexanes). When complete, the reaction mixture was diluted with EtOAc and washed with saturated aqueous NaHCO$_3$ then brine. The organic layer was dried over MgSO$_4$, filtered and concentrated in vacuo. The resulting residue was loaded onto a silica gel column from a minimal quantity of DCM. The product was eluted with 20% (increasing to 33%) EtOAc in hexanes. The product was isolated as a white foam solid 3.34 g, 4.98 mmol, 66% yield.

In a sealed tube protected nucleoside 28 (3.3 g, 4.92 mmol) was dissolved in 7N ammonia methanol (50 mL) and stirred overnight. The reaction mixture was concentrated onto a silica gel column, and the product was eluted with 5% (increasing to 20%) MeOH in DCM. The main spot was collected and re-purified on silica eluting isocratically with 13% MeOH in DCM. Finally, the product was purified by C18 ultra column eluting isocratically with 4% MeOH in Water. The product was collected and freeze dried to give a white solid 1.21 g, 4.23 mmol, 86% yield.

Example 30

2'-Ethynyl-2-aminopurine ribofuranoside (32)

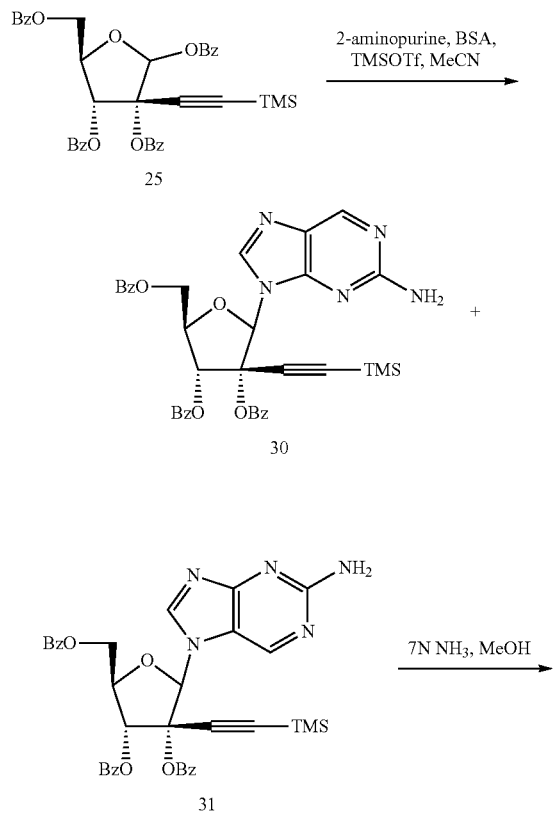

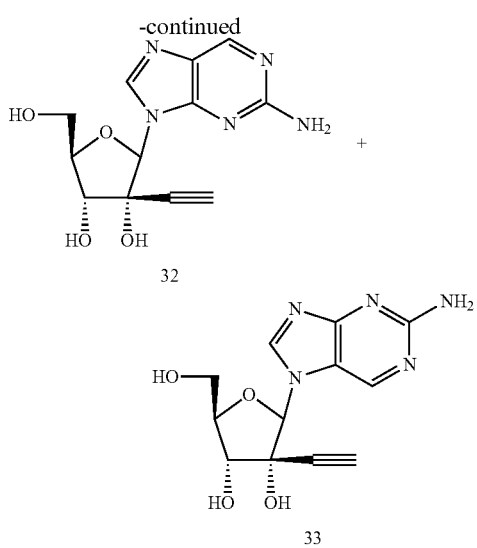

A stirred suspension of 2-aminopurine (0.459 g, 1.5 eq) and 25 (1.5 g, 1 eq) in acetonitrile (15 mL) were prepared. Next, BSA (2.49 mL, 4.5 eq) and TMSOTf (1.227 mL, 3 eq) were added. The reaction solution was then heated to 130° C. for 1 hour in a microwave. The reaction was quenched with 1.2 mL of 1M trethanolamine and was allowed to stir for 30 min. The reaction was concentrated onto celite under reduced pressure and applied to a silica gel column. The desired product was obtained as a mixture.

The above mixture was dissolved in 7N ammonia in methanol (40 mL) and was allowed to stir for 16h. The reaction was concentrated under reduced pressure onto celite. The product was purified by silica gel chromatography eluting with 0-15% methanol in DCM. Two products were obtained, the desired N9-32 (171 mg) and N7-33 (265 mg).

Example 31

2'-Ethynyluridine-5'-monophosphate bis-POM (34)

To a 25 mL pear-shaped flask charged with ((hydroxyphosphoryl)bis(oxy))bis(methylene) bis(2,2-dimethylpropanoate) (313 mg, 0.960 mmol) was added dry THF (4 mL) to give a colorless solution. This was vacuumed and charged with argon. Then triethylamine (147 µl, 1.056 mmol) was added dropwise. After stirring at rt for 30 min, compound 27 (148 mg, 0.480 mmol) was added. This was cooled to 0° C. and then N-ethyl-N-isopropylpropan-2-amine (334 µl, 1.920 mmol), bis(2-oxooxazolidin-3-yl)phosphinic chloride (306 mg, 1.200 mmol) and 3-nitro-1H-1,2,4-triazole (137 mg, 1.200 mmol) were added. The reaction was allowed to stir overnight warming to rt gradually. The reaction was diluted with EtOAc and quenched with saturated aqueous NaHCO$_3$. The organic layer was separated, dried over Na$_2$SO$_4$, filtered and concentrated in vacuo. The crude material was purified by ISCO silica gel column chromatography (12 g column) eluting from 100% DCM to 5% MeOH in DCM to afford a the desired product.

Example 32

2'-Ethynyluridine-5'-monophosphate mono-POM (35)

A solution of NaCl was prepared by dissolving 240 mg of sodium chloride into 24 mL water. The pH was adjusted to 7.3 with 2M sodium phosphate dibasic in water. A suspension of compound 34 was prepared, and the reaction was heated to 37° C. After 4d there was no reaction. An additional 240 mg of NaCl was added, and the reaction was stirred for a further 16h. The reaction looked to have progressed. The reaction was concentrated to 5 mL under reduced pressure at 25° C. The resulting residue was loaded onto a 100 g C18 column eluting with 0-100% acetonitrile in water. Fractions containing product were pooled, concentrated, and repurified using a 50 g C18 column. Fractions were pooled, concentrated, and lyophilized to provide 36 mg of desired product.

Example 33

2'-Ethynyl-5-fluorouridine-5'-monophosphate bis-POM (36)

To a stirred solution of ((hydroxyphosphoryl)bis(oxy))bis(methylene) bis(2,2-dimethylpropanoate) (230 mgs, 2 eq) and compound 29 (101 mgs, 1 eq) in THF (7 mL) was added triethylamine (0.1 mL, 2.2 eq). After 10 min the reaction was cooled to 0° C. and charged sequentially with Hunig's base (0.25 mL, 4 eq), BOPCl (225 mgs, 2.5 eq), and 3-nitro-1H-1,2,4-triazole (101 mgs, 2.5 eq). The reaction was allowed to stir for 14h. The reaction mixture was then concentrated onto celite under reduced pressure. The celite pad was placed on a sillica gel column, and the product was eluted with 1-7% methanol in DCM. The product (31 mgs) was obtained as a white solid.

Example 34

Alternative Method for Base Couplings

A mixture of nucleobase (9.05 mmol) and 25 (4.53 mmol) was co-evaporated with dry toluene (×3) then dried on the high vacuum line for two hours. The residue was taken up in dry MeCN (50 mL), BSA (4.4 mL, 18.11 mmol) was added, and the mixture was heated at 70° C. for one hour to allow for the complete dissolution of nucleobase. The mixture was allowed to cool to RT for the addition of SnCl$_4$ (1M in DCM, 18.1 mL, 18.1 mmol) via syringe, then heated at 70° C. overnight. Upon cooling to RT, the solvents were removed in vacuo and the residue taken up in DCM and pyridine to precipitate the Sn salts. After filtration through Celite, the organics were concentrated then taken up in ethyl acetate and washed with NaHCO$_3$ and brine. The organic layer was then dried, filtered and concentrated to afford a solid. Purification by column chromatography (SNAP 50 g, 0 to 100% EA in DCM) afforded recovered sugar donor and desired nucleoside. Trituration with ether afforded the desired nucleoside as a white solid.

Example 35

Cytidine Nucleosides Prepared Using the Alternative Method for Base Couplings and General Benzoyl Deprotection Conditions

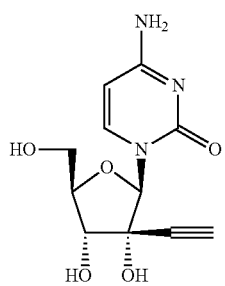

37

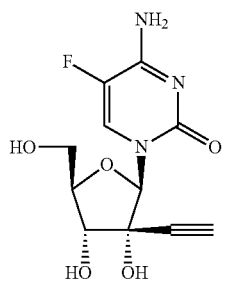

38

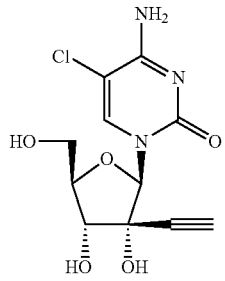

39

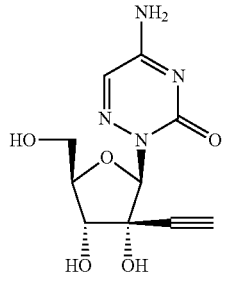

40

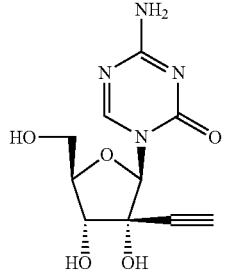

41

Example 36

N-tert-Butyloxycarbonyl-sphingosine (124)

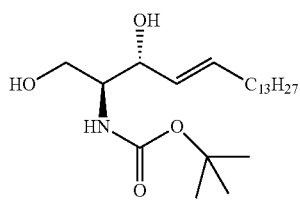

124

Prepared according to Boumendjel, Ahcene and Miller, Stephen *Journal of Lipid Research* 1994, 35, 2305.

A mixture of sphingosine (450 mg, 1.50 mmol) and di-tert-butyl dicarbonate (0.656 g, 3.01 mmol) in methylene chloride (100 mL) at 4° C. was treated dropwise with diisopropylethylamine (0.53 mL, 3.01 mmol). After gradual warming to rt, the mixture was stirred for an additional 12 h and then diluted with methylene chloride (100 mL) followed by a wash with water (30 mL) and brine (30 mL). The organic phase was dried over sodium sulfate, filtered and concentrated to dryness. The crude residue was purified by flash column chromatography over silica gel (19 mm×175 mm) using 50% ethyl acetate in hexanes to give N-tert-butyloxycarbonyl-sphingosine (540 mg, 90%) as a white solid.

$^1$H NMR (300 MHz, Chloroform-d) δ 5.77 (dt, J=15.4, 8.4 Hz, 1H), 5.52 (dd, J=15.4, 8.4 Hz, 1H), 3.93 (dd, J=11.4, 3.7 Hz, 1H), 3.70 (dd, J=11.4, 3.7 Hz, 1H), 3.59 (s, 3H), 2.05 (q, J=7.0 Hz, 2H), 1.52 (s, 9H), 1.25 (s, 22H), 0.87 (t, J=6.5 Hz, 3H).

Example 37

N-tert-Butyloxycarbonyl-sphingosine-1-O-dimethylphosphate (125)

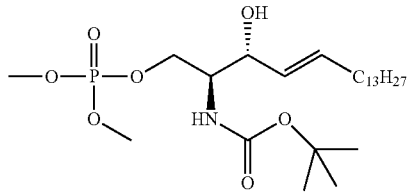

125

N-tert-Butyloxycarbonyl-sphingosine 124 (540 mg, 1.35 mmol) was rendered anhydrous by co-evaporation with anhydrous pyridine (2×12 mL). The residue was then dissolved in anhydrous pyridine and treated with carbon tetrabromide (622 mg, 1.88 mmol). The mixture was cooled to 0° C. and treated dropwise with a solution of trimethylphosphite (0.25 mL, 2.10 mmol) in anhydrous pyridine (3 mL) over a 30 min period. After an additional 12 h at rt, both LCMS and tlc (5% methanol in methylene chloride) analysis indicated complete conversion. The mixture was quenched with water (2 mL) and then concentrated to dryness. The resulting dark oil was dissolved in ethyl acetate (150 mL) and washed with 3% HCL solution (2×20 mL) followed by saturated sodium bicarbonate solution (30 mL). The organic layer was dried over sodium sulfate, filtered and concentrated. The crude residue was purified by flash column chromatography over silica gel (19 mm×175 mm) using 2% methanol in methylene chloride to give N-tert-butyloxycarbonyl-sphingosine-1-O-dimethylphosphate 125 (350 mg, 51%) as a gum.

$^1$H NMR (400 MHz, Chloroform-d) δ 5.82 (dt, J=15.4, 7.1 Hz, 1H), 5.48 (dd, J=15.4, 7.1 Hz, 1H), 4.99 (d, J=8.9 Hz, 1H), 4.32 (ddd, J=10.7, 8.0, 4.6 Hz, 1H), 4.11 (ddt, J=10.7, 7.4, 3.1 Hz, 2H), 3.77 (dd, J=11.1, 2.1 Hz, 6H), 2.01 (q, J=7.1 Hz, 2H), 1.41 (s, 9H), 1.34 (m, 2H), 1.23 (m, 20H), 0.86 (t, J=6.4 Hz, 3H).

$^{31}$P NMR (162 MHz, Chloroform-d) δ 2.00.

MS C17H25NO4 [M+Na+]; calculated: 330.2, found: 330.2.

Example 38

Sphingosine-1-phosphate (126)

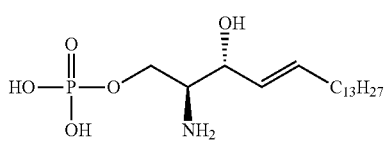

126

A solution of N-tert-butyloxycarbonyl-sphingosine-1-O-dimethylphosphate 125 (350 mg, 0.689 mmol) in anhydrous methylene chloride (8 mL) was treated dropwise with trimethylsilyl bromide (0.45 mL, 3.45 mmol) at 0° C. After warming to room temperature, the mixture was allowed to stir at rt for 6h and then concentrated to dryness. The resulting residue was co-evaporated with methylene chloride to remove excess trimethylsilyl bromide and then treated with 66% aqueous THF (6 mL). The resulting precipitate was collected by filtration to give sphingosine-1-phosphate 126 (218 mg, 83%) as a white solid.

$^1$H NMR (400 MHz, Methanol-d4+CD$_3$CO$_2$D) δ 5.84 (dt, J=15.5, 6.7 Hz, 1H), 5.46 (dd, J=15.5, 6.7 Hz, 1H), 4.33 (t, J=6.0 Hz, 1H), 4.13 (ddd, J=11.8, 7.7, 3.6 Hz, 1H), 4.03 (dt, J=11.8, 8.4 Hz, 1H), 3.47 (ddd, J=8.3, 4.8, 3.2 Hz, 1H), 2.10-1.99 (m, 2H), 1.37 (m, 2H), 1.24 (m, 20H), 0.83 (t, J=6.4 Hz, 3H).

$^{31}$P NMR (162 MHz, Chloroform-d) δ 0.69.

MS C$_{18}$H$_{38}$NO$_5$P [M−H$^+$]; calculated: 378.2, found: 378.2.

Example 39

N-Trifluoroacetyl-phytosphingosine (131)

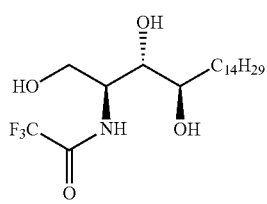

131

To a slurry of phytosphingosine (4 g, 12.6 mmol) and anhydrous powdered potassium carbonate (5.22 g, 37.8 mmol) in methylene chloride (85 mL) was added trifluoroacetic anhydride (1.96 mL, 13.9 mmol). The mixture was stirred at rt for 18 h and then diluted with methylene chloride (500 mL). The mixture was washed with water (100 mL). Methanol (60 mL) was added to break the emulsion. The organic phase was then dried over sodium sulfate, filtered and concentrated to give 131 (4.9 g, 94%) as a white solid $^1$H NMR (400 MHz, DMSO-d6) δ 8.90 (s, 1H), 4.90-4.68 (m, 1H), 4.56 (d, J=6.1 Hz, 1H), 4.43 (s, 1H), 3.97 (d, J=7.6 Hz, 1H), 3.65 (d, J=10.8 Hz, 1H), 3.46 (t, J=10.2 Hz, 1H), 3.32-3.16 (m, 1H), 1.42 (tt, J=15.7, 7.5 Hz, 2H), 1.20 (s, 24H), 0.83 t, J=6.8 Hz, 3H).

Example 40

1-O-tert-Butyldiphenylsilyl-2-N-trifluoroacetyl-phytosphingosine (132)

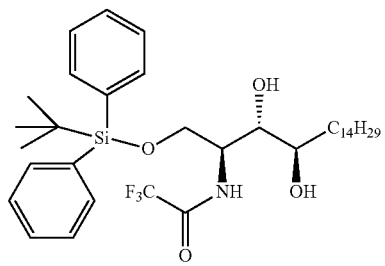

132

N-Trifluoroacetyl-phytosphingosine (131, 1.88 g, 4.5 mmol) in anhydrous pyridine (23 mL) was treated with DMAP (56 mg, 0.45 mmol) and then dropwise with tert-butyldiphenylsilyl chloride (1.38 g, 5.0 mmol). After 18 h concentrated to dryness. The resulting residue was dissolved in ethyl acetate (200 mL) and washed with saturated ammonium chloride (2×50 mL) and then brine (50 mL). The aqueous phases was back-extracted with ethyl acetate (50 mL). Combined organic phases were dried over sodium sulfate and concentrated to give crude 1-O-tert-Butyldiphenylsilyl-2-N-trifluoroacetyl-phytosphingosine 132 (3 g, 100%) as a gum. The material was used in the next step without further purification.

$^1$H NMR (400 MHz, Chloroform-d) δ 7.62 (m, 2H), 7.60-7.56 (m, 2H), 7.47-7.31 (m, 6H), 7.07 (d, J=8.4 Hz, 1H), 4.23 (dd, J=8.5, 4.1 Hz, 1H, 4.04 (dt, J=11.0, 2.5 Hz, 1H), 3.82 (ddd, J=11.0, 4.3, 1.8 Hz, 1H), 3.64 (dq, J=10.6, 6.0, 4.3 Hz, 2H), 1.45 (m, 2H), 1.39-1.15 (m, 24H), 1.05 (m, 9H), 0.94-0.80 (t, J=6.9 Hz 3H).

Example 41

1-O-tert-Butyldiphenylsilyl-3,4-O-isopropylidene-2-N-trifluoroacetyl-phytosphingosine (133)

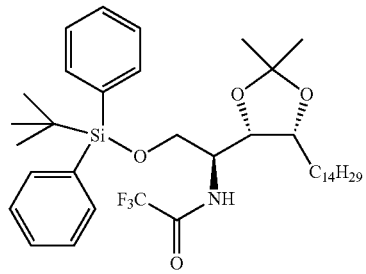

133

A solution of 1-O-tert-Butyldiphenylsilyl-2-N-trifluoroacetyl-phytosphingosine 132 (3 g, 4.5 mmol) in 1/1 (v/v) 2,2-dimethoxypropane/THF was treated with catalytic amount of p-toluenesulfonic acid (87 mg, 0.45 mmol) and allowed to stir for 16h at rt. The mixture was quenched with saturated sodium bicarbonate (30 mL) and then excess THF/2,2-dimethoxypropane was removed under vacuum. The mixture was extracted with ethyl acetate (200 mL). After washing with brine, the organic layer was dried over sodium sulfate, filtered and concentrated. The crude oil was purified by column chromatography (25 mm×175 mm) over silica gel with a hexanes/ethyl acetate mobile phase to give 133 (2.45 g, 78%).

$^1$H NMR (400 MHz, Chloroform-d) δ 7.68-7.63 (m, 2H), 7.63-7.57 (m, 2H), 7.39 (m, 6H), 6.54 (d, J=9.4 Hz, 1H), 4.23 (dd, J=8.2, 5.6 Hz, 1H), 4.12 (ddd, J=13.3, 6.9, 3.8 Hz, 2H), 3.96 (dd, J=10.5, 3.9 Hz, 1H), 3.69 (dd, J=10.5, 2.9 Hz, 1H), 1.52-1.36 (m, 2H), 1.33 (s, 3H), 1.31 (s, 3H), 1.24 (m, 24H), 1.03 (s, 9H), 0.86 (t, J=53.7, 6.9 Hz, 3H).

Example 42

3,4-O-Isopropylidene-2-N-Trifluoroacetyl-phytosphingosine (134)

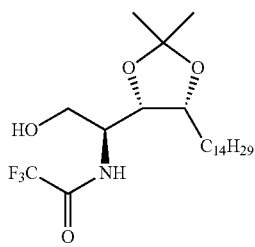

134

A solution of 1-O-tert-Butyldiphenylsilyl-3,4-O-isopropylidene-2-N-trifluoroacetyl-phytosphingosine 133 (2.45 g, 3.54 mmol) in THF (18 mL) was treated with tetrabutylammonium fluoride (4.25 mL of a 1.0 M solution in THF, 4.25 mmol) and stirred at rt for 12h. The mixture was diluted with ethyl acetate (100 mL) and saturated ammonium chloride (2×50 mL) and then brine (50 mL). The organic phase was dried over sodium sulfate, filtered, and concentrated to give a white solid that was further purified by column chromatography (25 mm×175 mm) over silica gel with a 9:1 hexanes:ethyl acetate mobile phase to afford 134 (1.5 g, 93%) as a white solid.

$^1$H NMR (300 MHz, Chloroform-d) δ 6.92 (d, J=8.7 Hz, 1H), 4.31-4.16 (m, 2H), 4.11 (dq, J=11.7, 3.7 Hz, 1H), 4.00 (dd, J=11.5, 2.6 Hz, 1H), 3.70 (dd, J=11.5, 3.6 Hz, 1H), 1.48 (s, 3H), 1.35 (s, 3H), 1.25 (m, 26H), 0.88 (t, J=6.9 Hz 3H).

Example 43

3,4-O-Isopropylidene-2-N-trifluoroacetyl-phytosphingosine-1-O-dimethylphosphate (135)

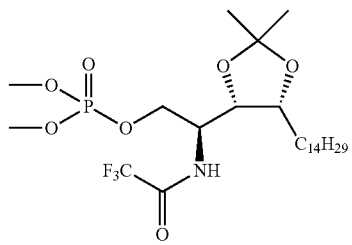

135

A solution of 3,4-O-Isopropylidene-2-N-Trifluoroacetyl-phytosphingosine 134 (630 mg, 1.39 mmol) was rendered anhydrous by co-evaporation with anhydrous pyridine (2×12 mL). The residue was then dissolved in anhydrous pyridine (12 mL) and treated with carbon tetrabromide (533 mg, 1.67 mmol). The mixture was cooled to 0° C. and treated dropwise with a solution of trimethylphosphite (0.23 mL, 1.95 mmol) in anhydrous pyridine (3 mL) over a 30 min period. After an additional 12 h at rt, both LCMS and tlc (5% methanol in methylene chloride) analysis indicated complete conversion. The mixture was quenched with water (2 mL) and then concentrated to dryness. The resulting dark oil was dissolved in ethyl acetate (100 mL) and washed with 3% HCL solution (2×20 mL) followed by saturated sodium bicarbonate solution (30 mL). The organic layer was dried over sodium sulfate, filtered and concentrated. The crude residue was purified by flash column chromatography over silica gel (19 mm×175 mm) using 2% methanol in methylene chloride to give 135 (650 mg, 83%).

$^1$H NMR (300 MHz, Chloroform-d) δ 7.42 (d, J=8.8 Hz, 1H), 4.36 (td, J=10.9, 5.0 Hz, 1H), 4.25 (m, 1H), 4.19 (m, J=6.5, 2.0 Hz, 3H), 3.77 (dd, J=11.2, 7.5 Hz, 6H), 1.44 (s, 3H), 1.33 (s, 3H), 1.25 (m, 26H), 0.87 (t, J=6.6 Hz, 3H).

$^{31}$P NMR (121 MHz, Chloroform-d) δ 1.69.

MS $C_{25}H_{47}F_3NO_7P$ [M−H$^+$]; calculated: 560.3, found: 560.2.

Example 44

3,4-O-Isopropylidene-2-N-trifluoroacetyl-phytosphingosine-1-phosphate (136)

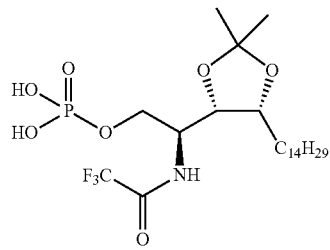

136

A solution of 3,4-O-Isopropylidene-2-N-trifluoroacetyl-phytosphingosine-1-O-dimethylphosphate 135 (650 mg, 1.16 mmol) in anhydrous methylene chloride (12 mL) was treated dropwise with trimethylsilyl bromide (0.81 mL, 6.23 mmol) at 0° C. After 12h at rt, the mixture was concentrated to dryness and the resulting residue co-evaporated with methylene chloride (3×50 mL) to remove excess trimethylsilyl bromide. The residue then was dissolved in cold (4° C.) solution of 1% NH$_4$OH while maintaining pH 7-8. After 10 min at rt, the mixture was concentrated to dryness, and the resulting solid triturated with methanol/acetonitrile. The solid was collected by filtration, washed with acetonitrile, and dried under high vacuum to give 136 (500 mg, 75%) as a white solid.

$^1$H NMR (300 MHz, Methanol-d4) δ 4.31 (dd, J=8.7, 5.4 Hz, 1H), 4.09 (m, 4H), 1.42 (s, 3H), 1.36 (s, 3H), 1.31 (m, 26H), 0.89 (t, J=6.4 Hz, 3H).

$^{31}$P NMR (121 MHz, Methanol-d$_4$) δ 1.28.

$^{19}$F NMR (282 MHz, Methanol-d$_4$) δ −77.13.

HRMS $C_{23}H_{42}F_3NO_7P$ [M−H$^+$]; calculated: 532.26565, found: 532.26630.

Example 45

2',3'-dideoxy-2'-fluoro-5'-(N-trifluoroacetyl-3,4-O-isopropylidene-phytosphingosine-1-phospho)-7-deazaguanosine (137)

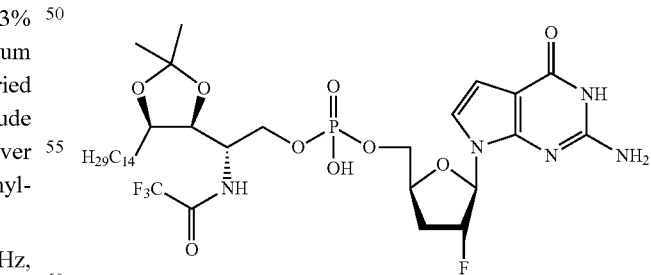

137

A mixture of N-trifluoroacetyl-phytosphingosine-1-phosphate 136 (200 mg, 0.373 mmol) and 2',3'-dideoxy-2'-fluoro-7-deazaguanine (100 mg, 0.373 mmol) was rendered anhydrous by co-evaporation with anhydrous pyridine (3×10 mL). The resulting residue then was dissolved in anhydrous pyridine (4 mL) and treated with diisopropylcarbodiimide (127 mg, 1.01 mmol) and HOBt (60 mg, 0.447 mmol). After 24 h at 75° C., the reaction mixture was cooled to rt and concentrated to dryness. The crude material was purified by flash column chromatography (19 mm×170 mm) over silica gel using a solvent gradient from 5 to 7.5% methanol in chloroform with 1% (v/v) NH$_4$OH to give 137 (80 mg, 27%) as a white solid.

$^1$H NMR (300 MHz, Methanol-d$_4$) δ 6.88 (d, J=3.8 Hz, 1H), 6.46 (d, J=3.8 Hz, 1H), 6.24 (d, J=19.9 Hz, 1H), 5.34 (dd, J=52.4, 4.6 Hz, 1H), 4.53 (s, 1H), 4.34-3.97 (m, 6H), 2.63-2.17 (m, 2H), 1.40 (s, 3H), 1.30 (s, 3H), 1.27 (m, 26H), 0.89 (t, J=6.6 Hz, 3H).

$^{31}$P NMR (121 MHz, Methanol-d$_4$) δ 12.50.

$^{19}$F NMR (282 MHz, Methanol-d$_4$) δ −77.10, −179.69-- 180.25 (m).

MS C$_{34}$H$_{52}$F$_4$N$_5$O$_9$P [M–H$^+$]; calculated: 781.3, found: 782.2.

Example 46

Experimental Procedure for Synthesis of Prodrugs

A solution of isopropyl 2-((chloro(phenoxy)phosphoryl)amino)propanoate (0.397 g, 1.300 mmol) in anhydrous THF (5 ml) was added to a −78° C. stirred solution of 2'-deoxy-2'-fluoronucleoside (0.812 mmol) and 1-methyl-1H-imidazole (0.367 ml, 4.63 mmol) in pyridine (10.00 ml). After 15 min the reaction was allowed to warm to room temperature and was stirred for an additional 3 hours. Next, the solvent was removed under reduced pressure. The crude product was dissolved in 120 ml of DCM and was washed with 20 ml 1 N HCl solution followed by 10 ml water. The organic phase was dried over sodium sulfate, filtered and concentrated in vacuo. The residues were separated over silica column (neutralized by TEA) using 5% MeOH in DCM as a mobile phase to yield the respective products as diastereomers.

Example 47

N-tert-Butyloxycarbonyl-phytosphingosine (174)

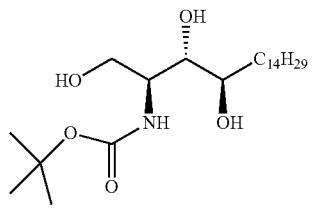

174

A suspension of phytosphingosine (10.6 g, 33.5 mmol) and triethylamine (5.6 ml, 40.2 mmol) in THF (250 mL) was treated dropwise with di-tert-butyl dicarbonate (8.6 mL, 36.9 mmol). After 12h at rt, the mixture was concentrated to dryness and the resulting white solid was recrystallized from ethyl acetate (80 mL) and then dried under high vacuum at 35° C. for 12h to give 174 (10.5 g, 75%).

$^1$H NMR (400 MHz, Chloroform-d) δ 5.31 (d, J=8.5 Hz, 1H), 3.89 (d, J=11.1 Hz, 1H), 3.83 (s, 2H), 3.74 (dd, J=11.1, 5.2 Hz, 1H), 3.65 (d, J=8.3 Hz, 1H), 3.61 (d, J=3.9 Hz, 1H), 1.43 (s, 9H), 1.23 (s, 27H), 0.86 (t, J=6.4 Hz, 3H).

Example 48

2-O-tert-Butyldiphenylsilyl-1-N-tert-butyloxycarbonyl-phytosphingosine (175)

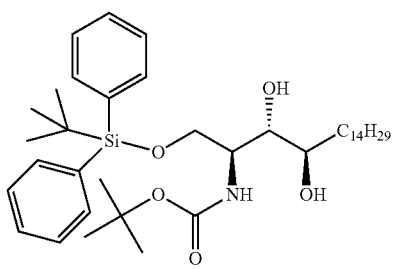

175

A solution of N-tert-Butyloxycarbonyl-phytosphingosine 174 (9.5 g, 22.65 mmol) and triethylamine (3.8 mL, 27.2 mmol) in anhydrous methylene chloride/DMF (120 mL/10 mL) was treated dropwise with tert-butylchlorodiphenylsilane (7 mL, 27.25 mmol). After 18h at rt, the mixture was diluted with methylene chloride (200 mL) and washed with 0.2N HCl (100 mL) and then brine (100 mL). The organic phase was dried over sodium sulfate, filtered and then concentrated to give 175 (14.9 g) as an oil which was used in the next reaction without further purification.

$^1$H NMR (400 MHz, Chloroform-d) δ 5.31 (d, J=8.5 Hz, 1H), 3.89 (d, J=11.1 Hz, 1H), 3.83 (m, 1H), 3.74 (dd, J=11.1, 5.2 Hz, 1H), 3.65 (d, J=8.3 Hz, 1H), 3.61 (d, J=3.9 Hz, 1H), 1.43 (s, 9H), 1.23 (s, 27H), 0.86 (t, J=6.4 Hz, 3H).

Example 49

2-O-tert-Butyldiphenylsilyl-1-N-tert-butyloxycarbonyl-3,4-O-isopropylidene-phytosphingosine (176)

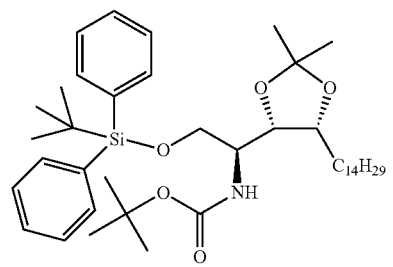

176

A solution of 2-O-tert-Butyldiphenylsilyl-1-N-tert-butyloxycarbonyl-phytosphingosine (175, 14.9 g, 22.65 mmol) in 1/1 (v/v) THF/2,2-dimethoxypropane was treated with catalytic para-toluenesulfonic acid (860 mg, 4.53 mmol). After 24h, the mixture was quenched with saturated sodium bicarbonate solution (50 mL). The mixture was concentrated and then dissolved in ethyl acetate (200 mL) and washed with brine (2×50 mL). The organic phase was dried over sodium sulfate, filtered and concentrated to give 176 (15.7 g) as a gum which was used in the next step without further purification.

$^1$H NMR (400 MHz, Chloroform-d) δ 7.66 (m, 4H), 7.51-7.27 (m, 6H), 4.78 (d, J=10.0 Hz, 1H), 4.18 (dd, J=9.3, 5.5 Hz, 1H), 3.89 (dd, J=9.9, 3.3 Hz, 1H), 3.80 (d, J=9.9 Hz, 1H), 3.72 (d, J=9.9 Hz, 1H), 1.45 (s, 9H), 1.42 (s, 3H), 1.35 (s, 3H), 1.25 (s, 27H), 1.05 (s, 9H), 0.87 (t, J=6.5 Hz, 3H).

Example 50

1-N-tert-butyloxycarbonyl-3,4-O-isopropylidene-phytosphingosine (177)

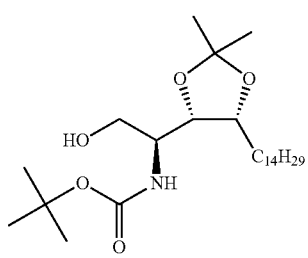

177

A solution of 2-O-tert-Butyldiphenylsilyl-1-N-tert-butyloxycarbonyl-3,4-O-isopropylidene-phytosphingosine 176 (15.7 g, 22.6 mmol) in THF at 0° C. was treated dropwise with a solution of tetrabutylammonium fluoride (1.0 M in THF, 24.9 mL, 24.9 mmol) over a 20 min period. After 16h at rt, tlc (3:1 hexanes:ethyl acetate) indicated complete conversion. The mixture was concentrated to dryness and the resulting residue was dissolved in ethyl acetate (300 mL) and washed with water (3×100 mL). The organic phase was dried over sodium sulfate, filtered and concentrated. The resulting oil purified by flash column chromatography (35 mm×180 mm) using a solvent gradient from 25 to 50% ethyl acetate in hexanes to give 177 (7.3 g, 71% over 3 steps) as a white solid.

$^1$H NMR (400 MHz, Chloroform-d) δ 4.93 (d, J=9.1, 1H), 4.16 (q, J=7.1, 6.4 Hz, 1H), 4.07 (t, J=6.5 Hz, 1H), 3.83 (dd, J=11.1, 2.4 Hz, 1H), 3.76 (m, 1H), 3.67 (dd, J=11.2, 3.6 Hz, 1H), 1.43 (s, 3H), 1.42 (s, 9H), 1.32 (s, 3H), 1.23 (s, 27H), 0.86 (t, J=6.9 Hz, 3H).

Example 51

General Procedure for the Preparation of 5'-Phosphoramidate Prodrugs
Synthesis of Chlorophosphoramidate:

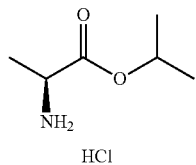

251

Thionyl chloride (80 g, 49.2 mL, 673 mmol) was added dropwise over a 30 min period to a suspension of L-alanine (50 g, 561 mmol) in isopropanol (500 mL). The mixture was heated to a gentle reflux for 5h and then concentrated by rotary evaporator (bath set at 60° C.). The resulting thick gum solidified upon trituration with ether (150 mL). The white powder was triturated a second time with ether (150 mL), collected by filtration while under a stream of argon, and then dried under high vacuum for 18h to give (S)-isopropyl 2-aminopropanoate hydrochloride (88 g, 94%).

$^1$H NMR (400 MHz, DMSO-d6) δ 8.62 (s, 3H), 5.10-4.80 (m, 1H), 3.95 (q, J=7.2 Hz, 1H), 1.38 (d, J=7.2 Hz, 3H), 1.22 (d, J=4.6 Hz, 3H), 1.20 (d, J=4.6 Hz, 3H).

Example 52

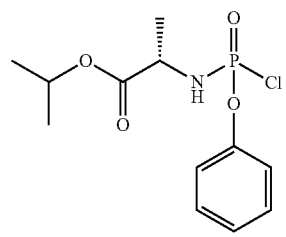

252

A solution of phenyl dichlorophosphate (30.9 g, 146 mmol) in dichloromethane (450 mL) was cooled to 0° C. then treated with (S)-isopropyl 2-aminopropanoate hydrochloride (24.5 g, 146 mmol). The mixture was further cooled to −78° C. and then treated dropwise with triethylamine (29.6 g, 40.8 mL, 293 mmol) over a 30 min period. The mixture continued to stir at −78° C. for an additional 2 h and then allowed to gradually warm to rt. After 18h the mixture was concentrated to dryness and the resulting gum dissolved in anhydrous ether (150 mL). The slurry was filtered while under a stream of argon, and the collected solid washed with small portions of anhydrous ether (3×30 mL). Combined filtrates were concentrated to dryness by rotary evaporator to give a 1:1 diastereomeric mixture of phosphochloridate (41.5 g, 93%) as pale yellow oil.

$^1$H NMR (300 MHz, Chloroform-d) δ 7.43-7.14 (m, 5H), 5.06 (m, 1H), 4.55 (dd, J=14.9, 7.0 Hz, 1H), 4.21-4.01 (m, 1H), 1.48 (d, J=7.0 Hz, 2H), 1.27 (d, J=6.2 Hz, 3H), 1.26 (d, J=5.8 Hz, 3H).

$^{31}$P NMR (121 MHz, Chloroform-d) δ 8.18 and 7.87.

Example 53

Synthesis of 2-chloro-4-nitrophenyl phosphoramidate

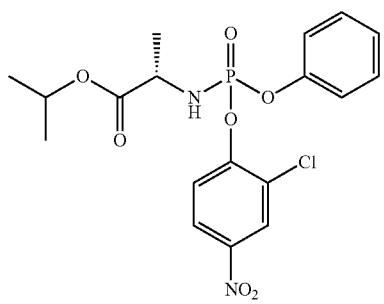

253

A solution of phenyl dichlorophosphate (60 g, 42.5 mL, 284 mmol) in dichloromethane (300 mL) was cooled to 0° C. and then treated with (S)-isopropyl 2-aminopropanoate hydrochloride (47.7 g, 284 mmol). The mixture was further cooled to −78° C. and treated dropwise with a solution of triethylamine (57.6 g, 79 mL, 569 mmol) in methylene chloride (300 mL) over a 1 h period. The reaction mixture was warmed to 0° C. for 30 min and then treated with a preformed mixture of 2-chloro-4-nitrophenol (46.9 g, 270 mmol) and triethylamine (28.8 g, 39.6 mL, 284 mmol) in dichloromethane (120 mL) over a 20 min period. After 2 h at 0° C., the mixture was filtered through a fritted funnel, and the collected filtrate concentrated to dryness. The crude gum was dissolved MTBE (500 mL) and washed with 0.2 M $K_2CO_3$ (2×100 mL) followed by 10% brine (3×75 mL). The organic phase was dried over sodium sulfate, filtered and concentrated to dryness by rotary evaporator to give a diastereomeric mixture (100 g, 93%) as a pale yellow oil.

$^1$H NMR (400 MHz, Chloroform-d) δ 8.33 (dd, J=2.7, 1.1 Hz, 1H, diastereomer 1), 8.31 (dd, J=2.7, 1.1 Hz, 1H, diastereomer 2), 8.12 (dd, J=9.1, 2.7 Hz, 1H), 7.72 (dt, J=9.1, 1.1 Hz, 1H), 7.40-7.31 (m, 2H), 7.28-7.19 (m, 6H), 5.01 (pd, J=6.3, 5.2 Hz, 1H), 4.22-4.08 (m, 1H), 3.96 (td, J=10.7, 9.1, 3.6 Hz, 1H), 1.43 (dd, J=7.0, 0.6 Hz, 3H), 1.40 (dd, J=7.2, 0.6 Hz, 3H, diastereomer 2), 1.25-1.20 (m, 9H).

Example 54

Separation of Compound 253 Diastereomers:

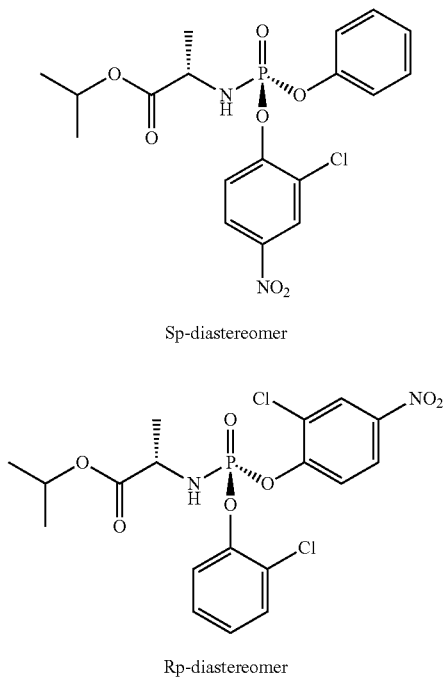

The diastereomeric mixture 253 (28 g, 63.2 mmol) was dissolved in 2:3 ethyl acetate:hexanes (100 mL) and cooled to −20° C. After 16 h, the resulting white solid was collected by filtration and dried under high vacuum to give a 16:1 $S_p$:$R_p$-diastereomeric mixture (5.5 g, 19.6%). The mother liquor was concentrated and the resulting residue dissolved in 2:3 ethyl acetate:hexanes (50 mL). After 16h at −10° C., the resulting white solid was collected and dried under high vacuum to give a 1:6 $S_p$:$R_p$-diastereomeric mixture (4 g, 14%). The 16:1 $S_p$:$R_p$-diastereomeric mixture (5.5 g, 12.4 mmol) was suspended in hot hexanes (50 mL) and treated slowly with ethyl acetate (approximately 10 mL) until complete dissolution. After cooling to 0° C., the resulting white solid was collected by filtration, washed with hexanes, and dried under high vacuum to give the $S_p$-diastereomer of 254 (4.2 g, 76%) as a single isomer.

$^1$H NMR ($S_p$-diastereomer, 400 MHz, Chloroform-d) δ 8.33 (dd, J=2.7, 1.1 Hz, 1H), 8.12 (dd, J=9.1, 2.7 Hz, 1H), 7.71 (dd, J=9.1, 1.2 Hz, 1H), 7.41-7.30 (m, 2H), 7.29-7.11 (m, 3H), 5.00 (m, 1H), 4.25-4.07 (m, 1H), 3.97 (dd, J=12.7, 9.4 Hz, 1H), 1.43 (d, J=7.0 Hz, 3H), 1.23 (d, J=2.2 Hz, 3H), 1.21 (d, J=2.2 Hz, 3H).

The 1:6 $S_p$:$R_p$-diastereomeric mixture (4 g, 12.4 mmol) was suspended in hot hexanes (50 mL) and treated slowly with ethyl acetate (approximately 5 mL) until complete dissolution. After cooling to 0° C., the resulting white solid was collected by filtration, washed with hexanes, and dried under high vacuum to give the $R_p$-diastereomer of 255 (3.2 g, 80%) as a single isomer. Absolute stereochemistry was confirmed by X-ray analysis.

$^1$H NMR ($R_p$-diastereomer, 400 MHz, Chloroform-d) δ 8.31 (dd, J=2.7, 1.1 Hz, 1H), 8.11 (dd, J=9.1, 2.7 Hz, 1H), 7.72 (dd, J=9.1, 1.2 Hz, 1H), 7.42-7.30 (m, 2H), 7.31-7.14 (m, 3H), 5.01 (p, J=6.3 Hz, 1H), 4.15 (tq, J=9.0, 7.0 Hz, 1H), 4.08-3.94 (m, 1H), 1.40 (d, J=7.0 Hz, 3H), 1.24 (d, J=3.5 Hz, 3H), 1.22 (d, J=3.5 Hz, 3H).

Example 55

General Procedure for Phosphoramidate Prodrug Formation:

The desired nucleoside (1 equivalent) to be converted into its 5'-phosphoramidate prodrug was dried in a vacuum oven at 50° C. overnight. The dry nucleoside is placed in a dry flask under an inert atmosphere and suspended in either dry THF or dry DCM to achieve a 0.05M solution. The flask was then cooled to 0° C., and the chlorophosphoramidate reagent (5 equivalents) was added to the suspended nucleoside. Next, 1-methylimidazole (8 equivalents) was added to the reaction mixture dropwise. The reaction was allowed to stir at room temperature for 12-72 hours. After the reaction was complete as judged by TLC, the reaction mixture was diluted with ethyl acetate. The diluted reaction mixture was then washed with saturated aqueous ammonium chloride solution. The aqueous layer was re-extracted with ethyl acetate. The combined organic layers were then washed with brine, dried over $MgSO_4$, filtered, and concentrated. The concentrated crude product was then purified on silica eluting with a gradient of DCM to 5% MeOH in DCM.

Example 56

General Procedure for Preparation of 5'-Triphosphates:

Nucleoside analogue was dried under high vacuum at 50° C. for 18h and then dissolved in anhydrous trimethylphosphate (0.3 M). After addition of Proton-Sponge® (1.5 molar equiv), the mixture was cooled to 0° C. and treated dropwise with phosphoryl chloride (1.3 molar equiv) via microsyringe over a 15 min period. The mixture continued stirring at 0° C. for 4 to 6 h while being monitored by tlc (7:2:1 isopropanol:conc. $NH_4OH$:water). Once greater than 85% conversion to the monophosphate, the reaction mixture was treated with a mixture of bis(tri-n-butylammonium pyrophosphate) (3 molar equiv) and tributylamine (6 molar equiv) in anhydrous DMF (1 mL). After 20 min at 0° C. with monitoring by tlc (11:7:2 $NH_4OH$:isopropanol:water), the mixture was treated with 20 mL of a 100 mM solution of triethylammonium bicarbonate (TEAB), stirred for 1h at rt and then extracted with ether (3×15 mL). The aqueous phase was then purified by anion-exchange chromatography over DEAE Sephadex® A-25 resin (11×200 mm) using a buffer gradient from 50 mM (400 mL) to 600 mM (400 mL) TEAB.

Fractions of 10 mL were analyzed by tlc (11:7:2 NH$_4$OH: isopropanol:water). Triphosphate (eluted @ 500 mM TEAB) containing fractions were combined and concentrated by rotary evaporator (bath <25° C.). The resulting solid was reconstituted in DI water (10 mL) and concentrated by lyophilization.

Example 57

5'-Triphosphates Synthesized Using the General Procedure for Preparation of 5'-Triphosphates

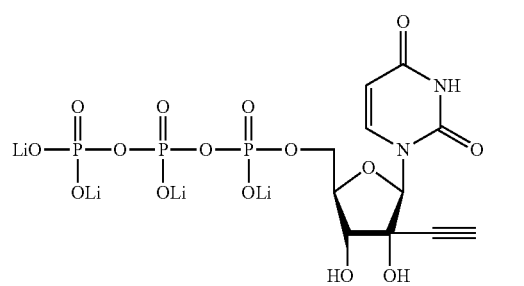

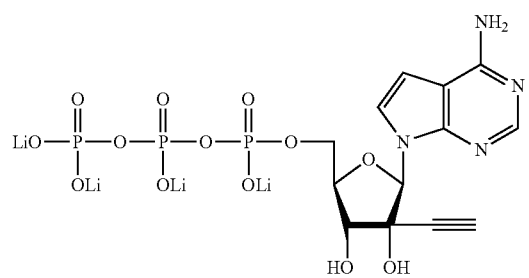

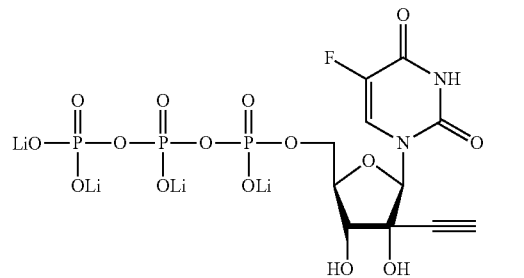

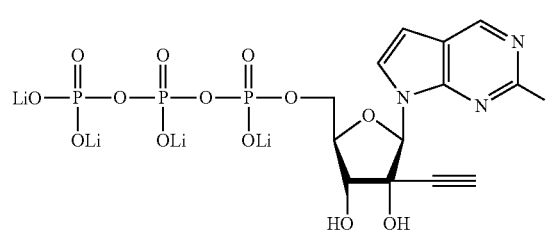

Example 58

Synthesis of (R)-2,2,2-trifluoro-N-(1-hydroxyoctadecan-2-yl)acetamide

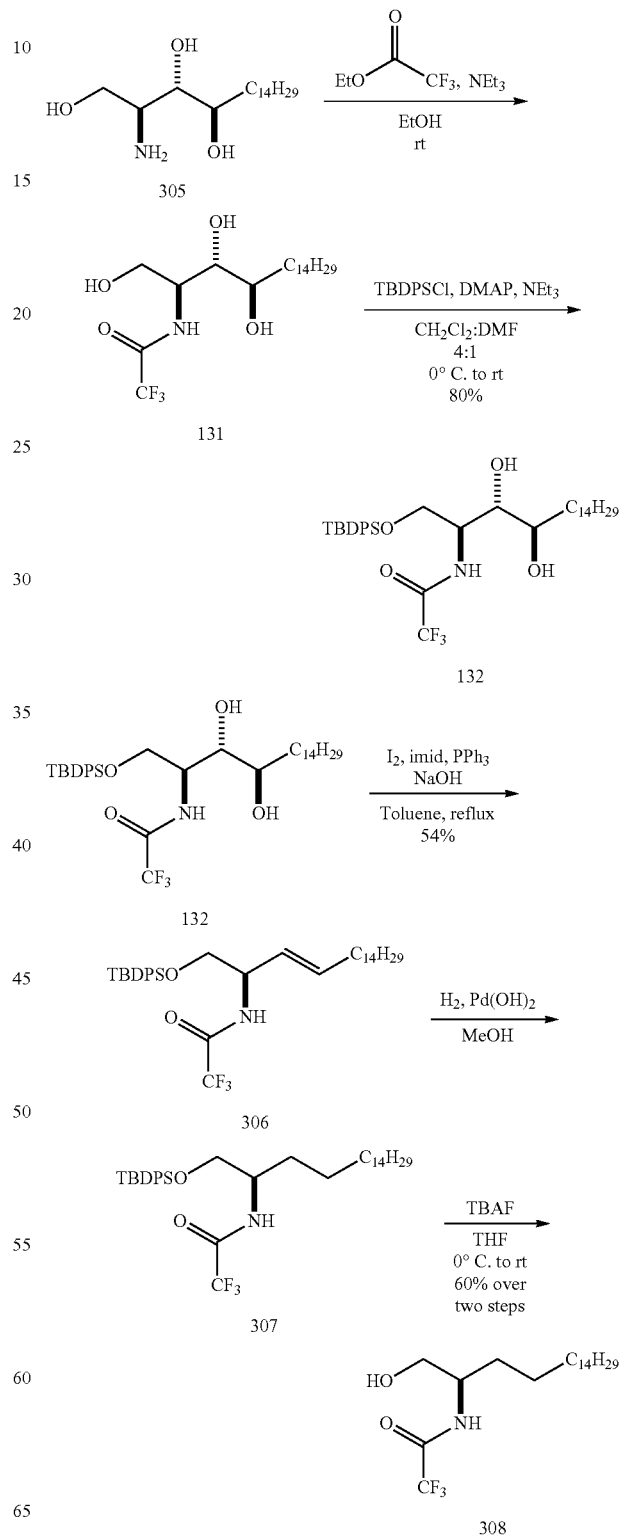

627
-continued

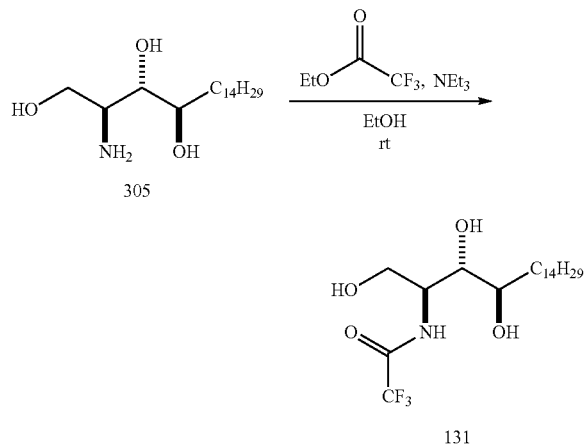

Phytosphingosine (15.75 mmol) was dissolved in EtOH (0.5M) and ethyl trifluoroacetate (15.75 mmol) was added dropwise. NEt₃ (24.41 mmol) was added next the reaction mixture stirred overnight. The solvent was removed in vacuo and the residue was taken up in EtOAc and brine, washed, dried and concentrated. The crude material that was a white powder was good enough to use in the next step without further purification. Characterization matched literature: Synthesis, 2011, 867.

Example 59

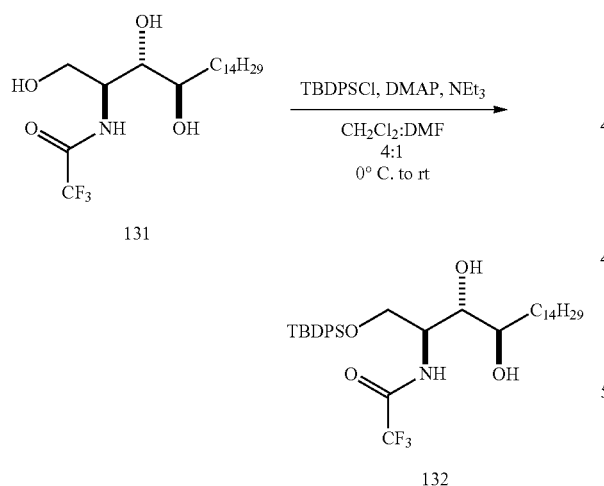

The primary alcohol (15.75 mmol), DMAP (1.575 mmol) and NEt₃ (39.4 mmol) were dissolved in CH₂Cl₂ and DMF (0.18M) mixture and cooled to 0° C. TBDPSCl (19.69 mmol) was added dropwise then the solution was allowed to warm to room temperature and stirred overnight.

NH₄Cl solution was added to quench. The reaction mixture was extracted with EtOAc and the combined organic layers were washed with water (×2) to remove DMF. It was then dried and concentrated. A column was run to purify the mixture. 10-20% EtOAc/Hex. Characterization matched literature: Synthesis, 2011, 867.

628
Example 60

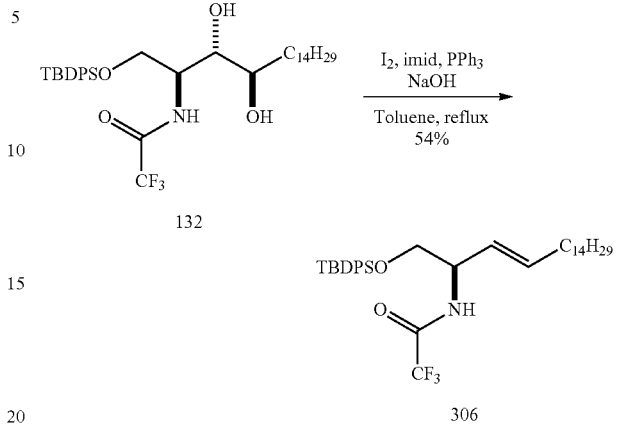

The diol (12.58 mmol), triphenylphosphine (50.3 mmol) and imidazole (50.03 mmol) were dissolved in toluene and reheated to reflux. The iodine (37.7 mmol) was then added slowly and the reaction mixture continued to be stirred at reflux. After three hours it was cooled to room temperature and 1 equivalent of iodine (12.58 mmol) was added followed by 8 equivalents of 1.5M NaOH (100.64 mmol). The reaction mixture was stirred until all the solids dissolved. The aqueous layer was removed in a separatory funnel and the organic layer was washed with Na₂S₂O₃ solution then NaHCO₃ solution then brine. It was dried and concentrated. A column was run to purify the mixture 0-20% EtOAc/Hex and a mixture of cis and trans was obtained but carried on to the next step.

δ ¹H NMR (400 MHz, Chloroform-d) δ 7.64 (ddt, J=7.8, 3.8, 1.7 Hz, 4H), 7.51-7.35 (m, 6H), 6.68 (dd, J=16.0, 8.2 Hz, 1H), 5.6-5.40 (m, 2H), 4.57-4.46 (m, 1H), 3.84-3.62 (m, 2H), 2.04 (q, J=7.0 Hz, 1H), 1.28-1.21 (m, 24H), 1.15-0.98 (m, 9H), 0.90 (t, J=6.8 Hz, 3H).

HRMS: 617.38759.

Example 61

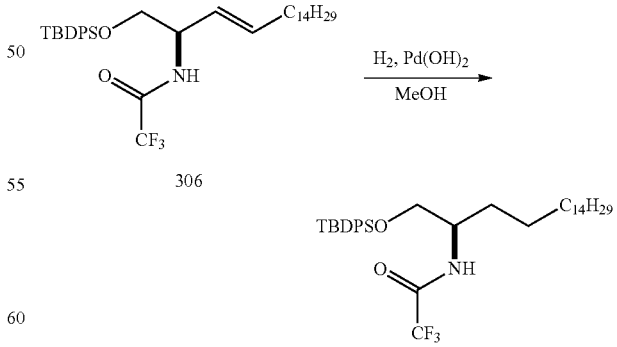

The alkene (2.91 mmol) was dissolved in MeOH (0.1M) and Pd(OH)₂/C (0.146 mmol) was added. A Parr Hydrogenator was used at 40 psi. The palladium catalyst was carefully filtered off through celite and rinsed with EtOAc. The crude material was used in the next step and provided quantitative yield.

Example 62

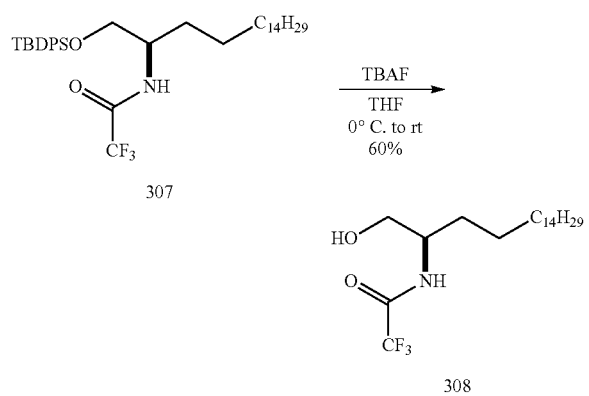

The silyl ether was dissolved in THF and cooled to 0° C. then TBAF was added dropwise. After stirring for 1 hour it was warmed to room temperature. After two hours NH$_4$Cl solution was added and it was extracted with EtOAc, washed with brine and dried and concentrated. A column was run 10-50% EtOAc/Hex.

$^1$H NMR (400 MHz, Chloroform-d) δ 7.60 (tt, J=7.0, 1.5 Hz, 2H), 7.48-7.33 (m, 4H), 3.73 3.61 (m, 1H), 1.24 (d, J=3.5 Hz, 18H), 1.05 (s, 6H), 0.86 (t, J=6.8 Hz, 3H). HRMS 381.28546.

Example 63

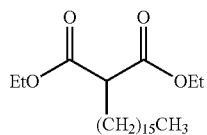

380

To 33.4 g sodium ethoxide solution (21% wt) in ethanol, diethyl malonate (15 g) and then 1-bromohexadecane (31.5 g) were added dropwise. After reflux for 8 hrs, ethanol was evaporated in vacuo. The remaining suspension was mixed with ice-water (200 ml) and extracted with diethyl ether (3×200 ml). The combined organic layers were dried over MgSO$_4$, filtered and the filtrate was evaporated in vacuo to yield a viscous oil residue. This residue was purified by column chromatography (silica: 500 g) using hexane/diethyl ether (12:1) as mobile phase to yield the main compound.

Example 64

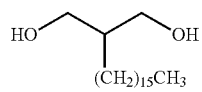

381

In a 250 mL round-bottomed flask was aluminum lithium hydride (2.503 g, 66.0 mmol) in Diethyl ether (90 ml) to give a suspension. To this suspension was added diethyl 2-hexadecylmalonate (18.12 g, 47.1 mmol) dropwise and the reaction was refluxed for 6 h. The reaction was followed up by TLC using PMA and H$_2$SO$_4$ as drying agents. The excess lithium aluminium hydride was destroyed by 200 ml of ice-water. 150 ml of 10% H$_2$SO$_4$ was added to dissolve aluminium hydrate. The reaction mixture was extracted by diethyl ether (100 ml×3). The organic layer including undissolved product was filtered. The collect solids were washed with ethyl acetate. The filtrate was dried over MgSO$_4$, filtered and concentrated under reduced pressure. The product was purified on silica (100 g) column eluting with Hexane:EtOAc (3:1) to (1:1).

Example 65

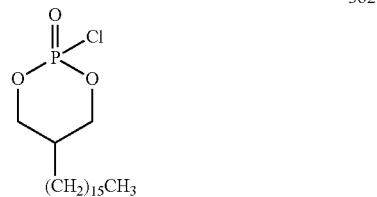

382

To a solution of 2-hexadecylpropane-1,3-diol (7.04 g, 23.43 mmol) in 100 ml of DCM was added dropwise phosphorous trichloride (3.59 g, 23.43 mmol) dissolved in 20 ml of DCM followed by triethylamine (6.53 ml, 46.9 mmol). The reaction was refluxed for one hour. TLC analysis showed that the starting material was consumed and two new spots formed. The mixture was concentrated to dryness, dissolved in dry diethyl ether and filtered. The filtrate was concentrated to yield the crude product (8.85 g) that was used in the next step without further purification.

Example 66

Synthesis of 5'-Deuterated Nucleoside Analogs

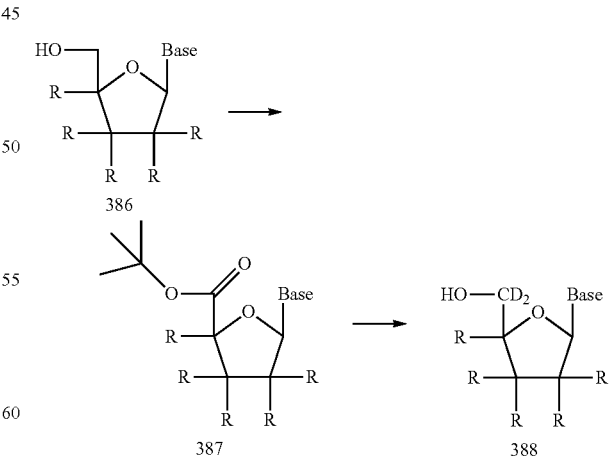

The nucleoside was suspended in methylene chloride (40 mL, partially soluble). After stirring at rt for 30 min the mixture was treated sequentially with PDC, acetic anhydride and then tert-butanol. The mixture continued to stir at room temperature. TLC (5% methanol in DCM) and LCMS indicated only a small amount of remaining starting material at 4 hours. The mixture was filtered through a pad of silica gel that was loaded into a 150 mL fritted funnel. The silica was eluted with ethyl acetate. The collected filtrate was concentrated by under reduced pressure. The crude dark oil was purified by chromatography over silica gel (25 mm×175 mm) with 2:1 hexanes:ethyl acetate to ethyl acetate gradient. The pure fractions were collected and concentrated to give of a white gum. The material was placed under high vacuum for 2 days and was used in the next step without further purification.

The 5'-protected nucleoside was dissolved in 200 proof ethanol and was then treated with solid sodium borodeuteride. The mixture became homogeneous and was then heated to 80° C. After 12h, a white/pale yellow precipitate formed. The mixture was allowed to cool to rt. TLC (5% methanol in methylene chloride) indicates complete conversion of starting material. The mixture was cooled to 0° C. with an ice-bath and then slowly quenched with acetic acid (approximately 1 mL). The clear solution was warmed to rt and then partitioned between ethyl acetate (30 mL) and brine (3 mL). The organic phase was concentrated and then purified by chromatography over silica gel (19 mm×180 mm) using a mobile phase of 5% methanol in methylene chloride.

Example 67

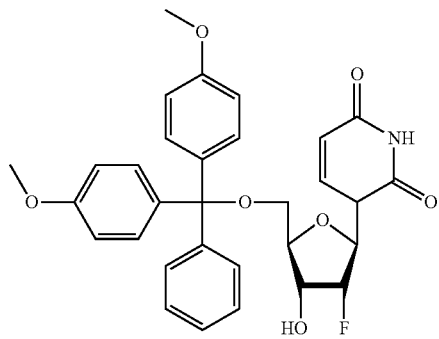

480

A solution of 2'-deoxy-2'-fluorouridine (6 g, 24.37 mmol) and 4,4'-(chloro(phenyl) methylene)-bis(methoxybenzene) (9.91 g, 29.2 mmol) in pyridine (48.7 ml) was stirred at rt for 16 hours. The mixture was treated with MeOH (20 mL), concentrated to dryness and was partitioned between water (50 mL) and EtOAc (250 mL). The aqueous phase was back extracted with EtOAc (50 mL) and the combined organic layers were washed with water (50 mL) and dried over Na$_2$SO$_4$. The solution was concentrated to give 2'-deoxy-2'-fluoro-5'-(4',4'-dimethoxytrityl)uridine (14 g, quant.) which was used without further purification.

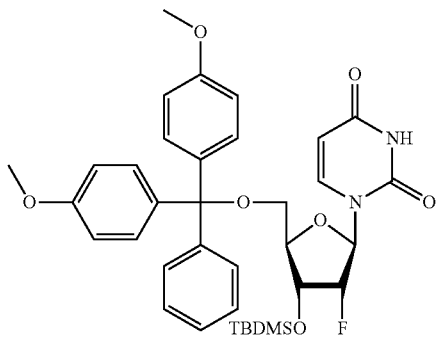

481

To a solution of 2'-deoxy-2'-fluoro-5'-(4',4'-dimethoxytrityl)uridine (13.37 g, 24.37 mmol) in methylene chloride (30 mL) were added 1H-imidazole (2.48 g, 36.6 mmol) and tert-butylchlorodimethylsilane (5.51 g, 36.6 mmol). The reaction was stirred for 16 hours and then was diluted with EtOAc (250 mL). The mixture was washed with saturated aqueous sodium bicarbonate (50 mL) and brine (50 mL), dried over Na$_2$SO$_4$, filtered and concentrated to give 2'-Deoxy-2'-fluoro-3'-O-(tert-butyldimethylsilyl)-5'-(4',4'-dimethoxytrityl)uridine (16 g, 99%). This product was used in the next step without further purification.

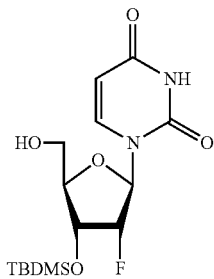

482

To a solution of 2'-deoxy-2'-fluoro-3'-O-(tert-butyldimethylsilyl)-5'-(4',4'-dimethoxytrityl) uridine (13.37 g, 20.17 mmol) in DCM (10 mL) were added acetic acid (20.19 ml, 353 mmol) and water (5 ml). The reaction was stirred at room temperature for 20 hours, diluted with EtOAc (250 mL), washed with saturated aqueous NaHCO$_3$ (2×100 mL) and brine (100 mL), dried (sodium sulfate), filtered and concentrated. The residue was purified by column chromatography over silica gel (1% MeOH in DCM, 2% MeOH in DCM) to afford 2'-deoxy-2'-fluoro-3'-O-(tert-butyldimethylsilyl)uridine (6.73 g, 93% yield) as a yellow solid.

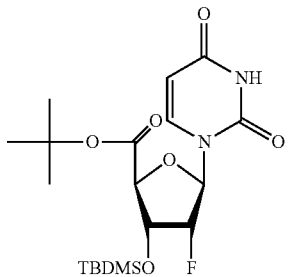

483

633

To a suspension of PDC (14.05 g, 37.3 mmol) in anhydrous DCM (37.3 ml)/DMF (9.34 ml) were added sequentially 2-methylpropan-2-ol (35.7 ml, 373 mmol), 2'-deoxy-2'-fluoro-3'-O-(tert-butyldimethylsilyl)uridine (6.73 g, 18.67 mmol) and acetic anhydride (17.62 ml, 187 mmol). After 18 hours, the mixture was quenched with absolute EtOH (5 mL), diluted with EtOAc (15 mL), dried over Na$_2$SO$_4$, filtered through Celite and concentrated. The crude residue was purified by column chromatography over silica gel using 1% MeOH in DCM to give (2S,3R,4R,5R)-tert-butyl 3-((tert-butyldimethylsilyl)oxy)-5-(2,4-dioxo-3,4-dihydropyrimidin-1(2H)-yl)-4-fluorotetrahydrofuran-2-carboxylate (6.72 g, 83%)

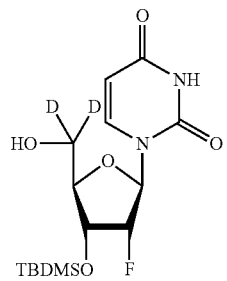

484

To a solution of (2S,3R,4R,5R)-tert-butyl 3-((tert-butyldimethylsilyl)oxy)-5-(2,4-dioxo-3,4-dihydropyrimidin-1(2H)-yl)-4-fluorotetrahydrofuran-2-carboxylate (3.29 g, 7.64 mmol) was added sodium borodeuteride (1.422 g, 30.6 mmol) in one portion. The reaction was stirred at 80° C. for 20 hours in a sealed tube. The mixture was cooled to room temperature and then quenched with acetic acid (6.99 ml, 122 mmol). The mixture was neutralized with saturated aqueous sodium bicarbonate and extracted with EtOAc. After concentrating, the resulting residue was purified by column chromatography over silica gel (Rf=0.5 hexane EtOAc 1:1) to give [5'-$^2$H2]-2'-deoxy-2'-fluoro-3'-O-(tert-butyldimethylsilyl)uridine (1 g, 36%).

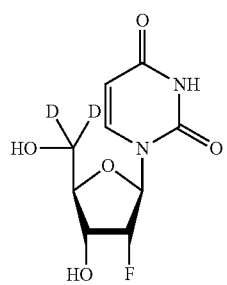

485

To a solution of [5'-$^2$H2]-2'-deoxy-2'-fluoro-3'-O-(tert-butyldimethylsilyl)uridine (200 mg, 0.552 mmol) in MeOH (6 mL) was added Dowex 50WX8 (H+ form) (6 g) in one portion. The mixture was stirred for 72 h, filtered and concentrated to give [5'-$^2$H2]-2'-deoxy-2'-fluorouridine (150 mg, quant.).

634

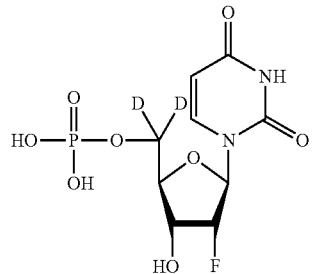

486

To a solution of phosphoryl trichloride (1.69 mL, 18.13 mmol) in trimethyl phosphate (2 mL) at 5° C., under N2, was added [5'-$^2$H2]-2'-deoxy-2'-fluorouridine (100 mg, 0.403 mmol) in small portions. The solution was stirred vigorously for 2h at 5° C. and then was quenched by dropwise addition of DI water (8 mL). The reaction mixture was extracted with chloroform (2×10 mL), and the aqueous phase was treated with concentrated with NH$_4$OH to pH 6.5, while keeping the solution below 30° C. The aqueous layer was extracted once more with chloroform (10 mL) and then concentrated to dryness. The residue was suspended in MeOH (15 mL), filtered, and concentrated. The resulting solid was purified by column chromatography over silica gel (7:2:1 iPrOH/conc. NH$_4$OH, H$_2$O, Rf=0.2). The product was further purified by column chromatography over DEAE using methanol followed by a mobile phase gradient from 0 to 100 mM aqueous ammonium bicarbonate. Fractions were concentrated to dryness, dissolved in water and lyophilized to give [5'-$^2$H2]-2'-deoxy-2'-fluorouridine-5'-monophosphate (27 mg, 20%) as an amorphous white solid.

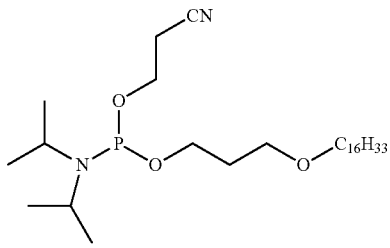

487

A suspension of 3-hexadecyloxypropan-1-ol (2.02 g, 6.72 mmol) and DIPEA (4.7 mL, 26.9 mmol) in anhydrous methylene chloride (45 mL) was treated dropwise over a 10 minute period with 3-((chloro(diisopropylamino)phosphino)oxy)propanenitrile (3 mL, 13.45 mmol). After 18 hours at room temperature, the mixture was quenched with saturated sodium bicarbonate solution (15 mL) and extracted with ethyl acetate (2×100 mL). Combined organic phases were concentrated to dryness, and the resulting crude residue purified by chromatography over silica gel (25 mm×140 mm) using a solvent gradient from 10 to 20% ethyl acetate in hexanes to give hexadecyloxypropyl-(2-cyanoethyl) diisopropylphosphoramidite (2.1 g, 65%) as a white solid.

$^1$H NMR (400 MHz, Chloroform-d) δ 3.89-3.54 (m, 6H), 3.49 (t, J=6.3 Hz, 2H), 3.39 (t, J=6.7 Hz, 2H), 2.64 (t, J=6.6 Hz, 2H), 1.87 (p, J=6.3 Hz, 2H), 1.57 (p, J=6.3 Hz, 2H), 1.25 (s, 26H), 1.18 (dd, J=6.8, 3.5 Hz, 12H), 0.87 (t, J=6.6 Hz, 3H).

$^{31}$P NMR (162 MHz, Chloroform-d) δ 147.40.

488

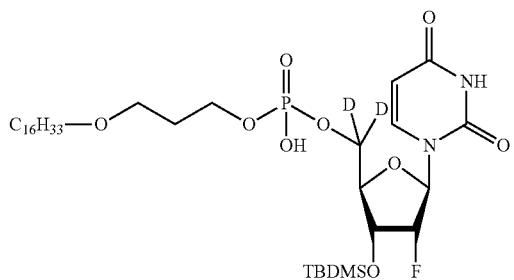

A solution of [5'-²H2]-2'-deoxy-2-fluoro-3'-O-(tert-butyldimethylsilyl)uridine (600 mg, 1.65 mmol) and hexadecyloxypropyl-(2-cyanoethyl) diisopropylphosphoramidite (1.65 g, 3.31 mmol) in anhydrous THF (22 mL) was treated dropwise with 1-H-tetrazole (14.7 mL of 0.45 M solution in acetonitrile, 6.62 mmol). After 16 hours at room temperature, the mixture was treated dropwise with tert-butyl hydroperoxide (1.5 mL of a 5.5 M solution in nonane, 8.28 mmol) and stirred at room temperature for 1 hour and then quenched with 1.0 M aqueous solution of sodium thiosulfate (40 mL). After 30 min, the mixture was extracted with ethyl acetate (2×80 mL). Combined organic phases were washed with brine (40 mL) and dried over sodium sulfate, filtered, and concentrated. The resulting residue was purified by column chromatography over silica gel (40 g) with a mobile phase gradient from 1% to 5% methanol in methylene chloride to give the cyanoethyl phosphate intermediate which without further purification was dissolved in methanol (30 mL) and treated with concentrated ammonium hydroxide (5 mL, 128 mmol). After 4 hours at room temperature, the mixture was concentrated to dryness. The resulting residue was purified by column chromatography over silica gel using a CombiFlash instrument equipped with a 40 g silica cartridge eluting with a solvent gradient from 5 to 25% methanol in methylene chloride to give [5'-²H₂]-2'-deoxy-2'-fluoro-3'-O-(tert-butyldimethylsilyl)-5'-((hexadecyloxypropyl) phospho)uridine (1 g, 82%) as a white foam.

489

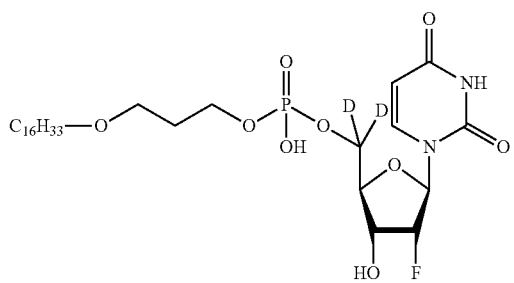

A solution of [5'-²H2]-2'-deoxy-2'-fluoro-3'-O-(tert-butyldimethylsilyl)-5'-((hexadecyloxypropyl) phospho)uridine (1 g, 1.38 mmol) in THF (15 mL) was treated with acetic acid (0.5 g, 8.28 mmol) and triethylammonium fluoride (1.2 g, 5.52 mmol). After 36 hours, the mixture was concentrated and the resulting residue eluted through a short column (11 mm×90 mm) of Dowex 50WX8 (H+ form) using methanol (120 mL) as the mobile phase. The product was further purified by column chromatography over silica gel (24 g) using a mobile phase gradient from 0 to 25% methanol in methylene chloride with 2.5% (v/v) ammonium hydroxide. Pure fractions were pooled and concentrated. The resulting solid was co-evaporated with methylene chloride (2×75 mL) and then dried under high vacuum for 19 hours to give [5'-²H₂]-2'-deoxy-2'-fluoro-5'-((hexadecyloxypropyl)phospho)-uridine (455 mg, 54%) as a white solid.

¹H NMR (400 MHz, Chloroform-d4/Methanol-d₄) δ 7.75 (d, J=8.1 Hz, 1H), 5.95 (dd, J=17.9, 1.6 Hz, 1H), 5.70 (d, J=8.1 Hz, 1H), 5.01 (ddd, J=52.8, 4.6, 1.7 Hz, 1H), 4.30 (ddd, J=20.7, 8.1, 4.5 Hz, 1H), 4.16-4.07 (m, 3H), 3.51 (t, J=6.2 Hz, 2H), 3.41 (t, J=6.7 Hz, 2H), 1.92 (p, J=7.6 Hz, 2H), 1.53 (p, J=7.6 Hz, 2H), 1.25 (s, 26H), 0.87 (d, J=7.6 Hz, 3H).

¹³C NMR (101 MHz, Chloroform-d4/Methanol-d₄) δ 164.31, 150.24, 140.33, 102.11, 94.19, 92.32, 88.88, 88.53, 80.83, 80.75, 71.18, 67.62, 67.45, 66.50, 66.40, 64.83, 64.77, 63.81, 31.81, 30.37, 30.29, 29.59, 29.57, 29.54, 29.51, 29.47, 29.41, 29.25, 26.00, 25.96, 22.57, 13.96.

³¹P NMR (162 MHz, Chloroform-d4/Methanol-d₄) δ −0.87.

HRMS C₂₈H₄₉D₂FN₂O₉P [M+H⁺]; calculated: 611.34359, found: 611.34363.

Example 68

Phosphoramidate Prodrugs Synthesized Using the General Procedure

EIDD-02464

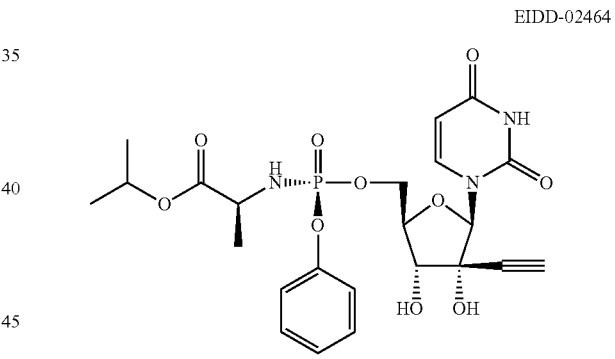

EIDD-02578

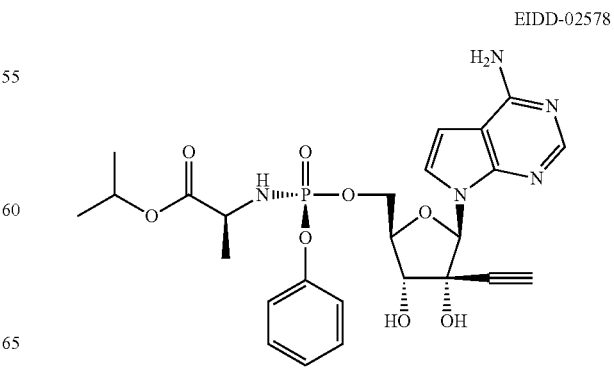

EIDD-02675

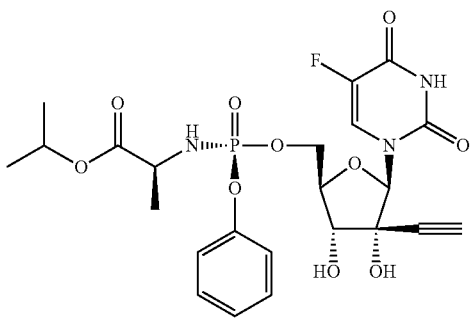

Example 69

Assay Protocols (1) Screening Assays for DENV, JEV, POWV, WNV, YFV, PTV, RVFV, CHIKV, EEEV, VEEV, WEEV, TCRV, PCV, JUNV, MPRLV Primary cytopathic effect (CPE) reduction assay. Four-concentration CPE inhibition assays are performed. Confluent or near-confluent cell culture monolayers in 96-well disposable microplates are prepared. Cells are maintained in MEM or DMEM supplemented with FBS as required for each cell line. For antiviral assays the same medium is used but with FBS reduced to 2% or less and supplemented with 50 µg/ml gentamicin. The test compound is prepared at four $\log_{10}$ final concentrations, usually 0.1, 1.0, 10, and 100 µg/ml or µM. The virus control and cell control wells are on every microplate. In parallel, a known active drug is tested as a positive control drug using the same method as is applied for test compounds. The positive control is tested with each test run. The assay is set up by first removing growth media from the 96-well plates of cells. Then the test compound is applied in 0.1 ml volume to wells at 2× concentration. Virus, normally at <100 50% cell culture infectious doses ($CCID_{50}$) in 0.1 ml volume, is placed in those wells designated for virus infection. Medium devoid of virus is placed in toxicity control wells and cell control wells. Virus control wells are treated similarly with virus. Plates are incubated at 37° C. with 5% $CO_2$ until maximum CPE is observed in virus control wells. The plates are then stained with 0.011% neutral red for approximately two hours at 37° C. in a 5% $CO_2$ incubator. The neutral red medium is removed by complete aspiration, and the cells may be rinsed 1× with phosphate buffered solution (PBS) to remove residual dye. The PBS is completely removed and the incorporated neutral red is eluted with 50% Sorensen's citrate buffer/50% ethanol (pH 4.2) for at least 30 minutes. Neutral red dye penetrates into living cells, thus, the more intense the red color, the larger the number of viable cells present in the wells. The dye content in each well is quantified using a 96-well spectrophotometer at 540 nm wavelength. The dye content in each set of wells is converted to a percentage of dye present in untreated control wells using a Microsoft Excel computer-based spreadsheet. The 50% effective ($EC_{50}$, virus-inhibitory) concentrations and 50% cytotoxic ($CC_{50}$, cell-inhibitory) concentrations are then calculated by linear regression analysis. The quotient of $CC_{50}$ divided by $EC_{50}$ gives the selectivity index (SI) value.

Secondary CPE Virus yield reduction (VYR) assay. This assay involves similar methodology to what is described in the previous paragraphs using 96-well microplates of cells. The differences are noted in this section. Eight half-$\log_{10}$ concentrations of inhibitor are tested for antiviral activity and cytotoxicity. After sufficient virus replication occurs, a sample of supernatant is taken from each infected well (three replicate wells are pooled) and held for the VYR portion of this test, if needed. Alternately, a separate plate may be prepared and the plate may be frozen for the VYR assay. After maximum CPE is observed, the viable plates are stained with neutral red dye. The incorporated dye content is quantified as described above. The data generated from this portion of the test are neutral red $EC_{50}$, $CC_{50}$, and SI values. Compounds observed to be active above are further evaluated by VYR assay. The VYR test is a direct determination of how much the test compound inhibits virus replication. Virus that was replicated in the presence of test compound is titrated and compared to virus from untreated, infected controls. Titration of pooled viral samples (collected as described above) is performed by endpoint dilution. This is accomplished by titrating $\log_{10}$ dilutions of virus using 3 or 4 microwells per dilution on fresh monolayers of cells by endpoint dilution. Wells are scored for presence or absence of virus after distinct CPE (measured by neutral red uptake) is observed. Plotting the $\log_{10}$ of the inhibitor concentration versus $\log_{10}$ of virus produced at each concentration allows calculation of the 90% (one $\log_{10}$) effective concentration by linear regression. Dividing $EC_{90}$ by the $CC_{50}$ obtained in part 1 of the assay gives the SI value for this test.

Example 70

(2) Screening Assays for Lassa Fever Virus (LASV)

Primary Lassafever virus assay. Confluent or near-confluent cell culture monolayers in 12-well disposable cell culture plates are prepared. Cells are maintained in DMEM supplemented with 10% FBS. For antiviral assays the same medium is used but with FBS reduced to 2% or less and supplemented with 1% penicillin/streptomycin. The test compound is prepared at four $log_{10}$ final concentrations, usually 0.1, 1.0, 10, and 100 μg/ml or μM. The virus control and cell control will be run in parallel with each tested compound. Further, a known active drug is tested as a positive control drug using the same experimental set-up as described for the virus and cell control. The positive control is tested with each test run. The assay is set up by first removing growth media from the 12-well plates of cells, and infecting cells with 0.01 MOI of LASV strain Josiah. Cells will be incubated for 90 min: 500 μl inoculum/M12 well, at 37° C., 5% $CO_2$ with constant gentle rocking. The inoculums will be removed and cells will be washed 2× with medium. Then the test compound is applied in 1 ml of total volume of media. Tissue culture supernatant (TCS) will be collected at appropriate time points. TCS will then be used to determine the compounds inhibitory effect on virus replication. Virus that was replicated in the presence of test compound is titrated and compared to virus from untreated, infected controls. For titration of TCS, serial ten-fold dilutions will be prepared and used to infect fresh monolayers of cells. Cells will be overlaid with 1% agarose mixed 1:1 with 2×MEM supplemented with 10% FBS and 1% penicillin, and the number of plaques determined. Plotting the $log_{10}$ of the inhibitor concentration versus $log_{10}$ of virus produced at each concentration allows calculation of the 90% (one $log_{10}$) effective concentration by linear regression.

Secondary Lassafever virus assay. The secondary assay involves similar methodology to what is described in the previous paragraphs using 12-well plates of cells. The differences are noted in this section. Cells are being infected as described above but this time overlaid with 1% agarose diluted 1:1 with 2×MEM and supplemented with 2% FBS and 1% penicillin/streptomycin and supplemented with the corresponding drug concentration. Cells will be incubated at 37° C. with 5% $CO_2$ for 6 days. The overlay is then removed and plates stained with 0.05% crystal violet in 10% buffered formalin for approximately twenty minutes at room temperature. The plates are then washed, dried and the number of plaques counted. The number of plaques is in each set of compound dilution is converted to a percentage relative to the untreated virus control. The 50% effective (EC50, virus-inhibitory) concentrations are then calculated by linear regression analysis.

Example 71

(3) Screening Assays for Ebola Virus (EBOV) and Nipah Virus (NIV)

Primary Ebola Nipah virus assay. Four-concentration plaque reduction assays are performed. Confluent or near-confluent cell culture monolayers in 12-well disposable cell culture plates are prepared. Cells are maintained in DMEM supplemented with 10% FBS. For antiviral assays the same medium is used but with FBS reduced to 2% or less and supplemented with 1% penicillin/streptomycin. The test compound is prepared at four $\log_{10}$ final concentrations, usually 0.1, 1.0, 10, and 100 μg/ml or μM. The virus control and cell control will be run in parallel with each tested compound. Further, a known active drug is tested as a positive control drug using the same experimental set-up as described for the virus and cell control. The positive control is tested with each test run. The assay is set up by first removing growth media from the 12-well plates of cells. Then the test compound is applied in 0.1 ml volume to wells at 2× concentration. Virus, normally at approximately 200 plaque-forming units in 0.1 ml volume, is placed in those wells designated for virus infection. Medium devoid of virus is placed in toxicity control wells and cell control wells. Virus control wells are treated similarly with virus. Plates are incubated at 37° C. with 5% $CO_2$ for one hour. Virus-compound inoculums will be removed, cells washed and overlaid with 1.6% tragacanth diluted 1:1 with 2×MEM and supplemented with 2% FBS and 1% penicillin/streptomycin and supplemented with the corresponding drug concentration. Cells will be incubated at 37° C. with 5% $CO_2$ for 10 days. The overlay is then removed and plates stained with 0.05% crystal violet in 10% buffered formalin for approximately twenty minutes at room temperature. The plates are then washed, dried and the number of plaques counted. The number of plaques is in each set of compound dilution is converted to a percentage relative to the untreated virus control. The 50% effective ($EC_{50}$, virus-inhibitory) concentrations are then calculated by linear regression analysis.

Secondary Ebola/NIpah virus assay with VYR component. The secondary assay involves similar methodology to what is described in the previous paragraphs using 12-well plates of cells. The differences are noted in this section. Eight half-$\log_{10}$ concentrations of inhibitor are tested for antiviral activity. One positive control drug is tested per batch of compounds evaluated. For this assay, cells are infected with virus. Cells are being infected as described above but this time incubated with DMEM supplemented with 2% FBS and 1% penicillin/streptomycin and supplemented with the corresponding drug concentration. Cells will be incubated for 10 days at 37° C. with 5% C02, daily observed under microscope for the number of green fluorescent cells. Aliquots of supernatant from infected cells will be taken daily and the three replicate wells are pooled. The pooled supernatants are then used to determine the compounds inhibitory effect on virus replication. Virus that was replicated in the presence of test compound is titrated and compared to virus from untreated, infected controls. For titration of pooled viral samples, serial ten-fold dilutions will be prepared and used to infect fresh monolayers of cells. Cells are overlaid with tragacanth and the number of plaques determined. Plotting the $\log_{10}$ of the inhibitor concentration versus $\log_{10}$ of virus produced at each concentration allows calculation of the 90% (one $\log_{10}$) effective concentration by linear regression.

Example 72

Anti-Dengue Virus Cytoprotection Assay:

Cell Preparation—BHK21 cells (Syrian golden hamster kidney cells, ATCC catalog #CCL-I 0), Vero cells (African green monkey kidney cells, ATCC catalog #CCL-81), or Huh-7 cells (human hepatocyte carcinoma) were passaged in DMEM supplemented with 10% FBS, 2 mM L-glutamine, 100 U/mL penicillin, and 100 μg/mL streptomycin in T-75 flasks prior to use in the antiviral assay. On the day preceding the assay, the cells were split 1:2 to assure they were in an exponential growth phase at the time of infection. Total cell and viability quantification was performed using a hemocytometer and Trypan Blue dye exclusion. Cell viability was greater than 95% for the cells to be utilized in the assay. The cells were resuspended at $3\times10^3$ ($5\times10^5$ for Vero cells and Huh-7 cells) cells per well in tissue culture medium and added to flat bottom microtiter plates in a volume of 100 μL. The plates were incubated at 37° C./5% $CO_2$ overnight to allow for cell adherence. Monolayers were observed to be approximately 70% confluent.

Virus Preparation—The Dengue virus type 2 New Guinea C strain was obtained from ATCC (catalog #VR-1584) and was grown in LLC-MK2 (Rhesus monkey kidney cells; catalog #CCL-7.1) cells for the production of stock virus pools. An aliquot of virus pretitered in BHK21 cells was removed from the freezer (−80° C.) and allowed to thaw slowly to room temperature in a biological safety cabinet. Virus was resuspended and diluted into assay medium (DMEM supplemented with 2% heat-inactivated FBS, 2 mM L-glutamine, 100 U/mL penicillin, and 100 μg/mL streptomycin) such that the amount of virus added to each well in a volume of 100 μL was the amount determined to yield 85 to 95% cell killing at 6 days post-infection.

Plate Format—Each plate contains cell control wells (cells only), virus control wells (cells plus virus), triplicate drug toxicity wells per compound (cells plus drug only), as well as triplicate experimental wells (drug plus cells plus virus).

Efficacy and Toxicity XTT-Following incubation at 37° C. in a 5% $CO_2$ incubator, the test plates were stained with the tetrazolium dye XTT (2,3-bis(2-methoxy-4-nitro-5-sulfophenyl)-5-[(phenylamino)carbonyl]-2H-tetrazolium hydroxide). XTT-tetrazolium was metabolized by the mitochondrial enzymes of metabolically active cells to a soluble formazan product, allowing rapid quantitative analysis of the inhibition of virus-induced cell killing by antiviral test substances. XTT solution was prepared daily as a stock of 1 mg/mL in RPMI 1640. Phenazine methosulfate (PMS) solution was prepared at 0.15 mg/mL in PBS and stored in the dark at −20° C. XTT/PMS stock was prepared immediately before use by adding 40 μL of PMS per ml of XTT solution. Fifty microliters of XTT/PMS was added to each well of the plate and the plate was reincubated for 4 hours at 37° C. Plates were sealed with adhesive plate sealers and shaken gently or inverted several times to mix the soluble formazan product and the plate was read spectrophotometrically at 450/650 nm with a Molecular Devices Vmax plate reader.

Data Analysis —Raw data was collected from the Softmax Pro 4.6 software and imported into a Microsoft Excel spreadsheet for analysis. The percent reduction in viral cytopathic effect compared to the untreated virus controls was calculated for each compound. The percent cell control value was calculated for each compound comparing the drug treated uninfected cells to the uninfected cells in medium alone.

Example 73

Anti-RSV Cytoprotection Assay:

Cell Preparation-HEp2 cells (human epithelial cells, ATCC catalog #CCL-23) were passaged in DMEM supplemented with 10% FBS, 2 mM L-glutamine, 100 U/mL penicillin, 100 µg/mL streptomycin 1 mM sodium pyruvate, and 0.1 mM NEAA, T-75 flasks prior to use in the antiviral assay. On the day preceding the assay, the cells were split 1:2 to assure they were in an exponential growth phase at the time of infection. Total cell and viability quantification was performed using a hemocytometer and Trypan Blue dye exclusion. Cell viability was greater than 95% for the cells to be utilized in the assay. The cells were resuspended at $1 \times 10^4$ cells per well in tissue culture medium and added to flat bottom microtiter plates in a volume of 100 µL. The plates were incubated at 37° C./5% $CO_2$ overnight to allow for cell adherence. Virus Preparation—The RSV strain Long and RSV strain 9320 were obtained from ATCC (catalog #VR-26 and catalog #VR-955, respectively) and were grown in HEp2 cells for the production of stock virus pools. A pretitered aliquot of virus was removed from the freezer (−80° C.) and allowed to thaw slowly to room temperature in a biological safety cabinet. Virus was resuspended and diluted into assay medium (DMEM supplemented with 2% heat-inactivated FBS, 2 mM L-glutamine, 100 U/mL penicillin, 100 µg/mL streptomycin, 1 mM sodium pyruvate, and 0.1 mM NEAA) such that the amount of virus added to each well in a volume of 100 µL was the amount determined to yield 85 to 95% cell killing at 6 days post-infection. Efficacy and Toxicity XTT-Plates were stained and analyzed as previously described for the Dengue cytoprotection assay.

Example 74

Anti-Influenza Virus Cytoprotection Assay:

Cell Preparation-MOCK cells (canine kidney cells, ATCC catalog #CCL-34) were passaged in DMEM supplemented with 10% FBS, 2 mM L-glutamine, 100 U/mL penicillin, 100 µg/mL streptomycin 1 mM sodium pyruvate, and 0.1 mM NEAA, T-75 flasks prior to use in the antiviral assay. On the day preceding the assay, the cells were split 1:2 to assure they were in an exponential growth phase at the time of infection. Total cell and viability quantification was performed using a hemocytometer and Trypan Blue dye exclusion. Cell viability was greater than 95% for the cells to be utilized in the assay. The cells were resuspended at $1 \times 10^4$ cells per well in tissue culture medium and added to flat bottom microtiter plates in a volume of 100 µL. The plates were incubated at 37° C./5% $CO_2$ overnight to allow for cell adherence.

Virus Preparation—The influenza A/PR/8/34 (ATCC #VR-95), A/CA/05/09 (CDC), A/NY/18/09 (CDC) and A/NWS/33 (ATCC #VR-219) strains were obtained from ATCC or from the Center of Disease Control and were grown in MDCK cells for the production of stock virus pools. A pretitered aliquot of virus was removed from the freezer (−80° C.) and allowed to thaw slowly to room temperature in a biological safety cabinet. Virus was resuspended and diluted into assay medium (DMEM supplemented with 0.5% BSA, 2 mM L-glutamine, 100 U/mL penicillin, 100 µg/mL streptomycin, 1 mM sodium pyruvate, 0.1 mM NEAA, and 1 µg/ml TPCK-treated trypsin) such that the amount of virus added to each well in a volume of 100 µL was the amount determined to yield 85 to 95% cell killing at 4 days post-infection. Efficacy and Toxicity XTT-Plates were stained and analyzed as previously described for the Dengue cytoprotection assay.

Example 75

Anti-Hepatitis C Virus Assay:

Cell Culture—The reporter cell line Huh-luc/neo-ET was obtained from Dr. Ralf Bartenschlager (Department of Molecular Virology, Hygiene Institute, University of Heidelberg, Germany) by ImQuest BioSciences through a specific licensing agreement. This cell line harbors the persistently replicating $I_{389}$luc-ubi-neo/NS3-3'/ET replicon containing the firefly luciferase gene-ubiquitin-neomycin phosphotransferase fusion protein and EMCV IRES driven NS3-5B HCV coding sequences containing the ET tissue culture adaptive mutations (E1202G, T12081, and K1846T). A stock culture of the Huh-luc/neo-ET was expanded by culture in DMEM supplemented with I 0% FCS, 2 mM glutamine, penicillin (100 U/mL)/streptomycin (100 µg/mL) and Ix nonessential amino acids plus 1 mg/mL G418. The cells were split 1:4 and cultured for two passages in the same media plus 250 µg/mL G418. The cells were treated with trypsin and enumerated by staining with trypan blue and seeded into 96-well tissue culture plates at a cell culture density $7.5 \times 10^3$ cells per well and incubated at 37° C. 5% $CO_2$ for 24 hours. Following the 24 hour incubation, media was removed and replaced with the same media minus the G418 plus the test compounds in triplicate. Six wells in each plate received media alone as a no-treatment control. The cells were incubated an additional 72 hours at 37° C. 5% $CO_2$ then anti-HCV activity was measured by luciferase endpoint. Duplicate plates were treated and incubated in parallel for assessment of cellular toxicity by XTT staining.

Cellular Viability—The cell culture monolayers from treated cells were stained with the tetrazolium dye XTT to evaluate the cellular viability of the Huh-luc/neo-ET reporter cell line in the presence of the compounds.

Measurement of Virus Replication-HCV replication from the replicon assay system was measured by luciferase activity using the britelite plus luminescence reporter gene kit according to the manufacturer's instructions (Perkin Elmer, Shelton, Conn.). Briefly, one vial of britelite plus lyophilized substrate was solubilized in 10 mL of britelite reconstitution buffer and mixed gently by inversion. After a 5 minute incubation at room temperature, the britelite plus reagent was added to the 96 well plates at 100 µL per well. The plates were sealed with adhesive film and incubated at room temperature for approximately 10 minutes to lyse the cells. The well contents were transferred to a white 96-well plate and luminescence was measured within 15 minutes using the Wallac 1450Microbeta Trilux liquid scintillation counter.

The data were imported into a customized Microsoft Excel 2007 spreadsheet for determination of the 50% virus inhibition concentration ($EC_{50}$).

Example 76

Anti-Parainfluenza-3 Cytoprotection Assay:

Cell Preparation—HEp2 cells (human epithelial cells, ATCC catalog #CCL-23) were passaged in DMEM supplemented with 10% FBS, 2 mM L-glutamine, 100 U/mL penicillin, 100 µg/mL streptomycin 1 mM sodium pyruvate, and 0.1 mM NEAA, T-75 flasks prior to use in the antiviral assay. On the day preceding the assay, the cells were split 1:2 to assure they were in an exponential growth phase at the time of infection. Total cell and viability quantification was performed using a hemocytometer and Trypan Blue dye exclusion. Cell viability was greater than 95% for the cells to be utilized in the assay. The cells were resuspended at $1\times10^4$ cells per well in tissue culture medium and added to flat bottom microtiter plates in a volume of 100 µL. The plates were incubated at 37° C./5% $CO_2$ overnight to allow for cell adherence.

Virus Preparation—The Parainfluenza virus type 3 SF4 strain was obtained from ATCC (catalog #VR-281) and was grown in HEp2 cells for the production of stock virus pools. A pretitered aliquot of virus was removed from the freezer (−80° C.) and allowed to thaw slowly to room temperature in a biological safety cabinet. Virus was resuspended and diluted into assay medium (DMEM supplemented with 2% heat-inactivated FBS, 2 mM L-glutamine, 100 U/mL penicillin, and 100 µg/mL streptomycin) such that the amount of virus added to each well in a volume of 100 µL was the amount determined to yield 85 to 95% cell killing at 6 days post-infection.

Plate Format—Each plate contains cell control wells (cells only), virus control wells (cells plus virus), triplicate drug toxicity wells per compound (cells plus drug only), as well a triplicate experimental wells (drug plus cells plus virus). Efficacy and Toxicity XTT—Following incubation at 37° C. in a 5% $CO_2$ incubator, the test plates were stained with the tetrazolium dye XTT (2,3-bis(2-methoxy-4-nitro-5-sulfophenyl)-5-[(phenylamino)carbonyl]-2H-tetrazol hydroxide). XTT-tetrazolium was metabolized by the mitochondrial enzymes of metabolically active cells to a soluble formazan product, allowing rapid quantitative analysis of the inhibition of virus-induced cell killing by antiviral test substances. XTT solution was prepared daily as a stock of 1 mg/mL in RPMI1640. Phenazine methosulfate (PMS) solution was prepared at 0.15 mg/mL in PBS and stored in the dark at −20° C. XTT/PMS stock was prepared immediately before use by adding 40 µL of PMS per ml of XTT solution. Fifty microliters of XTT/PMS was added to each well of the plate and the plate was reincubated for 4 hours at 3 7° C. Plates were sealed with adhesive plate sealers and shaken gently or inverted several times to mix the soluble fomlazan product and the plate was read spectrophotometrically at 450/650 nm with a Molecular Devices Vmax plate reader.

Data Analysis—Raw data was collected from the Softmax Pro 4.6 software and imported into a Microsoft Excel spreadsheet for analysis. The percent reduction in viral cytopathic effect compared to the untreated virus controls was calculated for each compound. The percent cell control value was calculated for each compound comparing the drug treated uninfected cells to the uninfected cells in medium alone.

Example 77

Influenza Polymerase Inhibition Assay:

Virus Preparation—Purified influenza virus A/PR/8/34 (1 ml) was obtained from Advanced Biotechnologies, Inc. (Columbia, Md.), thawed and dispensed into five aliquots for storage at −80° C. until use. On the day of assay set up, 20 µL of 2.5% Triton N-101 was added to 180 µL of purified virus. The disrupted virus was diluted 1:2 in a solution containing 0.25% Triton and PBS. Disruption provided the source of influenza ribonucleoprotein (RNP) containing the influenza RNA-dependent RNA polymerase and template RNA. Samples were stored on ice until use in the assay.

Polymerase reaction—Each 50 µL polymerase reaction contained the following: 5 µL of the disrupted RNP, 100 mM Tris-HCl (pH 8.0), 100 mM KCl, 5 mM $MgCl_2$. 1 mM dithiothreitol, 0.25% Triton N-101, 5 µCi of [$\alpha$-$^{32}$P] GTP, 100 µM ATP, 50 µM each (CTP, UTP), 1 µM GTP, and 200 µM adenyl (3'-5') guanosine. For testing the inhibitor, the reactions contained the inhibitor and the same was done for reactions containing the positive control (2'-Deoxy-2'-fluoroguanosine-5'-triphosphate). Other controls included RNP+ reaction mixture, and RNP+I % DMSO. The reaction mixture without the ApG primer and NTPs was incubated at 30° C. for 20 minutes. Once the ApG and NTPs were added to the reaction mixture, the samples were incubated at 30° C. for 1 hour then immediately followed by the transfer of the reaction onto glass-fiber filter plates and subsequent precipitation with 10% trichloroacetic acid (TCA). The plate was then washed five times with 5% TCA followed by one wash with 95% ethanol. Once the filter had dried, incorporation of [$\alpha$-$^{32}$P] GTP was measured using a liquid scintillation counter (Micro beta).

Plate Format—Each test plate contained triplicate samples of the three compounds (6 concentrations) in addition to triplicate samples of RNP+ reaction mixture (RNP alone), RNP+1% DMSO, and reaction mixture alone (no RNP).

Data Analysis—Raw data was collected from the Micro Beta scintillation counter. The incorporation of radioactive GTP directly correlates with the levels of polymerase activity. The "percent inhibition values" were obtained by dividing the mean value of each test compound by the RNP+1% DMSO control. The mean obtained at each concentration of 2DFGTP was compared to the RNP+ reaction control. The data was then imported into Microsoft Excel spreadsheet to calculate the $IC_{50}$ values by linear regression analysis.

Example 78

HCV Polymerase Inhibition Assay:

Activity of compounds for inhibition of HCV polymerase was evaluated using methods previously described (Lam eta!. 2010. Antimicrobial Agents and Chemotherapy 54(8): 3187-3196). HCV NS5B polymerase assays were performed in 20 µL volumes in 96 well reaction plates. Each reaction contained 40 ng/L purified recombinant NS5BΔ22 genotype-1b polymerase, 20 ng/L of HCV genotype-1b complimentary IRES template, 1 µM of each of the four natural ribonucleotides, 1 U/mL Optizyme RNAse inhibitor (Promega, Madison, Wis.), 1 mM $MgCl_2$, 0.75 mM $MnCl_2$, and 2 mM dithiothreitol (DTT) in 50 mM HEPES buffer (pH 7.5). Reaction mixtures were assembled on ice in two steps. Step 1 consisted of combining all reaction components except the natural nucleotides and labeled UTP in a polymerase reaction mixture. Ten microliters (10 µL) of the polymerase mixture was dispensed into individual wells of the 96 well reaction plate on ice. Polymerase reaction mixtures without NS5B polymerase were included as no enzyme controls. Serial half-logarithmic dilutions of test and control compounds, 2'-O-Methyl-CTP and 2'-O-Methyl-GTP (Trilink, San Diego, Calif.), were prepared in water and 5 µL of the serial diluted compounds or water alone (no compound control) were added to the wells containing the polymerase mixture. Five microliters of nucleotide mix (natural nucleotides and labeled UTP) was then added to the reaction plate wells and the plate was incubated at 27° C. for 30 minutes. The reactions were quenched with the addition of 80 µL stop solution (12.5 mM EDTA, 2.25 M NaCl, and 225 mM sodium citrate) and the RNA products were applied to a Hybond-N+ membrane (GE Healthcare, Piscataway, N.J.) under vacuum pressure using a dot blot apparatus. The membrane was removed from the dot blot apparatus and washed four times with 4×SSC (0.6 M NaCl, and 60 mM sodium citrate), and then rinsed one time with water and once with 100% ethanol. The membrane was air dried and exposed to a phosphoimaging screen and the image captured using a Typhoon 8600 Phospho imager. Following capture of the image, the membrane was placed into a Micro beta cassette along with scintillation fluid and the CPM in each reaction was counted on a Micro beta 1450. CPM data were imported into a custom Excel spreadsheet for determination of compound $IC_{50}$s.

Example 79

NS5B RNA-Dependent RNA Polymerase Reaction Conditions

Compounds were assayed for inhibition of NS5B-δ21 from HCV GT-1b Con-1. Reactions included purified recombinant enzyme, 1 u/µL negative-strand HCV IRES RNA template, and 1 µM NTP substrates including either [$^{32}P$]-CTP or [$^{32}P$]-UTP. Assay plates were incubated at 27° C. for 1 hour before quench. [32P] incorporation into macromolecular product was assessed by filter binding.

Example 80

Human DNA Polymerase Inhibition Assay:

The human DNA polymerase alpha (catalog #1075), beta (catalog #1077), and gamma (catalog #1076) were purchased from CHIMERx (Madison, Wis.). Inhibition of beta and gamma DNA polymerase activity was assayed in microtiter plates in a 50 uL reaction mixture containing 50 mM Tris-HCl (pH 8.7), KCl (10 mM for beta and 100 mM for gamma), 10 mM $MgCl_2$, 0.4 mg/mL BSA, 1 mM DTT, 15% glycerol, 0.05 mM of dCTP, dTTP, and dATP, 10 uCi [$^{32}P$]-alpha-dGTP (800 Ci/mmol), 20 ug activated calf thymus DNA and the test compound at indicated concentrations. The alpha DNA polymerase reaction mixture was as follows in a 50 uL volume per sample: 20 mM Tris-HCl (pH 8), 5 mM magnesium acetate, 0.3 mg/mL BSA, 1 mM DTT, 0.1 mM spermine, 0.05 mM of dCTP, dTTP, and dATP, 10 uCi [$^{32}P$]-alpha-dGTP (800 Ci/mmol), 20 ug activated calf thymus DNA and the test compound at the indicated concentrations. For each assay, the enzyme reactions were allowed to proceed for 30 minutes at 37° C. followed by the transfer onto glass-fiber filter plates and subsequent precipitation with 10% trichloroacetic acid (TCA). The plate was then washed with 5% TCA followed by one wash with 95% ethanol. Once the filter had dried, incorporation of radioactivity was measured using a liquid scintillation counter (Microbeta).

Example 81

HIV Infected PBMC Assay:

Fresh human peripheral blood mononuclear cells (PBMCs) were obtained from a commercial source (Biological Specialty) and were determined to be seronegative for HIV and HBV. Depending on the volume of donor blood received, the leukophoresed blood cells were washed several times with PBS. After washing, the leukophoresed blood was diluted 1:1 with Dulbecco's phosphate buffered saline (PBS) and layered over 15 mL of Ficoll-Hypaque density gradient in a 50 ml conical centrifuge tube. These tubes were centrifuged for 30 min at 600 g. Banded PBMCs were gently aspirated from the resulting interface and washed three times with PBS. After the final wash, cell number was determined by Trypan Blue dye exclusion and cells were re-suspended at 1×10^ cells/mL in RPMI 1640 with 15% Fetal Bovine Serum (FBS), 2 mmol/L L-glutamine, 2 ug/mL PHA-P, 100 U/mL penicillin and 100 ug/mL streptomycin and allowed to incubate for 48-72 hours at 37° C. After incubation, PBMCs were centrifuged and resuspended in tissue culture medium. The cultures were maintained until use by half-volume culture changes with fresh IL-2 containing tissue culture medium every 3 days. Assays were initiated with PBMCs at 72 hours post PHA-P stimulation.

To minimize effects due to donor variability, PBMCs employed in the assay were a mixture of cells derived from 3 donors. Immediately prior to use, target cells were resuspended in fresh tissue culture medium at 1×10^ cells/mL and plated in the interior wells of a 96-well round bottom microtiter plate at 50 uL/well. Then, 100 uL of 2× concentrations of compound-containing medium was transferred to the 96-well plate containing cells in 50 uL of the medium. AZT was employed as an internal assay standard.

Following addition of test compound to the wells, 50 uL of a predetermined dilution of HIV virus (prepared from 4× of final desired in-well concentration) was added, and mixed well. For infection, 50-150 $TCID_{50}$ of each virus was added per well (final MOI approximately 0.002). PBMCs were exposed in triplicate to virus and cultured in the presence or absence of the test material at varying concentrations as described above in the 96-well microtiter plates. After 7 days in culture, HIV-1 replication was quantified in the tissue culture supernatant by measurement of reverse transcriptase (RT) activity. Wells with cells and virus only served as virus controls. Separate plates were identically prepared without virus for drug cytotoxicity studies.

Reverse Transcriptase Activity Assay—Reverse transcriptase activity was measured in cell-free supernatants using a standard radioactive incorporation polymerization assay. Triatiated thymidine triphosphate (TTP; New England Nuclear) was purchased at 1 Ci/mL and 1 uL was used per enzyme reaction. A rAdT stock solution was prepared by mixing 0.5 mg/mL poly rAand 1.7 U/mL oligo dT in distilled water and was stored at −20° C. The RT reaction buffer was prepared fresh daily and consists of 125 uL of 1 mol/L EGTA, 125 uL of $dH_2O$, 125 uL of 20% Triton X-100, 50 uL of 1 mol/L Tris (pH 7.4), 50 uL of 1 mol/L DTT, and 40 uL of 1 mol/L $MgCl_2$. For each reaction, 1 uL of TTP, 4 uL of $dH_2O$, 2.5 uL of rAdT, and 2.5 uL of reaction buffer were mixed. Ten microliters of this reaction mixture was placed in a round bottom microtiter plate and 15 uL of virus-containing supernatant was added and mixed. The plate was incubated at 37° C. in a humidified incubator for 90 minutes. Following incubation, 10 uL of the reaction volume was spotted onto a DEAE filter mat in the appropriate plate format, washed 5 times (5 minutes each) in a 5% sodium phosphate buffer, 2 times (1 minute each) in distilled water, 2 times (1 minute each) in 70% ethanol, and then air dried. The dried filtermat was placed in a plastic sleeve and 4 mL of Opti-Fluor 0 was added to the sleeve. Incorporated radioactivity was quantified utilizing a Wallac 1450 Microbeta Trilux liquid scintillation counter.

Example 82

HBV:

HepG2.2.15 cells (100 L) in RPMI1640 medium with 10% fetal bovine serum was added to all wells of a 96-well plate at a density of $1\times10^4$ cells per well and the plate was incubated at 37° C. in an environment of 5% $CO_2$ for 24 hours. Following incubation, six ten-fold serial dilutions of test compound prepared in RPMI1640 medium with 10% fetal bovine serum were added to individual wells of the plate in triplicate. Six wells in the plate received medium alone as a virus only control. The plate was incubated for 6 days at 37° C. in an environment of 5% C02. The culture medium was changed on day 3 with medium containing the indicated concentration of each compound. One hundred microliters of supernatant was collected from each well for analysis of viral DNA by qPCR and cytotoxicity was evaluated by XTT staining of the cell culture monolayer on the sixth day.

Ten microliters of cell culture supernatant collected on the sixth day was diluted in qPCR dilution buffer (40 g/mL sheared salmon sperm DNA) and boiled for 15 minutes. Quantitative real time PCR was performed in 386 well plates using an Applied Biosystems 7900HT Sequence Detection System and the supporting SDS 2.4 software. Five microliters (5 µL) of boiled DNA for each sample and serial 10-fold dilutions of a quantitative DNA standard were subjected to real time Q-PCR using Platinum Quantitative PCR SuperMix-UDG (Invitrogen) and specific DNA oligonucleotide primers (IDT, Coralville, ID) HBV-AD38-qF1 (5'-CCG TCT GTG CCT TCT CAT CTG-3'), HBV-AD38-qR1 (5'-AGT CCA AGA GTY CTC TTA TRY AAG ACC TT-3'), and HBV-AD38-qP1 (5'-FAM CCG TGT GCA/ZEN/CTT CGC TTC ACC TCT GC-3'BHQ1) at a final concentration of 0.2 µM for each primer in a total reaction volume of 15 µL. The HBV DNA copy number in each sample was interpolated from the standard curve by the SDS.24 software and the data were imported into an Excel spreadsheet for analysis.

The 50% cytotoxic concentration for the test materials are derived by measuring the reduction of the tetrazolium dye XTT in the treated tissue culture plates. XTT is metabolized by the mitochondrial enzyme NADPH oxidase to a soluble formazan product in metabolically active cells. XTT solution was prepared daily as a stock of 1 mg/mL in PBS. Phenazine methosulfate (PMS) stock solution was prepared at 0.15 mg/mL in PBS and stored in the dark at −20° C. XTT/PMS solution was prepared immediately before use by adding 40 µL of PMS per 1 mL of XTT solution. Fifty microliters of XTT/PMS was added to each well of the plate and the plate incubated for 2-4 hours at 37° C. The 2-4 hour incubation has been empirically determined to be within linear response range for XTT dye reduction with the indicated numbers of cells for each assay. Adhesive plate sealers were used in place of the lids, the sealed plate was inverted several times to mix the soluble formazan product and the plate was read at 450 nm (650 nm reference wavelength) with a Molecular Devices SpectraMax Plus 384 spectrophotometer. Data were collected by Softmax 4.6 software and imported into an Excel spreadsheet for analysis.

Example 83

Dengue RNA-Dependent RNA Polymerase Reaction Conditions

RNA polymerase assay was performed at 30° C. using 100 µl reaction mix in 1.5 ml tube. Final reaction conditions were 50 mM Hepes (pH 7.0), 2 mM DTT, 1 mM $MnCl_2$, 10 mM KCl, 100 nM UTR-Poly A (self-annealing primer), 10 µM UTP, 26 nM RdRp enzyme. The reaction mix with different compounds (inhibitors) was incubated at 30° C. for 1 hour. To assess amount of pyrophosphate generated during polymerase reaction, 30 µl of polymerase reaction mix was mixed with a luciferase coupled-enzyme reaction mix (70 µl). Final reaction conditions of luciferase reaction were 5 mM $MgCl_2$, 50 mM Tris-HCl (pH 7.5), 150 mM NaCl, 200 µU ATP sulfurylase, 5 µM APS, 10 nM Luciferase, 100 µM D-luciferin. White plates containing the reaction samples (100 µl) were immediately transferred to the luminometer Veritas (Turner Biosystems, CA) for detection of the light signal.

Example 84

Procedure for Cell Incubation and Analysis

Huh-7 cells were seeded at 0.5×10^ cells/well in 1 mL of complete media in 12 well tissue culture treated plates. The cells were allowed to adhere overnight at 37°/5% C02. A 40 µM stock solution of test article was prepared in 100% DMSO. From the 40 µM stock solution, a 20 µM solution of test article in 25 ml of complete DMEM media was prepared. For compound treatment, the media was aspirated from the wells and 1 mL of the 20 µM solution was added in complete DMEM media to the appropriate wells. A separate plate of cells with "no" addition of the compound was also prepared. The plates were incubated at 37°/5% $CO_2$ for the following time points: 1, 3, 6 and 24 hours. After incubation at the desired time points, the cells were washed 2× with 1 mL of DPBS. The cells were extracted by adding 500 µl of 70% methanol/30% water spiked with the internal standard to each well treated with test article. The non-treated blank plate was extracted with 500 ul of 70% methanol/30% water per well. Samples were centrifuged at 16,000 rpm for 10 minutes at 4° C. Samples were analyzed by LC-MS/MS using an ABSCIEX 5500 QTRAP LC-MS/MS system with a Hypercarb (PGC) column.

Example 85

Zika RNA-Dependent RNA Polymerase Reaction Conditions

RNA polymerase assay was performed at 30° C. using 100 µl reaction mix in 1.5 ml tube. Final reaction conditions were 50 mM Hepes (pH 7.0), 2 mM DTT, 1 mM $MnCl_2$, 10 mM KCl, 100 nM UTR-Poly A (self-annealing primer), 10 µM UTP, 26 nM RdRp enzyme. The reaction mix with different compounds (inhibitors) was incubated at 30° C. for 1 hour. To assess amount of pyrophosphate generated during polymerase reaction, 30 µl of polymerase reaction mix was mixed with a luciferase coupled-enzyme reaction mix (70 µl). Final reaction conditions of luciferase reaction were 5 mM $MgCl_2$, 50 mM Tris-HCl (pH 7.5), 150 mM NaCl, 200 µU ATP sulfurylase, 5 µM APS, 10 nM Luciferase, 100 µM D-luciferin. White plates containing the reaction samples (100 µl) were immediately transferred to the luminometer Veritas (Turner Biosystems, CA) for detection of the light signal.

Example 86

Zika Infectious Assay Conditions

Vero cells were passaged in DMEM medium in T-75 flasks prior to use in the antiviral assay. On the day preceding the assay, the cells were split 1:2 to assure they were in exponential growth phase at the time of infection. The cells were resuspended at 5×10' cells per well in tissue culture medium and added to flat bottom microtiter plates in a volume of 100 mL. The plates were incubated at 37° C./5% $CO_2$ overnight to allow for cell adherence. Separately, Zika virus was titrated in LLCMK2 cells to define the inoculum for use in the antiviral assay. Virus was diluted in DMEM medium such that the amount of virus added to each well in a volume of 100 mL was the amount determined to achieve 85 to 95% cell killing at 5 days post-infection. Following incubation test plates were stained with XTT dye. XTT solution was prepared daily as a stock solution of 1 mg/mL in RPM11640. PMS solution was prepared at 0.15 mg/mL in PBS and stored in the dark at −20° C. XTT/PMS stock was prepared immediately before use by adding 40 mL of PMS per mL of XTT solution. Fifty microliters of XTT/PMS was added to each well of the plate, and the plate was reincubated for 4 hours at 37° C. Plates were sealed with adhesive plate sealers ad shaken gently to mix the soluble formazan product, and the plate was read spectrophotometrically read 450/650 nm with a Molecular Devices Vmax plate reader. The raw data was collected from Softmax Pro and imported into a Microsoft Excel XLfit4 spreadsheet for analysis using four parameter curve fit calculations.

Example 87

Mitochondrial RNA Polymerase Assay
POLRMT Enzyme Purification

A variant of human POLRMT coding sequence was amplified from a POLRMT cDNA plasmid (Accession: BC098387, Clone ID: 5264127, Dharmacon, CO) and cloned into a pMal-c5× vector under control of the tac promoter. For protein expression, the plasmid was transformed into Stellar competent cells (Clontech). Expression vector pMal-c5× contains a lacI gene which allows inducible expression of POLRMT in Stellar cells. The transformed cells were grown in LB medium containing 100 µg/ml ampicillin at 35° C. to an optical density of 1 at 600 nm. Cells were cooled down in a 4° C. fridge for 1 hour. $MgCl_2$ was added to final concentration of 1 mM. Protein expression was induced at 16° C. overnight by the addition of 0.4 mM IPTG. Cells were harvested by centrifugation at 4000×g for 20 min at 4° C. The cell pellet was stored at −80° C. until further processed. For protein purification, the cell pellet was re-suspended in sonication buffer (20 mM Tris-HCl pH 7.5, 10% glycerol, 500 mM NaCl, 0.5% Triton X-100, 10 mM DTT, 10 mM $MgCl_2$, 30 mM imidazole and 1× protease inhibitor cocktail). Cell disruption was performed on ice for 10 min using an ultrasound probe sonicator. The cell extract was clarified by centrifugation at 16,000×g for 20 min at 4° C. The supernatant was incubated with HisPur Ni-NTA agarose resin with gentle rocking for 15 minutes at 4° C. The resin was then washed 5 times with 10 volumes of wash buffer (20 mM Tris-HCl pH 7.5, 10% glycerol, 500 mM NaCl, 0.1% Triton X-100, 1 mM DTT, 2 mM $MgCl_2$) containing 30 mM imidazole and then once with the wash buffer containing 2M NaCl. The protein was eluted from the resin with 1 volume of elution buffer (20 mM Tris-HCl, pH 7.5, 10% glycerol, 50 mM NaCl, 0.5% Triton X-100, 10 mM DTT and 300 mM imidazole). The eluted enzyme was adjusted to 50% glycerol and stored at −80° C. before use. Protein identification was performed by mass spectrometry. The concentration of a targeted protein was measured by SDS-PAGE using BSA (Sigma, St. Louis, Mo.) as a standard.

Measurement of Ribonucleotide Analog Incorporation Efficiency

Different templates were designed to test individual analog rNTPs, Table 1. Different concentrations of tested ribonucleotide analogs were added to reaction mixtures containing 10 nM P/T and 20 nM POLRMT in a reaction buffer (5 mM Tris-HCl, pH 7.5, 10 mM DTT, 20 mM $MgCl_2$, 0.5% X-100, 10% glycerol) to initiate the reactions. The reactions were continued at 22° C. for different time and subsequently quenched with quenching buffer (8 M Urea, 90 mM Tris base, 29 mM taurine, 10 mM EDTA, 0.02% SDS and 0.1% bromophenol blue). The quenched samples were denatured at 95° C. for 15 min and the primer extension products were separated using 20% denaturing polyacrylamide gel electrophoresis (Urea PAGE) in 1×TTE buffer (90 mM Tris base, 29 mM Taurine and 0.5 mM EDTA). After electrophoresis, gels were scanned using an Odyssey infrared imaging system. The intensity of different RNA bands was quantified using Image Studio Software Lite version 4.0. The incorporation efficiencies of different rNTP analogs were evaluated by measurement the $K_{1/2}$ and corresponding Discrimination Values (ref. G Lu).

Primer Extension Polymerase Activity Assay

POLRMTs polymerase activity was determined in a primer extension reaction using a fluorescently labeled RNA primer/DNA template complex. A typical primer extension reaction was performed in a 20-µl reaction mixture containing reaction buffer (5 mM Tris-HCl, pH7.5, 10 mM DTT, 20 mM $MgCl_2$, 0.1% Triton X-100, 0.01 U RNasin, 10% glycerol), 10 nM P/T complex, and 20 nM POLRMT. The reaction was initiated by the addition of rNTPs at a final concentration of 100 µM, followed by incubation for 1 h at 22° C. The reactions were quenched by the addition of 20 µl quenching buffer (8 M Urea, 90 mM Tris base, 29 mM taurine, 10 mM EDTA, 0.02% SDS and 0.1% bromophenol blue). The quenched samples were denatured at 95° C. for 15 min and the primer extension products were separated using 20% denaturing polyacrylamide gel electrophoresis (Urea PAGE) in 1×TTE buffer (90 mM Tris base, 29 mM Taurine and 0.5 mM EDTA). After electrophoresis, gels were scanned using an Odyssey infrared imaging system (LI-COR Biosciences, Lincoln, Nebr.). The images were analyzed and the proper RNA bands were quantified using Image Studio software Lite version 4.0 (LI-COR Biosciences, Lincoln, Nebr.).

Example 88

ZIKV, DENV, and POLRMT Polymerase Assay Results

| ID and Structure | ZIKV Polymerase Assay | | DENV Polymerase Assay | | POLRMT Polymerase Assay | |
|---|---|---|---|---|---|---|
| | $K_{1/2}$ (µM) | Discrimination | $K_{1/2}$ (µM) | Discrimination | $K_{1/2}$ (µM) | Discrimination |
| EIDD-02780 | 1.1 | 6.4 | 0.97 | 11.4 | No incorporation | |
| EIDD-02689 | 11.9 | 5.08 | 1.6 | 14.83 | — | — |

Example 89

DENV Assay Results

| ID and Structure | DENV2 New Guinea C | |
|---|---|---|
| | Cell Line | $EC_{50}$ (µM) |
| EIDD-02578 | BHK21 | 27.7 |
| EIDD-02691 | Vero | >100 |

Example 90
Human Rhinovirus Assay Results
| ID and Structure | Cell Line | HRV-26 EC$_{50}$ (μM) |
|---|---|---|
| EIDD-02464 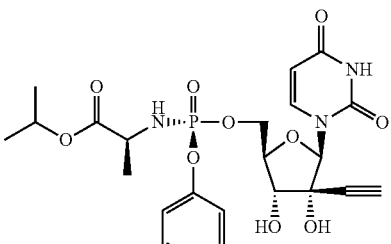 | HeLa | 3.22 |
| EIDD-02691 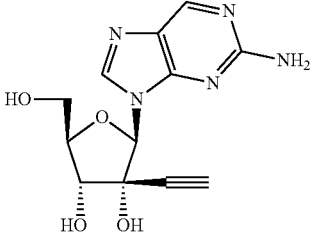 | HeLa | >100 |
Example 91
ZIKV Assay Results
| ID and Structure | Cell Line | ZIKV EC$_{50}$ (μM) |
|---|---|---|
| EIDD-02578 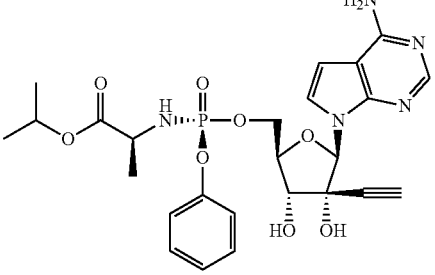 | Huh-7 | 0.001 |
| EIDD-02650 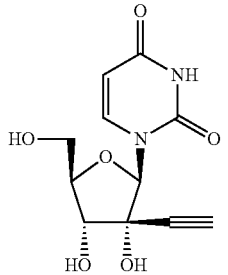 | Huh-7<br>Vero | >100<br>>100 |
| EIDD-02464 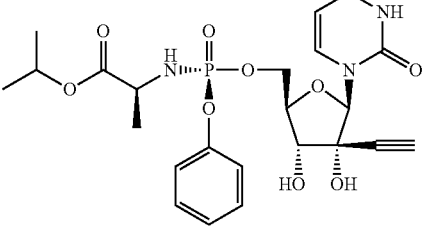 | Huh-7<br>Vero | 0.5<br>>100 |
| EIDD-02691 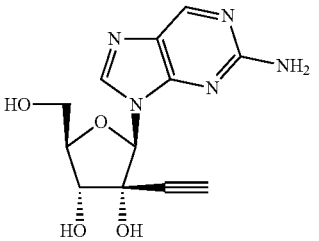 | HeLa | >100 |
| EIDD-02673 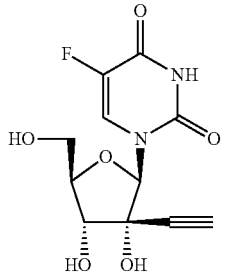 | Huh-7 | >100 |

655
-continued

| ID and Structure | ZIKV Cell Line | EC$_{50}$ (μM) |
|---|---|---|
| EIDD-02675 | Huh-7 Vero | 13 >100 |
| EIDD-02764 | Huh-7 | 5.3 |
| EIDD-02691 | Vero | >100 |

Example 92

Antiviral Assay Results for EIDD-02290

| ID and Structure | Virus | Cell Line | EC$_{50}$ (μM) |
|---|---|---|---|
| EIDD-02290 | RSV HRV DENV2 ZIKV | Huh-7 HeLa BHK Vero Huh-7 Vero Huh-7 | 90 0.05 7.76 7.56 0.24 1.06 0.31 |

656

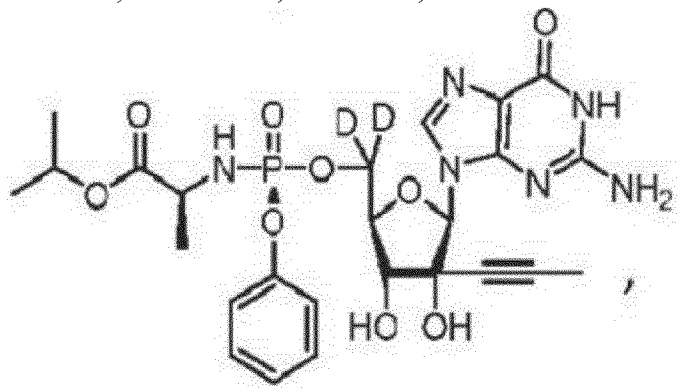

What is claimed is:

1. A compound of the following formula:

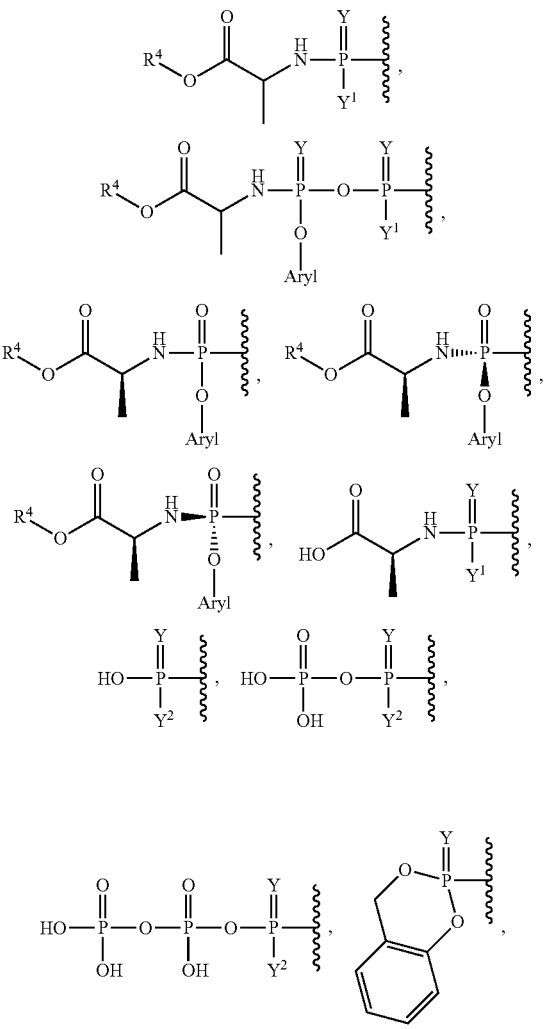

Formula XXXVIII or pharmaceutically acceptable salts thereof wherein,

X is $OCH_2$, $OCHMe$, $OCMe_2$, $OCHF$, $OCF_2$, or $OCD_2$;

W is N or $CR^7$;

Z is N or $CR^8$;

$R^1$ is selected from H or from one of the following formulae:

-continued

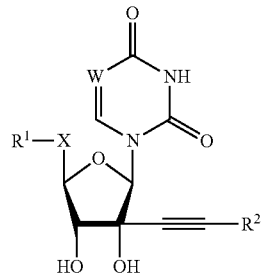

Y is O;
Y$^1$ is OH, OAryl, OAlkyl, or BH$_3^-$M$^+$;
Y$^2$ is OH or BH$_3^-$M$^+$;
Aryl is phenyl, 1-naphthyl, 2-naphthyl, aromatic, heteroaromatic group having 1 to 4 heteroatoms selected from nitrogen, oxygen and sulfur, and containing at least 1 carbon atom, 4-substituted phenyl, 4-chlorophenyl, or 4-bromophenyl;
R$^2$ is hydrogen, methyl, fluoromethyl, difluoromethyl, trifluoromethyl, ethyl, cyclopropyl, fluoro, hydroxymethyl, aminomethyl, vinyl, or cyclobutyl;

R$^4$ is hydrogen, methyl, ethyl, isopropyl, cyclopentyl, cyclohexyl, neopentyl, benzyl, alkyl, branched alkyl, cycloalkyl, or lipid substituent;
R$^5$ is hydrogen, deuterium, hydroxyl, cyano, azido, amino, substituted amino, aryl, heteroaryl group having 1 to 4 heteroatoms selected from nitrogen, oxygen and sulfur, and containing at least 1 carbon atom, substituted aryl, lipid substituent, C$_{1-22}$ alkoxy, C$_{1-22}$ alkyl, C$_{2-22}$ alkenyl, C$_{2-22}$ alkynyl, or substituted heteroaryl group having 1 to 4 heteroatoms selected from nitrogen, oxygen and sulfur, and containing at least 1 carbon atom;
R$^6$ is methyl, ethyl, tert-butyl, C$_{1-22}$ alkoxy, C$_{1-22}$ alkyl, branched alkyl, cycloalkyl, aryl, substituted aryl, or alkyoxy;
R$^7$ is H, D, hydroxyl, thiol, amino, C$_{1-4}$ alkyl, methyl, fluoromethyl, difluoromethyl, trifluoromethyl, hydroxymethyl, C$_{2-4}$ alkenyl, C$_{2-4}$ alkynyl, ethynyl, azido, fluoro, chloro, bromo, iodo, or cyano;
R$^8$ is D, C$_{1-4}$ alkyl, fluoro, chloro, bromo, or iodo; or
a compound of the following formula:

Formula XXXIX

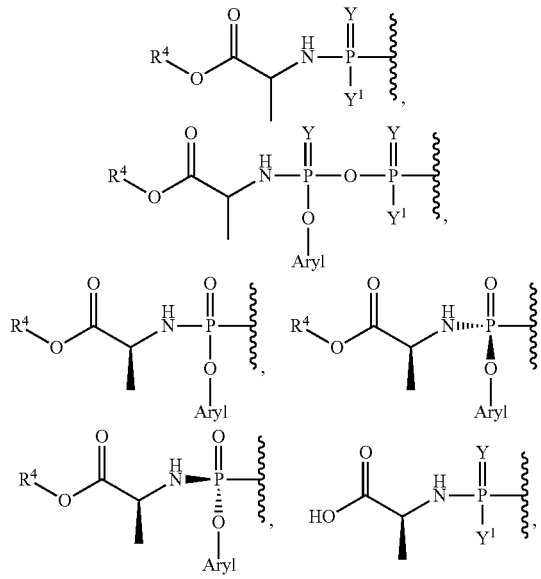

or pharmaceutically acceptable salts thereof wherein,
X is OCH$_2$, OCHMe, OCMe$_2$, OCHF, OCF$_2$, or OCD$_2$;
W is N or CR$^7$;
R$^1$ is selected from H or from one of the following formulae:

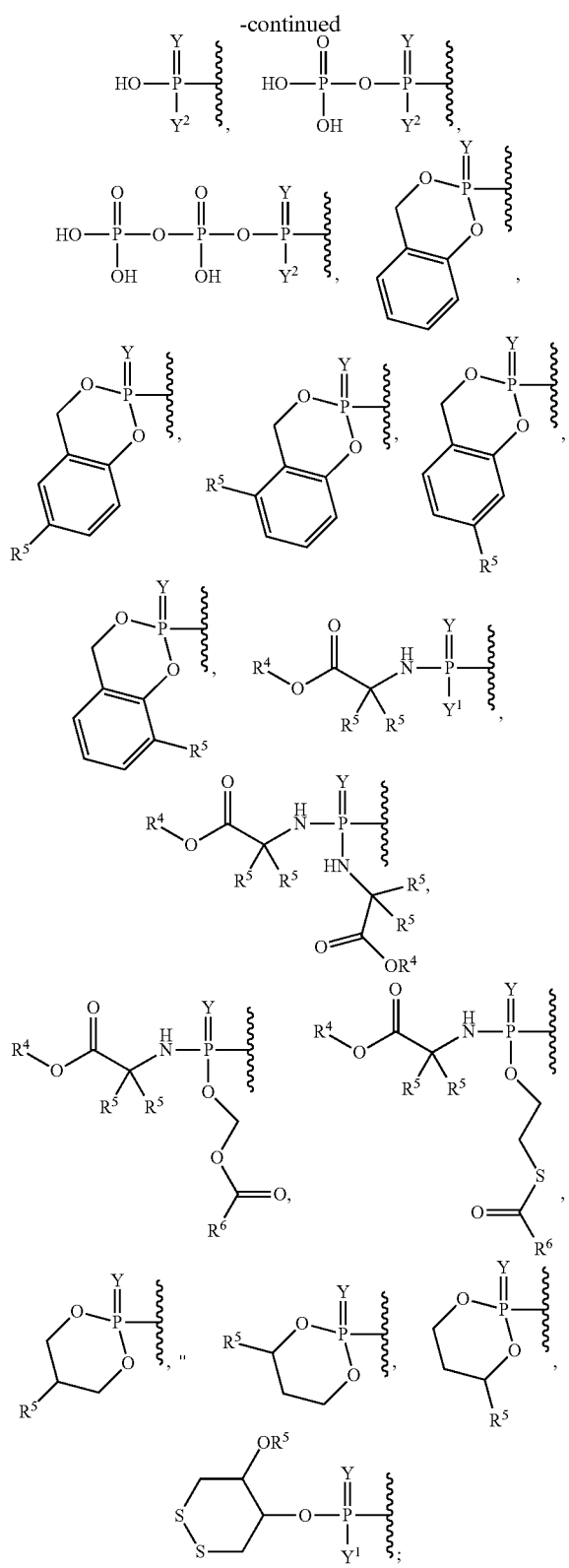

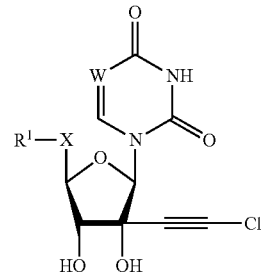

Y is O;
Y¹ is OH, OAryl, OAlkyl, or BH₃⁻M⁺;
Y² is OH or BH₃⁻M⁺;
Aryl is phenyl, 1-naphthyl, 2-naphthyl, aromatic, heteroaromatic group having 1 to 4 heteroatoms selected from nitrogen, oxygen and sulfur, and containing at least 1 carbon atom, 4-substituted phenyl, 4-chlorophenyl, or 4-bromophenyl;

R² is hydrogen, methyl, fluoromethyl, difluoromethyl, trifluoromethyl, ethyl, cyclopropyl, fluoro, hydroxymethyl, aminomethyl, vinyl, or cyclobutyl;

R⁴ is hydrogen, methyl, ethyl, isopropyl, cyclopentyl, cyclohexyl, neopentyl, benzyl, alkyl, branched alkyl, cycloalkyl, or lipid substituent;

R⁵ is hydrogen, deuterium, hydroxyl, cyano, azido, amino, substituted amino, aryl, heteroaryl group having 1 to 4 heteroatoms selected from nitrogen, oxygen and sulfur, and containing at least 1 carbon atom, substituted aryl, lipid substituent, $C_{1-22}$ alkoxy, $C_{1-22}$ alkyl, $C_{2-22}$ alkenyl, $C_{2-22}$ alkynyl, or substituted heteroaryl group having 1 to 4 heteroatoms selected from nitrogen, oxygen and sulfur, and containing at least 1 carbon atom;

R⁶ is methyl, ethyl, tert-butyl, $C_{1-22}$ alkoxy, $C_{1-22}$ alkyl, branched alkyl, cycloalkyl, aryl, substituted aryl group having 1 to 4 heteroatoms selected from nitrogen, oxygen and sulfur, and containing at least 1 carbon atom, or alkyoxy;

R⁷ is D, hydroxyl, thiol, amino, $C_{1-4}$ alkyl, methyl, fluoromethyl, difluoromethyl, trifluoromethyl, hydroxymethyl, $C_{2-4}$ alkenyl, $C_{2-4}$ alkynyl, ethynyl, azido, fluoro, chloro, bromo, iodo, or cyano; or a compound of the following formula:

Formula XL

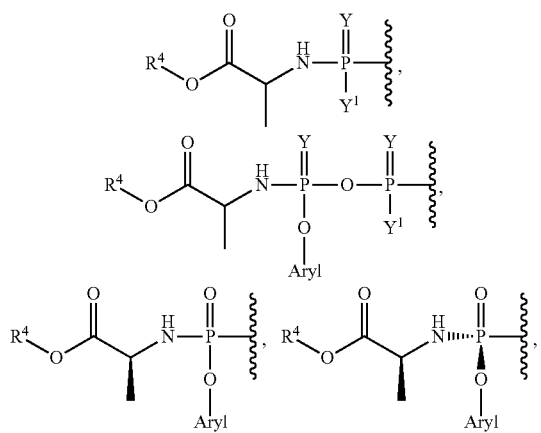

or pharmaceutically acceptable salts thereof wherein,
X is $OCMe_2$, OCHF, $OCF_2$, or $OCD_2$;
W is $CR^7$;
R¹ is selected from H or from one of the following formulae:

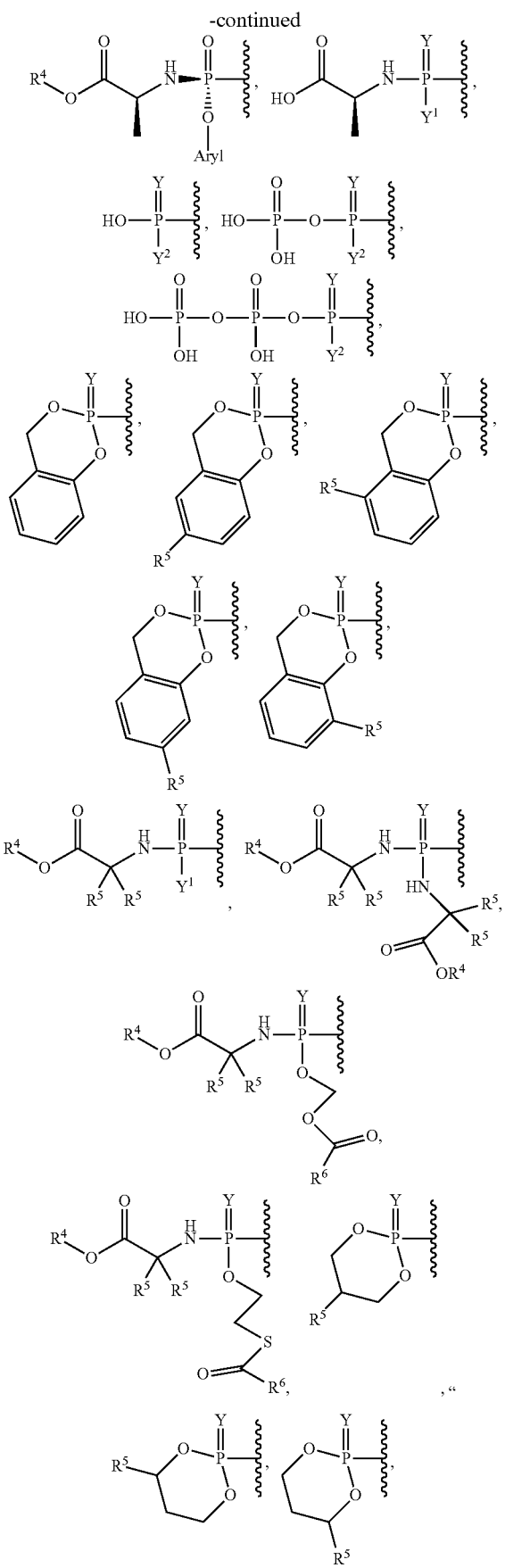

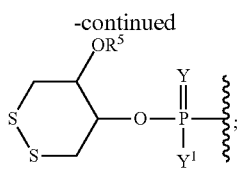

Y is O;
Y$^1$ is OH, OAryl, OAlkyl, or BH$_3^-$M$^+$;
Y$^2$ is OH or BH$_3^-$M$^+$;
Aryl is phenyl, 1-naphthyl, 2-naphthyl, aromatic, heteroaromatic group having 1 to 4 heteroatoms selected from nitrogen, oxygen and sulfur, and containing at least 1 carbon atom, 4-substituted phenyl, 4-chlorophenyl, or 4-bromophenyl;
R$^4$ is hydrogen, methyl, ethyl, isopropyl, cyclopentyl, cyclohexyl, neopentyl, benzyl, alkyl, branched alkyl, cycloalkyl, or lipid substituent;
R$^5$ is hydrogen, deuterium, hydroxyl, cyano, azido, amino, substituted amino, aryl, heteroaryl group having 1 to 4 heteroatoms selected from nitrogen, oxygen and sulfur, and containing at least 1 carbon atom, substituted aryl, lipid substituent, C$_{1-22}$ alkoxy, C$_{1-22}$ alkyl, C$_{2-22}$ alkenyl, C$_{2-22}$ alkynyl, or substituted heteroaryl group having 1 to 4 heteroatoms selected from nitrogen, oxygen and sulfur, and containing at least 1 carbon atom;
R$^6$ is methyl, ethyl, tert-butyl, C$_{1-22}$ alkoxy, C$_{1-22}$ alkyl, branched alkyl, cycloalkyl, aryl, substituted aryl, or alkyoxy;
R$^7$ is D; or
a compound of the following formula:

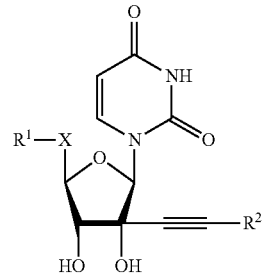

Formula XLI or pharmaceutically acceptable salts thereof wherein,
X is OCMe$_2$, OCHF, OCF$_2$, or OCD$_2$;
R$^1$ is selected from H or from one of the following formulae:

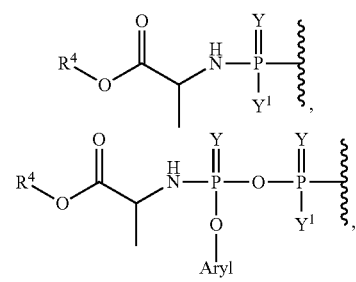

663

-continued

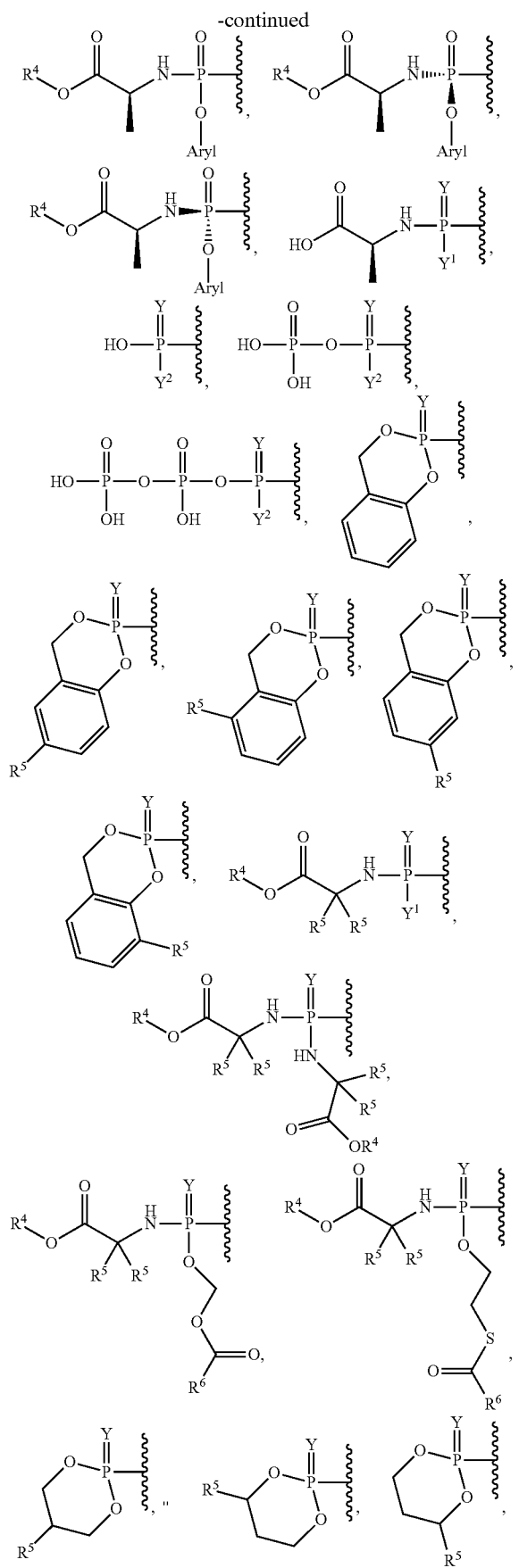

664

-continued

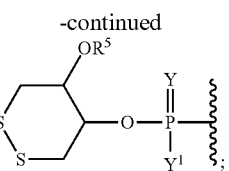

Y is O;

Y¹ is OH, OAryl, OAlkyl, or $BH_3^-M^+$;

Y² is OH or $BH_3^-M^+$;

Aryl is phenyl, 1-naphthyl, 2-naphthyl, aromatic, heteroaromatic group having 1 to 4 heteroatoms selected from nitrogen, oxygen and sulfur, and containing at least 1 carbon atom, 4-substituted phenyl, 4-chlorophenyl, or 4-bromophenyl;

R² is hydrogen, methyl, fluoromethyl, difluoromethyl, trifluoromethyl, ethyl, cyclopropyl, fluoro, hydroxymethyl, aminomethyl, vinyl, or cyclobutyl;

R⁴ is hydrogen, methyl, ethyl, isopropyl, cyclopentyl, cyclohexyl, neopentyl, benzyl, alkyl, branched alkyl, cycloalkyl, or lipid substituent;

R⁵ is hydrogen, deuterium, hydroxyl, cyano, azido, amino, substituted amino, aryl, heteroaryl group having 1 to 4 heteroatoms selected from nitrogen, oxygen and sulfur, and containing at least 1 carbon atom, substituted aryl, lipid substituent, $C_{1-22}$ alkoxy, $C_{1-22}$ alkyl, $C_{2-22}$ alkenyl, $C_{2-22}$ alkynyl, or substituted heteroaryl group having 1 to 4 heteroatoms selected from nitrogen, oxygen and sulfur, and containing at least 1 carbon atom;

R⁶ is methyl, ethyl, tert-butyl, $C_{1-22}$ alkoxy, $C_{1-22}$ alkyl, branched alkyl, cycloalkyl, aryl, substituted aryl, or alkyoxy, wherein when a moiety is substituted, the substituent is selected from halogen, hydroxy, alkyl, alkoxy, nitro, cyano, oxo, aryl, arylalkyl, heteroaryl, or heteroarylalkyl;

wherein the lipid substituent is selected from optionally substituted $C_{6-22}$ alkoxy; optionally substituted $C_{6-22}$ alkyl; optionally substituted aryl substituted with $C_{6-22}$ alkyl; or optionally substituted polyethylene glycol, wherein the lipid substituent optionally comprises an alcohol; amine; thiol; has one or more of its carbon units substituted with an oxygen, nitrogen, or sulfur; or the lipid substituent is unsaturated or polyunsaturated.

2. The compound of claim 1 selected from the following:

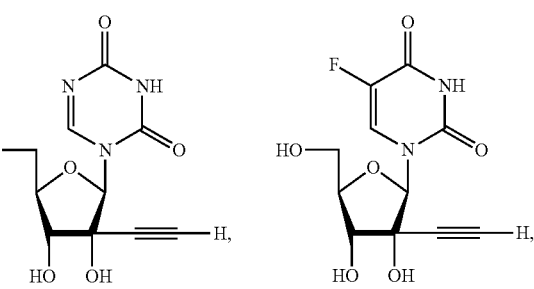

665
-continued
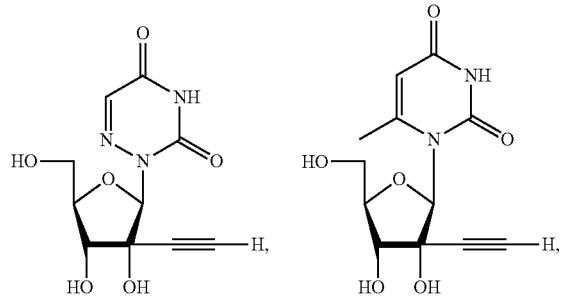
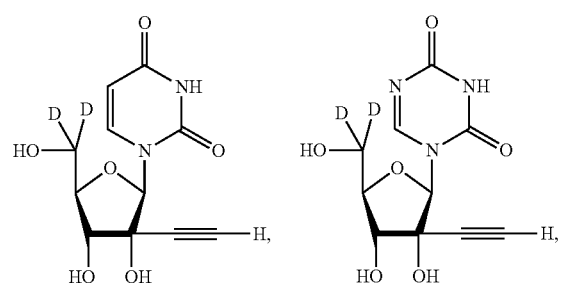
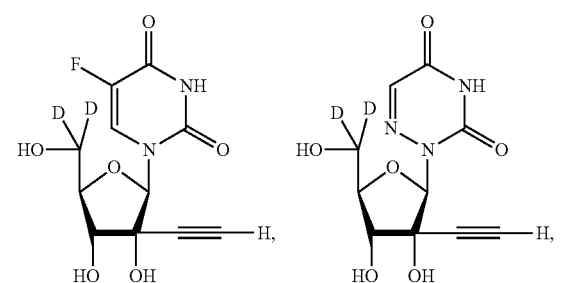
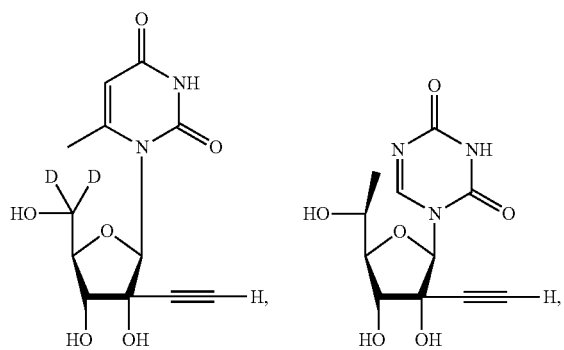
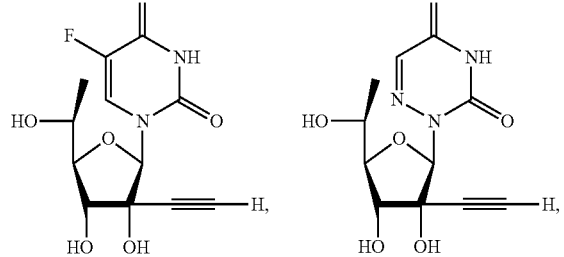
666
-continued
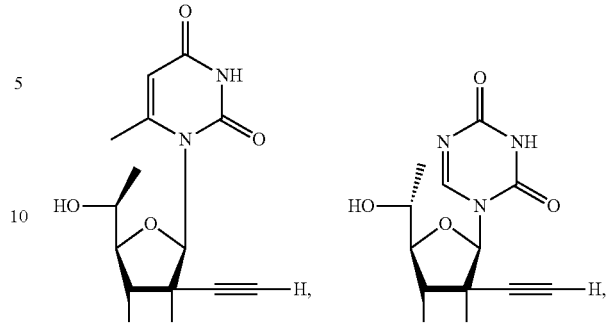
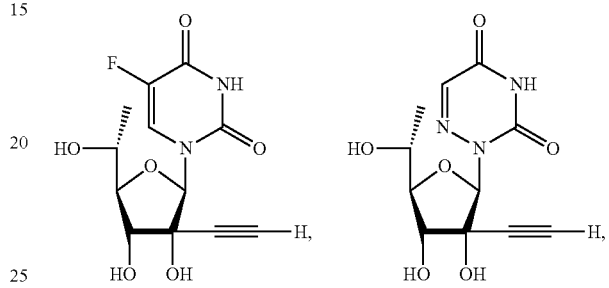
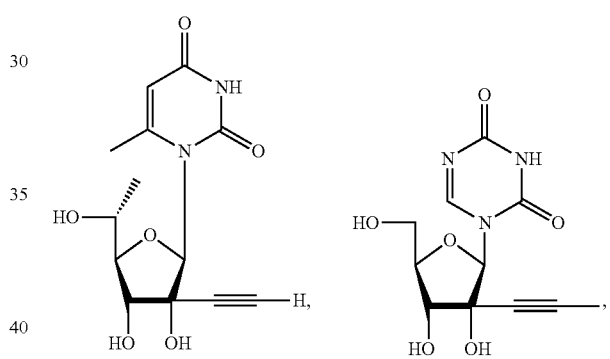
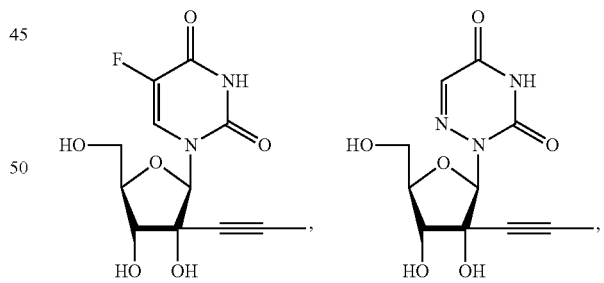
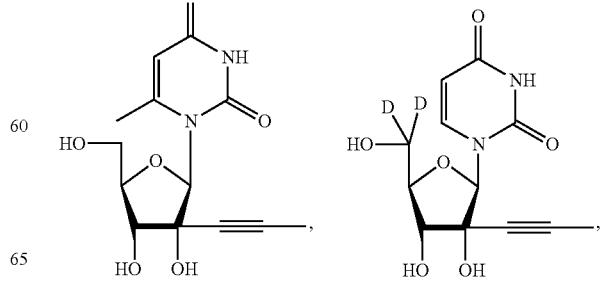

667
-continued
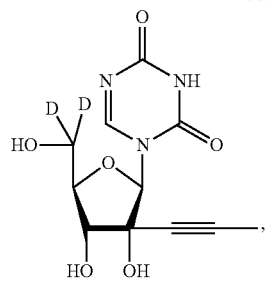 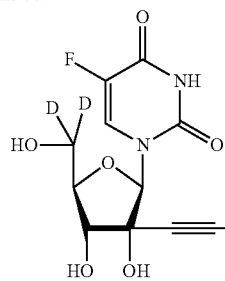
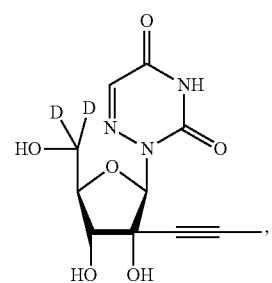 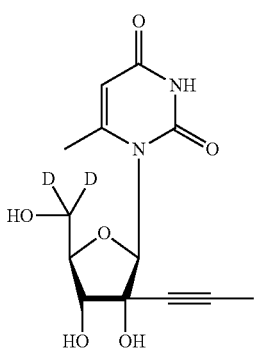
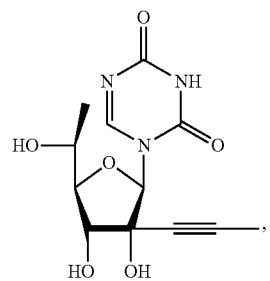 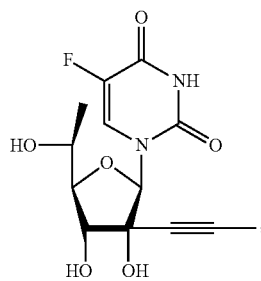
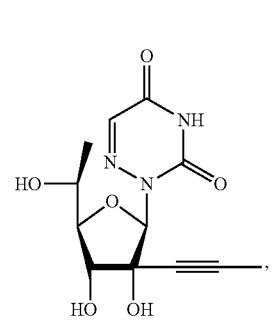 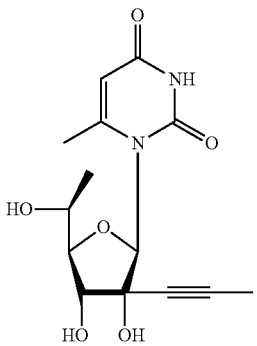
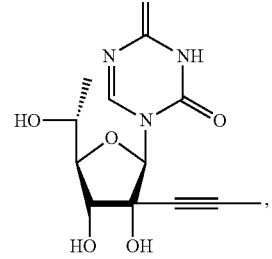 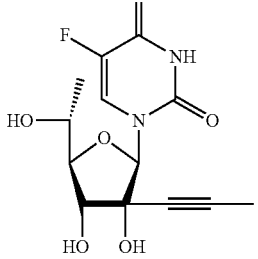
668
-continued
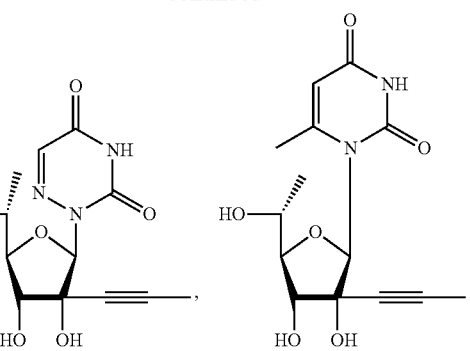
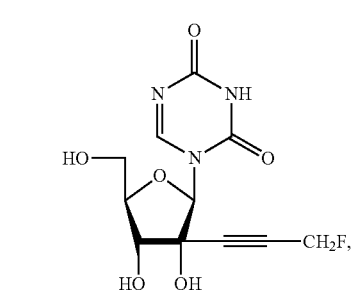
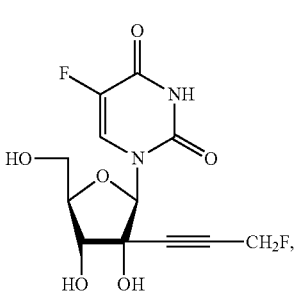
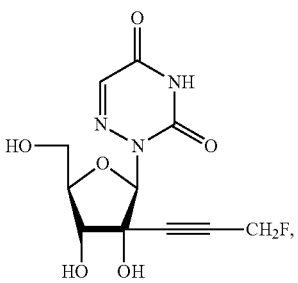
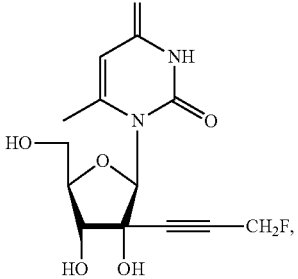

-continued
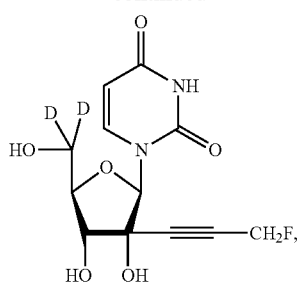
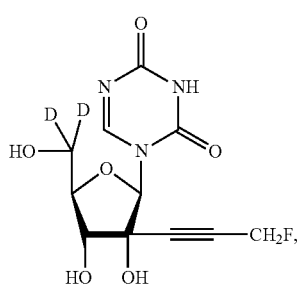
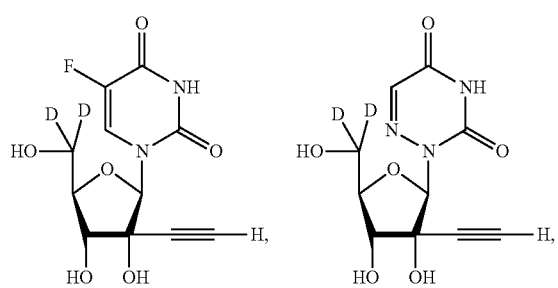
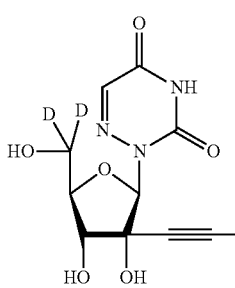
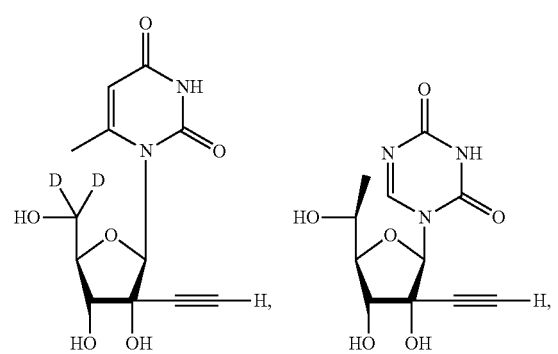
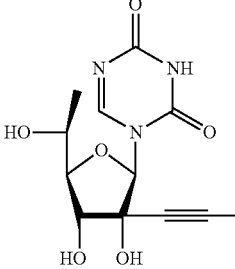
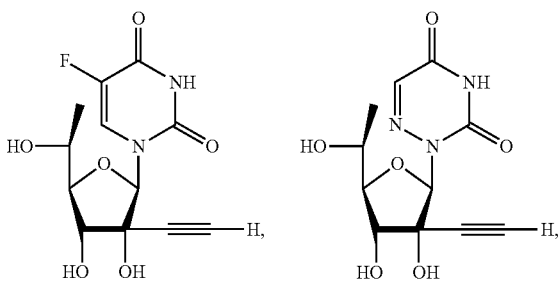
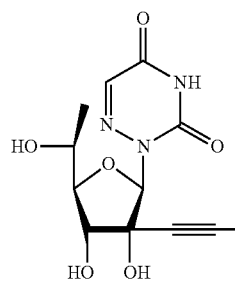
-continued
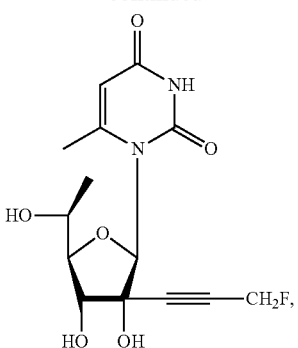
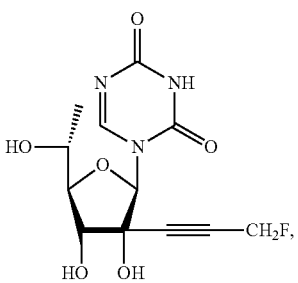
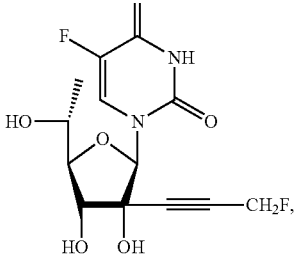
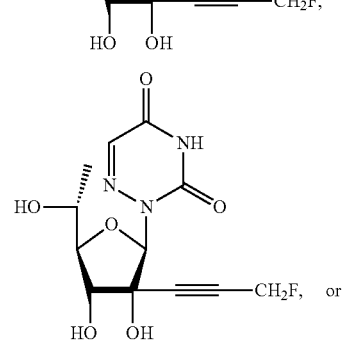
or
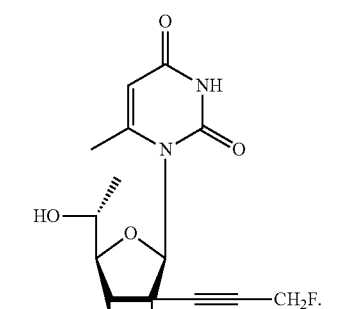

3. The compound of claim 1 selected from the following:
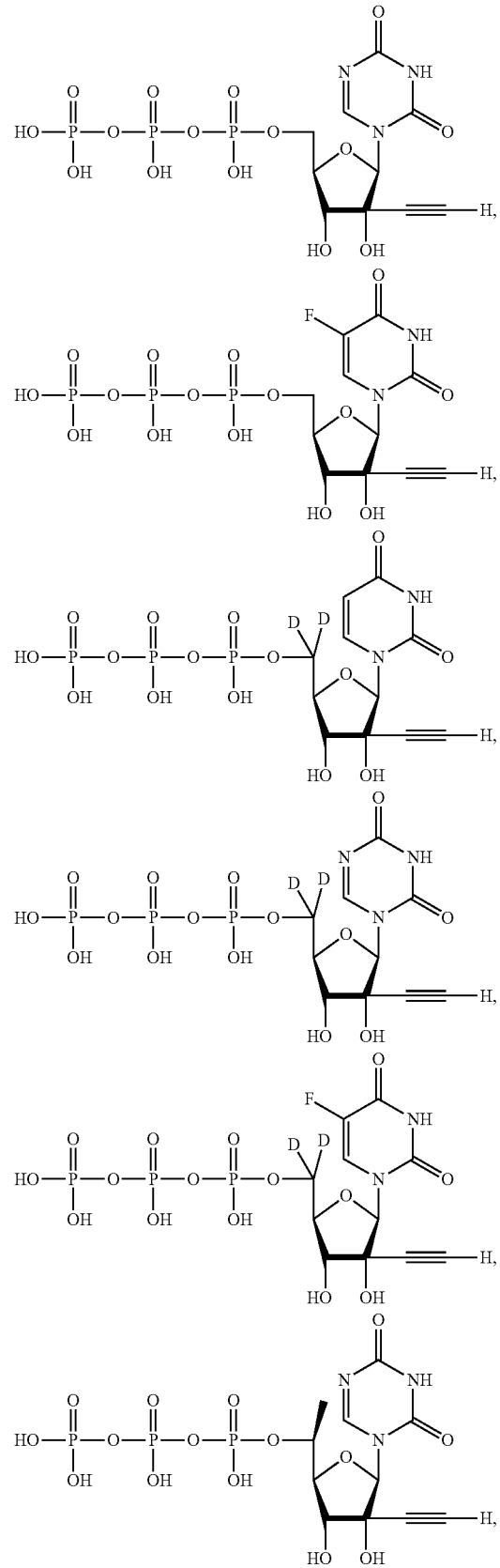
-continued
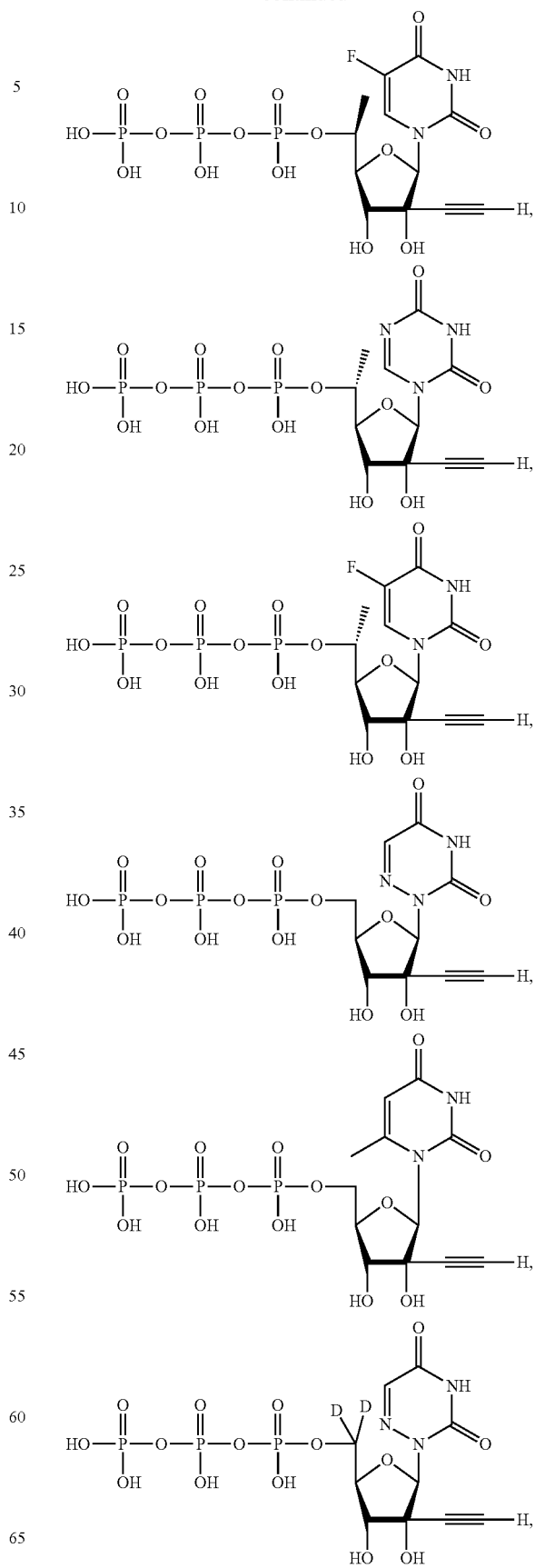

673
-continued
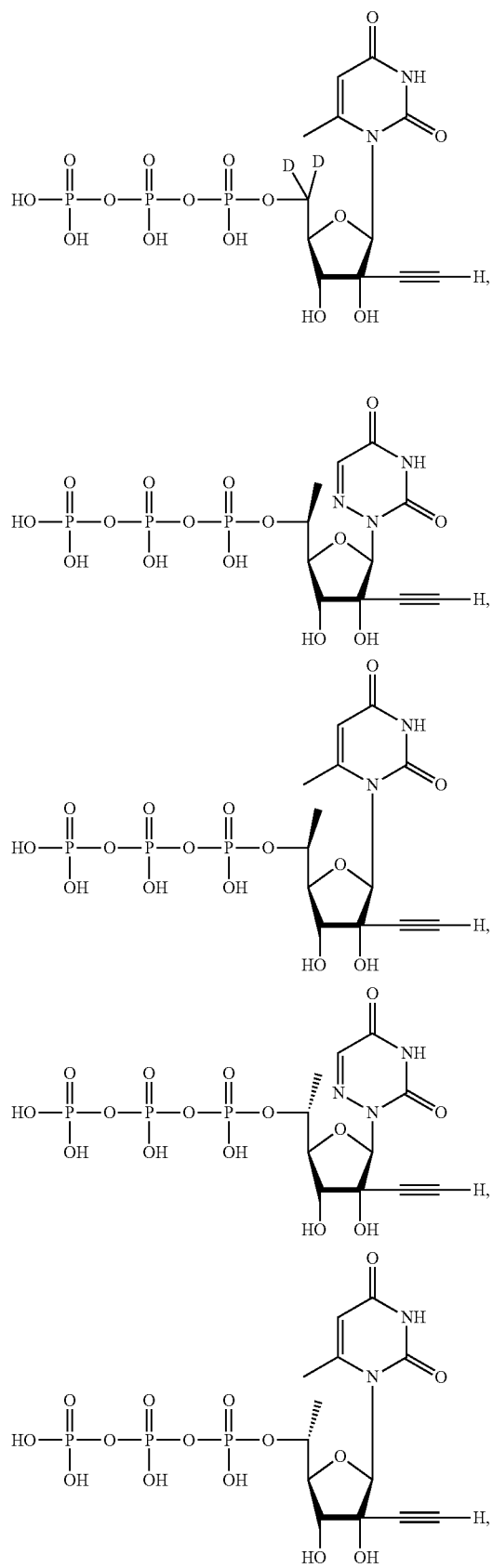
674
-continued
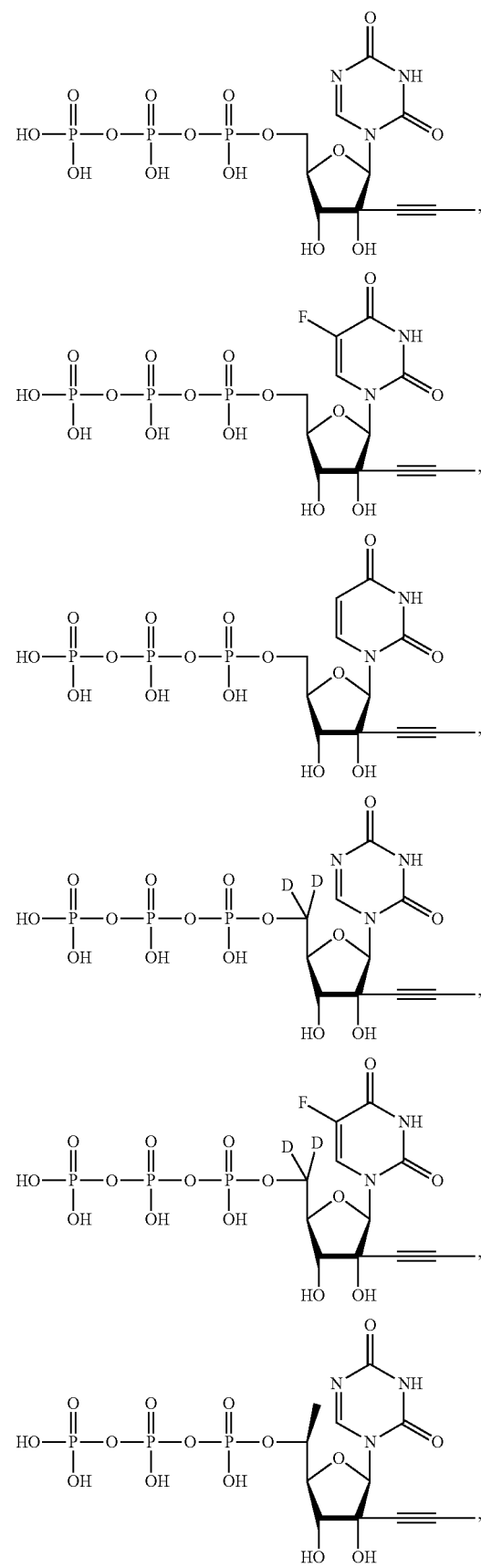

675
-continued
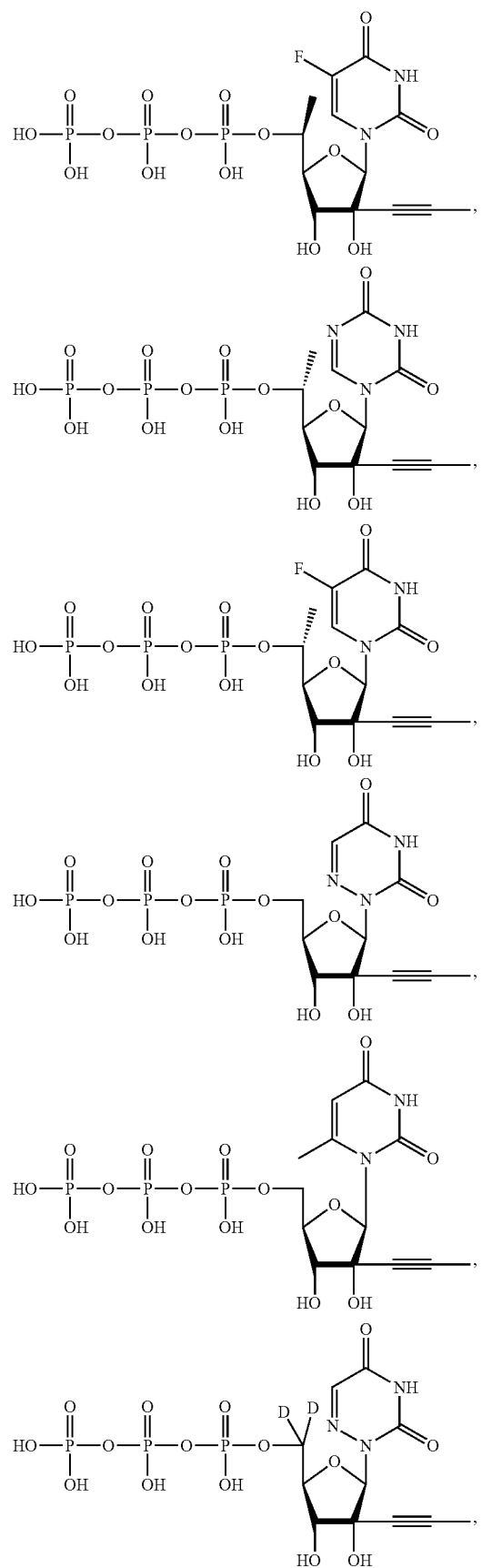
676
-continued
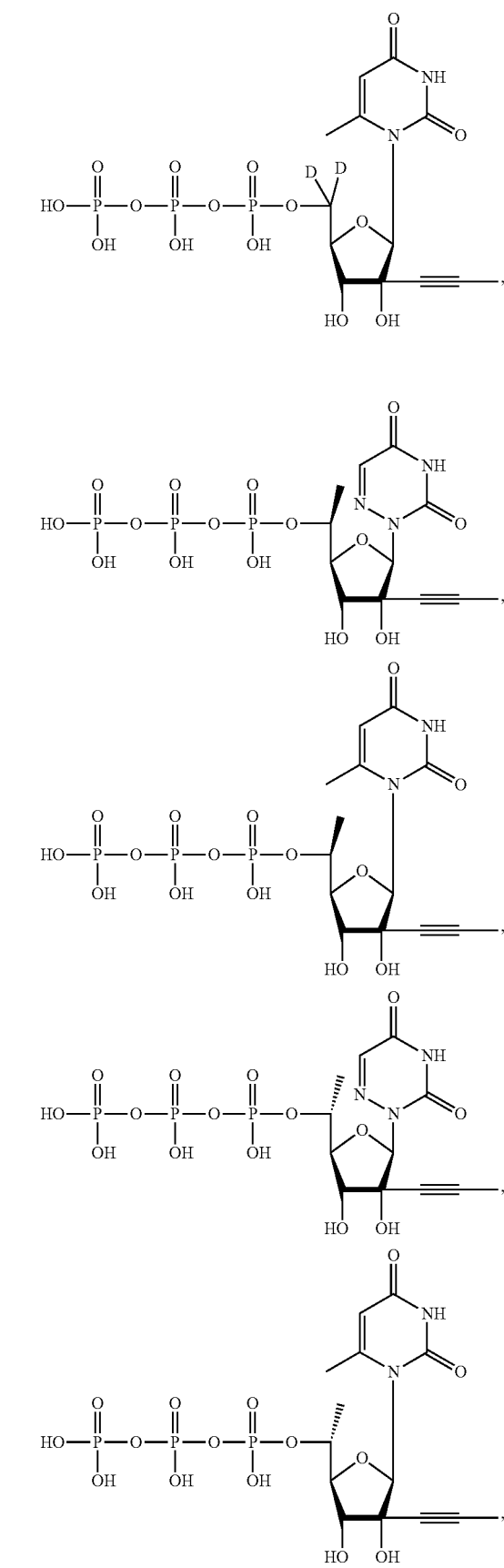

677
-continued
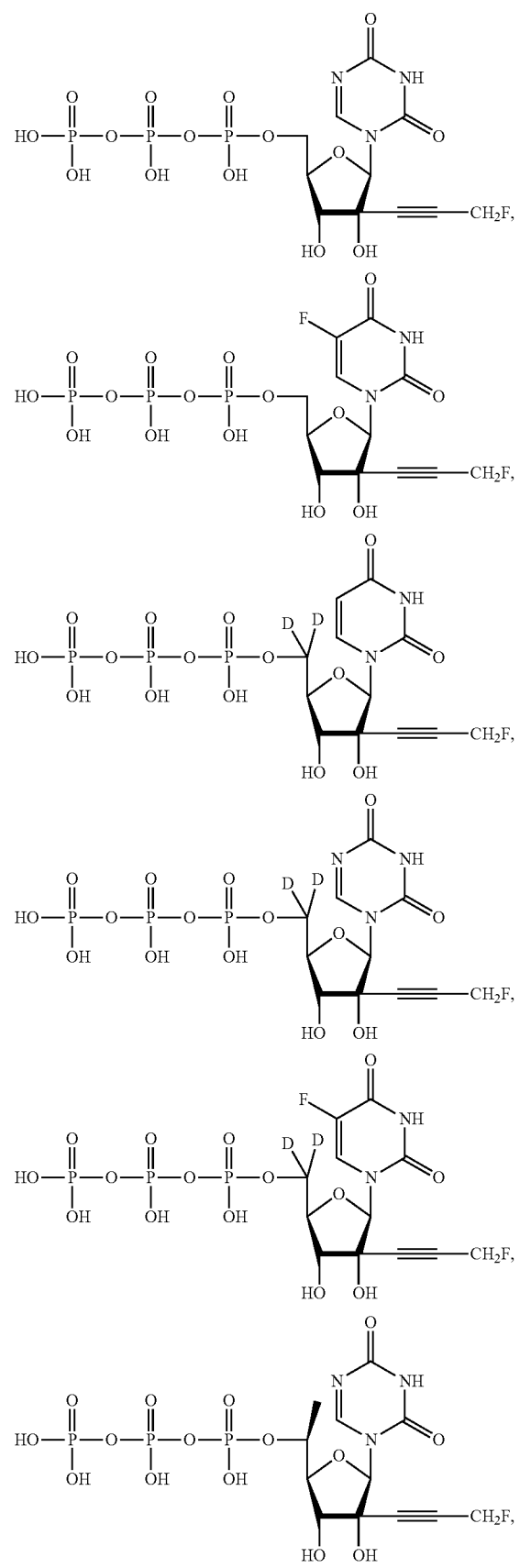
678
-continued
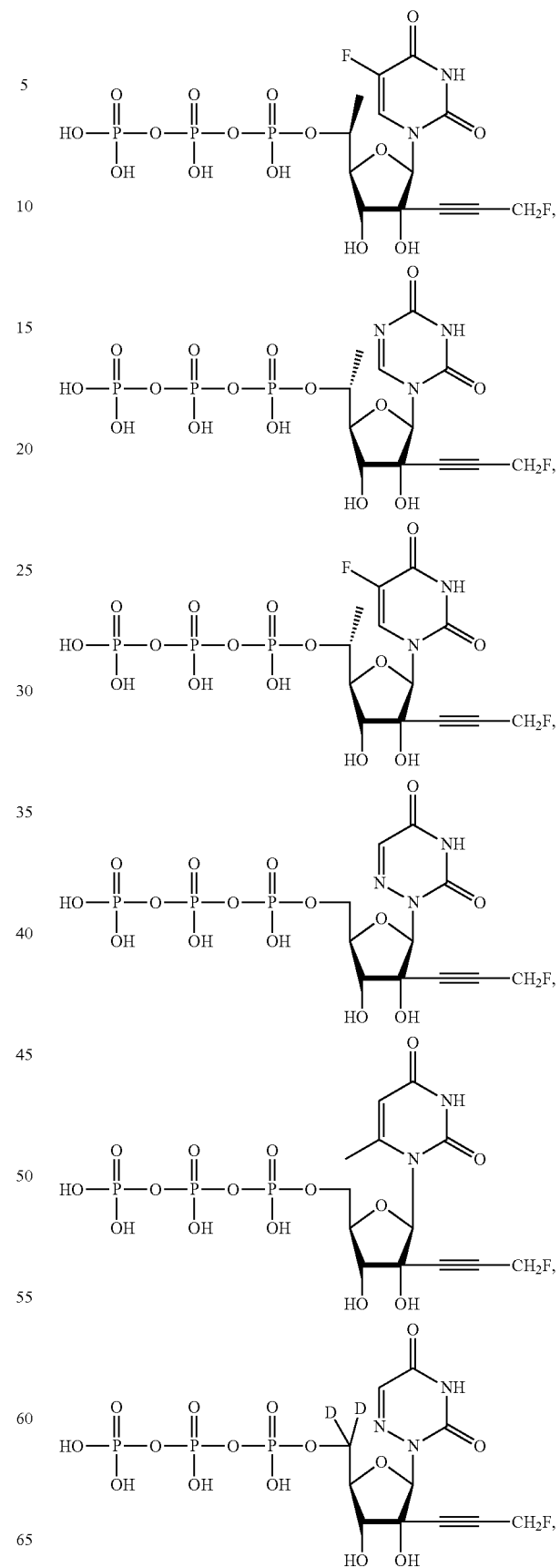

-continued
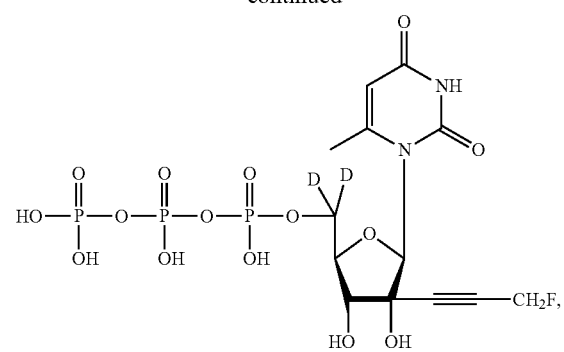
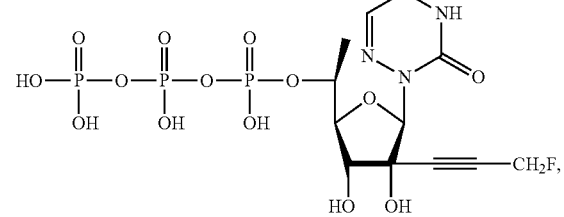
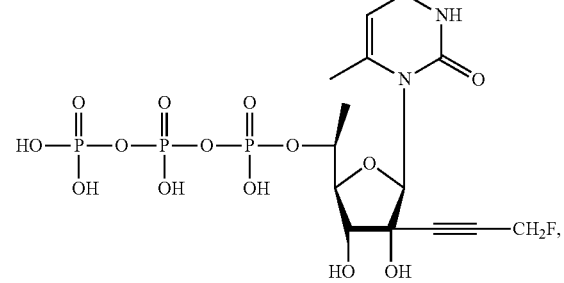
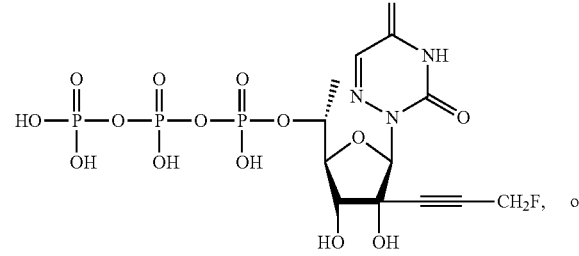
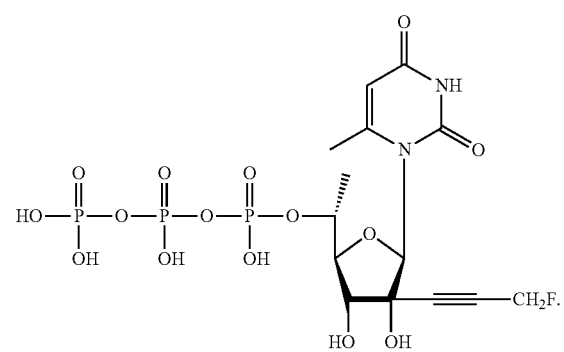
4. The compound of claim 1 selected from the following:
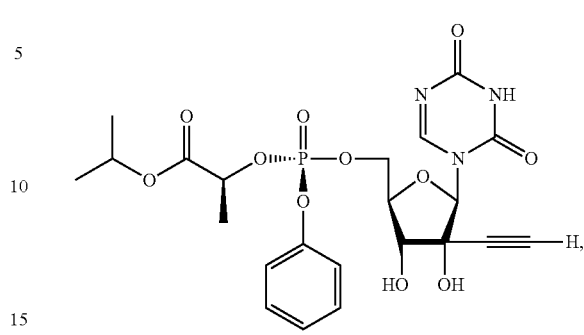
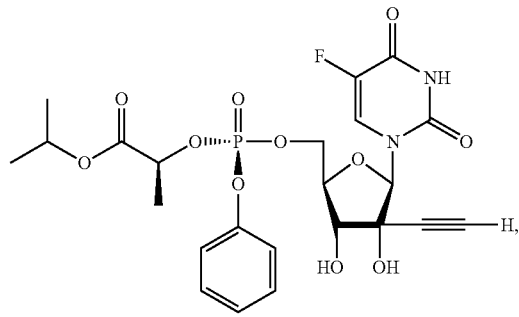
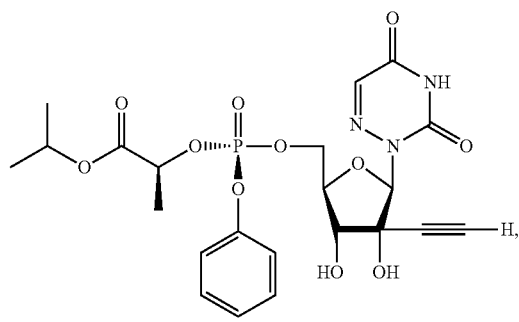
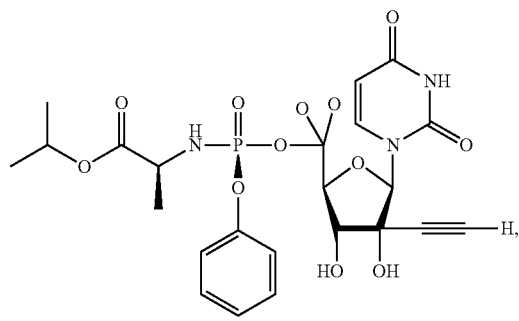
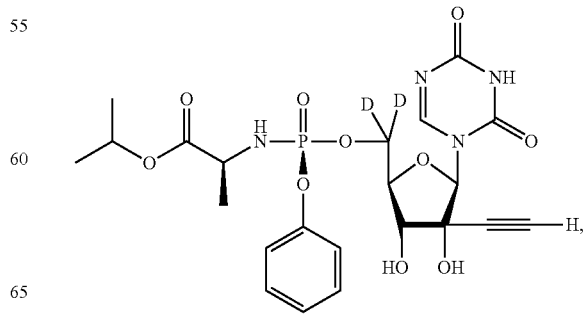

681
-continued
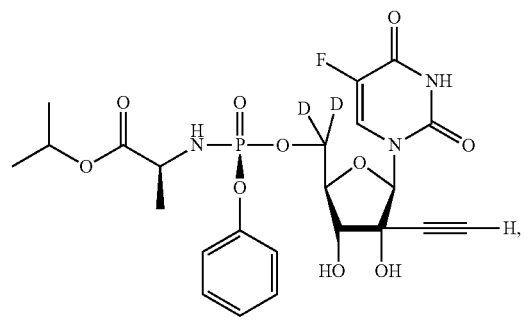
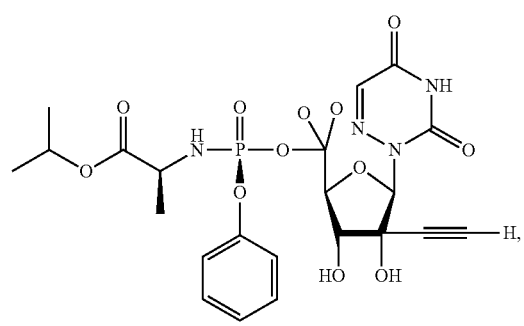
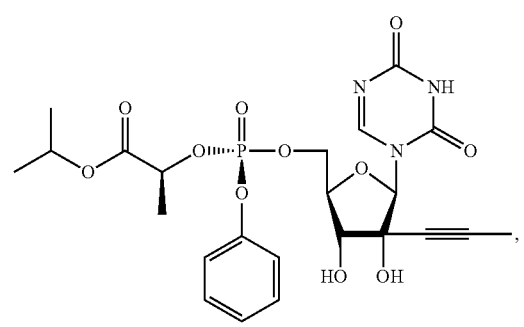
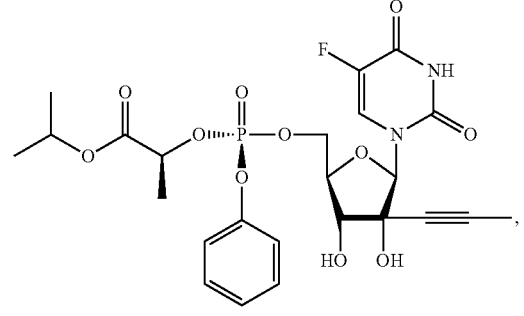
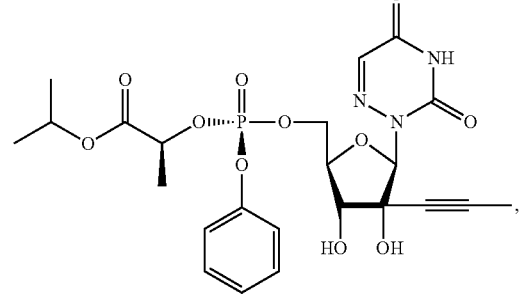
682
-continued
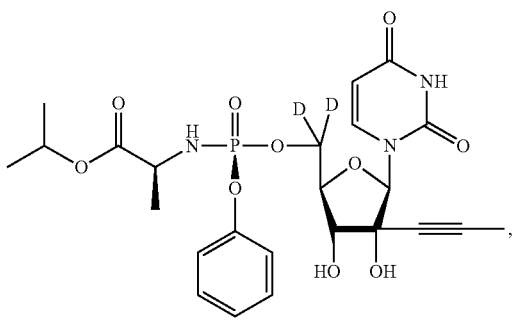
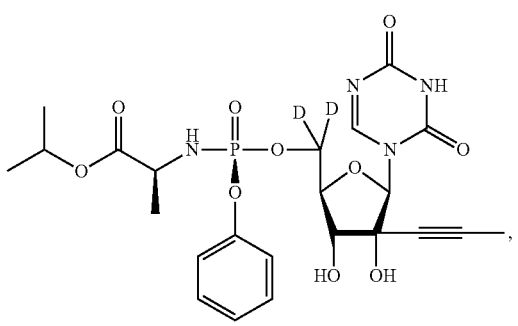
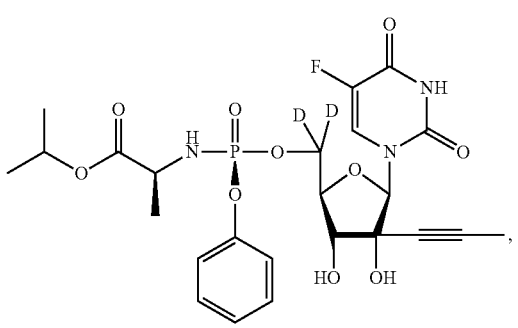
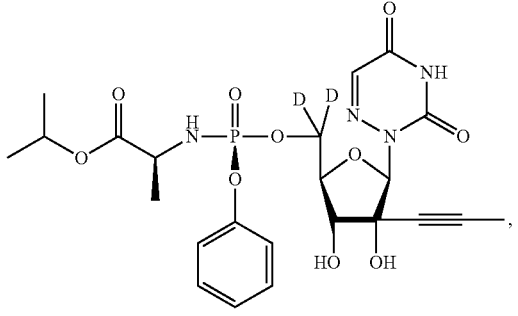
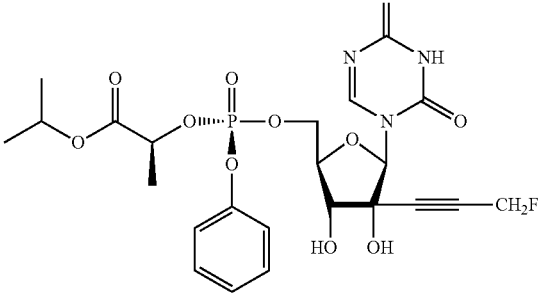

683
-continued

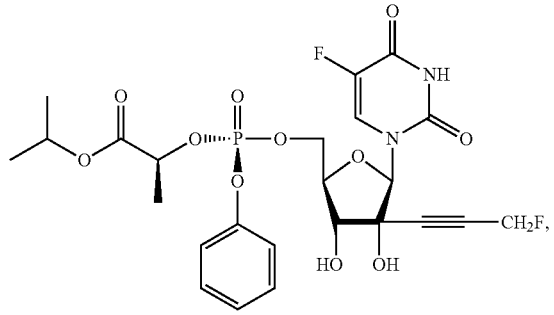

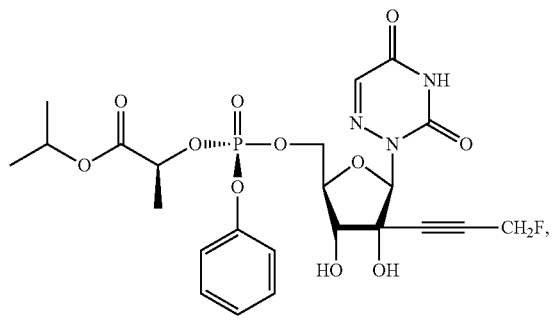

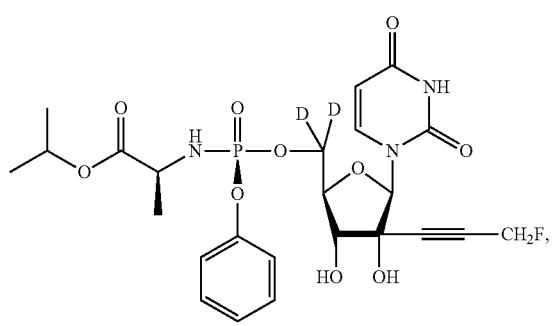

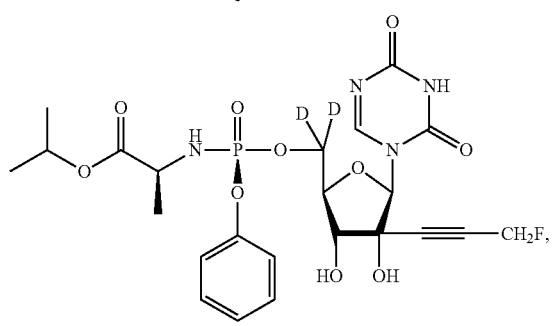

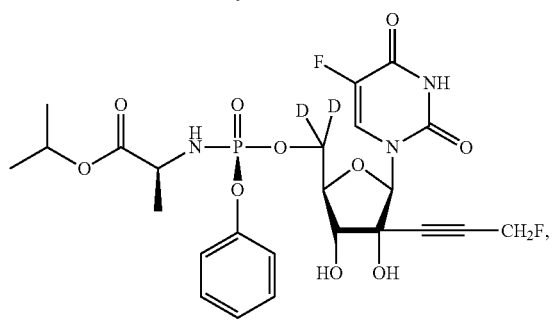

684
-continued

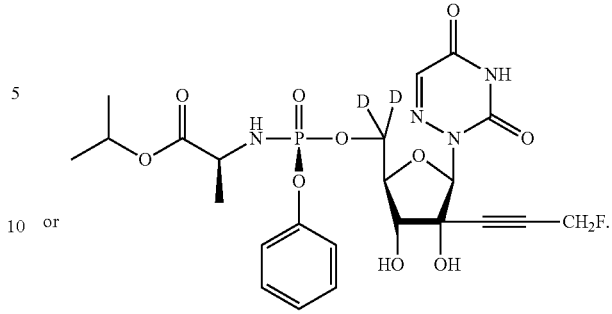

or

5. A pharmaceutical composition comprising a compound of claim 1, or its pharmaceutically acceptable salt, and a pharmaceutically acceptable carrier.

6. A liposomal composition comprising a compound of claim 1, or its pharmaceutically acceptable salt, and a pharmaceutically acceptable carrier.

7. A method of treating infections caused by RNA viruses selected from a flavivirus or a picornavirus comprising administering to a host in need an effective amount of a compound of claim 1, or a pharmaceutically acceptable salt thereof.

8. The method of claim 7, wherein the flavivirus is a tick-borne encephalitis virus, dengue, or a Zika virus.

9. A compound of the following formula:

Formula XLVIIa

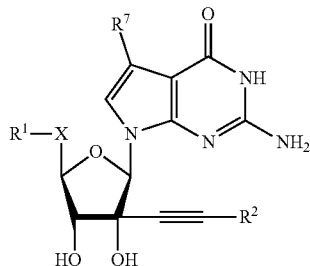

Formula XLVIIb

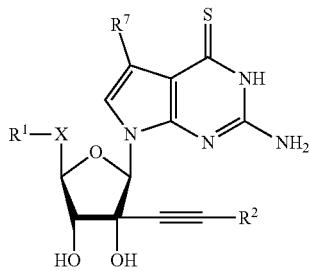

Formula XLVIIc

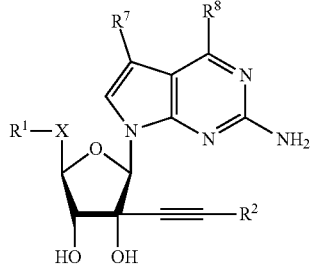

or pharmaceutically acceptable salts thereof wherein,

X is $OCH_2$, $OCHMe$, $OCMe_2$, $OCHF$, $OCF_2$, or $OCD_2$;

$R^1$ is selected from H or from one of the following formulae:

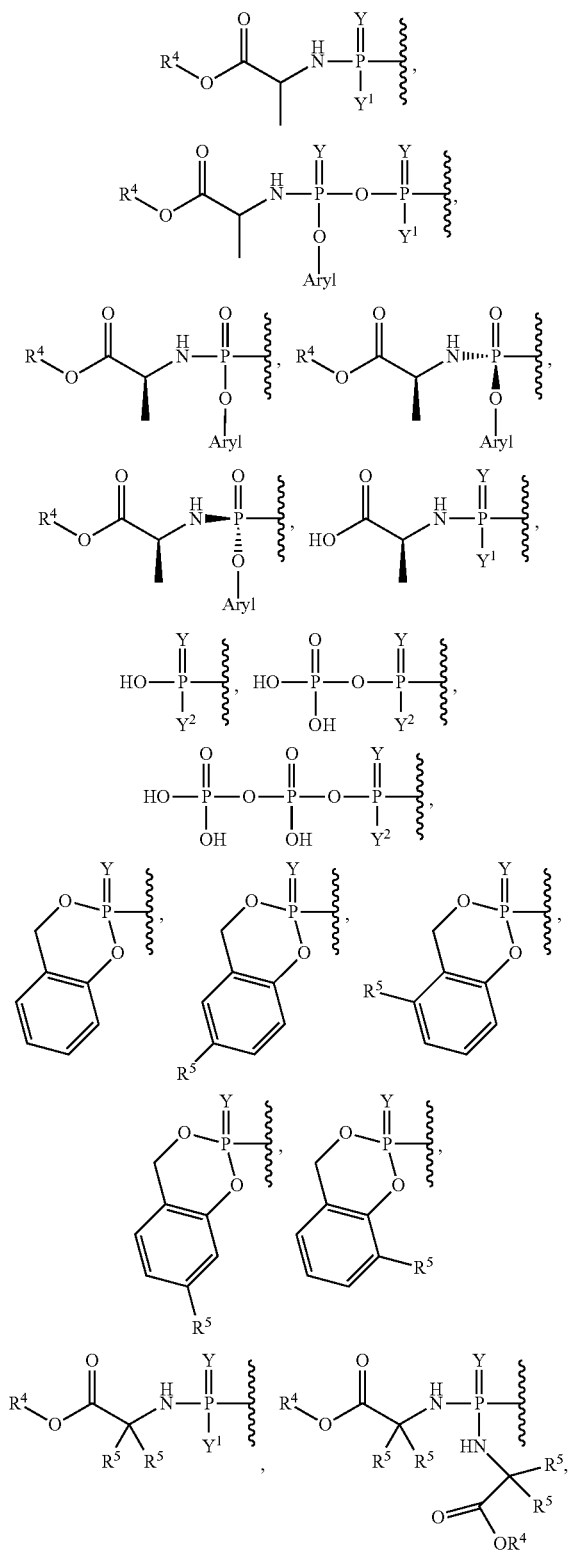
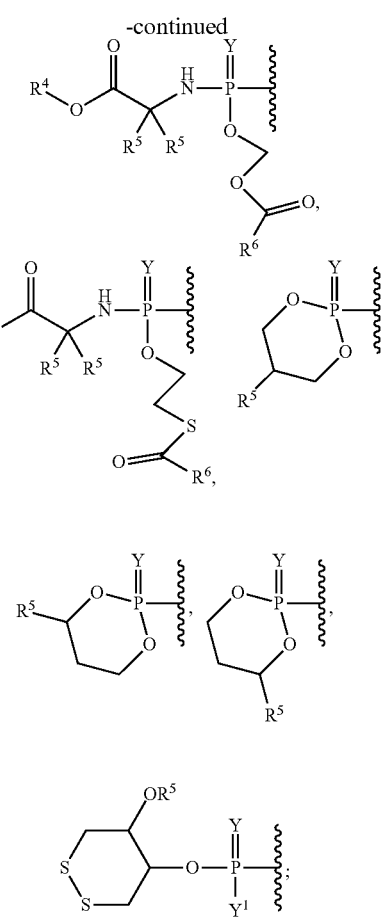

Y is O;

$Y^1$ is OH, OAryl, OAlkyl, or $BH_3^-M^+$;

$Y^2$ is OH or $BH_3^-M^+$;

Aryl is phenyl, 1-naphthyl, 2-naphthyl, aromatic, heteroaromatic group having 1 to 4 heteroatoms selected from nitrogen, oxygen and sulfur, and containing at least 1 carbon atom, 4-substituted phenyl, 4-chlorophenyl, or 4-bromophenyl;

$R^2$ is hydrogen, methyl, fluoromethyl, difluoromethyl, trifluoromethyl, ethyl, cyclopropyl, fluoro, hydroxymethyl, aminomethyl, vinyl, or cyclobutyl;

$R^4$ is hydrogen, methyl, ethyl, isopropyl, cyclopentyl, cyclohexyl, neopentyl, benzyl, alkyl, branched alkyl, cycloalkyl, or lipid substituent;

$R^5$ is hydrogen, deuterium, hydroxyl, cyano, azido, amino, substituted amino, aryl, heteroaryl group having 1 to 4 heteroatoms selected from nitrogen, oxygen and sulfur, and containing at least 1 carbon atom, substituted aryl, lipid substituent, $C_{1-22}$ alkoxy, $C_{1-22}$ alkyl, $C_{2-22}$ alkenyl, $C_{2-22}$ alkynyl, or substituted heteroaryl group having 1 to 4 heteroatoms selected from nitrogen, oxygen and sulfur, and containing at least 1 carbon atom;

$R^6$ is methyl, ethyl, tert-butyl, $C_{1-22}$ alkoxy, $C_{1-22}$ alkyl, branched alkyl, cycloalkyl, aryl, substituted aryl, or alkyoxy;

$R^7$ is H, D, hydroxyl, thiol, amino, $C_{1-4}$ alkyl, methyl, fluoromethyl, difluoromethyl, trifluoromethyl, hydroxymethyl, $C_{2-4}$ alkenyl, $C_{2-4}$ alkynyl, ethynyl, azido, fluoro, chloro, bromo, iodo, or cyano;

$R^8$ is H, D, $C_{1-4}$ alkyl, fluoro, chloro, bromo, or iodo; or a compound of the following formula:

Formula XLVIIIa

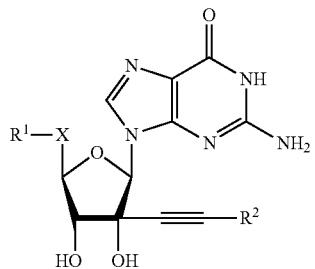

Formula XLVIIIb

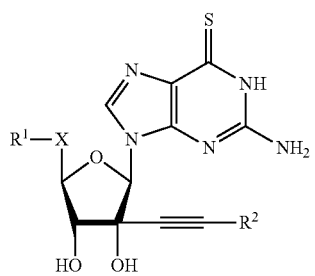

Formula XLVIIIc

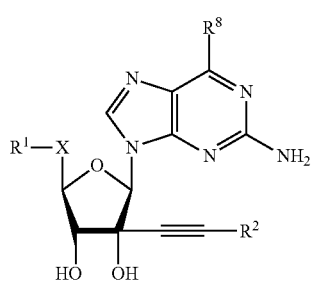

or pharmaceutically acceptable salts thereof wherein,
X is $OCH_2$, OCHMe, $OCMe_2$, OCHF, $OCF_2$, or $OCD_2$;
$R^1$ is selected from H or from one of the following formulae:

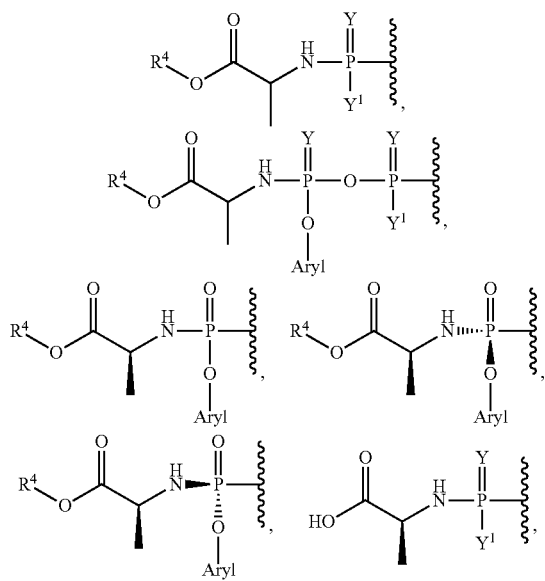

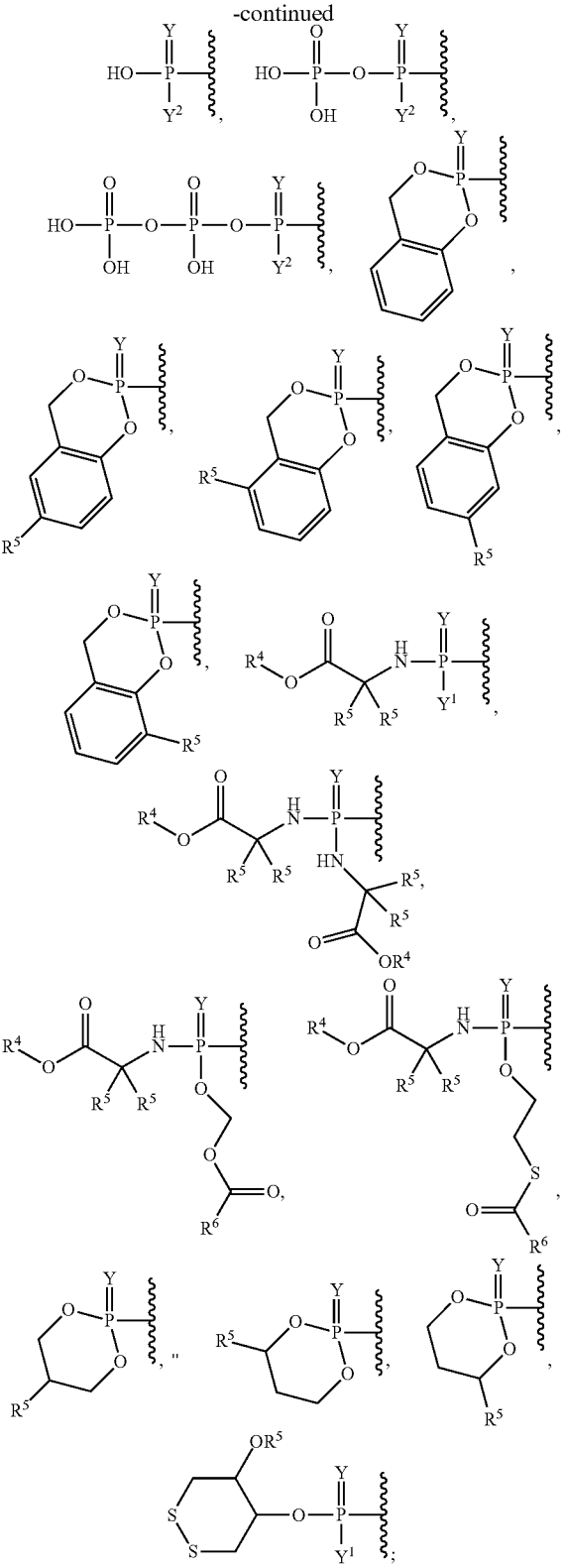

Y is O;
$Y^1$ is OH, OAryl, OAlkyl, or $BH_3^-M^+$;
$Y^2$ is OH or $BH_3^-M^+$;
Aryl is phenyl, 1-naphthyl, 2-naphthyl, aromatic, heteroaromatic group having 1 to 4 heteroatoms selected from nitrogen, oxygen and sulfur, and containing at least 1 carbon atom, 4-substituted phenyl, 4-chlorophenyl, or 4-bromophenyl;

$R^2$ is methyl, fluoromethyl, difluoromethyl, trifluoromethyl, cyclopropyl, fluoro, hydroxymethyl, aminomethyl, vinyl, or cyclobutyl;

$R^4$ is hydrogen, methyl, ethyl, isopropyl, cyclopentyl, cyclohexyl, neopentyl, benzyl, alkyl, branched alkyl, cycloalkyl, or lipid substituent;

$R^5$ is hydrogen, deuterium, hydroxyl, cyano, azido, amino, substituted amino, aryl, heteroaryl group having 1 to 4 heteroatoms selected from nitrogen, oxygen and sulfur, and containing at least 1 carbon atom, substituted aryl, lipid substituent, $C_{1-22}$ alkoxy, $C_{1-22}$ alkyl, $C_{2-22}$ alkenyl, $C_{2-22}$ alkynyl, or substituted heteroaryl group having 1 to 4 heteroatoms selected from nitrogen, oxygen and sulfur, and containing at least 1 carbon atom;

$R^6$ is methyl, ethyl, tert-butyl, $C_{1-22}$ alkoxy, $C_{1-22}$ alkyl, branched alkyl, cycloalkyl, aryl, substituted aryl, or alkyoxy;

$R^8$ is H, D, $C_{1-4}$ alkyl, fluoro, chloro, bromo, or iodo; or a compound of the following formula:

Formula XLIXa

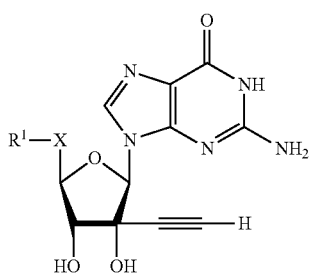

Formula XLIXb

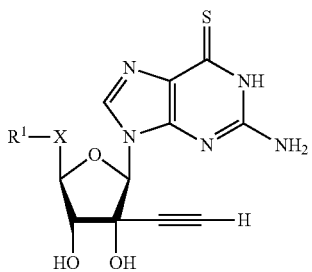

Formula XLIXc

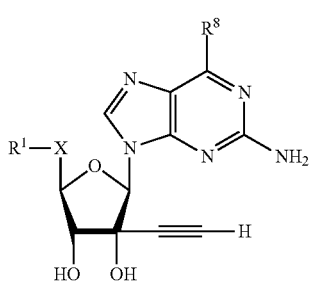

or pharmaceutically acceptable salts thereof wherein,

X is $OCHMe$, $OCMe_2$, $OCHF$, $OCF_2$, or $OCD_2$;

$R^1$ is selected from H or from one of the following formulae:

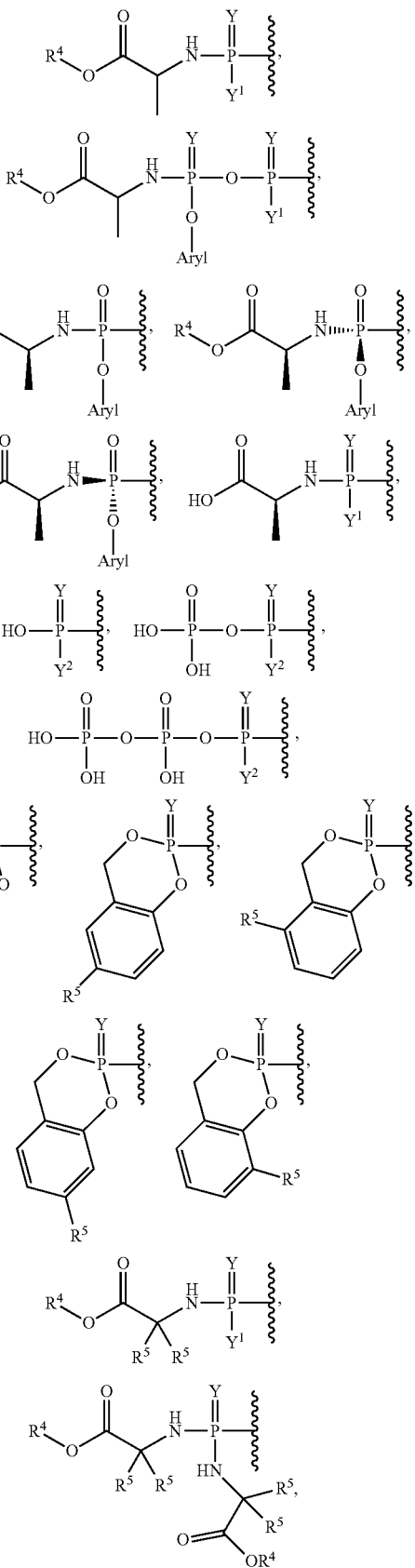

-continued

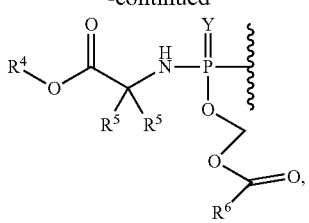

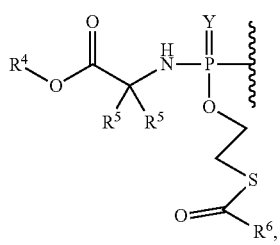

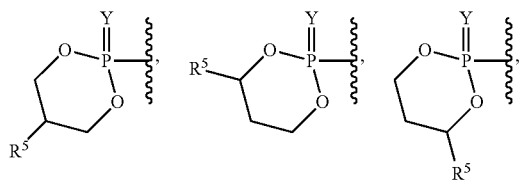

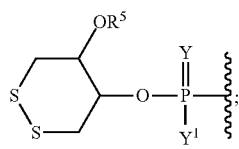

Y is O;
Y$^1$ is OH, OAryl, OAlkyl, or BH$_3^-$M$^+$;
Y$^2$ is OH or BH$_3^-$M$^+$;
Aryl is phenyl, 1-naphthyl, 2-naphthyl, aromatic, heteroaromatic group having 1 to 4 heteroatoms selected from nitrogen, oxygen and sulfur, and containing at least 1 carbon atom, 4-substituted phenyl, 4-chlorophenyl, or 4-bromophenyl;
R$^4$ is hydrogen, methyl, ethyl, isopropyl, cyclopentyl, cyclohexyl, neopentyl, benzyl, alkyl, branched alkyl, cycloalkyl, or lipid substituent;
R$^5$ is hydrogen, deuterium, hydroxyl, cyano, azido, amino, substituted amino, aryl, heteroaryl group having 1 to 4 heteroatoms selected from nitrogen, oxygen and sulfur, and containing at least 1 carbon atom, substituted aryl, lipid substituent, C$_{1-22}$ alkoxy, C$_{1-22}$ alkyl, C$_{2-22}$ alkenyl, C$_{2-22}$ alkynyl, or substituted heteroaryl group having 1 to 4 heteroatoms selected from nitrogen, oxygen and sulfur, and containing at least 1 carbon atom;
R$^6$ is methyl, ethyl, tert-butyl, C$_{1-22}$ alkoxy, C$_{1-22}$ alkyl, branched alkyl, cycloalkyl, aryl, substituted aryl, or alkyoxy;
R$^8$ is H, D, C$_{1-4}$ alkyl, fluoro, chloro, bromo, or iodo; or a compound of the following formula:

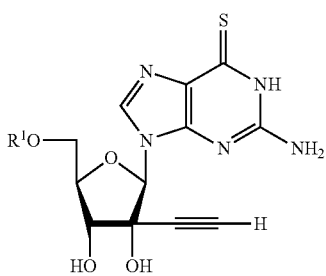

Formula La

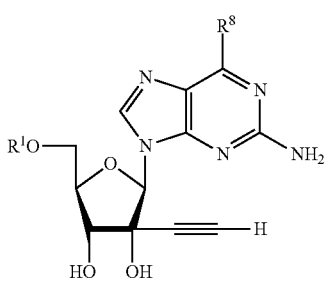

Formula Lb or pharmaceutically acceptable salts thereof wherein,
R$^1$ is selected from H or from one of the following formulae:

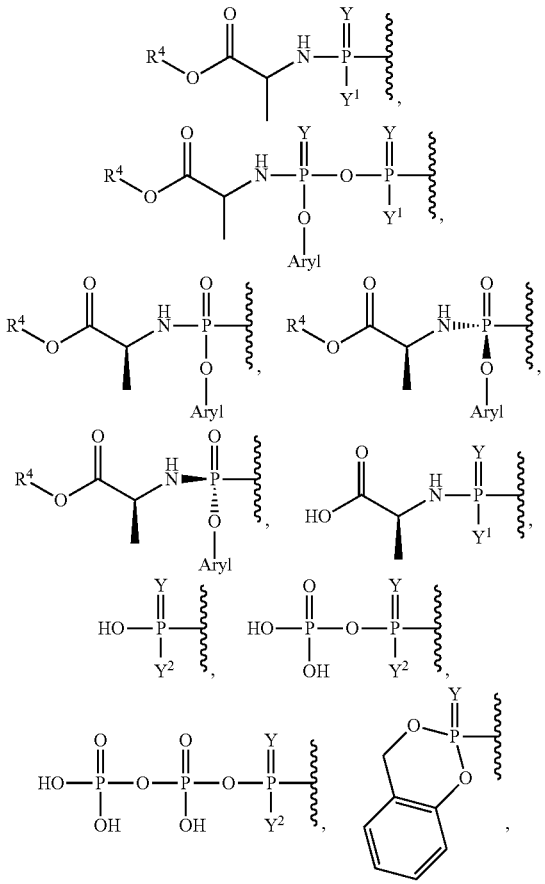

-continued

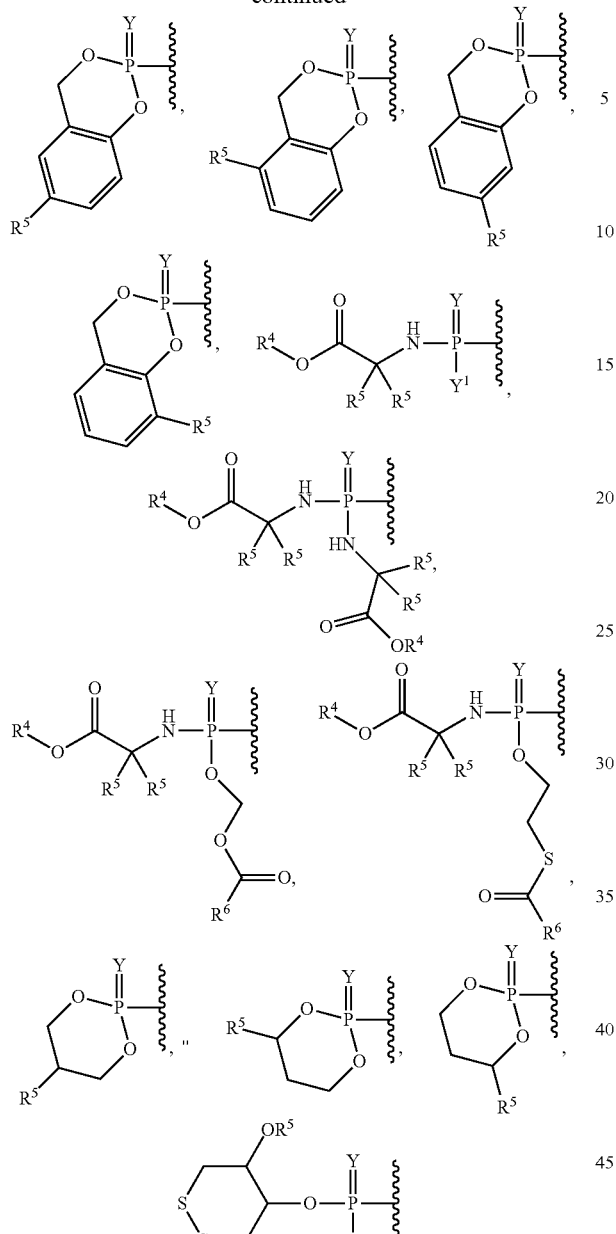

Y is O;
Y¹ is OH, OAryl, OAlkyl, or $BH_3^-M^+$;
Y² is OH or $BH_3^-M^+$;
Aryl is phenyl, 1-naphthyl, 2-naphthyl, aromatic, heteroaromatic group having 1 to 4 heteroatoms selected from nitrogen, oxygen and sulfur, and containing at least 1 carbon atom, 4-substituted phenyl, 4-chlorophenyl, or 4-bromophenyl;
R⁴ is hydrogen, methyl, ethyl, isopropyl, cyclopentyl, cyclohexyl, neopentyl, benzyl, alkyl, branched alkyl, cycloalkyl, or lipid substituent;
R⁵ is hydrogen, deuterium, hydroxyl, cyano, azido, amino, substituted amino, aryl, heteroaryl group having 1 to 4 heteroatoms selected from nitrogen, oxygen and sulfur, and containing at least 1 carbon atom, substituted aryl, lipid substituent, $C_{1-22}$ alkoxy, $C_{1-22}$ alkyl, $C_{2-22}$ alkenyl, $C_{2-22}$ alkynyl, or substituted heteroaryl group having 1 to 4 heteroatoms selected from nitrogen, oxygen and sulfur, and containing at least 1 carbon atom;
R⁶ is methyl, ethyl, tert-butyl, $C_{1-22}$ alkoxy, $C_{1-22}$ alkyl, branched alkyl, cycloalkyl, aryl, substituted aryl, or alkyoxy;
R⁸ is H, D, $C_{1-4}$ alkyl, fluoro, chloro, bromo, or iodo, wherein when a moiety is substituted, the substituent is selected from halogen, hydroxy, alkyl, alkoxy, nitro, cyano, oxo, aryl, arylalkyl, heteroaryl, or heteroarylalkyl;

wherein the lipid substituent is selected from optionally substituted $C_{6-22}$ alkoxy; optionally substituted $C_{6-22}$ alkyl; optionally substituted aryl substituted with $C_{6-22}$ alkyl; or optionally substituted polyethylene glycol, wherein the lipid substituent optionally comprises an alcohol; amine; thiol; has one or more of its carbon units substituted with an oxygen, nitrogen, or sulfur; or the lipid substituent is unsaturated or polyunsaturated.

10. The compound of claim 9 selected from the following:

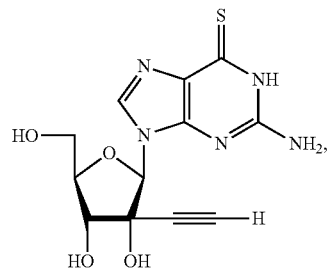

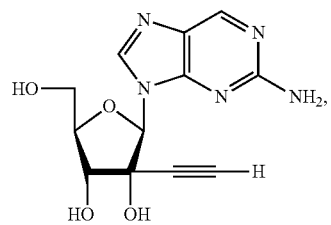

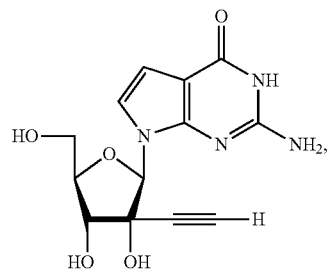

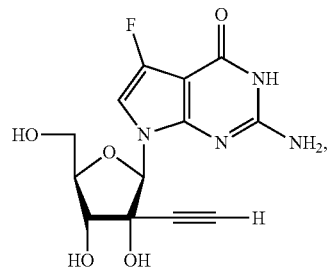

-continued
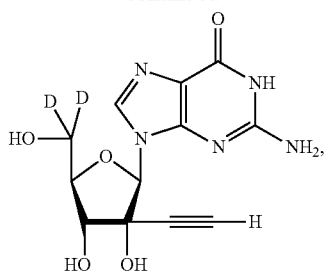
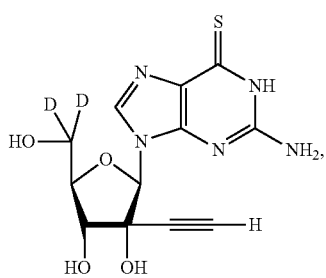
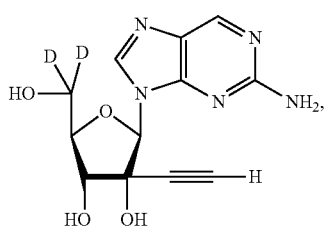
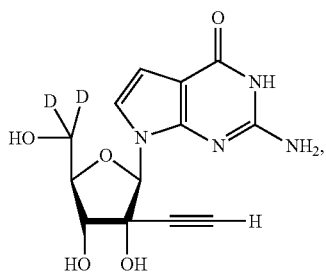
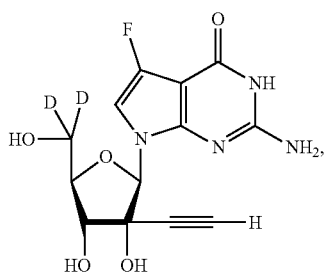
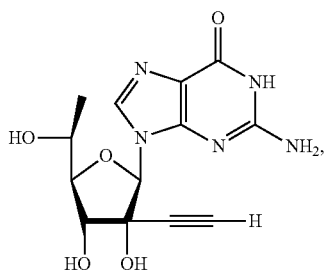
-continued
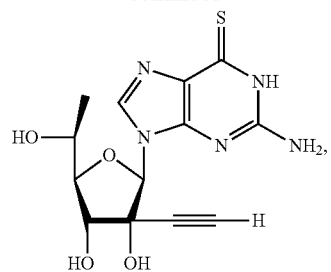
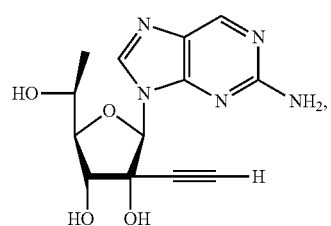
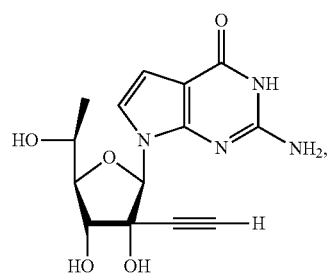
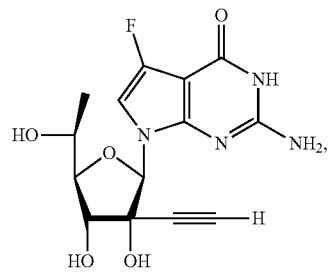
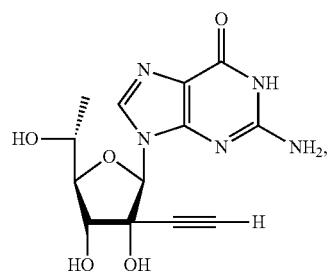
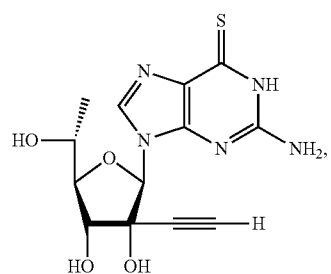

697
-continued
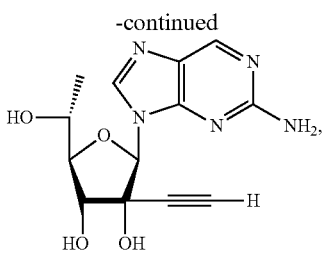
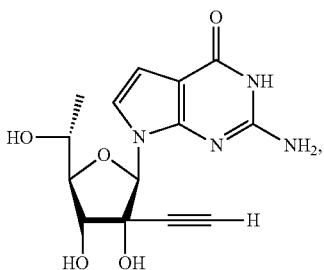
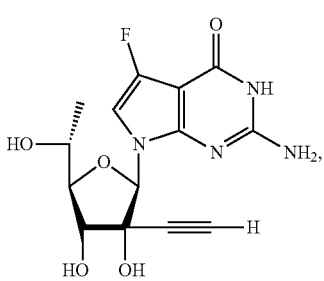
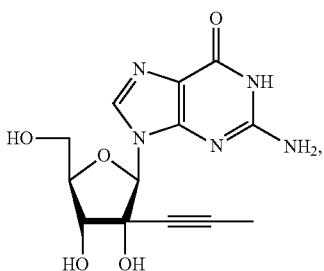
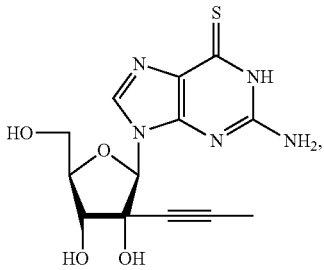
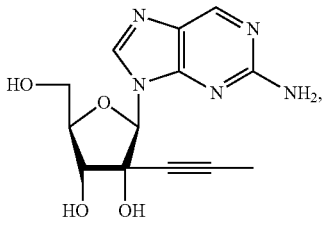
698
-continued
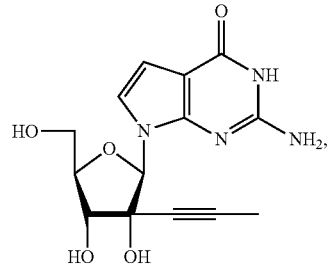
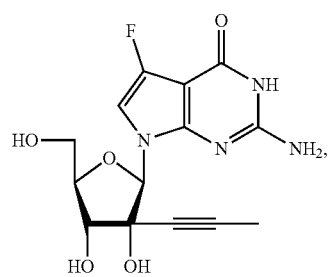
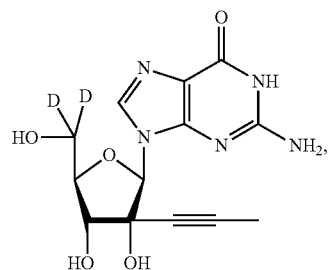
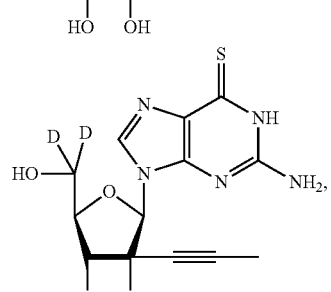
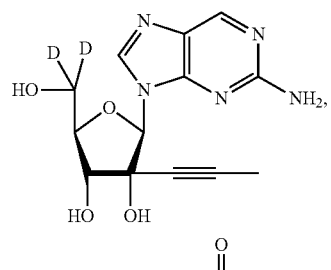
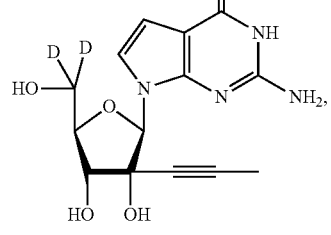

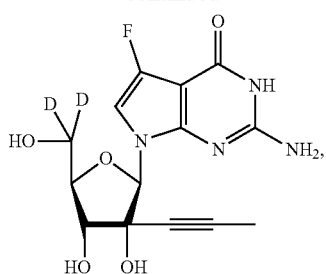
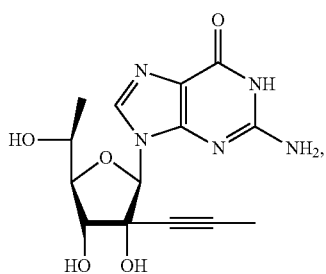
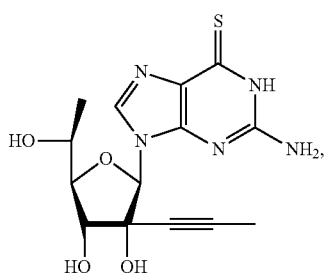
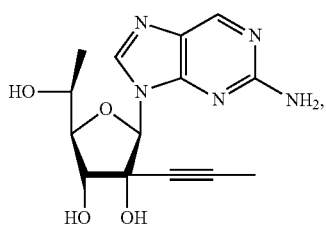
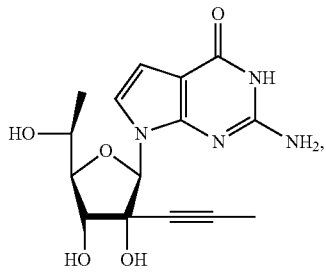
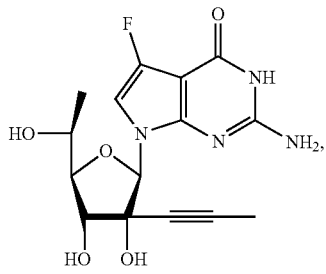
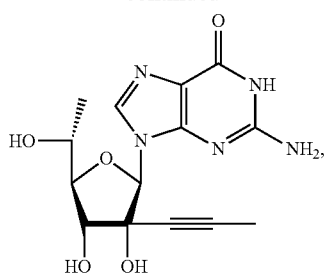
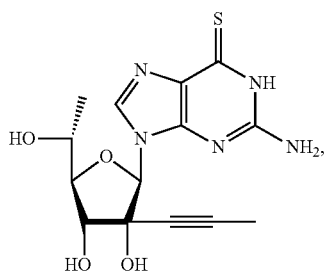
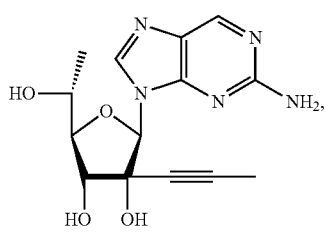
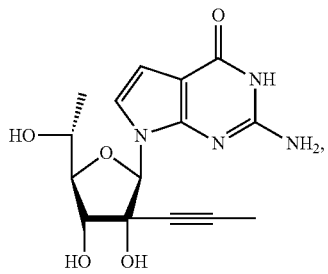
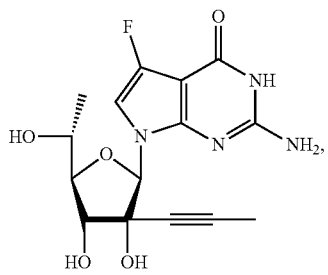
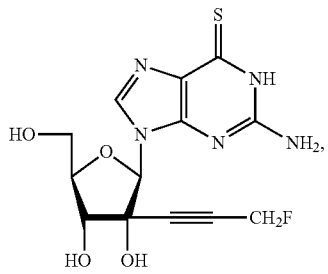

701
-continued
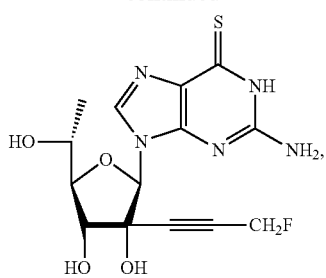
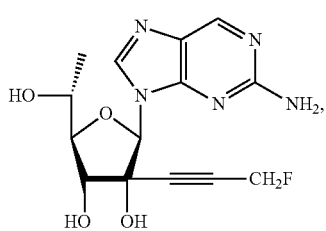
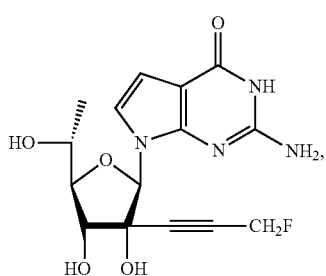
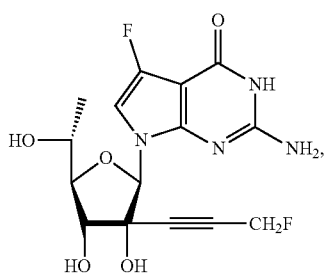
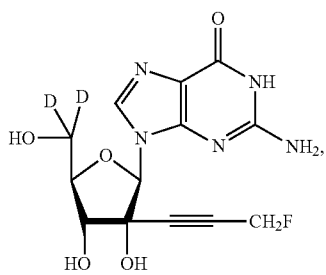
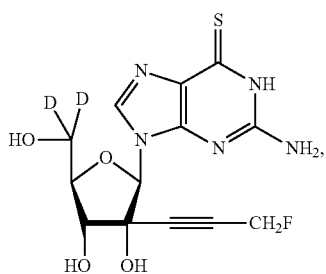
702
-continued
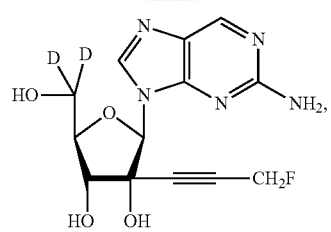
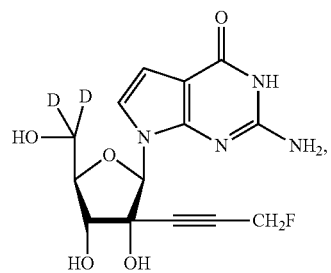
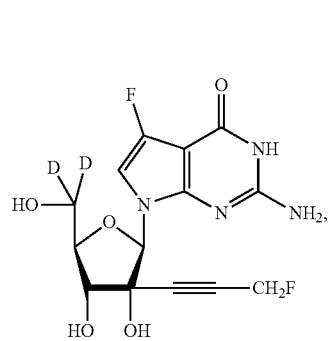
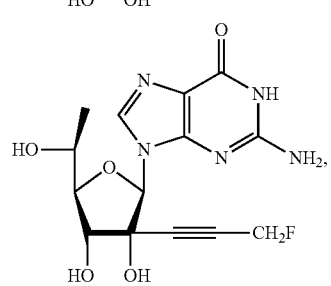
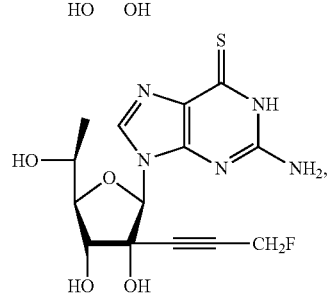
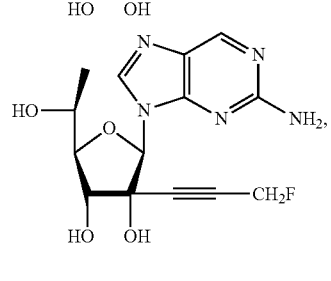

703
-continued
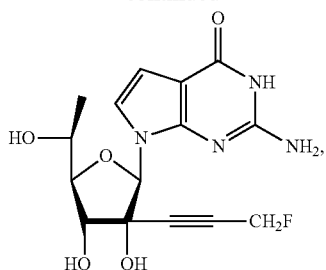
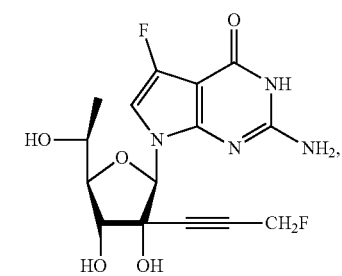
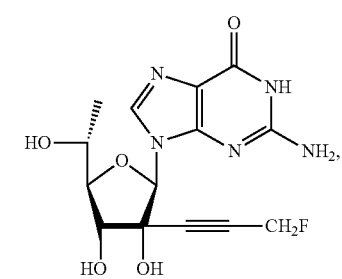
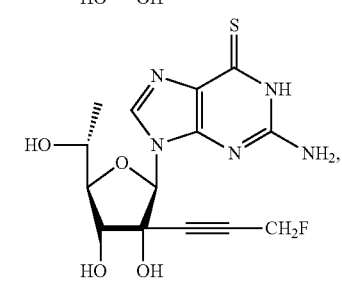
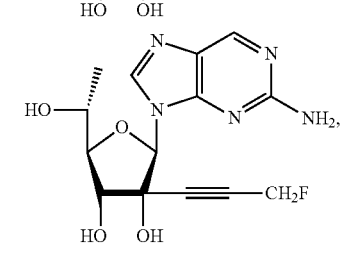
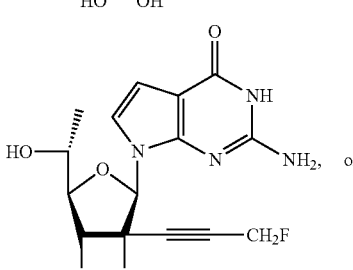 or
704
-continued
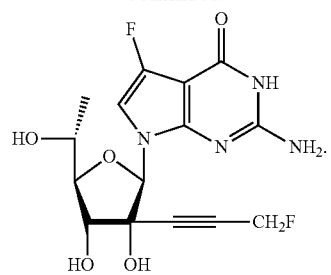
11. The compound of claim 9 selected from the following:
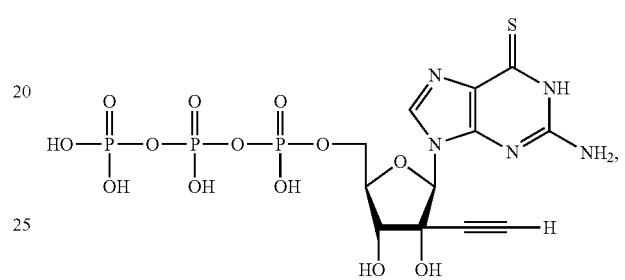
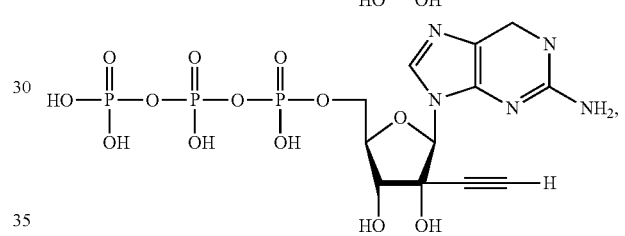
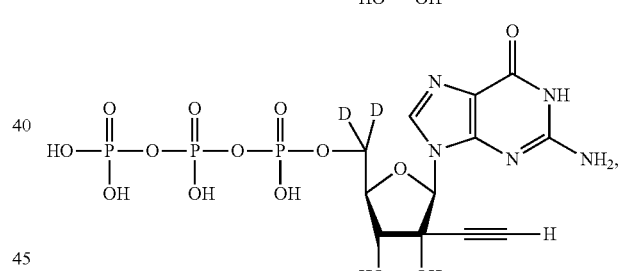
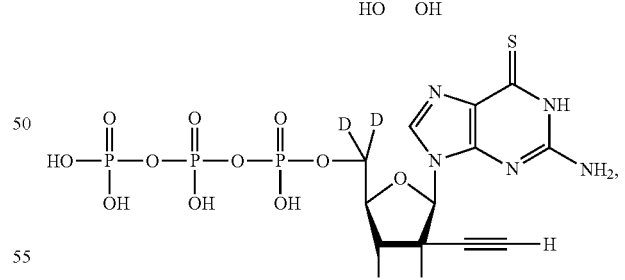
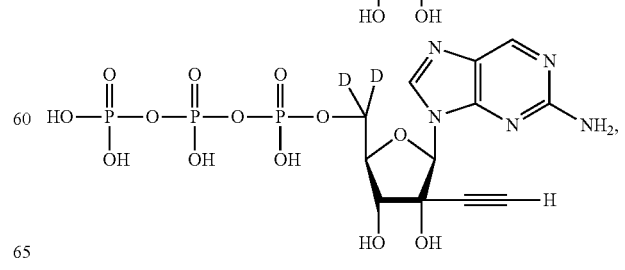

705
-continued
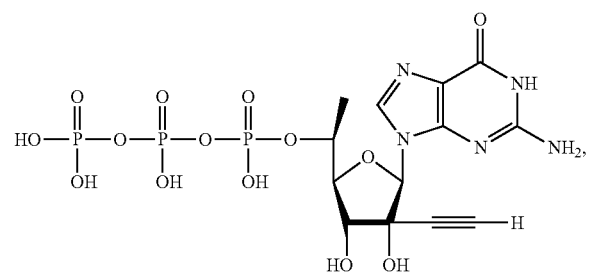
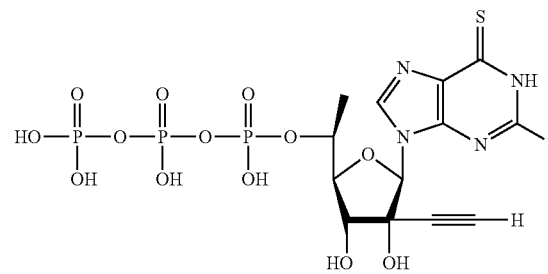
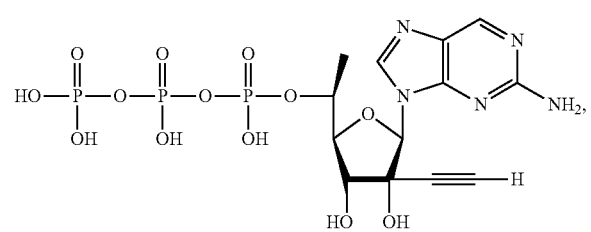
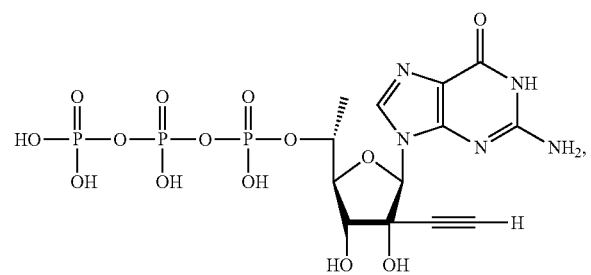
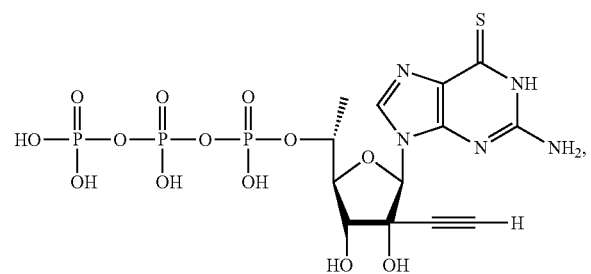
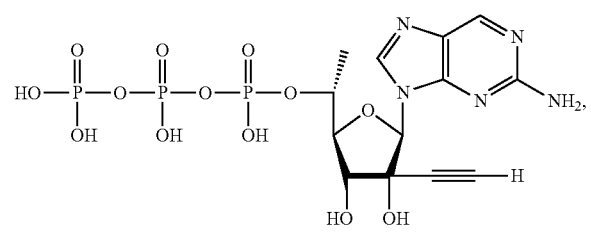
706
-continued
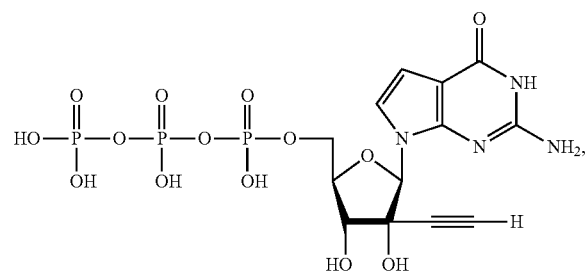
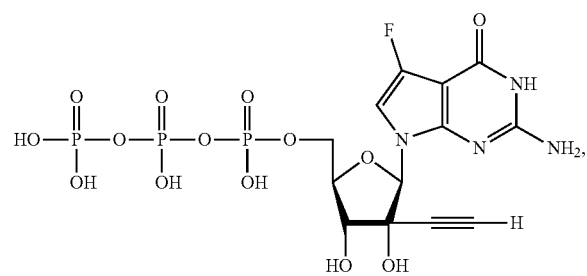
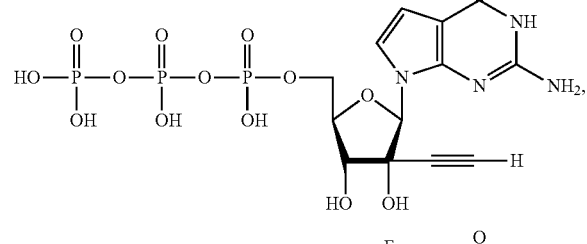
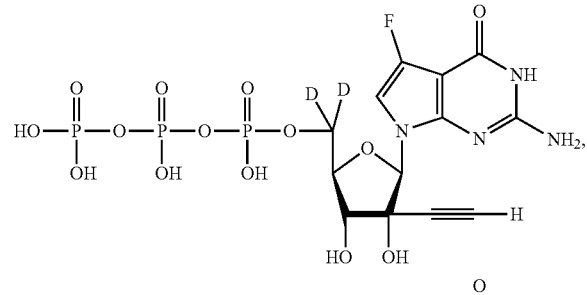
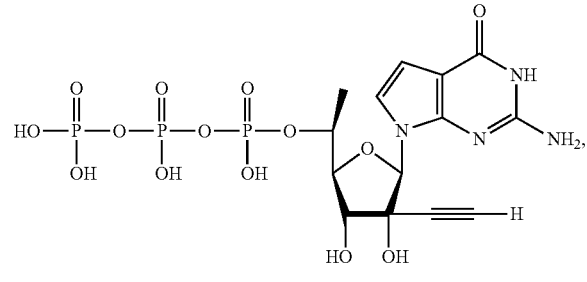
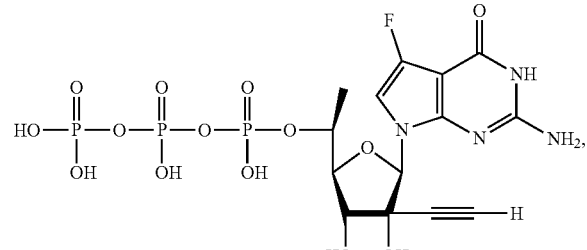

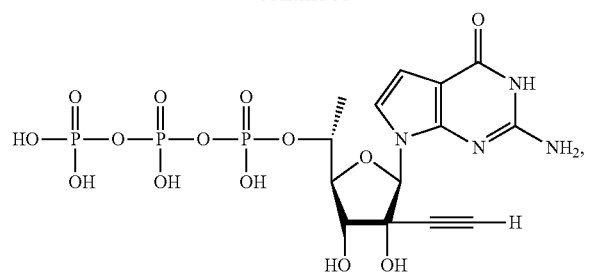
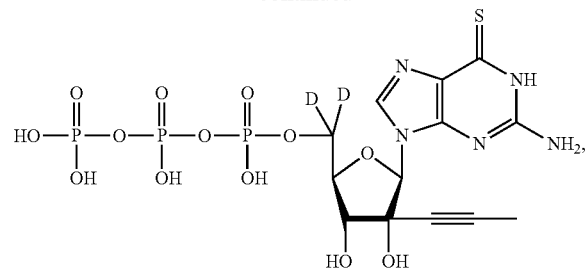
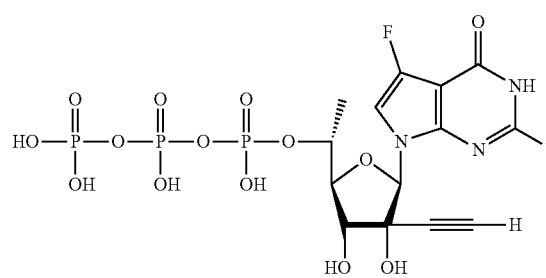
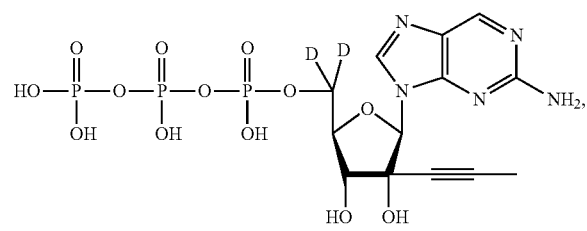
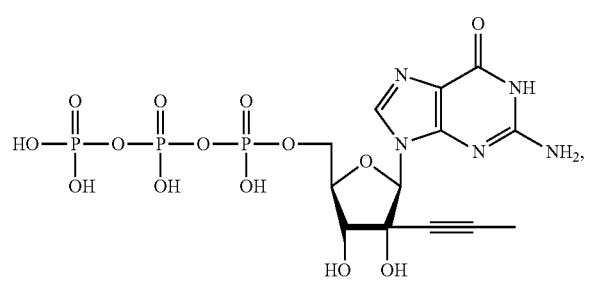
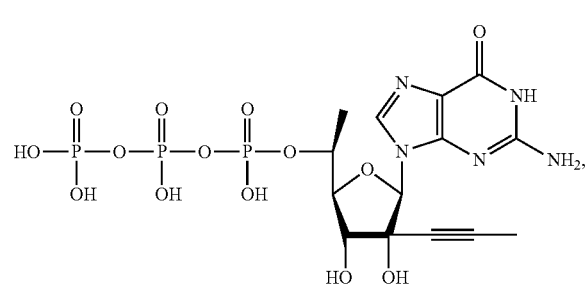
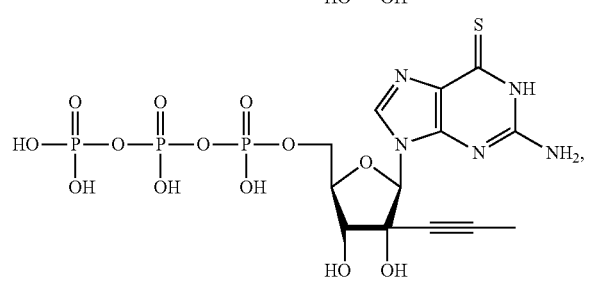
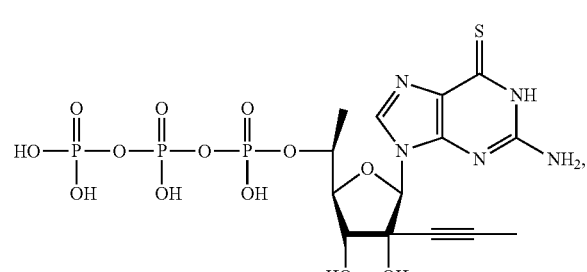
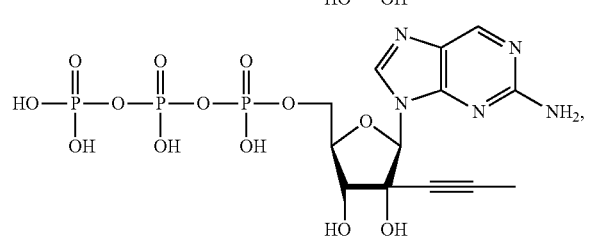
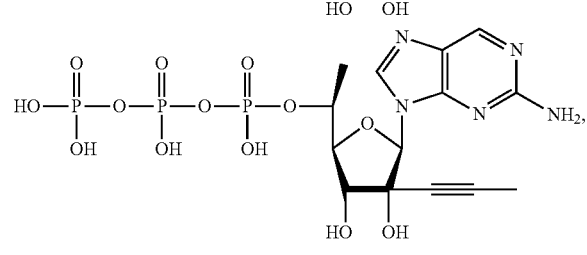
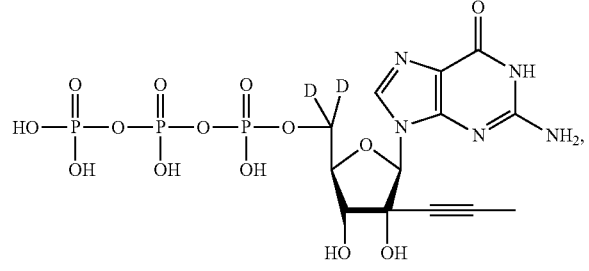
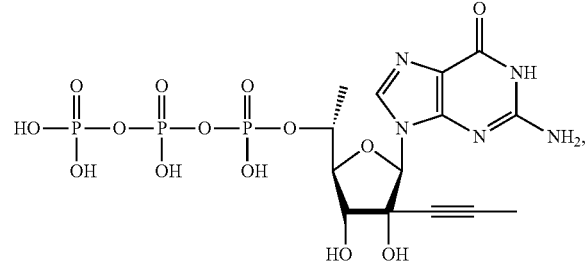

709
-continued
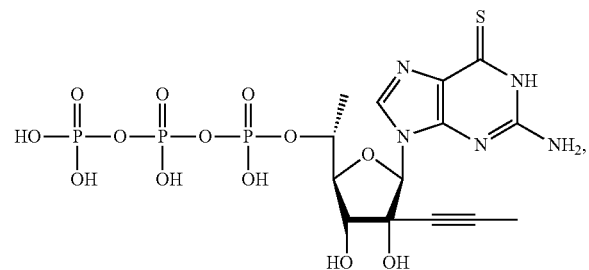
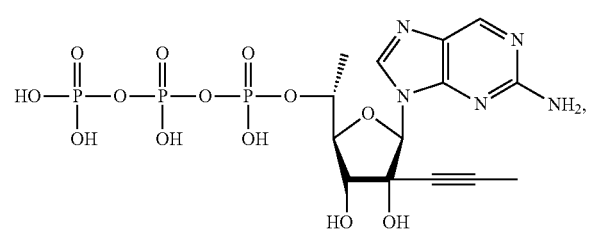
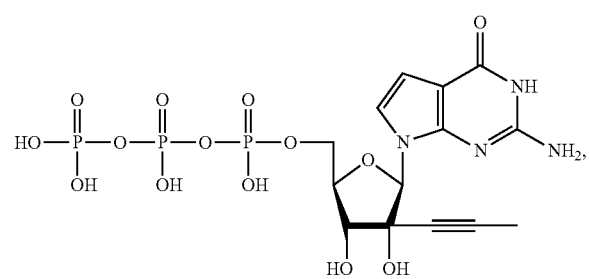
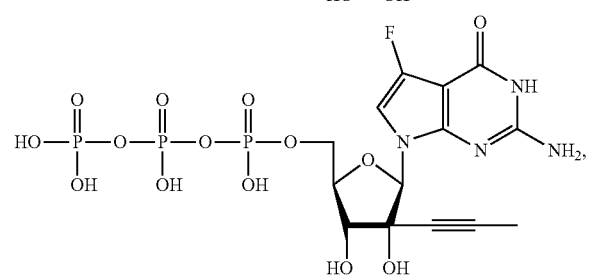
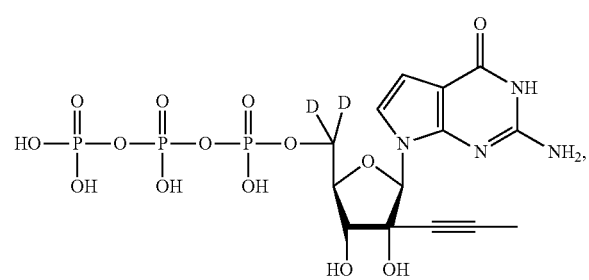
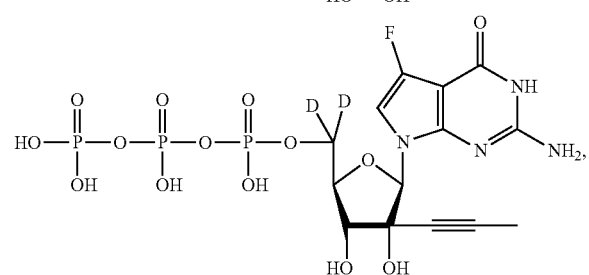
710
-continued
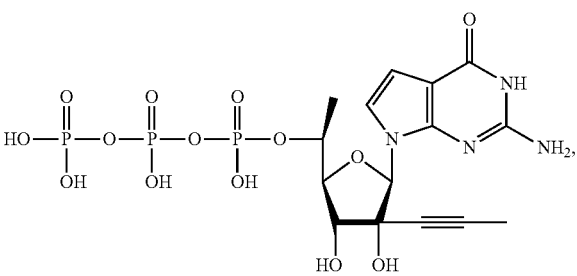
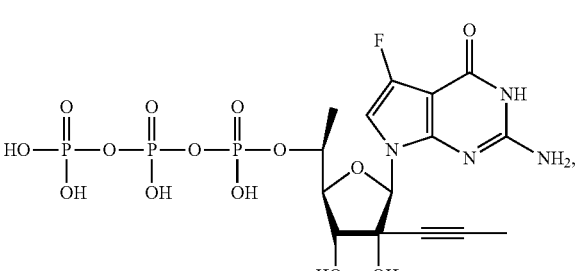
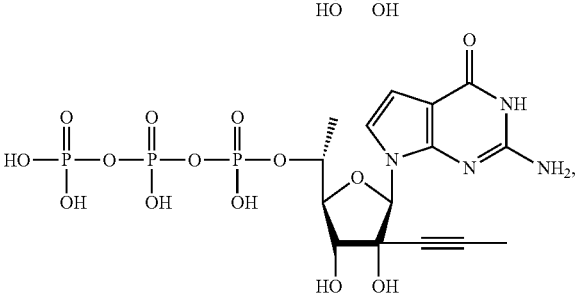
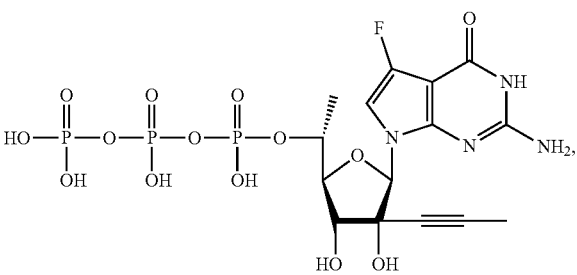
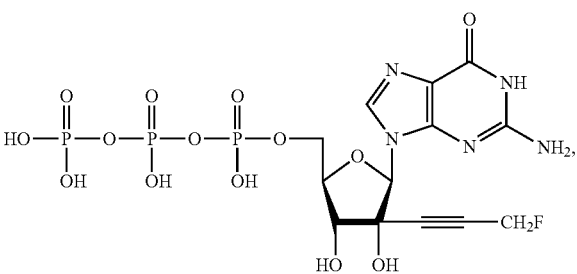
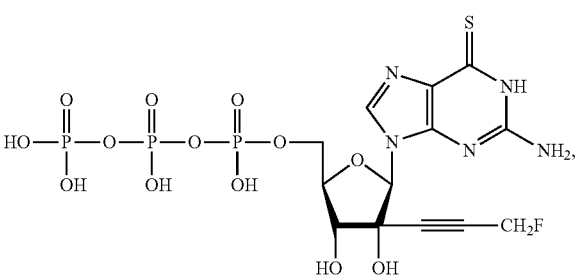

711
-continued
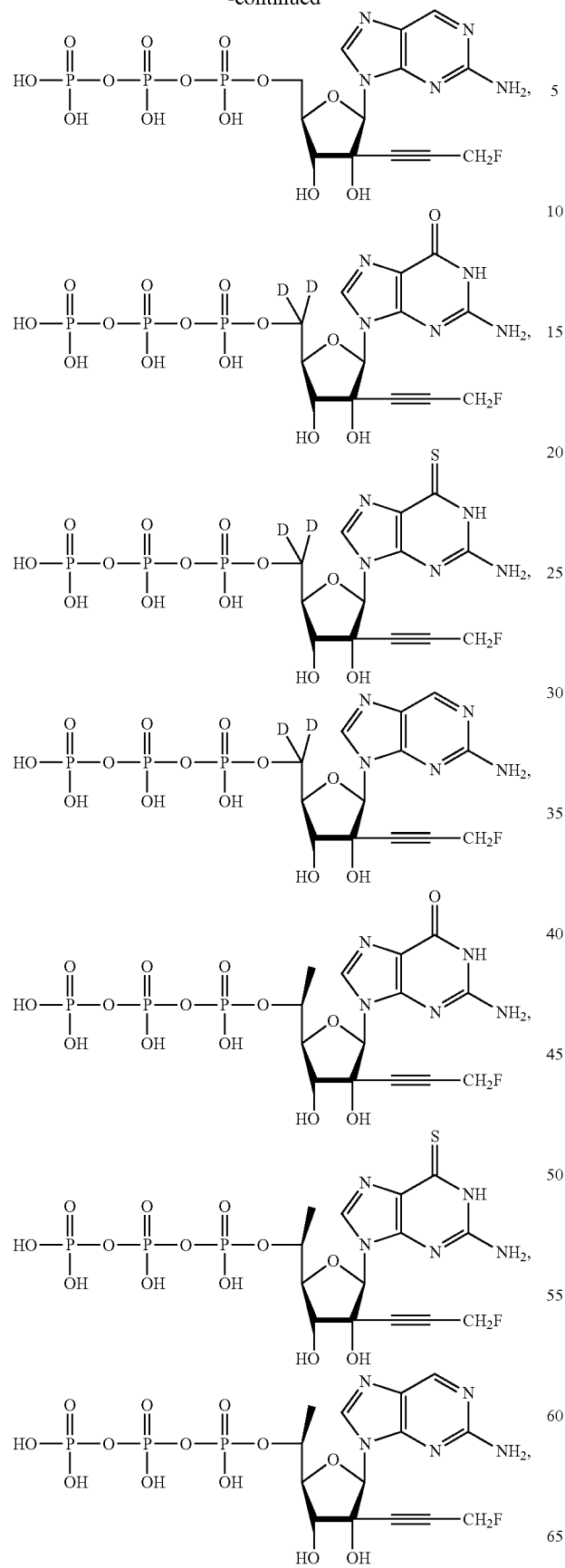
712
-continued
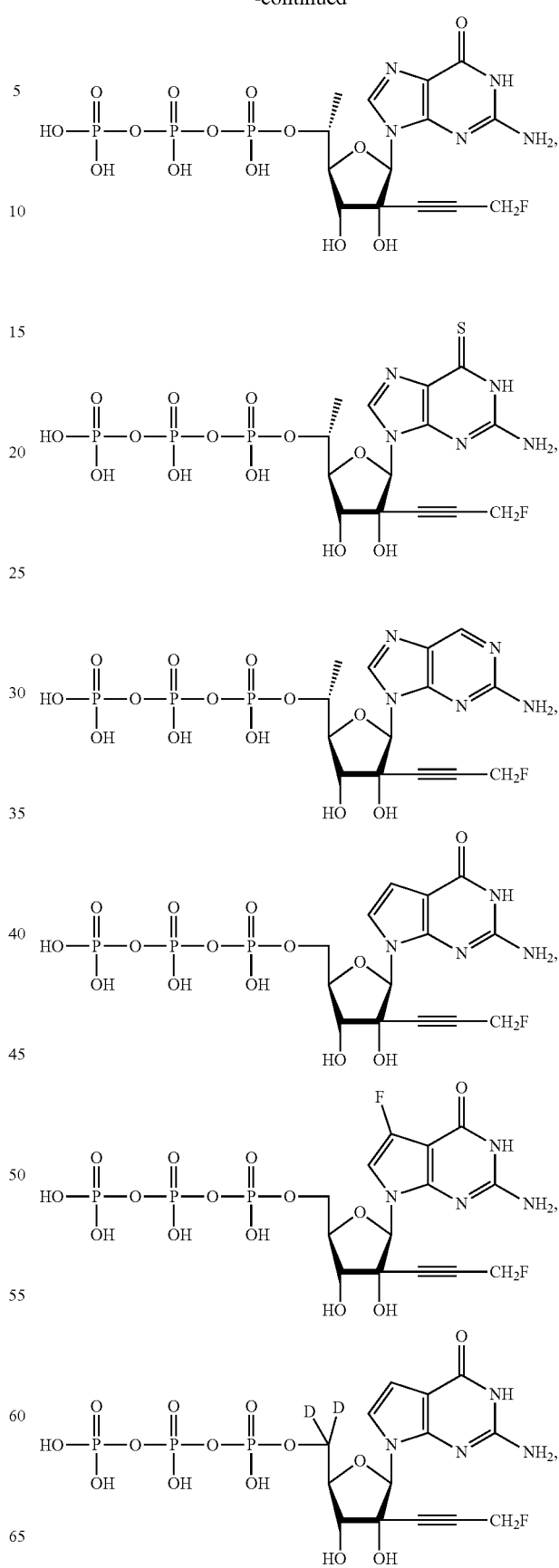

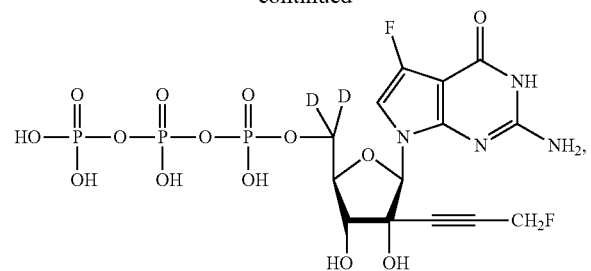
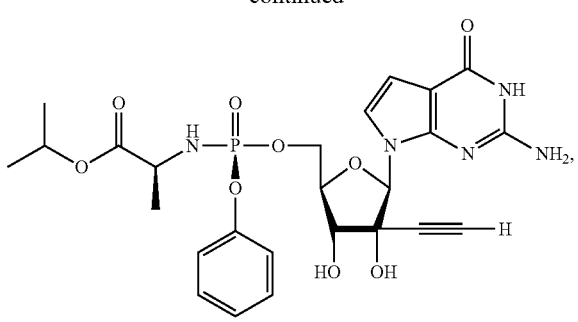
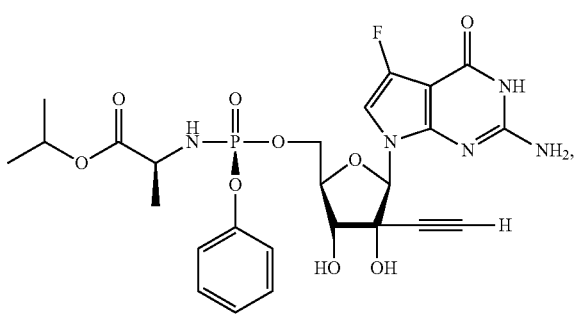
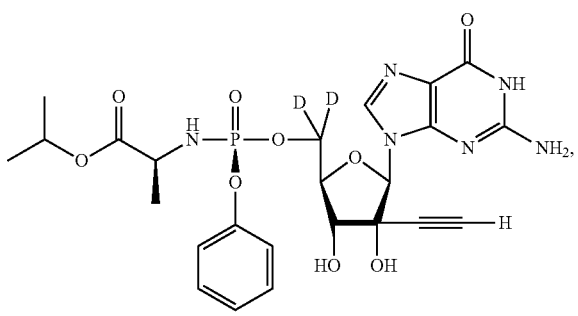
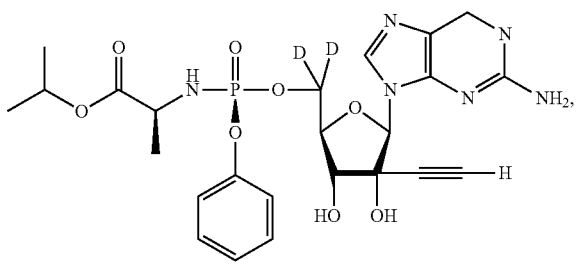
12. The compound of claim 9 selected from the following:
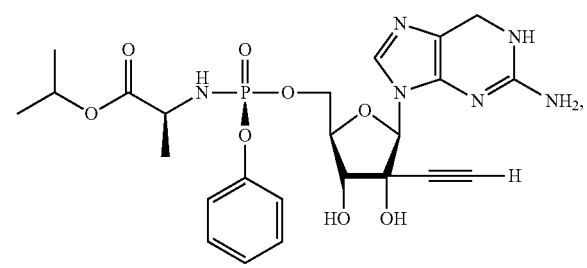
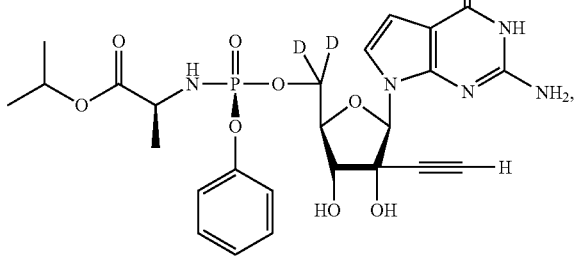

715
-continued
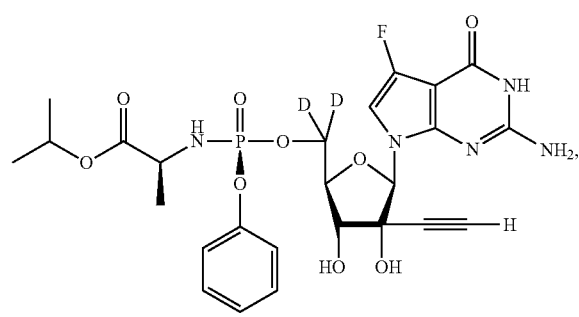
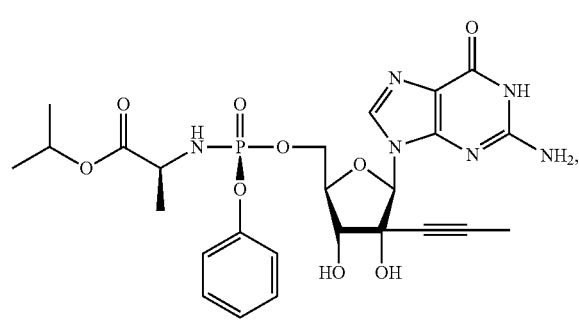
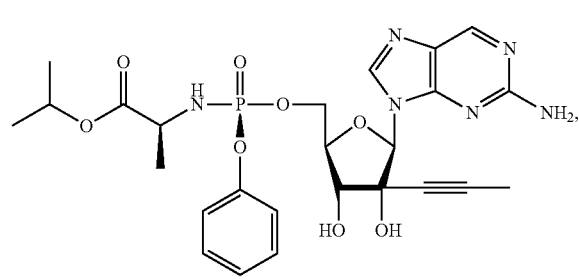
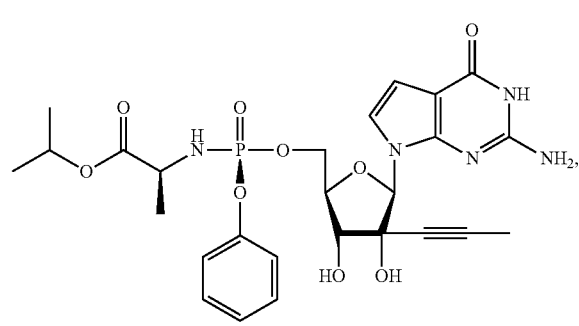
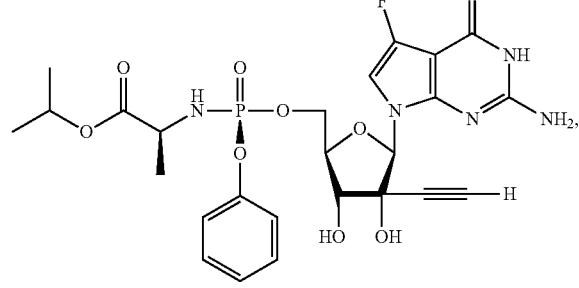
716
-continued
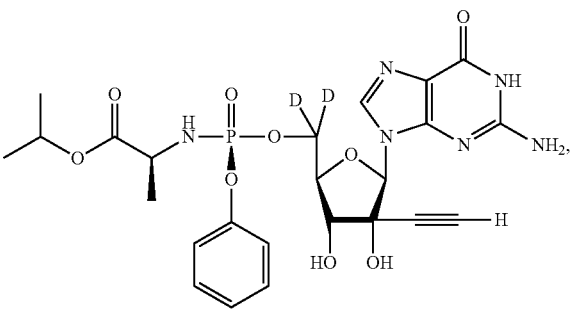
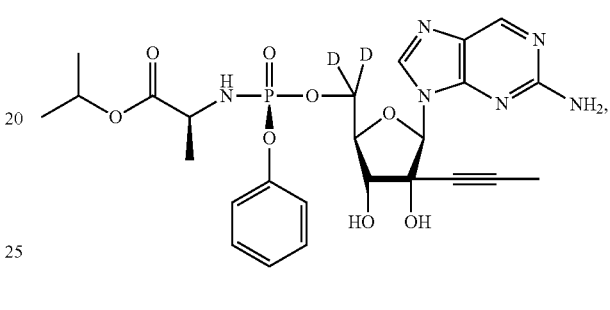
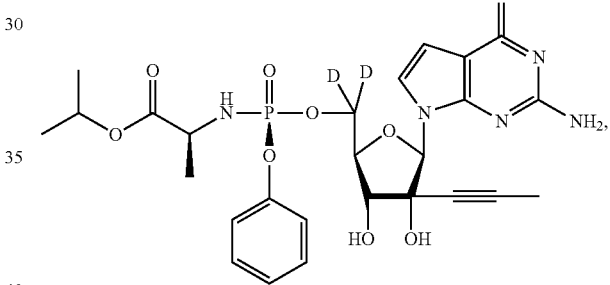
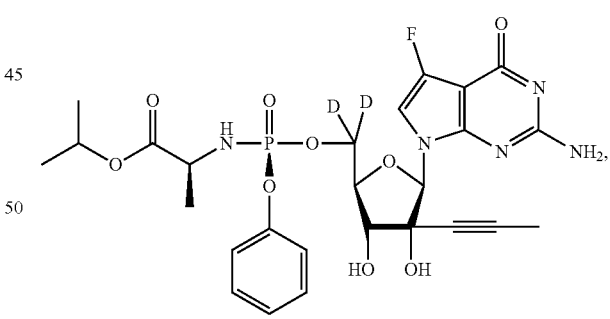
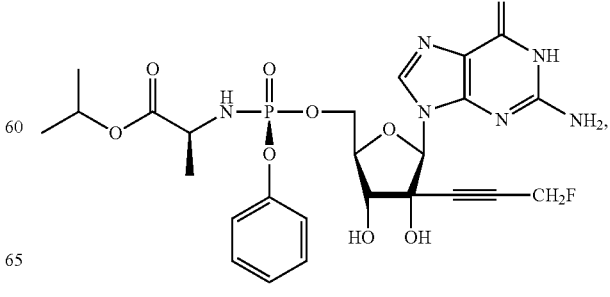

-continued

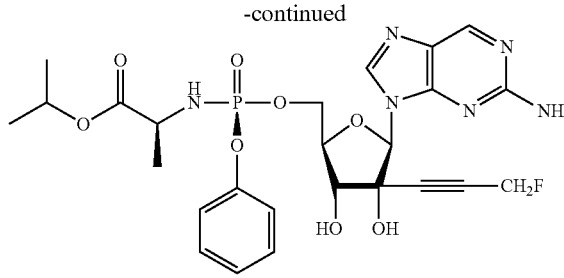

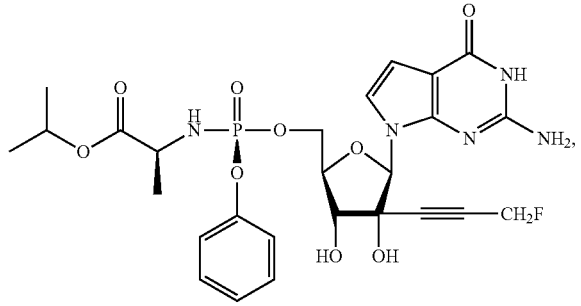

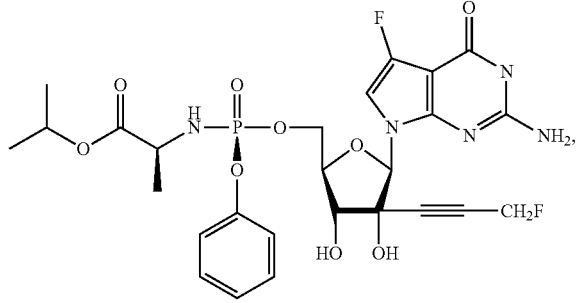

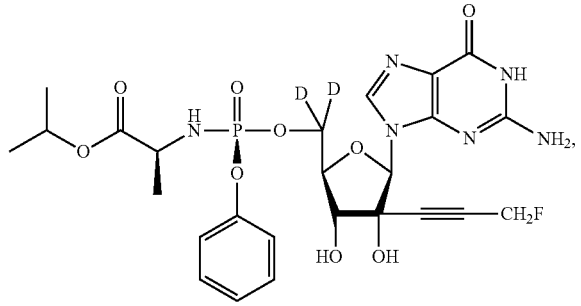

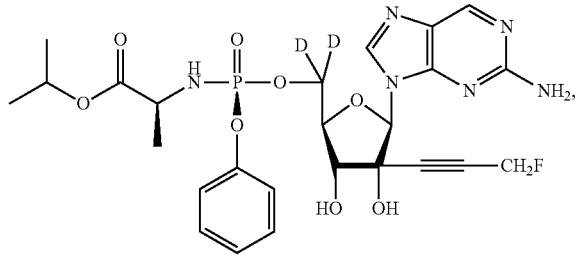

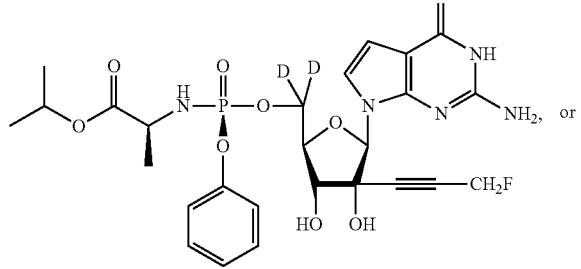

-continued

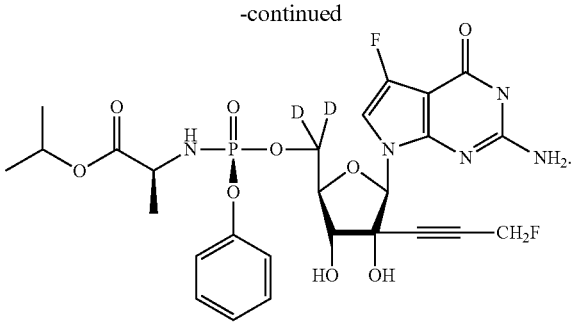

13. A method of treating infections caused by RNA viruses selected from a flavivirus or a picornavirus comprising administering to a host in need an effective amount of a compound of claim 9, or a pharmaceutically acceptable salt thereof.

14. The method of claim 13, wherein the flavivirus is a tick-borne encephalitis virus, dengue, or a Zika virus.

15. A compound of the following structure:

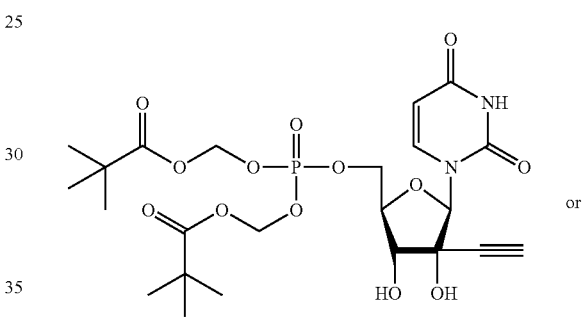

or

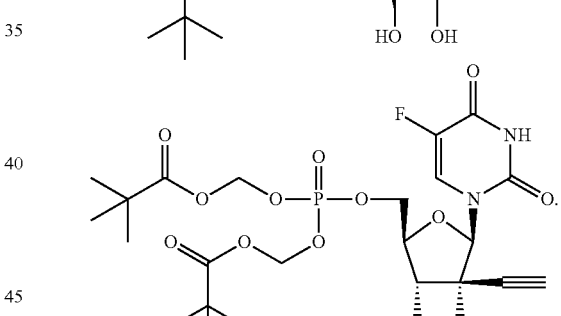

16. The compound of claim 15, having the following structure:

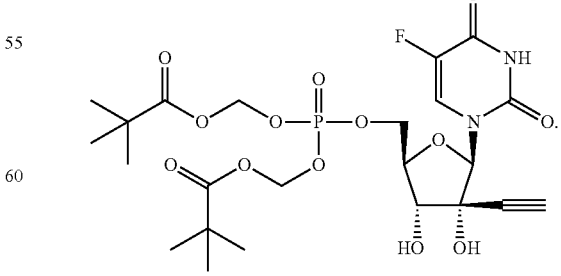

17. A method of treating infections caused by RNA viruses selected from a flavivirus or a picornavirus comprising administering to a host in need an effective amount of a compound of claim 15, or a pharmaceutically acceptable salt thereof.

18. The method of claim 17, wherein the flavivirus is a tick-borne encephalitis virus, dengue, or a Zika virus.

\* \* \* \* \*

UNITED STATES PATENT AND TRADEMARK OFFICE
CERTIFICATE OF CORRECTION

PATENT NO. : 11,192,914 B2  
APPLICATION NO. : 16/097382  
DATED : December 7, 2021  
INVENTOR(S) : Gregory Bluemling et al.

Page 1 of 4

It is certified that error appears in the above-identified patent and that said Letters Patent is hereby corrected as shown below:

In the Claims

Claim 2, Column 669, Lines 28-65, the six structures should appear as follows:

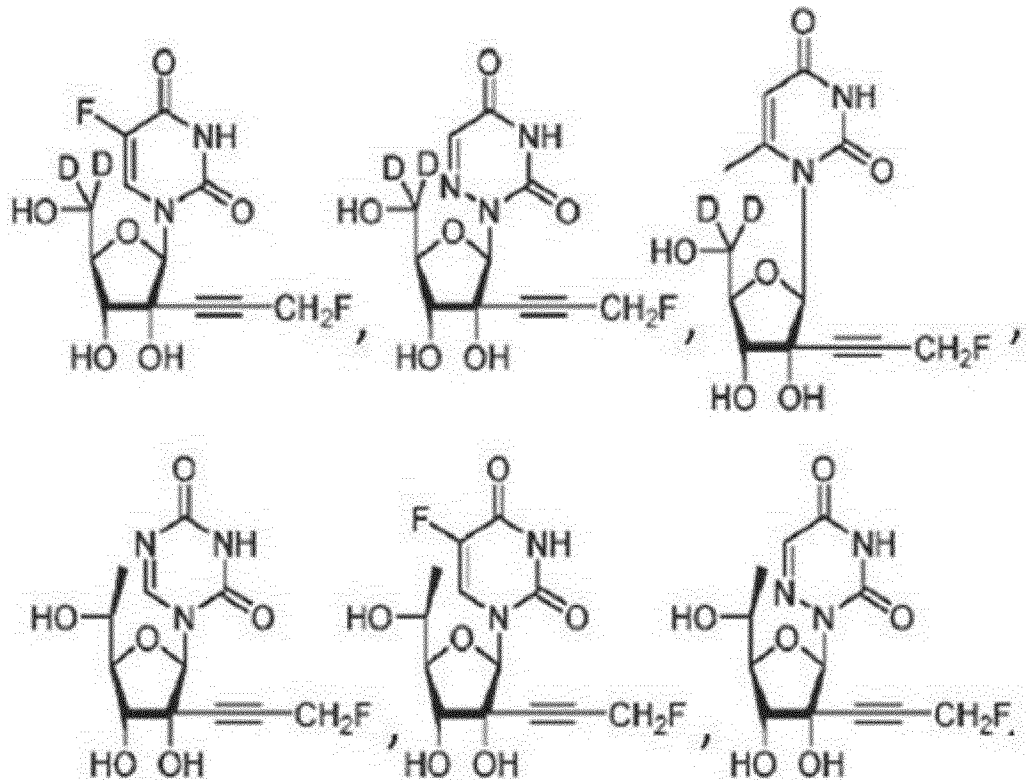

Signed and Sealed this  
Tenth Day of May, 2022

Katherine Kelly Vidal  
*Director of the United States Patent and Trademark Office*

Claim 3, Column 674, Lines 24-34, the structure should appear as follows:
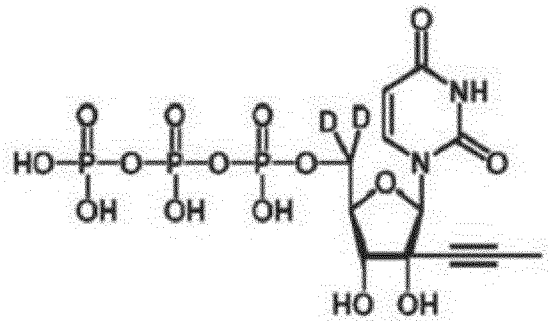
Claim 4, Column 681, Lines 16-27, the structure should appear as follows:
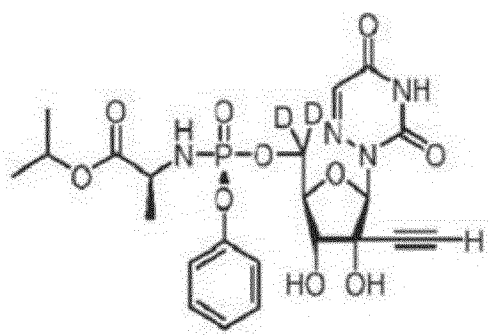
Claim 10, Column 700, Lines 56-66, the structure should appear as follows:
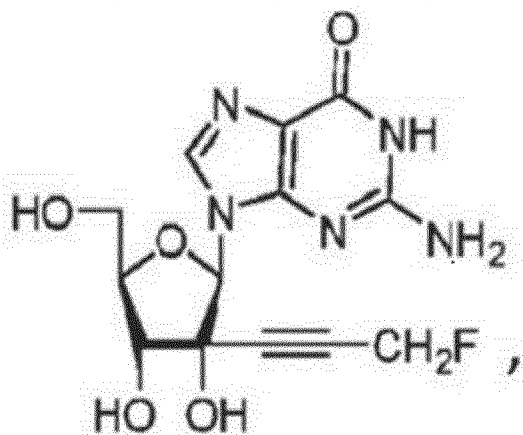

CERTIFICATE OF CORRECTION (continued)
U.S. Pat. No. 11,192,914 B2

Claim 10, Column 701, Lines 1-45, the first four structures should appear as follows:

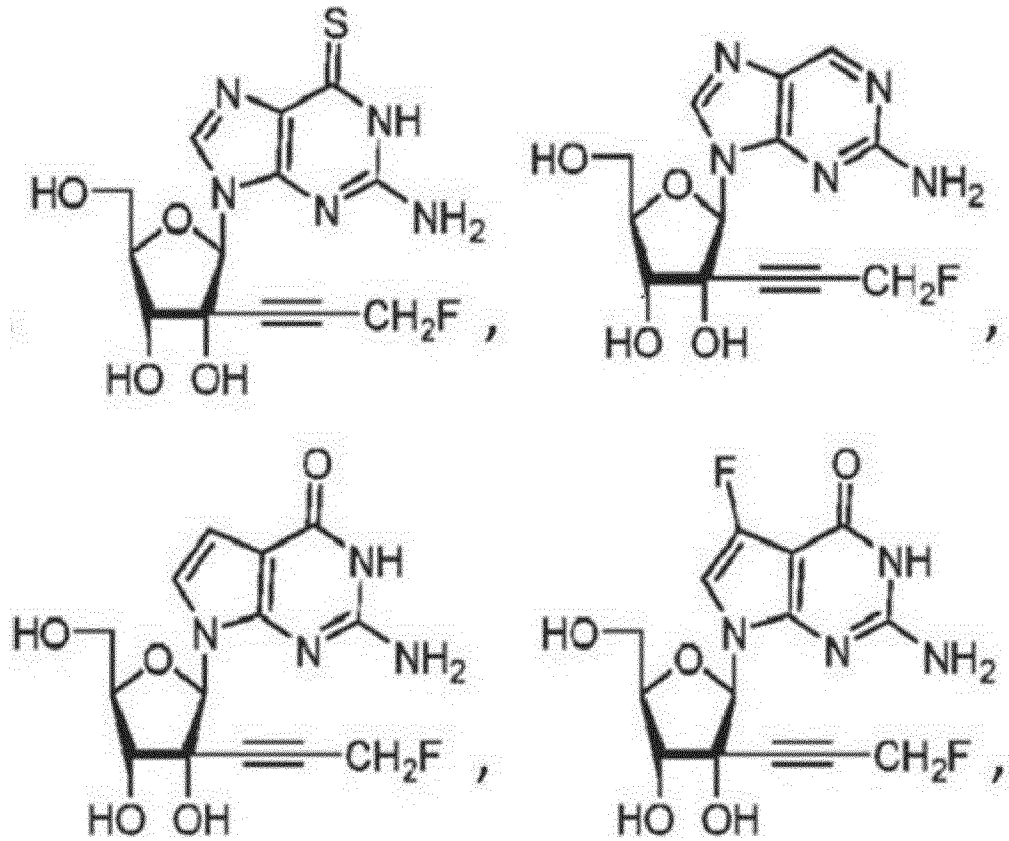

Claim 11, Column 706, Lines 25-35, the structure should appear as follows:

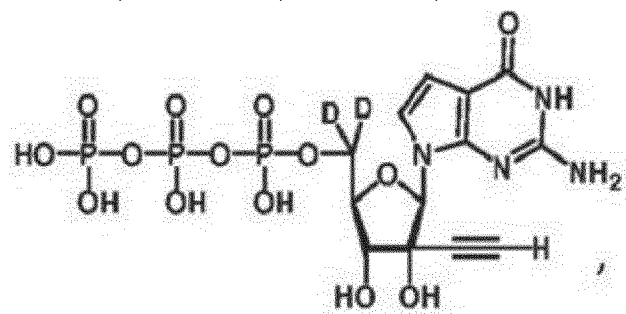

CERTIFICATE OF CORRECTION (continued)
U.S. Pat. No. 11,192,914 B2

Claim 11, Column 713, Lines 42-52, the structure should appear as follows:

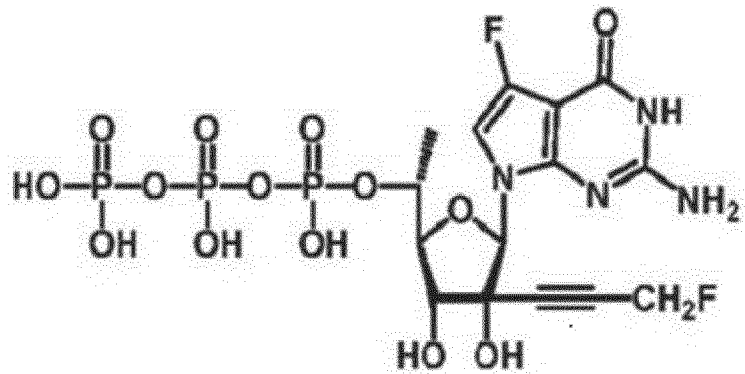

Claim 11, Column 715, Lines 55-65, the structure should appear as follows:

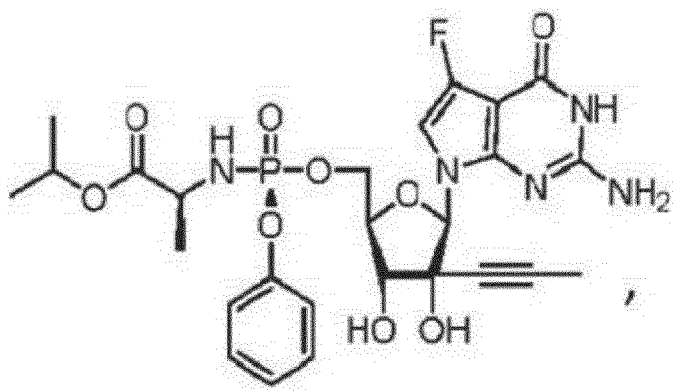

Claim 11, Column 716, Lines 1-13, the structure should appear as follows: